L 
US010287301B2

(12) United States Patent
Wiles et al.

(10) Patent No.: US 10,287,301 B2
(45) Date of Patent: *May 14, 2019

(54) ARYL, HETEROARYL, AND HETEROCYCLIC COMPOUNDS FOR TREATMENT OF MEDICAL DISORDERS

(71) Applicant: Achillion Pharmaceuticals, Inc., New Haven, CT (US)

(72) Inventors: Jason Allan Wiles, Madison, CT (US); Avinash S. Phadke, Branford, CT (US); Milind Deshpande, Madison, CT (US); Atul Agarwal, Hamden, CT (US); Dawei Chen, Guilford, CT (US); Venkat Rao Gadhachanda, Hamden, CT (US); Akihiro Hashimoto, Branford, CT (US); Godwin Pais, Hamden, CT (US); Qiuping Wang, Bethany, CT (US); Xiangzhu Wang, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/010,081

(22) Filed: Jun. 15, 2018

(65) Prior Publication Data
US 2018/0305375 A1 Oct. 25, 2018

Related U.S. Application Data

(63) Continuation of application No. 15/247,399, filed on Aug. 25, 2016, now Pat. No. 10,011,612.

(60) Provisional application No. 62/209,972, filed on Aug. 26, 2015.

(51) Int. Cl.
| | | |
|---|---|---|
| *C07D 513/04* | (2006.01) |
| *C07D 403/14* | (2006.01) |
| *C07D 403/06* | (2006.01) |
| *C07D 401/14* | (2006.01) |
| *C07D 471/04* | (2006.01) |
| *C07D 417/14* | (2006.01) |
| *C07D 487/04* | (2006.01) |
| *C07D 405/14* | (2006.01) |
| *C07D 409/14* | (2006.01) |
| *C07D 495/04* | (2006.01) |
| *C07D 493/04* | (2006.01) |
| *C07D 413/14* | (2006.01) |

(52) U.S. Cl.
CPC ......... *C07D 513/04* (2013.01); *C07D 401/14* (2013.01); *C07D 403/06* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 493/04* (2013.01); *C07D 495/04* (2013.01)

(58) Field of Classification Search
CPC .. C07D 513/04; C07D 403/14; C07D 403/06; C07D 401/14; C07D 471/04; C07D 417/14; C07D 485/04; C07D 405/14; C07D 409/14; C07D 495/04; C07D 493/04; C07D 413/14
See application file for complete search history.

(56) References Cited

U.S. PATENT DOCUMENTS

| | | |
|---|---|---|
| 6,489,476 B1 | 12/2002 | Dang et al. |
| 6,653,340 B1 | 11/2003 | Babu et al. |
| 2002/0133004 A1 | 9/2002 | Takaaki et al. |
| 2005/0228000 A1 | 10/2005 | Smallheer et al. |
| 2005/0267108 A1 | 12/2005 | Hsieh et al. |
| 2007/0155712 A1 | 7/2007 | Zahn et al. |
| 2008/0075720 A1 | 3/2008 | Holers et al. |
| 2008/0075728 A1 | 3/2008 | Newman et al. |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0295884 A1 | 11/2012 | Altmann et al. |
| 2013/0296377 A1 | 11/2013 | Adams et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0239837 A1 | 8/2015 | Wiles et al. |
| 2015/0239838 A1 | 8/2015 | Phadke et al. |
| 2015/0239868 A1 | 8/2015 | Pais et al. |

(Continued)

FOREIGN PATENT DOCUMENTS

| | | |
|---|---|---|
| WO | WO 1993/020099 A2 | 10/1993 |
| WO | WO 1995/029697 A1 | 11/1995 |

(Continued)

OTHER PUBLICATIONS

Gadhachanda et al., 2016, caplus an 2016:627420.*

(Continued)

*Primary Examiner* — Sun Jae Yoo
(74) *Attorney, Agent, or Firm* — Knowles Intellectual Property Strategies, LLC

(57) ABSTRACT

Compounds, methods of use, and processes for making inhibitors of complement Factor D comprising Formula I, or a pharmaceutically acceptable salt or composition thereof wherein R12 or R13 on the A group is an aryl, heteroaryl or heterocycle (R32) are provided. The inhibitors of Factor D described herein reduce the excessive activation of complement.

18 Claims, 61 Drawing Sheets

(56) References Cited

U.S. PATENT DOCUMENTS

| | | | |
|---|---|---|---|
| 2015/0239893 | A1 | 8/2015 | Wang et al. |
| 2015/0239894 | A1 | 8/2015 | Gadhachanda et al. |
| 2015/0239895 | A1 | 8/2015 | Gadhachanda et al. |
| 2015/0239919 | A1 | 8/2015 | Gadhachanda et al. |
| 2015/0239920 | A1 | 8/2015 | Gadhachanda et al. |
| 2015/0239921 | A1 | 8/2015 | Wiles et al. |

FOREIGN PATENT DOCUMENTS

| | | | |
|---|---|---|---|
| WO | WO 1999/048492 A1 | 9/1999 |
| WO | WO 2004/007501 A1 | 1/2004 |
| WO | WO 2004/045518 A2 | 6/2004 |
| WO | WO 2004/111041 A1 | 12/2004 |
| WO | WO 2008/047831 A1 | 4/2008 |
| WO | WO 2009/091826 A2 | 7/2009 |
| WO | WO 2012/093101 A1 | 7/2012 |
| WO | WO 2012/177782 A1 | 12/2012 |
| WO | WO 2013/166436 A1 | 11/2013 |
| WO | WO 2014/002051 A2 | 1/2014 |
| WO | WO 2014/002052 A1 | 1/2014 |
| WO | WO 2014/002053 A1 | 1/2014 |
| WO | WO 2014/002054 A1 | 1/2014 |
| WO | WO 2014/002057 A1 | 1/2014 |
| WO | WO 2014/002058 A2 | 1/2014 |
| WO | WO 2014/002059 A1 | 1/2014 |
| WO | WO 2014/005150 A1 | 1/2014 |
| WO | WO 2014/009833 A2 | 1/2014 |
| WO | WO 2014/037480 A1 | 3/2014 |
| WO | WO 2014/116880 A1 | 7/2014 |
| WO | WO 2015/008861 A1 | 1/2015 |
| WO | WO 2015/130784 A1 | 9/2015 |
| WO | WO 2015/130795 A1 | 9/2015 |
| WO | WO 2015/130806 A1 | 9/2015 |
| WO | WO 2015/130830 A1 | 9/2015 |
| WO | WO 2015/130838 A1 | 9/2015 |
| WO | WO 2015/130842 A2 | 9/2015 |
| WO | WO 2015/130845 A1 | 9/2015 |
| WO | WO 2015/130854 A1 | 9/2015 |
| WO | WO 2017/035348 A1 | 3/2017 |
| WO | WO 2017/035349 A1 | 3/2017 |
| WO | WO 2017/035351 A1 | 3/2017 |
| WO | WO 2017/035352 A1 | 3/2017 |
| WO | WO 2017/035353 A1 | 3/2017 |
| WO | WO 2017/035355 A1 | 3/2017 |
| WO | WO 2017/035357 A1 | 3/2017 |
| WO | WO 2017/035360 A1 | 3/2017 |
| WO | WO 2017/035361 A1 | 3/2017 |
| WO | WO 2017/035362 A1 | 3/2017 |
| WO | WO 2017/035401 A1 | 3/2017 |
| WO | WO 2017/035405 A1 | 3/2017 |
| WO | WO 2017/035408 A1 | 3/2017 |
| WO | WO 2017/035409 A1 | 3/2017 |
| WO | WO 2017/035411 A1 | 3/2017 |
| WO | WO 2017/035413 A1 | 3/2017 |
| WO | WO 2017/035415 A1 | 3/2017 |
| WO | WO 2017/035417 A1 | 3/2017 |
| WO | WO 2017/035418 A1 | 3/2017 |
| WO | WO 2017/098328 A2 | 6/2017 |
| WO | WO 2017/136395 A1 | 8/2017 |

OTHER PUBLICATIONS

Airey et al. "A Convenient Preparation of Thieno[3,2-c]pyrazole" Synthesis, 2014; 46: 96-100.

Barraclough et al. "Synthesis of (2S,3R)- and (@S,3S)-[3-2H1]-proline via highly selective hydrolysis of a silyl enol ether" Tetrahedron Letters, 2005; 46: 4653-4655.

Barraclough et al. "Two separate and distinct syntheses of stereospecifically deuteriated samples of (2S)-proline" Organic & Biomolecular Chemistry, 2006; 4: 1483-1491.

Cole et al. "Structure of 3,4-Dichloroisocoumarin-Inhibited Factor D" Acta Crystallographica, 1998; D54: 711-717.

Database Registry Chemical Abstracts Service, Columbus, Ohio, Accession No. RN1236248-20-6, Entered STN: Aug. 16, 2010.

Database Registry Chemical Abstracts Service, Columbus, Ohio, Accession No. RN1380849-41-1, Entered STN: Jul. 3, 2012.

De Luca et al. "HIV-1 integrase strand-transfer inhibitors: Design, synthesis and molecular modeling investigation" European Journal of Medicinal Chemistry, 2011; 46: 756-764.

Donthiri et al. "Copper-Catalyzed C—H Functionalization of Pyridines and Isoquinolines with Vinyl Azides: Synthesis of Imidazo Heterocycles" Journal of Organic Chemistry, 2014; 79: 11277-11284.

Dormoy et al. "Synthesis of N-t-Butoxycarbonyl-4,4-dideuterio-L-proline" Synthesis, 1986; 1: 81-82.

Hecker et al. "Liver-Targeted Prodrugs of 2'-C-Methyladenosine for Therapy of Hepatitis C Virus Infection" Journal of Medicinal Chemistry, 2007; 50(16): 3891-3896.

Hruby et al. "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments and effects of structural changes on carbon-13 NMR chemical shifts in peptides" Journal of the American Chemical Society, 1979; 101(1): 202-212.

International Search Report and Written Opinion for PCT/US2015/017523 dated May 14, 2015.

International Search Report and Written Opinion for PCT/US2015/017538 dated May 14, 2015.

International Search Report and Written Opinion for PCT/US2015/017554 dated May 14, 2015.

International Search Report and Written Opinion for PCT/US2015/017583 dated May 27, 2015.

International Search Report and Written Opinion for PCT/US2015/017593 dated Jun. 16, 2015.

International Search Report and Written Opinion for PCT/US2015/017597 dated Jan. 29, 2016.

International Search Report and Written Opinion for PCT/US2015/17600 dated May 27, 2015.

International Search Report and Written Opinion for PCT/US2015/017609 dated May 29, 2015.

International Search Report and Written Opinion for PCT/US2016/048688 dated Dec. 28, 2016.

International Search Report and Written Opinion for PCT/US2016/048690 dated Dec. 28, 2016.

International Search Report and Written Opinion for PCT/US2016/048693 dated Jan. 13, 2017.

International Search Report and Written Opinion for PCT/US2016/048695 dated Dec. 30, 2016.

International Search Report and Written Opinion for PCT/US2016/048696 dated Jan. 5, 2017.

International Search Report and Written Opinion for PCT/US2016/048701 dated Jan. 10, 2017.

International Search Report and Written Opinion for PCT/US2016/048704 dated Dec. 27, 2016.

International Search Report and Written Opinion for PCT/ US2016/048707 dated Jan. 5, 2017.

International Search Report and Written Opinion for PCT/ US2016/048709 dated Jan. 17, 2017.

International Search Report and Written Opinion for PCT/ US2016/048797 dated Jan. 5, 2017.

International Search Report and Written Opinion for PCT/ US2016/048779 dated Dec. 27, 2016.

International Search Report and Written Opinion for PCT/ US2016/048783 dated Feb. 3, 2017.

International Search Report and Written Opinion for PCT/ US2016/048795 dated Feb. 17, 2017.

International Search Report and Written Opinion for PCT/ US2016/048788 dated Jan. 5, 2017.

International Search Report and Written Opinion for PCT/ US2016/048793 dated Dec. 28, 2016.

International Search Report and Written Opinion for PCT/ US2016/048799 dated Dec. 28, 2016.

International Search Report and Written Opinion for PCT/ US2016/048787 dated Jan. 5, 2017.

International Search Report and Written Opinion for PCT/ US2016/048800 dated Jan. 5, 2017.

(56) References Cited

OTHER PUBLICATIONS

International Search Report and Written Opinion for PCT/US2016/048710 dated Jan. 5, 2017.
Kobayashi et al. "Carboxylation of alkynylsilanes with carbon dioxide mediated by cesium fluoride in DMSO" Organic & Biomolecular Chemistry, 2013; 11: 3773-3775.
Komiya et al., 2015, caplus an 2015:126147.
Kuang et al. "Synthesis of (Z)-1-bromo-1-alkenes and terminal alkynes from anti-2,3-dibromoalkanoic acids by microwave-induced reaction" Tetrahedron, 2006; 61(16): 4043-4052.
Mackay et al. "Rapid Synthesis of the N-Methylwelwitindolinone Skeleton" Organic Letters, 2005; 7: 3421-3424.
Okutani et al. "Conversion of Bromoalkenes into Alkynes by Wet Tetra-n-butylammonium Fluoride" Journal of Organic Chemistry, 2009; 74: 442-444.
PubChem CID 1129904 entered Jul. 10, 2005.
PubChem CID 59912842 entered Aug. 20, 2012.
Quesada et al. "One-pot conversion of activated alcohols into terminal alkynes using manganese dioxide in combination with the Bestmann—Ohira reagent" Tetrahedron Letters, 2005; 46: 6473-6476.
Roth et al. "Further Improvements of the Synthesis of Alkynes from Aldehydes" Synthesis, 2004; 1: 59-62.
Ruiz-Gomez et al. "Structure—Activity Relationships for Substrate-Based Inhibitors of Human Complement Factor B" Journal of Medicinal Chemistry, 2009; 52: 6042-6052.
Tandon et al. "Substrate specificity of human prolyl-4-hydroxylase" Bioorganic and Medicinal Chemistry Letters, 1998; 8(10): 1139-1144.
Tang et al. "Palladium-Catalyzed Carbonylative Sonogashira Coupling of Aryl Bromides via tert-Butyl Isocyanide Insertion" Journal of Organic Chemistry, 2013; 78(7): 3170-3175.
Peifer et al. "Design, Synthesis, and Biological Evaluation of Novel 3-Aryl-4-(1H-indole-3y1)-1,5-dihydro-2H-pyrrole-2-ones as Vascular Endothelial Growth Factor Receptor (VEGF-R) Inhibitors", J. Med. Chem. 2008, vol. 51, pp. 3814-3824.
Qu et al. "Recent Developments in Low Molecular Weight Complement Inhibitors", Mol. Immunol. 2009. vol. 47 (2-3). pp. 185-195.
U.S. Pat. No. 9,598,446 B2, U.S. Appl. No. 14/631,312, Gadhachanda et al., Mar. 21, 2017.
U.S. Pat. No. 9,643,986 B2, U.S. Appl. No. 14/630,959, Wiles et al., May 9, 2017.
U.S. Pat. No. 9,663,543 B2, U.S. Appl. No. 14/631,785, Wiles et al., May 30, 2017.
U.S. Pat. No. 9,695,205 B2, U.S. Appl. No. 14/631,233, Wang et al., Jul. 4, 2017.
U.S. Pat. No. 9,732,103 B2, U.S. Appl. No. 14/631,440, Wiles et al., Aug. 15, 2017.
U.S. Pat. No. 9,732,104 B2, U.S. Appl. No. 14/631,683, Wiles et al., Aug. 15, 2017.
U.S. Pat. No. 9,758,537 B2, U.S. Appl. No. 14/631,828, Phadke et al., Sep. 12, 2017.
U.S. Pat. No. 9,796,741 B2, U.S. Appl. No. 14/631,625, Wiles et al., Oct. 24, 2017.
U.S. Pat. No. 9,828,396 B2, U.S. Appl. No. 14/631,090, Pais et al., Nov. 28, 2017.
US 2016/0361329 A1, U.S. Appl. No. 15/246,049, Wiles et al., Dec. 15, 2016.
US 2016/0362398 A1, U.S. Appl. No. 15/245,712, Wiles et al., Dec. 15, 2016.
US 2016/0362399 A1, U.S. Appl. No. 15/245,788, Wiles et al., Dec. 15, 2016.
US 2016/0362432 A1, U.S. Appl. No. 15/245,945, Wiles et al., Dec. 15, 2016.
US 2016/0362433 A1, U.S. Appl. No. 15/245,872, Wiles et al., Dec. 15, 2016.
US 2017/0056428 A1, U.S. Appl. No. 15/247,429, Wiles et al., Mar. 2, 2017.
US 2017/0057950 A1, U.S. Appl. No. 15/247,440, Wiles et al., Mar. 2, 2017.
US 2017/0057983 A1, U.S. Appl. No. 15/247,424, Wiles et al., Mar. 2, 2017.
US 2017/0057993 A1, U.S. Appl. No. 15/247,410, Wiles et al., Mar. 2, 2017.
US 2017/0066783 A1, U.S. Appl. No. 15/247,399, Wiles et al., Mar. 9, 2017.
US 2017/0189410 A1, U.S. Appl. No. 15/463,701, Gadhachanda et al., Jul. 6, 2017.
US 2017/0226142 A1, U.S. Appl. No. 15/494,926, Wiles et al., Aug. 10, 2017.
US 2017/0260219 A1, U.S. Appl. No. 15/607,120, Wiles et al., Sep. 14, 2017.
US 2017/0298085 A1, U.S. Appl. No. 15/638,081, Wiles et al., Oct. 19, 2017.
US 2017/0298084 A1, U.S. Appl. No. 15/638,076, Wiles et al., Oct. 19, 2017.
US 2018/0022766 A1, U.S. Appl. No. 15/676,411, Wiles et al., Jan. 25, 2018.
US 2018/0022767 A1, U.S. Appl. No. 15/700,550, Wiles et al., Jan. 25, 2018.
US 2018/0030075 A1, U.S. Appl. No. 15/711,794, Wiles et al., Feb. 1, 2018.
US 2018/0072762 A1, U.S. Appl. No. 15/818,559, Wiles et al., Mar. 15, 2018.

* cited by examiner

FIG. 9C
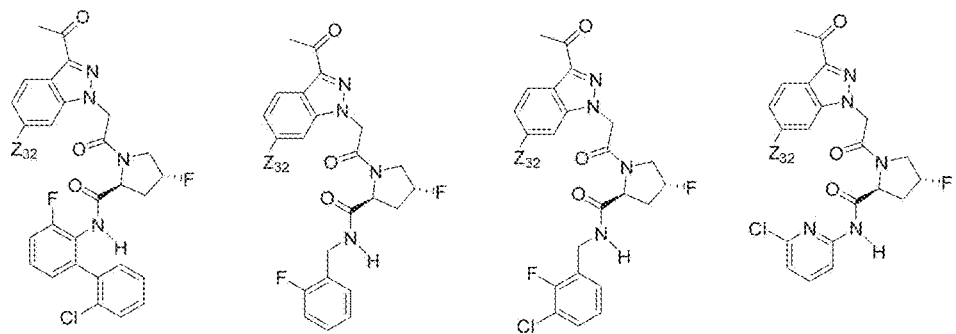
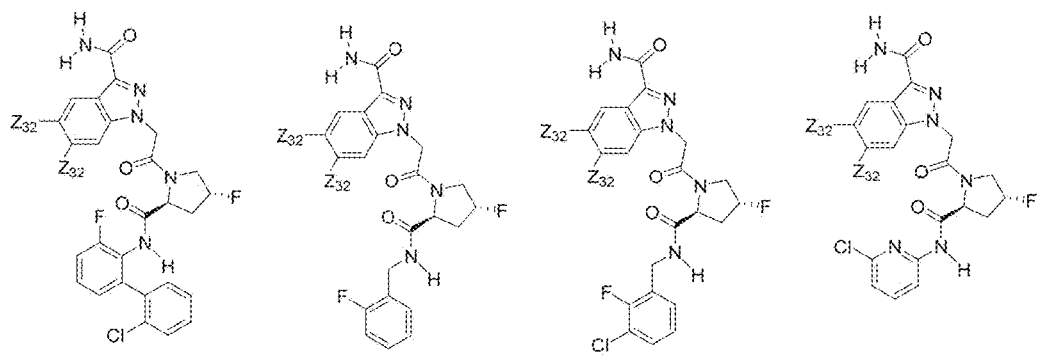
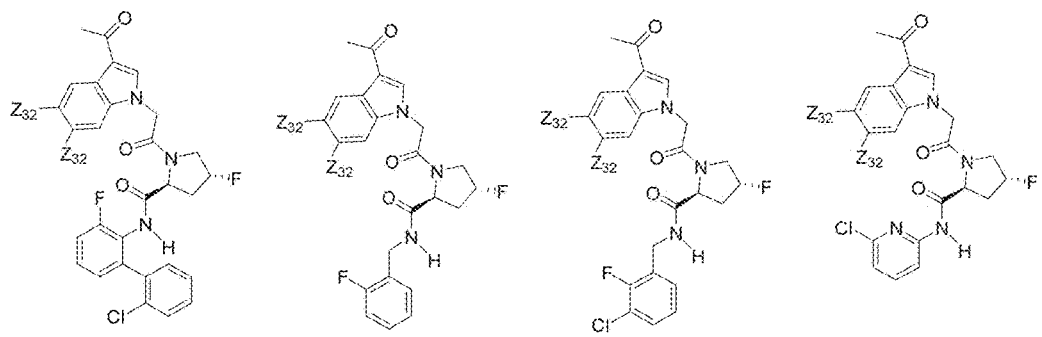

ARYL, HETEROARYL, AND HETEROCYCLIC COMPOUNDS FOR TREATMENT OF MEDICAL DISORDERS

CROSS-REFERENCE TO RELATED APPLICATIONS

This application is a continuation of U.S. application Ser. No. 15/247,399, filed Aug. 25, 2016, which claims the benefit of provisional U.S. Application No. 62/209,972, filed Aug. 26, 2015 and the entirety of the application is hereby incorporated by reference for all purposes.

BACKGROUND

An immune disorder occurs when the immune system is not performing in a normal manner. Inflammation is a protective response that involves the immune system, blood vessels, and molecular mediators. A wide variety of medical disorders are caused by detrimental immune or inflammatory responses, or the inability of a cell to respond to a normal immune or inflammatory process.

The complement system is a part of the innate immune system which does not adapt to changes over the course of the host's life, but instead is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. Complement Factor D plays an early and central role in activation of the alternative pathway of the complement cascade. Activation of the alternative complement pathway is initiated by spontaneous hydrolysis of a thioester bond within C3 to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning of Factor H, the alternative pathway of the complement cascade is overly activated leading to cellular damage. Inhibition of the alternative pathway under these circumstances is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Alexion Pharmaceutical's anti-C5 antibody eculizumab (Soliris®) is currently the only complement-specific antibody on the market, and is the first and only approved treatment for paroxysmal nocturnal hemoglobinuria (PNH). Exciluzimab is also approved for atypical hemolytic uremic syndrome (aHUS). However, many of the patients treated with eculizumab remain anemic, and many patients continue to require blood transfusions. In addition, treatment with eculizumab requires life-long intravenous injections. Thus, there is an unmet need to develop novel inhibitors of the complement pathway.

Other disorders that have been linked to the complement cascade include aHUS, hemolytic uremic syndrome (HUS), abdominal aortic aneurysm, hemodialysis complications, hemolytic anemia, or hemodialysis, neuromylitis (NMO), myasthenia gravis (MG), fatty liver, nonalcoholic steatohepatitis (NASH), liver inflammation, cirrhosis, liver failure, dermatomyocitis, and amyotrophic lateral sclerosis.

Factor D is an attractive target for inhibition or regulation of the complement cascade due to its early and essential role in the alternative complement pathway, and its potential role in signal amplification within the classical and lectin complement pathways. Inhibition of Factor D effectively interrupts the pathway and attenuates the formation of the membrane attack complex.

While initial attempts have been made to develop inhibitors of Factor D, there are currently no small molecule Factor D inhibitors in clinical trials. Examples of Factor D inhibitors or prolyl compounds are described in the following disclosures.

Biocryst Pharmaceuticals U.S. Pat. No. 6,653,340 titled "Compounds useful in the complement, coagulat and kallikrein pathways and method for their preparation" describes fused bicyclic ring compounds that are potent inhibitors of Factor D. Development of the Factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2014/

002051, WO2014/002052, WO2014/002053, WO2014/002054, WO2014/002057, WO2014/002058, WO2014/002059, WO2014/005150, and WO2014/009833.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B. V. and Yamanouchi Pharmaceutical Co. ITD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system.

On Feb. 25, 2015, Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

Given the wide variety of medical disorders that are caused by detrimental immune or inflammatory responses, new uses and compounds are needed for medical treatment. In one aspect, new uses and compounds are needed to mediate the complement pathway, and for example, which act as Factor D inhibitors for treatment of disorders in a host, including a human, associated with dysregulation of the complement cascade, or with undesired result of the complement cascade performing its normal function.

SUMMARY

In a first embodiment, the invention is the use of a compound of Formula I, or a pharmaceutically acceptable salt or composition thereof, wherein $R^{12}$ or $R^{13}$ on the A group is an aryl, heteroaryl, or heterocycle, including those compounds set out in Table 1, for the treatment of a disorder in a host, typically a human, wherein the disorder is selected from the group disclosed in the Detailed Description, Part IV, Section A. The compounds of Table 1 were first disclosed in PCT Patent Application No. PCT/US2015/017593 and U.S. patent application Ser. No. 14/631,625 titled "Aryl, Heteroaryl, and Heterocyclic Compounds for Treatment of Complement Mediated Disorders," however, not for the indications now provided in the Detailed Description, Part IV, Section A. The compound is provided in an effective amount to treat the disorder, and optionally in a pharmaceutically acceptable carrier. Therefore, in particular, this first embodiment includes uses of compounds to treat a disorder selected from the group disclosed in the Detailed Description, Part IV, Section A.

Non-limiting examples of disorders described in the Detailed Description, Part IV, Section A include: fatty liver and conditions stemming from fatty liver, nonalcoholic steatohepatitis (NASH), liver inflammation, cirrhosis, liver failure, dermatomyocitis, and amyotrophic lateral sclerosis. In another embodiment of Section A disorders, the active compound is used to modulate an immune response prior to, during, or after surgery or other medical procedure, or as adjunctive therapy to dampen the immune or inflammatory response during a pharmaceutical or biopharmaceutical drug treatment, a blood transfusion, or other allogenic tissue or fluid administration. In one embodiment, a Section A method is provided for the treatment or prevention of cytokine or inflammatory reactions in response to the administration of biotherapeutics (e.g. CAR T-cell therapy) in a host by administering an effective amount of a designated compound herein, or a pharmaceutically acceptable salt thereof, optionally in a pharmaceutically acceptable carrier.

Non-limiting examples of disorders in the Detailed Description, Part IV, Section B of this invention include paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease. In one aspect, an active compound or its salt or composition can be used to treat a medical disorder which is mediated by either a dysfunctional complement cascade or a disorder or abnormality of a cell that adversely affects the ability of the cell to engage in or respond to normal complement activity, for example, including but not limited to sparing certain cells from complement mediated lysis. PNH is one example of such a disorder, wherein host blood cells are missing the gene PIG-A that expresses a protein that protects the blood cells from complement mediated lysis. Other embodiments of Section B disorders include complement associated disorders that are induced by antibody-antigen interactions, a component of an immune or autoimmune disorder, hereditary angioedema, capillary leak syndrome, atypical hemolytic uremic syndrome (aHUS), hemolytic uremic syndrome (HUS), abdominal aortic aneurysm, hemodialysis complications, hemolytic anemia and hemodialysis.

In a second embodiment of the invention, an aryl, heteroaryl, or heterocycle compound is selected from Table 2 or an active compound that is prepared from or consists of moieties selected from FIGS. 1B, 1C, 2B, 2C, 2D, 2E, 3B, 3C, 3D, 3E, 3F, 3G, 3H, 3I, 3J, 3K, 3L, 3M, 3N, and 6A; and optionally 4B, 4C, 4D and 4E or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of Table 2 or an active compound that is prepared from or consisting of the moieties in the referenced Figures is used to treat a disorder associated with a dysfunction, including increased activity of the complement pathway that includes the administration of an effective amount of a compound selected from Table 2 or an active compound prepared from or consisting of the moieties in the referenced Figures or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in Table 2 or an active compound prepared from or consisting of the moieties in the referenced Figures in one embodiment is used to dampen or inhibit detrimental complement activity in a host, by administration of an effective amount in a suitable manner to a host in need thereof. Therefore, in particular, this second embodiment includes compound species, and uses of these species to treat disorders selected from the group disclosed in the Detailed Description, Part IV, Section A or B.

In a third embodiment of the invention, an aryl, heteroaryl, or heterocycle compound is provided selected from Table 3 or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of Table 3 is used to treat a disorder associated with a dysfunction, including increased activity, of the complement pathway that includes the administration of an effective amount of a compound selected from Table 3 or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. A compound selected from those in Table 3 in one embodiment is used to dampen or inhibit detrimental complement activity in a host, by administration of an effective amount in a suitable manner to a host in need thereof. Therefore, in particular, this third embodiment includes compound species and uses of these species to treat a disorder selected from the group disclosed in the Detailed Description, Part IV, Section A or B.

In a fourth embodiment of the invention, an aryl, heteroaryl, or heterocycle compound is provided that is prepared from or consists of moieties selected from FIGS. 1D, 1E, 5, 6A, 7A, 7B, 7C, 7D, 7E, and 8; and optionally 4B, 4C, 4D, 4E, or 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A. In one embodiment, the compound that is prepared from or consists of moieties selected from FIGS. 1D, 1E, 5, 6A, 7A, 7B, 7C, 7D, 7E, and 8; and optionally 4B, 4C, 4D, 4E, or 4F is used to treat a disorder associated with a dysfunction, including increased activity, of the complement pathway that includes the administration of an effective amount of the compound or an embodiment of the active compound, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in one embodiment provided herein is used to dampen or inhibit detrimental complement activity in a host, by administration of an effective amount in a suitable manner to a host in need thereof. Therefore, in particular, this fourth embodiment includes uses of these compounds to treat disorder selected from the group disclosed in the Detailed Description, Part IV, Section A.

In a fifth embodiment of the invention, an aryl, heteroaryl, or heterocycle compound is provided that is prepared from or consists of moieties selected from FIG. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, 6D, 7F or 7I; and optionally 4B, 4C, 4D, 4E, or 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, a compound that is prepared from or consists of moieties from FIG. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, 6D, 7F or 7I; and optionally 4B, 4C, 4D, 4E, or 4F is used to treat a disorder associated with a dysfunction, including increased activity, of the complement pathway that includes the administration of an effective amount of the compound or an embodiment of the active compound, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in one embodiment provided herein is used to dampen or inhibit detrimental complement activity in a host, by administration of an effective amount in a suitable manner to a host in need thereof. Therefore, in particular, this fifth embodiment includes compound species and uses of these species to treat disorder selected from the group disclosed in the Detailed Description, Part IV, Section A or B.

In a sixth embodiment of the invention, an aryl, heteroaryl, or heterocycle compound is provided that is prepared from or consists of moieties selected from FIGS. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, 6D, 7G, 7H, and 8; and optionally 4B, 4C, 4D, 4E, and 4F or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A. In one embodiment, the compound that is prepared from or consists of moieties selected from FIGS. 1B, 1C, 1D, 1E, 3A, 3B, 3C, 3D, 3E, 3F, 3G, 3H, 3I, 3J, 3K, 3L, 3M, 3N, 3O, 3P, 3Q, 5, 6A, 6B, 6C, 6D, 7G, 7H, and 8; and optionally 4B, 4C, 4D, 4E, and 4F is used to treat a disorder associated with a dysfunction, including increased activity, of the complement pathway that includes the administration of an effective amount of the compound or an embodiment of the active compound, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in one embodiment provided herein is used to dampen or inhibit detrimental complement activity in a host, by administration of an effective amount in a suitable manner to a host in need thereof. Therefore, in particular, this sixth embodiment includes uses of these species to treat disorder selected from the group disclosed in the Detailed Description, Part IV, Section A.

In a seventh embodiment of the invention, an aryl, heteroaryl, or heterocycle compound as described and used herein is selected from those depicted in FIGS. 9A, 9B, 9C, 9D, 9E, 9F, 9G and 9H, and FIGS. 6B, and 6C, or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of FIG. 9A, 9B, 9C, 9D, 9E, 9F, 9G or 9H, and FIGS. 6B, and 6C, is used to treat a disorder associated with a dysfunction, including increased activity of the complement pathway that includes the administration of an effective amount of a compound selected from FIG. 9A, 9B, 9C, 9D, 9E, 9F, 9G or 9H, and FIGS. 6B, and 6C, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in FIG. 9A, 9B, 9C, 9D, 9E, 9F, 9G or 9H, and FIGS. 6B and 6C, in one embodiment is used to dampen or inhibit detrimental complement activity in a host, by administration of an effective amount in a suitable manner to a host in need thereof. Therefore, in particular, this seventh embodiment includes compound species, and uses of these species to treat disorder selected from the group disclosed in the Detailed Description, Part IV, Section A or B.

In a eighth embodiment of the invention, an aryl, heteroaryl, or heterocycle compound as described and used herein is selected from those depicted in FIGS. 9A, 9B, 9C, 9D, 9E, 9F, 9G and 9H, and FIG. 6A, or a pharmaceutically acceptable composition, salt, isotopic analog or prodrug thereof, for the treatment of an immune or inflammatory disorder in a host, typically a human, including a disorder selected from the group disclosed in the Detailed Description, Part IV, Section A or B. In one embodiment, the compound of FIG. 9A, 9B, 9C, 9D, 9E, 9F, 9G or 9H, and FIG. 6A, is used to treat a disorder associated with a dysfunction, including increased activity of the complement pathway that includes the administration of an effective amount of a compound selected from FIG. 9A, 9B, 9C, 9D, 9E, 9F, 9G or 9H, and FIG. 6A, or a pharmaceutically acceptable salt thereof, optionally in a pharmaceutically acceptable carrier, as described in more detail below. In one embodiment, the disorder is associated with the alternative complement cascade pathway. In yet another embodiment, the disorder is associated with the complement classical pathway. In a further embodiment, the disorder is associated with the complement lectin pathway. The compound in FIG. 9A, 9B, 9C, 9D, 9E, 9F, 9G or 9H, and FIG. 6A, in one embodiment is used to dampen or inhibit detrimental complement activity in a host, by administration of an effective amount in a suitable manner to a host in need thereof. Therefore, in particular, this seventh embodiment includes compound species, and uses of these species to treat disorder selected from the group disclosed in the Detailed Description, Part IV, Section A or B.

Compounds disclosed herein or used as described herein may be administered in any desired route according to the direction of the healthcare provider, for example, oral, topical, parenteral, by inhalation or spray, sublingual, via implant, including ocular implant, transdermal, via buccal administration, rectal, as an ophthalmic solution, injection, including ocular injection, intravenous, intra-aortal, intracranial, subdermal, intraperitoneal, subcutaneous, transnasal, sublingual, or rectal or by other means, in dosage unit formulations optionally containing conventional pharmaceutically acceptable carriers, and in an immediate or controlled release fashion. For use in the eye, any of the compounds described herein can be administered to the eye in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtascleralscleral, circumcorneal, and tear duct injections, or through a mucus, mucin, or a mucosal barrier, in an immediate or controlled release fashion.

The compounds of Formula I are of the formula:

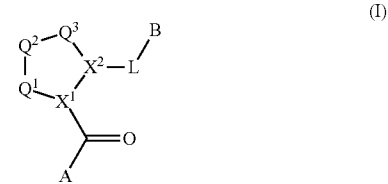

(I)

and the pharmaceutically acceptable salts and compositions thereof, wherein:

$Q^1$ is $N(R^1)$ or $C(R^1R^{1'})$;

$Q^2$ is $C(R^2R^{2'})$, $C(R^2R^{2'})$—$C(R^2R^{2'})$, S, O, $N(R^2)$ or $C(R^2R^{2'})O$;

$Q^3$ is $N(R^3)$, S, or $C(R^3R^{3'})$;

$X^1$ and $X^2$ are independently N, CH, or CZ, or $X^1$ and $X^2$ together are C=C; and wherein $Q^1$, $Q^2$, $Q^3$, $X^1$, and $X^2$ are selected such that a stable compound results.

Any of the structures illustrated herein, e.g., A, B, L or central core can be optionally substituted with 0, 1, 2, 3, or 4, as appropriate, and independently, selected from $R^{75}$, wherein $R^{75}$ is selected from hydrogen, halogen, hydroxyl, nitro, cyano, amino, $C_1$-$C_6$alkyl, $C_1$-$C_6$haloalkyl, $C_2$-$C_6$alkenyl, $C_2$-$C_6$alkynyl, $C_1$-$C_6$thioalkyl, $C_1$-$C_6$alkoxy, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O) NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP (O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), JNR$^9$P(O)(NHR$^{21}$)(NHR$^{22}$), -JNR$^9$P (O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S (O)$_2$R$^{22}$, -JOC(O)NR$^{21}$R$^{22}$, -JNR$^{21}$C(O)OR$^{22}$, -JNR$^{21}$OC (O)R$^{22}$, —(CH$_2$)$_{14}$C(O)NR$^{21}$R$^{22}$, -JC(O)NR$^{24}$R$^{25}$, -JNR$^9$C (O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, -JC(O)OR$^{23}$; each of which R$^{75}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_4$alkyl(mono- and di-C$_1$-C$_4$alkylNR$^9$R$^{10}$), C$_1$-C$_6$alkylester, C$_1$-C$_4$alkylamino, C$_1$-C$_4$hydroxylalkyl, C$_1$-C$_2$haloalkyl, C$_1$-C$_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, S(O)=NHR$^{21}$, SF$_5$, and JC(R$^9$)=NR$^{21}$ and SO$_2$OR$^{21}$.

R and R' (see FIG. 5) are independently selected from H, alkyl, cycloalkyl, cycloalkylalkyl, heterocycle, heterocycloalkyl, aryl, arylalkyl, heteroaryl, heteroarylalkyl wherein each group can be optionally substituted or any other substituent group herein that provides the desired properties. In some embodiments, the core ring includes one or more chiral carbon atoms. The invention includes the use of compounds with embodiments in which the chiral carbon can be provided as an enantiomer, or mixtures of enantiomers, including a racemic mixture. Where the core ring includes more than one stereocenter, all of the enantiomers and diastereomers are included in the invention as individual species.

Z is F, Cl, NH$_2$, CH$_3$, CH$_2$D, CHD$_2$, or CD$_3$.

R$^1$, R$^{1'}$, R$^2$, R$^{2'}$, R$^3$, and R$^{3'}$ are independently selected at each occurrence, as appropriate, and only where a stable compound results, from hydrogen, halogen, hydroxyl, nitro, cyano, amino, C$_1$-C$_6$alkyl, C$_2$-C$_6$alkenyl, C$_2$-C$_6$alkynyl, C$_1$-C$_6$alkoxy, C$_2$-C$_6$alkynyl, C$_2$-C$_6$alkanoyl, C$_1$-C$_6$thioalkyl, hydroxyC$_1$-C$_6$alkyl, aminoC$_1$-C$_6$alkyl, —C$_0$-C$_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, where R$^9$ and R$^{10}$ are independently selected at each occurrence from hydrogen, C$_1$-C$_6$alkyl, (C$_3$-C$_7$cycloalkyl)C$_0$-C$_4$alkyl, —C$_0$-C$_4$alkyl(C$_3$-C$_7$cycloalkyl), and —O—C$_0$-C$_4$alkyl(C$_3$-C$_7$cycloalkyl).

In alternative embodiments, R$^1$ and R$^{1'}$ or R$^3$ and R$^{3'}$ may be taken together to form a 3- to 6-membered carbocyclic spiro ring or a 3- to 6-membered heterocyclic spiro ring containing 1 or 2 heteroatoms independently selected from N, O, or S; R$^2$ and R$^{2'}$ may be taken together to form a 3- to 6-membered carbocyclic spiro ring; or R$^2$ and R$^{2'}$ may be taken together to form a 3- to 6-membered heterocyclic spiro ring; each of which spiro ring may be unsubstituted or substituted with 1 or more substituents independently selected from halogen (and in particular F), hydroxyl, cyano, —COOH, C$_1$-C$_4$alkyl (including in particular methyl), C$_2$-C$_4$alkenyl, C$_2$-C$_4$alkynyl, C$_1$-C$_4$alkoxy, C$_2$-C$_4$alkanoyl, hydroxyC$_1$-C$_4$alkyl, (mono- and di-C$_1$-C$_4$alkylamino)C$_0$-C$_4$alkyl, —C$_0$-C$_4$alkyl(C$_3$-C$_7$cycloalkyl), —O—C$_0$-C$_4$alkyl(C$_3$-C$_7$cycloalkyl), C$_1$-C$_2$haloalkyl, and C$_1$-C$_2$haloalkoxy.

In alternative embodiments, R$^1$ and R$^2$ may be taken together to form a 3-membered carbocyclic ring; R$^1$ and R$^2$ may be taken together to form a 4- to 6-membered carbocyclic or aryl ring or a 4- to 6-membered heterocyclic or heteroaryl ring containing 1 or 2 heteroatoms independently selected from N, O, and S; or R$^2$ and R$^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently selected from halogen (and in particular F), hydroxyl, cyano, —COOH, C$_1$-C$_4$alkyl (including in particular methyl), C$_2$-C$_4$alkenyl, C$_2$-C$_4$alkynyl, C$_1$-C$_4$alkoxy, C$_2$-C$_4$alkanoyl, hydroxyC$_1$-C$_4$alkyl, (mono- and di-C$_1$-C$_4$alkylamino)C$_0$-C$_4$alkyl, —C$_0$-C$_4$alkyl, —C$_0$-C$_4$alkyl(C$_3$-C$_7$cycloalkyl), —O—C$_0$-C$_4$alkyl(C$_3$-C$_7$cycloalkyl), C$_1$-C$_2$haloalkyl, and C$_1$-C$_2$haloalkoxy.

In alternative embodiments, R$^1$ and R$^{1'}$, R$^2$ and R$^{2'}$, or R$^3$ and R$^{3'}$ can be taken together to form a carbonyl group. In alternative embodiments, R$^1$ and R$^2$ or R$^2$ and R$^3$ can be taken together to form a carbon-carbon double bond.

Non-limiting examples of the

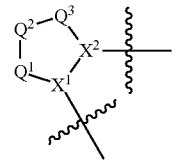

ring are illustrated, for example, in FIG. 5 (any of which can be otherwise substituted with R$^1$, R$^{1'}$, R$^2$, R$^{2'}$, R$^3$, and R$^{3'}$).

In an alternate embodiment, the

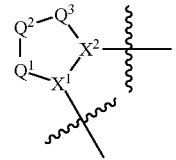

ring is replaced by one of the following core structures:

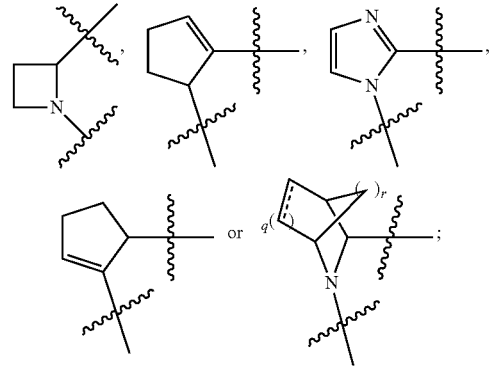

wherein q is 0, 1, 2 or 3 and r is 1, 2 or 3, ═══ is a single or double bond. Examples of core structures are provided in FIGS. 3B, 3C, 3D, 3E, 3F, 3G, 3H, 3I, 3J, 3K, 3L, 3M, 3N, 3O, 3P, 3Q, and 5.

A is a group selected from:

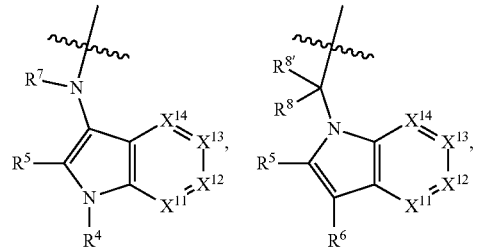

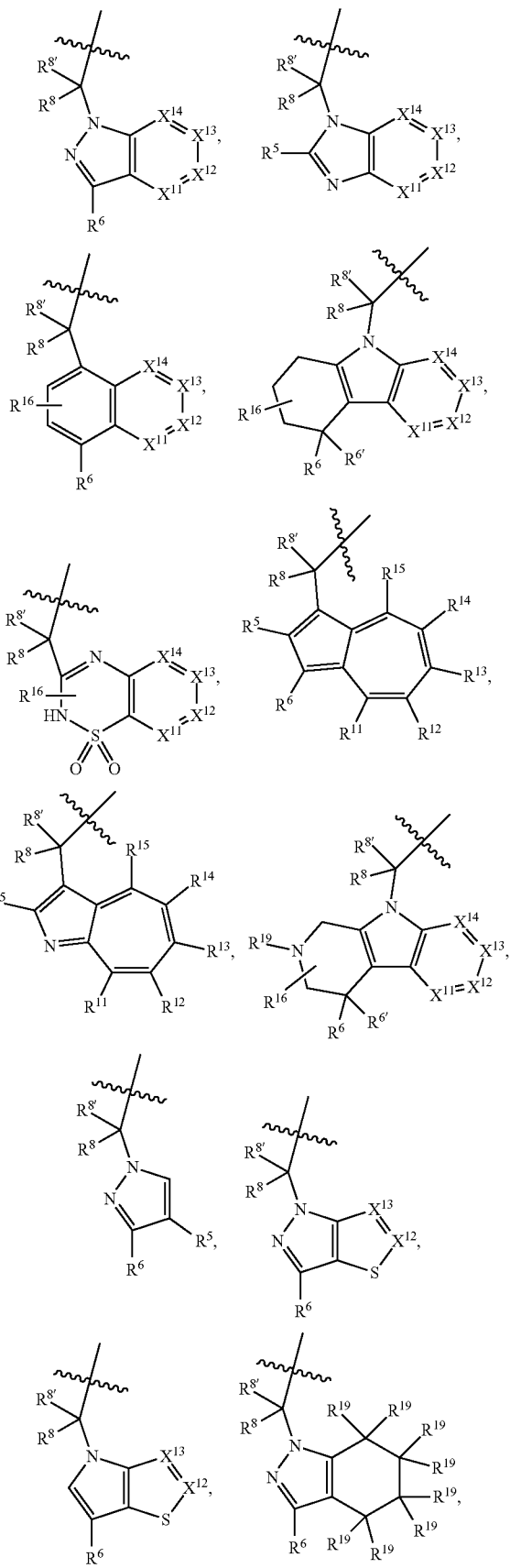

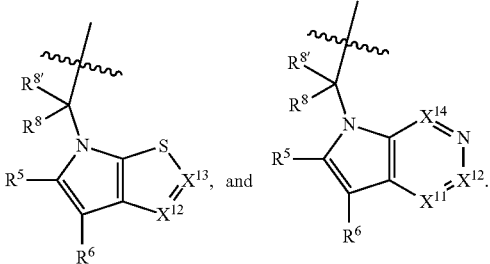

Examples of "A" groups are in FIGS. 1B, 1C, 1D, and 1E.

$R^4$ is selected from —CHO, —CONH$_2$, $C_2$-$C_6$alkanoyl, hydrogen, —SO$_2$NH$_2$, —C(CH$_2$)$_2$F, —CH(CF$_3$)NH$_2$, $C_1$-$C_6$alkyl, —C$_0$-C$_4$alkyl(C$_3$-C$_7$cycloalkyl), —C(O)C$_0$-C$_2$alkyl(C$_3$-C$_7$cycloalkyl),

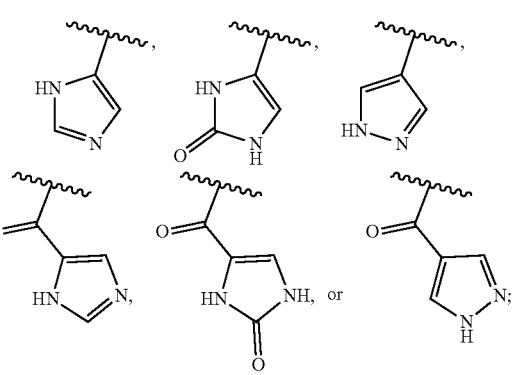

each of which $R^4$ other than hydrogen, —CHO, and —CONH$_2$, is unsubstituted or substituted with one or more of amino, imino, halogen, hydroxyl, cyano, cyanoimino, $C_1$-$C_2$alkyl, $C_1$-$C_2$alkoxy, —C$_0$-C$_2$alkyl(mono- and di-C$_1$-C$_4$alkylamino), $C_1$-$C_2$haloalkyl, and $C_1$-$C_2$haloalkoxy.

$R^5$ and $R^6$ are independently selected from —CHO, —C(O)NH$_2$, —C(O)NH(CH$_3$), $C_2$-$C_6$alkanoyl, hydrogen, hydroxyl, halogen, cyano, nitro, —COOH, —SO$_2$NH$_2$, vinyl, $C_1$-$C_6$alkyl (including methyl), $C_2$-$C_6$alkenyl, $C_1$-$C_6$alkoxy, —C$_0$-C$_4$alkyl(C$_3$-C$_7$cycloalkyl), —C(O)C$_0$-C$_4$alkyl(C$_3$-C$_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and —COOH may be substituted with one or more substituents independently selected from halogen, hydroxyl, amino, imino, cyano, cyanoimino, $C_1$-$C_2$alkyl, $C_1$-$C_4$alkoxy, —C$_0$-C$_2$alkyl(mono- and di-C$_1$-C$_4$alkylamino), $C_1$-$C_2$haloalkyl, and $C_1$-$C_2$haloalkoxy.

$R^{6'}$ is hydrogen, halogen, hydroxyl, $C_1$-$C_4$alkyl, —C$_0$-C$_4$alkyl(C$_3$-C$_7$cycloalkyl), or $C_1$-$C_4$alkoxy; or $R^6$ and $R^{6'}$ may be taken together to form an oxo, vinyl, or imino group.

$R^7$ is hydrogen, $C_1$-$C_6$alkyl, or —C$_0$-C$_4$alkyl(C$_3$-C$_7$cycloalkyl).

$R^8$ and $R^{8'}$ are independently selected from hydrogen, halogen, hydroxyl, $C_1$-$C_6$alkyl, —C$_0$-C$_4$alkyl(C$_3$-C$_7$cycloalkyl), $C_1$-$C_6$alkoxy, and (C$_1$-C$_4$alkylamino)C$_0$-C$_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may be selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), $C_1$-$C_2$haloalkyl, and $C_1$-$C_2$haloalkoxy.

$R^{19}$ is hydrogen, $C_1$-$C_6$alkyl, $C_2$-$C_6$alkenyl, $C_2$-$C_6$alkanoyl, —$SO_2C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), $C_0$-$C_4$alkyl(heteroaryl), and wherein $R^{19}$ other than hydrogen is unsubstituted or substituted with one or more substituents independently selected from halogen, hydroxyl, amino, —COOH, and —C(O)O$C_1$-$C_4$alkyl.

$X^{11}$ is N or $CR^{11}$.
$X^{12}$ is N or $CR^{12}$.
$X^{13}$ is N or $CR^{13}$.
$X^{14}$ is N or $CR^{14}$.
No more than 2 of $X^{11}$, $X^{12}$, $X^{13}$, and $X^{14}$ are N.

One of $R^{12}$ and $R^{13}$ is selected from $R^{31}$ and the other of $R^{12}$ and $R^{13}$ is selected from $R^{32}$. In an alternative embodiment, $R^{12}$ and $R^{13}$ are each independently selected from an $R^{32}$ moiety.

$R^{31}$ is selected from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)O$R^9$, $C_1$-$C_6$thioalkyl, —$C_0$-$C_4$alkyl$NR^9R^{10}$, —C(O)$NR^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —$CONH_2$ $C_1$-$C_2$haloalkyl, and $C_1$-$C_2$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is selected from aryl; saturated or unsaturated heterocycle (for example a 5-6 membered ring having 1, 2, or 3 heteroatoms independently selected from N, O, and S), wherein the heterocycle is bonded through a carbon atom in the heterocyclic ring to a carbon atom of ring A in the $R^{12}$ or $R^{13}$ position; and heteroaryl (for example a 5-6 membered ring having 1, 2, or 3 heteroatoms independently selected from N, O, and S), wherein the aryl, heterocycle or heteroaryl ring can be optionally substituted.

When A is an indole or indazole and $X^{12}$ is N, $X^{13}$ is $CR^{13}$, wherein $R^{13}$ is $R^{32}$.

When A is an indole or indazole and $X^{13}$ is N, $X^{12}$ is $CR^{12}$, wherein $R^{12}$ is $R^{32}$.

$R^{11}$, $R^{14}$, and $R^{15}$ are independently selected at each occurrence from hydrogen, halogen, hydroxyl, nitro, cyano, —O(PO)($OR^9$)$_2$, —(PO)($OR^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

L is a bond or is selected from the formulas

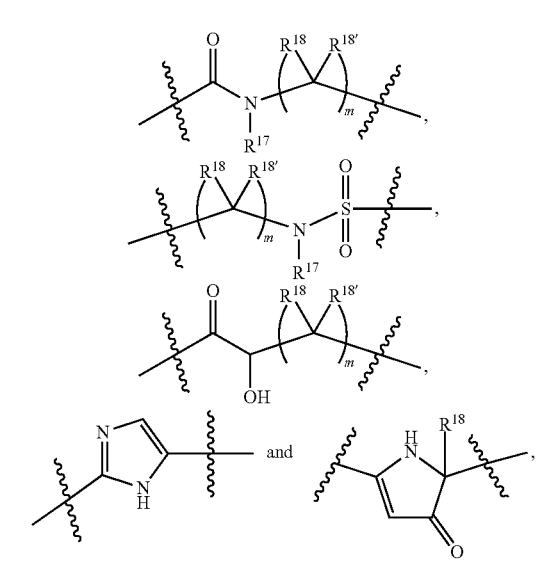

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

Linkers are also illustrated in FIGS. 4B, 4C, 4D, 4E, 4F, and 4G.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl), and B is unsubstituted or substituted with one or more substituents independently selected from $R^{33}$ and $R^{34}$, and 0 or 1 substituents selected from $R^{35}$ and $R^{36}$.

$R^{33}$ is independently selected from halogen, hydroxyl, —COOH, cyano, $C_1$-$C_6$alkyl, $C_2$-$C_6$alkanoyl, $C_1$-$C_6$alkoxy, —$C_0$-$C_4$alkyl$NR^9R^{10}$, —$SO_2R^9$, $C_1$-$C_2$haloalkyl, and $C_1$-$C_2$haloalkoxy.

$R^{34}$ is independently selected from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)$NR^9R^{23}$, -JOS$O_2OR^{21}$, —C(O)(CH$_2$)$_{1-4}$S(O)$R^{21}$, —O(CH$_2$)$_{1-4}$S(O)$NR^{21}R^{22}$, -JOP(O)($OR^{21}$)($OR^{22}$), -JP(O)($OR^{21}$)($OR^{22}$), -JOP(O)($OR^{21}$)$R^{22}$, -JP(O)($OR^{21}$)$R^{22}$, -JOP(O)$R^{21}R^{22}$, -JP(O)$R^{21}R^{22}$, -JSP(O)($OR^{21}$)($OR^{22}$), -JSP(O)($OR^{21}$)($R^{22}$), -JSP(O)($R^{21}$)($R^{22}$), -J$NR^9$P(O)(NHR$^{21}$)(NHR$^{22}$), -J$NR^9$P(O)($OR^{21}$)(NHR$^{22}$), -J$NR^9$P(O)($OR^{21}$)($OR^{22}$), -JC(S)$R^{21}$, -J$NR^{21}$SO$_2R^{22}$, -J$NR^9$S(O)$NR^{10}R^{22}$, -J$NR^9$SO$_2NR^{10}R^{22}$, -JSO$_2NR^9$COR$^{22}$, -JSO$_2NR^9$CONR$^{21}R^{22}$, -J$NR^{21}$SO$_2R^{22}$, -JC(O)$NR^{21}$SO$_2R^{22}$, -JC($NH_2$)$NR^{22}$, -JC($NH_2$)$NR^9$S(O)$_2R^{22}$, -JOC(O)$NR^{21}R^{22}$, -J$NR^{21}$C(O)$OR^{22}$, -J$NR^{21}$OC(O)$R^{22}$, —(CH$_2$)$_{1-4}$C(O)$NR^{21}R^{22}$, -JC(O)$NR^{24}R^{25}$, -J$NR^9$C(O)$R^{21}$, -JC(O)$R^{21}$, -J$NR^9$C(O)$NR^{10}R^{22}$, —CCR$^{21}$, —(CH$_2$)$_{1-4}$OC(O)$R^{21}$, and -JC(O)$OR^{23}$; each of which $R^{34}$ may be unsubstituted or substituted with one or more substituents independently selected from halogen, hydroxyl, nitro, cyano, amino, oxo, —B(OH)$_2$, —Si(CH$_3$)$_3$, —COOH, —$CONH_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

$R^{35}$ is independently selected from naphthyl, naphthyloxy, indanyl, (4- to 7-membered heterocycloalkyl)$C_0$-$C_4$alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which $R^{35}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy.

$R^{36}$ is independently selected from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently selected from N, O, B, and S, each of which $R^{36}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy.

In one embodiment $R^{36}$ is —$S(O)_2R^{21}$.

In one additional alternative embodiment B is selected from:

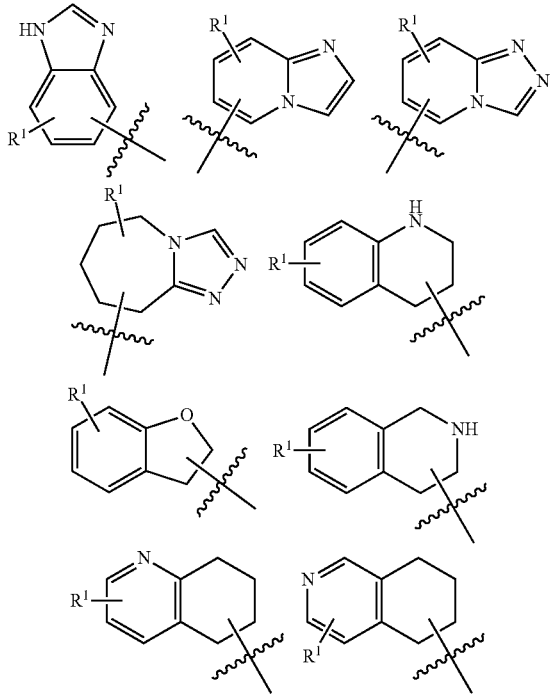

In one additional alternative embodiment $R^{36}$ is selected from:

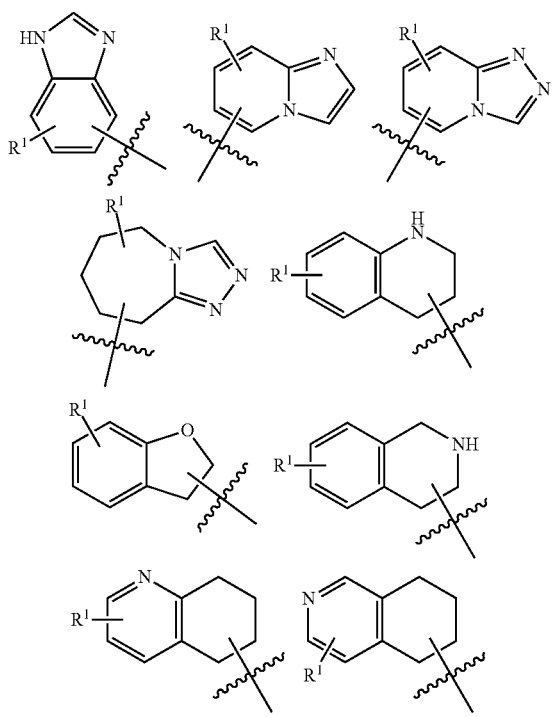

In one embodiment $R^1$ is selected from F, Cl, Br, and $C_1$-$C_6$alkyl.

In one embodiment $R^1$ is selected from hydroxyl and $C_1$-$C_6$alkoxy.

In one embodiment $R^1$ is selected from $C_2$-$C_6$alkynyl, $C_2$-$C_6$alkanoyl, and $C_1$-$C_6$thioalkyl.

In one embodiment $R^1$ is selected from amino$C_1$-$C_6$alkyl and —$C_0$-$C_4$alkylNR^9R^{10}$.

$R^{21}$ and $R^{22}$ are independently selected at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC_1$-$C_6$alkyl, —$C_1$-$C_4$alkylOC(O)$C_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, and each $R^{21}$ and $R^{22}$ can be optionally substituted.

$R^{23}$ is independently selected at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S, and each $R^{23}$ can be optionally substituted.

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings, and each $R^{24}$ and $R^{25}$ can be optionally substituted.

J is independently selected at each occurrence from a covalent bond, $C_1$-$C_4$alkylene, —$OC_1$-$C_4$alkylene, $C_2$-$C_4$alkenylene, and $C_2$-$C_4$alkynylene.

The present invention thus includes at least the following features:

(a) A heteroaryl compound of Formula I, including those compounds listed in Table 1, as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(b) A heteroaryl compound of Table 2 or Table 3 or an active compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure, dermatomyocitis; amyotrophic lateral sclerosis; and cytokine or inflammatory reactions in response to the administration of biotherapeutics (e.g. CAR T-cell therapy);

(c) A heteroaryl compound of Table 2 or Table 3 or an embodiment of the active compound as described in FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts and prodrugs thereof, for use in treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(d) A pharmaceutically acceptable composition of an ether compound of Table 2 or Table 3 or a ether compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, or its pharmaceutically acceptable salt in a pharmaceutically acceptable carrier;

(e) An ether compound selected from Table 2 or Table 3 or a compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts, prodrugs and pharmaceutically acceptable compositions thereof;

(f) A heteroaryl compound selected from Table 2 or Table 3 or a compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts and prodrugs thereof, for use in treating or preventing disorders mediated by the complement pathway, and for example, cascade Factor D;

(g) Use of a compound of Formula I, including those compounds listed in Table 1, as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(h) Use of a compound of Table 2 or Table 3 that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(i) Use of a compound of Table 2 or Table 3 or a compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts and prodrugs thereof, in the manufacture of a medicament for treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(j) A process for manufacturing a medicament intended for the therapeutic use for treating or preventing a disorder listed in the Detailed Description, Part IV, Section A or Section B, or generally for treating or preventing disorders mediated by complement cascade Factor D, including age-related macular degeneration (AMD), retinal degeneration, paroxysymal nocturnal hemoglobinuria (PNH), multiple sclerosis (MS), and rheumatoid arthritis (RA) and other disorders described further herein characterized in that a compound selected from Table 2 or Table 3 or a compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, is used in the manufacture;

(k) A compound selected from Table 2 or Table 3 or a compound that is prepared from or consists of moieties selected from FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein in substantially pure form (e.g., at least 90 or 95%):

(l) A heteroaryl compound of Formula I, including those compounds listed in Table 1, as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration;

(m) A heteroaryl compound of Table 2 or Table 3 or a compound that is prepared from or consists of moieties in FIG. 1B, 1C, 2B, 2C, 2D, 2E, 3B, 3C, 3D, 3E, 3F, 3G, 3H, 3I, 3J, 3K, 3L, 3M, 3N, 6A, and optionally 4B, 4C, 4D, 4E or 4F, as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration;

(n) A heteroaryl compound that is prepared from or consists of moieties selected from FIG. 1D or 1E; 5; 6A; 7A, 7B, 7C, 7D or 7E; and 8; optionally including a moiety of FIG. 4B, 4C, 4D, 4E or 4F, as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(o) A heteroaryl compound that is prepared from or consists of moieties selected from one of the following groups: (i) any of FIG. 1B, 1C, 1D or 1E; FIG. 5; any one of FIG. 6 and FIGS. 7F and 7I; optionally including a moiety of FIG. 4B, 4C, 4D, 4E or 4F (ii) FIG. 1B, 1C, 1D, 1E or 1F; FIG. 5, FIG. 6B, 6C, any of FIGS. 7A, 7B, 7C, 7D, 7E, 7F, 7G; and FIG. 8; optionally including a moiety of FIG. 4B, 4C, 4D, 4E or 4F (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; (vi) FIGS. 9A, 9B, 9C, 9D, 9E, 9F, 9G, 9H and any one of FIGS. 6A, 6B, 6C, 6D; as described herein, and pharmaceutically acceptable salts and prodrugs thereof, for use in treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure, dermatomyocitis; amyotrophic lateral sclerosis; and cytokine or inflammatory reactions in response to the administration of biotherapeutics (e.g. CAR T-cell therapy);

(p) A heteroaryl compound that is prepared from or consists of moieties selected from one of the following groups: (i) any of FIG. 1B, 1C, 1D or 1E; FIG. 5; any one of FIGS. 6A, 6B, 6C, 6D and FIGS. 7F and 7I, optionally including a moiety of FIG. 4B, 4C, 4D, 4E or 4F; (ii) FIG. 1B, 1C, 1D, 1E or 1F; FIG. 5, FIG. 6B, 6C, any of FIGS. 7A, 7B, 7C, 7D, 7E, 7F, 7G; and FIG. 8, optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or the species of (vi) FIGS. 9A, 9B, 9C, 9D, 9E, 9F, 9G, 9H, and any one of FIGS. 6A, 6B, 6C, 6D; as described herein, and pharmaceutically acceptable salts and prodrugs thereof, for use in treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(q) A pharmaceutically acceptable composition of a compound of any species consisting of moieties selected from one of the following groups: (i) any of FIG. 1B, 1C, 1D or 1E; FIG. 5; any one of FIGS. 6A, 6B, 6C, 6D and FIGS. 7F and 7I; optionally including a moiety of FIG. 4B, 4C, 4D, 4E or 4F (ii) FIG. 1B, 1C, 1D, 1E or 1F; FIG. 5, FIG. 6B, 6C, any of FIGS. 7A, 7B, 7C, 7D, 7E, 7F, 7G; and FIG. 8; optionally including a moiety of FIG. 4B, 4C, 4D, 4E or 4F (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or (vi) FIGS. 9A, 9B, 9C, 9D, 9E, 9F, 9G, 9H, and any one of FIG. 6A, 6B, 6C, 6D; or its pharmaceutically acceptable salt in a pharmaceutically acceptable carrier;

(r) A compound that is prepared from or consists of moieties selected from one of the following groups (i) any of FIG. 1B, 1C, 1D or 1E; FIG. 5; any one of FIGS. 6A, 6B, 6C, 6D and FIGS. 7F and 7I optionally including a moiety of FIG. 4B, 4C, 4D, 4E or 4F (ii) FIG. 1B, 1C, 1D, 1E or 1F; FIG. 5, FIGS. 6B and 6C, any of FIGS. 7A, 7B, 7C, 7D, 7E, 7F, 7G; and FIG. 8; optionally including a moiety of FIG. 4B, 4C, 4D, 4E or 4F (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; or (v) FIGS. 9A, 9B, 9C, 9D, 9E, 9F, 9G, and 9H, and FIGS. 6B and 6C, as described herein, and pharmaceutically acceptable salts, prodrugs and pharmaceutically acceptable compositions thereof;

(s) A compound that is prepared from or consists of moieties selected from one of the following groups (i) any of FIG. 1B, 1C, 1D or 1E; FIG. 5; any one of FIGS. 6A, 6B, 6C, 6D and FIGS. 7F and 7I; optionally including a moiety of FIG. 4B, 4C, 4D, 4E or 4F; (ii) FIG. 1B, 1C, 1D, 1E or 1F; FIG. 5, FIGS. 6B and 6C, any of FIGS. 7A, 7B, 7C, 7D, 7E, 7F, 7G; and FIG. 8; optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or (vi) FIGS. 9A, 9B, 9C, 9D, 9E, 9F, 9G, 9H, and FIGS. 6B and 6C, as described herein, and pharmaceutically acceptable salts and prodrugs thereof, for use in treating or preventing disorders mediated by the complement pathway, and for example, cascade Factor D;

(t) Use of a compound that is prepared from or consists of moieties selected from FIG. 1D or 1E; 5; 6A; 7A, 7B, 7C, 7D or 7E; and 8; optionally including a moiety of FIG. 4B, 4C, 4D, 4E or 4F as described herein, and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(u) Use of a compound of that is prepared from or consists of moieties selected from (i) any of FIG. 1B, 1C, 1D or 1E; FIG. 5; any one of FIGS. 6A, 6B, 6C, 6D and FIGS. 7F and 7I; optionally including a moiety of FIG. 4B, 4C, 4D, 4E or 4F (ii) FIG. 1B, 1C, 1D, 1E or 1F; FIG. 5, FIGS. 6B and 6C, any of FIGS. 7A, 7B, 7C, 7D, 7E, 7F, 7G; and FIG. 8; optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or (vi) FIGS. 9A, 9B, 9C, 9D, 9E, 9F, 9G, 9H, and FIGS. 6B and 6C, as described herein and pharmaceutically acceptable salts and prodrugs thereof, in the manufacture of a medicament for treating or preventing a disorder listed in the Detailed Description, Part IV, Section A, including but not limited to the development of fatty liver and conditions stemming from fatty liver, such as nonalcoholic steatohepatitis (NASH), liver inflammation, cirrhosis, liver failure; dermatomyocitis; amyotrophic lateral sclerosis; and cytokine or inflammatory reactions in response to biotherapeutics (e.g. CAR T-cell therapy);

(v) Use of a compound that is prepared from or consists of moieties selected from (i) any of FIG. 1B, 1C, 1D or 1E; FIG. 5; any one of FIGS. 6A, 6B, 6C, 6D and FIGS. 7F and 7I; optionally including a moiety of FIG. 4B, 4C, 4D, 4E or 4F (ii) FIG. 1B, 1C, 1D, 1E or 1F; FIG. 5, FIGS. 6B and 6C, any of FIGS. 7A, 7B, 7C, 7D, 7E, 7F, 7G; and FIG. 8; optionally including a moiety of FIG. 4 (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or (vi) FIGS. 9A, 9B, 9C, 9D, 9E, 9F, 9G, 9H, and FIGS. 6B and 6C, as described herein, and pharmaceutically acceptable salts and prodrugs thereof, in the manufacture of a medicament for treating or preventing a disorder listed in the Detailed Description, Part IV, Section B of this invention, including but not limited to paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(w) A process for manufacturing a medicament intended for the therapeutic use for treating or preventing a disorder listed in the Detailed Description, Part IV, Section A or Section B, or generally for treating or preventing disorders mediated by complement cascade Factor D, including age-related macular degeneration (AMD), retinal degeneration, paroxysmal nocturnal hemoglobinuria (PNH), multiple sclerosis (MS), and rheumatoid arthritis (RA) and other disorders described further herein characterized in that a compound selected for use is a compound that is prepared from or consists of moieties selected from (i) any of FIG. 1B, 1C, 1D or 1E; FIG. 5; any one of FIGS. 6A, 6B, 6C, 6D and FIGS. 7F and 7I; optionally including a moiety of FIG. 4B, 4C, 4D, 4E or 4F (ii) FIG. 1B, 1C, 1D, 1E or 1F; FIG. 5, FIGS. 6B and 6C, any of FIGS. 7A, 7B, 7C, 7D, 7E, 7F, 7G; and FIG. 8; optionally including a moiety of FIG. 4B, 4C, 4D, 4E or 4F (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or (vi) FIGS. 9A, 9B, 9C, 9D, 9E, 9F, 9G, 9H, and FIGS. 6B and 6C, as described herein is used in the manufacture;

(x) A compound that is prepared from or consists of moieties selected from (i) any of FIG. 1B, 1C, 1D or 1E; FIG. 5; any one of FIGS. 6A-D, and FIGS. 7F and 7I; optionally including a moiety of FIG. 4 (ii) FIG. 1B, 1C, 1D, 1E or 1F; FIG. 5, FIGS. 6B-6C, any of FIGS. 7A-G; and FIG. 8; optionally including a moiety of FIG. 4 (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; or (v) FIGS. 9A, 9B, 9C, 9D, 9E, 9F, 9G, 9H, and FIGS. 6B and 6C, as described herein as described herein in substantially pure form (e.g., at least 90 or 95%);

(y) A compound that is prepared from or consists of moieties selected from FIG. 1D or 1E; 5; 6A; 7A, 7B, 7C, 7D or 7E; and 8; optionally including a moiety of FIG. 4B, 4C, 4D, 4E or 4F; as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration; and (z) A compound of that is prepared from or consists of moieties selected from (i) any of FIG. 1B, 1C, 1D or 1E; FIG. 5; any one of FIGS. 6A, 6B, 6C, 6D and FIGS. 7F and 7I; optionally including a moiety of FIG. 4B, 4C, 4D, 4E or 4F; (ii) FIG. 1B, 1C, 1D, 1E or 1F; FIG. 5, FIGS. 6B and 6C, any of FIGS. 7A, 7B, 7C, 7D, 7E, 7F, 7G; and FIG. 8; optionally including a moiety of FIG. 4B, 4C, 4D, 4E or 4F; (iii) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, optionally including a moiety of FIG. 4B, 4C, 4D, 4E or 4F; (iv) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7F, and 7I, optionally including a moiety of FIG. 4B, 4C, 4D, 4E or 4F; (v) FIGS. 1B, 1C, 2B, 2C, 2D, 2E, 3B, 3C, 3D, 3E, 3F, 3G, 3H, 3I, 3J, 3K, 3L, 3M, 3N, 3O, 3P, 3Q, 6B, 6C, 6D, 7G, and 7H, optionally including a moiety of FIG. 4B, 4C, 4D, 4E or 4F; or (vi) FIGS. 9A, 9B, 9C, 9D, 9E, 9F, 9G, 9H, and FIGS. 6B and 6C, as described herein, and pharmaceutically acceptable salts and prodrugs thereof, for use in treating a medical disorder which is an inflammatory or immune condition, a disorder mediated by the complement cascade (including a dysfunctional cascade), a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

(aa) For each of (a) through (z) above, and otherwise herein, each assembly of moieties in the Figures and each active compound made therefrom or its use is considered and deemed specifically and individually disclosed, as such depiction is for convenience of space only and not intended to describe a only a genus or even a subgenus for such indication.

(bb) In another embodiment, any moiety of "A" (FIG. 1 B, C, D or E); any moiety of "B" ((FIG. 2 B, C, D, or E), FIG. 7 (A, B, C, D, E, F, G, H, or I) or FIG. 8); any moiety of the core ((FIG. 3 B, C, D, E, F, G, H, I, J, K, L, M, N, O, P or Q) or FIG. 5), any moiety of Linker (FIG. 4 B, C, D, E, F, or G) and any moiety of $R^{32}$ (FIG. 6 A, B, C, or D) can be combined to treat an indication of Section A; and the assembly of moieties from the Figures and each active compound made therefrom is considered and deemed specifically and individually disclosed, as such depiction is for convenience of space only and not intended to describe a only a genus or even a subgenus for such indication;

(cc) In another embodiment, any moiety of "A" (FIG. 1 B, C, D or E); any moiety of "B" ((FIG. 2 B, C, D, or E), FIG. 7 (A, B, C, D, E, F, G, H, or I) or FIG. 8); any moiety of the core ((FIG. 3 B, C, D, E, F, G, H, I, J, K, L, M, N, O, P or Q) or FIG. 5), any moiety of Linker (FIG. 4 B, C, D, E, F, or G) and any moiety of $R^{32}$ (FIG. 6 A, B, C, or D) can be combined to treat an indication of Section B with the proviso that there is at least one moiety selected from FIG. 1 (B or C); or FIG. 7 (F or I); FIG. 4G; or FIG. 6 (B or C); and the assembly of moieties from the Figures and each active compound made therefrom is considered and deemed specifically and individually disclosed, as such depiction is for convenience of space only and not intended to describe a only a genus or even a subgenus for such indication.

BRIEF DESCRIPTION OF THE FIGURES

FIGS. 3B, 3C, 3D, 3E, 3F, 3G, 3H, 3I, 3J, 3K, 3L, 3M, 3N, 3O, 3P, and 3Q provide non-limiting embodiments of the Central Core ring (C ring), wherein q is 0, 1, 2 or 3, r is 1, 2 or 3, ═══ is a single or double bond, and $R^{44}$, $R^{44'}$, $R^{45}$, $R^{45'}$ are defined below wherein each group can be optionally substituted.

FIGS. 9A, 9B, 9C, 9D, 9E, 9F, 9G and 9H provide non-limiting examples of compounds included in the present invention, wherein $Z_{32}$ is the same as $R^{32}$ as used herein.

DETAILED DESCRIPTION

I. Terminology

Figure 1A:
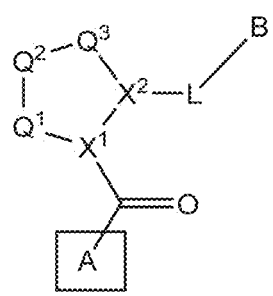
FIG. 1A is an illustration of Formula I which highlights the location of the A ring.
Figure 1B:
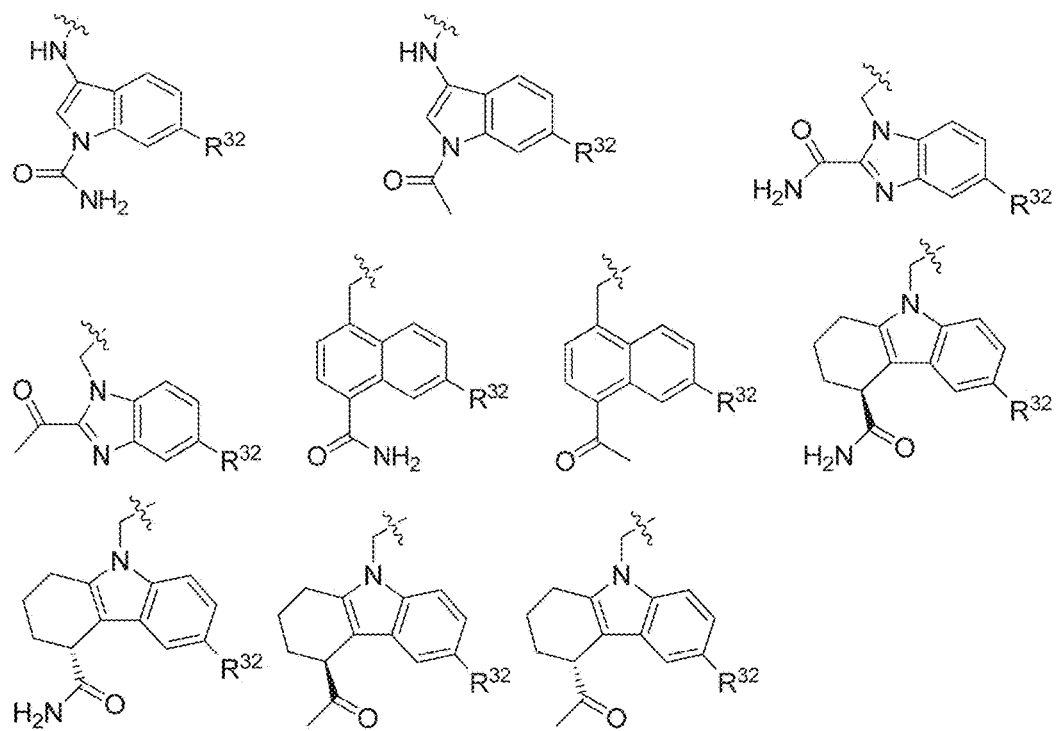
FIGS. 1B and 1C provide non-limiting embodiments of the A ring, wherein $R^{32}$ is defined below.
Figure 1C:
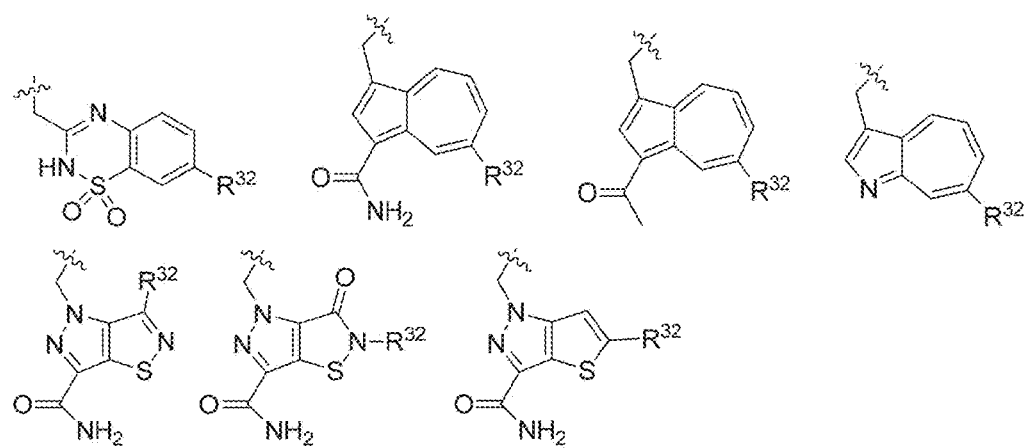
Figure 1D:
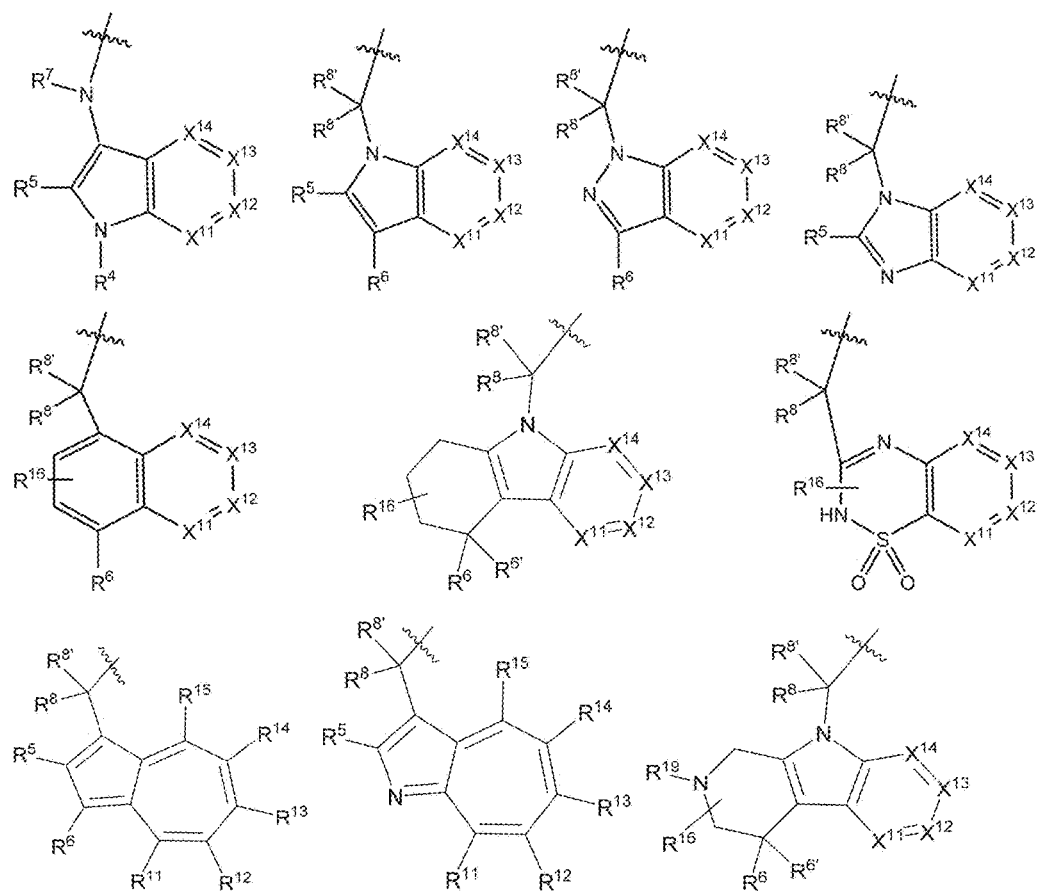
FIGS. 1D and 1E illustrate non-limiting embodiments of the A ring of FIG. 1A, wherein $R^4$, $R^5$, $R^6$, $R^7$, $R^8$, $R^{8'}$, $R^{11}$, $R^{12}$, $R^{13}$, $R^{14}$, $R^{15}$, $R^{16}$, $R^{19}$, $X^{11}$, $X^{12}$, $X^{13}$, and $X^{14}$ are defined below.
Figure 1E:
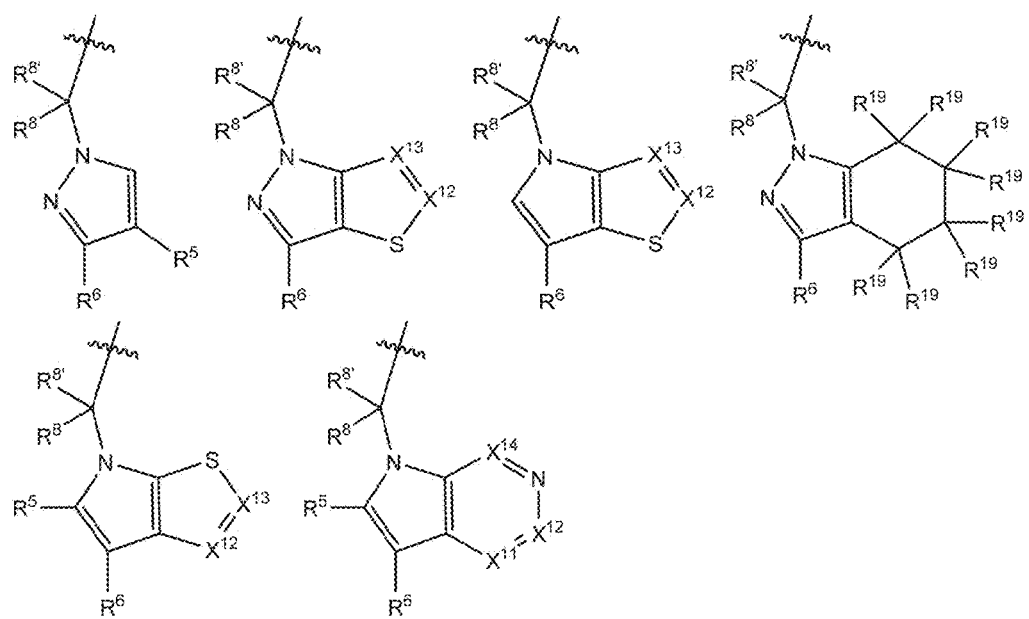
Figure 2A:
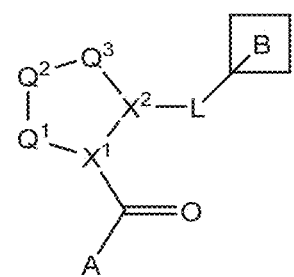
FIG. 2A illustrates the location of the B ring of Formula I.
Figure 2B:
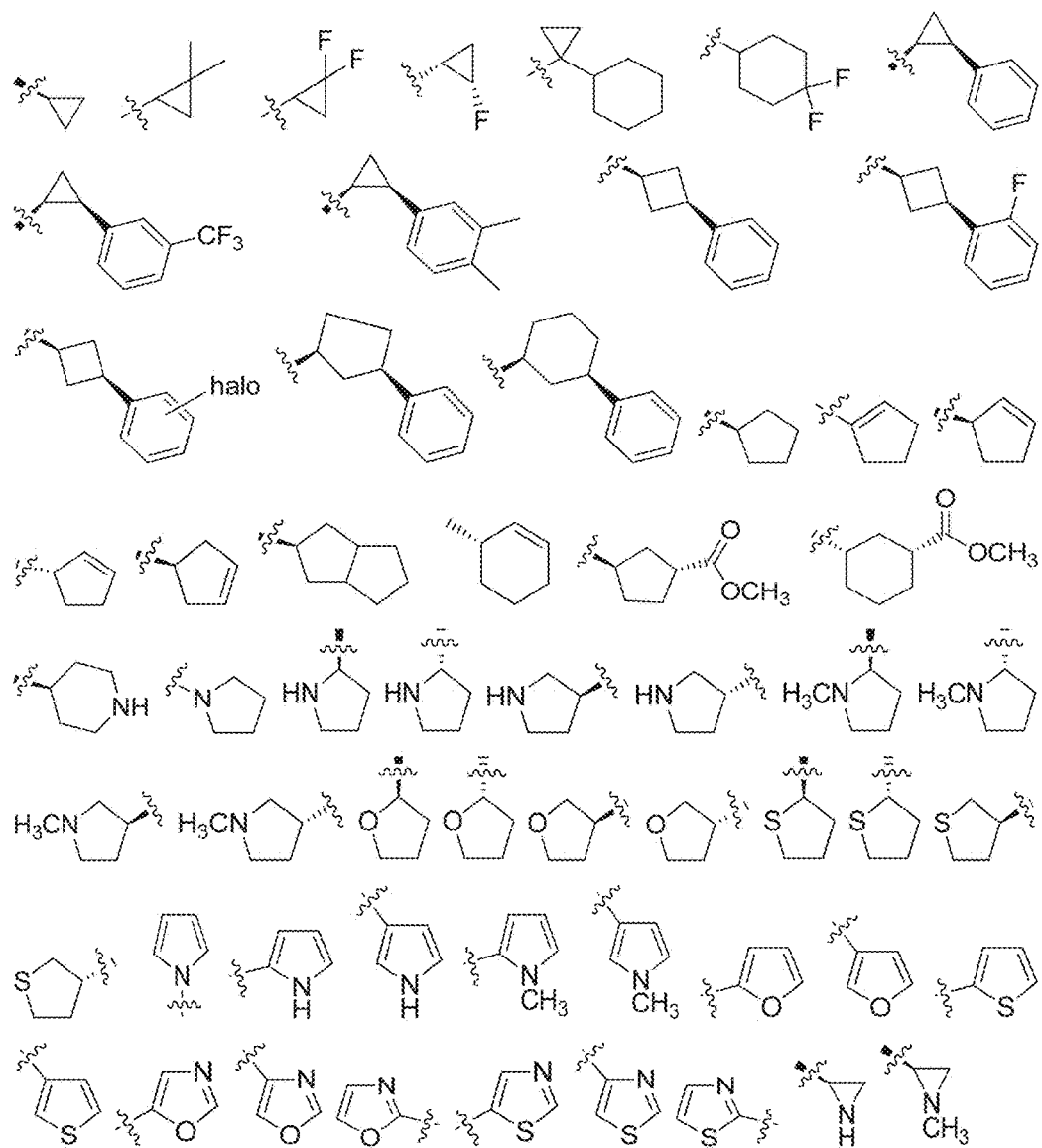
FIGS. 2B, 2C, 2D and 2E provide certain embodiments of the B ring, wherein "halo" can be F, Cl, Br, or I.
Figure 2C:
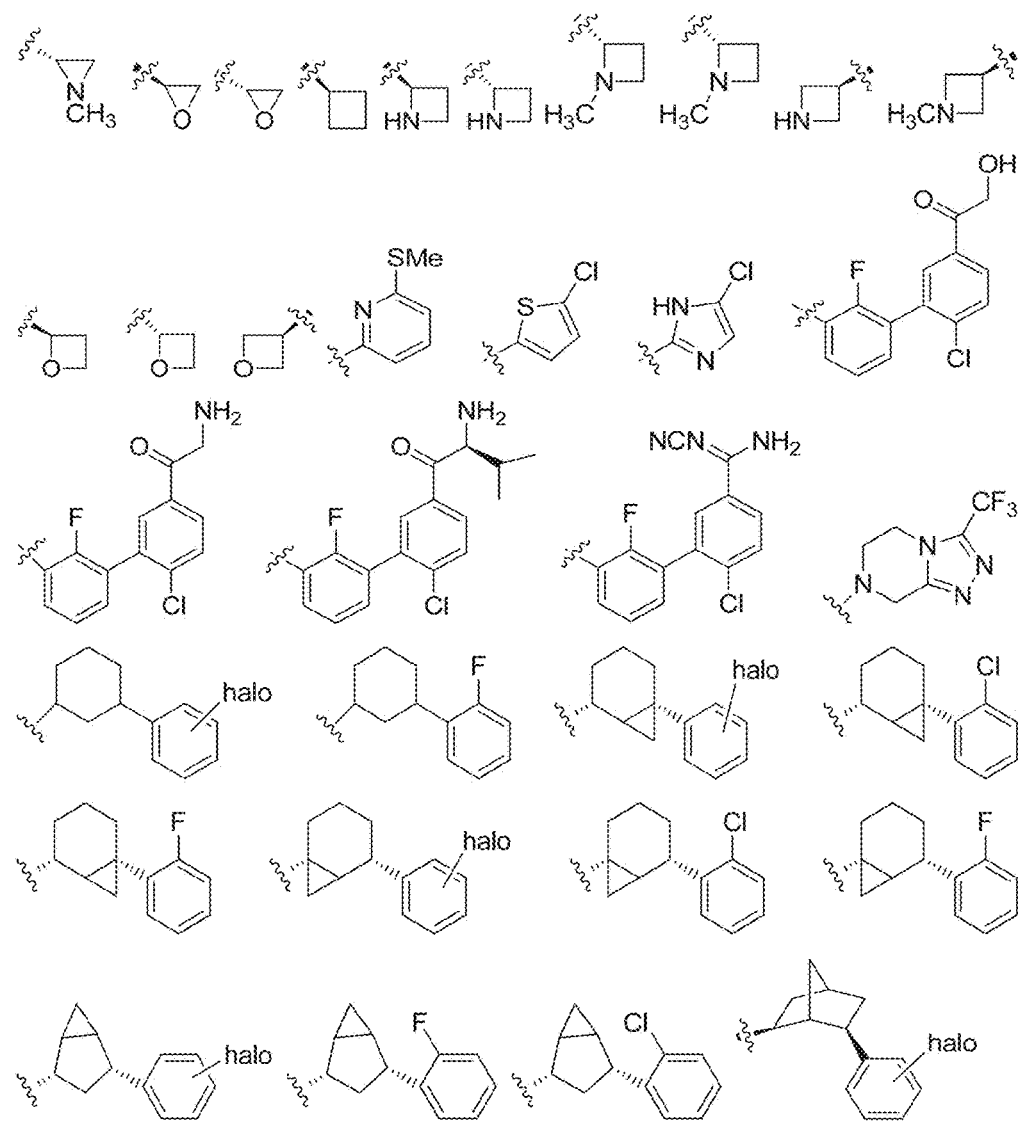
Figure 2D:
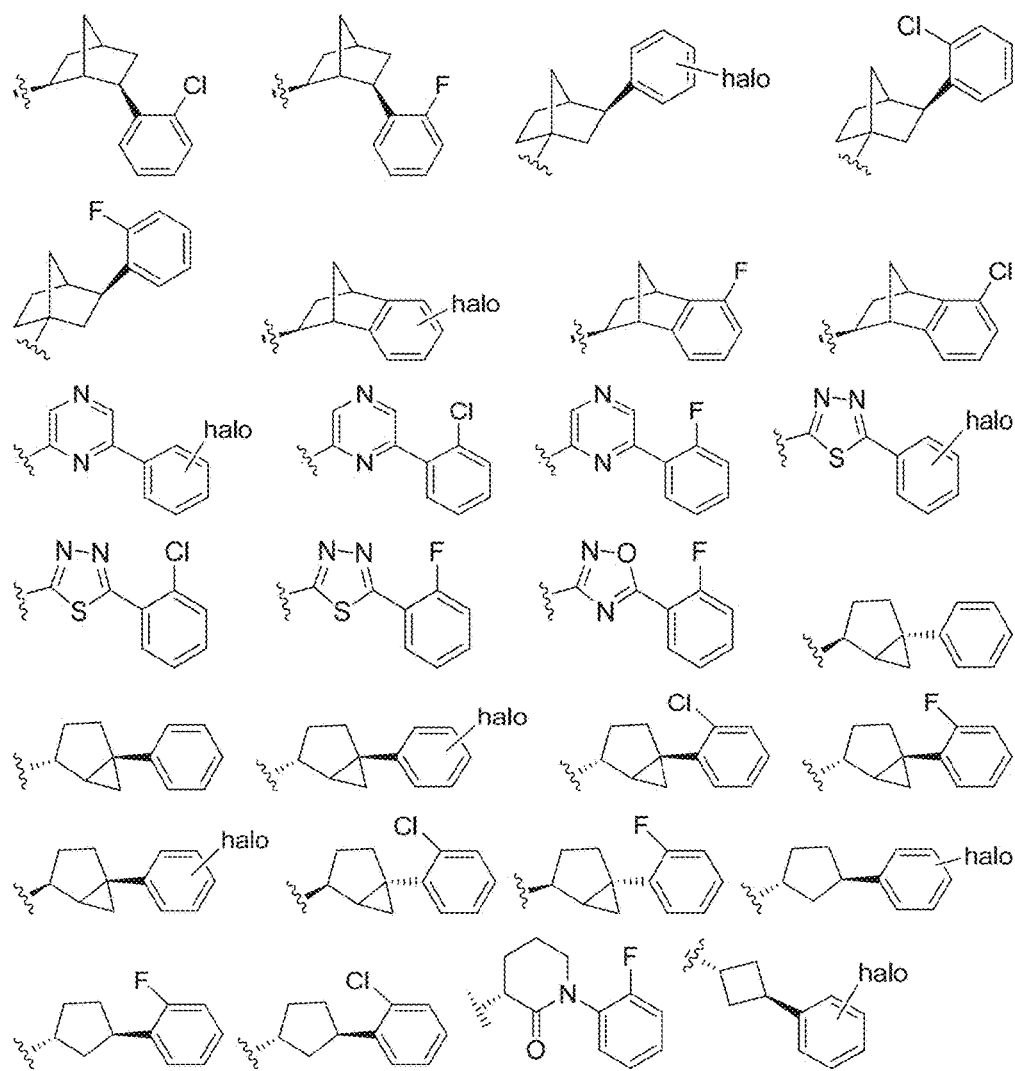
Figure 2E:
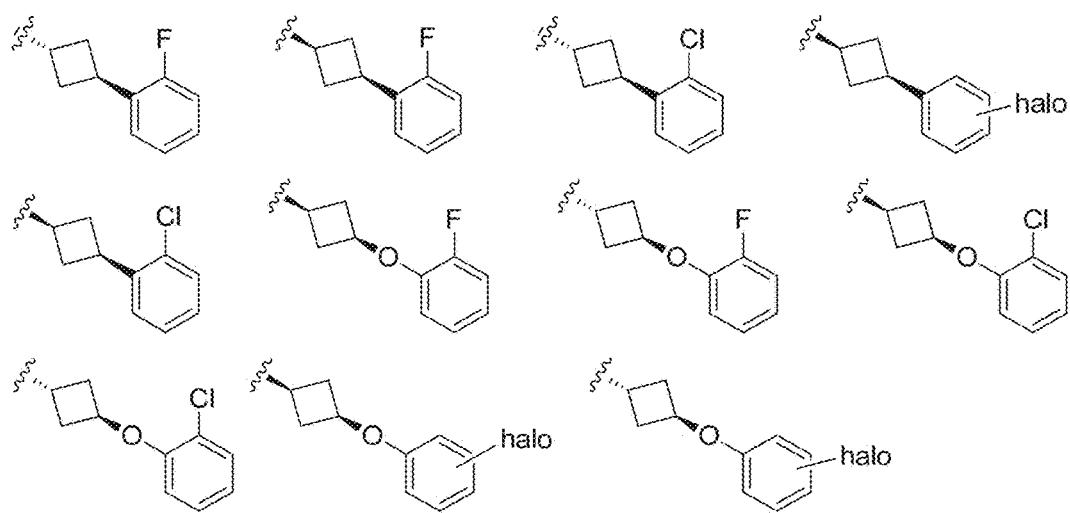
Figure 3A:
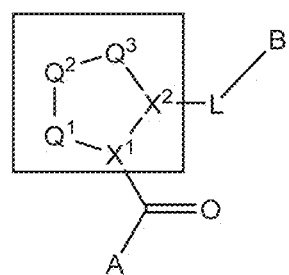
FIG. 3A illustrates the location of the Central Core of Formula I.
Figure 3B:
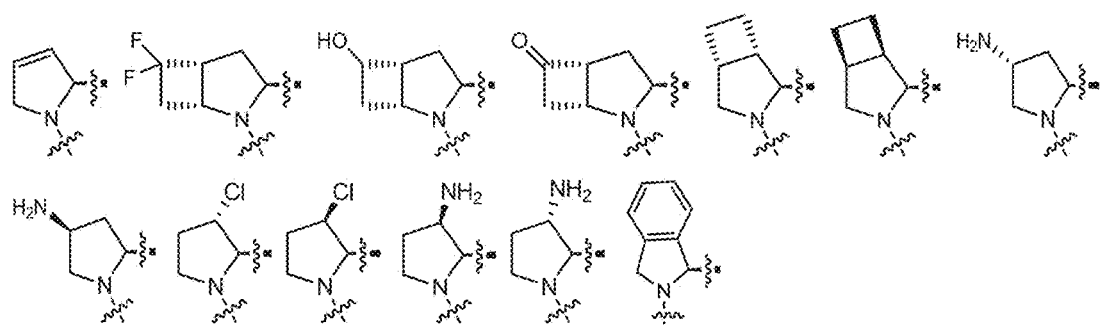
Figure 3C:
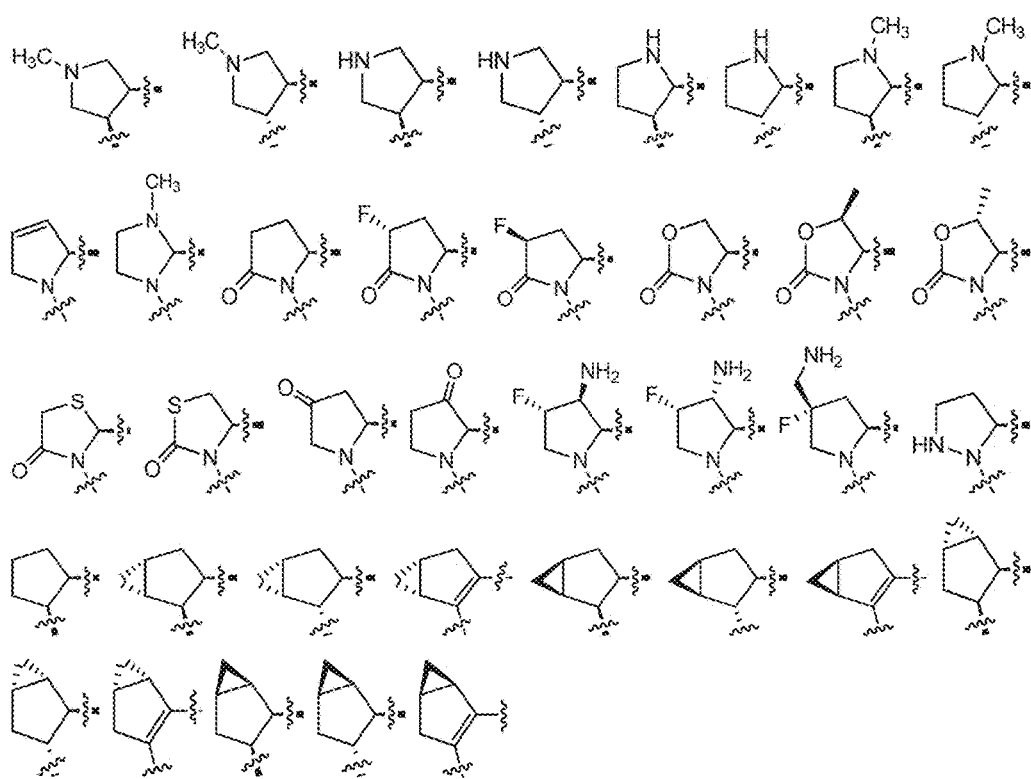
Figure 3D:
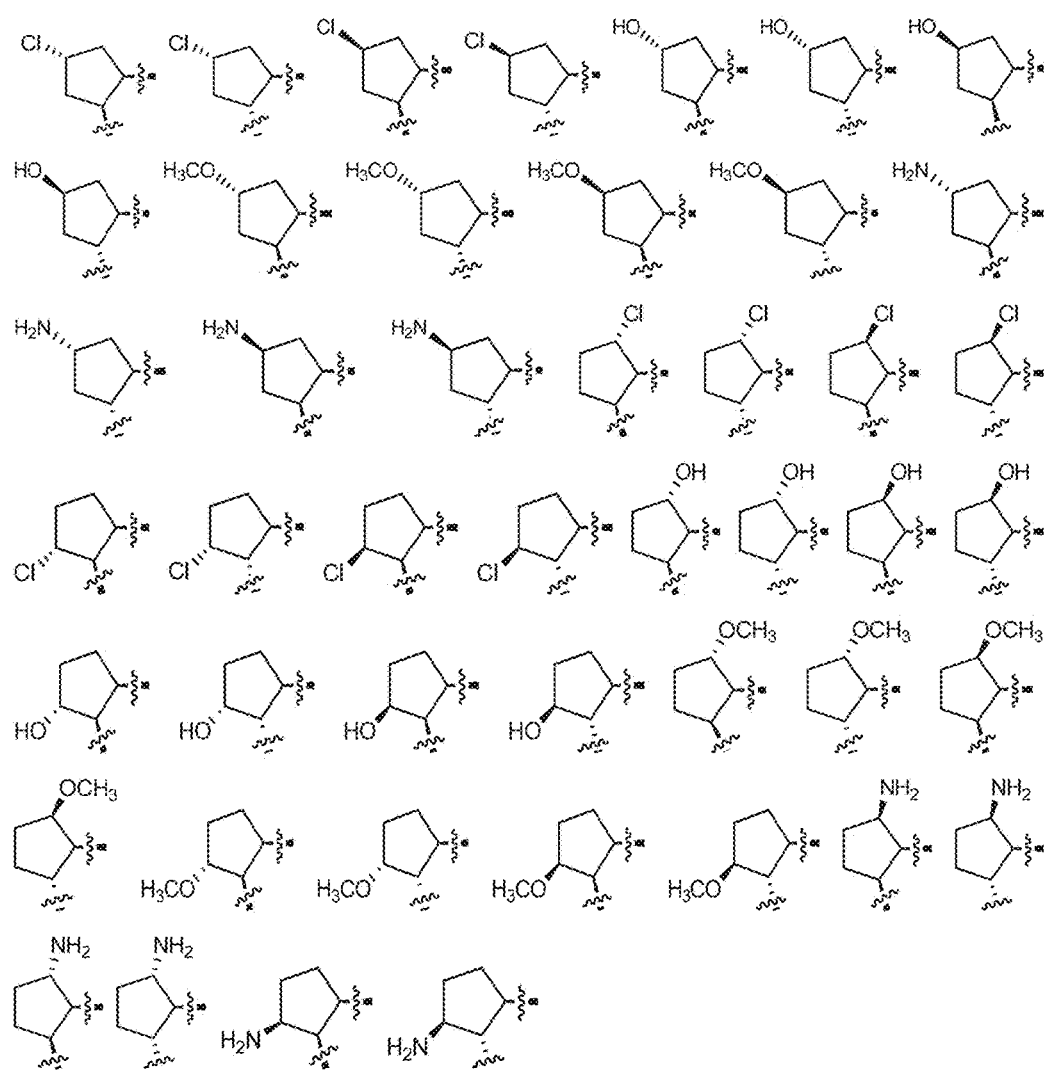
Figure 3E:
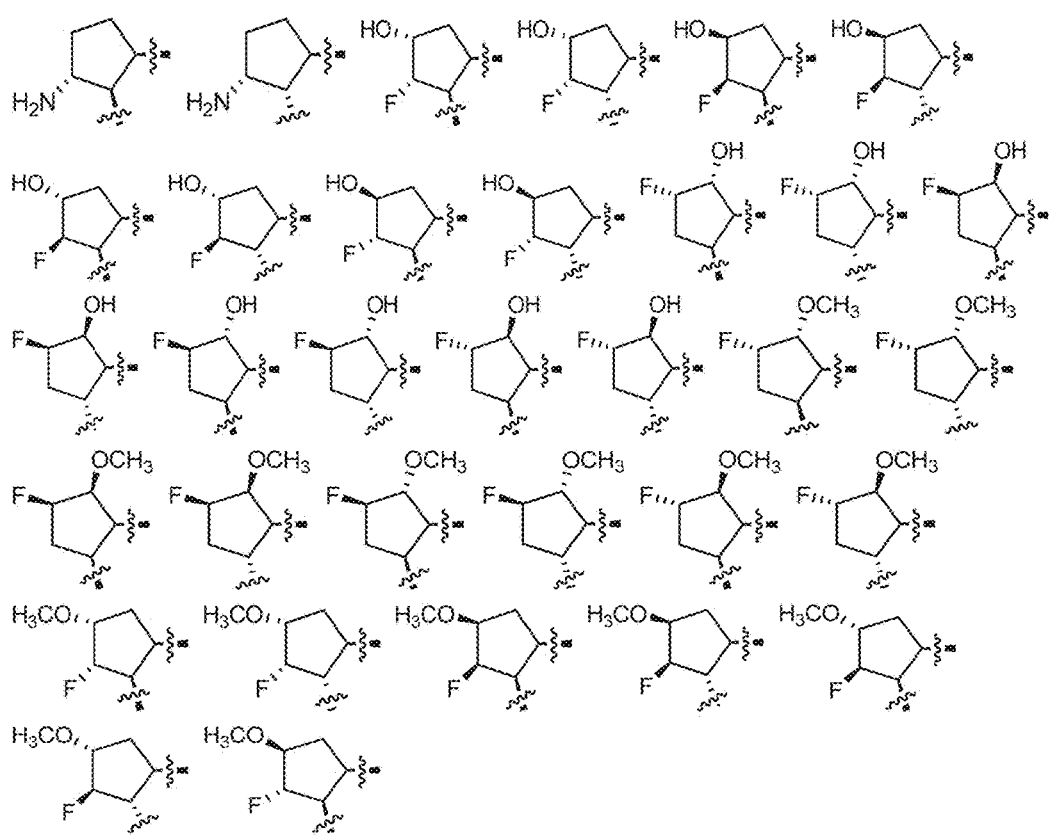
Figure 3F:
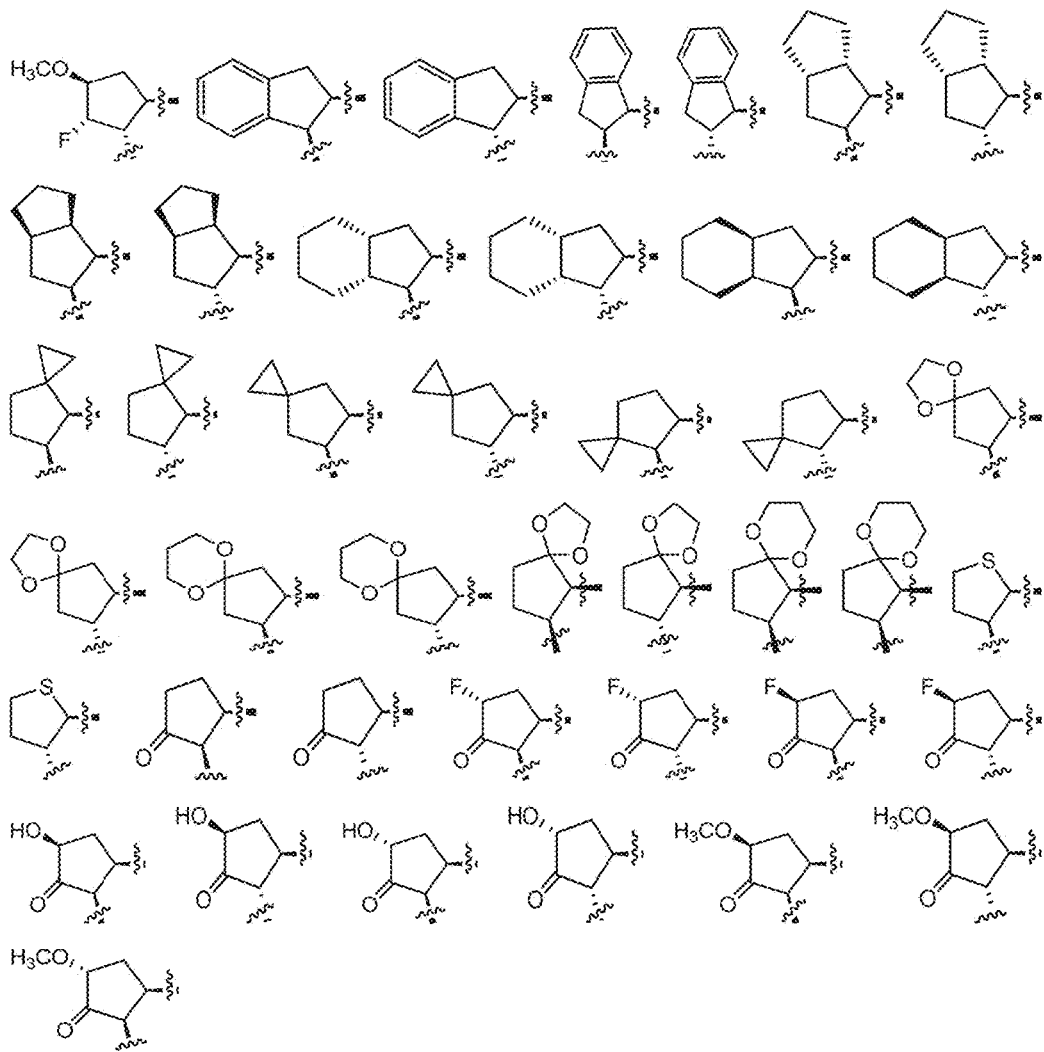
Figure 3G:
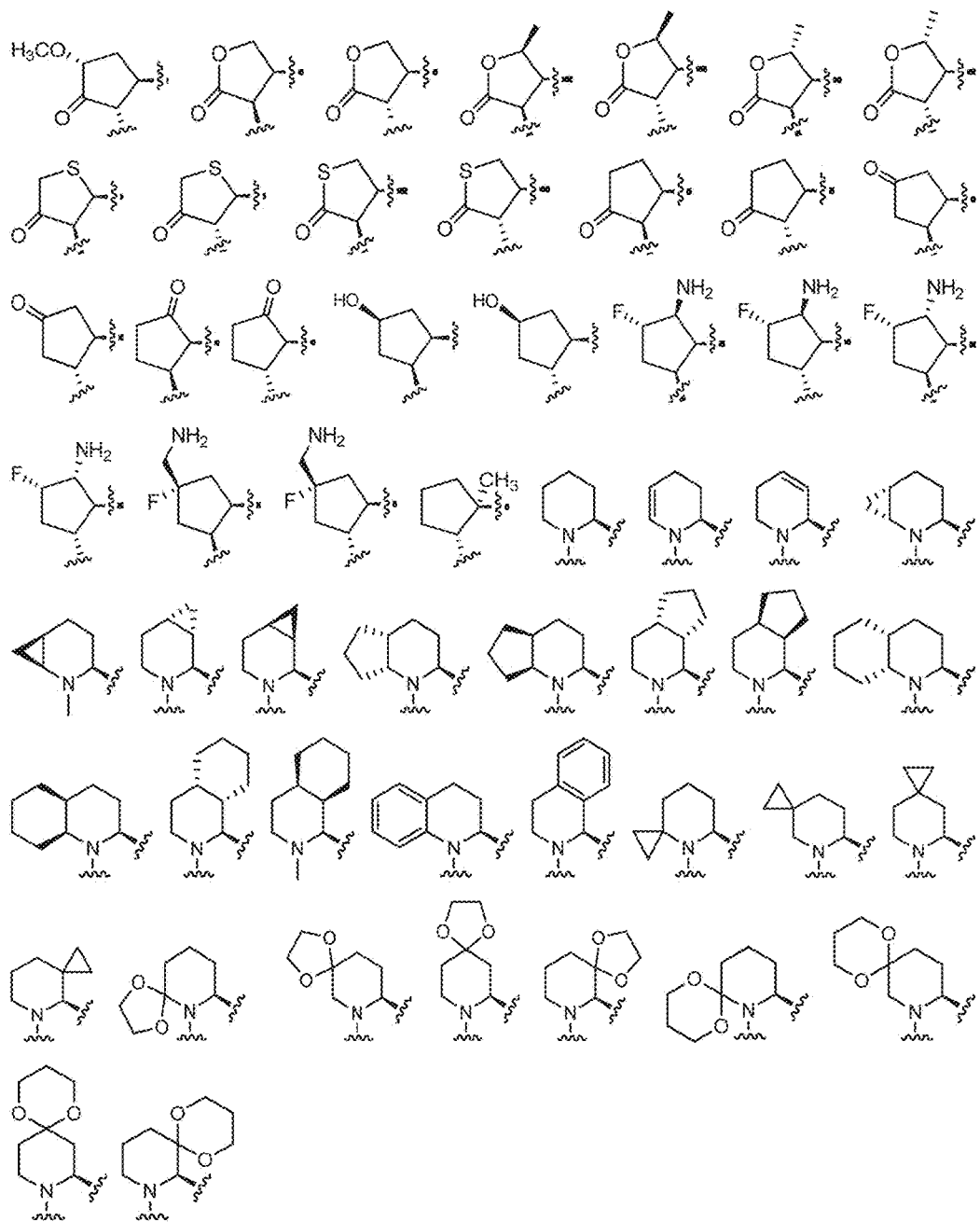
Figure 3H:
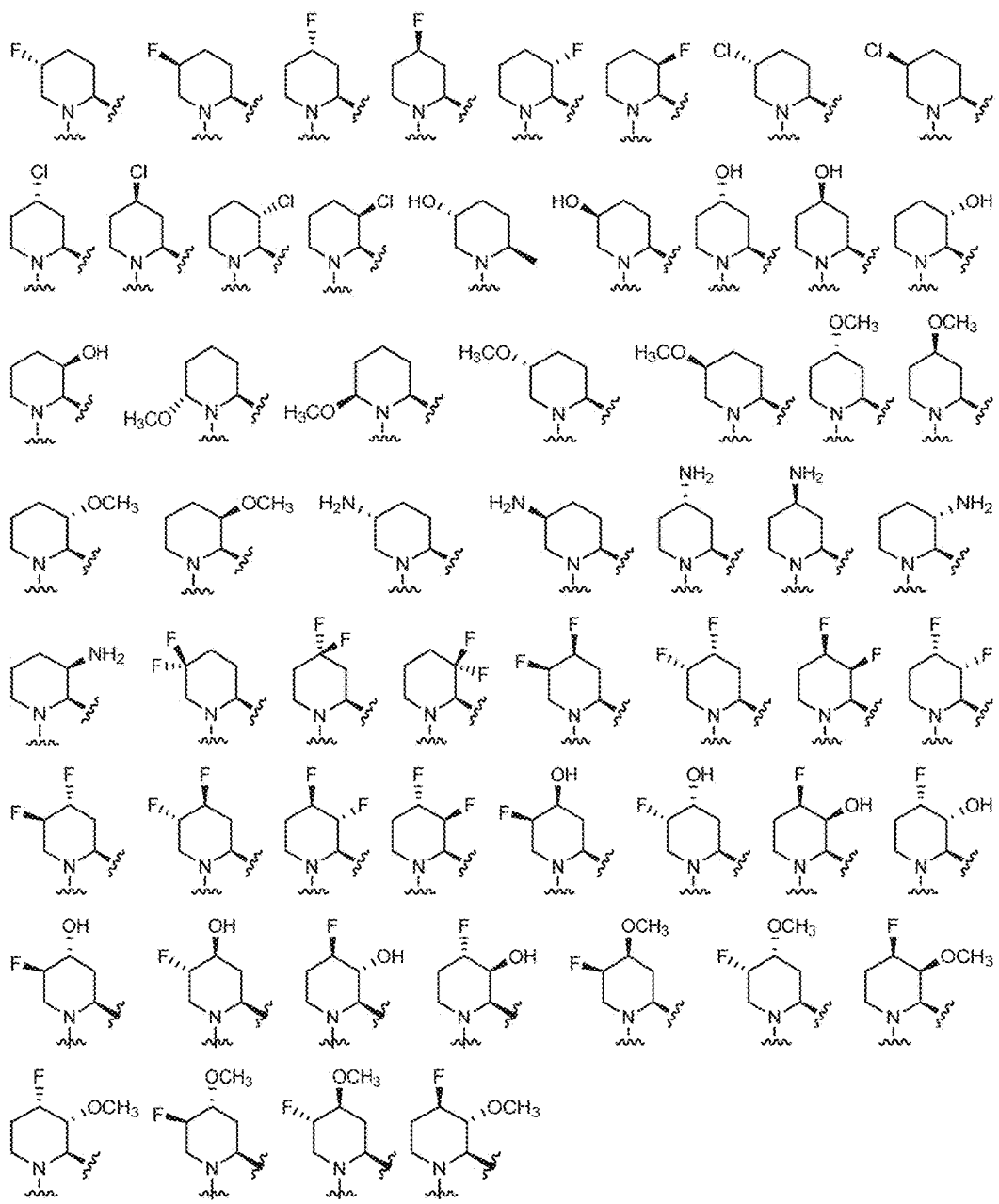
Figure 3I:
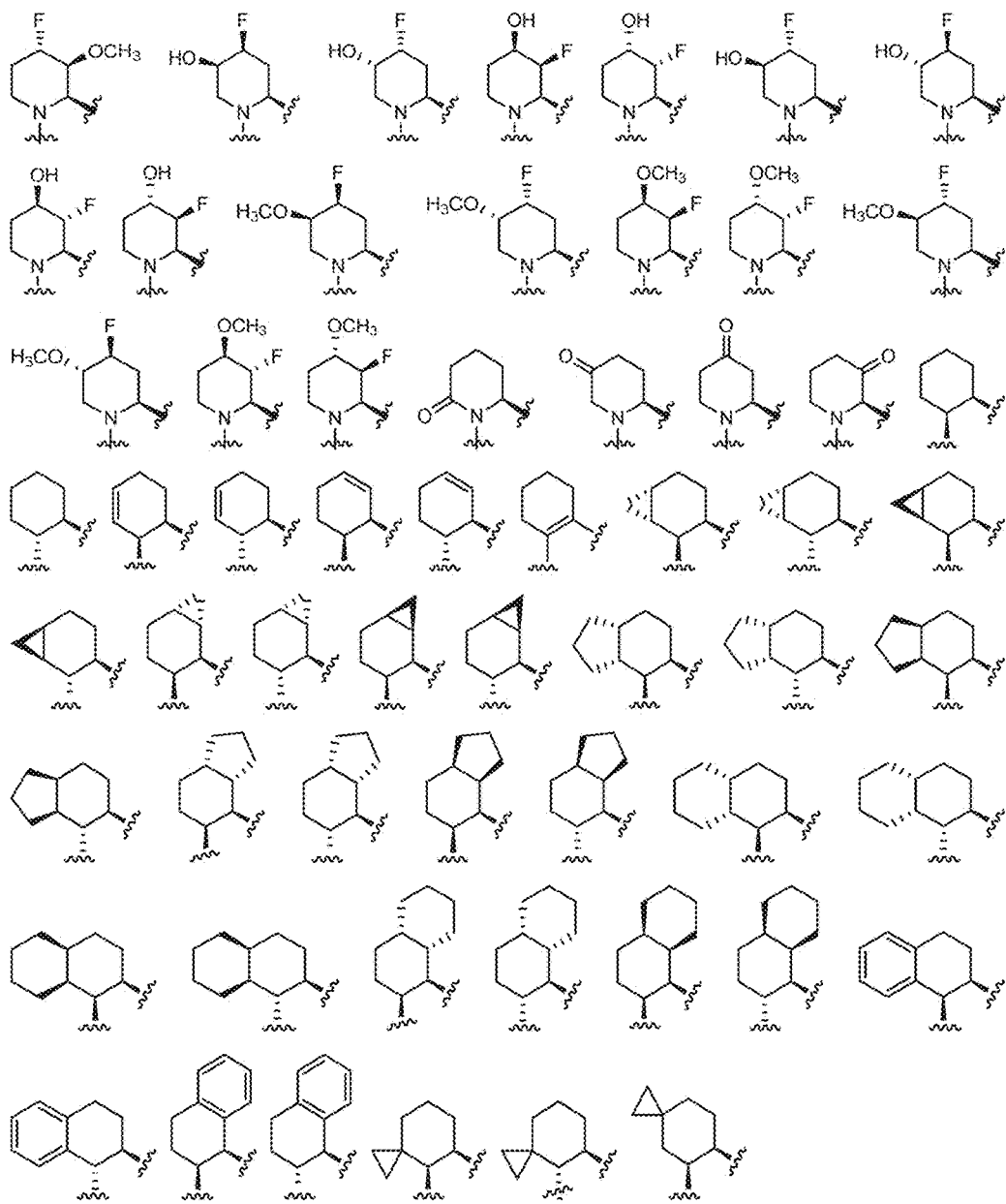
Figure 3J:
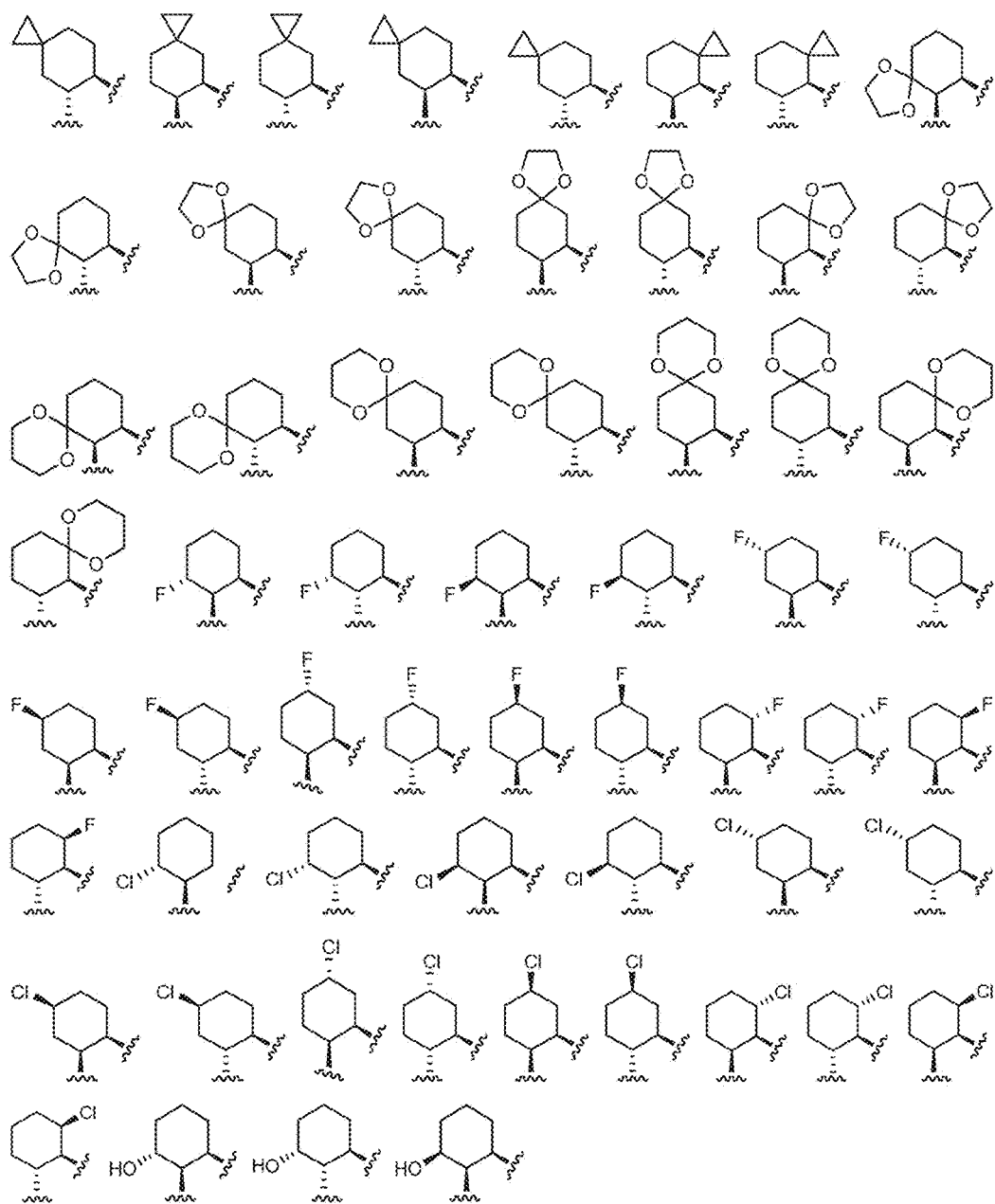
Figure 3K:
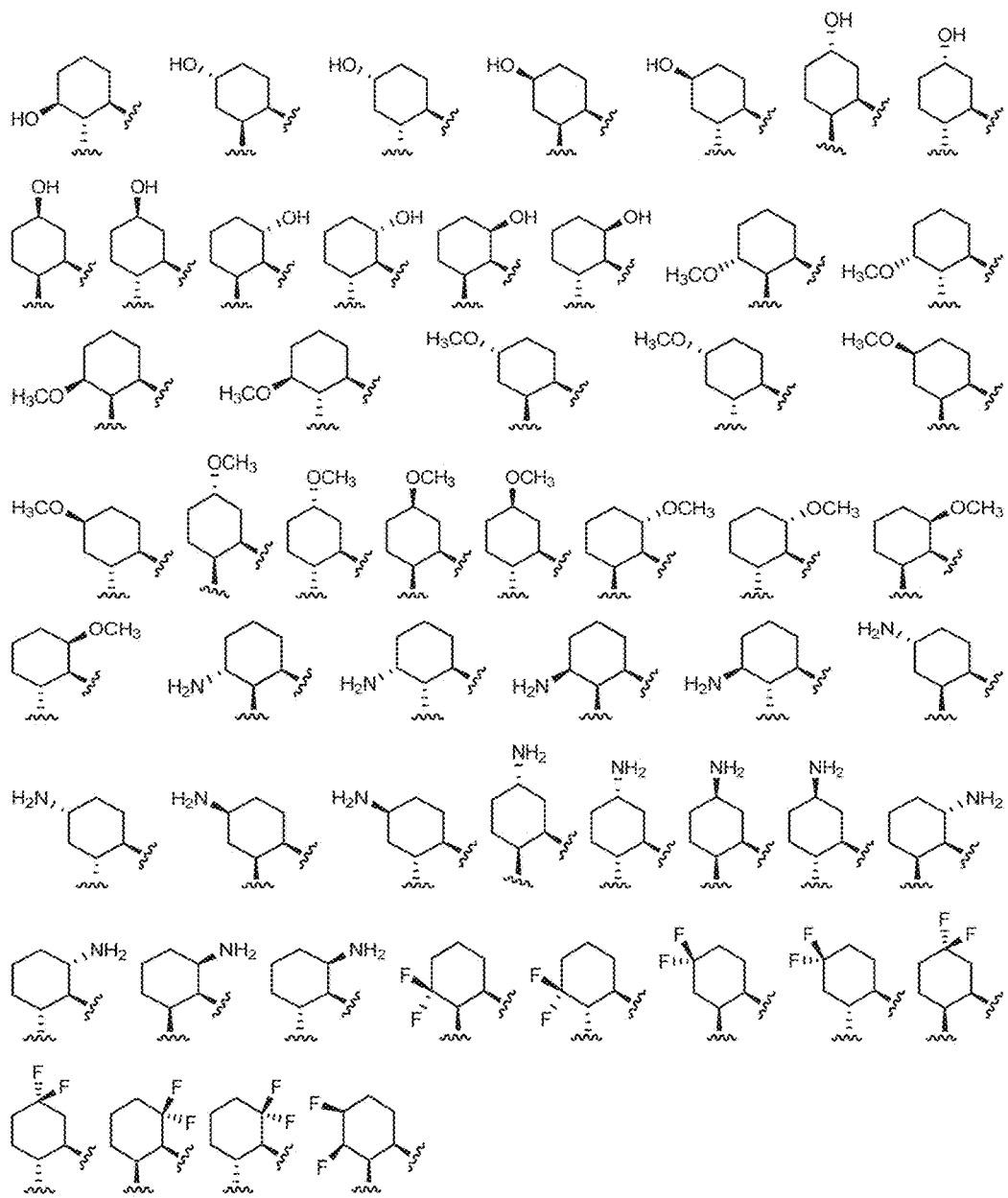
Figure 3L:
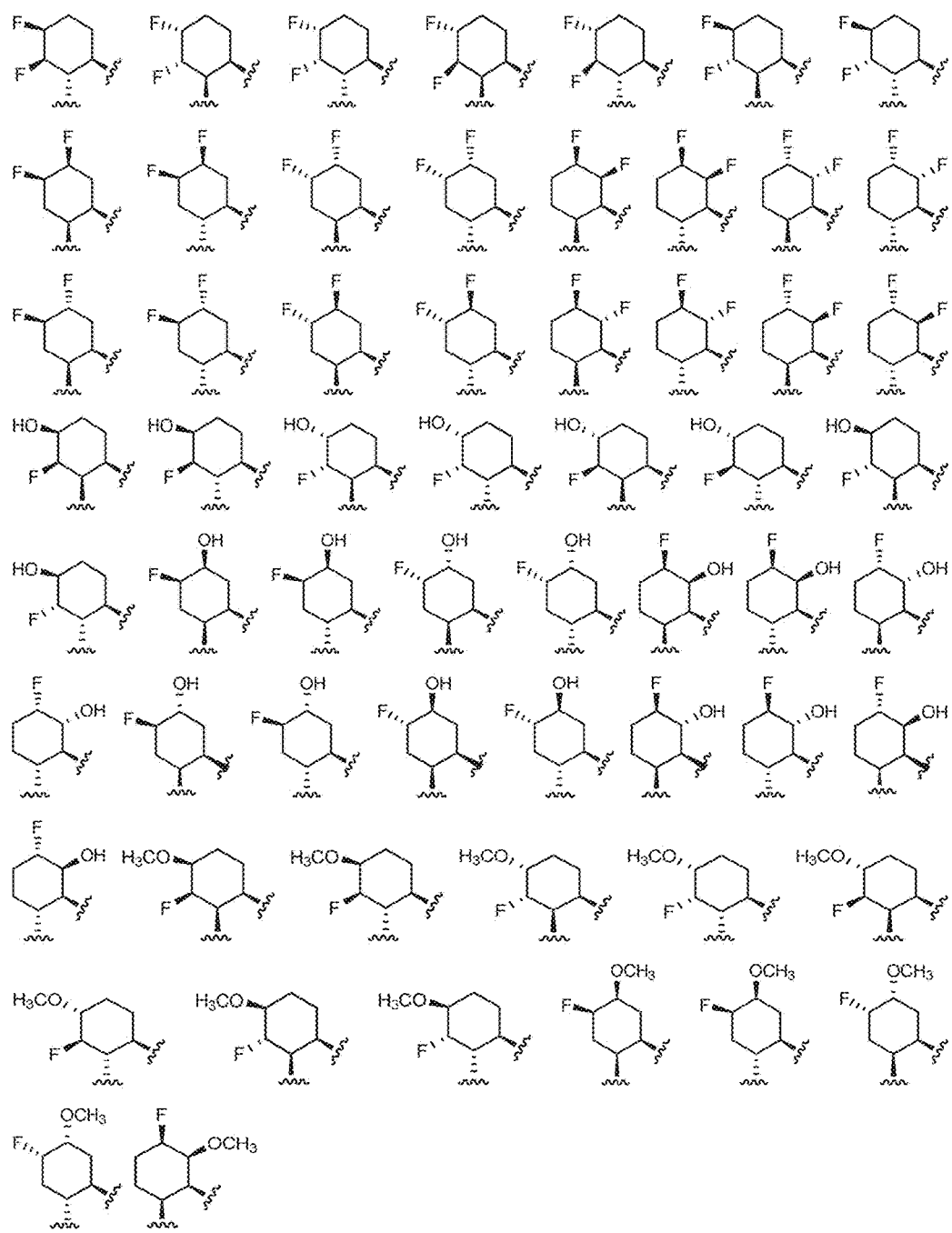
Figure 3M:
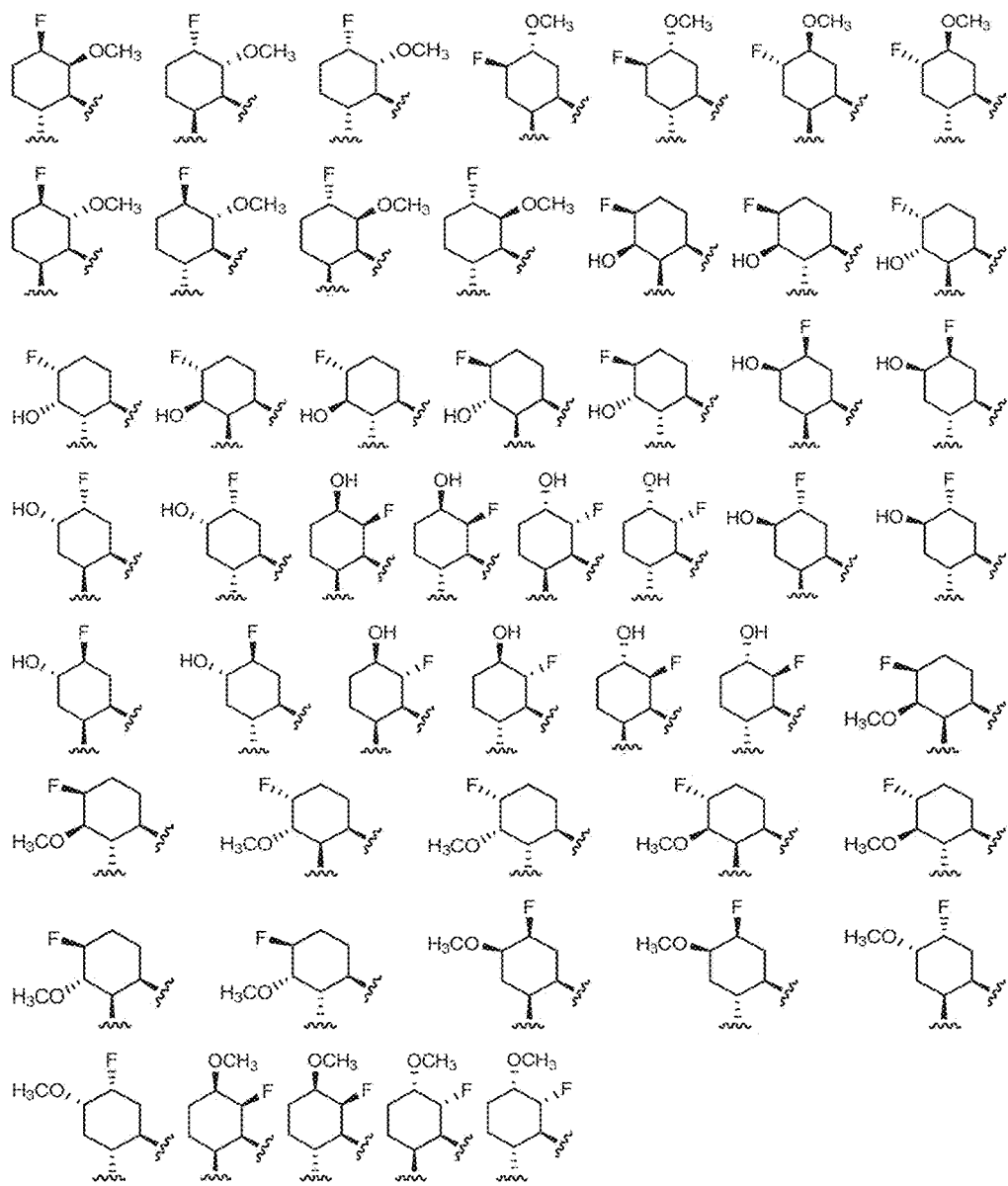
Figure 3N:
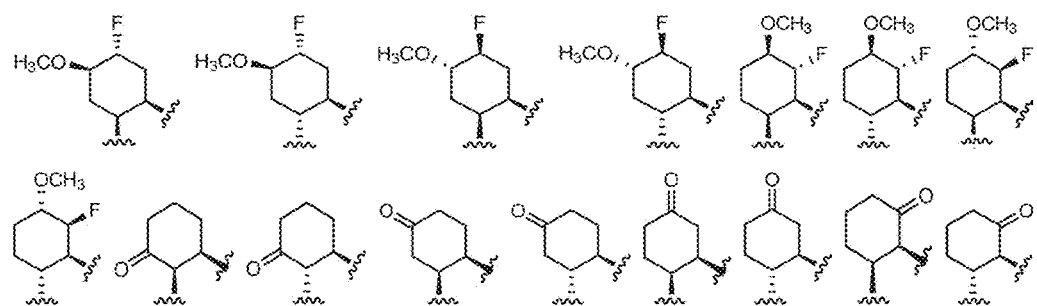
Figure 30:
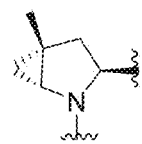
Figure 3P:
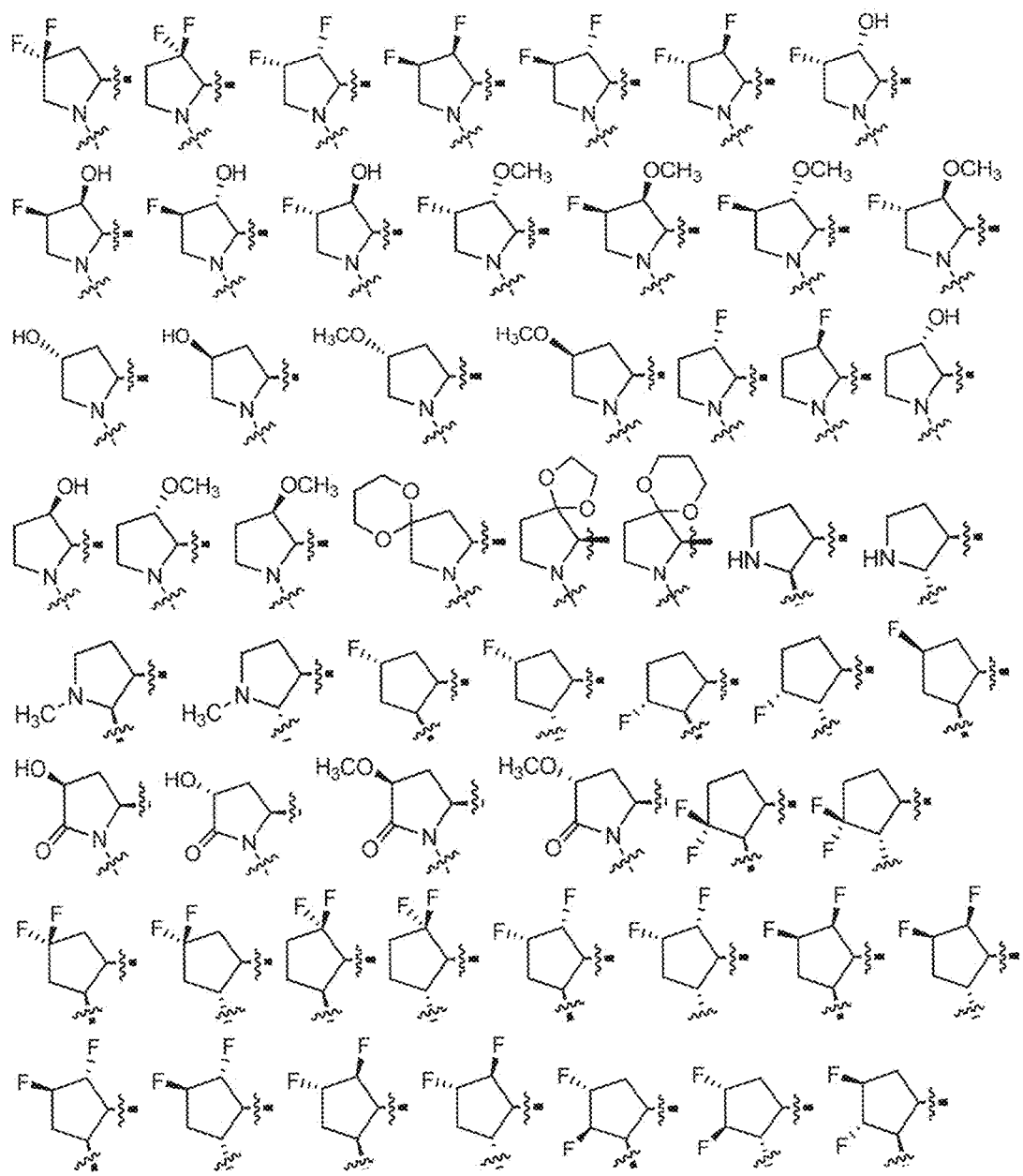
Figure 3Q:
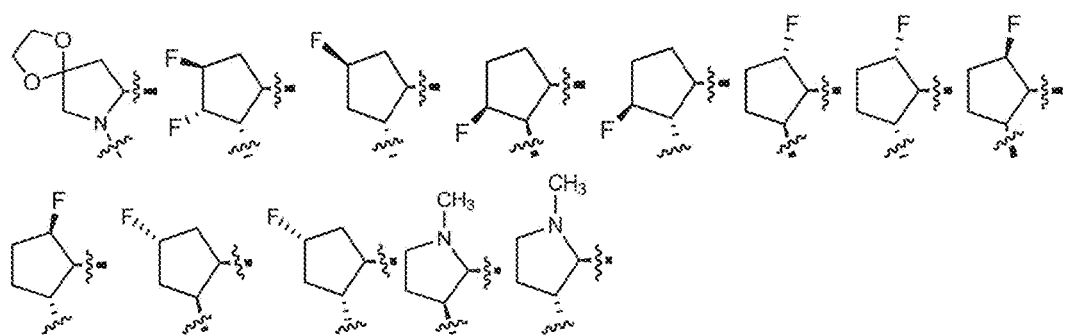
Figure 4A:
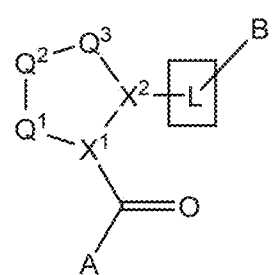
FIG. 4A illustrates the location of the Linker in Formula I.
Figure 4B:
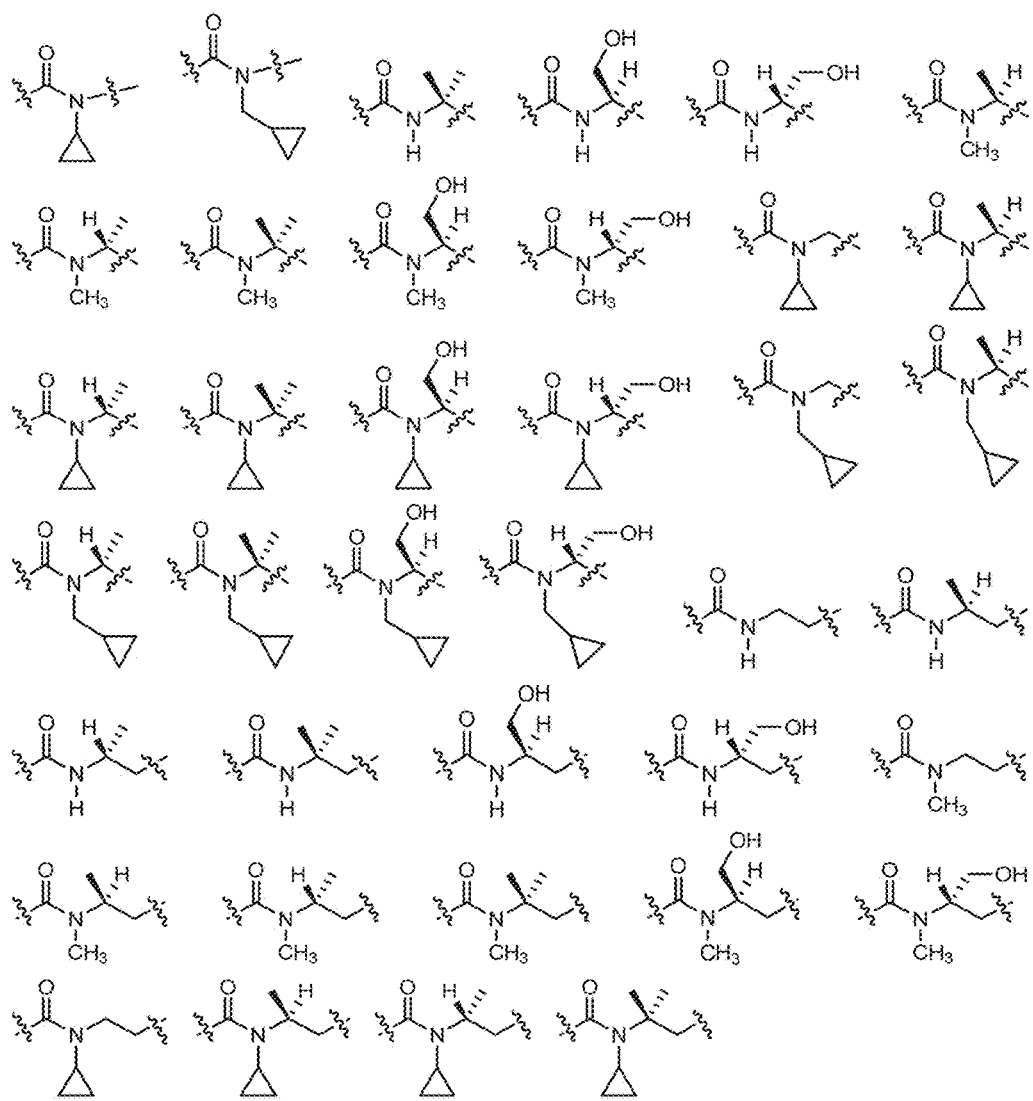
FIGS. 4B, 4C, 4D, 4E, 4F, and 4G, provide non-limiting specific embodiments of the Linker (L), wherein $R^{17}$, $R^{18}$, $R^{18'}$, and m are defined below.
Figure 4C:
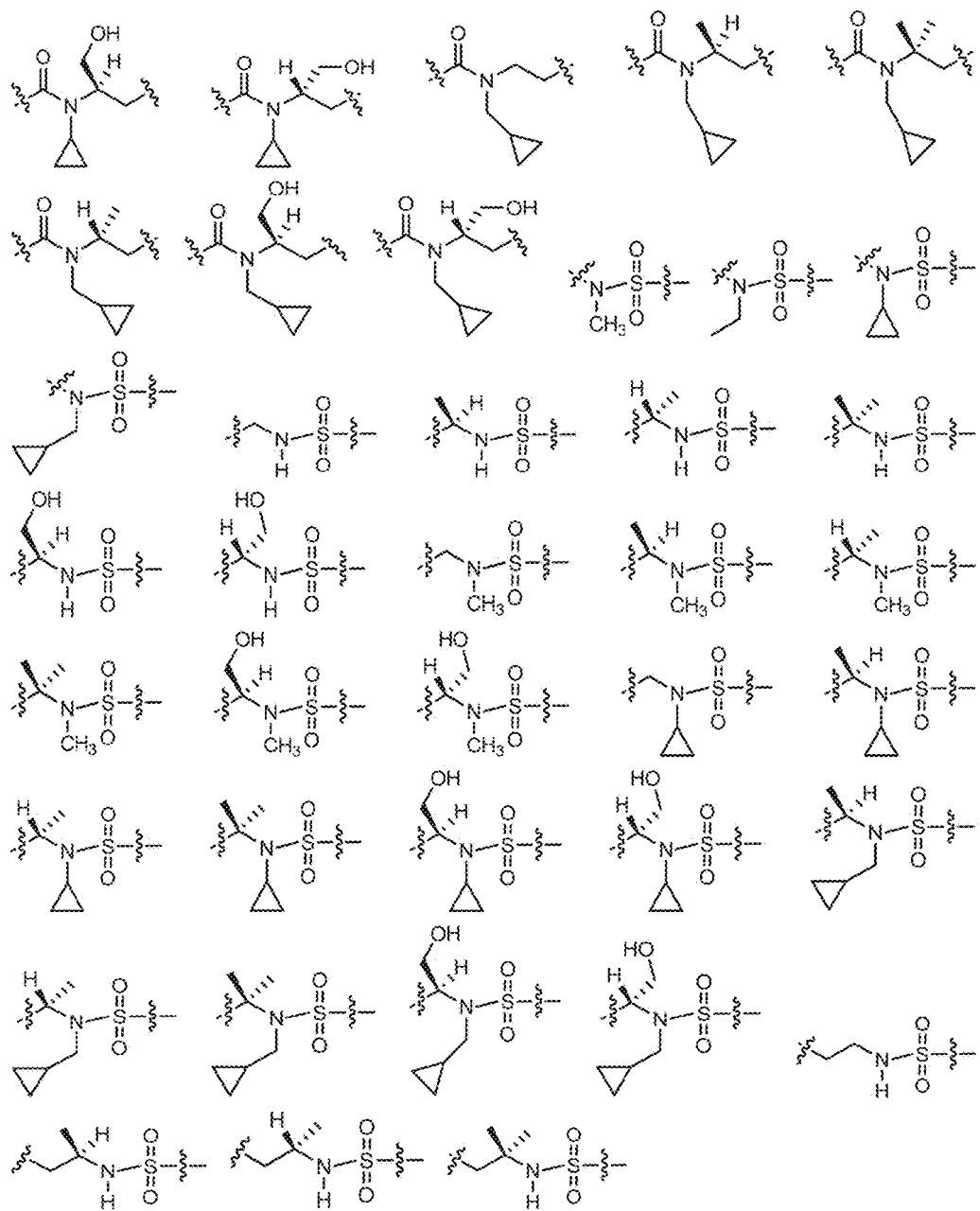
Figure 4D:
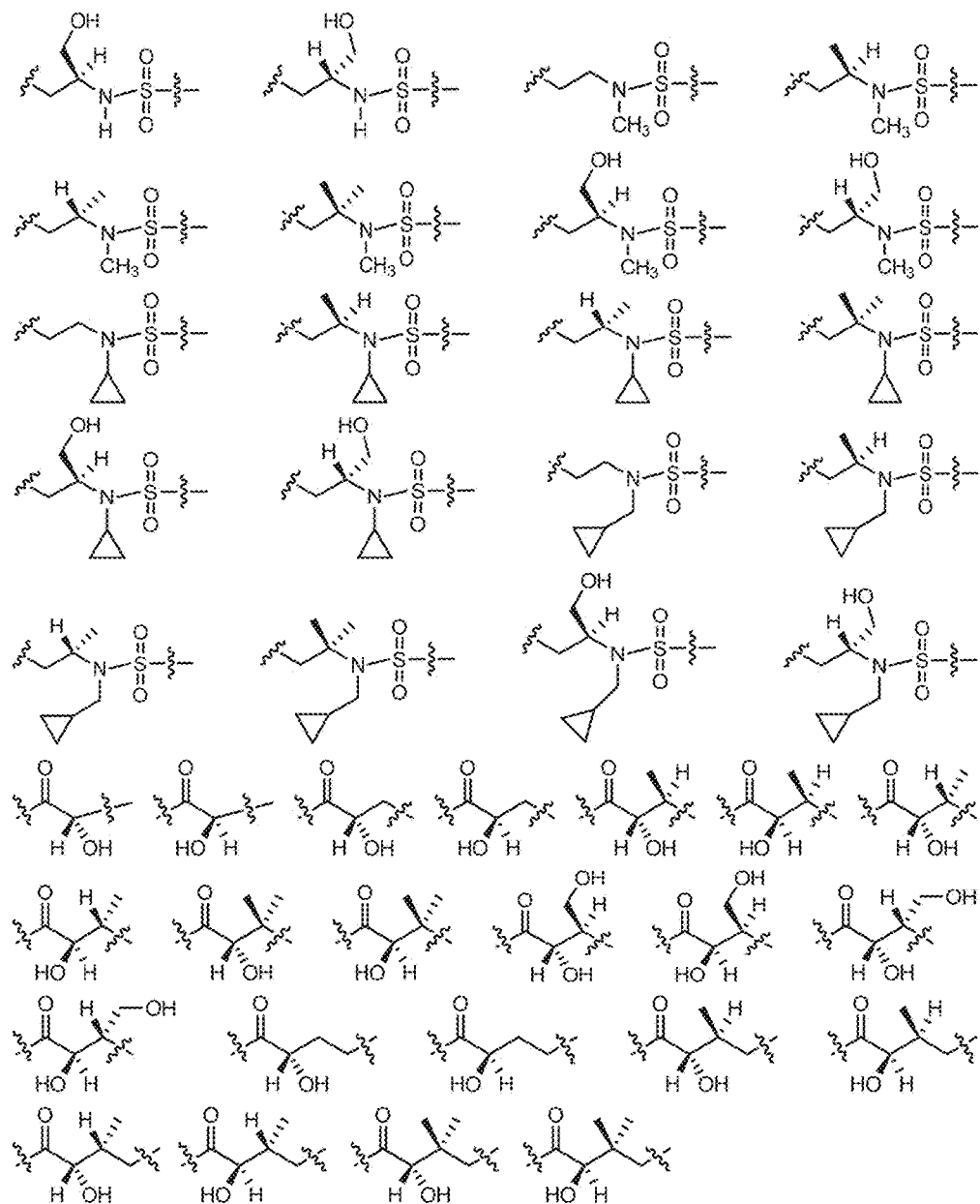
Figure 4E:
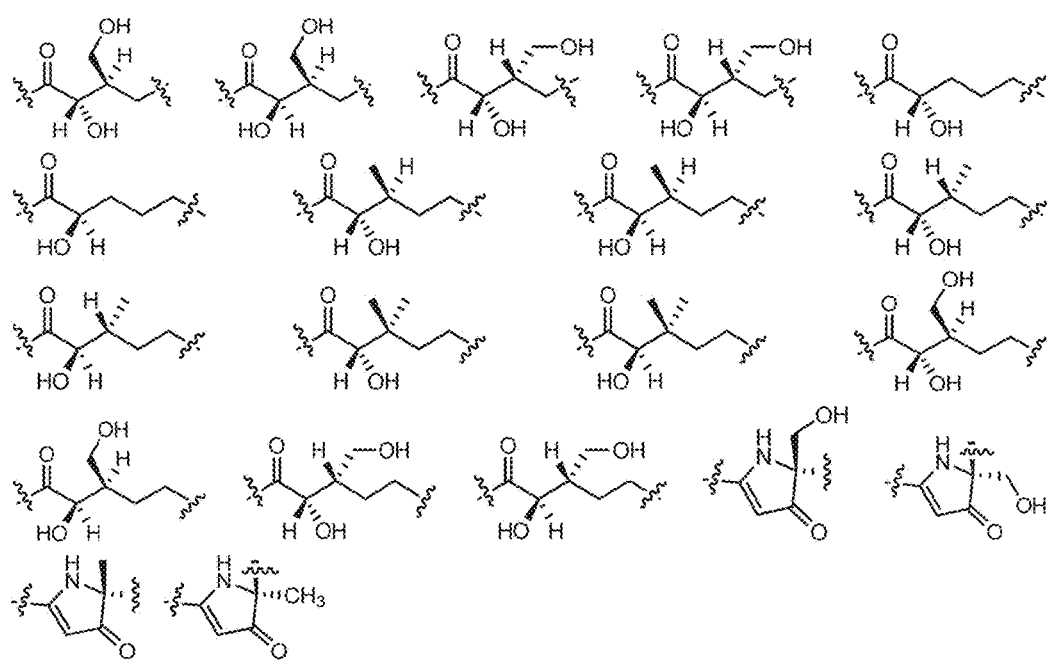
Figure 4F:
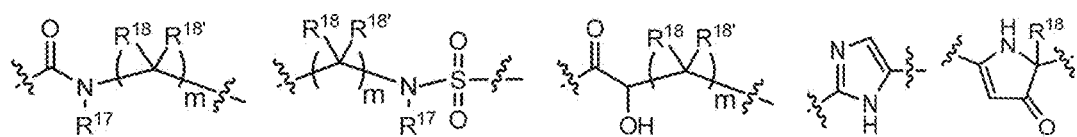
Figure 4G:
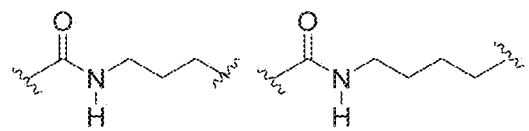

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixture of enantiomers, diastereomers, tautomers, racemates and other isomers, such as rotamers, as if each is specifically described, unless otherwise indicated in the text or drawing or otherwise indicated in context. "Formula I" includes all subgeneric groups of Formula I, such as Formula IA and Formula IB and also includes pharmaceutically acceptable salts of a compound of Formula I, unless clearly contraindicated by the context in which this phrase is used. "Formula I" also includes all subgeneric groups of Formula I, such as Formulas IC-ID, and Formulas II-XXX, and also includes pharmaceutically acceptable salts of all subgeneric groups of Formula I, such as Formulas IA-ID, and Formulas II-XXX, unless contraindicated by the context in which this phrase is used.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Table 2, Table 3, or an embodiment of the active compound as described in the Figures and the use of compounds of Formula I, Table 1 and Table 2 or an embodiment of the active compound as described in the Figures with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. In one embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom can be provided in any of A, B, L or the Central Core. In one embodiment, the substitution of a hydrogen atom for a deuterium atom occurs within an R group selected from any of R, R', $R^1$, $R^{1'}$, $R^2$, $R^{2'}$, $R^3$, $R^{3'}$, $R^4$, $R^5$, $R^6$, $R^{6'}$, $R^7$, $R^8$, $R^{8'}$, $R^9$, $R^{10}$, $R^{11}$, $R^{12}$, $R^{13}$, $R^{14}$, $R^{15}$, $R^{16}$, $R^{17}$, $R^{18}$, $R^{18'}$, $R^{19}$, $R^{21}$, $R^{22}$, $R^{23}$, $R^{24}$, $R^{25}$, $R^{26}$, $R^{27}$, $R^{28}$, $R^{29}$, $R^{31}$, $R^{32}$, $R^{33}$, $R^{34}$, $R^{35}$, $R^{36}$, $R^{75}$, $R^{101}$, and $R^{102}$.

For example, when any of R groups are, or contain for example through substitution, methyl, ethyl, or methoxy, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.). In some embodiments, an R group has a "'" designation, which in one embodiment can be deuterated. In certain other embodiments, when two substituents of the central core ring are combined to form a cyclopropyl ring, the unsubstituted methylene carbon may be deuterated.

The substitution of a hydrogen atom for a deuterium atom occurs within an R group when at least one of the variables within the R group is hydrogen (e.g., $^{2}H$ or D) or alkyl. For example, when any of R groups are, or contain for example through substitution, methyl or ethyl, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, etc.).

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the keto (C═O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., ═O) then two hydrogens on the atom are replaced. For example a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydroxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), $B(OH)_2$, phosphate, phosphonate and $C_1$-$C_2$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl ($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl. In one embodiment, the alkyl group is optionally substituted as described above.

In one embodiment, when a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, aminoalkyl, alkylene, alkenylene, alkynylene, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Non-limiting examples are $C_2$-$C_8$alkenyl, $C_2$-$C_6$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, $C_1$-$C_3$alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C=O) bridge. The carbonyl carbon is included in the number of carbons, that is $C_2$alkanoyl is a $CH_3(C=O)$— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O)Oalkyl.

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described above.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl substituent.

"Aminoalkyl" is an alkyl group as previously described, substituted with at least one amino substituent.

"Halo" or "halogen" indicates independently any of fluoro, chloro, bromo or iodo.

"Aryl" indicates an aromatic group containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7 or a 5 to 7-membered saturated or partially unsaturated cyclic group that optionally contains 1, or 3 heteroatoms independently selected from N, O, B, P, Si and/or S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic moiety of 3 to about 12, and more typically 3, 5, 6, 7 to 10 ring atoms in which at least one ring atom is a heteroatom selected from nitrogen, oxygen, phosphorus and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 6 to 10 ring members (4 to 9 carbon atoms and 1 to 6 heteroatoms selected from N, O, P, and S), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein.

"Heterocyclicoxy group" is a monocyclic heterocyclic ring or a bicyclic heterocyclic group as described previously linked to the group it substitutes via an oxygen, —O—, linker.

"Heteroaryl" indicates a stable monocyclic aromatic ring which contains from 1 to 3, or in some embodiments from 1, 2 or 3 heteroatoms selected from N, O, S, B or P with remaining ring atoms being carbon, or a stable bicyclic or tricyclic system containing at least one 4 to 7 or 5- to 7-membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 8- to 10-membered heteroaryl groups, that is, groups containing 8 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently selected from N, S, and O, with remaining ring atoms being carbon. In a typical embodiment, nitrogen is the heteroatm. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicate a secondary or tertiary alkylamino group, wherein the alkyl groups are independently selected alkyl groups, as defined herein. The point of attachment of the alkylamino group is on the nitrogen. Examples of mono- and di-alkylamino groups include ethylamino, dimethylamino, and methyl-propyl-amino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the complement Factor D pathway. Typically the host is a human. A "patient" or "host" or "subject" also refers to for example, a mammal, primate (e.g., human), cows, sheep, goat, horse, dog, cat, rabbit, rat, mice, fish, bird and the like.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Non-limiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound with at least one additional active agent," for example, in one embodiment can mean that the compound and the additional active agent(s) are provided simultaneously in a single dosage form, provided concomitantly in separate dosage forms, or provided in separate dosage forms for administration. In one embodiment, the compound administrations are separated by some amount of time that is within the time in which both the compound and the at least one additional active agent are within the blood stream of a patient. In certain embodiments the compound and the additional active agent need not be prescribed for a patient by the same medical care worker. In certain embodiments the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact. A "therapeutically effective amount" of a pharmaceutical composition/combination of this invention means an amount effective, when administered to a host, to provide a therapeutic benefit such as an amelioration of symptoms or reduction or diminution of the disease itself. In one embodiment, a therapeutically effective amount is an amount sufficient to prevent a significant increase or will significantly reduce the detectable level of complement Factor D in the patient's blood, serum, or tissues.

II. Detailed Description of the Active Compounds

PCT Patent Application No. PCT/US2015/017593 and U.S. patent application Ser. No. 14/631,625 titled "Aryl, Heteroaryl, and Heterocyclic Compounds for Treatment of Complement Mediated Disorders" defines a compound of Formula I as:

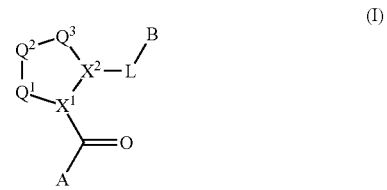

(I)

as well as the pharmaceutically acceptable salts and compositions thereof. In one embodiment, the invention is the use of a compound of Formula I, or a pharmaceutically acceptable salt or composition thereof, wherein $R^{12}$ or $R^{13}$ on the A group is an aryl, heteroaryl, or heterocycle, including those compounds set out in Table 1, for the treatment of a disorder in a host, typically a human, wherein the disorder is selected from the group disclosed in the Detailed Description, Part IV, Section A.

Formula I can be considered to have a central core, an L substituent, a B substituent (which can be an L-B substituent), and a (C=O)A substituent. Non-limiting examples of compounds falling within Formula I with variations in the variables e.g., A, B, $R^1$-$R^{3'}$, the central core, and L, are illustrated below. The disclosure includes the use of all combinations of these definitions so long as a stable compound results. In one embodiment, the compound of Formula I is selected from the compounds in Table 1 below.

In certain embodiments, any of the active compounds can be provided in its N-oxide form to a patient in need thereof. In a different embodiment, an N-oxide of one of the active compounds or a precursor of the active compound is used in a manufacturing scheme. In yet another embodiment, the N-oxide is a metabolite of administration of one of the active compounds herein, and may have independent activity. The N-oxide can be formed by treating the compound of interest with an oxidizing agent, for example a suitable peroxyacid or peroxide to generate an N-oxide compound. For example, a heteroaryl group, for example a pyridyl group, can be treated with an oxidizing agent such as sodium percarbonate in the presence of a rhenium-based catalyst under mild reaction conditions to generate an N-oxide compound. A person skilled in the art will understand that appropriate protecting groups may be necessary to carry out the chemistry. See, Jain, S. L. et al., "Rhenium-Catalyzed Highly Efficient Oxidations of Tertiary Nitrogen Compounds to N-Oxides Using Sodium Percarbonate as Oxygen Source, Synlett, 2261-2663, 2006.

In other embodiments, any of the active compounds with a sulfur can be provided in a corresponding oxidized form to a patient in need thereof, or can be used in a manufacturing scheme. A sulfur atom in a selected compound can be oxidized to form a sulfoxide

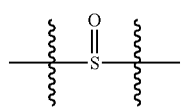 [SMILES: *S(*)=O]

or a sulfone

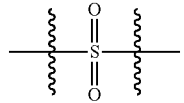 [SMILES: *S(*)(=O)=O]

according to known methods. For example, the compound 1,3,5-triazo-2,4,6-triphosphorine-2,2,4,4,6,6-tetrachloride (TAPC) is an efficient promoter for the oxidation of sulfides to sulfoxides. See, Bahrami, M. et al., "TAPC-Promoted Oxidation of sulfides and Deoxygenation of Sulfoxides", J. Org. Chem., 75, 6208-6213 (2010). Oxidation of sulfides with 30% hydrogen peroxide catalyzed by tantalum carbide provides sulfoxides in high yields, see, Kirihara, A., et al., "Tantalum Carbide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Sulfides can be oxidized to sulfones using, for example, niobium carbide as the catalyst, see, Kirihara, A., et al., "Tantalum Cardide or Niobium Carbide Catalyzed Oxidation of Sulfides with Hydrogen Peroxide: Highly Efficient and Chemoselective Syntheses of Sulfoxides and Sulfones", Synlett, 1557-1561 (2010). Urea-hydrogen peroxide adduct is a stable inexpensive and easily handled reagent for the oxidation of sulfides to sulfones, see Varma, R. S. and Naicker, K. P., "The Urea-Hydrogen Peroxide Complex: Solid-State Oxidative Protocols for Hydroxylated Aldehydes and Ketones (Dakin Reaction), Nitriles, Sulfides, and Nitrogen Heterocycles", Org. Lett., 1, 189-191 (1999). One skilled in the art will appreciate that other heteroatoms, such as nitrogen, may need to be protected and then deprotected while carrying out the oxidation of a sulfur atom to produce the desired compound.

Formulas II-XXX

In one aspect, the disclosure includes the use, as further described herein, of a compound or salt of Formula II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX and XXX. The variables shown in Formula II-XXX carry the definitions set forth in the SUMMARY section for Formula I or any of the definitions set forth in this disclosure.

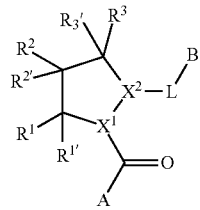

Formula II

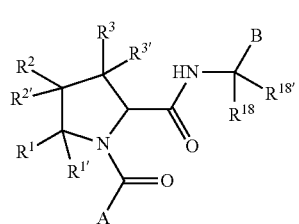

Formula III

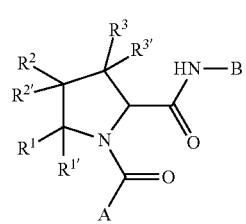

Formula IV

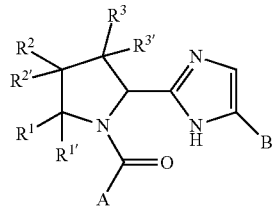

Formula V

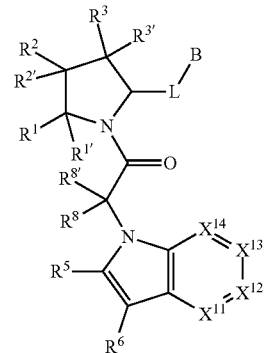

Formula VI

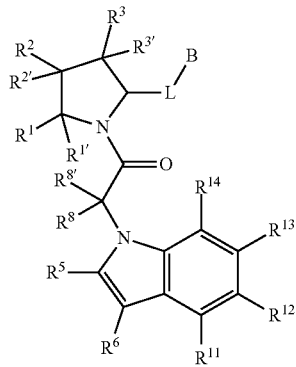

Formula VII

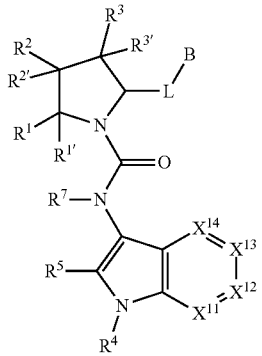

Formula VIII

-continued
Formula IX
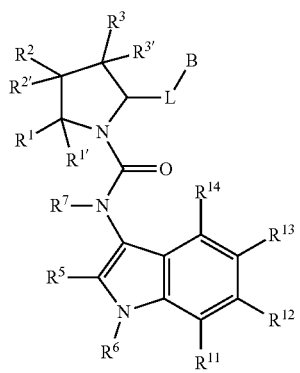
Formula X
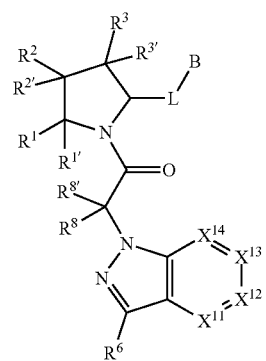
Formula XI
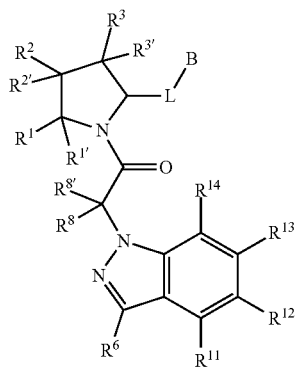
Formula XII
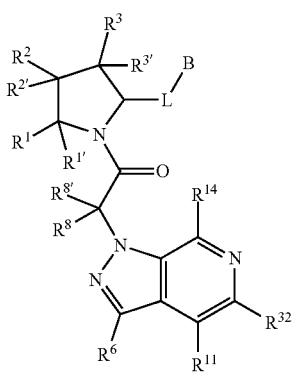
Formula XIII
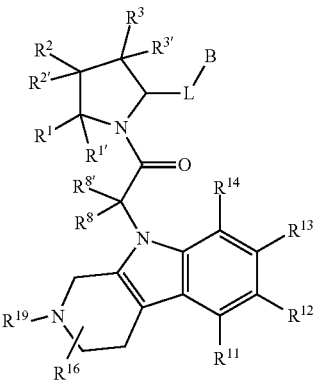
Formula XIV
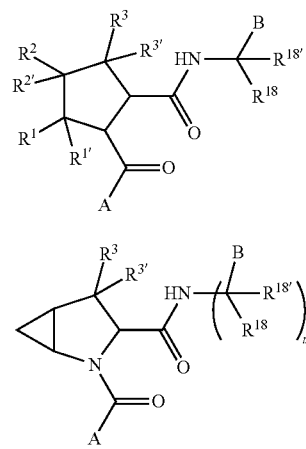
Formula XV
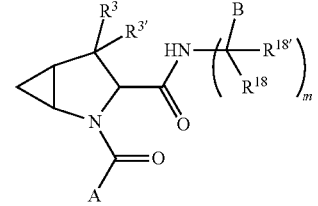
m is 0 or 1.
Formula XVI
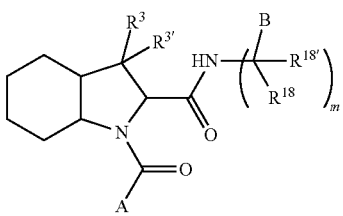
m is 0 or 1.
Formula XVII
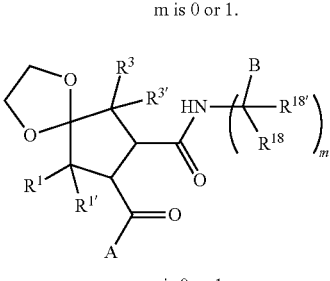
m is 0 or 1.
Formula XVIII
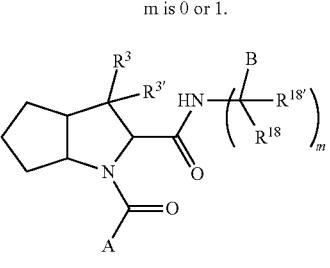
m is 0 or 1.

Formula XIX
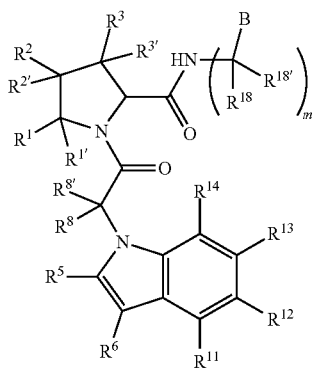
m is 0 or 1.
Formula XX
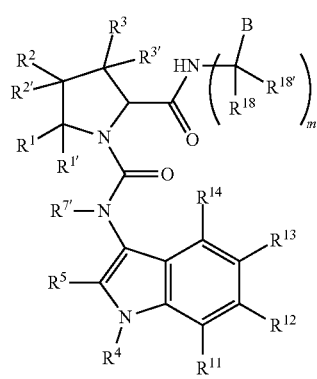
m is 0 or 1.
Formula XXI
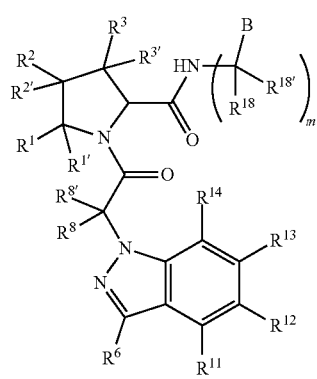
m is 0 or 1.
Formula XXII
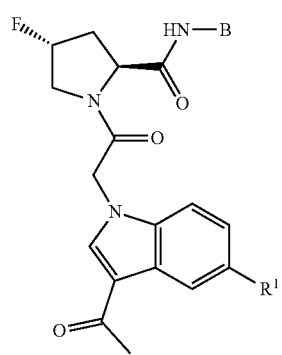
Formula XXIII
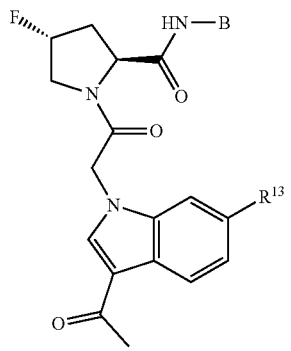
Formula XXIV
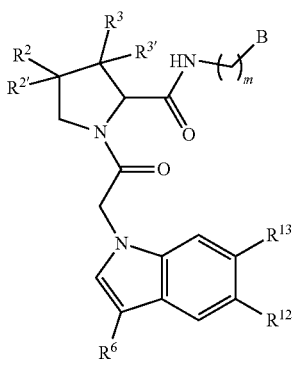
m is 0 or 1
Formula XXV
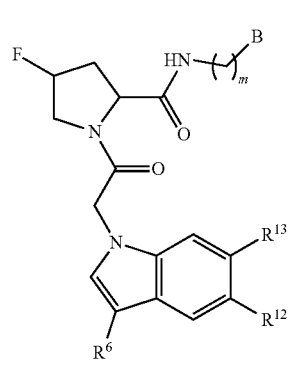
m is 0 or 1.
Formula XXVI
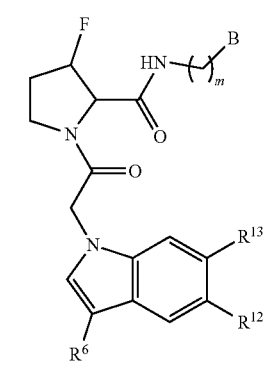
m is 0 or 1.

Formula XXVII

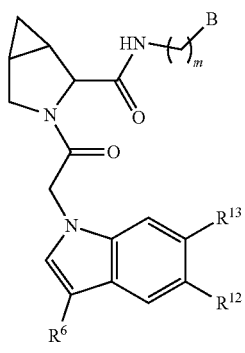

m is 0 or 1.

Formula XXVIII

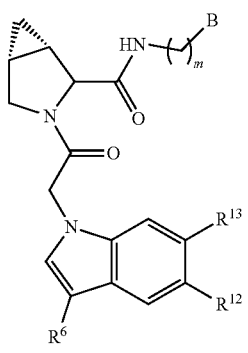

m is 0 or 1.

Formula XXIX

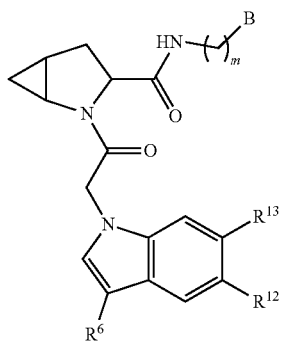

m is 0 or 1.

Formula XXX

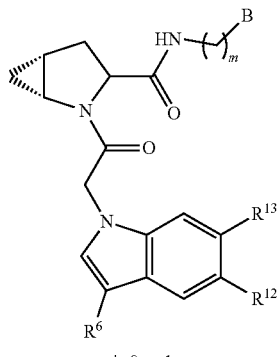

m is 0 or 1.

Additionally, the disclosure includes the use of compounds and salts of Formula I and pharmaceutically acceptable compositions thereof, and any of its subformulae (II-XXX) in which at least one of the following conditions is met in the embodiments described below.

The $R^{12}$ and $R^{13}$ Aryl, Heteroaryl, and Heterocycle Substituents

In one embodiment, the invention is the use of a compound of Formula I, or a pharmaceutically acceptable salt or composition thereof, wherein $R^{12}$ or $R^{13}$ on the A group is an aryl, heteroaryl, or heterocycle, including those compounds set out in Table 1, for the treatment of a disorder in a host, typically a human, wherein the disorder is selected from the group disclosed in the Detailed Description, Part IV, Section A.

One of $R^{12}$ and $R^{13}$ is selected from $R^{31}$ and the other of $R^{12}$ and $R^{13}$ is selected from $R^{32}$. In another embodiment, each of $R^{12}$ and $R^{13}$ can be independently selected from $R^{32}$.

$R^{31}$ is selected from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$, $C_1$-$C_2$haloalkyl, and $C_1$-$C_2$haloalkoxy, and each of which $R^{31}$ is also optionally substituted with one substituent selected from phenyl and 4- to 7-membered heterocycle containing 1, 2, or 3 heteroatoms independently selected from N, O, and S; which phenyl or 4- to 7-membered heterocycle is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is selected from aryl; saturated or unsaturated heterocycle (for example a 5-6 membered ring having 1, 2, or 3 heteroatoms independently selected from N, O, and S), wherein the heterocycle is bonded through a carbon atom in the heterocyclic ring to a carbon atom of ring A in the $R^{12}$ or $R^{13}$ position; and heteroaryl (for example a 5-6 membered ring having 1, 2, or 3 heteroatoms independently selected from N, O, and S), wherein the aryl, heterocycle or heteroaryl ring can be optionally substituted.

$R^{32}$ is the same as $Z^{32}$.

When A is an indole or indazole and $X^{12}$ is N, $X^{13}$ is CR$^{13}$, wherein $R^{13}$ is $R^{32}$.

When A is an indole or indazole and $X^{13}$ is N, $X^{12}$ is CR$^{12}$, wherein $R^{12}$ is $R^{32}$.

Non-limiting examples of $R^{32}$ include the structures of FIG. 6.

Non-Limiting $R^{12}/R^{13}$ Embodiments

In one embodiment, $R^{12}$ is $R^{32}$.

In one embodiment, $R^{13}$ is $R^{32}$.

In one embodiment, $R^{12}$ is $R^{32}$, which is aryl.

In one embodiment, $R^{12}$ is optionally substituted aryl.

In one embodiment, $R^{12}$ is an optionally substituted saturated or unsaturated heterocycle bonded through a carbon atom in the heterocyclic ring to a carbon atom of ring A in the $R^{12}$ position.

In one embodiment, $R^{12}$ is an optionally substituted heteroaryl.

In one embodiment, $R^{13}$ is an optionally substituted aryl.

In one embodiment, $R^{13}$ is an optionally substituted saturated or unsaturated heterocycle bonded through a carbon atom in the heterocyclic ring to a carbon atom of ring A in the $R^{13}$ position.

In one embodiment, $R^{13}$ is optionally substituted heteroaryl.

In one embodiment, $R^{12}$ is $R^{32}$, which is (5- or 6-membered unsaturated or aromatic heterocycle), having 1, 2, or 3 heteroatoms independently selected from N, O, and S, wherein the (5- or 6-membered unsaturated heterocycle) is bonded through a carbon atom to a carbon of $CR^{12}$ or $CR^{13}$.

In one embodiment, $R^{12}$ is $R^{32}$, which is (4- to 7-membered heterocycloalkyl) having 1, 2, or 3 heteroatoms independently selected from N, O, and S, wherein the (4- to 7-membered heterocycloalkyl) is bonded through a carbon atom to a carbon of $CR^{12}$ or $CR^{13}$.

In one embodiment, $R^{13}$ is $R^{32}$, which is aryl.

In one embodiment, $R^{13}$ is $R^{32}$, which is (5- or 6-membered unsaturated or aromatic heterocycle), having 1, 2, or 3 heteroatoms independently selected from N, O, and S, wherein the (5- or 6-membered unsaturated heterocycle) is bonded through a carbon atom to a carbon of $CR^{12}$ or $CR^{13}$.

In one embodiment, $R^{13}$ is $R^{32}$, which is (4- to 7-membered heterocycloalkyl) having 1, 2, or 3 heteroatoms independently selected from N, O, and S, wherein the (4- to 7-membered heterocycloalkyl) is bonded through a carbon atom to a carbon of $CR^{12}$ or $CR^{13}$.

In one embodiment, the disclosure provides the use of compounds of Formula I, wherein;
one of $R^{12}$ and $R^{13}$ is H and the other of $R^{12}$ and $R^{13}$ is $R^{32}$, where
$R^{32}$ is selected from aryl, which can be optionally substituted; (5- or 6-membered unsaturated or aromatic heterocycle), having 1, 2, or 3 heteroatoms independently selected from N, O, and S, wherein the (5- or 6-membered unsaturated or aromatic heterocycle) is bonded through a carbon atom to a carbon of $CR^{12}$ or $CR^{13}$, wherein the (5- or 6-membered unsaturated or aromatic heterocycle) can be optionally substituted; and (4- to 7-membered heterocycloalkyl) having 1, 2, or 3 heteroatoms independently selected from N, O, and S, wherein the (4- to 7-membered heterocycloalkyl) is bonded through a carbon atom to a carbon of $CR^{12}$ or $CR^{13}$, and the (4- to 7-membered heterocycloalkyl) can be optionally substituted.

In another embodiment, the disclosure provides the use of compounds of Formula I, wherein;
$R^1$, $R^{1'}$, $R^2$, and $R^{3'}$ are all hydrogen;
$R^2$ is fluoro and $R^3$ is hydrogen, $-C_0$-$C_4$alkyl($C_3$-$C_7$cycloalkyl), or $-O$-$C_0$-$C_4$alkyl($C_3$-$C_7$cycloalkyl);
$R^5$ is hydrogen, halogen, or $C_1$-$C_2$alkyl;
$R^{11}$, $R^{13}$, $R^{14}$, and $R^{15}$ if present, are independently selected at each occurrence from hydrogen, halogen, hydroxyl, amino, $C_1$-$C_4$alkyl, $C_1$-$C_4$alkoxy, $-C_0$-$C_2$alkyl (mono- and di-$C_1$-$C_2$alkylamino), trifluoromethyl, and trifluoromethoxy;
$X^{12}$ is $CR^{12}$; and
$R^{12}$ is selected from aryl, which can be optionally substituted; (5- or 6-membered unsaturated or aromatic heterocycle), having 1, 2, or 3 heteroatoms independently selected from N, O, and S, wherein the (5- or 6-membered unsaturated heterocycle) is bonded through a carbon atom to a carbon of $CR^{12}$ or $CR^{13}$, wherein the (5- or 6-membered unsaturated or aromatic heterocycle) can be optionally substituted; and (4- to 7-membered heterocycloalkyl) having 1, 2, or 3 heteroatoms independently selected from N, O, and S, wherein the (4- to 7-membered heterocycloalkyl) is bonded through a carbon atom to a carbon of $CR^{12}$ or $CR^{13}$, and the (4- to 7-membered heterocycloalkyl) can be optionally substituted.

In one embodiment, the disclosure provides the use of compounds of Formula I, wherein;
m is 0 or 1;
$R^2$ is halogen, $R^{2'}$ is hydrogen or halogen, and $R^3$ is hydrogen, halogen, $-C_0$-$C_4$alkyl($C_3$-$C_7$cycloalkyl), or $-O$-$C_0$-$C_4$alkyl($C_3$-$C_7$cycloalkyl);
$R^6$ is $-C(O)C_1$-$C_4$alkyl, $-C(O)NH_2$, $-C(O)CF_3$, $-C(O)(C_3$-$C_7$cycloalkyl), or -ethyl(cyanoimino);
one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where
$R^{32}$ is selected from aryl; saturated or unsaturated heterocycle (for example a 5-6 membered ring having 1, 2, or 3 heteroatoms independently selected from N, O, and S), wherein the heterocycle is bonded through a carbon atom in the heterocyclic ring to a carbon atom of ring A in the $R^{12}$ or $R^{13}$ position; and heteroaryl (for example a 5-6 membered ring having 1, 2, or 3 heteroatoms independently selected from N, O, and S), wherein the aryl, heterocycle or heteroaryl ring can be optionally substituted.

In one embodiment, the disclosure provides the use of compounds of Formula I, wherein one of $R^{12}$ and $R^{13}$ is hydrogen, hydroxyl, halogen, methyl, or methoxy; and the other of $R^{12}$ and $R^{13}$ is $R^{32}$, where
$R^{32}$ is selected from aryl, heteroaryl or heterocycle bonded to the A ring through a heterocyclic carbon atom;

In one embodiment, $R^{32}$ may be unsubstituted or substituted with one or more substituents independently selected from halogen, hydroxyl, nitro, cyano, amino, oxo, $-B(OH)_2$, $-Si(CH_3)_3$, $-COOH$, $-CONH_2$, $-P(O)(OH)_2$, $C_1$-$C_6$alkyl, $C_1$-$C_6$alkoxy, $-C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

Central Core Moiety

The central core moiety in Formula I is illustrated below:

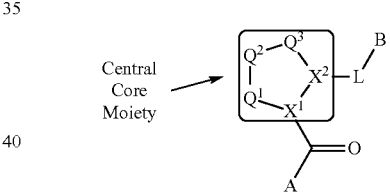

wherein:
$Q^1$ is $N(R^1)$ or $C(R^1R^{1'})$;
$Q^2$ is $C(R^2R^{2'})$, $C(R^2R^{2'})$—$C(R^2R^{2'})$, S, O, $N(R^2)$ or $C(R^2R^{2'})O$;
$Q^3$ is $N(R^3)$, S, or $C(R^3R^{3'})$;
$X^1$ and $X^2$ are independently N, CH, or CZ, or $X^1$ and $X^2$ together are C=C; and
wherein $Q^1$, $Q^2$, $Q^3$, $X^1$, and $X^2$ are selected such that a stable compound results.

Any of the structures illustrated herein, e.g., A, B, L or central core can be optionally substituted with 0, 1, 2, 3, or 4, as appropriate, and independently, selected from $R^{75}$, wherein $R^{75}$ is selected from hydrogen, halogen, hydroxyl, nitro, cyano, amino, $C_1$-$C_6$alkyl, $C_1$-$C_6$haloalkyl, $C_2$-$C_6$alkenyl, $C_2$-$C_6$alkynyl, $C_1$-$C_6$thioalkyl, $C_1$-$C_6$alkoxy, -$JC_3$-$C_7$cycloalkyl, $-B(OH)_2$, -$JC(O)NR^9R^{23}$, -$JOSO_2OR^{21}$, $-C(O)(CH_2)_{1-4}S(O)R^{21}$, $-O(CH_2)_{1-4}S(O)NR^{21}R^{22}$, $JOP(O)(OR^{21})(OR^{22})$, $-JP(O)(OR^{21})(OR^{22})$, $-JOP(O)(OR^{21})R^{22}$, $-JP(O)(OR^{21})R^{22}$, $-JOP(O)R^{21}R^{22}$, $-JP(O)R^{21}R^{22}$, $-JSP(O)(OR^{21})(OR^{22})$, $-JSP(O)(OR^{21})(R^{22})$, $-JSP(O)(R^{21})(R^{22})$, $JNR^9P(O)(NHR^{21})(NHR^{22})$, $-JNR^9P(O)(OR^{21})(NHR^{22})$, $-JNR^9P(O)(OR^{21})(OR^{22})$, $-JC(S)R^{21}$, $-JNR^{21}SO_2R^{22}$, $-JNR^9S(O)NR^{10}R^{22}$, $-JNR^9SO_2NR^{10}R^{22}$, $-JSO_2NR^9COR^{22}$, $-JSO_2NR^9CONR^{21}R^{22}$, $JNR^{21}SO_2R^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, JC(O)R$^{21}$, -JNR$^9$C(O)NR$^{10}$R$^{22}$, —CCR$^{21}$, —(CH$_2$)$_{1-4}$OC(O)R$^{21}$, -JC(O)OR$^{23}$; each of which R$^{75}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_4$alkyl(mono- and di-C$_1$-C$_4$alkylNR$^9$R$^{10}$), C$_1$-C$_6$alkylester, C$_1$-C$_4$alkylamino, C$_1$-C$_4$hydroxylalkyl, C$_1$-C$_2$haloalkyl, C$_1$-C$_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, S(O)=NHR$^{21}$, SF$_5$, and JC(R$^9$)=NR$^{21}$ and SO$_2$OR$^{21}$.

Non-limiting examples of the

Figure 5:
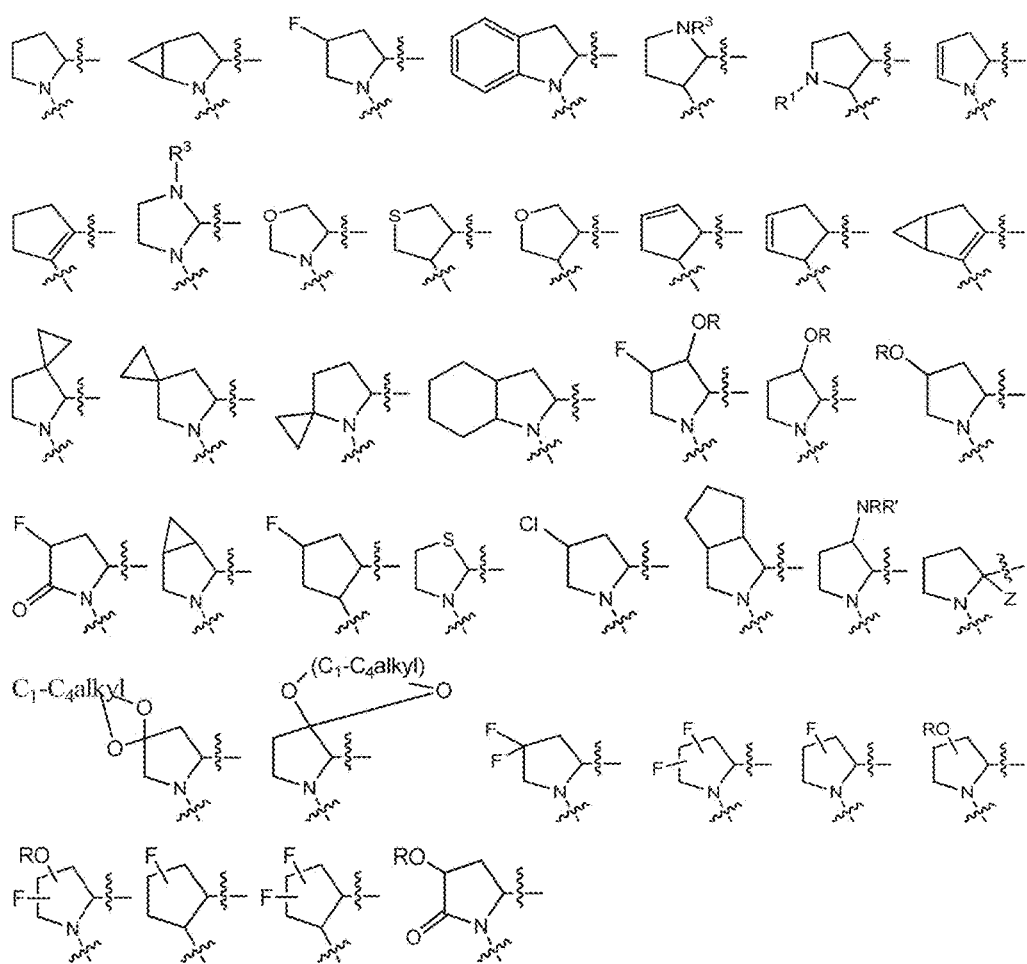
FIG. 5 provides non-limiting specific embodiments of the Central Core ring, wherein R, R', and $R^3$ are defined below.
Figure 6A:
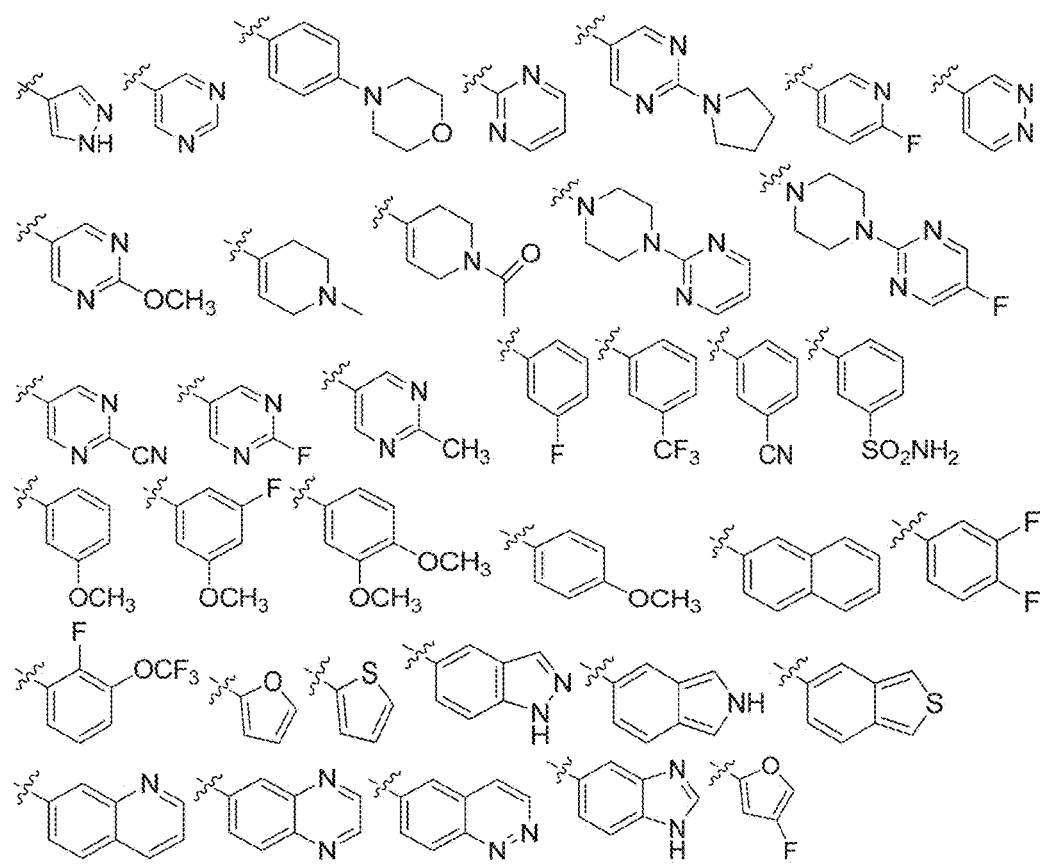
FIGS. 6A, 6B, 6C, and 6D provide non-limiting specific embodiments of $R^{32}$, wherein $R^{100}$ is defined below.
Figure 6B:
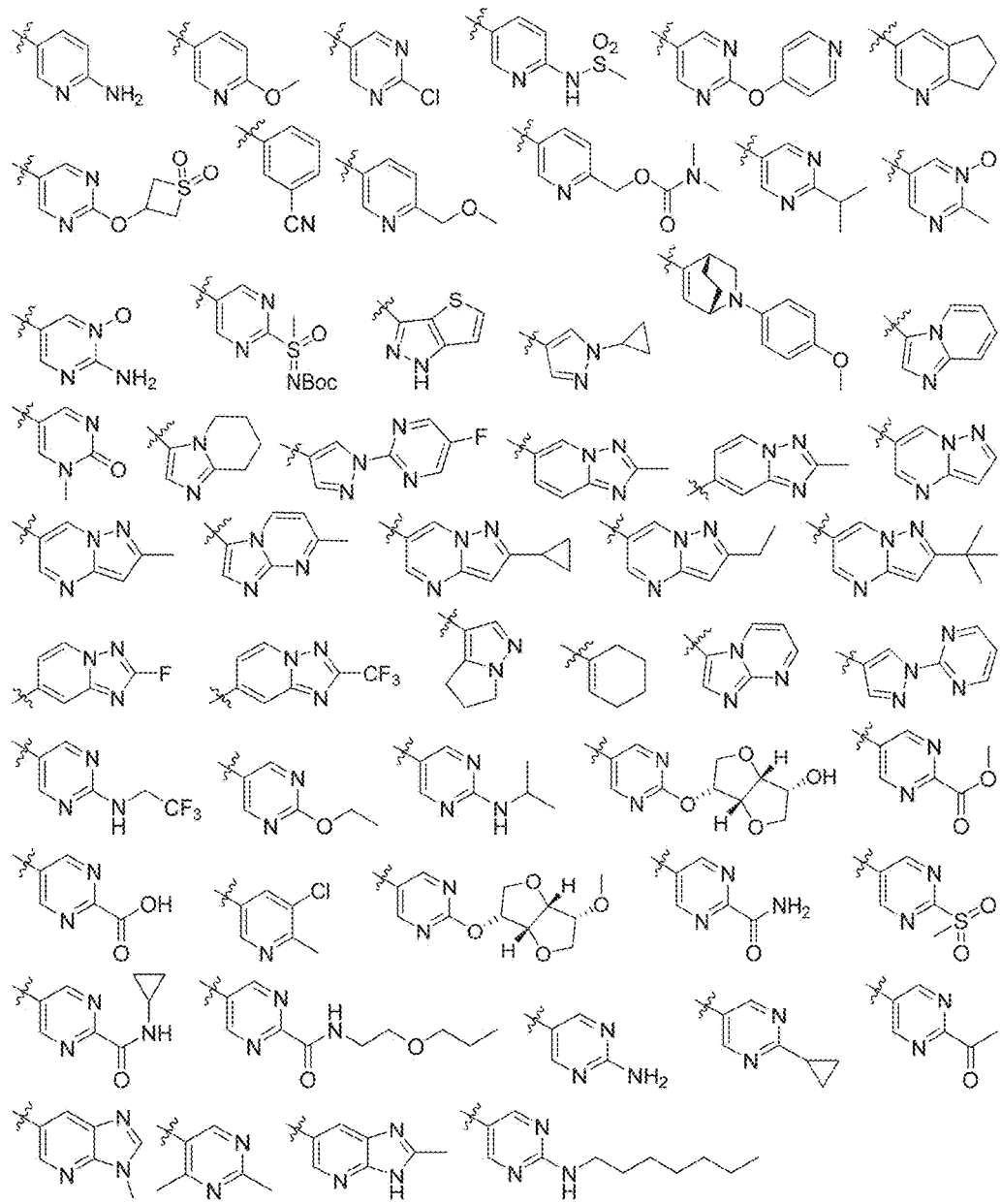
Figure 6C:
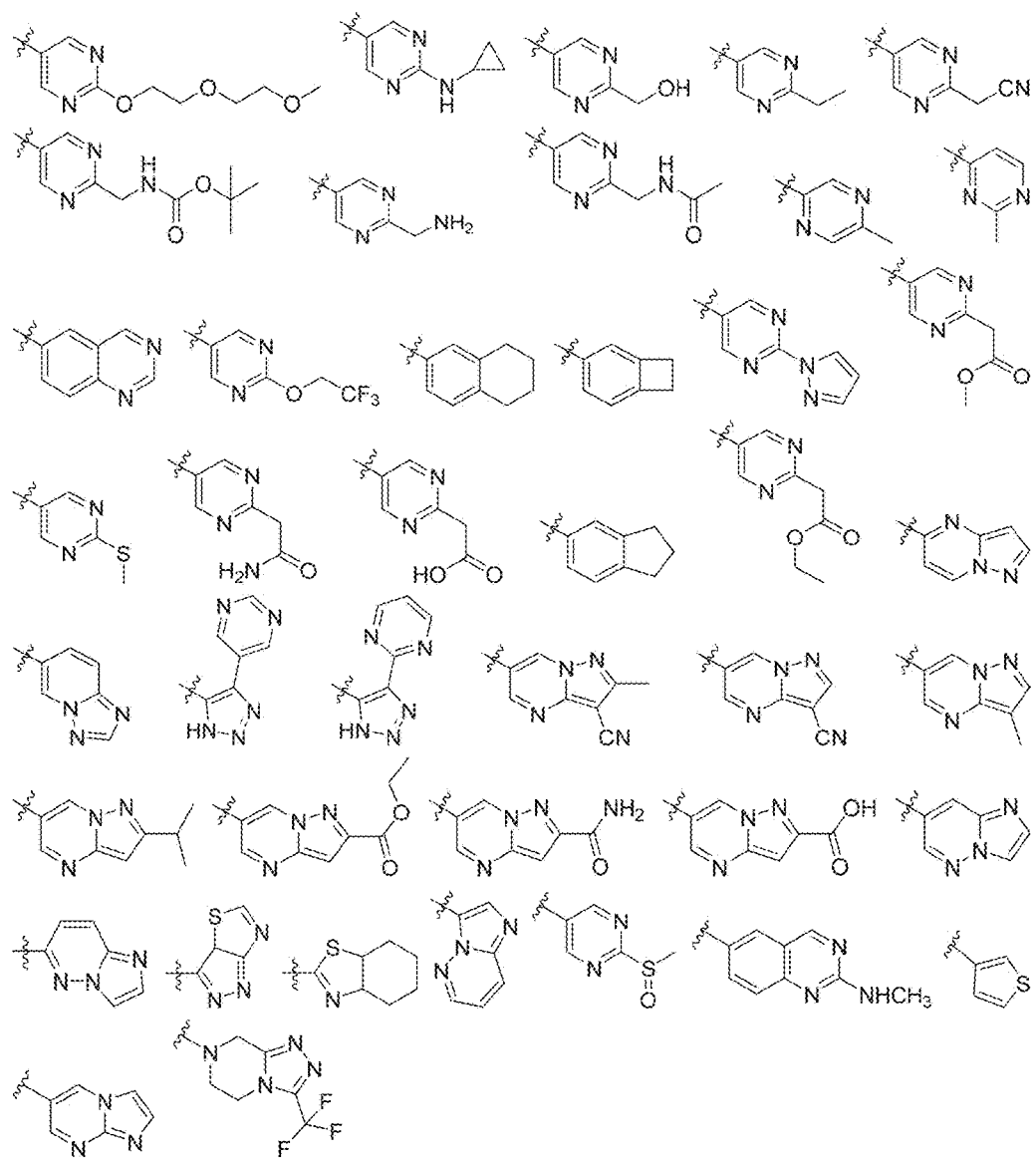
Figure 6D:
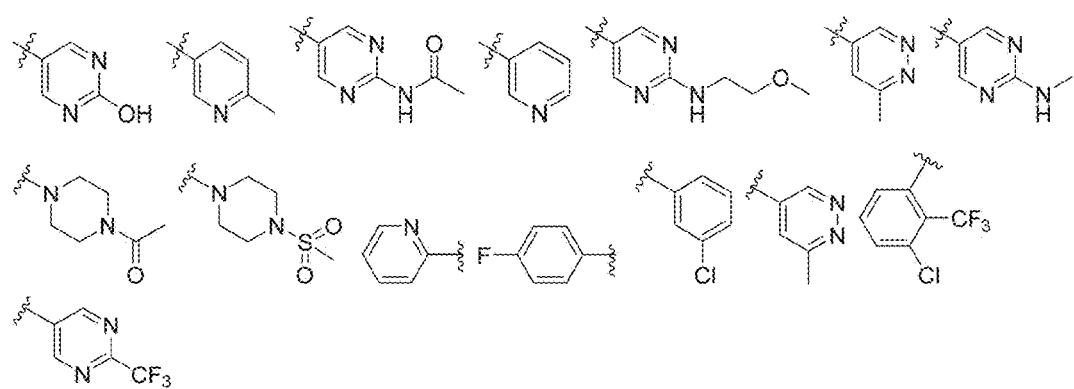
Figure 7A:
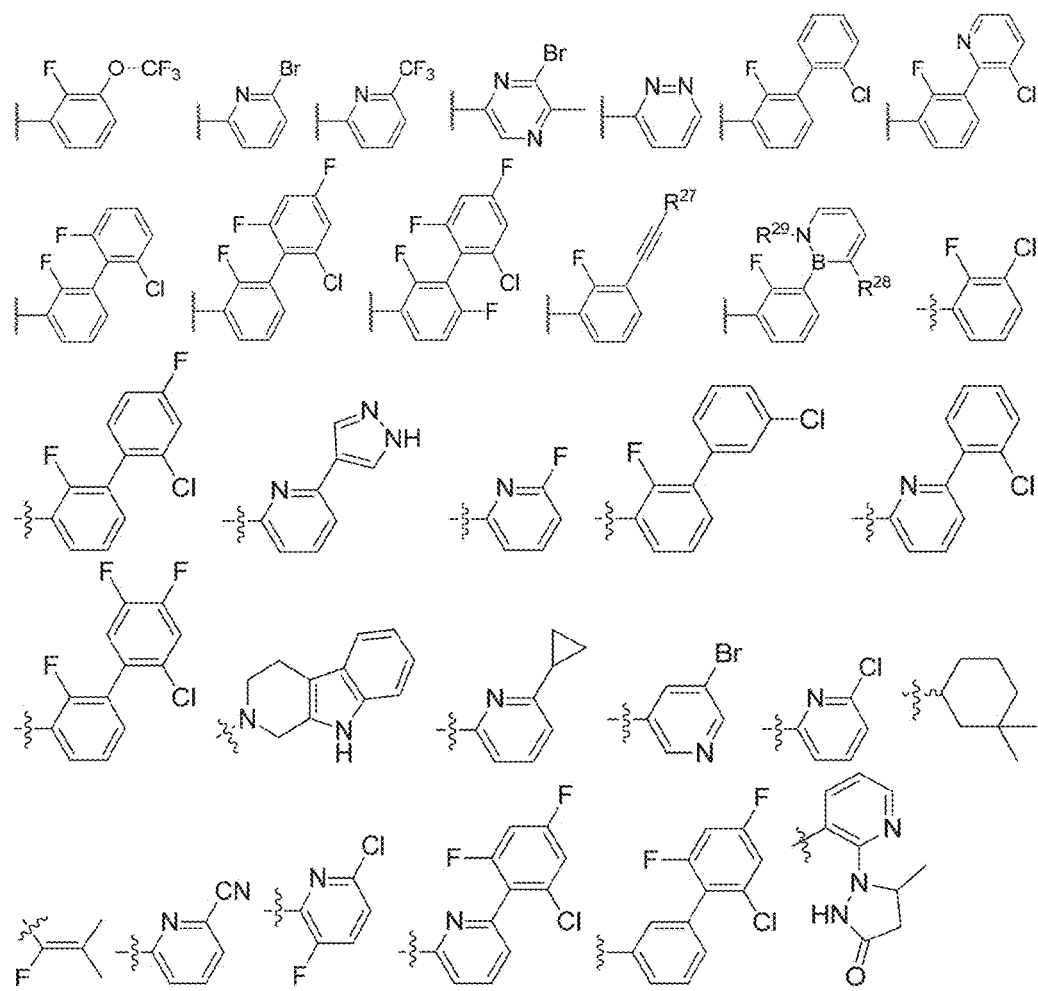
FIGS. 7A, 7B, 7C, 7D, 7E, 7F, 7G, 7H, and 7I provide non-limiting specific embodiments of the B ring, wherein $R^{27}$, $R^{28}$, and $R^{29}$ are defined below.
Figure 7B:
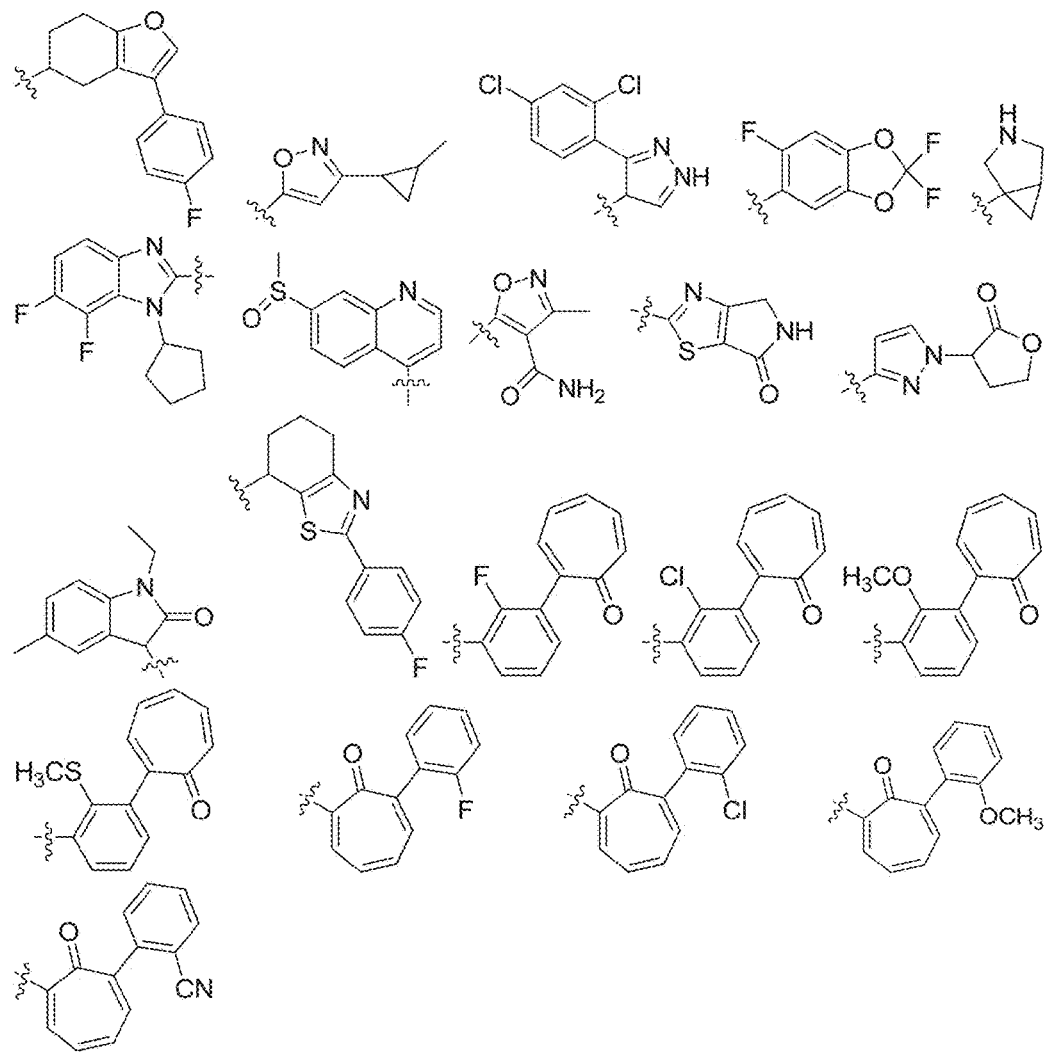
Figure 7C:
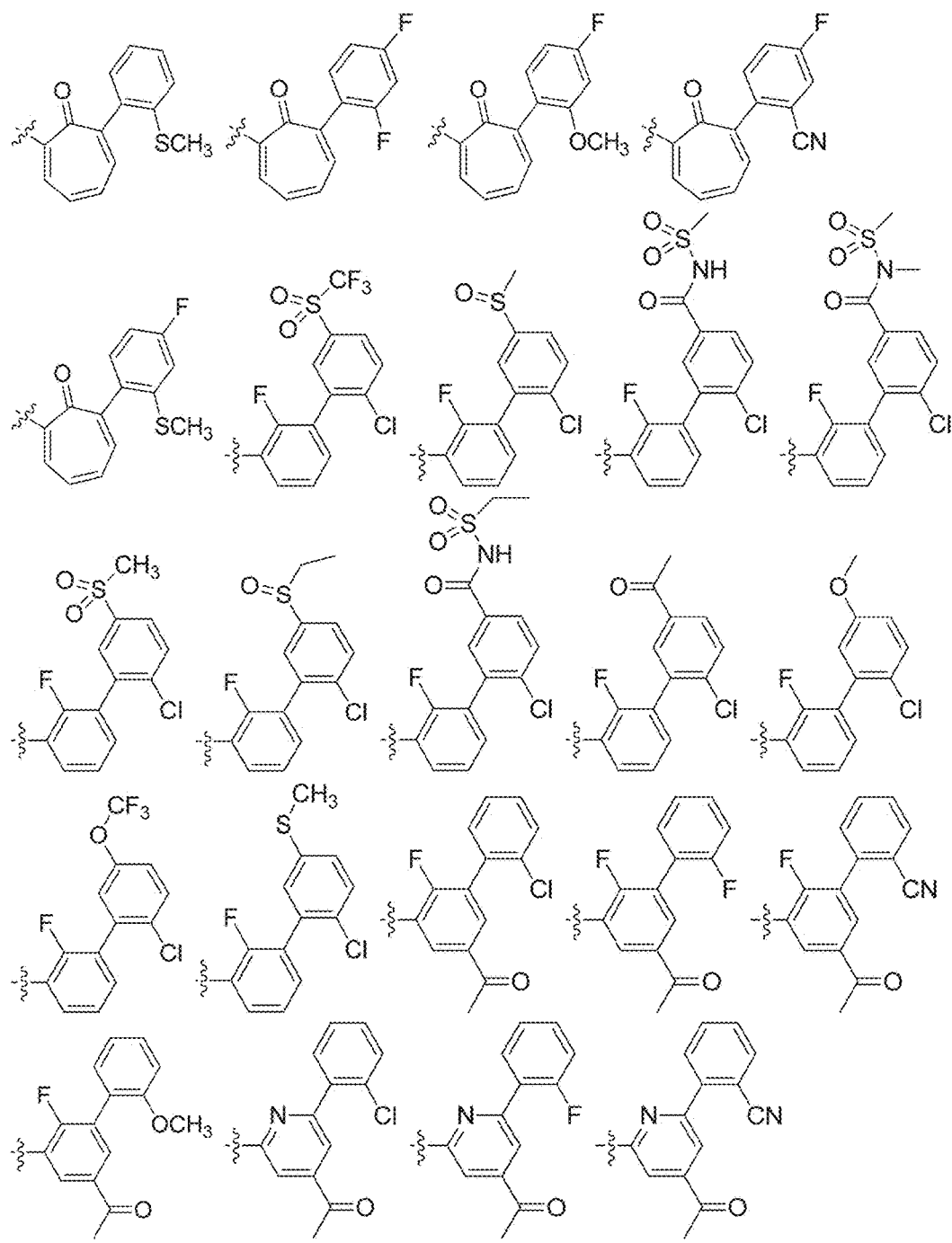
Figure 7D:
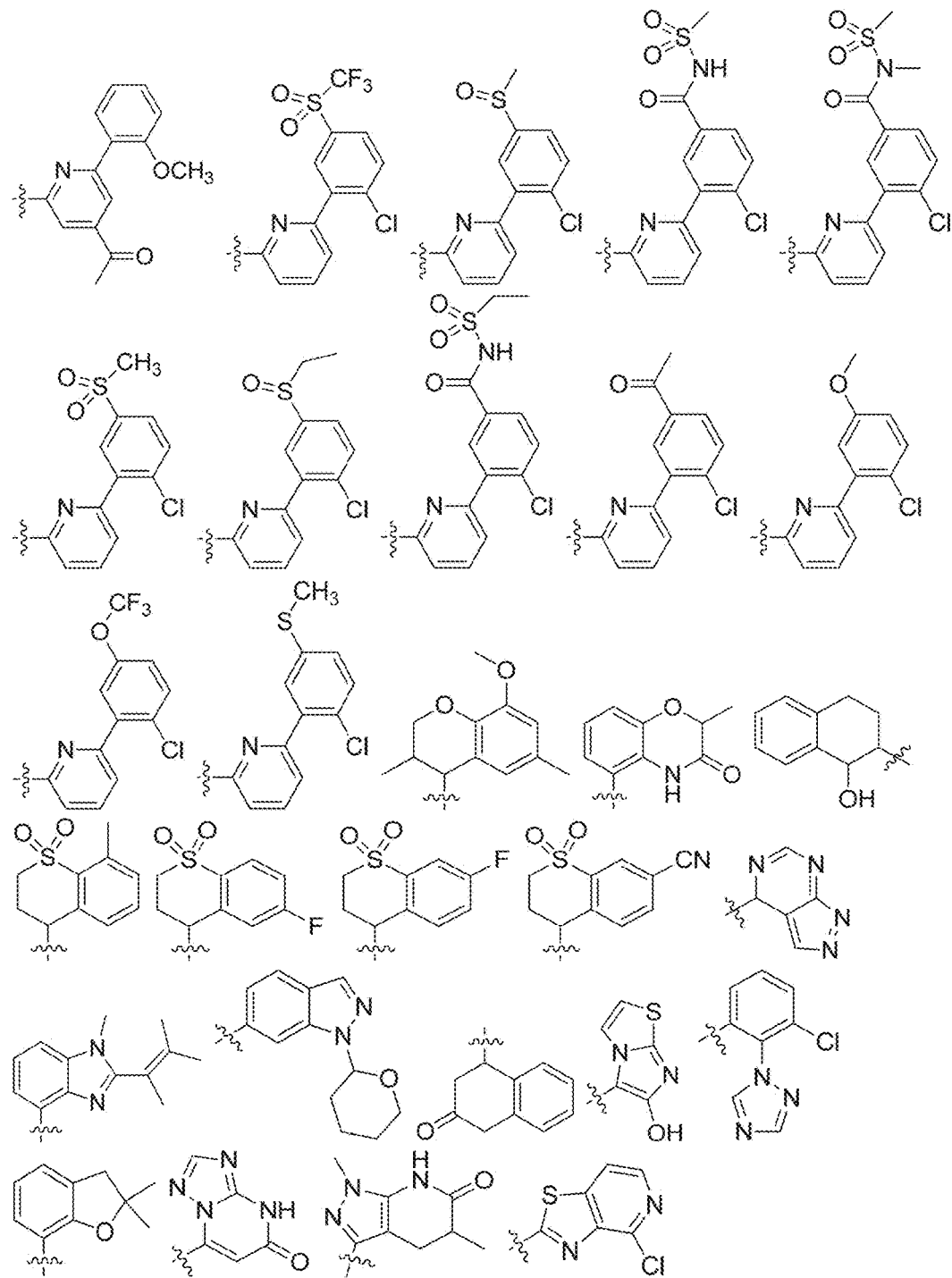
Figure 7E:
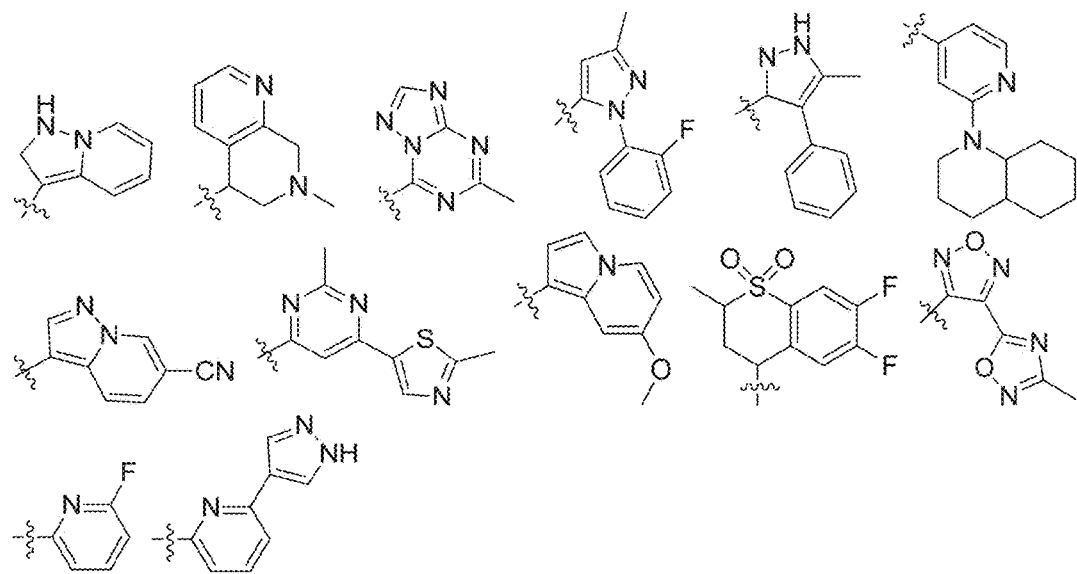
Figure 7F:
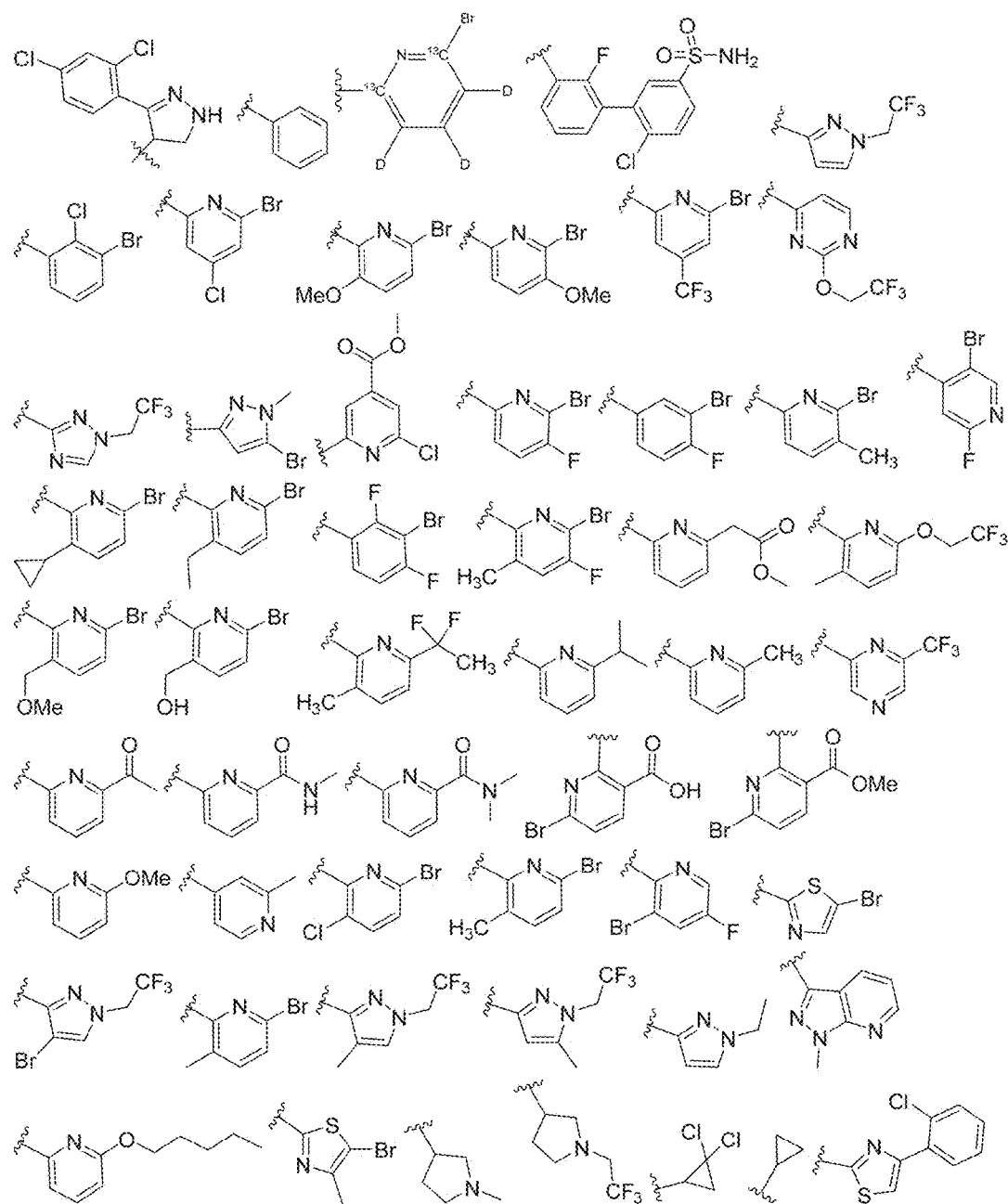
Figure 7G:
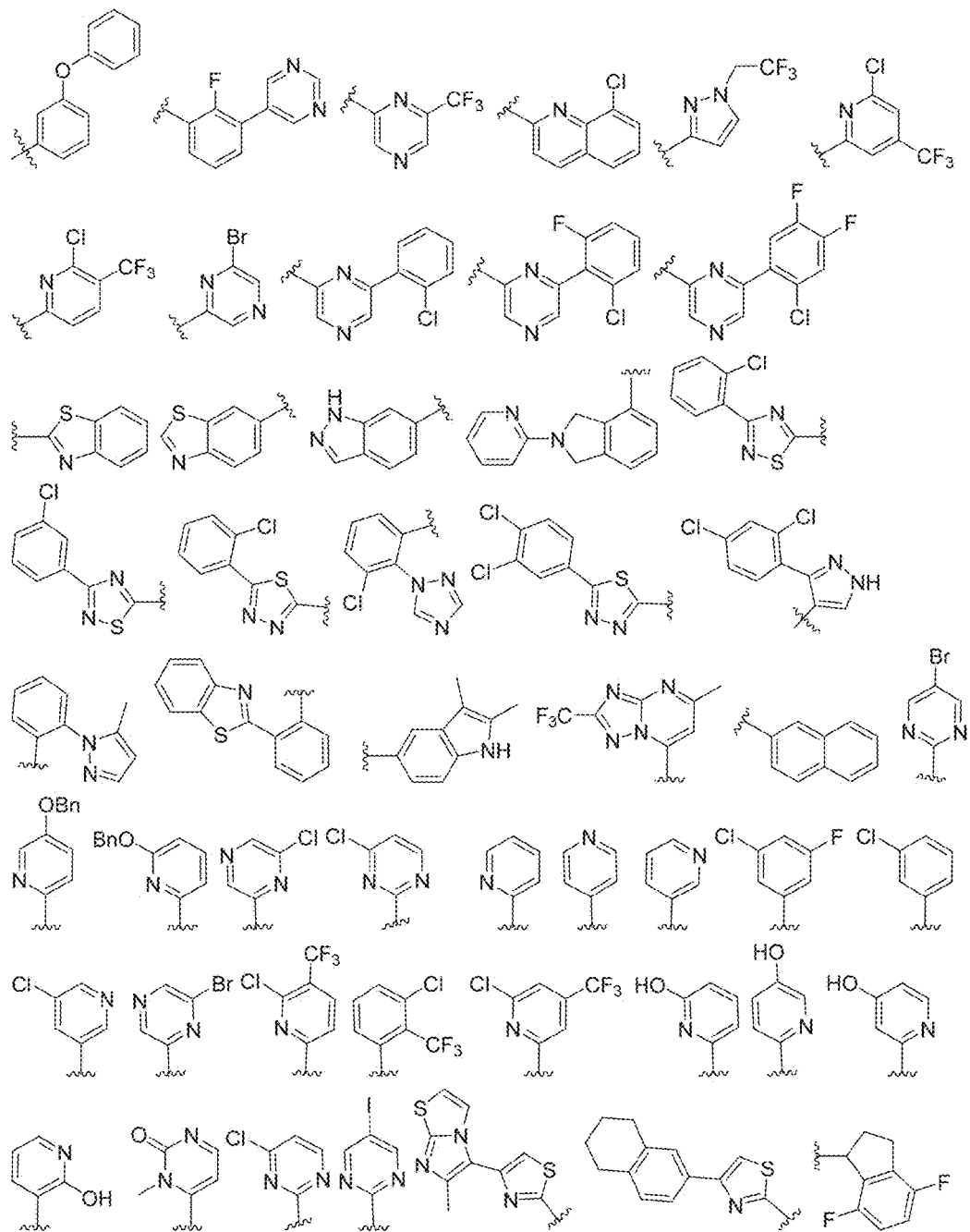
Figure 7H:
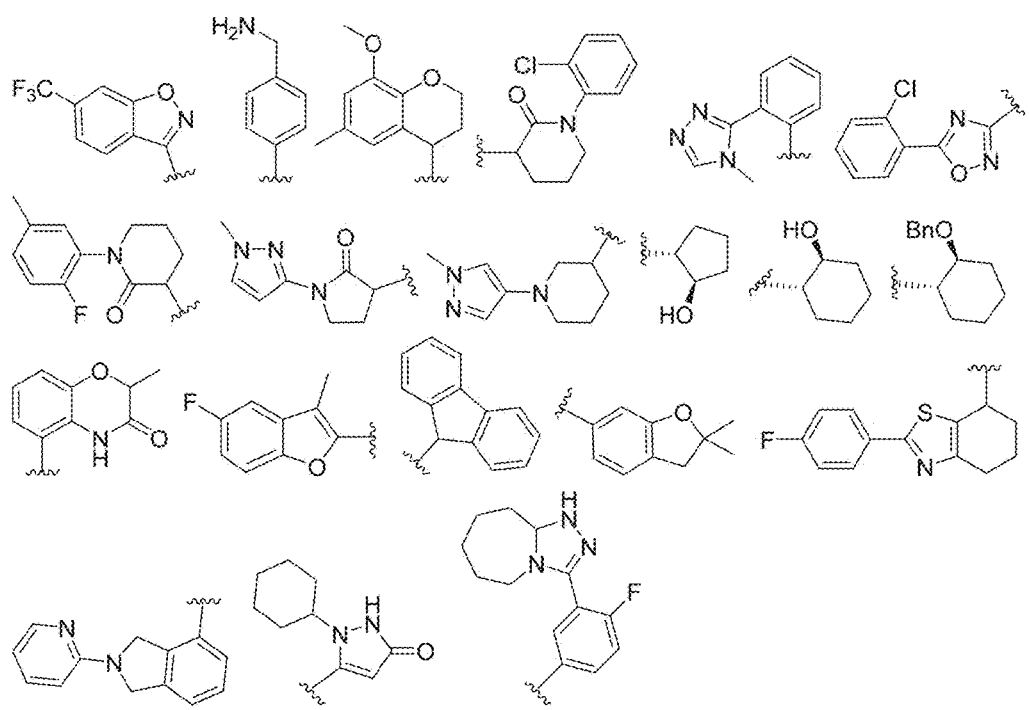
Figure 7I:
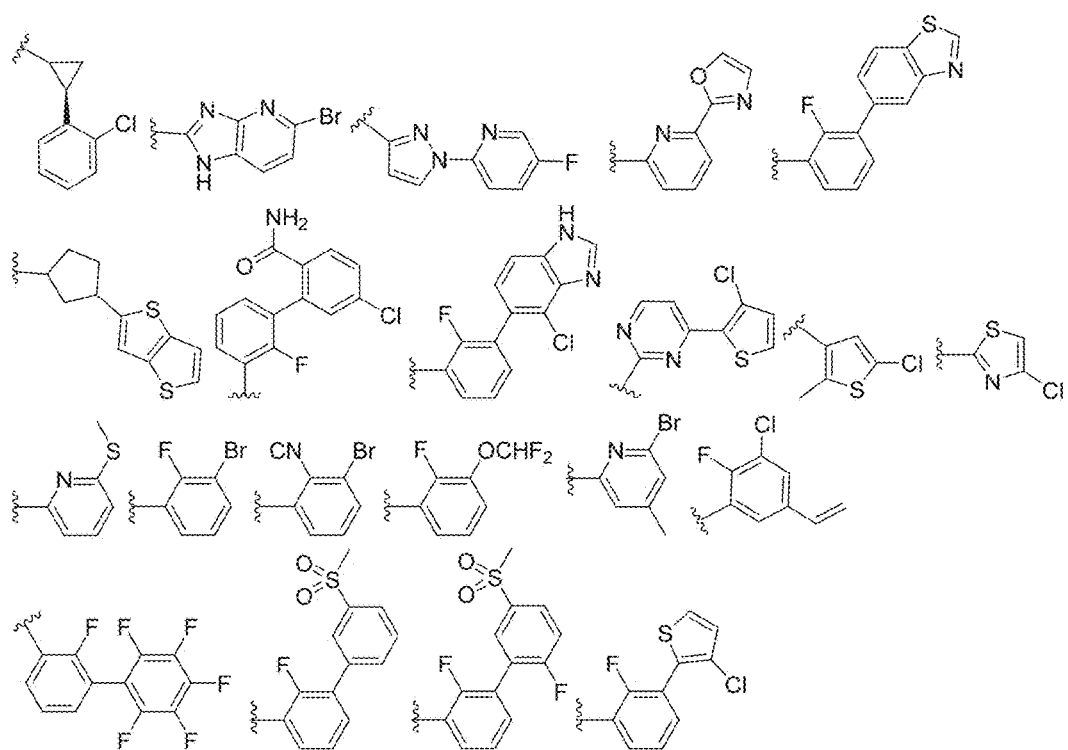

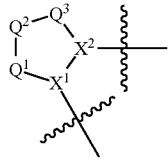

ring are illustrated in FIG. 5 (any of which can be otherwise substituted with R$^1$, R$^{1'}$, R$^2$, R$^{2'}$, R$^3$, and R$^{3'}$).

In an alternate embodiment, the

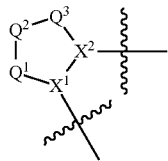

ring is replaced by one of the following core structures:

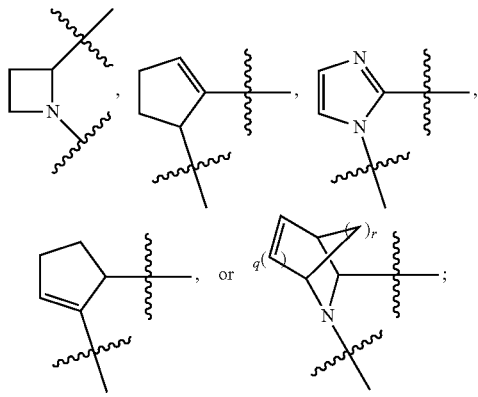

wherein q is 0, 1, 2 or 3 and r is 1, 2 or 3.

Any of the structures illustrated herein, e.g., A, B, L or central core can be optionally substituted with 0, 1, 2, 3, or 4, as appropriate, and independently, selected from R$^{75}$, wherein R$^{75}$ is selected from hydrogen, halogen, hydroxyl, nitro, cyano, amino, C$_1$-C$_6$alkyl, C$_1$-C$_6$haloalkyl, C$_2$-C$_6$alkenyl, C$_2$-C$_6$alkynyl, C$_1$-C$_6$thioalkyl, C$_1$-C$_6$alkoxy, -JC$_3$-C$_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, JNR$^{21}$SO$_2$R$^{22}$, -JC(O)NR$^{21}$SO$_2$R$^{22}$, -JC(NH$_2$)=NR$^{22}$, -JCH(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)NR$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, -JC(O)OR$^{23}$; each of which R$^{75}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, C$_1$-C$_6$alkyl, —C$_0$-C$_4$alkyl(C$_3$-C$_7$cycloalkyl), C$_1$-C$_6$alkoxy, —C$_0$-C$_4$alkyl(mono- and di-C$_1$-C$_4$alkylNR$^9$R$^{10}$), C$_1$-C$_6$alkylester, C$_1$-C$_4$alkylamino, C$_1$-C$_4$hydroxylalkyl, C$_1$-C$_2$haloalkyl, C$_1$-C$_2$haloalkoxy, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, S(O)=NHR$^{21}$, SF$_5$, and JC(R$^9$)=NR$^{21}$ and SO$_2$OR$^{21}$.

R and R' are independently selected from H, alkyl, cycloalkyl, cycloalkylalkyl, heterocycle, heterocycloalkyl, aryl, aralkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, NH$_2$, CH$_3$, CH$_2$D, CHD$_2$, or CD$_3$.

R$^1$, R$^{1'}$, R$^2$, R$^{2'}$, R$^3$, and R$^{3'}$ are independently selected at each occurrence, as appropriate, and only where a stable compound results, from hydrogen, halogen, hydroxyl, nitro, cyano, amino, C$_1$-C$_6$alkyl, C$_2$-C$_6$alkenyl, C$_2$-C$_6$alkynyl, C$_1$-C$_6$alkoxy, C$_2$-C$_6$alkynyl, C$_2$-C$_6$alkanoyl, C$_1$-C$_6$thioalkyl, hydroxyC$_1$-C$_6$alkyl, aminoC$_1$-C$_6$alkyl, —C$_0$-C$_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, C$_1$-C$_2$haloalkyl, and C$_1$-C$_2$haloalkoxy, where R$^9$ and R$^{10}$ are independently selected at each occurrence from hydrogen, C$_1$-C$_6$alkyl, (C$_3$-C$_7$cycloalkyl)C$_0$-C$_4$alkyl, —C$_0$-C$_4$alkyl(C$_3$-C$_7$cycloalkyl), and —O—C$_0$-C$_4$alkyl(C$_3$-C$_7$cycloalkyl).

Examples of central cores include, but are not limited to

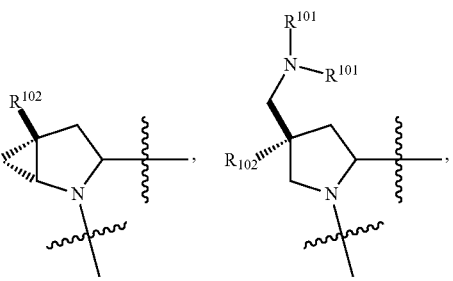

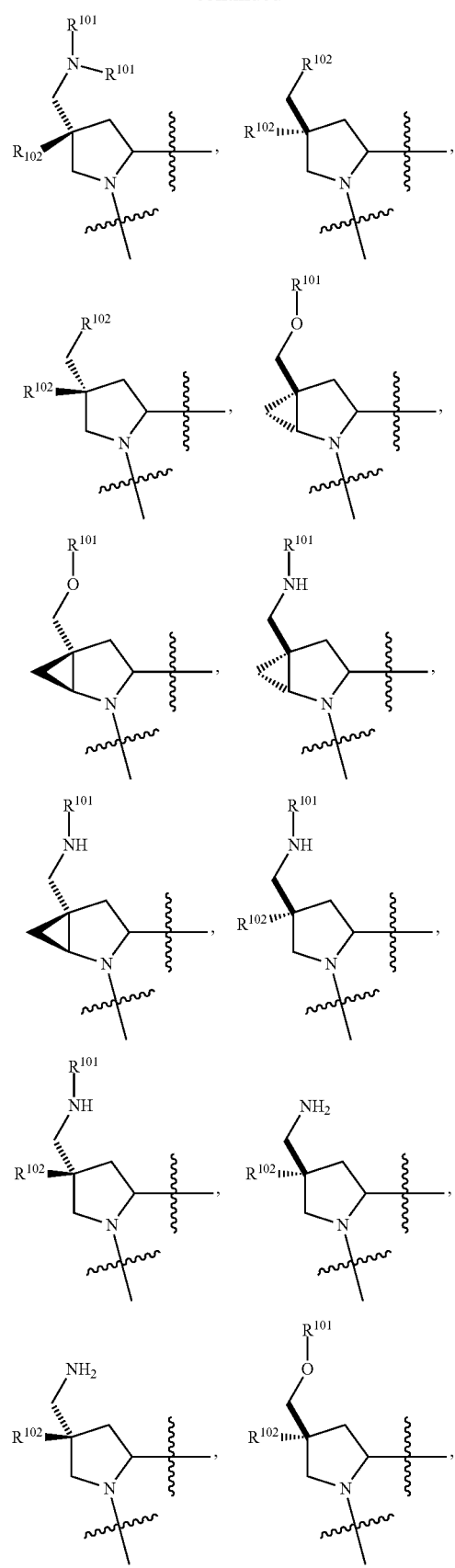
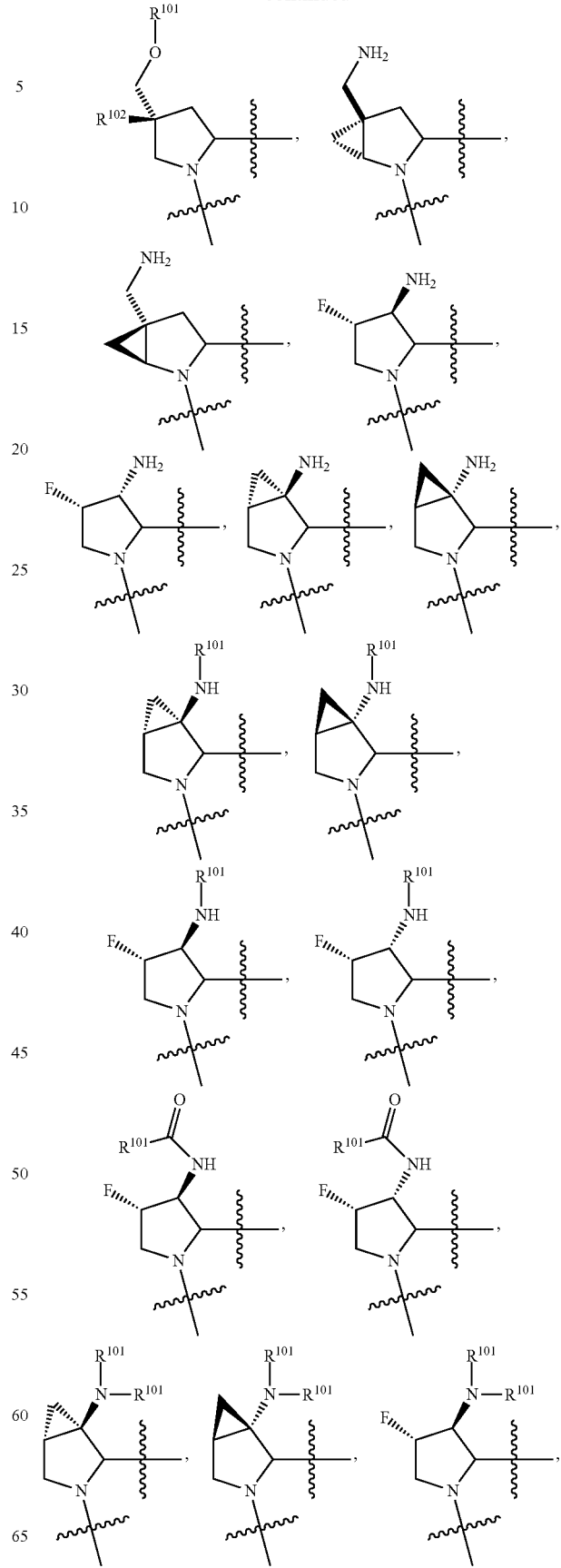

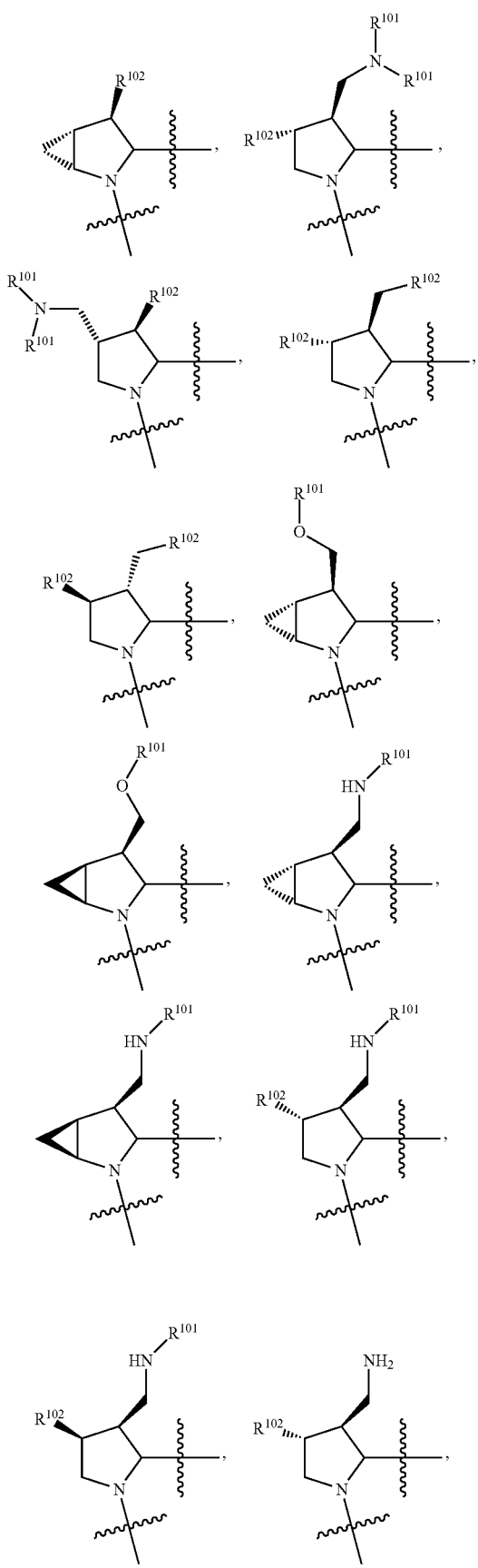
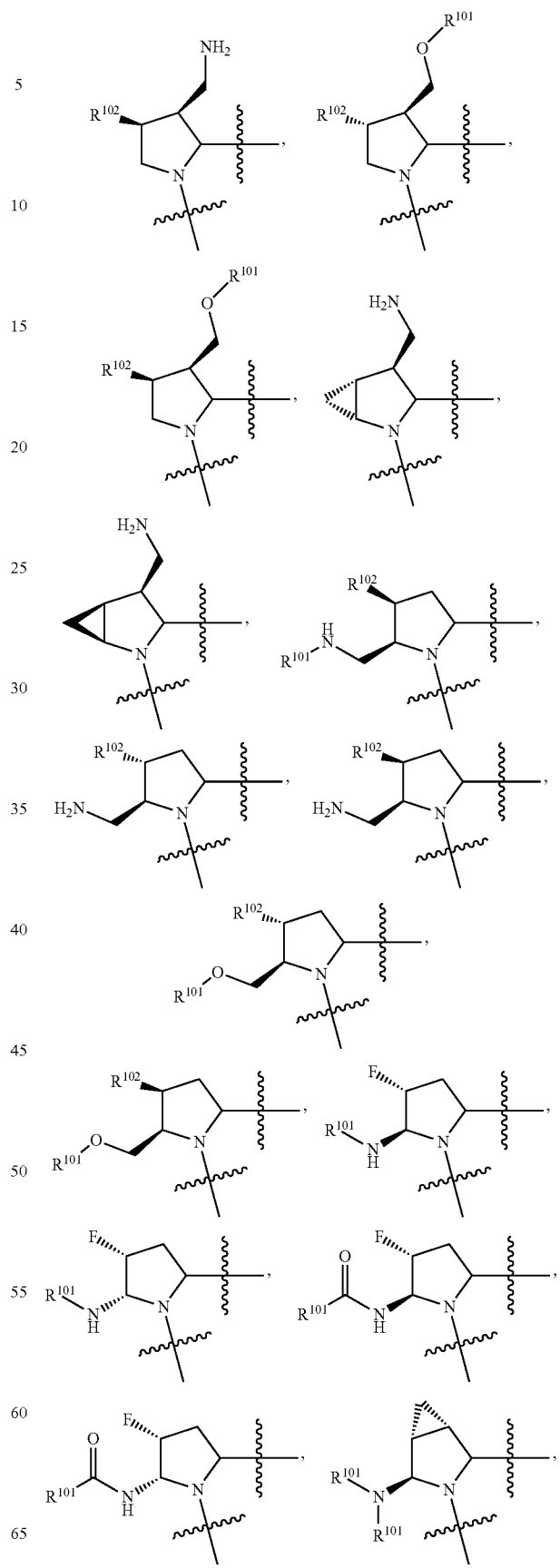

-continued

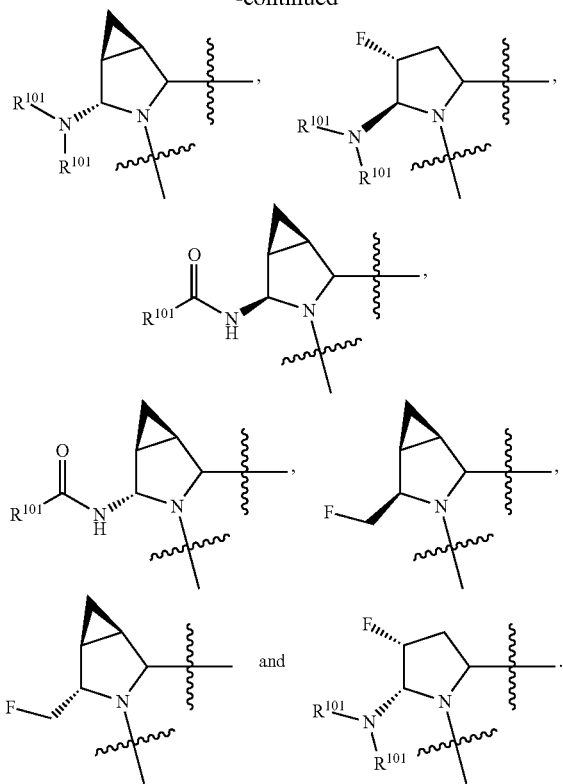

$R^{101}$ is $C_1$-$C_4$ alkyl or $C_3$-$C_7$ cycloalkyl.
$R^{102}$ is $C_1$-$C_4$ alkyl, fluorine, chlorine, or bromine.

Non-Limiting Central Core Embodiments

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently selected from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently selected from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently selected from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In one embodiment, the central core moiety is proline.

In one embodiment, the central core moiety is 4-fluoroproline.

In one embodiment, $R^1$, $R^{1'}$, $R^{2'}$, $R^3$, and $R^{3'}$, if present, are all hydrogen; and $R^2$ is fluoro.

In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen.

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

The disclosure includes the use of compounds of Formula I in which the central pyrrolidine is vinyl substituted, for example:

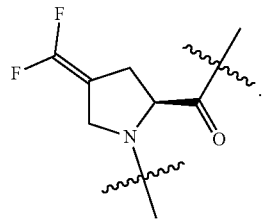 [SMILES: *C(=O)[C@@H]1CC(=C(F)F)CN1*]

In one embodiment, the compound of Formula I has the structure:

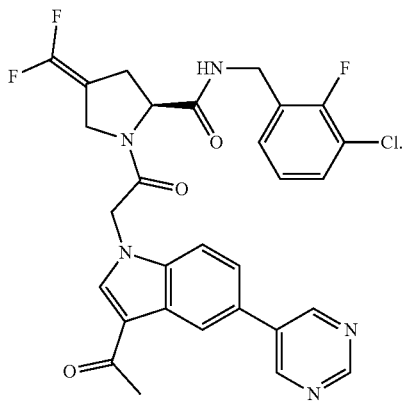 [SMILES: CC(=O)c1cn(CC(=O)N2CC(=C(F)F)C[C@H]2C(=O)NCc2cccc(Cl)c2F)c2ccc(-c3cncnc3)cc12]

In one embodiment, the central pyrrolidine is modified by addition of a second heteroatom to a pyrrolidine ring, such as N, O, S, Si, or B, for example:

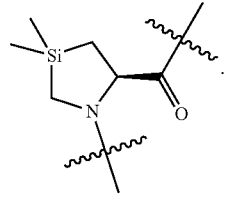 [SMILES: *C(=O)[C@@H]1C[Si](C)(C)CN1*]

Another modification within the scope of the disclosure is joining a substituent on the central pyrrolidine ring to $R^7$ or $R^8$ to form a 5- to 6-membered heterocyclic ring, for example:

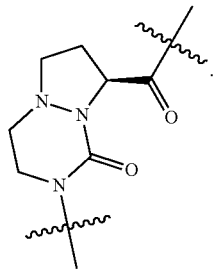 [SMILES: *C(=O)[C@@H]1CCN2CCN(*)C(=O)N12]

Example compounds having the modifications disclosed above include:

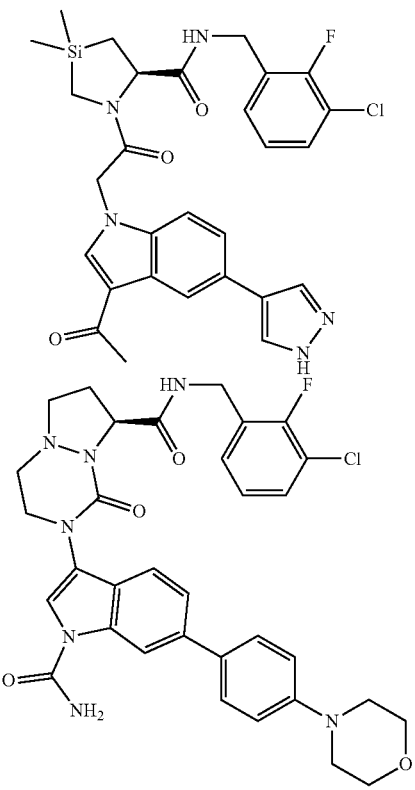

Central Core L-B Substituents

The central core L substituents and B substituents in Formula I are illustrated below:

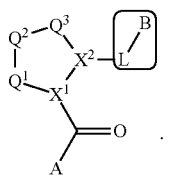

L is a bond or is selected from the formulas:

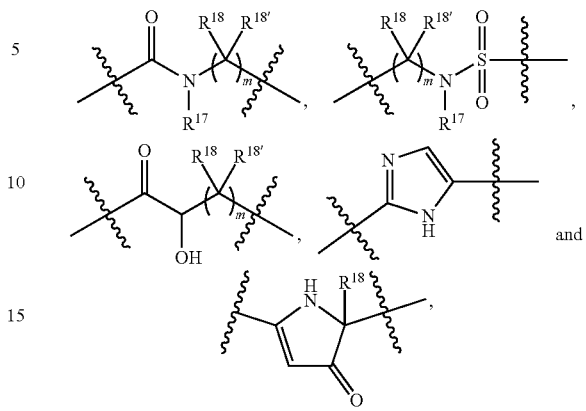

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently selected from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently selected from $R^{33}$ and $R^{34}$, and 0 or 1 substituents selected from $R^{35}$ and $R^{36}$:

$R^{33}$ is independently selected from halogen, hydroxyl, —COOH, cyano, $C_1$-$C_6$alkyl, $C_2$-$C_6$alkanoyl, $C_1$-$C_6$alkoxy, —$C_0$-$C_4$alkyl$NR^9R^{10}$, —$SO_2R^9$, $C_1$-$C_2$haloalkyl, and $C_1$-$C_2$haloalkoxy;

$R^{34}$ is independently selected from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)$NR^9R^{23}$, -JOSO$_2OR^{21}$, —C(O)(CH$_2$)$_{1-4}$S(O)$R^{21}$, —O(CH$_2$)$_{1-4}$S(O)$NR^{21}R^{22}$, -JOP(O)(OR$^{21}$)(OR$^{22}$), -JP(O)(OR$^{21}$)(OR$^{22}$), -JOP(O)(OR$^{21}$)$R^{22}$, -JP(O)(OR$^{21}$)$R^{22}$, -JOP(O)$R^{21}R^{22}$, -JP(O)$R^{21}R^{22}$, -JSP(O)(OR$^{21}$)(OR$^{22}$), -JSP(O)(OR$^{21}$)($R^{22}$), -JSP(O)($R^{21}$)($R^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)$R^{21}$, -JNR$^{21}$SO$_2R^{22}$, -JNR$^9$S(O)$NR^{10}R^{22}$, -JNR$^9$SO$_2NR^{10}R^{22}$, -JSO$_2NR^9COR^{22}$, -JSO$_2NR^9CONR^{21}R^{22}$, -JNR$^{21}$SO$_2R^{22}$, -JC(O)NR$^{21}$SO$_2R^{22}$, -JC(NH$_2$)$NR^{22}$, -JC(NH$_2$)$NR^9S(O)_2R^{22}$, -JOC(O)$NR^{21}R^{22}$, -JNR$^{21}$C(O)OR$^{22}$, -JNR$^{21}$OC(O)$R^{22}$, —(CH$_2$)$_{1-4}$C(O)$NR^{21}R^{22}$, -JC(O)$NR^{24}R^{25}$, -JNR$^9$C(O)$R^{21}$, -JC(O)$R^{21}$, -JNR$^9$C(O)$NR^{10}R^{22}$, —CCR$^{21}$, —(CH$_2$)$_{1-4}$OC(O)$R^{21}$, and -JC(O)$OR^{23}$; each of which $R^{34}$ may be unsubstituted or substituted with one or more substituents independently selected from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is independently selected from naphthyl, naphthyloxy, indanyl, (4- to 7-membered heterocycloalkyl)$C_0$-$C_4$alkyl containing 1 or 2 heteroatoms selected from N, O, and S, and bicyclic heterocycle containing 1, 2, or 3 heteroatoms independently selected from N, O, and S, and containing 4- to 7-ring atoms in each ring; each of which $R^{35}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy; and $R^{36}$ is independently selected from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently selected from N, O, B, and S, each of which $R^{36}$ is unsubstituted or substituted with one or more substituents independently selected from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy.

J is independently selected at each occurrence from a covalent bond, $C_1$-$C_4$alkylene, —$OC_1$-$C_4$alkylene, $C_2$-$C_4$alkenylene, and $C_2$-$C_4$alkynylene.

Examples of B moieties include, but are not limited to

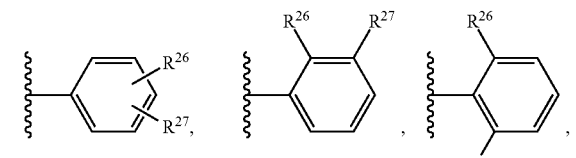

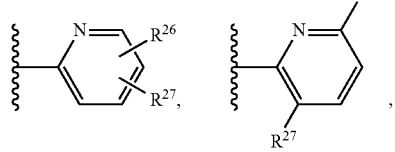

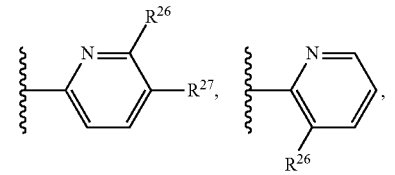

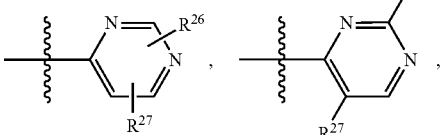

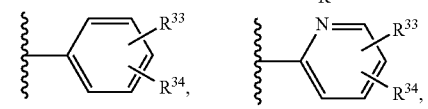

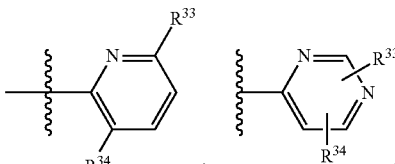

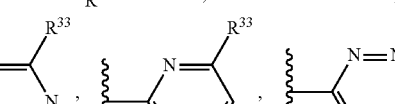

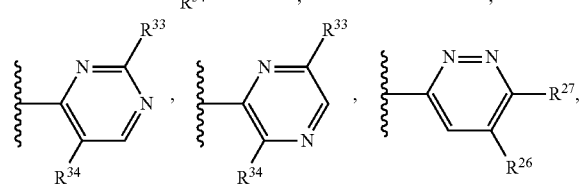

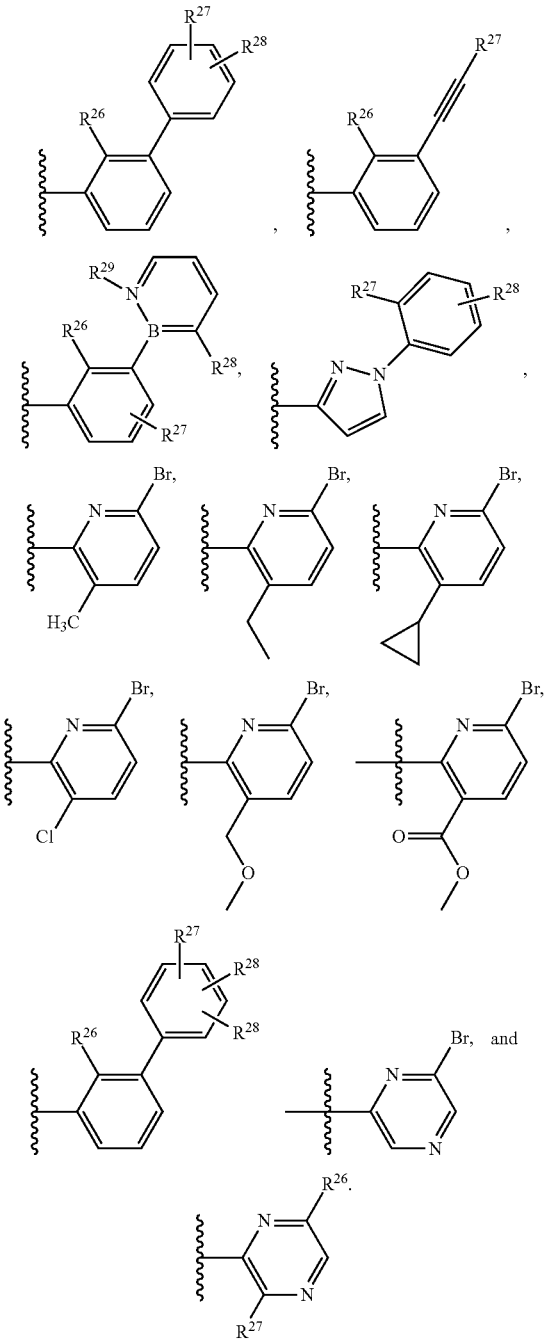

Non-Limiting L-B Embodiments

In one embodiment, -L-B— is

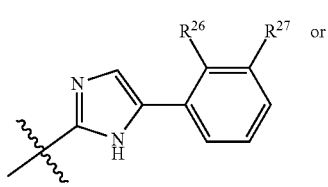

-continued

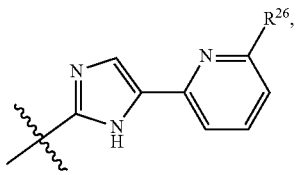

where

R$^{26}$ and R$^{27}$ are independently selected from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, —C$_0$-C$_4$alkyl (mono- and di-C$_1$-C$_6$alkylamino), —C$_0$-C$_4$alkyl(C$_3$-C$_7$cycloalkyl), —C$_0$-C$_4$alkoxy(C$_3$-C$_7$cycloalkyl), C$_1$-C$_2$haloalkyl, C$_1$-C$_2$haloalkoxy, and C$_1$-C$_2$haloalkylthio.

In another embodiment, -L-B— is

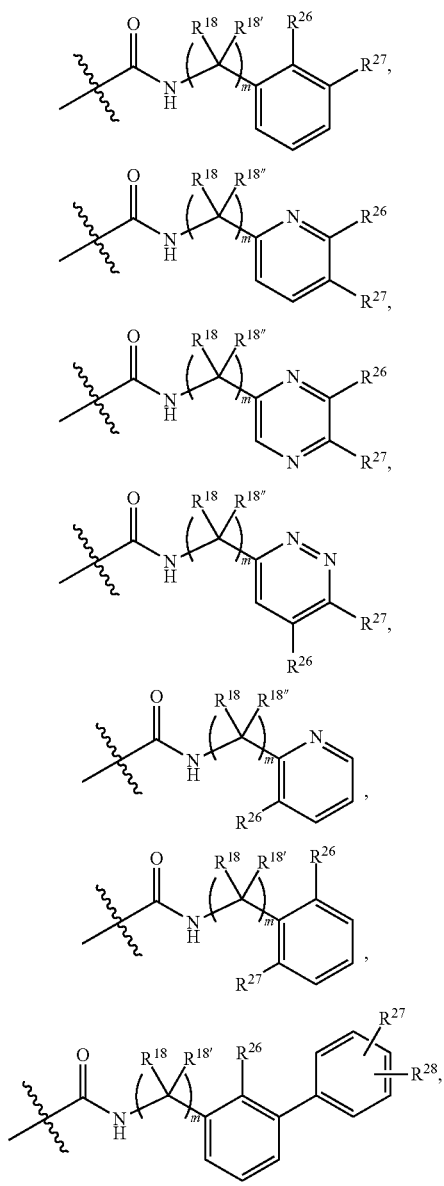

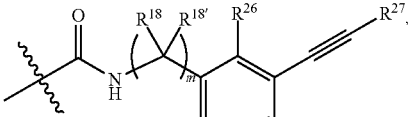

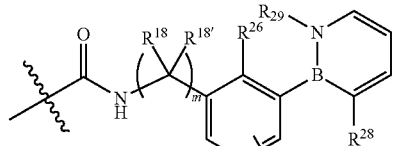

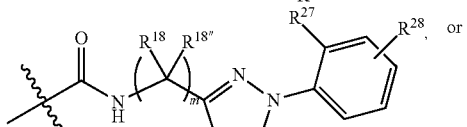

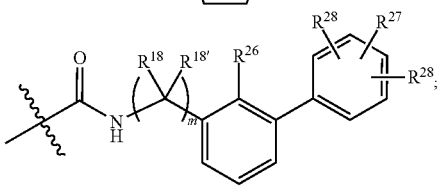

wherein

R$^{18}$ and R$^{18'}$ are independently selected from hydrogen, halogen, hydroxymethyl, and methyl; and m is 0 or 1; and R$^{26}$, R$^{27}$, and R$^{28}$ are independently selected from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, (mono- and di-C$_1$-C$_6$alkylamino)C$_0$-C$_4$alkyl, (C$_3$-C$_7$cycloalkyl)C$_0$-C$_4$alkyl, (aryl)C$_0$-C$_4$alkyl-, (heteroaryl)C$_0$-C$_4$alkyl-, and —C$_0$-C$_4$alkoxy(C$_3$-C$_7$cycloalkyl); each of which R$^{26}$, R$^{27}$, and R$^{28}$ other than hydrogen, halogen, hydroxyl, nitro, cyano, is unsubstituted or substituted with one or more substituents independently selected from halogen, hydroxyl, amino, C$_1$-C$_2$alkoxy, C$_1$-C$_2$haloalkyl, (C$_3$-C$_7$cycloalkyl)C$_0$-C$_4$alkyl-, and C$_1$-C$_2$haloalkoxy; and R$^{29}$ is hydrogen, C$_1$-C$_2$alkyl, C$_1$C$_2$haloalkyl or —Si(CH$_3$)$_2$C(CH$_3$)$_3$.

In one embodiment, m is 0.

In one embodiment, the disclosure further includes the use of compounds and salts of Formula I in which B is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B is phenyl, pyridyl, or indanyl each of which is unsubstituted or substituted with one or more substituents independently selected from hydrogen, halogen, hydroxyl, nitro, cyano, C$_1$-C$_6$alkyl, C$_2$-C$_6$alkenyl, C$_2$-C$_6$alkanoyl, C$_1$-C$_6$alkoxy, C$_1$-C$_6$thioalkyl, (mono- and di-C$_1$-C$_6$alkylamino)C$_0$-C$_4$alkyl, (C$_3$-C$_7$cycloalkyl)C$_0$-C$_4$alkyl, —C$_0$-C$_4$alkoxy(C$_3$-C$_7$cycloalkyl), (phenyl)C$_0$-C$_2$alkyl, (pyridyl)C$_0$-C$_2$alkyl; each of which substituents other than hydrogen, halogen, hydroxyl, nitro, cyano, is unsubstituted or substituted with one or more substituents independently selected from halogen, hydroxyl, amino, C$_1$-C$_2$alkyl, C$_1$-C$_2$alkoxy, —OSi(CH$_3$)$_2$C(CH$_3$)$_3$, —Si(CH$_3$)$_2$C(CH$_3$)$_3$, C$_1$-C$_2$haloalkyl, and C$_1$-C$_2$haloalkoxy.

In another embodiment, B is phenyl or pyridyl substituted with 1, 2, or 3 substituents selected from chloro, bromo, hydroxyl, —SCF$_3$, C$_1$-C$_2$alkyl, C$_1$-C$_2$alkoxy, trifluoromethyl, phenyl and trifluoromethoxy each of which substituents other than chloro, bromo, hydroxyl, —SCF$_3$, can be optionally substituted.

In certain embodiments, B is a 2-fluoro-3-chlorophenyl or a 2-fluoro-3-trifluoromethoxyphenyl group.

In one embodiment, B is pyridyl, optionally substituted with halogen, $C_1$-$C_2$alkoxy, and trifluoromethyl.

In one embodiment, B is phenyl, substituted with 1, 2, or 3 substituents independently selected from halogen, $C_1$-$C_2$alkyl, $C_1$-$C_2$alkoxy, trifluoromethyl, and optionally substituted phenyl.

In one embodiment, $R^{23}$ is independently selected at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently selected from N, O, and S, and (5- or 6-membered unsaturated or aromatic heterocycle)$C_0$-$C_4$alkyl having 1, 2, or 3 heteroatoms independently selected from N, O, and S.

In one embodiment, B is selected from FIG. 7, wherein $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.

Figure 8:
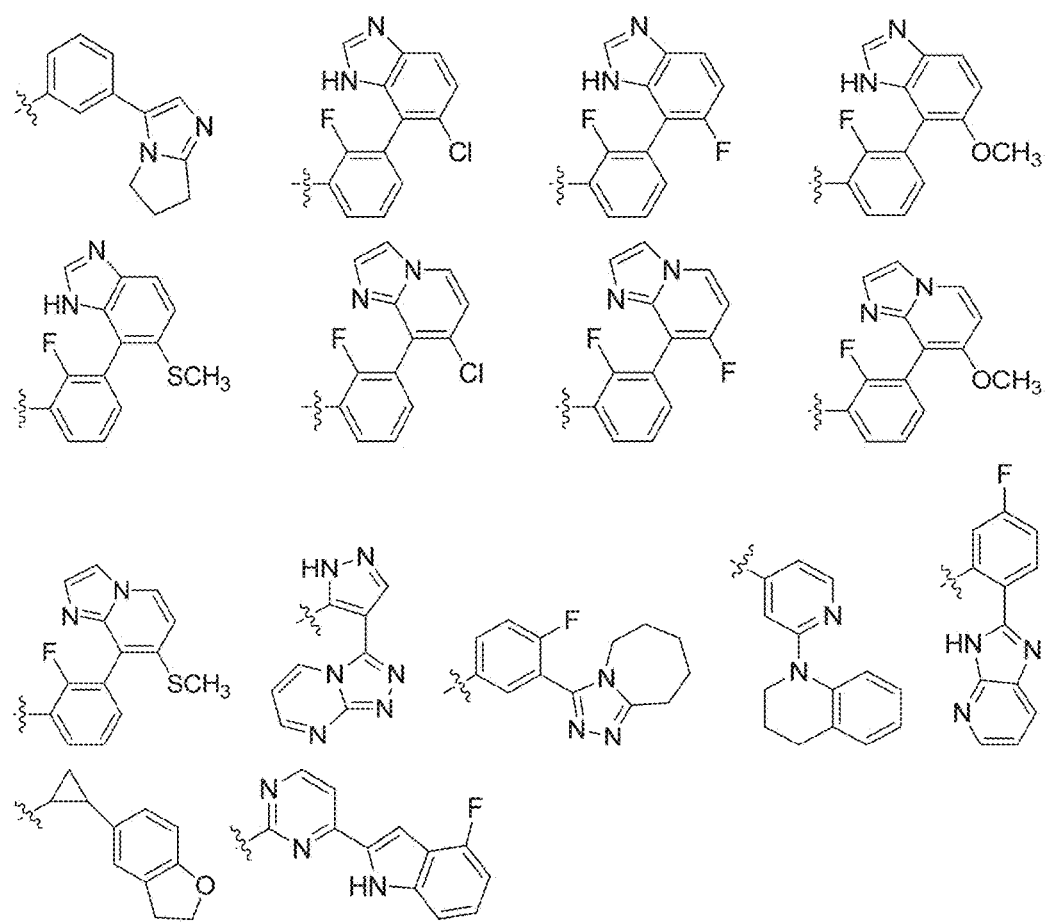
FIG. 8 provides non-limiting specific embodiments of the B ring.
Figure 9A:
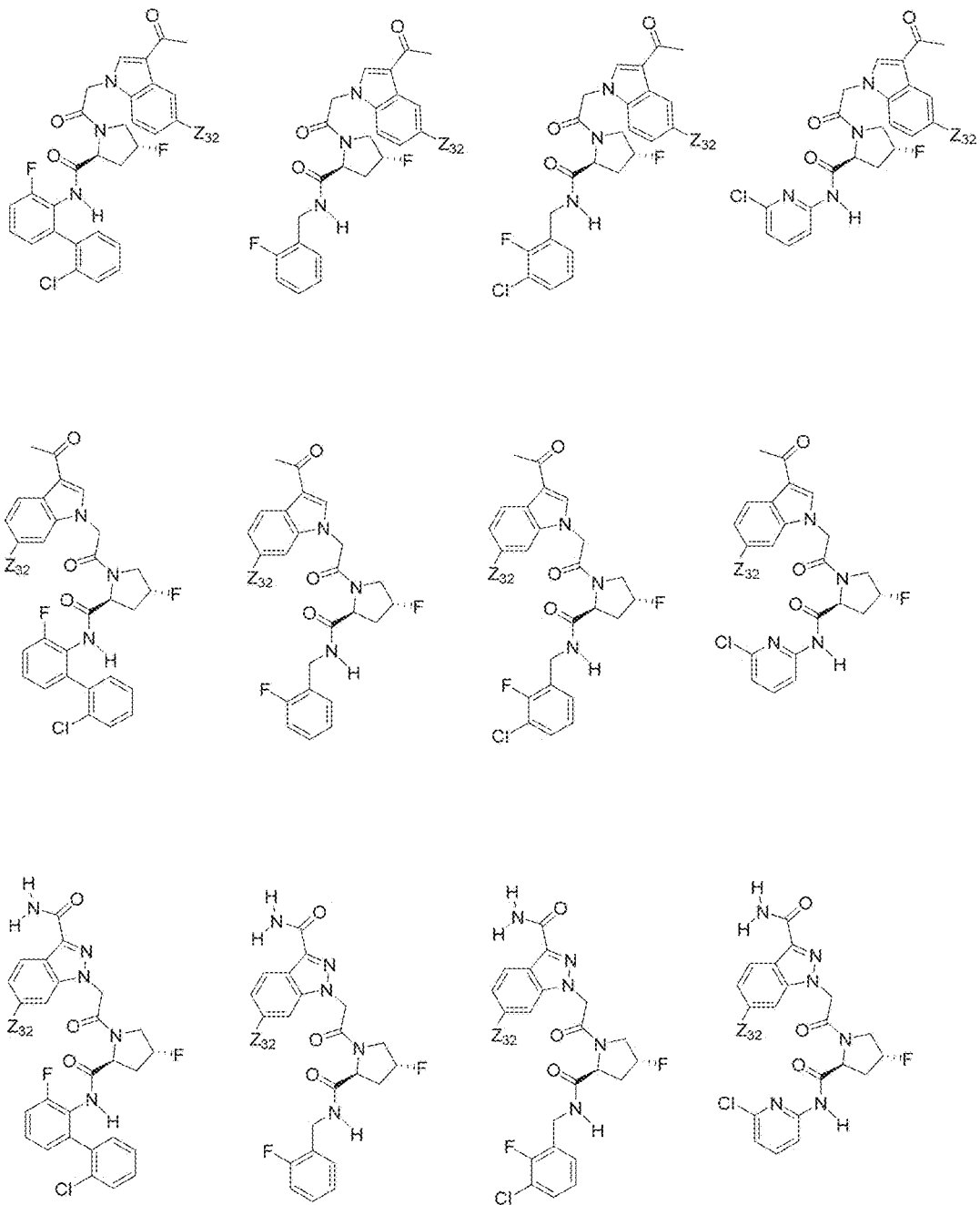
Figure 9B:
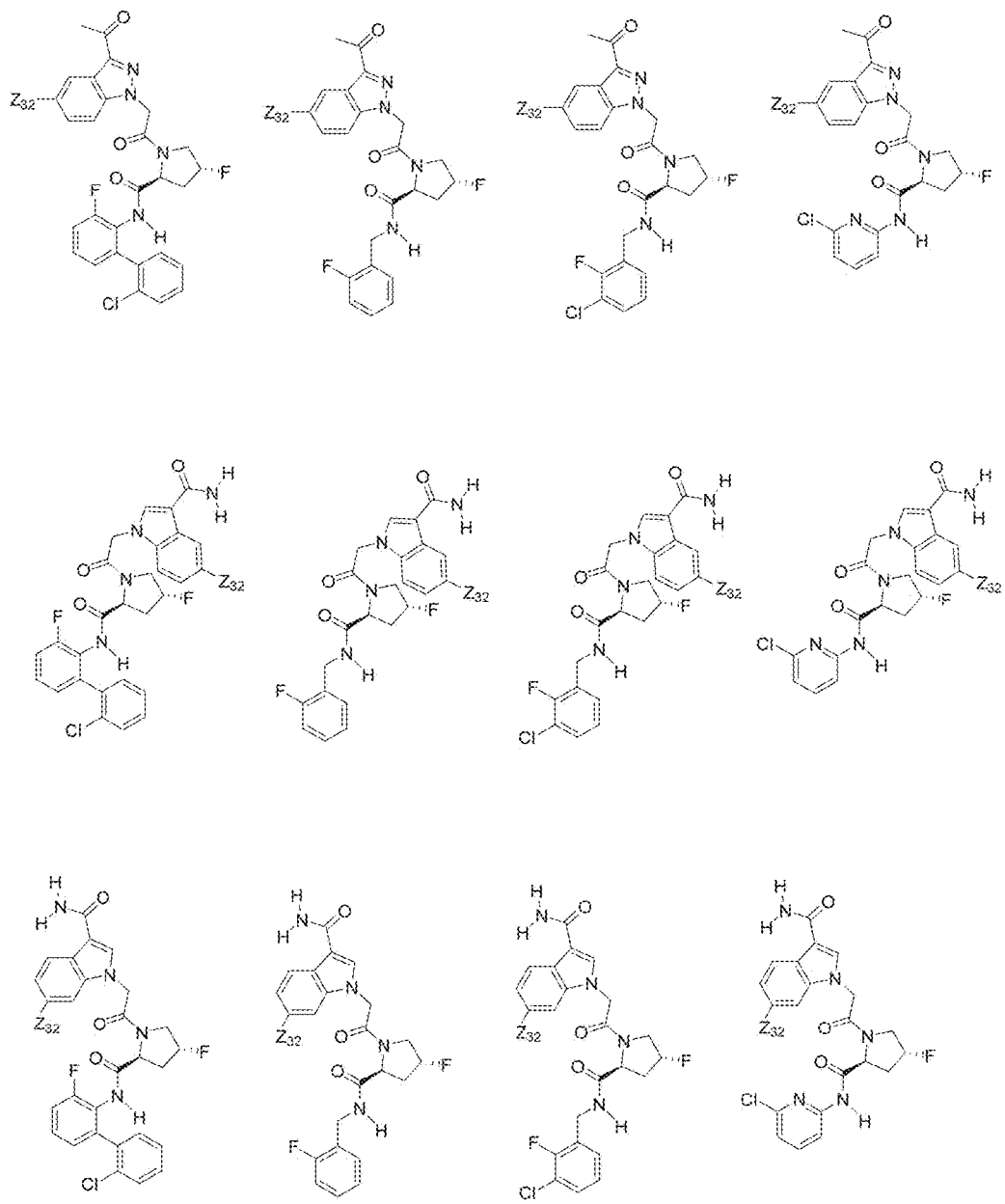
Figure 9D:
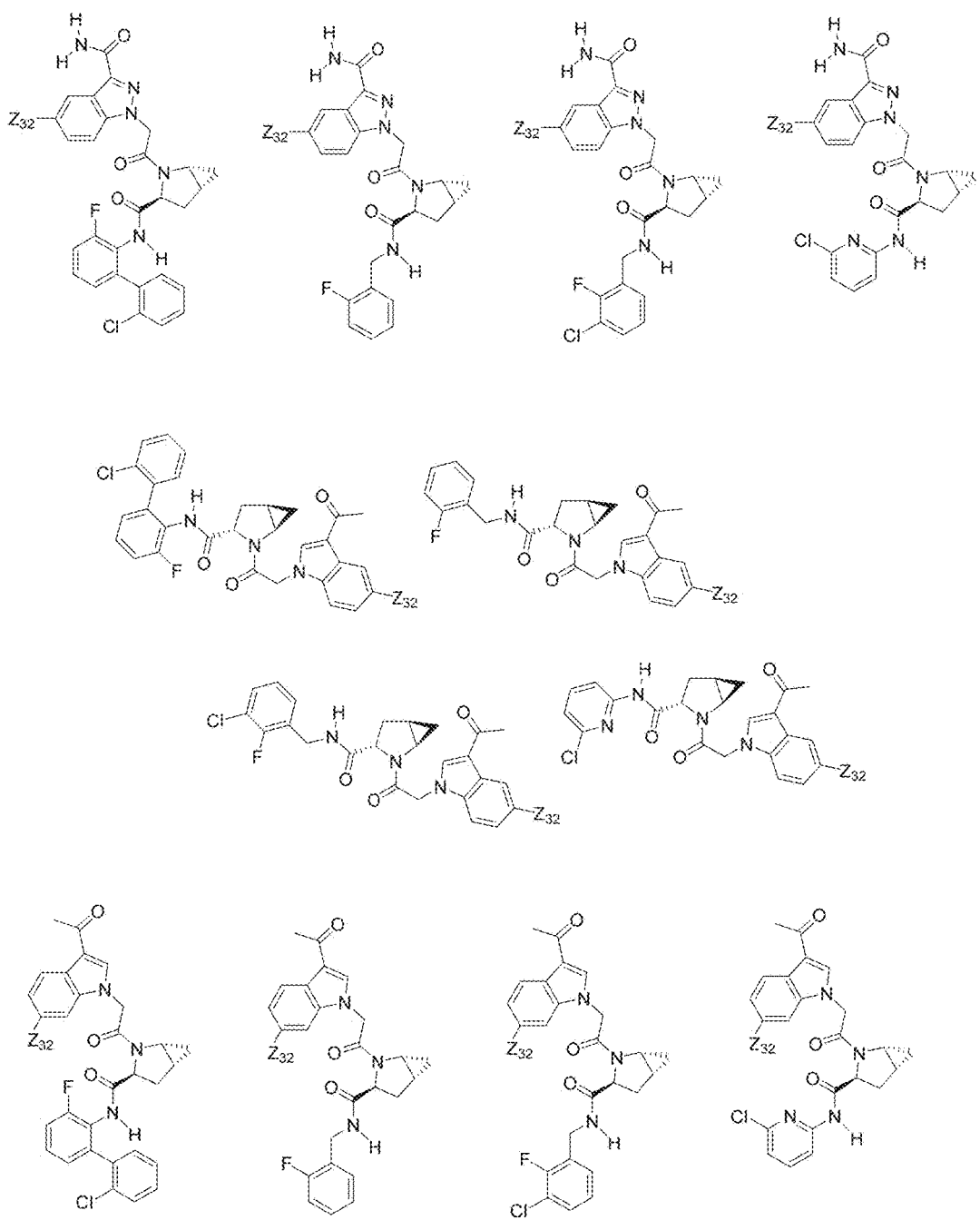
Figure 9E:
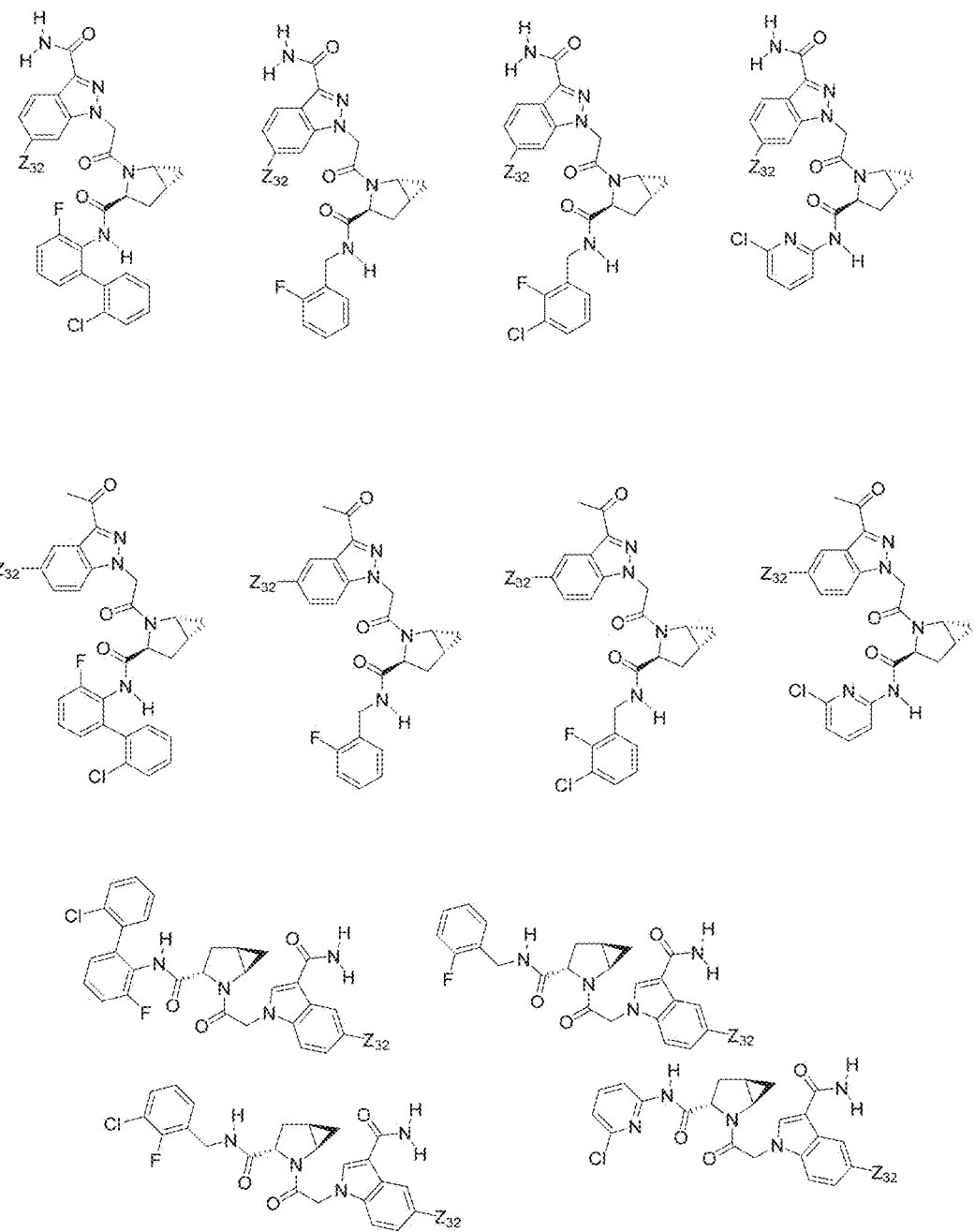
Figure 9F:
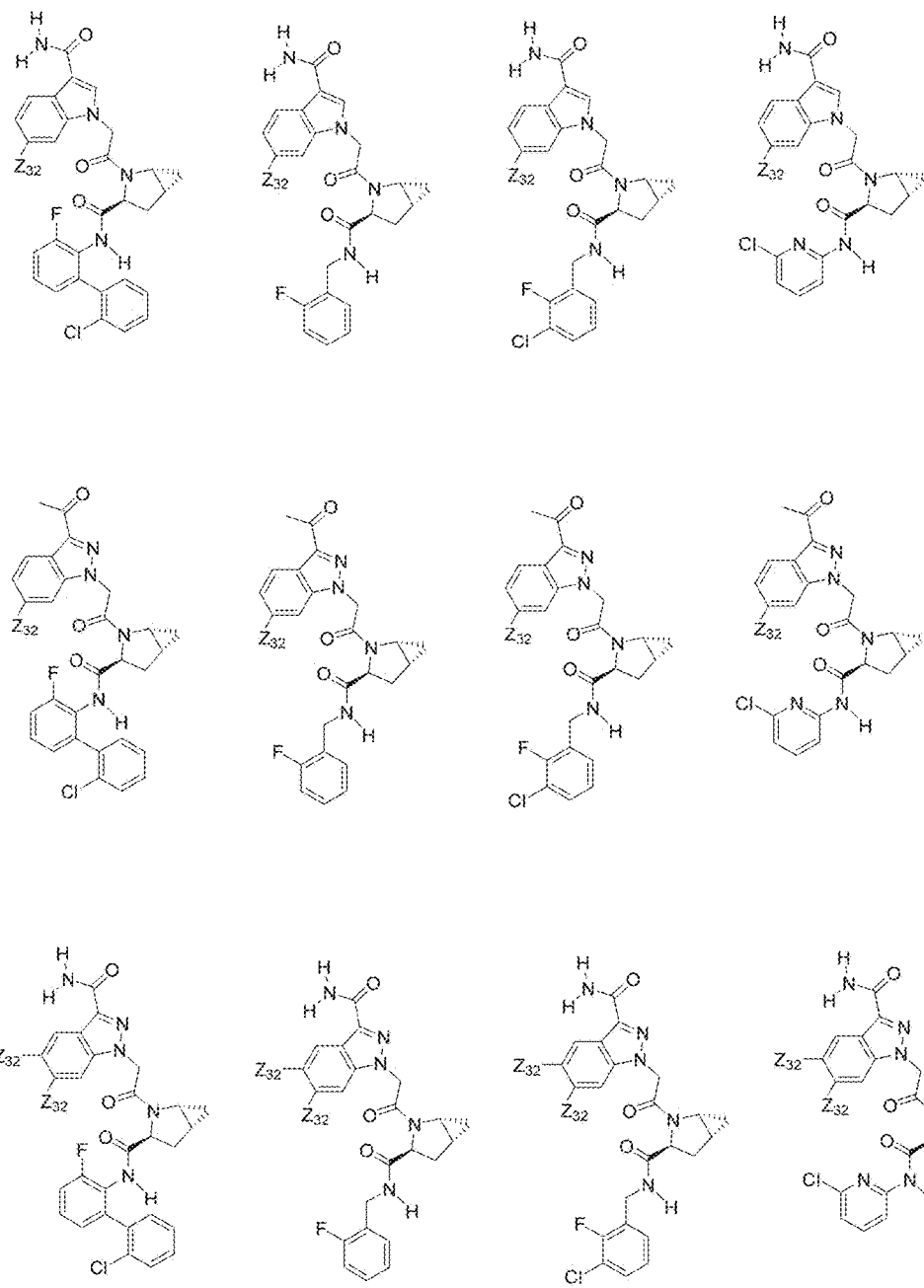
Figure 9G:
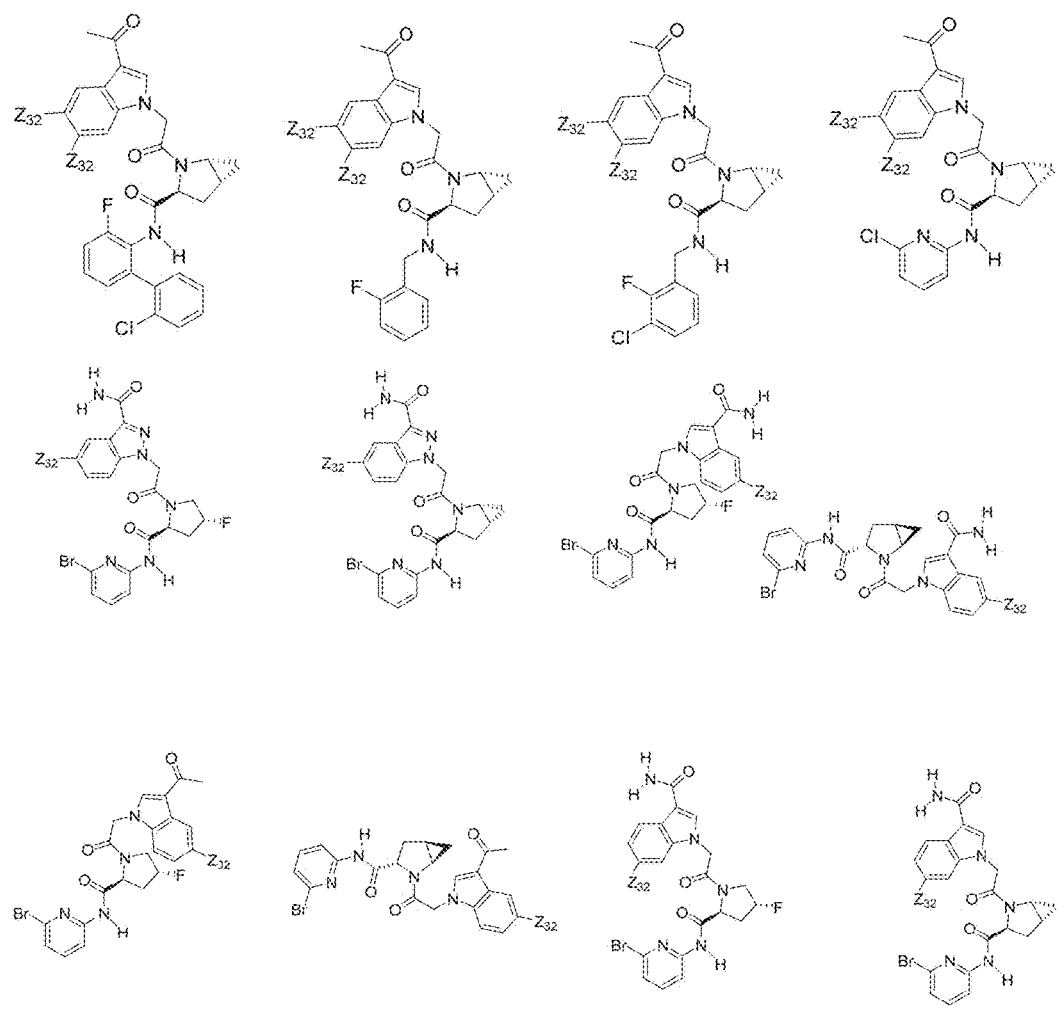
Figure 9H:
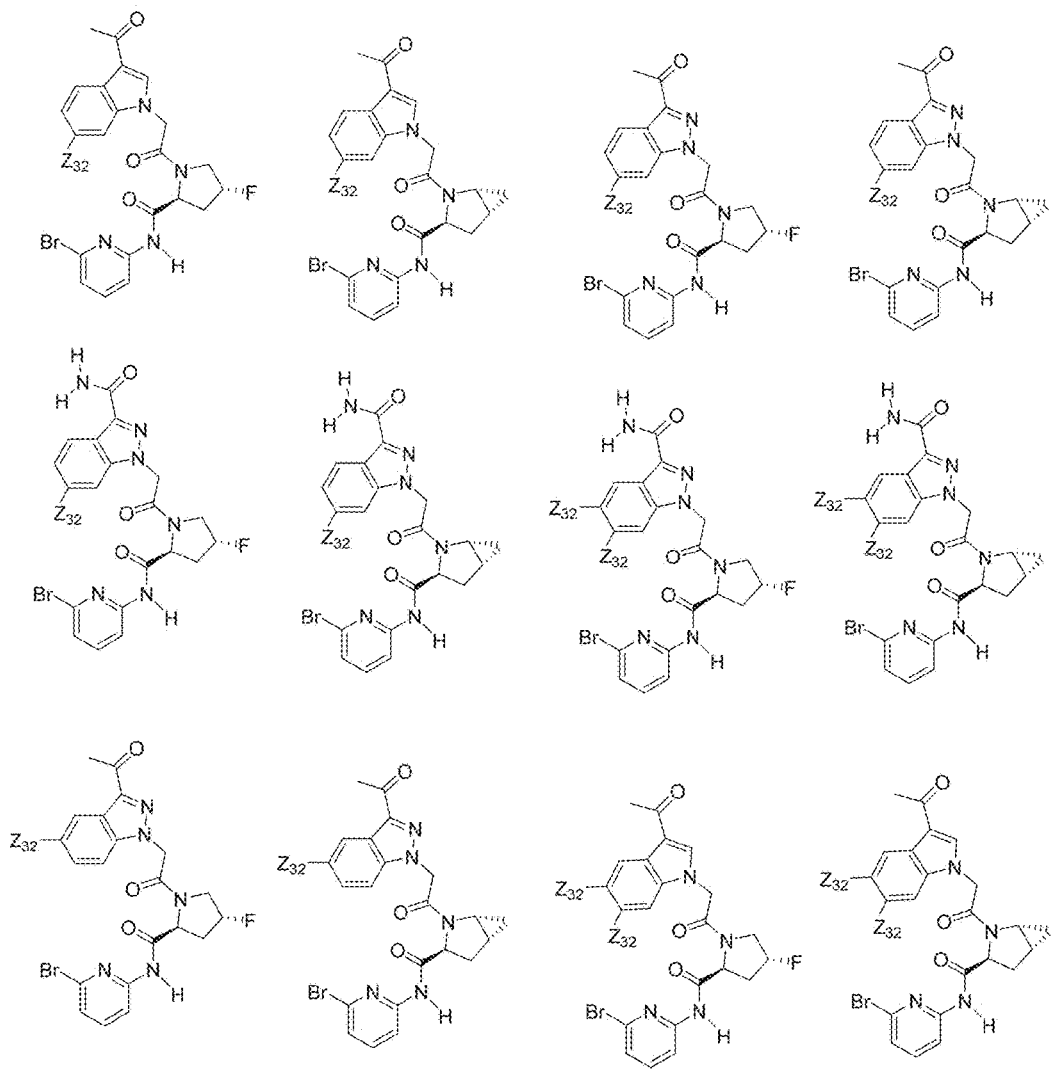

In an alternative embodiment, B is selected from FIG. 8.

Central Core (C=O)A Substituent

The central core (C=O)A substituent in Formula I is illustrated below:

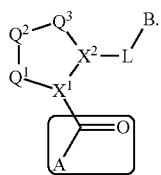

A is a group selected from:

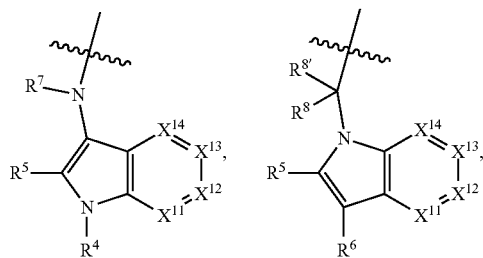

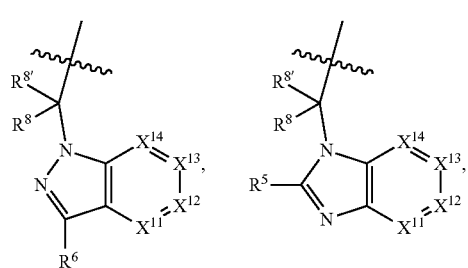

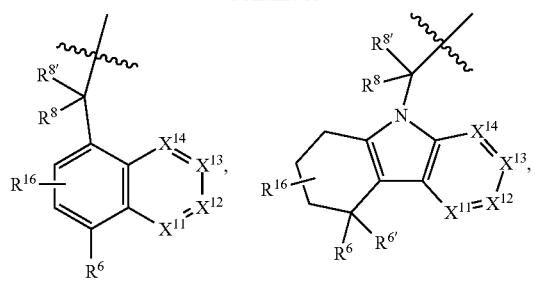

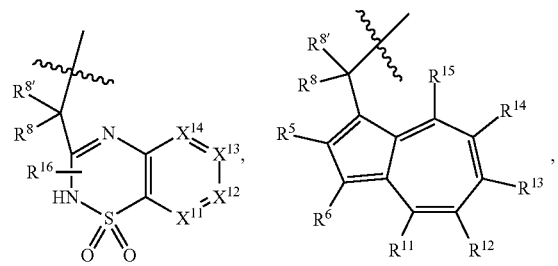

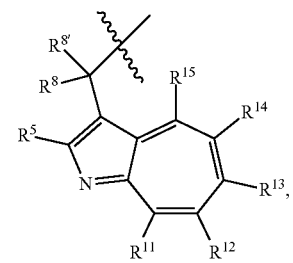

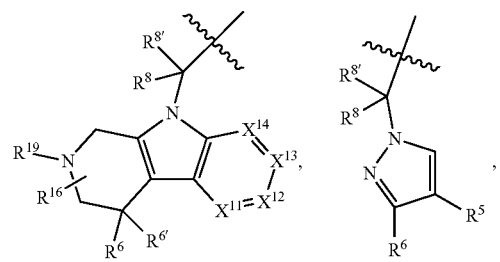

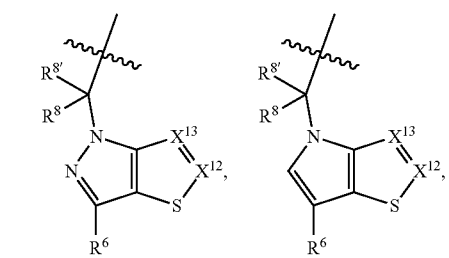

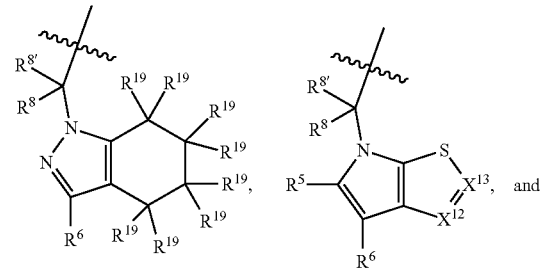

-continued

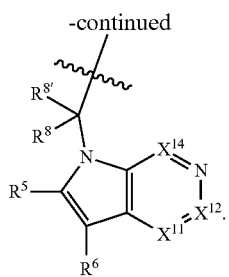

$R^4$ is selected from —CHO, —CONH$_2$, C$_2$-C$_6$alkanoyl, hydrogen, —SO$_2$NH$_2$, —C(CH$_2$)$_2$F, —CH(CF$_3$)NH$_2$, C$_1$-C$_6$alkyl, —C$_0$-C$_4$alkyl(C$_3$-C$_7$cycloalkyl), —C(O)C$_0$-C$_2$alkyl(C$_3$-C$_7$cycloalkyl),

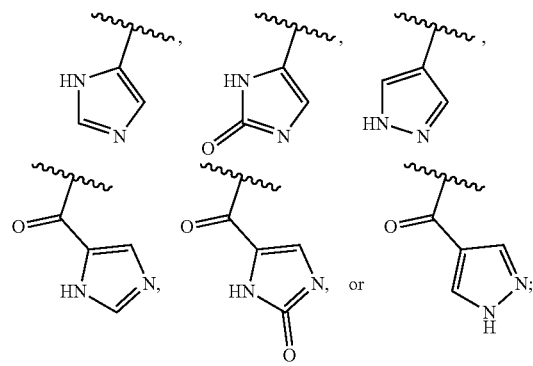

each of which $R^4$ other than hydrogen, —CHO, and —CONH$_2$, is unsubstituted or substituted with one or more of amino, imino, halogen, hydroxyl, cyano, cyanoimino, C$_1$-C$_2$alkyl, C$_1$-C$_2$alkoxy, —C$_0$-C$_2$alkyl(mono- and di-C$_1$-C$_4$alkylamino), C$_1$-C$_2$haloalkyl, and C$_1$-C$_2$haloalkoxy.

$R^5$ and $R^6$ are independently selected from —CHO, —C(O)NH$_2$, —C(O)NH(CH$_3$), C$_2$-C$_6$alkanoyl, hydrogen, hydroxyl, halogen, cyano, nitro, —COOH, —SO$_2$NH$_2$, vinyl, C$_1$-C$_6$alkyl (including methyl), C$_2$-C$_6$alkenyl, C$_1$-C$_6$alkoxy, —C$_0$-C$_4$alkyl(C$_3$-C$_7$cycloalkyl), —C(O)C$_0$-C$_4$alkyl(C$_3$-C$_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and —COOH may be substituted with one or more substituents independently selected from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

$R^{6'}$ is hydrogen, halogen, hydroxyl, C$_1$-C$_4$alkyl, —C$_0$-C$_4$alkyl(C$_3$-C$_7$cycloalkyl), or C$_1$-C$_4$alkoxy; or $R^6$ and $R^{6'}$ may be taken together to form an oxo, vinyl, or imino group.

$R^7$ is hydrogen, C$_1$-C$_6$alkyl, or —C$_0$-C$_4$alkyl(C$_3$-C$_7$cycloalkyl).

$R^8$ and $R^{8'}$ are independently selected from hydrogen, halogen, hydroxyl, C$_1$-C$_6$alkyl, —C$_0$-C$_4$alkyl(C$_3$-C$_7$cycloalkyl), C$_1$-C$_6$alkoxy, and (C$_1$-C$_4$alkylamino)C$_0$-C$_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may include one or more substituents independently selected from halogen, hydroxyl, nitro, cyano, C$_1$-C$_6$alkyl, C$_2$-C$_6$alkenyl, C$_2$-C$_6$alkanoyl, C$_1$-C$_6$alkoxy, —C$_0$-C$_4$alkyl(mono- and di-C$_1$-C$_6$alkylamino), —C$_0$-C$_4$alkyl(C$_3$-C$_7$cycloalkyl), C$_1$-C$_2$haloalkyl, and C$_1$-C$_2$haloalkoxy.

$R^{19}$ is hydrogen, C$_1$-C$_6$alkyl, C$_2$-C$_6$alkenyl, C$_2$-C$_6$alkanoyl, —SO$_2$C$_1$-C$_6$alkyl, (mono- and di-C$_1$-C$_6$alkylamino)C$_1$-C$_4$alkyl, —C$_0$-C$_4$alkyl(C$_3$-C$_7$cycloalkyl), —C$_0$-C$_4$alkyl(C$_3$-C$_7$heterocycloalkyl), —C$_0$-C$_4$alkyl(aryl), C$_0$-C$_4$alkyl(heteroaryl), and wherein $R^{19}$ other than hydrogen is unsubstituted or substituted with one or more substituents independently selected from halogen, hydroxyl, amino, —COOH, and —C(O)OC$_1$-C$_4$alkyl.

$X^{11}$ is N or CR$^{11}$.
$X^{12}$ is N or CR$^{12}$.
$X^{13}$ is N or CR$^{13}$.
$X^{14}$ is N or CR$^{14}$.
No more than 2 of $X^{11}$, $X^{12}$, $X^{13}$, and $X^{14}$ are N.

$R^{11}$, $R^{14}$, and $R^{15}$ are independently selected at each occurrence from hydrogen, halogen, hydroxyl, nitro, cyano, —O(PO)(OR$^9$)$_2$, —(PO)(OR$^9$)$_2$, C$_1$-C$_6$alkyl, C$_2$-C$_6$alkenyl, C$_2$-C$_6$alkynyl, C$_2$-C$_6$alkenyl(aryl), C$_2$-C$_6$alkenyl(cycloalkyl), C$_2$-C$_6$alkenyl(heterocycle), C$_2$-C$_6$alkenyl(heteroaryl), C$_2$-C$_6$alkynyl, C$_2$-C$_6$alkynyl(aryl), C$_2$-C$_6$alkynyl(cycloalkyl), C$_2$-C$_6$alkynyl(heterocycle), C$_2$-C$_6$alkynyl(heteroaryl), C$_2$-C$_6$alkanoyl, C$_1$-C$_6$alkoxy, C$_1$-C$_6$thioalkyl, —C$_0$-C$_4$alkyl(mono- and di-C$_1$-C$_6$alkylamino), —C$_0$-C$_4$alkyl(C$_3$-C$_7$cycloalkyl), —C$_0$-C$_4$alkoxy(C$_3$-C$_7$cycloalkyl), C$_1$-C$_2$haloalkyl, and C$_1$-C$_2$haloalkoxy.

In one embodiment, $R^5$ and $R^6$ are independently selected from —CHO, —C(O)NH$_2$, —C(O)NH(CH$_3$), C$_2$-C$_6$alkanoyl, and hydrogen.

In one embodiment, each $R^5$ and $R^6$ other than hydrogen, hydroxyl, cyano, and —COOH is unsubstituted or substituted with one or more substituents independently selected from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

In one embodiment, $R^8$ and $R^{8'}$ are independently hydrogen or methyl.

In one embodiment, $R^8$ and $R^{8'}$ are hydrogen.

In one embodiment, $R^7$ is hydrogen or methyl.

In one embodiment, $R^7$ is hydrogen.

Embodiments of Formulas IA, IB, IC, and ID

To further illustrate the invention, various embodiments of Formula IA, IB, IC and ID are provided. These are presented by way of example to show some of the variations among presented compounds to be used within the invention and can be applied to any of the Formulas I-XXX.

In one aspect, this disclosure includes the use of compounds and salts of Formula IA:

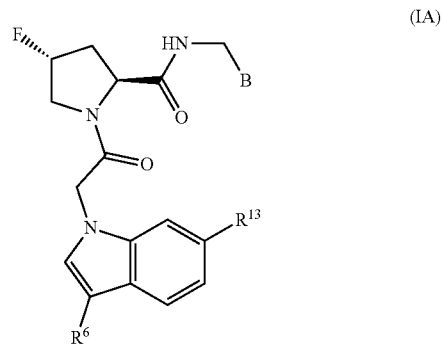

(IA)

where
R⁶, R¹³, and B may carry any of the definitions set forth herein for this variable.

In another aspect, this disclosure includes the use of compounds and salts of Formula IB, IC, and ID.

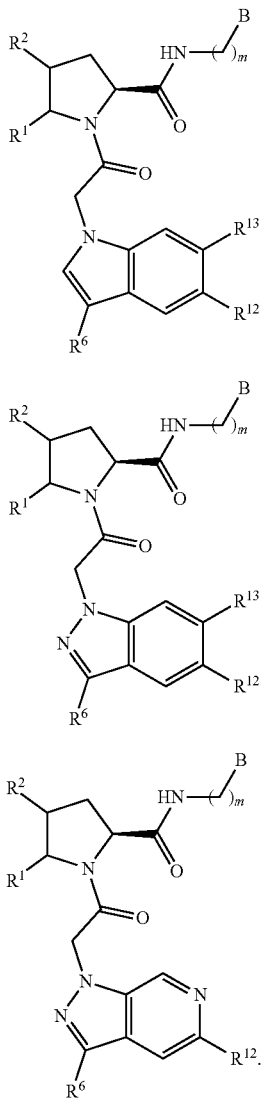

In Formulas IA, IB, IC, and ID, the variables may include any of the definitions set forth herein that results in a stable compound. In certain embodiments, the following conditions apply for Formula IB and IC.

In some embodiments, uses of compounds are provided, as described herein, comprising the administration of an effective amount of a compound of Formula IB or IC, wherein m=0, R¹ is H, R² is F, R⁶ is alkanoyl, R¹² is R³², R³² is heteroaryl, R¹³ is H, and B is heteroaryl.

In some embodiments, uses of compounds are provided, as described herein, comprising the administration of an effective amount of a compound of Formula IB or IC, wherein m=0, R¹ and R² are joined to form a 3 membered ring, R⁶ is alkanoyl, R¹² is R³², R³² is heteroaryl, R¹³ is H, and B is heteroaryl.

In some embodiments, uses of compounds are provided, as described herein, comprising the administration of an effective amount of a compound of Formula IB or IC, wherein m=0, R¹ is H, R² is F, R⁶ is amide, R¹² is R³², R³² is heteroaryl, R¹³ is H, and B is heteroaryl.

In some embodiments, uses of compounds are provided, as described herein, comprising the administration of an effective amount of a compound of Formula IB or IC, wherein m=0, R¹ and R² are joined to form a 3 membered ring, R⁶ is amide, R¹² is R³², R³² is heteroaryl, R¹³ is H, and B is heteroaryl.

In some embodiments, uses of compounds are provided, as described herein, comprising the administration of an effective amount of a compound of Formula IB or IC, wherein m=0, R¹ is H, R² is F, R⁶ is alkanoyl, R¹² is H, R¹³ is R³², R³² is heteroaryl, and B is heteroaryl.

In some embodiments, uses of compounds are provided, as described herein, comprising the administration of an effective amount of a compound of Formula IB or IC, wherein m=0, R¹ and R² are joined to form a 3 membered ring, R⁶ is alkanoyl, R¹² is H, R¹³ is R³², R³² is heteroaryl, and B is heteroaryl.

In some embodiments, uses of compounds are provided, as described herein, comprising the administration of an effective amount of a compound of Formula IB or IC, wherein m=0, R¹ is H, R² is F, R⁶ is amide, R¹² is H, R¹³ is R³², R³² is heteroaryl, and B is heteroaryl.

In some embodiments, uses of compounds are provided, as described herein, comprising the administration of an effective amount of a compound of Formula IB or IC, wherein m=0, R¹ and R² are joined to form a 3 membered ring, R⁶ is amide, R¹² is H, R¹³ is R³², R³² is heteroaryl, and B is heteroaryl.

In some embodiments, uses of compounds are provided, as described herein, comprising the administration of an effective amount of a compound of Formula IB or IC, wherein m=0, R¹ is H, R² is F, R⁶ is alkanoyl, R¹² is R³², R³² is heteroaryl, R¹³ is H, and B is phenyl.

In some embodiments, uses of compounds are provided, as described herein, comprising the administration of an effective amount of a compound of Formula IB or IC, wherein m=0, R¹ and R² are joined to form a 3 membered ring, R⁶ is alkanoyl, R¹² is R³², R³² is heteroaryl, R¹³ is H, and B is phenyl.

In some embodiments, uses of compounds are provided, as described herein, comprising the administration of an effective amount of a compound of Formula IB or IC, wherein m=0, R¹ is H, R² is F, R⁶ is amide, R¹² is R³², R³² is heteroaryl, R¹³ is H, and B is phenyl.

In some embodiments, uses of compounds are provided, as described herein, comprising the administration of an effective amount of a compound of Formula IB or IC, wherein m=0, R¹ and R² are joined to form a 3 membered ring, R⁶ is amide, R¹² is R³², R³² is heteroaryl, R¹³ is H, and B is phenyl.

In some embodiments, uses of compounds are provided, as described herein, comprising the administration of an effective amount of a compound of Formula IB or IC, wherein m=0, R¹ is H, R² is F, R⁶ is alkanoyl, R¹² is H, R¹³ is R³², R³² is heteroaryl, and B is phenyl.

In some embodiments, uses of compounds are provided, as described herein, comprising the administration of an effective amount of a compound of Formula IB or IC, wherein m=0, R¹ and R² are joined to form a 3 membered ring, R⁶ is alkanoyl, R¹² is H, R¹³ is R³², R³² is heteroaryl, and B is phenyl.

In some embodiments, uses of compounds are provided, as described herein, comprising the administration of an effective amount of a compound of Formula IB or IC, wherein m=0, $R^1$ is H, $R^2$ is F, $R^6$ is amide, $R^{12}$ is H, $R^{13}$ is $R^{32}$, $R^{32}$ is heteroaryl, and B is phenyl.

In some embodiments, uses of compounds are provided, as described herein, comprising the administration of an effective amount of a compound of Formula IB or IC, wherein m=0, $R^1$ and $R^2$ are joined to form a 3 membered ring, $R^6$ is amide, $R^{12}$ is H, $R^{13}$ is $R^{32}$, $R^{32}$ is heteroaryl, and B is phenyl.

In some embodiments, uses of compounds are provided, as described herein, comprising the administration of an effective amount of a compound of Formula IB or IC, wherein m=1, $R^1$ is H, $R^2$ is F, $R^6$ is alkanoyl, $R^{12}$ is $R^{32}$, $R^{32}$ is heteroaryl, $R^{13}$ is H, and B is heteroaryl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is alkanoyl, $R^{12}$ is $R^{32}$, $R^{32}$ is heteroaryl, $R^{13}$ is H, and B is heteroaryl.

In some embodiments, uses of compounds are provided, as described herein, comprising the administration of an effective amount of a compound of Formula IB or IC, wherein m=1, $R^1$ is H, $R^2$ is F, $R^6$ is amide, $R^{12}$ is $R^{32}$, $R^{32}$ is heteroaryl, $R^{13}$ is H, and B is heteroaryl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is amide, $R^{12}$ is $R^{32}$, $R^{32}$ is heteroaryl, $R^{13}$ is H, and B is heteroaryl.

In some embodiments, uses of compounds are provided, as described herein, comprising the administration of an effective amount of a compound of Formula IB or IC, wherein m=1, $R^1$ is H, $R^2$ is F, $R^6$ is alkanoyl, $R^{12}$ is H, $R^{13}$ is $R^{32}$, $R^{32}$ is heteroaryl, and B is heteroaryl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is alkanoyl, $R^{12}$ is H, $R^{13}$ is $R^{32}$, $R^{32}$ is heteroaryl, and B is heteroaryl.

In some embodiments, uses of compounds are provided, as described herein, comprising the administration of an effective amount of a compound of Formula IB or IC, wherein m=1, $R^1$ is H, $R^2$ is F, $R^6$ is amide, $R^{12}$ is H, $R^{13}$ is $R^{32}$, $R^{32}$ is heteroaryl, and B is heteroaryl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is amide, $R^{12}$ is H, $R^{13}$ is $R^{32}$, $R^{32}$ is heteroaryl, and B is heteroaryl.

In some embodiments, uses of compounds are provided, as described herein, comprising the administration of an effective amount of a compound of Formula IB or IC, wherein m=1, $R^1$ is H, $R^2$ is F, $R^6$ is alkanoyl, $R^{12}$ is $R^{32}$, $R^{32}$ is heteroaryl, $R^{13}$ is H, and B is phenyl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is alkanoyl, $R^{12}$ is $R^{32}$, $R^{32}$ is heteroaryl, $R^{13}$ is H, and B is phenyl.

In some embodiments, uses of compounds are provided, as described herein, comprising the administration of an effective amount of a compound of Formula IB or IC, wherein m=1, $R^1$ is H, $R^2$ is F, $R^6$ is amide, $R^{12}$ is $R^{32}$, $R^{32}$ is heteroaryl, $R^{13}$ is H, and B is phenyl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is amide, $R^{12}$ is $R^{32}$, $R^{32}$ is heteroaryl, $R^{13}$ is H, and B is phenyl.

In some embodiments, uses of compounds are provided, as described herein, comprising the administration of an effective amount of a compound of Formula IB or IC, wherein m=1, $R^1$ is H, $R^2$ is F, $R^6$ is alkanoyl, $R^{12}$ is H, $R^{13}$ is $R^{32}$, $R^{32}$ is heteroaryl, and B is phenyl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is alkanoyl, $R^{12}$ is H, $R^{13}$ is $R^{32}$, $R^{32}$ is heteroaryl, and B is phenyl.

In some embodiments, uses of compounds are provided, as described herein, comprising the administration of an effective amount of a compound of Formula IB or IC, wherein m=1, $R^1$ is H, $R^2$ is F, $R^6$ is amide, $R^{12}$ is H, $R^{13}$ is $R^{32}$, $R^{32}$ is heteroaryl, and B is phenyl.

In some embodiments, uses of compounds are provided, as described herein, comprising the administration of an effective amount of a compound of Formula IB or IC, wherein m=1, $R^1$ and $R^2$ are joined to form a 3 membered ring, $R^6$ is amide, $R^{12}$ is H, $R^{13}$ is $R^{32}$, $R^{32}$ is heteroaryl, and B is phenyl.

Embodiments of Formula VII

To further illustrate the invention, various embodiments of Formula VII are provided that can be used as further described in this application. In one aspect, the disclosure includes uses, as described herein, of compounds and salts of Formula VII:

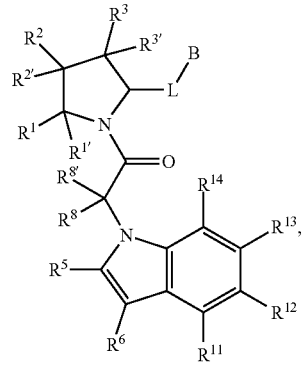

(VII)

wherein:

$R^1$, $R^2$, $R^{2'}$, and $R^3$ are independently selected from hydrogen, halogen, $C_1$-$C_4$alkyl, $C_1$-$C_4$alkoxy, —$C_0$-$C_2$alkyl$NR^9R^{10}$, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

$R^8$ and $R^{8'}$ are independently selected from hydrogen, halogen, and methyl;

$R^5$ is hydrogen, hydroxyl, cyano, —COOH, $C_1$-$C_6$alkyl, $C_1$-$C_6$alkoxy, $C_2$-$C_6$alkanoyl —$C_0$-$C_4$alkyl($C_3$-$C_7$cycloalkyl), —C(O)$C_0$-$C_4$alkyl($C_3$-$C_7$cycloalkyl, $C_1$-$C_2$haloalkyl, or $C_1$-$C_2$haloalkoxy;

$R^6$ is —C(O)CH$_3$, —C(O)NH$_2$, —C(O)CF$_3$, —C(O)(cyclopropyl), or -ethyl(cyanoimino); and $R^{11}$ and $R^{14}$ are independently selected from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —O$C_0$-$C_4$alkyl($C_3$-$C_7$cycloalkyl), $C_1$-$C_2$haloalkyl, and $C_1$-$C_2$haloalkoxy.

The use of prodrugs of Formula I and Table 1 for the treatment of a disorder in a host, typically a human, wherein the disorder is selected from the group disclosed in the Detailed Description, Part IV, Section A are within the scope of the disclosure. Prodrugs of compounds selected from Table 2 or an embodiment of the active compound as described in the Figures are also within the scope of the disclosure. The use of prodrugs of compounds selected from Table 2 or an embodiment of the active compound as described in the Figures for the treatment of a disorder in a host, typically a human, wherein the disorder is selected from the group disclosed in the Detailed Description, Part IV, Section A and Section B, are also within the scope of the disclosure.

Non-limiting examples of compounds falling within the scope of the invention are included in FIG. 9.

III. Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt. Thus, in one embodiment, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 25, 50, 100, 200, 250, 300, 400, 500, 600, 700, 750, 800, 900, 1000, 1100, 1200, 1300, 1400, 1500, 1600, or 1700 mg of active compound, or its salt. In one embodiment, the dosage form has at least about 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include any molar ratio of the active compound and additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent:active compound), or its salt, described herein. In one embodiment, the additional active agent is an anti-inflammatory or immunosuppressing agent.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes an active compound as described herein and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include a polymer for controlled delivery of the described compounds, including, but not limited to, a pluronic polymer, polyester (e.g., polylactic acid, poly(lactic-co-glycolic acid), polycaprolactone, polyvalerolactone, poly(1,3-dioxan-2one)); polyanhydride (e.g., poly(sebacic anhydride)); polyether (e.g., polyethylene glycol); polyurethane; polymethacrylate; polyacrylate; and polycyanoacrylate. In some embodiments, the polymer may be modified with polyethylene glycol (PEG), with a carbohydrate, and/or with an acyclic polyacetal derived from a polysaccharide. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles of a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794,000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or to deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

IV. Uses of Active Compounds for Treatment of Selected Disorders

In one aspect, an active compound or its salt or composition, as described herein is used to treat a medical disorder which is an inflammatory or immune condition, a disorder mediated by the complement cascade (including a dysfunctional cascade) including a complement D-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

Section A Disorders

In one embodiment, the invention is the use of a compound of Formula I, or a pharmaceutically acceptable salt or composition thereof, as well as the compounds of Table 1, Table 2, Table 3 or an embodiment of the active compound as described in the Figures for the treatment of a disorder as described in this Section A herein.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of a compound of Formula I, Table 1, Table 2, Table 3 or an embodiment of the active compound as described in the Figures or a pharmaceutically acceptable salt thereof, optionally in a pharmaceutically acceptable carrier. In one embodiment of the present invention, a method is provided for treating nonalcoholic steatohepatitis (NASH) in a host by administering an effective amount of a compound of Formula I, Table 1, Table 2, Table 3 or an embodiment of the active compound as described in the Figures, or a pharmaceutically acceptable salt thereof, optionally in a pharmaceutically acceptable carrier.

In another embodiment, the active compound is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a host in need thereof an effective amount of a composition comprising a compound of the current invention. In one embodiment, the present invention provides a method of treating or preventing amyotrophic lateral sclerosis by administering to a host in need thereof an effective amount of a composition comprising a compound of the current invention.

In another embodiment, a method is provided for the treatment or prevention of cytokine or inflammatory reactions in response to the administration of biotherapeutics (e.g. CAR T-cell therapy or monoclonal antibody therapy) in a host by administering an effective amount of a compound of Formula I, Table 1, Table 2, Table 3 or an embodiment of the active compound as described in the Figures, or a pharmaceutically acceptable salt thereof, optionally in a pharmaceutically acceptable carrier, or a pharmaceutically acceptable salt thereof, optionally in a pharmaceutically acceptable carrier. Various types of cytokine or inflammatory reactions may occur in response to biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal. Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" *Transplantation* (1989) 47(4):606-8; Chatenoud L, et al. "In vivo cell activation following OKT3 administration. Systemic cytokine release and modulation by corticosteroids" *Transplantation* (1990) 49(4):697-702; and Lim L C, Koh L P, and Tan P. "Fatal cytokine release syndrome with chimeric anti-CD20 monoclonal antibody rituximab in a 71-year-old patient with chronic lymphocytic leukemia" *J. Clin Oncol.* (1999) 17(6):1962-3.

Also contemplated herein, is the use of a compound of Formula I, Table 1, Table 2, Table 3 or an embodiment of the active compound as described in the Figures, or a pharmaceutically acceptable salt thereof, optionally in a pharmaceutically acceptable carrier to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging CD19/CD3-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In yet another embodiment, the disorder is selected from:
(i) vitritis, sarcoidosis, syphilis, tuberculosis, or Lyme disease;
(ii) retinal vasculitis, Eales disease, tuberculosis, syphilis, or toxoplasmosis;
(iii) neuroretinitis, viral retinitis, or acute retinal necrosis;
(iv) varicella zoster virus, herpes simplex virus, cytomegalovirus, Epstein-Barr virus, lichen planus, or Dengue-associated disease (e.g., hemorraghic Dengue Fever);
(v) Masquerade syndrome, contact dermatitis, trauma induced inflammation, UVB induced inflammation, eczema, granuloma annulare, or acne.

In an additional embodiment, the disorder is selected from:
(i) acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA);
(ii) antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy;
(iii) allergic bronchopulmonary aspergillosis, allergic neuritis, drug allergy, radiation-induced lung injury, eosinophilic pneumonia, radiographic contrast media allergy, bronchiolitis obliterans, or interstitial pneumonia;

(iv) amyotrophic lateral sclerosis, parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia;

(v) Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from:
(i) atopic dermatitis, dermatitis, dermatomyositis, dermatomyositis bullous pemphigoid, scleroderma, sclerodermatomyositis, psoriatic arthritis, pemphigus vulgaris, cutaneous lupus, discoid lupus erythematosus, chilblain lupus erythematosus, or lupus erythematosus-lichen planus overlap syndrome;

(ii) cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis;

(iii) angioedema, low platelets (HELLP) syndrome, sickle cell disease, platelet refractoriness, red cell casts, or typical or infectious hemolytic uremic syndrome (tHUS);

(iv) hematuria, hemodialysis, hemolysis, hemorrhagic shock, immunothrombocytopenic purpura (ITP), thrombotic thrombocytopenic purpura (TTP), idiopathic thrombocytopenic purpura (ITP), drug-induced thrombocytopenia, autoimmune hemolytic anemia (AIHA), azotemia, blood vessel and/or lymph vessel inflammation, rotational atherectomy, or delayed hemolytic transfusion reaction;

(v) British type amyloid angiopathy, Buerger's disease, bullous pemphigoid, C1q nephropathy, cancer, or catastrophic antiphospholipid syndrome.

In another embodiment, the disorder is selected from:
(i) wet AMD, dry AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, or RPE degeneration;

(ii) pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen;

(iii) chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita;

(iv) essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments;

(v) hepatitis, hepatitis A, hepatitis B, hepatitis C or human immunodeficiency virus (HIV), (vi) a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae;

(vii) *Neisseria meningitidis*, shiga toxin *E. coli*-related hemolytic uremic syndrome (STEC-HUS), *Streptococcus*, or poststreptococcal glomerulonephritis.

In a further embodiment, the disorder is selected from:
(viii) hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis;

(ix) inclusion body myositis, intestinal ischemia, iridocyclitis, iritis, juvenile chronic arthritis, Kawasaki's disease (arteritis), or lipiduria;

(x) membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder;

(xi) multiple organ failure, multiple system atrophy (MSA), myotonic dystrophy, Niemann-Pick disease type C, chronic demyelinating diseases, or progressive supranuclear palsy;

(xii) spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis;

In one embodiment, a compound described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis, ischemic-reperfusion injury of the eye.

In one embodiment, a method for the treatment of sickle cell in a host is provided that includes the administration of an effective amount of a compound described herein, or its salt, optionally in a pharmaceutically acceptable carrier. In one embodiment, a method for the treatment of immuno-thrombocytopenic purpura (ITP), thrombotic thrombocytopenic purpura (TTP), or idiopathic thrombocytopenic purpura (ITP) in a host is provided that includes the administration of an effective amount of a compound described herein, or its salt, optionally in a pharmaceutically acceptable carrier. In one embodiment, a method for the treatment of ANCA-vasculitis in a host is provided that includes the administration of an effective amount of a compound described herein, or its salt, optionally in a pharmaceutically acceptable carrier. In one embodiment, a method for the treatment of IgA nephropathy in a host is provided that includes the administration of an effective amount of a compound described herein, or its salt, optionally in a pharmaceutically acceptable carrier. In one embodiment, a method for the treatment of rapidly progressing glomerulonephritis (RPGN), in a host is provided that includes the administration of an effective amount of a compound described herein, or its salt, optionally in a pharmaceutically acceptable carrier. In one embodiment, a method for the treatment of lupus nephritis, in a host is provided that includes the administration of an effective amount of a compound described herein, or its salt, optionally in a pharmaceutically acceptable carrier. In one embodiment, a method for the treatment of hemorraghic dengue fever, in a host is provided that includes the administration of an effective amount of a compound described herein, or its salt, optionally in a pharmaceutically acceptable carrier.

Section B Disorders

The compound of Table 2 or Table 3 or their pharmaceutically acceptable salts or pharmaceutical compositions are useful for treating any of the disorders described herein. In one embodiment, the compound is useful for treating or preventing a disorder that is mediated by the complement pathway, and in particular, a pathway that is modulated by complement Factor D. In another embodiment, the compound is effective to treat the named disorder, albeit through a different mechanism.

In certain embodiments, the disorder is an inflammatory disorder, an immune disorder, an autoimmune disorder, or complement Factor D related disorders in a host. In one embodiment, the disorder is an ocular disorder or an eye disorder.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), panuveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from age-related macular degeneration, glaucoma, diabetic retinopathy, neuromyelitis optica (NMO), vasculitis, hemodialysis, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion, or uveitis (including Behcet's disease and other sub-types of uveitis).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Complement mediated disorders that may be treated or prevented by the compounds of Table 2 or Table 3 include, but are not limited to:
(i) paroxysmal nocturnal hemoglobinuria (PNH), hereditary angioedema, capillary leak syndrome, atypical hemolytic uremic syndrome (aHUS), hemolytic uremic syndrome (HUS), abdominal aortic aneurysm, hemodialysis complications, hemolytic anemia, or hemodialysis;
(ii) myasthenia gravis, multiple sclerosis, C3 glomerulonephritis (C3GNs), MPGN II (dense deposit disease), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome;
(iii) inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), Crohn's disease, rheumatoid arthritis, inflammatory bowel disease, lupus nephritides, arthritis, immune complex disorders and autoimmune diseases, systemic lupus, or lupus erythematosus;
(iv) ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes;
(v) Alzheimer's dementia, stroke, schizophrenia, traumatic brain injury, trauma, Parkinson's disease, epilepsy, transplant rejection, prevention of fetal loss, biomaterial reactions (e.g. in hemodialysis, implants), hyperacute allograft rejection, xenograft rejection, transplantation, psoriasis, burn injury, thermal injury including burns or frostbite;
(vi) asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of paroxysmal nocturnal hemoglobinuria (PNH) is provided that includes the administration of an effective amount of a compound selected from Table 2 or Table 3, or a pharmaceutically acceptable salt thereof, optionally in a pharmaceutically acceptable carrier.

In another embodiment, a method for the treatment of age-related macular degeneration (AMD) is provided that includes the administration of an effective amount of a compound selected from Table 2 or Table 3, or a pharmaceutically acceptable salt thereof, optionally in a pharmaceutically acceptable carrier.

In another embodiment, a method for the treatment of rheumatoid arthritis is provided that includes the administration of an effective amount of a compound selected from Table 2 or Table 3, or a pharmaceutically acceptable salt thereof, optionally in a pharmaceutically acceptable carrier.

In another embodiment, a method for the treatment of multiple sclerosis is provided that includes the administration of an effective amount of a compound selected from Table 2 or Table 3, or a pharmaceutically acceptable salt thereof, optionally in a pharmaceutically acceptable carrier.

In another embodiment, a method for the treatment of myasthenia gravis is provided that includes the administration of an effective amount of a compound selected from Table 2 or Table 3, or a pharmaceutically acceptable salt thereof, optionally in a pharmaceutically acceptable carrier.

In another embodiment, a method for the treatment of atypical hemolytic uremic syndrome (aHUS) is provided that includes the administration of an effective amount of a compound selected from Table 2 or Table 3, or a pharmaceutically acceptable salt thereof, optionally in a pharmaceutically acceptable carrier.

In another embodiment, a method for the treatment of C3 glomerulonephritis is provided that includes the administration of an effective amount of a compound selected from Table 2 or Table 3, or a pharmaceutically acceptable salt thereof, optionally in a pharmaceutically acceptable carrier.

In another embodiment, a method for the treatment of abdominal aortic aneurysm is provided that includes the administration of an effective amount of a compound selected from Table 2 or Table 3, or a pharmaceutically acceptable salt thereof, optionally in a pharmaceutically acceptable carrier.

In another embodiment, a method for the treatment of neuromyelitis optica (NMO) is provided that includes the administration of an effective amount of a compound selected from Table 2 or Table 3, or a pharmaceutically acceptable salt thereof, optionally in a pharmaceutically acceptable carrier.

In some embodiments, the present invention provides methods of treating or preventing an inflammatory disorder or a complement related disease, by administering to a host in need thereof an effective amount of a compound selected from Table 2 or Table 3 of the invention. In some embodiments, the present invention provides methods of treating or preventing an inflammatory disorder more generally, an immune disorder, autoimmune disorder, or complement Factor D related disorder, by providing an effective amount of a compound or pharmaceutically acceptable salt of a compound selected from Table 2 or Table 3 to patient with a Factor D mediated inflammatory disorder. A compound selected from Table 2 or Table 3 may be provided as the only active agent or may be provided together with one or more additional active agents.

In one embodiment, a method for the treatment of a disorder associated with a dysfunction in the complement cascade is provided that includes the administration of an effective amount of a compound selected from Table 2 or Table 3, or a pharmaceutically acceptable salt thereof, optionally in a pharmaceutically acceptable carrier. In one embodiment, a method of inhibiting activation of the alternative complement pathway in a host is provided that includes the administration of an effective amount of a compound selected from Table 2 or Table 3, or a pharmaceutically acceptable salt thereof, optionally in a pharmaceutically acceptable carrier. In one embodiment, a method of modulating Factor D activity in a host is provided that includes the administration of an effective amount of a compound selected from Table 2 or Table 3, or a pharmaceutically acceptable salt thereof, optionally in a pharmaceutically acceptable carrier.

In an additional alternative embodiment, the compound selected from Table 2 or Table 3, or a pharmaceutically acceptable salt thereof, optionally in a pharmaceutically acceptable carrier is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of a compound of Table 2 or Table 3, or a pharmaceutically acceptable salt thereof, optionally in a pharmaceutically acceptable carrier, to a host in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, a compound selected from Table 2 or Table 3, or a pharmaceutically acceptable salt thereof, optionally in a pharmaceutically acceptable carrier, is used in the treatment of lupus. Non-limiting examples of lupus include lupus erythematosus, cutaneous lupus, discoid lupus erythematosus, chilblain lupus erythematosus, lupus erythematosus-lichen planus overlap syndrome.

Lupus erythematosus is a generic category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment a compound of Table 2 or Table 3 or a pharmaceutically acceptable salt thereof, optionally in a pharmaceutically acceptable carrier, is provided at an effective dose to treat a patient with type 1 diabetes. In one embodiment a compound of Table 2 or Table 3, or a pharmaceutically acceptable salt thereof, optionally in a pharmaceutically acceptable carrier, is provided at an effective dose to treat a patient with type 2 diabetes.

Type 1 diabetes is an autoimmune disease. An autoimmune disease results when the body's system for fighting infection (the immune system) turns against a part of the body. The pancreas then produces little or no insulin.

V. Combination Therapy

In additional embodiments, an effective amount of an active compound or its salt or composition as described herein may be provided in combination or alternation with or preceded by, concomitant with or followed by, an effective amount of at least one additional therapeutic agent, for example, for treatment of a disorder listed herein. Non-limiting examples of additional therapeutic agents for such combination therapy are provided below.

In one embodiment, an effective amount of an active compound or its salt or composition as described herein may be provided in combination or alternation with an effective amount of at least one additional inhibitor of the complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble complement regulator, a therapeutic antibody (monoclonal or polyclonal), complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant).

In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab.

In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In another embodiment, an active compound as described herein can be administered in combination or alternation with an immune checkpoint inhibitor. Non-limiting examples of checkpoint inhibitors are anti-PD-1 or anti-PDL1 antibodies (for example, Nivolumab, Pembrolizumab, Pidilizumab and Atezolizumab) and anti-CTLA4 antibodies (Ipilimumab and Tremelimumab).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble complement regulators: Soluble complement receptor 1 (TP10) (Avant Immunotherapeutics); sCR1-sLe$^x$/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix);

Receptor agonists: PMX-53 (Peptech Ltd.); JPE-137 (Jerini); JSM-7717 (Jerini);

Others: Recombinant human MBL (rhMBL; Enzon Pharmaceuticals).

Imides and glutarimide derivatives such as thalidomide, lenalidomide, pomalidomide;

Additional non-limiting examples that can be used in combination or alternation with an active compound or its salt or composition as described herein include the following.

| Non-limiting examples of potential therapeutics for combination therapy | | | |
|---|---|---|---|
| Name | Target | Company | Class of Molecule |
| LFG316 | C5 | Novartis/Morphosys | Monoclonal antibody |
| 4(1MEW)APL-1,APL-2 | C3/C3b | Apella | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101,PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |

Non-limiting examples of potential therapeutics for combination therapy

| Name | Target | Company | Class of Molecule |
| --- | --- | --- | --- |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-3 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Opthterion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |

In one embodiment, an active compound or its salt or composition as described herein may be provided together with a compound that inhibits an enzyme that metabolizes an administered protease inhibitor. In one embodiment, a compound or salt may be provided together with ritonavir.

In one embodiment, an active compound or its salt or composition as described herein may be provided in combination with a complement C5 inhibitor or C5 convertase inhibitor. In another embodiment, an active compound or its salt or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits complement factor D. In one embodiment of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2014/002051, WO2014/002052, WO2014/002053, WO2014/002054, WO2014/002057, WO2014/002058, WO2014/002059, WO2014/005150, WO2014/009833, WO 2013/164802, WO 2015/009616, WO 2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus and combinations thereof.

In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more nonsteroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656, 667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methylpropanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a host in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); and pegaptanib (Macugen®; OSI Pharmaceuticals and Pfizer); Bevacizumab (Avastin; Genentech/Roche); anecortane acetate, squalamine lactate, and corticosteroids, including, but not limited to, triamcinolone acetonide.

In one embodiment, the present invention provides a method of treating or preventing paroxysmal nocturnal hemoglobinuria (PNH) by administering to a host in need thereof an effective amount of an active compound or its salt or composition as described herein with an additional inhibitor of the complement system or another active compound with a different biological mechanism of action. In another embodiment, the present invention provides a method of treating or preventing paroxysmal nocturnal hemoglobinuria (PNH) by administering to a host in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a host in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes.

In one embodiment, the present invention provides a method of treating or preventing rheumatoid arthritis by administering to a host in need thereof an effective amount of a composition comprising an active compound or its salt or composition as described herein in combination or alternation with an additional inhibitor of the complement system, or an active agent that functions through a different mechanism of action. In another embodiment, the present invention provides a method of treating or preventing rheumatoid arthritis by administering to a host in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a host in need thereof an effective amount of an active compound or its salt or composition as described herein in combination or alternation with an additional inhibitor of the complement system, or an active agent that functions through a different mechanism of action. In another embodiment, the present invention provides a method of treating or preventing multiple sclerosis by administering to a host in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), SoluMedrol (methylprednisolone), High-dose oral Deltasone (prednisone), H.P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In one embodiment, the adoptive cell transfer therapy includes the use of a chimeric antigen receptor T-Cell (CAR T). In one embodiment, the adoptive cell transfer therapy includes the use of a chimeric antigen receptor T-Cell (CAR T) or a dendritic cell to treat a hematologic or solid tumor, for example, a B-cell related hematologic cancer. In one embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, chronic hemolysis, neuromyelitis optica, or transplantation rejection.

In one embodiment, an active compound or its salt or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a host in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In one embodiment, an active compound or its salt or composition as described herein may be provided in combination with azathioprine for the treatment of Lupus.

In one embodiment, an active compound or its salt or composition as described herein may be provided in combination with a non-steroidal anti-inflammatory drug for the treatment of Lupus.

In one embodiment, an active compound or its salt or composition as described herein may be provided in combination with a corticosteroid for the treatment of Lupus.

In one embodiment, an active compound or its salt or composition as described herein may be provided in combination with a belimumab (Benlysta) for the treatment of Lupus.

In one embodiment, an active compound or its salt or composition as described herein may be provided in combination with hydroxychloroquine (Plaquenil) for the treatment of Lupus.

In one embodiment, an active compound or its salt or composition as described herein may be provided in combination with sifalimumab for the treatment of Lupus.

In one embodiment, an active compound or its salt or composition as described herein may be provided in combination with OMS721 (Omeros) for the treatment of a complement mediated disorder. In one embodiment, an active compound or its salt or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, an active compound or its salt or composition as described herein may be provided in combination with a corticosteroid for the treatment or prevention of cytokine or inflammatory reactions in response to the administration of biotherapeutics. In another embodiment, an active compound or its salt or composition as described herein may be provided in combination with etarnercept for the treatment or prevention of cytokine or inflammatory reactions in response to the administration of biotherapeutics. In another embodiment, an active compound or its salt or composition as described herein may be provided in combination with tocilizumab for the treatment or prevention of cytokine or inflammatory reactions in response to the administration of biotherapeutics. In another embodiment, an active compound or its salt or composition as described herein may be provided in combination with etarnercept and tocilizumab for the treatment or prevention of cytokine or inflammatory reactions in response to the administration of biotherapeutics. In another embodiment, an active compound or its salt or composition as described herein may be provided in combination with infliximab for the treatment or prevention of cytokine or inflammatory reactions in response to the administration of biotherapeutics. In another embodiment, an active compound or its salt or composition as described herein may be provided in combination with golimumab for the treatment or prevention of cytokine or inflammatory reactions in response to the administration of biotherapeutics.

VI. Combinations for Prophylactic or Concommitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host concomitantly with the prophylactic administration of a vaccine against a bacterial infection. In one embodiment, the complement mediated disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host and, during the administration period of the compound or salt, a vaccine against a bacterial infection is administered to the host. In one embodiment, the disorder is PNH or aHUS. In one embodiment, the host has received an organ or other tissue or biological fluid transplant. In one embodiment, the host is also administered eculizumab.

In one aspect of the present invention, the host is administered an active compound or its salt or composition as described herein in combination with an antibiotic compound for the duration of factor D inhibitor administration. In one embodiment, the disorder is PNH or aHUS. In one embodiment, the host has received an organ or other tissue or biological fluid transplant. In one embodiment, the host is also administered eculizumab.

In one aspect of the present invention, an active compound or its salt or composition as described herein is administered to a host following the prophylactic administration of a vaccine against a bacterial infection, and in combination with an antibiotic compound for the duration of factor D inhibitor administration. In one embodiment, the complement mediated disorder is PNH or aHUS. In one embodiment, the host has received an organ or other tissue or biological fluid transplant. In one embodiment, the host is also administered eculizumab.

In one embodiment, the host, prior to receiving an active compound or its salt or composition as described herein, is vaccinated against a bacterial infection caused by the bacterium *Neisseria meningitidis*. In one embodiment, the host is vaccinated against a bacterial infection caused by the bacterium *Haemophilus influenzae*. In one embodiment, the *Haemophilus influenzae* is *Haemophilus influenzae* serotype B (Hib). In one embodiment, the host is vaccinated against a bacterial infection caused by *Streptococcus pneumoniae*. In one embodiment, the host is vaccinated against a bacterial infection caused by the bacterium *Nisseria meningitidis, Haemophilus influenzae*, or *Streptococcus pneumoniae*, or a combination of one or more of *Nisseria meningitidis, Haemophilus influenzae*, or *Streptococcus pneumoniae*. In one embodiment, the host is vaccinated against a bacterial infection caused by the bacterium *Nisseria meningitidis, Haemophilus influenzae*, and *Streptococcus pneumoniae*.

In other embodiments, the host is vaccinated against a bacterial infection caused by a bacterium selected from a Gram-negative bacterium. In one embodiment, the host is vaccinated against a bacterial infection caused by a bacterium selected from a Gram-positive bacterium. In one embodiment, the host is vaccinated against a bacterial infection caused by the bacterium *Nisseria meningitidis, Haemophilus influenzae*, or *Streptococcus pneunemoniae*, or a combination of one or more of *Nisseria meningitidis, Haemophilus influenzae*, or *Streptococcus pneumoniae*, and one or more of, but not limited to, *Bacillus anthracis, Bordetella pertussis, Clostridium tetani, Corynebacterium diphtheria, Coxiella bumetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the host is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *haemophilus* b conjugate (prp-t) vaccine (ActHIB, Sanofi; Hibrix, GSK), *haemophilus* b conjugate (hboc) vaccine (HibTITER, Neuron Biotech), *haemophilus* b conjugate (prp-omp) vaccine (PedvaxHIB, Merck), *haemophilus* b conjugate (prp-t) vaccine/meningococcal conjugate vaccine (MenHibrix, GSK), *haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *haemophilus* influenza tybe b (Pentacel, Sanofi), and/or diphtheria, and pertussis (Tdap; Boostrix, GSK; Adacel, Sanofi), or a combination thereof.

As described above, a host receiving a compound of the present invention to treat disorder is prophylactically administered an antibiotic compound in addition to a factor D inhibitor described herein. In one embodiment, the host is administered an antibiotic compound for the duration of administration of the active compound to reduce the development of a bacterial infection. Antibiotic compounds for concomitant administration with a factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen), azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen), oxacillin (Prostaphlin), penicillin G (Pentids), penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin), bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the host is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

VII. Process of Preparation of Active Compounds

Abbreviations (Boc)$_2$O di-tert-butyl dicarbonate
CAN Acetonitrile
AcOEt, EtOAc ethyl acetate
CH$_3$OH, MeOH Methanol
CsF Cesium fluoride
CuI Cuprous iodide
DCM, CH$_2$Cl$_2$ Dichloromethane
DIEA, DIPEA N,N-diisopropylethylamine
DMA N,N-dimethylacetamide DMF N,N-dimethylformamide
DMSO Dimethylsulfoxide
DPPA Diphenyl phosphoryl azide
$Et_3N$, TEA Triethylamine
EtOAc Ethylacetate
EtOH Ethanol
HATU 1-[Bis(dimethylamino)methylene]-1H-1,2,3-triazolo[4,5-b]pyridinium 3-oxide hexafluorophosphate
HCl Hydrochloric acid
$^iPr_2Net$ N,N-diisopropylethylamine
$K_2CO_3$ Potassium carbonate
LiOH Lithium hydroxide
MTBE Methyl $^t$butylether
$Na_2SO_4$ Sodium sulfate
NaCl Sodium chloride
NaH Sodium hydride
$NaHCO_3$ Sodium bicarbonate
$NEt_3$ Trimethylamine
Pd $(OAc)_2$ Palaldium acetate
$Pd(dppf)Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(0)
$Pd_2(dba)_3$ Tris(dibenzylideneacetone)dipalladium(0)
$PPh_3$ Triphenylphosphine
RT Room temperature
tBuOK potassium tert-butoxide
TEA Trimethylamine
TFA trifluoroacetic acid
$Tf_2O$ trifluoromethanesulfonic anhydride
TFA Trifluoroacetic acid
THF Tetrahydrofuran
TMSBr Bromotrimethylsilane
$t_R$ Retention time
Zn $(CN)_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7 µm
Column Temperature: 40° C.
Mobile Phase: Solvent A: $H_2O$+0.05% FA; Solvent B: $CH_3CN$+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)

LC Method B
Instrument: Shimadzu LC-2010A HT
Column: Athena, C18-WP, 50×4.6 mm, 5 µm
Column Temperature: 40° C.
Mobile Phase: Solvent A: $H_2O/CH_3OH/FA$=90/10/0.1; Solvent B: $H_2O/CH_3OH/FA$=10/90/0.1
Flow Rate: 3 mL/min
Gradient: 0.4 min @ 30% B, 3.4 min gradient (30-100% B), then 0.8 min @ 100% B
Detection: UV (220/254 nm)

LC Method C
Instrument: Agilent 1100/1200 series LC system with DAD detector
Column: Atlantis dC18 (250×4.6) mm, 5 m
Column Temperature: Ambient
Mobile Phase A: 0.1% TFA in water, Mobile Phase B: Acetonitrile
Flow Rate: 1.0 mL/min
Gradient:

| | Time (min) | | | | |
|---|---|---|---|---|---|
| | 0.0 | 15 | 20 | 23 | 30 |
| % B | 10 | 100 | 100 | 10 | 10 |

Detection: (210-400 nm)

LC Method D
Instrument: Shimadzu LC 20AD system with PDA detector
Column: Phenomenex Gemini NX C18 (150×4.6) mm, 5 µm
Column Temperature: Ambient
Mobile Phase A: 10 mM $NH_4OAC$ in water, Mobile Phase B: Acetonitrile
Flow Rate: 1.0 mL/min
Gradient:

| | Time (min) | | | | |
|---|---|---|---|---|---|
| | 0.0 | 15 | 20 | 23 | 30 |
| % B | 10 | 100 | 100 | 10 | 10 |

Detection: (210-400 nm)

Example 1. General Route of Synthesis

A compound of the present invention can be prepared, for example, from a central core. In one embodiment, for example, the central core Structure 1 is an N-protected aminoacid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A-COOH) to generate a second amide bond, forming a compound within Formula I. The chemistry is illustrated in Route 1.

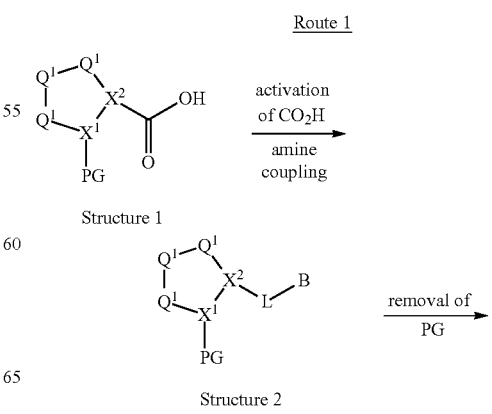

Route 1

Structure 1

Structure 2

-continued

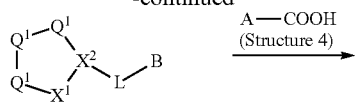

Structure 3

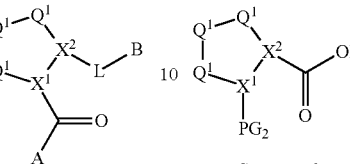

Formula I

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

Route 2

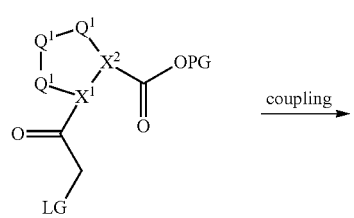

Structure 5

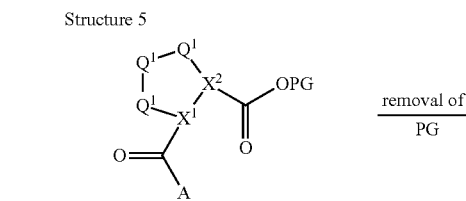

Structure 6

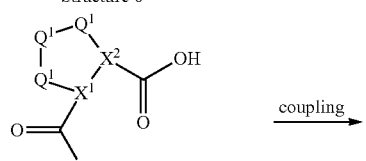

Structure 7

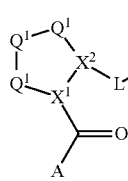

Formula I

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

Route 3

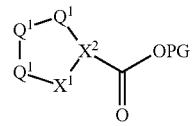

Structure 8

Structure 9

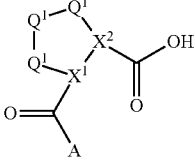

Structure 6

Structure 7

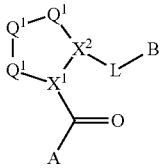

Formula I

In an alternate embodiment, a heteroaryl or aryl moiety, 4-1, is coupled to a central core to generate 4-2. The protected acid, 4-2 is deblocked to form the carboxylic acid, 4-3. The carboxylic acid is then coupled to form an amide (L-B) which is 4-4. The heteroaryl or aryl moiety, A', can then be further derivatized to add substituents at the $X^{11}$, $X^{12}$, $X^{13}$ and $X^{14}$ positions to generate compounds of Formula I. This chemistry is illustrated in Route 4.

Route 4

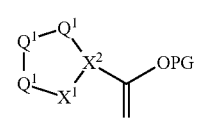

4-1

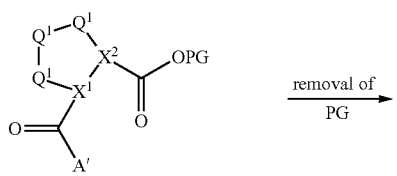

4-2

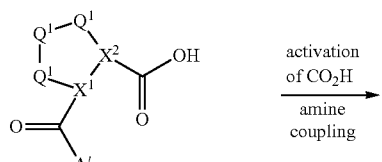

4-3

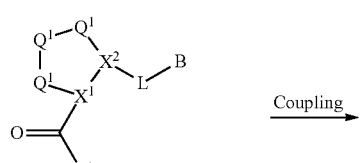

4-4

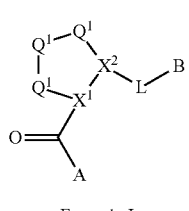

Formula I

In an alternate embodiment, Structure 5-1 is coupled to an acid, Structure 5-2, to generate Structure 5-3. The carboxylic acid, Structure 5-3, is deblocked to generate a carboxylic acid which is Structure 5-4. Carboxylic acid Structure 5-4 is coupled to an amine to form the product amide (L-B) which is a compound within Formula I. This chemistry is illustrated in Route 5.

Route 5

Structure 5-1

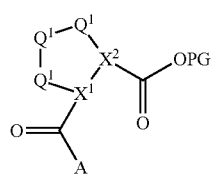

Structure 5-3

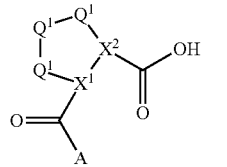

Structure 5-4

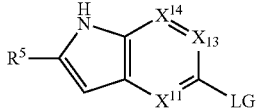

Formula I

In an alternate embodiment, a heteroaryl compound of Structure 10 is acylated to generate a compound of Structure 11, wherein LG is a leaving group. As an example, the leaving group can be a halide, for example bromide. Structure 11 is coupled to Structure 12 to generate Structure 13. In some embodiments, $LG_1$ is a leaving group. In some embodiments, the $LG_1$ is a halide. Structure 13 is coupled to an aryl, heteroaryl or heterocylic compound to generate Structure 14. In some embodiments, Structure 13 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 14 is treated with an organic acid such as, but not limited to, trifluoroacetic acid to generate Structure 15. Structure 15 is coupled to Structure 3 from Route 1 to generate a compound within Formula I. This chemistry is illustrated in Route 6.

Route 6

Structure 10

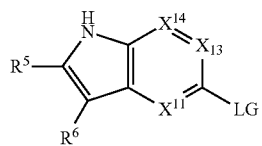

Structure 11

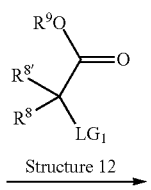

Structure 12

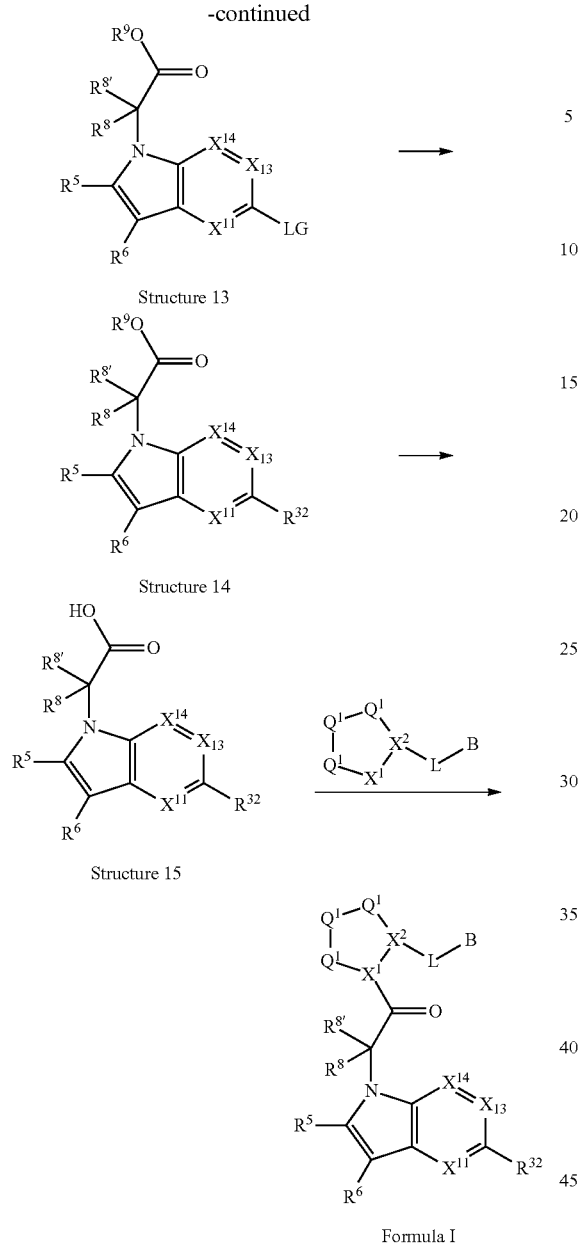

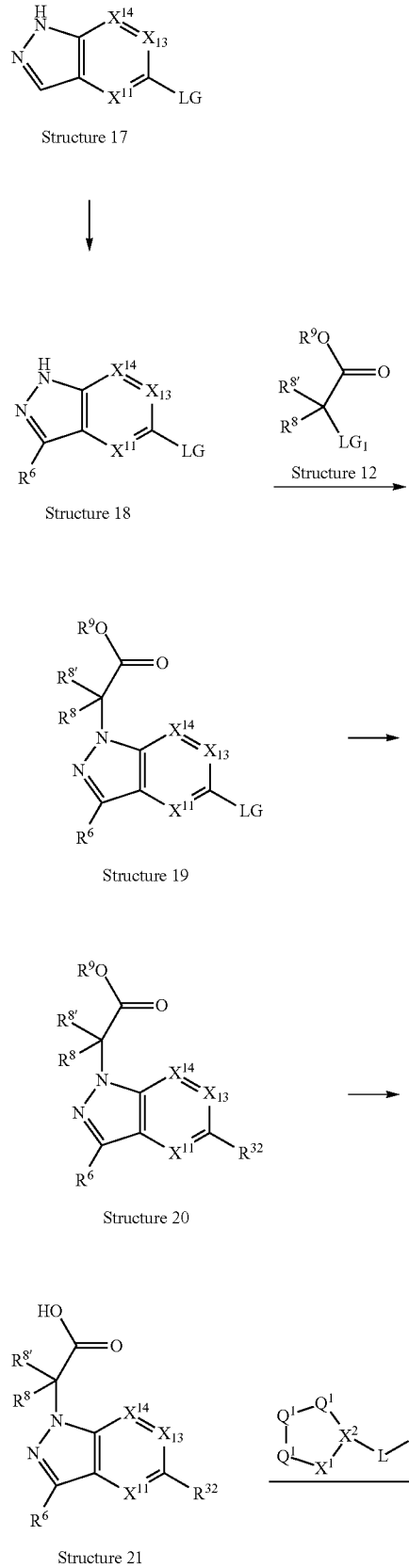

Route 7

Structure 17

Structure 18

Structure 12

Structure 19

Structure 20

Structure 21

In an alternate embodiment, a heteroaryl compound of Structure 17 is acylated to generate a compound of Structure 18, wherein LG is a leaving group. As an example, the leaving group can be a halide, for example bromide. Structure 18 is coupled to an activated ester, Structure 12 from Route 6, wherein $LG_1$ can be a halogen to generate Structure 19.

Structure 19 is coupled to an aryl, heteroaryl or heterocylic compound to generate Structure 20. In some embodiments, Structure 19 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 20 is treated with an organic acid such as, but not limited to, trifluoroacetic acid to generate Structure 21. Structure 21 is coupled to Structure 3 from Route 1 to generate a compound within Formula I. This chemistry is illustrated in Route 7.

-continued

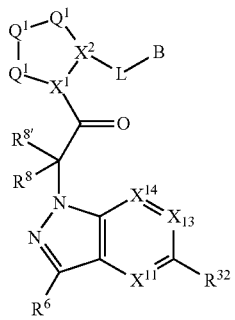

Formula I

In an alternate embodiment, a heteroaryl compound of Structure 8-1 is acylated to generate a compound of Structure 8-2, wherein LG is a leaving group. As an example, the leaving group can be a halide, for example bromide. Structure 8-2 is coupled to Structure 8-3 to generate Structure 8-4. In some embodiments, $LG_1$ is a leaving group. In some embodiments, the $LG_1$ is a halide.

Structure 8-4 is coupled to an aryl, heteroaryl or heterocylic compound to generate Structure 8-5. In some embodiments, Structure 8-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 8-5 is treated with an organic acid such as, but not limited to, trifluoroacetic acid to generate Structure 8-6. Structure 8-6 is coupled to Structure 3 from Route 1 to generate a compound within Formula I. This chemistry is illustrated in Route 8.

Route 8

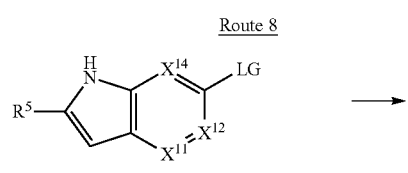

Structure 8-1

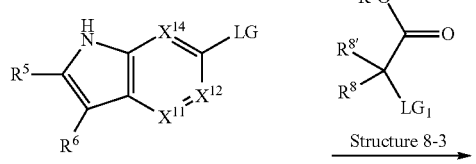 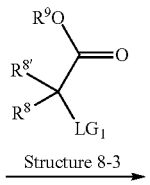

Structure 8-3

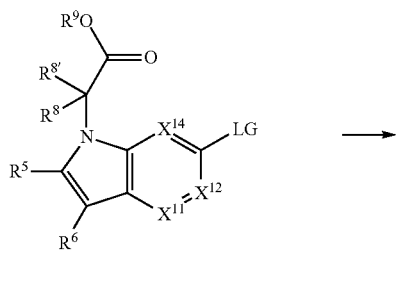

Structure 8-4

-continued

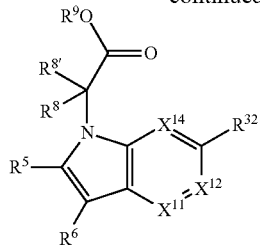 

Structure 8-5

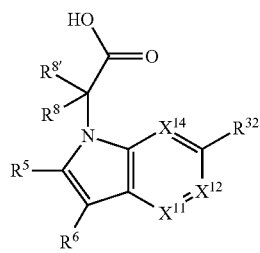 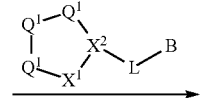

Structure 8-6

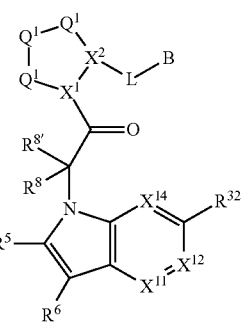

Formula I

In an alternate embodiment, a heteroaryl compound of Structure 9-1 is acylated to generate a compound of Structure 9-2, wherein LG is a leaving group. As an example, the leaving group can be a halide, for example bromide. Structure 9-2 is coupled to an activated ester, Structure 9-3, wherein $LG_1$ can be a halide to generate Structure 9-4. Structure 9-4 is coupled to an aryl, heteroaryl or heterocylic compound to generate Structure 9-5. In some embodiments, Structure 9-4 is treated with an aryl, heteroaryl or heterocylic boronic acid, an organometallic catalyst, a base and an organic solvent. In some embodiments, the organometallic catalyst is tetrakis(triphenylphosphine)palladium (0). In some embodiments, the base is cesium carbonate. In some embodiments, the organic solvent is DMF. Structure 9-5 is treated with an organic acid such as, but not limited to, trifluoroacetic acid to generate Structure 9-6. Structure 9-6 is coupled to Structure 3 from Route 1 to generate a compound within Formula I. This chemistry is illustrated in Route 9.

Route 9
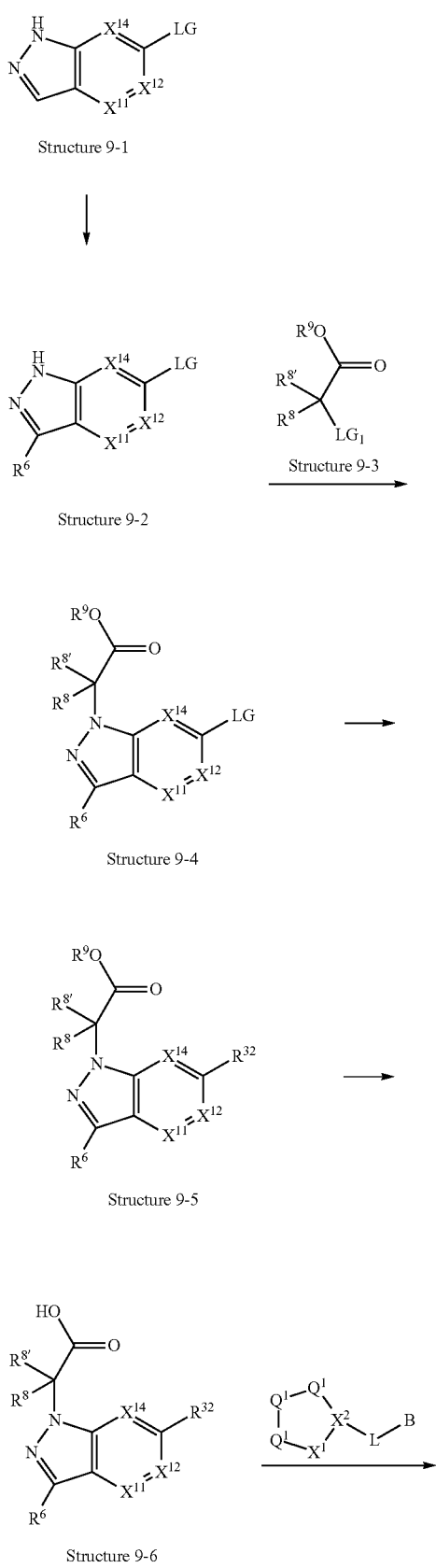
In an alternate embodiment, Structure 10-1 is coupled to an amine to generate an amide (L-B), and Structure 10-2. Structure 10-2, is coupled to an amine to generate compounds within Formula I. This chemistry is illustrated in Route 10.
Route 10
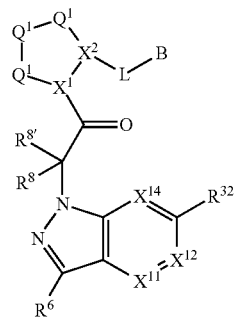
Example 2. Examples of Central Synthons

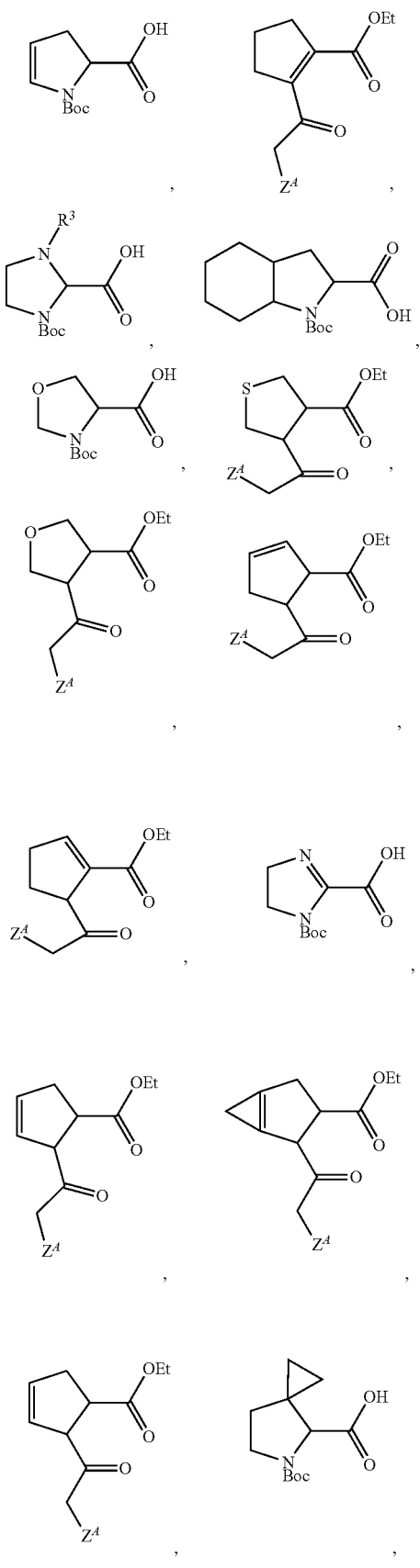
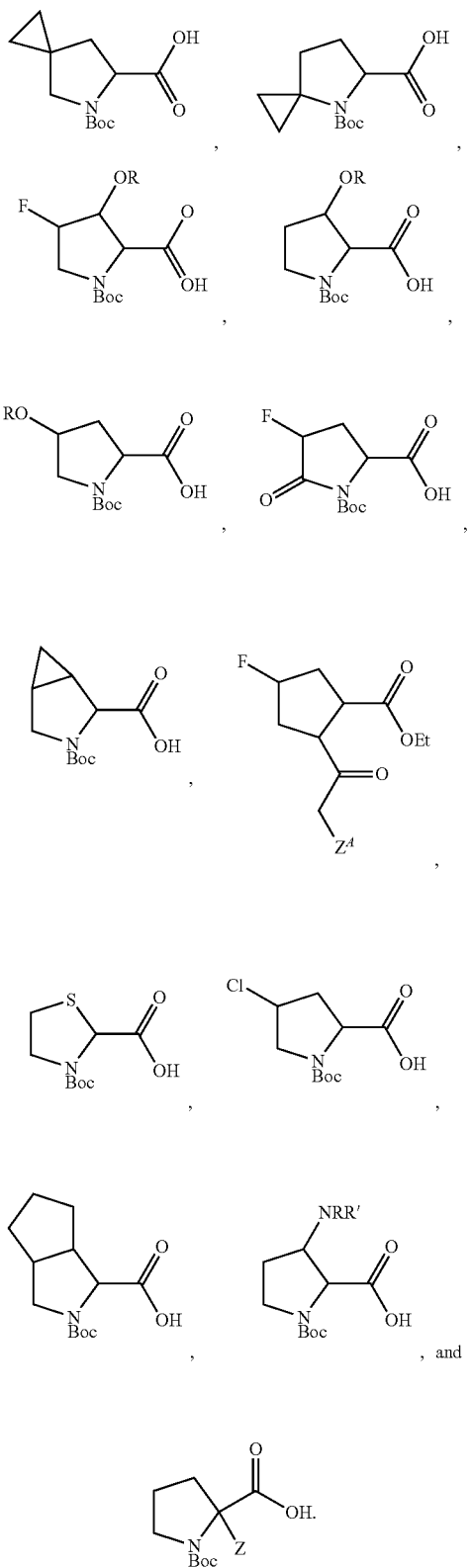
$Z^A$ is halogen.
In one embodiment, deuterated L-proline synthons are disclosed. Deuterated synthons include, but are not limited to, for example, the following compounds:

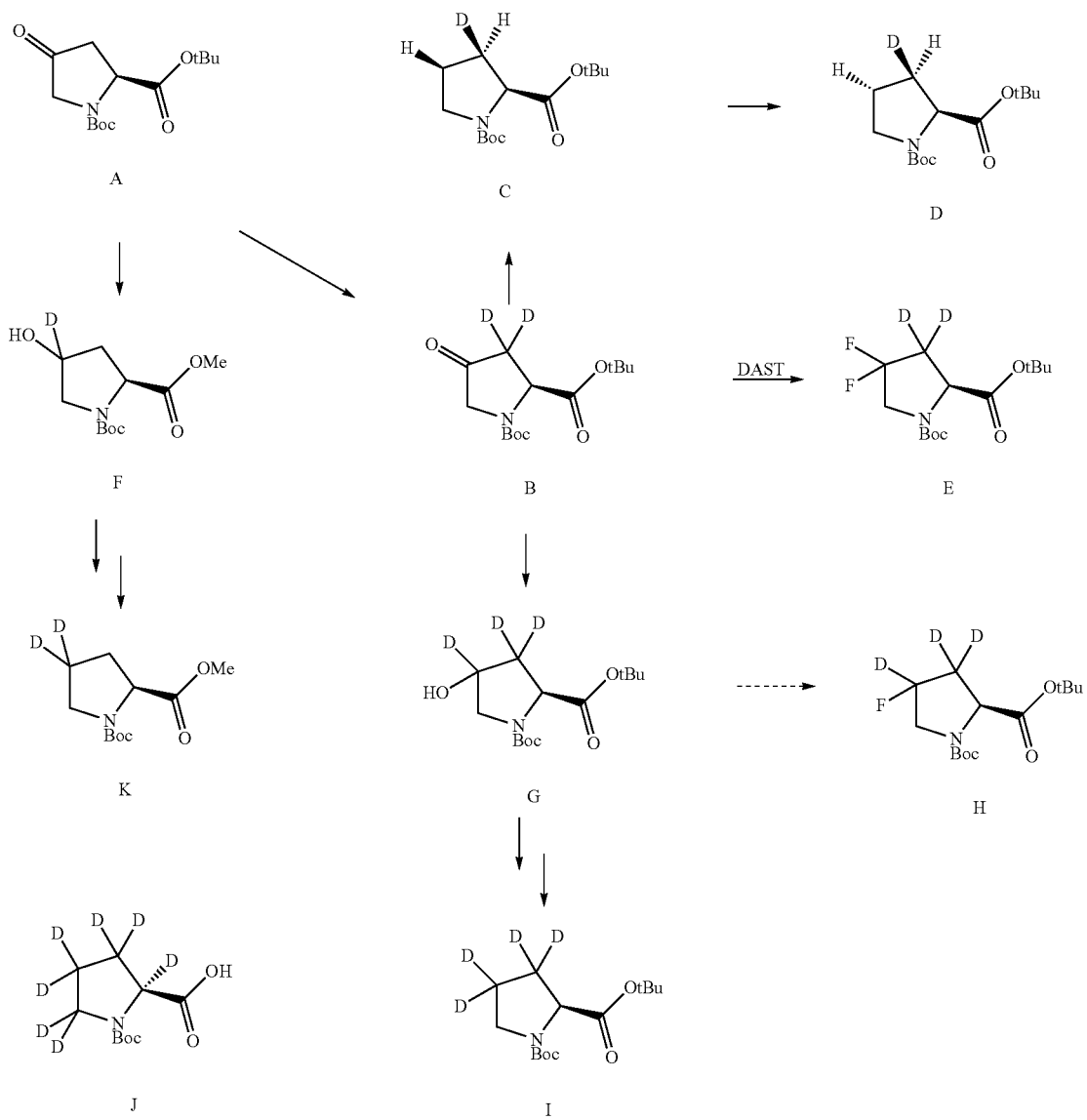

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.-R.; Castro, B. Synthesis 1986, 81-82. Compound F can be used to generate Structure K. See, Dormoy, J.-R.; Castro, B. Synthesis 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.-R.; Castro, B. Synthesis 1986, 81-82. Structure G can be used to generate Structure I. Structure J can be prepared according to Hruby, V. J. et al. J. Am. Chem. Soc. 1979, 101, 202-212. Structures A-J can be used to prepare compounds of Formula I.

Example 3. Preparation of Central-L-B Synthons

Routes 1a, 1b and 1c.

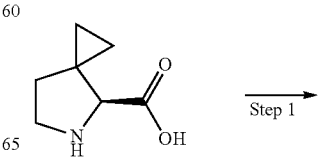

(1a)

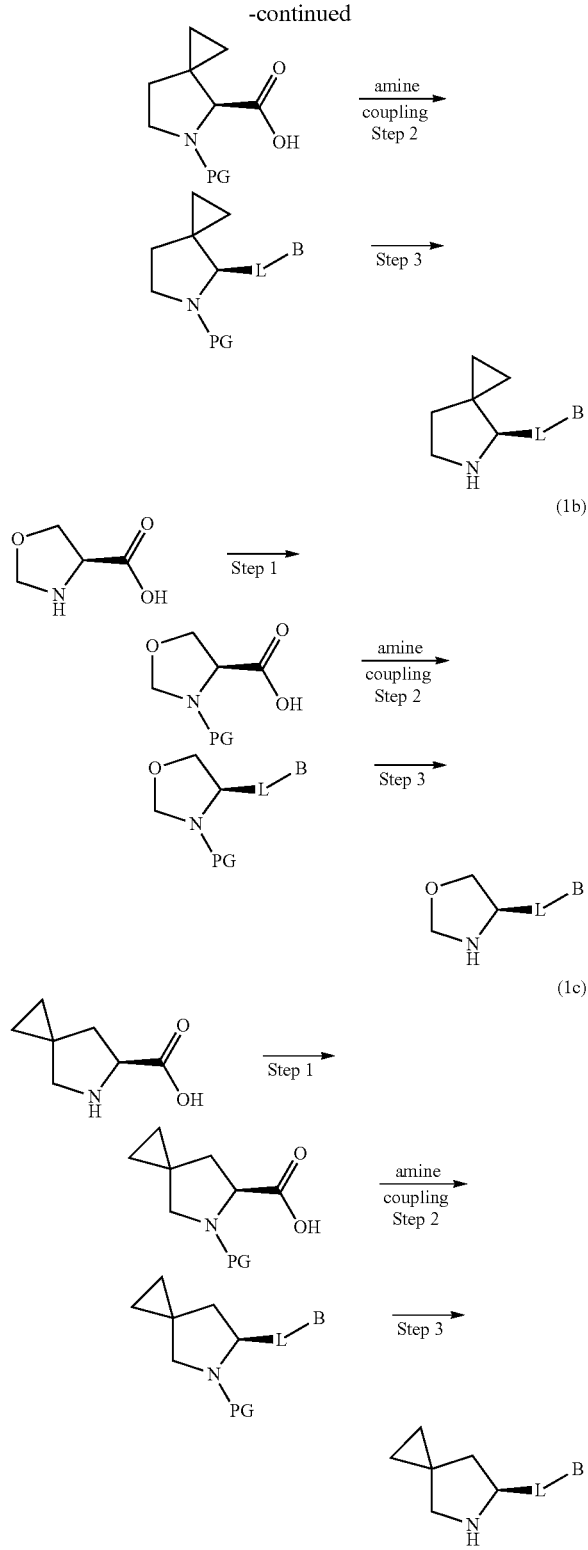

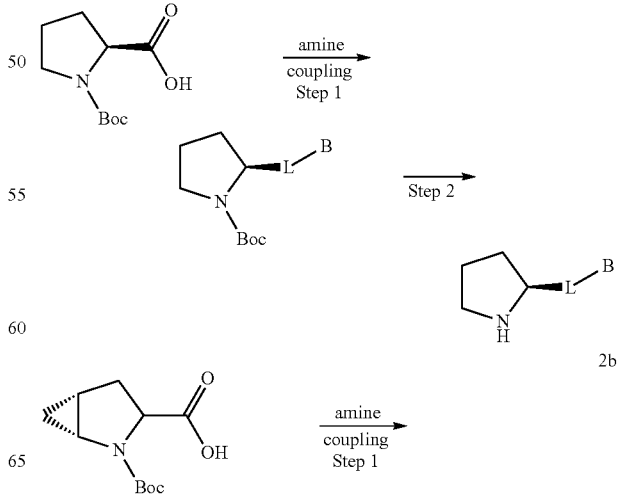

ment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)—, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4] heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

Routes 2a, 2b, 2c, and 2d.

In Route 1a, 5-azaspiro[2.4]heptane-4,5-dicarboxylic acid, 5-(1,1-dimethylethyl) ester, (4S)—, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodi-

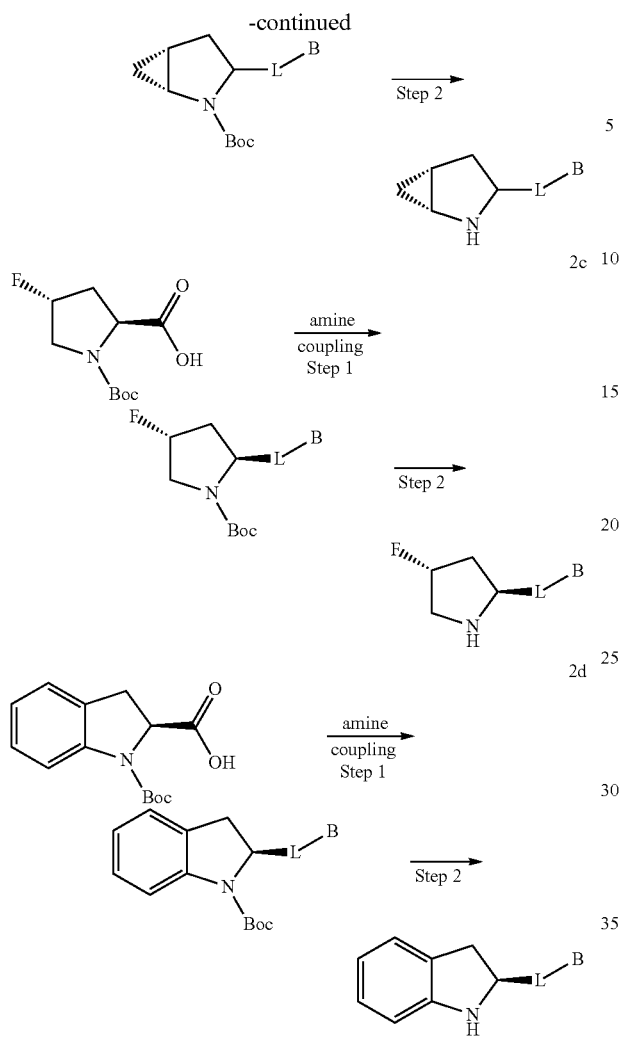

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

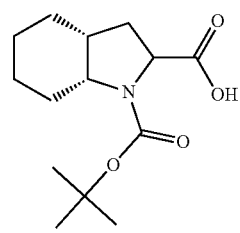 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S, 5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR, 6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl] amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

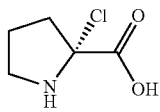

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Examples of Embodiments of Active Compounds

The Figures provide additional examples of the moieties of the active compounds described herein, namely, A, B, L, and the central core. All combinations of the A, B, L, and central core are considered specifically and individually disclosed, and are provided by groupings only for efficiency.

Example 5. Synthesis of Selected Aryl, Hetroaryl, and Heterocyclic Compounds of Formula I Synthesis of (2S,4R)-1-(2-(3-Acetyl-5-(2-methoxy-pyrimidin-5-yl)-1H-indol-1-yl)acetyl)-N-(2'-chloro-2-fluoro-[1,1'-biphenyl]-3-yl)-4-fluoropyrrolidine-2-carboxamide (197)

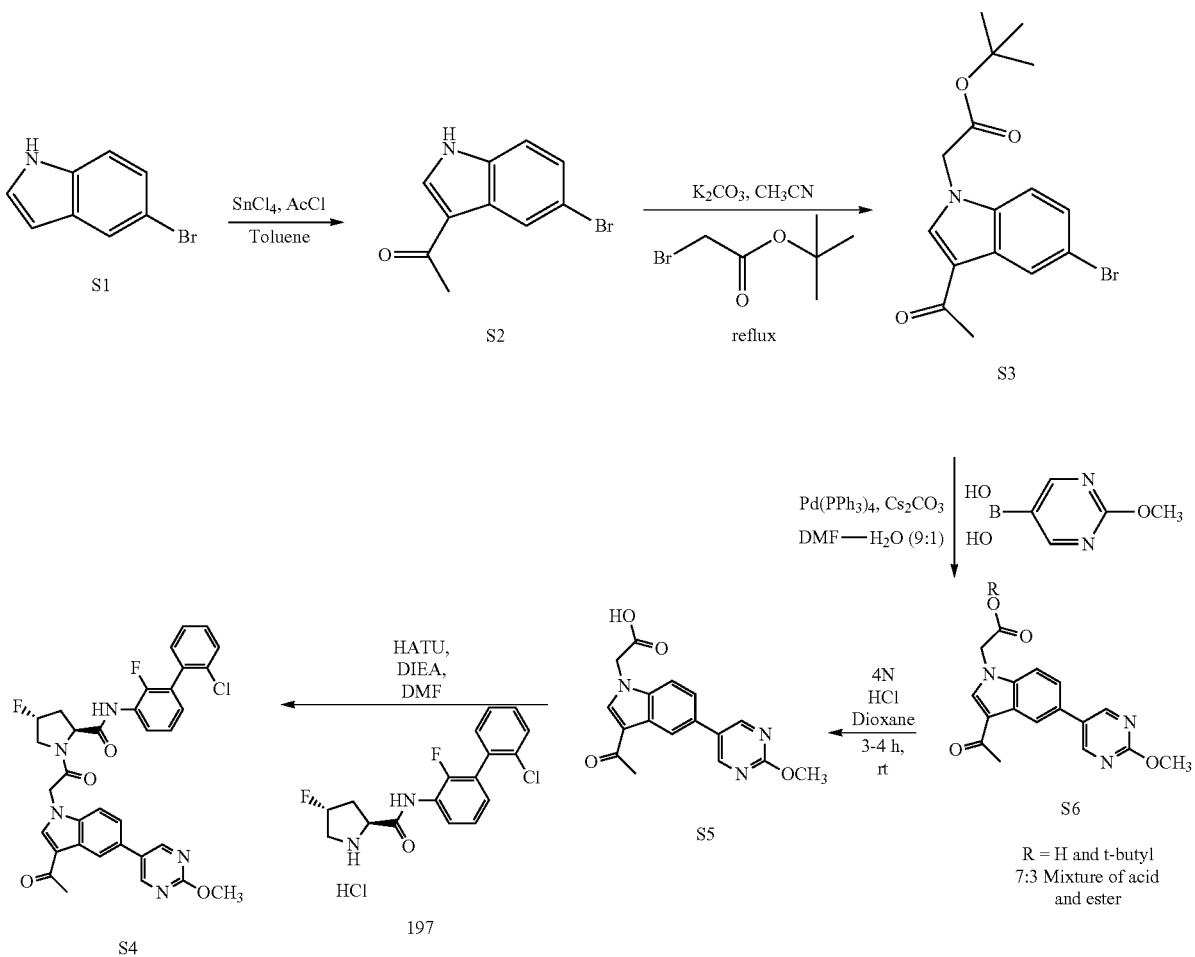

Scheme 1

1-(5-Bromo-1H-indol-3-yl)ethanone (S2) was prepared from 5-bromoindole according to the procedure of MacKay et al. (MacKay, J. A.; Bishop, R.; Rawal, V. H. Org. Lett. 2005, 7, 3421-3424.)

tert-Butyl 2-(3-acetyl-5-bromo-1H-indol-1-yl)acetate (S3)

A mixture of 3.9 g (16.4 mmol) of 1-(5-bromo-1H-indol-3-yl)ethanone, 2.63 mL (18.02 mmol) of tert-butyl bromoacetate and 2.50 g (18.02 mmol) potassium carbonate in anhydrous acetonitrile (80 mL) was refluxed for 5 h. The reaction mixture was then cooled to room temperature and the solvent was removed under reduced pressure. The residue was taken in a 1:1 mixture of CH$_2$Cl$_2$ and water (100 mL: 100 mL). The two layers were separated and the organic layer was washed with water (2×100 mL). Finally, the organic layer was dried (Na$_2$SO$_4$) and concentrated. The resulting residue was stirred with 50 mL of heptane for 30 min, cooled in an ice bath and filtered, washing the solid with cold heptane (10 mL). This cream colored solid was dried under high vacuum to give 5.6 g of tert-butyl 2-(3-acetyl-5-bromo-1H-indol-1-yl)acetate.

tert-Butyl 2-(3-acetyl-5-(2-methoxypyrimidin-5-yl)-1H-indol-1-yl)acetate (S4)

A mixture of 351 mg (1 equiv) of S3, (2-methoxypyrimidin-5-yl)boronic acid (230 mg. 1.5 equiv), cesium carbonate (650 mg, 2 equiv) in DMF (15 mL) and water (1.5 mL) was purged with argon in a pressure vessel for 5 min. Tetrakis(triphenylphosphine)palladium (0) (57 mg, 0.05 equiv) was then added under argon and the pressure vessel was sealed and heated at 100° C. overnight. The reaction mixture was cooled to room temperature and the solvent was removed under reduced pressure. The crude product (7:3 mixture of acid and ester) was used directly in the next synthetic step.

2-(3-Acetyl-5-(2-methoxypyrimidin-5-yl)-1H-indol-1-yl)acetic acid (S5)

tert-Butyl 2-(3-acetyl-5-(2-methoxypyrimidin-5-yl)-1H-indol-1-yl)acetate (crude from above reaction), was taken in 4N HCl dioxane (20 mL) and the resulting reaction mixture was stirred at room temperature for 4 h. After completion of the reaction, the solvent was removed under reduced pressure. The remaining material was used directly in the next synthetic step.

(2S,4R)-1-(2-(3-Acetyl-5-(2-methoxypyrimidin-5-yl)-1H-indol-1-yl)acetyl)-N-(2'-chloro-2-fluoro-[1,1'-biphenyl]-3-yl)-4-fluoropyrrolidine-2-carboxamide (S6)

Compound S5 (100 mg, 1 equiv) from the previous step was dissolved in DMF (10 mL), and iPr$_2$NEt (0.269 mL, 5 equiv) was added. This was followed by the addition of (2S,4R)—N-(3-chloro-(2S,4R)—N-(6-chloropyridin-2-yl)-4-fluoropyrrolidine-2-carboxamide hydrochloride (111 mg, 1 equiv) at 5° C. HATU (263 mg, 2.1 equiv) was then added slowly at this same temperature and the reaction mixture was stirred for 3 h at rt. After completion of the reaction, which was monitored by HPLC, the reaction mixture was added to water (50 mL+10 g NaCl) and extracted with DCM (2×25 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (ISCO eluted with DCM/CH3OH) to give S6. $^1$H NMR (400 MHz, DMSO-d$_6$): (major rotamer) δ 2.13-2.3 (m, 1H), 2.45 (s, 3H), 2.68-2.70 (m, 1H), 3.95-4.05 (m, 4H), 4.16-4.24 (m, 1H), 4.78 (t, J=8 Hz, 1H), 5.28 (d, J=20 Hz, 1H), 5.45 (d, J=20 Hz, 1H), 5.50-5.63 (m, 1H), 7.04-7.08 (m, 1H), 7.20-7.24 (m, 1H), 7.37-7.61 (m, 7H), 7.75-7.78 (m, 1H), 7.94-7.98 (m, 1H), 8.31 (s, 1H), 8.88 (s 1H), 8.97 (s 1H); $^{19}$F NMR (376 MHz, DMSO-d$_6$): (major rotamer) δ −126.64, −175.79. LC (method A): tR=2.16 min. LC/MS (EI) m/z: [M+H]+ calcd for C$_{34}$H$_{28}$ClF$_2$N$_5$O$_4$, 643; found, 644.

(2S,4R)—N-(2'-Chloro-2-fluoro-[1,1'-biphenyl]-3-yl)-4-fluoropyrrolidine-2-carboxamide hydrochloride

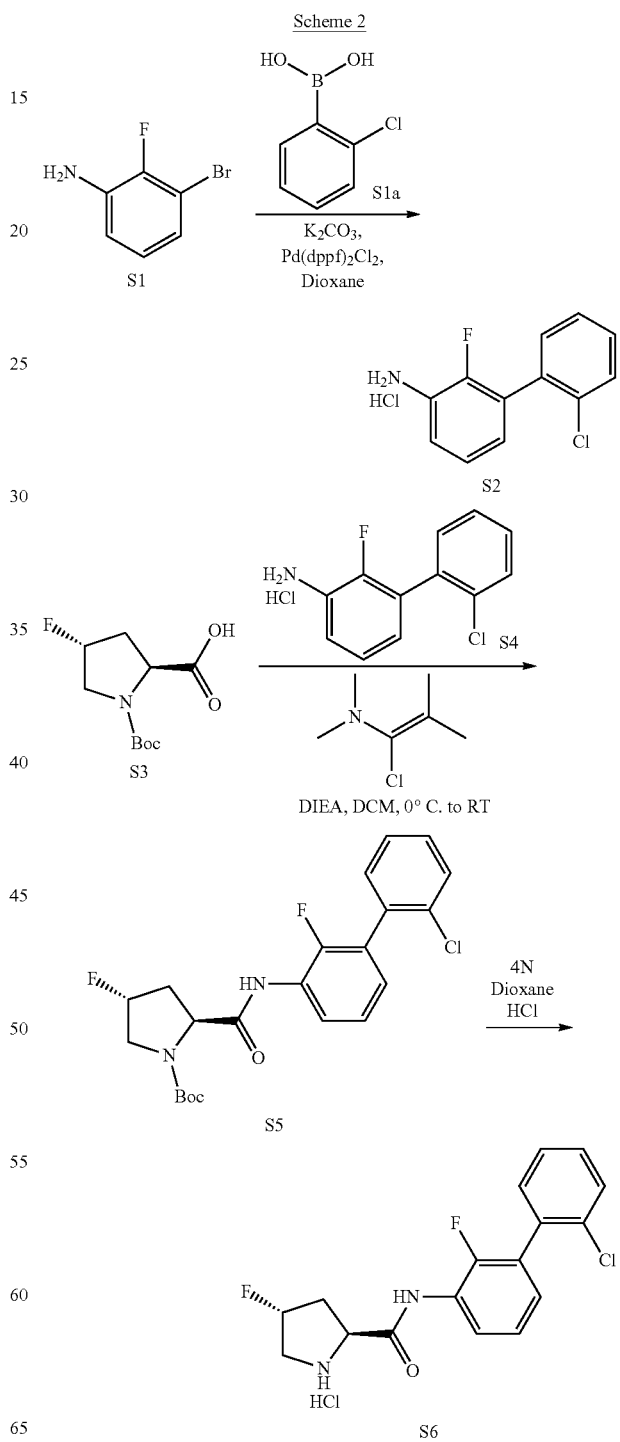

2'-Chloro-2-fluoro-[1,1'-biphenyl]-3-amine hydrochloride (S2)

A mixture of S1 (30 g), S1a (60 g), $K_2CO_3$ (91 g) and $Pd(dppf)_2Cl_2$ (19.25 g) in solvent (dioxane 400 mL, $H_2O$ 100 mL) was purged with argon in a pressure vessel for 5 min and stirred for 15 h at 100° C. The solvent was removed under reduced pressure and the remaining residue was purified by flash column chromatography. The purified material was then dissolved in MeOH and treated with HCl/MeOH. The solvent was removed and the remaining solid was washed with IPA-heptane (1/1) to afford S2.

(2S,4R)-tert-Butyl 2-((2'-chloro-2-fluoro-[1,1'-biphenyl]-3-yl)carbamoyl)-4-fluoropyrrolidine-1-carboxylate (S5)

To an ice-cold solution of S3 (530 mg) in 20 mL of $CH_2Cl_2$, 1-chloro-N,N,2-trimethyl-1-propenylamine (0.333 mL, 1.1 equiv) was added dropwise with stirring. The stirring was continued for 3 h at this temperature and solid S4 (640 mg, 1.1 equiv) was added followed by 1.12 mL of $iPr_2NEt$ (3 equiv). The cooling bath was removed and the reaction mixture was stirred overnight at rt. After completion of the reaction, which was monitored by HPLC, the reaction mixture was added to water (20 mL) and extracted with DCM (2×25 mL). The organic layer was washed successively with an aqueous solution of $NaHCO_3$ (20 mL), water (20 mL), and brine (20 mL), then dried over $Na_2SO_4$ and concentrated under reduced pressure. The remaining residue was purified by flash column chromatography (ISCO eluted with Hexanes/EtOAC) to give S5.

(2S,4R)—N-(2'-Chloro-2-fluoro-[1,1'-biphenyl]-3-yl)-4-fluoropyrrolidine-2-carboxamide hydrochloride (S6)

(2S,4R)-tert-Butyl 2-((2'-chloro-2-fluoro-[1,1'-biphenyl]-3-yl)carbamoyl)-4-fluoropyrrolidine-1-carboxylate S5 (700 mg) was taken in 4N HCl dioxane (25 mL) and the resulting reaction mixture was stirred at room temperature for 3 h. After completion of the reaction, which was monitored by HPLC, the solvent was removed under reduced pressure. The remaining residue 197 was used directly in the next synthetic step (preparation of S6 in Scheme 1).

Example 6. Additional Exemplary Syntheses of Aryl, Hetroaryl, and Heterocyclic Compounds as Described Herein (2S,4R)-1-(2-(3-Acetyl-5-(pryridazin-4-yl)-1H-indol-1-yl)acetyl)-N-(2'-chloro-2-fluoro-[1,1'-biphenyl]-3-yl)-4-fluoropyrrolidine-2-carboxamide (20)

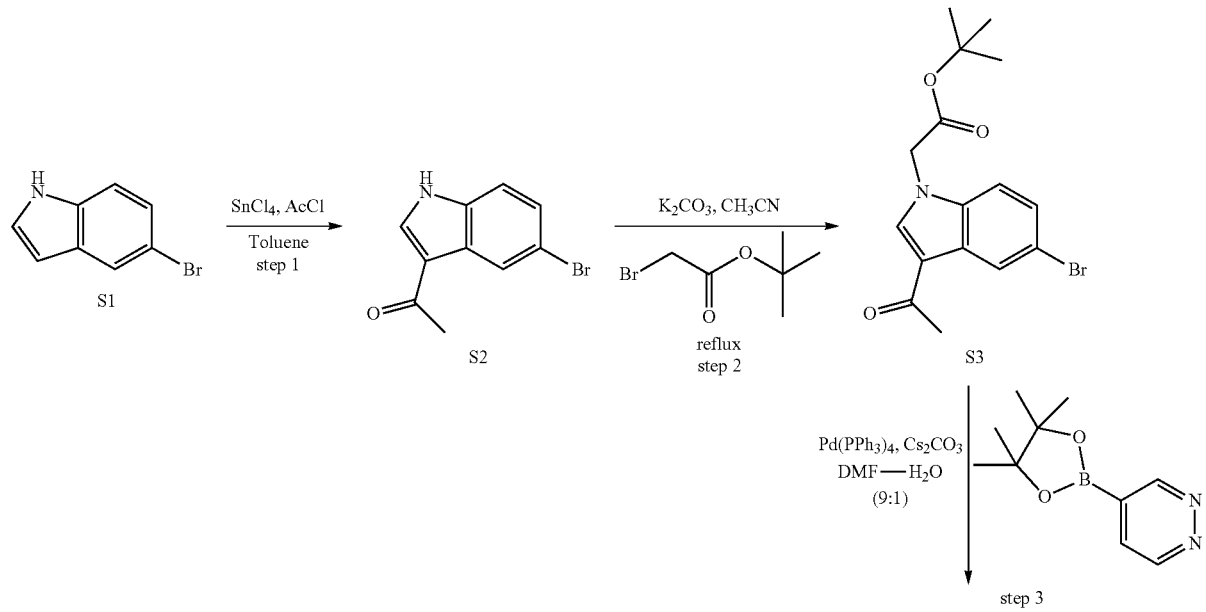

Scheme 3

-continued

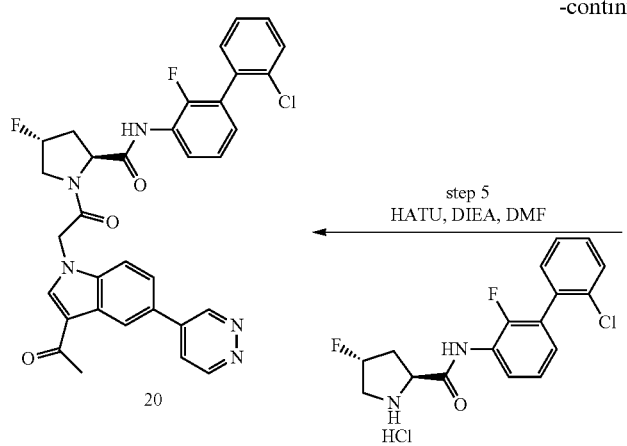

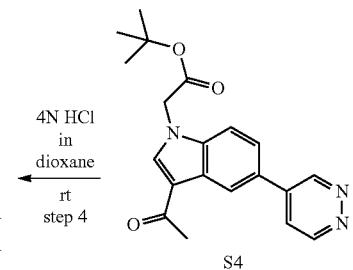

Step 1: 1-(5-Bromo-1H-indol-3-yl)ethanone

The title compound was prepared from 5-bromoindole according to the procedure of MacKay et al. (MacKay, J. A.; Bishop, R.; Rawal, V. H. *Org. Lett.* 2005, 7, 3421-3424.)

Step 2: Tert-Butyl 2-(3-acetyl-5-bromo-1H-indol-1-yl)acetate (S2)

A mixture of 1-(5-bromo-1H-indol-3-yl)ethanone (3.9 g, 16.4 mmol), tert-butyl bromoacetate (2.63 mL, 18.02 mmol), and potassium carbonate (2.50 g, 18.02 mmol) in anhydrous acetonitrile (80 mL) was refluxed for 5 h. The reaction mixture was then cooled to room temperature and the solvent was removed under reduced pressure. The residue was taken in a 1:1 mixture of DCM and water (100 mL: 100 mL). The two layers were separated and the organic layer was washed with water (2×100 mL). Finally, the organic layer was dried ($Na_2SO_4$) and concentrated. The resulting residue was stirred with 50 mL of heptane for 30 min, cooled in an ice bath and filtered where the solid was washed with cold heptane (10 mL). This cream colored solid was dried under high vacuum to give 5.6 g of tert-butyl 2-(3-acetyl-5-bromo-1H-indol-1-yl)acetate.

Step 3: tert-Butyl 2-(3-acetyl-5-(pyridazin-4-yl)-1H-indol-1-yl)acetate (S3)

A mixture of tert-butyl 2-(3-acetyl-5-bromo-1H-indol-1-yl)acetate (351 mg, 1 equiv), 4-(4,4,5,5-tetramethyl-1,3,2-dioxaborolan-2-yl)pyridazine (250 mg, 1.5 equiv), cesium carbonate (700 mg, 2 equiv), DMF (15 mL), and water (1.5 mL) was purged with argon in a pressure vessel for 5 min. Tetrakis(triphenylphosphine)palladium (0) (57 mg, 0.05 equiv) was then added under argon and the pressure vessel was sealed and heated at 100° C. overnight. The reaction mixture was cooled to room temperature and the solvent was removed under reduced pressure. The crude product was used directly in the next synthetic step.

Step 4: 2-(3-Acetyl-5-(pyridazin-4-yl)-1H-indol-1-yl)acetic acid (S4)

tert-Butyl 2-(3-acetyl-5-(pyridazin-4-yl)-1H-indol-1-yl)acetate (crude from above reaction) was taken in 4 N HCl in dioxane (20 mL) and the resulting reaction mixture was stirred at room temperature for 4 h. The solvent was removed under reduced pressure and the remaining material was used directly in the next synthetic step.

Step 5: (2S,4R)-1-(2-(3-Acetyl-5-(pryridazin-4-yl)-1H-indol-1-yl)acetyl)-N-(2'-chloro-2-fluoro-[1,1'-biphenyl]-3-yl)-4-fluoropyrrolidine-2-carboxamide (20)

2-(3-Acetyl-5-(pyridazin-4-yl)-1H-indol-1-yl)acetic acid (100 mg, 1 equiv) was dissolved in DMF (10 mL), and DIEA (0.269 mL, 5 equiv) was added. This was followed by the addition of (2S,4R)—N-(3-chloro-(2S,4R)—N-(6-chloropyridin-2-yl)-4-fluoropyrrolidine-2-carboxamide hydrochloride (111 mg, 1 equiv) at 5° C. HATU (263 mg, 2.1 equiv) was then added slowly at this same temperature and the reaction mixture was stirred for 3 h at rt. The reaction mixture was then added to water (50 mL+10 g solid NaCl) and extracted with DCM (2×25 mL). The organic layer was washed successively with an aqueous solution of $NaHCO_3$ (20 mL), water (20 mL), and brine (20 mL), then dried over $Na_2SO_4$ and concentrated under reduced pressure. The remaining residue was purified by flash column chromatography (eluted with DCM/MeOH) to give 20. $^1$H NMR (400 MHz, DMSO-$d_6$): (major rotamer) δ 2.13-2.30 (m, 1H), 2.45 (s, 3H), 2.58-2.68 (m, 1H), 3.95-4.05 (m, 1H), 4.13-4.22 (m, 1H), 4.75 (t, J=8 Hz, 1H), 5.28 (d, J=20 Hz, 1H), 5.45 (d, J=20 Hz, 1H), 5.50-5.63 (m, 1H), 7.06-7.10 (m, 1H), 7.31-7.49 (m, 4H), 7.51-7.61 (m, 1H), 7.65-7.80 (m, 1H), 7.92-8.03 (m, 2H), 8.35 (s, 1H), 8.61 (s 1H), 9.23 (d, 1H), 9.61 (s, 1H), 9.97 (s, 1H); $^{19}$F NMR (376 MHz, DMSO-$d_6$): (major rotamer) δ −126.74, −175.78. LC (method A): $t_R$=2.58 min. LC/MS (EI) m/z: [M+H]$^+$ 614.

tert-Butyl 2-(5-bromo-3-carbamoyl-1H-indazol-1-yl)acetate

Scheme 4

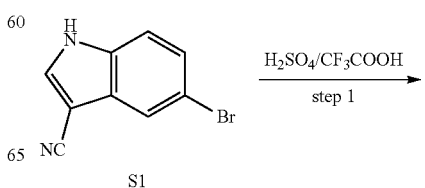

131

132

1-(2-((2S,4R)-2-((2'-Chloro-2-fluoro-[1,1'-biphenyl)
carbamoyl)-4-fluoropyrrolidin-1-yl)-2-oxoethyl)-5-
(1H-pyrazol-4-yl)-1H-indazole-3-carboxamide (1)

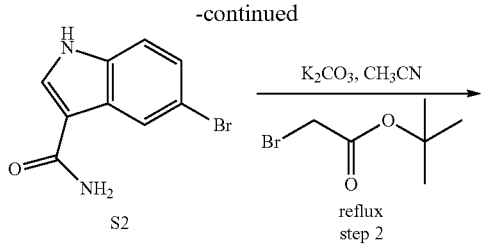

Scheme 5

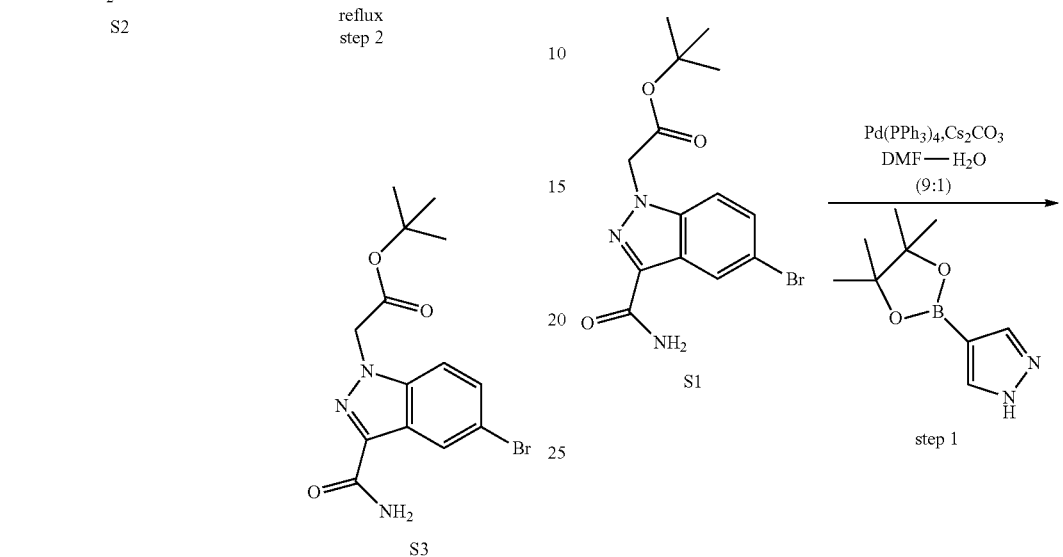

Step 1: 5-Bromo-1H-indole-3-carboxamide (S2)

A mixture of 5-bromo-1H-indole-3-carbonitrile (10 g) in TFA (160 mL) and sulfuric acid (40 mL) was stirred at room temperature for 4 h. The reaction mixture was then poured into ice, and the precipitated solid was collected by filtration, washed with water, and dried in vacuo to give 5-bromo-1H-indole-3-carboxamide.

Step 2: tert-Butyl 2-(5-bromo-3-carbamoyl-1H-indazol-1-yl)acetate (S3)

A mixture of 5-bromo-1H-indole-3-carboxamide (9.8 g, 41.66 mmol), tert-butyl bromoacetate (6.67 mL, 1.1 equiv), and potassium carbonate (6.32 g, 1.1 equiv) in anhydrous acetonitrile (100 mL) was refluxed for 5 h. The reaction mixture was then cooled to room temperature and the solvent was removed under reduced pressure. The residue was taken in a mixture of DCM and water. The two layers were separated and the organic layer was washed with water, dried (Na$_2$SO$_4$), and concentrated. The remaining residue was purified by flash column chromatography (eluted with DCM/MeOH) to give tert-butyl 2-(5-bromo-3-carbamoyl-1H-indazol-1-yl)acetate.

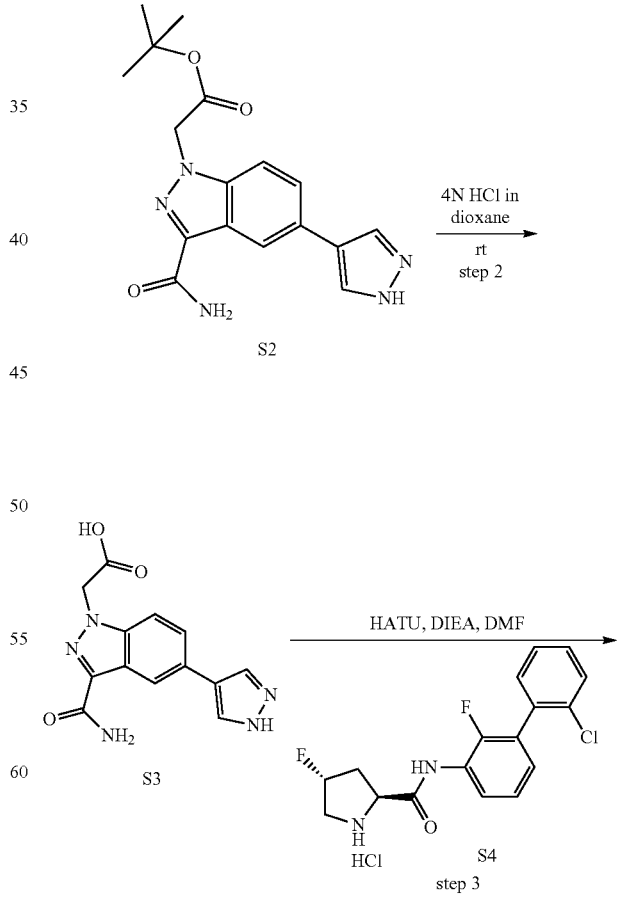

-continued

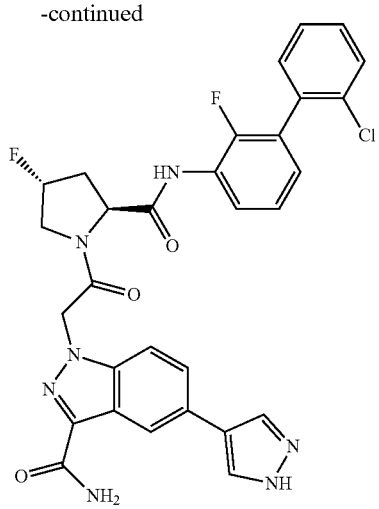

1

Step 1: tert-Butyl 2-(3-carbamoyl-5-(1H-pyrazol-4-yl)-1H-indazol-1-yl)acetate (S2)

A mixture of tert-butyl-2-(5-bromo-3-carbamoyl-1H-indazol-1-yl)acetate (211 mg, 1 equiv), 4-(4,4,5,5-tetramethyl-1,3,2-dioxaborolan-2-yl)-1H-pyrazole (140 mg), cesium carbonate (391 mg, 2 equiv), DMF (10 mL), and water (1.0 mL) was purged with argon in a pressure vessel for 5 min. Tetrakis(triphenylphosphine)palladium (0) (35 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(1H-pyrazol-4-yl)-1H-indazol-1-yl)acetic acid (S3)

tert-Butyl 2-(3-carbamoyl-5-(1H-pyrazol-4-yl)-1H-indazol-1-yl)acetate (crude from above reaction) was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-((2S,4R)-2-((2'-Chloro-2-fluoro-[1,1'-biphenyl)carbamoyl)-4-fluoropyrrolidin-1-yl)-2-oxoethyl)-5-(1H-pyrazol-4-yl)-1H-indazole-3-carboxamide (1)

2-(3-Carbamoyl-5-(1H-pyrazol-4-yl)-1H-indazol-1-yl) acetic acid (100 mg, 1 equiv) was dissolved in DMF, (10 mL) and DIEA (0.269 mL, 5 equiv) was added. This was followed by the addition of (2S,4R)—N-(3-chloro-(2S,4R)—N-(6-chloropyridin-2-yl)-4-fluoropyrrolidine-2-carboxamide hydrochloride (111 mg, 1 equiv) at 5° C. HATU (263 mg, 2.1 equiv) was then added slowly at this same temperature and the reaction mixture was stirred for 3 h at room temperature. The reaction mixture was then added to water (50 mL+10 g solid NaCl) and extracted with DCM (2×25 mL). The organic layer was washed successively with an aqueous solution of NaHCO₃ (20 mL), water (20 mL), and brine (20 mL), then dried over Na₂SO₄ and concentrated under reduced pressure. The remaining residue was purified by flash column chromatography (eluted with DCM/MeOH) to give 1. $^1$H NMR (400 MHz, DMSO-$d_6$): (major rotamer) δ 2.01-2.21 (m, 1H), 2.49-2.55 (m, 1H), 3.80-3.92 (m, 1H), 4.08-4.21 (m, 1H), 4.61 (t, 1H), 5.47-5.62 (m, 3H), 7.05 (t, 1H), 7.15 (t, J=8.0 Hz, 1H), 7.31-7.40 (m, 4H), 7.49-7.62 (m, 5H), 7.77 (m, 1H), 8.21 (s, 1H); $^{19}$F NMR (376 MHz, DMSO-$d_6$): (major rotamer) δ −126.75, −175.87. LC (method A): $t_R$=1.79 min. LC/MS (EI) m/z: [M+H]⁺ 604.

1-(2-((2S,4R)-2-((2'-Chloro-2-fluoro-[1,1'-biphenyl)carbamoyl)-4-fluoropyrrolidin-1-yl)-2-oxoethyl)-5-(pyrimidin-5-yl)-1H-indazole-3-carboxamide (2)

Scheme 6

-continued

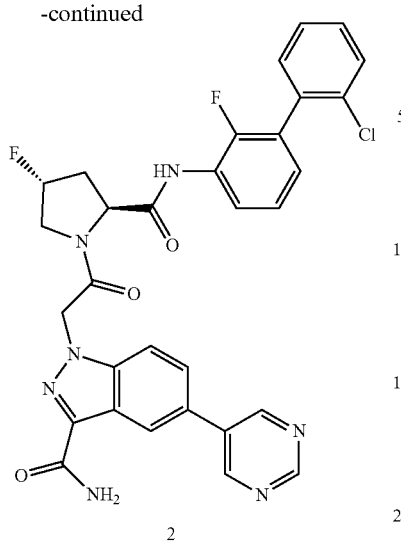

2

Step 1: tert-Butyl 2-(3-carbamoyl-5-(pyrimidin-5-yl)-1H-indazol-1-yl)acetate (S2)

A mixture of tert-butyl-2-(5-bromo-3-carbamoyl-1H-indazol-1-yl)acetate (211 mg), pyrimidin-5-ylboronic acid (82 mg), cesium carbonate (391 mg, 2 equiv), DMF (9 mL), and water (1.0 mL) was purged with argon in a pressure vessel for 5 min. Tetrakis(triphenylphosphine)palladium (0) (40 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(pyrimidin-5-yl)-1H-indazol-1-yl)acetic acid (S3)

tert-butyl 2-(3-carbamoyl-5-(pyrimidin-5-yl)-1H-indazol-1-yl)acetate (crude from above reaction), was taken in 4N HCl dioxane (5 mL) and the resulting reaction mixture was stirred at room temperature for 4 h. The solvent was removed under reduced pressure and the remaining material was used directly in the next synthetic step.

Step 3: 1-(2-((2S,4R)-2-((2'-Chloro-2-fluoro-[1,1'-biphenyl)carbamoyl)-4-fluoropyrrolidin-1-yl)-2-oxoethyl)-5-(pyrimidin-5-yl)-1H-indazole-3-carboxamide (2)

2-(3-Carbamoyl-5-(pyrimidin-5-yl)-1H-indazol-1-yl)acetic acid (45 mg, 1 equiv) from the previous step was dissolved in DMF (10 mL) and DIEA (0.12 mL, 5 equiv) was added, which was followed by the addition of (2S,4R)—N-(3-chloro-(2S,4R)—N-(6-chloropyridin-2-yl)-4-fluoropyrrolidine-2-carboxamide hydrochloride (50 mg, 1 equiv) at 5° C. HATU (118 mg, 2.1 equiv) was then added slowly at this same temperature and the reaction mixture was stirred for 3 h at rt. The reaction mixture was then added to water (25 mL+5 g solid NaCl) and extracted with DCM (2×15 mL). The organic layer was washed successively with an aqueous solution of NaHCO$_3$ (10 mL), water (10 mL), and brine (10 mL), then dried over Na$_2$SO$_4$ and concentrated under reduced pressure. The remaining residue was purified by flash column chromatography (eluted with DCM/MeOH) to give 2. $^1$H NMR (400 MHz, DMSO-d$_6$): (major rotamer) δ 2.11-2.29 (m, 1H), 2.51-2.62 (m, 1H), 3.89-4.08 (m, 1H), 4.18-4.30 (m, 1H), 4.76 (t, 1H), 5.48-5.76 (m, 3H), 7.06 (t, 1H), 7.23 (t, J=8.0 Hz, 1H), 7.37-7.48 (m, 4H), 7.57 (m, 1H), 7.72-7.88 (m, 2H), 7.86 (t, 1H), 8.47 (s, br, 1H), 9.15 (s, 2H), 9.21 (s, 1H), 9.99 (s, 1H); $^{19}$F NMR (376 MHz, DMSO-d$_6$): (major) δ −126.69, −175.86. LC (method A): t$_R$=1.82 min. LC/MS (EI) m/z: [M+H]+ 616.

1-(2-((2S,4R)-2-((2'-Chloro-2-fluoro-[1,1'-biphenyl]-3-yl)carbamoyl)-4-fluoropyrrolidin-1-yl)-2-oxo-ethyl)-5-(2-pyrrolidin-1-yl)pyrimidin-5-yl)-1H-indazole-3-carboxamide (10)

Scheme 7

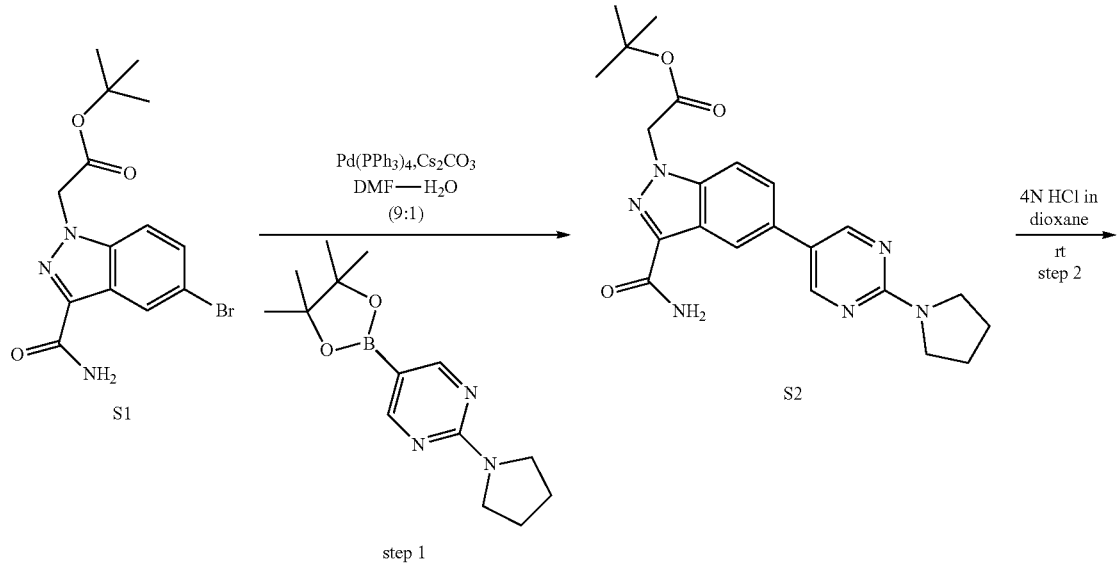

step 1

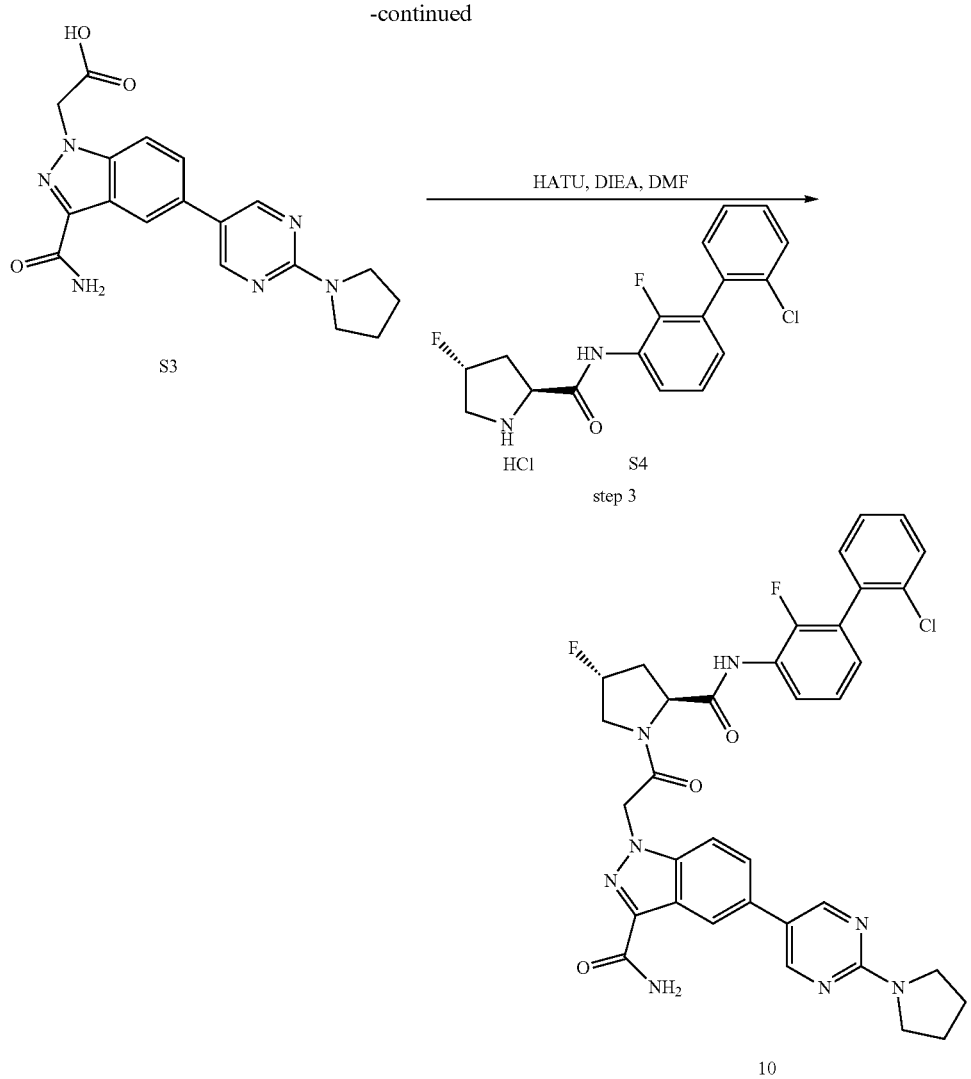

Step 1: tert-Butyl 2-(3-carbamoyl-5-(2-pyrrolidin-1-yl)pyrimidin-5-yl)-1H-indazol-1-yl)acetate (S2)

A mixture of tert-butyl-2-(5-bromo-3-carbamoyl-1H-indazol-1-yl)acetate (316 mg), 2-(pyrrolidin-1-yl)-5-(4,4,5,5-tetramethyl-1,3,2-dioxaborolan-2-yl)pyrimidin (271 mg), cesium carbonate (350 mg, 2 equiv), DMF (10 mL), and water (1.5 mL) was purged with argon in a pressure vessel for 5 min. Tetrakis(triphenylphosphine)palladium (0) (57 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(2-pyrrolidin-1-yl)pyrimidin-5-yl)-1H-indazol-1-yl)acetic acid (S3)

tert-Butyl 2-(3-carbamoyl-5-(2-pyrrolidin-1-yl)pyrimidin-5-yl)-1H-indazol-1-yl)acetate (crude from above reaction), was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-((2S,4R)-2-((2'-Chloro-2-fluoro-[1,1'-biphenyl]-3-yl)carbamoyl)-4-fluoropyrrolidin-1-yl)-2-oxoethyl)-5-(2-pyrrolidin-1-yl)pyrimidin-5-yl)-1H-indazole-3-carboxamide (10)

2-(3-Carbamoyl-5-(2-pyrrolidin-1-yl)pyrimidin-5-yl)-1H-indazol-1-yl)acetic acid (110 mg, 1 equiv) was dissolved in DMF (10 mL) and DIEA (0.3 mL) was added, which was followed by the addition of (2S,4R)—N-(3-chloro-(2S,4R)—N-(6-chloropyridin-2-yl)-4-fluoropyrrolidine-2-carboxamide hydrochloride (110 mg, 1 equiv) at 5° C. HATU (118 mg) was then added slowly at this same temperature and the reaction mixture was stirred for 3 h at rt. The reaction mixture was then added to water (50 mL+10 g solid NaCl) and extracted with DCM (2×20 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (eluted with DCM/MeOH) to give 10. $^1$H NMR (400 MHz, DMSO-d$_6$): (major rotamer) δ 1.96 (m, 4H), 2.07-2.25 (m, 1H), 2.49-2.62 (m, 1H), 3.53 (m, 4H), 3.78-3.92 (m, 1H), 4.18-4.27 (m, 1H), 4.66 (t, 1H), 5.45-5.51 (m, 1H), 5.58-5.69 (m, 2H), 7.04 (t, 1H), 7.21 (t, J=8.0 Hz, 1H), 7.32-7.48 (m, 4H), 7.53-7.69 (m, 4H), 7.95 (m, 1H), 8.24 (s, 1H), 9.97 (s, 1H); $^{19}$F NMR (376 MHz, DMSO-d$_6$): (major rotamer) δ −126.70, −175.88. LC (method A): $t_R$=2.33 min. LC/MS (EI) m/z: [M+H]$^+$ 685.

1-(2-((2S,4R)-2-((2'-Chloro-2-fluoro-[1,1'-biphenyl]-3-yl)carbamoyl)-4-fluoropyrrolidin-1-yl)-2-oxoethyl)-5-(6-fluoropyridin-3-yl)-1H-indazole-3-carboxamide (12)

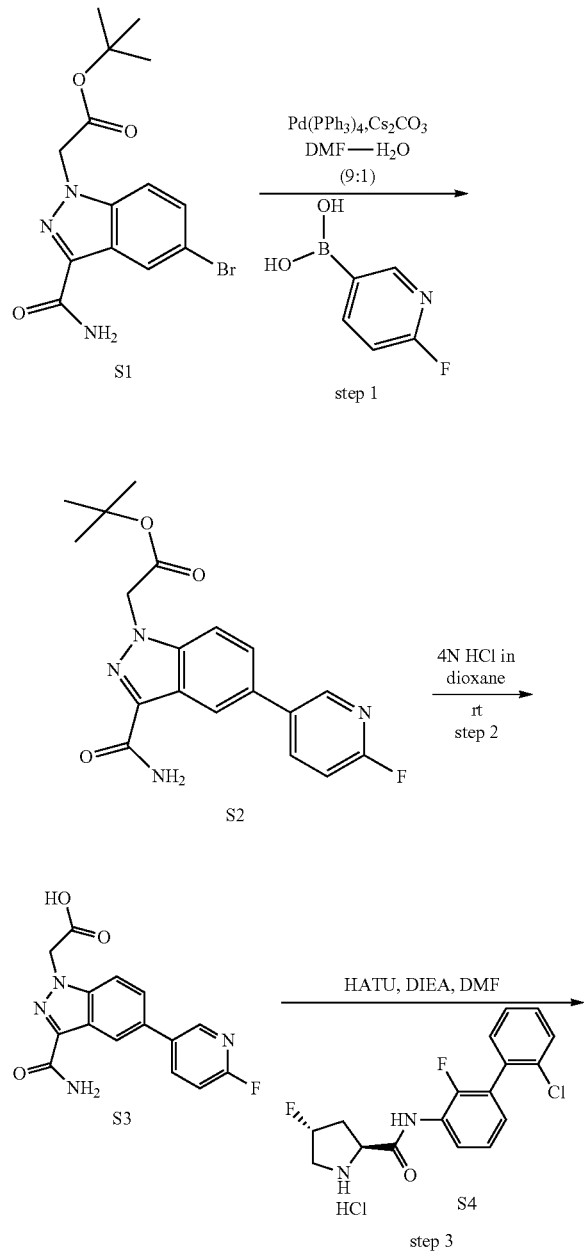

Step 1: tert-Butyl 2-(3-carbamoyl-5-(6-fluoropyridin-3-yl)-1H-indazol-1-yl)acetate (S2)

A mixture of tert-butyl-2-(5-bromo-3-carbamoyl-1H-indazol-1-yl)acetate (211 mg), 6-fluoropyridin-3-ylboronic acid (135 mg), cesium carbonate (350 mg, 2 equiv), DMF (9 mL), and water (1.0 mL) was purged with argon in a pressure vessel for 5 min. Tetrakis(triphenylphosphine)palladium (0) (50 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(6-fluoropyridin-3-yl)-1H-indazol-1-yl)acetic acid (S3)

tert-Butyl 2-(3-carbamoyl-5-(6-fluoropyridin-3-yl)-1H-indazol-1-yl)acetate (crude from above reaction), was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-((2S,4R)-2-((2'-Chloro-2-fluoro-[1,1'-biphenyl]-3-yl)carbamoyl)-4-fluoropyrrolidin-1-yl)-2-oxoethyl)-5-(6-fluoropyridin-3-yl)-1H-indazole-3-carboxamide (12)

2-(3-Carbamoyl-5-(6-fluoropyridin-3-yl)-1H-indazol-1-yl)acetic acid (110 mg, 1 equiv) was dissolved in DMF (10 mL), and DIEA (0.3 mL) was added which was followed by the addition of (2S,4R)—N-(3-chloro-(2S,4R)—N-(6-chloropyridin-2-yl)-4-fluoropyrrolidine-2-carboxamide hydrochloride (110 mg, 1 equiv) at 5° C. HATU (118 mg) was then added slowly at this same temperature and the reaction mixture was stirred for 3 h at rt. The reaction mixture was then added to water (50 mL+10 g solid NaCl) and extracted with DCM (2×20 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (eluted with DCM/MeOH) to give 12. $^1$H NMR (400 MHz, DMSO-$d_6$): (major rotamer) δ 2.10-2.32 (m, 1H), 2.49-2.65 (m, 1H), 3.88-4.06 (m, 1H), 4.18-4.29 (m, 1H), 4.73 (t, 1H), 5.95-5.74 (m, 3H), 7.05 (t, 1H), 7.21 (t, J=8.0 Hz, 1H), 7.31-7.48 (m, 5H), 7.46 (m, 1H), 8.27 (m, 1H), 8.39 (s, 1H), 8.55 (s, 1H), 9.98 (s, 1H); $^{19}$F NMR (376 MHz, DMSO-$d_6$): (major rotamer) δ −125.25, −175.87. LC (method A): $t_R$=2.43 min. LC/MS (EI) m/z: [M+H]$^+$ 633.

(1R,3S,5R)—N-(6-Bromopyridin-2-yl)-2-azabicyclo[3.1.0]hexane-3-carboxamide Hydrochloride

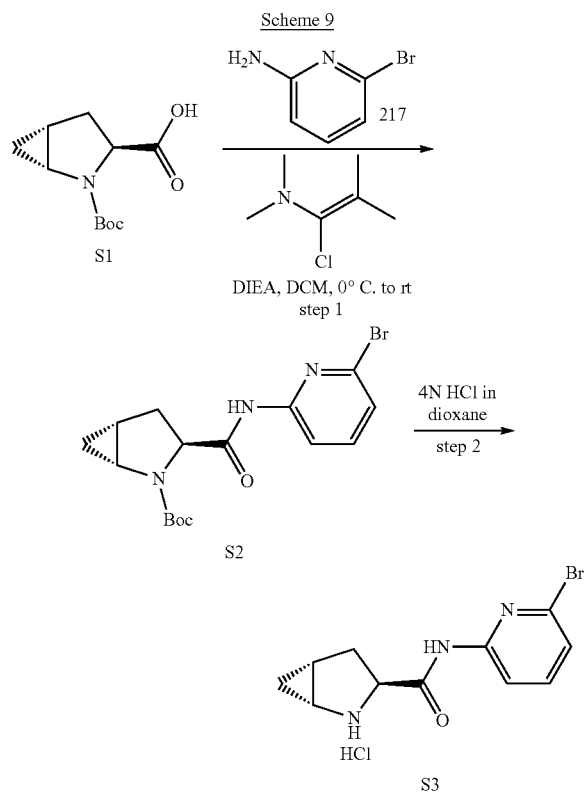

Step 1: (1R,3S,5R)-tert-Butyl 3-((6-bromopyridin-2-yl)carbamoyl)-2-azabicyclo[3.1.0]hexane-2-carboxylate (S2)

To an ice-cold solution of (1R,3S,5R)-tert-butoxycarbonyl)-2-azabicyclo[3.1.0]hexane-2-carboxylic acid (1.5 g) in DCM (20 mL) was added 1-chloro-N,N,2-trimethyl-1-propenylamine (998 mg, 1.1 equiv) dropwise with stirring. The stirring was continued for 3 h at this temperature, and then solid 6-bromopyridin-2-amine (1.3 g, 1.1 equiv) was added, followed by DIEA (3.34 mL, 3 equiv). The cooling bath was removed and the reaction mixture was stirred overnight at room temperature. The reaction mixture was then added to water (20 mL) and extracted with DCM (2×25 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (eluted with hexanes/EtOAc) to give (1R,3S,5R)-tert-butyl 3-((6-bromopyridin-2-yl)carbamoyl)-2-azabicyclo[3.1.0]hexane-2-carboxylate.

Step 2: (1R,3S,5R)—N-(6-Bromopyridin-2-yl)-2-azabicyclo[3.1.0]hexane-3-carboxamide Hydrochloride (S3)

(1R,3S,5R)-tert-Butyl 3-((6-bromopyridin-2-yl)carbamoyl)-2-azabicyclo[3.1.0]hexane-2-carboxylate (500 mg) was taken in 4 N HCl in dioxane (25 mL) and the resulting reaction mixture was stirred at room temperature for 3 h. The solvent was removed under reduced pressure and the remaining residue was used directly in the next synthetic step.

1-(2-((1R,3S,5R)-3-((6-Bromopyridin-2-yl)carbamoyl)-2-azabicyclo[3.1.0]hexan-2-yl-2-oxoethyl)5-(pyrimidin-5-yl)-1H-indazole-3-carboxamide (4)

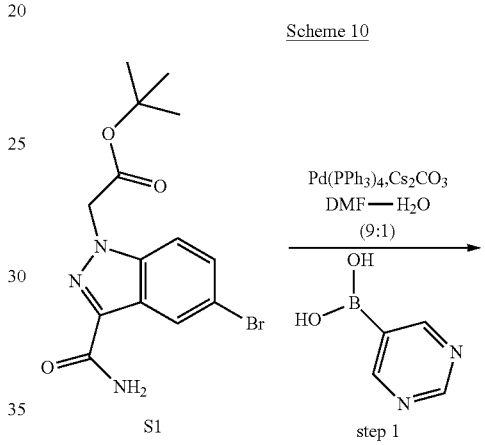
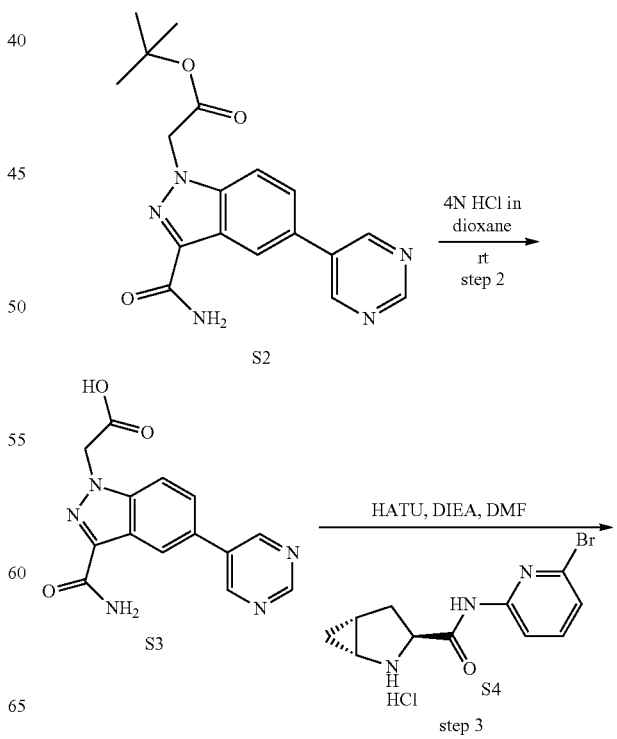

-continued

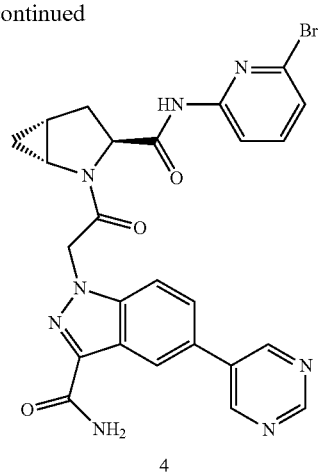

4

Step 1: tert-Butyl 2-(3-carbamoyl-5-(pyrimidin-5-yl)-1H-indazol-1-yl)acetate (S2)

A mixture of tert-butyl-2-(5-bromo-3-carbamoyl-1H-indazol-1-yl)acetate (211 mg), pyrimidin-5-yl boronic acid (135 mg), cesium carbonate (350 mg, 2 equiv), DMF (9 mL), and water (1.0 mL) was purged with argon in a pressure vessel for 5 min. Tetrakis(triphenylphosphine)palladium (0) (50 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(pyrimidin-5-yl)-1H-indazol-1-yl)acetic acid (S3)

tert-Butyl 2-(3-carbamoyl-5-(pyrimidin-5-yl)-1H-indazol-1-yl)acetate (crude from above reaction) was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-((1R,3S,5R)-3-((6-Bromopyridin-2-yl)carbamoyl)-2-azabicyclo[3.1.0]hexan-2-yl-2-oxoethyl)5-(pyrimidin-5-yl)-1H-indazole-3-carboxamide (4)

2-(3-Carbamoyl-5-(pyrimidin-5-yl)-1H-indazol-1-yl)acetic acid (110 mg) from the previous step was dissolved in DMF (20 mL) and DIEA (0.3 mL) was added, which was followed by the addition of (1R,3S,5R)—N-(6-bromopyridin-2-yl)-2-azabicyclo[3.1.0]hexane-3-carboxamide hydrochloride (126 mg) at 5° C. HATU (350 mg) was then added slowly at this same temperature and the reaction mixture was stirred for 3 h at rt. The reaction mixture was then added to water (50 mL+10 g solid NaCl) and extracted with DCM (2×20 mL). The organic layer was washed successively with an aqueous solution of NaHCO₃ (20 mL), water (20 mL), and brine (20 mL), then dried over Na₂SO₄ and concentrated under reduced pressure. The remaining residue was purified by flash column chromatography (eluted with DCM/MeOH) to give 4. ¹H NMR (400 MHz, DMSO-d₆300): (major rotamer) δ 0.75 (m, 1H), 1.02 (m, 1H), 1.85 (m, 1H), 2.16-2.35 (m, 2H), 3.80 (m, 1H), 4.42 (m, 1H), 5.54 (d, 1H), 5.86 (d, 1H), 7.32 (t, 1H), 7.48 (br s, 1H), 7.68-7.88 (m, 4H), 8.03 (d, 1H), 8.46 (s, 1H), 9.23 (s, 2H), 10.76 (s, 1H); LC (method A): $t_R$=1.42 min. LC/MS (EI) m/z: [M+H]⁺ 561.

1-(2-((1R,3S,5R)-3-((6-Bromopyridin-2-yl)carbamoyl)-2-azabicyclo[3.1.0]hexan-2-yl-2-oxoethyl)5-((2-pyrrolidin-1-yl)pyrimidin-5-yl)-1H-indazole-3-carboxamide (11)

Scheme 11

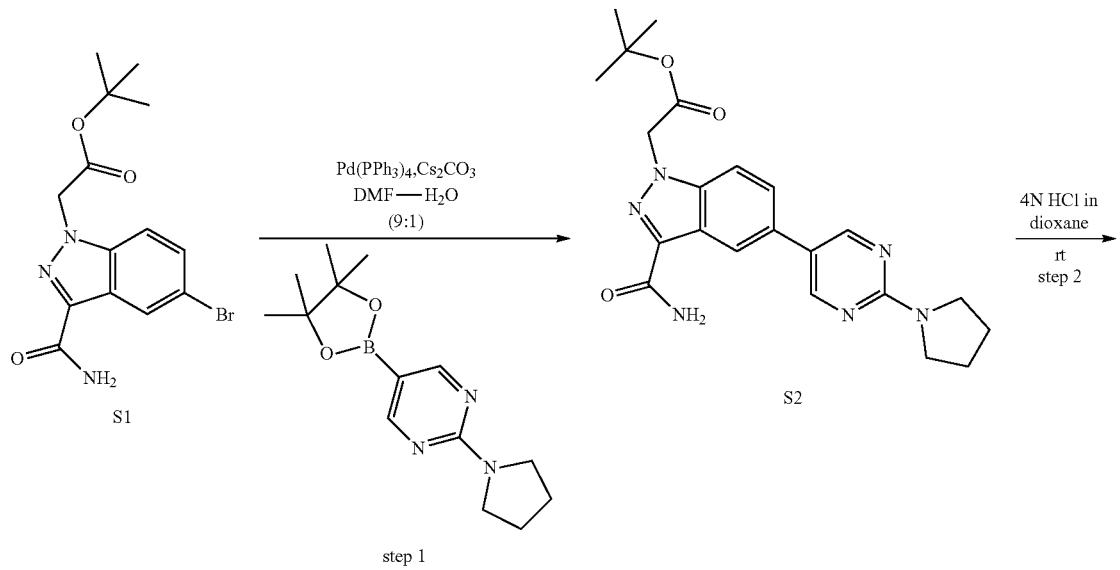

step 1

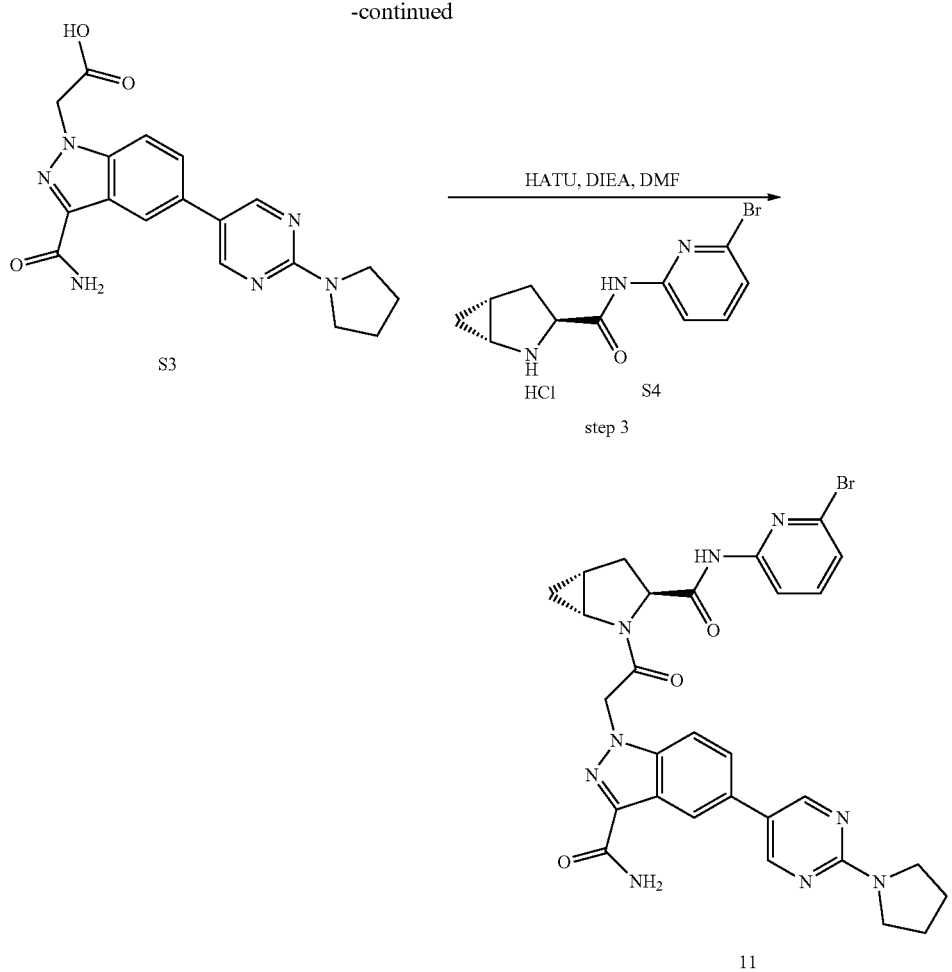

Step 1: tert-Butyl 2-(3-carbamoyl-5-(2-pyrrolidin-1-yl)pyrimidin-5-yl)-1H-indazol-1-yl)acetate (S2)

A mixture of tert-butyl-2-(5-bromo-3-carbamoyl-1H-indazol-1-yl)acetate (316 mg), 2-(pyrrolidin-1-yl)-5-(4,4,5,5-tetramethyl-1,3,2-dioxaborolan-2-yl)pyrimidine (271 mg), cesium carbonate (350 mg), DMF (10 mL), and water (1.5 mL) was purged with argon in a pressure vessel for 5 min. Tetrakis(triphenylphosphine)palladium (0) (57 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(2-pyrrolidin-1-yl)pyrimidin-5-yl)-1H-indazol-1-yl)acetic acid (S3)

tert-Butyl 2-(3-carbamoyl-5-(2-pyrrolidin-1-yl)pyrimidin-5-yl)-1H-indazol-1-yl)acetate (crude from above reaction) was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-(((1R,3S,5R)-3-((6-Bromopyridin-2-yl)carbamoyl)-2-azabicyclo[3.1.0]hexan-2-yl-2-oxoethyl)5-((2-pyrrolidin-1-yl)pyrimidin-5-yl)-1H-indazole-3-carboxamide (11)

2-(3-Carbamoyl-5-(2-pyrrolidin-1-yl)pyrimidin-5-yl)-1H-indazol-1-yl)acetic acid (131 mg) from the previous step was dissolved in DMF (20 mL) and DIEA (0.25 mL) was added, which was followed by the addition of (1R,3S,5R)—N-(6-bromopyridin-2-yl)-2-azabicyclo[3.1.0]hexane-3-carboxamide hydrochloride (110 mg) at 5° C. HATU (240 mg) was then added slowly at this same temperature and the reaction mixture was stirred for 3 h at rt. The reaction mixture was then added to water (50 mL+10 g solid NaCl) and extracted with DCM (2×20 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (eluted with DCM/MeOH) to give 11. $^1$H NMR (400 MHz, DMSO-d$_6$): (major rotamer) δ 0.74 (m, 1H), 1.01 (m, 1H), 1.25 (m, 1H), 1.86-1.98 (m, 5H), 2.13-2.38 (m, 2H), 3.56 (m, 4H), 3.80 (m, 1H), 4.42 (m, 1H), 5.51 (d, 1H), 5.82 (d, 1H), 7.19 (d, J=6.8 Hz, 1H), 7.40 (br s, 1H), 7.64-7.72 (m, 4H), 8.01 (d, 1H), 8.27 (s, 1H), 8.66 (s, 2H), 10.75 (s, 1H); LC (method A): t$_R$=1.82 min. LC/MS (EI) m/z: [M+H]$^+$ 630.

147

(2S,4R)—N-(6-Bromopyridin-2-yl)-4-fluoropyrrolidine-2-carboxamide Hydrochloride

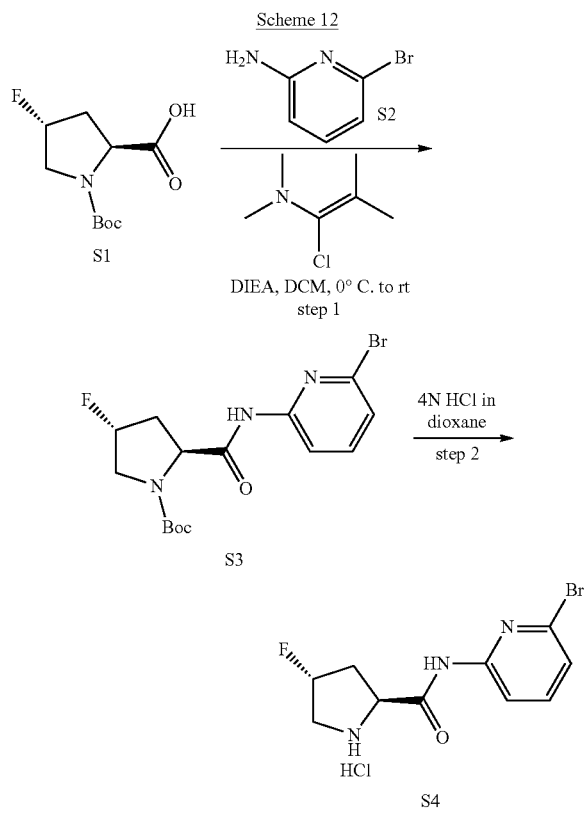

148

Step 1: (2S,4R)-1-tert-Butyl 2-((6-bromopyridin-2-yl)carbamoyl)-4-fluoropyrrolidine-1-carboxylate (S3)

To an ice-cold solution of (2S,4R)-1-tert-butoxycarbonyl)-4-fluoropyrrolidine-2-carboxylic acid (1.59 g) in DCM (20 mL), was added 1-chloro-N,N,2-trimethyl-1-propenylamine (998 mg, 1.1 equiv) dropwise with stirring. The stirring was continued for 3 h at this temperature, and then solid 6-bromopyridin-2-amine (1.3 g, 1.1 equiv) was added, followed by DIEA (3.34 mL, 3 equiv). The cooling bath was removed and the reaction mixture was stirred overnight at rt. The reaction mixture was then added to water (20 mL) and extracted with DCM (2×25 mL). The organic layer was washed successively with an aqueous solution of $NaHCO_3$ (20 mL), water (20 mL), and brine (20 mL), then dried over $Na_2SO_4$ and concentrated under reduced pressure. The remaining residue was purified by flash column chromatography (eluted with hexanes/EtOAc) to give (2S,4R)-1-tert-Butyl 2-((6-bromopyridin-2-yl)carbamoyl)-4-fluoropyrrolidine-1-carboxylate.

Step 2: (2S,4R)—N-(6-Bromopyridin-2-yl)-4-fluoropyrrolidine-2-carboxamide Hydrochloride (S4)

(2S,4R)-1-tert-Butyl 2-((6-bromopyridin-2-yl)carbamoyl)-4-fluoropyrrolidine-1-carboxylate (1.5 g) was taken in 4 N HCl in dioxane (25 mL) and the resulting reaction mixture was stirred at room temperature for 3 h. The solvent was removed under reduced pressure and the remaining residue was used directly in the next synthetic step.

1-(2-((2S,4R)-2-((6-Bromopyridin-2-yl)carbamoyl)-4-fluoropyrrolidin-1-yl)-2-oxoethyl)-5-(4-morpholinophenyl)-1H-indazole-3-carboxamide (3)

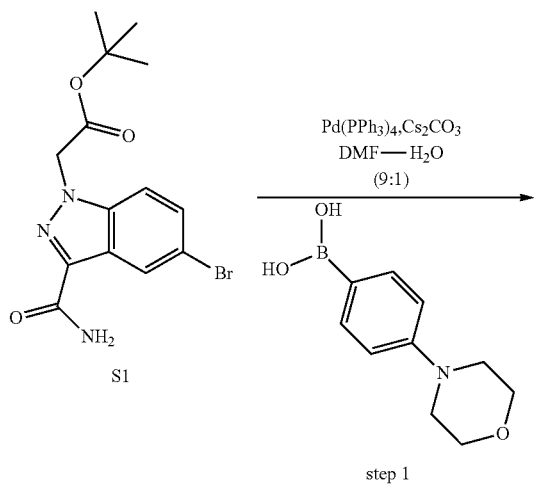

-continued
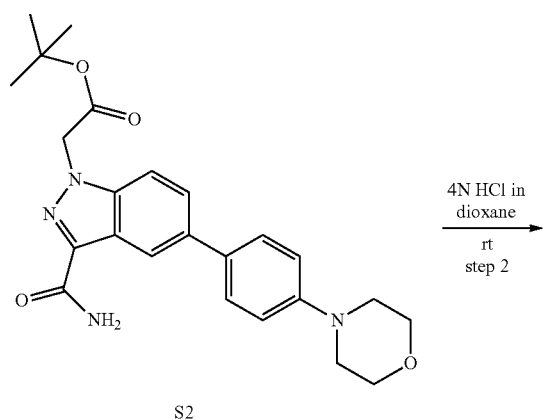
S2
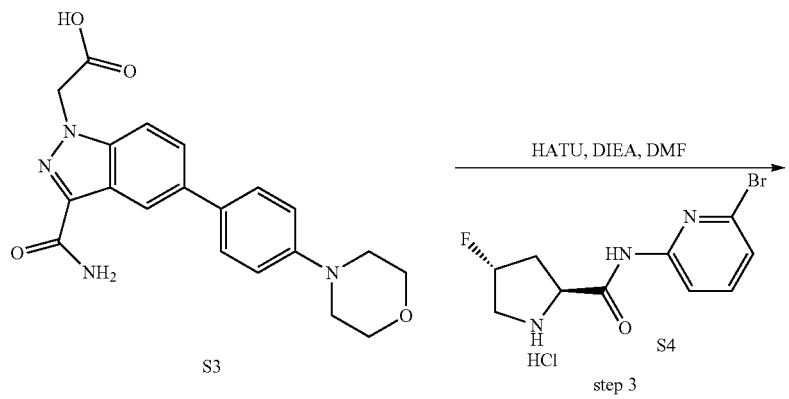
S3    S4
      HCl
      step 3
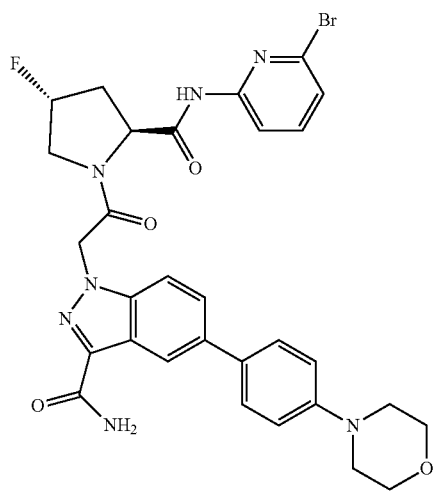
3

Step 1: tert-Butyl 2-(3-carbamoyl-5-(4-morpholinophenyl)-1H-indazol-1-yl)acetate (S2)

A mixture of tert-butyl-2-(5-bromo-3-carbamoyl-1H-indazol-1-yl)acetate (316 mg), (4-morpholinophenyl)boronic acid (224 mg), cesium carbonate (585 mg, 2 equiv), DMF (20 mL), and water (2 mL) was purged with argon in a pressure vessel for 5 min. Tetrakis(triphenylphosphine)palladium (0) (45 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(4-morpholinophenyl)-1H-indazol-1-yl)acetic acid (S3)

tert-Butyl 2-(3-carbamoyl-5-(4-morpholinophenyl)-1H-indazol-1-yl)acetate (crude from above reaction) was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-((2S,4R)-2-((6-Bromopyridin-2-yl)carbamoyl)-4-fluoropyrrolidin-1-yl)-2-oxoethyl)-5-(4-morphlinophenyl)-1H-indazole-3-carboxamide (3)

2-(3-Carbamoyl-5-(4-morpholinophenyl)-1H-indazol-1-yl)acetic acid (177 mg, 1 equiv) from the previous step was dissolved in DMF (10 mL), and DIEA (0.25 mL) was added. This was followed by the addition of (2S,4R)—N-(6-bromopyridin-2-yl)-4-fluoropyrrolidine-2-carboxamide hydrochloride (118 mg, 1 equiv) at 5° C. HATU (248 mg) was then added slowly at this same temperature and the reaction mixture was stirred for 3 h at rt. The reaction mixture was then added to water (50 mL+10 g solid NaCl) and extracted with DCM (2×20 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (eluted with DCM/MeOH) to give 3. 1H NMR (400 MHz, DMSO-d$_6$): (major rotamer) δ 2.07-2.22 (m, 1H), 2.49-2.61 (m, 1H), 3.12-3.18 (m, 4H), 3.73-3.78 (m, 4H), 3.86-4.09 (m, 1H), 4.13-4.25 (m, 1H), 4.66 (t, J=8.4 Hz, 1H), 5.42-5.48 (m, 1H), 5.58-5.70 (m, 2H), 7.04 (t, J=6.4 Hz, 1H), 7.31 (t, J=8.0 Hz, 1H), 7.35-7.52 (m, 1H), 7.50-7.58 (d, J=8.4 Hz, 2H), 7.63-7.75 (m, 4H), 8.02 (d, J=8 Hz, 1H), 8.32 (s, 1H), 10.99 (s, 1H); $^{19}$F NMR (376 MHz, DMSO-d$_6$): (major) δ −175.70. LC (method A): t$_R$=1.82 min. LC/MS (EI) m/z: [M+H]$^+$ 650.

(1R,3S,5R)—N-(2'-Chloro-2-fluoro-[1,1'-biphenyl]-3-yl)2-azabicyclo[3.1.0]hexane-3-carboxamide Hydrochloride Scheme 14

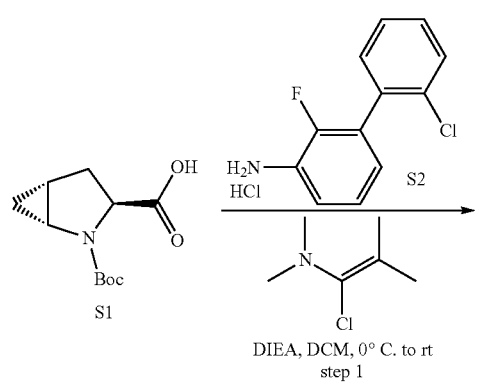

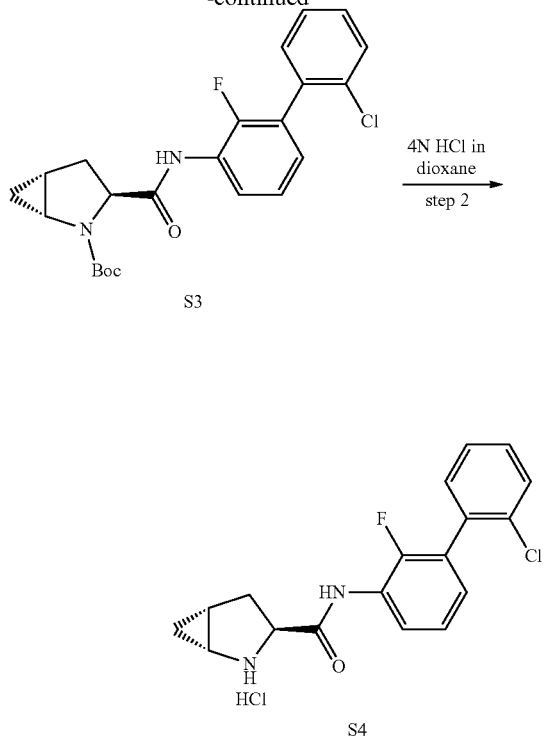

Step 1: (1R,3S,5R)-tert-Butyl 3-((2'-chloro-2-fluoro-[1,1'-biphenyl]-3-yl)carbamoyl)2-azabicyclo[3.1.0]hexane-2-carboxylate (S3)

To an ice-cold solution of (1R,3S,5R)-tert-butoxycarbonyl)-2-azabicyclo[3.1.0]hexane-2-carboxylic acid (1.13 g) in DCM (20 mL) was added 1-chloro-N,N,2-trimethyl-1-propenylamine (731 mg, 1.1 equiv) dropwise with stirring. The stirring was continued for 3 h at this temperature, and then solid of 2'-chloro-2-fluoro-[1,1'-biphenyl]-3-amine hydrochloride (1.3 g, 1 equiv) was added, followed by DIEA (2.45 mL). The cooling bath was removed and the reaction mixture was stirred overnight at room temperature. The reaction mixture was then added to water (20 mL) and extracted with DCM (2×25 mL). The organic layer was washed successively with an aqueous solution of NaHCO$_3$ (20 mL), water (20 mL), and brine (20 mL), then dried over Na$_2$SO$_4$ and concentrated under reduced pressure. The remaining residue was purified by flash column chromatography (eluted with hexanes/EtOAc) to give (1R,3S,5R)-tert-Butyl 3-((2'-chloro-2-fluoro-[1,1'-biphenyl]-3-yl)carbamoyl)2-azabicyclo[3.1.0]hexane-2-carboxylate.

Step 2: (1R,3S,5R)—N-(2'-Chloro-2-fluoro-[1,1'-biphenyl]-3-yl)2-azabicyclo[3.1.0]hexane-3-carboxamide Hydrochloride (S4)

(1R,3S,5R)-tert-Butyl 3-((2'-chloro-2-fluoro-[1,1'-biphenyl]-3-yl)carbamoyl)2-azabicyclo[3.1.0]hexan-2-carboxylate (700 mg) was taken in 4 N HCl in dioxane (25 mL) and the resulting reaction mixture was stirred at room temperature for 3 h. The solvent was removed under reduced pressure and the remaining residue was used directly in the next synthetic step.

1-(2-(((1R,3S, R)-3-((2'-Chloro-2-fluoro-[1,1'-biphenyl]-3-yl)carbamoyl)-azabicyclo[3.1.0]hexan-2-yl)-2-oxoethyl)-5-(pyrimidin-5-yl)-1H-indazole-3-carboxamide (6)

Scheme 15

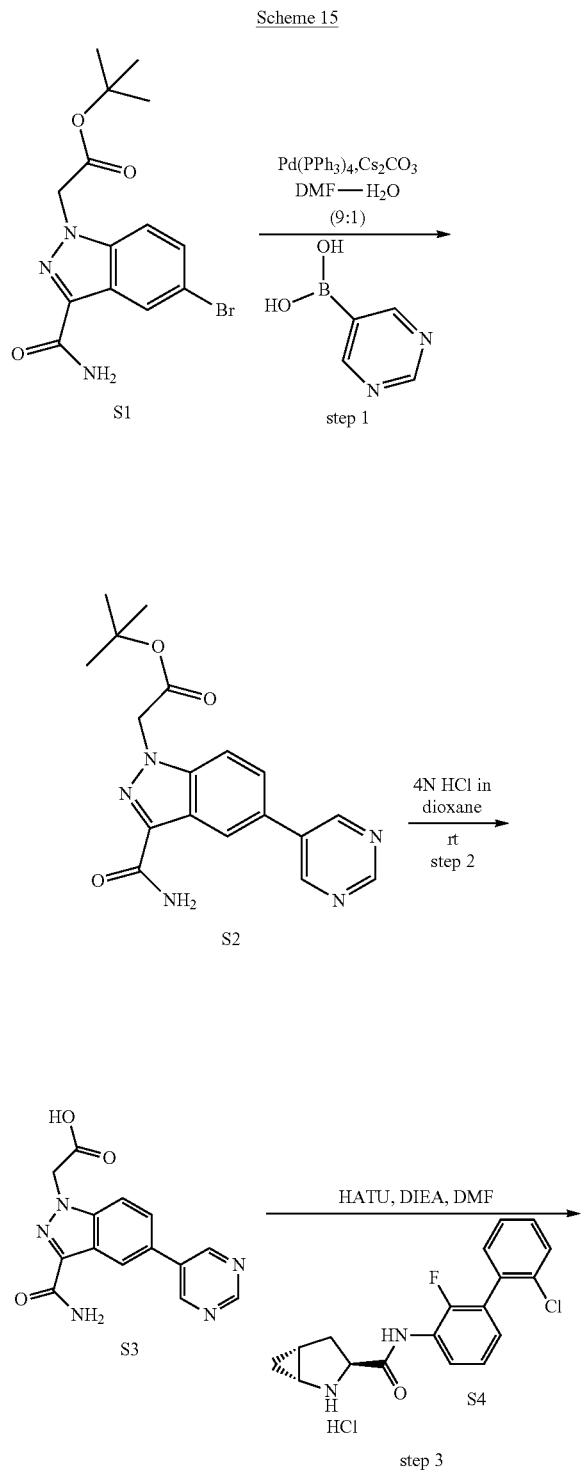

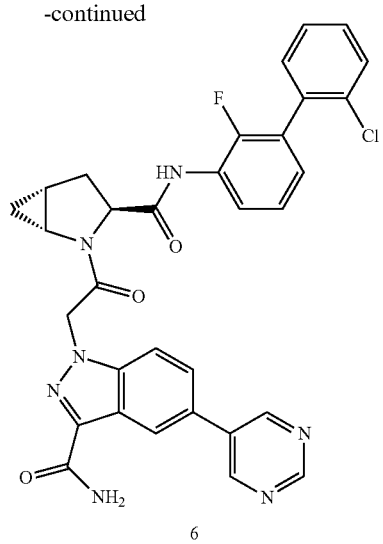

6

Step 1: tert-Butyl 2-(3-carbamoyl-5-(pyrimidin-5-yl)-1H-indazol-1-yl)acetate (S2)

A mixture of tert-butyl-2-(5-bromo-3-carbamoyl-1H-indazol-1-yl)acetate (211 mg), pyrimidin-5-ylboronic acid (82 mg), cesium carbonate (391 mg, 2 equiv), DMF (9 mL), and water (1.0 mL) was purged with argon in a pressure vessel for 5 min. Tetrakis(triphenylphosphine)palladium (0) (40 mg) was then added under argon and the pressure vessel was sealed and heated at 100° C. overnight. The reaction mixture was cooled to room temperature and the solvent was removed under reduced pressure. The crude product was used directly in the next synthetic step.

Step 2: 2-(3-Carbamoyl-5-(pyrimidin-5-yl)-1H-indazol-1-yl)acetic acid tert-Butyl 2-(3-carbamoyl-5-(pyrimidin-5-yl)-1H-indazol-1-yl)acetate (crude from above reaction) was taken in 4 N HCl in dioxane (5 mL) and the resulting reaction mixture was stirred at room temperature for 4 h. The solvent was removed under reduced pressure and the remaining material was used directly in the next synthetic step.

Step 3: 1-(2-(((1R,3S,5R)-3-((2'-Chloro-2-fluoro-[1,1'-biphenyl]-3-yl)carbamoyl)-azabicyclo[3.1.0]hexan-2-yl)-2-oxoethyl)-5-(pyrimidin-5-yl)-1H-indazole-3-carboxamide (6)

2-(3-Carbamoyl-5-(pyrimidin-5-yl)-1H-indazol-1-yl)acetic acid (131 mg, 1 equiv) from the previous step was dissolved in DMF (10 mL) and DIEA (0.33 mL, 5 equiv) was added, which was followed by the addition of (1R,3S,5R)—N-(2'-chloro-2-fluoro-[1,1'-biphenyl]-3-yl)2-azabicyclo[3.1.0]hexane-3-carboxamide Hydrochloride (131 mg, 1 equiv) at 5° C. HATU (350 mg, 2.1 equiv) was then added slowly at this same temperature and the reaction mixture was stirred for 3 h at rt. The reaction mixture was then added to water (25 mL+5 g solid NaCl) and extracted with DCM (2×15 mL). The organic layer was washed successively with an aqueous solution of NaHCO$_3$ (10 mL), water (10 mL), and brine (10 mL), then dried over Na$_2$SO$_4$ and concentrated under reduced pressure. The remaining residue was purified by flash column chromatography (eluted with DCM/MeOH) to give 6. $^1$H NMR (400 MHz, DMSO-d$_6$): (major rotamer) δ 0.73 (m, 1H), 1.07 (m, 1H), 1.26 (m, 1H), 1.90 (m, 1H), 2.28-2.35 (m, 2H), 3.78-3.83 (m, 1H), 4.54 (m, 1H), 5.52 (d, 1H), 5.84 (d, 1H), 7.07 (t, J=6.4 Hz, 1H), 7.27 (t, J=8.0 Hz, 1H), 7.35-7.58 (m, 4H), 7.55 (d, 1H), 7.72-7.84 (m, 4H), 8.47 (s, 1H), 9.72 (s, 1H); $^{19}$F NMR (376 MHz, DMSO-$d_6$): (major) δ −126.54. LC (method A): $t_R$=1.96 min. LC/MS (EI) m/z: [M+H]+ 610.

tert-Butyl 2-(3-carbamoyl-5-chloro-1H-pyrazolo[3,4-c]pyridine-1-yl)acetate

Scheme 16

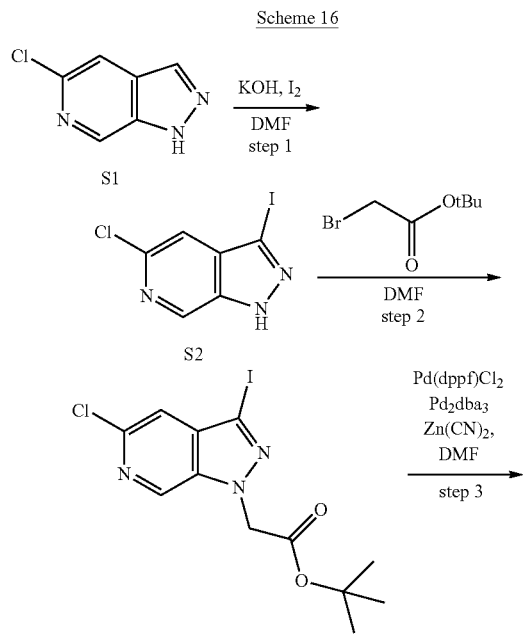

Step-1: 5-Chloro-3-iodo-1H-pyrazolo[3,4]pyridine (S2)

To a solution of 5-chloro-1H-pyrazolo[3,4-c]pyridine (15 g, 1 equiv) in DMF (150 mL) was added iodine (37.2 g, 1.5 equiv) and potassium hydroxide (13.7 g, 2.5 equiv) at 0° C. The reaction mixture was stirred at room temperature for 12 h and then diluted with 10% aqueous sodium thiosulfate (250 mL) and extracted with EtOAc. The combined organic extracts were washed with brine and then dried. The obtained solid (15 g) was slurried with MTBE, filtered and dried.

Step-2: tert-Butyl 2-(5-chloro-3-iodo-1H-pyrazolo[3,4]pyridine-1-yl)acetate (S3)

To a mixture of 5-chloro-3-iodo-1H-pyrazolo[3,4]pyridine (14 g, 1 equiv) and potassium carbonate (8.3 g, 1.2 equiv) in DMF (140 mL) was added tert-butyl bromoacetate (8.9 mL, 1.2 equiv) dropwise at room temperature and the resulting mixture was stirred at 50° C. for 3 h. The reaction mixture was then poured into water and extracted with EtOAc; the combined organic extracts were concentrated under reduced pressure. The material obtained was taken to next step without further purification.

Step-3: tert-Butyl 2-(5-chloro-3-cyano-1H-pyrazolo[3,4-c]pyridine-1-yl)acetate (S4)

A mixture of tert-butyl 2-(5-chloro-3-iodo-1H-pyrazolo[3,4]pyridine-1-yl)acetate (12.5 g, 1 equiv), Zn(CN)2 (4.5 g, 1.2 equiv), Pd (dppf)Cl$_2$ (2.6 g, 0.1 equiv), Pd$_2$(dba)$_3$ (2.9 g, 0.1 equiv), water (25 mL), and DMF (125 mL) was stirred at 100° C. for 5 h under an atmosphere of nitrogen. The reaction mixture was diluted with EtOAc and then washed successively with water, saturated aqueous NaHCO$_3$, and brine. The combined organic layer was concentrated under reduced pressure. The crude residue was purified by silica gel column chromatography (hexane/EtOAc) to give the title compound.

Step-4: tert-Butyl 2-(3-carbamoyl-5-chloro-1H-pyrazolo[3,4-c]pyridine-1-yl)acetate (S5)

A mixture of tert-butyl 2-(5-chloro-3-cyano-1H-pyrazolo[3,4-c]pyridine-1-yl)acetate (5.7 g, 1 equiv), acetaldoxime (2.3 g, 2 equiv), Pd(OAc)$_2$ (0.22 g, 0.05 equiv), and PPh$_3$ (0.54 g, 0.1 equiv) in aqueous ethanol (143 mL, H$_2$O/EtOH (29 mL/114 mL) was heated to 90° C. for 3 h under an atmosphere of nitrogen. The reaction mixture was filtered through Celite and the solvent was removed under reduced pressure. The crude residue was purified by silica gel column chromatography (hexane/EtOAc) to give the title compound (3.5 g).

1-(2-((2S,4R)-2-((2'-Chloro-2-fluoro-[1,1'-biphenyl]-3-yl)carbamoyl)-4-fluoropyrrolidin-1-yl)-2-oxo-ethyl)-5-(pyrimidin-5-yl)-1H-pyrazolo[3,4-c]pyridine-3-carboxamide (19)

Scheme 17

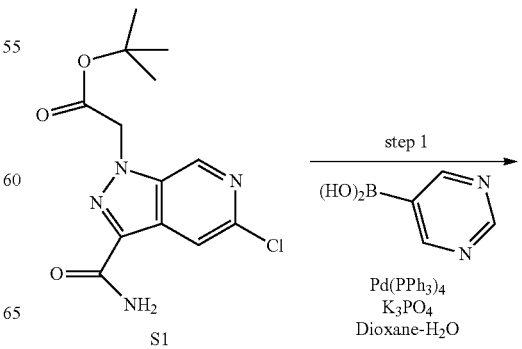

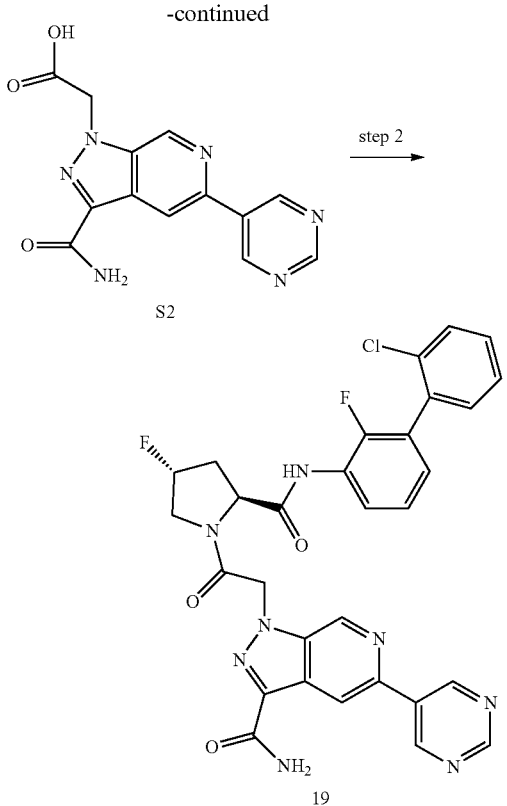

Step 1: 2-(3-Carbamoyl-5-(pyrimidin-5-yl)-1H-pyrazolo[3,4-c]pyridin-1-yl)acetic acid (S2)

A mixture of tert-butyl 2-(3-carbamoyl-5-chloro-1H-pyrazolo[3,4-c]pyridin-1-yl)acetate (311 mg, 1 mmol), pyrimidin-5-ylboronic acid (248 mg, 2 mmol), K$_3$PO$_4$ (634 mg, 3 mmol), dioxane (9 mL), and water (1 mL) was degassed and refilled with argon three times. To this mixture was added Pd(PPh$_3$)$_4$ (58 mg, 0.05 mmol) under an atmosphere of argon, and the reaction mixture was heated in a 85° C. oil bath overnight. Additional Pd(PPh$_3$)$_4$ (58 mg, 0.05 mmol) was added to the solution and the reaction was kept at 85° C. for an additional 24 h. The reaction was cooled to room temperature and the volatiles were removed under reduced pressure. The remaining residue was acidified with 10% aqueous citric acid (10 mL) and extracted with ethyl acetate (20 mL). The organic layer was discarded and the aqueous phase was evaporated to dryness. The remaining solid was loaded on a pad of silica gel and flushed with methanol. The methanol solution was concentrated and co-evaporated with toluene. The obtained solid was dried under high vacuum and used in the next step without further purification.

Step 2: 1-(2-((2S,4R)-2-((2'-Chloro-2-fluoro-[1,1'-biphenyl]-3-yl)carbamoyl)-4-fluoropyrrolidin-1-yl)-2-oxoethyl)-5-(pyrimidin-5-yl)-1H-pyrazolo[3,4-c]pyridine-3-carboxamide (19)

To a mixture of 2-(3-carbamoyl-5-(pyrimidin-5-yl)-1H-pyrazolo[3,4-c]pyridin-1-yl)acetic acid (77 mg, 0.26 mmol), HATU (120 mg, 0.32 mmol, 1.2 equiv), (2S,4R)—N-(2'-chloro-2-fluoro-[1,1'-biphenyl]-3-yl)-4-fluoropyrrolidine-2-carboxamide hydrochloride (96 mg, 0.26 mmol), and DMF (2.5 mL) was added DIEA (0.15 mL, 0.86 mmol) at room temperature. The reaction mixture was stirred for 30 min at room temperature and then the volatiles were removed under reduced pressure. The remaining residue was subjected to preparative HPLC to afford 40.9 mg of title product. $^1$H NMR (400 MHz, DMSO-d$_6$): (major rotamer) δ 2.17-2.25 (m, 1H), 2.49-2.57 (m, 1H), 3.86-3.99 (m, 1H), 4.13-4.22 (m, 1H), 4.73 (t, J=8.4 Hz, 1H), 5.57-5.61 (m, 1H), 5.65-5.84 (m, 2H), 6.99 (t, J=6.4 Hz, 1H), 7.14 (t, J=8.0 Hz, 1H), 7.28-7.42 (m, 4H), 7.50-7.58 (m, 1H), 7.83-7.92 (m, 2H), 8.58 (s, 1H), 9.15 (s, 1H), 9.23 (s, 1H), 9.38 (s, 2H), 9.95 (s, 1H); $^{19}$F NMR (376 MHz, DMSO-d$_6$): (major rotamer) δ −126.77, −175.85. LC (method A): t$_R$=2.47 min. LC/MS (EI) m/z: [M+H]$^+$ 617.

Scheme 18: Synthesis of (2S,4R)-1-(2-(3-Acetyl-5-(4-acetylpiperazin-1-yl)-1H-indol-1-yl)acetyl)-N-(2'-chloro-2-fluoro-[1,1'-biphenyl]-3-yl)-4-fluoropyrrolidine-2-carboxamide (16)

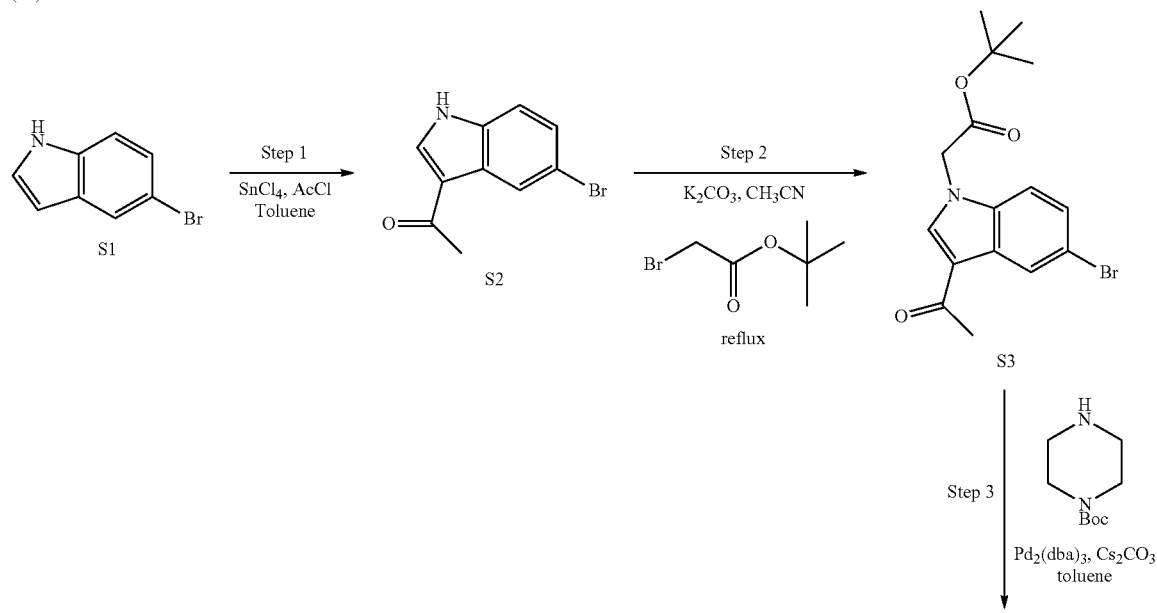

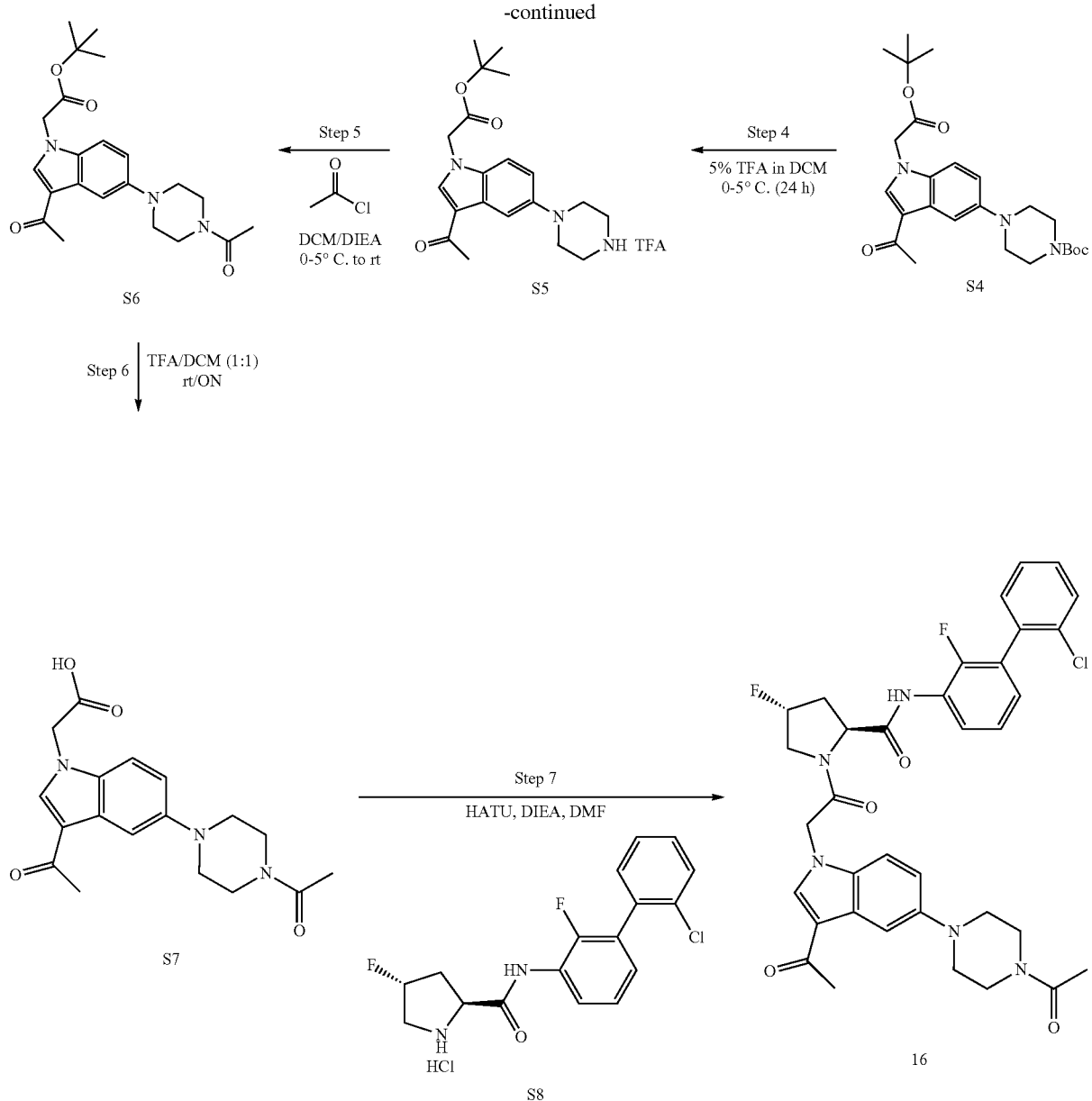

Step 1: 1-(5-Bromo-1H-indol-3-yl)ethanone (S2)

1-(5-Bromo-1H-indol-3-yl)ethanone was prepared from 5-bromoindole according to the procedure of MacKay et al. (MacKay, J. A.; Bishop, R.; Rawal, V. H. *Org. Lett.* 2005, 7, 3421-3424.)

Step 2: tert-Butyl 2-(3-acetyl-5-bromo-1H-indol-1-yl)acetate (S3)

A mixture of 1-(5-bromo-1H-indol-3-yl)ethanone (3.9 g, 16.4 mmol), tert-butyl bromoacetate (2.63 mL (18.02 mmol), and potassium carbonate (2.50 g, 18.02 mmol) in anhydrous acetonitrile (80 mL) was refluxed for 5 h. The reaction mixture was then cooled to room temperature and the solvent was removed under reduced pressure. The residue was taken in a 1:1 mixture of DCM and water (100 mL: 100 mL). The two layers were separated and the organic layer was washed with water (2×100 mL). Finally, the organic layer was dried (Na$_2$SO$_4$) and concentrated. The resulting residue was stirred with 50 mL of heptane for 30 min, cooled in an ice bath and the solid was filtered, washed with cold heptane (10 mL). The solid was dried under high vacuum to give tert-butyl 2-(3-acetyl-5-bromo-1H-indol-1-yl)acetate (5.6 g).

Step 3: tert-Butyl 4-(3-acetyl-1-(2-(tert-butoxy)-2-oxoethyl)-1H-indol-5-yl)piperazine-1-carboxylate (S4)

A mixture of tert-butyl 2-(3-acetyl-5-bromo-1H-indol-1-yl)acetate (379 mg), tert-butyl piperazine-1-carboxylate (223 mg, 1.2 equiv), cesium carbonate (489 mg, 1.4 equiv), (S)-(−)-2,2-bis(diphenylphosphino)-1,1-binaphthyl (40 mg), and toluene (8 mL) was purged with argon for 5 min. Tris(dibenzylideneacetone)dipalladium (0) (40 mg) was then added under argon and the reaction mixture was heated at 100° C. overnight. The reaction mixture was cooled to room temperature and the solvent was removed under reduced pressure. The crude product was purified by column chromatography (EtOAc in hexanes gradient) to give tert-butyl 4-(3-acetyl-1-(2-(tert-butoxy)-2-oxoethyl)-1H-indol-5-yl)piperazine-1-carboxylate (89 mg).

Step 4: tert-Butyl 2-(3-acetyl-5-(piperazin-1-yl)-1H-indol-1-yl)acetate TFA Salt (S5)

tert-Butyl 4-(3-acetyl-1-(2-(tert-butoxy)-oxoethyl-1H-indole-5-yl)piperazine-1-carboxylate (65 mg) was taken in 5% TFA (0.5 mL) in DCM (10 mL) at 0-5° C. and the resulting reaction mixture was stirred at 0-5° C. for 24 h. The solvent was then removed under reduced pressure and the remaining material was used directly in the next synthetic step.

Step 5: tert-Butyl 2-(3-acetyl-5-(4-acetylpiperazin-1-yl)-1H-indol-1-yl)acetate (S6)

The TFA salt of tert-butyl 2-(3-acetyl-5-(piperazin-1-yl)-1H-indol-1-yl)acetate from step 4 was dissolved in DCM (4 mL) and DIEA (0.14 mL, excess) was added, then followed by the addition of AcCl (0.02 mL, 1 equiv) at 0-5° C. After stirring for 10 min, the reaction mixture was diluted with EtOAc (10 mL) and water (4 mL). The EtOAc layer was separated, washed with brine (15 mL), dried (Na$_2$SO$_4$), and evaporated to dryness under reduced pressure. The remaining material was used directly in the next step.

Step 6: 2-(3-Acetyl-5-(4-acetylpiperazin-1-yl)-1H-indol-1-yl)acetic acid (S7)

tert-Butyl 2-(3-acetyl-5-(4-acetylpiperazin-1-yl)-1H-indol-1-yl)acetate from the previous step was dissolved in DCM (5 mL) and TFA (1 mL) was added. The reaction mixture was stirred overnight at room temperature. The solvent was then removed under reduced pressure and the remaining material was used directly in the next synthetic step.

Step 7: (2S,4R)-1-(2-(3-Acetyl-5-(4-acetylpiperazin-1-yl)-1H-indol-1-yl)acetyl)-N-(2'-chloro-2-fluoro-[1,1'-biphenyl]-3-yl)-4-fluoropyrrolidine-2-carboxamide (S8)

To a solution of 2-(3-acetyl-5-(4-acetylpiperazin-1-yl)-1H-indol-1-yl)acetic acid from step 6 in DMF (5 mL) was added DIEA (0.13 mL, 3 equiv) followed by (2S,4R)—N-(3-chloro-(2S,4R)—N-(6-chloropyridin-2-yl)-4-fluoropyrrolidine-2-carboxamide hydrochloride (108 mg, 1.1 equiv). HATU (120 mg, 1.2 equiv) was then added slowly and the reaction mixture was stirred for 18 h at room temperature. The reaction mixture was then added to water (10 mL) and extracted with EtOAc (2×15 mL). The separated organic layer was washed successively with an aqueous solution of NaHCO$_3$ (10 mL), water (10 mL), and brine (10 mL), then dried over Na$_2$SO$_4$ and concentrated under reduced pressure. The remaining residue was purified by column chromatography (eluted with DCM/CH$_3$OH) to give the title compound. $^1$H NMR (400 MHz, DMSO-d$_6$): (major rotamer) δ 2.18 (s, 3H), 2.24-2.41 (m, 1H), 2.50 (s, 3H), 2.64-2.78 (m, 1H), 3.08-3.19 (m, 4H), 3.69-3.80 (m, 4H), 3.91-4.09 (m, 1H), 4.16-4.27 (m, 1H), 4.78 (t, J=8 Hz, 1H), 5.16 (d, J=17 Hz, 1H), 5.26 (d, J=17 Hz, 1H), 5.45-5.61 (m, 1H), 7.04-7.08 (m, 1H), 7.18-7.25 (m, 1H), 7.38-7.47 (m, 4H), 7.51-7.56 (m, 1H), 7.86-7.90 (s, 1H), 7.93-7.98 (m, 1H), 8.12 (s, 1H); $^{19}$F NMR (376 MHz, DMSO-d$_6$): (major rotamer) δ −128.56, −178.51. LC (method A): t$_R$=2.30 min. LC/MS (EI) m/z: [M+H]$^+$ 664.

(2S,4R)-1-(2-(3-Acetyl-5-(4-(methylsulfonyl)piperazin-1-yl)-1H-indol-1-yl)acetyl)-N-(2'-chloro-2-fluoro-[1,1'-biphenyl]-3-yl)-4-fluoropyrrolidine-2-carboxamide (33)

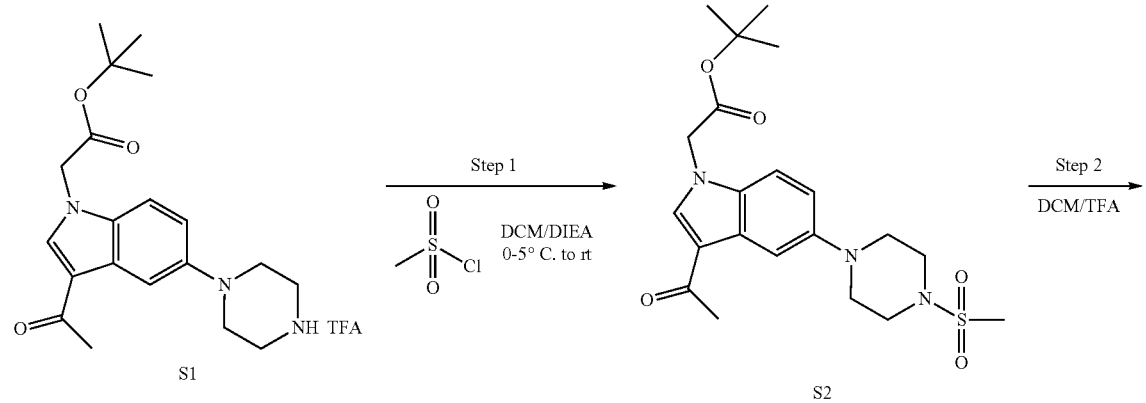

Scheme 19.

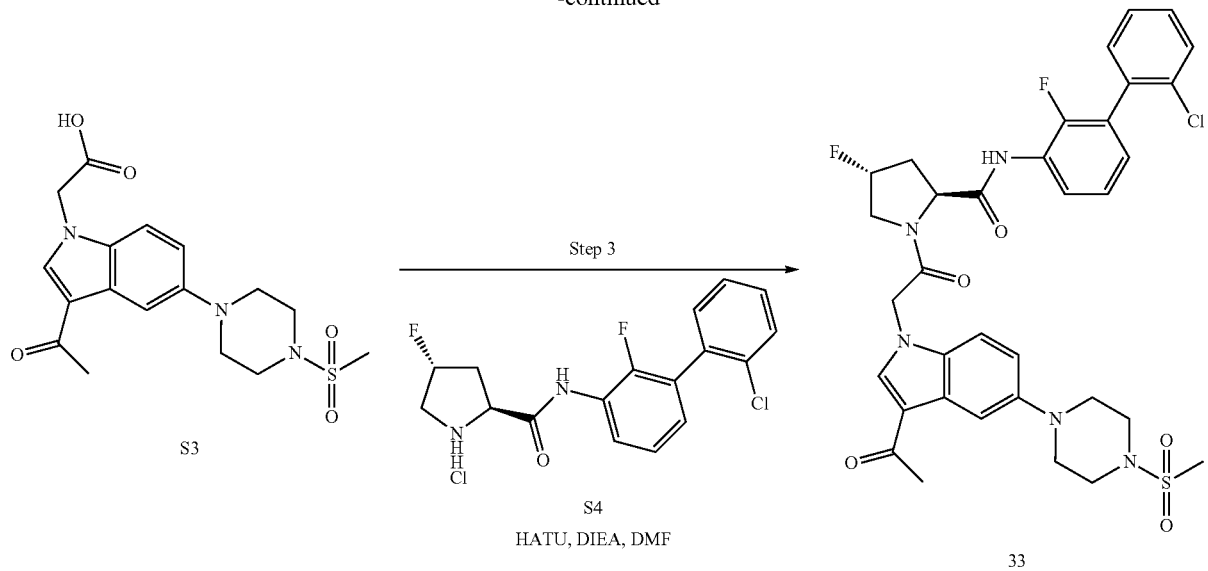

Step 1: tert-Butyl 2-(3-acetyl-5-(4-(methylsulfonyl)piperazin-1-yl)-1H-indol-1-yl)acetate (S2)

The TFA salt of tert-butyl 2-(3-acetyl-5-(piperazin-1-yl)-1H-indol-1-yl)acetate (90 mg) was dissolved in DCM (4 mL). To this solution was added DIEA (0.14 mL) followed by methylsulfonyl chloride (0.06 mL) at 0-5° C. After stirring for 10 min, the reaction mixture was diluted with EtOAc (10 mL) and water (4 mL). The separated organic layer was washed with brine (15 mL), dried (Na$_2$SO$_4$), and evaporated to dryness under reduced pressure. The remaining material was used directly in the next step.

Step 2: 2-(3-Acetyl-5-(4-(methylsulfonyl)piperazin-1-yl)-1H-indol-1-yl)acetic acid (S3)

tert-Butyl 2-(3-acetyl-5-(4-(methylsulfonyl)piperazin-1-yl)-1H-indol-1-yl)acetate was dissolved in DCM (5 mL) and TFA (1 mL) was added. The reaction mixture was stirred overnight at room temperature and then the solvent was removed under reduced pressure. The title compound was used directly in the next step.

Step 3: (2S,4R)-1-(2-(3-Acetyl-5-(4-(methylsulfonyl)piperazin-1-yl)-1H-indol-1-yl)acetyl)-N-(2'-chloro-2-fluoro-[1,1'-biphenyl]-3-yl)-4-fluoropyrrolidine-2-carboxamide (33)

DIEA (0.17 mL, 4 equiv) followed by (2S,4R)—N-(3-chloro-(2S,4R)—N-(6-chloropyridin-2-yl)-4-fluoropyrrolidine-2-carboxamide hydrochloride (102 mg, 1.1 equiv) was added to a solution of 2-(3-acetyl-5-(4-(methylsulfonyl)piperazin-1-yl)-1H-indol-1-yl)acetic acid in DMF (5 mL). HATU (120 mg, 1.2 equiv) was then added slowly and the reaction mixture was stirred for 18 h at room temperature. The reaction mixture was then added to water (10 mL) and extracted with EtOAc (2×15 mL). The organic layer was washed successively with an aqeuous solution of NaHCO$_3$ (10 mL), water (10 mL), and brine (10 mL), dried over Na$_2$SO$_4$ and concentrated under reduced pressure. The remaining residue was purified by HPLC to give the title compound. $^1$H NMR (400 MHz, DMSO-d$_6$): (major rotamer) δ 2.18 (s, 3H), 2.27-2.42 (m, 1H), 2.50 (s, 3H), 2.67-2.80 (m, 1H), 2.98 (s, 3H), 3.52 (m, 8H), 3.95-4.29 (m, 2H), 4.78 (t, J=8 Hz, 1H), 5.21 (d, J=18 Hz, 1H), 5.35 (d, J=18 Hz, 1H), 5.42-5.63 (m, 1H), 7.04-7.08 (m, 1H), 7.14-7.20 (m, 1H), 7.22-7.29 (m, 1H), 7.30-7.42 (m, 3H), 7.43-7.51 (m, 3H), 7.93-7.96 (m, 1H), 8.15 (s, 1H); $^{19}$F NMR (376 MHz, DMSO-d$_6$): (major rotamer) δ −128.49, −178.41. LC (method A): t$_R$=2.09 min. LC/MS (EI) m/z: [M+H]$^+$ 698.

(2S,4R)-1-(2-(3-Acetyl-5-(1-acetyl-1,2,3,6-tetrahydropyridin-4-yl)-1H-indol-1-yl)acetyl)-N-(2'-chloro-2-fluoro-[1,1'-biphenyl]-3-yl)-4-fluoropyrrolidine-2-carboxamide (28)

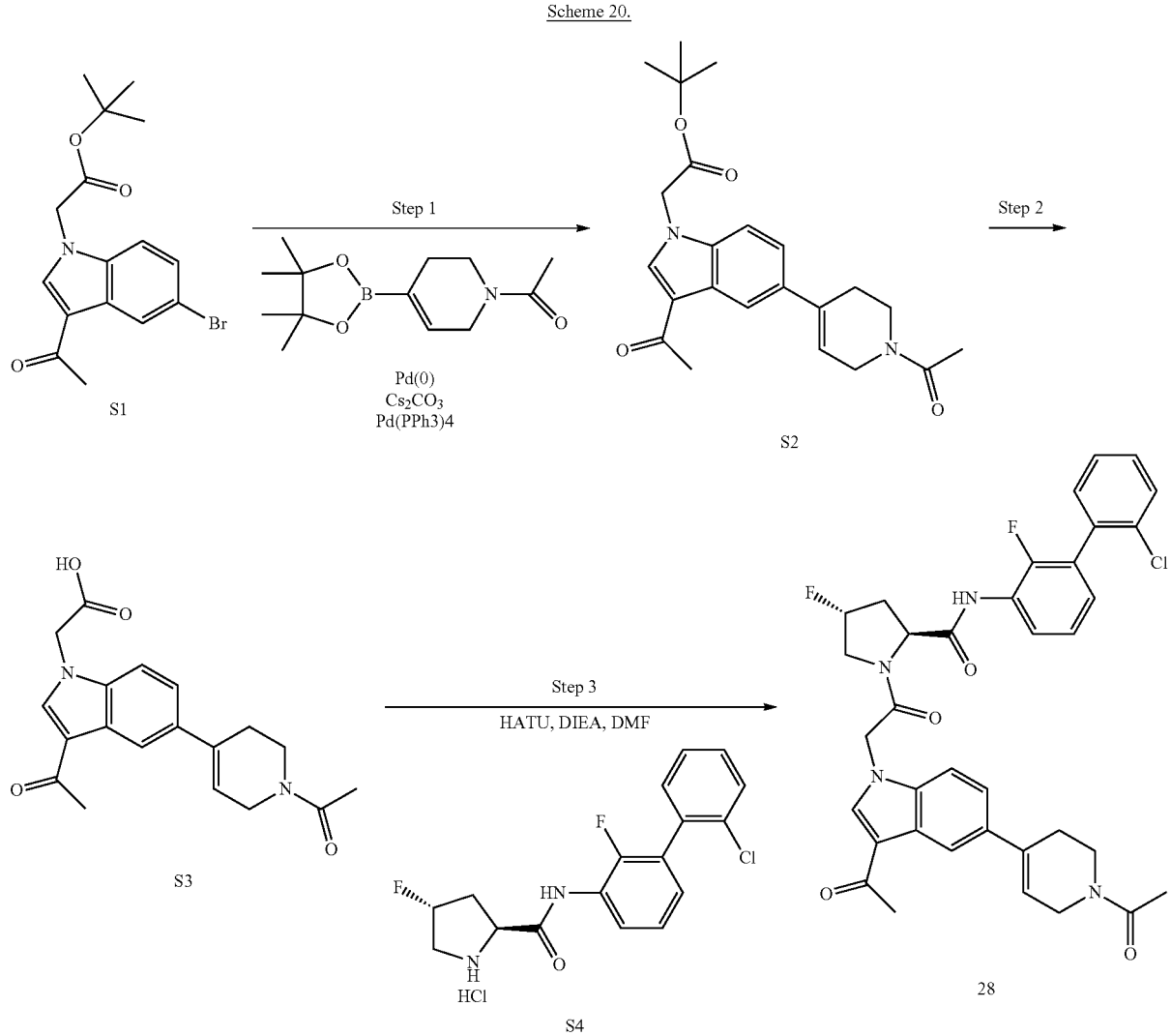

Scheme 20.

Step 1: tert-Butyl 2-(3-acetyl-5-(1-acetyl-1,2,3,6-tetrahydropyridin-4-yl)-1H-indol-1-yl)acetate (S2)

A mixture of tert-butyl 2-(3-acetyl-5-bromo-1H-indol-1-yl)acetate (113 mg, 0.32 mmol), 1-(4-(4,4,5,5-tetramethyl-1,3,2-dioxaborolan-2-yl)-5,6-dihydropyridin-1(2H)-yl)ethanone (80 mg. 0.32 mmol), cesium carbonate (209 mg, 0.64 mmol), and DMF (10 mL) was purged with argon in a pressure vessel for 5 min. Tetrakis(triphenylphosphine)palladium (0) (18 mg, 0.016 mmol) was then added under argon and the pressure vessel was sealed and heated at 90° C. overnight. The reaction mixture was cooled to room temperature and the solvent was removed under reduced pressure. The remaining crude product was used directly in the next synthetic step.

Step 2: 2-(3-Acetyl-5-(1-acetyl-1,2,3,6-tetrahydropyridin-4-yl)-1H-indol-1-yl)acetic acid (S3)

tert-Butyl 2-(3-acetyl-5-(1-acetyl-1,2,3,6-tetrahydropyridin-4-yl)-1H-indol-1-yl)acetate was taken up in 4 N HCl in dioxane (10 mL) and the resulting reaction mixture was stirred at room temperature for 4 hours. The solvent was then removed under reduced pressure and the title compound was used directly in the next synthetic step.

Step 3: (2S,4R)-1-(2-(3-Acetyl-5-(1-acetyl-1,2,3,6-tetrahydropyridin-4-yl)-1H-indol-1-yl)acetyl)-N-(2'-chloro-2-fluoro-[1,1'-biphenyl]-3-yl)-4-fluoropyrrolidine-2-carboxamide (28)

The title compound was prepared from 2-(3-acetyl-5-(1-acetyl-1,2,3,6-tetrahydropyridin-4-yl)-1H-indol-1-yl)acetic acid (100 mg, 0.29 mmol) and (2S,4R)—N-(3-chloro-(2S, 4R)—N-(6-chloropyridin-2-yl)-4-fluoropyrrolidine-2-carboxamide hydrochloride (110 mg, 0.29 mmol) in a manner similar to that described above for (2S,4R)-1-(2-(3-acetyl-5-(4-acetylpiperazin-1-yl)-1H-indol-1-yl)acetyl)-N-(2'-chloro-2-fluoro-[1,1'-biphenyl]-3-yl)-4-fluoropyrrolidine-2-carboxamide. $^1$H NMR (400 MHz, DMSO-$d_6$): (major rotamer) δ 2.05-2.07 (s, 3H), δ 2.31-2.38 (m, 1H), 2.50 (s, 3H), 2.50-2.70 (m, 3H), 3.73-3.79 (m, 2H), 4.01-4.31 (m, 4H), 4.85 (t, J=8.4 Hz, 1H), 5.28-5.50 (m, 2H), 5.64 (d, J=52.8 Hz, 1H), 6.18 (s, 1H), 7.16 (t, J=6.8 Hz, 1H), 7.31 (t, J=7.6 Hz, 1H), 7.41-7.68 (m, 6H), 8.04 (t, J=7.6 Hz, 1H), 8.30 (d, J=8 Hz, 1H), 8.35 (s, 1H), 10.05 (s, 1H); $^{19}$F NMR (376 MHz, DMSO-$d_6$): (major rotamer) δ −126.64, −175.81. LC (method A): $t_R$=2.07 min. LC/MS (EI) m/z: [M+H]$^+$ 659.

(2S,4R)-1-(2-(3-Acetyl-5-(2-methylpyrimidin-5-yl)-1H-indazol-1-yl)acetyl)-N-(5'-carbamoyl-2'-chloro-2-fluoro-[1,1'-biphenyl]-3-yl)-4-fluoropyrrolidine-2-carboxamide Scheme 21

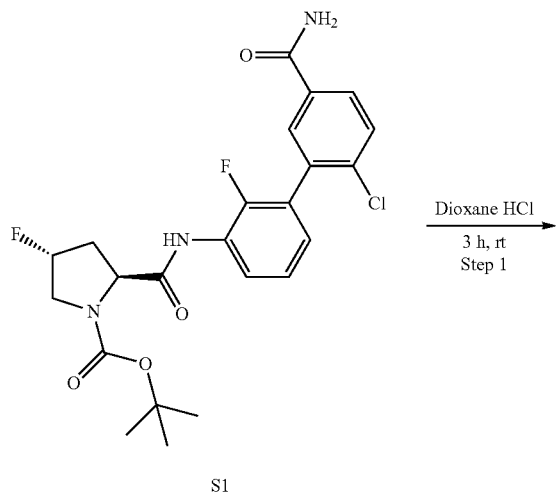

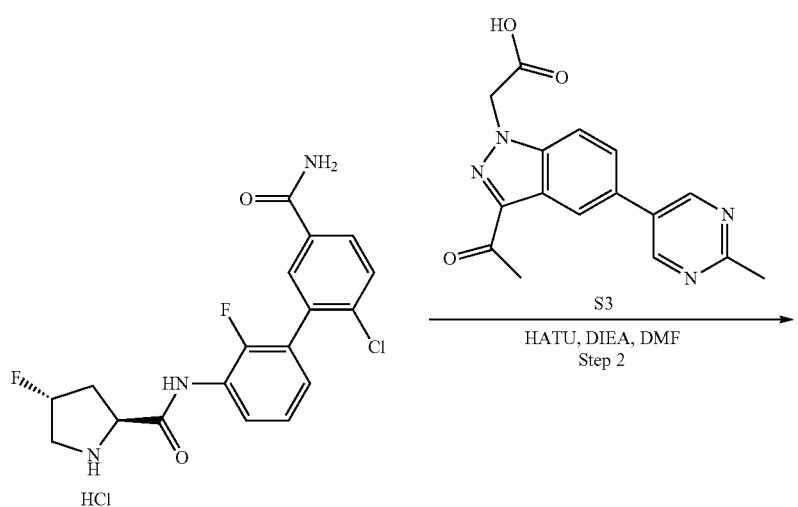

-continued

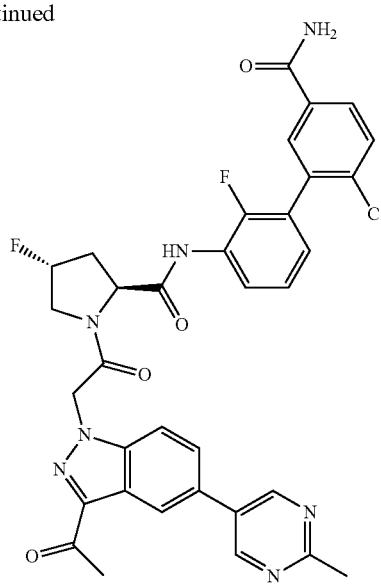

S4

Step 1: (2S,4R)—N-(5'-Carbamoyl-2'-chloro-2-fluoro-[1,1'-biphenyl]-3-yl)-4-fluoropyrrolidine-2-carboxamide hydrochloride (S2)

To a solution of compound S1 (1 equiv) in 1,4-dioxane (3 vol) at 0° C. under an atmosphere of nitrogen was added 4 N HCl in 1,4-dioxane (10 vol). The reaction was stirred at room temperature for 3 hours and concentrated to afford the title compound, which was used directly in the next step.

Step 2: (2S,4R)-1-(2-(3-Acetyl-5-(2-methylpyrimidin-5-yl)-1H-indazol-1-yl)acetyl)-N-(5'-carbamoyl-2'-chloro-2-fluoro-[1,1'-biphenyl]-3-yl)-4-fluoropyrrolidine-2-carboxamide (S3)

To a solution of compound S2 (1 equiv) in DMF (10 vol) at 0° C. under an atmosphere of nitrogen was added 2-(3-acetyl-5-(2-methylpyrimidin-5-yl)-1H-indazol-1-yl)acetic acid (S3, 1 equiv), HATU (2.1 equiv), and DIPEA (5 equiv). The reaction mixture was stirred at room temperature for 3 h. The reaction mixture was quenched with water (30 vol), extracted with DCM, washed with brine, dried over anhydrous $Na_2SO_4$, filtered, and then concentrated. The remaining residue was purified by column chromatography on silica gel (MeOH/DCM) to give compound S4. $^1H$ NMR (400 MHz, DMSO-$d_6$): δ 10.01 (s, 1H), 9.03 (s, 2H), 8.43 (s, 1H), 8.08 (s, 1H), 8.01 (t, J=18.8 Hz, 1H), 7.93 (d, J=8.0 Hz, 1H), 7.86 (m, 3H), 7.68 (d, J=12.8 Hz, 1H), 7.45 (s, 1H), 7.25 (t, J=8.0 Hz, 1H), 7.12 (t, J=6.8 Hz, 1H), 5.85 (d, J=17.20 Hz, 1H), 5.66-5.51 (m, 2H), 4.78 (t, J=8.40 Hz, 1H), 4.30-4.21 (m, 1H), 4.09-3.97 (m, 1H), 2.7 (s, 3H), 2.6 (s, 3H), 2.56-2.51 (m, 1H), 2.30-2.14 (m, 1H). $^{19}F$ NMR (376 MHz, DMSO-$d_6$): δ −175.67. LC (method A): $t_R$=1.68 min. LC/MS (EI) m/z: [M+H]$^+$ 672.

(2S,4R)-1-(2-(3-Acetyl-5-(5-chloro-6-methylpyridin-3-yl)-1H-indol-1-yl)acetyl)-N-(2'-chloro-2-fluoro-[1,1'-biphenyl]-3-yl)-4-fluoropyrrolidine-2-carboxamide Scheme 22

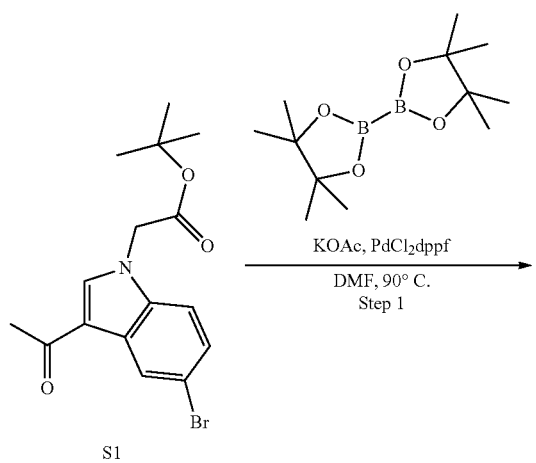

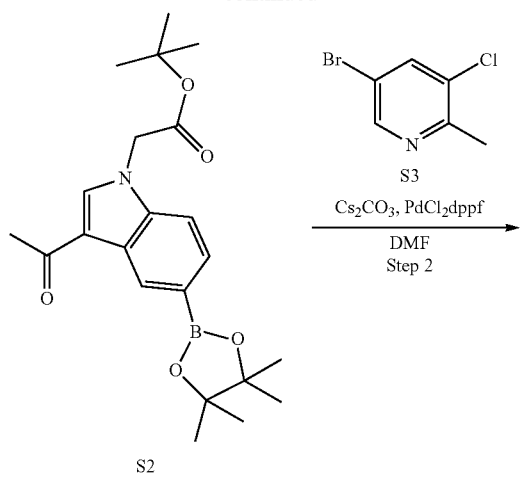

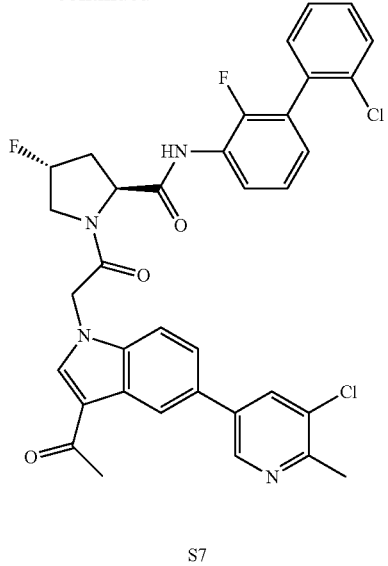

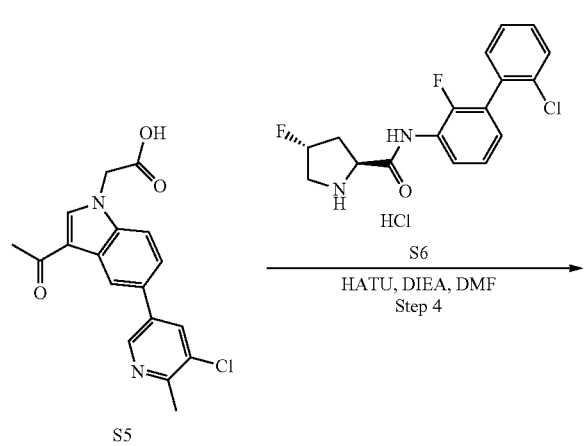

Step 1: tert-Butyl 2-(3-acetyl-5-(4, 4, 5,5-tetramethyl-1,3,2-dioxaborolan-2-yl)-1H-indol-1-yl)acetate (S2)

A mixture of tert-butyl 2-(3-acetyl-5-bromo-1H-indol-1-yl)acetate (51, 1.35 g, 1 equiv), 4,4,4'4',5,5,5',5'-octamethyl-2,2'-bi(1,3,2-dioxabolane (1.2 g. 1.1 equiv) and potassium acetate (1.13 g, 3 equiv) in DMF (50 mL) was purged with argon for 5 min. 1,1'-Bis(diphenylphosphino)ferrocenedichloropalladium(II) (188 mg, 0.06 equiv) was then added under argon and the reaction mixture was heated at 90° C. overnight. The reaction mixture was cooled to room temperature and diluted with EtOAc (70 mL) and water (30 mL). The organic layer was then separated, washed with brine (3×35 mL), dried, and concentrated. The crude product was purified by column chromatography on silica gel (EtOAc in hexanes, gradient) to give 975 mg (64% yield) of tert-butyl 2-(3-acetyl-5-(4, 4, 5,5-tetramethyl-1,3,2-dioxaborolan-2-yl)-1H-indol-1-yl)acetate (S2).

Step 2: tert-Butyl 2-(3-acetyl-5-(5-chloro-6-methylpyridin-3-yl)-1H-indol-1-yl)acetate (S4)

A mixture of tert-butyl 2-(3-acetyl-5-(4, 4, 5,5-tetramethyl-1,3,2-dioxaborolan-2-yl)-1H-indol-1-yl)acetate (S2, 100 mg, 1 equiv), 5-bromo-3-chloro-2-methylpyridine (S3, 62 mg, 1.2 equiv), and cesium carbonate (230 mg, 2.8 equiv) in DMF (8 mL) was purged with argon for 5 min. 1,1'-Bis(diphenylphosphino)ferrocenedichloropalladium(II) (14 mg, 0.06 equiv) was then added under argon and the reaction mixture was heated to 90° C. overnight. The reaction mixture was cooled to room temperature and diluted with EtOAc (20 mL) and water (10 ml). The organic layer was then separated, washed with brine (3×15 mL), dried, and the solvent was removed under reduced pressure. The crude product was purified by column chromatography on silica gel (5% MeOH in DCM) to give 100 mg of tert-butyl 2-(3-acetyl-5-(5-chloro-6-methylpyridin-3-yl)-1H-indol-1-yl)acetate (S4) as a yellow solid.

Step 3: 2-(3-Acetyl-5-(5-chloro-6-methylpyridin-3-yl)-1H-indol-1-yl)acetic acid (S5)

tert-Butyl 2-(3-acetyl-5-(5-chloro-6-methylpyridin-3-yl)-1H-indol-1-yl)acetate (S4) from above was taken up 4 N HCl in dioxane (10 mL) and the resulting reaction mixture was stirred at room temperature for 4 h. The solvent was removed under reduced pressure and the title compound was used directly in the next synthetic step.

Step 4: (2S,4R)-1-(2-(3-Acetyl-5-(5-chloro-6-methylpyridin-3-yl)-1H-indol-1-yl)acetyl)-N-(2'-chloro-2-fluoro-[1,1'-biphenyl]-3-yl)-4-fluoropyrrolidine-2-carboxamide (S7)

2-(3-Acetyl-5-(5-chloro-6-methyl-3-yl)-1H-indol-1-yl)acetic acid (S5, 100 mg, 1 equiv) from the previous step was dissolved in DMF (10 mL) and iPr$_2$NEt (0.17 mL, 3 equiv) was added, which was followed by the addition of (2S, 4R)—N-(3-chloro-(2S,4R)—N-(6-chloropyridin-2-yl)-4-fluoropyrrolidine-2-carboxamide hydrochloride (S6, 110 mg, 0.95 equiv). HATU (122 mg, 1 equiv) was then added and the reaction mixture was stirred for 3 h at rt. After completion of the reaction, which was monitored by HPLC, the reaction mixture was diluted with EtOAc (20 mL) and water (10 mL). The separated organic layer was washed with brine (3×15 mL), dried over Na$_2$SO$_4$, and concentrated under reduced pressure. The remaining residue was purified by column chromatography on silica gel (MeOH/DCM) to give the title compound S7 (81 mg, 40% yield). $^1$H NMR (400 MHz, DMSO-d$_6$): (major rotamer) δ 2.13-2.30 (m, 1H), 2.45 (s, 3H), 2.61 (s, 3H), 2.58-2.68 (m, 1H), 3.91-4.08 (m, 1H), 4.12-4.25 (m, 1H), 4.73 (t, J=8 Hz, 1H), 5.29 (d, J=20 Hz, 1H), 5.46 (d, J=20 Hz, 1H), 5.43-5.55 (m, 1H), 7.06-7.10 (m, 1H), 7.18-7.25 (m, 1H), 7.27-7.72 (m, 6H), 7.91-8.00 (m, 1H), 8.09 (s, 1H), 8.32 (s, 1H), 8.42 (s, 1H), 8.71 (s, 1H), 9.97 (s, 1H); $^{19}$F NMR (376 MHz, DMSO-d$_6$): (major rotamer) δ −126.65, −175.78. LC (method A): $t_R$=2.61 min. LC/MS (EI) m/z: [M+H]$^+$ 661.

rac-2-(2-(3-Acetyl-5-(2-methylpyrimidin-5-yl)-1H-indol-1-yl)acetyl)-N-(2'-chloro-2-fluoro-[1,1'biphenyl]-3-yl)pyrazolidine-3-carboxamide Scheme 23

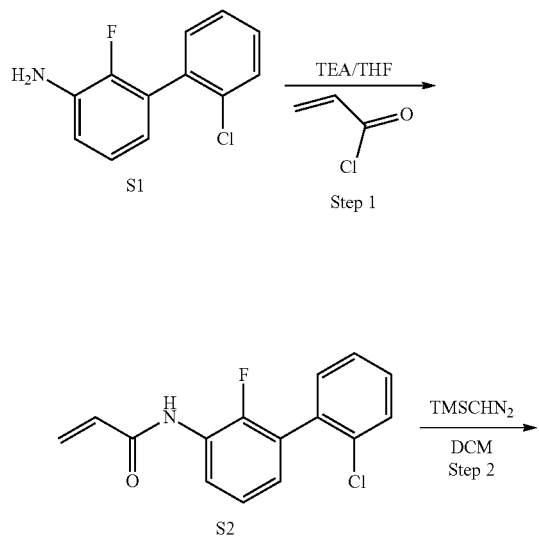

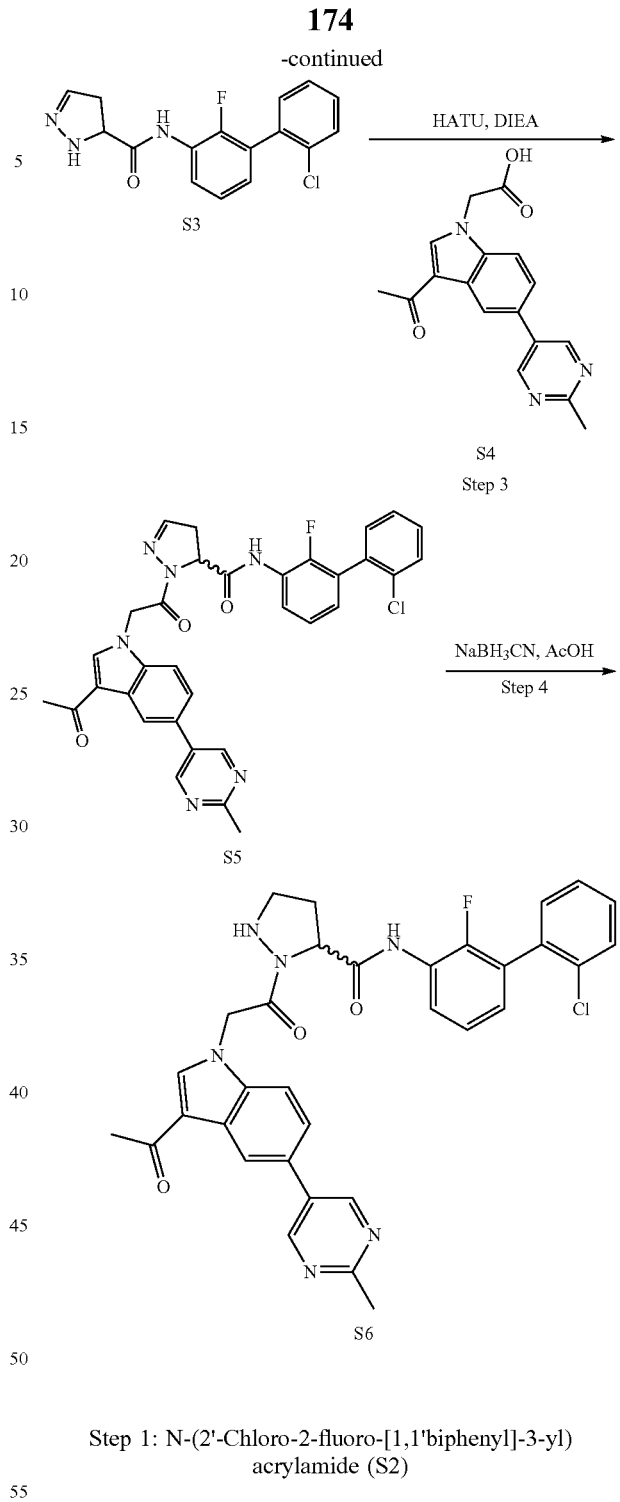

Step 1: N-(2'-Chloro-2-fluoro-[1,1'biphenyl]-3-yl)acrylamide (S2)

To a solution of 2'chloro-2-fluoro-[1,1'-biphenyl]-3-amine (328 mg) and TEA (0.53 mL, 1.2 equiv) in THF (5 mL) was added acryloyl chloride (0.12 mL, 1.2 equiv) dropwise. The reaction mixture was stirred at 25° C. for 2 h. The reaction mixture was diluted with EtOAc (10 mL), washed with HCl (1 N, 1 mL), extracted with EtOAc (10 mL), and the combined organic layers were dried, filtered, and evaporated to dryness. The crude residue was purified by chromatography on silica gel (EtOAc in hexanes, gradient) to give N-(2'-chloro-2-fluoro-[1,1'biphenyl]-3-yl)acrylamide as white solid (299 mg, 86%).

Step 2: N-(2'-Chloro-2-fluoro-[1,1'biphenyl]-3-yl)-4,5-dihydro-1H-pyrazole-5-carboxamide (S3)

To a solution of N-(2'-chloro-2-fluoro-[1,1'biphenyl]-3-yl)acrylamide (299 mg) in a mixture of toluene (15 mL) and hexanes (10 mL) was added trimethylsilyldiazomethane (1.1 mL, 2 M in hexanes, 2 equiv). The reaction mixture was stirred at room temperature for 20 h. The volatiles were removed under reduced pressure and then DCM (15 mL) was added followed by TFA (0.1 mL, 1.1 equiv). The reaction mixture was stirred at room temperature for 1 h, quenched with 5% aq. NaHCO$_3$, and extracted with DCM (15 mL). The organic layer was dried and evaporated to dryness. The remaining residue was purified by column chromatography on silica gel (EtOAc in hexanes, gradient) to give N-(2'-chloro-2-fluoro-[1,1'biphenyl]-3-yl)-4,5-dihydro-1H-pyrazole-5-carboxamide, 100 mg, 31%) as a clear oil.

Step 3: rac-1-(2-(3-Acetyl-5-(2-methylpyrimidin-5-yl)-1H-indol-1-yl)acetyl)-N-(2'-chloro-2-fluoro-[1,1'biphenyl]-3-yl)-4,5-dihydro-1H-pyrazole-5-carboxamide (S5)

2-(3-Acetyl-5-(2-methylpyrimidin-5-yl)-1H-indol-1-yl)acetic acid (93 mg) was dissolved in DMF (10 mL) and iPr$_2$NEt (0.15 mL, 3 equiv). This was followed by the addition of N-(2'-chloro-2-fluoro-[1,1'biphenyl]-3-yl)-4,5-dihydro-1H-pyrazole-5-carboxamide (250, 100 mg, 1.03 equiv). HATU (130 mg, 1.2 equiv) was then added slowly and the reaction mixture was stirred for 3 h at rt. The reaction mixture was added to water (20 mL), extracted with DCM (2×25 mL). The organic layer was washed with water (20 mL) and brine (2×20 mL), then dried over Na$_2$SO$_4$ and concentrated under reduced pressure. The remaining residue was purified by column chromatography (MeOH/DCM) to give 1-(2-(3-acetyl-5-(2-methylpyrimidin-5-yl)-1H-indol-1-yl)acetyl)-N-(2'-chloro-2fluoro-[1,1'biphenyl]-3-yl)-4,5-dihydro-1H-pyrazole-5-carboxamide (35 mg, 19%). $^1$H NMR (400 MHz, DMSO-d$_6$): (major rotamer) δ 2.49 (s, 3H), 2.71 (s, 3H), 3.15-3.21 (m, 1H), 3.65-3.79 (m, 2H), 5.11-5.16 (m, 1H), 5.61 (br, 2H), 7.08-7.12 (m, 1H), 7.41-7.52 (m, 4H), 7.62 (br, 3H), 7.99-8.03 (m, 1H), 8.45 (d, J=7.8 Hz, 2H), 9.00 (s, 2H) 10.2 (s, 1H). $^{19}$F NMR (376 MHz, DMSO-d$_6$): (major rotamer) δ -128.78. LC (method A): t$_R$=2.09 min. LC/MS (EI) m/z: [M+H]$^+$ 609.

Step 4: rac-2-(2-(3-Acetyl-5-(2-methylpyrimidin-5-yl)-1H-indol-1-yl)acetyl)-N-(2'-chloro-2-fluoro-[1,1'biphenyl]-3-yl)pyrazolidine-3-carboxamide (S6)

To a solution of rac-1-(2-(3-acetyl-5-(2-methylpyrimidin-5-yl)-1H-indol-1-yl)acetyl)-N-(2'-chloro-2-fluoro-[1,1'biphenyl]-3-yl)-4,5-dihydro-1H-pyrazole-5-carboxamide (30 mg) in glacial acetic acid (5 mL) was added NaCNBH$_3$ (6 mg, 2 equiv) at room temperature. The reaction mixture was stirred for 2 h and volatiles were removed in vacuo. The remaining material was treated with EtOAc (8 mL) and saturated aq. K$_2$CO$_3$ (5 mL). The organic layer was separated, dried, and concentrated. The residue was purified by HPLC (MeCN in water gradient) to give the TFA salt of rac-2-(2-(3-acetyl-5-(2-methylpyrimidin-5-yl)-1H-indol-1-yl)acetyl)-N-(2'-chloro-2-fluoro-[1,1'biphenyl]-3-yl)pyrazolidine-3-carboxamide (5.3 mg). $^1$H NMR (400 MHz, DMSO-d$_6$): (major rotamer) δ 2.22 (s, 3H), 2.43 (s, 3H), 3.05-3.12 (m, 1H), 3.45-3.51 (m, 2H), 4.56 (s, 2H), 5.02-5.11 (m, 1H), 5.55 (br, 2H), 6.89 (m, 1H), 7.08-7.12 (m, 1H), 7.21-7.27 (m, 1H), 7.38-7.49 (m, 6H), 7.61 (br, 1H), 7.94-8.01 (m, 1H), 8.11 (s, 1H), 8.39 (s, 1H). $^{19}$F NMR (376 MHz, DMSO-d$_6$): (major rotamer) δ -126

(2S,4R)-1-(2-(3-Acetyl-5-(3-methyl-3H-imidazo[4,5-b]pyridin-6-yl)-1H-indazol-1-yl)acetyl)-N-(6-bromopyridin-2-yl)-4-fluoropyrrolidine-2-carboxamide

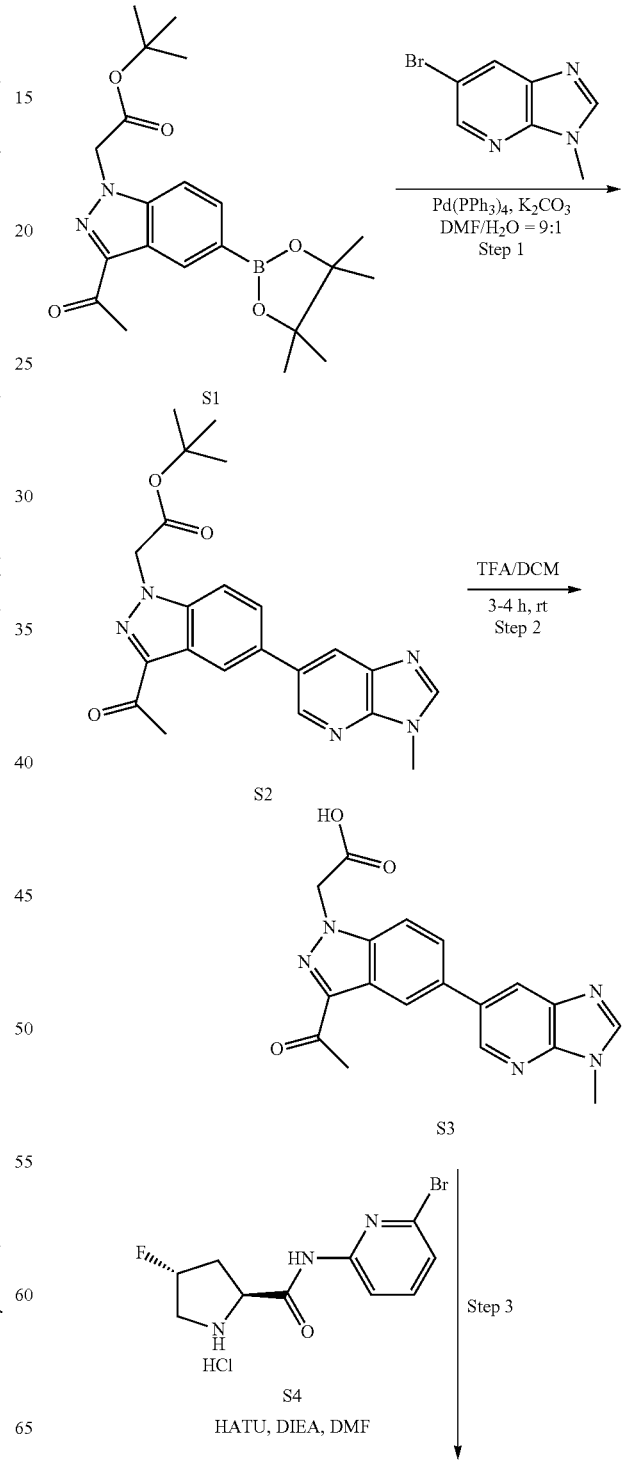

Scheme 24

-continued

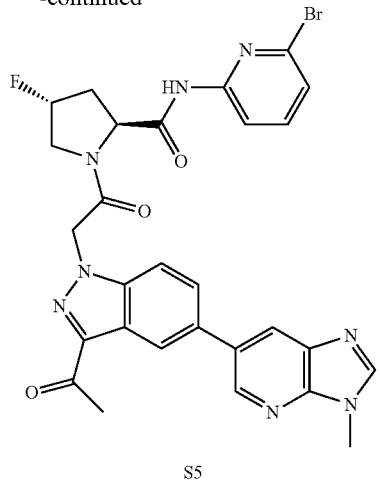

S5

Step 1: tert-Butyl 2-(3-acetyl-5-(3-methyl-3H-imidazo[4,5-b]pyridin-6-yl)-1H-indazol-1-yl)acetate (S2)

To a solution of 6-bromo-3-methyl-3H-imidazo[4,5-b]pyridine (S1, 1 equiv) in DMF/H$_2$O (9:1, 10 vol) was added compound S1 (1 equiv), K$_2$CO$_3$ (2 equiv) and tetrakis(triphenylphosphine)palladium (0.1 equiv). The reaction mixture was stirred at 90° C. for 5 h and then concentrated under reduced pressure. The remaining residue was purified by column chromatography on silica gel to give compound S2.

Step 2: 2-(3-Acetyl-5-(3-methyl-3H-imidazo[4,5-b]pyridin-6-yl)-1H-indazol-1-yl)acetic acid (S3)

To a solution of compound S2 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(3-methyl-3H-imidazo[4,5-b]pyridin-6-yl)-1H-indazol-1-yl)acetyl)-N-(6-bromopyridin-2-yl)-4-fluoropyrrolidine-2-carboxamide (S5)

To a solution of compound S3 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound S5. $^1$H NMR (400 MHz, DMSO-d$_6$): δ 11.00 (s, 1H), 8.70 (s, 1H), 8.53 (s, 1H), 8.41 (s, 1H), 8.34 (s, 1H), 8.04 (d, J=8.0 Hz, 1H), 7.88 (d, J=8.8 Hz, 1H), 7.83 (d, J=8.8 Hz, 1H), 7.71 (t, J=8.0 Hz, 1H), 7.32 (d, J=7.6 Hz, 1H), 5.84 (d, J=17.20 Hz, 1H), 5.65 (d, J=17.20 Hz, 1H), 5.62-5.50 (m, 1H), 4.68 (t, J=8.4 Hz, 1H), 4.25 (dd, J=22.40, 12.40 Hz, 1H), 4.0 (dd, J=43.1, 23.8 Hz, 1H), 3.9 (s, 3H), 2.7 (s, 3H), 2.61-2.58 (m, 1H), 2.26-2.10 (m, 1H). $^{19}$F NMR (376 MHz, DMSO-d$_6$): δ −175.67. LC (method A): t$_R$=1.95 min. LC/MS (EI) m/z: [M+H]$^+$ 619.

(2S,4R)-1-(2-(3-Acetyl-5-(imidazo[1,2-a]pyrimidin-3-yl)-1H-indazol-1-yl)acetyl)-N-(6-bromopyridin-2-yl)-4-fluoropyrrolidine-2-carboxamide (259)

Scheme 25

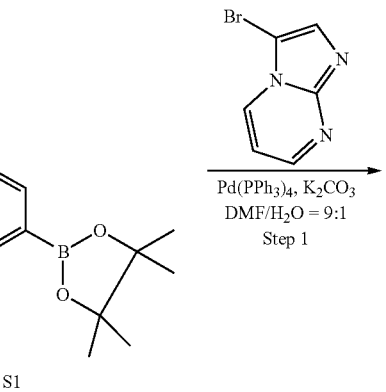

S1

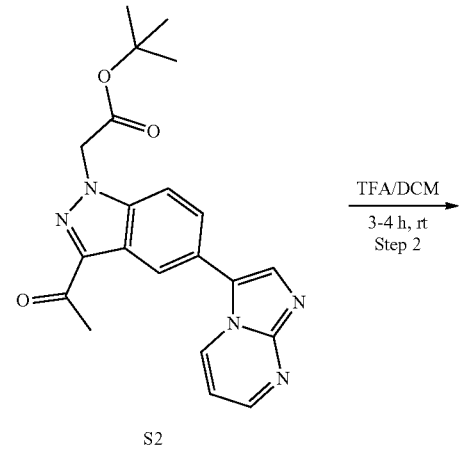

S2

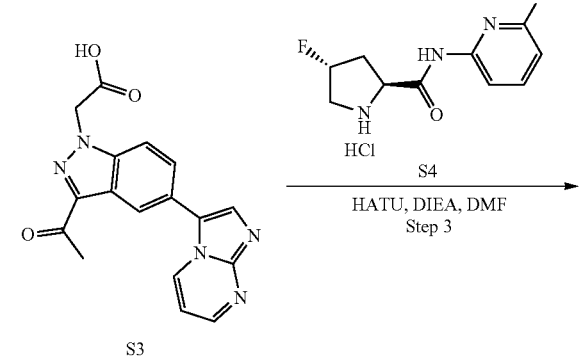

S3

-continued

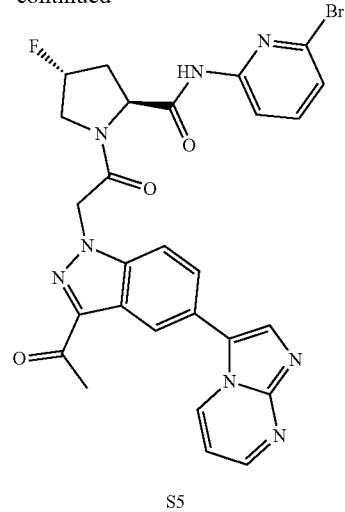

S5

Step 1: tert-Butyl 2-(3-acetyl-5-(imidazo[1,2-a]pyrimidin-3-yl)-1H-indazol-1-yl)acetate (S2)

To a solution of 3-bromoimidazo[1,2-a]pyrimidine (2, 1 equiv) in DMF/H$_2$O (9:1, vol) was added compound S1 (1 equiv), K$_2$CO$_3$ (2 equiv) and tetrakis(triphenylphosphine) palladium (0.1 equiv). The reaction mixture was stirred at 90° C. for 5 h and then concentrated. The remaining residue was purified by column chromatography on silica gel to give compound S2.

Step 2: 2-(3-Acetyl-5-(imidazo[1,2-a]pyrimidin-3-yl)-1H-indazol-1-yl)acetic acid (S3)

To a solution of compound S2 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (2S,4R)-1-(2-(3-Acetyl-5-(imidazo[1,2-a]pyrimidin-3-yl)-1H-indazol-1-yl)acetyl)-N-(6-bromopyridin-2-yl)-4-fluoropyrrolidine-2-carboxamide (S5)

To a solution of compound S3 (1 equiv) in DMF (10 vol) at 0° C. under an atmosphere of nitrogen, (2S,4R)—N-(6-bromopyridin-2-yl)-4-fluoropyrrolidine-2-carboxamide hydrochloride (1 equiv), HATU (2.1 equiv), and DIPEA (5 equiv) were added. The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound S5. $^1$H NMR (400 MHz, DMSO-d$_6$): δ 11.00 (s, 1H), 8.96 (d, J=6.8 Hz, 1H), 8.61-8.60 (m, 1H), 8.38 (s, 1H), 8.04 (d, J=8.0 Hz, 1H), 7.98 (s, 1H), 7.90 (d, J=8.8 Hz, 1H), 7.79 (d, J=8.8 Hz, 1H), 7.71 (t, J=8.0 Hz, 1H), 7.33 (d, J=7.6 Hz, 1H), 7.15-7.12 (m, 1H), 5.87 (d, J=17.20 Hz, 1H), 5.67 (d, J=17.20 Hz, 1H), 5.63-5.50 (m, 1H), 4.69 (t, J=8.40 Hz, 1H), 4.3 (dd, J=22.6, 12.4 Hz, 1H), 4.0 (dd, J=37.5, 12.4 Hz, 1H), 2.7 (s, 3H), 2.61-2.55 (m, 1H), 2.26-2.12 (m, 1H). $^{19}$F NMR (376 MHz, DMSO-d$_6$): δ −175.66. LC (method A): t$_R$=2.47 min. LC/MS (EI) m/z: [M+H]$^+$ 605.

(S)-1-(2-(3-Acetyl-5-(2-methylpyrimidin-5-yl)-1H-indazol-1-yl)acetyl)-N-(6-bromo pyridin-2-yl)-4-oxopyrrolidine-2-carboxamide Scheme 26

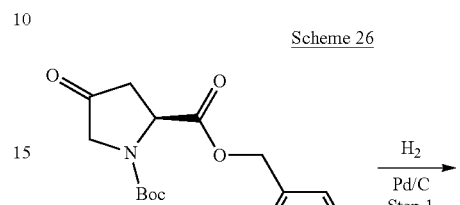

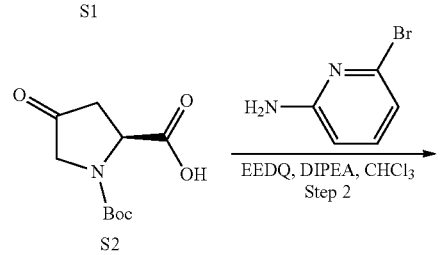

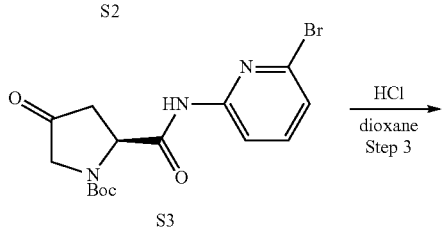

Step 1: (S)-1-(tert-Butoxycarbonyl)-4-oxopyrrolidine-2-carboxylic acid (S2)

To a solution of compound S1 (0.16 g, 0.5 mmol) in anhydrous EtOH (10 mL) was added 10% Pd/C (0.05 g). The resulting mixture was degassed twice and stirred under an atmosphere of $H_2$ (balloon) for 2 h. After filtration, the filtrate was concentrated to give compound S2 (0.10 g, 87% yield). LC-MS: m/z 230 (M+H)$^+$.

Step 2: (S)-tert-Butyl 2-(6-bromopyridin-2-ylcarbamoyl)-4-oxopyrrolidine-1-carboxylate (S3)

To a mixture of compound S2 (0.10 g, 0.43 mmol), 6-bromopyridin-2-amine (0.076 g, 0.43 mmol), and DIPEA (0.15 mL, 0.87 mmol) in CHCl$_3$ (5 mL) was added EEDQ (0.22 g, 0.87 mmol). The resulting mixture was stirred at 80° C. overnight. The reaction mixture was concentrated and the residue was purified by column chromatography on silica gel (eluted with petroleum ether/ethyl acetate=10:1) to give compound S3 (0.08 g, yield 48%) as a yellow solid. LC-MS: m/z 384 (M+H)$^+$.

Step 3: (S)—N-(6-Bromopyridin-2-yl)-4-oxopyrrolidine-2-carboxamide (S4)

To a solution of compound S3 (0.08 g, 0.2 mmol) in dioxane (2 mL) at room temperature was added saturated HCl/dioxane solution (2 mL). The reaction mixture was stirred at room temperature for 2 h and then concentrated to give compound S4 (0.06 g, yield 95%). LC-MS: m/z 284 (M+H)$^+$.

Step 4: (S)-1-(2-(3-Acetyl-5-(2-methylpyrimidin-5-yl)-1H-indazol-1-yl)acetyl)-N-(6-bromo pyridin-2-yl)-4-oxopyrrolidine-2-carboxamide (S6)

To a solution of compound S5 (60 mg, 0.19 mmol), compound S4 (58 mg, 0.19 mmol), and DIPEA (0.06 mL, 0.38 mmol) in DMF (2 mL) at room temperature was added HATU (0.14 g, 0.38 mmol). The resulting mixture was stirred at room temperature overnight and then concentrated. The residue was purified by prep-HPLC (eluted with CH$_3$CN/water) to give compound S6 (20 mg, yield 19%) as a white solid. $^1$H-NMR: 8.99 (s, 1H), 8.82 (s, 2H), 8.48 (s, 1H), 7.90 (d, J=8.0 Hz, 1H), 7.52 (s, 1H), 7.42 (t, J=8.0 Hz, 1H), 7.14 (d, J=8.0 Hz, 1H), 5.23 (dd, J=24 Hz, 16 Hz, 2H), 5.11 (d, J=8 Hz, 1H), 4.14 (d, J=16 Hz, 1H), 3.99 (d, J=16 Hz, 1H), 2.84 (d, J=16 Hz, 1H), 2.74 (s, 3H), 2.70-2.65 (m, 1H), 2.62 (s, 3H). LC-MS: m/z 576 (M+H)$^+$.

(S)-1-(2-(3-Acetyl-5-(2-methylpyrimidin-5-yl)-1H-indazol-1-yl)acetyl)-N-(6-bromo pyridin-2-yl)-4,4-difluoropyrrolidine-2-carboxamide Scheme 27

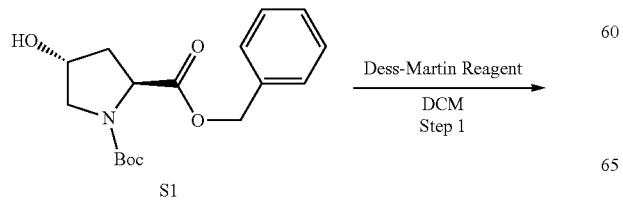

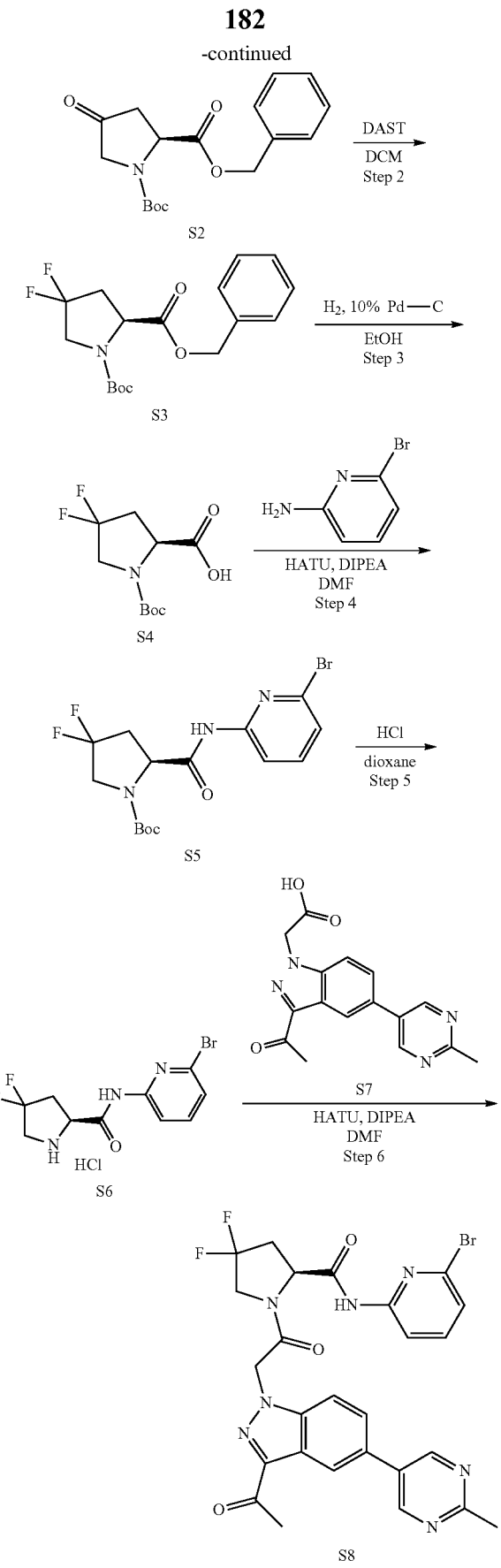

Step 1: (S)-2-Benzyl 1-tert-butyl 4-oxopyrrolidine-1,2-dicarboxylate (S2)

To a solution of compound S1 (3.2 g, 10 mmol) in anhydrous DCM (100 mL) at 0° C. was added Dess-Martin periodinane (6.6 g, 15 mmol). The reaction mixture was stirred at room temperature for 16 h and then quenched with saturated aq. NaHCO$_3$ (100 mL). The resulting mixture was extracted with DCM (150 mL×2). The combined organic layers were washed with brine, dried over anhydrous Na$_2$SO$_4$, filtered, and then concentrated. The residue was purified by column chromatography on silica gel to afford compound S2 (2.5 g, 78% yield). LC-MS: m/z 320 (M+H)$^+$.

Step 2: (S)-2-Benzyl 1-tert-butyl 4,4-difluoropyrrolidine-1,2-dicarboxylate (S3)

To a solution of compound S2 (0.25 g, 0.8 mmol) in anhydrous DCM (10 mL) at −78° C. was added DAST (0.64 g, 4 mmol). The reaction mixture was stirred at room temperature overnight and then quenched with saturated aq. NaHCO$_3$ (50 mL). The resulting mixture was extracted with DCM (50 mL×2). The organic layer was separated, dried over anhydrous Na$_2$SO$_4$, filtered, and then concentrated. The residue was purified by column chromatography on silica gel to afford compound S3 (0.19 g, 70% yield). LC-MS: m/z 342 (M+H)$^+$.

Step 3: (S)-1-(tert-Butoxycarbonyl)-4,4-difluoropyrrolidine-2-carboxylic acid (S4)

To a solution of compound S3 (0.19 g, 0.56 mmol) in anhydrous EtOH (10 mL) was added 10% Pd/C (0.05 g). The resulting mixture was degassed twice and stirred under an atmosphere of H$_2$ (balloon) for 2 h. After filtration, the filtrate was concentrated to give compound S4 (0.13 g, 95% yield). LC-MS: m/z 252 (M+H)$^+$.

Step 4: (S)-tert-Butyl 2-(2'-chloro-2-fluorobiphenyl-3-ylcarbamoyl)-4,4-difluoropyrrolidine-1-carboxylate (S5)

To a solution of compound S4 (0.13 g, 0.53 mmol), compound S5 (0.12 g, 0.53 mmol), and DIPEA (0.1 mL, 0.60 mmol) in DMF (2 mL) at room temperature, HATU (0.2 g, 0.53 mmol) was added. The resulting mixture was stirred at room temperature overnight and then concentrated. The residue was purified by column chromatography on silica gel to give compound S5 (0.15 g, yield 60%) as a yellow oil. LC-MS: m/z 406 (M+H)$^+$.

Step 5: (S)—N-(2'-Chloro-2-fluorobiphenyl-3-yl)-4,4-difluoropyrrolidine-2-carboxamide (S6)

To a solution of compound S5 (0.15 g, 0.33 mmol) in dioxane (5 mL) at room temperature was added saturated HCl/dioxane solution (5 mL). The reaction mixture was stirred at room temperature for 2 h and then concentrated to give compound S6 (0.11 g, yield 95%). LC-MS: m/z 306 (M+H)$^+$.

Step 6: (S)-1-(2-(3-Acetyl-5-(2-methylpyrimidin-5-yl)-1H-indazol-1-yl)acetyl)-N-(6-bromo pyridin-2-yl)-4,4-difluoropyrrolidine-2-carboxamide (S8)

To a solution of compound S7 (110 mg, 0.3 mmol), compound S6 (120 mg, 0.3 mmol), and DIPEA (0.2 mL, 1.2 mmol) in DMF (2 mL) at room temperature, HATU (0.2 g, 0.6 mmol) was added. The resulting mixture was stirred at room temperature overnight and then concentrated. The residue was purified by prep-HPLC (eluted with CH$_3$CN/water) to give compound S8 (20 mg, yield 18%) as a white solid. $^1$H-NMR: 8.98 (s, 2H), 8.43 (s, 1H), 7.92 (t, J=8.0 Hz, 1H), 7.72-7.64 (m, 2H), 7.50 (t, J=8.0 Hz, 1H), 7.15 (d, J=8.0 Hz, 1H), 5.48 (dd, J=24 Hz, 16 Hz, 2H), 5.41-5.25 (m, 1H), 4.32-4.19 (m, 2H), 2.85-2.79 (m, 1H), 2.65 (s, 3H), 2.59 (s, 3H), 2.51-2.43 (s, 1H). LC-MS: m/z 598 (M+H)$^+$.

(2S,4R)-1-(2-(3-Acetyl-5-(3-cyano-2-methylpyrazolo[1,5-a]pyrimidin-6-yl)-1H-indazol-1-yl)acetyl)-N-(6-bromopyridin-2-yl)-4-fluoropyrrolidine-2-carboxamide

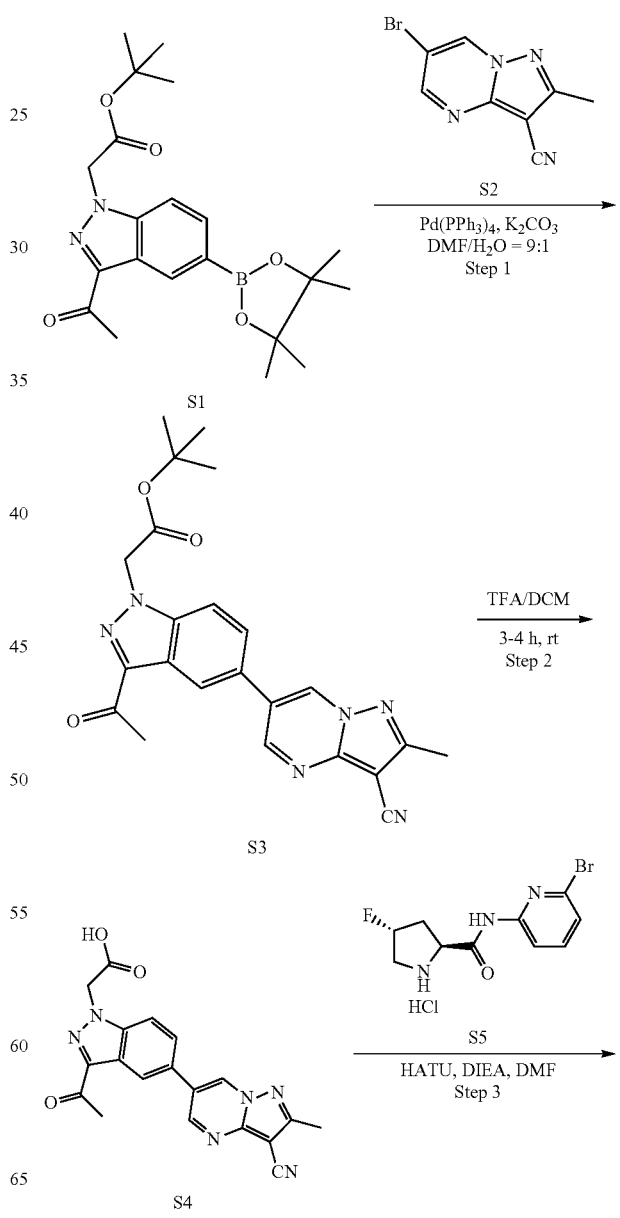

Scheme 28

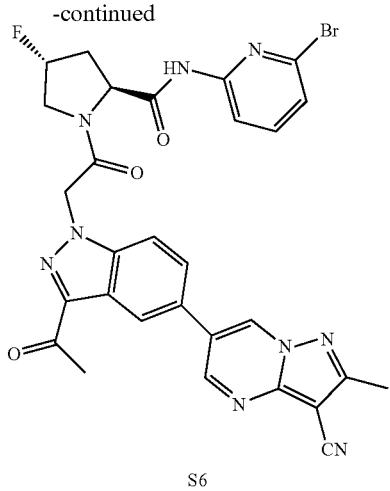

S6

Step 1: tert-Butyl2-(3-acetyl-5-(3-cyano-2-methyl-pyrazolo[1,5-a]pyrimidin-6-yl)-1H-indazol-1-yl)acetate (S3)

To a solution of 6-bromo-2-methylpyrazolo[1,5-a]pyrimidine-3-carbonitrile (1 equiv) in DMF/H2O (9:1, 10 vol) was added compound S1 (1 equiv), K₂CO₃ (2 equiv) and tetrakis(triphenylphosphine) palladium (0.1 equiv). The reaction mixture was stirred at 90° C. for 5 h and then concentrated. The residue was purified by column chromatography on silica gel to give compound S2.

Step 2: 2-(3-Acetyl-5-(3-cyano-2-methylpyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (2S,4R)-1-(2-(3-Acetyl-5-(3-cyano-2-methylpyrazolo[1,5-a]pyrimidin-6-yl)-1H-indazol-1-yl)acetyl)-N-(6-bromopyridin-2-yl)-4-fluoropyrrolidine-2-carboxamide (S5)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv) and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound S6. ¹H NMR (400 MHz, DMSO-d₆): δ 10.99 (s, 1H), 9.65 (s, 1H), 9.18 (s, 1H), 8.53 (s, 1H), 8.03 (d, J=8.0 Hz, 1H), 7.95-7.87 (m, 2H), 7.71 (t, J=8.0 Hz, 1H), 7.33 (d, J=8.0 Hz, 1H), 5.86 (d, J=17.2 Hz, 1H), 5.66 (d, J=17.2 Hz, 1H), 5.63-5.50 (m, 1H), 4.69 (t, J=8.40 Hz, 1H), 4.25 (dd, J=22.20, 12.80 Hz, 1H), 4.04 (dd, J=33.80, 12.80 Hz, 1H), 2.66 (s, 3H), 2.63-2.61 (m, 1H), 2.6 (s, 3H), 2.25-2.12 (m, 1H). ¹⁹F NMR (376 MHz, DMSO-d₆): δ −175.65. LC (method A): $t_R$=2.07 min. LC/MS (EI) m/z: [M+H]⁺ 644.

(2S,4R)-1-(2-(3-Acetyl-5-(2-methylpyrazolo[1,5-a]pyrimidin-6-yl)-1H-indol-1-yl)acetyl)-N-(6-bromopyridin-2-yl)-4-fluoropyrrolidine-2-carboxamide Scheme 29

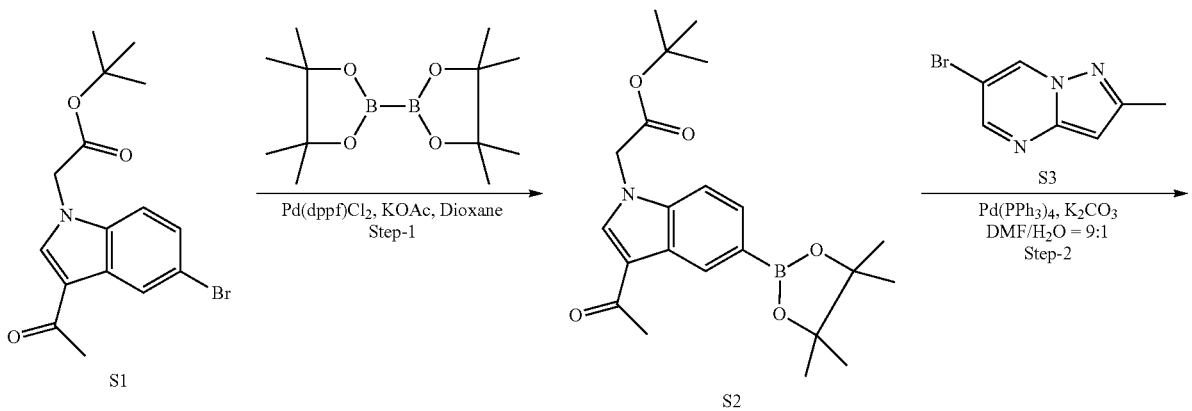

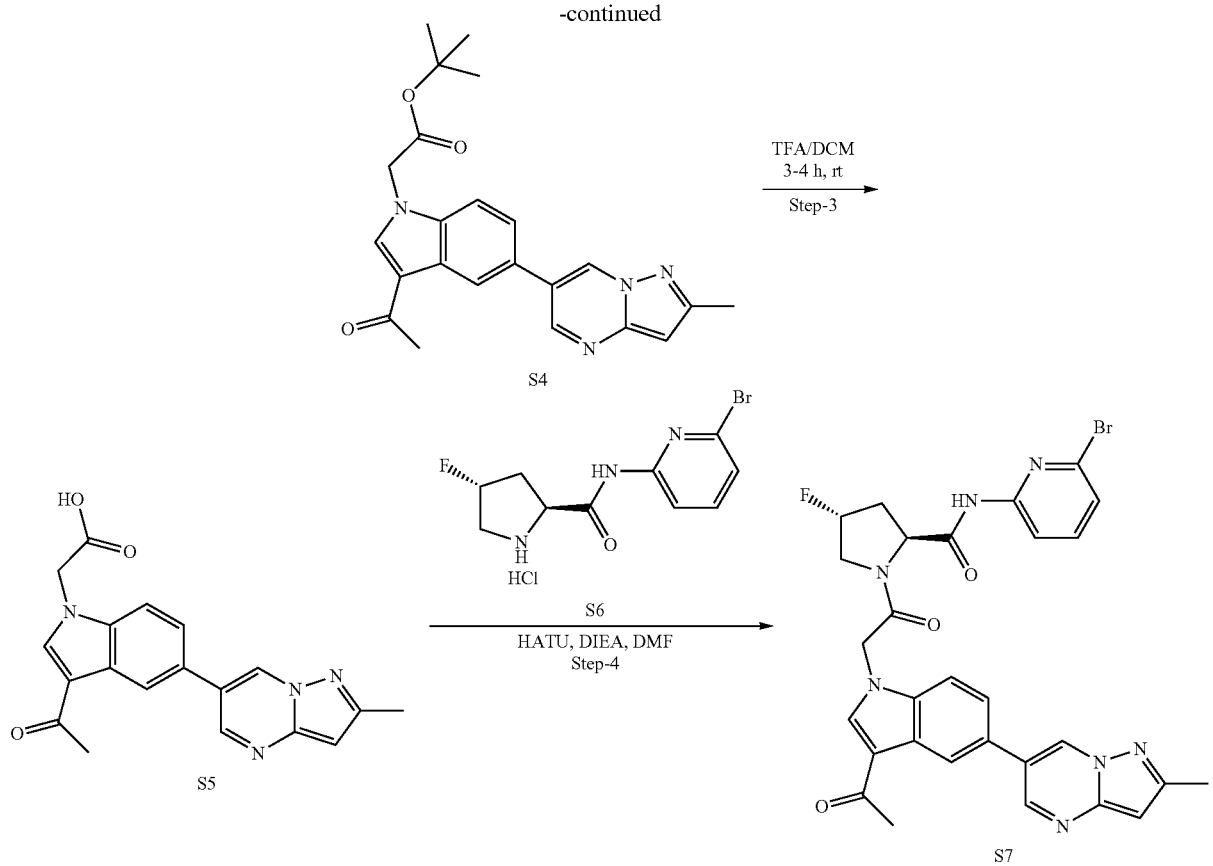

Step 1: tert-Butyl 2-(3-acetyl-5-(4,4,5,5-tetramethyl-1,3,2-dioxaborolan-2-yl)-1H-indol-1-yl)acetate (S2)

In one portion, Pd(dppf)Cl$_2$ (2.71 g, 3.7 mmol) was to a mixture of compound S1 (26 g, 74.1 mmol), AcOK (21.8 g, 222.1 mmol), and 4,4,4',4',5,5,5',5'-octamethyl-2,2'-bi(1,3,2-dioxaborolane) (22.6 g, 88.9 mmol) in dioxane (200 mL). The resulting mixture was stirred at 90° C. under nitrogen for 3 h. After cooling the reaction mixture to room temperature, the mixture was filtered through Celite and washed with dioxane (30 mL). The filtrate was concentrated under high vacuum and the residue was purified by column chromatography (silica gel, petroleum ether/ethyl acetate=5:1) to give the title compound.

Step 2: tert-Butyl 2-(3-acetyl-5-(2-methylpyrazolo[1,5-a]pyrimidin-6-yl)-1H-indol-1-yl)acetate (S4)

K$_2$CO$_3$ (0.138 g, 1 mmol) and Pd(PPh$_3$)$_4$ (0.029 g, 0.025 mmol) were added to a solution of compound S3 (0.200 g, 0.5 mmol) and compound S2 (0.105 g, 0.5 mmol) in DMF (20 mL)/water (2 mL). The reaction mixture was stirred at 95° C. under argon for 3 h. The reaction mixture was then added to water (100 mL+10 g solid NaCl) and extracted with DCM (2×15 mL). The organic layer was washed successively with an aqueous solution of NaHCO$_3$ (10 mL), water (10 mL), and brine (10 mL), then dried over Na$_2$SO$_4$ and concentrated under reduced pressure. The remaining residue was purified by column chromatography (silica gel, DCM/MeOH) to give the title compound.

Step 3: 2-(3-Acetyl-5-(2-methylpyrazolo[1,5-a]pyrimidin-6-yl)-1H-indol-1-yl)acetic acid (S5)

To a solution of compound S4 (200 mg) in DCM (5 mL) was added TFA (5 mL). The resulting mixture was stirred at room temperature for 4 h and then concentrated to afford crude product S5, which was used in the next step without further purification.

Step 4: (2S,4R)-1-(2-(3-Acetyl-5-(2-methylpyrazolo[1,5-a]pyrimidin-6-yl)-1H-indol-1-yl)acetyl)-N-(6-bromopyridin-2-yl)-4-fluoropyrrolidine-2-carboxamide (S7)

Compound S5 (105 mg) was dissolved in DMF (5 mL) and DIPEA (0.260 mL) was added. This was followed by the addition of (2S,4R)—N-(6-bromopyridin-2-yl)-4-fluoropyrrolidine-2-carboxamide hydrochloride (0.096 g) at 5° C. HATU (240 mg) was then added slowly and the reaction mixture was stirred for 3 h at rt. The reaction mixture was then added to water (25 mL+5 g solid NaCl) and extracted with DCM (2×15 mL). The organic layer was washed successively with an aqueous solution of NaHCO$_3$ (10 mL), water (10 mL), and brine (10 mL), dried over Na$_2$SO$_4$, and concentrated under reduced pressure. The remaining residue was purified by column chromatography (silica gel, DCM/MeOH) to give the title compound. $^1$H NMR (400 MHz, DMSO-d$_6$): (major rotamer) δ 2.08-2.25 (m, 1H), 2.47 (S, 3H), 2.48 (S, 3H), 2.58-2.63 (m, 1H), 3.94-4.06 (m, 1H), 4.16-4.24 (m, 1H), 4.70 (t, J=12 Hz, 1H), 5.3 (d, J=16, 1H), 5.45 (d, J=16 Hz, 1H), 5.50-5.63 (m, 1H), 6.56 (s, 1H), 7.31

(d, J=8 Hz, 1H), 7.61-7.67 (m, 2H), 7.71 (t, J=8 Hz, 1H), 8.04 (d, J=8 Hz, 1H), 8.32 (s, 1H), 8.46 (s, 1H), 8.81 (d, 1H), 9.23 (d, 1H), 11.01 (s, 1H). $^{19}$F NMR (376 MHz, CDCl$_3$): δ −175.61. LC (method A): $t_R$=1.82 min. LC/MS (EI) m/z: [M+H]+ 618.

(2S,4R)-1-(2-(3-Acetyl-5-(2-(undec-10-enylamino) pyrimidin-5-yl)-1H-indazol-1-yl)acetyl)-N-(3-chloro-2-fluoro-5-vinylbenzyl)-4-fluoropyrrolidine-2-carboxamide

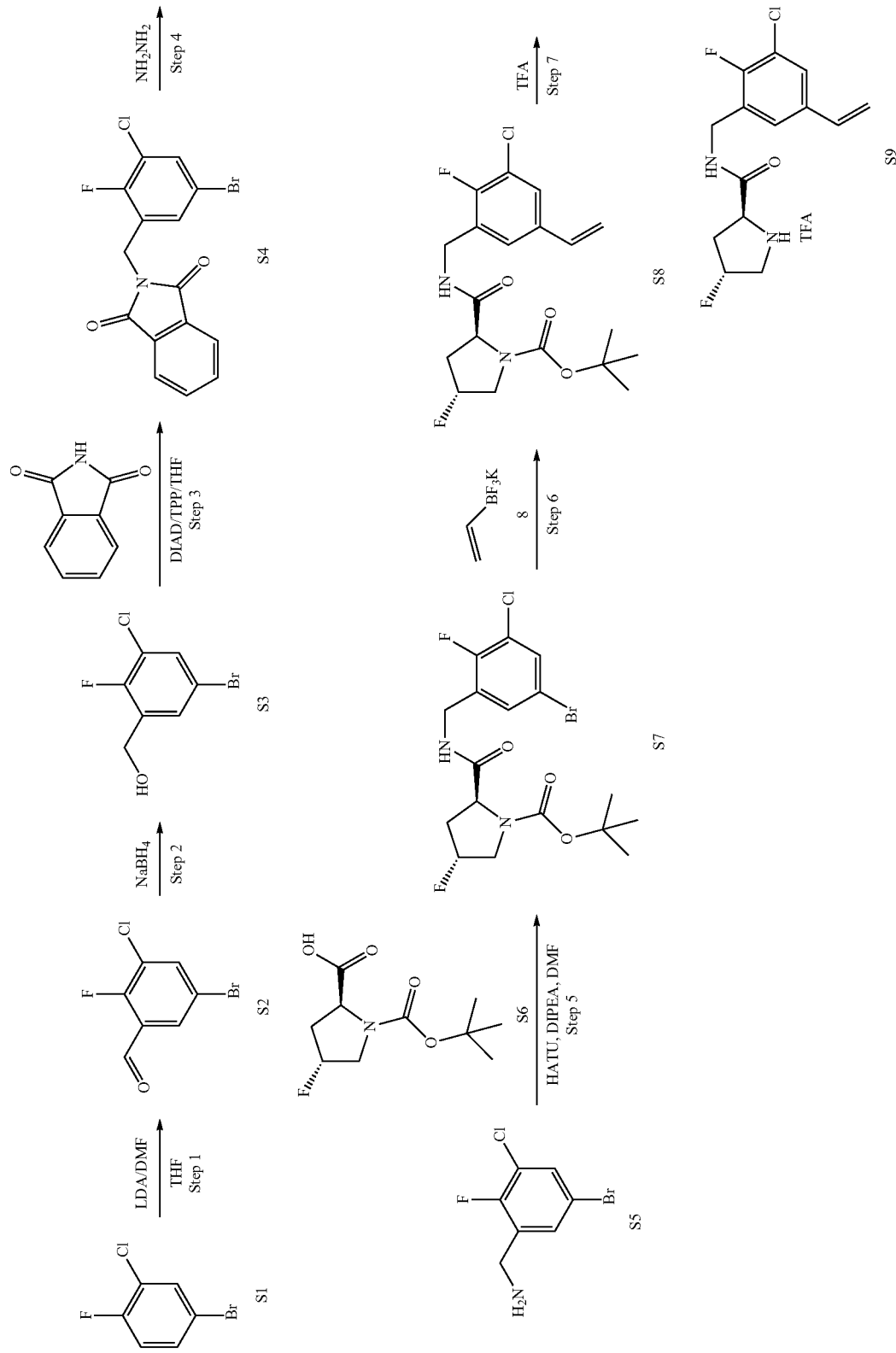

-continued
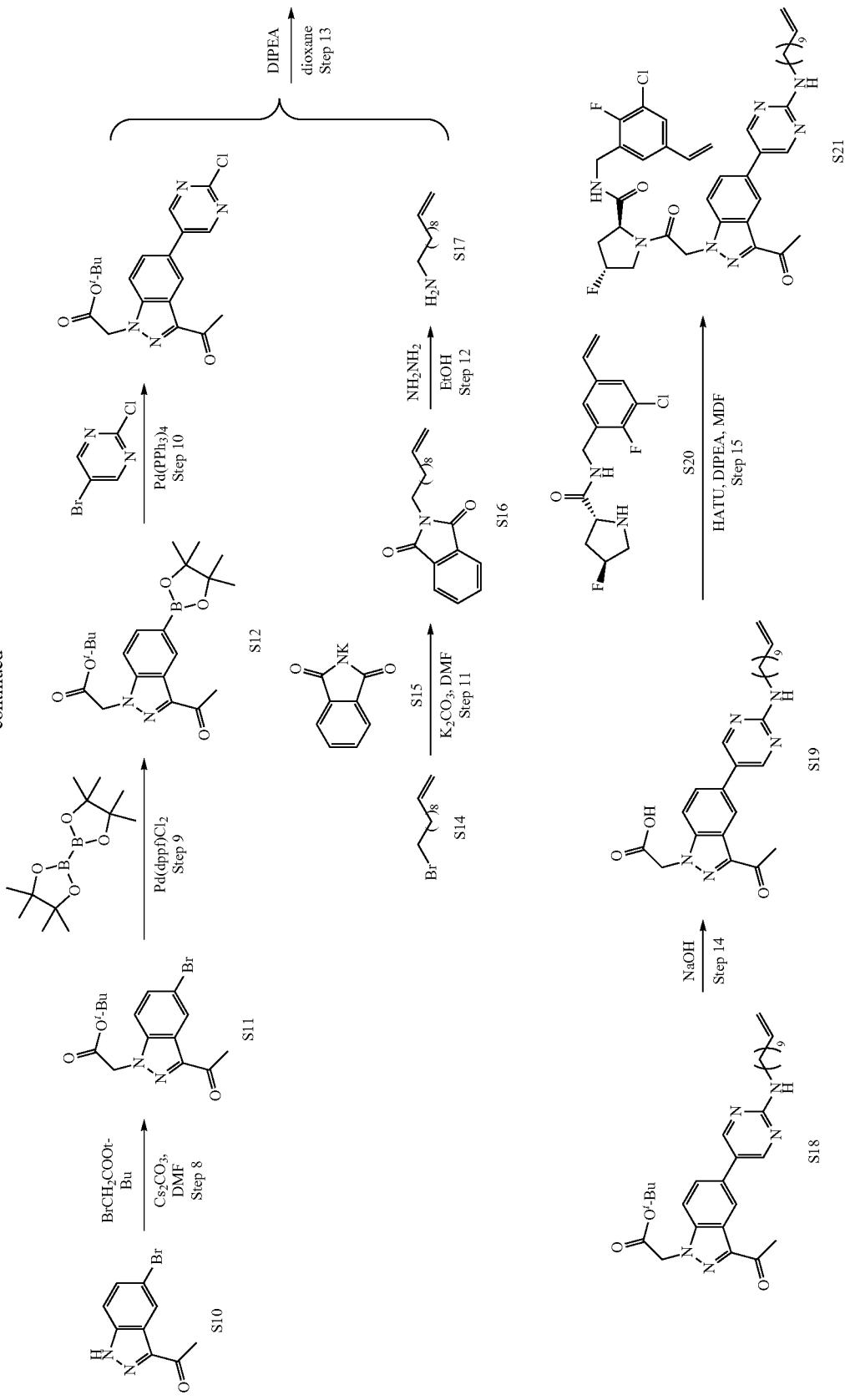

Step 1: 5-Bromo-3-chloro-2-fluorobenzaldehyde (S2)

To a dry-ice/ethanol cooled solution of compound S1 (20.0 g, 0.95 mol) in THF (200 mL) was added 2 M LDA (52 mL, 1.05 mol) dropwise over 30 min. After addition, the reaction mixture was stirred at this temperature for 30 min followed by the addition of DMF (10.5 g, 1.43 mol). The reaction was stirred for 30 min and warmed to room temperature slowly. The reaction mixture was then quenched with aq. $NH_4Cl$ (100 mL) and extracted with ethyl acetate (500 mL). The organic phase was washed with brine, dried over anhydrous $Na_2SO_4$, filtered, and concentrated. The residue was purified by column chromatography on silica gel (eluted with petroleum ether/ethyl acetate=1:0 to 50:1) to give compound S2 (10 g, yield 40%) as a yellow oil.

Step 2: (5-Bromo-3-chloro-2-fluorophenyl)methanol (S3)

To an ice-water cooled solution of compound S2 (18.0 g, 0.076 mol) in THF (150 mL) was added $NaBH_4$ (4.3 g, 0.114 mol). The reaction mixture was stirred at this temperature for 1 h. Then the reaction mixture was quenched slowly with aq. $NH_4Cl$ and extracted with ethyl acetate (500 mL). The organic phase was washed with brine, dried over anhydrous $Na_2SO_4$, filtered, and then concentrated. The residue was purified by column chromatography on silica gel (eluted with petroleum ether/ethyl acetate=100:1 to 20:1) to give compound S3 (10 g, yield 55%) as a white solid.

Step 3: 2-(5-Bromo-3-chloro-2-fluorobenzyl)isoindoline-1,3-dione (S4)

To an ice-water cooled solution of compound S3 (17.0 g, 0.071 mol), isoindoline-1,3-dione (15.7 g, 0.106 mol), and triphenylphosphine (22.4 g, 0.085 mol) in THF (100 mL) was added DIAD (28.7 g, 0.142 mol). The reaction mixture was stirred at room temperature overnight and then concentrated. The residue was purified by column chromatography on silica gel (eluted with petroleum ether/ethyl acetate=100:1 to 10:1) to give compound S4 (10 g, yield 55%) as a white solid.

Step 4. (5-Bromo-3-chloro-2-fluorophenyl)methanamine (S5)

A mixture of compound S4 (14 g, 37.98 mmol) and $NH_2NH_2\cdot H_2O$ (2.28 g, 45.58 mmol) in EtOH (70 mL) was stirred at 80° C. for 5 h. After cooling to room temperature, the reaction mixture was filtered. Following concentration, the residue was purified by prep-HPLC to afford compound S5 (6 g, yield 67%) as a white solid.

Step 5: (2S,4R)-Tert-Butyl 2-(5-bromo-3-chloro-2-fluorobenzylcarbamoyl)-4-fluoropyrrolidine-1-carboxylate (S6)

To a solution of compound S5 (3.5 g, 15.0 mmol), compound S6 (3.94 g, 16.5 mmol), and DIPEA (5.82 g, 45.02 mmol) in DMF (20 mL) was added HATU (12.55 g, 33 mmol). The resulting mixture was stirred at room temperature overnight and then concentrated. The residue was purified by prep-HPLC (eluted with $CH_3CN$/water) to give compound S7 (1.2 g, yield 18%) as a white solid.

Step 6: (2S,4R)-tert-Butyl 2-(3-chloro-2-fluoro-5-vinylbenzylcarbamoyl)-4-fluoropyrrolidine-1-carboxylate (S8)

$Pd(dppf)Cl_2$ (0.18 g, 0.242 mmol) was added to a solution of compound S7 (1.1 g, 2.42 mmol), vinyltrifluoroboric acid potassium salt (0.65 g, 4.85 mmol), and TEA (0.49 g, 4.85 mmol) in EtOH (5 mL) at room temperature under nitrogen. The resulting mixture was stirred under nitrogen at 80° C. for 3 h and then concentrated. The residue was diluted with water (50 mL) and extracted with ethyl acetate (50 mL). The organic phase was washed with brine, dried over anhydrous $Na_2SO_4$, filtered, and then concentrated. The residue was purified by column chromatography on silica gel (eluted with petroleum ether/ethyl acetate=1:0 to 20:1) to give compound S8 (0.9 g, yield 87%) as a white solid.

Step 7: (2S,4R)—N-(3-Chloro-2-fluoro-5-vinylbenzyl)-4-fluoropyrrolidine-2-carboxamide (S9)

To a solution of compound S8 (0.8 g, 2 mmol) in DCM (5 mL) was added TFA (5 mL). The resulting mixture was stirred at room temperature for 1 h and then concentrated to afford crude S9 (0.8 g) as a brown solid, which was used in the next step without further purification.

Step 8: tert-Butyl 2-(3-acetyl-5-bromo-1H-indazol-1-yl)acetate (S11)

To a solution of compound S10 (11.0 g, 0.046 mol) and tert-butyl 2-bromoacetate (10.8 g, 0.055 mol) in DMF (50 mL) at room temperature was added $Cs_2CO_3$ (12.7 g, 0.092 mol). After addition, the mixture was stirred at room temperature overnight and then quenched with water (500 mL). The resulting mixture was extracted with ethyl acetate (500 mL). The organic phase was washed with brine, dried over anhydrous $Na_2SO_4$, filtered, and then concentrated. The residue was purified by column chromatography on silica gel (eluted with petroleum ether/ethyl acetate=1:0 to 20:1) to give compound S11 (11.6 g, yield 71%) as a white solid.

Step 9: tert-Butyl 2-(3-acetyl-5-(4,4,5,5-tetramethyl-1,3,2-dioxaborolan-2-yl)-1H-indazol-1-yl)Acetate (S12)

$Pd(dppf)Cl_2$ (1.1 g, 0.0014 mol) was added to a solution of compound S11 (5.0 g, 0.014 mol), 4,4,4',4',5,5,5',5'-octamethyl-2,2'-bi(1,3,2-dioxaborolane) (4.3 g, 0.017 mol), and KOAc (4.2 g, 0.042 mol) in 1,4-dioxane (100 mL) at room temperature under nitrogen. The reaction mixture was stirred under nitrogen protection at 120° C. for 2 h and then concentrated. Water (100 mL) was added and the mixture was extracted with ethyl acetate (100 mL). The organic phase was washed with brine, dried over anhydrous $Na_2SO_4$, filtered, and then concentrated. The residue was purified by column chromatography on silica gel (eluted with petroleum ether/ethyl acetate=100:1 to 7:1) to give compound S12 (5.0 g, yield 89%) as a white solid.

Step 10: tert-Butyl 2-(3-acetyl-5-(2-chloropyrimidin-5-yl)-1H-indazol-1-yl)acetate (S13)

$Pd(PPh_3)_4$ (0.145 g, 0.125 mmol) was added to a solution of compound S12 (0.5 g, 1.25 mmol), 5-bromo-2-chloropyrimidine (0.265 g, 1.38 mmol), and $K_2CO_3$ (0.52 g, 3.75 mmol) in 1,4-dioxane (10 mL)/water (2 mL) at room temperature under nitrogen. The reaction mixture was stirred under nitrogen protection at 120° C. for 2 h and then concentrated. Water (50 mL) was added and the mixture was extracted with ethyl acetate (50 mL). The organic phase was washed with brine, dried over anhydrous $Na_2SO_4$, filtered, and then concentrated. The residue was purified by column chromatography on silica gel (eluted with petroleum ether/ethyl acetate=100:1 to 2:1) to give compound S13 (0.2 g, yield 65%) as a white solid.

Step 11: 2-(Undec-10-enyl)isoindoline-1,3-dione (S16)

A mixture of compound S14 (5 g, 21.44 mmol) and potassium salt (4.4 g, 22.0 mmol) in DMF (50 mL) was stirred at 80° C. overnight and then quenched with water (100 mL). The resulting mixture was extracted with ethyl acetate (200 mL). The organic phase was washed with brine, dried over anhydrous $Na_2SO_4$, filtered, and then concentrated. The residue was purified by column chromatography on silica gel (eluted with petroleum ether/ethyl acetate=100:1 to 10:1) to give compound S16 (5 g, yield 78%) as a yellow oil.

Step 12: Undec-10-en-1-amine (S17)

A mixture of compound S16 (5 g, 16.7 mmol) and $NH_2NH_2.H_2O$ (0.92 g, 18.4 mmol) in EtOH (50 mL) was stirred at 80° C. for 5 h. After cooling to room temperature, the mixture was filtered and the filtrate was concentrated to afford crude compound S17 (2 g, yield 70%) as a white solid.

Step 13: tert-Butyl 2-(3-acetyl-5-(2-(undec-10-enylamino)pyrimidin-5-yl)-1H-indazol-1-yl)acetate (S18)

A mixture of compound S13 (75 mg, 0.194 mmol) and compound S17 (33 mg, 0.194 mmol) in 1,4-dioxane (5 mL) was stirred at 80° C. overnight and then concentrated. The residue was purified by column chromatography on silica gel (eluted with petroleum ether/ethyl acetate=5:1 to 1:1) to give compound S18 (70 mg, yield 70%) as a yellow solid.

Step 14: 2-(3-Acetyl-5-(2-(undec-10-enylamino)pyrimidin-5-yl)-1H-indazol-1-yl)acetic acid (S19)

To a solution of compound S18 (0.2 g, 0.384 mmol) in THF (5 mL)/$H_2O$ (1 mL) was added NaOH (0.015 g, 0.384 mmol). The reaction mixture was stirred at room temperature overnight and then acidified with aq. citric acid to adjust to pH of 5. The resulting mixture was extracted with ethyl acetate (50 mL). The organic layer was washed with brine, dried over anhydrous $Na_2SO_4$, filtered, and then concentrated to give compound S19 (0.15 g yield 88%) as a brown solid that was used without further purification.

Step 15: (2S,4R)-1-(2-(3-Acetyl-5-(2-(undec-10-enylamino)pyrimidin-5-yl)-1H-indazol-1-yl)acetyl)-N-(3-chloro-2-fluoro-5-vinylbenzyl)-4-fluoropyrrolidine-2-carboxamide (S21)

HATU (776 mg, 2.043 mmol) was added to a solution of compound S19 (430 mg, 0.929 mmol), compound S18 (446 mg, 1.11 mmol), and DIPEA (599 mg, 4.644 mmol) in DMF (10 mL) at room temperature. The reaction mixture was stirred at room temperature overnight and concentrated. The residue was purified by prep-HPLC (eluted with $CH_3CN$/water) to give compound S20 (500 mg, yield 72%) as a white solid.

(R)-2-(6-Bromopyridin-2-yl)-1-((2S,4R)-4-fluoropyrrolidin-2-yl)ethanol

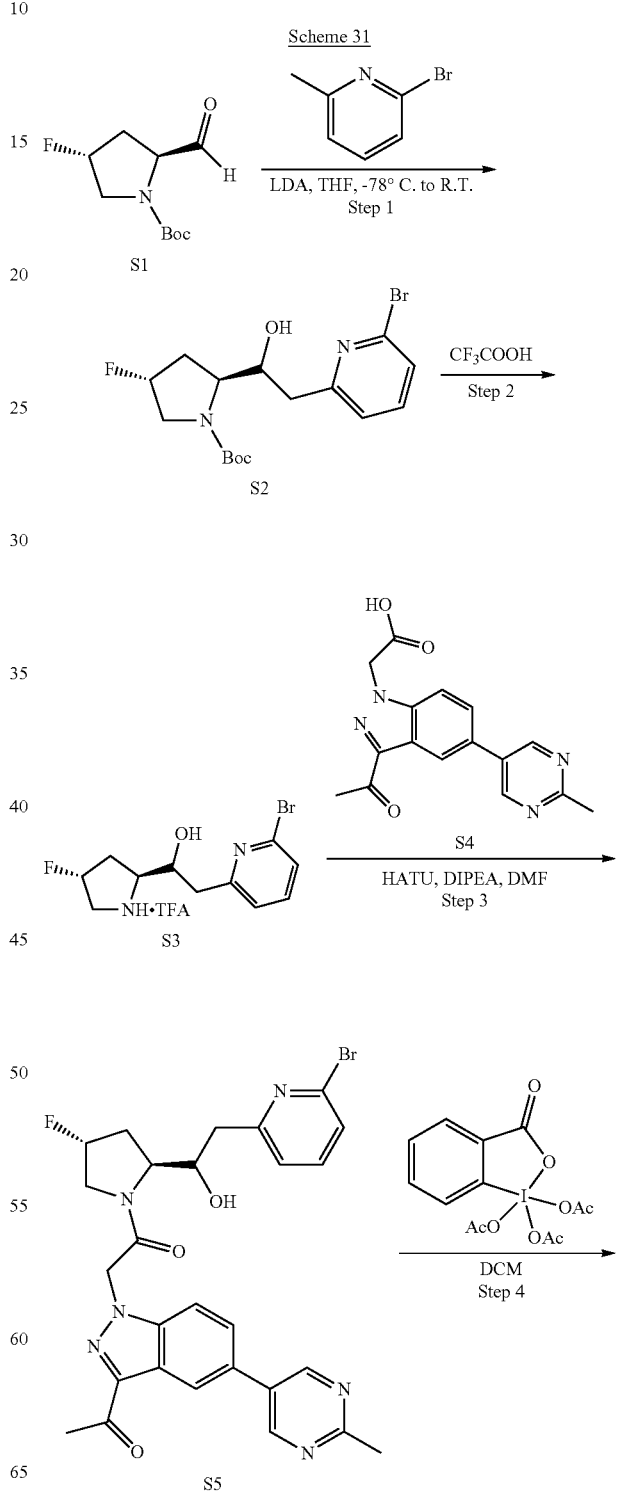

-continued

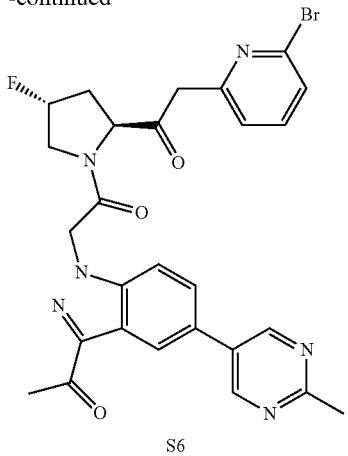

S6

Step 1: (2S,4R)-tert-Butyl 2-((R)-2-(6-bromopyridin-2-yl)-1-hydroxyethyl)-4-fluoropyrrolidine-1-carboxylate (S2)

To a dry-ice/ethanol cooled solution of 2-bromo-6-methylpyridine (80 mg, 0.46 mmol) in THF (2 mL) was added LDA (0.5 mL, 0.5 mmol). After addition, the reaction mixture was stirred at room temperature for 30 min and cooled to −70° C. This was followed by the addition of compound S1 (100 mg, 0.46 mmol). After stirring at this temperature for 30 min, the reaction mixture was quenched with aq. $NaHCO_3$ (10 mL). The reaction mixture was extracted with ethyl acetate (20 mL). The organic phase was washed with brine, dried over anhydrous $Na_2SO_4$, filtered, and then concentrated. The residue was purified by column chromatography on silica gel (eluted with petroleum ether/ethyl acetate=100:1 to 4:1) to give compound S2 (60 mg, yield 35%) as a yellow oil.

Step 2: (R)-2-(6-Bromopyridin-2-yl)-1-((2S,4R)-4-fluoropyrrolidin-2-yl)ethanol (S3)

To a solution of compound S2 (60 mg, 0.15 mmol) in dry DCM (1 mL) was added TFA (1 mL) in portions. After stirring at room temperature for 1 h, the reaction mixture was concentrated to give crude compound (50 mg, yield 95%) as a yellow oil. This material was used in the next synthetic step without purification.

6-(3-Acetyl-1-(2-((2S,4R)-2-((6-Bromopyridin-2-yl)carbamoyl)-4-fluoropyrrolidin-1-yl)-2-oxoethyl)-1H-indazol-5-yl)pyrazolo[1,5-a]pyrimidine-2-carboxamide (288)

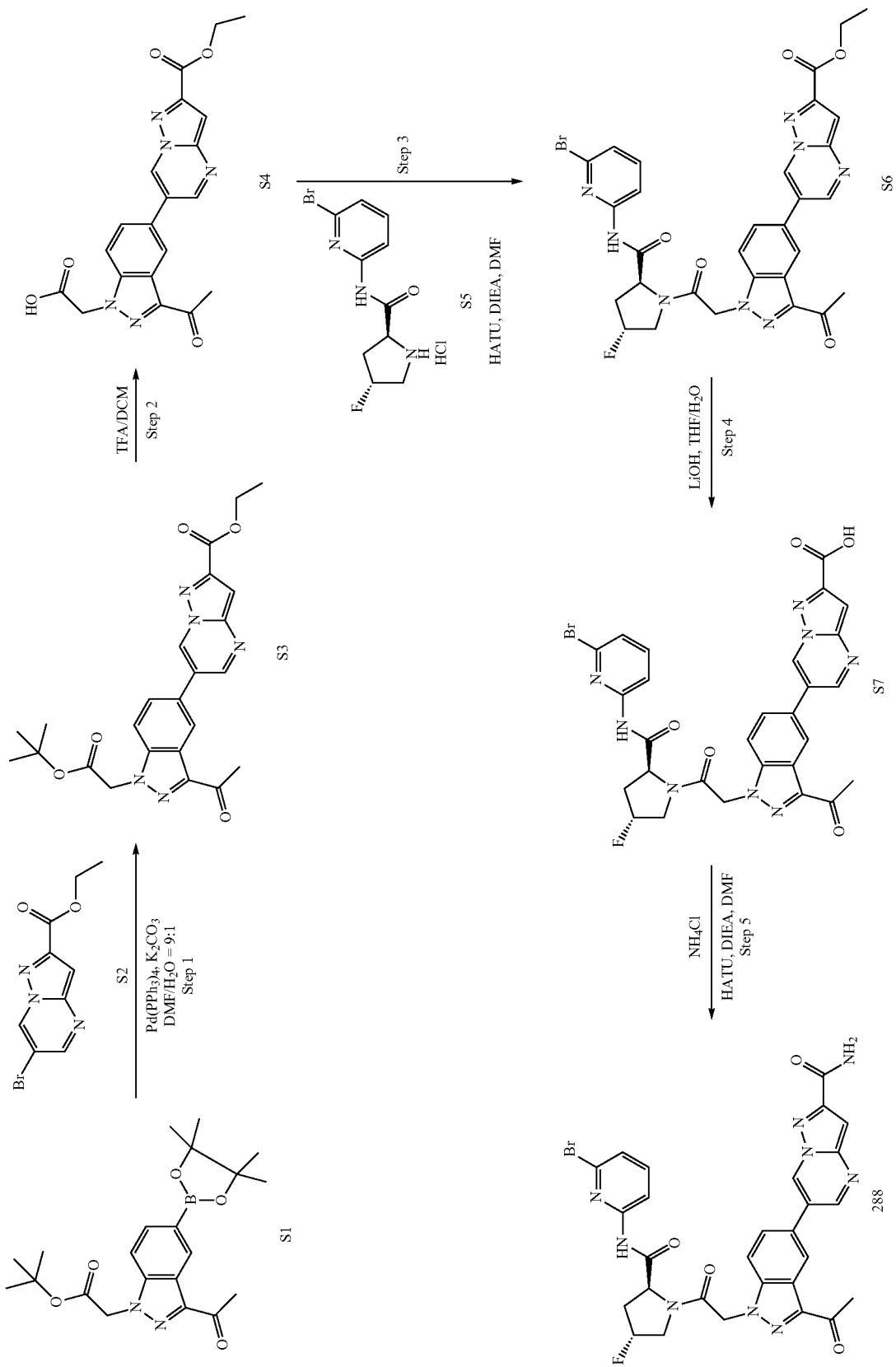

Step 1: Ethyl-6-(3-acetyl-1-(2-(tert-butoxy)-2-oxo-ethyl)-1H-indazol-5-yl)pyrazolo[1,5-a]pyrimidine-2-carboxylate (S3)

To a solution of ethyl 6-bromopyrazolo[1,5-a]pyrimidine-2-carboxylate (2, 1 equiv) in DMF/H$_2$O (9:1, 20 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S2.

Step 2: 2-(3-Acetyl-5-(2-(ethoxycarbonyl)pyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: Ethyl 6-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrazolo[1,5-a]pyrimidine-2-carboxylate (S6)

(2S,4R)—N-(6-bromopyridin-2-yl)-4-fluoropyrrolidine-2-carboxamide hydrochloride (1 equiv), HATU (2.1 equiv), and DIPEA (5 equiv) were added to a solution of compound S4 (1 equiv) in DMF (10 vol) at 0° C. under an atmosphere of nitrogen. The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel using (MeOH/DCM) to give compound S6.

Step 4: 6-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrazolo[1,5-a]pyrimidine-2-carboxylic acid (S7)

To a solution of compound S6 (1 equiv) in THF/H$_2$O (8:2, 10 vol) was added LiOH (3.3 equiv). The reaction mixture was stirred at room temperature for 4 h and then quenched with 4 N HCl. The resulting mixture was extracted with ethyl acetate. The organic layer was separated, dried over anhydrous Na$_2$SO$_4$, filtered, and then concentrated. The residue was purified by column chromatography on silica gel (MeOH/DCM) to give compound S7.

Step 5: 6-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrazolo[1,5-a]pyrimidine-2-carboxamide (288)

To a solution of compound S7 (1 equiv) in DMF (10 vol) at 0° C. was added NH$_4$Cl (3 equiv), DIPEA (5 equiv), and HATU (2.1 equiv). The reaction mixture was stirred at room temperature for 3 h and then diluted with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 288. $^1$H NMR (400 MHz, DMSO-d$_6$): δ 10.99 (s, 1H), 9.43 (s, 1H), 9.02 (s, 1H), 8.52 (s, 1H), 8.03 (d, J=8.0 Hz, 1H), 7.95 (d, J=10.0 Hz, 1H), 7.89-7.82 (m, 2H), 7.71 (t, J=8.0 Hz, 1H), 7.64 (s, 1H), 7.33 (d, J=7.6 Hz, 1H), 7.14 (s, 1H), 5.86 (d, J=17.20 Hz, 1H), 5.75 (d, J=17.20 Hz, 1H), 5.64-5.50 (m, 1H), 4.69 (t, J=8.40 Hz, 1H), 4.2 (dd, J=22.0, 12.0 Hz, 1H), 4.1 (dd, J=28.1, 12.4 Hz, 1H), 2.7 (s, 3H), 2.60-2.58 (m, 1H), 2.26-2.09 (m, 1H). $^{19}$F NMR (376 MHz, DMSO-d$_6$): δ −175.66. LC (method A): t$_R$=1.55 min. LC/MS (EI) m/z: [M+H]$^+$ 648.

(2S,4R)-1-(2-(3-Acetyl-5-(1H-thieno[3,2-c]pyrazol-3-yl)-1H-indazol-1-yl)acetyl)-N-(6-bromopyridin-2-yl)-4-fluoropyrrolidine-2-carboxamide (291)

Scheme 33

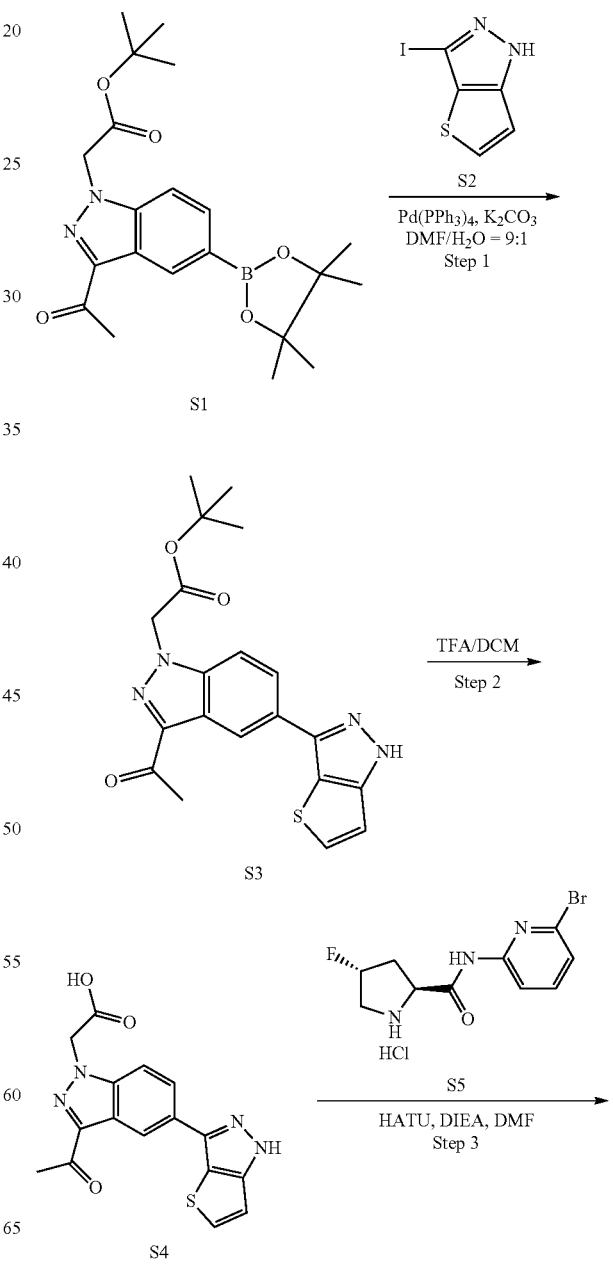

205
-continued

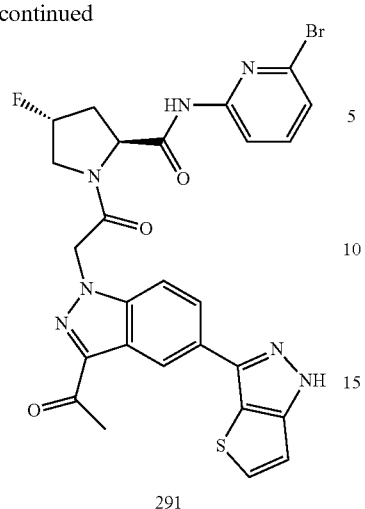

291

Step 1: tert-Butyl 2-(3-acetyl-5-(1H-thieno[3,2-c]pyrazol-3-yl)-1H-indazol-1-yl)acetate (S2)

To a solution of 3-iodo-1H-thieno[3,2-c]pyrazole (1 equiv) in DMF/H$_2$O (9:1, 10 vol) was added compound S2 (1 equiv), K$_2$CO$_3$ (2 equiv) and tetrakis(triphenylphosphine)palladium (0.1 equiv). The reaction mixture was stirred at 90° C. for 5 h and then concentrated. The remaining residue was purified by column chromatography on silica gel to give compound S3.

Step 2: 2-(3-Acetyl-5-(1H-thieno[3,2-c]pyrazol-3-yl)-1H-indazol-1-yl)acetic acid (S3)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (2S,4R)-1-(2-(3-Acetyl-5-(1H-thieno[3,2-c]pyrazol-3-yl)-1H-indazol-1-yl)acetyl)-N-(6-bromopyridin-2-yl)-4-fluoropyrrolidine-2-carboxamide (291)

To a solution of compound S4 (1 equiv) in DMF (10 vol) at 0° C. under an atmosphere nitrogen atmosphere was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 291. $^1$H NMR (400 MHz, DMSO-d$_6$): δ 10.92 (s, 1H), 8.49 (s, 1H), 7.96 (d, J=8.0 Hz, 2H), 7.74 (d, J=8.8 Hz, 1H), 7.69 (d, J=5.2 Hz, 1H), 7.62 (t, J=7.6 Hz, 1H), 7.25 (d, J=7.6 Hz, 1H), 7.14 (d, J=5.2 Hz, 1H), 5.75 (d, J=17.2 Hz, 1H), 5.55 (d, J=17.2 Hz, 1H), 5.55-5.42 (m, 1H), 4.61 (t, J=8.00 Hz, 1H), 4.16 (dd, J=21.60, 12.40 Hz, 1H), 3.97 (dd, J=34.50, 11.00 Hz, 1H), 2.58 (s, 3H), 2.55-2.43 (m, 1H), 2.18-2.00 (m, 1H). $^{19}$F NMR (376 MHz, DMSO-d$_6$): δ −175.68. LC (method A): t$_R$=1.95 min. LC/MS (EI) m/z: [M+H]$^+$ 610.

206
(2S,4R)-1-(2-(3-Acetyl-5-(3a,4,5,6,7,7a-hexahydrobenzo[d]thiazol-2-yl)-1H-indazol-1-yl)acetyl)-N-(6-bromopyridin-2-yl)-4-fluoropyrrolidine-2-carboxamide (297)

Scheme 34

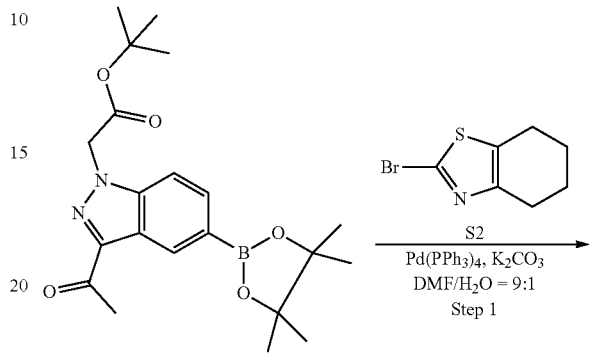

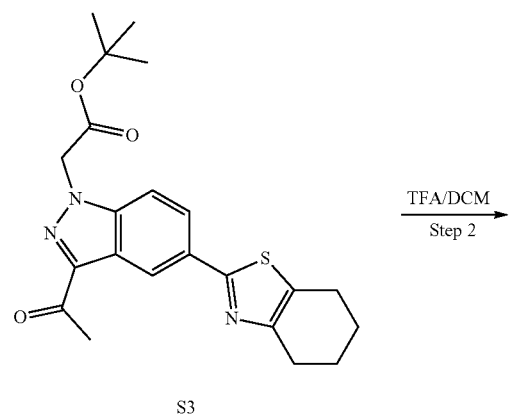

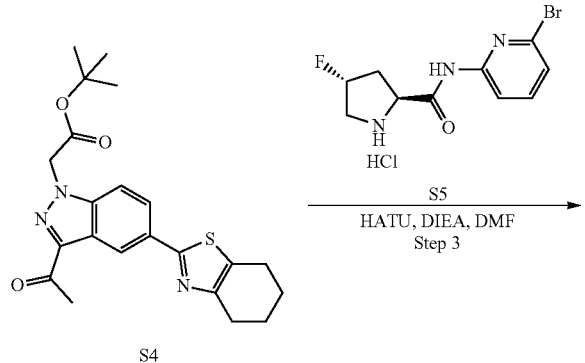

-continued

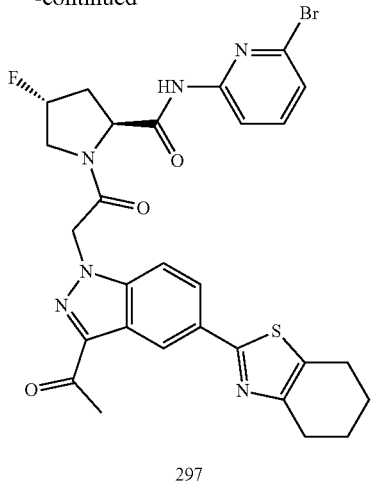

297

Step 1: tert-Butyl 2-(3-acetyl-5-(3a,4,5,6,7,7a-hexahydrobenzo[d]thiazol-2-yl)-1H-indazol-1-yl)acetate (S3)

To a solution of 2-bromo-3a,4,5,6,7,7a-hexahydrobenzo[d]thiazole (1 equiv) in DMF/H$_2$O (9:1, 10 vol) was added compound S2 (1 equiv), K$_2$CO$_3$ (2 equiv), and tetrakis(triphenylphosphine)palladium (0.1 equiv). The reaction mixture was stirred at 90° C. for 5 h and then concentrated. The residue was purified by column chromatography on silica gel to give compound S3.

Step 2: 2-(3-Acetyl-5-(3a,4,5,6,7,7a-hexahydrobenzo[d]thiazol-2-yl)-1H-indazol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (2S,4R)-1-(2-(3-Acetyl-5-(3a,4,5,6,7,7a-hexahydrobenzo[d]thiazol-2-yl)-1H-indazol-1-yl)acetyl)-N-(6-bromopyridin-2-yl)-4-fluoropyrrolidine-2-carboxamide (297)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 297. $^1$H-NMR (400 MHz, DMSO-d$_6$): δ 10.99 (s, 1H), 8.65 (s, 1H), 8.03 (d, J=8.0 Hz, 1H), 7.99 (d, J=9.6 Hz, 1H), 7.78 (d, J=9.2 Hz, 1H), 7.71 (t, J=8.0 Hz, 1H), 7.32 (d, J=7.6 Hz, 1H), 5.83 (d, J=17.6 Hz, 1H), 5.62 (d, J=17.2 Hz, 1H), 5.62-5.49 (m, 1H), 4.67 (t, J=8.40 Hz, 1H), 4.22 (dd, J=22.0, 12.40 Hz, 1H), 4.04 (dd, J=37.60, 12.40 Hz, 1H), 2.81-2.80 (m, 4H), 2.64 (s, 3H), 2.61-2.54 (m, 1H), 2.25-2.08 (m, 1H), 1.90-1.80 (m, 4H). $^{19}$F NMR (376 MHz, DMSO-d$_6$): δ −175.65. LC (method A): t$_R$=2.57 min. LC/MS (EI) m/z: [M+H]$^+$ 625.

(2R,4R)-1-(2-(5-(2-((2,5,8,11,14-Pentaoxahexadecan-16-yl)oxy)pyrimidin-5-yl)-3-acetyl-1H-indazol-1-yl)acetyl)-N-(3-bromophenyl)-4-fluoropyrrolidine-2-carboxamide (316)

Scheme 35

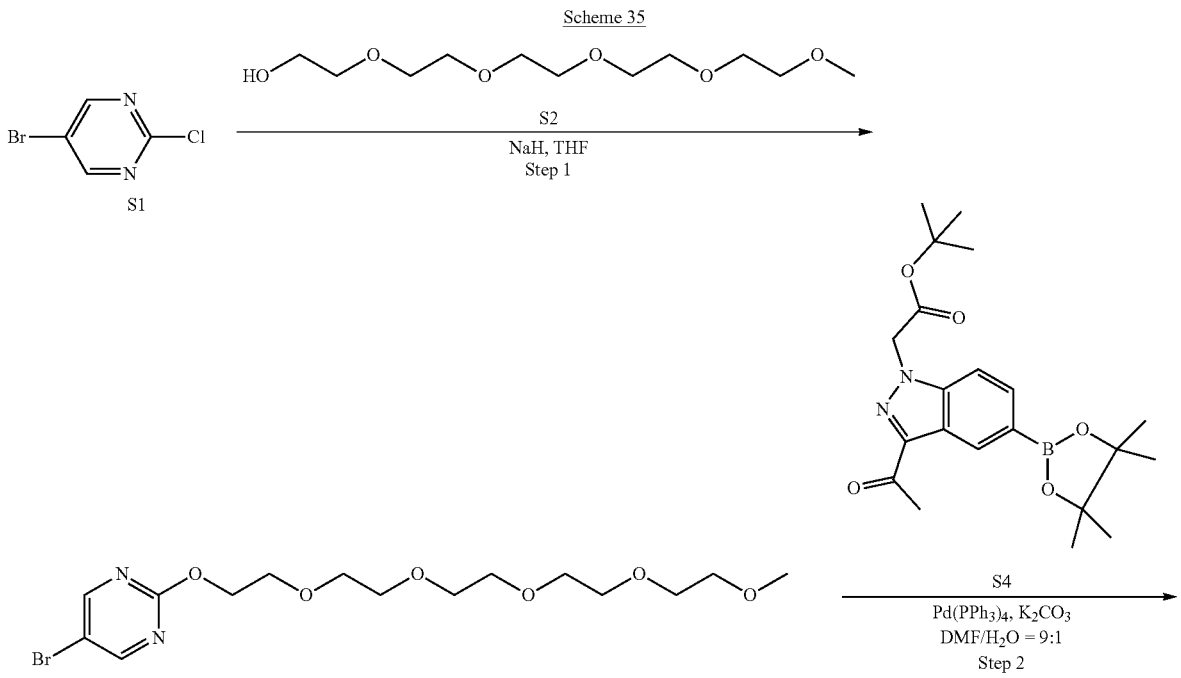

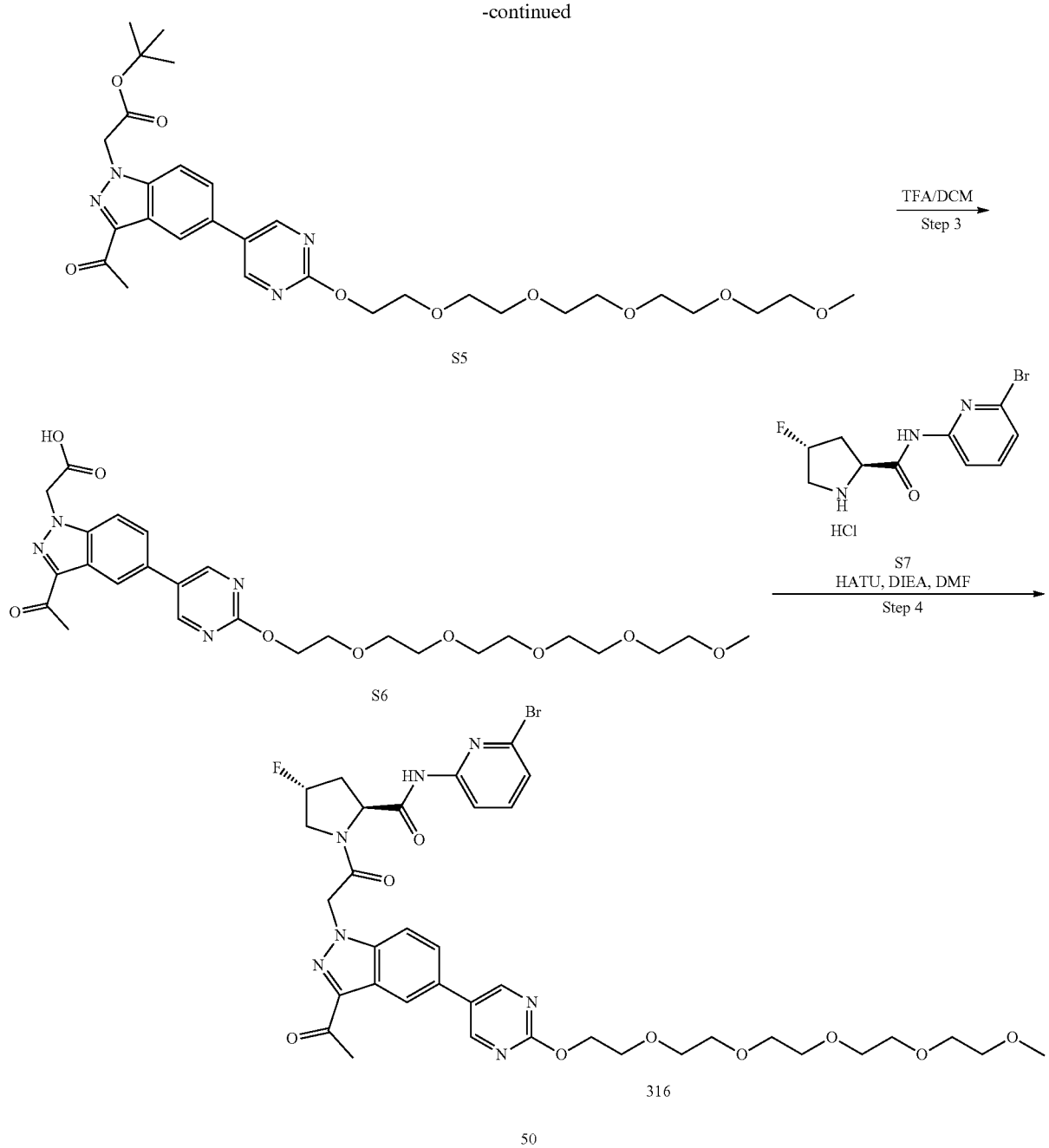

Step 1: 2-(2,5,8,11,14-Pentaoxahexadecan-16-yloxy)-5-bromopyrimidine (S3)

To a solution of 2,5,8,11,14-pentaoxahexadecan-16-ol (1.2 equiv) in THF (10 vol) at 0° C. under an atmosphere of nitrogen was added NaH (1.3 equiv) and stirred at 0° C. for 15 min. To the reaction mixture was added compound S1 (1.2 equiv) and the resulting mixture was stirred at 0° C. for 1 h. The reaction mixture was then concentrated and the remaining residue was purified by column chromatography on silica gel to give compound S3.

Step 2: tert-Butyl-2-(5-(2-((2,5,8,11,14-pentaoxahexadecan-16-yl)oxy)pyrimidin-5-yl)-3-acetyl-1H-indazol-1-yl)acetate (S5)

To a solution of compound S3 (1 equiv) in DMF/H$_2$O (9:1, 10 vol) was added compound S4 (1 equiv), K$_2$CO$_3$ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S5.

Step 3: 2-(5-(2-((2,5,8,11,14-Pentaoxahexadecan-16-yl)oxy)pyrimidin-5-yl)-3-acetyl-1H-indazol-1-yl) acetic acid (S6)

To a solution of compound S5 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 4: (2R,4R)-1-(2-(5-(2-((2,5,8,11,14-Pentaoxa-hexadecan-16-yl)oxy)pyrimidin-5-yl)-3-acetyl-1H-indazol-1-yl)acetyl)-N-(3-bromophenyl)-4-fluoropyrrolidine-2-carboxamide (316)

To a solution of compound S6 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound S8. $^1$H NMR (400 MHz, DMSO-$d_6$): δ 10.99 (s, 1H), 8.94 (s, 2H), 8.38 (s, 1H), 8.03 (d, J=8.4 Hz, 1H), 7.83 (s, 2H), 7.71 (t, J=7.6 Hz, 1H), 7.32 (d, J=7.6 Hz, 1H), 5.83 (d, J=17.2 Hz, 1H), 5.64 (d, J=17.2 Hz, 1H), 5.58-5.49 (m, 1H), 4.68 (t, J=8.40 Hz, 1H), 4.49 (t, J=4.40 Hz, 2H), 4.24 (dd, J=22.40, 12.40 Hz, 1H), 4.09 (dd, J=20.20, 18.00 Hz, 1H), 3.80 (t, J=4.40 Hz, 2H), 3.63-3.62 (m, 2H), 3.57-3.56 (m, 2H), 3.52-3.50 (m, 10H), 3.43-3.41 (m, 2H), 3.2 (s, 3H), 2.6 (s, 3H), 2.58-2.54 (m, 1H), 2.25-2.08 (m, 1H). $^{19}$F NMR (376 MHz, DMSO-$d_6$): δ −175.67. LC (method A): $t_R$=1.96 min. LC/MS (EI) m/z: [M+H]$^+$ 816.

(4R)-1-(2-(3-Acetyl-6-hydroxy-5-(2-methylpyrimidin-5-yl)-1H-indol-1-yl)acetyl)-N-(2'-chloro-2-fluoro-[1,1'-biphenyl]-3-yl)-4-fluoropyrrolidine-2-carboxamide (320)

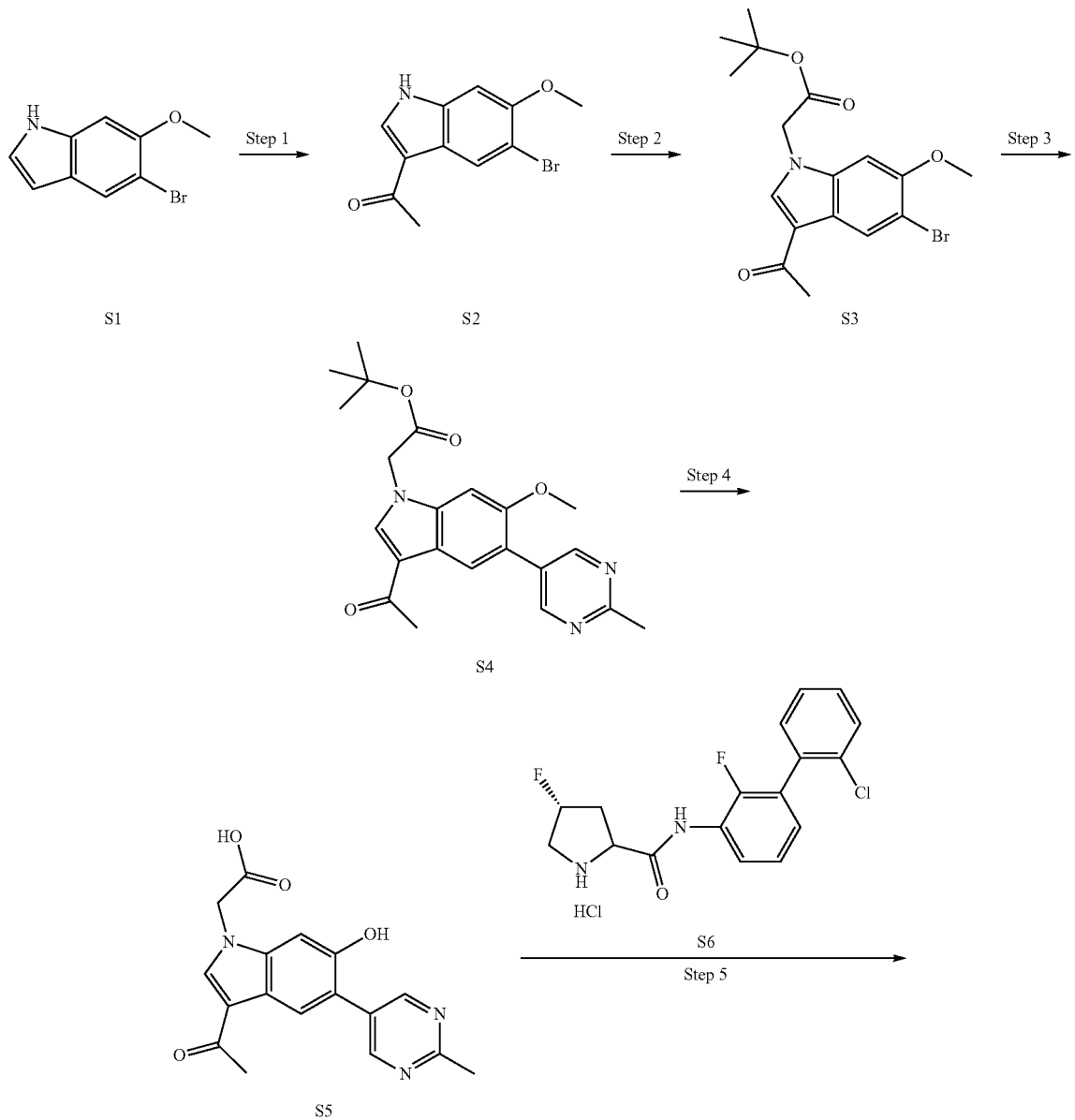

Scheme 36

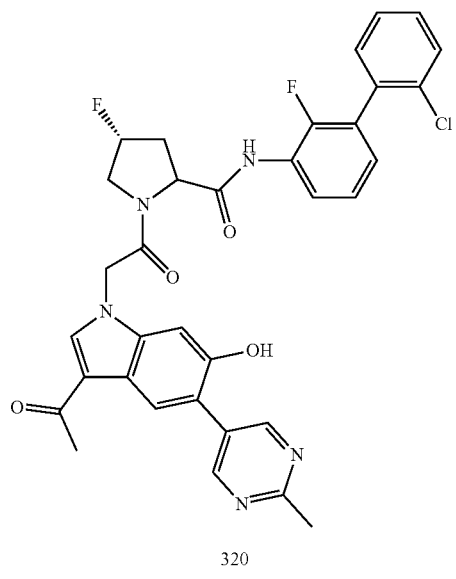

320

Step 1: 1-(5-Bromo-6-methoxy-1H-indol-3-yl)ethan-1-one (S2)

5-Bromo-6-methoxy-1H-indole (1.01 g, 4.47 mmol) in DCM (20 mL) was treated with $Et_2AlCl$ in hexane (1.0 M, 6.71 mL, 1.5 equiv) at 0° C. for 1 h. AcCl (0.479 mL, 6.71 mmol) in DCM (mL) was added and the reaction mixture was stirred for an additional 1 h. To this mixture was added 5% aq. citric acid (100 mL) and the reaction was stirred at room temperature for 1 h. The resulting brick-colored solid was collected by filtration and dried to give 1-(5-bromo-6-methoxy-1H-indol-3-yl)ethan-1-one (0.62 g).

Step 2: tert-Butyl 2-(3-acetyl-5-bromo-6-methoxy-1H-indol-1-yl)acetate (S3)

A mixture of 1-(5-bromo-6-methoxy-1H-indol-3-yl)ethan-1-one (0.62 g, 2.31 mmol), tert-butyl 2-bromoacetate (0.375 mL, 2.54 mmol), and $K_2CO_3$ (0.35 g, 2.54 mmol) in acetonitrile (20 mL) was refluxed for 6 h. The reaction mixture was allowed to cool to room temperature, filtered, and concentrated to give tert-butyl 2-(3-acetyl-5-bromo-6-methoxy-1H-indol-1-yl)acetate (0.88 g).

Step 3: tert-Butyl 2-(3-acetyl-6-methoxy-5-(2-methylpyrimidin-5-yl)-1H-indol-1-yl)acetate (S4)

To a mixture of tert-butyl 2-(3-acetyl-5-bromo-6-methoxy-1H-indol-1-yl)acetate (0.88 g, 2.3 mmol) and 2-methyl-5-(4,4,5,5-tetramethyl-1,3,2-dioxaborolan-2-yl)pyrimidine (0.61 g, 2.76 mmol) in DMF-water (20 mL/2 mL) was added $Cs_2CO_3$ (1.5 g, 4.6 mmol) and $Pd(PPh_3)_4$ (0.132 g, 0.115 mmol) in succession. The mixture was stirred at 80° C. under an atmosphere of argon for 3 h. The solvent was removed under reduced pressure and the remaining residue was purified by column chromatography on silica gel (50% EtOAc in hexanes) to give tert-butyl 2-(3-acetyl-6-methoxy-5-(2-methylpyrimidin-5-yl)-1H-indol-1-yl)acetate (0.85 g) as a pale yellow solid.

Step 4: 2-(3-Acetyl-6-hydroxy-5-(2-methylpyrimidin-5-yl)-1H-indol-1-yl)acetic acid (S5)

A mixture of 2-(3-acetyl-6-hydroxy-5-(2-methylpyrimidin-5-yl)-1H-indol-1-yl)acetic acid (0.102 g, 0.258 mmol) and anhydrous $Na_2S$ (0.1 g, 1.29 mmol) in NMP (2 mL) was heated at 145° C. for 5 h. The mixture was purified by HPLC to give 2-(3-acetyl-6-hydroxy-5-(2-methylpyrimidin-5-yl)-1H-indol-1-yl)acetic acid (0.064 g) as a yellow solid.

Step 5: (4R)-1-(2-(3-Acetyl-6-hydroxy-5-(2-methyl-pyrimidin-5-yl)-1H-indol-1-yl)acetyl)-N-(2'-chloro-2-fluoro-[1,1'-biphenyl]-3-yl)-4-fluoropyrrolidine-2-carboxamide (S7)

A mixture of 2-(3-acetyl-6-hydroxy-5-(2-methylpyrimidin-5-yl)-1H-indol-1-yl)acetic acid (64 mg, 0.197 mmol) and (2S,4R)—N-(2'-chloro-2-fluoro-[1,1'-biphenyl]-3-yl)-4-fluoropyrrolidine-2-carboxamide hydrochloride (77 mg, 0.207 mmol) in DMF (2 mL) was treated with TBTU (95 mg, 0.296 mmol) followed by DIEA (0.103 mL, 0.59 mmol) at room temperature for 1 h. An aq. solution of $NaHCO_3$ (15 mL) was added and the solid was collected by filtration. This solid was purified by column chromatography on silica gel (10% MeOH in DCM) to give (4R)-1-(2-(3-acetyl-6-hydroxy-5-(2-methylpyrimidin-5-yl)-1H-indol-1-yl)acetyl)-N-(2'-chloro-2-fluoro-[1,1'-biphenyl]-3-yl)-4-fluoropyrrolidine-2-carboxamide (81 mg).

(4R)-1-(2-(3-Acetyl-6-hydroxy-5-(2-methylpyrimidin-5-yl)-1H-indol-1-yl)acetyl)-N-(6-bromopyridin-2-yl)-4-fluoropyrrolidine-2-carboxamide (328)

Scheme 37

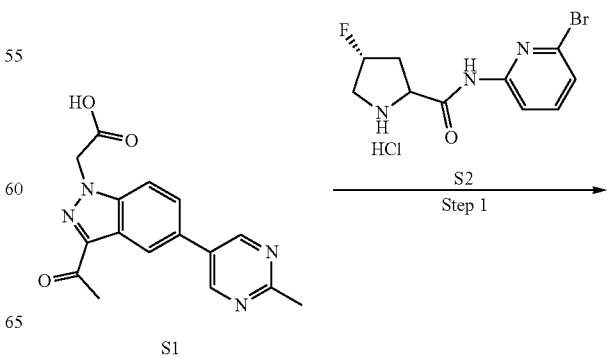

-continued

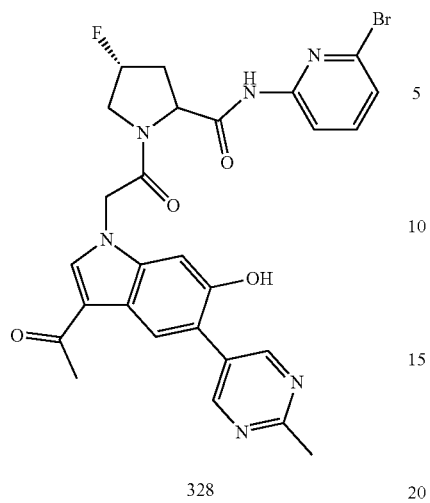

328

A mixture of 2-(3-acetyl-6-hydroxy-5-(2-methylpyrimidin-5-yl)-1H-indol-1-yl)acetic acid (101 mg, 0.311 mmol) and (4R)—N-(6-bromopyridin-2-yl)-4-fluoropyrrolidine-2-carboxamide hydrochloride (101 mg, 0.311 mmol) in DMF (3 mL) was treated with TBTU (0.15 g, 0.466 mmol) followed by DIEA (0.324 mL, 1.87 mmol) at room temperature for 1 h. An aq. solution of NaHCO₃ (15 mL) was added and the solid was collected by filtration. This solid was purified by column chromatography on silica gel to give (4R)-1-(2-(3-acetyl-6-hydroxy-5-(2-methylpyrimidin-5-yl)-1H-indol-1-yl)acetyl)-N-(6-bromopyridin-2-yl)-4-fluoropyrrolidine-2-carboxamide (0.099 g).

(2S,4R)—N-benzyl-4-fluoropyrrolidine-2-carboxamide hydrochloride

Scheme 38

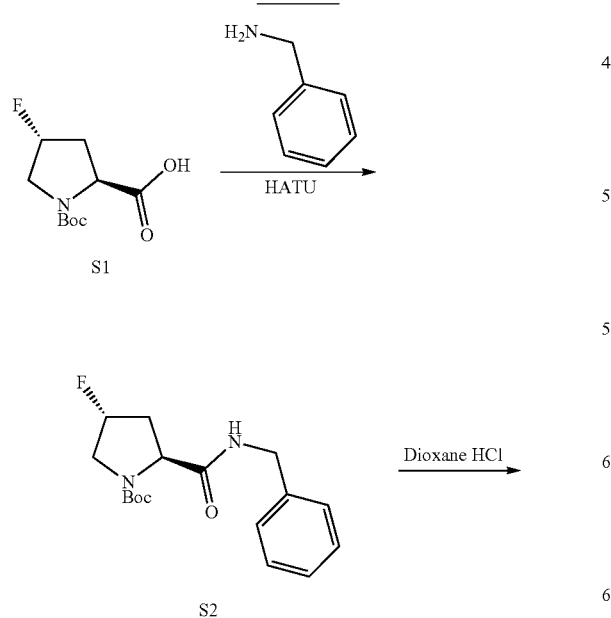

-continued

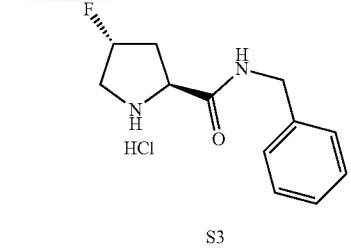

S3

To a solution of (2S,4R)-1-(tert-butoxycarbonyl)-4-fluoropyrrolidine-2-carboxylic acid (1 equiv) in DMF (10 mL) at 0° C. under nitrogen atmosphere was added benzyl amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous Na₂SO₄, filtered and then concentrated. The residue was purified by column chromatography on silica gel using DCM/MeOH to afford tert-butyl (2S,4R)-2-(benzylcarbamoyl)-4-fluoropyrrolidine-1-carboxylate. To a solution of tert-butyl (2S,4R)-2-(benzylcarbamoyl)-4-fluoropyrrolidine-1-carboxylate (1 equiv) in 1,4-dioxane (3 vol) at 0° C. under nitrogen atmosphere was added 4 N HCl in 1,4-dioxane (10 mL) and stirred at room temperature for 3 h. The reaction mixture was concentrated to afford (2S,4R)—N-benzyl-4-fluoropyrrolidine-2-carboxamide hydrochloride.

(2S,4R)-4-Fluoro-N-phenethylpyrrolidine-2-carboxamide hydrochloride

Scheme 39

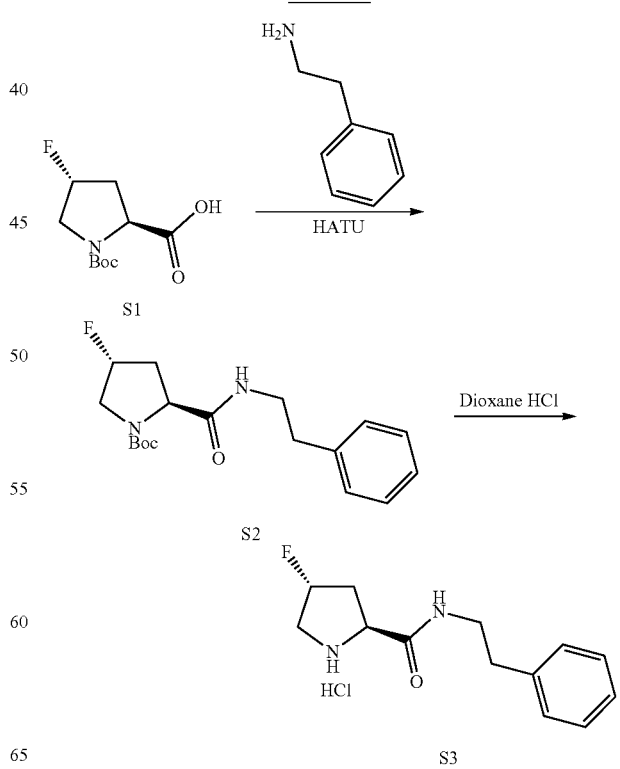

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 2-phenylethan-1-amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to afford tert-butyl (2S,4R)-4-fluoro-2-(phenethylcarbamoyl)pyrrolidine-1-carboxylate. To a solution of tert-butyl (2S,4R)-4-fluoro-2-(phenethylcarbamoyl)pyrrolidine-1-carboxylate (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to afford (2S,4R)-4-fluoro-N-phenethylpyrrolidine-2-carboxamide hydrochloride.

(2S,4R)-4-Fluoro-N-(3-phenylpropyl)pyrrolidine-2-carboxamidehydrochloride

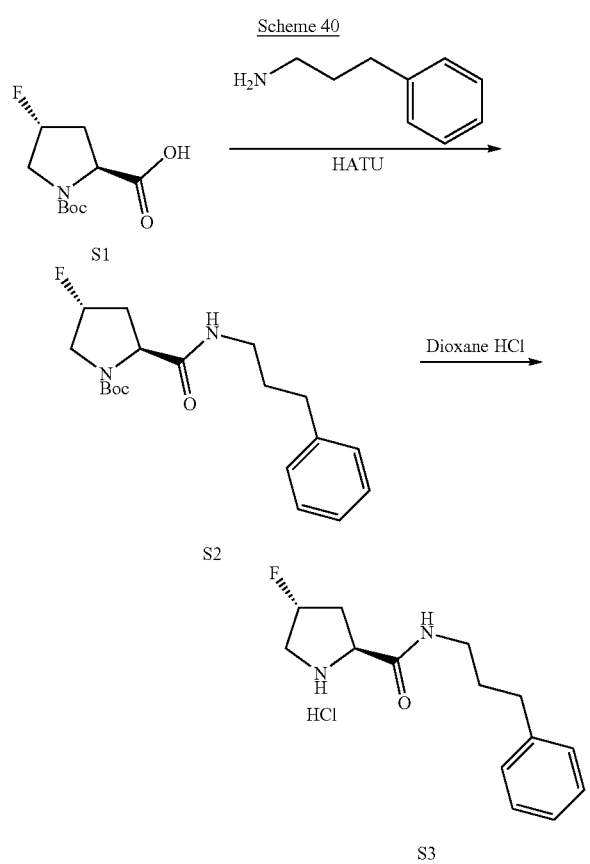

To a solution of (2S,4R)-1-(tert-butoxycarbonyl)-4-fluoropyrrolidine-2-carboxylic acid (1 equiv) in DMF (10 mL) at 0° C. under nitrogen atmosphere was added 3-phenylpropan-1-amine (1.2 equiv), HATU (1.5 equiv) and DIPEA (3 equiv). The reaction mixture was stirred at room temperature for 3 h. After completion of the reaction, the reaction mixture was quenched with water (30 vol). The resulting mixture was extracted with DCM. The organic layer was washed with brine, dried over anhydrous $Na_2SO_4$, filtered and then concentrated. The residue was purified by column chromatography on silica gel using DCM/MeOH to afford tert-butyl (2S,4R)-4-fluoro-2-((3-phenylpropyl)carbamoyl) pyrrolidine-1-carboxylate. To a solution of tert-butyl (2S, 4R)-4-fluoro-2-((3-phenylpropyl)carbamoyl)pyrrolidine-1-carboxylate (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to afford (2S,4R)-4-fluoro-N-(3-phenylpropyl)pyrrolidine-2-carboxamidehydrochloride.

(2S,4R)-4-Fluoro-N-(4-phenylbutyl)pyrrolidine-2-carboxamide

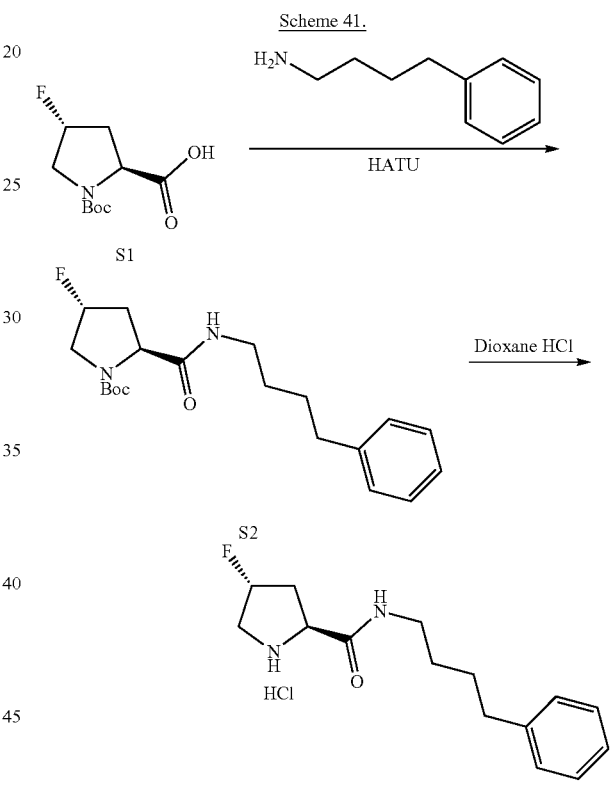

To a solution of (2S,4R)-1-(tert-butoxycarbonyl)-4-fluoropyrrolidine-2-carboxylic acid (1 equiv) in DMF (10 mL) at 0° C. under nitrogen atmosphere was added 4-phenylbutan-1-amine (1.2 equiv), HATU (1.5 equiv) and DIPEA (3 equiv). The reaction mixture was stirred at room temperature for 3 h. After completion of the reaction, the reaction mixture was quenched with water (30 mL). The resulting mixture was extracted with DCM. The organic layer was washed with brine, dried over anhydrous $Na_2SO_4$, filtered and then concentrated. The residue was purified by column chromatography on silica gel using DCM/MeOH to afford tert-butyl (2S,4R)-4-fluoro-2-((4-phenylbutyl)carbamoyl) pyrrolidine-1-carboxylate. To a solution of tert-butyl (2S, 4R)-4-fluoro-2-((4-phenylbutyl)carbamoyl)pyrrolidine-1-carboxylate (1 equiv) in 1,4-dioxane (3 mL) at 0° C. under nitrogen atmosphere was added 4 N HCl in 1,4-dioxane (10 vol) and the reaction was stirred at room temperature for 3 h. The reaction mixture was concentrated to afford (2S,4R)-4-fluoro-N-(4-phenylbutyl)pyrrolidine-2-carboxamide.

(2S,4R)-1-(2-(3-Acetyl-5-(2-methylpyrazolo[1,5-a]pyrimidin-6-yl)-1H-indol-1-yl)acetyl)-N-benzyl-4-fluoropyrrolidine-2-carboxamide (685)

(2S,4R)-1-(2-(3-Acetyl-5-(2-methylpyrazolo[1,5-a]pyrimidin-6-yl)-1H-indol-1-yl)acetyl)-4-fluoro-N-phenethylpyrrolidine-2-carboxamide (686)

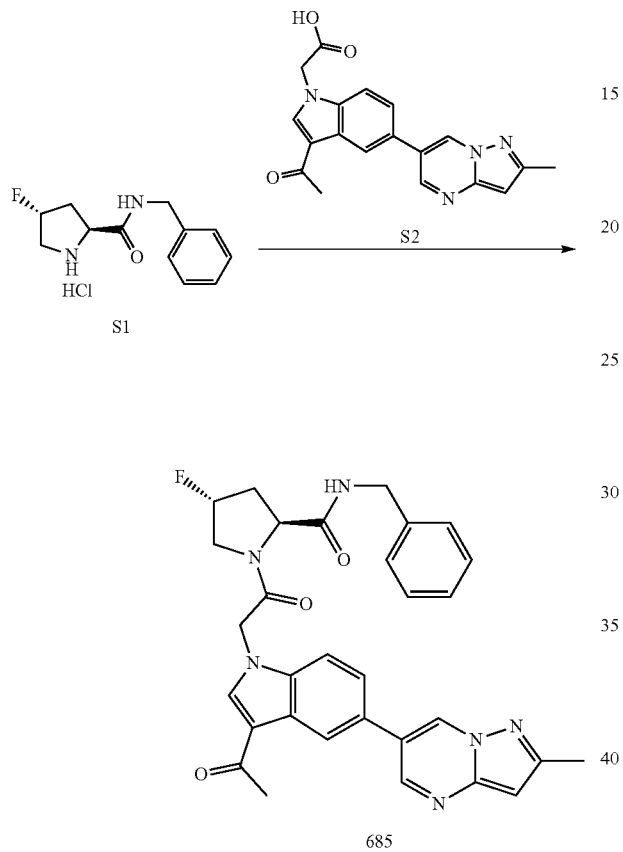

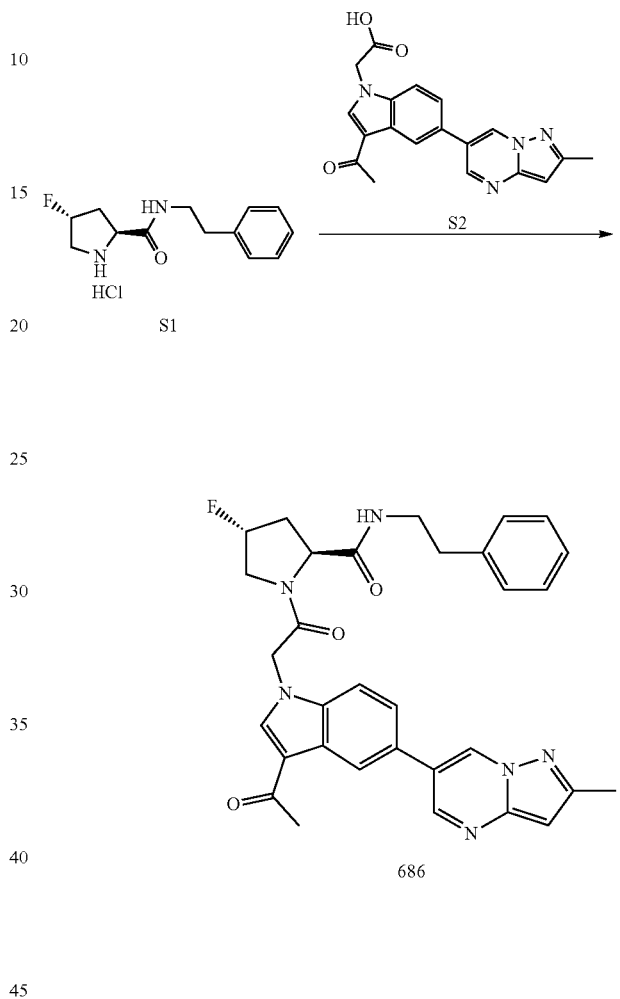

To a solution of S1 (1 equiv) in DMF (10 mL) at 0° C. under nitrogen atmosphere was added S2 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 685.

$^1$H NMR (400 MHz, DMSO-$d_6$) δ 9.24 (s, 1H), 8.82 (s, 1H), 8.53-8.47 (m, 2H), 8.31 (s, 1H), 7.61 (s, 2H), 7.38-7.28 (m, 5H), 6.56 (s, 1H), 5.57-5.41 (m, 2H), 5.26-5.21 (m, 1H), 4.45 (t, J=8.8 Hz, 1H), 4.32-4.12 (m, 3H), 3.98-3.31 (m, 1H), 2.49 (s, 3H), 2.48 (s, 3H), 2.47-2.46 (m, 1H), 2.15-2.00 (m, 1H).

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 686.

$^1$H NMR (400 MHz, DMSO-$d_6$) δ 9.22 (s, 1H), 8.82 (s, 1H), 8.46 (m, 1H), 8.31 (s, 1H), 8.18-8.15 (m, 1H), 7.66-7.60 (m, 2H), 7.26-7.13 (m, 5H), 6.56 (s, 1H), 5.53-5.37 (m, 2H), 5.23-5.19 (m, 1H), 4.35 (t, J=8.4 Hz, 1H), 4.15-4.13 (m, 1H), 3.94-3.92 (m, 1H), 3.39-3.38 (m, 1H), 3.31-3.16 (m, 2H), 2.67 (s, 3H), 2.47 (s, 3H), 2.46-2.45 (m, 1H), 2.05-1.98 (m, 2H).

(2S,4R)-1-(2-(3-Acetyl-5-(2-methylpyrazolo[1,5-a]pyrimidin-6-yl)-1H-indol-1-yl)acetyl)-4-fluoro-N-(3-phenylpropyl)pyrrolidine-2-carboxamide (687)

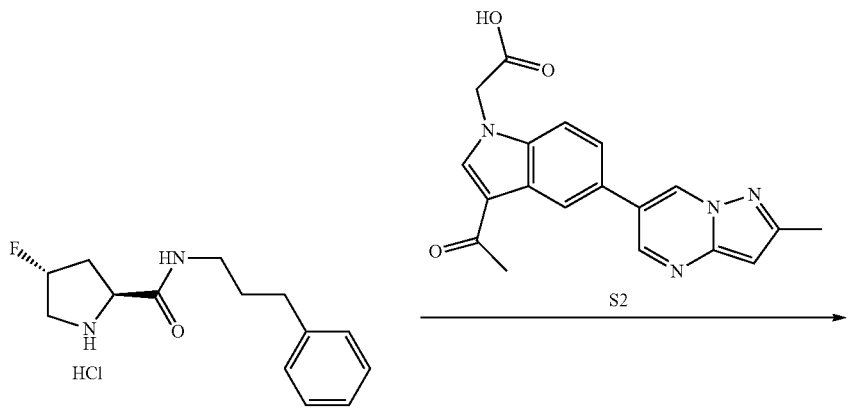

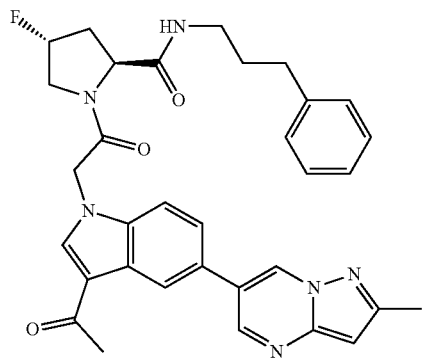

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 687.

$^1$H NMR (400 MHz, DMSO-$d_6$) δ 9.20 (s, 1H), 8.81 (s, 1H), 8.47 (m, 1H), 8.32 (s, 1H), 8.07-8.04 (m, 1H), 7.64-7.56 (m, 2H), 7.22-7.06 (m, 4H), 6.57 (s, 1H), 5.57-5.41 (m, 2H), 5.26-5.21 (m, 1H), 4.37 (t, J=8.4 Hz, 1H), 4.21-4.12 (m, 1H), 4.00-3.91 (m, 1H), 3.32-3.31 (m, 1H), 3.09-3.02 (m, 2H), 2.67-2.65 (m, 1H), 2.47 (s, 3H), 2.46 (s, 3H), 2.45-2.44 (m, 1H), 2.11-2.00 (m, 1H), 1.64-1.61 (m, 2H).

(2S,4R)-1-(2-(3-Acetyl-5-(2-methylpyrazolo[1,5-a]pyrimidin-6-yl)-1H-indol-1-yl)acetyl)-4-fluoro-N-(4-phenylbutyl)pyrrolidine-2-carboxamide (688)

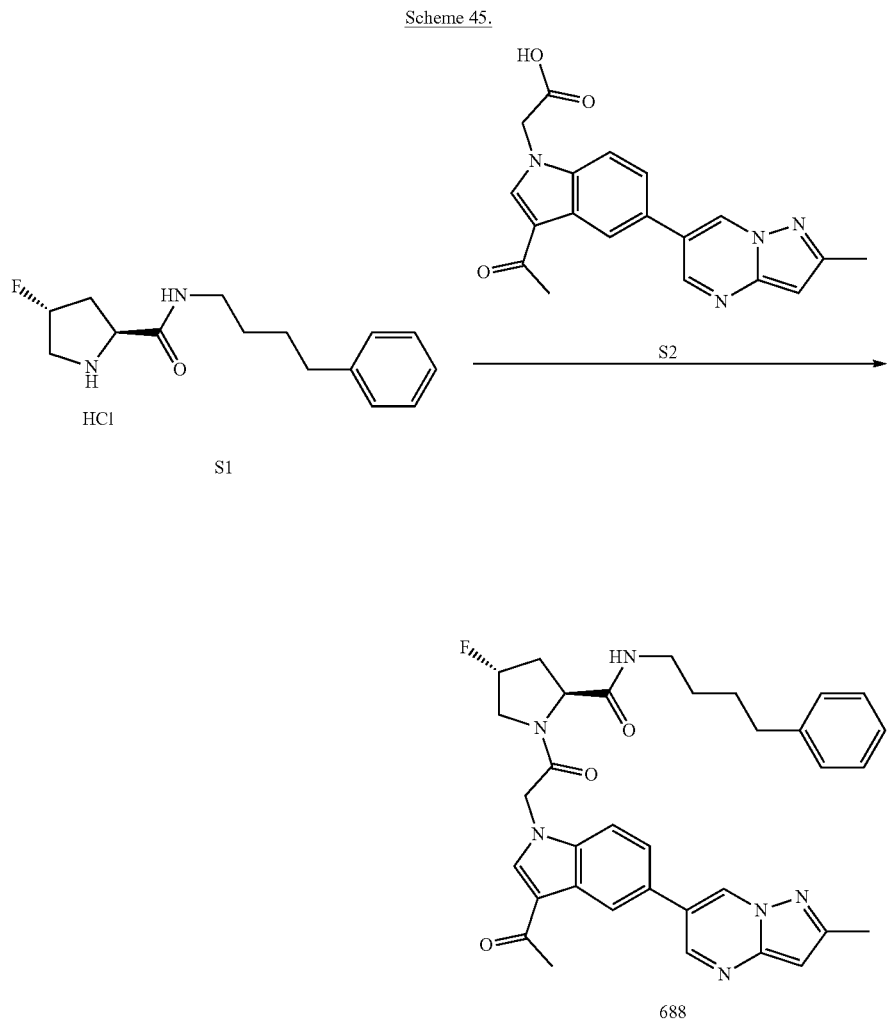

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 688.

$^1$H NMR (400 MHz, DMSO-$d_6$) δ 9.24 (s, 1H), 8.81 (s, 1H), 8.53-8.47 (m, 2H), 7.98 (s, 1H), 7.62-7.45 (m, 2H), 7.17-7.09 (m, 5H), 6.56 (s, 1H), 5.56-5.21 (m, 3H), 4.35-4.33 (m, 1H), 4.12-4.10 (m, 2H), 3.61-3.59 (m, 1H), 3.13-3.11 (m, 2H), 2.52-2.51 (m, 1H), 2.49 (s, 3H), 2.48 (s, 3H), 2.47-2.46 (m, 2H), 1.76-1.75 (m, 2H), 1.50-1.45 (m, 2H).

N-(2-((2R,4R)-4-Fluoropyrrolidin-2-yl)ethyl)benzenesulfonamide hydrochloride

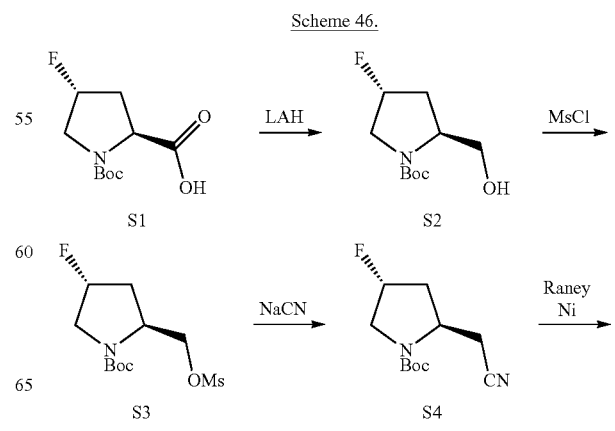

-continued

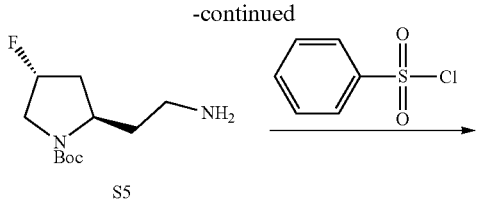

S5

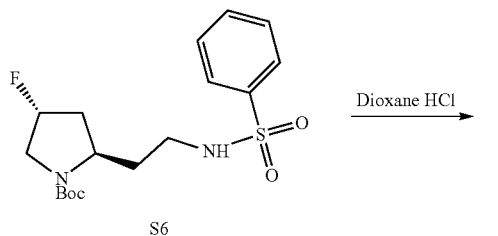

S6

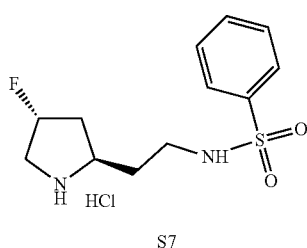

S7 tert-Butyl (2S,4R)-4-fluoro-2-(hydroxymethyl)pyrrolidine-1-carboxylate (S2)

To a solution of (2S,4R)-1-(tert-butoxycarbonyl)-4-fluoropyrrolidine-2-carboxylic acid (1 equiv) in THF (10 vol) at 0° C. was added boron hydride-tetrahydrofuran complex (2.1 equiv). The reaction mixture was stirred at room temperature for 2 h and then cooled at 0° C. The resulting mixture was quenched with saturated $K_2CO_3$ solution and extracted with ethyl acetate. The organic layer was separated, dried over anhydrous $Na_2SO_4$, filtered and then concentrated. The residue was purified by column chromatography on silica gel using DCM/MeOH to afford the title compound.

tert-butyl (2R,4R)-2-(cyanomethyl)-4-fluoropyrrolidine-1-carboxylate (S4)

To a solution of tert-butyl (2S,4R)-4-fluoro-2-(hydroxymethyl)pyrrolidine-1-carboxylate (1 equiv) in DCM (20 Vol) at 0° C. was added methane sulfonyl chloride (1.5 equiv) and triethylamine (3 equiv). The reaction mixture was stirred at 0° C. for 1 h. The resulting mixture was diluted with ethyl acetate, washed with 1N HCl and saturated $NaHCO_3$ solution. The organic layer was separated, dried over anhydrous $Na_2SO_4$, filtered and then concentrated. Crude tert-butyl (2S,4R)-4-fluoro-2-(((methylsulfonyl)oxy)methyl)pyrrolidine-1-carboxylate was dissolved in DMSO (10 Vol) and sodium cyanide (3 equiv) was added. The reaction mixture was stirred at 50° C. for 15 h. The resulting mixture was cooled to room temperature and quenched with water and was extracted with ethyl acetate. The organic layer was separated, dried over anhydrous $Na_2SO_4$, filtered and then concentrated. The residue was purified by column chromatography on silica gel using hexane/EtOAc to give tert-butyl (2R,4R)-2-(cyanomethyl)-4-fluoropyrrolidine-1-carboxylate.

tert-butyl (2R,4R)-2-(2-aminoethyl)-4-fluoropyrrolidine-1-carboxylate (S5)

To a solution of tert-butyl (2R,4R)-2-(cyanomethyl)-4-fluoropyrrolidine-1-carboxylate (1 equiv) in methanol (5 Vol) was added raney Ni (1.2 equiv) and triethylamine (2 equiv). The reaction mixture was stirred at room temperature at 3.5 milli bar pressure under hydrogen atmosphere for 16 h. The resulting mixture was filtered and then concentrated. The residue was purified by column chromatography on silica gel using DCM/MeOH to give tert-butyl (2R,4R)-2-(2-aminoethyl)-4-fluoropyrrolidine-1-carboxylate.

tert-butyl (2R,4R)-4-fluoro-2-(2-(phenylsulfonamido)ethyl)pyrrolidine-1-carboxylate (S6)

To a solution of tert-butyl (2R,4R)-2-(2-aminoethyl)-4-fluoropyrrolidine-1-carboxylate (1 equiv) in THF (10 vol) at 0° C. under nitrogen atmosphere was added benzene sulfonyl chloride (1.5 equiv) and triethylamine (3 equiv). The reaction mixture was stirred at room temperature for 16 h and then concentrated. The residue was purified by column chromatography on silica gel using hexane/EtOAc to give tert-butyl (2R,4R)-4-fluoro-2-(2-(phenyl sulfonamido)ethyl)pyrrolidine-1-carboxylate.

N-(2-((2R,4R)-4-fluoropyrrolidin-2-yl)ethyl)benzenesulfonamide (S7)

To a solution of tert-butyl (2R,4R)-4-fluoro-2-(2-(phenylsulfonamido)ethyl)pyrrolidine-1-carboxylate (1 equiv) in 1,4-dioxane (2 vol) at 0° C. was added 4 N HCl in dioxane (10 vol). The reaction mixture was stirred at room temperature for 4 h and then concentrated. The residue was taken in MTBE and stirred for 30 min. The resultant solid was filtered and dried to give N-(2-((2R,4R)-4-fluoropyrrolidin-2-yl)ethyl)benzenesulfonamide hydrochloride.

N-(2-((2R,4R)-1-(2-(3-acetyl-5-(2-methylpyrazolo[1,5-a]pyrimidin-6-yl)-1H-indol-1-yl)acetyl)-4-fluoropyrrolidin-2-yl)ethyl)benzenesulfonamide (697)

Scheme 47.

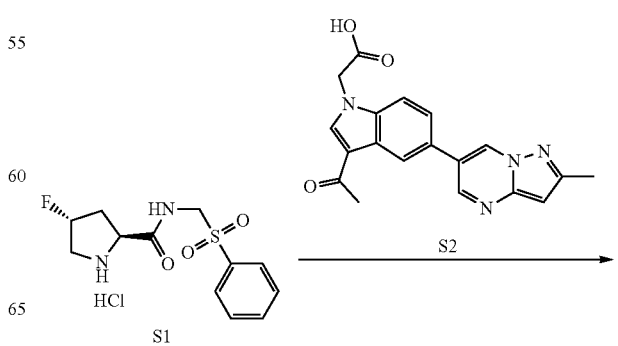

227

-continued

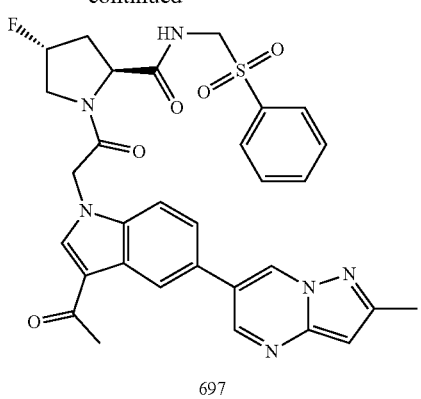

697

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 697.

$^1$H NMR (400 MHz, DMSO-$d_6$) δ 9.21 (s, 1H), 8.83 (s, 1H), 8.48 (s, 1H), 8.34 (s, 1H), 7.76 (d, J=7.2 Hz, 1H), 7.64-7.54 (m, 6H), 6.57 (s, 1H), 5.46-5.32 (m, 2H), 5.20-5.16 (m, 1H), 4.10-4.02 (m, 2H), 3.80-3.68 (m, 1H), 2.75-2.67 (m, 2H), 2.48 (s, 3H), 2.46 (s, 3H), 2.34-2.32 (m, 1H), 2.19-1.99 (m, 2H), 1.52-1.47 (m, 1H).

(2S,4R)-1-(2-(3-Acetyl-5-(2-methylpyrimidin-5-yl)-1H-indol-1-yl)acetyl)-N-benzyl-4-fluoropyrrolidine-2-carboxamide (442)

Scheme 48.

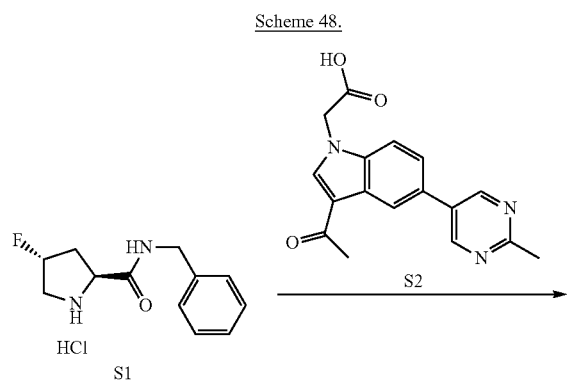

228

-continued

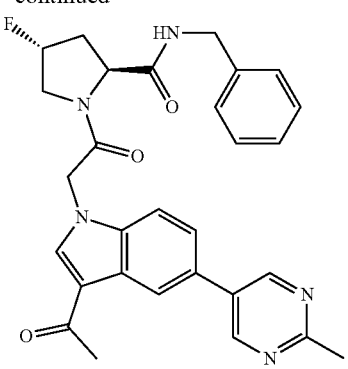

442

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 442.

$^1$H NMR (400 MHz, DMSO-$d_6$) δ 8.98-8.97 (m, 2H), 8.53-8.25 (m, 2H), 7.60-7.57 (m, 2H), 7.37-7.18 (m, 5H), 5.57-5.20 (m, 3H), 4.88-4.70 (m, 1H), 4.45-4.41 (m, 1H), 4.27-4.10 (m, 2H), 3.97-3.88 (m, 1H), 2.66 (s, 3H), 2.45 (s, 3H), 2.44-2.42 (m, 1H), 2.15-2.00 (m, 1H).

(2S,4R)-1-(2-(3-Acetyl-5-(2-methylpyrimidin-5-yl)-1H-indol-1-yl)acetyl)-4-fluoro-N-phenethylpyrrolidine-2-carboxamide (443)

Scheme 49.

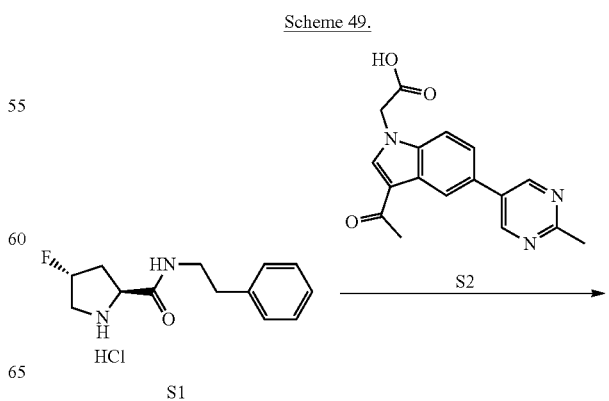

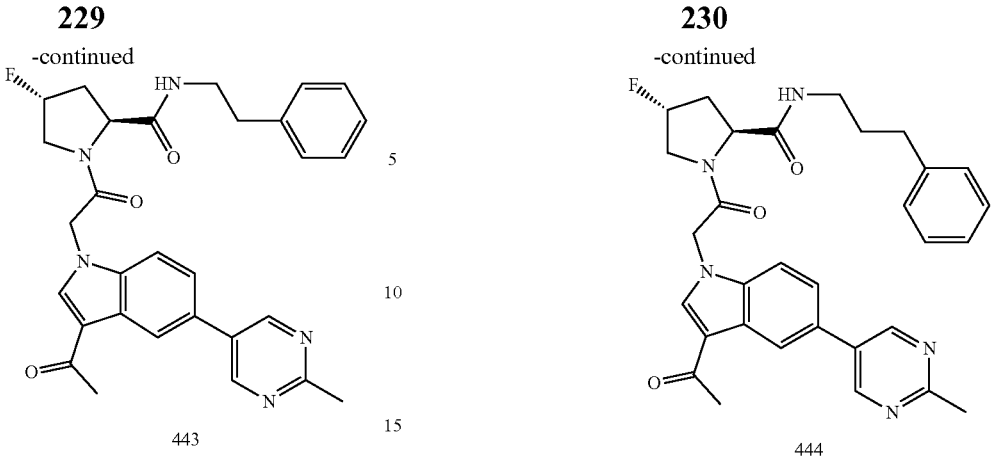

443

444

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 443.

$^1$H NMR (400 MHz, DMSO-$d_6$) δ 8.99 (s, 2H), 8.44 (s, 1H), 8.33 (m, 1H), 8.14-8.11 (m, 1H), 7.63 (m, 2H), 7.26-7.15 (m, 5H), 5.54-5.38 (m, 2H), 5.25-5.13 (m, 1H), 4.34 (t, J=8.4 Hz, 1H), 4.14-4.09 (m, 1H), 3.93-3.84 (m, 1H), 3.55-3.43 (m, 1H), 3.28-3.16 (m, 2H), 2.82-2.79 (m, 1H), 2.64 (s, 3H), 2.47 (s, 3H), 2.42-2.39 (m, 1H), 2.05-1.96 (m, 1H).

(2S,4R)-1-(2-(3-Acetyl-5-(2-methylpyrimidin-5-yl)-1H-indol-1-yl)acetyl)-4-fluoro-N-(3-phenylpropyl)pyrrolidine-2-carboxamide (444)

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 444.

$^1$H NMR (400 MHz, DMSO-$d_6$) δ 8.94 (s, 2H), 8.45 (s, 1H), 8.32 (m, 1H), 8.06-8.04 (m, 1H), 7.63 (d, J=8.8 Hz, 1H), 7.54 (d, J=8.8 Hz, 1H), 7.21-7.05 (m, 5H), 5.57-5.40 (m, 2H), 5.26-5.21 (m, 1H), 4.36 (t, J=8.4 Hz, 1H), 4.18-4.10 (m, 1H), 3.98-3.89 (m, 1H), 3.29-3.28 (m, 1H), 3.10-2.99 (m, 2H), 2.68 (s, 3H), 2.67-2.65 (m, 1H), 2.44 (s, 3H), 2.43-2.42 (m, 1H), 2.15-1.98 (m, 1H), 1.64-1.60 (m, 2H).

(2S,4R)-1-(2-(3-Acetyl-5-(2-methylpyrimidin-5-yl)-1H-indol-1-yl)acetyl)-4-fluoro-N-(4-phenylbutyl)pyrrolidine-2-carboxamide (461)

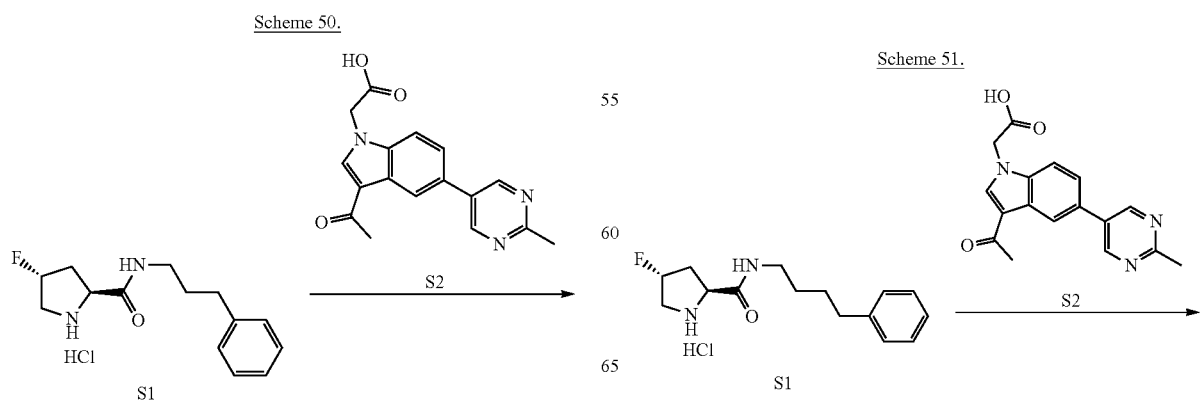

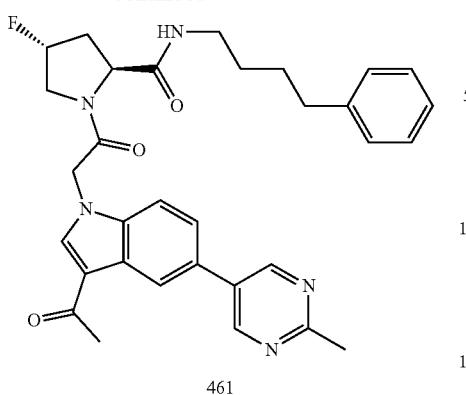

461

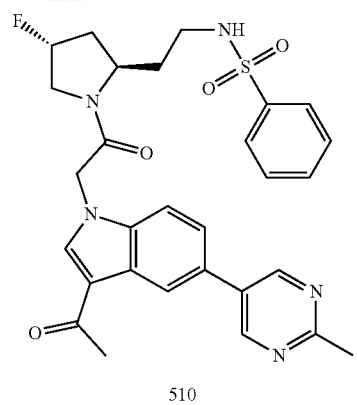

510

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 461.

$^1$H NMR (400 MHz, DMSO-$d_6$) δ 8.98 (s, 2H), 8.44 (s, 1H), 8.34 (s, 1H), 7.97-7.95 (m, 1H), 7.62-7.60 (m, 1H), 7.19-7.06 (m, 5H), 5.55-5.37 (m, 2H), 5.24-5.20 (m, 1H), 4.33 (t, J=8 Hz, 1H), 4.14-4.12 (m, 1H), 4.00-3.94 (m, 1H), 3.21-3.19 (m, 1H), 3.08-2.97 (m, 2H), 2.66 (s, 3H), 2.65-2.64 (m, 1H), 2.45 (s, 3H), 2.10-1.98 (m, 2H), 1.38-1.32 (m, 4H).

N-(2-((2R,4R)-1-(2-(3-Acetyl-5-(2-methylpyrimidin-5-yl)-1H-indol-1-yl)acetyl)-4-fluoropyrrolidin-2-yl)ethyl)benzenesulfonamide (510)

To a solution of S2 (1 equiv) in DMF (10 vol) at 0° C. under nitrogen atmosphere was added S1 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 510.

$^1$H NMR (400 MHz, DMSO-$d_6$) δ 8.99 (s, 2H), 8.45 (s, 1H), 8.34 (s, 1H), 7.79-7.75 (m, 2H), 7.63-7.51 (m, 6H), 5.45-5.31 (m, 2H), 5.20-5.13 (m, 1H), 4.09-4.01 (m, 2H), 3.80-3.67 (m, 1H), 2.75-2.73 (m, 2H), 2.68 (s, 3H), 2.47 (s, 3H), 2.39-2.38 (m, 1H), 2.07-2.05 (m, 1H), 1.95-1.91 (m, 1H), 1.55-1.51 (m, 1H).

(2S,4R)-1-(2-(3-Acetyl-5-(2-methylpyrimidin-5-yl)-1H-indazol-1-yl)acetyl)-N-(3-bromophenyl)-4-fluoropyrrolidine-2-carboxamide (507)

Scheme 52.

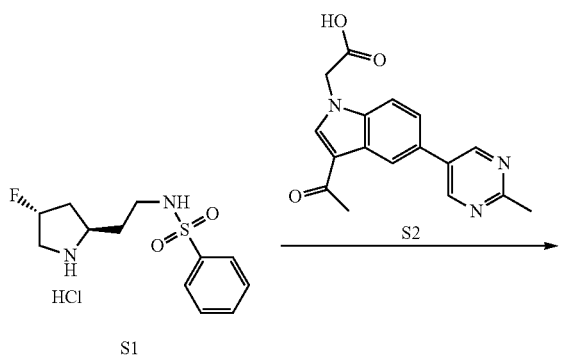

Scheme 53.

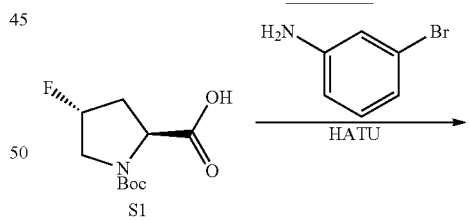

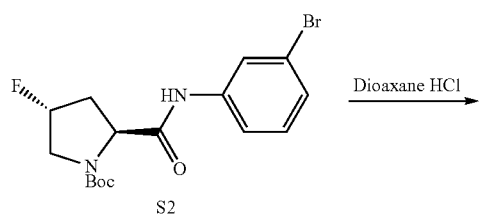

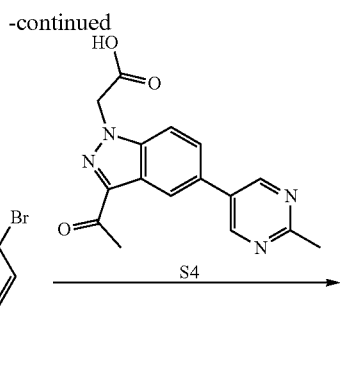

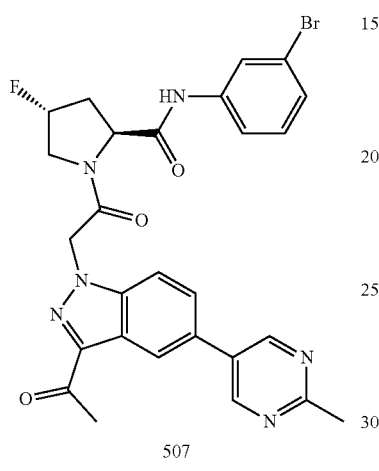

Step 1: tert-Butyl (2S,4R)-2-((3-bromophenyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 3-bromoaniline (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S2.

Step 2: (2S,4R)—N-(3-Bromophenyl)-4-fluoropyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-N-(3-bromophenyl)-4-fluoropyrrolidine-2-carboxamide (507)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 507.

$^1$H NMR (400 MHz, DMSO-$d_6$) δ 10.31 (s, 1H), 9.04 (s, 2H), 8.43 (s, 1H), 7.91-7.87 (m, 3H), 7.41 (d, J=7.32 Hz, 1H), 7.25-7.23 (m, 2H), 5.88-5.84 (m, 1H), 5.69-5.52 (m, 2H), 4.52 (t, J=7.4 Hz, 1H), 4.29-4.20 (m, 1H), 4.09-3.99 (m, 1H), 2.68 (s, 3H), 2.65 (s, 3H), 2.64-2.62 (m, 1H), 2.24-2.11 (m, 1H).

(2S,4R)-1-(2-(3-Acetyl-5-(2-methylpyrimidin-5-yl)-1H-indazol-1-yl)acetyl)-N-(3-bromo-4-fluorophenyl)-4-fluoropyrrolidine-2-carboxamide (509)

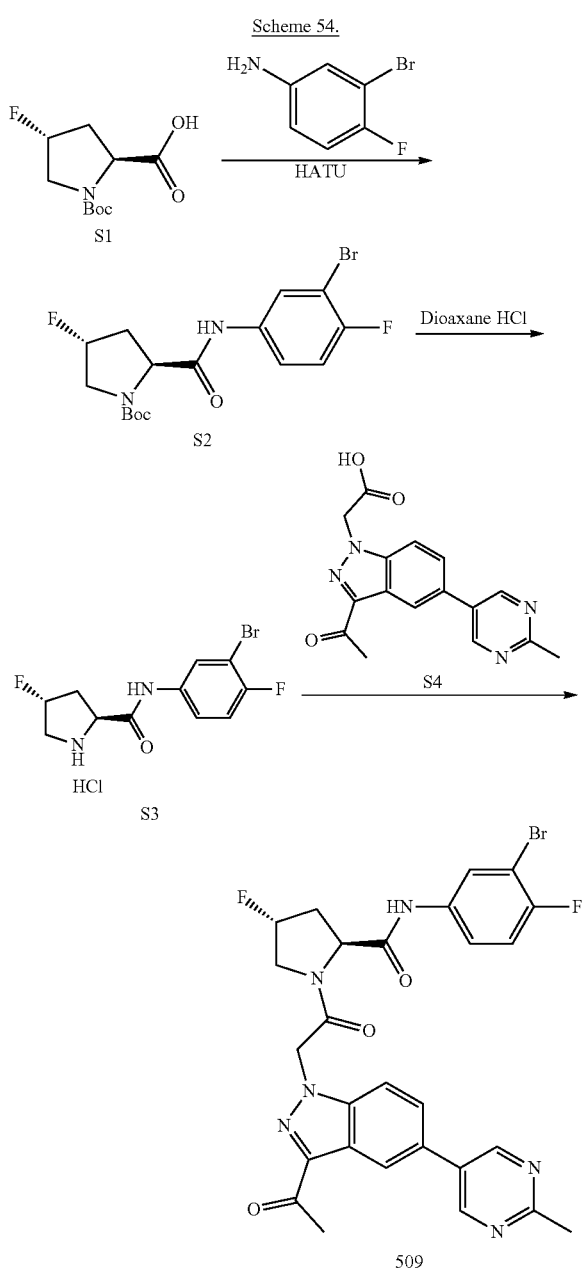

235

Step 1: tert-Butyl (2S,4R)-2-((3-bromo-4-fluorophenyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 3-bromo-4-fluoroaniline (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound S2.

Step 2: (2S,4R)—N-(3-Bromo-4-fluorophenyl)-4-fluoropyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-N-(3-bromo-4-fluorophenyl)-4-fluoropyrrolidine-2-carboxamide (509)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 509.

$^1$H NMR (400 MHz, DMSO-d$_6$) δ 10.34 (s, 1H), 9.04 (s, 2H), 8.43 (s, 1H), 7.99 (d, J=2.4 Hz, 1H), 7.89-7.84 (m, 2H), 7.45-7.41 (m, 1H), 7.34-7.29 (m, 1H), 5.88-5.77 (m, 1H), 5.69-5.52 (m, 2H), 4.50 (t, J=7.8 Hz, 1H), 4.29-4.20 (m, 1H), 4.08-3.96 (m, 1H), 2.68 (s, 3H), 2.65 (s, 3H), 2.64-2.63 (m, 1H), 2.25-2.00 (m, 1H).

(2S,4R)-1-(2-(3-Acetyl-5-(2-methylpyrimidin-5-yl)-1H-indazol-1-yl)acetyl)-N-(3-bromo-2,4-difluorophenyl)-4-fluoropyrrolidine-2-carboxamide (524)

Scheme 55.

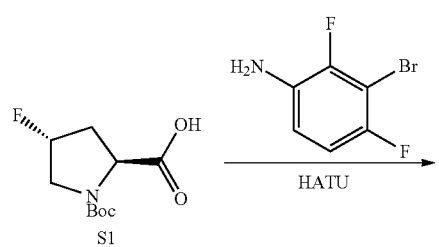

236

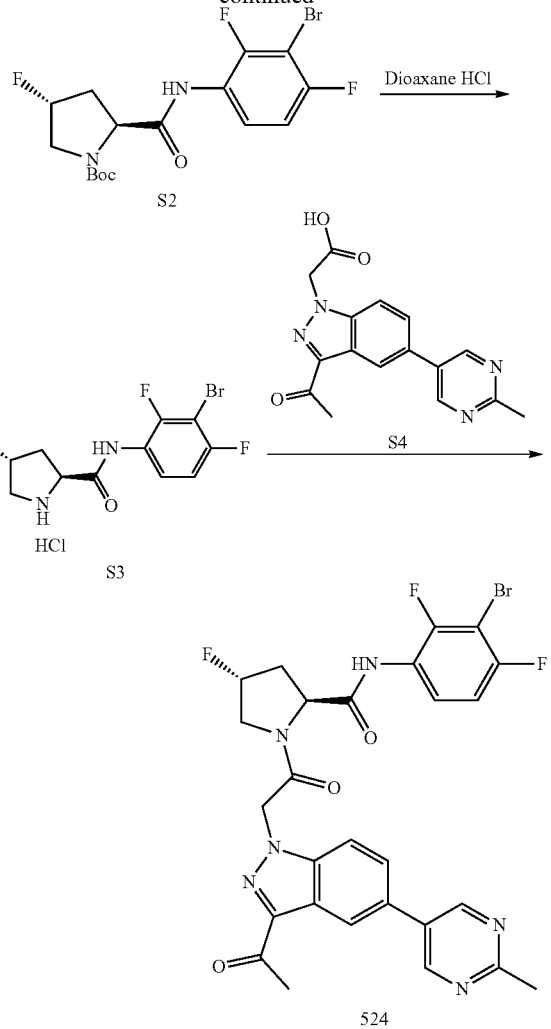

Step 1: tert-Butyl (2S,4R)-2-((3-bromo-2,4-difluorophenyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 3-bromo-2,4-difluoroaniline (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound S2.

Step 2: (2S,4R)—N-(3-Bromo-2,4-difluorophenyl)-4-fluoropyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-N-(3-bromo-2,4-difluorophenyl)-4-fluoropyrrolidine-2-carboxamide (524)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 524.

$^1$H NMR (400 MHz, DMSO-$d_6$) δ 10.09 (s, 1H), 9.05 (s, 2H), 8.44 (s, 1H), 7.89-7.73 (m, 3H), 7.26-7.22 (m, 1H), 5.88-5.79 (m, 1H), 5.67-5.51 (m, 2H), 4.69 (t, J=8.8 Hz, 1H), 4.29-4.21 (m, 1H), 4.07-3.96 (m, 1H), 2.69 (s, 3H), 2.65 (s, 3H), 2.64-2.62 (m, 1H), 2.25-2.05 (m, 1H).

(2S,4R)-1-(2-(3-Acetyl-5-(2-methylpyrimidin-5-yl)-1H-indazol-1-yl)acetyl)-N-(3-chlorophenyl)-4-fluoropyrrolidine-2-carboxamide (508)

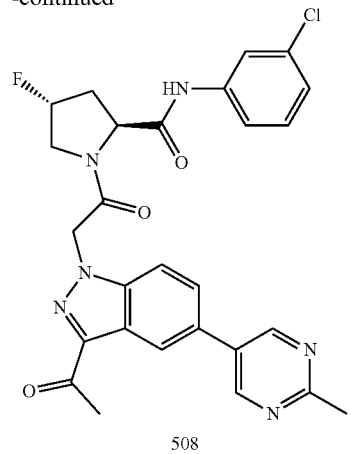

508

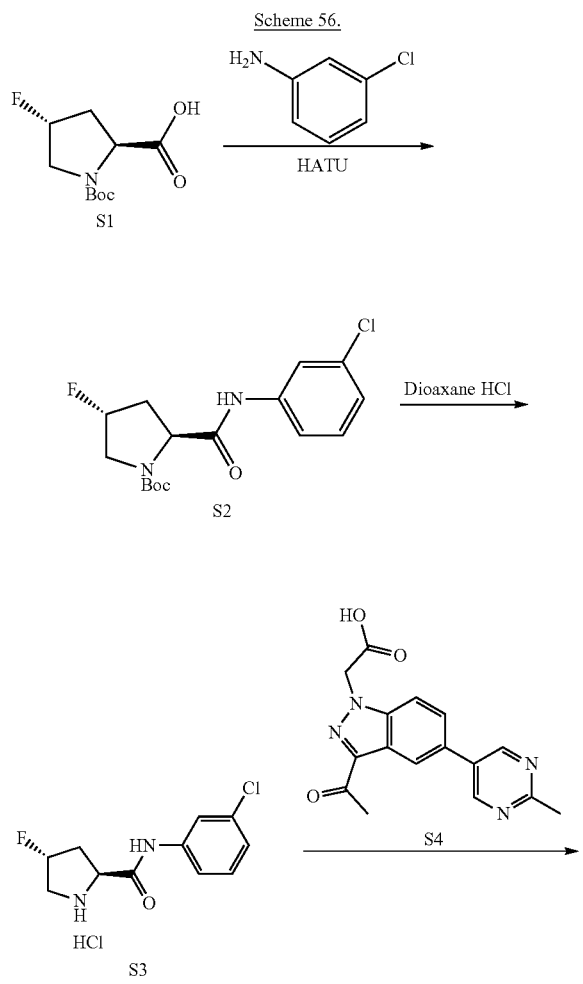

Step 1: tert-Butyl (2S,4R)-2-((3-chlorophenyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 3-chloroaniline (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S2.

Step 2: (2S,4R)—N-(3-Chlorophenyl)-4-fluoropyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Aetyl-5-(2-methylpyrimidin-5-yl)-1H-indazol-1-yl)acetyl)-N-(3-chlorophenyl)-4-fluoropyrrolidine-2-carboxamide (508)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 508.

$^1$H NMR (400 MHz, DMSO-$d_6$) δ 10.37 (s, 1H), 9.05 (s, 2H), 8.43 (s, 1H), 7.89 (s, 2H), 7.77 (s, 1H), 7.38-7.29 (m, 2H), 7.10-7.08 (m, 1H), 5.88-5.76 (m, 1H), 5.69-5.52 (m, 2H), 4.52 (t, J=7.4 Hz, 1H), 4.31-4.20 (m, 1H), 4.15-4.00 (m, 1H), 2.69 (s, 3H), 2.66 (s, 3H), 2.65-2.62 (m, 1H), 2.21-2.05 (m, 1H).

239

(2S,4R)-1-(2-(3-Acetyl-5-(2-methylpyrimidin-5-yl)-1H-indazol-1-yl)acetyl)-4-fluoro-N—(((S)-1-methyl-pyrrolidin-3-yl)methyl)pyrrolidine-2-carboxamide (568)

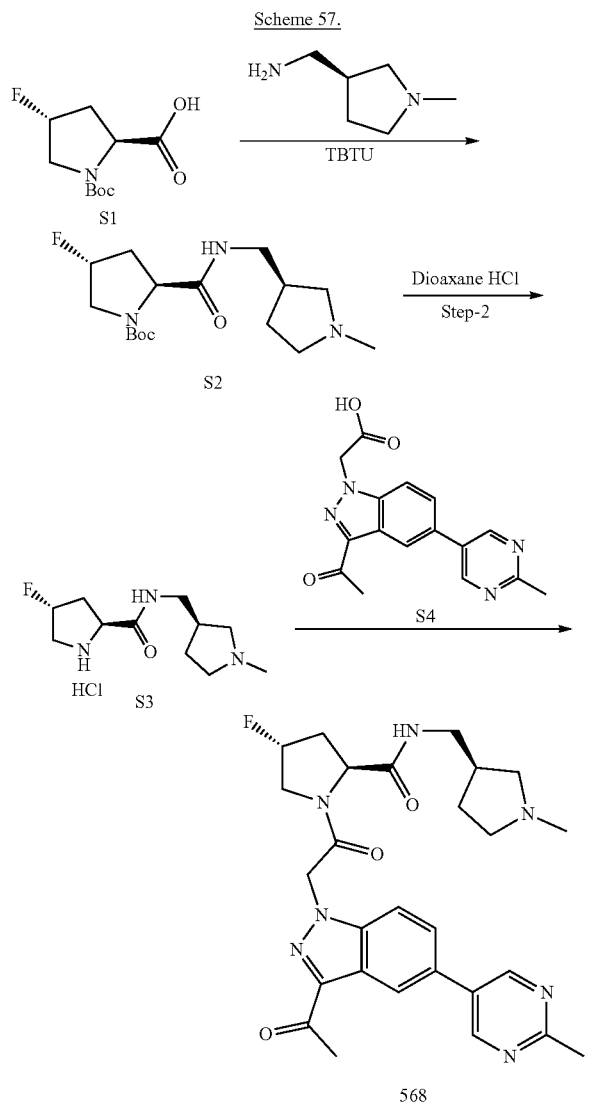

Step 1: tert-Butyl (2S,4R)-4-fluoro-2-((((S)-1-methylpyrrolidin-3-yl)methyl)carbamoyl)pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (S)-(1-methylpyrrolidin-3-yl)methanamine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound S2.

240

Step 2: (2S,4R)-4-Fluoro-N—(((S)-1-methylpyrrolidin-3-yl)methyl)pyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-4-fluoro-N—(((S)-1-methylpyrrolidin-3-yl)methyl)pyrrolidine-2-carboxamide (568)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 568.

$^1$H NMR (400 MHz, DMSO-d$_6$) δ 9.05 (s, 2H), 8.44-8.25 (m, 2H), 7.90-7.82 (m, 2H), 5.87-5.81 (m, 1H), 5.64-5.57 (m, 2H), 4.37-4.35 (m, 1H), 4.33-4.16 (m, 1H), 4.02-3.97 (m, 2H), 3.37-3.35 (m, 2H), 3.15-2.95 (m, 2H), 2.82-2.81 (m, 1H), 2.56 (s, 3H), 2.54 (s, 3H), 2.49 (s, 3H), 2.36-2.32 (m, 2H), 2.11-2.01 (m, 2H), 1.79-1.77 (m, 1H).

(2S,4R)-1-(2-(3-acetyl-5-(2-methylpyrimidin-5-yl)-1H-indazol-1-yl)acetyl)-4-fluoro-N—(((R)-1-methylpyrrolidin-3-yl)methyl)pyrrolidine-2-carboxamide (569)

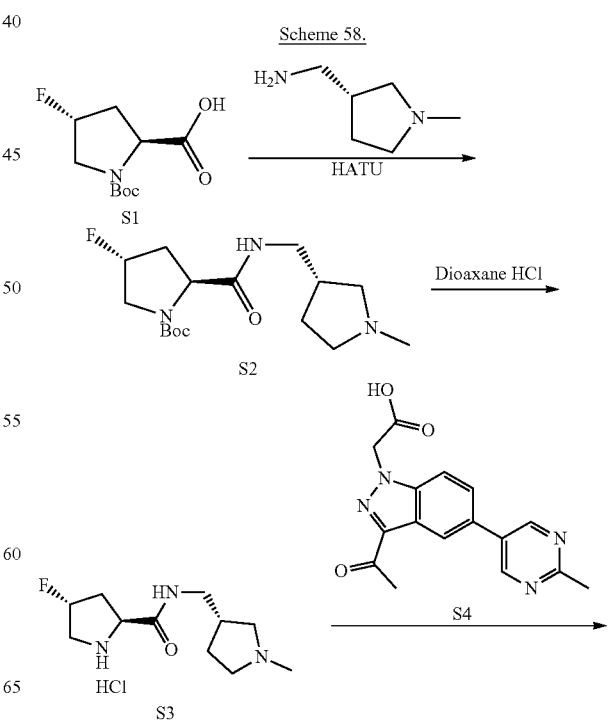

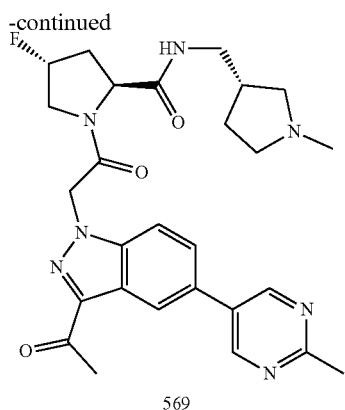

569

Step 1: tert-butyl (2S,4R)-4-Fluoro-2-((((R)-1-methylpyrrolidin-3-yl)methyl)carbamoyl)pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (R)-(1-methylpyrrolidin-3-yl)methanamine (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using DCM/MeOH to give compound S2.

Step 2: (2S,4R)-4-Fluoro-N—(((R)-1-methylpyrrolidin-3-yl)methyl)pyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-4-fluoro-N—(((R)-1-methylpyrrolidin-3-yl)methyl)pyrrolidine-2-carboxamide (569)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using DCM/MeOH to give compound 569.

$^1$H NMR (400 MHz, DMSO-d$_6$) δ 9.05 (s, 2H), 8.44 (s, 1H), 8.29-8.27 (m, 1H), 7.90-7.84 (m, 2H), 5.85-5.73 (m, 2H), 5.62-5.46 (m, 1H), 4.33-4.25 (m, 1H), 4.22-4.16 (m, 1H), 4.00-3.91 (m, 2H), 3.38-3.26 (m, 2H), 3.16-3.06 (m, 3H), 2.82 (s, 3H), 2.80 (s, 3H), 2.46 (s, 3H), 2.45-2.43 (m, 1H), 2.10-2.00 (m, 2H), 1.84-1.82 (m, 1H), 1.75-1.45 (m, 1H).

(2S,4R)-1-(2-(3-Acetyl-5-(2-methylpyrimidin-5-yl)-1H-indazol-1-yl)acetyl)-4-fluoro-N-((1-(2,2,2-trifluoroethyl)pyrrolidin-3-yl)methyl)pyrrolidine-2-carboxamide (550)

Scheme 59.

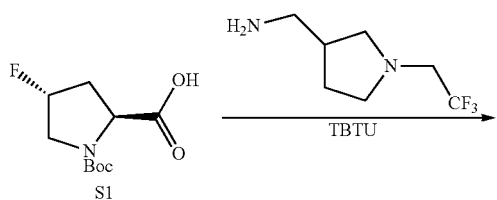

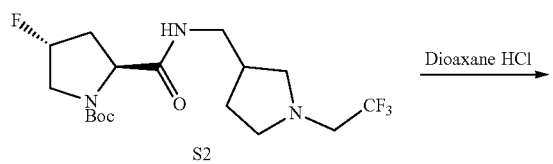

-continued

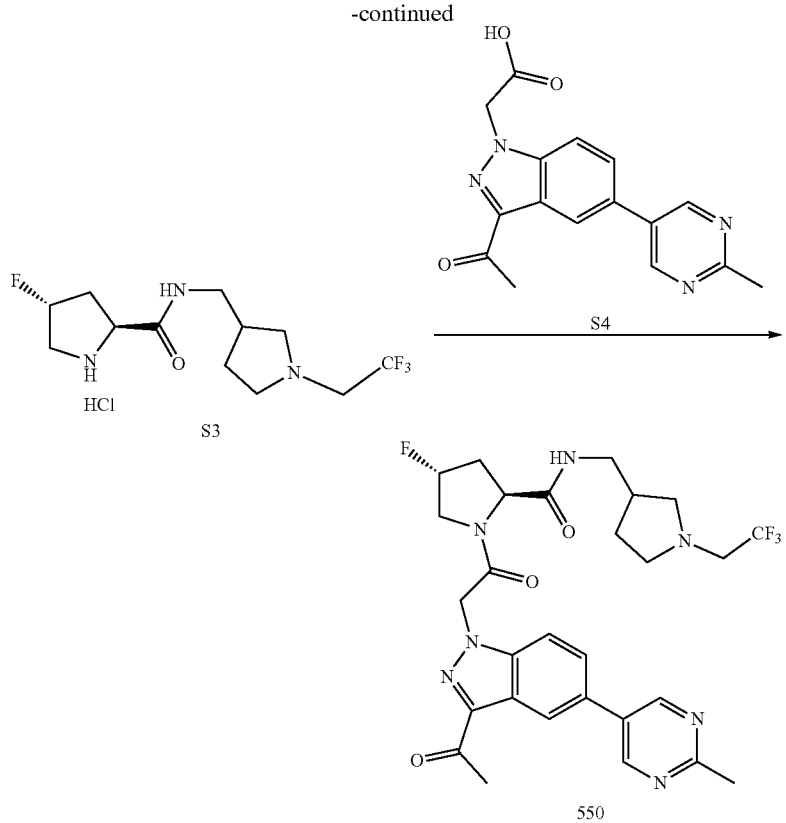

Step 1: tert-Butyl (2S,4R)-4-fluoro-2-(((1-(2,2,2-trifluoroethyl)pyrrolidin-3-yl)methyl)carbamoyl) pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (1-(2,2,2-trifluoroethyl)pyrrolidin-3-yl)methanamine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S2.

Step 2: (2S,4R)-4-Fluoro-N-((1-(2,2,2-trifluoroethyl)pyrrolidin-3-yl)methyl)pyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-4-fluoro-N-((1-(2,2,2-trifluoroethyl)pyrrolidin-3-yl)methyl)pyrrolidine-2-carboxamide (S4)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 550.

$^1$H NMR (400 MHz, DMSO-$d_6$) δ 9.00 (s, 2H), 8.44 (s, 1H), 8.08-8.06 (m, 1H), 7.89-7.82 (m, 2H), 5.82-5.60 (m, 1H), 5.56-5.44 (m, 2H), 4.35 (t, J=8.4 Hz, 1H), 4.20-4.15 (m, 1H), 4.00-3.85 (m, 1H), 3.18-2.98 (m, 6H), 2.69 (s, 3H), 2.65 (s, 3H), 2.58-2.56 (m, 2H), 2.31-2.15 (m, 1H), 2.21-2.15 (m, 2H), 1.75-1.73 (m, 1H), 1.36-1.34 (m, 1H).

(2S,4R)-1-(2-(3-Acetyl-5-(2-methylpyrimidin-5-yl)-1H-indazol-1-yl)acetyl)-N—((R)-1-((R)-2,2-dichlorocyclopropyl)ethyl)-4-fluoropyrrolidine-2-carboxamide (570)

Scheme 60.

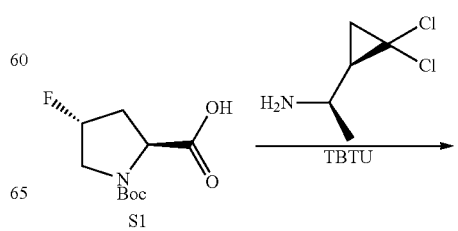

-continued

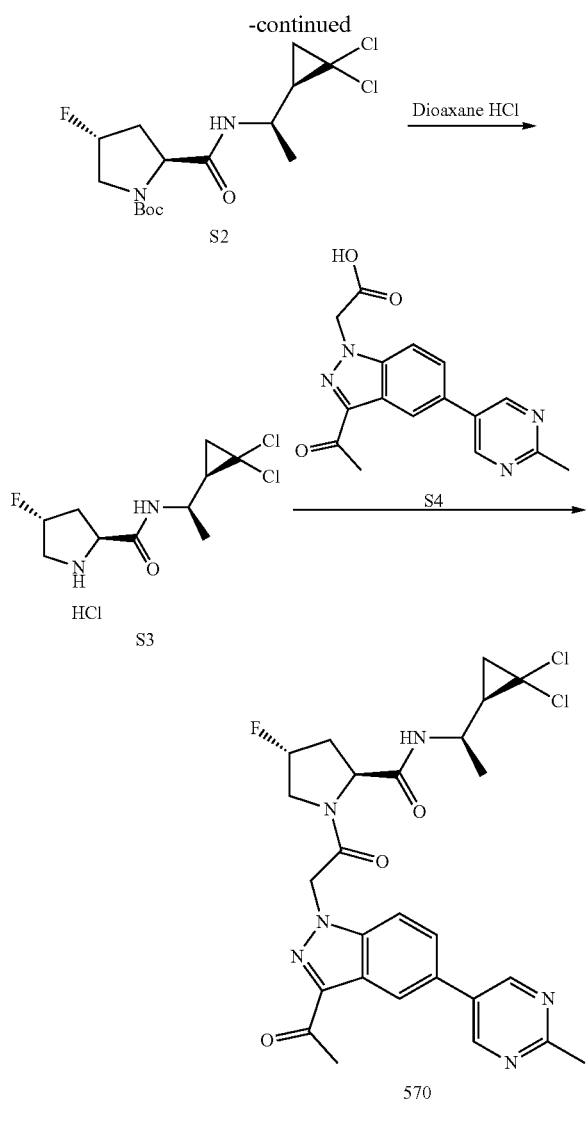

Step 1: tert-Butyl (2S,4R)-2-(((R)-1-((R)-2,2-dichlorocyclopropyl)ethyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (R)-1-((R)-2,2-dichlorocyclopropyl)ethan-1-amine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S2.

Step 2: (2S,4R)—N—((R)-1-((R)-2,2-Dichlorocyclopropyl)ethyl)-4-fluoropyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-N—((R)-1-((R)-2,2-dichlorocyclopropyl)ethyl)-4-fluoropyrrolidine-2-carboxamide (570)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 570.

$^1$H NMR (400 MHz, DMSO-$d_6$) δ 9.06 (s, 2H), 8.44 (s, 1H), 7.87 (d, J=8.8 Hz, 2H), 5.85-5.80 (m, 1H), 5.60-5.56 (m, 1H), 5.14-4.89 (m, 1H), 4.42-4.18 (m, 1H), 4.05-3.85 (m, 1H), 3.51-3.50 (m, 2H), 2.70 (s, 3H), 2.67 (s, 3H), 1.93-1.87 (m, 2H), 1.44-1.42 (m, 1H), 1.27-1.24 (m, 2H), 1.12 (d, J=6.4 Hz, 3H).

(2S,4R)-1-(2-(3-acetyl-5-(2-methylpyrimidin-5-yl)-1H-indazol-1-yl)acetyl)-4-fluoro-N-(2-fluoro-3-methylbut-2-en-1-yl)pyrrolidine-2-carboxamide (474)

Scheme 61.

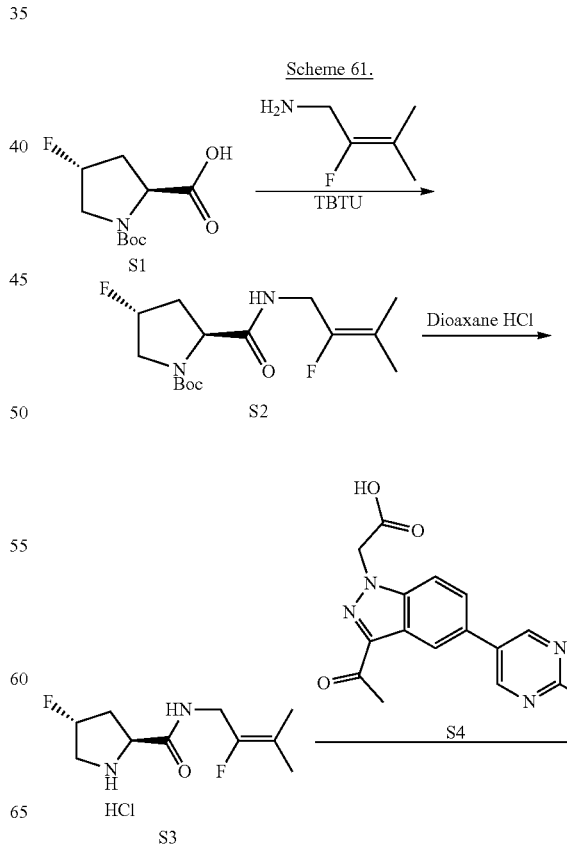

-continued

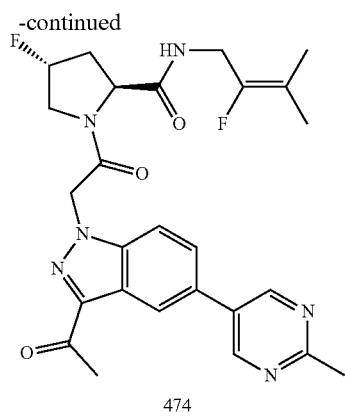

474

Step 1: tert-Butyl (2S,4R)-4-fluoro-2-((2-fluoro-3-methylbut-2-en-1-yl)carbamoyl)pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 2-fluoro-3-methylbut-2-en-1-amine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound S2.

Step 2: (2S,4R)-4-Fluoro-N-(2-fluoro-3-methylbut-2-en-1-yl)pyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-4-fluoro-N-(2-fluoro-3-methylbut-2-en-1-yl)pyrrolidine-2-carboxamide (S5)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 474.

$^1$H NMR (400 MHz, DMSO-d$_6$) δ 9.05 (s, 2H), 8.44 (s, 1H), 8.34-8.33 (m, 1H), 7.90-7.82 (m, 2H), 5.82-5.78 (m, 1H), 5.60-5.43 (m, 2H), 4.39 (t, J=8.0 Hz, 1H), 4.24-3.76 (m, 4H), 2.69 (s, 3H), 2.65 (s, 3H), 2.42-2.41 (m, 1H), 2.12-2.00 (m, 1H), 1.61 (s, 3H), 1.56 (s, 3H).

(2S,4R)-1-(2-(3-Acetyl-5-(2-methylpyrimidin-5-yl)-1H-indazol-1-yl)acetyl)-4-fluoro-N—((R)-3-fluoro-4-methylpent-3-en-2-yl)pyrrolidine-2-carboxamide (613)

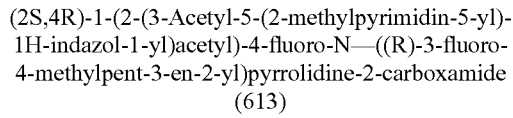

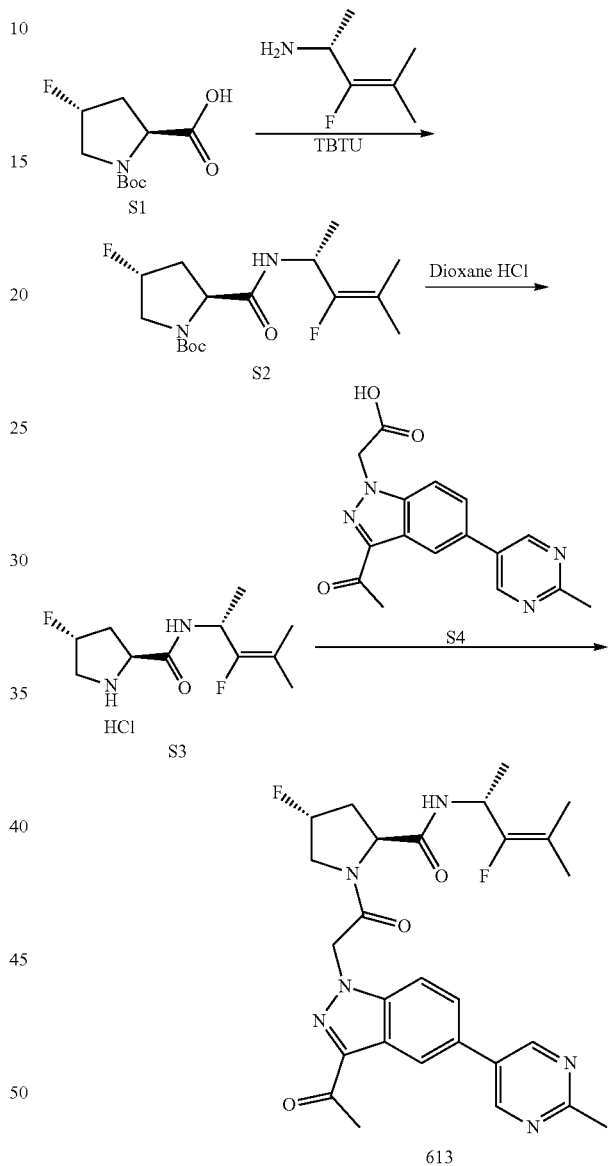

613

Step 1: tert-Butyl (2S,4R)-4-fluoro-2-(((R)-3-fluoro-4-methylpent-3-en-2-yl)carbamoyl)pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (R)-3-fluoro-4-methylpent-3-en-2-amine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH-J to give compound S2.

Step 2: (2S,4R)-4-Fluoro-N—((R)-3-fluoro-4-methylpent-3-en-2-yl)pyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-4-fluoro-N—((R)-3-fluoro-4-methylpent-3-en-2-yl)pyrrolidine-2-carboxamide (613)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 613.

$^1$H NMR (400 MHz, DMSO-d$_6$) δ 9.05 (s, 2H), 8.44 (s, 1H), 8.28 (d, J=7.8 Hz, 1H), 7.88-7.82 (m, 2H), 5.82-5.78 (m, 1H), 5.61-5.41 (m, 2H), 4.81-4.74 (m, 1H), 4.41 (t, J=8.2 Hz, 1H), 4.24-4.14 (m, 1H), 4.00-3.91 (m, 1H), 2.69 (s, 3H), 2.65 (s, 3H), 2.49-2.48 (m, 1H), 2.11-1.97 (m, 1H), 1.60 (s, 3H), 1.59 (s, 3H), 1.15 (d, J=6.9 Hz, 3H).

(2S,4R)-1-(2-(3-Acetyl-5-(2-methylpyrimidin-5-yl)-1H-indazol-1-yl)acetyl)-4-fluoro-N—((S)-3-fluoro-4-methylpent-3-en-2-yl)pyrrolidine-2-carboxamide (614)

Scheme 63.

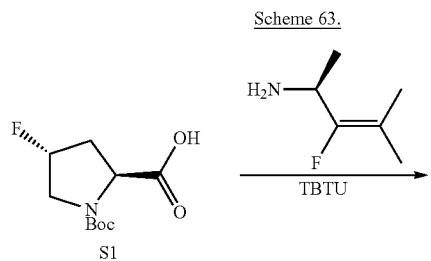

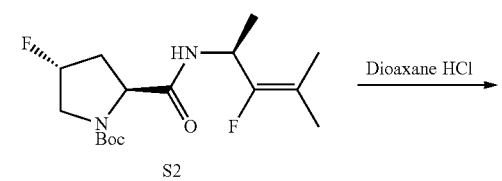

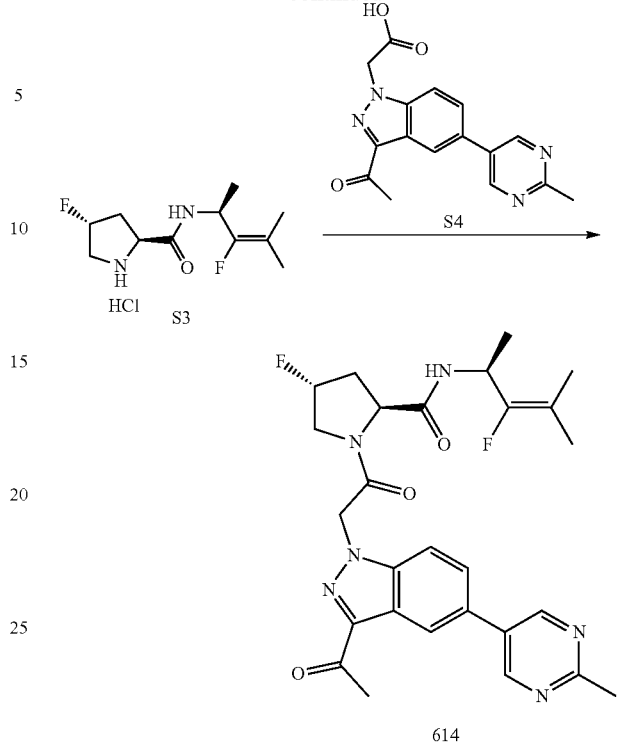

Step 1: tert-Butyl (2S,4R)-4-fluoro-2-(((S)-3-fluoro-4-methylpent-3-en-2-yl)carbamoyl)pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (S)-3-fluoro-4-methylpent-3-en-2-amine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound S2.

Step 2: (2S,4R)-4-Fluoro-N—((S)-3-fluoro-4-methylpent-3-en-2-yl)pyrrolidine-2-carboxamide hydrochloride e (S3)

To a solution of compound S2 (1 equiv) in 1,4-dioxane (3 vol) at 0° C. under nitrogen atmosphere was added 4 N HCl in 1,4-dioxane (10 vol) and the reaction was stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-4-fluoro-N—((S)-3-fluoro-4-methylpent-3-en-2-yl)pyrrolidine-2-carboxamide (614)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 614.

$^1$H NMR (400 MHz, DMSO-$d_6$) δ 9.05 (s, 2H), 8.44 (s, 1H), 8.25 (d, J=7.8 Hz, 1H), 7.88-7.85 (m, 2H), 5.83-5.43 (m, 3H), 4.81-4.74 (m, 1H), 4.39 (t, J=8.2 Hz, 1H), 4.20-4.14 (m, 1H), 4.00-3.91 (m, 1H), 2.69 (s, 3H), 2.65 (s, 3H), 2.49-2.48 (m, 1H), 2.11-1.97 (m, 1H), 1.57 (s, 3H), 1.50 (s, 3H), 1.15 (d, J=6.9 Hz, 3H).

(2S,4R)-1-(2-(3-Acetyl-5-(2-methylpyrimidin-5-yl)-1H-indazol-1-yl)acetyl)-N-((1R,2S)-2-(2-chlorophenyl)cyclopropyl)-4-fluoropyrrolidine-2-carboxamide (527) and (2S,4R)-1-(2-(3-acetyl-5-(2-methylpyrimidin-5-yl)-1H-indazol-1-yl)acetyl)-N-((1S,2R)-2-(2-chlorophenyl)cyclopropyl)-4-fluoropyrrolidine-2-carboxamide (526)

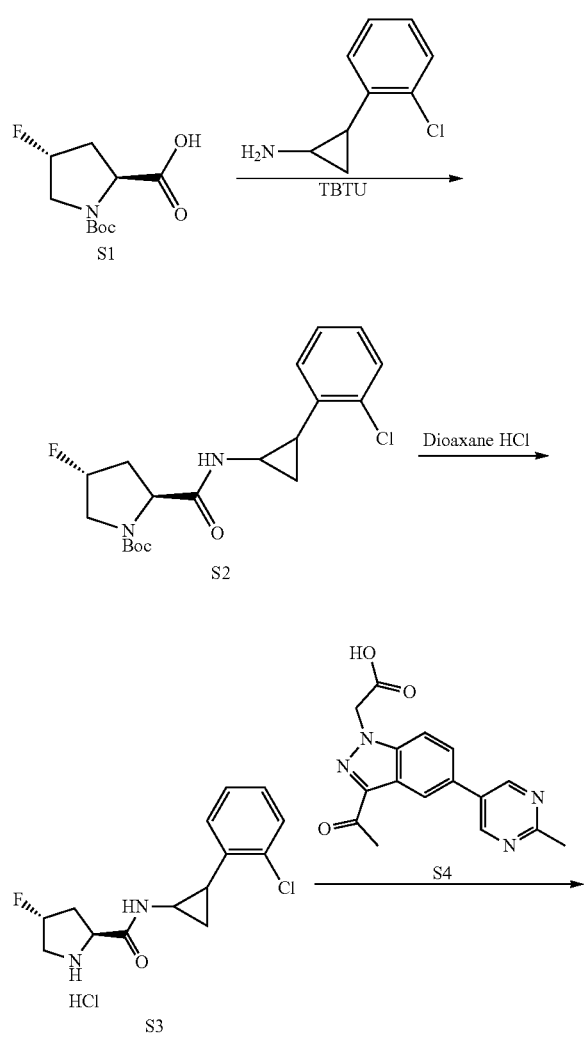

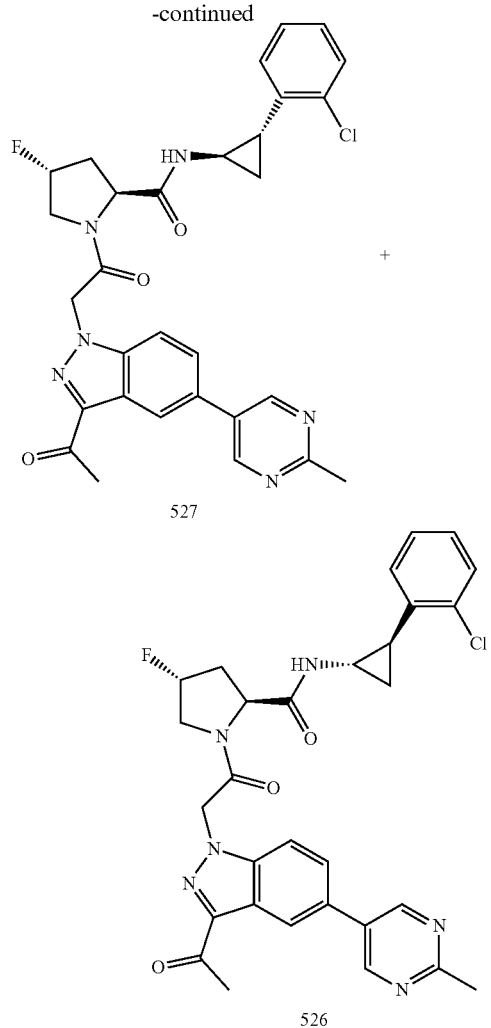

Step 1: tert-Butyl (2S,4R)-2-((2-(2-chlorophenyl)cyclopropyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 2-(2-chlorophenyl)cyclopropan-1-amine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S2.

Step 2: (2S,4R)—N-(2-(2-Chlorophenyl)cyclopropyl)-4-fluoropyrrolidine-2-carboxamidehydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step 3: (2S,4R)-1-(2-(3-Acetyl-5-(2-methylpyrimidin-5-yl)-1H-indazol-1-yl)acetyl)-N-((1R,2S)-2-(2-chlorophenyl)cyclopropyl)-4-fluoropyrrolidine-2-carboxamide (527) and (2S,4R)-1-(2-(3-Acetyl-5-(2-methylpyrimidin-5-yl)-1H-indazol-1-yl)acetyl)-N-((1S,2R)-2-(2-chlorophenyl)cyclopropyl)-4-fluoropyrrolidine-2-carboxamide (526)

To a solution of compound S3 (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give racemic product. This racemic product was purified by SFC to give compound 527 as one isomer and compound 526 was another isomer.

527: $^1$H NMR (400 MHz, DMSO-$d_6$) δ 9.04 (s, 2H), 8.43 (s, 1H), 8.37 (d, J=4.4 Hz, 1H), 7.87-7.80 (m, 2H), 7.41-7.37 (m, 1H), 7.24-7.15 (m, 2H), 7.06-7.04 (m, 1H), 5.82-5.78 (m, 1H), 5.71-5.44 (m, 2H), 4.31 (t, J=8.8 Hz, 1H), 4.19-4.14 (m, 1H), 4.01-3.96 (m, 1H), 2.93-2.90 (m, 1H), 2.68 (s, 3H), 2.66 (s, 3H), 2.44-2.42 (m, 1H), 2.11-2.08 (m, 1H), 1.20-1.09 (m, 3H).

526: $^1$H NMR (400 MHz, DMSO-$d_6$) δ 9.03 (s, 2H), 8.42 (s, 1H), 8.36 (d, J=4.8 Hz, 1H), 7.83-7.82 (m, 2H), 7.36-7.33 (m, 1H), 7.22-7.14 (m, 2H), 7.07-7.05 (m, 1H), 5.82-5.78 (m, 1H), 5.60-5.44 (m, 2H), 4.32 (t, J=8.8 Hz, 1H), 4.25-4.12 (m, 1H), 4.00-3.96 (m, 1H), 2.94-2.91 (m, 1H), 2.68 (s, 3H), 2.66 (s, 3H), 2.35-2.32 (m, 1H), 2.16-2.12 (m, 1H), 1.35-1.31 (m, 1H), 1.23-1.22 (m, 1H), 1.16-1.10 (m, 1H).

(2S,4R)-1-(2-(3-Acetyl-5-(2-methylpyrimidin-5-yl)-1H-indazol-1-yl)acetyl)-N-(((3S,5S,7S)-adamantan-1-yl)methyl)-4-fluoropyrrolidine-2-carboxamide (612)

Scheme 65.

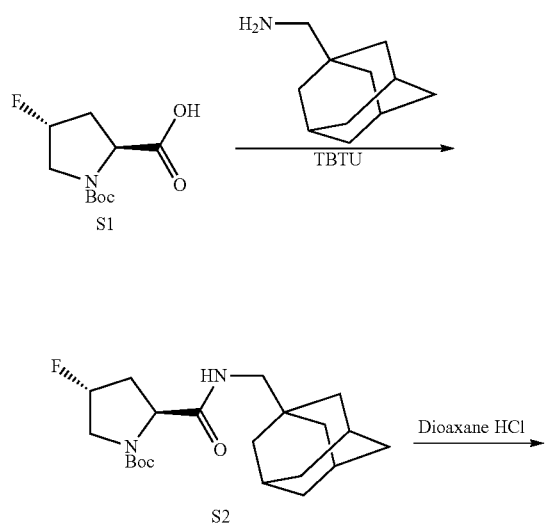

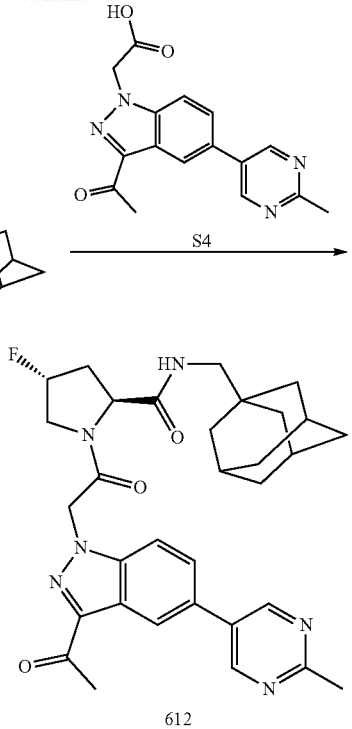

Step 1: tert-Butyl (2S,4R)-2-((((3S,5S,7S)-adamantan-1-yl)methyl)carbamoyl)-4-fluoropyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added (S)-3-fluoro-4-methylpent-3-en-2-amine (1.2 equiv), TBTU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S2.

Step 2: (2S,4R)—N-(((3S,5S,7S)-Adamantan-1-yl)methyl)-4-fluoropyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step 3: (2S,4R)-1-(2-(3-acetyl-5-(2-Methylpyrimidin-5-yl)-1H-indazol-1-yl)acetyl)-N-(((3S,5S,7S)-adamantan-1-yl)methyl)-4-fluoropyrrolidine-2-carboxamide (612)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using DCM/MeOH to give compound 612.

¹H NMR (400 MHz, DMSO-d₆) δ 9.06-9.04 (m, 2H), 8.44 (m, 1H), 7.88-7.82 (m, 3H), 5.83-5.78 (m, 1H), 5.61-5.43 (m, 2H), 4.46-4.42 (m, 1H), 4.23-4.12 (m, 1H), 4.00-3.88 (m, 3H), 2.90-2.85 (m, 1H), 2.69 (s, 3H), 2.64 (s, 3H), 2.63-2.62 (m, 1H), 2.13-1.98 (m, 1H), 1.91-1.92 (m, 1H), 1.83-1.82 (m, 2H), 1.63-1.24 (m, 12H).

(2S,4R)-1-(2-(3-Acetyl-5-(2-((1,1-dioxidothietan-3-yl)oxy)pyrimidin-5-yl)-1H-indazol-1-yl)acetyl)-N-(6-bromopyridin-2-yl)-4-fluoropyrrolidine-2-carboxamide (591)

Scheme 66.

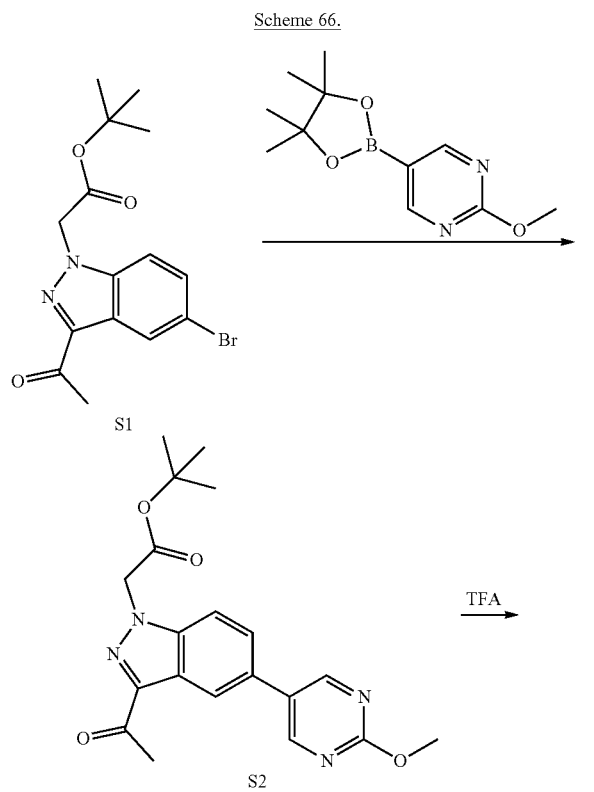

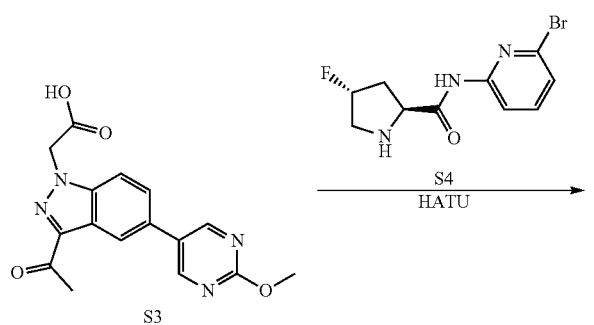

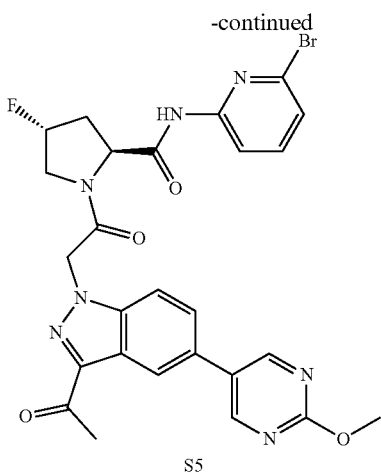

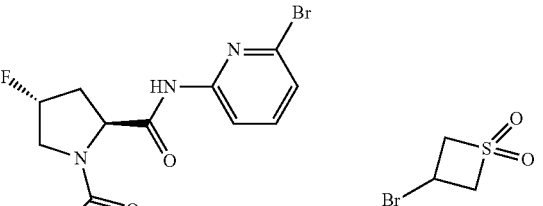

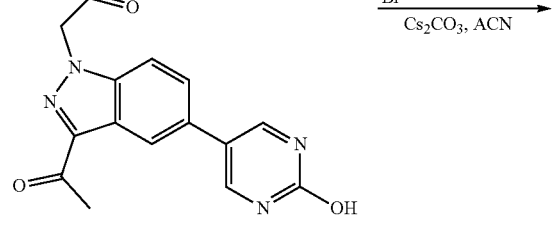

Step 1: tert-Butyl 2-(3-acetyl-5-(2-methoxypyrimidin-5-yl)-1H-indazol-1-yl)acetate (S2)

To a solution of tert-butyl 2-(3-acetyl-5-bromo-1H-indazol-1-yl)acetate (1 equiv) in dioxane (20 vol) was added 2-methoxy-5-(4,4,5,5-tetramethyl-1,3,2-dioxaborolan-2-yl)pyrimidine (1.2 equiv) and 1 M Na₂CO₃ (3 equiv). After degassing with nitrogen, Pd(PPh₃)₄ (0.05 equiv) was added to the reaction mixture. The resulting mixture was stirred at 90° C. for 12 h and then cooled to room temperature. Water was added to the reaction mixture and the resulting mixture was extracted with ethyl acetate. The organic layer was separated, dried over anhydrous Na₂SO₄, filtered and then concentrated. The residue was purified by column chromatography on silica gel using Hexane/EtOAc to give compound S2.

Step 2: 2-(3-Acetyl-5-(2-methoxypyrimidin-5-yl)-1H-indazol-1-yl)acetic acid (S3)

To a solution of compound S2 (1 equiv) in DCM (10 vol) at 0° C. under nitrogen atmosphere was added TFA (10 vol). The reaction mixture was heated to 50° C. for 3 h. After completion of the reaction, the reaction mixture was concentrated to give compound S3.

Step 3: (2S,4R)-1-(2-(3-Acetyl-5-(2-methoxypyrimidin-5-yl)-1H-indazol-1-yl)acetyl)-N-(6-bromopyridin-2-yl)-4-fluoropyrrolidine-2-carboxamide (S5)

To a solution of compound S3 (1 equiv) in DMF (10 vol) at 0° C. under nitrogen atmosphere was added S4 (1.2 equiv), HATU (1.5 equiv) and DIPEA (5 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound S5.

Step 4: (2S,4R)-1-(2-(3-Acetyl-5-(2-hydroxypyrimidin-5-yl)-1H-indazol-1-yl)acetyl)-N-(6-bromopyridin-2-yl)-4-fluoropyrrolidine-2-carboxamide (S6)

To a solution of compound S5 (1 equiv) in ACN (10 vol) at 0° C. under nitrogen atmosphere was added TMSCl (2.5 equiv) and NaI (2 equiv). The reaction mixture was stirred at room temperature for 16 h. After completion of the reaction, the reaction mixture was concentrated and quenched with water. The resulting solid was filtered, dried to give compound S6.

Step 5: (2S,4R)-1-(2-(3-Acetyl-5-(2-((1,1-dioxidothietan-3-yl)oxy)pyrimidin-5-yl)-1H-indazol-1-yl)acetyl)-N-(6-bromopyridin-2-yl)-4-fluoropyrrolidine-2-carboxamide (591)

To a solution of compound S6 (1 equiv) in ACN (10 vol) was added cesium carbonate (3 equiv) and 3-bromothietane 1,1-dioxide (2 equiv). The reaction mixture was stirred at room temperature for 16 h. After completion of the reaction, the reaction mixture was concentrated and quenched with water. The resulting solid was filtered, dried, and then purified by preparative purification to give compound 591.

$^1$H NMR (400 MHz, DMSO-$d_6$) δ 11.09 (s, 1H), 9.01 (s, 1H), 8.58 (s, 1H), 8.35 (s, 1H), 8.03 (d, J=5.4 Hz, 1H), 7.80-7.71 (m, 2H), 7.33 (d, J=6.4 Hz, 1H), 7.23-6.98 (m, 1H), 5.85-5.76 (m, 1H), 5.63 (d, J=15.2 Hz, 1H), 5.49 (s, 1H), 5.26 (s, 1H), 4.99-4.97 (m, 2H), 4.27-4.19 (m, 3H), 4.08-4.05 (m, 1H), 3.99-3.96 (m, 1H), 2.64 (s, 3H), 2.33-2.28 (m, 1H), 2.21-2.11 (m, 1H).

tert-butyl 2-(3-Carbamoyl-5-(4,4,5,5-tetramethyl-1,3,2-dioxaborolan-2-yl)-1H-indol-1-yl)acetate

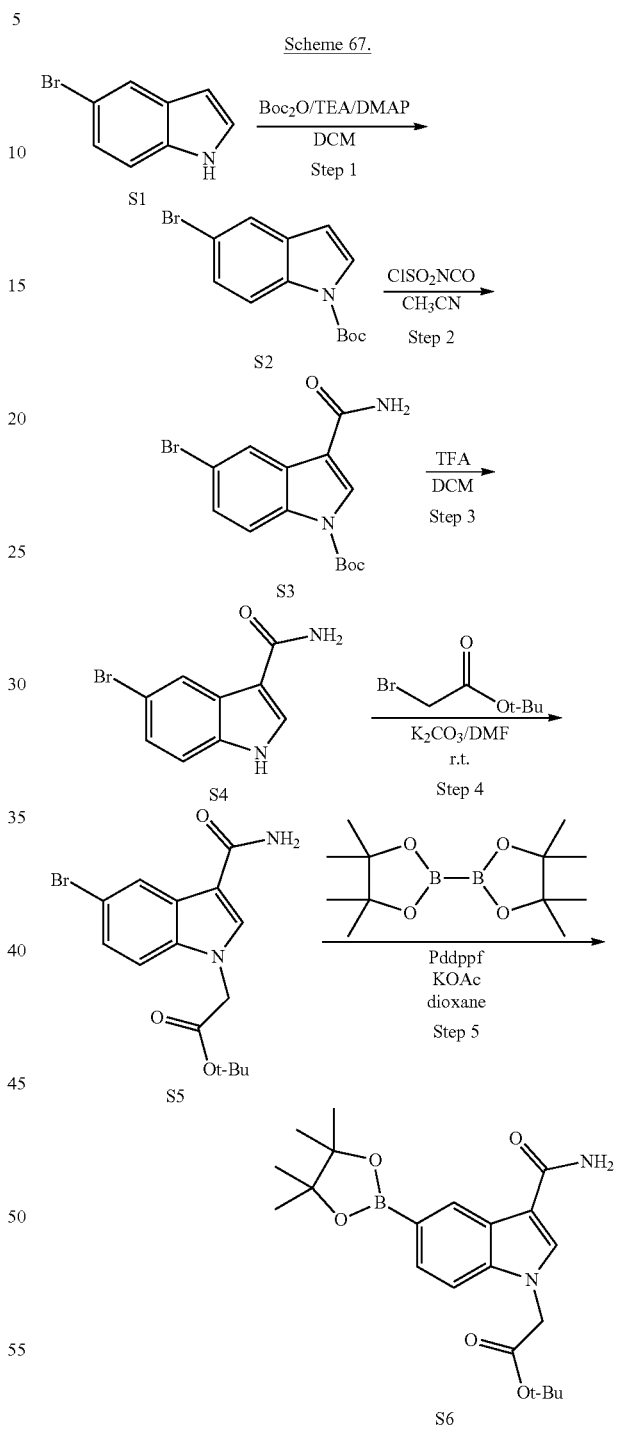

Scheme 67.

Step 1: tert-Butyl 5-bromo-1H-indole-1-carboxylate (S2)

To a solution of compound S1 (30 g, 0.15 mol) in DCM (300 mL) at 0° C. was added $Et_3N$ (64 mL, 0.46 mol), DMAP (5.6 g, 0.046 mol). This was followed by addition of $Boc_2O$ (50 g, 0.23 mol) in portions. The reaction mixture was stirred at room temperature for 16 hrs. The mixture was diluted with DCM (200 mL) and washed with water and brine, dried over anhydrous Na$_2$SO$_4$, filtered and concentrated to dryness. The residue was purified by column chromatography on silica gel (eluted with petroleum ether: ethyl acetate=50:1) to give the title compound (44 g, 97% yield) as white solid. LC/MS (ESI) m/z: 240 (M-56+H)$^+$.

Step 2: tert-Butyl 5-bromo-3-carbamoyl-1H-indole-1-carboxylate (S3)

To a solution of compound S2 (10 g, 33.7 mmol) in MeCN (100 mL) was added chlorosulfonyl isocyanate (3.1 mL, 35.6 mmol) dropwise at 0° C. The reaction was stirred at room temperature overnight. Acetone (200 mL) and H$_2$O (25 mL) was dropwise added at 0° C., followed by dropwise addition of aq. KOH solution (5 mL, 10% wt). The reaction was stirred at room temperature for 30 min and extracted with EtOAc (50 mL×2). The combined organic phases were washed with brine, dried over anhydrous Na$_2$SO$_4$, and then concentrated to give the title compound (7.4 g, 64.8% yield) as white solid. LC/MS (ESI) m/z: 339 (M+H)$^+$.

Step 3: 5-Bromo-1H-indole-3-carboxamide (S4)

To a solution of compound S3 (7.4 g, 21.8 mmol) in DCM (100 mL), TFA was added dropwise (15 mL) and the reaction was stirred at room temperature for 2 hrs. The reaction mixture was concentrated and co-evaporated with toluene twice to give the title compound (7.5 g, 100% yield) as yellow solid, which was directly used to the next reaction without further purification. LC/MS (ESI) m/z: 239 (M+H)$^+$ Step 4: tert-Butyl 2-(5-bromo-3-carbamoyl-1H-indol-1-yl)acetate (S5)

To a mixture of compound S4 (7.5 g, 21.8 mmol) and K$_2$CO$_3$ (9.04 g, 65.45 mmol) in DMF (100 mL) was added tert-butyl 2-bromoacetate (6.2 mL, 43.5 mmol) dropwise at 0° C. The reaction mixture was stirred at room temperature overnight. The mixture was diluted with EtOAc and washed with water and brine, dried over anhydrous Na$_2$SO$_4$, filtered and concentrated to give crude product, which was washed with petroleum ether and dried under vacuum to give the title compound (6.7 g, 87.0% yield) as a white solid. LC/MS (ESI) m/z: 353 (M+H)$^+$.

Step 5: tert-Butyl 2-(3-carbamoyl-5-(4,4,5,5-tetramethyl-1,3,2-dioxaborolan-2-yl)-1H-indol-1-yl)acetate (S6)

To a solution of compound S5 (4 g, 11.36 mmol) in dioxane (40 mL) was added 4,4,4',4',5,5,5',5'-octamethyl-2,2'-bi(1,3,2-dioxaborolane) (4.4 g, 17.04 mmol), KOAc (2.2 g, 22.72 mmol), and PdCl$_2$(dppf) (416 mg, 0.568 mmol). The reaction mixture was stirred at 90° C. under N$_2$ for overnight. After filtration, water was added and the resulting mixture was extracted with ethyl acetate (20 mL×3). The organic phase was washed with brine, dried over anhydrous Na$_2$SO$_4$, filtered and then concentrated. The residue was purified by column chromatography on silica gel (eluted with DCM/MeOH=50:1 to 30:1) to give S6 (4.2 g, 92.3% yield) as a white solid. LC/MS (ESI) m/z: 401 (M+H)$^+$.

2-(3-Carbamoyl-5-(2-methylpyrimidin-5-yl)-1H-indol-1-yl)acetic acid

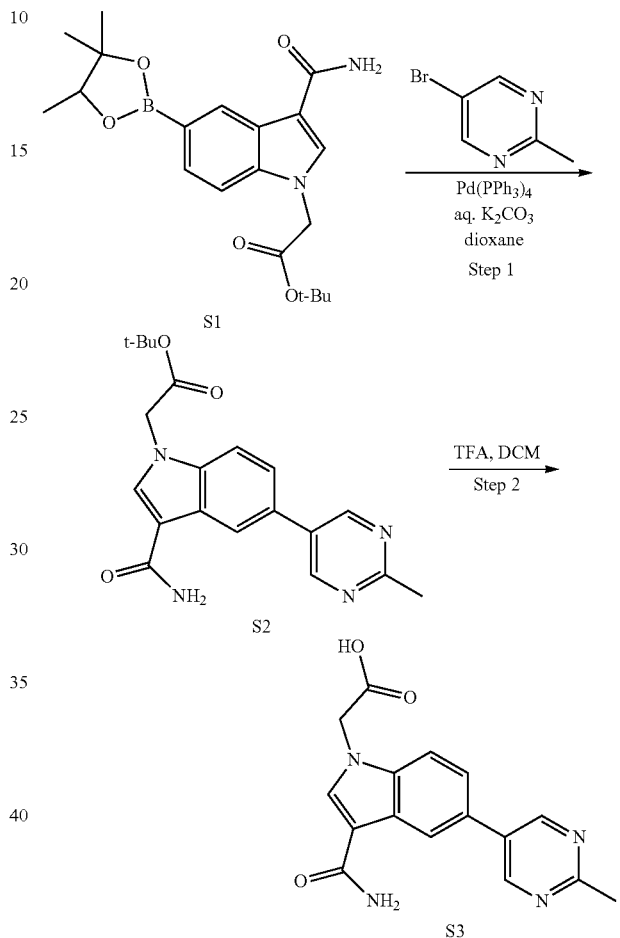

Scheme 68.

Step 1: tert-Butyl 2-(3-carbamoyl-5-(2-methylpyrimidin-5-yl)-1H-indol-1-yl)acetate (S2)

To a mixture of S1 (2 g, 4.99 mmol) and 5-bromo-2-methyl pyrimidine (1.04 g, 5.98 mmol) in dioxane (20 mL) was added aq. K$_2$CO$_3$ solution (7.5 mL, 7.5 mmol, 1 M). The mixture was degassed under N$_2$ atmosphere three times. Pd(PPh$_3$)$_4$ (289 mg, 0.25 mmol) was added under N$_2$ atmosphere and the reaction was stirred at 100° C. under N$_2$ atmosphere for 16 hrs. The reaction mixture was cooled and diluted with EtOAc, washed with water and brine, dried and concentrated. The residue was purified by column chromatography on silica gel eluted with PE/EtOAc (10:1 to 1:1) to give the title compound (1.49 g, 81.6% yield) as white solid. LC/MS (ESI) m/z: 367 (M+H)$^+$.

Step 2: tert-Butyl 2-(3-carbamoyl-5-(2-methylpyrimidin-5-yl)-1H-indol-1-yl)acetate (S3)

To a solution of S2 (1.49 g, 4.06 mmol) in DCM was added TFA dropwise at 0° C. The reaction mixture was stirred at room temperature for 2 hrs. The mixture was concentrated to dryness and washed with diethyl ether and dried under vacuum to give S3 (1.1 g, 87.3% yield) as yellow solid. LC/MS (ESI) m/z: 311 (M+H)+.

(1R,3S,4S)—N-(6-Methylpyridin-2-yl)-2-azabicyclo[2.2.1]heptane-3-carboxamide hydrochloride

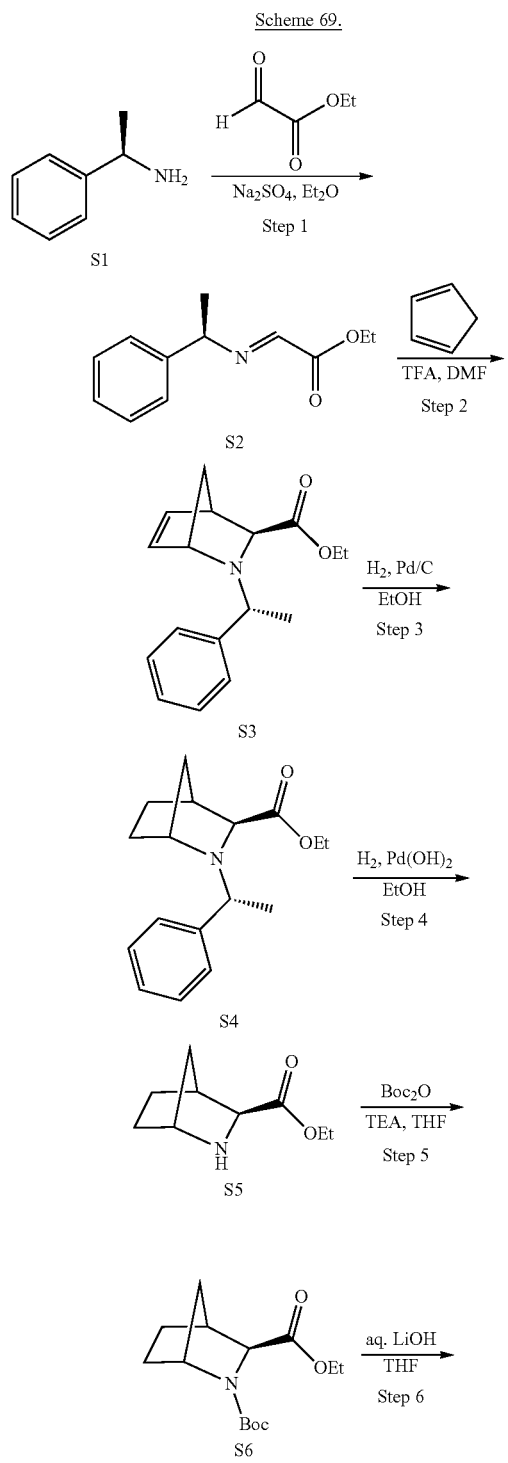

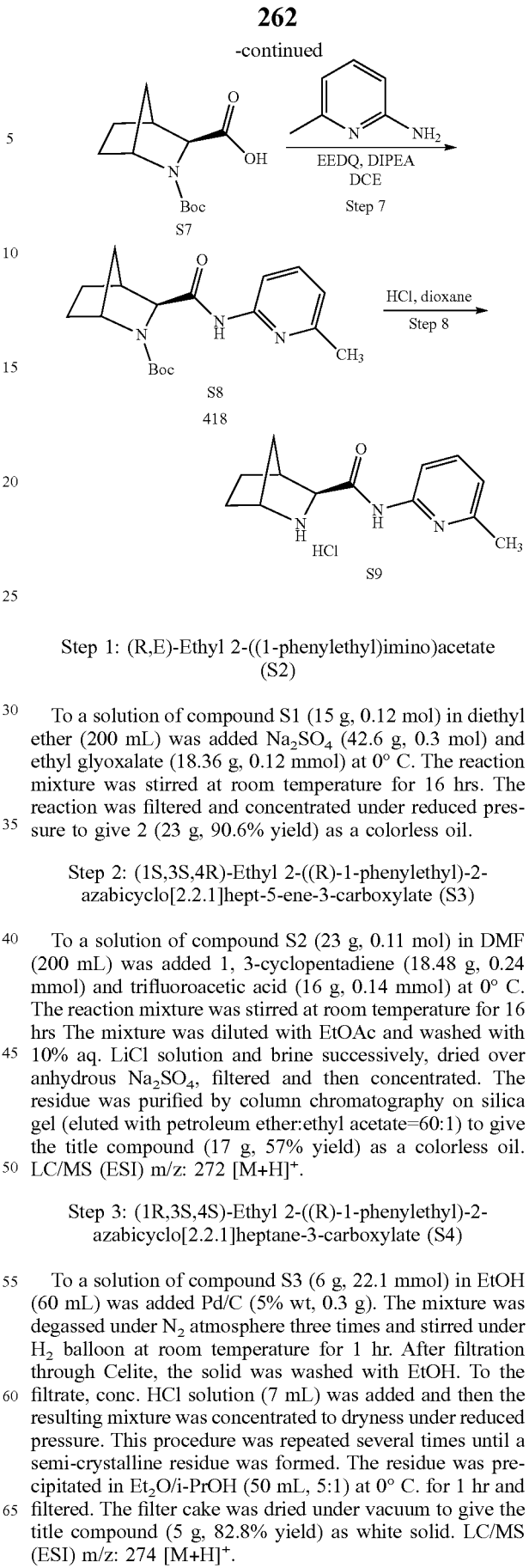

Step 1: (R,E)-Ethyl 2-((1-phenylethyl)imino)acetate (S2)

To a solution of compound S1 (15 g, 0.12 mol) in diethyl ether (200 mL) was added Na₂SO₄ (42.6 g, 0.3 mol) and ethyl glyoxalate (18.36 g, 0.12 mmol) at 0° C. The reaction mixture was stirred at room temperature for 16 hrs. The reaction was filtered and concentrated under reduced pressure to give 2 (23 g, 90.6% yield) as a colorless oil.

Step 2: (1S,3S,4R)-Ethyl 2-((R)-1-phenylethyl)-2-azabicyclo[2.2.1]hept-5-ene-3-carboxylate (S3)

To a solution of compound S2 (23 g, 0.11 mol) in DMF (200 mL) was added 1, 3-cyclopentadiene (18.48 g, 0.24 mmol) and trifluoroacetic acid (16 g, 0.14 mmol) at 0° C. The reaction mixture was stirred at room temperature for 16 hrs The mixture was diluted with EtOAc and washed with 10% aq. LiCl solution and brine successively, dried over anhydrous Na₂SO₄, filtered and then concentrated. The residue was purified by column chromatography on silica gel (eluted with petroleum ether:ethyl acetate=60:1) to give the title compound (17 g, 57% yield) as a colorless oil. LC/MS (ESI) m/z: 272 [M+H]+.

Step 3: (1R,3S,4S)-Ethyl 2-((R)-1-phenylethyl)-2-azabicyclo[2.2.1]heptane-3-carboxylate (S4)

To a solution of compound S3 (6 g, 22.1 mmol) in EtOH (60 mL) was added Pd/C (5% wt, 0.3 g). The mixture was degassed under N₂ atmosphere three times and stirred under H₂ balloon at room temperature for 1 hr. After filtration through Celite, the solid was washed with EtOH. To the filtrate, conc. HCl solution (7 mL) was added and then the resulting mixture was concentrated to dryness under reduced pressure. This procedure was repeated several times until a semi-crystalline residue was formed. The residue was precipitated in Et₂O/i-PrOH (50 mL, 5:1) at 0° C. for 1 hr and filtered. The filter cake was dried under vacuum to give the title compound (5 g, 82.8% yield) as white solid. LC/MS (ESI) m/z: 274 [M+H]+.

Step 4: (1R,3S,4S)-Ethyl 2-azabicyclo[2.2.1]heptane-3-carboxylate (S5)

A solution of compound S4 (5 g, 18.3 mmol) in ethanol (10 mL) was degassed under $N_2$ atmosphere for three times and Pd(OH)$_2$ (500 mg, 10% wt) was added. The mixture was degassed again and stirred under $H_2$ balloon at room temperature for 16 hrs. The mixture was filtered and the filtrate was concentrated under reduced pressure to give the title compound (3.3 g, 98.5% yield) as a colorless oil. LC/MS (ESI) m/z: 170 [M+H]$^+$.

Step 5: (1R,3S,4S)-2-tert-Butyl 3-ethyl 2-azabicyclo[2.2.1]heptane-2,3-dicarboxylate (S6)

Triethylamine (7.5 mL, 54 mmol) and di-tert-butyl dicarbonate (7.85 g, 36 mmol) were added to a solution of compound S5 (3.3 g, 18 mmol) in DCM (30 mL) at room temperature. The reaction mixture was stirred at room temperature for 16 hrs and then diluted with DCM. The resulting mixture was washed with water and brine, dried over anhydrous $Na_2SO_4$, filtered and then concentrated. The residue was purified by column chromatography on silica gel (eluted with petroleum ether:ethyl acetate=20:1) to give the title compound (3.6 g, 71% yield) as a colorless oil. LC/MS (ESI) m/z: 214 [M+H−56]$^+$.

Step 6: (1R,3S,4S)-2-(tert-Butoxycarbonyl)-2-azabicyclo[2.2.1]heptane-3-carboxylic acid (S7)

To a solution of compound S6 (3.6 g, 0.18 mmol) in THF (20 mL) was added aq. NaOH solution (2 M, 27 mL, 0.54 mmol) at room temperature. The reaction mixture was stirred at room temperature for 16 hrs and washed with ethyl acetate (20 mL×2). The aqueous phase was acidified to pH=3 with aq. HCl (1 M) and extracted with DCM twice. The combined organic phases were dried over anhydrous $Na_2SO_4$, filtered and then concentrated to give the title compound (3.2 g, 99.2% yield) as white solid. LC/MS (ESI) m/z: 186 [M+H−56]$^+$.

Step 7: (1R,3S,4S)-tert-Butyl-3-((6-methylpyridin-2-yl)carbamoyl)-2-azabicyclo[2.2.1]heptane-2-carboxylate (S8)

To a solution of compound S7 (2 g, 8.3 mmol) in 1,2-Dichloroethane (20 ml) was added N-Ethoxycarbonyl-2-ethoxy-1,2-dihydroquinoline (4.1 g, 16.6 mmol) and 2-Amino-6-methylpyridine (0.9 g, 8.3 mmol) at 0° C. The reaction mixture was stirred at 85° C. for 16 hrs and concentrated to dryness to give crude product, which was purified by column chromatography on silica gel (eluted with petroleum ether:ethyl acetate=10:1) to give the title compound (2.1 g, 79% yield) as white solid. LC/MS (ESI) m/z: 276 [M+H−56]$^+$.

Step 8: (1R,3S,4S)—N-(6-Methylpyridin-2-yl)-2-azabicyclo[2.2.1]heptane-3-carboxamide (S9)

To a solution of compound S8 (2.1 g, 6.5 mmol) in dioxane (15 mL) was added HCl dioxane solutions (15 mL) at 0° C. The reaction was stirred at room temperature for 3 hrs and concentrated to dryness to give compound S9 (2.3 g, 99.7% yield) as yellow solid, which was directly used to the next reaction without purification. LC/MS (ESI) m/z: 232 [M+H]$^+$.

2-(3-Carbamoyl-5-(2-methylpyrazolo[1,5-a]pyrimidin-6-yl)-1H-indol-1-yl)acetic acid

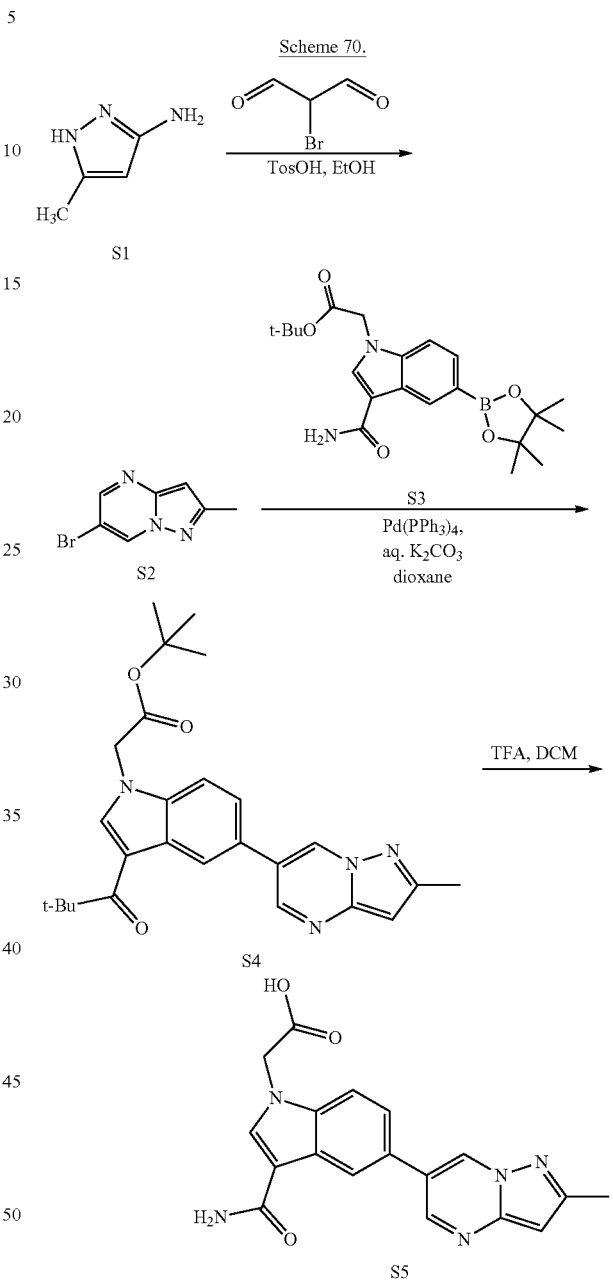

Scheme 70.

Step 1: 6-Bromo-2-methylpyrazolo[1,5-a]pyrimidine (S2)

To a solution of 5-methyl-1H-pyrazol-3-amine (1.0 g, 10.31 mmol) in EtOH (2 mL) was added 2-bromomalonaldehyde (1.56 g, 10.31 mmol) and 4-methylbenzenesulfonic acid (91 mg, 0.52 mmol) in succession. The reaction mixture was stirred at 80° C. overnight and concentrated. The residue was purified by column chromatography on silica gel eluted with PE/EtOAc (50:1 to 5:1) to give the title compound (540 mg, 25.0% yield); LC/MS (ESI) m/z: 212 [M+H]$^+$.

Step 2: tert-Butyl 2-(3-carbamoyl-5-(2-methylpyrazolo[1,5-a]pyrimidin-6-yl)-1H-indol-1-yl)acetate (S3)

To a mixture of S2 (490 mg, 1.22 mmol) and 6-bromo-2-methylpyrazolo[1,5-a]pyrimidine (286 mg, 1.35 mmol) in dioxane (10 mL) was added aq. $K_2CO_3$ solution (2 mL, 2 mmol, 1 M). The mixture was degassed under $N_2$ atmosphere for three times. After addition of $Pd(PPh_3)_4$ (70 mg, 0.06 mmol) under $N_2$ atmosphere, the reaction mixture was stirred at 100° C. under $N_2$ atmosphere for 16 hrs. The reaction mixture was cooled and diluted with EtOAc. The resulting mixture was washed with water and brine, dried over anhydrous $Na_2SO_4$ and concentrated to dryness. The residue was purified by column chromatography on silica gel eluted with DCM/MeOH (100:1 to 40:1) to give the title compound (290 mg, 58.6% yield) as white solid. LC/MS (ESI) m/z: 406 $[M+H]^+$.

Step 3: 2-(3-Carbamoyl-5-(2-methylpyrazolo[1,5-a]pyrimidin-6-yl)-1H-indol-1-yl)acetic acid (S4)

To a solution of tert-butyl 2-(3-carbamoyl-5-(2-methylpyrazolo[1, 5-a]pyrimidin-6-yl)-1H-indol-1-yl) acetate (290 mg, 0.72 mmol) in DCM (2 mL) was added TFA (2 mL). The reaction mixture was stirred at room temperature for 2 hrs and concentrated to dryness to give S5 (240 mg, 96% yield) as yellow solid, which was used directly in the next step; LC-MS: LC/MS (ESI) m/z: 350 $[M+H]^+$.

2-(3-Carbamoyl-5-(2-methylpyrimidin-5-yl)-1H-pyrazolo[3,4-d]thiazol-1-yl)acetic acid

Scheme 71.

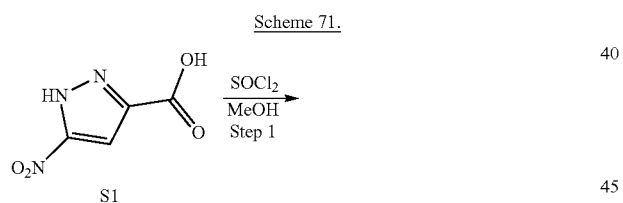

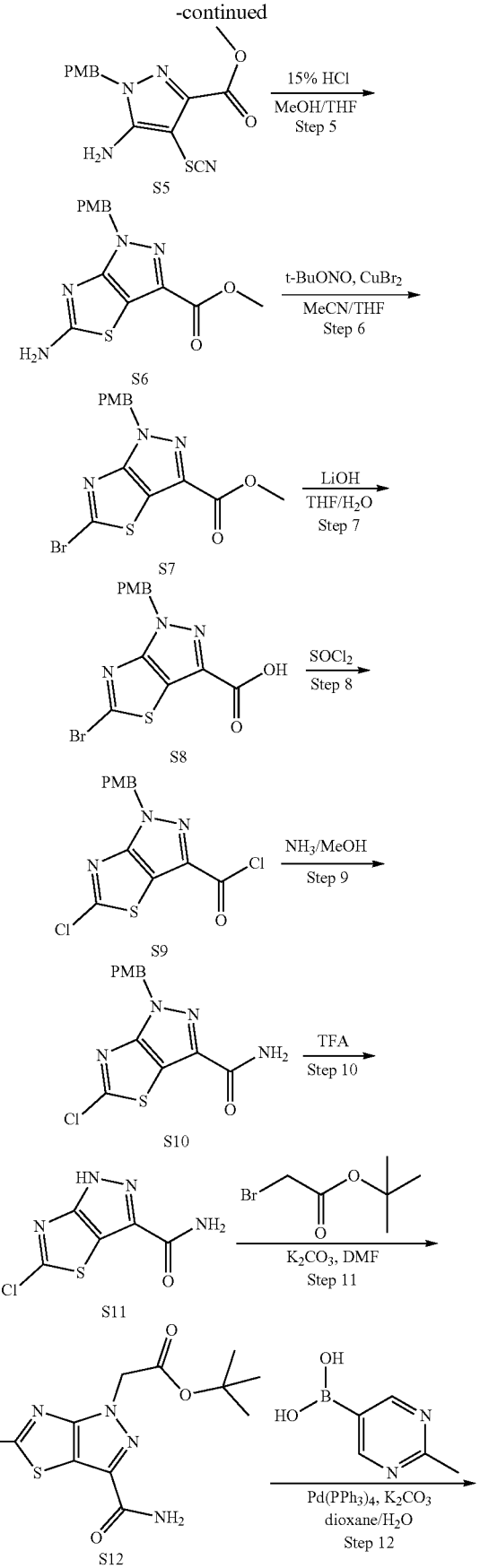

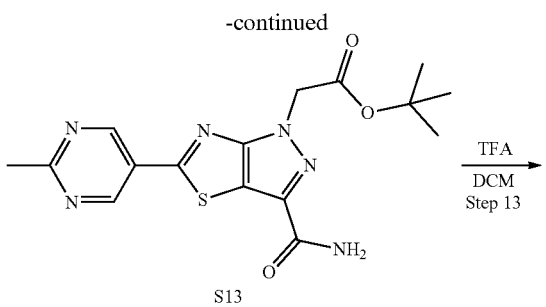

S13

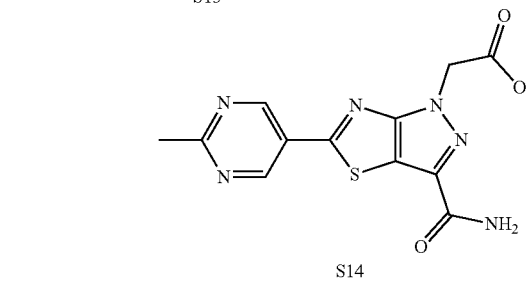

S14

Step 1: Methyl 5-nitro-1H-pyrazole-3-carboxylate (S2)

To a mixture of compound S1 (50 g, 0.318 mol) in MeOH (500 mL) was added $SOCl_2$ (190 g, 1.59 mol) dropwise at 0° C. The reaction mixture was stirred at 80° C. for 6 hrs and then concentrated under reduced pressure to give the title compound (54.0 g, 98.2% yield) as white solid, which was directly used to the next reaction without further purification. LC/MS (ESI) m/z: 170 (M−H)⁻.

Step 2: Methyl 1-(4-methoxybenzyl)-5-nitro-1H-pyrazole-3-carboxylate (S3)

To a mixture of compound S2 (54.0 g, 0.316 mol) and $K_2CO_3$ (87.1 g, 0.63 mol) in DMF (400 mL) was added PMBCl (59.2 g, 0.38 mol). Then the reaction mixture was stirred at 80° C. for 3 hrs. After cooling, the mixture was diluted with aq. LiCl (500 mL, 10%) and extracted with EtOAc (400 mL×2). The combined organic layers were washed with brine, dried over anhydrous $Na_2SO_4$, filtered and then concentrated. The residue was recrystallized with PE/EtOAc (2/1) to give the title compound (40.4 g, 43.9% yield) as yellow solid.

Step 3: Methyl 5-amino-1-(4-methoxybenzyl)-1H-pyrazole-3-carboxylate (S4)

To a mixture of compound S3 (40.4 g, 138.8 mmol) in MeOH/THF (400 mL, 1:1) was added 10% Pd/C (4 g). The reaction mixture was stirred at room temperature overnight under a $H_2$ balloon. After filtration, the filtrate was concentrated to dryness to give the title compound (33.7 g, yield 93.1%) as yellow oil, which was directly used to the next reaction without further purification. LC/MS (ESI) m/z: 262 (M+H)⁺.

Step 4: Methyl 5-amino-1-(4-methoxybenzyl)-4-thiocyanato-1H-pyrazole-3-carboxylate (S5)

To a mixture of compound S4 (33.7 g, 128.6 mmol) and KSCN (37.4 g, 385.9 mmol) in EtOH (300 mL) was added a solution of $Br_2$ (41.1 g, 257.2 mmol) in EtOH (200 mL) dropwise. Then the reaction mixture was stirred at 0° C. for 16 hrs. The mixture was basified with aq. $Na_2CO_3$ solution to pH=9 at 0° C. and extracted with EtOAc (400 mL×2). The combined organic phases were dried over anhydrous $Na_2SO_4$ and concentrated to dryness. The residue was recrystallized with THF/PE (1/1) to give the title compound (23.0 g, 55.9% yield) as white solid. LC/MS (ESI) m/z: 319 [M+H]⁺.

Step 5: Methyl 5-amino-1-(4-methoxybenzyl)-1H-pyrazolo[3,4-d]thiazole-3-carboxylate (S6)

To a mixture of compound S5 (23.0 g, 72.1 mmol) in EtOH (160 mL) and $H_2O$ (108 mL) was added conc. HCl (60 mL). The reaction was stirred at 90° C. for 2 hrs and concentrated under reduced pressure. The residue was recrystallized with EtOAc/PE (1/2) to give the title compound (12.2 g, yield 53.1%) as white solid. LC/MS (ESI) m/z: 319 (M+H)⁺.

Step 6: Methyl 5-bromo-1-(4-methoxybenzyl)-1H-pyrazolo[3,4-d]thiazole-3-carboxylate (S7)

To a mixture of compound S5 (12.2 g, 38.3 mmol) and $CuBr_2$ (17.2 g, 76.6 mmol) in dry MeCN/THF (175 mL, 1:4) was added t-BuONO (5.92 g, 57.45 mmol) at 0° C. under $N_2$ atmosphere dropwise. After stirring for 1 h at 0° C., the resulting mixture was quenched with aq. $Na_2S_2O_3$ (150 mL, 5%) and extracted with DCM (80 mL×2). The combined organic phases were washed with brine, dried over anhydrous $Na_2SO_4$, filtered and concentrated. The residue was purified by column chromatography on silica gel (eluted with petroleum ether: ethyl acetate=30:1 to 10:1) to give the title compound (4.59 g, 31.4% yield) as yellow oil. LC/MS (ESI) m/z: 382 (M+H)⁺.

Step 7: 5-Bromo-1-(4-methoxybenzyl)-1H-pyrazolo[3,4-d]thiazole-3-carboxylic acid (S8)

To a mixture of compound S6 (4.59 g, 12.0 mmol) in $THF/H_2O$ (50 mL, 4:1, v/v) was added $LiOH \cdot H_2O$ (1.01 g, 24.0 mmol). The reaction mixture was stirred at room temperature for 1 hr and then acidified with aq. HCl solution (1 M) to pH=5. The mixture was extracted with DCM/MeOH (30 mL×2, 20:1, v/v). The combined organic phases were washed with brine, dried over anhydrous $Na_2SO_4$, filtered and concentrated to give the title compound (4.04 g, 91.5% yield) as white solid. LC/MS (ESI) m/z: 368 (M+H)⁺.

Step 8: 5-Chloro-1-(4-methoxybenzyl)-1H-pyrazolo[3,4-d]thiazole-3-carbonyl chloride (S9)

A solution of compound S7 (4.04 g, 10.98 mmol) in $SOCl_2$ (30 mL) was stirred at 70° C. for 4 hrs. After cooling, the mixture was concentrated to dryness and the residue was co-evaporated with toluene twice to give the title compound (3.75 g, 100% yield) as yellow oil, which was directly used to the next reaction without further purification.

Step 9: 5-Chloro-1-(4-methoxybenzyl)-1H-pyrazolo[3,4-d]thiazole-3-carboxamide (S10)

To a solution of compound S8 (3.75 g, 10.97 mmol) in dry THF (25 mL) at 0° C. was added $NH_3$/MeOH solution (2 M, 15 mL) dropwise. The reaction mixture was stirred at 0° C. for 30 min and then concentrated. The residue was purified by column chromatography on silica gel (eluted with petroleum ether:ethyl acetate=15:1 to 3:1) to give the title compound (3.25 g, 92.1% yield) as white solid. LC/MS (ESI) m/z: 323 (M+H)+.

Step 10: 5-Chloro-1H-pyrazolo[3,4-d]thiazole-3-carboxamide (S11)

A solution of compound S9 (3.25 g, 10.1 mmol) in TFA (30 mL) was stirred at 70° C. for 4 hrs. The mixture was concentrated to dryness and the residue was co-evaporated with toluene twice, dried under vacuum to give the title compound (3.03 g, 94.9% yield) as a brown solid. The title compound was carried forward with any further purification. LC/MS (ESI) m/z: 203 (M+H)+.

Step 11: tert-Butyl 2-(3-carbamoyl-5-chloro-1H-pyrazolo[3,4-d]thiazol-1-yl)acetate (S12)

To a mixture of compound S10 (3.03 g, 9.59 mmol) and $K_2CO_3$ (3.97 g, 28.77 mmol) in DMF (30 mL) was added tert-butyl bromoacetate (2.62 g, 13.43 mmol.). The reaction mixture was stirred at room temperature for 16 hrs. The mixture was diluted with EtOAc and washed with 10% aq. LiCl solution and brine successively, dried over anhydrous $Na_2SO_4$, filtered and concentrated. The residue was purified by column chromatography on silica gel (eluted with petroleum ether:ethyl acetate=10:1 to 3:1) to give the title compound (2.01 g, 66.2% yield) as yellow solid. LC/MS (ESI) m/z: 317 (M+H)+.

Step 12: tert-Butyl 2-(3-carbamoyl-5-(2-methylpyrimidin-5-yl)-1H-pyrazolo[3,4-d]thiazol-1-yl)acetate (S13)

To a mixture of compound S11 (300 mg, 0.84 mmol) and $K_2CO_3$ (292 mg, 2.1 mmol) in dioxane/$H_2O$ (10 mL, 9:1) was added 2-methylpyrimidin-5-ylboronic acid (138 mg, 1 mmol.) and Pd(PPh3)4 (100 mg, 0.08 mmol). The reaction was degassed under $N_2$ for three times and stirred at 90° C. for 4 hrs under $N_2$ atmosphere. After cooling, the mixture was diluted with saturated aq. $NaHCO_3$ (10 mL) and extracted with EtOAc (20 mL×2). The combined organic phases were washed with brine, dried over anhydrous $Na_2SO_4$, filtered and concentrated. The residue was purified by column chromatography on silica gel (eluted with DCM:MeOH=50:1 to 20:1) to give the title compound (121 mg, 38.4% yield) as white solid. LC/MS (ESI) m/z: 375 (M+H)+.

Step 13: 2-(3-Carbamoyl-5-(2-methylpyrimidin-5-yl)-1H-pyrazolo[3,4-d]thiazol-1-yl)acetic acid (S14)

To a mixture of compound S12 (121 mg, 0.32 mmol) in DCM (2 mL) was added TFA (1 mL) and the reaction mixture was stirred at room temperature for 2 hrs and then concentrated under reduced pressure to give compound S13 (130 mg, 100% yield) as a brown solid. The title compound was used without any further purification. LC/MS (ESI) m/z: 319 (M+H)+.

2-(3-Carbamoyl-5-(2-methylpyrazolo[1,5-a]pyrimidin-6-yl)-1H-pyrazolo[3,4-d]thiazol-1-yl)acetic acid

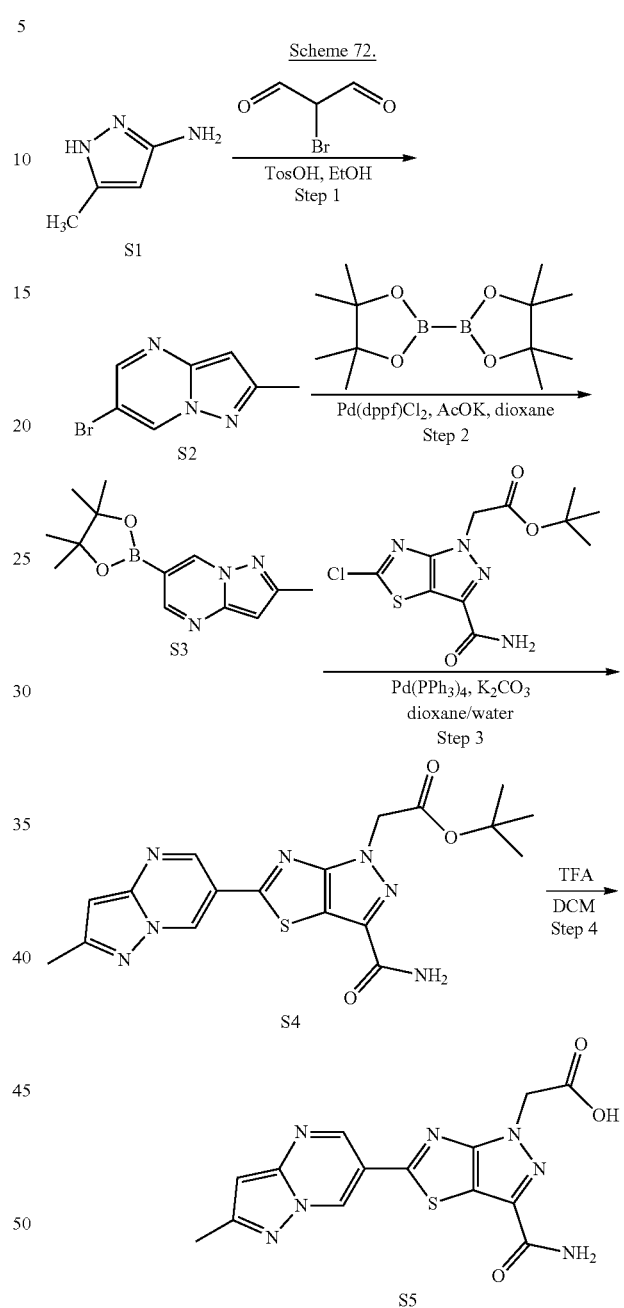

Scheme 72.

Step 1: 6-Bromo-2-methylpyrazolo[1,5-a]pyrimidine (S2)

To a mixture of 5-methyl-1H-pyrazol-3-amine (6.43 g, 0.066 mol) in EtOH (40 mL) in the presence of 4-methylbenzenesulfonic acid (0.63 g, 3.0 mmol) was added 2-bromomalonaldehyde (10.0 g, 0.066 mol). The reaction mixture was stirred at 80° C. overnight under a $N_2$ atmosphere and concentrated. The residue was purified by column chromatography on silica gel (eluted with PE/EtOAc (100:1 to 10:1) to give the title compound (3.0 g, 21.4% yield). LC/MS (ESI) m/z: 212 (M+H)+.

Step 2: 2-Methyl-6-(4,4,5,5-tetramethyl-1,3,2-dioxa-borolan-2-yl)pyrazol[1,5-a]pyrimidine (S3)

A round-bottom flask was charged with 6-bromo-2-methylpyrazolo[1, 5-a]pyrimidine (2.97 g, 14.08 mmol), 4, 4, 4', 4', 5, 5, 5', 5'-octamethyl-2, 2'-bi(1, 3, 2-dioxaborolane) (4.29 g, 16.89 mmol), AcOK (4.14 g, 42.23 mmol), Pd(dppf)Cl$_2$ (0.52 g, 0.70 mmol) and 1, 4-dioxane (40 mL). The reaction mixture was stirred at 85° C. for 2 hrs under N$_2$ atmosphere. After dilution with EtOAc, the resulting mixture was washed with water and brine, dried over anhydrous Na$_2$SO$_4$ and concentrated. The residue was purified by column chromatography on silica gel (eluted with PE/EtOAc=100:1 to 5:1) to give the title compound (3.05 g, 83.7% yield) as a white solid. LC/MS (ESI) m/z: 260 (M+H)$^+$.

Step 3: tert-Butyl 2-(3-carbamoyl-5-(2-methylpyra-zolo[1,5-a]pyrimidin-6-yl)-1H-pyrazolo[3,4-d]thiazol-1-yl)acetate (S4)

Tert-butyl 2-(3-carbamoyl-5-chloro-1H-pyrazolo[3,4-d]thiazol-1-yl)acetate (253 mg, 0.8 mmol.) and Pd(PPh$_3$)$_4$ (93 mg, 0.08 mmol) were added to a mixture of compound S3 (230 mg, 0.88 mmol) and K$_2$CO$_3$ (276 mg, 2 mmol) in dioxane/H$_2$O (15 mL, 4:1 The mixture was degassed under N$_2$ atmosphere three times and stirred at 95° C. for 5 hrs under N$_2$ atmosphere. After dilution with saturation with aq. NaHCO$_3$ (10 mL), the mixture was extracted with EtOAc (20 mL×2). The combined organic phases were washed with brine, dried over anhydrous Na$_2$SO$_4$, filtered and concentrated. The residue was purified by column chromatography on silica gel (eluted with PE:EtOAc=20:1 to 3:1) to give the title compound (211 mg, 63.7% yield) as a white solid. LC/MS (ESI) m/z: 414 (M+H)$^+$.

Step 4: 2-(3-Carbamoyl-5-(2-methylpyrazolo[1,5-a]pyrimidin-6-yl)-1H-pyrazolo[3,4-d]thiazol-1-yl) acetic acid (S5)

To a mixture of compound S4 (140 mg, 0.34 mmol) in DCM (3 mL) was added TFA (1 mL). The reaction mixture was stirred at room temperature for 2 hrs and concentrated under reduced pressure to give compound S5 (142 mg, 100% yield) as a brown solid. The title compound was used without further purification. LC/MS (ESI) m/z: 358 (M+H)$^+$.

(2S,4R)-4-Fluoro-N-(3-(thieno[3,2-b]thiophen-2-yl)cyclopentyl)pyrrolidine-2-carbothioamide

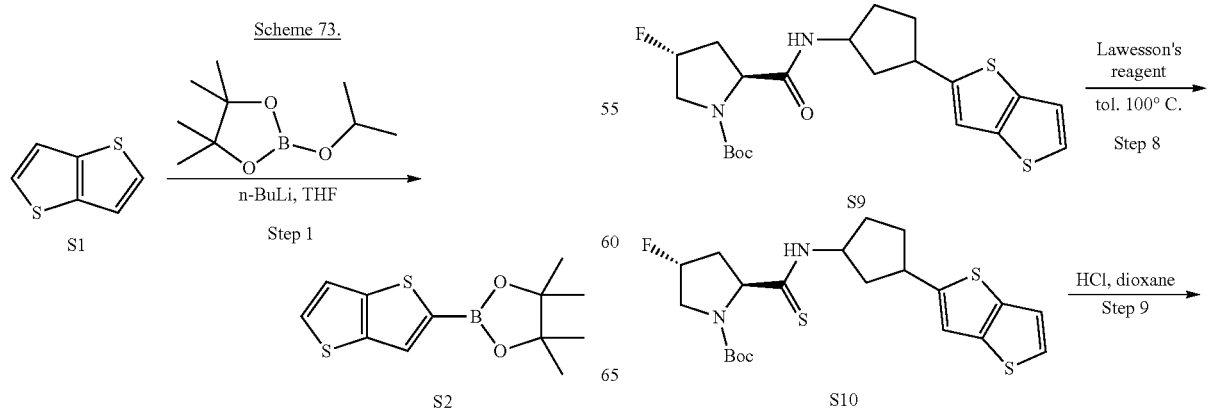

-continued

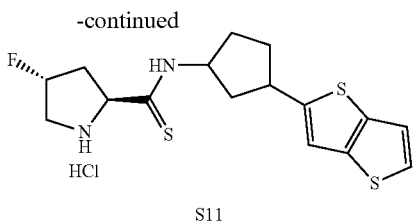

S11

Step 1: 4,4,5,5-Tetramethyl-2-(thieno[3,2-b]thiophen-2-yl)-1,3,2-dioxaborolane (S2)

To a solution of S1 (5 g, 35.65 mmol) in THF (70 mL) was added n-BuLi (1.6 M in hexanes, 23.4 mL, 37.4 mmol) at −70° C. dropwise for 30 ruin with stirring under $N_2$ atmosphere. After addition, the reaction was stirred at the same temperature for 30 min and 2-isopropoxy-4,4,5,5-tetramethyl-1,3,2-dioxaborolane (7.29 g, 39.2 mmol) was added. The reaction mixture was allowed to warm to room temperature and stirred for 16 hrs. After quenched with saturated aq. $NH_4Cl$ solution at 0° C., the mixture was extracted with EtOAc twice. The combined organic layers were washed with brine, dried over anhydrous $Na_2SO_4$ and to give the title compound (8.1 g, 85.4% yield) as light green solid.

Step 2: 2-(3-Oxocyclopentyl)isoindoline-1,3-dione (S4)

To a slurry of cyclopentenone (5 g, 60.9 mmol) and phthalimide (9 g, 61.1 mol) in MeOH (440 mL) was added aqueous $Na_2CO_3$ solution (2 M, 4 mL, 8 mmol) dropwise at 0° C. for 30 min. The reaction mixture was stirred at room temperature for 16 hrs. After filtration, the filter cake was washed with cooled MeOH and dried under vacuum to give the title compound (6.8 g, 48.7° % yield) as white solid. LCMS: LC/MS (ESI) m/z: 230 [M+H]$^+$.

Step 3: 3-(1,3-Dioxoisoindolin-2-yl)cyclopent-1-enyl trifluoromethanesulfonate (S5)

To a mixture of DIPEA (5.32 g, 41.17 mmol) and S4 (5.9 g, 25.73 mmol) in DCM (100 mL) was added $Tf_2O$ (8.7 g, 30.9 mmol) dropwise at 0° C. for 30 min. The reaction mixture was stirred at 0° C. for 16 hrs. After dilution with DCM, the mixture was washed with aq. $NH_4Cl$ solution and aq. $NaHCO_3$ solution successively. The organic phase was dried over anhydrous $Na_2SO_4$, filtered and concentrated to give crude product, which was purified by column chromatography on silica gel (eluted with petroleum ether:ethyl acetate=4:1) to give the title compound (6.3 g, 67.7% yield) as off-white solid.

Step 4: 2-(3-(Thieno[3,2-b]thiophen-2-yl)cyclopent-2-enyl)isoindoline-1,3-dione (S6)

To a mixture of S5 (6.3 g, 17.4 mmol) and 2 (4.8 g, 17.4 mmol) in DME/water (100 mL/30 mL) was added CsF (3.96 g, 26.1 mmol). The mixture was degassed under $N_2$ three times and then $Pd(PPh_3)_4$ was added in one portion under $N_2$ atmosphere. The resulting mixture was degassed again and stirred at 70° C. under $N_2$ atmosphere for 16 hrs. After cooling to room temperature, the mixture was filtered. The filter cake was washed with water and cooled, washed with ethanol and dried under vacuum to give the title compound (5.9 g, 96.4% yield) as pale solid. LCMS: LC/MS (ESI) m/z: 352 [M+H]$^+$.

Step 5: 3-(Thieno[3,2-b]thiophen-2-yl)cyclopent-2-enamine (S7)

To a slurry of S6 (5.9 g, 16.78 mmol) in EtOH (100 mL) was added hydrazine hydrate (4.94 g, 83.9 mmol, 85%) and the reaction mixture was stirred at reflux for 2 hrs. The mixture was cooled to 0° C. and diluted with EtOH (50 mL) and filtered. The filter cake was washed with cooled EtOH and the filtrate was concentrated to dryness to give crude product, which was purified by column chromatography on silica gel (eluted with DCM:MeOH=20:1) to give S7 (3.3 g, 88.85% yield) as yellow solid. LCMS: LC/MS (ESI) m/z: 222 [M+H]$^+$.

Step 6: 3-(Thieno[3,2-b]thiophen-2-yl)cyclopentanamine (S8)

To a solution of S7 (3 g, 13.55 mmol) in EtOH (50 mL) was added conc. HCl (3 mL), The mixture was degassed under $N_2$ atmosphere three times and Pd/C (300 mg, 10%) was added. The resulting mixture was degassed under $N_2$ atmosphere and stirred under $H_2$ balloon at 45° C. for 32 hrs. After filtration, the filter cake was washed with EtOH twice. The combined filtrates were concentrated to give the title compound (2.3 g, 75.99% yield) as foam-like solid. LCMS: LC/MS (ESI) m/z: 224 [M+H]$^+$.

Step 7: (2S,4R)-tert-Butyl 4-fluoro-2-(3-(thieno[3,2-b]thiophen-2-yl)cyclopentylcarbamoyl)pyrrolidine-1-carboxylate (S9)

To a mixture of S8 (500 mg, 2.24 mmol) and (2S,4R)-1-(tert-butoxycarbonyl)-4-fluoropyrrolidine-2-carboxylic acid (522 mg, 2.24 mmol) in DMF (10 mL) was added HATU (1.1 g, 2.91 mmol) followed by DIPEA (434 mg, 3.36 mmol) at 0° C. The reaction mixture was stirred at room temperature for 16 hrs. After dilution with EtOAc, the mixture was washed with 10% aq. LiCl solution. The organic phase was dried over anhydrous $Na_2SO_4$, filtered and concentrated to give crude product, which was purified by column chromatography on silica gel (eluted with DCM:MeOH=40:1) to give the title compound (580 mg, 59.04% yield) as light yellow solid. LC/MS (ESI) m/z: 383 [M+H−56]$^+$.

Step 8: (2S,4R)-tert-Butyl 4-fluoro-2-((3-(thieno[3,2-b]thiophen-2-yl)cyclopentyl)carbamothioyl)pyrrolidine-1-carboxylate (S10)

To a solution of compound S9 (440 mg, 1 mmol) in toluene (6 L) was added Lawesson's Reagent (202 mg, 0.5 mmol) at 0° C. The reaction mixture was heated at 80° C. for 16 hrs and concentrated to dryness. The residue was purified by silica gel chromatography with (petroleum ether:ethyl acetate=5:1) to give the title compound (220 mg, 48.5% yield) as yellow solid. LC-MS (ESI) found: 455 [M+1]$^+$.

Step 2: (2S,4R)-4-Fluoro-N-(3-(thieno[3,2-b]thiophen-2-yl)cyclopentyl)pyrrolidine-2-carbothioamide hydrochloride (S11)

A mixture of compound S10 (220 mg, 0.48 mmol) and HCl/1.4-dioxane (15 mL, 1 M) was stirred at room temperature for 3 hrs. The reaction mixture was concentrated under high vacuum. The residue was washed with diethyl ether and dried under vacuum to give S11 (170 mg, 90.6% yield) as yellow solid, which was directly used to the next reaction without purification. LC-MS (ESI) found: 355 [M+1]+.

(3S)-tert-butyl 3-(6-Bromopyridin-2-ylcarbamoyl)-5-(hydroxymethyl)-2-azabicyclo[3.1.0]hexane-2-carboxylate

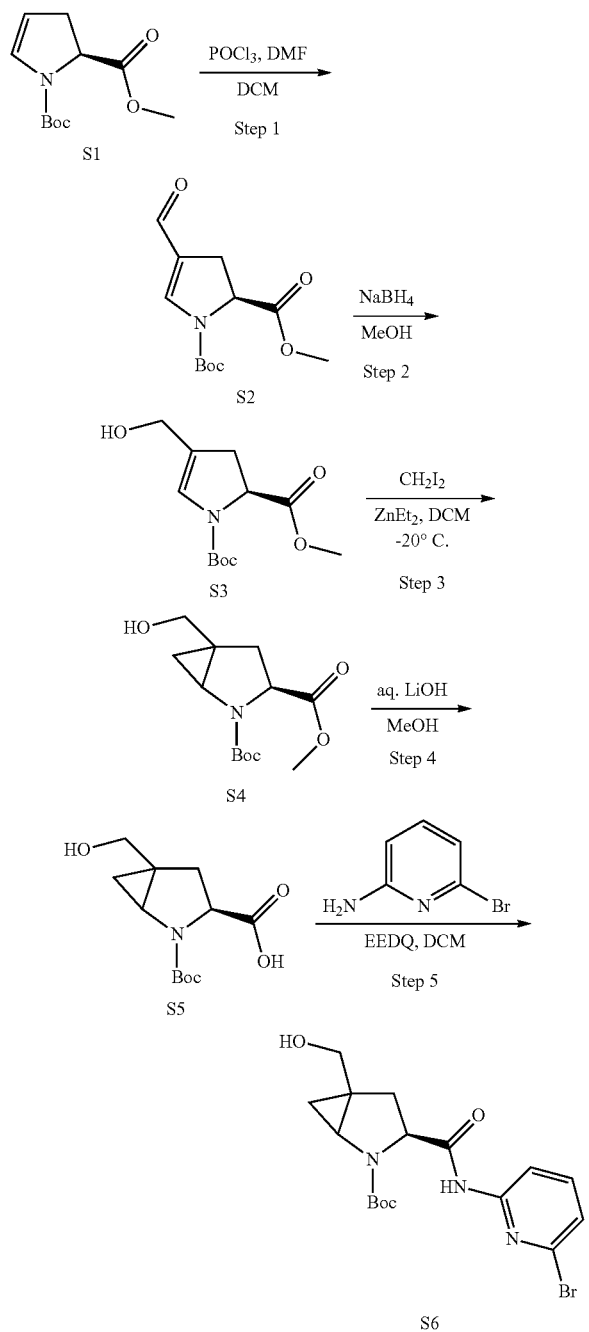

Scheme 74.

Step 1: (S)-Methyl 4-formyl-2,3-dihydro-1H-pyrrole-2-carboxylate (S2)

POCl$_3$ (2.7 g, 17.6 mmol) was added dropwise to ice-cooled DMF (2.6 g, 35.2 mmol) under N$_2$ atmosphere. The reaction was stirred at 0° C. for 30 min and then diluted with dry DCM (50 mL). A solution of S1 (2 g, 8.8 mmol) in DCM (20 mL) was added to the mixture dropwise at 0° C. for 30 min. The reaction mixture was stirred at room temperature for 1 hr and slowly poured into ice-cooled 2 M aq. NaOH solution. The resulting mixture was extracted with DCM (50 mL*2). The combined organic layers were washed with water and brine, dried and concentrated to give a residue, which was purified by silica gel column (eluted with petroleum ether:ethyl acetate=10:1 to 5:1) to give the title compound (1.9 g, 84.6% yield) as a light yellow oil.

Step 2: (S)-1-tert-Butyl 2-methyl 4-(hydroxymethyl)-2,3-dihydro-1H-pyrrole-1,2-dicarboxylate (S3)

To a solution of the compound S2 (1.9 g, 7.44 mmol) in DCM (20 mL) and MeOH (10 mL) was added NaBH$_4$ (23 mg, 1.44 mmol) in portions at −70° C. The reaction was stirred at 0° C. for 30 min and quenched with saturated aq. NH$_4$Cl solution (10 mL). The resulting mixture was extracted with DCM twice and the combined organic layers were washed with brine, dried over anhydrous Na$_2$SO$_4$, filtered and concentrated to give a residue, which was purified by silica gel column (eluted with petroleum ether:ethyl acetate=10:1 to 3:1) to give the title compound (1.7 g, 88.8% yield) as a colorless oil.

Step 3: (3S)-2-tert-Butyl 3-methyl 5-(hydroxymethyl)-2-azabicyclo[3.1.0]hexane-2,3-dicarboxylate (S4)

To a solution of the compound S3 (1.5 g, 5.83 mmol) in DCM (20 mL) was added diethylzinc hexane solution (1 M, 17.5 mL, 17.5 mmol) dropwise followed by Diiodomethane (4.68 g, 17.5 mmol) at −20° C. under N$_2$ atmosphere. The reaction was stirred at −20° C. for 2 hrs and quenched with aqueous NH$_4$Cl solution. The resulting mixture was extracted with DCM twice. The combined organic layers were washed with water and brine, dried over anhydrous Na$_2$SO$_4$, filtered and concentrated to give a residue, which was purified by silica gel column (eluted with petroleum ether:ethyl acetate=10:1 to 3:1) to give the title compound (1.2 g, 75.8% yield) as a colorless oil.

Step 4: (3S)-2-(tert-Butoxycarbonyl)-5-(hydroxymethyl)-2-azabicyclo[3.1.0]hexane-3-carboxylic acid (S5)

To a solution of compound S4 (150 mg, 0.55 mmol) in THF (5 mL) was added aq. LiOH solution (3 mL, 3 mmol). The reaction was stirred at room temperature for 2 hrs and concentrated. The residue was acidified with 1 N HCl solution to pH=~3. The resulting mixture was extracted with EtOAc twice. The combined organic layer was washed with brine, dried over anhydrous Na$_2$SO$_4$, filtered and concentrated to give the title compound (110 mg, 78.2% yield) as a white solid.

Step 5: (3S)-tert-Butyl 3-(6-bromopyridin-2-ylcarbamoyl)-5-(hydroxymethyl)-2-azabicyclo[3.1.0]hexane-2-carboxylate (S6)

To a mixture of the compound S5 (110 mg, 0.43 mmol), 6-bromopyridin-2-amine (74 mg, 0.43 mmol) and EEDQ (210 mg, 0.85 mmol) in 1,2-DCE (5 mL) was added DIPEA (165 mg, 1.29 mmol). The reaction was stirred at 90° C. for 16 hrs and concentrated. The residue was purified by silica gel column (eluted with petroleum ether:ethyl acetate=10:1 to 2:1) to give the title compound S6 (120 mg, 67.7% yield) as yellow solid. LC/MS (ESI) m/z: 412 (M+H)$^+$.

(2S,4R)-2-Benzyl 1-tert-butyl 4-fluoro-4-(hydroxymethyl)pyrrolidine-1,2-dicarboxylate

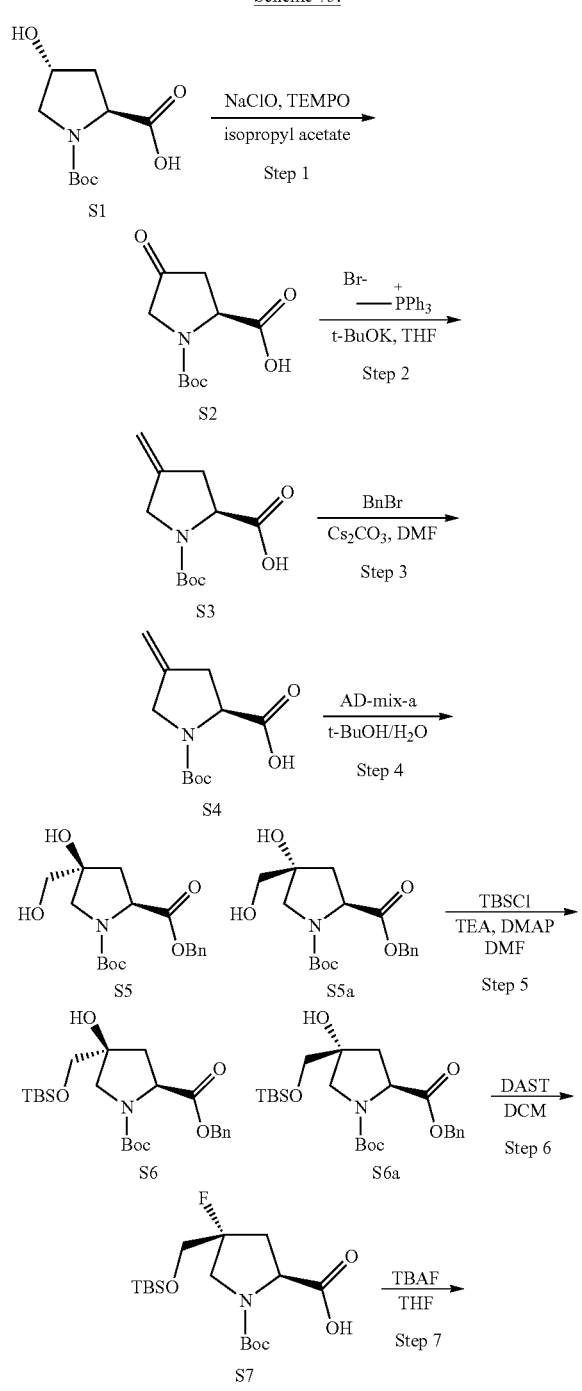

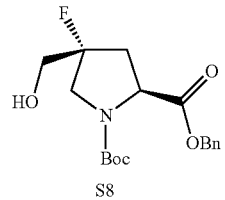 [SMILES: CC(C)(C)OC(=O)N1C[C@@](F)(CO)C[C@H]1C(=O)OCc1ccccc1 ; "S8"]

Step 1: (S)-1-(tert-Butoxycarbonyl)-4-oxopyrrolidine-2-carboxylic acid (S2)

To a solution of (2R,4)-1-(tert-butoxycarbonyl)-4-hydroxypyrrolidine-2-carboxylic acid (20 g, 86.6 mmol) in isopropylacetate (100 mL) was added TEMPO (675 mg, 4.3 mmol) at 0° C. A solution of aq. NaClO (10 wt %, 61.8 g, 104.0 mmol) was added dropwise to the reaction mixture at 0-5° C. The reaction was allowed to warm to room temperature and stirred at room temperature for 1 hr. The organic layer was separated and the aqueous layer was treated with 1 M aq. KHSO$_4$ solution and extracted with isopropyl acetate (2×30 mL). The combined organic layers were washed with 5% Na$_2$S$_2$O$_3$ (100 mL), brine, dried over anhydrous Na$_2$SO$_4$, filtered and evaporated. The residue was triturated with acetonitrile (20 mL), filtered and concentrated to give the title compound (5.0 g, 25.3% yield) as white solid.

Step 2: (S)-1-(tert-Butoxycarbonyl)-4-methylenepyrrolidine-2-carboxylic acid (S3)

To a mixture of methyltriphenylphosphonium bromide (11.7 g, 32.7 mmol) in THF (150 mL) was rapidly added potassium tert-butoxide (3.67 g, 32.7 mmol) while maintaining the temperature around 0° C. The reaction mixture was allowed to warm to room temperature and stirred at room temperature for 2 hrs. The mixture was cooled to 0° C. and (S)-1-(tert-butoxycarbonyl)-4-oxopyrrolidine-2-carboxylic acid (5 g, 21.8 mmol) was added in portions. The reaction was allowed to warm to room temperature and stirred at room temperature for 30 min. After quenching with addition of saturated aq. NaHCO$_3$ solution, the mixture was washed with ether (2×50 mL). The aqueous was acidified with 2 N HCl to pH=~2 and extracted with ethyl acetate (2×50 mL). The combined organic layers were washed with brine, dried over anhydrous Na$_2$SO$_4$, filtered and evaporated under reduced pressure to give the title compound (5.1 g) as a yellow oil, which was without further purification for next step.

Step 3: (S)-4-Methylene-pyrrolidine-1,2-dicarboxylicacid2-benzylester1-tert-butylester (S4)

To a solution of (S)-1-(tert-butoxycarbonyl)-4-methylenepyrrolidine-2-carboxylic acid (5 g, 22 mmol) in DMF (100 mL) were added benzyl bromide (4.9 g, 28.6 mmol) and cesium carbonate 9.3 g, 28.6 mmol) at 0° C. The reaction was stirred at room temperature overnight. The mixture was partitioned between water (100 mL) and EtOAc (100 mL). The organic layer was washed with brine, dried over anhydrous Na$_2$SO$_4$, and concentrated under reduced pressure. The residue was purified by chromatography on silica gel (PE:EtOAc=50:1 to 40:1) to give S4 (5.1 g, 73.0% yield) as light yellow oil.

Step 4: (2S,4S)-4-Hydroxy-4-hydroxymethyl-pyrrolidine-1,2-dicarboxylic acid 2-benzyl ester 1-tert-butylester (s5) and (2S,4R)-4-Hydroxy-4-hydroxymethyl-pyrrolidine-1,2-dicarboxylic acid 2-benzyl ester 1-tert-butyl ester (S5a)

A solution of AD-mix-alpha (22.2 g, 18.7 mmol) in t-BuOH (80 mL) and water (80 mL) was stirred until both phases were clear and then the mixture was cooled to 0° C. (S)-4-Methylene-pyrrolidine-1,2-dicarboxylic acid 2-benzyl ester 1-tert-butyl ester (4.96 g, 15.6 mmol) was added and the reaction mixture was stirred at room temperature overnight. The reaction mixture was quenched by addition of sodiumsulfite at 0° C. and then allowed to reach room temperature and stirred for 1 hr. After extraction with DCM (3×50 mL), the organic phases were combined, dried over anhydrous Na$_2$SO$_4$, filtered and concentrated under reduced pressure. The residue was purified by chromatography on silica gel (PE:EtOAc=1:1) to give a mixture of S5 and S5a (3.8 g, 69.2% yield) as yellow solid.

Step 5: (2S,4S)-4-(tert-Butyl-dimethyl-silanyloxymethyl)-4-hydroxy-pyrrolidine-1,2-dicarboxylic acid 2-benzylester and 1-tert-butyl ester (S6) and (2S,4R)-4-(tert-Butyl-dimethylsilanyloxymethyl)-4-hydroxy-pyrrolidine-1,2-dicarboxylic acid 2-benzyl ester 1-tert-butyl ester (S6a)

To a solution of (2S,4S)-4-hydroxy-4-hydroxymethyl-pyrrolidine-1,2-dicarboxylic acid 2-benzyl ester 1-tert-butyl ester and (2S,4S)-4-hydroxy-4-hydroxymethyl-pyrrolidine-1,2-dicarboxylic acid 2-benzyl ester 1-tert-butyl ester (3.8 g, 10.8 mmol) in DMF (80 mL) were added tert-butyl dimethylchlorosilane (3.2 g, 21.6 mmol), triethylamine (3.0 mL, 21.6 mmol) and DMAP (134 mg, 1.1 mmol). The reaction was stirred at room temperature overnight and then poured into ice-cooled saturated aq. NaHCO$_3$ solution (50 mL). The resulting mixture was extracted with DCM (3×20 mL). The combined organic layers were dried over anhydrous Na$_2$SO$_4$, filtered and concentrated under reduced pressure. The residue was purified by chromatography on silica gel (PE:EtOAc=25:1 to 20:1) to give S6a (800 mg, 16.0% yield) and S6 (3.5 g, 70.0% yield) as yellow oil.

Step 6: (2S,4R)-4-(tert-Butyl-dimethyl-silanyloxymethyl)-4-fluoro-pyrrolidine-1,2-dicarboxylic acid 2-benzylester 1-tert-butyl ester (S7)

To a solution of (2S,4S)-4-(tert-butyl-dimethyl-silanyloxymethyl)-4-hydroxy-pyrrolidine-1,2-dicarboxylic acid 2-benzyl ester 1-tert-butyl ester (2.0 g, 4.3 mmol) in DCM (20 mL) was added DAST (1.0 g, 6.55 mmol) dropwise at −70° C. The reaction mixture was stirred at room temperature overnight and poured into ice-cooled saturated aq. NaHCO$_3$ solution (50 mL). The resulting mixture was extracted with DCM (3×20 mL). The combined organic layers were dried over anhydrous Na$_2$SO$_4$, filtered and concentrated under reduced pressure. The residue was purified by chromatography on silica gel (PE:EtOAc=25:1 to 20:1) to give the desired product (1.4 g, 70% yield) as yellow oil.

Step 7: (2S,4R)-4-Fluoro-4-hydroxymethyl-pyrrolidine-1,2-dicarboxylic acid 2-benzyl ester 1-tert-butyl ester (S8)

To a solution of (2S,4R)-4-(tert-butyl-dimethyl-silanyloxymethyl)-4-fluoro-pyrrolidine-1,2-dicarboxylicacid 2-benzyl ester 1-tert-butyl ester (1.4 g, 3.0 mmol) in THF (15 mL) was added 1 M TBAF in THF (6 mL, 6.0 mmol) at room temperature. The reaction was stirred at room temperature for 30 min. The mixture was poured into ice-water and extracted with EtOAc. The organic layer was dried over anhydrous Na$_2$SO$_4$, filtered and concentrated under reduced pressure. The residue was purified by chromatography on silica gel (PE:EtOAc=4:1 to 2:1) give S8 (950 mg, 90.0% yield) as yellow oil. LC/MS (ESI) m/z: 354 (M+H)$^+$.

(1R,3S,5R)—N-(6-Bromopyridin-2-yl)-5-methyl-2-azabicyclo[3.1.0]hexane-3-carboxamide

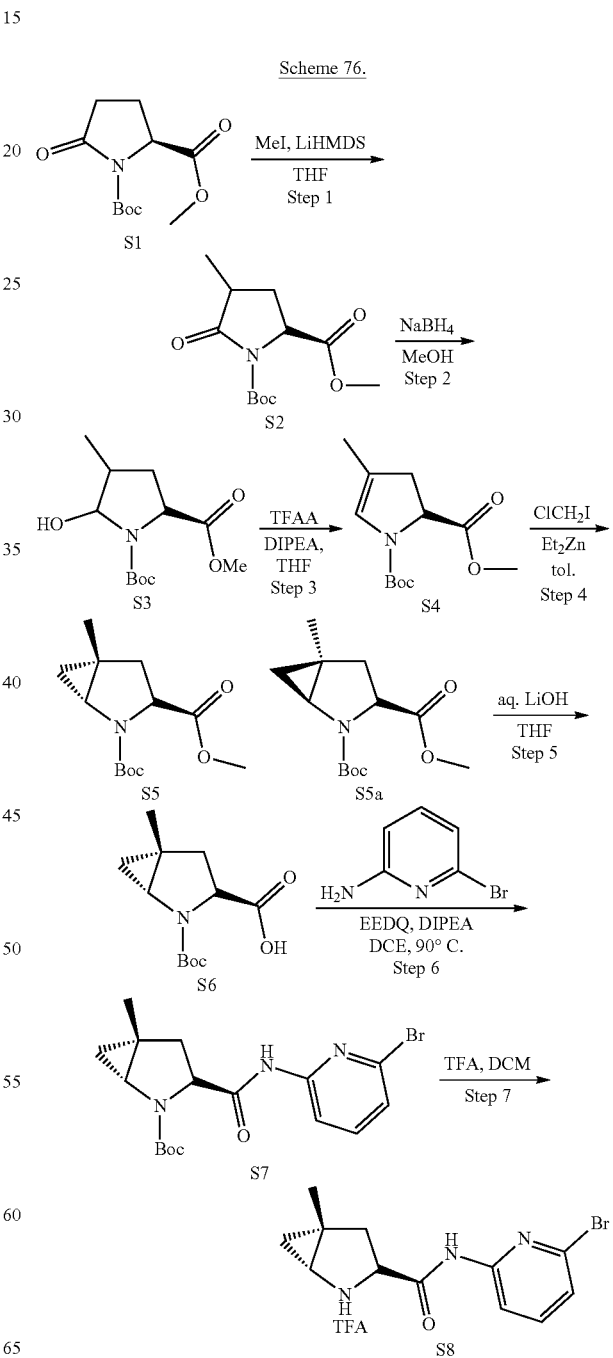

Scheme 76.

Step 1: (2S)-1-tert-Butyl 2-methyl 4-methyl-5-oxopyrrolidine-1,2-dicarboxylate (S2)

To a solution of N-Boc-L-pyroglutamic acid methyl ester (86 g, 0.354 mol) in THF (500 mL) was added LiHMDS (354 mL, 1.0 M in THF) at −70° C. dropwise for 1 hr. The reaction was stirred at −70° C. for 45 min and iodomethane (100.5 g, 0.708 mol) was added dropwise. The reaction was stirred at −70° C. for 2 hours and then at room temperature overnight. The reaction was quenched with acetic acid (50 mL) and water (500 mL). The volatiles were removed under reduced pressure and the mixture was extracted with EtOAc twice. The combined organic layers were washed with water and brine, dried over anhydrous $Na_2SO_4$, filtered and concentrated to dryness. The residue was purified by column chromatography on silica gel (eluted with petroleum ether: ethyl acetate=5:1 to 2:1) to give the title compound (53 g, 58.2% yield) as light yellow oil.

Step 2: (2S)-1-tert-Butyl 2-methyl 5-hydroxy-4-methylpyrrolidine-1,2-dicarboxylate (S3)

To a solution of compound S2 (53 g, 0.206 mol) in MeOH (500 mL) at −10° C. to −15° C. was added $NaBH_4$ (10.9 g, 0.29 mol) in small portions. The reaction was stirred at −15° C. for 6 hrs and quenched by dropwise addition of water (300 mL). The volatiles were removed under reduced pressure and the mixture was extracted with EtOAc twice. The combined organic phases were dried over anhydrous $Na_2SO_4$, filtered and concentrated to give the title compound (43 g, 80.5% yield), which was directly used in the next step without purification.

Step 3: (S)-1-tert-Butyl 2-methyl 4-methyl-2,3-dihydro-1H-pyrrole-1,2-dicarboxylate (S4)

To a solution of compound S3 (43 g, 166 mmol) in THF (500 mL) was added DIPEA (118 g, 913 mmol) and the mixture was cooled to −65° C. Trifluoroacetic acid anhydride (56 g, 216 mmol) was added dropwise to the mixture at −65° C. over 30 min. The reaction was stirred at −65° C. for 1 hrs and then room temperature for 2 hrs. The reaction was quenched with water (400 mL). The volatiles were removed under reduced pressure and the mixture was extracted with EtOAc twice. The combined organic phases were dried over anhydrous $Na_2SO_4$ and concentrated to dryness. The residue was purified by silica gel column chromatography (PE/EtOAc=15/1) to give the title compound (23 g, 57.4% yield) as a yellow oil.

Step 4: (1R,3S,5R)-2-tert-Butyl 3-methyl 5-methyl-2-azabicyclo[3.1.0]hexane-2,3-dicarboxylate (S5) & (1S,3S,5S)-2-tert-Butyl 3-methyl 5-methyl-2-azabicyclo[3.1.0]hexane-2,3-dicarboxylate (S5a)

Diethylzinc (1 M in toluene, 572 mL, 572 mmol) was added dropwise over 20 min to a cooled (−23° C.) toluene (115 mL) solution of compound S4 (23 g, 95 mmol) and the reaction was stirred at −20° C. for 30 min. Chloroiodomethane (35 g, 286 mmol) was added dropwise and the reaction mixture was stirred at −21° C. for 30 hrs. After addition of saturated aq. $NaHCO_3$ (100 mL) at −20° C., the reaction mixture was stirred at room temperature for 10 min. The resulting mixture was filtered and the filter cake was washed with toluene. The filtrate was extracted with EtOAc and the organic layer was washed with brine, dried over anhydrous $Na_2SO_4$, filtered and concentrated to dryness to give crude product, which was purified by column chromatography on silica gel (eluted with petroleum ether:ethyl acetate=60:1 to 10:1) to give the title compound S5 (2.2 g, 9.1% yield) and S5a (5.9 g, 24.3% yield) as a yellow oil. S5 (Rf=0.2, PE/EtOAc=3/1): $^1$H NMR (400 MHz, $CDCl_3$): 4.0 (m, 1H), 3.76 (s, 3H), 3.32-3.16 (m, 1H), 2.43 (m, 1H), 2.01 (m, 1H), 1.44 (s, 9H), 1.35 (s, 3H), 0.76-0.66 (m, 2H). S5a (Rf=0.35, PE/EtOAc=3/1): $^1$H NMR (400 MHz, $CDCl_3$): 4.65-4.52 (m, 1H), 3.72 (s, 3H), 3.28-3.17 (m, 1H), 2.44-2.32 (m, 1H), 2.16-2.10 (m, 1H), 1.51-1.42 (two s, 9H), 1.24 (s, 3H), 1.07 (m, 1H), 0.69-0.60 (m, 1H).

Step 5: (1R,3S,5R)-2-(tert-Butoxycarbonyl)-5-methyl-2-azabicyclo[3.1.0]hexane-3-carboxylic acid (S6)

To a solution of (1R, 3S, 5R)-2-tert-butyl 3-ethyl 5-methyl-2-azabicyclo[3.1.0]hexane-2, 3-dicarboxylate (0.32 g, 1.19 mmol) in THF (5 mL) was added aq. LiOH solution (3 mL, 1M) and the reaction was stirred at room temperature for 3 hrs. The volatiles were removed under reduced pressure and the mixture was washed with diethyl ether twice. The aqueous layer was acidified with citric acid and extracted with EtOAc twice. The combined organic layers were washed with water and brine, dried over anhydrous $Na_2SO_4$ and concentrated to give compound S6 (150 mg, 52.4% yield) as yellow solid, which was directly used in the next step. LCMS: LC/MS (ESI) m/z: 242 $[M+H]^+$.

Step 6: (1R,3S,5R)-tert-Butyl 3-(6-bromopyridin-2-ylcarbamoyl)-5-methyl-2-azabicyclo[3.1.0]hexane-2-carboxylate (S7)

To a solution of (1R, 3S, 5R)-2-(tert-butoxycarbonyl)-methyl-2-azabicyclo [3.1.0] hexane-3-carboxylic acid (0.15 g, 0.62 mmol) in 1,2-dichloroethane was added ethyl 2-ethoxyquinoline-1(2H)-carboxylate (0.31 g, 1.24 mmol), DIPEA (0.24 g, 1.87 mmol) and 6-bromopyridin-2-amine (0.11 g, 0.62 mmol) and the reaction was stirred at 90° C. under $N_2$ atmosphere overnight. The mixture was diluted with EtOAc and washed with water and brine, dried over anhydrous $Na_2SO_4$ and concentrated. The residue was purified by column chromatography on silica gel eluted with PE/acetone (PE/EtOAc=20:1 to 3:1) to give compound 7 (0.16 g, 65.1% yield) as light yellow solid. LCMS: LC/MS (ESI) m/z: 396 $[M+H]^+$

Step 7: (1R, 3S, 5R)—N-(6-Bromopyridin-2-yl)-5-methyl-2-azabicyclo [3.1.0] hexane-3-carboxamide TFA Salt (S8)

To a solution of (1R, 3S, 5R)-tert-butyl 3-(6-bromopyridin-2-ylcarbamoyl)-5-methyl-2-azabicyclo [3.1.0] hexane-2-carboxylate (160 mg, 0.4 mmol) in DCM (6 mL) was added TFA (3 mL), then the reaction was stirred at room temperature for 1 h. The mixture was concentrated and the residue was washed with $Et_2O$ to give S8 (170 mg, 100% yield) as yellow solid, which was directly used to the reaction. LCMS: LC/MS (ESI) m/z: 296 $[M+H]^+$.

(S)-1-(2-(3-Acetyl-5-(2-methylpyrimidin-5-yl)-1H-indazol-1-yl)acetyl)-N-(6-bromopyridin-2-yl)-4-oxopyrrolidine-2-carboxamide (250)

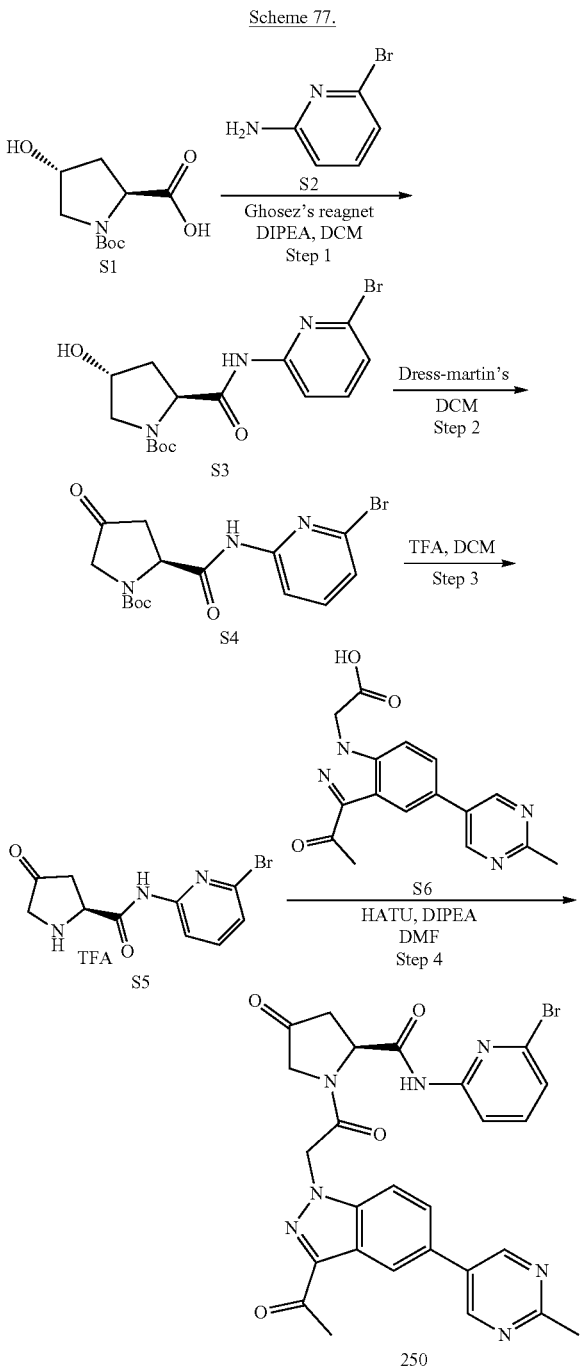

Step 1: (2S, 4S)-tert-Butyl 2-(6-bromopyridin-2-ylcarbamoyl)-4-hydroxypyrrolidine-1-carboxylate (S1)

To a solution of (2S, 4R)-1-(tert-butoxycarbonyl)-4-hydroxypyrrolidine-2-carboxylic acid (400 mg, 1.73 mmol) in DCM (15 mL) was added 1-chloro-N, N, 2-trimethylprop-1-en-1-amine (346 mg, 2.6 mmol) dropwise at 0° C. The reaction mixture was stirred at 0° C. for 3 hrs. Then 6-bromopyridin-2-amine (300 mg, 1.74 mmol) was added to the mixture, followed by DIPEA (670 mg, 5.2 mmol). After stirring at room temperature overnight, the mixture was washed with aq. NaHCO$_3$ solution and brine successively, dried over anhydrous Na$_2$SO$_4$ and concentrated. The obtained crude product was purified by column chromatography on silica gel eluted with PE/EtOAc (30:1 to 2:1) to give the title compound (210 mg, 31.2% yield) as white solid; LC/MS (ESI) m/z: 386 (M+H)$^+$.

Step 2: (R)-tert-Butyl 2-(6-bromopyridin-2-ylcarbamoyl)-4-oxopyrrolidine-1-carboxylate (S2)

To a solution of S3 (100 mg, 0.259 mmol) in DCM (3 mL) was added Dess-Martin' reagent (163 mg, 0.39 mmol) at 0° C. The reaction mixture was stirred at room temperature for 3 hrs and then diluted with DCM. The resulting mixture was washed with aq. NaHCO3 solution and brine successively, dried over anhydrous Na$_2$SO$_4$ and concentrated. The obtained crude product was purified by column chromatography on silica gel eluted with PE/EtOAc (20:1 to 2:1) to give the title compound (45 mg, 45.2% yield) as yellow solid. LC/MS (ESI) m/z: 384 (M+H)$^+$.

Step 3: (S)—N-(6-Bromopyridin-2-yl)-4-oxopyrrolidine-2-carboxamide (S3)

To a solution of compound S4 (45 mg, 11.7 mmol) in DCM (2 mL) was added TFA (1 mL). The reaction mixture was stirred at room temperature for 16 hrs and then evaporated under reduced to give the title compound (40 mg, 100% yield) as yellow solid, which was directly used to the next reaction without further purification. LC/MS (ESI) m/z: 284 (M+H)$^+$.

Step 4: (S)-1-(2-(3-Acetyl-5-(2-methylpyrimidin-5-yl)-1H-indazol-1-yl)acetyl)-N-(6-bromopyridin-2-yl)-4-oxopyrrolidine-2-carboxamide (S4)

To a mixture of compound S6 (30 mg, 0.095 mmol), compound S5 (29 mg, 0.95 mmol) and DIPEA (0.06 mL, 0.38 mmol) in DMF (2 mL) was added HATU (70 mg, 0.19 mmol). The reaction was stirred at room temperature overnight. The mixture was diluted with water and brine, dried and concentrated to give crude product, which was purified by prep-HPLC (eluted with CH$_3$CN/water) to give the title compound (10 mg, 9.5% yield) as a white solid. $^1$H-NMR (400 MHz, DMSO-d6) δ 8.99 (s, 1H), 8.82 (s, 2H), 8.48 (s, 1H), 7.90 (d, J=8.0 Hz, 1H), 7.52 (s, 1H), 7.42 (t, J=8.0 Hz, 1H), 7.14 (d, J=8.0 Hz, 1H), 5.23 (dd, J=24 Hz, 16 Hz, 2H), 5.11 (d, J=8 Hz, 1H), 4.14 (d, J=16 Hz, 1H), 3.99 (d, J=16 Hz, 1H), 2.84 (d, J=16 Hz, 1H), 2.74 (s, 3H), 2.70-2.65 (m, 1H), 2.62 (s, 3H). LC/MS (ESI) m/z: 576 (M+H)$^+$.

285

(S)-1-(2-(3-Acetyl-5-(2-methylpyrimidin-5-yl)-1H-indazol-1-yl) acetyl)-N-(6-bromopyridin-2-yl)-5-oxopyrrolidine-2-carboxamide (271)

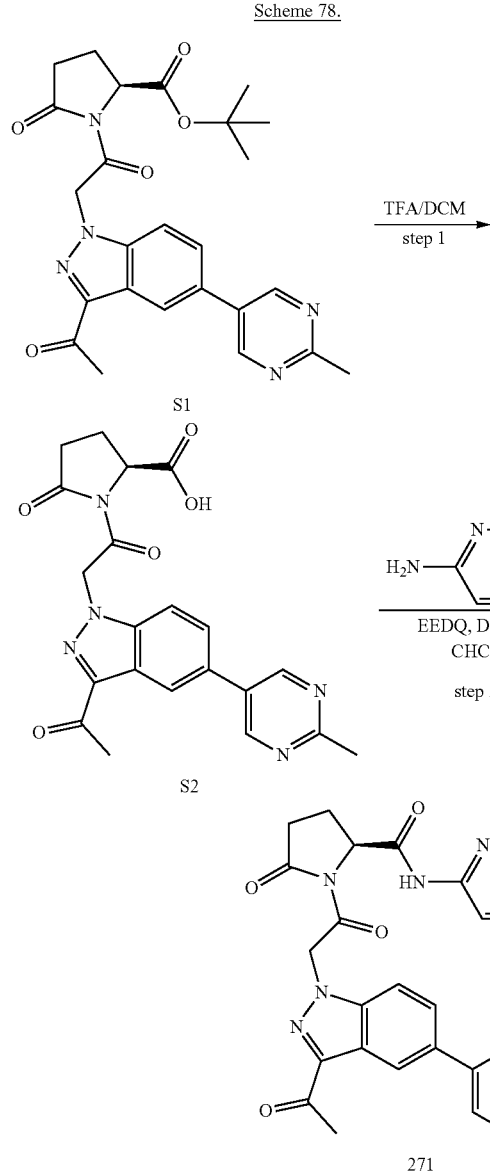

Step 1: (S)-1-(2-(3-Acetyl-5-(2-methylpyrimidin-5-yl)-1H-indazol-1-yl) acetyl)-5-oxopyrrolidine-2-carboxylic acid (S1)

To a solution of (S)-tert-butyl 1-(2-(3-acetyl-5-(2-methylpyrimidin-5-yl)-1H-indazol-1-yl) acetyl)-5-oxopyrrolidine-2-carboxylate (150 mg, 0.31 mmol) in DCM (4 mL) was added TFA (3 mL). The reaction was stirred at room temperature for 2 hrs and then concentrated. The residue was washed with Et$_2$O to give the title compound (130 mg, 98.4% yield); LC/MS (ESI) m/z: 422 [M+H]$^+$.

286

Step 2: (S)-1-(2-(3-Acetyl-5-(2-methylpyrimidin-5-yl)-1H-indazol-1-yl) acetyl)-N-(6-bromopyridin-2-yl)-5-oxopyrrolidine-2-carboxamide (S2)

To a solution of S2 (130 mg, 0.31 mmol) in CHCl$_3$ was added ethyl 2-ethoxyquinoline-1(2H)-carboxylate (114 mg, 0.46 mmol), DIPEA (120 mg, 0.93 mmol) and 6-bromopyridin-2-amine (53 mg, 0.31 mmol). The reaction was refluxed under N$_2$ atmosphere overnight. The mixture was concentrated and the residue was purified by prep-HPLC to give the title compound (10 mg, 5.6% yield); $^1$H NMR (400 MHz, DMSO-d6) δ 11.22 (s, 1H), 9.03 (s, 2H), 8.43 (s, 1H), 8.02 (d, J=8.4 Hz, 1H), 7.91-7.82 (m, 2H), 7.73 (t, J=8.0 Hz, 1H), 7.35 (d, J=7.6 Hz, 1H), 6.01 (q, J=18.4 Hz, 2H), 4.91 (dd, J=9.2, 2.8 Hz, 1H), 2.75 (m, 2H), 2.68 (s, 3H), 2.64 (s, 3H), 2.48-2.39 (m, 1H), 2.11 (ddd, J=17.2, 8.0, 4.0 Hz, 1H); LC/MS (ESI) m/z: 576 [M+H]$^+$.

(2S,3R)-1-(2-(3-Acetyl-5-(2-methylpyrimidin-5-yl)-1H-indazol-1-yl)acetyl)-3-amino-N-(6-bromopyridin-2-yl)pyrrolidine-2-carboxamide (270)

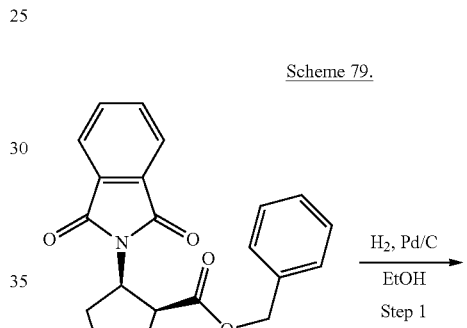

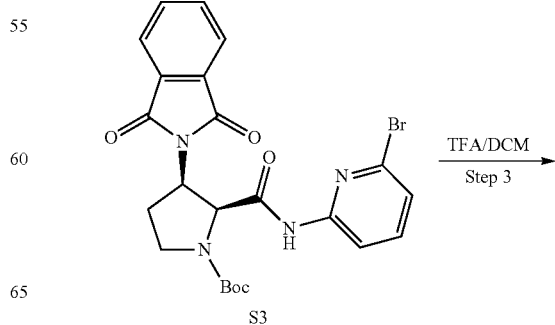

287
-continued

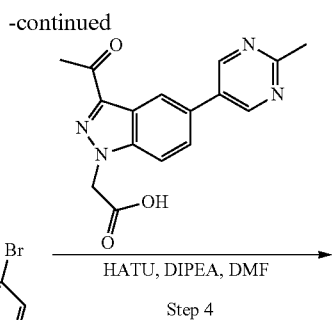

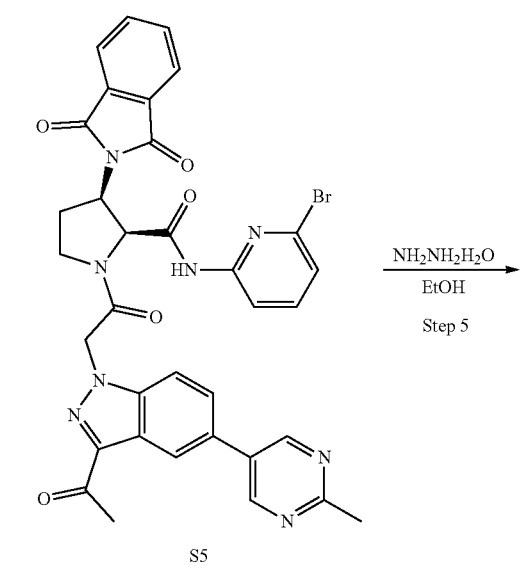

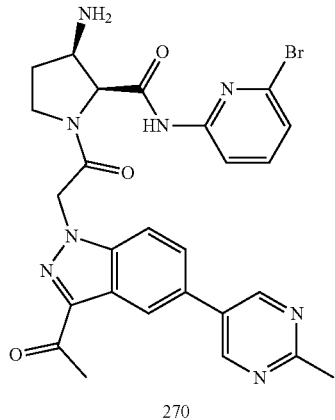

Step 1: (2S, 3R)-1-(tert-Butoxycarbonyl)-3-(1, 3-dioxoisoindolin-2-yl) pyrrolidine-2-carboxylic acid (S2)

To a solution of ((2S, 3R)-2-benzyl 1-tert-butyl 3-(1, 3-dioxoisoindolin-2-yl) pyrrolidine-1, 2-dicarboxylate (1.0 g, 2.22 mmol) in EtOH (50 mL) was added Pd/C (350 mg, 10% wt). The reaction was stirred overnight under $H_2$ balloon at room temperature. After filtration through Celite, the filtrate was concentrated to give the title compound (757 mg, 94.6% yield), which was directly used in the next step; LC/MS (ESI) m/z: 361 $[M+H]^+$.

288

Step 2: (2S, 3R)-tert-butyl 2-(6-Bromopyridin-2-ylcarbamoyl)-3-(1, 3-dioxoisoindolin-2-yl) pyrrolidine-1-carboxylate (S3)

To a solution of (2S, 3R)-1-(tert-butoxycarbonyl)-3-(1, 3-dioxoisoindolin-2-yl) pyrrolidine-2-carboxylic acid (300 mg, 0.83 mmol) in $CHCl_3$ was added ethyl 2-ethoxyquinoline-1(2H)-carboxylate (309 mg, 1.25 mmol), DIPEA (322 mg, 2.50 mmol) and 6-bromopyridin-2-amine (143 mg, 0.83 mmol). The reaction was stirred under $N_2$ atmosphere overnight. The mixture was concentrated and the residue was purified by column chromatography on silica gel eluted with PE/EtOAc (30:1 to 2:1) to give the title compound (135 mg, 31.5%); LC/MS (ESI) m/z: 515 $[M+H]^+$ Step 3: (2S, 3R)—N-(6-Bromopyridin-2-yl)-3-(1, 3-dioxoisoindolin-2-yl) pyrrolidine-2-carboxamide (S4)

To a solution of (2S, 3R)-tert-butyl 2-(6-bromopyridin-2-ylcarbamoyl)-3-(1, 3-dioxoisoindolin-2-yl) pyrrolidine-1-carboxylate (135 mg, 0.26 mmol) in DCM (3 mL) was added TFA (1 mL) and the reaction was stirred at room temperature for 2 hrs. The mixture was concentrated and the residue was washed with $Et_2O$ to give the title compound (105 mg, 96.6% yield) as yellow solid. LC/MS (ESI) m/z: 415 $[M+H]^+$.

Step 4: (2S, 3R)-1-(2-(3-Acetyl-5-(2-methylpyrimidin-5-yl)-1H-indazol-1-yl) acetyl)-N-(6-bromopyridin-2-yl)-3-(1, 3-dioxoisoindolin-2-yl) pyrrolidine-2-carboxamide (S5)

To a mixture of (2S, 3R)—N-(6-bromopyridin-2-yl)-3-(1, 3-dioxoisoindolin-2-yl) pyrrolidine-2-carboxamide (100 mg, 0.24 mmol), 2-(3-acetyl-5-(2-methylpyrimidin-5-yl)-1H-indazol-1-yl) acetic acid (90 mg, 0.29 mmol) and DIPEA (156 mg, 1.21 mmol) in DMF (3 mL) was added HATU (202 mg, 0.53 mmol). The reaction was stirred at room temperature overnight and diluted with $H_2O$. The resulting mixture was extracted with EtOAc, washed by brine, dried over anhydrous $Na_2SO_4$ and concentrated. The obtained crude product was purified by prep-HPLC to give the title compound (75 mg, 44% yield) as white solid. LC/MS (ESI) m/z: 707 $[M+H]^+$.

Step 5: (2S, 3R)-1-(2-(3-Acetyl-5-(2-methylpyrimidin-5-yl)-1H-indazol-1-yl) acetyl)-3-amino-N-(6-bromopyridin-2-yl) pyrrolidine-2-carboxamide (S6)

To a solution of (2S, 3R)-1-(2-(3-acetyl-5-(2-methylpyrimidin-5-yl)-1H-indazol-1-yl) acetyl)-N-(6-bromopyridin-2-yl)-3-(1,3-dioxoisoindolin-2-yl) pyrrolidine-2-carboxamide (50 mg, 0.071 mmol) in EtOH (2 mL) was added hydrazine hydrate (20 mg, 0.4 mmol). The reaction was refluxed overnight and concentrated. The residue was purified by prep-HPLC to give the title compound (5 mg, 12.3% yield) as white solid $^1H$ NMR (400 MHz, $CD_3OD$) δ 8.90 (s, 2H), 8.44 (s, 1H), 7.98 (d, J=8.0 Hz, 1H), 7.69 (s, 2H), 7.52 (t, J=8.0 Hz, 1H), 7.17 (d, J=7.6 Hz, 1H), 5.52 (s, 2H), 4.61 (dd, J=9.2 Hz, 4.4 Hz, 1H), 4.04 (dd, J=10.8, 5.6 Hz, 1H), 3.88 (s, 1H), 3.79 (dd, J=11.2, 4.0 Hz, 1H), 3.42-3.36, 3.05-3.02 (m, 1H), 2.65 (s, 3H), 2.59 (s, 3H), 2.13-1.88. (m, 2H); LC/MS (ESI) m/z: 577 [M+H]⁺.

(2S,4R)-1-(2-(3-Acetyl-5-(2-methylpyrimidin-5-yl)-1H-indazol-1-yl)acetyl)-N-(6-bromopyridin-2-yl)-4-hydroxypyrrolidine-2-carboxamide (231)

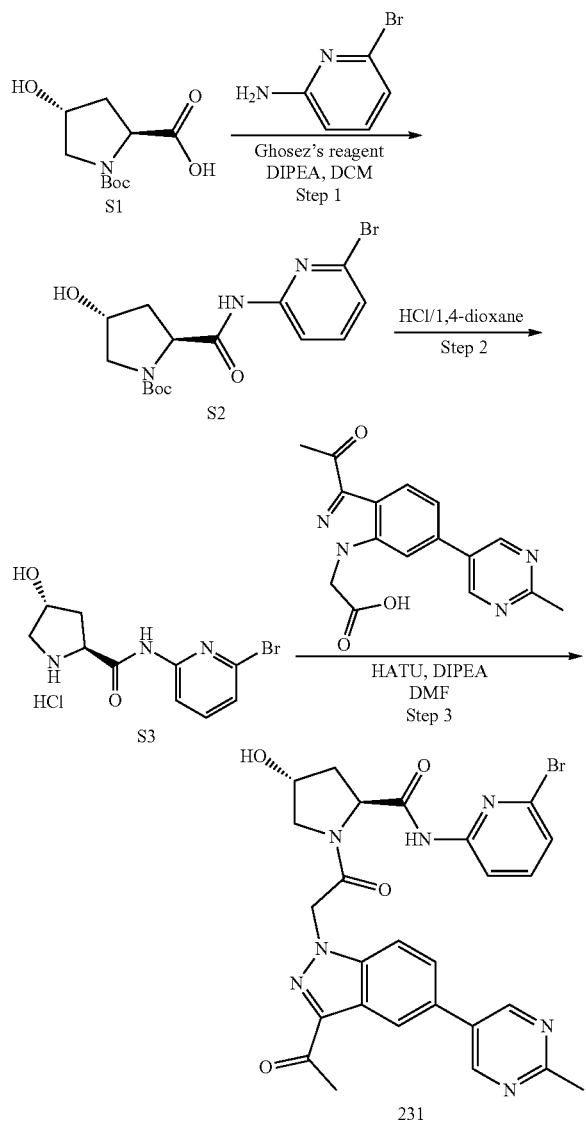

231

Step 1: (2S, 4S)-tert-Butyl 2-(6-bromopyridin-2-ylcarbamoyl)-4-hydroxypyrrolidine-1-carboxylate (S2)

To a solution of (2S, 4R)-1-(tert-butoxycarbonyl)-4-hydroxypyrrolidine-2-carboxylic acid (400 mg, 1.73 mmol) in DCM (15 mL) was added 1-chloro-N, N, 2-trimethylprop-1-en-1-amine (346 mg, 2.6 mmol) dropwise at 0° C. The reaction was stirred at 0° C. for 3 hrs. Then 6-bromopyridin-2-amine (300 mg, 1.74 mmol) was added to the mixture, followed by DIPEA (670 mg, 5.2 mmol). The reaction was stirred at room temperature overnight. The mixture was washed with aq. NaHCO₃ solution and brine successively, dried over anhydrous Na₂SO₄ and concentrated. The obtained crude product was purified by column chromatography on silica gel eluted with PE/EtOAc (30:1 to 2:1) to give the title compound (210 mg, 31.2% yield) as white solid; LC/MS (ESI) m/z: 386 (M+H)⁺.

Step 2: (2S, 4R)—N-(6-Bromopyridin-2-yl)-4-hydroxypyrrolidine-2-carboxamide (S3)

A round-bottom flask was charged with (2S, 4S)-tert-butyl 2-(6-bromopyridin-2-ylcarbamoyl)-4-hydroxypyrrolidine-1-carboxylate (80 mg, 0.21 mmol) and HCl/dioxane (2 mL). The reaction was stirred at room temperature for 1 hr and then concentrated to dryness to give the title compound (50 mg, 84.7% yield) as yellow solid, which was used directly in the next step; LC/MS (ESI) m/z: 286 [M+H]⁺.

Step 3: (2S,4R)-1-(2-(3-Acetyl-5-(2-methylpyrimidin-5-yl)-1H-indazol-1-yl)acetyl)-N-(6-bromopyridin-2-yl)-4-hydroxypyrrolidine-2-carboxamide (S4)

To a mixture of (2S, 4R)—N-(6-bromopyridin-2-yl)-4-hydroxypyrrolidine-2-carboxamide (50 mg, 0.18 mmol) and 2-(3-acetyl-6-(2-methylpyrimidin-5-yl)-1H-indazol-1-yl) acetic acid (66 mg, 0.21 mmol) in DMF (2 mL) was added DIPEA (91 mg, 0.70 mmol) and HATU (147 mg, 0.39 mmol). The reaction was stirred at room temperature overnight and diluted with water. The resulting mixture was extracted with EtOAc twice. The combined organic phases were washed with brine, dried over anhydrous Na₂SO₄ and concentrated to dryness. The obtained crude product was purified by prep-HPLC to give the title compound (15 mg, 14.8% yield) as white solid. ¹H NMR (400 MHz, CD3OD) δ 8.88 (s, 2H), 8.40 (s, 1H), 7.95 (d, J=8.4 Hz, 1H), 7.73-7.60 (m, 2H), 7.48 (t, J=8.0 Hz, 1H), 7.13 (dd, J=8.0, 0.4 Hz, 1H), 5.52-5.31 (m, 2H), 4.64 (t, J=8.0 Hz, 1H), 4.51 (s, 1H), 3.87 (dd, J=10.8, 4.4 Hz, 1H), 3.72 (d, J=10.8 Hz, 1H), 2.65 (s, 3H), 2.59 (s, 3H), 2.36-2.20 (m, 1H), 2.13-2.02 (m, 1H); LC/MS (ESI) m/z: 578 [M+H]⁺.

(2S,4S)-1-(2-(3-Acetyl-5-(2-methylpyrimidin-5-yl)-1H-indazol-1-yl)acetyl)-N-(6-bromopyridin-2-yl)-4-hydroxypyrrolidine-2-carboxamide (249)

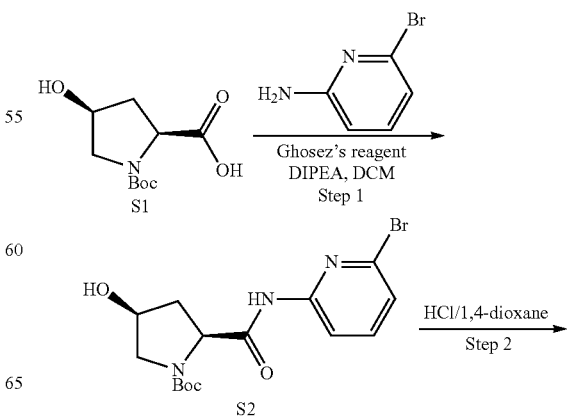

291

-continued

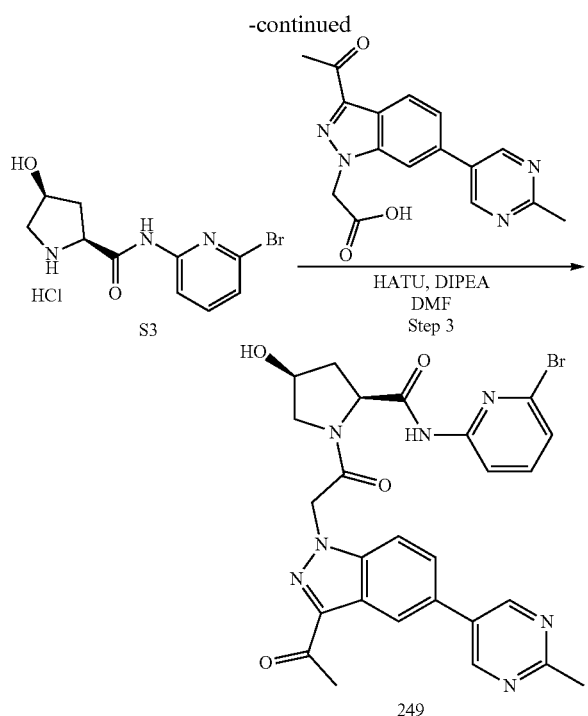

Step 1: (2S,4S)-tert-Butyl 2-(6-bromopyridin-2-ylcarbamoyl)-4-hydroxypyrrolidine-1-carboxylate (S2)

To a solution of (2S, 4R)-1-(tert-butoxycarbonyl)-4-hydroxypyrrolidine-2-carboxylic acid (400 mg, 1.73 mmol) in DCM (15 mL) was added 1-chloro-N, N, 2-trimethylprop-1-en-1-amine (346 mg, 2.6 mmol) dropwise at 0° C. The reaction was stirred at 0° C. for 3 hrs. Then 6-bromopyridin-2-amine (300 mg, 1.74 mmol) was added, followed by DIPEA (670 mg, 5.2 mmol). The reaction was stirred at room temperature overnight. The mixture was washed with aq. NaHCO₃ solution and brine successively, dried over anhydrous Na₂SO₄ and concentrated. The obtained crude product was purified by column chromatography on silica gel eluted with PE/EtOAc (30:1 to 2:1) to give the title compound (170 mg, 25.4% yield) as white solid; LC/MS (ESI) m/z: 386 (M+H)⁺.

Step 2: (2S, 4S)—N-(6-Bromopyridin-2-yl)-4-hydroxypyrrolidine-2-carboxamide hydrochloride (S3)

A round-bottom flask was charged with (2S, 4S)-tert-butyl 2-(6-bromopyridin-2-ylcarbamoyl)-4-hydroxypyrrolidine-1-carboxylate (80 mg, 0.21 mmol) and HCl/dioxane (2 mL), and the reaction was stirred at room temperature for 1 hr. The mixture was concentrated to dryness to give the title compound (75 mg, 100 yield) as yellow solid, which was used directly in the next step; LC/MS (ESI) m/z: 286 [M+H]⁺.

Step 3: (2S, 4S)-1-(2-(3-Acetyl-5-(2-methylpyrimidin-5-yl)-1H-indazol-1-yl)acetyl)-N-(6-bromopyridin-2-yl)-4-hydroxypyrrolidine-2-carboxamide (249)

To a mixture of (2S, 4S)—N-(6-bromopyridin-2-yl)-4-hydroxypyrrolidine-2-carboxamide (80 mg, 0.28 mmol) and 2-(3-acetyl-5-(2-methylpyrimidin-5-yl)-1H-indazol-1-yl)

292 acetic acid (105 mg, 0.38 mmol) in DMF (2 mL) was added DIPEA (145 mg, 1.12 mmol) and HATU (235 mg, 0.62 mmol). The reaction was stirred at room temperature overnight. The mixture was diluted with water, extracted with EtOAc twice. The combined organic phases were washed with brine, dried over anhydrous Na₂SO₄ and concentrated to dryness. The obtained crude product was purified by prep-HPLC to give the title compound (20 mg, 12.3% yield) as a white solid. ¹H NMR (400 MHz, CDCl₃) δ 9.22 (s, 1H), 8.82 (s, 2H), 8.48 (s, 1H), 7.98 (d, J=8.4 Hz, 1H), 7.55-7.41 (m, 3H), 7.14 (d, J=7.6 Hz, 1H), 5.36-5.20 (m, 2H), 4.72 (dd, J=24.8, 9.2 Hz, 2H), 4.53 (s, 1H), 3.90-3.67 (m, 2H), 2.73 (s, 3H), 2.63 (s, 3H), 2.30 (d, J=14.4 Hz, 1H), 2.23-2.11 (m, 1H); LC/MS (ESI) m/z: 578 [M+H]⁺.

(S)-1-(2-(3-Acetyl-5-(2-methylpyrimidin-5-yl)-1H-indazol-1-yl)acetyl)-N-(6-bromopyridin-2-yl)pyrrolidine-2-carboxamide (230)

Scheme 82.

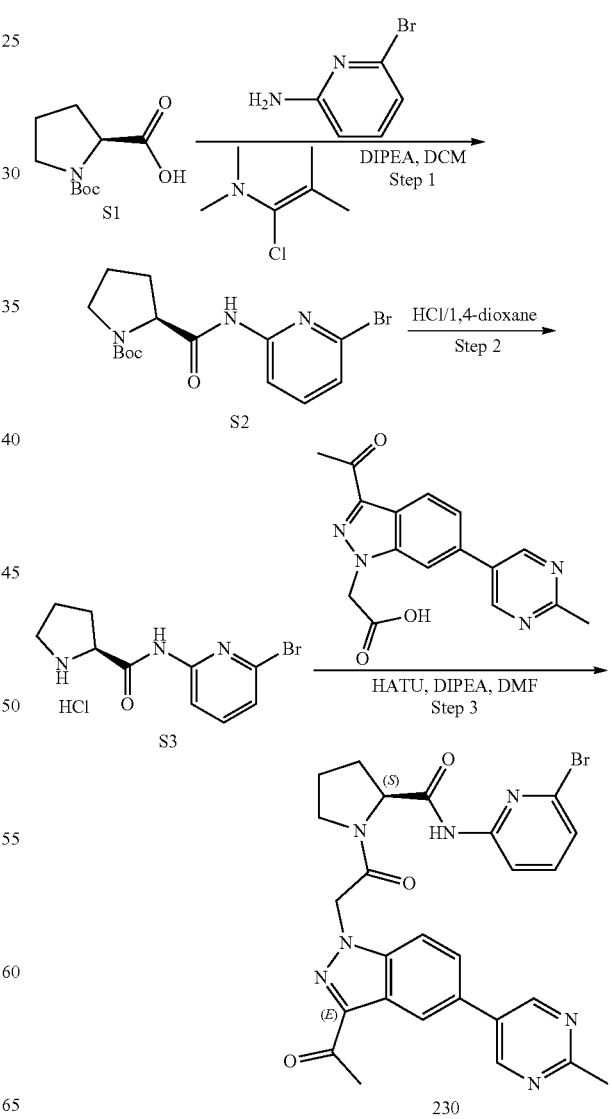

Step 1: (S)-tert-Butyl 2-(6-bromopyridin-2-ylcarbamoyl) pyrrolidine-1-carboxylate (S1)

To a solution of (S)-1-(tert-butoxycarbonyl) pyrrolidine-2-carboxylic acid (500 mg, 2.32 mmol) in DCM (10 mL) was added 1-chloro-N, N, 2-trimethylprop-1-en-1-amine (464 mg, 3.49 mmol) dropwise at 0° C. The reaction was stirred at 0° C. for 3 hrs. Then 6-bromopyridin-2-amine (440 mg, 2.56 mmol) was added followed by DIPEA (899 mg, 6.97 mmol) at 0° C. The reaction was stirred at room temperature overnight. The mixture was washed with aq. NaHCO$_3$ solution and brine successively, dried over anhydrous Na$_2$SO$_4$ and concentrated to dryness. The obtained crude product was purified by column chromatography on silica gel eluted with PE/EtOAc (30:1 to 10:1) to give the title compound (790 mg, 92.1% yield) as white solid; LC/MS (ESI) m/z: 370 [M+H]$^+$.

Step 2: (S)—N-(6-Bromopyridin-2-yl) pyrrolidine-2-carboxamide hydrochloride (S2)

A round-bottom flask was charged with (S)-tert-butyl 2-(6-bromopyridin-2-ylcarbamoyl) pyrrolidine-1-carboxylate (790 mg, 2.14 mmol) and HCl/dioxane (4 M, 10 mL). The reaction was stirred at room temperature overnight and concentrated to dryness to give the title compound (535 mg, 92.9% yield) as a yellow solid, which was used directly in the next step; LC/MS (ESI) m/z: 270 [M+H]$^+$.

Step 3: (S)-1-(2-(3-Acetyl-6-(2-methylpyrimidin-5-yl)-1H-indazol-1-yl) acetyl-N-(6-bromopyridin-2-yl) pyrrolidine-2-carboxamide (230)

The titled compound was prepared according the procedure for example Scheme 81. $^1$H NMR (400 MHz, CDCl$_3$) δ 8.92 (s, 1H), 8.82 (s, 2H), 8.48 (s, 1H), 7.98 (d, J=8.4 Hz, 1H), 7.63-7.51 (m, 2H), 7.42 (t, J=8.0 Hz, 1H), 7.11 (d, J=8.0 Hz, 1H), 5.40-5.09 (m, 2H), 4.62 (dd, J=8.0, 2.4 Hz, 1H), 3.77-3.54 (m, 2H), 2.73 (s, 3H), 2.65 (s, 3H), 2.36-2.21 (m, 1H), 2.21-2.10 (m, 1H), 2.09-1.89 (m, 2H); LC/MS (ESI) m/z: 562 [M+H]$^+$.

(2S, 4R)-1-(2-(3-Acetyl-5-(2-methylpyrimidin-5-yl)-1H-indazol-1-yl) acetyl)-4-fluoro-N-(1-(2, 2, 2-trifluoroethyl) pyrrolidin-3-yl) pyrrolidine-2-carboxamide (610)

Scheme 83.

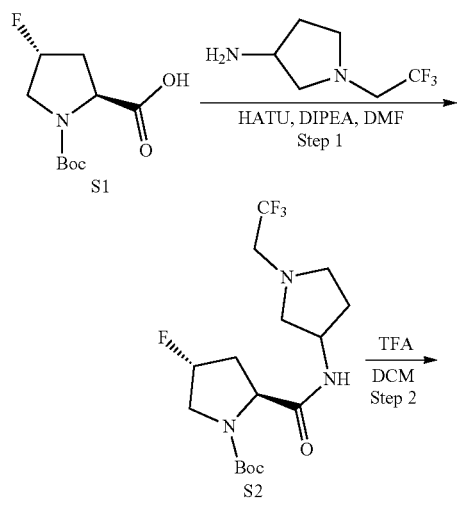

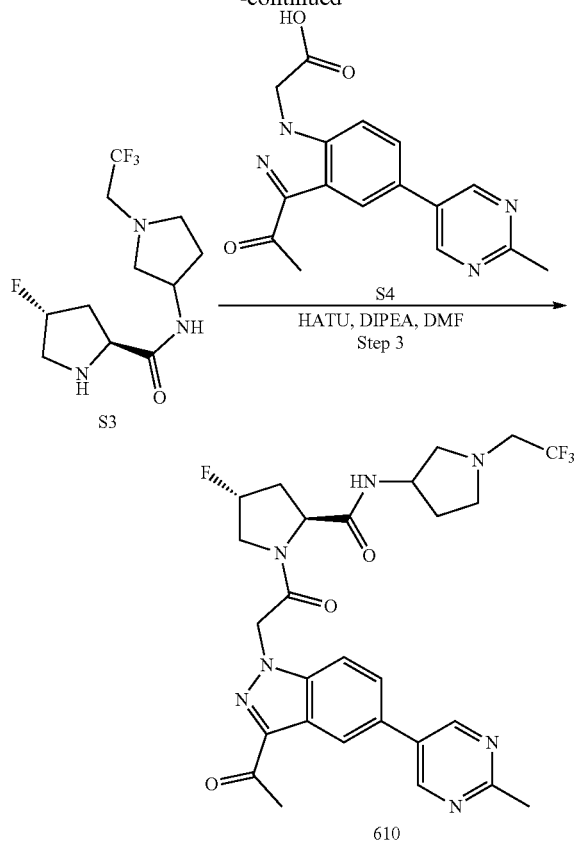

Step 1: (2S, 4R)-tert-Butyl-4-fluoro-2-(1-(2, 2, 2-trifluoroethyl) pyrrolidin-3-ylcarbamoyl) pyrrolidine-1-carboxylate (S2)

To a mixture of (2S, 4R)-1-(tert-butoxycarbonyl)-4-fluoropyrrolidine-2-carboxylic acid (69 mg, 0.30 mmol) and 1-(2, 2, 2-trifluoroethyl) pyrrolidin-3-amine (50 mg, 0.30 mmol) in DMF (2 mL) was added DIPEA (154 mg, 1.19 mmol) and HATU (226 mg, 0.60 mmol). The reaction was stirred at room temperature for 2 hrs. The mixture was diluted with water and extracted with EtOAc. The organic layer was washed by brine, dried over anhydrous Na$_2$SO$_4$ and concentrated. The obtained crude product was purified by column chromatography on silica gel eluted with PE/EtOAc (30:1 to 3:1) to give the title compound (110 mg, 96.4% yield) as white solid; LC/MS (ESI) m/z: 384 [M+H]$^+$.

Step 2: (2S, 4R)-4-Fluoro-N-(1-(2, 2, 2-trifluoroethyl) pyrrolidin-3-yl) pyrrolidine-2-carboxamide (S3)

To a solution of (2S, 4R)-tert-butyl 4-fluoro-2-(1-(2, 2, 2-trifluoroethyl) pyrrolidin-3-ylcarbamoyl) pyrrolidine-1-carboxylate (110 mg, 0.29 mmol) in DCM (2 mL) was added TFA (2 mL) and the reaction was stirred at room temperature for 2 hrs. The mixture was concentrated to dryness to give the title compound (80 mg, 98.4% yield) as yellow solid, which was used directly in the next step; LC/MS (ESI) m/z: 284 [M+H]$^+$

Step 3: (2S, 4R)-1-(2-(3-Acetyl-5-(2-methylpyrimidin-5-yl)-1H-indazol-1-yl) acetyl)-4-fluoro-N-(1-(2, 2, 2-trifluoroethyl) pyrrolidin-3-yl) pyrrolidine-2-carboxamide (610)

To a mixture of (2S, 4R)-4-fluoro-N-(1-(2, 2, 2-trifluoroethyl) pyrrolidin-3-yl) pyrrolidine-2-carboxamide (80 mg, 0.28 mmol) and S4 (88 mg, 0.28 mmol) in DMF (2 mL) was added DIPEA (182 mg, 1.41 mmol) and HATU (236 mg, 0.62 mmol). The reaction was stirred at room temperature for 2 hrs. The mixture was diluted with water and extracted with EtOAc. The organic layer was washed with 10% aq. LiCl solution and brine successively, dried over anhydrous Na$_2$SO$_4$ and concentrated. The obtained crude product was purified by prep-HPLC to give the title compound (60 mg, 37.0% yield) as white solid. $^1$H NMR (400 MHz, DMSO-d6) δ 9.04 (s, 2H), 8.44 (s, 1H), 8.18 (dd, J=7.2, 2.8 Hz, 1H), 7.92-7.75 (m, 2H), 5.85-5.28 (m, 3H), 4.44-3.83 (m, 4H), 3.51 (dd, J=37.2, 10.8 Hz, 1H), 3.25-3.11 (m, 2H), 2.89-2.73 (m, 2H), 2.69 (s, 3H), 2.65 (s, 3H), 2.59 (dd, J=15.6, 7.6 Hz, 1H), 2.49-2.27 (m, 2H), 2.21-1.93 (m, 2H), 1.75-1.47 (m, 1H); LC/MS (ESI) m/z: 576 [M+H]$^+$.

(1R, 3S, 5R)-2-(2-(3-acetyl-5-(2-methylpyrimidin-5-yl)-1H-indazol-1-yl) acetyl)-N-(1-(2, 2, 2-trifluoroethyl) pyrrolidin-3-yl)-2-azabicyclo [3.1.0] hexane-3-carboxamide (611)

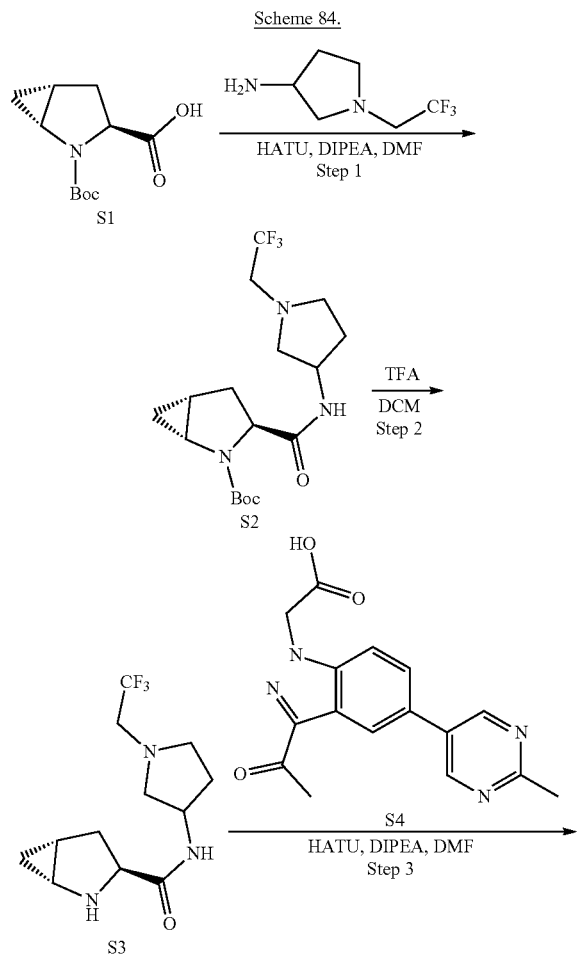

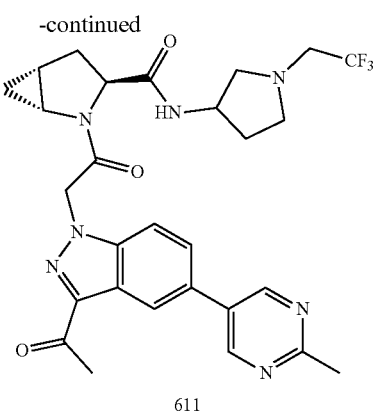

611

Step 1: Synthesis of (1R, 3S, 5R)-tert-Butyl 3-(1-(2, 2, 2-trifluoroethyl) pyrrolidin-3-ylcarbamoyl)-2-azabicyclo [3.1.0] hexane-2-carboxylate (S2)

To a solution of (1R, 3S, 5R)-2-(tert-butoxycarbonyl)-2-azabicyclo[3.1.0]hexane-3-carboxylic acid (68 mg, 0.30 mmol) and 1-(2, 2, 2-trifluoroethyl) pyrrolidin-3-amine (50 mg, 0.30 mmol) in DMF (2 mL) was added DIPEA (154 mg, 1.19 mmol) and HATU (226 mg, 0.60 mmol). The reaction was stirred at room temperature for 2 hrs. The mixture was diluted with water and extracted with EtOAc. The organic layer was washed with 10% aq. LiCl solution and brine successively, dried over anhydrous Na$_2$SO$_4$ and concentrated. The obtained crude product was purified by column chromatography on silica gel eluted with PE/EtOAc (30:1 to 3:1) to give the title compound (65 mg, 58.0% yield) as white solid. LC/MS (ESI) m/z: 378 [M+H]$^+$.

Step 2: Synthesis of (1R, 3S, 5R)—N-(1-(2, 2, 2-Trifluoroethyl) pyrrolidin-3-yl)-2-azabicyclo [3.1.0] hexane-3-carboxamide (S3)

To a solution of (1R, 3S, 5R)-tert-butyl 3-(1-(2, 2, 2-trifluoroethyl) pyrrolidin-3-ylcarbamoyl)-2-azabicyclo [3.1.0] hexane-2-carboxylate (65 mg, 0.17 mmol) in DCM (2 mL) was added TFA (1 mL). The reaction was stirred at room temperature for 2 hrs and concentrated to give the title compound (60 mg, 100% yield) which was used directly in the next step; LC/MS (ESI) m/z: 278 [M+H]$^+$.

Step 3: Synthesis of (1R, 3S, 5R)-2-(2-(3-Acetyl-5-(2-methylpyrimidin-5-yl)-1H-indazol-1-yl) acetyl)-N-(1-(2, 2, 2-trifluoroethyl) pyrrolidin-3-yl)-2-azabicyclo [3.1.0] hexane-3-carboxamide (611)

To a mixture of ((1R, 3S, 5R)—N-(1-(2, 2, 2-trifluoroethyl) pyrrolidin-3-yl)-2-azabicyclo [3.1.0] hexane-3-carboxamide (47 mg, 0.17 mmol) and S4 (53 mg, 0.17 mmol) in DMF (2 mL) was added DIPEA (109 mg, 0.85 mmol) and HATU (142 mg, 0.37 mmol). The reaction mixture was stirred at room temperature for 2 hrs. The mixture was diluted with water and extracted with EtOAc. The organic layer was washed with 10% aq. LiCl solution and brine successively, dried over anhydrous Na$_2$SO$_4$ and concentrated. The obtained crude product was purified by prep-HPLC to give the title compound (25 mg, 25.9% yield) as white solid. $^1$H NMR (400 MHz, DMSO-d6) δ 9.05 (s, 2H), 8.44 (s, 1H), 7.94 (d, J=7.2 Hz, 1H), 7.91-7.85 (m, 2H), 5.93 (dd, J=17.2, 1.6 Hz, 1H), 5.57 (d, J=17.2 Hz, 1H), 4.27-4.06

(m, 2H), 3.75 (t, J=4.8 Hz, 1H), 3.32-3.16 (m, 2H), 2.86-2.75 (m, 2H), 2.69 (s, 1H), 2.66 (s, 1H), 2.64-2.55 (m, 1H), 2.48-2.39 (m, 1H), 2.26-2.15 (m, 1H), 2.13-1.94 (m, 2H), 1.91-1.80 (m, 1H), 1.65-1.51 (m, 1H), 1.07-0.95 (m, 1H), 0.79-0.74 (m, 1H); LC/MS (ESI) m/z: 570 [M+H]$^+$.

(R)-1-(2-(3-acetyl-5-(2-Methylpyrimidin-5-yl)-1H-indazol-1-yl)acetyl)-N-(6-bromopyridin-2-yl)-3,3-dimethyl-1,3-azasilolidine-5-carboxamide (514)

Scheme 85.

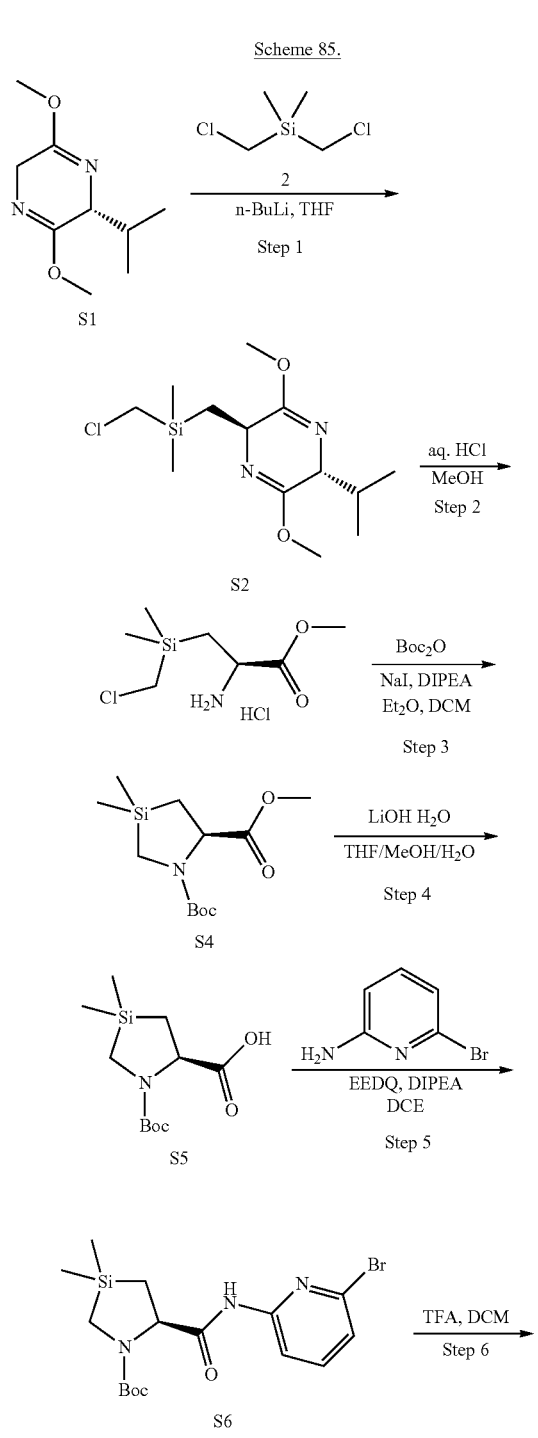

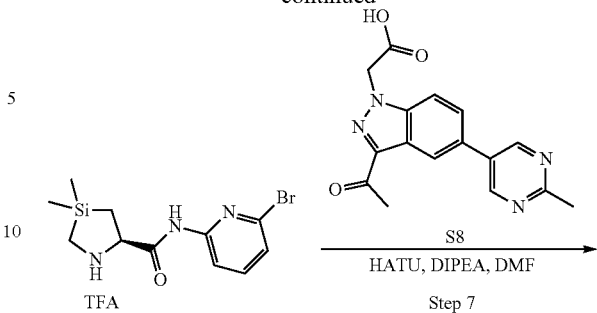

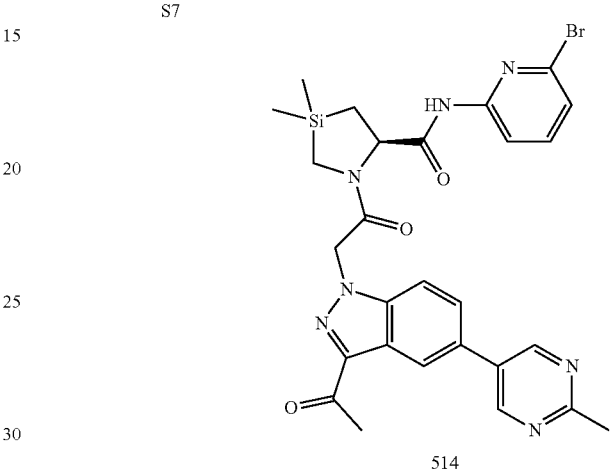

Step 1: (2R, 5R)-2-(((Chloromethyl) dimethylsilyl) methyl)-5-isopropyl-3, 6-dimethoxy-2, 5-dihydropyrazine (S2)

To a solution of (R)-2-isopropyl-3, 6-dimethoxy-2, 5-dihydropyrazine (500 mg, 2.72 mmol) and bis(chloromethyl) dimethylsilane (636 mg, 4.08 mmol) in THF (10 mL) under N$_2$ atmosphere in a dry ice/acetone bath was slowly n-BuLi (1.6 M in hexane, 2 mL, 3.2 mmol) via an injection syringe. After addition, the reaction was stirred at room temperature overnight. The reaction mixture was cooled to 0° C. and quenched by dropwise addition of water. The resulting mixture was extracted with EtOAc. The organic layer was washed by brine, dried over anhydrous Na$_2$SO$_4$ and concentrated. The obtained crude product was purified by column chromatography on silica gel eluted with PE/EtOAc (100:1 to 30:1) to give the title compound (640 mg, 77.5% yield); LC/MS (ESI) m/z: 305 [M+H]$^+$.

Step 2: (R)-Methyl 2-amino-3-((chloromethyl)dimethylsilyl)propanoate hydrochloride (S3)

To a solution of (2R, 5R)-2-(((chloromethyl) dimethylsilyl) methyl)-5-isopropyl-3, 6-dimethoxy-2, 5-dihydropyrazine (0.62 g, 2.04 mmol) in MeOH (4.8 mL) was added 10% aq. HCl (1 mL) and the reaction was stirred at room temperature for 3 hrs. The mixture was concentrated to dryness to give the title compound (280 mg, 79.4% yield) as yellow syrup, which was used directly in the next step; LC/MS (ESI) m/z: 174 [M+H]$^+$.

Step 3: (R)-1-tert-Butyl 5-methyl 3, 3-dimethyl-1, 3-azasilolidine-1, 5-dicarboxylate (S4)

To a solution of (R)-methyl 2-amino-3-((chloromethyl) dimethylsilyl) propanoate hydrochloride (430 mg, 1.75 mmol) and NaI (308 mg, 2.06 mmol) in DCM (6 mL) and Et₂O (10 mL) was slowly added DIPEA via an injection syringe at 0° C. Then the reaction was stirred at room temperature for 4 hrs. Di-tert-butyl dicarbonate (762 mg, 3.5 mmol) was added and the reaction was stirred at room temperature overnight. After diluted with DCM, the resulting mixture was washed with water and brine, dried over anhydrous Na₂SO₄ and concentrated. The obtained crude product was washed purified by column chromatography on silica gel eluted with PE/EtOAc (100:1 to 60:1) to give the title compound (290 mg, 60.6% yield) as white solid. m/z (ES+): 274 [M+H]⁺.

Step 4: (R)-1-(tert-Butoxycarbonyl)-3, 3-dimethyl-1, 3-azasilolidine-5-carboxylic acid (S5)

To a solution of (R)-1-tert-butyl 5-methyl 3, 3-dimethyl-1, 3-azasilolidine-1, 5-dicarboxylate (290 mg, 1.06 mmol) in THF (2 mL) and MeOH (3 mL) was added aq. LiOH solution (2 mL, 1 M) (268 mg, 6.37 mmol) and the reaction was stirred at room temperature overnight. The mixture was diluted with water and washed with EtOAc. The aqueous layer was acidified with 1 M aq. HCl to pH=~3 and extracted with EtOAc twice. The combined organic phases were washed with brine, dried over anhydrous Na₂SO₄, filtered and concentrated to give the title compound (201 mg, 72.7% yield) as a white solid. m/z (ES+): 260 [M+H]⁺.

Step 5: (R)-tert-Butyl 5-(6-bromopyridin-2-ylcarbamoyl)-3, 3-dimethyl-1, 3-azasilolidine-1-carboxylate (S6)

To a solution of (R)-1-(tert-butoxycarbonyl)-3, 3-dimethyl-1, 3-azasilolidine-5-carboxylic acid (0.12 g, 0.46 mmol) in 1,2-dichloroethane was added ethyl 2-ethoxyquinoline-1(2H)-carboxylate (0.23 g, 0.93 mmol), DIPEA (0.18 g, 1.39 mmol) and 6-bromopyridin-2-amine (80 mg, 0.46 mmol). The reaction was stirred at 90° C. under N₂ atmosphere overnight. The mixture was concentrated and the residue was purified by column chromatography on silica gel eluted with PE/EtOAc (50:1 to 20:1) to give the title compound (0.15 g, 78.5% yield) as yellow solid; LC/MS (ESI) m/z: 414 [M+H]⁺.

Step 6: (R)—N-(6-Bromopyridin-2-yl)-3, 3-dimethyl-1, 3-azasilolidine-5-carboxamide (S7)

To a solution of (R)-tert-butyl 5-(6-bromopyridin-2-ylcarbamoyl)-3, 3-dimethyl-1, 3-azasilolidine-1-carboxylate (100 mg, 0.24 mmol) in DCM (2 mL) was added TFA (1 mL). The reaction mixture was stirred at room temperature for 1 hr and concentrated to dryness. The residue was washed with Et₂O to give the title compound (75 mg, 99.0% yield) as yellow solid. LC/MS (ESI) m/z: 314 [M+H]⁺.

Step 7: (R)-1-(2-(3-Acetyl-5-(2-methylpyrimidin-5-yl)-1H-indazol-1-yl) acetyl)-N-(6-bromopyridin-2-yl)-3, 3-dimethyl-1, 3-azasilolidine-5-carboxamide (514)

To a mixture of (R)—N-(6-bromopyridin-2-yl)-3, 3-dimethyl-1, 3-azasilolidine-5-carboxamide (40 mg, 0.13 mmol), S8 (44 mg, 0.14 mmol) and DIPEA (82 mg, 0.64 mmol) in DMF (2 mL) was added HATU (107 mg, 0.28 mmol) and the reaction was stirred at room temperature for 1 hr. The mixture was diluted with EtOAc and washed with water and brine, dried over anhydrous Na₂SO₄ and concentrated. The obtained crude product was purified by prep-HPLC to give the title compound (30 mg, 39.0% yield) as white solid. ¹H NMR (400 MHz, DMSO-d6) δ 11.84 (s, 1H), 9.03 (s, 2H), 8.42 (s, 1H), 8.00 (d, J=8.0 Hz, 1H), 7.91-7.77 (m, 2H), 7.69 (t, J=8.0 Hz, 1H), 7.30 (d, J=7.6 Hz, 1H), 5.90-5.57 (m, 2H), 4.94 (dd, J=10.8, 3.6 Hz, 1H), 3.18 (dd, J=17.6, 13.2 Hz, 2H), 2.68 (s, 3H), 2.64 (s, 3H), 1.31 (dd, J=15.2, 10.8 Hz, 1H), 1.05 (dd, J=15.2, 3.6 Hz, 1H), 0.37-0.23 (m, 6H); LC/MS (ESI) m/z: 606 [M+H]⁺.

(2S,3S,4S)-1-(2-(3-Acetyl-5-(2-methylpyrimidin-5-yl)-1H-indazol-1-yl)acetyl)-3-amino-N-(6-bromopyridin-2-yl)-4-fluoropyrrolidine-2-carboxamide (427) and (2R,3S,4R)-1-(2-(3-Acetyl-5-(2-methylpyrimidin-5-yl)-1H-indazol-1-yl)acetyl)-4-amino-N-(6-bromopyridin-2-yl)-3-fluoropyrrolidine-2-carboxamide (428)

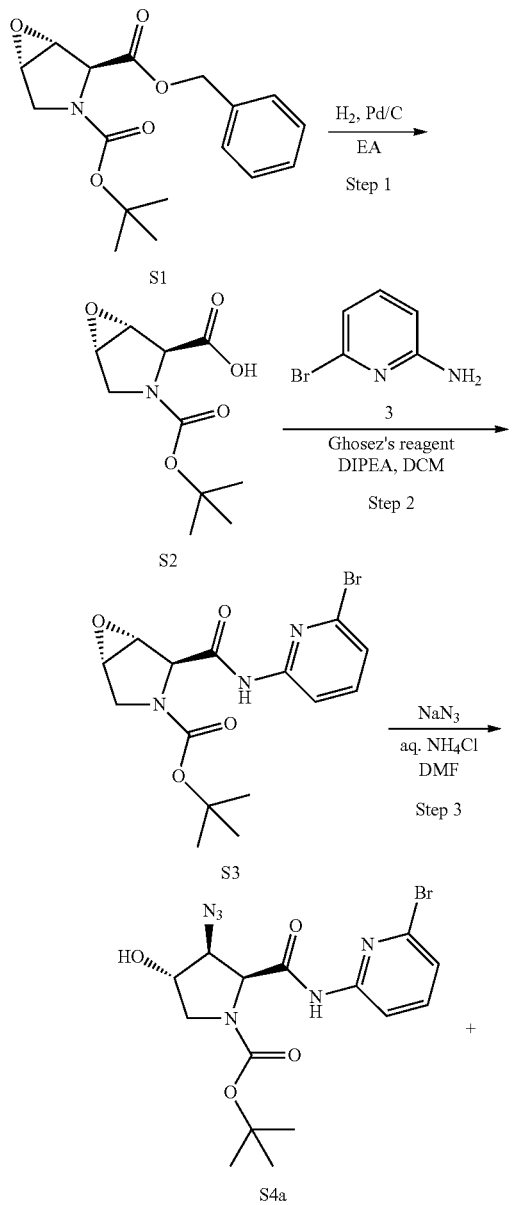

Scheme 86.

301
-continued
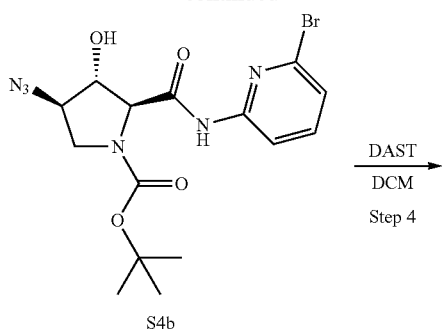
S4b
→ DAST / DCM / Step 4 →
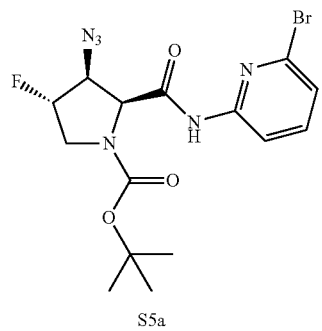
S5a
+
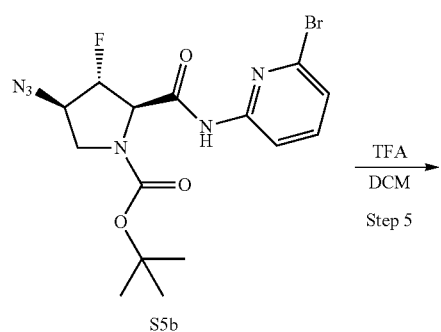
S5b
→ TFA / DCM / Step 5 →
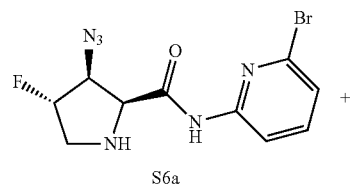
S6a
+
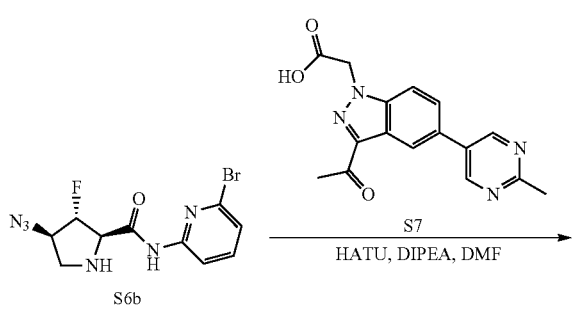
S6b
→ S7, HATU, DIPEA, DMF →
302
-continued
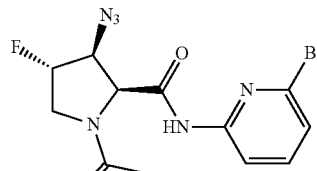
S8a
+
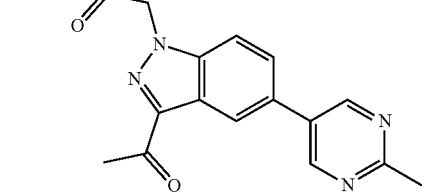
S8b
→ PPh₃ / THF/H₂O →
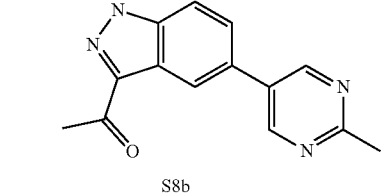
427
+
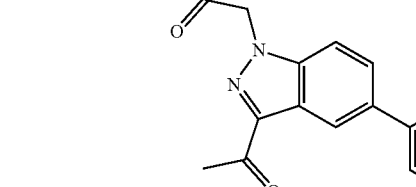
428

Step 1: (1R,2S,5S)-3-(tert-Butoxycarbonyl)-6-oxa-3-azabicyclo[3.1.0]hexane-2-carboxylic acid (S2)

To a mixture of compound S1 (1 g, 3.12 mmol) in EtOAc (30 mL) was added Pd/C (100 mg, 10%) and the reaction mixture was degassed under N₂ for three times and stirred under a H₂ balloon at room temperature for 16 hrs. The mixture was filtered and the filtrate was concentrated to give the title compound (710 mg, 99% yield) as yellow oil, which was directly used to the next reaction without further purification. LC/MS (ESI) m/z: 230 (M+H)⁺.

Step 2: (1R,2S,5S)-tert-butyl 2-(6-Bromopyridin-2-ylcarbamoyl)-6-oxa-3-azabicyclo[3.1.0]hexane-3-carboxylate (S3)

To a solution of compound S2 (360 mg, 1.56 mmol) in dry DCM (12 mL) was added Ghosez's reagent (228 mg, 1.72 mmol) at 0° C. under N₂ atmosphere. The reaction was stirred at 0° C. for 3 hrs and 6-bromopyridin-2-amine (270 mg, 1.56 mmol) and DIPEA (609 mg, 4.68 mmol) were added into the above mixture. The reaction was stirred at room temperature for 16 hrs. The mixture was diluted with water (30 mL) and extracted with ethyl acetate (40 mL×2). The combined organic phases were washed with brine, dried over anhydrous Na₂SO₄, filtered and concentrated. The residue was purified by column chromatography on silica gel (eluted with DCM:Ethyl acetate=100:0 to 100:1) to give the title compound (400 mg, 67% yield). LC/MS (ESI) m/z: 384 (M+H)⁺.

Step 3: (2S,3S,4S)-tert-butyl 3-azido-2-(6-Bromopyridin-2-ylcarbamoyl)-4-hydroxypyrrolidine-1-carboxylate (S4a) and (2S,3R,4R)-tert-Butyl 4-azido-2-(6-bromopyridin-2-ylcarbamoyl)-3-hydroxypyrrolidine-1-carboxylate (S4b)

To a mixture of compound S3 (307 mg, 0.8 mmol) in DMF (6 mL) was added NH₄Cl (87 mg, 1.6 mmol), H₂O (432 mg, 24 mmol) and NaN₃ (312 mg, 4.8 mmol). The reaction mixture was heated to 100° C. for 1 hr. After cooling to room temperature, the mixture was diluted with EtOAc. The resulting mixture was washed with water, 10% aq. LiCl solution and brine successively, dried over anhydrous Na₂SO₄, filtered and concentrated. The residue was purified by column chromatography on silica gel (eluted with DCM:Ethyl acetate=20:1 to 2:1) to give the title mixture of S4a and S4b (228 mg, 67% yield). LC/MS (ESI) m/z: 427 (M+H)⁺.

Step 4: (2S,3S,4S)-tert-butyl 3-azido-2-(6-Bromopyridin-2-ylcarbamoyl)-4-fluoropyrrolidine-1-carboxylate (S5a) and (2R,3R,4R)-tert-Butyl 4-azido-2-(6-bromopyridin-2-ylcarbamoyl)-3-fluoropyrrolidine-1-carboxylate (S5b)

To a mixture of compound S4a and S4b (228 mg, 0.534 mmol) in DCM (12 mL) was added DAST (260 mg, 1.6 mmol) at −78° C. under N₂ atmosphere. The reaction was stirred at this temperature first for 2 hrs and then at room temperature for 16 hrs. The reaction was quenched with water (30 mL) and extracted with DCM (20 mL×2). The combined organic phases were washed with brine, dried over anhydrous Na₂SO₄, filtered and concentrated. The residue was purified by column chromatography on silica gel (eluted with DCM:Ethyl acetate=50:1 to 10:1) to give a mixture of S5a and S5b (95 mg, 42% yield) as light yellow solid. LC/MS (ESI) m/z: 429 (M+H)⁺.

Step 5: (2S,3S,4S)-3-azido-N-(6-Bromopyridin-2-yl)-4-fluoropyrrolidine-2-carboxamide (S6a) and (2R,3R,4R)-4-azido-N-(6-Bromopyridin-2-yl)-3-fluoropyrrolidine-2-carboxamide (S6b)

To a mixture of compound S5a and S5b (95 mg, 0.222 mmol) in DCM (1 mL) was added TFA (1 mL) and the reaction mixture was stirred at room temperature for 1 hr. Then the mixture was concentrated to dryness to give a mixture of S6a and S6b (80 mg, 82% yield) as a brown solid, which was directly used to the next reaction without further purification. LC/MS (ESI) m/z: 329 (M+H)⁺.

Step 6: (2S,3S,4S)-1-(2-(3-acetyl-5-(2-Bethylpyrimidin-5-yl)-1H-indazol-1-yl)acetyl)-3-azido-N-(6-bromopyridin-2-yl)-4-fluoropyrrolidine-2-carboxamide (S8a) and (2R,3R,4R)-1-(2-(3-Acetyl-5-(2-methylpyrimidin-5-yl)-1H-indazol-1-yl)acetyl)-4-azido-N-(6-bromopyridin-2-yl)-3-fluoropyrrolidine-2-carboxamide (S8b)

To a mixture of compound S6a and S6b (74 mg, 0.222 mmol), compound S7 (76 mg, 0.244 mmol) and DIPEA (87 mg, 0.166 mmol) in DMF (3 mL) were added HATU (169 mg, 0.444 mmol). The reaction was stirred at room temperature overnight. After dilution with EtOAc, the resulting mixture was washed with water and brine, dried over anhydrous Na₂SO₄ and concentrated. The residue was purified by column chromatography on silica gel (eluted with DCM:MeOH=100:0 to 50:1) to give a mixture of S8a and S8b (101 mg, 72% yield) as yellow solid. LC/MS (ESI) m/z: 621 (M+H)⁺.

Step 7: (2S,3S,4S)-1-(2-(3-Acetyl-5-(2-methylpyrimidin-5-yl)-1H-indazol-1-yl)acetyl)-3-amino-N-(6-bromopyridin-2-yl)-4-fluoropyrrolidine-2-carboxamide (427) and (2R,3S,4R)-1-(2-(3-Acetyl-5-(2-methylpyrimidin-5-yl)-1H-indazol-1-yl)acetyl)-4-amino-N-(6-bromopyridin-2-yl)-3-fluoropyrrolidine-2-carboxamide (428)

To a mixture of compound S8a and S8b (100 mg, 0.16 mmol) in THF/H₂O (8.8 mL, 10:1) was added PPh₃ (84 mg, 0.32 mmol). The reaction mixture was heated to 40° C. for 60 hrs. After cooling, the mixture was diluted with water (30 mL) and extracted with ethyl acetate (30 mL×2). The combined organic phases were washed with brine, dried over anhydrous Na₂SO₄, filtered and concentrated, the residue was purified via prep-HPLC to give the title compound 427 (16 mg, 17.1% yield) and 428 (5 mg, 5.2% yield) as a white solid.

428: ¹H-NMR (400 MHz, CDCl3) δ: 10.85 (s, 1H), 9.05 (d, J=7.0 Hz, 2H), 8.43 (s, 1H), 8.06 (d, J=8.1 Hz, 1H), 7.78-7.90 (m, 2H), 7.71 (t, J=8.0 Hz, 1H), 7.36 (d, J=7.7 Hz, 1H), 5.82 (d, J=17.3 Hz, 1H), 5.64 (d, J=17.2 Hz, 1H), 5.00-5.30 (m, 2H), 4.70 (d, J=7.2 Hz, 1H), 4.27 (ddd, J=30.6, 12.0, 4.2 Hz, 1H), 4.07 (dd, J=19.9, 12.5 Hz, 1H), 3.76-3.85 (m, 1H), 3.34 (s, 1H), 2.69 (s, 3H), 2.63 (s, 3H). LC/MS (ESI) m/z: 595 (M+H)⁺.

429: ¹H-NMR (400 MHz, CDCl₃) δ: 10.76 (s, 1H), 9.06 (s, 2H), 8.46 (s, 1H), 8.03 (d, J=8.1 Hz, 1H), 7.83-7.95 (m, 2H), 7.78 (t, J=8.0 Hz, 1H), 7.42 (d, J=7.6 Hz, 1H), 5.91 (d,

J=17.6 Hz, 1H), 5.47-5.63 (m, 3H), 4.79 (s, 1H), 4.34 (s, 1H), 4.24 (d, J=17.8 Hz, 2H), 3.49-3.54 (m, 1H), 2.62-2.73 (m, 5H), 2.31-2.35 (m, 1H).
(2S,3S,4S)-3-Acetamido-1-(2-(3-acetyl-5-(2-methyl-pyrimidin-5-yl)-1H-indazol-1-yl)acetyl)-N-(6-bromopyridin-2-yl)-4-fluoropyrrolidine-2-carboxamide (512) and (2R,3S,4R)-4-Acetamido-1-(2-(3-acetyl-5-(2-methylpyrimidin-5-yl)-1H-indazol-1-yl)acetyl)-N-(6-bromopyridin-2-yl)-3-fluoropyrrolidine-2-carboxamide (513)
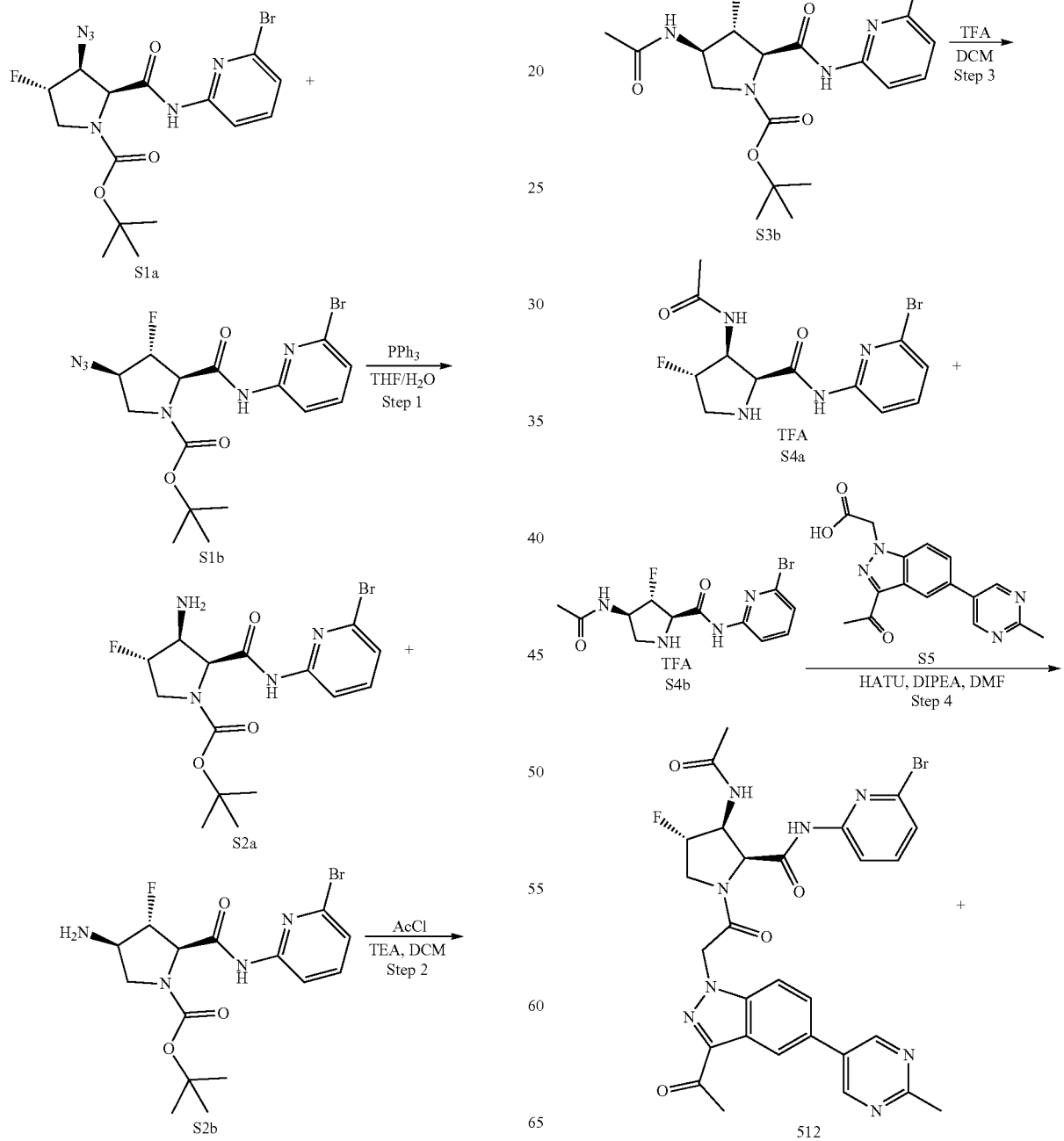

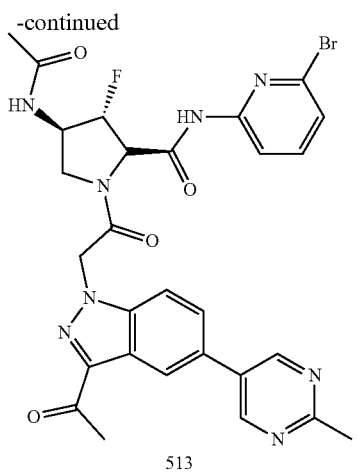

513

Step 1: (2S,3S,4S)-tert-Butyl 3-amino-2-(6-bromopyridin-2-ylcarbamoyl)-4-fluoropyrrolidine-1-carboxylate (S2a) and (2R,3S,4R)-tert-butyl 4-amino-2-(6-bromopyridin-2-ylcarbamoyl)-3-fluoropyrrolidine-1-carboxylate (S2b)

To a mixture of compound S1a and S1b (585 mg, 1.36 mmol) in THF/H$_2$O (30 mL, 5:1) was added PPh$_3$ (500 mg, 1.91 mmol). The reaction mixture was heated to 40° C. for 70 hrs. After cooling to room temperature, the mixture was diluted with water (40 mL) and extracted with ethyl acetate (40 mL×2). The combined organic phases were washed with brine, dried over anhydrous Na$_2$SO$_4$, filtered, concentrated, purified by column chromatography on silica gel to give a mixture of S2a and S2b (500 mg, 91% yield). LC/MS (ESI) m/z: 403 (M+H)$^+$.

Step 2: (2S,3S,4S)-tert-Butyl 3-acetamido-2-(6-bromopyridin-2-ylcarbamoyl)-4-fluoropyrrolidine-1-carboxylate (S3a) and (2R,3S,4R)-tert-butyl 4-acetamido-2-(6-bromopyridin-2-ylcarbamoyl)-3-fluoropyrrolidine-1-carboxylate (S3b)

To a mixture of compound S2a and S2b (120 mg, 0.3 mmol) in dry DCM (15 mL) was added Et$_3$N (92 mg, 0.9 mmol) and acetyl chloride (34 mg, 0.42 mmol) at 0° C. The reaction was stirred at room temperature for 1 hr. Then the mixture was diluted with water (20 mL) and extracted with ethyl acetate (20 mL×2). The combined organic phases were washed with brine, dried over anhydrous Na$_2$SO$_4$, filtered and concentrated to give a mixture of S3a and S3b (130 mg, 97% yield) as a yellow solid. LC/MS (ESI) m/z: 445 (M+H)$^+$.

Step 3: (2S,3S,4S)-3-Acetamido-N-(6-bromopyridin-2-yl)-4-fluoropyrrolidine-2-carboxamide (S4a) and (2R,3R,4R)-4-azido-N-(6-bromopyridin-2-yl)-3-fluoropyrrolidine-2-carboxamide (S4)

To a mixture of compound S3a and S3b (130 mg, 0.29 mmol) in DCM (2 mL) was added TFA (2 mL) and the reaction was stirred at room temperature for 1 hr. Then the mixture was concentrated under reduced pressure to give a mixture of S4a and S4b (100 mg, 78% yield) without further purification. LC/MS (ESI) m/z: 345 (M+H)$^+$.

Step 4: (2S,3S,4S)-3-Acetamido-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide (512) and (2R,3S,4R)-4-acetamido-1-(2-(3-acetyl-5-(2-methylpyrimidin-5-yl)-1H-indazol-1-yl)acetyl)-N-(6-bromopyridin-2-yl)-3-fluoropyrrolidine-2-carboxamide (513)

To a solution of compound S4a and S4b (100 mg, 0.3 mmol), S5 (100 mg, 0.33 mmol) and DIPEA (117 mg, 0.9 mmol) in DMF (3 mL) was added HATU (228 mg, 0.6 mmol). The reaction was stirred overnight. The mixture was diluted with EtOAc and washed with 10% aq. LiCl solution and brine, dried over anhydrous Na$_2$SO$_4$ and concentrated to dryness. The residue was purified via prep-HPLC to give a mixture of 512 (41 mg, 21% yield) and 513 (14 mg, 7% yield) as a white solid. LC/MS (ESI) m/z: 637 (M+H)$^+$.

512: $^1$H-NMR (400 MHz, CDCl3) δ: 11.02 (s, 1H), 9.04 (d, J=2.0 Hz, 2H), 8.40-8.47 (m, 1H), 8.24 (d, J=8.6 Hz, 1H), 8.00 (d, J=8.1 Hz, 1H), 7.80-7.91 (m, 2H), 7.71 (t, J=8.0 Hz, 1H), 7.36 (d, J=7.6 Hz, 1H), 5.80 (d, J=17.3 Hz, 1H), 5.62 (d, J=17.3 Hz, 1H), 5.20-5.39 (m, 1H), 4.80-4.96 (m, 2H), 4.28-4.40 (m, 1H), 4.06-4.14 (m, 1H), 2.64 (d, J=16.4 Hz, 6H), 1.75 (s, 3H). LC/MS (ESI) m/z: 637 (M+H)$^+$.

513: $^1$H-NMR (400 MHz, CDCl3) δ: 11.19 (s, 1H), 9.04 (s, 2H), 8.43 (s, 1H), 8.21 (d, J=6.1 Hz, 1H), 8.02 (d, J=8.1 Hz, 1H), 7.89 (dd, J=6.8, 5.3 Hz, 2H), 7.71-7.78 (m, 1H), 7.37 (d, J=7.6 Hz, 1H), 5.81 (d, J=17.2 Hz, 1H), 5.66 (d, J=17.4 Hz, 1H), 5.09-5.26 (m, 1H), 4.74 (d, J=23.2 Hz, 1H), 4.52-4.60 (m, 1H), 4.23-4.30 (m, 1H), 3.79 (dd, J=10.9, 5.4 Hz, 1H), 2.56-2.80 (m, 6H), 1.85 (s, 3H). LC/MS (ESI) m/z: 637 (M+H)$^+$.

(2S,3S,4S)-1-(2-(3-Acetyl-5-(2-methylpyrimidin-5-yl)-1H-indazol-1-yl)acetyl)-N-(6-bromopyridin-2-yl)-4-fluoro-3-hydroxypyrrolidine-2-carboxamide (346)

Scheme 88.

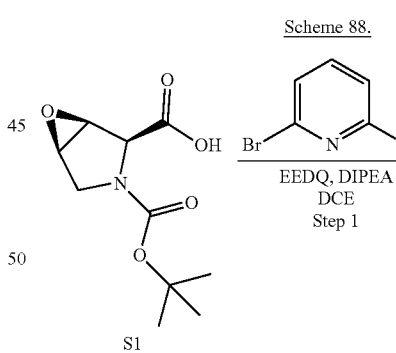

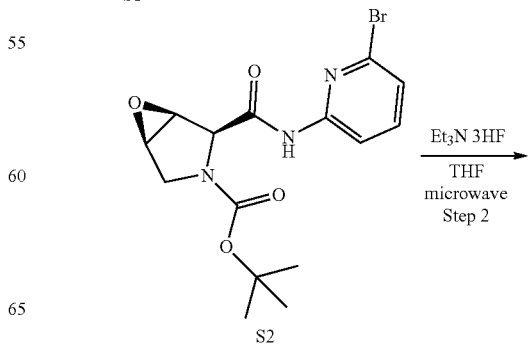

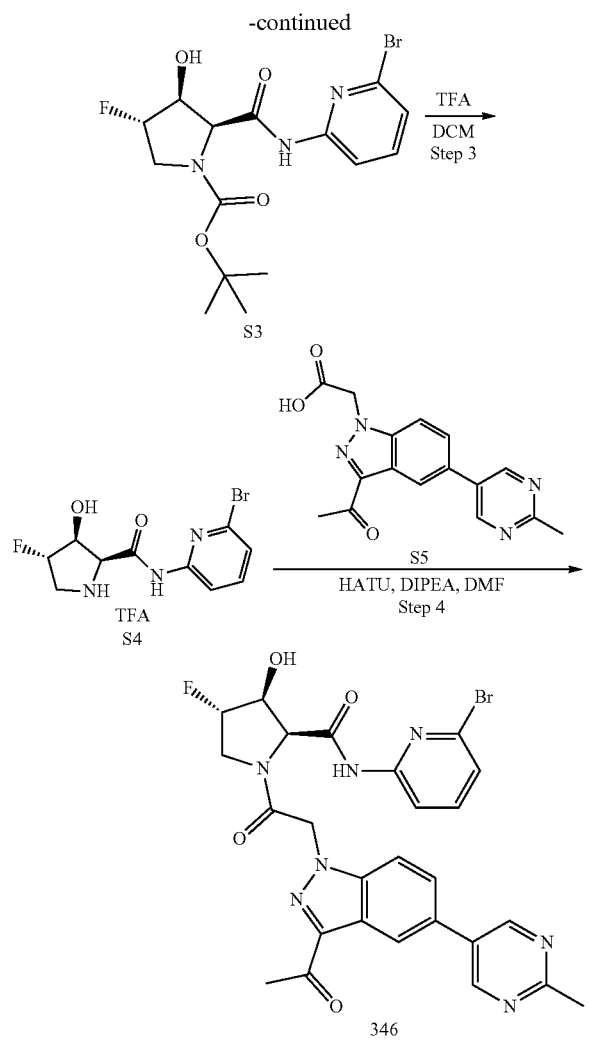

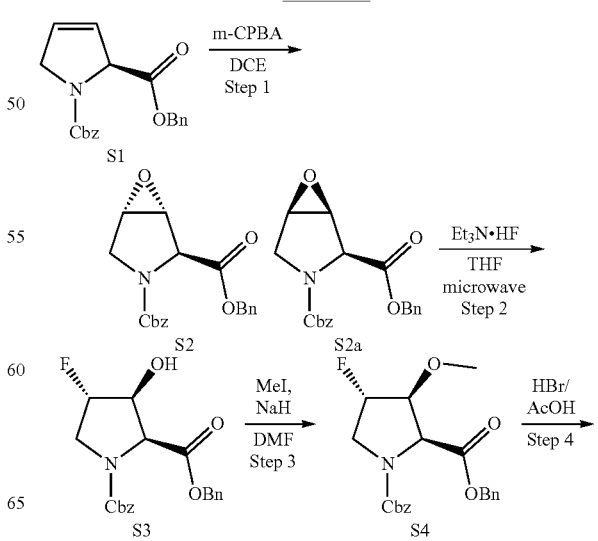

over anhydrous Na₂SO₄, filtered and concentrated. The residue was purified by column chromatography on silica gel (eluted with DCM:MeOH=100:0 to 20:1) to give the title compound (20 mg, 9% yield) as a colorless oil. LC/MS (ESI) m/z: 404 (M+H)⁺.

Step 3: (2S,3S,4S)—N-(6-Bromopyridin-2-yl)-4-fluoro-3-hydroxypyrrolidine-2-carboxamide (S4)

To a mixture of compound S3 (20 mg, 0.05 mmol) in DCM (1 mL) was added TFA (0.3 mL) and the reaction was stirred at room temperature for 1 hr. Then the mixture was concentrated to dryness to give the title compound (20 mg, 97% yield) as a brown solid, which was directly used to the next reaction without further purification. LC/MS (ESI) m/z: 304 (M+H)⁺.

Step 4: (2S,3S,4S)-1-(2-(3-Acetyl-5-(2-methylpyrimidin-5-yl)-1H-indazol-1-yl)acetyl)-N-(6-bromopyridin-2-yl)-4-fluoro-3-hydroxypyrrolidine-2-carboxamide (346)

To a solution of compound S4 (20 mg, 0.05 mmol), S5 (18 mg, 0.055 mmol) and DIPEA (20 mg, 0.15 mmol) in DMF (2 mL) was added HATU (38 mg, 0.1 mmol). The reaction was stirred at room temperature overnight. The mixture was diluted with 10% of LiCl solution and extracted with EtOAc three times. The combined organic phases were washed with brine, dried over anhydrous Na₂SO₄, filtered and then concentrated. The residue was purified by prep-HPLC (eluted with CH₃CN/water) to give the title compound 346 (3 mg, 10% yield) as a white solid. ¹H-NMR (400 MHz, CDCl3) δ: 10.78 (s, 1H), 9.03 (s, 2H), 8.43 (s, 1H), 8.05 (d, J=8.1 Hz, 1H), 7.66-7.92 (m, 3H), 7.32 (d, J=7.7 Hz, 1H), 6.04-6.14 (m, 1H), 5.66-5.85 (m, 2H), 5.20-5.25 (m, 1H), 5.07-5.13 (m, 1H), 4.67-4.74 (m, 1H), 4.52-4.62 (m, 1H), 4.09-4.17 (m, 1H), 2.67 (d, J=13.9 Hz, 3H), 2.44 (s, 3H). LC/MS (ESI) m/z: 596 (M+H)⁺.

(2S,3S,4S)-1-(2-(3-Acetyl-5-(2-methylpyrimidin-5-yl)-1H-indazol-1-yl)acetyl)-N-(6-bromopyridin-2-yl)-4-fluoro-3-methoxypyrrolidine-2-carboxamide (393)

Scheme 89.

Step 1: (1S,2S,5R)-tert-Butyl 2-(6-bromopyridin-2-ylcarbamoyl)-6-oxa-3-azabicyclo[3.1.0]hexane-3-carboxylate (S2)

To a solution of compound S1 (1145 mg, 5 mmol) in DCE (20 mL) was added 6-bromopyridin-2-amine (860 mg, 5 mmol), EEDQ (2232 mg, 9 mmol) and DIPEA (1950 mg, 15 mmol). The reaction was stirred at reflux overnight under N₂ atmosphere. After cooling to room temperature, the mixture was concentrated to dryness and the residue was purified by column chromatography on silica gel (eluted with petroleum ether:ethyl acetate=12:1 to 2:1) to give the title compound (208 mg, 11% yield) as a yellow solid. LC/MS (ESI) m/z: 384 (M+H)⁺.

Step 2: (2S,3S,4S)-tert-Butyl 2-(6-bromopyridin-2-ylcarbamoyl)-4-fluoro-3-hydroxypyrrolidine-1-carboxylate (S3)

To a mixture of compound S2 (208 mg, 0.54 mmol) in THF (1.5 mL) was added triethylamine trihydrofluoride (6 mL). The reaction was stirred at 130° C. for 40 min under microwave condition. Then the reaction was quenched with aq. NaHCO₃ and extracted with ethyl acetate (30 mL×2). The combined organic phases were washed with brine, dried

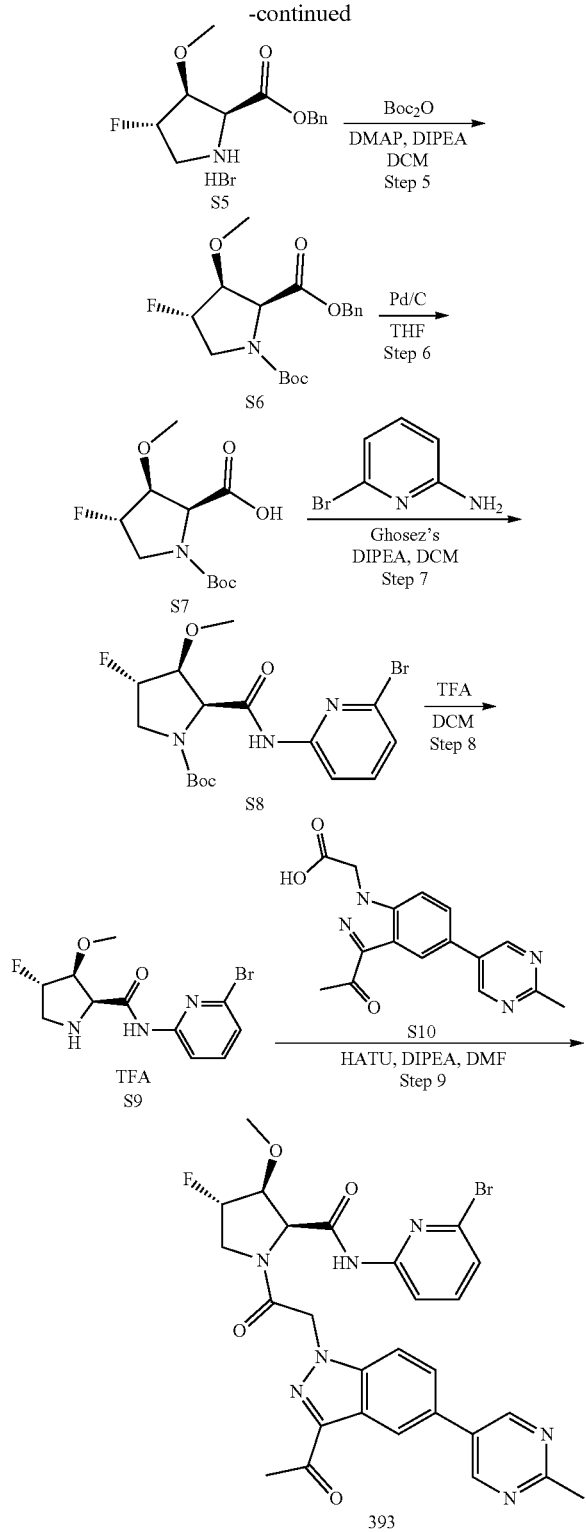

Step 1: (1R,2S,5S)-Dibenzyl 6-oxa-3-azabicyclo[3.1.0]hexane-2,3-dicarboxylate and (1S,2S,5R)-dibenzyl 6-oxa-3-azabicyclo[3.1.0]hexane-2,3-dicarboxylate (S2)

To a mixture of compound S1 (10.5 g, 31.16 mmol) in DCE (120 mL) was added m-CPBA (7 g, 40.5 mmol) and the reaction mixture was refluxed for 5 hrs. After cooling to room temperature, the reaction was quenched with aq. $Na_2S_2O_3$ solution (20%, 200 mL) and extracted with DCM (200 mL×2). The combined organic phases were washed with brine, dried over anhydrous $Na_2SO_4$, filtered and then concentrated. The residue was purified by column chromatography on silica gel (eluted with petroleum ether:ethyl acetate=100:0 to 20:1) to give the title compound S2 (5 g, 45% yield) and compound S2a (1.8 g, 17% yield) as white solid. LC/MS (ESI) m/z: 354 (M+H)$^+$.

Step 2: ((2S,3S,4S)-Dibenzyl 4-fluoro-3-hydroxy-pyrrolidine-1,2-dicarboxylate (S3)

To a mixture of compound S2 (550 mg, 1 mmol) in THF (1 mL) was added triethylamine trihydrofluoride (5 mL). The reaction was stirred at 130° C. for 3 hrs in a microwave reactor. The reaction was quenched with aq. $NaHCO_3$ solution and extracted with ethyl acetate (30 mL×2). The combined organic phases were washed with brine, dried over anhydrous $Na_2SO_4$, filtered and concentrated. The residue was purified by column chromatography on silica gel (eluted with DCM:MeOH=100:0 to 20:1) to give the title compound (430 mg, 73% yield) as a colorless oil. LC/MS (ESI) m/z: 374 (M+H)$^+$.

Step 3: (2S,3S,4S)-Dibenzyl 4-fluoro-3-methoxypyrrolidine-1,2-dicarboxylate (S4)

To a mixture of compound S3 (430 mg, 1.15 mmol) in dry DMF (10 ml) was added NaH (48 mg, 1.21 mmol) in portions at 0° C. and the reaction was stirred for 30 min. After addition of MeI (654 mg, 4.6 mmol), the reaction mixture was stirred at 0° C. for another 30 min. The reaction was quenched with aq. LiCl solution (10%, 40 mL) and extracted with ethyl acetate (30 mL×2). The combined organic phases were washed with brine, dried over anhydrous $Na_2SO_4$, filtered and concentrated. The residue was purified by column chromatography on silica gel (eluted with petroleum ether:ethyl acetate=100:0 to 10:1) to give the title compound S5 (430 mg, 96% yield) as yellow solid. LC/MS (ESI) m/z: 388 (M+H)$^+$.

Step 4: (2S,3S,4S)-Benzyl 4-fluoro-3-methoxypyrrolidine-2-carboxylate hydrobromide (S5)

Compound S4 (400 mg, 1.03 mmol) was added to HBr/AcOH solution (20 mL, 18%, w/w) at 0° C. and the reaction was stirred at room temperature for 2 hrs. The mixture was concentrated to dryness and the residue was washed with $Et_2O$ (20 mL), filtered and dried under vacuum to give the title compound (310 mg, 90.0% yield) as a light yellow solid, which was directly used to the next reaction without further purification. LC/MS (ESI) m/z: 254 (M+H)$^+$.

Step 5: (2S,3S,4S)-2-Benzyl 1-tert-butyl 4-fluoro-3-methoxypyrrolidine-1,2-dicarboxylate (S6)

To a mixture of compound S5 (295 mg, 1.16 mmol) and $Boc_2O$ (381 mg, 1.76 mmol) in DCM (10 mL) was added DIPEA (454 mg, 3.5 mmol) and DMAP (10 mg, cat. amount). The reaction was stirred at room temperature for 16 hrs. The mixture was diluted with water (30 mL) and extracted with DCM (30 mL×2). The combined organic phases were washed with brine, dried over anhydrous Na₂SO₄, filtered and concentrated. The residue was purified by column chromatography on silica gel (eluted with petroleum ether:ethyl acetate=40:1 to 10:1) to give the title compound (290 mg, 89% yield). LC/MS (ESI) m/z: 354 (M+H)⁺.

Step 6: (2S,3S,4S)-1-(tert-Butoxycarbonyl)-4-fluoro-3-methoxypyrrolidine-2-carboxylic acid (S7)

To a solution of compound S6 (280 mg, 1 mmol) in THF (10 mL) was added Pd/C (50 mg, 10%) and the reaction mixture was stirred at room temperature for 16 hrs under a H₂ balloon. Then the mixture was filtered and the filtrate was concentrated to dryness to give the title compound (200 mg, 99% yield) as yellow oil. LC/MS (ESI) m/z: 264 (M+H)⁺.

Step 7: (2S,3S,4S)-tert-Butyl 2-(6-bromopyridin-2-ylcarbamoyl)-4-fluoro-3-methoxypyrrolidine-1-carboxylate (S8)

To a mixture of compound S7 (20 mg, 0.08 mmol) in dry DCM (8 mL) was added 1-chloro-N,N,2-trimethylpropenylamine (12 mg, 0.088 mmol) at 0° C. under N₂ atmosphere and the reaction was stirred at 0° C. for 3 hrs, followed by addition of 6-bromopyridin-2-amine (28 mg, 0.16 mmol) and DIPEA (42 mg, 0.32 mmol). Then the reaction was stirred at room temperature for 16 hrs. The mixture was diluted with DCM and washed with saturated aq. NaHCO₃ solution and brine successively, dried over anhydrous Na₂SO₄, filtered, and concentrated. The residue was purified via pre-TLC to give the title compound (30 mg, 88% yield). LC/MS (ESI) m/z: 418 (M+H)⁺.

Step 8: (2S,3S,4S)—N-(6-Bromopyridin-2-yl)-4-fluoro-3-methoxypyrrolidine-2-carboxamide (S9)

To a mixture of compound S8 (30 mg, 0.072 mmol) in DCM (1 mL) was added TFA (0.5 mL) and the reaction mixture was stirred at room temperature for 1 hr. Then the mixture was concentrated under reduced pressure to give the title compound (31 mg, 100% yield) as a yellow solid, which was directly used to the next reaction without further purification. LC/MS (ESI) m/z: 318 (M+H)⁺.

Step 9: (2S,3S,4S)-1-(2-(3-Acetyl-5-(2-methylpyrimidin-5-yl)-1H-indazol-1-yl)acetyl)-N-(6-bromopyridin-2-yl)-4-fluoro-3-methoxypyrrolidine-2-carboxamide (393)

To a solution of compound S8 (30 mg, 0.072 mmol), S9 (25 mg, 0.08 mmol) and DIPEA (29 mg, 0.216 mmol) in DMF (2 mL) was added HATU (55 mg, 0.144 mmol). The resulting was stirred at room temperature overnight. The mixture was diluted with EtOAc and washed with 10% aq. LiCl solution and brine successively, dried over anhydrous Na₂SO₄, filtered and then concentrated. The residue was purified by prep-HPLC (eluted with CH₃CN/water) to give the title compound (2 mg, yield 5%) as a white solid. ¹H-NMR (400 MHz, CDCl3) δ: 10.98 (s, 1H), 9.03 (s, 2H), 8.42 (s, 1H), 8.04 (d, J=8.4 Hz, 1H), 7.86 (s, 1H), 7.71 (t, J=8.0 Hz, 1H), 7.33 (d, J=7.7 Hz, 1H), 7.23 (d, J=7.5 Hz, 1H), 5.75 (d, J=25.6 Hz, 2H), 5.46-5.53 (m, 1H), 5.34-5.40 (m, 1H), 4.89 (d, J=7.2 Hz, 1H), 4.30-4.38 (m, 1H), 4.11 (d, J=17.3 Hz, 1H), 3.41 (s, 3H), 2.66 (d, J=15.5 Hz, 3H), 2.48 (s, 3H). LC/MS (ESI) m/z: 610 (M+H)⁺.

(2S,3S,4S)-1-(2-(3-Acetyl-5-(2-methylpyrimidin-5-yl)-1H-indazol-1 yl)acetyl)-2-((6-bromopyridin-2-yl)carbamoyl)-4-fluoropyrrolidin-3-yl acetate (452)

Scheme 90.

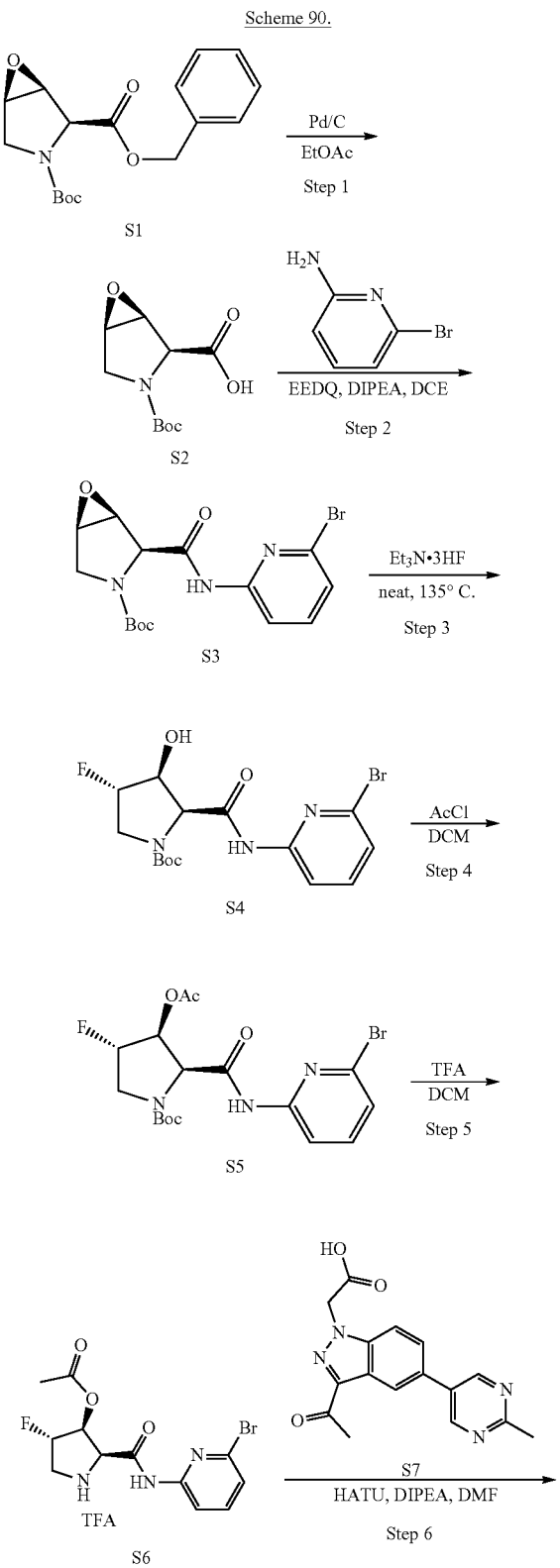

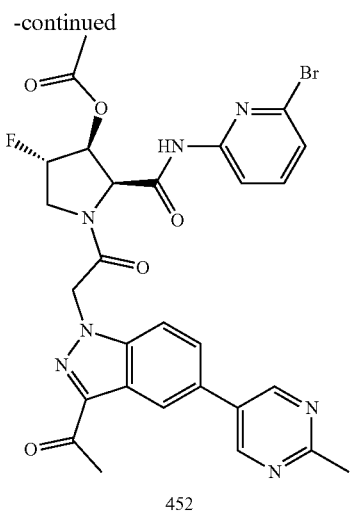

452

Step 1: (1S,2S,5R)-3-(tert-Butoxycarbonyl)-6-oxa-3-azabicyclo[3.1.0]hexane-2 carboxylic acid (S2)

To a solution of (1S,2S,5R)-2-benzyl 3-tert-butyl 6-oxa-3-azabicyclo[3.1.0]hexane 2,3-dicarboxylate (2.0 g, 6.26 mmol) in EtOAc (20 mL) was added Pd/C (200 mg, 10%) and the reaction was stirred at room temperature under a H$_2$ balloon overnight. The mixture was filtered and the filtrate was evaporated under reduced pressure to give the title compound (1.4 g, 97.5% yield) as yellow solid, which was directly used to the next reaction without further purification.

Step 2: (1S,2S,5R)-tert-Butyl 2-((6-bromopyridin-2-yl)carbamoyl)-6-oxa-3 azabicyclo[3.1.0]hexane-3-carboxylate (S3)

To a solution of (1S,2S,5R)-3-(tert-butoxycarbonyl)-6-oxa-3-azabicyclo[3.1.0]hexane 2-carboxylic acid (400 mg, 1.75 mmol), 6-bromopyridin-2-amine (330 mg, 1.92 mmol) in DCE (10 mL) was added EEDQ (865 mg, 3.50 mmol). The reaction mixture was stirred at 90° C. overnight and evaporated under reduced pressure. The residue was purified by chromatography on silica gel (PE:EtOAc=5:1 to 3:1) to give the title compound (160 mg, 23.8% yield) as a brown solid.

Step 3: (2S,3S,4S)-tert-Butyl 2-((6-bromopyridin-2-yl)carbamoyl)-4-fluor-3-hydroxypyrrolidine-1-carboxylate (S4)

A solution of (1S,2S,5R)-tert-butyl 2-((6-bromopyridin-2-yl)carbamoyl)-6-oxa-3 azabicyclo[3.1.0]hexane-3-carboxylate (200 mg, 0.52 mmol) in THF (0.05 mL) was added Et$_3$N'3HF (841 mg, 5.2 mmol) in a sealed tube. Then the reaction was stirred at 135° C. for 30 minutes. The mixture was partitioned with EtOAc and water. The organic layer was washed with brine, dried over anhydrous Na$_2$SO$_4$ and concentrated under reduced pressure. The residue was purified by chromatography on silica gel (PE:EtOAc=8:1 to 4:1) to give the title compound (46 mg, 21.9% yield) as white solid.

Step 4: (2S,3S,4S)-tert-Butyl 3-acetoxy-2-((6-bromopyridin-2-yl)carbamoyl)-4-fluoropyrrolidine-1-carboxylate (S5)

To a mixture of (2S,3S,4S)-tert-butyl 2-((6-bromopyridin-2-yl)carbamoyl)-4-fluoro-3-hydroxypyrrolidine-1-carboxy-late (45 mg, 0.11 mmol), TEA (26 mg, 0.24 mmol) and DMAP (1.2 mg, 0.01 mmol) in DCM (3 mL) was added acetyl chloride (14.5 mg, 0.19 mmol). The reaction was stirred at room temperature for 3 hrs. The mixture was partitioned with EtOAc and water. The organic layer was washed with brine, dried over anhydrous Na$_2$SO$_4$ and concentrated under reduced pressure. The residue was purified by pre-TLC (PE:EtOAc=2:1) to give the title compound (22 mg, 41.5% yield) as a light yellow oil.

Step 5: (2S,3S,4S)-2-((6-Bromopyridin-2-yl)carbamoyl)-4-fluoropyrrolidin-3-yl acetate (S6)

To a solution of (2S,3S,4S)-tert-butyl 3-acetoxy-2-((6-bromopyridin-2-yl)carbamoyl)-4-fluoropyrrolidine-1-carboxylate (22 mg, 0.049 mmol) in DCM (1 mL) was added TFA (0.5 mL) at 0° C. and the reaction was stirred at room temperature for 1 hr and evaporated under reduced pressure to give the title compound (20 mg, 100% yield), which was directly used to the next reaction without further purification.

Step 6: (2S,3S,4S)-1-(2-(3-Acetyl-5-(2-methylpyrimidin-5-yl)-1H-indazol-1-yl) acetyl)-2-((6-bromopyridin-2-yl)carbamoyl)-4-fluoropyrrolidin-3-yl acetate (S7)

A mixture of compound S6 (22 mg, 0.05 mmol), S7 (17.1 mg, 0.055 mmol), HATU (28.5 mg, 0.075 mmol) and DIPEA (0.03 mL, 0.15 mmol) in DMF (2 mL) was stirred at room temperature overnight. The mixture was partitioned with EtOAc and water. The organic layer was washed with brine, dried over anhydrous Na$_2$SO$_4$ and concentrated under reduced pressure. The residue was purified by prep-HPLC to give the title compound (8.6 mg, yield 27.0%) as white solid. $^1$H NMR (400 MHz, DMSO-d6) δ: 11.04 (s, 1H), 9.04 (d, J=1.9 Hz, 2H), 8.43 (s, 1H), 7.97 (d, J=8.1 Hz, 1H), 7.88 (d, J=1.1 Hz, 2H), 7.73 (t, J=8.0 Hz, 1H), 7.35 (d, J=7.7 Hz, 1H), 5.87 (d, J=17.3 Hz, 1H), 5.74 (d, J=17.4 Hz, 1H), 5.66 (m, 1H), 5.49 (s, 1H), 4.92 (d, J=6.2 Hz, 1H), 4.29-4.18 (m, 2H), 2.66 (d, J=13.7 Hz, 6H), 1.94 (s, 3H). LC/MS (ESI) m/z: 638 (M+H)$^+$.

(1R,3S,5S)-2-(2-(3-Acetyl-5-(2-Methylpyrimidin-5-yl)-1H-indazol-1-yl)acetyl)-N-(6-bromopyridin-2-yl)-5-(hydroxymethyl)-2-azabicyclo[3.1.0]hexane-3-carboxamide (392) & (1S,3S,5R)-2-(2-(3-Acetyl-5-(2-methylpyrimidin-5-yl)-1H-indazol-1-yl)acetyl)-N-(6-bromopyridin-2-yl)-5-(hydroxymethyl)-2-azabicyclo[3.1.0]hexane-3-carboxamide (383)

Scheme 91.

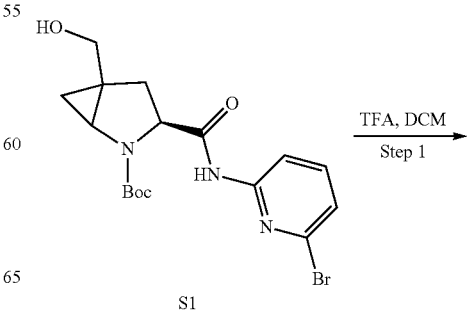

S1

317

-continued

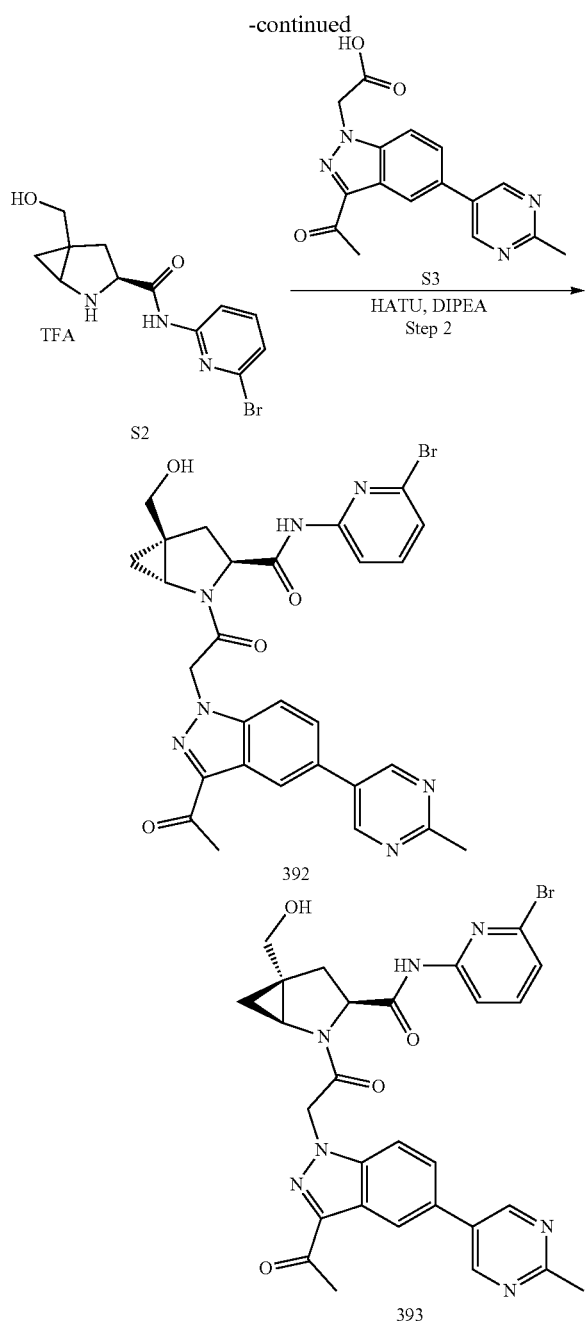

Step 1: (3S)—N-(6-Bromopyridin-2-yl)-5-(hydroxymethyl)-2-azabicyclo[3.1.0]hexane-3-carboxamide (S2)

To a solution of compound S1 (50 mg, 0.12 mmol) in DCM (1 mL) was added TFA (0.5 mL) at 0° C. The reaction was stirred at room temperature for 1 hr and evaporated under reduced pressure to give the title compound S2 (50 mg, 100% yield), which was directly used to the next reaction without further purification.

318

Step 2: (1R,3S,5S)-2-(2-(3-Acetyl-5-(2-Methylpyrimidin-5-yl)-1H-indazol-1-yl)acetyl)-N-(6-bromopyridin-2-yl)-5-(hydroxymethyl)-2-azabicyclo[3.1.0]hexane-3-carboxamide (392) & (1S,3S,5R)-2-(2-(3-Acetyl-5-(2-methylpyrimidin-5-yl)-1H-indazol-1-yl)acetyl)-N-(6-bromopyridin-2-yl)-5-(hydroxymethyl)-2-azabicyclo[3.1.0]hexane-3-carboxamide (383)

To a mixture of the compound S2 (40 mg, 0.13 mmol), S3 (40 mg, 0.13 mmol) and HATU (74 mg, 0.2 mmol) in DMF (3 mL) was added DIPEA (51 mg, 0.4 mmol). The reaction was stirred at room temperature for 16 hrs. The mixture was partitioned with EtOAc and water. The organic layer was washed with brine, dried over anhydrous Na$_2$SO$_4$ and concentrated under reduced pressure. The residue was purified by prep-HPLC to give 392 (5.6 mg, 7.1% yield) and 383 (3.9 mg, 4.9% yield) as white solid.

392: $^1$H NMR (400 MHz, CDCl$_3$) δ 8.94 (d, J=26.7 Hz, 3H), 8.58 (s, 1H), 8.07 (d, J=8.0 Hz, 1H), 7.65 (dd, J=8.7, 1.6 Hz, 1H), 7.59-7.48 (m, 2H), 7.22 (d, J=7.7 Hz, 1H), 5.56-5.44 (m, 2H), 4.86 (d, J=8.3 Hz, 1H), 4.05 (d, J=11.6 Hz, 1H), 3.41 (dd, J=7.2, 4.5 Hz, 2H), 2.79 (t, J=21.1 Hz, 7H), 2.22 (dd, J=13.9, 8.4 Hz, 1H), 1.38 (t, J=5.8 Hz, 2H), 1.06 (dd, J=5.7, 2.6 Hz, 1H), 0.88 (s, 2H). LC/MS (ESI) m/z: 604 (M+H)$^+$.

383: $^1$H NMR (400 MHz, CDCl$_3$) δ 9.02 (d, J=19.7 Hz, 3H), 8.60 (s, 1H), 8.04 (d, J=8.5 Hz, 1H), 7.67 (d, J=9.4 Hz, 2H), 7.53 (dd, J=10.2, 5.7 Hz, 1H), 7.21 (d, J=7.7 Hz, 1H), 5.53 (d, J=11.9 Hz, 2H), 5.03 (d, J=7.3 Hz, 1H), 3.90 (d, J=11.2 Hz, 1H), 3.65 (d, J=11.2 Hz, 1H), 3.57 (d, J=3.7 Hz, 1H), 2.88 (s, 3H), 2.73 (s, 3H), 2.58-2.46 (m, 2H), 1.30 (d, J=4.0 Hz, 2H), 1.01 (t, J=6.2 Hz, 1H). LC/MS (ESI) m/z: 604 (M+H)$^+$.

(1R,3S,5S)-2-(2-(3-Acetyl-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide (416) & (1S,3S,5R)-2-(2-(3-Acetyl-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide (417)

Scheme 92.

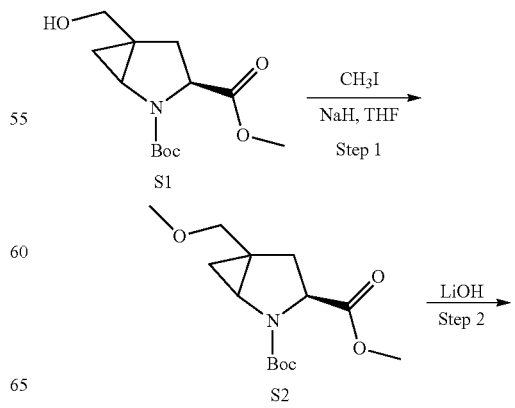

-continued

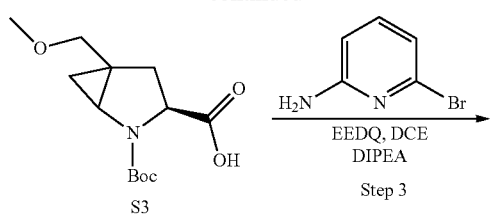

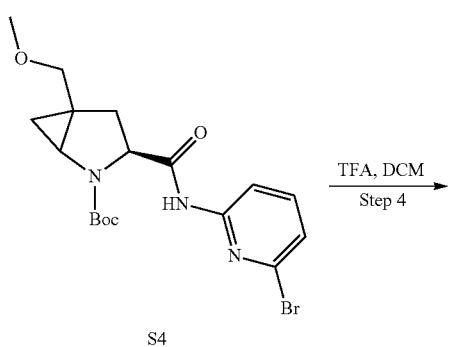

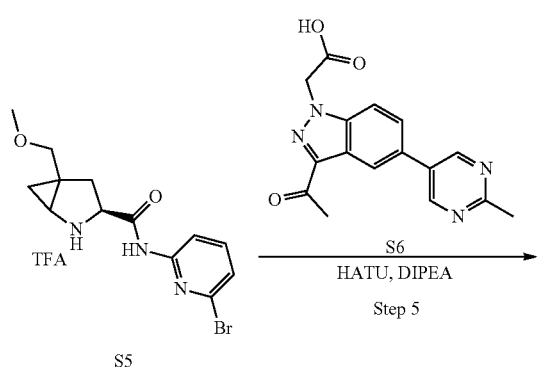

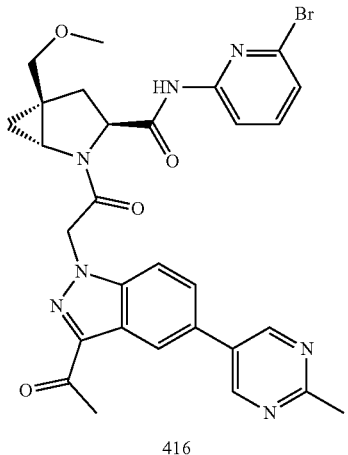

416

-continued

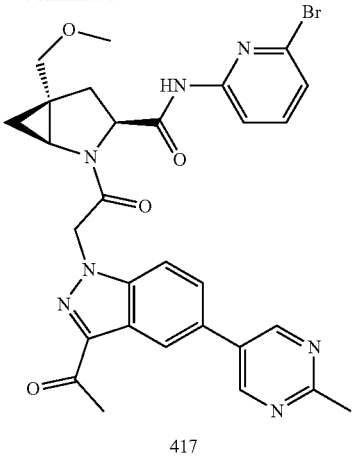

417

Step 1: (3S)-2-tert-Butyl 3-methyl-(methoxymethyl)-2-azabicyclo[3.1.0]hexane-2,3-dicarboxylate (S2)

To a solution of the compound S1 (180 mg, 0.66 mmol) in THF (5 mL) was added NaH (65 mg, 1.65 mmol, 60% dispersion in mineral oil). The reaction was stirred at 0° C. for 1 hr. MeI (280 mg, 2.0 mmol) was added to the mixture and the reaction was stirred at 0° C. for another 2 hrs. The reaction was quenched with aq. NH$_4$Cl solution and extracted with EtOAc twice. The combined organic layers were washed with brine and dried over anhydrous Na$_2$SO$_4$, filtered, and concentrated to give the crude product, which was purified by silica gel column (eluted with petroleum ether:ethyl acetate=5:1 to 2:1) to give the title compound (140 mg, 74% yield) as a colorless oil.

Step 2: (3S)-2-(tert-Butoxycarbonyl)-5-(methoxymethyl)-2-azabicyclo[3.1.0]hexane-3-carboxylic acid (S4)

To a solution of the compound S2 (140 mg, 0.49 mmol) in THF (2 mL) was added aq. LiOH solution (1 mL, 1 M). The reaction was stirred at room temperature for 2 hrs and then concentrated. The residue was acidified by adding 1 N aq. HCl solution to pH 3. The resulting mixture was extracted with EtOAc twice and the combined organic phases were washed with brine, dried over anhydrous Na$_2$SO$_4$ and concentrated to give the title compound (120 mg, 90% yield) as a white solid.

Step 3: (3S)-tert-Butyl 3-(6-bromopyridin-2-ylcarbamoyl)-5-(methoxymethyl)-2-azabicyclo[3.1.0] hexane-2-carboxylate (S5)

To a solution of the compound S3 (120 mg, 0.44 mmol), 6-bromopyridin-2-amine (77 mg, 0.44 mmol) and EEDQ (217 mg, 0.88 mmol) in 1,2-DCE (5 mL) was added DIPEA (170 mg, 1.32 mmol). The reaction was stirred at 90° C. for 16 hrs and concentrated. The residue was purified by silica gel column (eluted with petroleum ether:ethyl acetate=10:1 to 2:1) to give the title compound (55 mg, 29.3% yield) as white solid.

Step 4: (3S)—N-(6-Bromopyridin-2-yl)-5-(methoxymethyl)-2-azabicyclo[3.1.0]hexane-3-carboxamide (S6)

To a solution of the compound S4 (30 mg, 0.073 mmol) in DCM (1 mL) was added TFA (0.5 mL). The reaction was stirred at room temperature for 1.5 hrs and then concentrated to dryness to give the title compound (30 mg, 100% yield) as yellow solid, which was directly used to the next reaction without purification.

Step 5: (1R,3S,5S)-2-(2-(3-Acetyl-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide (416) & (1S,3S,5R)-2-(2-(3-Acetyl-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide (417)

To a solution of the compound S5 (30 mg, 0.73 mmol), S6 (22.6 mg, 0.73 mmol) and HATU (41.8 mg, 0.11 mmol) in DMF (2 mL) was added DIPEA (18.7 mg, 0.145 mmol). The reaction was stirred at room temperature for 16 hrs. The mixture was partitioned with EtOAc and water. The organic layer was washed with brine, dried over anhydrous Na$_2$SO$_4$ and concentrated under reduced pressure. The residue was purified by prep-HPLC to give 416 (5.5 mg, 12.2% yield) and 417 (3.1 mg, 6.86% yield) as white solid.

416: $^1$H NMR (400 MHz, CDCl$_3$) δ 8.91 (s, 3H), 8.58 (s, 1H), 8.10 (d, J=8.1 Hz, 1H), 7.69-7.64 (m, 1H), 7.58-7.51 (m, 2H), 7.21 (d, J=7.6 Hz, 1H), 5.51 (s, 2H), 4.74-4.71 (m, 1H), 3.54 (t, J=6.3 Hz, 2H), 3.41 (d, J=8.4 Hz, 4H), 2.81 (s, 3H), 2.72 (d, J=8.3 Hz, 4H), 2.32 (dd, J=13.8, 9.1 Hz, 1H), 1.42-1.34 (m, 2H), 1.00-0.93 (m, 1H). LC/MS (ESI) m/z: 619 (M+H)$^+$.

417: $^1$H NMR (400 MHz, CDCl$_3$) δ 8.93 (d, J=19.8 Hz, 3H), 8.56 (s, 1H), 8.03 (d, J=8.0 Hz, 1H), 7.67-7.58 (m, 2H), 7.51 (dd, J=9.7, 6.1 Hz, 1H), 7.20 (d, J=7.7 Hz, 1H), 5.57-5.42 (m, 2H), 5.06-4.94 (m, 1H), 3.66-3.52 (m, 2H), 3.42-3.21 (m, 4H), 2.81 (s, 3H), 2.72 (s, 3H), 2.56 (dd, J=13.2, 2.6 Hz, 1H), 2.50-2.42 (m, 1H), 1.27-1.21 (m, 1H), 0.97 (t, J=6.2 Hz, 1H). LC/MS (ESI) m/z: 619 (M+H)$^+$.

(3S)-2-(2-(3-Acetyl-5-(2-methylpyrimidin-5-yl)-1H-indazol-1-yl)acetyl)-5-(aminomethyl)-N-(6-bromopyridin-2-yl)-2-azabicyclo[3.1.0]hexane-3-carboxamide (454)

Scheme 93.

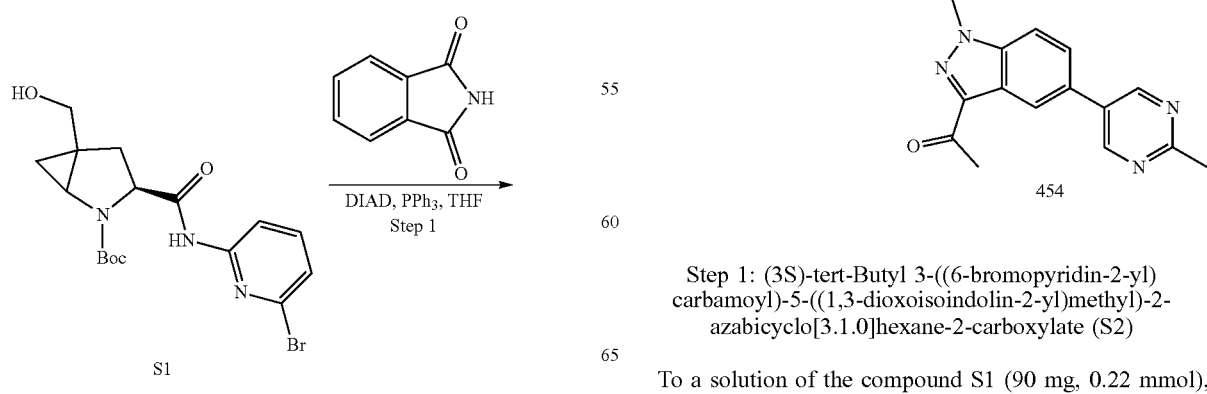

Step 1: (3S)-tert-Butyl 3-((6-bromopyridin-2-yl)carbamoyl)-5-(((1,3-dioxoisoindolin-2-yl)methyl)-2-azabicyclo[3.1.0]hexane-2-carboxylate (S2)

To a solution of the compound S1 (90 mg, 0.22 mmol), isoindoline-1,3-dione (32 mg, 0.22 mmol) and PPh$_3$ (175 mg, 0.66 mmol) in THF (3 mL) was added DIAD (133 mg, 0.66 mmol) dropwise at 0° C. under N₂ atmosphere. The reaction was stirred at room temperature for 16 hrs and concentrated to dryness. The residue was purified by silica gel column (eluted with petroleum ether:ethyl acetate=10:1 to 3:1) to give the title compound (110 mg, 93% yield) as a light yellow solid.

Step 2: (3S)—N-(6-Bromopyridin-2-yl)-5-((1,3-dioxoisoindolin-2-yl)methyl)-2-azabicyclo[3.1.0]-hexane-3-carboxamide (S3)

To a solution of the compound S2 (110 mg, 0.20 mmol) in DCM (2 mL) was added TFA (1 mL). The reaction was stirred at room temperature for 2 hrs and concentrated to dryness to give the title compound (120 mg, 100% yield), which was directly used to the next reaction without purification.

Step 3: (3S)-2-(2-(3-Acetyl-5-(2-methylpyrimidin-5-yl)-1H-indazol-1-yl)acetyl)-N-(6-bromopyridin-2-yl)-5-((1,3-dioxoisoindolin-2-yl)methyl)-2-azabicyclo[3.1.0]hexane-3-carboxamide (S4)

To a mixture of the compound S3 (110 mg, 0.2 mmol), S4 (65 mg, 0.2 mmol) and HATU (91.2 mg, 0.24 mmol) in DMF (2 mL) was added DIPEA (108 mg, 0.8 mmol). The reaction was stirred at room temperature for 16 hrs. The mixture was partitioned with EtOAc and water. The organic layer was washed with brine, dried over anhydrous Na₂SO₄ and concentrated under reduced pressure. The crude product was purified by silica gel column eluted with (DCM/MeOH=10/1) to give the title compound (80 mg, 54% yield) as white solid.

Step 3: (3S)-2-(2-(3-Acetyl-5-(2-methylpyrimidin-5-yl)-1H-indazol-1-yl)acetyl)-5-(aminomethyl)-N-(6-bromopyridin-2-yl)-2-azabicyclo[3.1.0]hexane-3-carboxamide (454)

To a solution of the compound S5 (80 mg, 0.11 mmol) in EtOH (5 mL) was added hydrazine hydrate (0.2 mL, 85%). The reaction was stirred at 50° C. for 3 hrs and then cooled to room temperature. The mixture was filtered. The filtrate was concentrated to dryness and the crude product was purified by prep-HPLC to give the title compound (3.6 mg, 5.4% yield) as a white solid. ¹H NMR (400 MHz, CD3OD) δ 9.01 (d, J=3.7 Hz, 2H), 8.55 (s, 1H), 8.03 (d, J=8.3 Hz, 1H), 7.81 (d, J=8.7 Hz, 2H), 7.61 (dd, J=13.7, 5.8 Hz, 1H), 7.25 (d, J=7.7 Hz, 1H), 5.74 (dd, J=28.0, 6.4 Hz, 1H), 5.34 (t, J=4.6 Hz, 1H), 5.08 (d, J=9.2 Hz, 1H), 3.93 (d, J=3.6 Hz, 1H), 3.42 (d, J=13.7 Hz, 1H), 3.08 (d, J=36.7 Hz, 1H), 2.70 (dd, J=19.2, 15.6 Hz, 7H), 2.38 (dd, J=13.7, 3.2 Hz, 1H), 2.21-2.16 (m, 1H), 1.69 (s, 1H), 1.23 (d, J=5.6 Hz, 1H).

(1R,3S,5R)-2-(2-(3-Acetyl-5-(2-methylpyrimidin-5-yl)-1H-indazol-1-yl)acetyl)-N-(6-bromopyridin-2-yl)-5-((dimethylamino)methyl)-2-azabicyclo[3.1.0]hexane-3-carboxamide (577) & (1S,3S,5S)-2-(2-(3-acetyl-5-(2-methylpyrimidin-5-yl)-1H-indazol-1-yl)acetyl)-N-(6-bromopyridin-2-yl)-5-((dimethylamino)methyl)-2-azabicyclo[3.1.0]hexane-3-carboxamide (578)

Scheme 94.

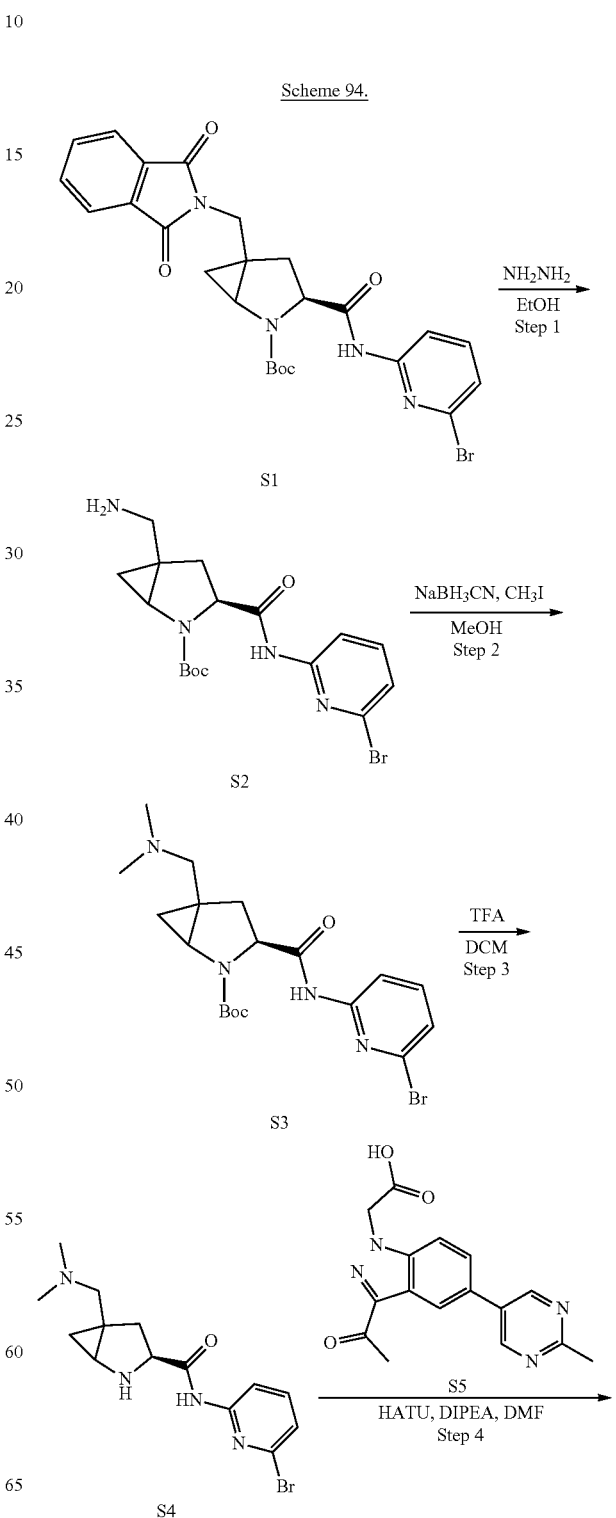

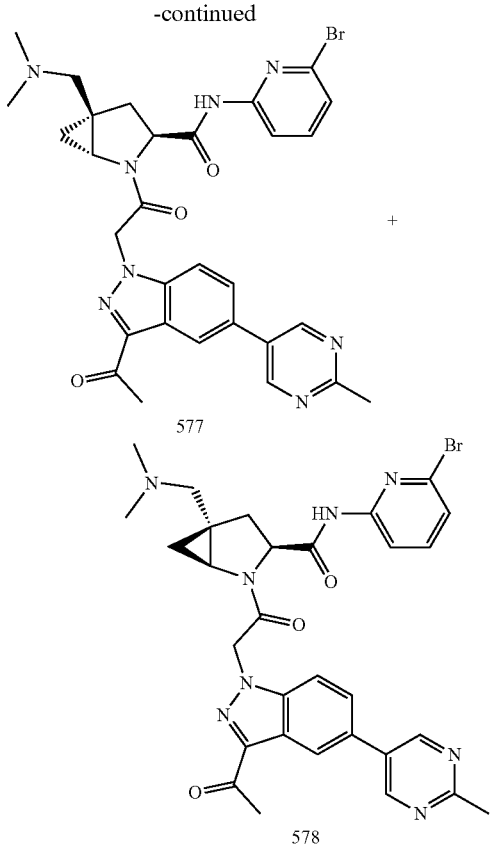

Step 1: (3S)-tert-Butyl 5-(aminomethyl)-3-((6-bromopyridin-2-yl)carbamoyl)-2-azabicyclo[3.1.0]hexane-2-carboxylate (S2)

To a solution of the compound S1 (190 mg, 0.35 mmol) in EtOH (5 mL) was added hydrazine hydrate (0.5 mL, 85%). The reaction was stirred at 50° C. for 3 hrs and cooled to room temperature. The mixture was filtered and the filtrate was concentrated to dryness. The crude product was purified by silica gel column eluted with (DCM/MeOH=50/1) to give the title compound (140 mg, 97% yield) as a white solid. LC/MS (ESI) m/z: 411 (M+H)$^+$.

Step 2: (3S)-tert-Butyl 5-(aminomethyl)-3-((6-bromopyridin-2-yl)carbamoyl)-2-azabicyclo[3.1.0]hexane-2-carboxylate (S3)

To a solution of the compound S2 (140 mg, 0.34 mmol) in MeOH (5 mL) was added NaBH$_3$CN (43 rag, 0.68 mmol) and aqueous 15% formaldehyde solution (0.5 mL). The reaction was stirred at room temperature for 30 min and concentrated to dryness. The residue was purified by silica gel column eluted with DCM/MeOH=30/1 to give the title compound (90 compound (140 mg, 68% yield) as white solid. LC/MS (ESI) m/z: 439 (M+H)$^+$.

Step 3: (3S)—N-(6-Bromopyridin-2-yl)-5-((dimethylamino)methyl)-2-azabicyclo[3.1.0]hexane-3-carboxamide (S4)

To a solution of the compound S3 (90 mg, 0.20 mmol) in DCM (3 mL) was added TFA (1 mL). The reaction was stirred at room temperature for 1.5 hrs and then concentrated under reduced pressure to give the title compound (85 mg, 100% yield) as yellow solid, which was directly used to the next reaction without further purification. LC/MS (ESI) m/z: 339 (M+H)$^+$.

Step 4: (1R,3S,5R)-2-(2-(3-Acetyl-5-(2-methylpyrimidin-5-yl)-1H-indazol-1-yl)acetyl)-N-(6-bromopyridin-2-yl)-5-((dimethylamino)methyl)-2-azabicyclo[3.1.0]hexane-3-carboxamide (577) & (1S,3S,5S)-2-(2-(3-Acetyl-5-(2-methylpyrimidin-5-yl)-1H-indazol-1-yl)acetyl)-N-(6-bromopyridin-2-yl)-5-((dimethylamino)methyl)-2-azabicyclo[3.1.0] hexane-3-carboxamide (578)

The title compound was prepared according the procedure for Scheme 92.

577: $^1$H NMR (400 MHz, CD3OD) δ 9.00 (s, 2H), 8.54 (s, 1H), 8.07 (d, J=8.1 Hz, 1H), 7.79 (d, J=1.3 Hz, 2H), 7.62 (t, J=7.9 Hz, 1H), 7.27 (d, J=7.7 Hz, 1H), 5.82 (d, J=17.1 Hz, 1H), 5.66 (d, J=17.1 Hz, 1H), 4.66 (s, 1H), 3.91 (dd, J=6.2, 2.9 Hz, 1H), 3.54 (d, J=13.4 Hz, 1H), 3.14 (d, J=13.5 Hz, 1H), 2.90 (s, 6H), 2.72 (d, J=20.9 Hz, 7H), 2.48 (dd, J=13.7, 4.6 Hz, 1H), 2.03 (d, J=6.0 Hz, 1H), 1.44 (s, 1H). LC/MS (ESI) m/z: 637 (M+H)$^+$.

578: $^1$H NMR (400 MHz, CD3OD) δ 9.00 (s, 2H), 8.54 (dt, J=2.5, 1.3 Hz, 1H), 8.05 (dd, J=16.3, 8.2 Hz, 1H), 7.79 (t, J=1.3 Hz, 2H), 7.61 (dt, J=9.1, 8.0 Hz, 1H), 7.25 (dd, J=10.4, 7.7 Hz, 1H), 5.81 (d, J=17.1 Hz, 1H), 5.66 (dd, J=17.1, 3.8 Hz, 1H), 5.09 (d, J=11.3 Hz, 1H), 3.87 (d, J=5.1 Hz, 1H), 3.47 (dd, J=38.9, 13.3 Hz, 1H), 2.91 (d, J=13.2 Hz, 1H), 2.86-2.55 (m, 13H), 2.43 (ddd, J=34.6, 13.6, 4.1 Hz, 1H), 1.77 (d, J=4.7 Hz, 1H), 1.36-1.23 (m, 1H). LC/MS (ESI) m/z: 637 (M+H)$^+$.

(2S,4S)-1-(2-(3-Acetyl-5-(2-methylpyrimidin-5-yl)-1H-indazol-1-yl)acetyl)-4-(aminomethyl)-N-(6-bromopyridin-2-yl)-4-fluoropyrrolidine-2-carboxamide (395)

Scheme 95.

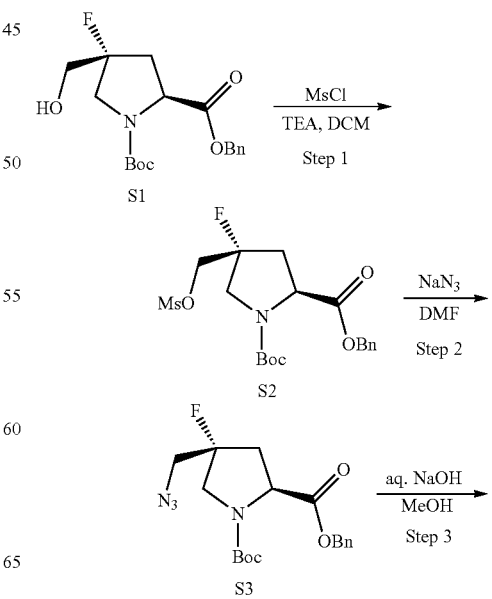

327
-continued

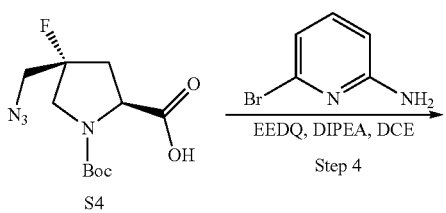

S4

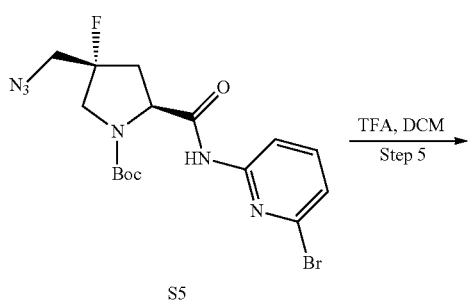

S5

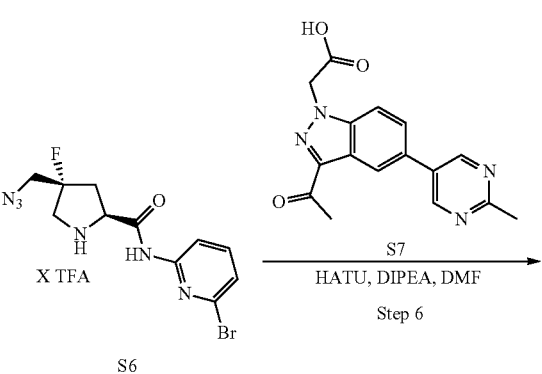

S6

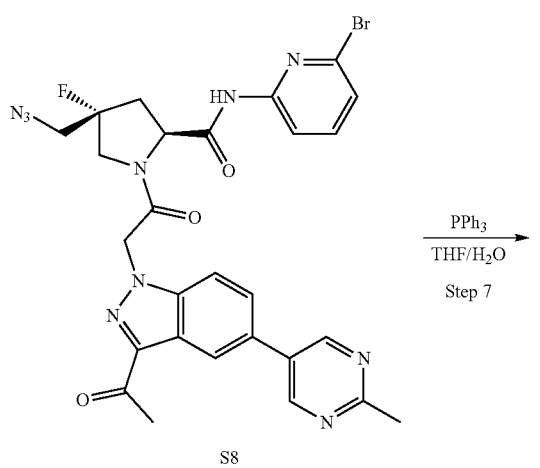

S8

328
-continued

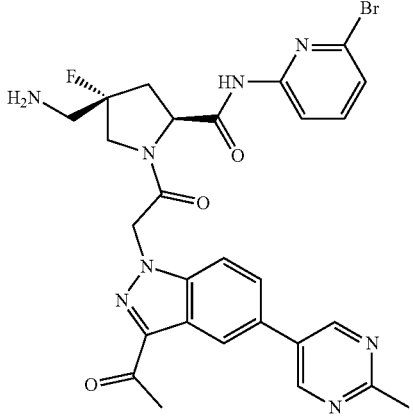

395

Step 1: (2S,4R)-4-Azidomethyl-4-fluoro-pyrrolidine-1,2-dicarboxylic acid 2-benzyl ester 1-tert-butyl ester (S2)

To a solution of (2S,4R)-4-fluoro-4-hydroxymethyl-pyrrolidine-1,2-dicarboxylic acid 2-benzyl ester 1-tert-butyl ester (950 mg, 2.7 mmol) in DCM (10 mL) was added TEA (0.75 mL, 5.4 mmol) and a solution of MsCl (371 mg, 3.2 mmol) in DCM (2 mL) at 0° C. Then the reaction was stirred at room temperature for 1 hr. The mixture was poured into ice water (30 mL) and extracted with DCM (3×20 mL). The combined organic layers were dried over anhydrous $Na_2SO_4$ and concentrated under reduced pressure to give compound S2 (1.0 g, crude), which was carried forward without further purification.

Step 2: (2S,4R)-2-Benzyl 1-tert-butyl 4-(azidomethyl)-4-fluoropyrrolidine-1,2-dicarboxylate (S3)

To a solution of (2S,4R)-4-azidomethyl-4-fluoro-pyrrolidine-1,2-dicarboxylic acid 2-benzyl ester 1-tert-butyl ester (950 mg, 2.2 mmol) in DMF (30 mL) was added $NaN_3$ (900 mg, 13.2 mmol) and the reaction was stirred at 80° C. overnight. The mixture was poured into ice water (30 mL) and extracted with EtOAc (3×20 mL). The combined organic layers were washed with brine, dried over anhydrous $Na_2SO_4$ and concentrated under reduced pressure. The residue was purified by chromatography on silica gel (PE:EtOAc=15:1 to 5:1) to give compound S3 (690 mg, 83.0% yield) as light oil.

Step 3: (2S,4R)-4-(Azidomethyl)-1-(tert-butoxycarbonyl)-4-fluoropyrrolidine-2-carboxylic acid (S4)

To a solution of (2S,4R)-2-benzyl 1-tert-butyl 4-(azidomethyl)-4-fluoropyrrolidine-1,2-dicarboxylate (690 mg, 1.8 mmol) in MeOH (8 mL) was added a 1 M aq. NaOH solution (3.6 mL, 3.6 mmol) at 0° C. and the reaction mixture was stirred at room temperature for 1 hr. The mixture was diluted with water (15 mL) and the volatiles were removed under reduced pressure. The residue was washed with $Et_2O$ (2×10 mL) and acidified with 2 N HCl to pH~3. The resulting mixture was extracted with EtOAc (2×15 mL) and the combined organic layers were dried over anhydrous $Na_2SO_4$ and concentrated under reduced pressure to give compound S4 (480 mg, 92.5% yield) as light oil.

Step 4: (2S,4R)-tert-Butyl 4-(azidomethyl)-2-((6-bromopyridin-2-yl)carbamoyl)-4-fluoropyrrolidine-1-carboxylate (S5)

A mixture of (2S,4R)-4-(azidomethyl)-1-(tert-butoxycarbonyl)-4-fluoropyrrolidine-2-carboxylic acid (480 mg, 1.67 mmol), 6-bromopyridin-2-amine (316 mg, 1.84 mmol), DIPEA (539 mg, 4.18 mmol) and EEDQ (825 mg, 3.34 mmol) in DCE (10 mL) was stirred at 90° C. overnight. The mixture was evaporated under reduced pressure and the residue was purified by chromatography on silica gel (PE:EtOAC=20:1 to 4:1) to give compound S5 (510 mg, 69.1% yield) as light oil.

Step 5: (2S,4R)-4-(Azidomethyl)-N-(6-bromopyridin-2-yl)-4-fluoropyrrolidine-2-carboxamide (S6)

To a solution of (2S,4R)-tert-butyl 4-(azidomethyl)-2-((6-bromopyridin-2-yl) carbamoyl)-4-fluoropyrrolidine-1-carboxylate (200 mg) in DCM (3.0 mL) was added TFA (1 mL) at 0° C. and the reaction mixture was stirred at room temperature for 1 hr. The mixture was evaporated under reduced pressure to give compound S6 (180 mg, 100% yield), which was directly used to the next reaction without further purification.

Step 6: (2S,4R)-1-(2-(3-Acetyl-5-(2-methylpyrimidin-5-yl)-1H-indazol-1-yl)acetyl)-4-(azidomethyl)-N-(6-bromopyridin-2-yl)-4-fluoropyrrolidine-2-carboxamide (S8)

A mixture of (2S,4R)-4-(azidomethyl)-N-(6-bromopyridin-2-yl)-4-fluoropyrrolidine-2-carboxamide (180 mg, 0.47 mmol), 2-(3-acetyl-5-(2-methylpyrimidin-5-yl)-1H-indazol-1-yl)acetic acid (161 mg, 0.52 mmol), HATU (270 mg, 0.71 mmol) and DIPEA (0.24 mL, 1.41 mmol) in DMF (4 mL) was stirred at room temperature overnight. The mixture was partitioned with EtOAc and water. The organic layer was washed with brine, dried over anhydrous Na$_2$SO$_4$ and concentrated under reduced pressure. The residue was purified by chromatography on silica gel (DCM:MeOH=80:1 to 60:1) to give aS (200 mg, yield 67.1% yield) as white solid. $^1$H NMR (400 MHz, DMSO-d$_6$) δ 11.02 (s, 1H), 9.03 (s, 2H), 8.42 (d, J=1.0 Hz, 1H), 8.02 (d, J=8.2 Hz, 1H), 7.85 (dd, J=7.3, 5.2 Hz, 2H), 7.71 (t, J=8.0 Hz, 1H), 7.33 (d, J=7.3 Hz, 1H), 5.87 (d, J=17.3 Hz, 1H), 5.64 (d, J=17.2 Hz, 1H), 4.71 (t, J=8.6 Hz, 1H), 4.32 (m, 1H), 4.07-3.92 (m, 2H), 3.90-3.79 (m, 1H), 2.66 (d, J=15.0 Hz, 6H), 2.62-2.55 (m, 1H), 2.17 (m, 1H). LC/MS (ESI) m/z: 635 (M+H)$^+$.

Step 7: (2S,4S)-1-(2-(3-Acetyl-5-(2-methylpyrimidin-5-yl)-1H-indazol-1-yl)acetyl)-4-(aminomethyl)-N-(6-bromopyridin-2-yl)-4-fluoropyrrolidine-2-carboxamide (395)

To a solution of (2S,4R)-1-(2-(3-acetyl-5-(2-methylpyrimidin-5-yl)-1H-indazol-1-yl)acetyl)-4-(azidomethyl)-N-(6-bromopyridin-2-yl)-4-fluoropyrrolidine-2-carboxamide (100 mg, 0.16 mmol) in THF (3 mL) was added PPh$_3$ (50 mg, 0.19 mmol) and water (0.3 mL) at 0° C. Then the reaction mixture was stirred at 30° C. overnight. The mixture was partitioned with EtOAc and water, the combined organic layer was washed with brine, dried over anhydrous Na$_2$SO$_4$ and concentrated under reduced pressure. The residue was purified by prep-HPLC to give S9 (10 mg, 10.2% yield) as white solid. $^1$H NMR (400 MHz, DMSO-d$_6$) δ 11.01 (s, 1H), 9.03 (s, 2H), 8.42 (s, 1H), 8.22 (s, 1H), 8.03 (d, J=8.2 Hz, 1H), 7.86 (s, 2H), 7.71 (t, J=8.0 Hz, 1H), 7.32 (d, J=7.6 Hz, 1H), 5.82 (d, J=17.3 Hz, 1H), 5.59 (d, J=17.2 Hz, 1H), 4.69 (t, J=8.5 Hz, 1H), 4.12 (m, 3H), 3.07 (d, J=18.6 Hz, 2H), 2.68 (s, 3H), 2.63 (s, 3H), 2.58-2.52 (m, 1H), 2.50-2.44 (m, 1H), 2.18 (m, 1H). LC/MS (ESI) m/z: 609 (M+H)$^+$.

(2S,4R)-1-(2-(3-Acetyl-5-(2-methylpyrimidin-5-yl)-1H-indazol-1-yl)acetyl)-N-(6-bromopyridin-2-yl)-4-fluoro-4-(hydroxymethyl)pyrrolidine-2-carboxamide (400)

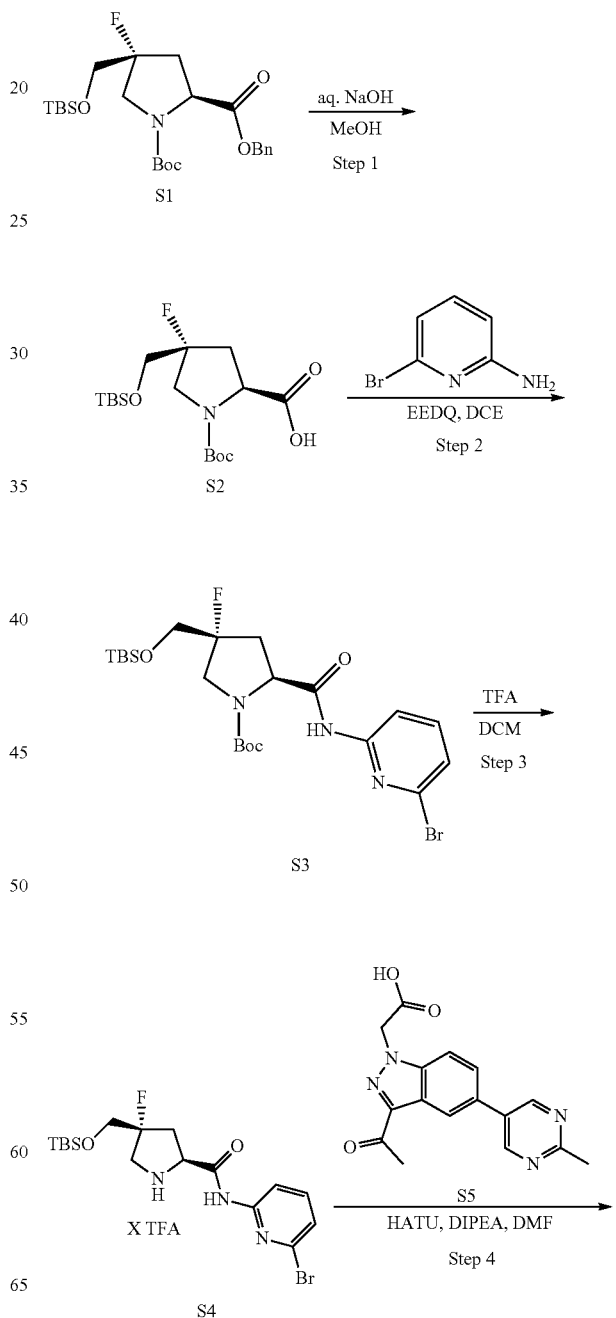

Scheme 96.

-continued

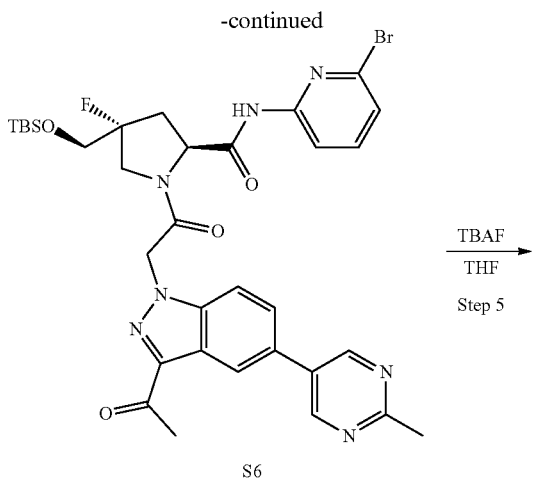

S6

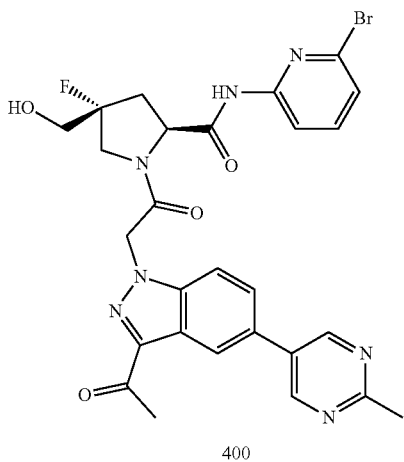 [SMILES: CC(=O)c1nn(CC(=O)N2C[C@@](F)(CO)C[C@H]2C(=O)Nc2cccc(Br)n2)c2ccc(-c3cnc(C)nc3)cc12 ; "400"]

400

Step 1: (2S,4R)-1-(tert-Butoxycarbonyl)-4-(((tert-butyldimethylsilyl)oxy)methyl)-4-fluoropyrrolidine-2-carboxylic acid (S2)

To a solution of (2S,4R)-2-benzyl 1-tert-butyl 4-(((tert-butyldimethylsilyl)oxy)methyl)-4-fluoropyrrolidine-1,2-dicarboxylate (115 mg, 0.25 mmol) in MeOH (3 mL) was added a 1 M aq. NaOH solution (0.5 mL, 0.5 mmol) at 0° C. and the reaction mixture was stirred at room temperature for 1 hr. The mixture was diluted with water (15 mL) and the volatiles were removed under reduced pressure. The residue was washed with $Et_2O$ (2×10 mL) and acidified with 2 N HCl to pH~3. The mixture was extracted with EtOAc (2×15 mL) and the combined organic layers were dried over anhydrous $Na_2SO_4$, filtered, and concentrated under reduced pressure to give the desired product (62 mg, 64.0% yield) as light oil.

Step 2: (2S,4R)-tert-Butyl 2-((6-bromopyridin-2-yl)carbamoyl)-4-(((tert-butyldimethylsilyl)oxy)methyl)-4-fluoropyrrolidine-1-carboxylate (S3)

A mixture of (2S,4R)-1-(tert-butoxycarbonyl)-4-(((tert-butyldimethyl silyl)oxy)methyl)-4-fluoropyrrolidine-2-carboxylic acid (62 mg, 0.16 mmol), 6-bromopyridin-2-amine (31 mg, 0.18 mmol), DIPEA (53 mg, 0.41 mmol) and EEDQ (79 mg, 0.32 mmol) in DCE (3 mL) was stirred at 90° C. overnight. The mixture was evaporated under reduced pressure and the residue was purified by chromatography on silica gel (PE:A=20:1 to 4:1) to give the desired product (51 mg, 58.9% yield) as a yellow oil.

Step 3: (2S,4R)—N-(6-Bromopyridin-2-yl)-4-(((tert-butyldimethylsilyl)oxy)methyl)-4-fluoropyrrolidine-2-carboxamide (S4)

To a solution of (2S,4R)-tert-butyl 4-(azidomethyl)-2-((6-bromopyridin-2-yl) carbamoyl)-4-fluoropyrrolidine-1-carboxylate (50 mg, 0.092 mmol) in DCM (3.0 mL) was added TFA (1 mL) at 0° C. and the reaction mixture was stirred at room temperature for 1 hr. The mixture was evaporated under reduced pressure to give the desired product (50 mg, 100% yield), which was directly used to the next reaction without further purification.

Step 4: (2S,4R)-1-(2-(3-Acetyl-5-(2-methylpyrimidin-5-yl)-1H-indazol-1-yl)acetyl)-N-(6-bromopyridin-2-yl)-4-(((tert-butyldimethylsilyl)oxy)methyl)-4-fluoropyrrolidine-2-carboxamide (S6)

To a mixture of (2S,4R)—N-(6-bromopyridin-2-yl)-4-(((tert-butyldimethyl silyl)oxy)methyl)-4-fluoropyrrolidine-2-carboxamide (50 mg, 0.12 mmol), S6 (40 mg, 0.13 mmol) and HATU (68 mg, 0.18 mmol) in DMF (2 mL) was added DIPEA (0.06 mL, 0.36 mmol). The reaction was stirred at room temperature overnight. The mixture was partitioned with EtOAc and water. The organic layer was washed with brine, dried over anhydrous sodium sulfate and concentrated under reduced pressure to give the crude product (80 mg), which was directly used to the next reaction without further purification.

Step 5: (2S,4R)-1-(2-(3-Acetyl-5-(2-methylpyrimidin-5-yl)-1H-indazol-1-yl)acetyl)-N-(6-bromopyridin-2-yl)-4-fluoro-4-(hydroxymethyl)pyrrolidine-2-carboxamid (400)

To a solution of (2S,4R)-4-(tert-butyl-dimethyl-silanyloxymethyl)-4-fluoro-pyrrolidine-1,2-dicarboxylicacid 2-benzyl ester 1-tert-butyl ester (80 mg) in THF (2 mL) at room temperature was added 1 M TBAF in THF (0.12 mL, 0.12 mmol). The reaction was stirred at room temperature for 30 min and poured into ice-water. The resulting mixture was extracted with EtOAc, dried over anhydrous $Na_2SO_4$, filtered and concentrated under reduced pressure. The residue was purified by prep-HPLC to give the desired product (20 mg, 27.3% yield) as white solid. $^1H$ NMR (400 MHz, DMSO-$d_6$) δ 11.00 (s, 1H), 9.03 (s, 2H), 8.42 (t, J=1.2 Hz, 1H), 8.02 (d, J=8.1 Hz, 1H), 7.86 (d, J=1.2 Hz, 2H), 7.71 (t, J=8.0 Hz, 1H), 7.32 (d, J=7.3 Hz, 1H), 5.83 (d, J=17.3 Hz, 1H), 5.62 (d, J=17.2 Hz, 1H), 4.70 (t, J=8.6 Hz, 1H), 4.23-4.01 (m, 2H), 3.78-3.66 (m, 2H), 2.68 (s, 3H), 2.64 (s, 3H), 2.49-2.41 (m, 1H), 2.24-2.09 (m, 1H). LC/MS (ESI) m/z: 610 (M+H)$^+$.

333

(2S,4R)-1-(2-(3-Acetyl-5-(2-methylpyrimidin-5-yl)-1H-indazol-1-yl) acetyl)-N-(6-bromopyridin-2-yl)-4-fluoro-4-(fluoromethyl)pyrrolidine-2-carboxamide (415)

Scheme 97.

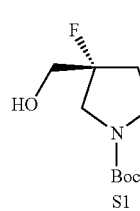

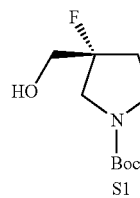

334

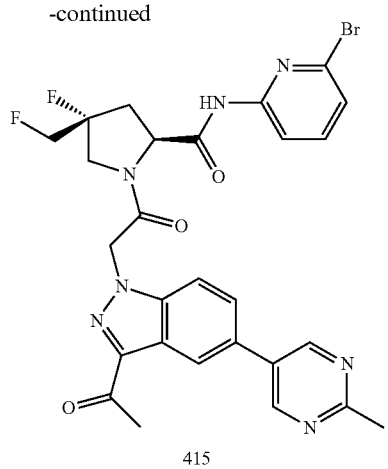

415

Step 1: (2S,4R)-2-Benzyl 1-tert-butyl 4-fluoro-4-(fluoromethyl)pyrrolidine-1,2-dicarboxylate (S2)

BAST (400 mg, 1.81 mmol) was added to a solution of (2S,4R)-2-benzyl 1-tert-butyl 4-fluoro-4-(hydroxymethyl) pyrrolidine-1,2-dicarboxylate (160 mg, 0.45 mmol) in $CHCl_3$ (5 mL) at 0° C. and the reaction mixture was stirred at 60° C. overnight. The mixture was poured into ice water and extracted with DCM. The organic layer was washed with brine, dried over anhydrous $Na_2SO_4$ and concentrated under reduced pressure. The residue was purified by chromatography on silica gel (PE:EtOAc=20:1 to 10:1) to give the desired product (120 mg, 75.1% yield) as light oil.

Step 2: (2S,4R)-1-(tert-Butoxycarbonyl)-4-fluoro-4-(fluoromethyl)pyrrolidine-2-carboxylic acid (S3)

To a solution of (2S,4R)-2-benzyl 1-tert-butyl 4-fluoro-4-(fluoromethyl) pyrrolidine-1,2-dicarboxylate (120 mg, 0.34 mmol) in MeOH (3 mL) was added 1 M aq. NaOH solution (0.68 mL, 0.68 mmol) at 0° C. and the reaction mixture was stirred at room temperature for 1 hr. The mixture was diluted with water and the volatiles were removed under reduced pressure. The residue was washed with $Et_2O$ (2×10 mL). The aqueous layer was acidified with 2 N HCl to pH~3 and extracted with EtOAc (2×15 mL). The combined organic layers were dried over anhydrous $Na_2SO_4$ and concentrated under reduced pressure to give the desired product (82 mg, 90.9% yield) as light oil.

Step 3: (2S,4R)-tert-Butyl 2-((6-bromopyridin-2-yl) carbamoyl)-4-fluoro-4-(fluoromethyl)pyrrolidine-1-carboxylate (S4)

To a mixture of (2S,4R)-1-(tert-butoxycarbonyl)-4-fluoro-4-(fluoromethyl)pyrrolidine-2-carboxylic acid (82 mg, 0.31 mmol), 6-bromopyridin-2-amine (90 mg, 0.34 mmol) in DCE (4 mL) was added DIPEA (100 mg, 0.77 mmol) and EEDQ (153 mg, 0.62 mmol). The reaction was stirred at 90° C. overnight. The mixture was evaporated under reduced pressure and the residue was purified by chromatography on silica gel (PE:EtOAc=15:1 to 5:1) to give the desired product (85 mg, 65.2% yield) as a light oil.

Step 4: (2S,4R)—N-(6-Bromopyridin-2-yl)-4-fluoro-4-(fluoromethyl)pyrrolidine-2-carboxamide (S5)

To a solution of (2S,4R)-tert-butyl 4-(azidomethyl)-2-((6-bromopyridin-2-yl) carbamoyl)-4-fluoropyrrolidine-1-carboxylate (80 mg, 0.19 mmol) in DCM (3.0 mL) was added TFA (1 mL) at 0° C. and the reaction mixture was stirred at room temperature for 1 hr. The mixture was evaporated under reduced pressure to give the desired product (90 mg, 100% yield) as a yellow solid, which was directly used to the next reaction without further purification.

Step 5: (2S,4R)-1-(2-(3-Acetyl-5-(2-methylpyrimidin-5-yl)-1H-indazol-1-yl)acetyl)-N-(6-bromopyridin-2-yl)-4-fluoro-4-(fluoromethyl)pyrrolidine-2-carboxamide (416)

To a mixture of (2S,4R)—N-(6-bromopyridin-2-yl)-4-fluoro-4-(fluoromethyl) pyrrolidine-2-carboxamide (80 mg, 0.25 mmol), S6 (93.3 mg, 0.30 mmol), HATU (143 mg, 0.38 mmol) in DMF (4 mL) was added DIPEA (0.12 mL, 0.75 mmol). The reaction was stirred at room temperature overnight. The mixture was partitioned with EtOAc and water. The organic layer was washed with brine, dried over anhydrous $Na_2SO_4$ and concentrated under reduced pressure. The residue was purified by prep-HPLC to give the desired product (40 mg, 26.1% yield) as white solid. $^1$H NMR (400 MHz, DMSO-d6) δ 11.04 (s, 1H), 9.04 (s, 2H), 8.42 (s, 1H), 8.02 (d, J=8.2 Hz, 1H), 7.89-7.84 (m, 2H), 7.71 (t, J=8.0 Hz, 1H), 7.33 (d, J=7.7 Hz, 1H), 5.86 (d, J=mdd, J=19.8, 12.1 Hz, 1H), 4.12 (m, 1H), 2.68 (s, 3H), 2.64 (s, 3H), 2.61-2.55 (m, 1H), 2.29-2.16 (m, 1H). LC/MS (ESI) m/z: 612 (M+H)$^+$.

(2S,4R)-1-(2-(3-Acetyl-5-(2-methylpyrimidin-5-yl)-1H-indazol-1-yl)acetyl)-N-(6-bromo-3-methylpyridin-2-yl)-4-fluoro-4-(fluoromethyl)pyrrolidine-2-carboxamide (511)

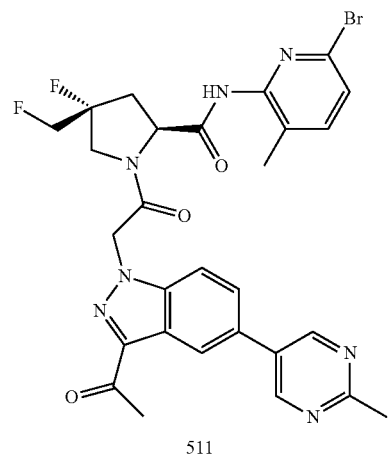

511

The titled compound was prepared according the procedure from Scheme 97 from appropriate starting materials. $^1$H NMR (400 MHz, DMSO-d6) δ 10.51 (s, 1H), 9.04 (s, 2H), 8.44 (s, 1H), 7.89-7.78 (m, 2H), 7.61 (d, J=8.0 Hz, 1H), 7.43 (d, J=7.9 Hz, 1H), 5.90-5.81 (m, 1H), 5.62 (d, J=17.3 Hz, 1H), 4.94 (d, J=21.9 Hz, 1H), 4.82 (d, J=22.2 Hz, 1H), 4.69 (t, J=8.4 Hz, 1H), 4.32 (m, 1H), 4.10 (m, 1H), 2.69 (s, 3H), 2.64 (s, 3H), 2.26 (m, 2H), 2.00 (s, 3H). LC/MS (ESI) m/z: 626 (M+H)$^+$.

(2S,4R)-1-(2-(3-Acetyl-5-(2-methylpyrimidin-5-yl)-1H-indazol-1-yl)acetyl)-N-(6-bromopyridin-2-yl)-4-fluoro-4-methylpyrrolidine-2-carboxamide (418)

Scheme 98.

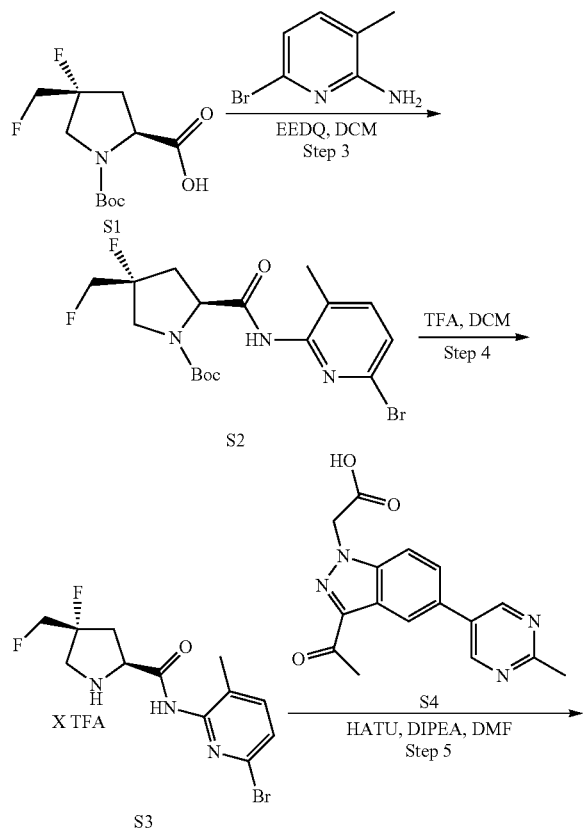

Scheme 99.

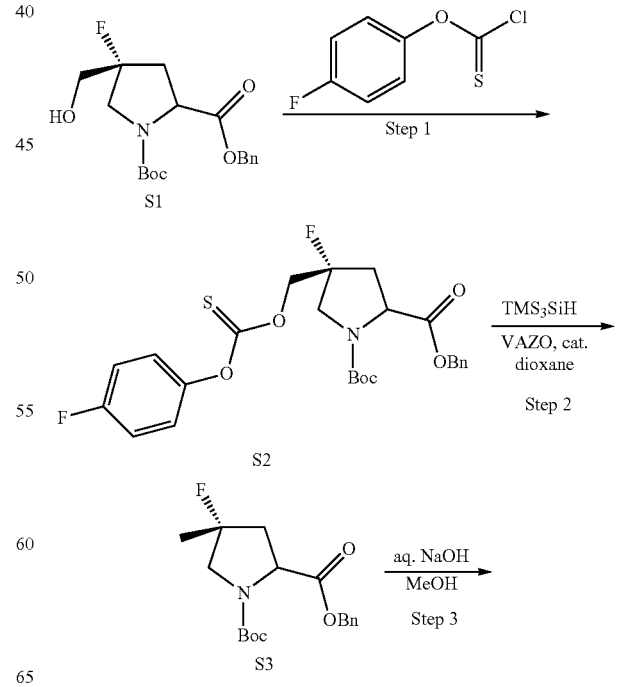

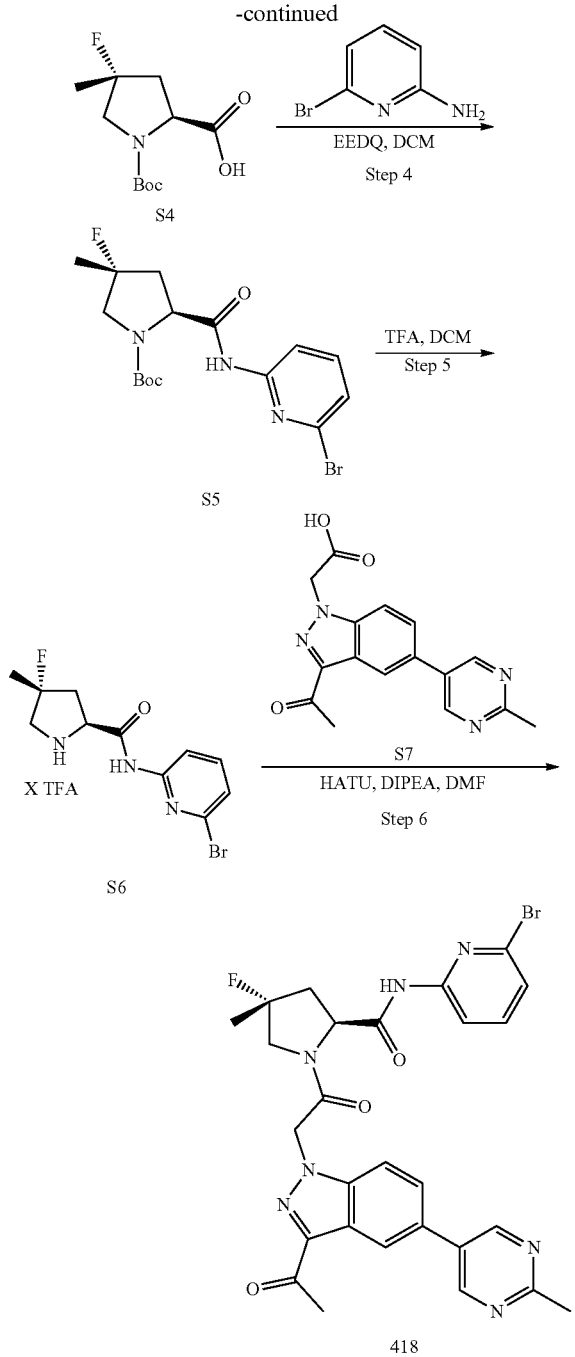

chromatography on silica gel (PE:EtOAc=20:1 to 10:1) to give the desired product (167 mg, 70.0% yield) as light oil.

Step 2: (2S,4R)-4-Fluoro-4-methyl-pyrrolidine-1,2-dicarboxylicacid2-benzylester1-tert-butylester (S3)

To a solution of (2S,4R)-4-Fluoro-4-(4-fluoro-phenoxy-thiocarbonyloxymethyl)-pyrrolidine-1,2-dicarboxylicacid2-benzylester1-tert-butylester (167 mg, 0.33 mmol) in 1,4-dioxane (4 mL) was added 2,2'-azobis(2-methylpropionitrile) (27 mg, 0.16 mmol) and tris(trimethylsilyl) silane (122 mg, 0.77 mmol). The reaction was at 105° C. for 30 min and at room temperature for 1 hr. The mixture was concentrated to dryness and the residue was purified by chromatography on silica gel (PE:EtOAc=15:1 to 50:1) to give the desired product (85 mg, 76.4% yield) as a light oil.

Step 3: (2S,4R)-4-Fluoro-4-methyl-pyrrolidine-1,2-dicarboxylicacid1-tert-butylester (S4)

To a solution of (2S,4R)-4-Fluoro-4-methyl-pyrrolidine-1,2-dicarboxylicacid-2-benzylester1-tert-butylester (85 mg, 0.25 mmol) in MeOH (3 mL) was added 1 M aq. NaOH solution (0.50 mL, 0.50 mmol) at 0° C. and the reaction was stirred at room temperature for 1 hr. The mixture was diluted with water (5 mL) and the volatiles were removed under reduced pressure. The residue was washed with Et₂O (2×5 mL). The water layer was acidified with 2 N aq. HCl to pH~3 and extracted with EtOAc (2×10 mL). The combined organic layers were dried over anhydrous Na₂SO₄ and concentrated under reduced pressure to give the desired product (60 mg, 95.9% yield) as light yellow solid.

Step 4: (2S,4R)-tert-Butyl 2-((6-bromopyridin-2-yl)carbamoyl)-4-fluoro-4-methylpyrrolidine-1-carboxylate (S5)

A mixture of (2S,4R)-4-Fluoro-4-methyl-pyrrolidine-1,2-dicarboxylicacid1-tert-butylester (60 mg, 0.24 mmol), 6-bromopyridin-2-amine (46 mg, 0.27 mmol), DIPEA (77.5 mg, 0.6 mmol) and EEDQ (118 mg, 0.48 mmol) in DCE (3 mL) was stirred at 90° C. overnight. The mixture was evaporated under reduced pressure and the residue was purified by chromatography on silica gel (PE:EtOAc=15:1 to 5:1) to give the desired product (55 mg, 57.1% yield) as white solid.

Step 5: (2S,4R)—N-(6-Bromopyridin-2-yl)-4-fluoro-4-methylpyrrolidine-2-carboxamide (S6)

To a solution of (2S,4R)-tert-butyl 2-((6-bromopyridin-2-yl)carbamoyl)-4-fluoro-4-methylpyrrolidine-1-carboxylate (55 mg, 0.137 mmol) in DCM (3.0 mL) was added TFA (1 mL) at 0° C. and the reaction mixture was stirred at room temperature for 1 hr. The mixture was evaporated under reduced pressure to give the desired product (50 mg, 100% yield) as a yellow solid, which was directly used to the next reaction without further purification.

Step 6: (2S,4R)-1-(2-(3-Acetyl-5-(2-methylpyrimidin-5-yl)-1H-indazol-1-yl)acetyl)-N-(6-bromopyridin-2-yl)-4-fluoro-4-methylpyrrolidine-2-carboxamide (418)

To a mixture of (2S,4R)—N-(6-bromopyridin-2-yl)-4-fluoro-4-methylpyrrolidine-2-carboxamide (50 mg, 0.17 mmol), 2-(3-acetyl-5-(2-methylpyrimidin-5-yl)-1H-indazol-1-yl)acetic acid (56 mg, 0.18 mmol) and HATU (99 mg, 0.26 mmol) in DMF (3 mL) was added DIPEA (0.08 mL, 0.51 mmol). The reaction was stirred at room temperature overnight. The mixture was partitioned with EtOAc and water. The organic layer was washed with brine, dried over anhydrous $Na_2SO_4$ and concentrated under reduced pressure. The residue was purified by prep-HPLC to give the desired product (11 mg, 10.9% yield) as white solid. $^1$H NMR (400 MHz, DMSO-d6) δ 10.99 (s, 1H), 9.03 (s, 2H), 8.42 (s, 1H), 8.02 (d, J=8.1 Hz, 1H), 7.90-7.80 (m, 2H), 7.70 (t, J=8.0 Hz, 1H), 7.32 (d, J=7.7 Hz, 1H), 5.82 (d, J=17.3 Hz, 1H), 5.60 (d, J=17.3 Hz, 1H), 4.75-4.63 (m, 1H), 4.22 (m, 1H), 3.92 (d, 1H), 2.68 (s, 3H), 2.64 (s, 3H), 2.09 (m, 2H), 1.62 (d, J=20.9 Hz, 3H). LC/MS (ESI) m/z: 594 (M+H)$^+$.

(2S,4R)-1-(2-(3-Acetyl-5-(2-methylpyrimidin-5-yl)-1H-indazol-1-yl)acetyl)-N-(6-bromopyridin-2-yl)-4-fluoro-4-(methoxymethyl)pyrrolidine-2-carboxamide (419)

Scheme 100.

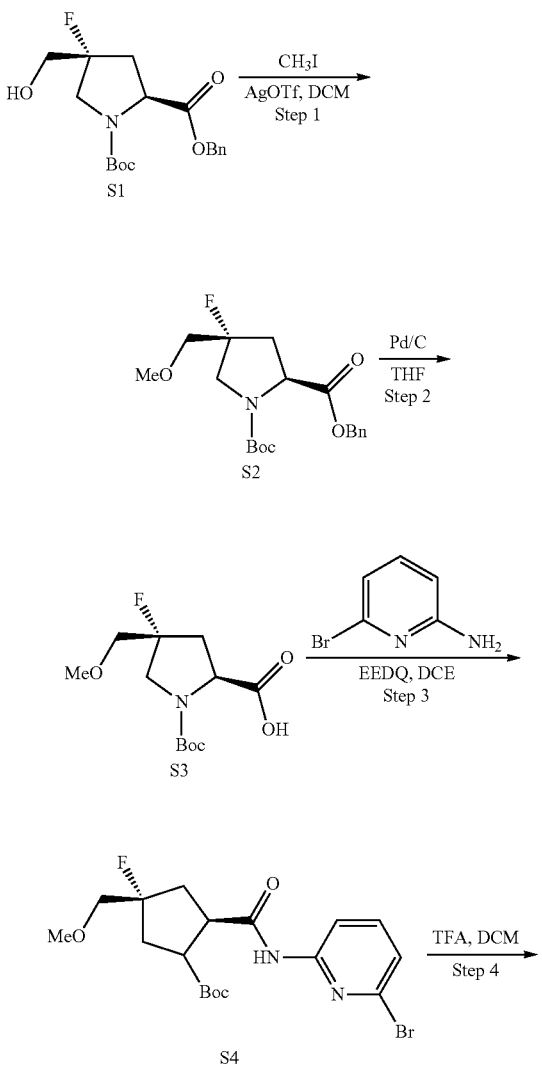

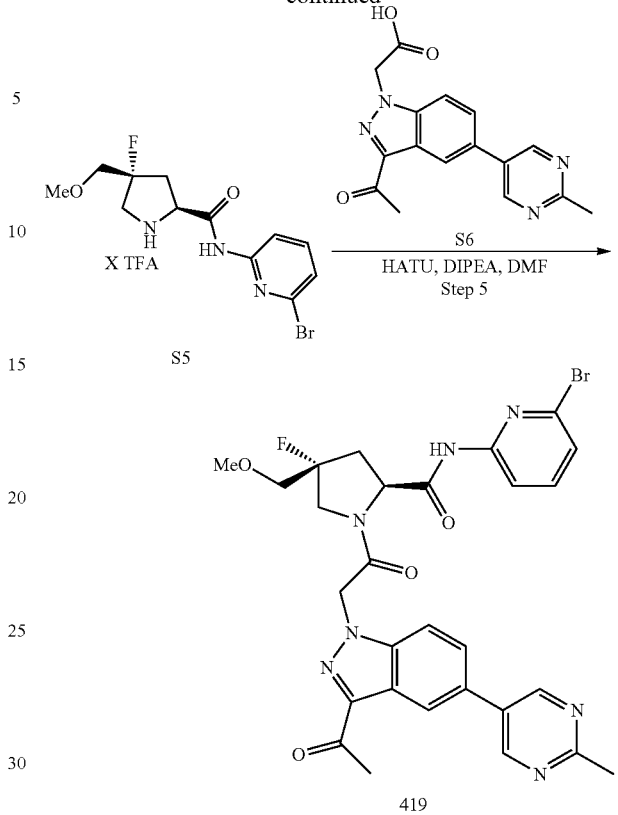

Step 1: (2S,4R)-2-Benzyl 1-tert-butyl 4-fluoro-4-(methoxymethyl)pyrrolidine-1,2-dicarboxylate (S1)

To a solution of (2S,4R)-2-benzyl 1-tert-butyl 4-fluoro-4-(hydroxymethyl)pyrrolidine-1,2-dicarboxylate (90 mg, 0.25 mmol) in DCM (3 mL) was added silver trifluoromethanesulfonate (103 mg, 0.40 mmol) and 2,6-di-tert-butylpyridine (105 mg, 0.51 mmol). The reaction mixture was cooled to 0° C. (external temperature) and MeI (72 mg, 0.51 mmol) was slowly added. The resulting slurry was stirred at 0° C. for 1.5 hrs and then at room temperature for 1.5 hrs. The mixture was filtered and the filtrate was evaporated under reduced pressure. The residue was purified by chromatography on silica gel (PE:EtOAc=15:1 to 5:1) to give the desired product (50 mg, 54.5% yield) as light oil.

Step 2: (2S,4R)-1-(tert-Butoxycarbonyl)-4-fluoro-4-(methoxymethyl)pyrrolidine-2-carboxylic acid (S2)

A solution of (2S,4R)-2-benzyl 1-tert-butyl 4-fluoro-4-(methoxymethyl)pyrrolidine-1,2-dicarboxylate (50 mg) in THF (3 mL) was degassed under $N_2$ atmosphere and stirred under a $H_2$ balloon at room temperature overnight. The reaction mixture was filtered and the filtrate was evaporated under reduced pressure to give the desired product (28 mg) as light yellow oil.

Step 3: (2S,4R)-tert-Butyl 2-((6-bromopyridin-2-yl)carbamoyl)-4-fluoro-4-(methoxy methyl)pyrrolidine-1-carboxylate (S3)

To a mixture of (2S,4R)-1-(tert-butoxycarbonyl)-4-fluoro-4-(methoxymethyl)pyrrolidine-2-carboxylic acid (28 mg, 0.10 mmol), 6-bromopyridin-2-amine (19.1 mg, 0.11 mmol) in DCE (3 mL) was added DIPEA (26 mg, 0.2 mmol) and EEDQ (49.4 mg, 0.20 mmol). The reaction was stirred at 90° C. overnight. The mixture was evaporated under reduced pressure and the residue was purified by chromatography on silica gel (PE:EtOAc=15:1 to 5:1) to give the desired product (32 mg, 74.2% yield) as light oil.

Step 4: (2S,4R)—N-(6-Bromopyridin-2-yl)-4-fluoro-4-(methoxymethyl)pyrrolidine-2-carboxamide (S4)

To a solution of (2S,4R)-tert-butyl 2-((6-bromopyridin-2-yl)carbamoyl)-4-fluoro-4-(methoxy methyl)pyrrolidine-1-carboxylate (32 mg) in DCM (1.0 mL) was added TFA (0.3 mL) at 0° C. and the reaction mixture was stirred at room temperature for 1 hr. The mixture was evaporated under reduced pressure to give the desired product (32 mg, 100%), which was directly used to the next reaction without further purification.

Step 5: (2S,4R)-1-(2-(3-Acetyl-5-(2-methylpyrimidin-5-yl)-1H-indazol-1-yl)acetyl)-N-(6-bromopyridin-2-yl)-4-fluoro-4-(methoxymethyl)pyrrolidine-2-carboxamide (419)

To a mixture of (2S,4R)—N-(6-bromopyridin-2-yl)-4-fluoro-4-(methoxymethyl)pyrrolidine-2-carboxamide (41 mg, 0.12 mmol), S6 (42.2 mg, 0.14 mmol) and HATU (68.4 mg, 0.18 mmol) in DMF (3 mL) was added DIPEA (0.06 mL, 0.36 mmol). The reaction was stirred at room temperature overnight and then partitioned with EtOAc and water. The organic layer was washed with brine, dried over anhydrous Na$_2$SO$_4$ and concentrated under reduced pressure. The residue was purified by prep-HPLC to give the desired product (8 mg, 10.6% yield) as white solid. $^1$H NMR (400 MHz, DMSO-d6) δ 11.01 (s, 1H), 9.03 (s, 2H), 8.42 (s, 1H), 8.02 (d, J=8.2 Hz, 1H), 7.86 (d, J=1.7 Hz, 2H), 7.71 (t, J=8.0 Hz, 1H), 7.33 (d, J=7.7 Hz, 1H), 5.85 (d, J=17.3 Hz, 1H), 5.63 (d, J=17.3 Hz, 1H), 4.70 (t, J=8.5 Hz, 1H), 4.24 (m, 1H), 4.04 (m, 1H), 3.74 (m, 2H), 3.40 (s, 3H), 2.67 (d, 6H), 2.57 (m, 1H), 2.15 (m, 1H). LC/MS (ESI) m/z: 624 (M+H)$^+$.

(1R,2S,5S)-3-(2-(3-Acetyl-5-(2-methylpyrimidin-5-yl)-1H-indazol-1-yl)acetyl)-N-(6-bromopyridin-2-yl)-3-azabicyclo[3.1.0]hexane-2-carboxamide (413)

Scheme 101.

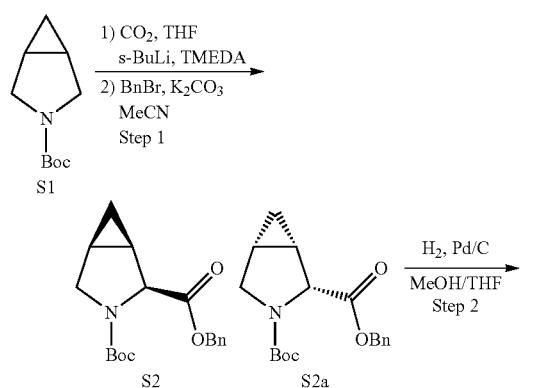

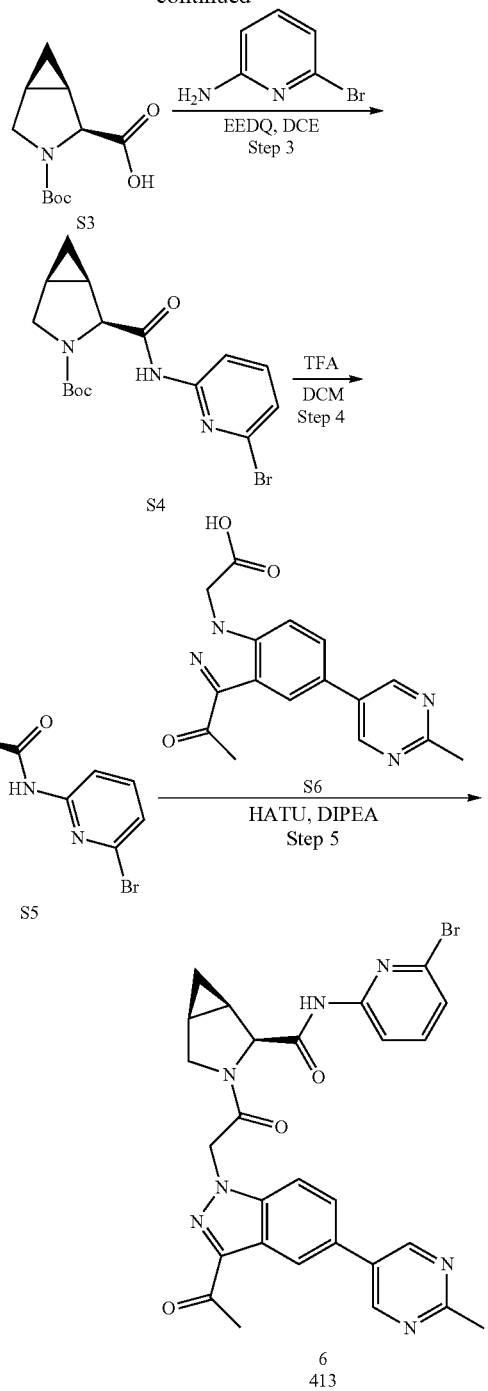

(1R,2S,5S)-2-Benzyl 3-tert-butyl 3-azabicyclo [3.1.0]hexane-2,3-dicarboxylate & (1S,2R,5R)-2-benzyl 3-tert-butyl 3-azabicyclo[3.1.0]hexane-2,3-dicarboxylate (S2)

To a mixture of S1 (6.5 g, 35.5 mmol) and TMEDA (8.5 mL, 56.8 mmol) in dry THF (130 mL) was added sec-BuLi solution (53.2 mL, 53.2 mmol, 1M)) at −60° C. for 20 min under N$_2$ atmosphere. After 3 hrs at −65° C., dry CO$_2$ gas was purged through the reaction mixture for 20 min. The reaction was quenched by dropwise addition of 150 mL of water at −60° C. Most of the THF was distilled and the aqueous phase was washed twice with 150 mL of MTBE. To the aqueous phase were added of 25% aqueous KHSO₄ solution until the pH<3 and the resulting mixture was extracted three times with EtOAc. The combined organic phases were washed with brine, dried over anhydrous Na₂SO₄, filtered, and concentrated to give a residue (2.9 g).

The residue was dissolved with MeCN (60 mL), K₂CO₃ (3.5 g, 25.6 mmol) and BnBr (3.3 g, 19.2 mmol) was added into the solution. The reaction mixture was stirred at room temperature for 16 hrs. The volatiles were removed under reduce pressure and the mixture was diluted with EtOAc and washed with water and brine. The organic layer was dried over anhydrous Na₂SO₄, filtered and concentrated. The residue was purified by chromatography on silica gel (PE: acetone=80:1 to 10:1) to give racemic product, which was purified by preparative chiral-HPLC to give the desired product S2 (1.9 g, 16.8% yield) and S2a (1.9 g, 16.8% yield) as yellow solid. Chiral HPLC condition: OJ-H (150×4.6 mm, 5 um) column, hexane/EtOH=95/5, retention time: S2=3.74 min, S2A=4.59 min.

Step 2: (1R,2S,5S)-3-(tert-Butoxycarbonyl)-3-azabicyclo[3.1.0]hexane-2-carboxylic acid (S3)

To a solution of the compound S2 (1.5 g, 4.7 mmol) in MeOH (25 mL) was added Pd/C (140 mg, 10% wt). The mixture was degassed under N₂ for three times and stirred under a H₂ balloon at room temperature for 2 hrs. The mixture was filtered and the filtrated was concentrated to dryness to give the desired product (1.05 g, 98% yield) as a white solid.

Step 3: (1R,2S,5S)-tert-Butyl 2-(6-bromopyridin-2-ylcarbamoyl)-3-azabicyclo[3.1.0]hexane-3-carboxylate (S4)

To a mixture of the compound S3 (500 mg, 2.2 mmol), 6-bromopyridin-2-amine (460 mg, 2.65 mmol) and EEDQ (1.1 g, 4.4 mmol) in 1,2-DCE (10 mL) was added DIPEA (850 mg, 6.6 mmol). The reaction was stirred at 90° C. for 16 hrs. The mixture was concentrated and purified by silica gel column (eluted with EtOAc/PE=1/3) to give the desired product (510 mg, 60.6% yield) as light yellow solid.

Step 4: N-(6-Bromopyridin-2-yl)-3-azabicyclo[3.1.0]hexane-2-carboxamide (S5)

To a solution of the compound S4 (200 mg, 0.52 mmol) in DCM (6 mL) was added TFA (3 mL). The reaction was stirred at room temperature for 1.5 hrs. The mixture was concentrated to dryness to give the desired product (210 mg, 100% yield) as yellow solid, which was directly used to the next reaction without purification.

Step 5: 3-(2-(3-Acetyl-5-(2-methylpyrimidin-5-yl)-1H-indazol-1-yl)acetyl)-N-(6-bromopyridin-2-yl)-3-azabicyclo[3.1.0]hexane-2-carboxamide (413)

To a solution of the compound S5 (200 mg, 0.71 mmol), S6 (220 mg, 0.71 mmol) and HATU (323 mg, 0.85 mmol) in DMF (5 mL) was added DIPEA (274 mg, 2.13 mmol). The reaction was stirred at room temperature for 16 hrs. The mixture diluted with EtOAc and washed with 10% aq. LiCl solution and brine, dried over anhydrous sodium sulfate, filtered and concentrated to give crude product, which was purified by preparative HPLC to give the desired product (70 mg, 17% yield) as white solid. ¹H NMR (400 MHz, DMSO) δ 10.87 (s, 1H), 9.04 (s, 2H), 8.41 (s, 1H), 8.01 (d, J=8.2 Hz, 1H), 7.92-7.79 (m, 2H), 7.69 (t, J=8.0 Hz, 1H), 7.31 (d, J=7.7 Hz, 1H), 5.61 (s, 2H), 4.63 (d, J=5.2 Hz, 1H), 4.10-3.85 (m, 2H), 2.65 (t, J=12.9 Hz, 6H), 1.94 (d, J=45.5 Hz, 2H), 0.90-0.64 (m, 2H). LC/MS (ESI) m/z: 574 (M+H)⁺.

(1S,2R,5R)-3-(2-(3-Acetyl-5-(2-methylpyrimidin-5-yl)-1H-indazol-1-yl)acetyl)-N-(6-bromopyridin-2-yl)-3-azabicyclo[3.1.0]hexane-2-carboxamide (414)

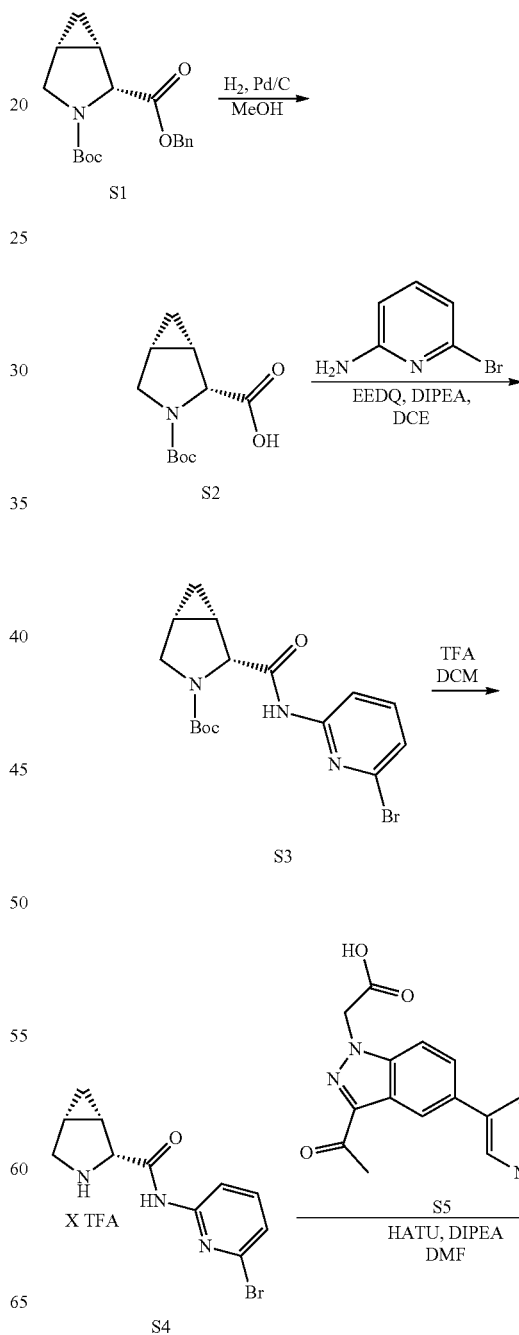

Scheme 102.

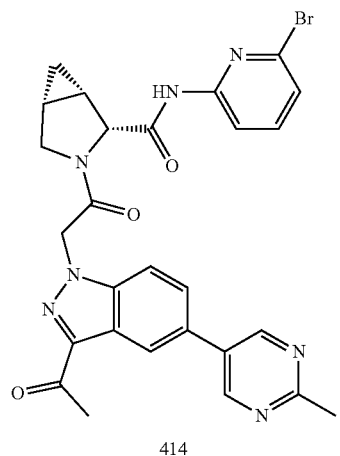

414

The titled compound was prepared according the procedure from Scheme 101 from appropriate starting materials. ¹H NMR (400 MHz, CDCl₃) δ: 10.85 (s, 1H), 9.03 (s, 2H), 8.41 (s, 1H), 8.01 (d, J=8.2 Hz, 1H), 7.86 (s, 2H), 7.69 (t, J=8.0 Hz, 1H), 7.30 (d, J=7.7 Hz, 1H), 5.65-5.53 (m, 2H), 4.63 (d, J=5.3 Hz, 1H), 4.02 (dd, J=9.8, 5.4 Hz, 1H), 3.92 (d, J=9.6 Hz, 1H), 2.65 (t, J=13.0 Hz, 6H), 1.99 (dd, J=9.8, 6.9 Hz, 1H), 1.91-1.84 (m, 1H), 0.81 (dd, J=8.9, 4.5 Hz, 1H), 0.77-0.69 (m, 1H). LC/MS (ESI) m/z: 574 (M+H)⁺.

(1R,2S,5S)-3-(2-(3-Acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide (488)

Scheme 103.

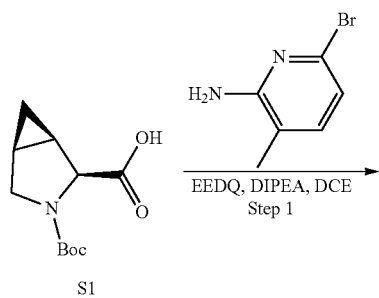

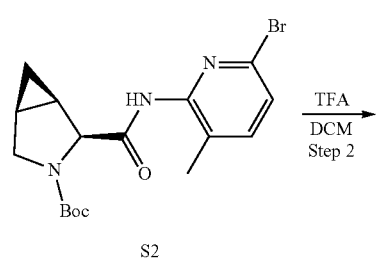

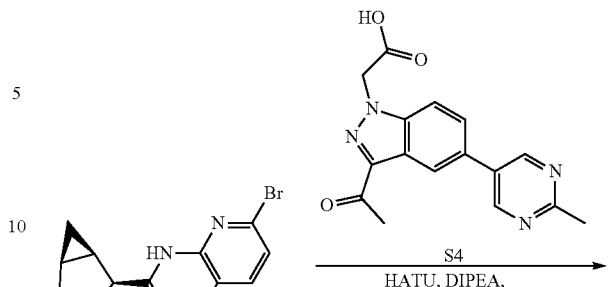

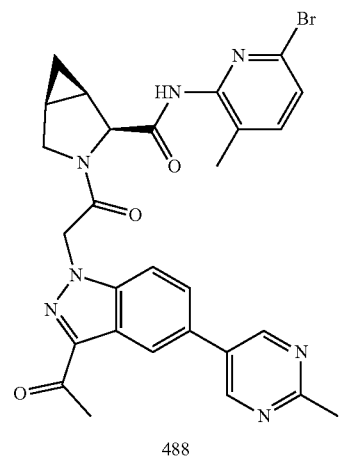

488

Step 1: (1R, 2S, 5S)-tert-Butyl 2-(6-bromo-3-methylpyridin-2-ylcarbamoyl)-3-azabicyclo [3.1.0] hexane-3-carboxylate (S2)

To a solution of (1R, 2S, 5S)-3-(tert-butoxycarbonyl)-3-azabicyclo[3.1.0]hexane-2-carboxylic acid (0.19 g, 0.84 mmol) in 1,2-dichloroethane was added ethyl 2-ethoxyquinoline-1(2H)-carboxylate (0.35 g, 1.40 mmol), DIPEA (0.36 g, 2.8 mmol) and 6-bromo-3-methylpyridin-2-amine (80 mg, 0.46 mmol). The reaction was stirred at 90° C. under N₂ atmosphere overnight. The mixture was concentrated and the residue was purified by column chromatography on silica gel eluted with PE/EtOAc (100:1 to 30:1) to give the desired product (0.12 g, 43.0% yield); LC/MS (ESI) m/z: 396 [M+H]+

Step 2: (1R, 2S, 5S)—N-(6-Bromo-3-methylpyridin-2-yl)-3-azabicyclo[3.1.0]hexane-2-carboxamide TFA Salt (S3)

To a solution of (1R, 2S, 5S)-tert-butyl 2-(6-bromo-3-methylpyridin-2-ylcarbamoyl)-3-azabicyclo[3.1.0]hexane-3-carboxylate (120 mg, 0.30 mmol) in DCM (2 mL) was added TFA (1 mL). The reaction was stirred at room temperature for 2 hrs. The mixture was concentrated to dryness and the residue was washed with Et₂O to give the desired product (85 mg, 94.9% yield); LC/MS (ESI) m/z: 296[M+H]+.

Step 3: (1R,2S,5S)-3-(2-(3-Acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide (488)

To a solution of (1R, 2S, 5S)—N-(6-bromo-3-methylpyridin-2-yl)-3-azabicyclo [3.1.0] hexane-2-carboxamide (85 mg, 0.29 mmol), S4 (98 mg, 0.32 mmol) and DIPEA (186 mg, 1.44 mmol) in DMF (2 mL) was added HATU (241 mg, 0.63 mmol). The reaction was stirred at room temperature for 1 hr. The mixture was diluted with EtOAc and washed with 10% aq. LiCl solution and brine, dried over anhydrous Na$_2$SO$_4$ and concentrated. The obtained crude product was purified by prep-HPLC to give the title compound (50 mg, 29.6% yield) as white solid. $^1$H NMR (400 MHz, DMSO-d6) δ: 10.35 (s, 1H), 9.10 (s, 2H), 8.48 (s, 1H), 7.96-7.84 (m, 2H), 7.65 (d, J=8.0 Hz, 1H), 7.47 (d, J=8.0 Hz, 1H), 5.76-5.47 (m, 2H), 4.65 (d, J=5.2 Hz, 1H), 4.16-4.05 (m, 1H), 3.95 (d, J=9.6 Hz, 1H), 2.74 (s, 3H), 2.70 (s, 3H), 2.16-2.05 (m, 4H), 2.00-1.83 (m, 1H), 0.96-0.56 (m, 2H); LC/MS (ESI) m/z: 588 [M+H]+.

(1R,3S,5R)-2-(2-(3-Acetyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide (372)

Scheme 104.

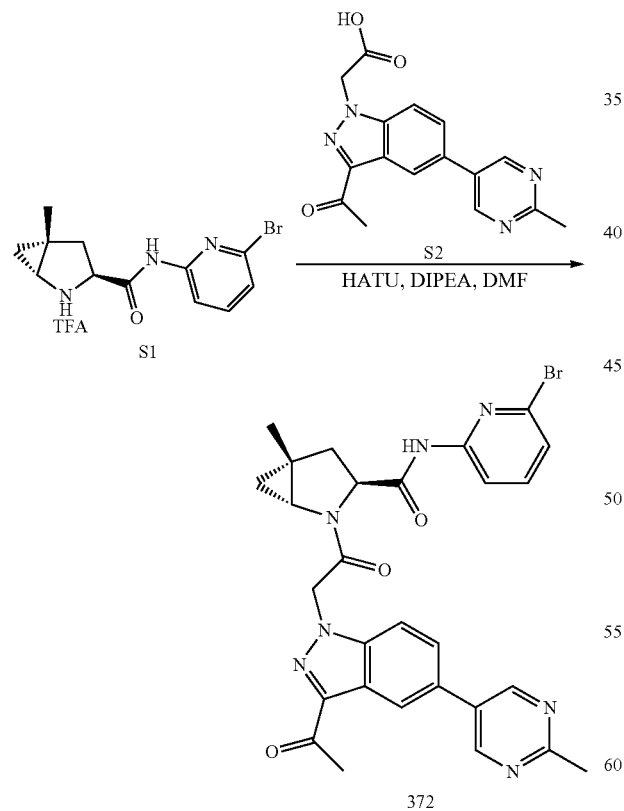

To a solution of compound S1 (43 mg, 0.11 mmol), S2 (34 mg, 0.11 mmol) and DIPEA (57 mg, 0.44 mmol) in DMF (2 mL) was added HATU (83 mg, 0.22 mmol), then the reaction was stirred at room temperature for 1 hr. The mixture was diluted with EtOAc and washed with 10% aq. LiCl solution and brine successively, dried over anhydrous Na$_2$SO$_4$, filtered and concentrated to dryness to give the crude product, which was purified by prep-HPLC to give the title compound (19 mg, 29.3% yield) as white solid; $^1$H NMR (400 MHz, DMSO-d6) δ 10.78 (s, 1H), 9.04 (s, 2H), 8.43 (s, 1H), 8.03 (d, J=8.2 Hz, 1H), 7.87 (s, 2H), 7.71 (t, J=8.0 Hz, 1H), 7.32 (d, J=7.8 Hz, 1H), 5.96 (d, J=17.3 Hz, 1H), 5.57 (d, J=17.2 Hz, 1H), 4.45-4.38 (m, 1H), 3.65-3.60 (m, 1H), 2.65 (t, J=14.7 Hz, 6H), 2.45 (s, 1H), 1.99 (dd, J=13.3, 5.7 Hz, 1H), 1.30 (s, 3H), 0.97 (d, J=3.5 Hz, 2H). LC/MS (ESI) m/z: 588 (M+H)$^+$.

(1S,3S,5S)-2-(2-(3-Acetyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide (382)

Scheme 105.

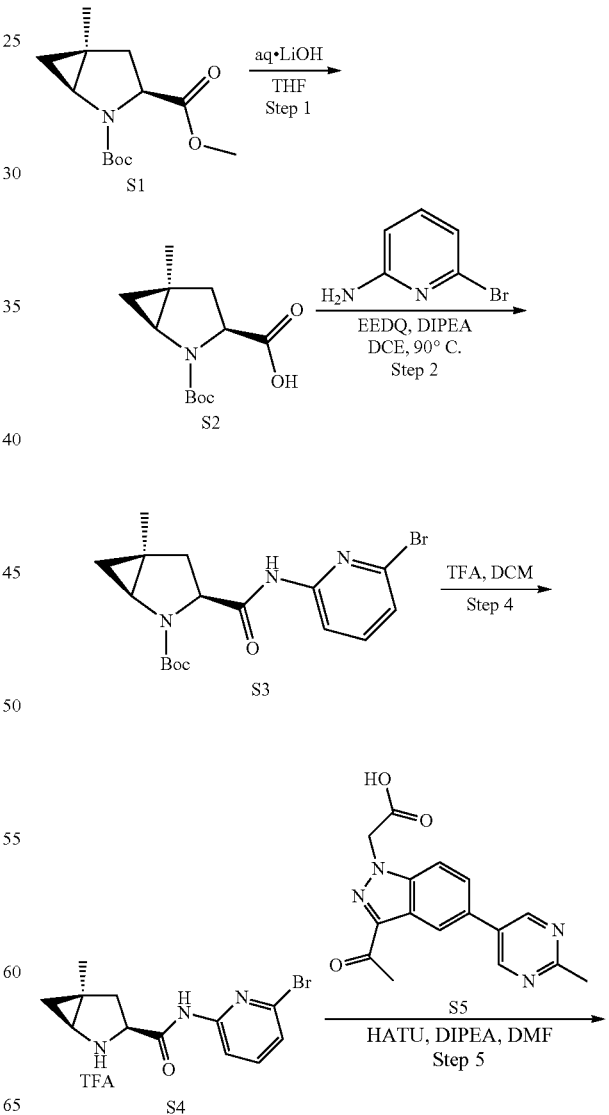

-continued

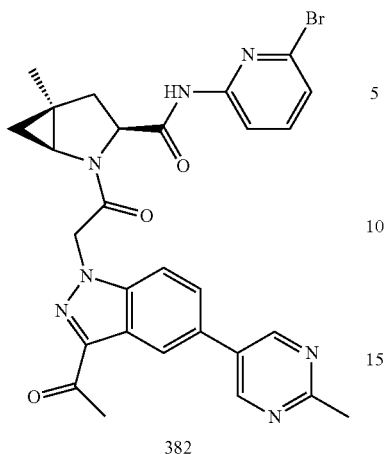

382

The titled compound was prepared according the procedure from Scheme 104 from appropriate starting materials. ¹H NMR (400 MHz, CDCl₃) δ 8.99 (s, 1H), 8.90 (s, 2H), 8.57 (s, 1H), 8.03 (d, J=8.0 Hz, 1H), 7.70-7.60 (m, 2H), 7.51 (t, J=7.6 Hz, 1H), 7.20 (d, J=7.2 Hz, 1H), 5.51 (dd, J=34, 16.4 Hz, 2H), 4.99 (dd, J=10.4, 2.0 Hz, 1H), 3.34 (dd, J=6.0, 2.4 Hz, 1H), 2.81 (s, 3H), 2.73 (s, 3H), 2.62 (dd, J=13.6, 2.4 Hz, 1H), 2.19 (t, J=11.6 Hz, 1H), 1.35 (s, 3H), 1.15 (dd, J=6.4, 2.4 Hz, 1H), 0.78 (t, J=6.0 Hz, 1H); LC/MS (ESI) m/z: 588 (M+H)⁺.

(1R,3S,5R)-2-(2-(3-Acetyl-5-(2-aminopyrimidin-5-yl)-1H-indazol-1-yl)acetyl)-N-(6-bromopyridin-2-yl)-5-methyl-2-azabicyclo[3.1.0]hexane-3-carboxamide (480)

Scheme 106.

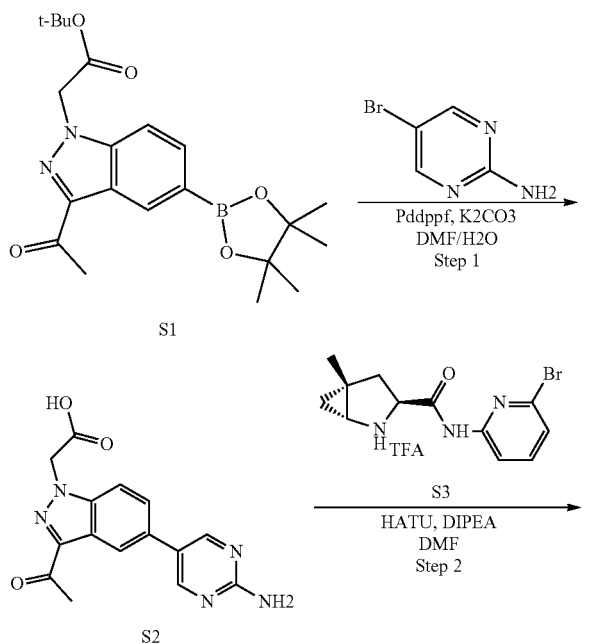

-continued

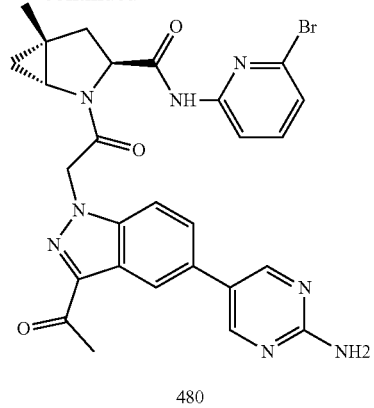

480

Step 1: 2-(3-acetyl-5-(2-Aminopyrimidin-5-yl)-1H-indazol-1-yl)acetic acid (S2)

To a mixture of compound S1 (100 mg, 0.25 mmol) and 5-bromopyrimidin-2-amine (47.8 mg, 0.27 mmol) in DMF/water (5 mL/1.5 mL) was added K₂CO₃ (69 mg, 0.5 mmol). The mixture was degassed under N₂ atmosphere three times and Pddppf (15 mg, 0.018 mmol) was added under N₂ atmosphere. The reaction was stirred at 100° C. under N₂ atmosphere for 16 hrs. The mixture was diluted with water and washed with EtOAc three times. The aqueous layer was acidified by adding 1 N aq. HCl solution to pH~3 and the mixture was filtered. The filter cake was washed with water, dried under vacuum to give the title compound (56 mg, 71.9% yield) as a gray solid. LC/MS (ESI) m/z: 312 (M+H)⁺.

Step 2: (1R,3S,5R)-2-(2-(3-Acetyl-5-(2-aminopyrimidin-5-yl)-1H-indazol-1-yl)acetyl)-N-(6-bromopyridin-2-yl)-5-methyl-2-azabicyclo[3.1.0]hexane-3-carboxamide (480)

The titled compound was prepared according the procedure from Scheme 104 from appropriate starting materials. ¹H NMR (400 MHz, DMSO-d6) δ 10.78 (s, 1H), 8.59 (s, 2H), 8.27 (s, 1H), 8.04 (d, J=8.2 Hz, 1H), 7.80-7.69 (m, 3H), 7.33 (d, J=7.4 Hz, 1H), 6.81 (s, 2H), 5.93 (d, J=17.3 Hz, 1H), 5.54 (d, J=17.2 Hz, 1H), 4.42 (dd, J=8.9, 5.8 Hz, 1H), 3.63 (t, J=4.1 Hz, 1H), 2.62 (d, J=16.9 Hz, 3H), 2.46 (d, J=9.2 Hz, 1H), 2.02-1.96 (m, 1H), 1.27 (d, J=23.5 Hz, 3H), 0.97 (d, J=3.9 Hz, 2H). LC/MS (ESI) m/z: 589 (M+H)⁺.

351

(1R,3S,5R)-2-(2-(3-Acetyl-5-(2-methoxypyrimidin-5-yl)-1H-indazol-1-yl)acetyl)-N-(6-bromopyridin-2-yl)-5-methyl-2-azabicyclo[3.1.0]hexane-3-carboxamide (486)

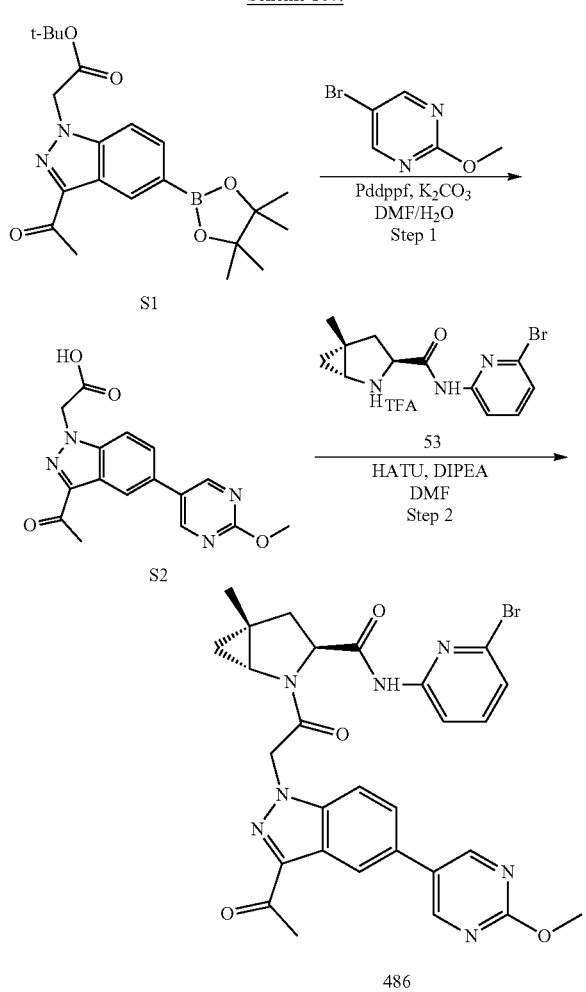

Step 1: 2-(3-Acetyl-5-(2-methoxypyrimidin-5-yl)-1H-indazol-1-yl)acetic acid (S2)

To a mixture of compound S1 (100 mg, 0.25 mmol) and 5-bromo-2-methoxypyrimidine (51 mg, 0.27 mmol) in DMF/water (5 mL/1.5 mL) was added $K_2CO_3$ (69 mg, 0.5 mmol). The reaction was degassed under $N_2$ atmosphere for three times and Pddppf (15 mg, 0.018 mmol) was added under $N_2$ atmosphere. The reaction mixture was stirred at 100° C. under $N_2$ atmosphere for 16 hrs. The mixture was diluted with water and washed with EtOAc three times. The aqueous layer was acidified by adding 1 N aq. HCl solution to pH=~3 and the mixture was filtered. The filter cake was washed with water, dried under vacuum to give the title compound (49 mg, 60.7% yield) as white solid. LC/MS (ESI) m/z: 327 (M+H)$^+$.

352

Step 2: (1R,3S,5R)-2-(2-(3-Aetyl-5-(2-methxypyrimidin-5-yl)-1H-indazol-1-yl)acetyl)-N-(6-bromopyridin-2-yl)-5-methyl-2-azabicyclo[3.1.0]hexane-3-carboxamide (486)

The titled compound was prepared according the procedure from Scheme 104 from appropriate starting materials. $^1$H NMR (400 MHz, DMSO-d6) δ: 11.15 (s, 1H), 9.27 (s, 1H), 8.95 (s, 2H), 8.54 (d, J=4.4 Hz, 1H), 8.38 (s, 1H), 7.86 (d, J=8.3 Hz, 1H), 7.82 (dd, J=8.8, 1.6 Hz, 1H), 5.96 (d, J=17.3 Hz, 1H), 5.58 (d, J=17.2 Hz, 1H), 4.44 (dd, J=9.1, 5.9 Hz, 1H), 3.99 (s, 3H), 3.65 (dd, J=5.3, 2.5 Hz, 1H), 2.69-2.63 (m, 3H), 2.47 (s, 1H), 2.04 (dd, J=13.2, 6.0 Hz, 1H), 1.37-1.27 (m, 3H), 1.28-1.15 (m, 1H), 1.03-0.93 (m, 2H). LC/MS (ESI) m/z: 604 (M+H)$^+$.

(1R,3S,5R)-2-(2-(3-Acetyl-5-(2-methylpyrimidin-5-yl)-1H-indazol-1-yl)acetyl)-N-(6-bromo-4-methoxypyridin-2-yl)-5-methyl-2-azabicyclo[3.1.0]hexane-3-carboxamide (484)

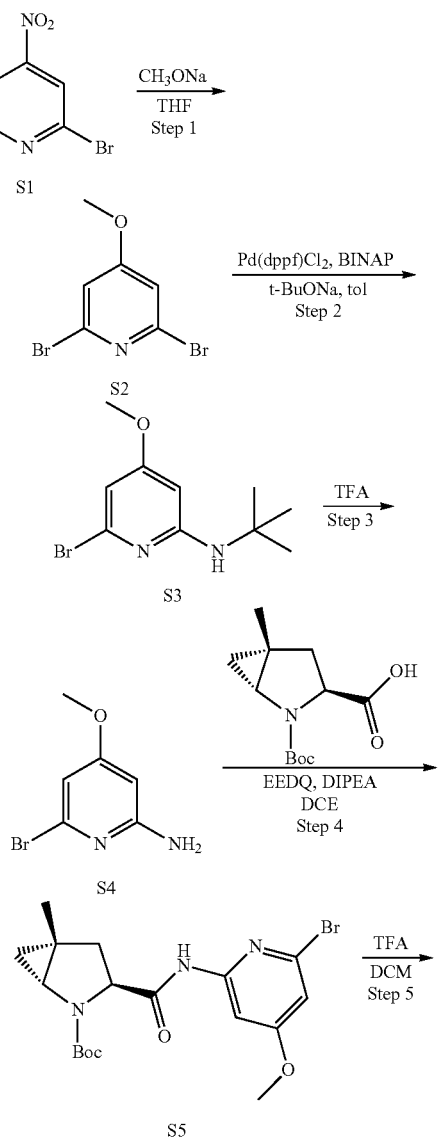

Step 1: 2,6-Dibromo-4-methoxypyridine (S2)

To a solution of compound S1 (2 g, 7.11 mmol) in THF (15 mL) was added MeONa/MeOH solution (1.2 mL, 6.05 mmol, 1.3 M). The reaction was stirred at room temperature for 2 hrs and quenched with water. The resulting mixture was extracted with EtOAc twice. The combined organic phases were washed with brine, dried over anhydrous $Na_2SO_4$, filtered and concentrated to dryness. The residue was purified by silica gel column eluted with (PE/Acetone=30/1) to give the title compound (1.45 g, 70% yield) as a white solid.

Step 2: 6-Bromo-N-(tert-butyl)-4-methoxypyridin-2-amine (S3)

To a solution of the compound S2 (500 mg, 1.87 mmol), BINAP (58 mg, 0.09 mmol), 2-methylpropan-2-amine (205 mg, 2.81 mmol) and t-BuONa (450 mg, 3.75 mmol) in toluene (10 mL) was added Pd(dppf)Cl$_2$ (85 mg, 0.09 mmol). The reaction was stirred at 90° C. for 16 hrs under $N_2$ atmosphere. The mixture was diluted with EtOAc and washed with brine, dried over anhydrous $Na_2SO_4$, filtered and concentrated. The residue was purified by silica gel column eluted with PE/Acetone=5/1 to give the title compound (150 mg, 25% yield) as a yellow solid.

Step 3: 6-Bromo-4-methoxypyridin-2-amine 4 TFA Salt (S4)

A solution of compound S3 (100 mg, 0.38 mmol) in TFA (3 mL) was stirred at 70° C. for 3 hrs. The mixture was concentrated to dryness to give the title compound (90 mg, 89% yield) as a yellow solid, which was directly used to the next reaction without purification.

Step 4: (1R,3S,5R)-tert-Butyl 3-((6-bromo-4-methoxypyridin-2-yl)carbamoyl)-5-methyl-2-azabicyclo[3.1.0]hexane-2-carboxylate (S5)

To a solution of the compound S4 (70 mg, 0.34 mmol), (1R,3S,5R)-2-(tert-butoxycarbonyl)-5-methyl-2-azabicyclo[3.1.0]hexane-3-carboxylic acid (83 mg, 0.34 mmol) and EEDQ (170 mg, 0.69 mmol) in 1,2-DCE (5 mL) was added DIPEA (135 mg, 1.02 mmol). The reaction was stirred at 90° C. for 16 hrs and then concentrated to dryness. The residue was purified by silica gel column with (EtOAc/PE=1/3 to 1/1) to give the title compound (90 mg, 62% yield) as a yellow solid.

Step 5: (1R,3S,5R)—N-(6-Bromo-4-methoxypyridin-2-yl)-5-methyl-2-azabicyclo[3.1.0]hexane-3-carboxamide TFA Salt (S6)

To a solution of the compound S5 (90 mg, 0.21 mmol) in DCM (3 mL) was added TFA (1 mL). The reaction was stirred at room temperature for 2 hrs. The mixture was concentrated to dryness to give the title compound (95 mg, 100% yield) as a yellow solid, which was directly used to the next reaction without purification.

Step 6: (1R,3S,5R)-2-(2-(3-Acetyl-5-(2-methylpyrimidin-5-yl)-1H-indazol-1-yl)acetyl)-N-(6-bromo-4-methoxypyridin-2-yl)-5-methyl-2-azabicyclo[3.1.0]hexane-3-carboxamide (484)

To a solution of the compound S6 (89 mg, 0.21 mmol), S7 (80 mg, 0.26 mmol) and HATU (120 mg, 0.31 mmol) in DMF (3 mL) was added DIPEA (80 mg, 0.63 mmol). The reaction was stirred at room temperature for 16 hrs. The mixture was diluted with EtOAc and washed with 10% aq. LiCl solution and brine, dried over anhydrous $Na_2SO_4$, filtered and concentrated to dryness. The residue was purified by silica gel column with PE/Acetone=2/1 to give the title compound (46 mg, 35.4% yield) as a white solid. $^1$H NMR (400 MHz, DMSO-d6) δ: 10.73 (s, 1H), 9.05 (s, 2H), 8.44 (s, 1H), 7.88 (d, J=1.1 Hz, 2H), 7.65 (d, J=1.8 Hz, 1H), 6.96 (d, J=2.0 Hz, 1H), 5.96 (d, J=17.3 Hz, 1H), 5.58 (d, J=17.2 Hz, 1H), 4.42 (dd, J=9.0, 5.8 Hz, 1H), 3.83 (s, 3H), 3.62 (d, J=4.1 Hz, 1H), 2.68 (d, J=13.4 Hz, 6H), 2.46 (d, J=9.1 Hz, 1H), 1.98 (dd, J=13.3, 5.7 Hz, 1H), 1.30 (s, 3H), 0.97 (d, J=3.8 Hz, 2H). LC/MS (ESI) m/z: 618 (M+H)$^+$.

(1R,3S,5R)-2-(2-(3-Acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (485)

Scheme 110.

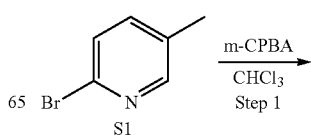

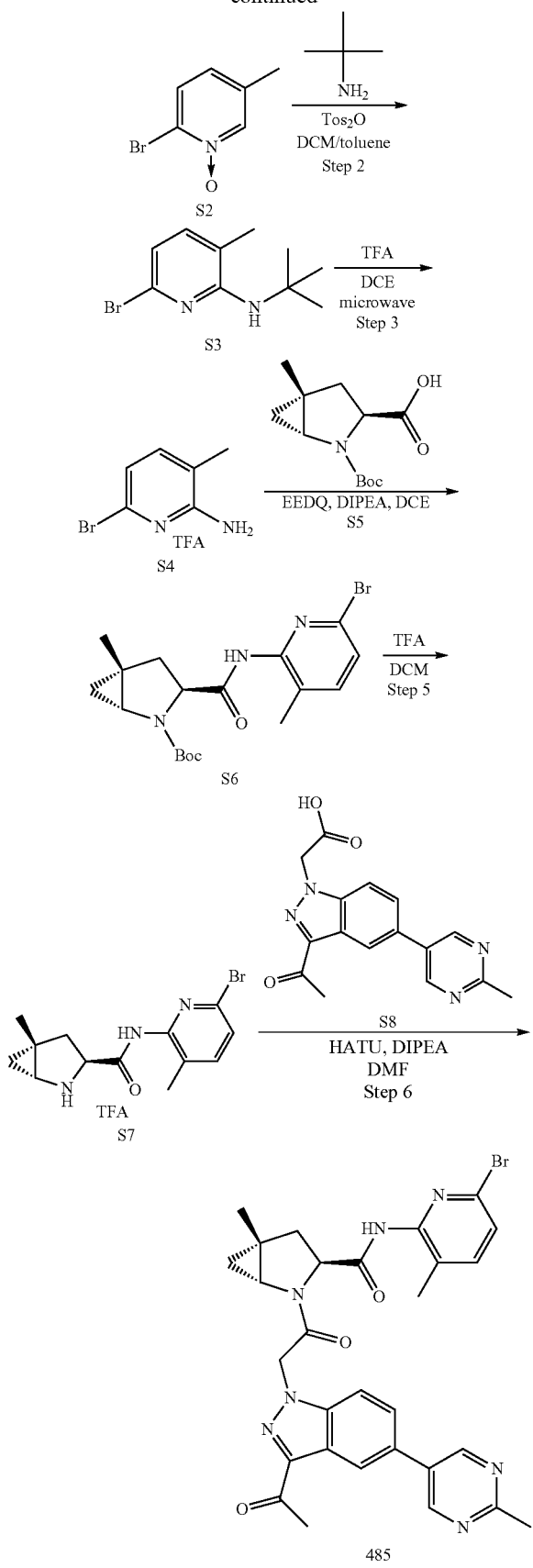

Step 1: 2-Bromo-5-methylpyridine 1-oxide (S2)

To a mixture of 2-bromo-5-methylpyridine (4.0 g, 23.3 mmol) in CHCl$_3$ (20 mL) was added m-CPBA (5.2 g, 29.8 mmol) and the reaction was stirred at 50° C. for 3 hrs. The mixture was cooled and filtered. The filtrate was washed with 5% aqueous NaOH solution and the organic layer was separated, dried over anhydrous Na$_2$SO$_4$ and concentrated to dryness. The residue was purified by column chromatography on silica gel (eluted with DCM:MeOH=100:0 to 100:1) to give the title compound (3.1 g, 71% yield) as a colorless oil. LC/MS (ESI) m/z: 188 (M+H)$^+$.

Step 2:
6-Bromo-N-tert-butyl-3-methylpyridin-2-amine (S3)

To a solution of 2-bromo-5-methylpyridine 1-oxide (1.18 g, 6.28 mmol) in toluene (22 mL) was added 2-methylpropan-2-amine (3.21 g, 44 mmol) and a solution of 4-methylbenzenesulfonic anhydride (6.76 g, 20.74 mmol) in DCM (48 mL) dropwise at 0° C. The reaction mixture was stirred at 0° C. for 2 hrs and filtered. The filtrate was concentrated under reduced pressure to give a residue, which was purified by column chromatography on silica gel (eluted with PE:EtOAc=30:1) to give the title compound (280 mg, 18% yield) as a white solid. LC/MS (ESI) m/z: 243 (M+H)$^+$.

Step 3: 6-Bromo-3-methyl-2-aminopyridinium trifluoroacetate (S4)

To a mixture of 6-bromo-N-tert-butyl-3-methylpyridin-2-amine (280 mg, 1.15 mmol) in DCE (1 mL) was added TFA (1 mL). The reaction was heated to 90° C. for 25 min in a microwave reactor. The mixture was cooled and concentrated under reduced pressure. The residue was re-crystallized with Et$_2$O/PE to give the title compound (340 mg, 86% yield) as white solid. LC/MS (ESI) m/z: 187 (M+H)$^+$.

Step 4: (1R,3S,5R)-tert-Butyl 3-(6-bromo-3-methylpyridin-2-ylcarbamoyl)-5-methyl-2-azabicyclo[3.1.0]hexane-2-carboxylate (S5)

To a solution of compound (1R,3S,5R)-2-(tert-butoxycarbonyl)-5-methyl-2-azabicyclo[3.1.0]hexane-3-carboxylic acid (186 mg, 0.77 mmol), compound S5 (230 mg, 0.77 mmol) and EEDQ (384 mg, 1.54 mmol) in DCE (20 mL) was added DIPEA (410 mg, 3.08 mmol). The reaction was stirred at reflux overnight under N$_2$ atmosphere. The mixture was concentrated and the residue was purified by column chromatography on silica gel (eluted with petroleum ether:ethyl acetate=10:1 to 3:1) to give the title compound (220 mg, 72.7% yield) as a yellow solid. LC/MS (ESI) m/z: 410 (M+H)$^+$.

Step 5: (1R,3S,5R)—N-(6-Bromo-3-methylpyridin-2-yl)-5-methyl-2-azabicyclo[3.1.0]hexane-3-carboxamide (S6)

To a mixture of compound S6 (220 mg, 0.56 mmol) in DCM (2 mL) was added TFA (2 mL) and the reaction was stirred at room temperature for 2 hrs. The mixture was concentrated to dryness to give the title compound (220 mg, 100 yield) as a brown solid, which was directly used to the next reaction without further purification. LC/MS (ESI) m/z: 310 (M+H)$^+$.

Step 6: (1R,3S,5R)-2-(2-(3-Acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (485)

To a solution of S7 (168 mg, 0.54 mmol), compound S8 (220 mg, 0.54 mmol) and DIPEA (210 mg, 1.62 mmol) in DMF (10 mL) was added HATU (412 mg, 1.08 mmol) at 0° C. The reaction was stirred at room temperature overnight. The mixture was diluted with EtOAc, washed with 10% aq. LiCl solution and brine successively, dried over anhydrous Na$_2$SO$_4$, filtered and then concentrated. The residue was purified by prep-HPLC (eluted with CH$_3$CN/water) to give the title compound (71 mg, 21.8% yield) as a white solid. $^1$H NMR (400 MHz, DMSO-d6) δ: 10.29 (s, 1H), 9.05 (s, 2H), 8.45 (s, 1H), 7.86 (d, J=1.6 Hz, 2H), 7.63 (d, J=8.0 Hz, 1H), 7.45 (d, J=7.9 Hz, 1H), 5.93 (d, J=17.3 Hz, 1H), 5.58 (d, J=17.2 Hz, 1H), 4.41 (dd, J=9.3, 5.1 Hz, 1H), 3.60 (dd, J=5.4, 2.4 Hz, 1H), 2.69 (s, 3H), 2.65 (s, 3H), 2.53-2.59 (m, 1H), 2.00-2.09 (m, 4H), 1.33 (s, 3H), 0.98-1.07 (m, 2H). LC/MS (ESI) m/z: 602 (M+H)$^+$.

1-(2-((1R,3S,4S)-3-(6-Methylpyridin-2-ylcarbamoyl)-2-azabicyclo[2.2.1]heptan-2-yl)-2-oxoethyl)-5-(2-methylpyrimidin-5-yl)-1H-indole-3-carboxamide (473)

Scheme 111.

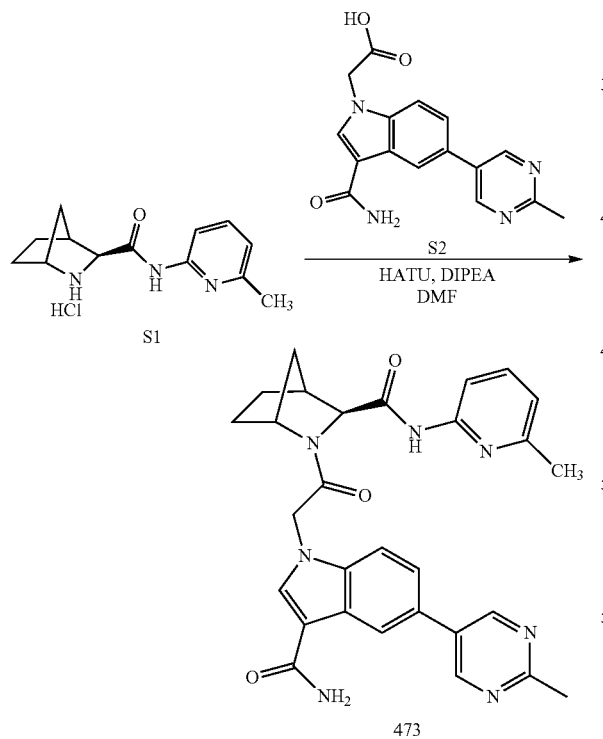

The titled compound was prepared according the procedure from Scheme 110 from appropriate starting materials. $^1$H NMR (400 MHz, CDCl$_3$) δ: 9.10 (s, 2H), 8.43 (d, J=48.3 Hz, 2H), 8.09 (d, J=7.8 Hz, 1H), 7.89 (s, 1H), 7.52 (d, J=4.7 Hz, 3H), 7.19 (d, J=7.2 Hz, 1H), 5.58 (s, 1H), 4.92 (d, J=17.0 Hz, 1H), 4.53 (s, 1H), 4.27 (s, 1H), 2.89 (s, 3H), 2.74 (s, 3H), 2.04 (s, 1H), 1.98-1.97 (m, 1H), 1.95-1.94 (m, 1H), 1.76 (s, 2H), 1.60 (s, 1H), 1.44 (s, 1H). LC/MS (ESI) m/z: 524 (M+H)$^+$.

5-(2-Methylpyrazolo[1,5-a]pyrimidin-6-yl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (691)

Scheme 112.

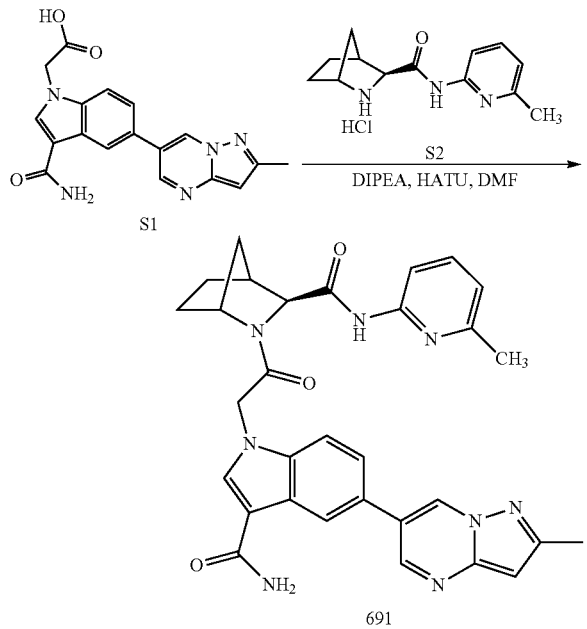

The titled compound was prepared according the procedure from Scheme 110 from appropriate starting materials. $^1$H NMR (400 MHz, DMSO-d6) δ: 10.47 (s, 1H), 9.26 (d, J=1.6 Hz, 1H), 8.86 (d, J=2.4 Hz, 1H), 8.42 (s, 1H), 8.05-7.96 (m, 1H), 7.86-7.46 (m, 4H), 6.99 (d, J=7.6 Hz, 1H), 6.56 (s, 1H), 5.44 (d, J=17.2 Hz, 1H), 5.16 (dd, J=17.2, 7.2 Hz, 1H), 4.73-4.38 (m, 2H), 2.68 (s, 1H), 2.46 (s, 3H), 2.39 (s, 3H), 2.11 (d, J=9.6 Hz, 1H), 1.93-1.66 (m, 3H), 1.60-1.27 (m, 2H); LC/MS (ESI) m/z: 563 [M+H]$^+$.

1-(2-((1R,3S,4S)-3-(6-Methylpyridin-2-ylcarbamoyl)-2-azabicyclo[2.2.1]heptan-2-yl)-2-oxoethyl)-5-(pyridin-3-yl)-1H-indole-3-carboxamide (501)

Scheme 113.

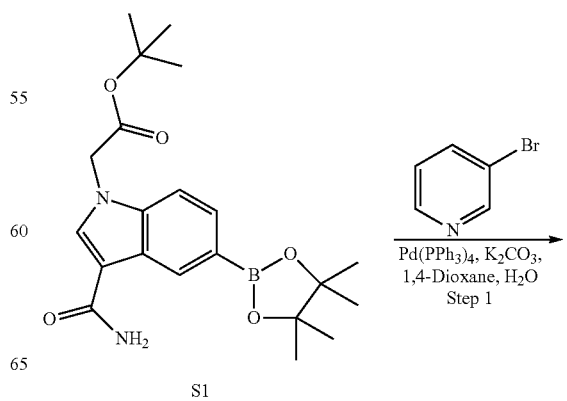

-continued

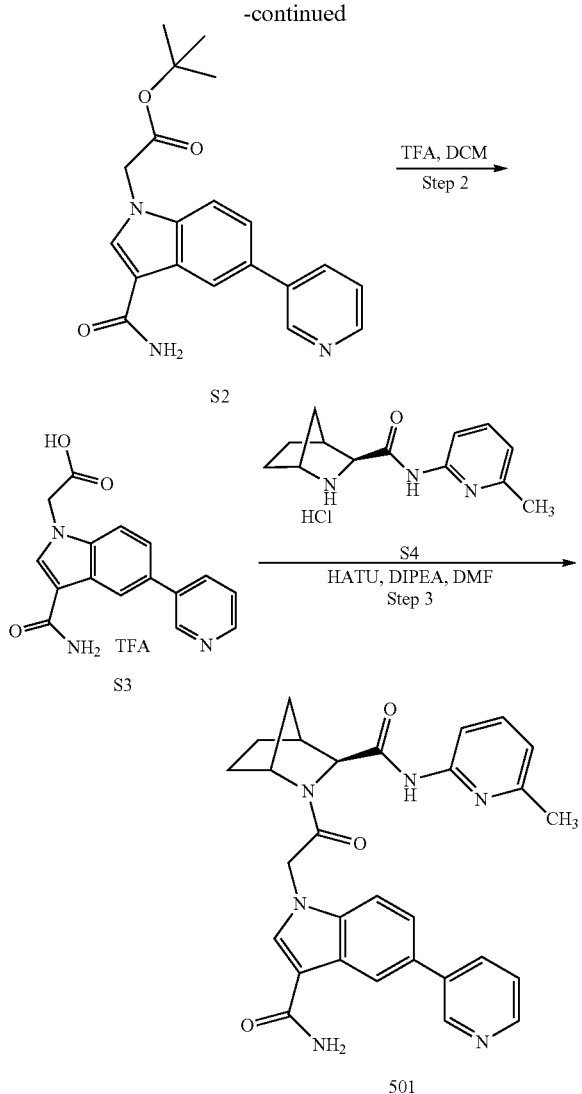

Step 1: tert-Butyl 2-(3-carbamoyl-5-(pyridin-3-yl)-1H-indol-1-yl)acetate (S2)

To a mixture of S1 (200 mg, 0.5 mmol), 3-bromopyridine (95 mg, 0.6 mmol), and K$_2$CO$_3$ (138 mg, 1 mmol) in 1,4-Dioxane (4 mL) and water (1 mL) was added Pd(PPh$_3$)$_4$ (30 mg, 0.025 mmol). The reaction was degassed under N$_2$ three times and stirred at 120° C. for 2 hrs under N$_2$ atmosphere. The mixture was diluted with EtOAc and washed with water and brine, dried over anhydrous Na$_2$SO$_4$, filtered and concentrated. The residue was purified by silica gel column (eluted with DCM/MeOH=50/1 to 20:1) to give the title compound (110 mg, 62.6% yield) as a gray solid. LCMS: LC/MS (ESI) m/z: 352 [M+H]$^+$

Step 2: 2-(3-Carbamoyl-5-(pyridin-3-yl)-1H-indol-1-yl)acetic acid TFA Salt (S3)

To a solution of the compound S2 (100 mg, 0.28 mmol) in DCM (3 mL) was added TFA (1 mL). The reaction was stirred at room temperature for 2 hrs. The mixture was concentrated to dryness to give the title compound (105 mg, 100% yield) as a white solid. LCMS: LC/MS (ESI) m/z: 296 [M+H]$^+$

Step 3: 1-(2-(((1R,3S,4S)-3-((6-Methylpyridin-2-yl)carbamoyl)-2-azabicyclo[2.2.1]heptan-2-yl)-2-oxo-ethyl)-5-(pyridin-3-yl)-1H-indole-3-carboxamide (501)

To a solution of the compound S3 (50 mg, 0.127 mmol), S4 (34.1 mg, 0.127 mmol) and HATU (72 mg, 0.19 mmol) in DMF (3 mL) was added DIPEA (65.6 mg, 0.51 mmol) at 0° C. The reaction was stirred at room temperature for 16 hrs. The mixture was diluted with EtOAc and washed with water and brine, dried over anhydrous Na$_2$SO$_4$, filtered and concentrated to give crude product, which was purified by prep-HPLC to give the title compound (11 mg, 17.0% yield) as white solid. $^1$H NMR (400 MHz, DMSO-d6) δ: 10.43 (s, 1H), 8.89 (s, 1H), 8.54 (s, 1H), 8.41 (s, 1H), 8.17-7.69 (m, 4H), 7.66-7.38 (m, 4H), 6.97 (dd, J=31.3, 7.5 Hz, 1H), 5.42 (d, J=17.2 Hz, 1H), 5.15 (dd, J=17.1, 6.4 Hz, 1H), 4.67-4.54 (m, 1H), 4.13 (s, 1H), 2.80 (d, J=105.1 Hz, 1H), 2.40 (d, J=17.9 Hz, 3H), 2.10 (d, J=9.7 Hz, 1H), 1.89-1.65 (m, 3H), 1.62-1.27 (m, 2H). LCMS: LC/MS (ESI) m/z: 509 [M+H]$^+$.

1-(2-((1R,3S,4S)-3-(6-Methylpyridin-2-ylcarbamoyl)-2-azabicyclo[2.2.1]heptan-2-yl)-2-oxoethyl)-5-(6-methylpyridin-3-yl)-1H-indole-3-carboxamide (490)

Scheme 114.

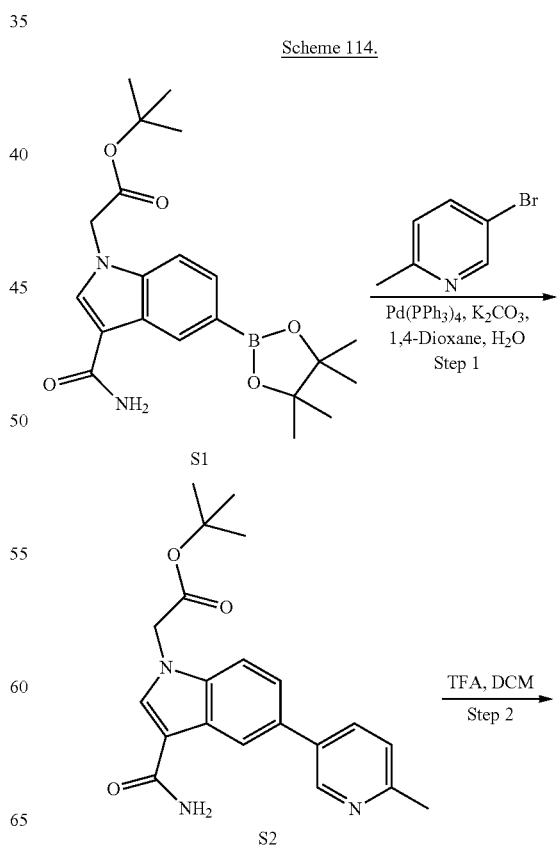

361

-continued

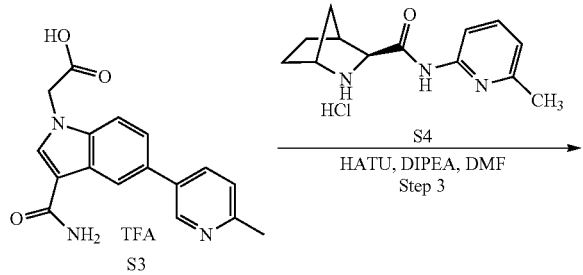

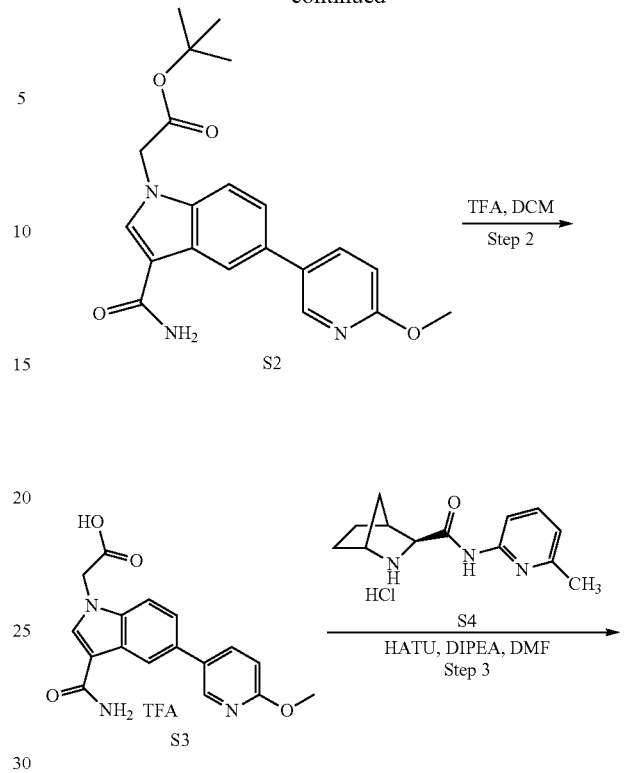

The titled compound was prepared according the procedure from Scheme 113 from appropriate starting materials. $^1$H NMR (400 MHz, DMSO-d6) δ 10.49 (s, 1H), 8.79 (d, J=2.4 Hz, 1H), 8.43 (d, J=1.2 Hz, 1H), 8.00-8.07 (m, 3H), 7.87-7.89 (m, 1H), 7.54-7.68 (m, 4H), 7.39 (d, J=8.0 Hz, 1H), 6.99 (d, J=7.6 Hz, 1H), 5.44-5.49 (m, 1H), 5.18-5.22 (m, 1H), 4.69 (s, 1H), 4.18 (s, 1H), 2.72 (s, 1H), 2.56 (s, 3H), 2.44 (s, 3H), 2.15 (d, J=5.6 Hz, 1H), 1.84 (s, 3H), 1.48-1.57 (m, 2H). LC/MS (ESI) m/z: 523 (M+H)$^+$.

5-(6-Methoxypyridin-3-yl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (730)

Scheme 115.

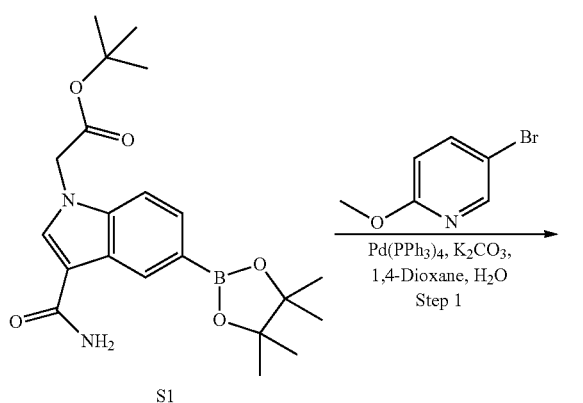

362

-continued

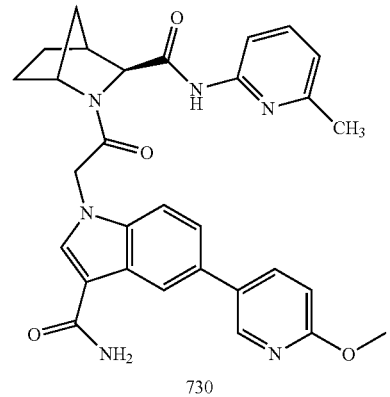

The titled compound was prepared according the procedure from Scheme 113 from appropriate starting materials. $^1$H NMR (400 MHz, DMSO-d$_6$) δ 10.43 (s, 1H), 8.45 (d, J=2.4 Hz, 1H), 8.33 (d, J=1.6 Hz, 1H), 8.03-7.97 (m, 2H), 7.83 (d, J=8.4 Hz, 1H), 7.76-7.40 (m, 4H), 6.93 (t, J=7.6 Hz, 2H), 5.40 (d, J=17.6 Hz, 1H), 5.13 (dd, J=17.2, 8.4 Hz, 1H), 4.63 (s, 1H), 4.58-4.43 (m, 1H), 4.13 (s, 1H), 3.90 (s, 3H), 2.67 (s, 1H), 2.39 (s, 3H), 2.19-2.07 (m, 1H), 1.80-1.61 (m, 3H), 1.60-1.40 (m, 2H); LCMS: LC/MS (ESI) m/z: 539 [M+H]$^+$.

363

5-(6-Aminopyridin-3-yl)-1-(2-(((1R,3S,4S)-3-(6-methylpyridin-2-ylcarbamoyl)-2-azabicyclo[2.2.1]heptan-2-yl)-2-oxoethyl)-1H-indole-3-carboxamide (498)

Scheme 116.

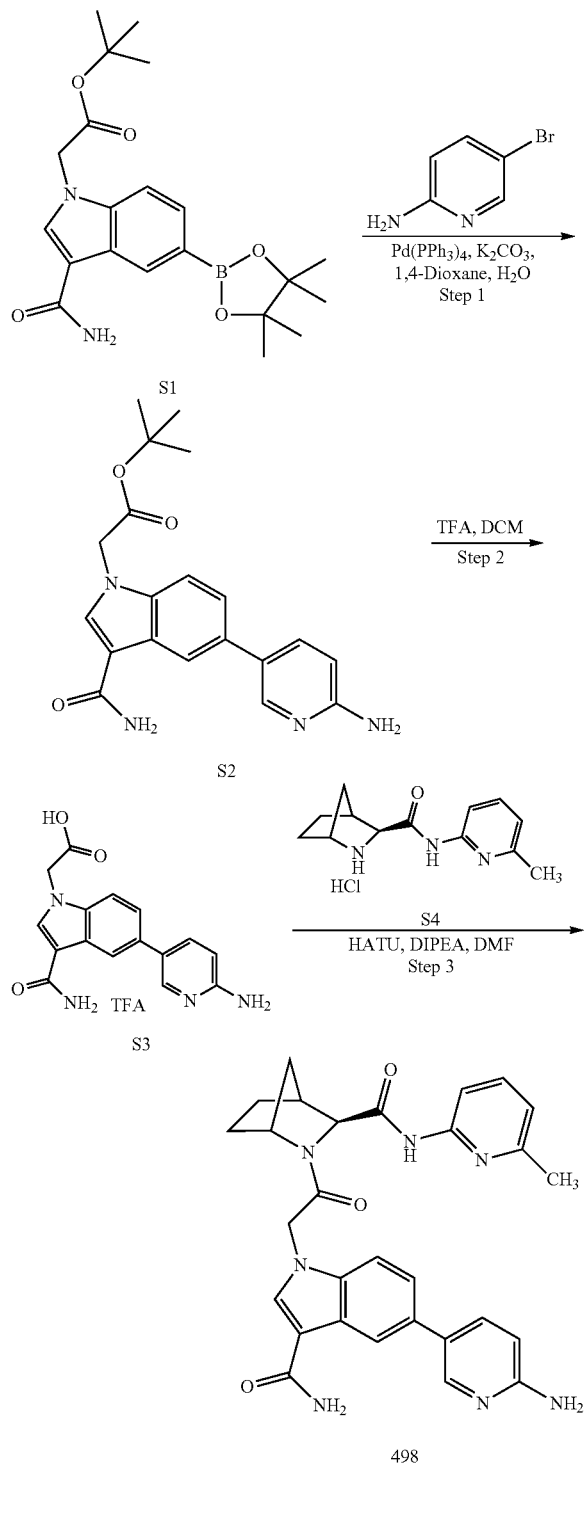

The titled compound was prepared according the procedure from Scheme 113 from appropriate starting materials.

364

$^1$H NMR (400 MHz, DMSO-d$_6$) δ: 10.42 (s, 1H), 8.21-8.25 (dd, J=14.4, 1.6 Hz, 2H), 7.96 (s, 1H), 7.81-7.83 (d, J=8.0 Hz, 1H), 7.70-7.76 (m, 1H), 7.60-7.64 (t, 1H), 7.45-7.47 (d, J=8.4 Hz, 1H), 7.36-7.38 (m, 1H), 6.92-6.94 (d, J=7.6 Hz, 1H), 6.58-6.61 (d, J=8.8 Hz, 1H), 6.11-6.15 (br, 2H), 5.34-5.39 (d, J=17.2 Hz, 1H), 5.07-5.13 (m, 1H), 4.62 (m, 1H), 4.11 (m, 1H), 2.66 (m, 1H), 2.38 (s, 3H), 2.08-2.10 (m, 1H), 1.77 (m, 3H), 1.41-1.48 (m, 2H). LCMS: LC/MS (ESI) m/z: 524 [M+H]$^+$.

5-(6-Fluoropyridin-3-yl)-1-(2-(((1R,3S,4S)-3-(6-methylpyridin-2-ylcarbamoyl)-2-azabicyclo[2.2.1]heptan-2-yl)-2-oxoethyl)-1H-indole-3-carboxamide (500)

Scheme 117.

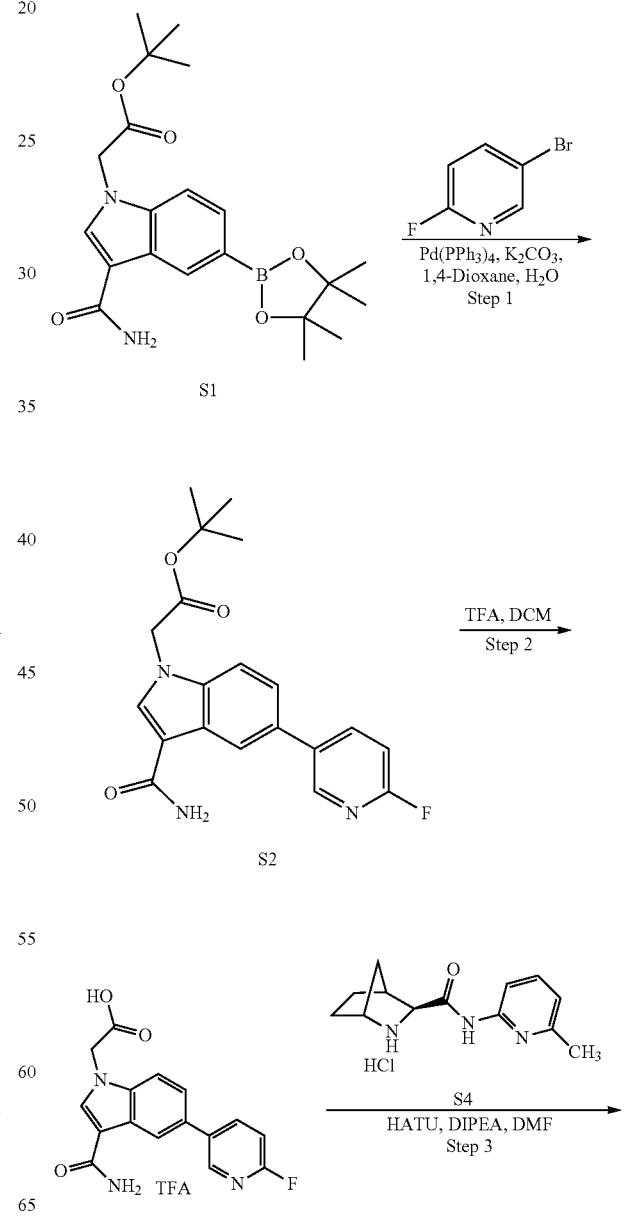

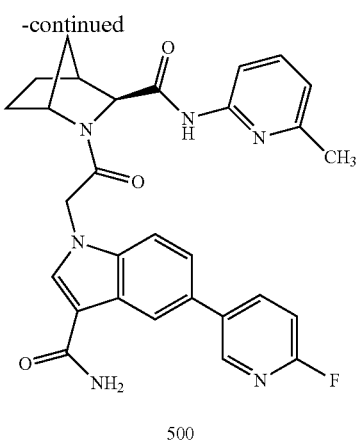
500
The titled compound was prepared according the procedure from Scheme 113 from appropriate starting materials. ¹H NMR (400 MHz, CDCl₃) δ: 9.08 (s, 1H), 8.42 (d, J=2.3 Hz, 1H), 8.30 (d, J=6.2 Hz, 1H), 8.00 (td, J=8.2, 2.6 Hz, 1H), 7.92 (d, J=8.2 Hz, 1H), 7.85 (s, 1H), 7.54 (dd, J=14.3, 6.4 Hz, 1H), 7.44-7.34 (m, 2H), 7.00-6.95 (m, 1H), 6.86 (d, J=7.5 Hz, 1H), 6.02 (d, 2H), 5.13 (d, 1H), 4.95 (d, 1H), 4.78 (d, J=8.0 Hz, 1H), 4.34 (s, 1H), 4.22 (s, 1H), 2.96 (d, 1H), 2.43 (d, J=4.4 Hz, 1H), 2.39 (s, 3H), 2.22 (d, J=10.4 Hz, 1H), 1.87 (d, J=4.7 Hz, 1H), 1.54 (d, J=10.6 Hz, 2H). LC/MS (ESI) m/z: 527 (M+H)⁺.
1-(2-(((1R,3S,4S)-3-(6-Methylpyridin-2-ylcarbamoyl)-2-azabicyclo[2.2.1]heptan-2-yl)-2-oxoethyl)-5-(quinolin-7-yl)-1H-indole-3-carboxamide (499)
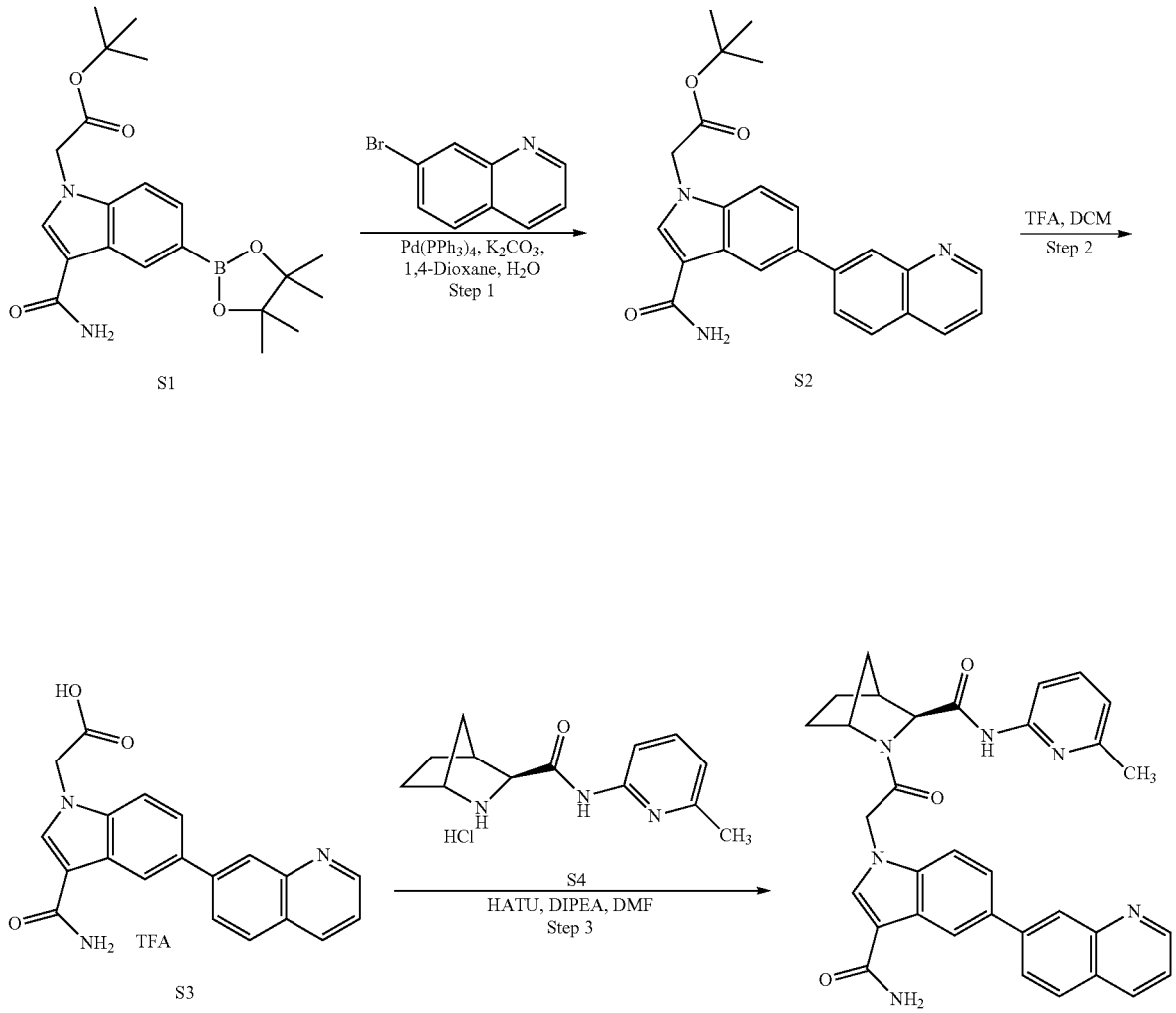

The titled compound was prepared according the procedure from Scheme 113 from appropriate starting materials. $^1$H NMR (400 MHz, CDCl$_3$) δ: 9.13 (s, 1H), 8.92 (d, J=4.2 Hz, 1H), 8.48 (s, 1H), 8.34 (d, J=9.5 Hz, 1H), 8.16 (t, J=6.8 Hz, 1H), 7.97-7.90 (m, 1H), 7.90-7.84 (m, 3H), 7.66 (t, J=7.6 Hz, 1H), 7.55 (t, J=7.8 Hz, 1H), 7.41-7.36 (m, 2H), 6.84 (d, J=7.5 Hz, 1H), 6.07 (d, J=38.0 Hz, 2H), 5.12 (d, 1H), 4.92 (d, 1H), 4.76 (s, 1H), 4.32 (s, 1H), 4.21 (s, 1H), 2.94 (d, 1H), 2.41 (s, 1H), 2.39 (s, 3H), 2.18 (d, J=10.5 Hz, 1H), 1.53 (dd, 3H). LC/MS (ESI) m/z: 559 (M+H)$^+$.

5-(6,7-Dihydro-5H-cyclopenta[b]pyridin-3-yl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (535)

Step 1: 4-Bromo-1H-pyrazol-1-amine (S2)

To a solution of compound S1 (1 g, 6.8 mmol) in H$_2$O (15 mL) was added NaOH (544 mg, 13.6 mmol) and sulfamic acid (1.32 g, 13.6 mmol) at 0° C. After addition, the reaction was stirred at room temperature for 2 hrs. The mixture was diluted with EtOAc and washed with water and brine, dried over anhydrous Na$_2$SO$_4$, filtered, and concentrated to dryness to give the title compound (1 g, crude) as a white solid.

Step 2: 5-Bromo-1,2,3-triazine (S3)

To a solution of compound S2 (1 g, crude) in DCM (15 mL) and water (5 mL) was added NaIO$_4$ (2 g, 9.3 mmol). The reaction was stirred at room temperature for 16 hrs. The mixture was diluted with DCM and washed with water, brine, dried over anhydrous Na$_2$SO$_4$, filtered, and concen-

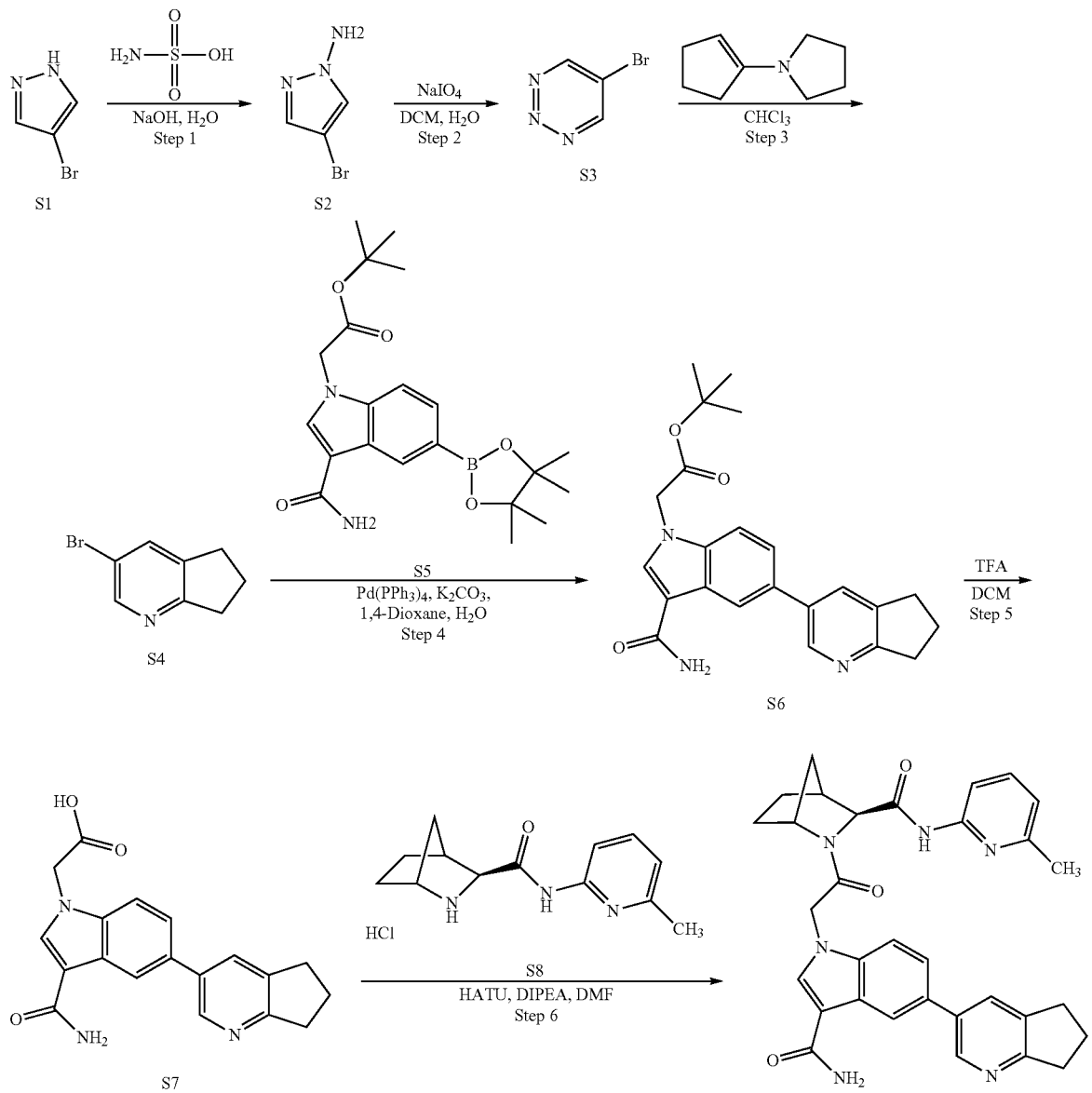

Scheme 119.

535 trated. The residue was purified by silica gel column (eluted with EtOAc/PE=1/5) to give the title compound (710 mg, 65.2% yield) as a purple solid.

Step 3: 3-Bromo-6,7-dihydro-5H-cyclopenta[b]pyridine (S4)

To a solution of compound S3 (400 mg, 2.5 mmol) in CHCl₃ (10 mL) was added 1-(cyclopent-1-en-1-yl)pyrrolidine (516 mg, 3.8 mmol). The reaction was stirred at 45° C. for 16 hrs. The reaction mixture was diluted with DCM and washed water, brine, dried over anhydrous Na₂SO₄, filtered, and concentrated. The residue was purified by silica gel column (eluted with EtOAc/PE=1/10) to give the title compound (170 mg, 34.3% yield) as a gray solid.

Step 4: tert-Butyl 2-(3-carbamoyl-5-(6,7-dihydro-5H-cyclopenta[b]pyridin-3-yl)-1H-indol-1-yl)acetate (S6)

To a mixture of compound S4 (160 mg, 0.81 mmol), S5 (150 mg, 0.38 mmol), and K₂CO₃ (155 mg, 1.1 mmol) in 1,4-dioxane (5 mL) and water (2 mL) was added Pd(PPh₃)₄ (30 mg, 0.025 mmol). The mixture was degassed under N₂ atmosphere three times and the reaction was stirred at 110° C. under N₂ atmosphere for 2 hrs. The mixture was diluted with EtOAc and washed with water and brine, dried over anhydrous Na₂SO₄ and concentrated to dryness. The residue was purified by silica gel chromatography (eluted with DCM/MeOH=50/1) to give the title compound (90 mg, 60.5% yield) as yellow solid. LC/MS (ESI) m/z: 392 (M+H)⁺.

Step 5: 2-(3-Carbamoyl-5-(6,7-dihydro-5H-cyclopenta[b]pyridin-3-yl)-1H-indol-1-yl)acetic acid (S7)

To a solution of the compound S6 (30 mg, 0.08 mmol) in DCM (1 mL) was added TFA (0.2 mL). The reaction was stirred at room temperature for 2 hrs. The mixture was concentrated to dryness to give compound S7 (30 mg, 100% yield) as yellow solid, which was directly used to the next reaction without purification as a TFA salt. LC/MS (ESI) m/z: 336 (M+H)⁺.

Step 6: 5-(6,7-Dihydro-5H-cyclopenta[b]pyridin-3-yl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (535)

To a solution of the compound S7 (30 mg, 0.08 mmol), S8 (20 mg, 0.08 mmol) and HATU (45 mg, 0.12 mmol) in DMF (1 mL) was added DIPEA (32 mg, 0.25 mmol). The reaction was stirred at room temperature for 16 hrs. The mixture was diluted with EtOAc and washed with 10% aq. LiCl solution and brine, dried over anhydrous Na₂SO₄, filtered and concentrated to dryness. The residue was purified by Prep-TLC (DCM/MeOH=10/1) to give the title compound (8 mg, 16% yield) as white solid. ¹H NMR (400 MHz, DMSO-d₆) δ 10.43 (s, 1H), 8.56 (s, 1H), 8.36 (d, J=1.3 Hz, 1H), 8.03-7.95 (m, 1H), 7.89-7.69 (m, 2H), 7.62 (t, J=7.9 Hz, 1H), 7.47 (ddd, J=24.0, 21.8, 8.5 Hz, 2H), 7.07-6.90 (m, 2H), 5.35 (dd, J=41.9, 18.4 Hz, 1H), 5.21-5.06 (m, 1H), 4.65-4.45 (m, 1H), 4.12 (s, 1H), 2.96 (dt, J=18.2, 7.5 Hz, 4H), 2.66 (s, 1H), 2.40 (d, J=17.8 Hz, 3H), 2.11 (p, J=7.5 Hz, 3H), 1.85 (d, J=50.5 Hz, 3H), 1.54-1.37 (m, 2H), 1.34-1.14 (m, 2H). LC/MS (ESI) m/z: 549 (M+H)⁺.

5-(Imidazo[1,2-a]pyrimidin-3-yl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (695)

Scheme 120.

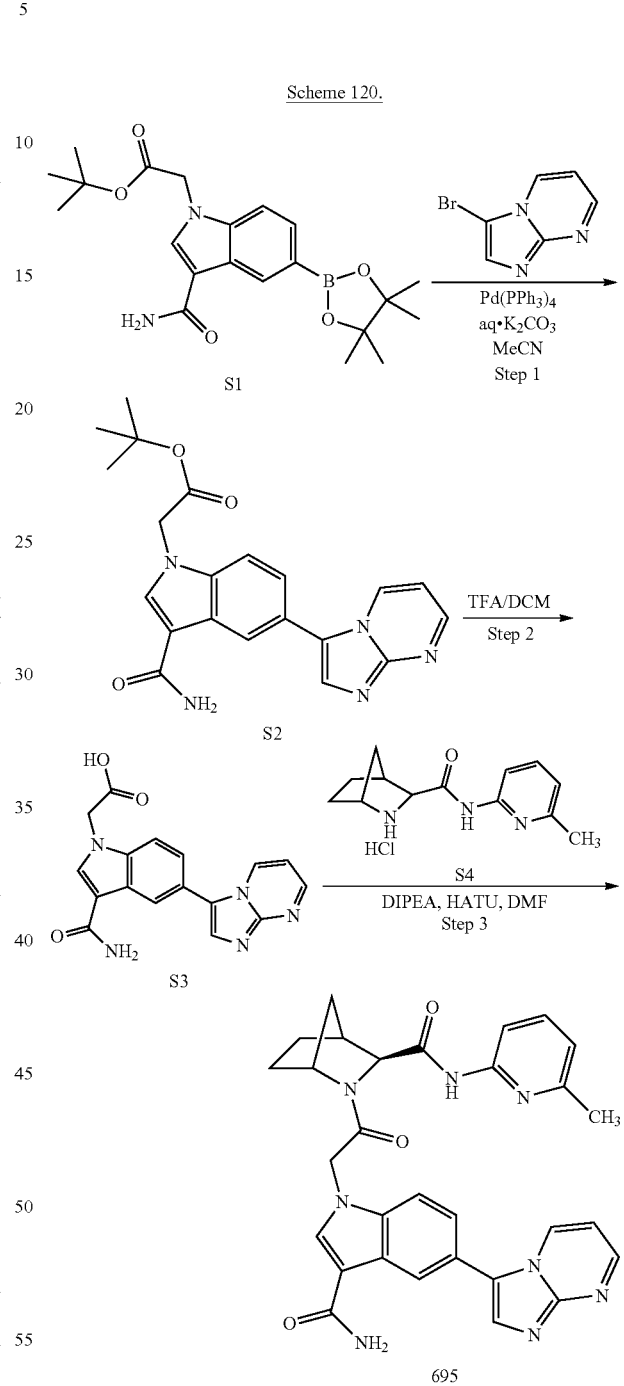

Step 1: tert-Butyl 2-(3-carbamoyl-5-(imidazo[1,2-a]pyrimidin-3-yl)-1H-indol-1-yl)acetate (S1)

To a mixture of S1 (140 mg, 0.35 mmol) and 3-bromoimidazo[1,2-a]pyrimidine (82 mg, 0.42 mmol) in CH₃CN (3 mL) was added aq. K₂CO₃ solution (0.7 mL, 0.7 mmol, 1M). The mixture was degassed under N₂ for three times stirred at 80° C. under N₂ atmosphere for 16 hrs. The mixture was diluted with EtOAc, washed with water and brine, dried over anhydrous Na$_2$SO$_4$ and concentrated to dryness. The residue was purified by silica gel chromatography (dichloromethane:methanol=100:1) to give the title compound (70 mg, 51.2% yield) as white solid. LC-MS (ESI) found: 392 [M+1]$^+$.

Step 2: 2-(3-Carbamoyl-5-(imidazo[1,2-a]pyrimidin-3-yl)-1H-indol-1-yl)acetic acid (S2)

To a solution of compound S2 (70 mg, 0.18 mmol) in DCM (3 mL) was added TFA (1 mL) at 0° C. The reaction mixture was stirred at room temperature for 3 hrs. The reaction was concentrated under vacuum to give a residue, which was co-evaporated with toluene three times to give the title compound (70 mg, 100% yield) as brown solid, which was directly used to the next reaction without purification. LC-MS (ESI) found: 336 [M+1]+.

Step 3: 5-(Imidazo[1,2-a]pyrimidin-3-yl)-1-(2-((1R, 3S,4S)-3-((6-methylpyridin-2-yl)carbamoyl)-2-azabicyclo[2.2.1]heptan-2-yl)-2-oxoethyl)-1H-indole-3-carboxamide (695)

To a mixture compound S3 (70 mg, 0.18 mmol) and S4 (41 mg, 0.18 mmol) in DMF (3 mL) was added DIPEA (92.9 mg, 0.72 mmol) and HATU (137 mg, 0.36 mmol) at 0° C. The reaction was stirred at room temperature for 16 hrs. The mixture was diluted with EtOAc, washed with 10% aq. LiCl solution and brine successively, dried over anhydrous Na$_2$SO$_4$, filtered and concentrated to dryness. The residue was purified by prep-HPLC to give the title compound (25 mg, 25.3% yield) as white solid. $^1$H NMR (400 MHz, CD$_3$OD) δ 9.26 (dd, J=7.0, 1.7 Hz, 1H), 9.05 (dd, J=4.3, 1.6 Hz, 1H), 8.49 (d, J=1.3 Hz, 1H), 8.25 (s, 1H), 8.07 (s, 1H), 7.76 (dd, J=11.0, 7.7 Hz, 3H), 7.57 (ddd, J=10.2, 7.7, 3.0 Hz, 2H), 7.08 (d, J=8.1 Hz, 1H), 5.50 (d, J=17.3 Hz, 1H), 5.27 (d, J=17.3 Hz, 1H), 4.69 (s, 1H), 4.19 (s, 1H), 2.87 (s, 1H), 2.66 (s, 1H), 2.49 (d, J=5.8 Hz, 3H), 2.23 (d, J=9.8 Hz, 1H), 1.96 (d, J=10.6 Hz, 2H), 1.67 (dd, J=42.3, 20.6 Hz, 2H). LC-MS (ESI) found: 549 [M+1]$^+$.

1-(2-((1R,3S,4S)-3-(6-Methylpyridin-2-ylcarbamoyl)-2-azabicyclo[2.2.1]heptan-2-yl)-2-oxoethyl)-5-(5,6,7,8-tetrahydroimidazo[1,2-a]pyridin-3-yl)-1H-indole-3-carboxamide (698)

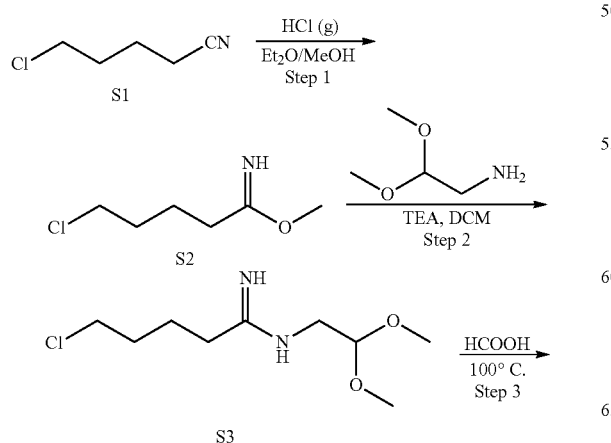

Scheme 121.

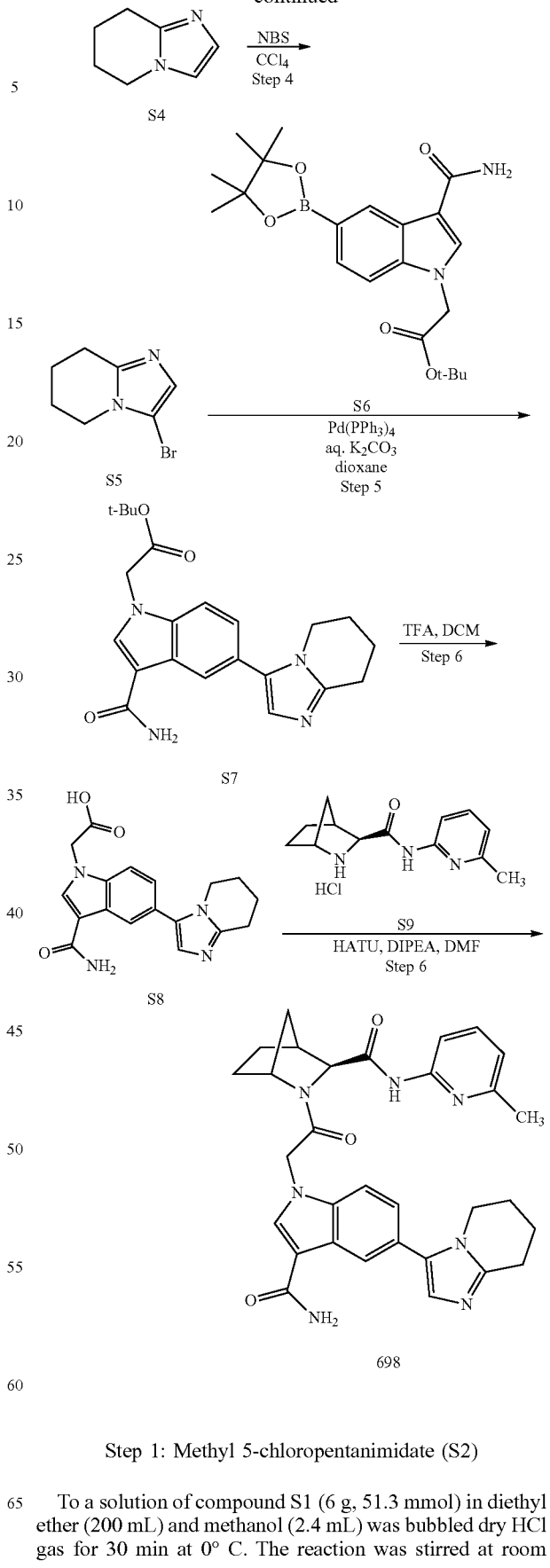

Step 1: Methyl 5-chloropentanimidate (S2)

To a solution of compound S1 (6 g, 51.3 mmol) in diethyl ether (200 mL) and methanol (2.4 mL) was bubbled dry HCl gas for 30 min at 0° C. The reaction was stirred at room temperature for 3 hrs. The mixture was concentrated to give the title compound (17 g, 99.9% yield) as white solid.

Step 2:
5-Chloro-N-(2,2-dimethoxyethyl)pentanimidamide (S3)

To a solution of compound S2 (17 g, 51.3 mmol) in DCM (200 mL) was added 2,2-dimethoxyethanamine (4.4 g, 41.0 mmol) and TEA (10.4 g, 102.6 mmol) at 0° C. The reaction was stirred at room temperature for 16 hrs. The resulting mixture was extracted with DCM. The combined organic phases were washed with brine, dried over anhydrous Na₂SO₄, filtered and then concentrated. The residue was purified by column chromatography on silica gel (eluted with petroleum ether:ethyl acetate=30:1) to give the title compound (7 g, 61.5% yield) as colorless oil.

Step 3: 5,6,7,8-Tetrahydroimidazo[1,2-a]pyridine (S4)

A solution of compound S3 (7 g, 31.5 mmol) in formic acid (60 mL) was stirred at 100° C. for 6 hrs. The mixture was concentrated to give a residue, which was purified by column chromatography on silica gel (dichloromethane:methanol=20:1) to give the title compound (3.3 g, 85.9% yield) as a colorless oil. LC-MS (ESI) found: 123 [M+1]⁺.

Step 4: 3-Bromo-5,6,7,8-tetrahydroimidazo[1,2-a]pyridine (S5)

To a solution of compound S4 (2 g, 16.4 mmol) in carbon tetrachloride (20 mL) was added NBS (2.9 g, 16.4 mmol). The reaction was stirred at room temperature for 16 hrs. The mixture was diluted with DCM, washed with brine, dried over anhydrous Na₂SO₄, filtered and then concentrated to dryness. The residue was purified by column chromatography on silica gel (dichloromethane:methanol=100:1 to 20:1) to give the title compound (510 mg, 15.4% yield) as a yellow solid. LC-MS (ESI) found: 202 [M+1]⁺.

Step 5 to 7: 1-(2-((1R,3S,4S)-3-(6-Methylpyridin-2-ylcarbamoyl)-2-azabicyclo[2.2.1]heptan-2-yl)-2-oxoethyl)-5-(5,6,7,8-tetrahydroimidazo[1,2-a]pyridin-3-yl)-1H-indole-3-carboxamide (698)

The titled compound was prepared according the procedure from Scheme 120 from appropriate starting materials. ¹H NMR (400 MHz, CD3OD) δ: 8.23 (s, 1H), 8.04-7.79 (m, 2H), 7.59 (dd, J=22.7, 8.2 Hz, 2H), 7.32 (d, J=10.0 Hz, 1H), 7.14 (s, 1H), 6.96 (d, J=7.5 Hz, 1H), 5.30 (dd, J=72.2, 17.2 Hz, 2H), 4.64 (s, 1H), 4.09 (d, J=59.3 Hz, 3H), 2.93 (d, J=70.3 Hz, 3H), 2.44 (d, J=17.3 Hz, 3H), 2.19 (d, J=10.3 Hz, 1H), 1.99 (s, 4H), 1.96-1.80 (m, 3H), 1.66 (dd, J=31.5, 20.5 Hz, 2H). LC-MS (ESI) found: 552 [M+1]⁺.

1-(2-((1R,3S,4S)-3-(6-Methylpyridin-2-ylcarbamoyl)-2-azabicyclo[2.2.1]heptan-2-yl)-2-oxoethyl)-5-(1H-thieno[3,2-c]pyrazol-3-yl)-1H-indole-3-carboxamide (704)

Scheme 122.

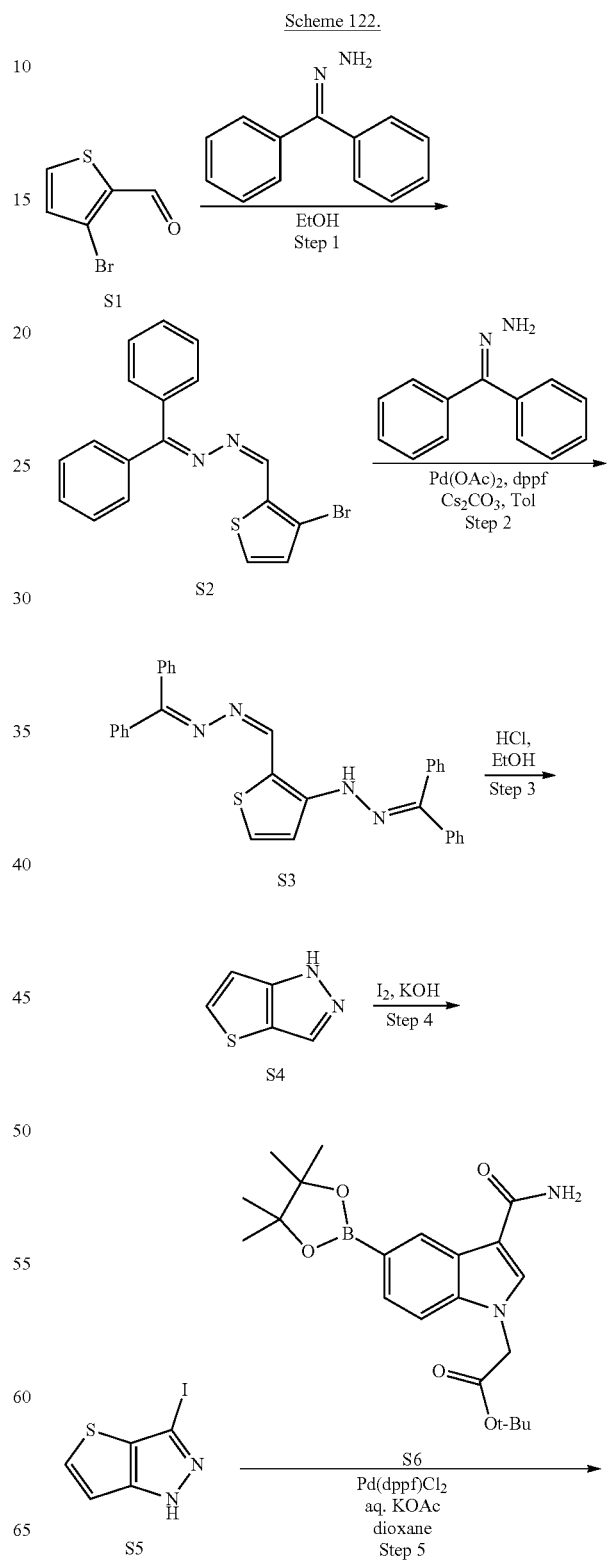

-continued

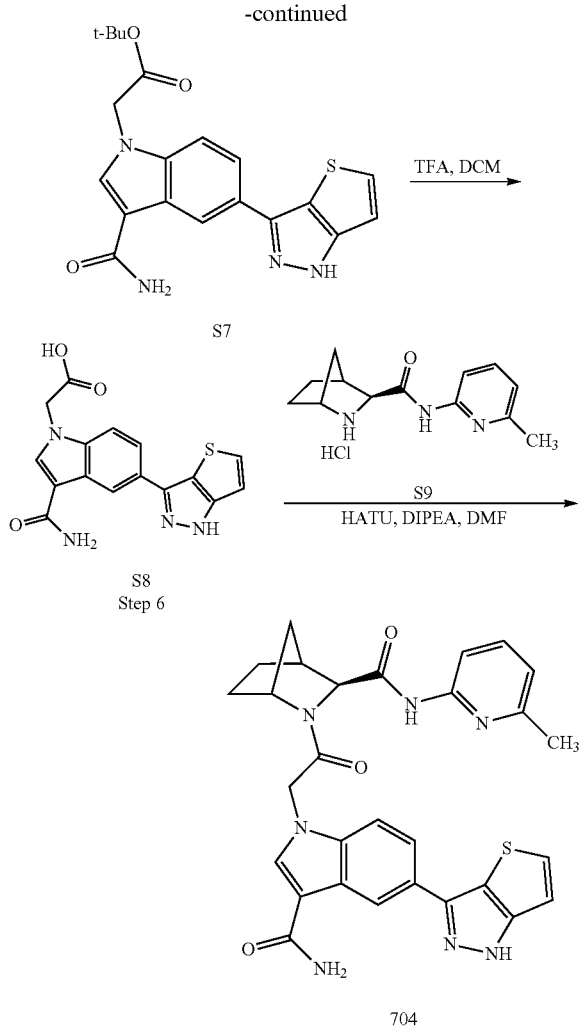

Step 1: (Z)-1-((3-Bromothiophen-2-yl)methylene)-2-(diphenylmethylene)hydrazine (S2)

To a solution of compound S1 (2 g, 10.5 mmol) in EtOH (30 mL) was added (diphenylmethylene)hydrazine (2.26 g, 11.6 mmol) at 0° C. The reaction mixture was stirred at 65° C. for 4 hrs. The mixture was concentrated and purified by silica gel chromatography with (petroleum ether:ethyl acetate=100:1) to give the title compound (3.5 g, 90.6% yield) as yellow oil. LC-MS (ESI) found: 369 [M+1]+.

Step 2: (Z)-1-(Diphenylmethylene)-2-((3-(2-(diphenylmethylene)hydrazinyl)thiophen-2-yl)methylene)hydrazine (S3)

To a solution of compound S2 (3.5 g, 9.5 mmol) in toluene (30 mL) was added (diphenylmethylene)hydrazine (2.23 g, 11.4 mmol) and cesium carbonate (5.26 g, 16.15 mmol), Pd(OAc)$_2$ (427 mg, 1.9 mol), and dppf (792 mg, 1.43 mmol) at 0° C. The mixture was degassed under N$_2$ atmosphere for three times and stirred at 100° C. under N$_2$ atmosphere for 16 hrs. The mixture was filtered and the filtrate was concentrated to dryness. The residue was purified by silica gel chromatography with (petroleum ether:ethyl acetate=100:1) to give the title compound (2.5 g, 54.3% yield) as brown oil. LC-MS (ESI) found: 485 [M+1]+.

Step 3: 1H-Thieno[3,2-c]pyrazole (S4)

To a solution of compound S3 (2.5 g, 5.16 mmol) in EtOH (20 mL) was added conc. HCl (10 mL) and the reaction was stirred at 85° C. for 1 hr. Then the reaction was cooled to room temperature, diluted with water and neutralized with Na$_2$CO$_3$. The mixture was extracted with EtOAc and the organic layer was washed with brine then dried over anhydrous MgSO$_4$ and concentrated. The residue was purified by silica gel chromatography with (petroleum ether: ethyl acetate=1:1) to give the title compound (300 mg, 46.9% yield) as brown solid. LC-MS (ESI) found: 125 [M+1]+.

Step 4: 3-Iodo-1H-thieno[3,2-c]pyrazole (S5)

To a solution of compound S4 (300 mg, 2.42 mmol) was in DMF (10 mL) was added potassium hydroxide (475 mg, 4.84 mmol) and iodine (925 mg, 3.63 mmol) at 0° C. The reaction mixture was stirred at room temperature for 3 hrs. The reaction was quenched with 10% aqueous Na$_2$S$_2$O$_3$ solution and diluted with water. The mixture was extracted with ethyl acetate twice. The combined organic phases were washed with 10% aq. LiCl solution and brine successively, dried over anhydrous MgSO$_4$ and concentrated, which was purified by silica gel chromatography with (petroleum ether: ethyl acetate=1:1) to give the title compound (450 mg, 74.4% yield) as brown solid. LC-MS (ESI) found: 251 [M+1]+.

Step 5: tert-Butyl 2-(3-carbamoyl-5-(1H-thieno[3,2-c]pyrazol-3-yl)-1H-indol-1-yl)acetate (S7)

To a solution compound S5 (50 mg, 0.2 mmol) in 1,4-dioxane (2 mL) and water (0.5 mL) was added compound S6 (80 mg, 0.2 mmol) and potassium carbonate (39.2 mg, 0.4 mmol) and Pd(PPh$_3$)$_4$ (10 mg) at 0° C. under N$_2$ atmosphere. The mixture was degassed under N$_2$ atmosphere for three times and stirred at 85° C. under N$_2$ atmosphere for 16 hrs. The mixture was diluted with water and extracted with EtOAc twice. The combined organic phases were dried over anhydrous Na$_2$SO$_4$, which was purified by silica gel chromatography (dichloromethane:methanol=100:1 to 10:1) to give the title compound (30 mg, 37.9% yield) as a white solid. LC-MS (ESI) found: 397 [M+1]+.

Step 6: 2-(3-Carbamoyl-5-(1H-thieno[3,2-c]pyrazol-3-yl)-1H-indol-1-yl)acetic acid (S8)

To a solution of compound S7 (30 mg, 0.08 mmol) in Dichloromethane (3 mL) was added TFA (3 mL) dropwise at 0° C. The reaction was stirred at room temperature for 3 hrs. The mixture was concentrated under vacuum to give a residue, which was co-evaporated with toluene to give the title compound (50 mg, 100% yield) as a brown solid. LC-MS (ESI) found: 342 [M+1]+.

Step 7: 1-(2-((1R,3S,4S)-3-((6-Methylpyridin-2-yl)carbamoyl)-2-azabicyclo[2.2.1]heptan-2-yl)-2-oxoethyl)-5-(1H-thieno[3,2-c]pyrazol-3-yl)-1H-indole-3-carboxamide (704)

To a mixture compound S8 (50 mg, 0.08 mmol) and S9 (19 mg, 0.13 mmol) in N,N-Dimethylformamide (1 mL) was added and DIPEA (41.28 mg, 0.32 mmol) and HATU (61 mg, 0.16 mmol) at 0° C. The reaction was stirred at room temperature overnight. The mixture was diluted with ethyl acetate and washed with 10% aq. LiCl solution and brine, dried over anhydrous Na₂SO₄, filtered and concentrated to dryness. The residue was purified by prep-HPLC to give the title compound (2 mg, 4.5% yield) as white solid. $^1$H NMR (400 MHz, CD3OD) δ: 8.63 (s, 1H), 7.96 (s, 1H), 7.88-7.79 (m, 2H), 7.62 (dd, J=9.6, 6.6 Hz, 2H), 7.57 (d, J=8.7 Hz, 1H), 7.08 (d, J=5.3 Hz, 1H), 6.96 (d, J=7.5 Hz, 1H), 5.37 (d, J=17.4 Hz, 1H), 5.24 (s, 1H), 4.58 (s, 3H), 4.18 (s, 1H), 3.48 (s, 1H), 3.34 (s, 1H), 3.13 (s, 1H), 2.84 (s, 1H), 2.43 (d, J=5.3 Hz, 3H), 2.20 (d, J=10.3 Hz, 1H), 1.92 (s, 2H), 1.82 (s, 1H), 1.68 (d, J=9.5 Hz, 1H), 1.58 (d, J=10.7 Hz, 1H), 1.39 (d, J=44.2 Hz, 2H). LC-MS (ESI) found: 554 [M+1]⁺.

5-(5,6-Dihydro-4H-pyrrolo[1,2-b]pyrazol-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide (703)

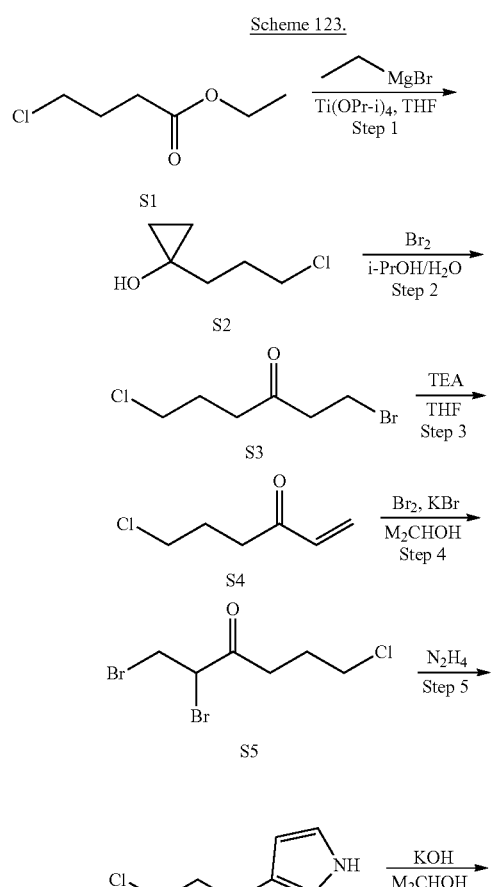

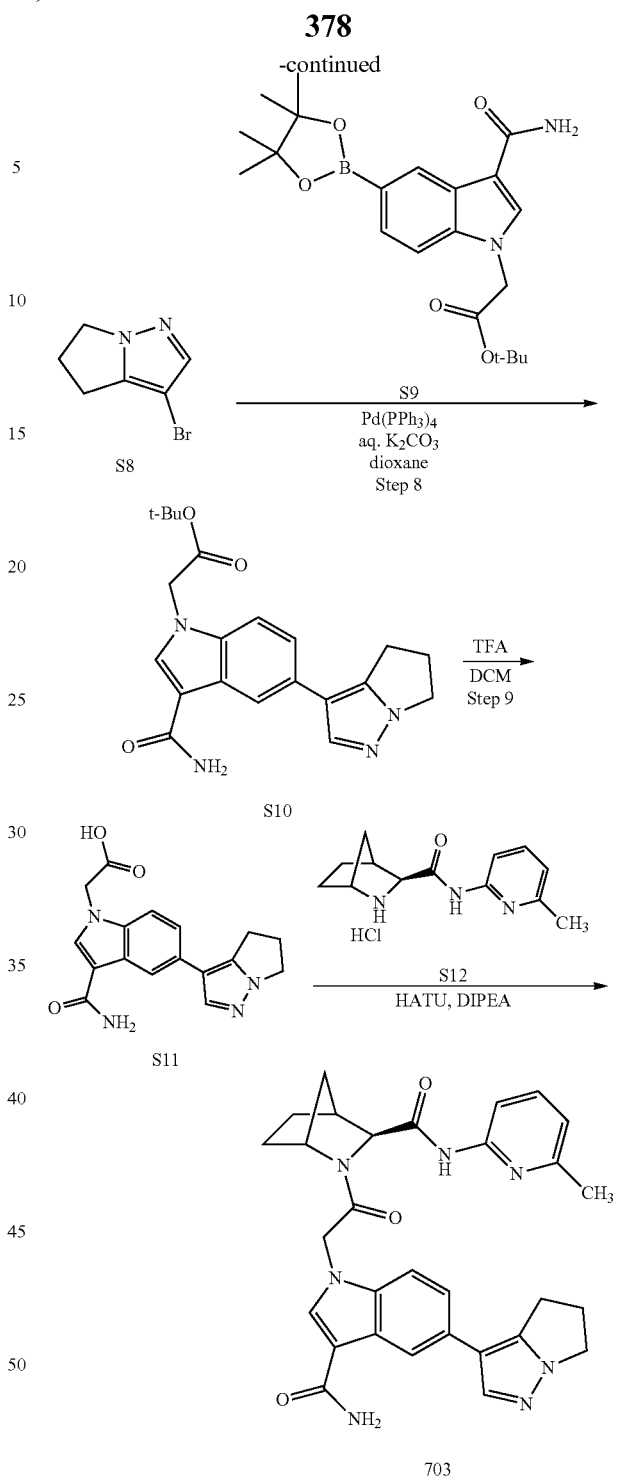

Step 1: 1-(3-Chloropropyl)cyclopropanol (S2)

To a solution of ethyl 4-chlorobutanoate (12.3 g, 81.6 mmol) in THF (200 mL) was added titanium isopropoxide (2.2 mL, 8.2 mmol) and ethylmagnesiumbromide (3.0 M in diethyl ether, 55 mL, 163.2 mmol) dropwise at ambient temperature. After 1.5 hrs, the reaction mixture was quenched with 10% aq. HCl at 0° C. The mixture was extracted with diethyl ether and the combined organic phases were washed with saturated aqueous sodium bicarbonate solution and brine, dried over magnesium sulfate, and concentrated under reduced pressure. The residue was purified by chromatography on silica gel (eluted with DCM/MeOH=50:1 to 40:1) to give the title compound (5.3 g, 48.6% yield) as a light oil.

Step 2: 1-Bromo-6-chlorohexan-3-one (S3)

Bromine (6.8 g, 43.5 mmol) was added slowly to a solution of 1-(3-chloropropyl)cyclopropanol (5.3 g, 39.6 mmol) in i-PrOH/$H_2O$ (24 mL/6 mL) at 0° C. The reaction mixture was stirred at ambient temperature for 1 hr and then quenched with water (15 mL). The resulting mixture was extracted with ethyl acetate (3×30 mL). The combined organic layers were dried over anhydrous $Na_2SO_4$, filtered, and concentrated under reduced pressure to give the title compound (7.9 g, crude) as yellow oil, which was used without further purification.

Step 3: 6-Chlorohex-1-en-3-one (S4)

Triethylamine (8.3 mL, 55.9 mmol) was slowly added to a solution of 1-bromo-6-chlorohexan-3-one (7.9 g, crude) in THF (80 mL) at ambient temperature. After 16 hours, the reaction mixture was concentrated under reduced pressure to give the title compound (6.0 g, crude), which was used without further purification.

Step 4: 1,2-Dibromo-6-chlorohexan-3-one (S5)

To a solution of 6-chlorohex-1-en-3-one (6 g, 45.25 mmol) in i-PrOH/$H_2O$ (50 mL/10 mL) at 0° C. were added potassium bromide (6.4 g, 54.3 mmol) and bromine (7.9 g, 49.8 mmol). After 1 hr, the reaction mixture was quenched with water (50 mL) and extracted with ethyl acetate (3×50 mL). The combined organic layers were washed with 5% aq. $Na_2S_2O_4$ solution, dried over anhydrous $Na_2SO_4$, filtered, and concentrated under reduced pressure to give the title compound (7.8 g, 58.9% yield) as a yellow oil.

Step 5: 3-(3-Chloropropyl)-1H-pyrazole (S6)

To a solution of 1,2-dibromo-6-chlorohexan-3-one (7.8 g, 26.9 mmol) in i-PrOH/$H_2O$ (25 mL/5 mL) at ambient temperature was added hydrazine hydrate (6.7 g, 134.5 mmol). After 16 hours, the reaction was quenched with water (15 mL) and extracted with ethyl acetate (3×10 mL). The organic layers were dried over anhydrous $Na_2SO_4$, filtered, and concentrated under reduced pressure to give the title compound (1.5 g, 38.5% yield) as a yellow oil. LC-MS (ESI) found: 145 $[M+1]^+$.

Step 6: 5,6-Dihydro-4H-pyrrolo[1,2-b]pyrazole (S7)

To a solution of 3-(3-chloropropyl)-1H-pyrazole (500 mg, 3.5 mmol) in i-PrOH/$H_2O$ (5 mL/1 mL) was added potassium hydroxide (389 mg, 6.9 mmol) and then the reaction mixture was stirred at 90° C. for 2 hrs. The reaction mixture was cooled to ambient temperature, extracted with DCM (3×20 mL). The organic layers were combined, dried over anhydrous magnesium sulfate, filtered, and concentrated under reduced pressure. The residue was purified by chromatography on silica gel (PE:EtOAc=6:1 to 2:1) to give the title compound (150 mg, 39.6% yield) as brown oil. LC-MS (ESI) found: 109 $[M+1]^+$.

Step 7: 3-Bromo-5,6-dihydro-4H-pyrrolo[1,2-b]pyrazole (S8)

To a solution of 5,6-dihydro-4H-pyrrolo[1,2-b]pyrazole (150 mg, 1.39 mmol) and sodium acetate (114 mg, 1.39 mmol) in acetic acid (1.5 mL) at 0° C. was added bromine (197.5 mg, 1.25 mmol). After 10 minutes, the reaction mixture was neutralized with saturated aqueous sodium bicarbonate and extracted with ethyl acetate (3×20 mL). The organic layers were combined, washed with 5% $Na_2S_2O_4$, dried over anhydrous $Na_2SO_4$, and concentrated under reduced pressure. The residue was purified by chromatography on silica gel (PE:EtOAc=6:1 to 4:1) to give the title compound (120 mg, yield 46.4%) as white solid.

Step 8: tert-Butyl 2-(3-carbamoyl-5-(5,6-dihydro-4H-pyrrolo[1,2-b]pyrazol-3-yl)-1H-indol-1-yl)acetate (S10)

To a mixture of tert-butyl 2-(3-carbamoyl-5-(4,4,5,5-tetramethyl-1,3,2-dioxaborolan-2-yl)-1H-indol-1-yl)acetate (189 mg, 0.48 mmol), 3-bromo-5,6-dihydro-4H-pyrrolo[1,2-b]pyrazole (80.0 mg, 0.22 mmol) in 1,4-dioxane (5 mL) and water (1 mL) were added Pd(PPh$_3$)$_4$ (25 mg, 0.02 mmol) and $K_2CO_3$ (149 mg, 1.08 mmol). The reaction mixture was degassed under $N_2$ atmosphere for three times and stirred at 80° C. under $N_2$ atmosphere overnight. The mixture was diluted with EtOAc and washed with water and brine, dried over anhydrous $Na_2SO_4$, filtered and concentrated to dryness. The residue was purified by chromatography on silica gel (DCM:MeOH=80:1 to 60:1) to afford the desired compound (65 mg, 35.6% yield) as white solid.

Step 9: 2-(3-Carbamoyl-5-(5,6-dihydro-4H-pyrrolo[1,2-b]pyrazol-3-yl)-1H-indol-1-yl) acetic acid (S11)

To a solution of tert-butyl 2-(3-carbamoyl-5-(5,6-dihydro-4H-pyrrolo[1,2-b]pyrazol 3-yl)-1H-indol-1-yl)acetate (30 mg, 0.0788 mmol) in DCM (1 mL) was added TFA (0.5 mL) at 0° C. and the reaction was stirred at room temperature for 1 hr. The mixture was evaporated under reduced pressure to afford the desired compound (31 mg, 100% yield) as yellow solid, which was directly used to the next reaction without further purification.

Step 10: 5-(5,6-Dihydro-4H-pyrrolo[1,2-b]pyrazol-3-yl)-1-(2-((1R,3S,4S)-3-((6-ethypyridin-2-yl)carbamoyl)-2-azabicyclo[2.2.1]heptan-2-yl)-2-oxoethyl)-1H-indole-3-carboxamide (703)

To a mixture of 2-(3-carbamoyl-5-(5,6-dihydro-4H-pyrrolo[1,2-b]pyrazol-3-yl)-1H indol-1-yl)acetic acid (30 mg, 0.07 mmol), (1R,3S,4S)—N-(6-methylpyridin-2-yl)-2 azabicyclo[2.2.1]heptane-3-carboxamide (26.8 mg, 0.08 mmol), HATU (42 mg, 0.11 mmol) in DMF (2 mL) was added DIPEA (0.04 mL, 0.22 mmol) at room temperature overnight. The reaction was stirred overnight and then partitioned with EtOAc and water. The organic layer was washed with brine, dried over anhydrous $Na_2SO_4$ and concentrated under reduced pressure. The residue was purified by prep-HPLC to afford the desired product (11 mg, 29.2% yield) as white solid. $^1$H NMR (400 MHz, DMSO-d$_6$) δ: 10.43 (s, 1H), 8.25-8.13 (m, 2H), 7.93 (s, 1H), 7.82 (d, J=12.0 Hz, 2H), 7.62 (m, 1H), 7.40 (d, J=8.6 Hz, 1H), 7.35-7.25 (m, 2H), 6.94 (d, J=7.4 Hz, 1H), 5.33 (d, J=17.1 Hz, 1H), 5.09 (d, J=17.2 Hz, 1H), 4.61 (s, 1H), 4.13-4.07 (m, 3H), 3.09-3.05 (m, 2H), 2.67-2.61 (m, 3H), 2.38 (s, 3H), 2.09 (d, J=9.5 Hz, 1H), 1.77 (d, J=8.0 Hz, 3H), 1.46 (m, 2H). LC-MS (ESI) found: 538 [M+1]+.

1-(2-((2S,4R)-4-Fluoro-2-(6-methylpyridin-2-ylcarbamoyl)pyrrolidin-1-yl)-2-oxoethyl)-5-(2-methylpyrimidin-5-yl)-1H-pyrazolo[3,4-d]thiazole-3-carboxamide (715)

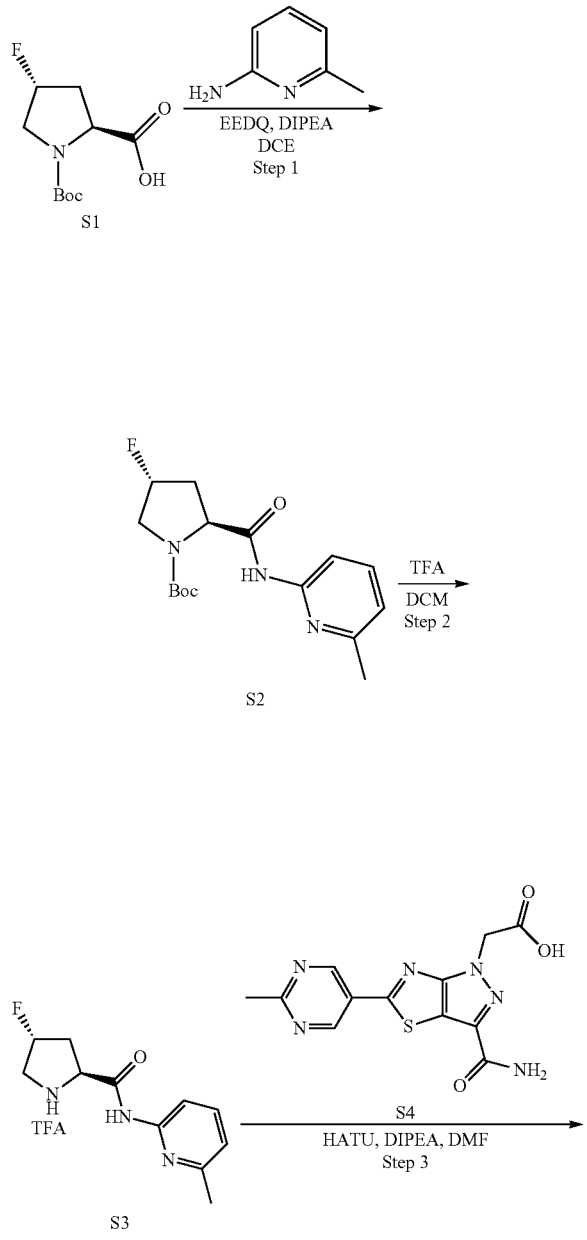

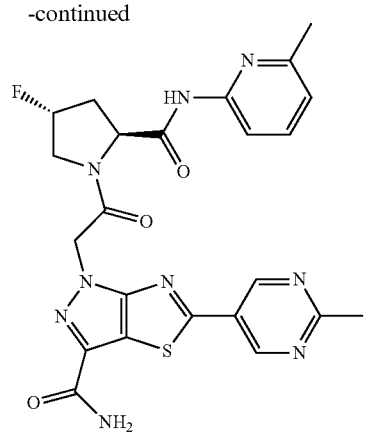

715

Step 1: (2S,4R)-tert-Butyl 4-fluoro-2-(6-methylpyridin-2-ylcarbamoyl)pyrrolidine-1-carboxylate (S2)

To a mixture of compound S1 (7.0 g, 0.03 mol) in DCE (60 mL) was added ethyl 2-ethoxyquinoline-1 (2H)-carboxylate (14.84 g, 0.06 mol), N, N'-diisopropylethylamine (11.63 g, 0.09 mol) and 6-methylpyridin-2-amine (3.24 g, 0.03 mol). The reaction was stirred at 90° C. under $N_2$ atmosphere overnight. Then the mixture was cooled, quenched with water and extracted with DCM twice. The combined organic layers were washed with brine, dried over anhydrous $Na_2SO_4$ and concentrated. The residue was purified by column chromatography on silica gel (eluted with PE/EtOAc=30:1 to 2:1) to give the title compound (9.50 g, 97.9% yield) as white solid. LC/MS (ESI) m/z: 324 (M+H)+.

Step 2: (2S,4R)-tert-Butyl 4-fluoro-2-(6-methylpyridin-2-ylcarbamoyl)pyrrolidine-1-carboxylate TFA Salt (S3)

To a mixture of compound S2 (9.50 g, 0.0291 mol) in DCM (20 mL) was added TFA (10 mL) at 0° C. and the reaction was stirred at room temperature for 2 hrs. The mixture was concentrated and the residue was washed with $Et_2O$ to give the title compound (6.3 g, 96.0% yield) as yellow solid. LC/MS (ESI) m/z: 224 (M+H)+.

Step 3: 1-(2-((2S,4R)-4-Fluoro-2-(6-methylpyridin-2-ylcarbamoyl)pyrrolidin-1-yl)-2-oxoethyl)-5-(2-methylpyrimidin-5-yl)-1H-pyrazolo[3,4-d]thiazole-3-carboxamide (715)

To a solution of S3 (27 mg, 0.064 mmol), compound S4 (32 mg, 0.096 mmol) and DIPEA (32 mg, 0.243 mmol) in DMF (1 mL) was added HATU (62 mg, 0.162 mmol). The reaction was stirred at room temperature for 4 hrs. Then the mixture was diluted with EtOAc and washed with 10% aq. LiCl solution and brine successively, dried over anhydrous $Na_2SO_4$, filtered and concentrated. The residue was purified by prep-HPLC (eluted with $CH_3CN$/water) to give the title compound (4.0 mg, 12.1% yield) as white solid. 1H-NMR (400 MHz, $CD_3OD$) δ 9.21 (s, 2H), 8.18-8.48 (m, 2H), 7.84 (d, J=8.3 Hz, 1H), 7.56-7.61 (m, 1H), 6.94 (d, J=7.6 Hz, 1H), 5.63 (m, 1H), 5.50 (m, 1H), 5.43 (d, J=9.9 Hz, 1H), 4.21-4.29 (m, 1H), 3.91-4.10 (m, 2H), 2.70-2.76 (m, 4H), 2.36 (s, 3H), 2.29-2.22 (m, 1H). LC/MS (ESI) m/z: 524 (M+H)+.

1-(2-((2S,4R)-4-Fluoro-2-(6-methylpyridin-2-ylcarbamoyl)pyrrolidin-1-yl)-2-oxoethyl)-5-(2-methylpyrazolo[1,5-a]pyrimidin-6-yl)-1H-pyrazolo[3,4-d]thiazole-3-carboxamide (714)

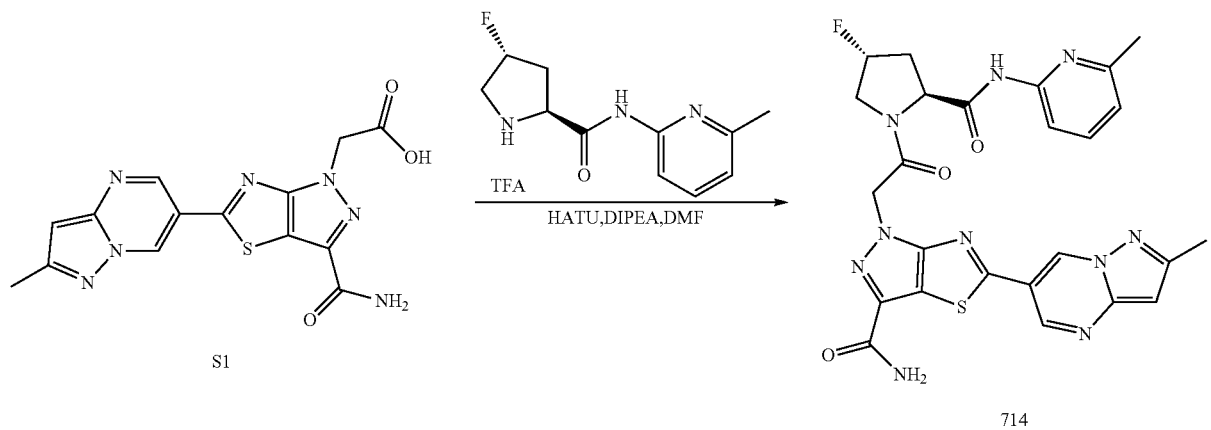

The titled compound was prepared according the procedure from Scheme 124 from appropriate starting materials. $^{1}$H NMR (400 MHz, CD$_3$OD) δ 9.41 (s, 1H), 8.97 (d, J=2.2 Hz, 1H), 8.46 (s, 2H), 7.85 (d, J=8.4 Hz, 1H), 7.50-7.67 (m, 1H), 6.84 (d, J=7.5 Hz, 1H), 6.61 (s, 1H), 5.38-5.64 (m, 3H), 4.14-4.36 (m, 1H), 3.92-4.07 (m, 1H), 3.66-3.78 (m, 1H), 2.62-2.77 (m, 1H), 2.53 (s, 3H), 2.38 (s, 3H), 2.22-2.31 (m, 1H). LC/MS (ESI) m/z: 563 (M+H)$^{+}$.

(2S,4R)-1-(2-(3-Acetyl-5-(2-methylpyrimidin-5-yl)-1H-indazol-1-yl)acetyl)-N-((E)-3-(3-chlorophenyl)-2-fluorobut-2-en-1-yl)-4-fluoropyrrolidine-2-carboxamide (523)

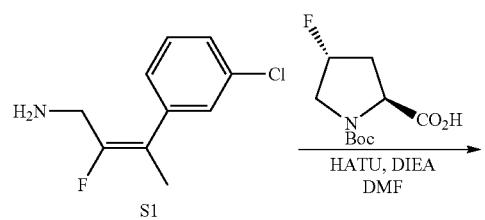

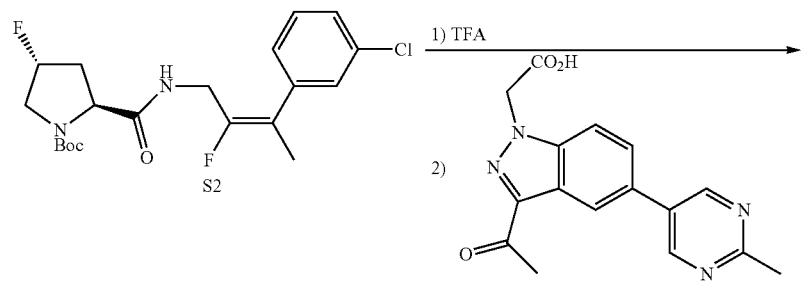

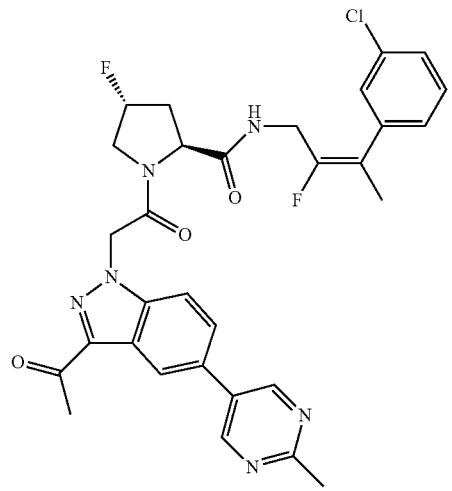

523 tert-Butyl (2S,4R)-2-(((E)-3-(3-chlorophenyl)-2-fluorobut-2-en-1-yl)carbamoyl)-4-fluoropyrrolidine-1-carboxylate (S2)

(2S,4R)-1-(tert-butoxycarbonyl)-4-fluoropyrrolidine-2-carboxylic acid (0.163 g) was dissolved in DMF (1.5 mL) and $^i$Pr$_2$NEt (555 µL) was added followed by the sequential addition of (E)-3-(3-chlorophenyl)-2-fluorobut-2-en-1-amine hydrochloride (0.150 g) and HATU (0.291 g) slowly at 5° C. The reaction mixture was then stirred for 30 min at RT. DMF was removed under reduced pressure and residue was purified by ISCO (eluent: 0-0.5% MeOH in CH$_2$Cl$_2$) to 0.12 g of white foam.

(2S,4R)-1-(2-(3-Acetyl-5-(2-methylpyrimidin-5-yl)-1H-indazol-1-yl)acetyl)-N-((E)-3-(3-chlorophenyl)-2-fluorobut-2-en-1-yl)-4-fluoropyrrolidine-2-carboxamide (523)

tert-Butyl (2S,4R)-2-(((E)-3-(3-chlorophenyl)-2-fluorobut-2-en-1-yl)carbamoyl)-4-fluoropyrrolidine-1-carboxylate (0.12 g) was dissolved in CH$_2$Cl$_2$ (1 mL) and equal volume of TFA was added. The mixture was stirred for 30 min at rt. Then the volatiles were removed under reduced pressure. The residue was dissolved in DMF (1 mL) and $^i$Pr$_2$NEt (252 µL) was added, followed by the sequential addition of 2-(3-acetyl-5-(2-methylpyrimidin-5-yl)-1H-indazol-1-yl)acetic acid (0.094 g) and HATU (0.132 g) slowly at 5° C. The reaction mixture was then stirred for 30 min at RT, poured into water (10 mL) and the solid was isolated by filtration, washed with water and dried in vacuo. The solid was then purified by ISCO (eluent: 0-2.5% MeOH in CH$_2$Cl$_2$) to get a white solid. $^1$H-NMR (DMSO-d$_6$) (major rotamer): δ 0.76-0.77 (m, 1H), 0.98-1.03 (m, 1H), 1.82-1.86 (m, 1H), 1.93 (d, J=3.2 Hz, 3H), 2.06-2.12 (m, 1H), 2.199-2.26 (m, 1H), 2.62 (s, 3H), 3.69-3.73 (m, 1H), 3.77-3.86 (m, 2H), 4.23 (dd, J=9.2, 4.4 Hz, 1H), 5.53 (d, J=17.2 Hz, 1H), 5.84 (d, J=17.2 Hz, 1H), 7.29-7.37 (m, 5H), 7.42 (s, 1H), 7.47 (t, J=7.2 Hz, 1H), 7.68 (d, J=8.4 Hz, 1H), 8.17 (s, 1H), 8.18 (d, J=8 Hz, 1H). $^{19}$F-NMR (DMSO-d$_6$) (major rotamer): δ −112.1.

1-(2-((1R,3S,5R)-3-(5'-Acetyl-2'-chloro-2-fluorobi-phenyl-3-ylcarbamoyl)-2-azabicyclo[3.1.0]hexan-2-yl)-2-oxoethyl)-5-(2-methylpyrazolo[1,5-a]pyrimi-din-6-yl)-1H-pyrazolo[3,4-d]thiazole-3-carboxamide (716)

Scheme 127.

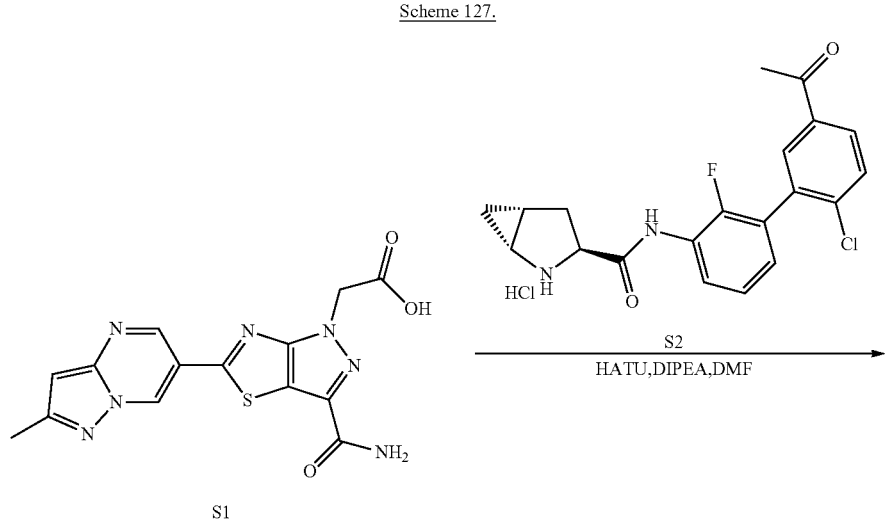

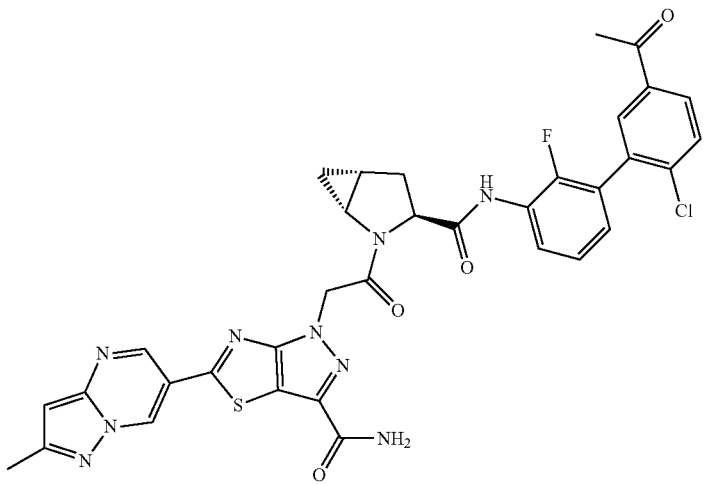

To a solution of compound S1 (60 mg, 0.14 mmol), S2 (52 mg, 0.13 mmol) and DIPEA (55 mg, 0.42 mmol) in DMF (2 mL) was added HATU (106 mg, 0.28 mmol). The reaction was stirred at room temperature for 1 hr. Then the mixture was diluted with EtOAc and washed with 10% aq. LiCl solution and brine successively, dried over anhydrous Na$_2$SO$_4$, filtered and concentrated. The residue was purified by prep-HPLC (eluted with CH$_3$CN/water) to give the title compound (50.1 mg, 50.3% yield) as a white solid. $^1$H NMR (400 MHz, DMSO-d$_6$) δ: 9.84 (s, 1H), 9.63-9.73 (m, 1H), 9.02 (d, J=2.2 Hz, 1H), 7.85-8.01 (m, 3H), 7.72 (d, J=8.4 Hz, 1H), 7.61 (s, 1H), 7.24 (t, J=8.0 Hz, 1H), 7.12 (t, J=6.4 Hz, 1H), 6.70 (s, 1H), 5.81 (d, J=17.1 Hz, 1H), 5.48 (d, J=17.1 Hz, 1H), 4.56 (dd, J=8.8, 5.3 Hz, 1H), 3.80-3.87 (m, 1H), 2.58 (s, 3H), 2.49 (s, 3H), 2.20-2.37 (m, 3H), 1.86-1.96 (m, 1H), 1.01-1.09 (m, 1H), 0.68-0.76 (m, 1H).

1-(2-((1R,3S,5R)-3-(5'-Acetyl-2'-chloro-2-fluorobiphenyl-3-ylcarbamoyl)-2-azabicyclo[3.1.0]hexan-2-yl)-2-oxoethyl)-5-(2-methylpyrimidin-5-yl)-1H-pyrazolo[3,4-d]thiazole-3-carboxamide (717)

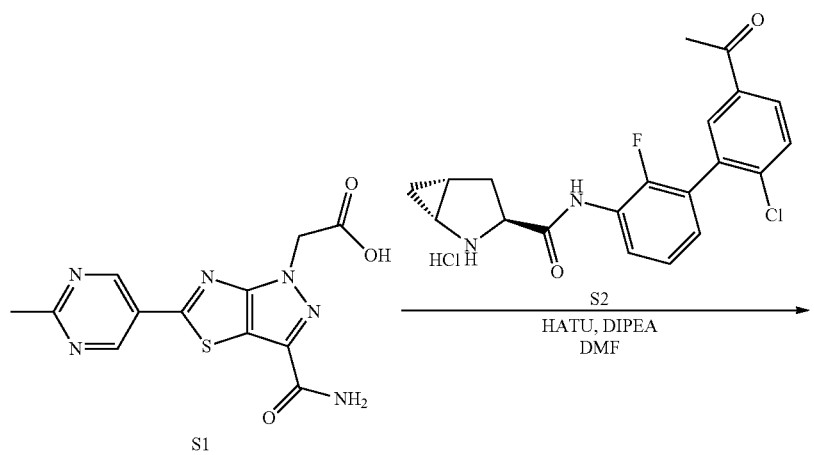

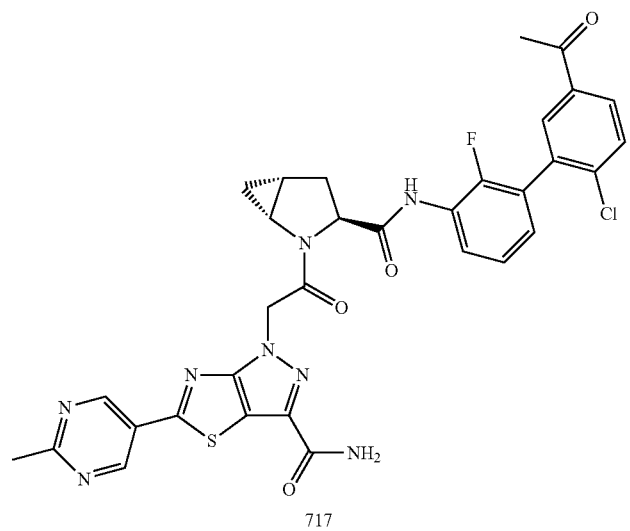

The titled compound was prepared according the procedure from Scheme 124 from appropriate starting materials. ¹H NMR (400 MHz, CDCl₃) δ: 9.11 (d, J=9.4 Hz, 2H), 8.98 (s, 1H), 8.33 (t, J=7.1 Hz, 1H), 7.95-7.77 (m, 2H), 7.53 (t, J=6.1 Hz, 1H), 7.19 (t, J=8.3 Hz, 1H), 7.07-6.94 (m, 1H), 6.68 (s, 1H), 5.52 (s, 2H), 5.41 (s, 1H), 4.88 (dd, J=8.6, 2.8 Hz, 1H), 3.50-3.37 (m, 1H), 3.13-2.98 (m, 1H), 2.81 (d, J=5.7 Hz, 3H), 2.59 (s, 3H), 2.09 (dd, J=12.3, 8.6 Hz, 2H), 0.88 (t, J=6.6 Hz, 1H), 0.81 (td, 1H). LC/MS (ESI) m/z: 673 (M+H)⁺.

(2S,4R)-4-Fluoro-N-(2-fluoro-3-(trifluoromethoxy)phenyl)pyrrolidine-2-carboxamide hydrochloride (S3)

Scheme 129.

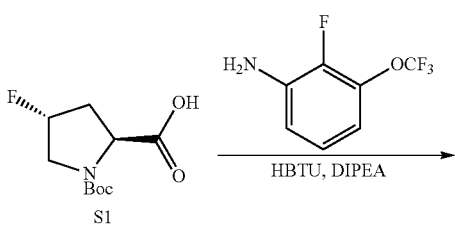

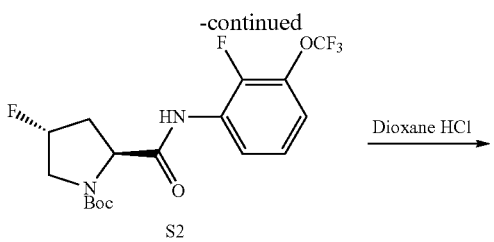

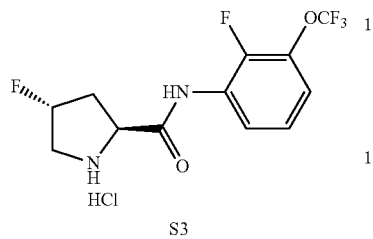

Step 1: tert-Butyl (2S,4R)-4-fluoro-2-((2-fluoro-3-(trifluoromethoxy)phenyl)carbamoyl)pyrrolidine-1-carboxylate (S2)

To a solution of (2S,4R)-1-(tert-butoxycarbonyl)-4-fluoropyrrolidine-2-carboxylic acid (1 equiv) in DMF (10 vol) at 0° C. under nitrogen atmosphere was added 2-fluoro-3-(trifluoromethoxy)aniline (1.2 equiv), HBTU (1.5 equiv) and DIPEA (3 equiv). The reaction mixture was stirred at room temperature for 12 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 1239.

Step 2: (2S,4R)-4-Fluoro-N-(2-fluoro-3-(trifluoromethoxy)phenyl)pyrrolidine-2-carboxamide hydrochloride (S3)

To a solution of S2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give S3.

(2S,4R)-1-(2-(3-Acetyl-5-((1S,4R)-2-(4-methoxyphenyl)-2-azabicyclo[2.2.2]oct-5-en-5-yl)-1H-indazol-1-yl)acetyl)-N-(6-bromopyridin-2-yl)-4-fluoropyrrolidine-2-carboxamide (721)

Scheme 130.

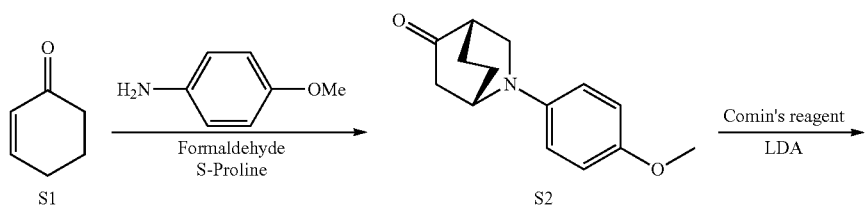

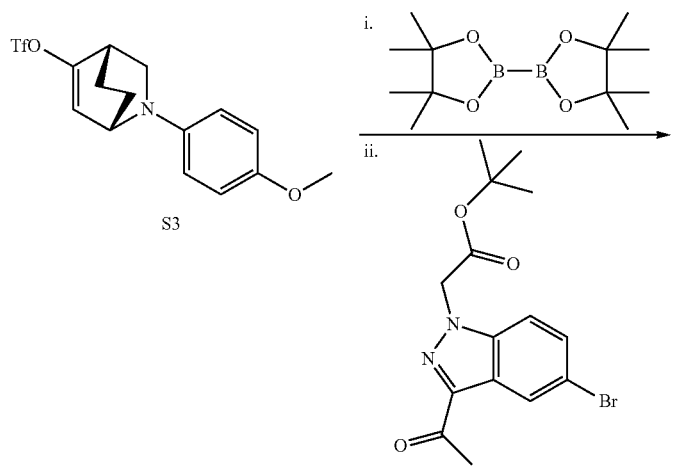

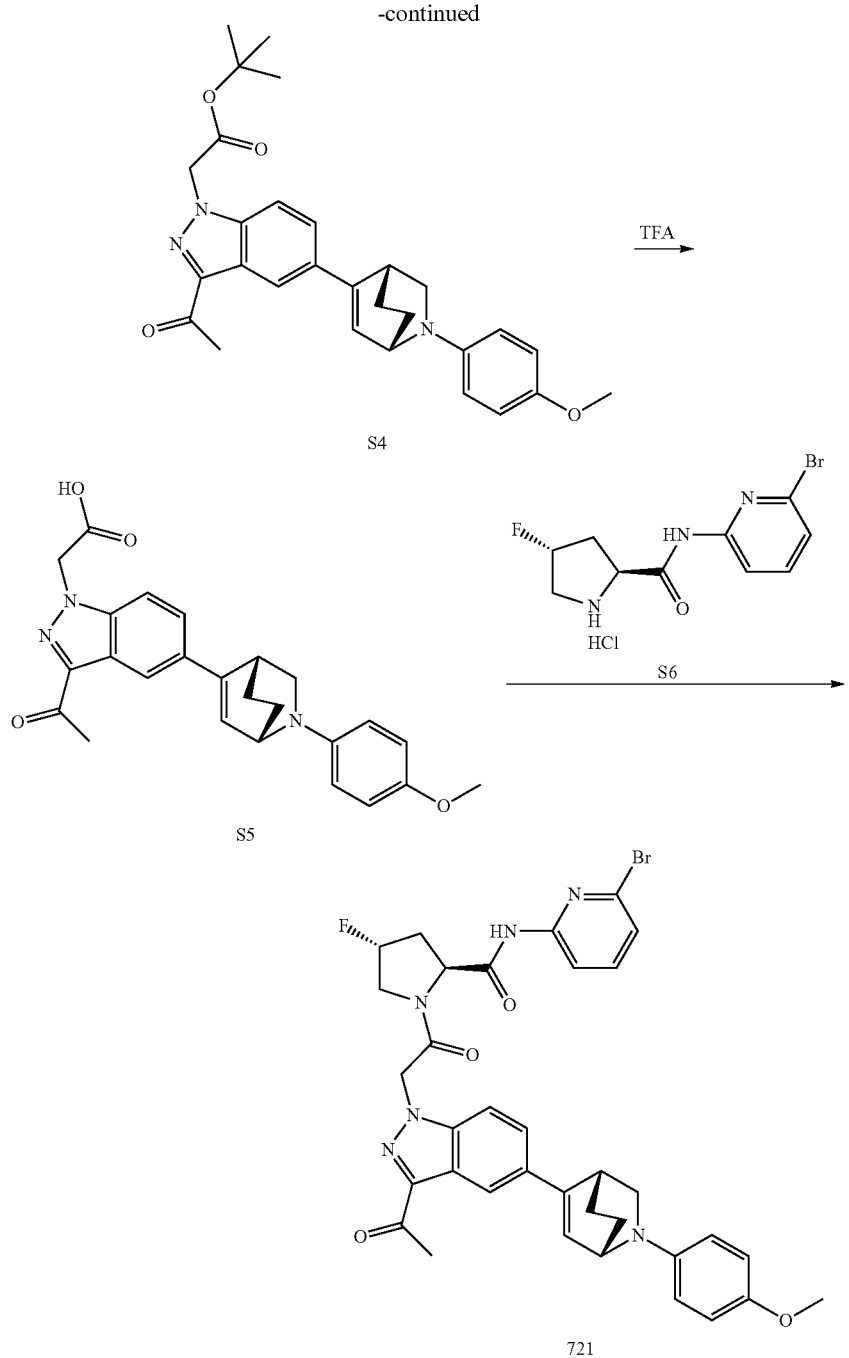

Step-1: (1S,4S)-2-(4-Methoxyphenyl)-2-azabicyclo[2.2.2]octan-5-one (S2)

To a solution of cyclohex-2-en-1-one (1 equiv) in DMSO (10 vol) was added aqueous formaldehyde (0.5 equiv), p-anisidine (0.55 equiv) and (S)-proline (0.3 equiv). The reaction mixture was stirred at 50° C. for 24 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using Hexane/EtOAc to give compound S2.

Step 2: (1S,4S)-2-(4-Methoxyphenyl)-2-azabicyclo[2.2.2]oct-5-en-5-yl trifluoromethanesulfonate (S3)

To a solution of compound S2 (1 equiv) in THF (10 vol) at −78° C. under nitrogen atmosphere was added LDA (2 M in THF) (1.2 equiv) and stirred at −78° C. for 30 minutes. Comin's reagent (1.1 equiv) was added to the reaction mixture at the same temperature and stirred for 2 h. After completion of the reaction, the reaction mixture was quenched with water. The resulting mixture was extracted with EtOAc. The organic layer was washed with brine, dried over anhydrous Na₂SO₄, filtered and then concentrated. The residue was purified by column chromatography on silica gel using Hexane/EtOAc to give compound S3.

Step-3: tert-butyl 2-(3-Acetyl-5-((1S,4R)-2-(4-methoxyphenyl)-2-azabicyclo[2.2.2]oct-5-en-5-yl)-1H-indazol-1-yl)acetate (S4)

To a solution of compound S3 (1 equiv) in 1,4-dioxane (10 vol) at 0° C. under nitrogen atmosphere was added 4,4,4',4',5,5,5',5'-octamethyl-2,2'-bi(1,3,2-dioxaborolane) (1.1 equiv), potassium acetate (3 equiv) and $PdCl_2$(dppf) (0.07 equiv). The reaction mixture was stirred at 60° C. for 18 h. The reaction mixture was cooled to room temperature. tert-butyl 2-(3-acetyl-5-bromo-1H-indazol-1-yl)acetate (1 equiv), water (0.7 vol), $Cs_2CO_3$ (5.5 equiv) and bis(tri-tert-butylphosphine)palladium(0) (0.13 equiv) was added to the reaction mixture and stirred at 60° C. for 15 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using Hexane/EtOAc to give compound S4.

Step-4: 2-(3-Acetyl-5-((1S,4R)-2-(4-methoxyphenyl)-2-azabicyclo[2.2.2]oct-5-en-5-yl)-1H-indazol-1-yl)acetic acid (S5)

To a solution of compound S4 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S5.

Step-5: (2S,4R)-1-(2-(3-Acetyl-5-((1S,4R)-2-(4-methoxyphenyl)-2-azabicyclo[2.2.2]oct-5-en-5-yl)-1H-indazol-1-yl)acetyl)-N-(6-bromopyridin-2-yl)-4-fluoropyrrolidine-2-carboxamide (721)

To a solution of compound 5 (1 equiv) in DMF (10 vol) at 0° C. under nitrogen atmosphere was added S6 (1.5 equiv), HATU (1.5 equiv) and DIPEA (5 equiv). The reaction mixture was stirred at room temperature for 12 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 721.

$^1$H NMR (400 MHz, CD3OD) δ 8.48 (s, 1H), 8.07 (d, J=7.6 Hz, 1H), 7.81 (m, 1H), 7.72 (d, J=8.8 Hz, 1H), 7.68-7.58 (m, 1H), 7.39-7.38 (m, 2H), 7.27-7.24 (m, 1H), 7.07-7.05 (m, 2H), 6.75 (s, 1H), 5.71-5.67 (m, 1H), 5.58-5.44 (m, 2H), 4.78-4.74 (m, 1H), 4.62-4.61 (m, 1H), 4.30-4.25 (m, 1H), 4.11-3.96 (m, 3H), 3.83 (s, 3H), 3.45-3.42 (m, 1H), 2.70 (s, 3H), 2.42-2.10 (s, 3H), 1.75-1.71 (m, 4H).

(2S,4R)-1-(2-(3-Acetyl-5-(2-methylpyrimidin-5-yl)-1H-indol-1-yl)ethyl)-4-fluoro-N-(2-fluoro-3-(trifluoromethoxy)phenyl)pyrrolidine-2-carboxamide (594)

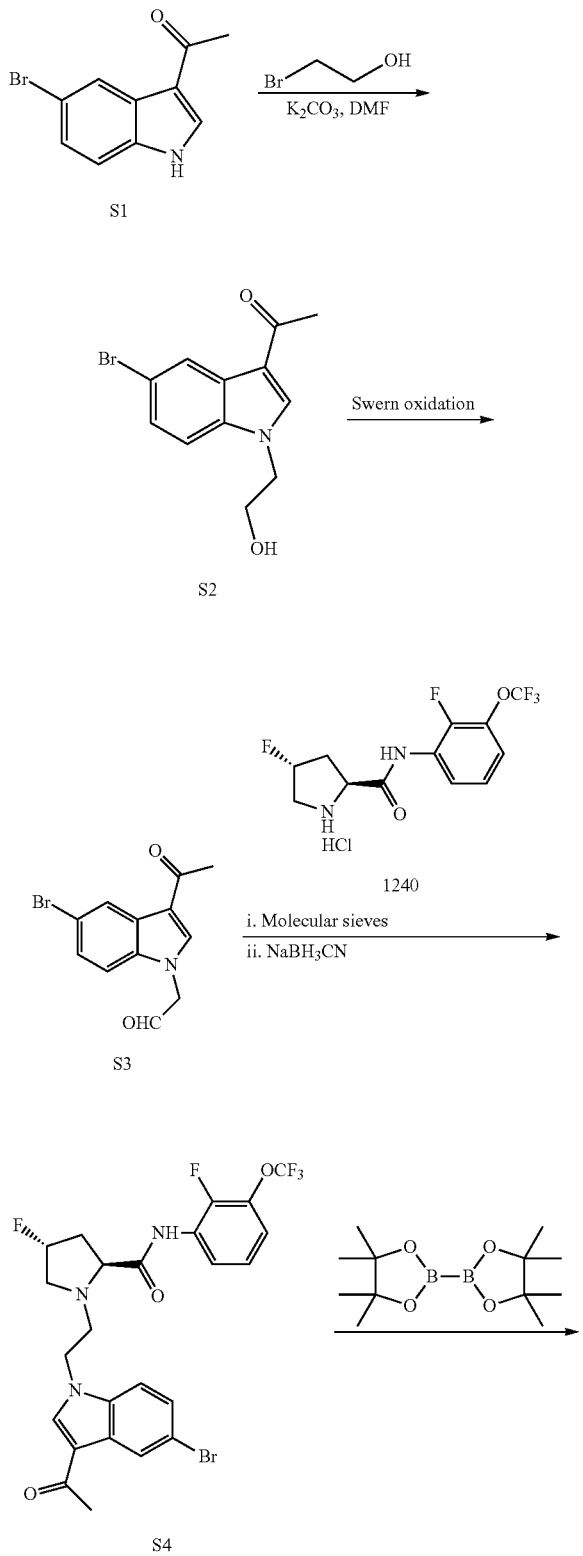

Scheme 131.

-continued

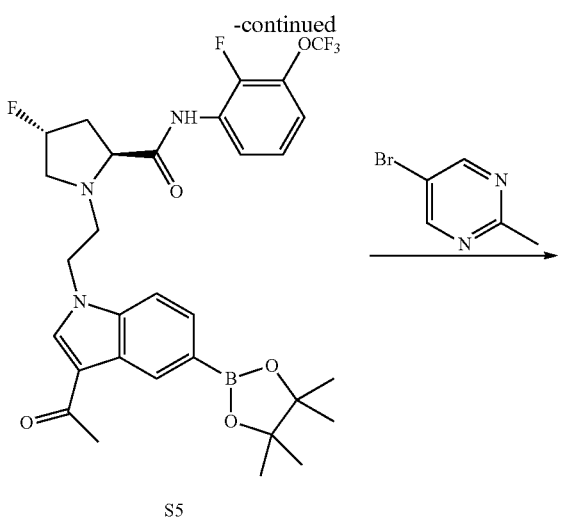

S5

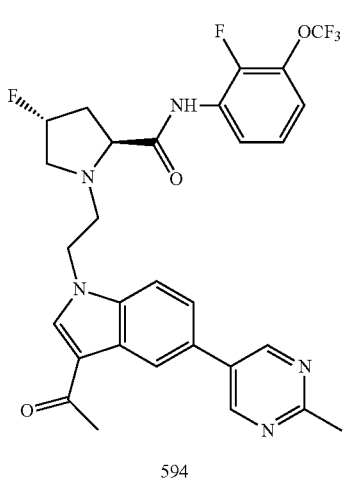

594

Step-1: 1-(5-Bromo-1-(2-hydroxyethyl)-1H-indol-3-yl)ethan-1-one (S2)

To a solution of 1-(5-bromo-1H-indol-3-yl)ethan-1-one (1 equiv) in DMF (10 vol) was added potassium carbonate (3 equiv) and 2-bromoethan-1-ol (2.5 equiv). The reaction mixture was stirred at 80° C. for 12 h. After completion of the reaction, the reaction mixture was filtered through celite and then concentrated. The residue was purified by column chromatography on silica gel using Hexane/EtOAc to give compound SL.

Step 2: 2-(3-Acetyl-5-bromo-1H-indol-1-yl)acetaldehyde (S3)

To a solution of oxalyl chloride (1.3 equiv) in DCM (20 vol) at −78° C. under nitrogen atmosphere was added DMSO (1.4 equiv). The reaction mixture was stirred at the same temperature for 30 minutes and then 1-(5-bromo-1-(2-hydroxyethyl)-1H-indol-3-yl)ethan-1-one (1 equiv) was added to the reaction mixture and stirred at −78° C. for 2 h. The reaction mixture was cooled to 0° C. TEA (4 equiv) was added to the reaction mixture and stirred at 0° C. for 1 h. After completion of the reaction, the reaction mixture was quenched with water. The resulting mixture was extracted with DCM. The organic layer was washed with 1.5 N HCl, 10% $NaHCO_3$ and brine, dried over anhydrous $Na_2SO_4$, filtered and then concentrated to give compound S2.

Step-3: (2S,4R)-1-(2-(3-Acetyl-5-bromo-1H-indol-1-yl)ethyl)-4-fluoro-N-(2-fluoro-3-(trifluoromethoxy)phenyl)pyrrolidine-2-carboxamide (S4)

To a solution of compound S3 (1 equiv) in MeOH (10 vol) at 0° C. under nitrogen atmosphere was added S4 (1.2 equiv), molecular sieves (5%, w/w) and acetic acid (catalytic amount). The reaction mixture was stirred at room temperature for 3 h. Sodium cyanoborohydride (1.5 equiv) was added to the reaction mixture and stirred at room temperature for 12 h. After completion of the reaction, the reaction mixture was filtered through celite and then concentrated. The residue was purified by column chromatography on silica gel using Hexane/EtOAc to give compound S4.

Step-4: (2S,4R)-1-(2-(3-Acetyl-5-(4,4,5,5-tetramethyl-1,3,2-dioxaborolan-2-yl)-1H-indol-1-yl)ethyl)-4-fluoro-N-(2-fluoro-3-(trifluoromethoxy)phenyl)pyrrolidine-2-carboxamide (S5)

To a solution of compound S4 (1 equiv) in 1,4-dioxane (20 vol) was added 4,4,4',4',5,5,5',5'-octamethyl-2,2'-bi(1,3,2-dioxaborolane) (1.5 equiv) and potassium acetate (3 equiv). After degassing with nitrogen, $Pd(dppf)Cl_2$ (0.1 equiv) was added to the reaction mixture. The resulting mixture was stirred at 100° C. for 12 h and then cooled to room temperature. Water was added to the reaction mixture and the resulting mixture was extracted with ethyl acetate. The organic layer was separated, dried over anhydrous $Na_2SO_4$, filtered and then concentrated. The residue was purified by column chromatography on silica gel using Hexane/EtOAc to give compound S5.

Step-5: (2S,4R)-1-(2-(3-Acetyl-5-(2-methylpyrimidin-5-yl)-1H-indol-1-yl)ethyl)-4-fluoro-N-(2-fluoro-3-(trifluoromethoxy)phenyl)pyrrolidine-2-carboxamide (594)

To a solution of compound S5 (1 equiv) in $DMF/H_2O$ (9:1, 10 vol) at room temperature was added 5-bromo-2-methylpyrimidine (1 equiv) and potassium carbonate (2 equiv). After degassing with nitrogen, $Pd(PPh_3)_4$ (0.05 equiv) was added to the reaction mixture. The resulting mixture was stirred at 90° C. for 3 h and then cooled to room temperature. Water was added to the reaction mixture and the resulting mixture was extracted with ethyl acetate. The organic layer was separated, dried over anhydrous $Na_2SO_4$, filtered and then concentrated. The residue was purified by column chromatography on silica gel using DCM/MeOH to give compound 594.

$^1$H NMR (400 MHz, CD3OD) δ 8.88 (s, 2H), 8.37-8.33 (s, 2H), 7.69 (d, J=8.8 Hz, 1H), 7.55-7.52 (m, 1H), 7.41-7.37 (m, 1H), 7.07-6.99 (m, 2H), 5.33-5.20 (m, 1H), 4.50-4.49 (m, 2H), 3.75-3.63 (m, 2H), 3.49-3.41 (m, 1H), 3.25-3.22 (m, 1H), 3.14-3.04 (m, 1H), 2.75 (s, 3H), 2.57 (s, 3H), 2.56-2.55 (m, 1H), 2.08-1.98 (m, 1H).

399
(2S,4R)-1-(2-(3-Acetyl-5-(2-methylpyrazolo[1,5-a]pyrimidin-6-yl)-1H-indol-1-yl)ethyl)-4-fluoro-N-(2-fluoro-3-(trifluoromethoxy)phenyl)pyrrolidine-2-carboxamide (701)

400
(2S,4R)—N-(6-Bromopyridin-2-yl)-4fluoro-1-(2-(5-(2-methylpyrimidin-5-yl)-3-sulfamoyl-1H-indol-1-yl)acetyl)pyrrolidine-2-carboxamide (326)

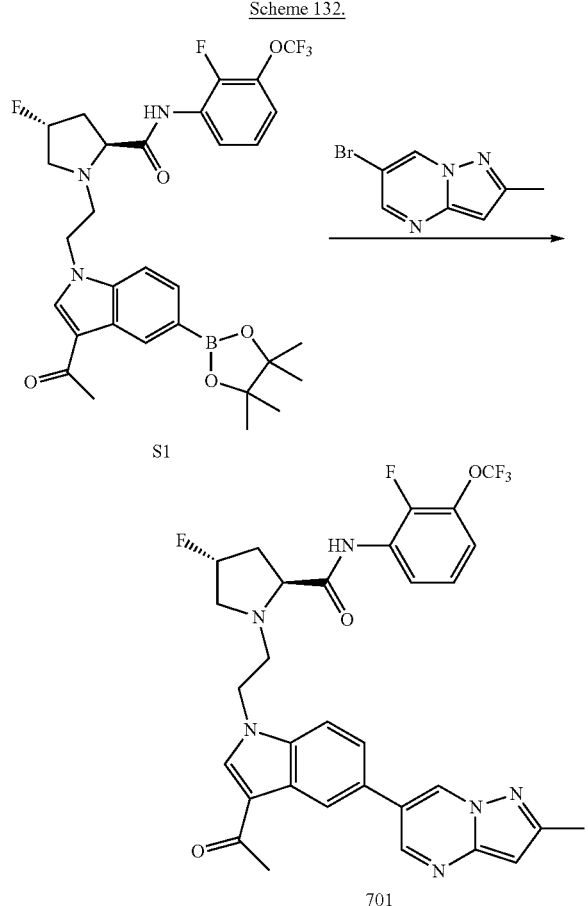

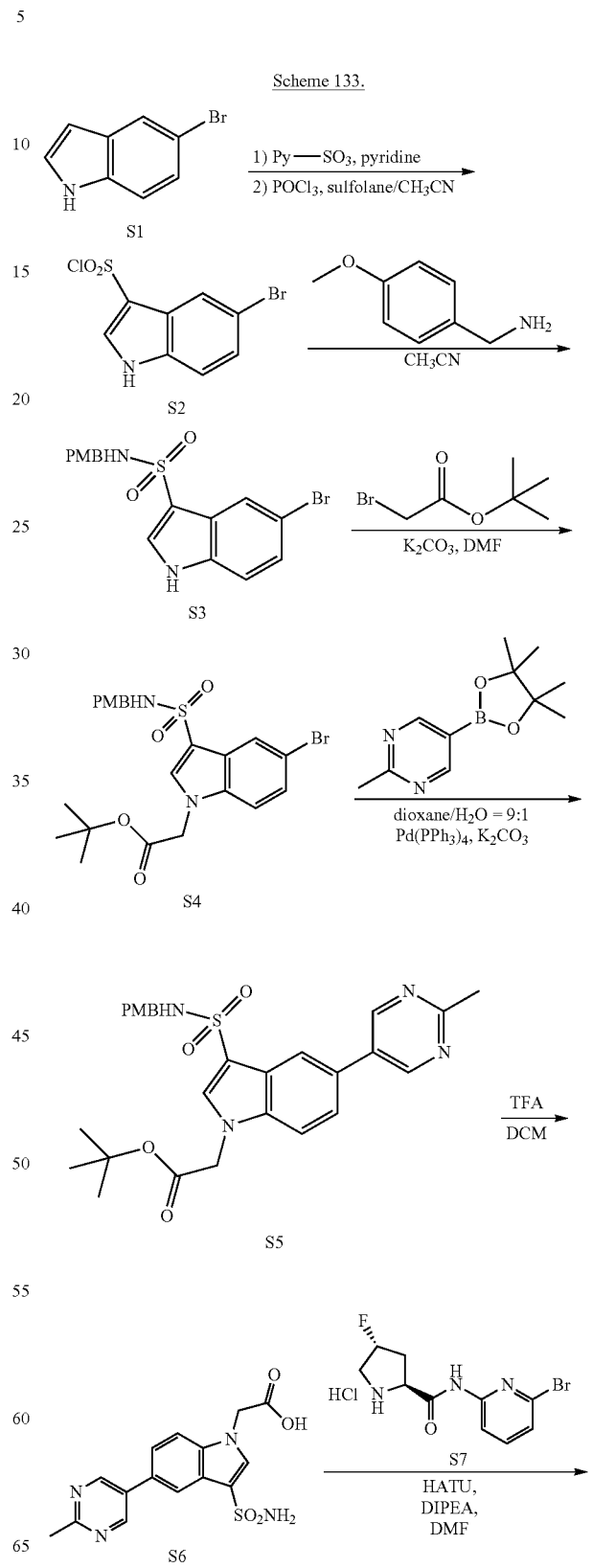

To a solution of (2S,4R)-1-(2-(3-acetyl-5-(4,4,5,5-tetramethyl-1,3,2-dioxaborolan-2-yl)-1H-indol-1-yl)ethyl)-4-fluoro-N-(2-fluoro-3-(trifluoromethoxy)phenyl)pyrrolidine-2-carboxamide (1 equiv) in DMF/H₂O (9:1, 10 vol) at room temperature was added 6-bromo-2-methylpyrazolo[1,5-a]pyrimidine (1 equiv) and potassium carbonate (2 equiv). After degassing with nitrogen, Pd(PPh₃)₄ (0.05 equiv) was added to the reaction mixture. The resulting mixture was stirred at 90° C. for 3 h and then cooled to room temperature. Water was added to the reaction mixture and the resulting mixture was extracted with ethyl acetate. The organic layer was separated, dried over anhydrous Na₂SO₄, filtered and then concentrated. The residue was purified by column chromatography on silica gel using DCM/MeOH to give compound 701.

¹H NMR (400 MHz, CD3OD) δ 8.47 (s, 1H), 8.69 (s, 1H), 8.34 (s, 1H), 8.30 (s, 1H), 7.67 (d, J=8.5 Hz, 1H), 7.54-7.51 (m, 1H), 7.41-7.40 (m, 1H), 7.06-7.04 (m, 2H), 6.53 (s, 1H), 5.33-5.22 (m, 1H), 4.50-4.48 (m, 2H), 3.77-3.64 (m, 2H), 3.43-3.38 (m, 1H), 3.27-3.24 (m, 1H), 3.17-3.07 (m, 1H), 2.57 (s, 3H), 2.54 (s, 3H), 2.53-2.51 (m, 1H), 2.12-1.98 (m, 1H).

-continued

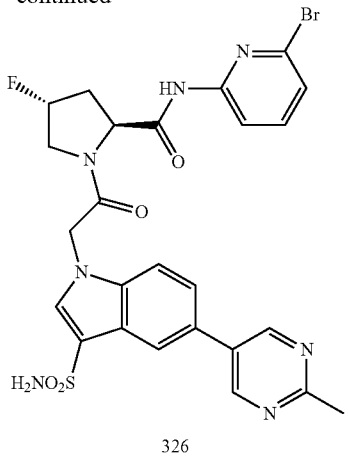

326

Step 1: 5-Bromo-1H-indole-3-sulfonyl chloride (S2)

A solution of 5-bromo-1H-indole (3.0 g, 15.39 mmol) and pyridine sulfur trioxide (2.45 g, 15.39 mmol) in pyridine (15 mL) was stirred under reflux for 2 hrs, and then the reaction was cooled to room temperature, diluted with water and extracted with EtOAc. The aqueous layer was concentrated to dryness. The residue was dissolved in sulfolane/$CH_3CN$ (v/v=1:1). The resulting mixture was cooled to 0° C., and $POCl_3$ was added dropwise. Then the mixture was heated to 70° C. for 1 hr and slowly poured into ice-water. After filtration, the filter cake was washed with water and dried under vacuum to give the title compound (2.3 g, 51.1% yield) as a yellow solid. LCMS: m/z (ES+): 294 [M+H]$^+$.

Step 2: 5-Bromo-N-(4-methoxybenzyl)-1H-indole-3-sulfonamide (S3)

To a solution of 5-bromo-1H-indole-3-sulfonyl chloride (100 mg, 0.34 mmol) in MeCN (5 mL) was added (4-methoxyphenyl) methanamine (47 mg, 0.34 mmol) and the reaction was stirred at room temperature overnight. The mixture was diluted with $H_2O$ and extracted with EtOAc, washed by brine, dried over anhydrous $Na_2SO_4$ and concentrated. The obtained crude product was purified by column chromatography on silica gel eluted with PE/EtOAc (30:1 to 2:1) to give the title compound (120 mg, 89.2% yield) as a yellow solid. LCMS: m/z (ES+): 266 [M+H]$^+$.

Step 3: tert-Butyl 2-(5-bromo-3-(N-(4-methoxybenzyl) sulfamoyl)-1H-indol-1-yl) acetate (S4)

To a solution of 5-bromo-N-(4-methoxybenzyl)-1H-indole-3-sulfonamide (50 mg, 0.13 mmol) in DMF (15 mL) was added $K_2CO_3$ (53 mg, 0.38 mmol) and tert-butyl 2-bromoacetate (25 mg, 0.13 mmol). The reaction was stirred at room temperature overnight. The mixture was diluted with $H_2O$ and extracted with EtOAc, washed by brine, dried over anhydrous $Na_2SO_4$ and concentrated. The obtained crude product was purified by column chromatography on silica gel eluted with PE/EtOAc (30:1 to 2:1) to give the title compound (50 mg, 77.5% yield) as yellow solid. LCMS: m/z (ES+): 509 [M+H]$^+$.

Step 4: tert-Butyl 2-(3-(N-(4-methoxybenzyl)sulfamoyl)-5-(2-methylpyrimidin-5-yl)-1H-indol-1-yl) acetate (S5)

To a mixture of tert-butyl 2-(5-bromo-3-(N-(4-methoxybenzyl) sulfamoyl)-1H-indol-1-yl) acetate (50 mg, 0.098 mmol), 2-methyl-5-(4,4,5,5-tetramethyl-1,3,2-dioxaborolan-2-yl)pyrimidine (20 mg, 0.089 mmol), $K_2CO_3$ (31 mg, 0.22 mmol) in dioxane/$H_2O$ (v/v=9:1) was added tetrakis (triphenylphosphine) palladium(0) (10 mg, 0.0089 mmol) under $N_2$ atmosphere. The reaction was stirred at 120° C. for 2 hrs under $N_2$ atmosphere. After diluted with EtOAc, the mixture was washed with water and brine, dried over anhydrous $Na_2SO_4$ and concentrated. The obtained crude product was purified by column chromatography on silica gel eluted with DCM/MeOH (100:1 to 50:1) to give the title compound (40 mg, 78.4% yield) as yellow solid. LCMS: m/z (ES+): 523 [M+H]$^+$.

Step 5: 2-(5-(2-Methylpyrimidin-5-yl)-3-sulfamoyl-1H-indol-1-yl) acetic acid (S6)

To a solution of tert-butyl 2-(3-(N-(4-methoxybenzyl) sulfamoyl)-5-(2-methylpyrimidin-5-yl)-1H-indol-1-yl) acetate (40 mg, 0.077 mmol) in DCM (1 mL) was added TFA (1 mL) and the reaction was stirred at room temperature for 2 hrs. The mixture was concentrated to dryness to give the title compound (26 mg, 98.1% yield) as a yellow sold, which was used directly in the next step. LCMS: m/z (ES+): 347 [M+H]$^+$.

Step 6: (2S,4R)—N-(6-Bromopyridin-2-yl)-4-fluoro-1-(2-(5-(2-methylpyrimidin-5-yl)-3-sulfamoyl-1H-indol-1-yl)acetyl)pyrrolidine-2-carboxamide (326)

To a mixture of 2-(5-(2-methylpyrimidin-5-yl)-3-sulfamoyl-1H-indol-1-yl) acetic acid (26 mg, 0.075 mmol), S7 (26 mg, 0.09 mmol) in DMF (1 mL) are added DIPEA (48 mg, 0.38 mmol) and HATU (63 mg, 0.17 mmol). The reaction was stirred at room temperature for 1.5 hrs. The mixture was diluted with EtOAc and washed with 10% aq. LiCl solution and brine successively. The organic layer was dried over anhydrous $Na_2SO_4$ and concentrated. The obtained crude product was purified by prep-HPLC to give the title compound (5 mg, 10.9% yield) as white solid. $^1$H-NMR (400 MHz, DMSO-d$_6$) δ: 11.01 (s, 1H), 9.07 (s, 2H), 8.21 (s, 1H), 8.03 (d, J=8.0 Hz, 1H), 7.86 (s, 1H), 7.72-7.62 (m, 2H), 7.34-7.30 (m, 2H), 5.74-5.19 (m, 3H), 4.79-4.59 (m, 1H), 4.25-3.91 (m, 2H), 2.68 (s, 3H), 2.36-2.32 (m, 1H), 2.26-2.14 (m, 1H). LCMS: m/z (ES+): 616 [M+H]$^+$.

1-(2-((1R,3S,4S)-3-((6-Methylpyridin-2-yl)carbamoyl)-2-azabicyclo[2.2.1]heptan-2-yl)-2-oxoethyl)-5-(naphthalen-2-yl)-1H-indole-3-carboxamide (489)

Scheme 135.

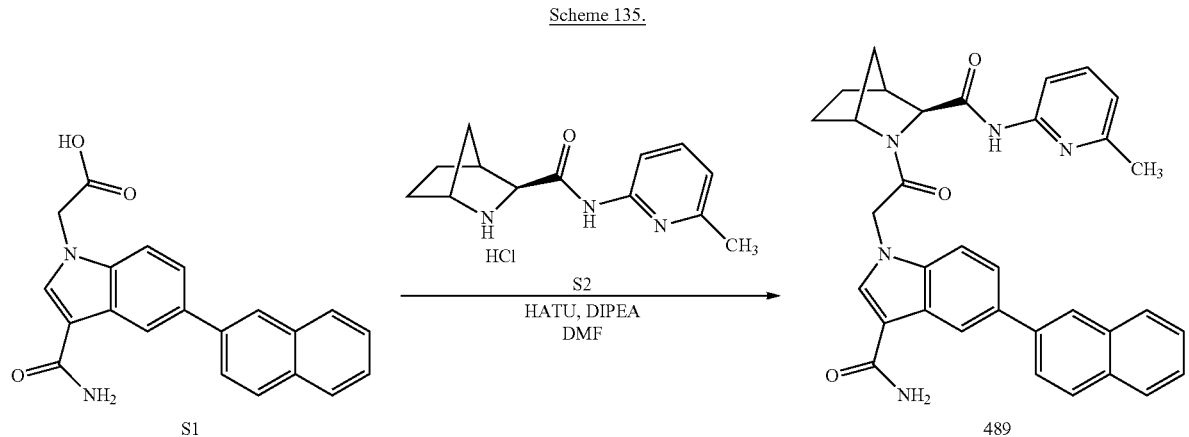

To a mixture of compound S1 and S2 in DMF (1 mL) was added DIPEA and HATU at 0° C. The reaction was stirred at room temperature for 16 hrs. The mixture was diluted with EtOAc and washed with 10% aq. LiCl solution and brine successively. The organic layer was dried over anhydrous $Na_2SO_4$, filtered and concentrated to dryness. The residue was purified by prep-TLC (DCM/MeOH=20:1) to give 489. $^1$H NMR (400 MHz, CDCl$_3$) δ 8.35 (s, 1H), 8.00 (t, J=17.7 Hz, 2H), 7.87-7.74 (m, 5H), 7.57 (d, J=8.1 Hz, 3H), 7.46-7.35 (m, 3H), 6.89-6.83 (m, 1H), 5.69 (d, J=56.7 Hz, 2H), 5.35-5.00 (m, 1H), 4.88-4.62 (m, 2H), 4.31-3.98 (m, 2H), 2.90 (s, 1H), 2.37 (d, J=15.6 Hz, 3H), 2.20-1.98 (m, 2H), 1.38 (s, 1H). LC/MS (ESI) m/z: 558 (M+H)$^+$.

5-(3-Cyanophenyl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (497)

Scheme 136.

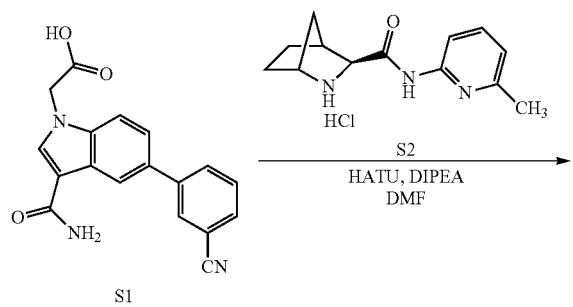

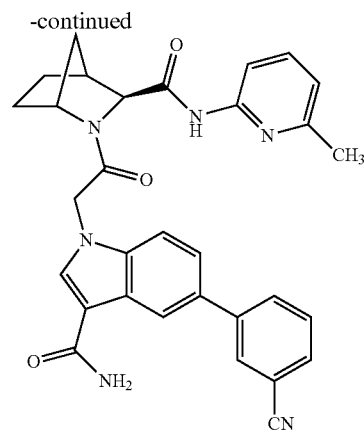

The titled compound was prepared according to the synthesis from Scheme 135 from appropriate starting materials. $^1$H NMR (400 MHz, DMSO-d$_6$) δ: 10.44 (s, 1H), 8.42 (s, 1H), 8.13 (d, J=1.6 Hz, 1H), 8.00 (dd, J=22.6, 9.0 Hz, 2H), 7.85-7.72 (m, 2H), 7.72-7.60 (m, 2H), 7.56 (dd, J=6.4, 1.5 Hz, 2H), 6.98 (dd, J=31.5, 7.5 Hz, 2H), 5.43 (d, J=17.2 Hz, 1H), 5.15 (dd, J=17.0, 5.8 Hz, 1H), 4.70-4.42 (m, 2H), 4.13 (s, 1H), 2.67 (s, 1H), 2.46-2.31 (m, 3H), 2.11 (d, J=9.5 Hz, 1H), 1.81-1.58 (m, 3H), 1.47 (dd, J=27.0, 9.1 Hz, 2H). LC/MS (ESI) m/z: 533 (M+H)$^+$.

1-(2-((1R,3S,4S)-3-(6-Methylpyridin-2-ylcarbamoyl)-2-azabicyclo[2.2.1]heptan-2-yl)-2-oxoethyl)-5-(5,6,7,8-tetrahydronaphthalen-2-yl)-1H-indole-3-carboxamide (515)

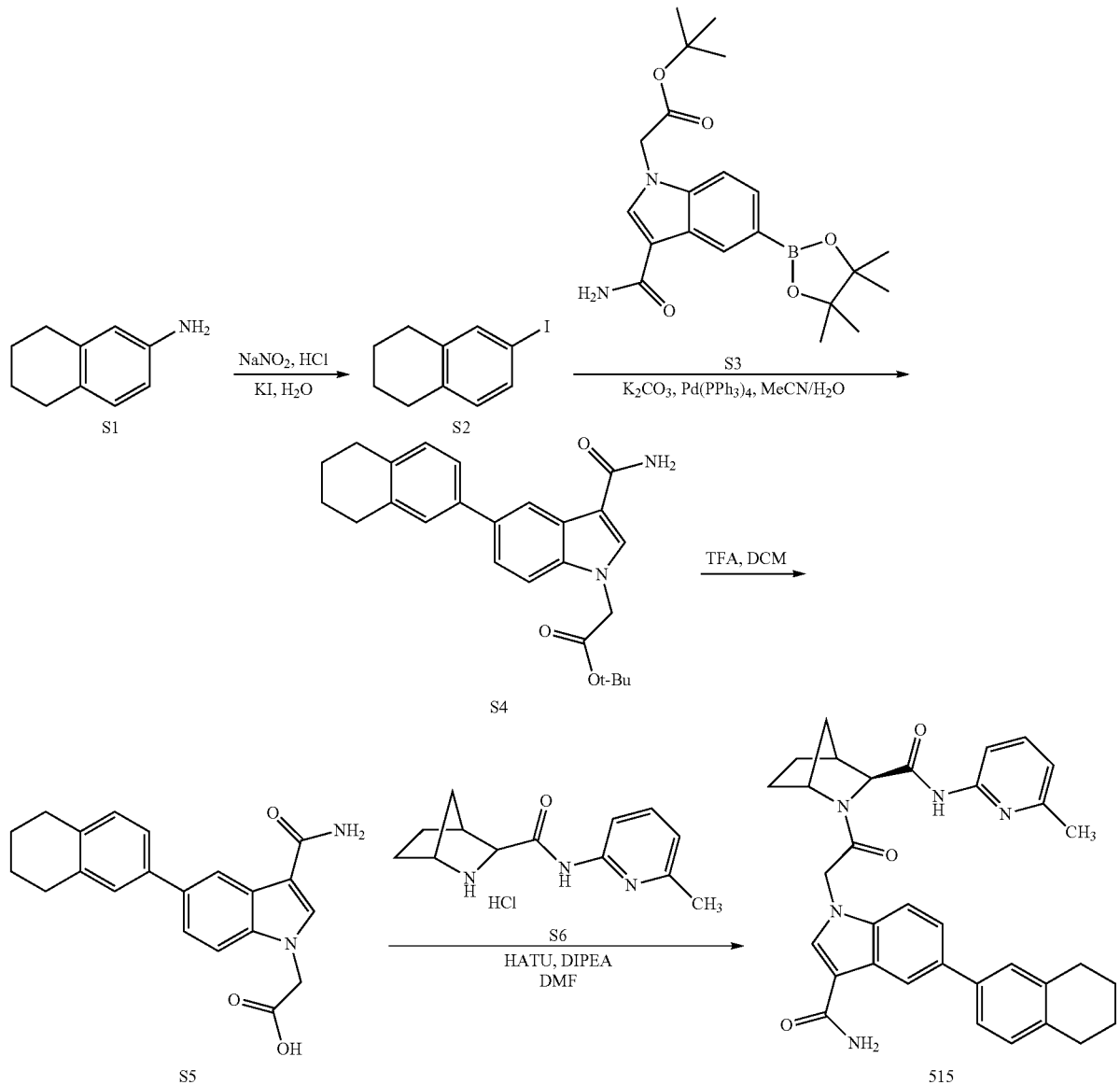

Scheme 137.

Step 1: 6-Iodo-1,2,3,4-tetrahydronaphthalene (S2)

To a suspension of compound S1 (1 g, 6.8 mmol) in 15% HCl (w/w, 6 mL) was added a solution of sodium nitrite (563 mg, 8.16 mmol) in water (2.5 mL) drop-wise over 15 min at 0-5° C. After addition was completed, the mixture was stirred at 0° C. for 1 hr. Potassium iodide (1.35 g, 8.16 mmol) was added in one portion. The reaction mixture was stirred at room temperature for 3 hrs and 60° C. for 1 hr. The resulting mixture was extracted with diethyl ether (10 mL×2). The combined organic layers are washed with sat. $NaHCO_3$ and brine, dried over anhydrous $Na_2SO_4$, filtered and concentrated. The residue was purified by column chromatography on silica gel (eluted with petroleum ether) to give compound S2 (750 mg, 42.8% yield) as a colorless oil.

Step 2: tert-Butyl 2-(3-carbamoyl-5-(5,6,7,8-tetrahydronaphthalen-2-yl)-1H-indol-1-yl)acetate (S4)

To a solution of compound S2 (154.8 mg, 0.60 mmol), S3 (200 mg, 0.50 mmol) and $K_2CO_3$ (207 mg, 1.50 mmol) in MeCN (4 ml)/water (1 mL) was added $Pd(PPh_3)_4$ (28.8 mg, 0.025 mmol) at room temperature under nitrogen. The reaction was stirred under nitrogen protection at 90° C. for 2 hrs and then concentrated. Water (10 mL) was added and the mixture was extracted with ethyl acetate (5 mL×2). The organic phase are washed with brine, dried over anhydrous Na$_2$SO$_4$, filtered and then concentrated. The residue was purified by silica gel chromatography (DCM:MeOH=80:1) to give compound S4 (185 mg, 73.1% yield) as a brown oil.

Step 3: 2-(3-Carbamoyl-5-(5,6,7,8-tetrahydronaphthalen-2-yl)-1H-indol-1-yl)acetic acid TFA Salt (S5)

To a mixture of compound S4 (180 mg, 0.44 mmol) in dichloromethane (2 mL) was added TFA (1 mL) drop-wise at 0° C. The reaction was stirred at room temperature for 12 hrs. The mixture was concentrated under reduced pressure to give a residue. Co-evaporated of the residue with toluene (2 mL×2) to give compound S5 (200 mg, 100% yield) as a brown oil, which was used in the next step without purification.

Step 4: 1-(2-((1R,4S)-3-(6-Methylpyridin-2-ylcarbamoyl)-2-azabicyclo[2.2.1]heptan-2-yl)-2-oxoethyl)-5-(5,6,7,8-tetrahydronaphthalen-2-yl)-1H-indole-3-carboxamide (515)

To a solution of compound S5 (70 mg, 0.11 mmol) and S6 (47 mg, 0.15 mmol) in DMF (2 ml), was added DIPEA (0.085 mL, 0.52 mmol) and HATU (98 mg, 0.26 mmol). The reaction was stirred at room temperature overnight. The mixture was poured into ice-water and the precipitated solid was collected by filtration. Purification with pre-TLC gives compound 515 (13 mg, 11.6% yield) as a white solid. $^1$H NMR (400 MHz, DMSO-d$_6$) δ: 10.42 (s, 1H), 8.34 (s, 1H), 7.97 (s, 1H), 7.81-7.83 (m, 1H), 7.60-7.64 (m, 1H), 7.41-7.48 (m, 6H), 7.12 (d, J=8.0 Hz, 1H), 6.93 (d, J=7.6 Hz, 1H), 5.35-5.39 (m, 1H), 5.09-5.14 (m, 1H), 4.62 (s, 1H), 4.12 (s, 1H), 2.66-2.80 (m, 6H), 2.42 (s, 3H), 2.09 (d, J=9.2 Hz, 1H), 1.76-1.78 (m, 6H), 1.42-1.48 (m, 2H). LC/MS (ESI) m/z: 562 (M+H)$^+$.

5-(1,2-Dihydrocyclobutabenzen-4-yl)-1-(2-((1R,3S,4S)-3-(6-methylpyridin-2-ylcarbamoyl)-2-azabicyclo[2.2.1]heptan-2-yl)-2-oxoethyl)-1H-indole-3-carboxamide (536)

Scheme 138

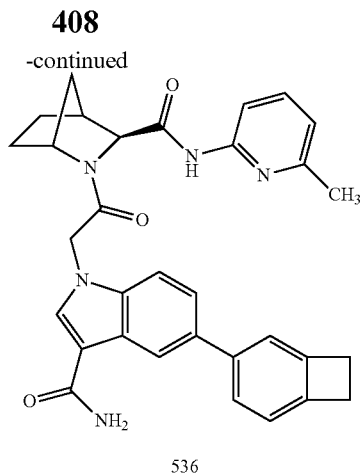

536

The titled compound was prepared according to the synthesis from Scheme 135 from appropriate starting materials. $^1$H NMR (400 MHz, DMSO-d$_6$) δ: 10.43 (s, 1H), 8.31 (d, J=0.9 Hz, 1H), 7.97 (s, 1H), 7.82 (d, J=8.0 Hz, 1H), 7.62 (t, J=8.0 Hz, 1H), 7.49-7.37 (m, 3H), 7.34 (s, 1H), 7.15 (d, J=8.0 Hz, 1H), 6.93 (d, J=7.6 Hz, 1H), 5.38 (d, J=17.6 Hz, 1H), 5.11 (dd, J=17.2, 6.8 Hz, 1H), 4.62 (s, 1H), 4.50 (dd, J=28.8, 17.2 Hz, 1H), 4.12 (s, 1H), 3.18 (d, J=2.8 Hz, 4H), 2.66 (s, 1H), 2.40 (s, 3H), 2.09 (d, J=9.6 Hz, 1H), 1.81-1.58 (m, 2H), 1.53-1.22 (m, 2H); LC/MS (ESI) m/z: 534 (M+H)$^+$.

(1R,3S,5R)-2-(2-(3-Acetyl-5-(2-methylpyrimidin-5-yl)-1H-indazol-1-yl)acetyl)-N-(3-cyclopropyl-2-fluorobut-2-en-1-yl)-2-azabicyclo[3.1.0]hexane-3-carboxamide (551)

Scheme 139

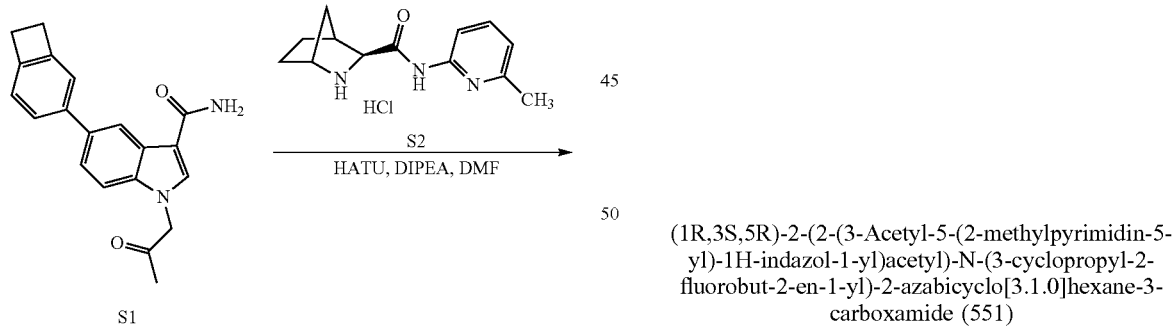

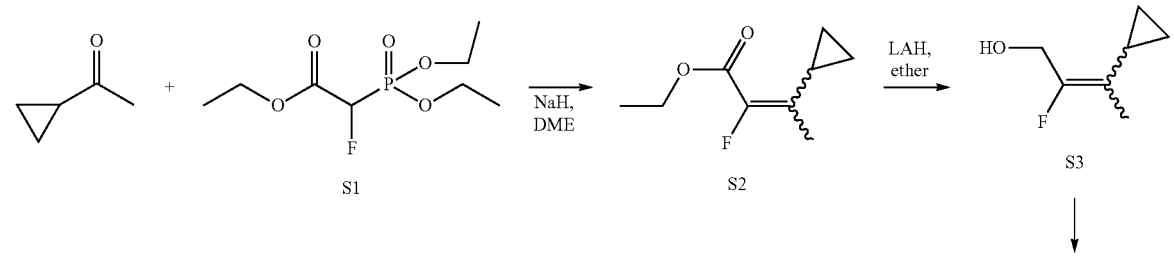

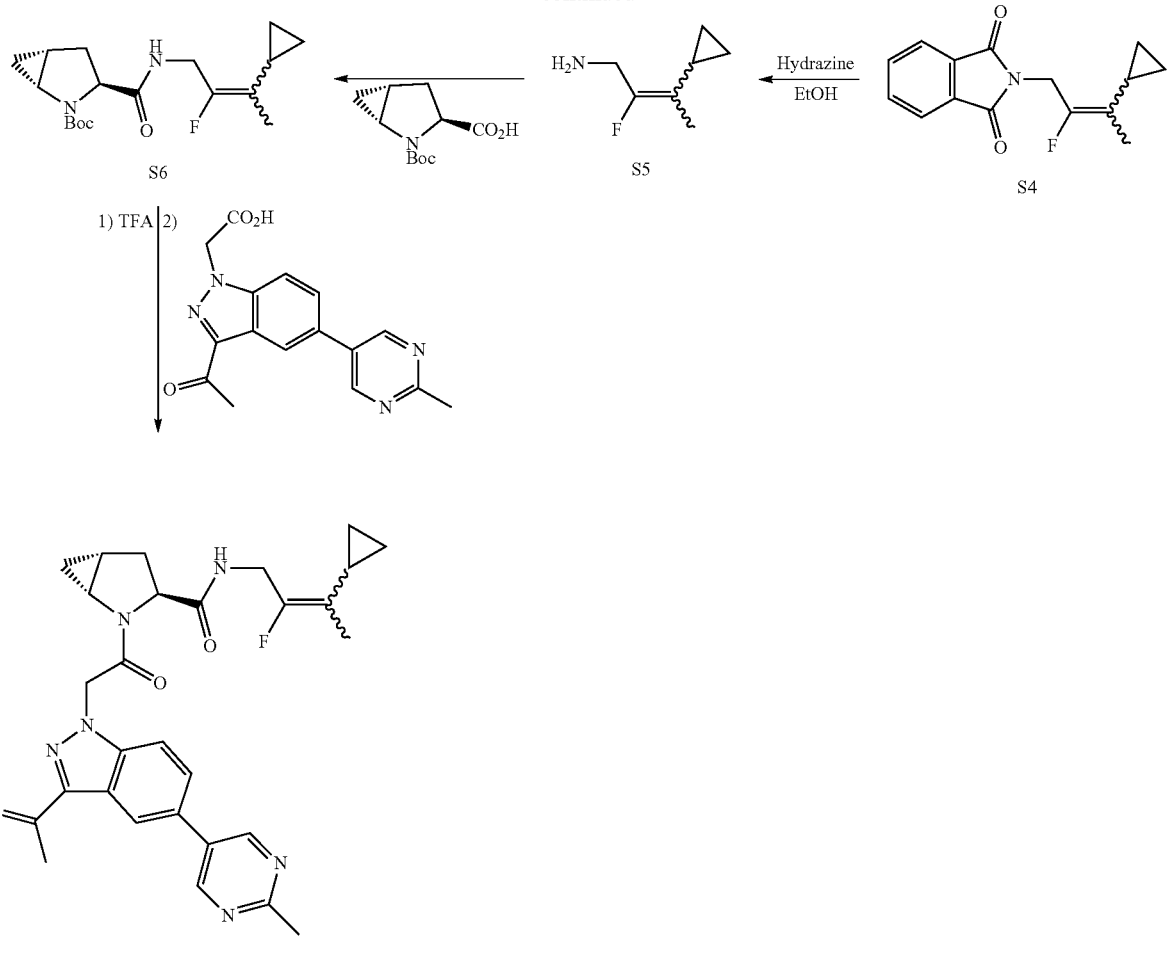

Ethyl 3-cyclopropyl-2-fluorobut-2-enoate

Same procedure as for the synthesis of ethyl (E)-2-fluoro-3-phenylbut-2-enoate, but starting from 1-(3-chlorophenyl)ethan-1-one. The crude product was purified on an ISCO (eluent: 0-0.4% EtOAc in hexanes) to afford an inseparable mixture of (E)- and (Z)-isomers as a light yellow oil.

(1R,3S,5R)-2-(2-(3-Acetyl-5-(2-methylpyrimidin-5-yl)-1H-indazol-1-yl)acetyl)-N-(3-cyclopropyl-2-fluorobut-2-en-1-yl)-2-azabicyclo[3.1.0]hexane-3-carboxamide (551)

The title compound was prepared according to the procedure described for the synthesis of (1R,3S,5R)-2-(2-(3-acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide from (E)-2-fluoro-3-phenylbut-2-enoate except that the starting compound was ethyl 3-cyclopropyl-2-fluorobut-2-enoate. The crude product was purified by ISCO (eluent: 0-2.5% MeOH in $CH_2Cl_2$) to get white solid. $^1$H NMR (400 MHz, DMSO) (major rotamer) δ 0.42-0.58 (m, 4H), 0.75-0.82 (m, 1H), 1.02 (-1.06 (m, 1H), 1.30 (dd, J=3.2, 14.6 Hz, 3H), 1.58-1.62 (m, 1H), 1.77-1.86 (m, 1H), 2.08-2.14 (m, 1H), 2.17-2.28 (m, 1H), 2.66 (s, 3H), 2.69 (s, 3H), 3.69-3.76 (m, 1H), 3.83-4.08 (m, 2H), 4.24-4.28 (m, 1H), 5.58 (d, J=17.2 Hz, 1H), 5.90 (d, J=17.2 Hz, 1H), 7.86 (s, 2H), 8.10-8.19 (m, 1H), 8.44 (s, 1H), 9.05 (s, 2H). $^{19}$F-NMR (DMSO-$d_6$) (major rotamer): δ -112.6.

1-(2-((2S,4R)-2-((6-Bromopyridin-2-yl)carbamoyl)-4-fluoropyrrolidin-1-yl)-2-oxoethyl)-4-(2-(methylamino)quinazolin-6-yl)-1H-pyrazole-3-carboxamide (723)

Scheme 140.

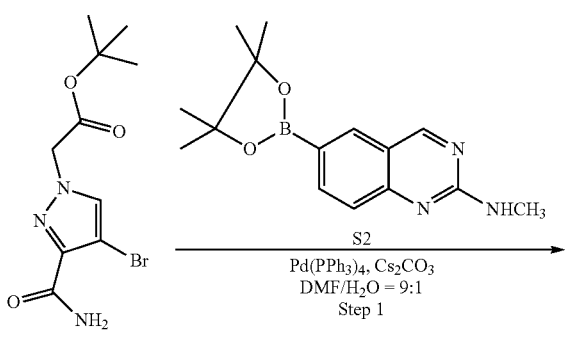

-continued

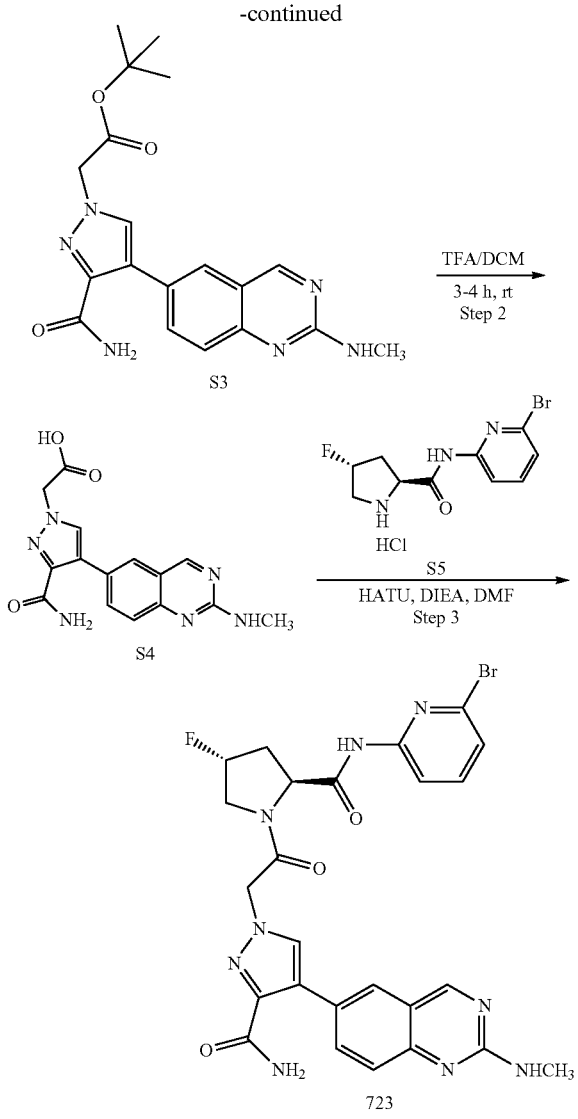

Step 1: tert-Butyl 2-(3-carbamoyl-4-(2-(methylamino)quinazolin-6-yl)-1H-pyrazol-1-yl)acetate (S3)

To a solution of N-methyl-6-(4,4,5,5-tetramethyl-1,3,2-dioxaborolan-2-yl)quinazolin-2-amine (1 equiv) in DMF/H₂O (9:1, 10 vol) was added compound S1 (1 equiv), Cs₂CO₃ (3 equiv), and tetrakis(triphenylphosphine)palladium (0.1 equiv). The reaction mixture was stirred at 90° C. for 5 h and then concentrated under reduced pressure. The residue was purified by column chromatography on silica gel (MeOH/DCM) to give compound S3.

Step 2: 2-(3-Carbamoyl-4-(2-(methylamino)quinazolin-6-yl)-1H-pyrazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: 1-(2-((2S,4R)-2-((6-Bromopyridin-2-yl)carbamoyl)-4-fluoropyrrolidin-1-yl)-2-oxoethyl)-4-(2-(methylamino)quinazolin-6-yl)-1H-pyrazole-3-carboxamide (723)

To a solution of compound S4 (1 equiv) in DMF (10 vol) at 0° C. under an atmosphere of nitrogen was added (2S,4R)—N-(6-bromopyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 723. $^1$H NMR (400 MHz, DMSO-d$_6$) δ 2.04-2.26 (m, 1H), 2.52-2.63 (m, 1H), 2.91 (d, J=4.8 Hz, 3H), 3.77-3.95 (m, 1H), 4.05-4.19 (m, 1H), 4.71 (t, J=8.5 Hz, 1H), 5.17 (d, J=16.8 Hz, 1H), 5.36 (d, J=16.9 Hz, 1H), 5.51 (d, J=52.3 Hz, 1H), 7.20-7.31 (m, 2H), 7.35 (d, J=7.7 Hz, 1H), 7.43 (d, J=8.3 Hz, 2H), 7.73 (t, J=8.0 Hz, 1H), 7.85-7.91 (m, 1H), 7.95 (d, J=2.1 Hz, 1H), 8.01 (s, 1H), 8.03-8.09 (m, 1H), 9.05 (s, 1H), 11.06 (s, 1H). $^{19}$F NMR (376 MHz, DMSO-d$_6$): δ -175.82. LC (method A): tR=1.13 min. LC/MS (EI) m/z: [M+H]$^+$ 596.

1-(2-((2S,4R)-2-((6-Bromopyridin-2-yl)carbamoyl)-4-fluoropyrrolidin-1-yl)-2-oxoethyl)-1'-(5-fluoropyrimidin-2-yl)-1H,1'H-[4,4'-bipyrazole]-3-carboxamide (729)

Scheme 141.

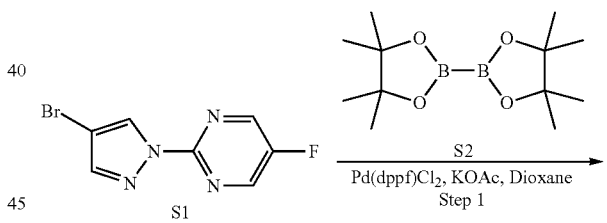

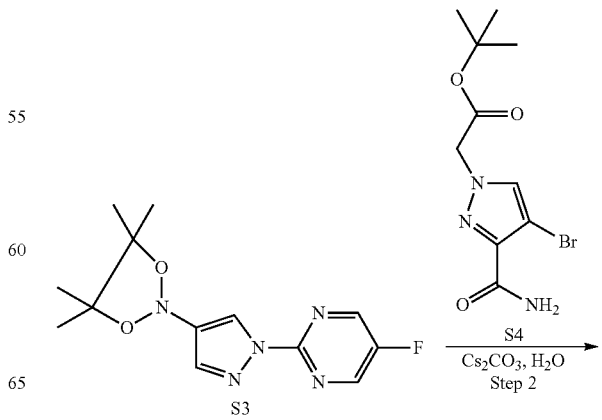

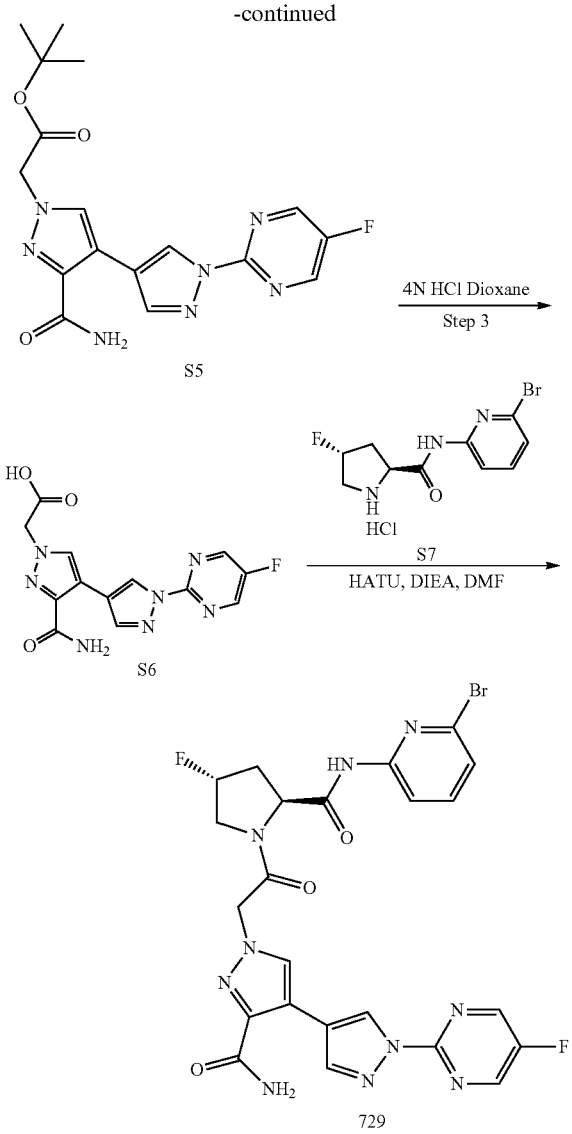

Step 1: 5-Fluoro-2-(4-(4,4,5,5-tetramethyl-1,3,2-dioxaborolan-2-yl)-1H-pyrazol-1-yl)pyrimidine (S3)

To a mixture of compound S1 (1 equiv), AcOK (3 equiv), and compound S2 (1.2 equiv) in dioxane (10 vol) stirred at room temperature under nitrogen was added Pd(dppf)Cl$_2$ (0.05 equiv) in one portion. The resulting mixture was stirred at 90° C. under nitrogen for 3 h. After cooling the reaction mixture to room temperature and directly used in the next step.

Step 2: tert-Butyl 2-(3-carbamoyl-1'-(5-fluoropyrimidin-2-yl)-1H,1'H-[4,4'-bipyrazol]-1-yl)acetate (S5)

To a solution of compound S3 (1 equiv) in dioxane and water (9:1 vol) at room temperature under an atmosphere of nitrogen was added CS$_2$CO$_3$ (3 equiv) and compound S4. The resulting mixture was stirred at 90° C. under nitrogen for 3 h. After cooling the reaction mixture to room temperature, the mixture was filtered through Celite and washed with dioxane. The filtrate was concentrated under high vacuum and The residue was purified by column chromatography on silica gel (EtOAc/DCM) to give compound S5.

Step 3: 2-(3-Carbamoyl-1'-(5-fluoropyrimidin-2-yl)-1H,1'H-[4,4'-bipyrazol]-1-yl)acetic acid (S6)

To a solution of compound S5 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 4: 1-(2-((2S,4R)-2-((6-Bromopyridin-2-yl)carbamoyl)-4-fluoropyrrolidin-1-yl)-2-oxoethyl)-1'-(5-fluoropyrimidin-2-yl)-1H,1'H-[4,4'-bipyrazole]-3-carboxamide (729)

To a solution of compound S6 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give the title compound. $^1$H NMR (400 MHz, DMSO-d$_6$) δ 2.03-2.25 (m, 1H), 2.52-2.62 (m, 1H), 3.76-3.93 (m, 1H), 4.13 (dd, J=12.7, 21.8 Hz, 1H), 4.71 (q, J=8.5, 9.6 Hz, 1H), 5.16 (d, J=16.9 Hz, 1H), 5.37 (d, J=17.0 Hz, 1H), 5.51 (d, J=52.2 Hz, 1H), 7.25-7.31 (m, 1H), 7.35 (d, J=7.7 Hz, 1H), 7.50 (d, J=17.0 Hz, 1H), 7.73 (t, J=8.0 Hz, 1H), 8.06 (d, J=8.2 Hz, 1H), 8.25 (d, J=5.8 Hz, 2H), 8.96 (s, 2H), 9.24 (d, J=3.7 Hz, 1H), 11.08 (s, 1H). $^{19}$F NMR (376 MHz, DMSO-d$_6$): δ −175.88, −142.72. LC (method A): t$_R$=1.32 min. LC/MS (EI) m/z: [M+H]$^+$ 601.

1-(2-((2S,4R)-2-((6-Bromopyridin-2-yl)carbamoyl)-4-fluoropyrrolidin-1-yl)-2-oxoethyl)-1'-cyclopropyl-1H,1'H-[4,4'-bipyrazole]-3-carboxamide (726)

Scheme 142

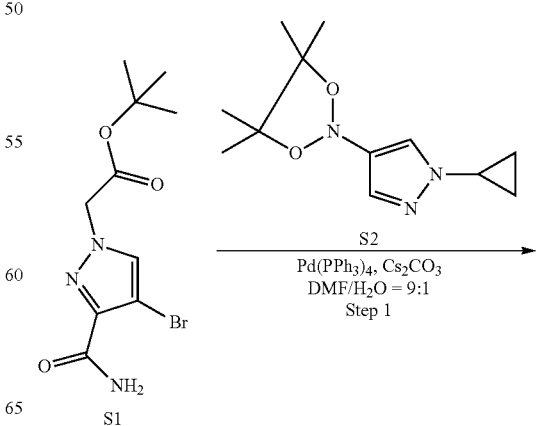

415

-continued

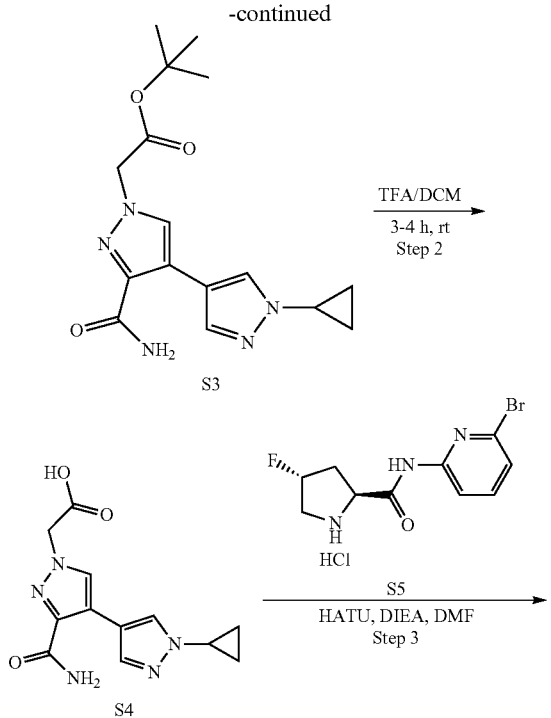

Step 1: tert-Butyl 2-(3-carbamoyl-1'-cyclopropyl-1H,1'H-[4,4'-bipyrazol]-1-yl)acetate (S3)

To a solution of 1-cyclopropyl-4-(4,4,5,5-tetramethyl-1,3,2-dioxaborolan-2-yl)-1H-pyrazole (S2, 1 equiv) in DMF/H₂O (9:1, 10 vol) was added compound S1 (1 equiv), Cs₂CO₃ (3 equiv), and tetrakis(triphenylphosphine)palladium (0.1 equiv). The reaction mixture was stirred at 90° C. for 5 h and then concentrated under reduced pressure. The residue was purified by column chromatography on silica gel (MeOH/DCM) to give compound S3.

Step 2: 2-(3-Carbamoyl-1'-cyclopropyl-1H,1'H-[4,4'-bipyrazol]-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

416

Step 3: 1-(2-((2S,4R)-2-((6-Bromopyridin-2-yl)carbamoyl)-4-fluoropyrrolidin-1-yl)-2-oxoethyl)-1'-cyclopropyl-1H,1'H-[4,4'-bipyrazole]-3-carboxamide (726)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 726. $^1$H NMR (400 MHz, DMSO-d₆) δ 0.86-1.08 (m, 4H), 2.01-2.25 (m, 1H), 2.53-2.63 (m, 1H), 3.66-3.75 (m, 1H), 3.76-3.92 (m, 1H), 4.11 (dd, J=12.6, 21.5 Hz, 1H), 4.70 (d, J=8.3 Hz, 1H), 5.11 (d, J=16.9 Hz, 1H), 5.31 (d, J=16.9 Hz, 1H), 5.50 (d, J=52.2 Hz, 1H), 7.18 (s, 1H), 7.33-7.38 (m, 2H), 7.70-7.79 (m, 2H), 7.99 (s, 1H), 8.03-8.08 (m, 1H), 8.24 (s, 1H), 11.06 (s, 1H). $^{19}$F NMR (376 MHz, DMSO-d₆): δ −175.88. LC (method A): $t_R$=1.28 min. LC/MS (EI) m/z: [M+H]$^+$ 545.

4-(1-acetyl-1,2,3,6-Tetrahydropyridin-4-yl)-1-(2-((2S,4R)-2-((6-bromopyridin-2-yl)carbamoyl)-4-fluoropyrrolidin-1-yl)-2-oxoethyl)-1H-pyrazole-3-carboxamide (727)

Scheme 143.

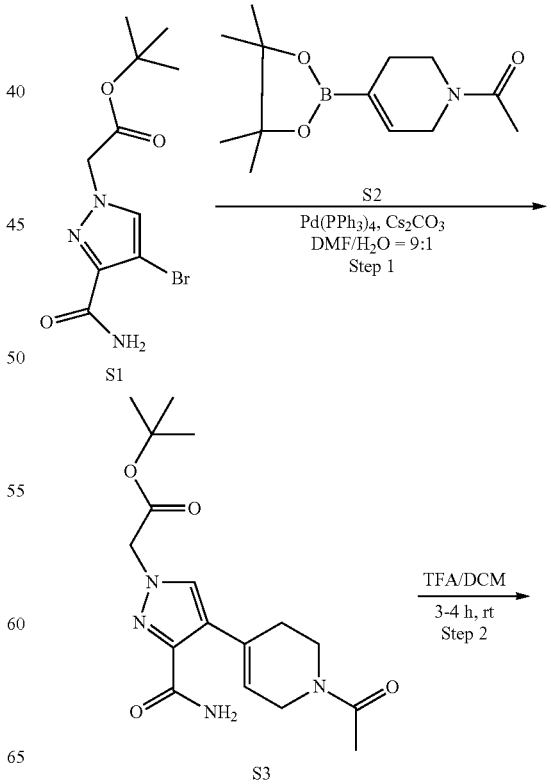

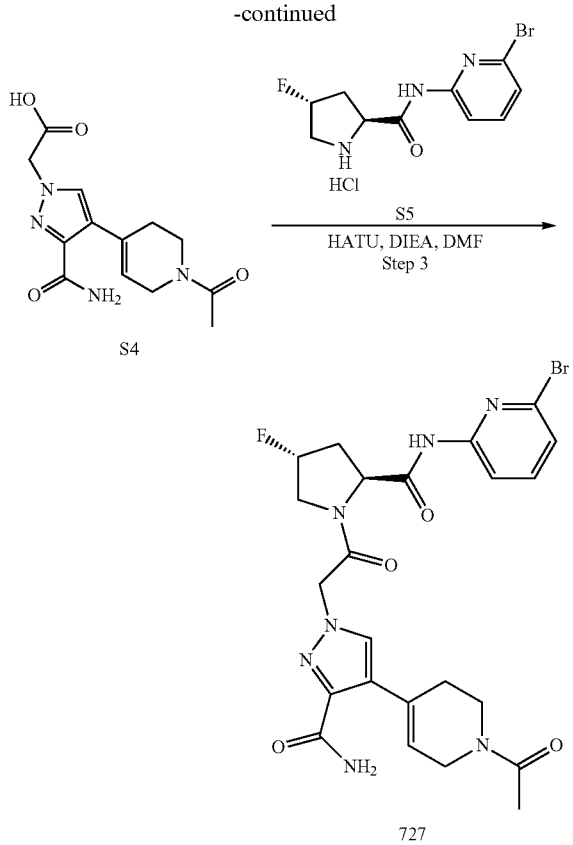

temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 727. $^1$H NMR (400 MHz, DMSO-$d_6$) δ 1.95-2.25 (m, 4H), 2.31-2.48 (m, 2H), 2.53-2.62 (m, 1H), 3.52-3.62 (m, 2H), 3.73-3.91 (m, 1H), 3.96-4.15 (m, 3H), 4.67 (t, J=8.5 Hz, 1H), 5.08 (d, J=16.8 Hz, 1H), 5.26 (d, J=16.9 Hz, 1H), 5.49 (d, J=52.2 Hz, 1H), 6.03 (d, J=33.3 Hz, 1H), 7.19 (s, 1H), 7.35 (d, J=7.6 Hz, 2H), 7.66-7.78 (m, 2H), 8.05 (d, J=8.2 Hz, 1H), 11.06 (s, 1H). $^{19}$F NMR (376 MHz, DMSO-$d_6$): δ −175.82. LC (method A): $t_R$=1.08 min. LC/MS (EI) m/z: [M+H]$^+$ 562.

3-Acetyl-1-(2-((2S,4R)-2-((6-bromopyridin-2-yl)carbamoyl)-4-fluoropyrrolidin-1-yl)-2-oxoethyl)-N,N-dimethyl-5-(2-methylpyrimidin-5-yl)-1H-indazole-6-carboxamide (722)

Scheme 144.

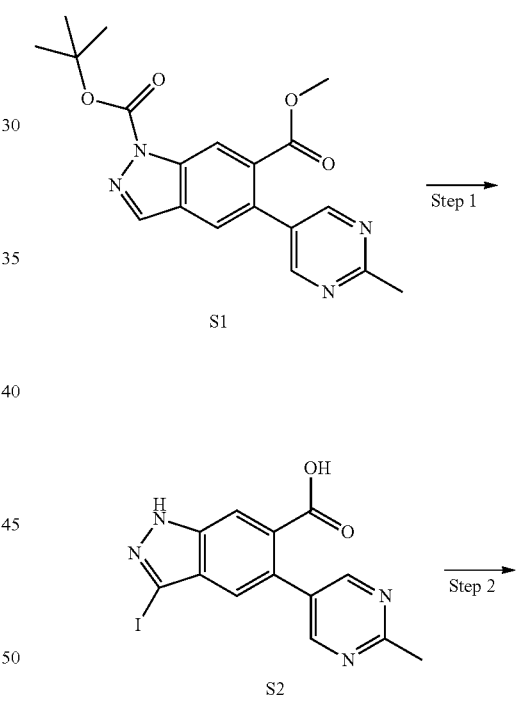

Step 1: tert-Butyl 2-(4-(1-acetyl-1,2,3,6-tetrahydropyridin-4-yl)-3-carbamoyl-1H-pyrazol-1-yl)acetate (S3)

To a solution of 1-(4-(4,4,5,5-tetramethyl-1,3,2-dioxaborolan-2-yl)-3,6-dihydropyridin-1(2H)-yl)ethan-1-one (S2, 1 equiv) in DMF/H$_2$O (9:1, 10 vol) was added compound 1 (1 equiv), $Cs_2CO_3$ (3 equiv), and tetrakis(triphenylphosphine)palladium (0.1 equiv). The reaction mixture was stirred at 90° C. for 5 h and then concentrated under reduced pressure. The residue was purified by column chromatography on silica gel (MeOH/DCM) to give compound S3.

Step 2: 2-(4-(1-Acetyl-1,2,3,6-tetrahydropyridin-4-yl)-3-carbamoyl-1H-pyrazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: 4-(1-Acetyl-1,2,3,6-tetrahydropyridin-4-yl)-1-(2-((2S,4R)-2-((6-bromopyridin-2-yl)carbamoyl)-4-fluoropyrrolidin-1-yl)-2-oxoethyl)-1H-pyrazole-3-carboxamide (727)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room

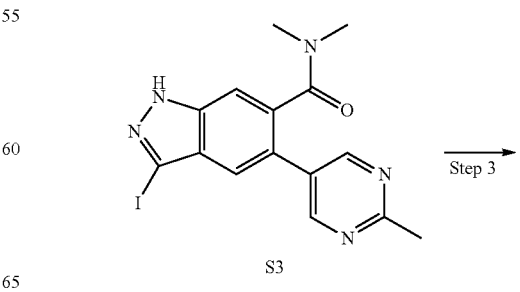

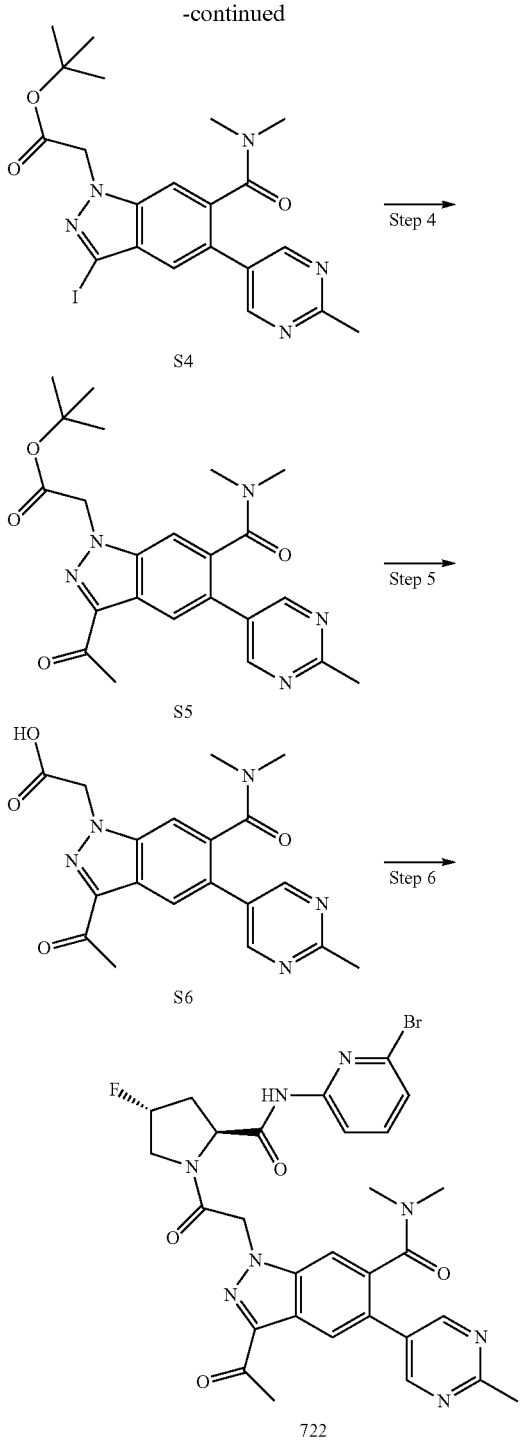

Step 1: 3-Iodo-5-(2-methylpyrimidin-5-yl)-1H-indazole-6-carboxylic acid (S2)

To the solution of 1-(tert-butyl) 6-methyl 5-(2-methylpyrimidin-5-yl)-1H-indazole-1,6-dicarboxylate (177 mg, 0.48 mmol) in anhydrous methanol (3.0 ml), sodium methoxide (25% in methanol) (1.0 mL) was added. The mixture was stirred at room temperature for 20 minutes, and then iodine (127 mg, 0.50 mmol) was added in one portion. The mixture was stirred for additional 1 hr, and quenched with water (1 mL). Then, the solution was heated to reflux for 1 hr. The solution was cooled to rt, and the volatiles are removed. The residue was acidified with 10% citric acid and the solid was collected, washed with water and dried (162 mg) for next step use.

Step 2: 3-Iodo-N,N-dimethyl-5-(2-methylpyrimidin-5-yl)-1H-indazole-6-carboxamide (S3)

To the suspension of 3-iodo-5-(2-methylpyrimidin-5-yl)-1H-indazole-6-carboxylic acid (777 mg, 2.0 mmol) in DMF (10 mL), the solution of dimethylamine in THF (2M, 7.0 mL) was added slowly at room temperature. The suspension becomes solution. To the solution, HATU (1.91 g, 5.0 mmol) was added in portions. The mixture was stirred for 3.0 hours, and the volatiles are removed. The remaining material was treated with saturated $NaHCO_3$ and extracted with ethyl acetate. The combined organic phase was washed with brine and dried over $MgSO_4$. The solution was filtered and the filtrate was concentrated. The remaining material was used for next step.

Step 3: tert-Butyl 2-(6-(dimethylcarbamoyl)-3-iodo-5-(2-methylpyrimidin-5-yl)-1H-indazol-1-yl)acetate (S4)

The residue from above step was dissolved in $CH_3CN$. To the solution, tert-butyl 2-bromoacetate (644 mg, 0.48 mL, 3.3 mmol) and solid $K_2CO_3$ (622 mg, 4.5 mmol) are added. The mixture was stirred over night at room temperature. The reaction mixture was filtered. The cake was rinsed with additional $CH_3CN$. The combined filtrate was concentrated, and the resulting residue was purified to afford 618 mg of title product.

Step 4: tert-Butyl 2-(3-acetyl-6-(dimethylcarbamoyl)-5-(2-methylpyrimidin-5-yl)-1H-indazol-1-yl)acetate (S5)

To the degassed solution of 3-iodo-N,N-dimethyl-5-(2-methylpyrimidin-5-yl)-1H-indazole-6-carboxamide (618 mg, 1.18 mmol) in DMF (10 mL), tributyl(1-ethoxyvinyl)stannane (642 mg, 0.60 mL, 1.78 mmol) and $Pd(PPh_3)_4$ (0.12 mmol) are added under argon. The mixture was heated at 100° C. overnight and then cooled to room temperature. To the solution, aqueous HCl (1N, 15 mL) was added, and the mixture was stirred for 30 minutes at room temperature. The volatiles are removed, and the residue was mixed with ethyl acetate and water. The organic layer was separated from aqueous phase, and washed with brine. The organic phase was dried over $MgSO_4$. The solution was filtered through a short pad of silica gel. The filtrate was concentrated and the residue was purified to provide 438 mg of title product.

Step 5: 2-(3-Acetyl-6-(dimethylcarbamoyl)-5-(2-methylpyrimidin-5-yl)-1H-indazol-1-yl)acetic acid (S6)

Tert-butyl 2-(3-acetyl-6-(dimethylcarbamoyl)-5-(2-methylpyrimidin-5-yl)-1H-indazol-1-yl)acetate (44 mg, 0.1 mmol) was dissolved in DCM (1.50 mL) and treated with TFA (0.50 mL). The mixture was stirred overnight at room temperature. The volatiles are evaporated under reduced pressure. The remaining material was co-evaporated with toluene twice. The residue was used for next step without further purification.

Step 6: 3-acetyl-1-(2-(((2S,4R)-2-((6-bromopyridin-2-yl)carbamoyl)-4-fluoropyrrolidin-1-yl)-2-oxo-ethyl)-N,N-dimethyl-5-(2-methylpyrimidin-5-yl)-1H-indazole-6-carboxamide (722)

To the solution of (2S,4R)—N-(6-bromopyridin-2-yl)-4-fluoropyrrolidine-2-carboxamide hydrochloride (35 mg, 0.11 mmol), 2-(3-acetyl-6-(dimethylcarbamoyl)-5-(2-methylpyrimidin-5-yl)-1H-indazol-1-yl)acetic acid (0.1 mmol) from above step in DMF (1.0 mL), HATU (1.5 eq) was added, followed by dropwise addition of DIEA (4.0 eq) at room temperature. The mixture was stirred for 1 h at room temperature and the solution was purified by preparative HPLC to afford 43.1 mg of the title compound. $^1$H NMR (400 MHz, DMSO-$d_6$): (major rotamer) δ 2.02-2.17 (m, 1H), 2.47-2.61 (m, 1H), 2.52 (s, 3H), 2.58 (s, 3H), 2.60 (s, 3H), 2.77 (s, 3H), 3.88-4.00 (m, 1H), 4.08-4.17 (m, 1H), 4.61 (t, J=8.4 Hz, 1H), 5.51 (d, J=52.4 Hz, 1H), 5.58-5.80 (m, 2H), 7.25 (d, J=7.6 Hz, 1H), 7.64 (t, J=8.0 Hz, 1H), 7.78 (s, 1H), 7.94 (d, J=8.0 Hz, 1H), 8.13 (s, 1H), 8.62 (s, 2H), 10.93 (s, 1H) ppm. $^{19}$F NMR (376 MHz, DMSO-$d_6$): (major rotamer) δ −175.56; LC (method A): $t_R$=1.48 min. LC/MS (EI) m/z: [M+H]$^+$ 651.25

(S)—N-(6-Bromopyridin-2-yl)azetidine-2-carboxamide hydrochloride

Scheme 145.

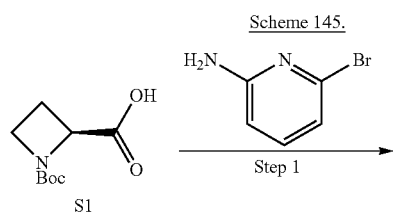

Step 1: tert-Butyl (S)-2-((6-bromopyridin-2-yl)carbamoyl)azetidine-1-carboxylate (S2)

To a solution of (S)-1-(tert-butoxycarbonyl)azetidine-2-carboxylic acid (1 equiv) in DCM (10 vol) at 0° C. under nitrogen atmosphere was added Ghosez's reagent. The reaction mixture was stirred at same temperature for 3 h and then 6-bromopyridin-2-amine (1 equiv), DIPEA (3 equiv) was added to the reaction mixture and the reaction mixture was stirred at room temperature for 16 h. After completion of the reaction, the reaction mixture was quenched with water (30 vol). The resulting mixture was extracted with DCM. The organic layer was washed with brine, dried over anhydrous Na$_2$SO$_4$, filtered and then concentrated. The residue was purified by column chromatography on silica gel using Hexane/EtOAc to give compound 2.

Step 2: (S)—N-(6-Bromopyridin-2-yl)azetidine-2-carboxamide hydrochloride (S3)

To a solution of compound 2 (1 equiv) in 1,4-dioxane (3 vol) at 0° C. under nitrogen atmosphere was added 4 N HCl in 1,4-dioxane (10 vol) and stirred at room temperature for 3 h and then concentrated. The residue was taken in MTBE and stirred for 30 min. The resultant solid was filtered and dried to give S3.

(S)-1-(2-(3-a=Acetyl-5-(2-methylpyrimidin-5-yl)-1H-indol-1-yl)acetyl)-N-(6-methylpyridin-2-yl)azetidine-2-carboxamide (481)

Scheme 146.

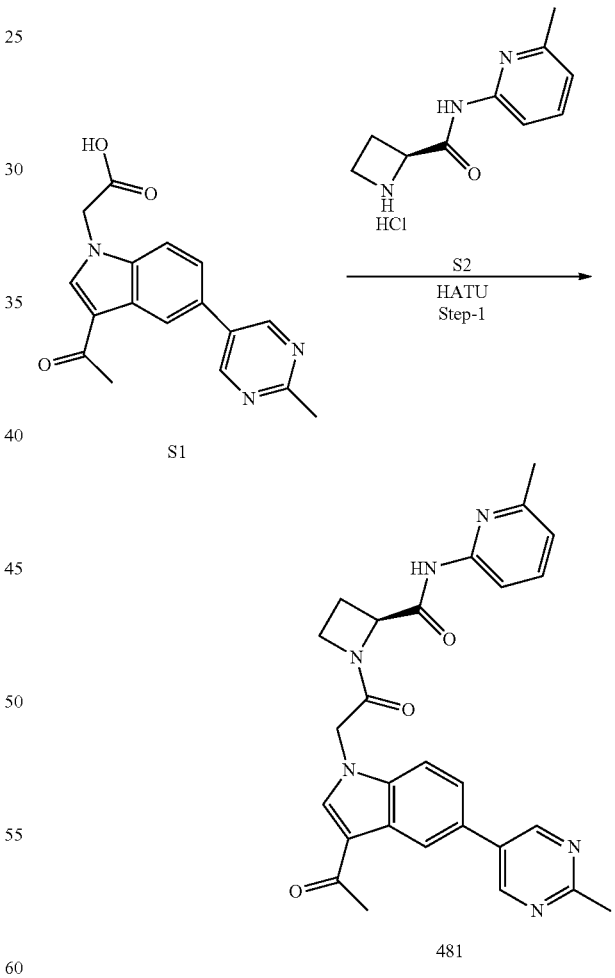

To a solution of S1 (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic

423 layer was washed with brine, dried over anhydrous Na₂SO₄, filtered and then concentrated. The residue was purified by column chromatography on silica gel using DCM/MeOH to give compound 481.

¹H NMR (400 MHz, DMSO-d₆) 10.48 (s, 1H), 9.00 (s, 2H), 8.45 (d, J=4.4 Hz, 1H), 8.35 (d, J=8.2 Hz, 1H), 7.91-7.63 (m, 4H), 7.03-6.97 (m, 1H), 5.16-5.10 (m, 2H), 5.03-4.99 (m, 1H), 4.33-4.28 (m, 1H), 3.89-3.86 (m, 1H), 2.71 (s, 3H), 2.48 (s, 3H), 2.43 (s, 3H), 2.33-2.32 (m, 2H).

(S)-1-(2-(3-Acetyl-5-(2-methylpyrazolo[1,5-a]pyrimidin-6-yl)-1H-indol-1-yl)acetyl)-N-(6-methylpyridin-2-yl)azetidine-2-carboxamide (692)

Scheme 147

To a solution of S1 (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using DCM/MeOH to give compound 692.

¹H NMR (400 MHz, DMSO-d₆) 10.50 (s, 1H), 9.26-9.25 (m, 1H), 8.83-8.82 (m, 1H), 8.47-8.46 (m, 1H), 8.36-8.34 (m, 1H), 8.02-7.90 (m, 1H), 7.76-7.65 (m, 3H), 7.03-6.99 (m, 1H), 6.57 (s, 1H), 5.21-5.17 (m, 2H), 5.11-5.09 (m, 1H), 4.32-4.31 (m, 1H), 3.89-3.88 (m, 1H), 2.46 (s, 3H), 2.45 (s, 3H), 2.44 (s, 3H), 2.42-2.38 (m, 2H).

424

(S)-1-(2-(3-Acetyl-5-(pyridin-3-yl)-1H-indazol-1-yl)acetyl)-N-(6-methylpyridin-2-yl)azetidine-2-carboxamide (548)

Scheme 148

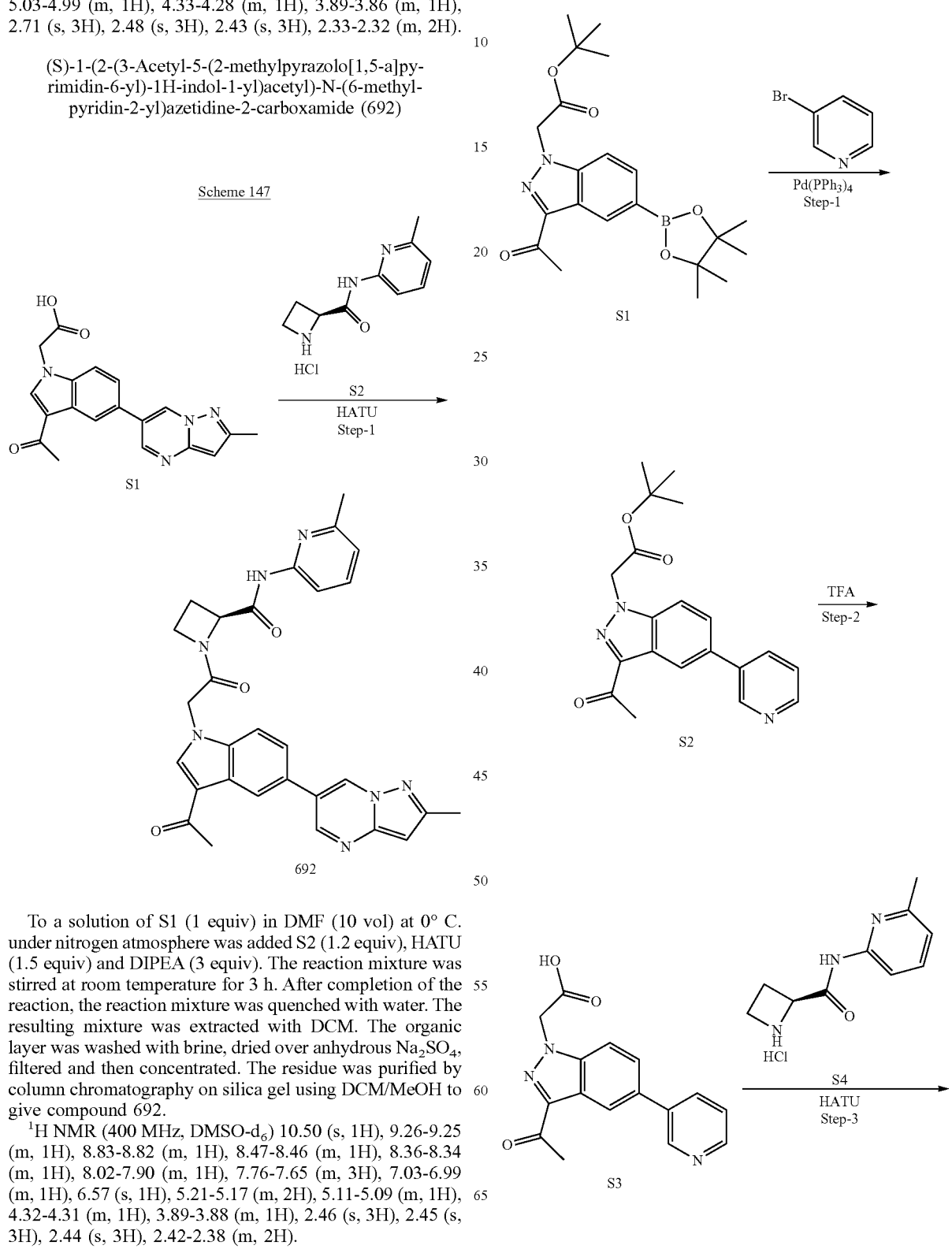

-continued

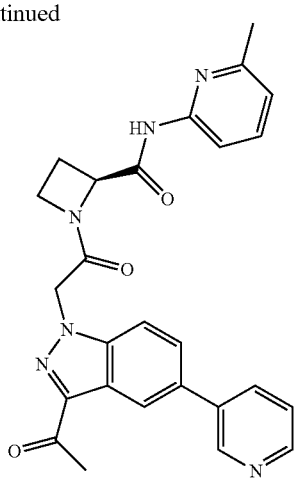

548

Step-1: tert-Butyl 2-(3-acetyl-5-(pyridin-3-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H₂O (8:2, 10 vol) at room temperature was added 3-bromopyridine (1.2 equiv) and cesium carbonate (2 equiv). After degassing with nitrogen, Pd(PPh₃)₄ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na₂SO₄, filtered and then concentrated. The residue was purified by column chromatography on silica gel using Hexane/EtOAc to give compound S1.

Step-2: 2-(3-Acetyl-5-(pyridin-3-yl)-1H-indazol-1-yl)acetic acid (S3)

To a solution of compound S2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S2.

Step-3: (S)-1-(2-(3-Acetyl-5-(pyridin-3-yl)-1H-indazol-1-yl)acetyl)-N-(6-methylpyridin-2-yl)azetidine-2-carboxamide (548)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using DCM/MeOH to give compound 548.

¹H NMR (400 MHz, DMSO-d₆) 10.46 (s, 1H), 8.93-8.89 (m, 1H), 8.61 (d, J=4.4 Hz, 1H), 8.40 (d, J=8.2 Hz, 1H), 8.15-8.08 (m, 1H), 7.91-7.65 (m, 4H), 7.54-7.51 (m, 1H), 7.00-6.96 (m, 1H), 5.52-5.47 (m, 2H), 5.17-5.02 (m, 1H), 4.35-4.31 (m, 1H), 3.89-3.87 (m, 1H), 2.66 (s, 3H), 2.61-2.59 (m, 1H), 2.38 (s, 3H), 2.37-2.33 (m, 1H).

(S)-1-(2-(3-Acetyl-5-(6-methylpyridin-3-yl)-1H-indazol-1-yl)acetyl)-N-(6-methylpyridin-2-yl)azetidine-2-carboxamide (588)

Scheme 149

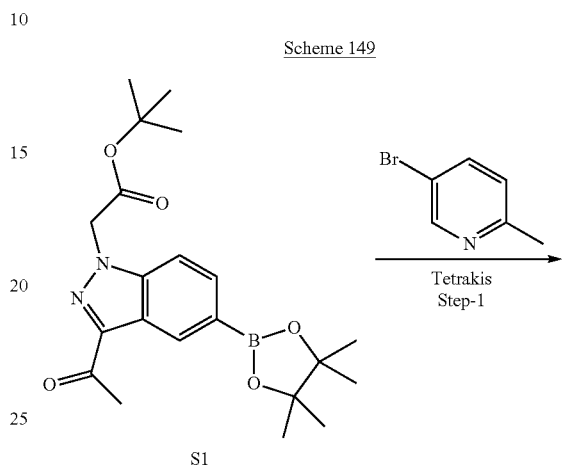

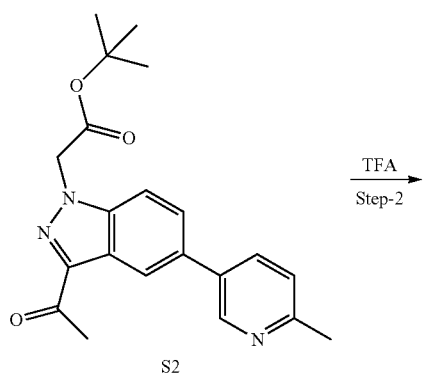

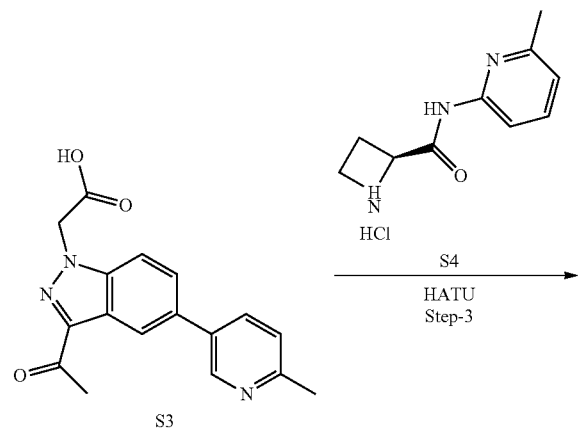

-continued

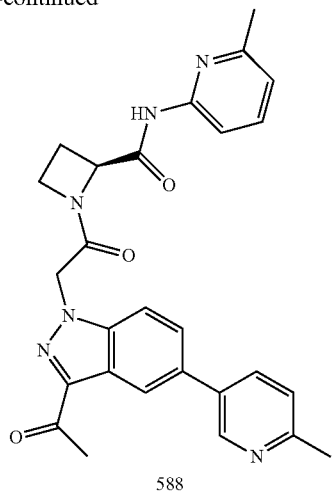

588

Step-1: tert-Butyl 2-(3-acetyl-5-(6-methylpyridin-3-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 5-bromo-2-methylpyridine (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(6-methylpyridin-3-yl)-1H-indazol-1-yl)acetic acid (S3)

To a solution of compound S2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(6-methylpyridin-3-yl)-1H-indazol-1-yl)acetyl)-N-(6-methylpyridin-2-yl)azetidine-2-carboxamide (588)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 588.

$^1$H NMR (400 MHz, DMSO-d$_6$) 10.44 (s, 1H), 8.77-8.73 (m, 1H), 8.37-8.35 (m, 1H), 8.02-7.64 (m, 5H), 7.37 (d, J=8.0 Hz, 1H), 7.00-6.96 (m, 1H), 5.50-5.44 (m, 2H), 5.15-4.99 (m, 1H), 4.33-4.29 (m, 1H), 3.88-3.87 (m, 1H), 2.68 (s, 3H), 2.67-2.65 (m, 1H), 2.52 (s, 3H), 2.38 (s, 3H), 2.37-2.36 (m, 1H).

(S)-1-(2-(3-Acetyl-5-(6-methoxypyridin-3-yl)-1H-indazol-1-yl)acetyl)-N-(6-methylpyridin-2-yl)azetidine-2-carboxamide (546)

Scheme 150

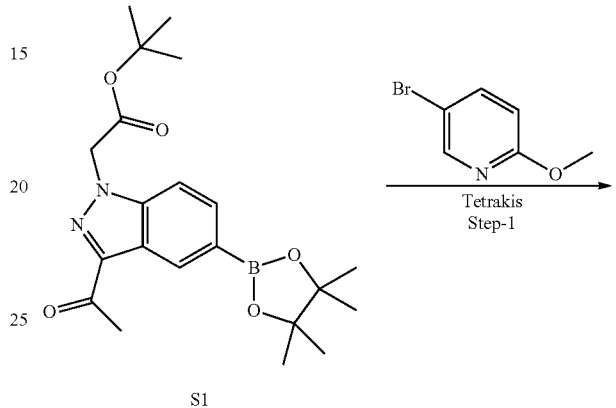

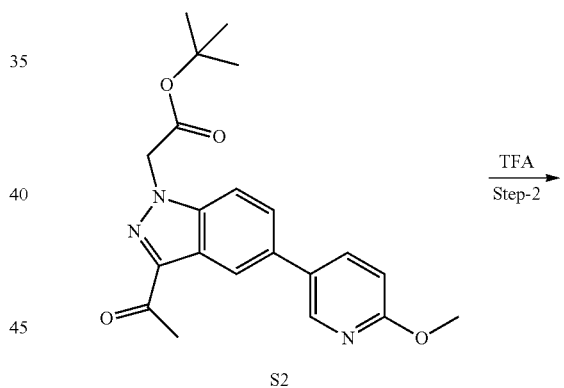

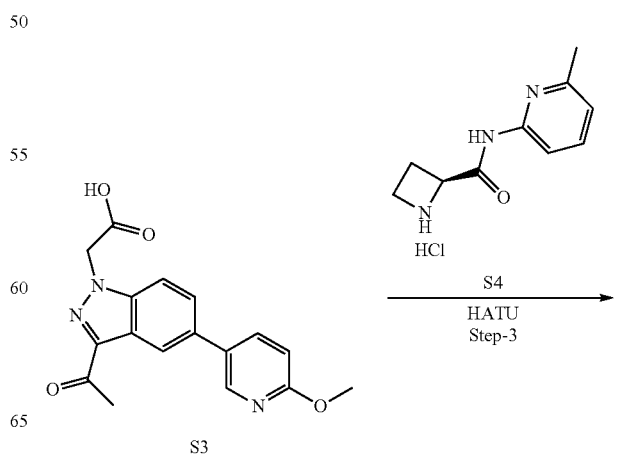

-continued

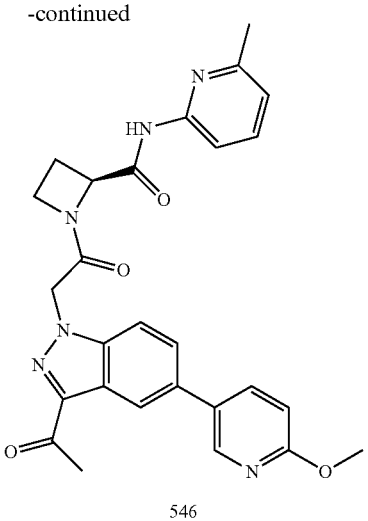

546

Step-1: tert-Butyl 2-(3-acetyl-5-(6-methoxypyridin-3-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 5-bromo-2-methoxypyridine (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(6-methoxypyridin-3-yl)-1H-indazol-1-yl)acetic acid (S3)

To a solution of compound 2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(6-methoxypyridin-3-yl)-1H-indazol-1-yl)acetyl)-N-(6-methylpyridin-2-yl)azetidine-2-carboxamide (546)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 546.
$^1$H NMR (400 MHz, DMSO-d$_6$) 10.46 (s, 1H), 8.50-8.46 (m, 1H), 8.32 (d, J=9.6 Hz, 1H), 8.07-7.65 (m, 5H), 7.01-6.94 (m, 2H), 5.50-5.49 (m, 2H), 5.15-4.98 (m, 1H), 4.34-4.30 (m, 1H), 3.91 (s, 3H), 3.90-3.89 (m, 1H), 2.65 (s, 3H), 2.63-2.60 (m, 1H), 2.37 (s, 3H), 2.33-2.32 (m, 1H).

(S)-1-(2-(3-Acetyl-5-(6-fluoropyridin-3-yl)-1H-indazol-1-yl)acetyl)-N-(6-methylpyridin-2-yl)azetidine-2-carboxamide (549)

Scheme 151

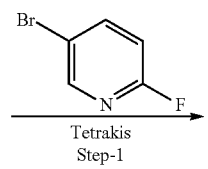

S1

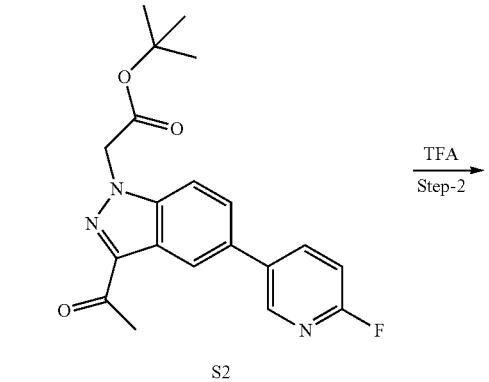

S2

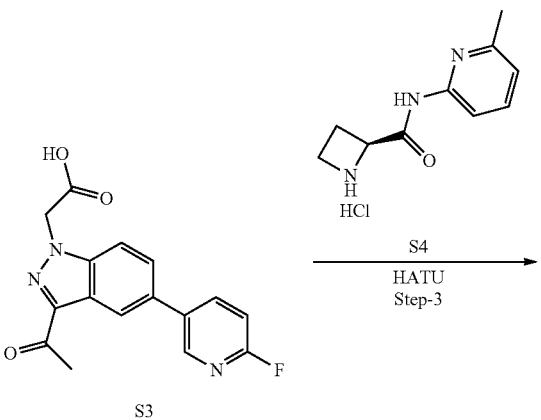

S3

431
-continued

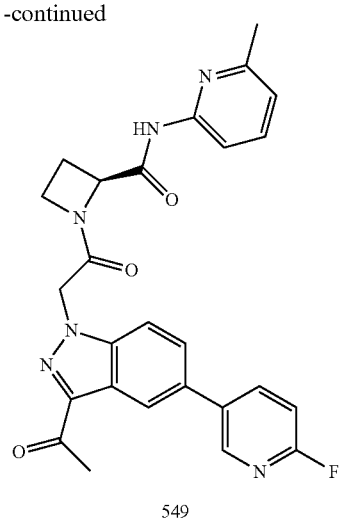

549

Step-1: tert-Butyl 2-(3-acetyl-5-(6-fluoropyridin-3-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 5-bromo-2-fluoropyridine (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(6-fluoropyridin-3-yl)-1H-indazol-1-yl)acetic acid (S3)

To a solution of compound S2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(6-fluoropyridin-3-yl)-1H-indazol-1-yl)acetyl)-N-(6-methylpyridin-2-yl)azetidine-2-carboxamide (549)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 549.

$^1$H NMR (400 MHz, DMSO-d$_6$) 10.45 (s, 1H), 8.57-8.52 (m, 1H), 8.38-8.28 (m, 2H), 7.96-7.64 (m, 4H), 7.30 (d, J=6.4 Hz, 1H), 7.00-6.95 (m, 1H), 5.51-5.45 (m, 2H), 5.16-4.99 (m, 1H), 4.37-4.30 (m, 1H), 3.90-3.86 (m, 1H), 2.66 (s, 3H), 2.60-2.58 (m, 1H), 2.36 (s, 3H), 2.35-2.33 (m, 1H).

432

(S)-1-(2-(3-Acetyl-5-(3-cyanophenyl)-1H-indazol-1-yl)acetyl)-N-(6-methylpyridin-2-yl)azetidine-2-carboxamide (547)

Scheme 152

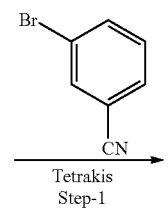

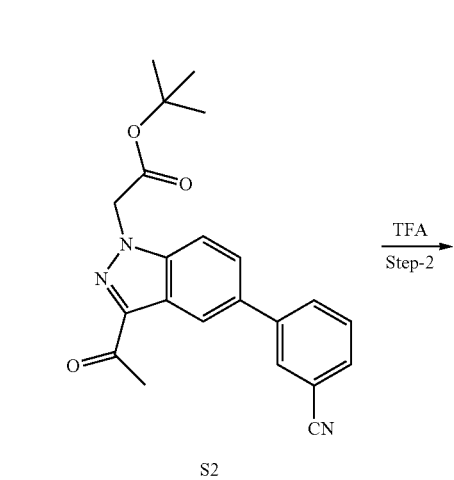

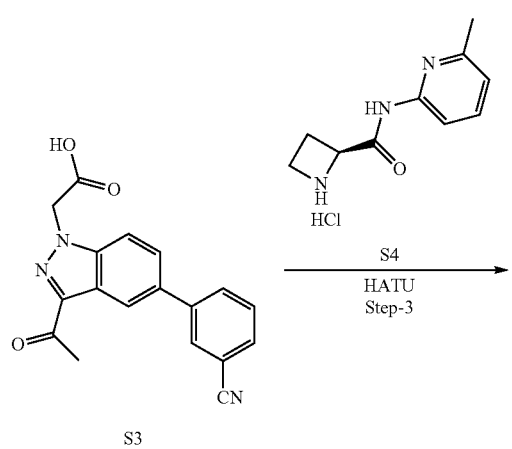

-continued

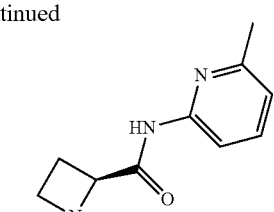

547

Step-1: tert-Butyl 2-(3-acetyl-5-(3-cyanophenyl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 3-bromobenzonitrile (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(3-cyanophenyl)-1H-indazol-1-yl)acetic acid (S3)

To a solution of compound S2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(3-cyanophenyl)-1H-indazol-1-yl)acetyl)-N-(6-methylpyridin-2-yl)azetidine-2-carboxamide (547)

To a solution of compound 3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 547.
$^1$H NMR (400 MHz, DMSO-d$_6$) 10.46 (s, 1H), 8.43-8.40 (m, 1H), 8.21-8.20 (m, 1H), 8.13-7.82 (m, 5H), 7.74-7.65 (m, 2H), 7.00-6.96 (m, 1H), 5.52-5.47 (m, 2H), 5.17-5.01 (m, 1H), 4.35-4.31 (m, 1H), 3.91-3.89 (m, 1H), 2.73 (s, 3H), 2.69-2.66 (m, 1H), 2.37 (s, 3H), 2.34-2.33 (m, 1H).

(S)-1-(2-(3-Acetyl-5-(quinolin-7-yl)-1H-indazol-1-yl)acetyl)-N-(6-methylpyridin-2-yl)azetidine-2-carboxamide (590)

Scheme 153

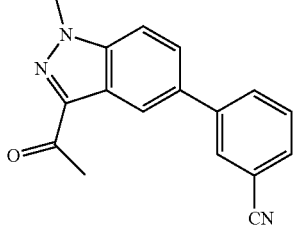

S1

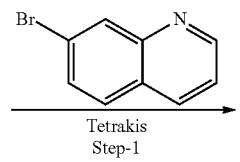

Tetrakis
Step-1

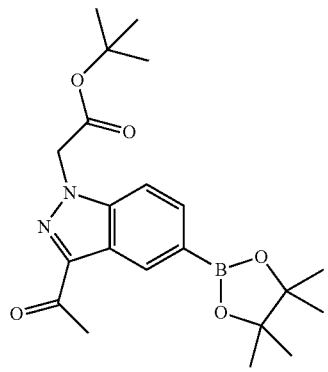

S2

TFA
Step-2

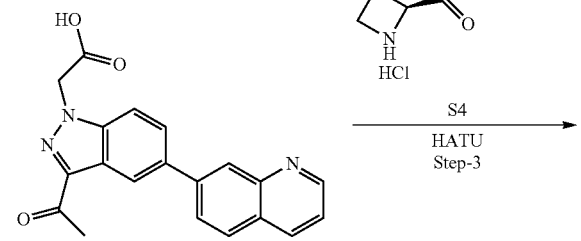

S4
HATU
Step-3

S3

-continued

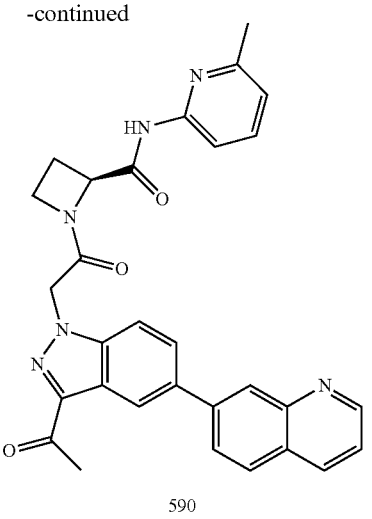

590

Step-1: tert-Butyl 2-(3-acetyl-5-(quinolin-7-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H₂O (8:2, 10 vol) at room temperature was added 7-bromoquinoline (1.2 equiv) and cesium carbonate (2 equiv). After degassing with nitrogen, Pd(PPh₃)₄ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na₂SO₄, filtered and then concentrated. The residue was purified by column chromatography on silica gel using Hexane/EtOAc to give compound S2.

Step-2: 2-(3-Acetyl-5-(quinolin-7-yl)-1H-indazol-1-yl)acetic acid (S3)

To a solution of compound 2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(quinolin-7-yl)-1H-indazol-1-yl)acetyl)-N-(6-methylpyridin-2-yl)azetidine-2-carboxamide (590)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na₂SO₄, filtered and then concentrated. The residue was purified by column chromatography on silica gel using DCM/MeOH to give compound 590.

¹H NMR (400 MHz, DMSO-d₆) 10.48 (s, 1H), 8.97 (s, 1H), 8.56-8.54 (m, 1H), 8.43 (d, J=8.2 Hz, 1H), 8.31-8.27 (m, 1H), 8.14-8.12 (m, 1H), 8.05-7.86 (m, 4H), 7.70-7.68 (m, 1H), 7.58-7.55 (m, 1H), 6.99-6.97 (m, 1H), 5.54-5.48 (m, 2H), 5.19-5.18 (m, 1H), 4.34-4.33 (m, 1H), 3.91-3.90 (m, 1H), 2.74 (s, 3H), 2.73-2.72 (m, 1H), 2.34 (s, 3H), 2.33-2.32 (m, 1H).

(S)-1-(2-(3-Acetyl-5-(naphthalen-2-yl)-1H-indazol-1-yl)acetyl)-N-(6-methylpyridin-2-yl)azetidine-2-carboxamide (587)

Scheme 154

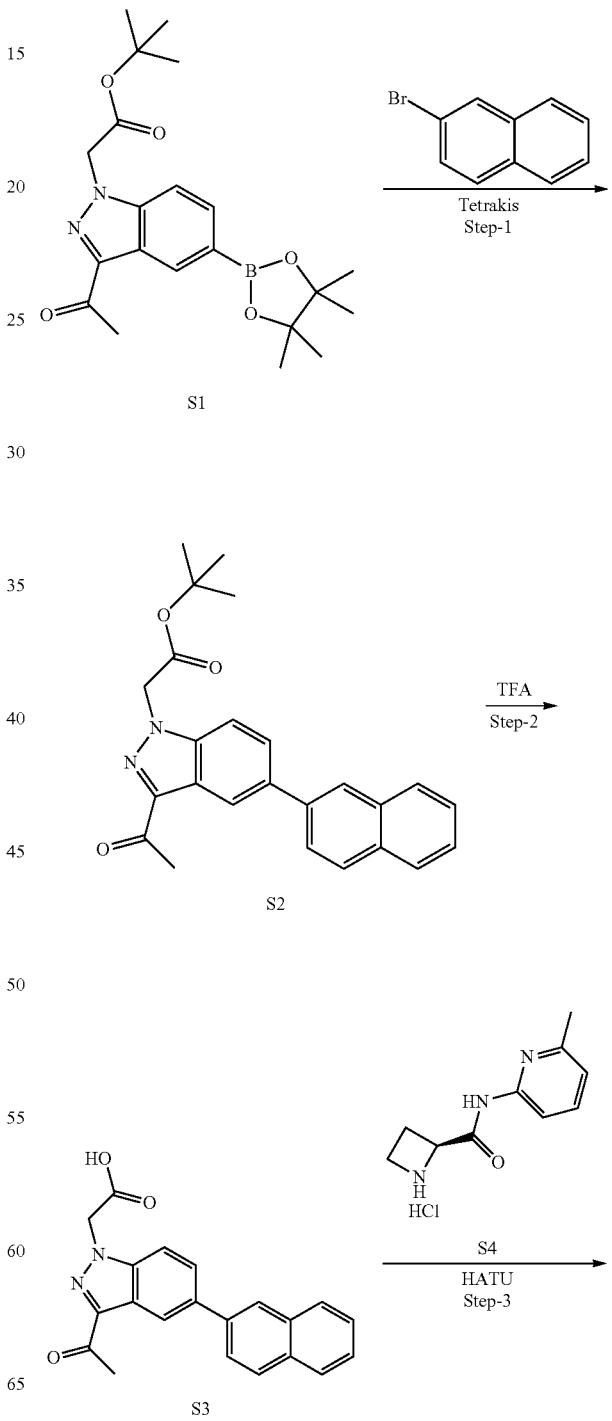

437

-continued

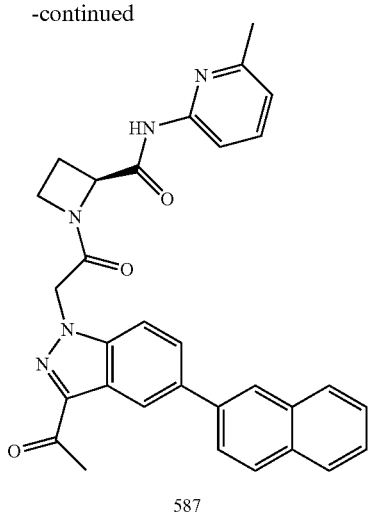

587

Step-1: tert-Butyl 2-(3-acetyl-5-(naphthalen-2-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 2-bromonaphthalene (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(naphthalen-2-yl)-1H-indazol-1-yl)acetic acid (S3)

To a solution of compound 2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(naphthalen-2-yl)-1H-indazol-1-yl)acetyl)-N-(6-methylpyridin-2-yl)azetidine-2-carboxamide (587)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 587.

$^1$H NMR (400 MHz, DMSO-d$_6$) 10.47 (s, 1H), 8.53-8.51 (m, 1H), 8.27-8.21 (m, 1H), 8.06-7.82 (m, 7H), 7.13-7.59 (m, 3H), 7.01-6.97 (m, 1H), 5.53-5.47 (m, 2H), 5.18-5.02 (m, 1H), 4.33-4.32 (m, 1H), 3.92-3.91 (m, 1H), 2.89-2.88 (m, 1H), 2.73 (s, 3H), 2.33 (s, 3H), 2.32-2.31 (m, 1H).

438

(S)-1-(2-(3-Acetyl-5-(2,3-dihydro-1H-inden-5-yl)-1H-indazol-1-yl)acetyl)-N-(6-methylpyridin-2-yl)azetidine-2-carboxamide (573)

Scheme 155.

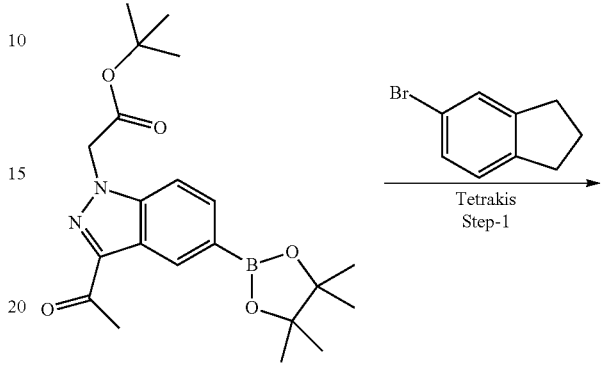

S1

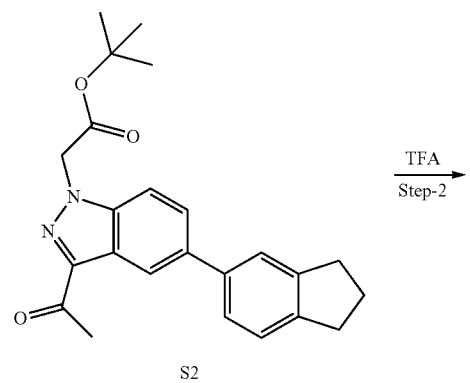

S2

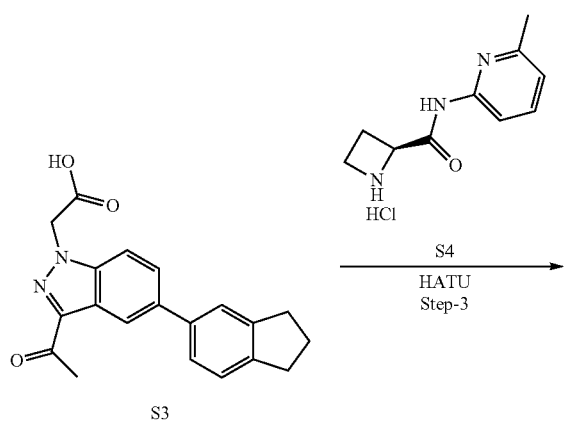

S3

439
-continued

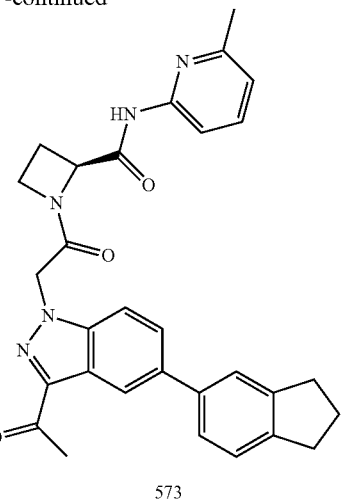

573

Step-1: tert-Butyl 2-(3-acetyl-5-(2,3-dihydro-1H-inden-5-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 5-bromo-2,3-dihydro-1H-indene (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-aAcetyl-5-(2,3-dihydro-1H-inden-5-yl)-1H-indazol-1-yl)acetic acid (S3)

To a solution of compound 2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(2,3-dihydro-1H-inden-5-yl)-1H-indazol-1-yl)acetyl)-N-(6-methylpyridin-2-yl)azetidine-2-carboxamide (573)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 573.
$^1$H NMR (400 MHz, CD$_3$OD) 8.34 (s, 1H), 7.83-7.81 (m, 2H), 7.76-7.72 (m, 1H), 7.64 (s, 1H), 7.50-7.49 (m, 1H), 7.42-7.41 (m, 1H), 7.33-7.28 (m, 1H), 7.12-7.03 (m, 1H), 5.42-5.25 (m, 2H), 5.13-5.05 (m, 1H), 4.36-4.32 (m, 1H),

440

4.11-4.08 (m, 1H), 2.99-2.94 (m, 4H), 2.70 (s, 3H), 2.51 (s, 3H), 2.50-2.49 (m, 2H), 2.15-2.10 (m, 2H).

(S)-1-(2-(3-Acetyl-5-(imidazo[1,2-a]pyrimidin-3-yl)-1H-indazol-1-yl)acetyl)-N-(6-methylpyridin-2-yl)azetidine-2-carboxamide (709)

Scheme 156

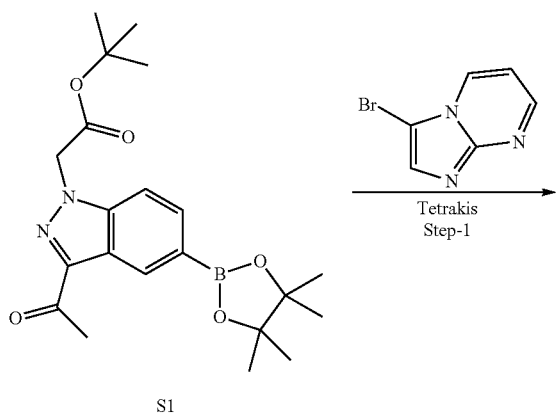

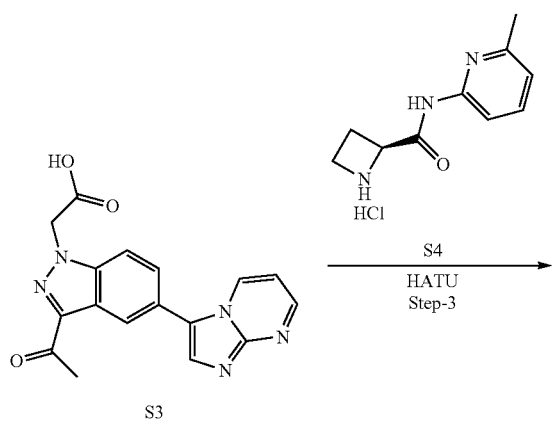

-continued

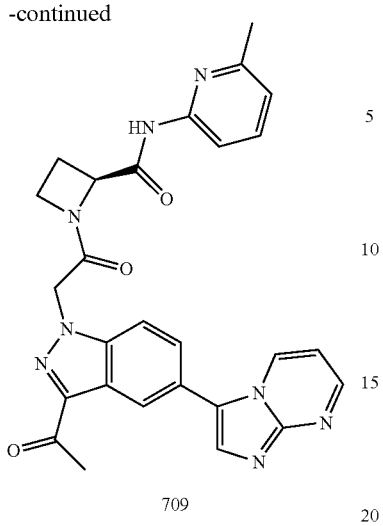

709

Step-1: tert-Butyl 2-(3-acetyl-5-(imidazo[1,2-a]pyrimidin-3-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetateacetate (1 equiv) in DMF/H$_2$O (8:2, 10 vol) at room temperature was added 3-bromoimidazo[1,2-a]pyrimidine (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(imidazo[1,2-a]pyrimidin-3-yl)-1H-indazol-1-yl)acetic acid (S3)

To a solution of compound S2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(imidazo[1,2-a]pyrimidin-3-yl)-1H-indazol-1-yl)acetyl)-N-(6-methylpyridin-2-yl)azetidine-2-carboxamide (709)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 709.

$^1$H NMR (400 MHz, DMSO-d$_6$) 10.47 (s, 1H), 8.99-8.93 (m, 1H), 8.61 (d, J=4.0 Hz, 1H), 8.38 (d, J=9.6 Hz, 1H), 7.97-7.66 (m, 5H), 7.15-7.14 (m, 1H), 7.01-6.97 (m, 1H), 5.53-5.49 (m, 2H), 5.25-5.16 (m, 1H), 4.36-4.33 (m, 1H), 3.92-3.88 (m, 1H), 2.68-2.67 (m, 1H), 2.66 (s, 3H), 2.39 (s, 3H), 2.38-2.37 (m, 1H).

(S)-1-(2-(3-Acetyl-5-(5,6,7,8-tetrahydroimidazo[1,2-a]pyridin-3-yl)-1H-indazol-1-yl)acetyl)-N-(6-methylpyridin-2-yl)azetidine-2-carboxamide (705)

Scheme 157

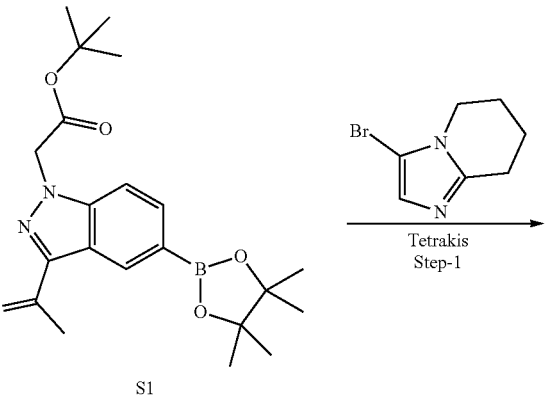

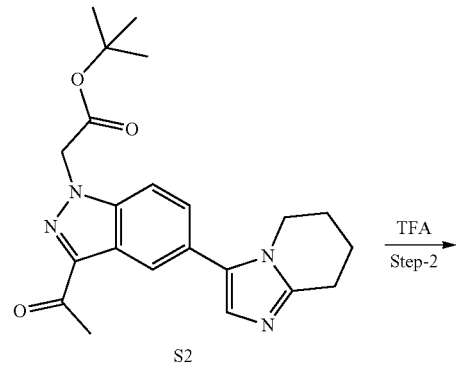

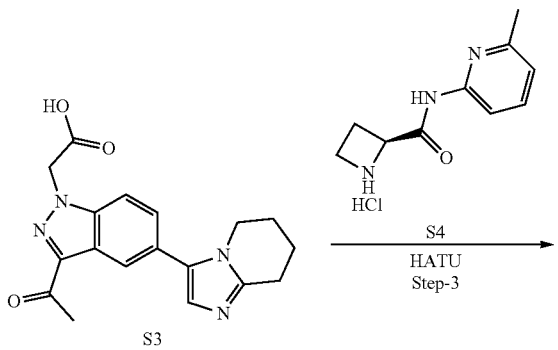

-continued

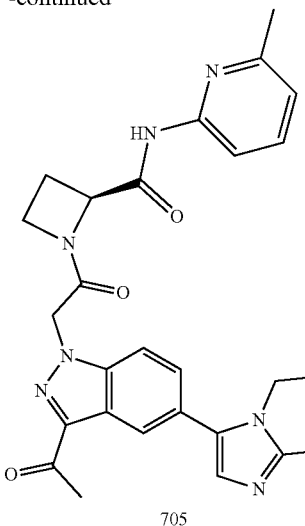

705

Step-1: tert-Butyl 2-(3-acetyl-5-(5,6,7,8-tetrahydroimidazo[1,2-a]pyridin-3-yl)-1H-indazol-1-yl)acetate (S2)

To a solution of tert-butyl 2-(3-acetyl-5-(4,4,5,5-tetramethyl-1,3,2-dioxaborolan-2-yl)-1H-indazol-1-yl)acetate (1 equiv) in DMF/H$_2$O (8:2, 10 vol) at room temperature was added 3-bromo-5,6,7,8-tetrahydroimidazo[1,2-a]pyridine (1.2 equiv) and cesium carbonate (2 equiv). After degassing with nitrogen, Pd(PPh$_3$)$_4$ (0.05 equiv) was added to the reaction mixture. The resulting mixture was stirred at 80° C. for 3 h and then cooled to room temperature. Water was added to the reaction mixture and the resulting mixture was extracted with ethyl acetate. The organic layer was separated, dried over anhydrous Na$_2$SO$_4$, filtered and then concentrated. The residue was purified by column chromatography on silica gel using Hexane/EtOAc to give compound S2.

Step-2: 2-(3-Acetyl-5-(5,6,7,8-tetrahydroimidazo[1,2-a]pyridin-3-yl)-1H-indazol-1-yl)acetic acid (S3)

To a solution of compound 2 (1 equiv) in DCM (10 vol) at 0° C. was added TFA (5 vol). The reaction mixture was stirred at 50° C. for 3 h and then concentrated. The residue was taken in MTBE and stirred for 30 min. The resultant solid was filtered and dried to give compound S3.

Step-3: (S)-1-(2-(3-Acetyl-5-(5,6,7,8-tetrahydroimidazo[1,2-a]pyridin-3-yl)-1H-indazol-1-yl)acetyl)-N-(6-methylpyridin-2-yl)azetidine-2-carboxamide (705)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 705.

$^1$H NMR (400 MHz, DMSO-d$_6$) 10.45 (s, 1H), 8.20-8.18 (m, 1H), 7.97-7.58 (m, 4H), 7.21-7.18 (m, 1H), 7.01-6.96 (m, 1H), 5.50-5.48 (m, 2H), 5.23-5.00 (m, 1H), 4.33-4.32 (m, 1H), 3.97-3.86 (m, 3H), 2.87-2.85 (m, 2H), 2.66 (s, 3H), 2.65-2.64 (m, 1H), 2.32 (s, 3H), 2.31-2.30 (m, 1H), 1.91-1.90 (m, 4H).

(S)-1-(2-(3-Acetyl-5-(2-methylpyrimidin-5-yl)-1H-indazol-1-yl)acetyl)-N-(6-bromopyridin-2-yl)azetidine-2-carboxamide (542)

Scheme 158

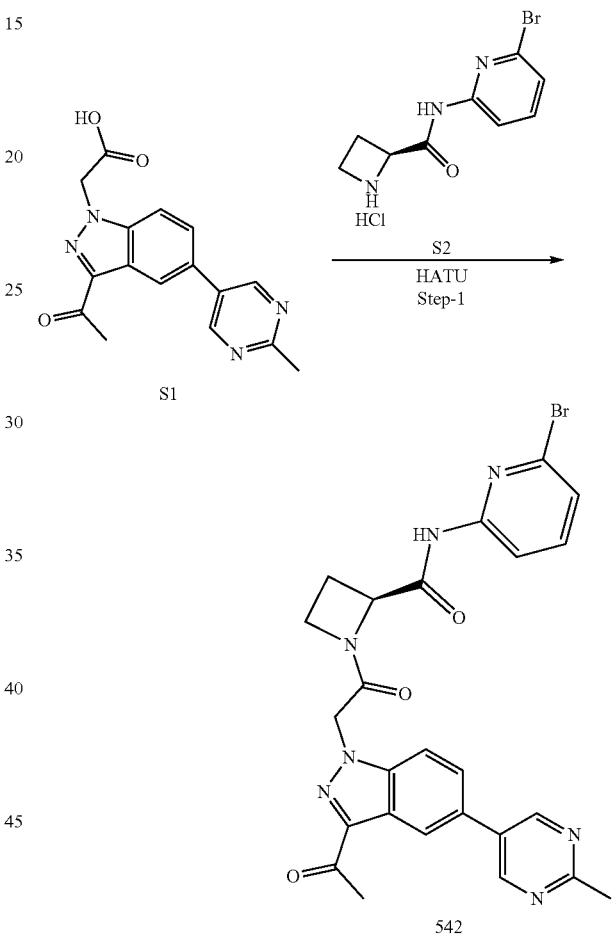

Step-1: (S)-1-(2-(3-Acetyl-5-(2-methylpyrimidin-5-yl)-1H-indazol-1-yl)acetyl)-N-(6-bromopyridin-2-yl)azetidine-2-carboxamide (542)

To a solution of S1 (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 3 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 542.

$^1$H NMR (400 MHz, DMSO-d$_6$) 10.90 (s, 1H), 9.05-9.01 (m, 2H), 8.43 (d, J=10.0 Hz, 1H), 8.11-8.09 (m, 1H), 7.90-7.74 (m, 3H), 7.36 (dd, J=8.0 Hz, 1.6 Hz, 1H), 5.52-5.47 (m, 2H), 5.00-4.96 (m, 1H), 4.34-4.30 (m, 1H), 3.91-3.87 (m, 1H), 2.69 (s, 3H), 2.66 (s, 3H), 2.39-2.25 (m, 2H).

(S)—N-(6-Methylpyridin-2-yl)pyrrolidine-2-carboxamide

Scheme 159.

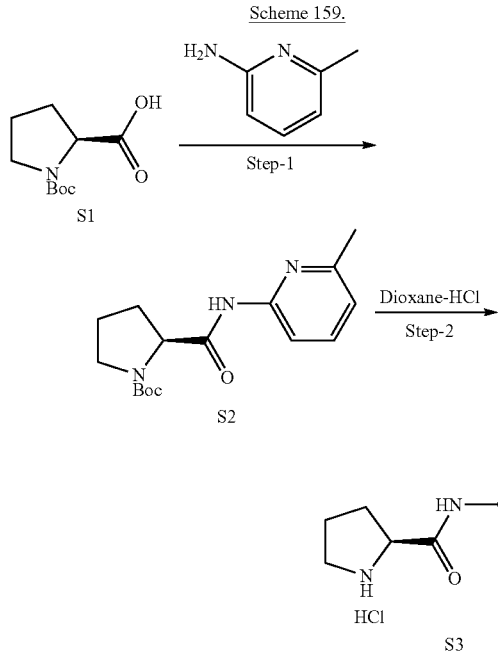

Step 1: tert-Butyl (S)-2-((6-methylpyridin-2-yl)carbamoyl)pyrrolidine-1-carboxylate (S2)

To a solution of (tert-butoxycarbonyl)-L-proline (1 equiv) in DCM (10 vol) at 0° C. under nitrogen atmosphere was added Ghosez's reagent. The reaction mixture was stirred at same temperature for 3 h and then 6-methylpyridin-2-amine (1 equiv), DIPEA (3 equiv) was added to the reaction mixture and the reaction mixture was stirred at room temperature for 16 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using Hexane/EtOAc to give compound S2.

Step 2: (S)—N-(6-Methylpyridin-2-yl)pyrrolidine-2-carboxamide hydrochloride (S3)

To a solution of compound S2 (1 equiv) in 1,4-dioxane (3 vol) at 0° C. under nitrogen atmosphere was added 4 N HCl in 1,4-dioxane (10 vol) and stirred at room temperature for 3 h and then concentrated. The residue was taken in MTBE and stirred for 30 min. The resultant solid was filtered and dried to give S3.

(S)-1-(2-(3-Acetyl-5-(pyridin-3-yl)-1H-indazol-1-yl)acetyl)-N-(6-methylpyridin-2-yl)pyrrolidine-2-carboxamide (525)

Scheme 160.

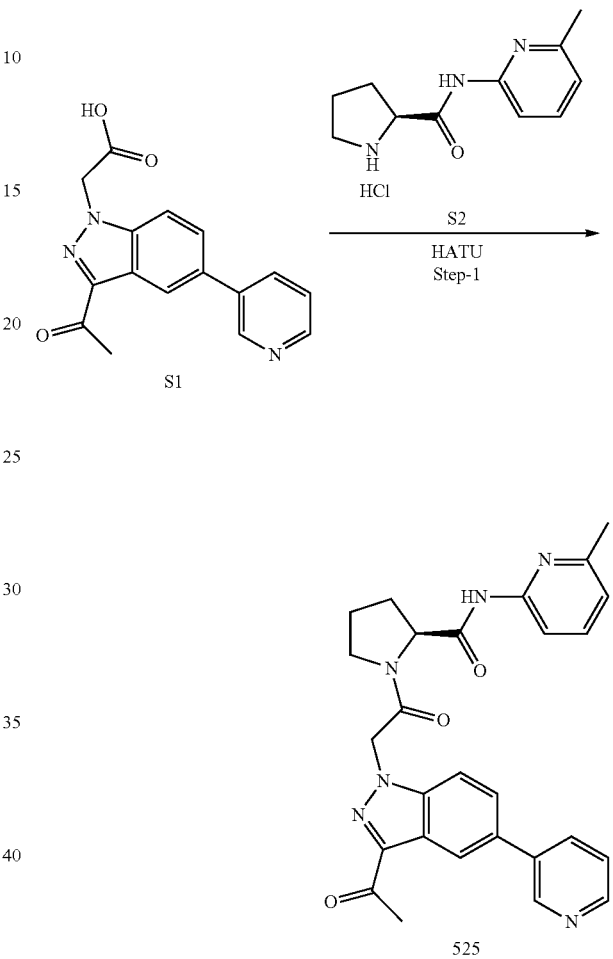

To a solution of 2-(3-acetyl-5-(pyridin-3-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous Na$_2$SO$_4$, filtered and then concentrated. The residue was purified by column chromatography on silica gel using DCM/MeOH to give compound 525.

$^1$H NMR (400 MHz, DMSO-d$_6$) δ 10.46 (s, 1H), 8.94 (s, 1H), 8.62 (s, 1H), 8.40 (s, 1H), 8.14 (d, J=7.6 Hz, 1H), 7.89-7.80 (m, 3H), 7.65-7.54 (m, 2H), 6.93 (d, J=7.6 Hz, 1H), 5.78-5.66 (m, 2H), 4.61-4.59 (m, 1H), 3.85-3.76 (m, 2H), 2.65 (s, 3H), 2.37 (s, 3H), 2.23-1.87 (m, 4H).

447
(S)-1-(2-(3-Acetyl-5-(6-methylpyridin-3-yl)-1H-indazol-1-yl)acetyl)-N-(6-methylpyridin-2-yl)pyrrolidine-2-carboxamide (586)

448
(S)-1-(2-(3-Acetyl-5-(6-methoxypyridin-3-yl)-1H-indazol-1-yl)acetyl)-N-(6-methylpyridin-2-yl)pyrrolidine-2-carboxamide (543)

Scheme 161

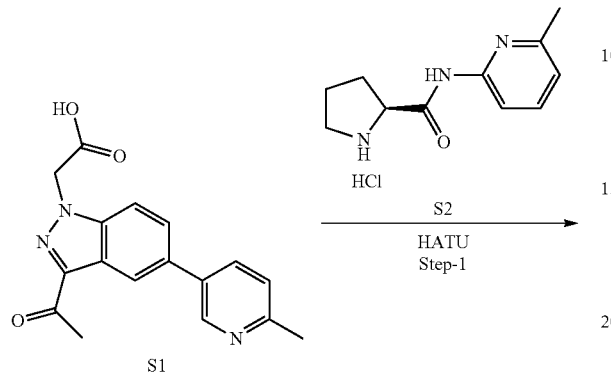

Scheme 162

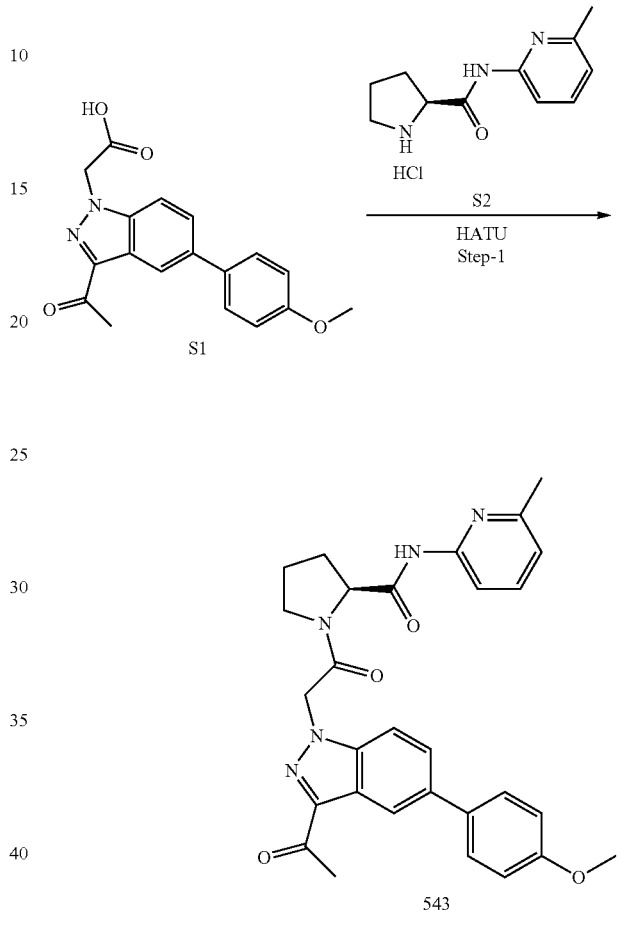

To a solution of 2-(3-acetyl-5-(6-methylpyridin-3-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 543.

$^1$H NMR (400 MHz, DMSO-$d_6$) δ 10.46 (s, 1H), 8.77 (s, 1H), 8.37 (s, 1H), 8.00 (d, J=10.8 Hz, 1H), 7.85-7.82 (m, 3H), 7.65-7.61 (m, 1H), 7.37 (d, J=8.0 Hz, 1H), 6.94 (d, J=7.2 Hz, 1H), 5.72-5.67 (m, 2H), 4.60-4.59 (m, 1H), 3.85-3.78 (s, 2H), 2.69 (s, 3H), 2.60 (s, 3H), 2.37 (s, 3H), 2.20-1.91 (m, 4H).

To a solution of 2-(3-acetyl-5-(6-methoxypyridin-3-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 543.

$^1$H NMR (400 MHz, DMSO-$d_6$) δ 10.45 (s, 1H), 8.48 (s, 1H), 8.31 (s, 1H), 8.04 (dd, J=11.2 Hz, 2.4 Hz, 1H), 7.78-7.74 (m, 3H), 7.62-7.60 (m, 1H), 6.94-6.92 (m, 2H), 5.67-5.64 (m, 2H), 4.61-4.58 (m, 1H), 3.90 (s, 3H), 3.85-3.77 (m, 2H), 2.68 (s, 3H), 2.42 (s, 3H), 2.20-1.92 (m, 4H).

449
(S)-1-(2-(3-Acetyl-5-(6-fluoropyridin-3-yl)-1H-indazol-1-yl)acetyl)-N-(6-methylpyridin-2-yl)pyrrolidine-2-carboxamide (545)

450
(S)-1-(2-(3-Acetyl-5-(3-cyanophenyl)-1H-indazol-1-yl)acetyl)-N-(6-methylpyridin-2-yl)pyrrolidine-2-carboxamide (544)

Scheme 163

Scheme 164

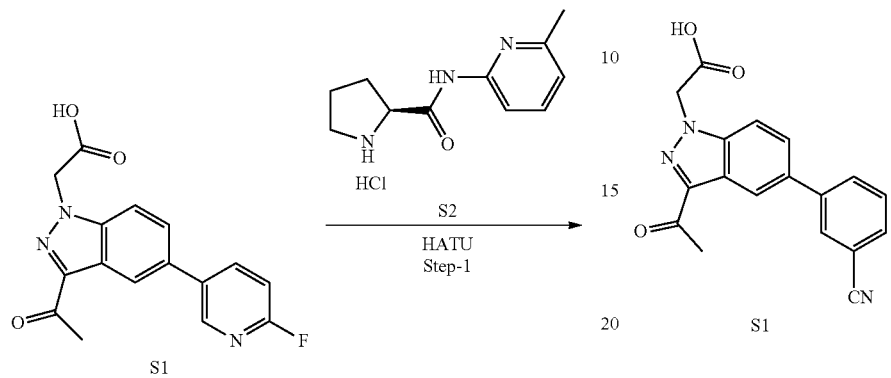
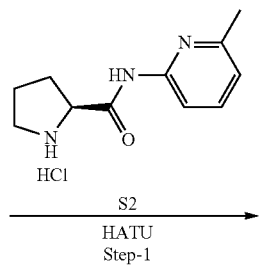

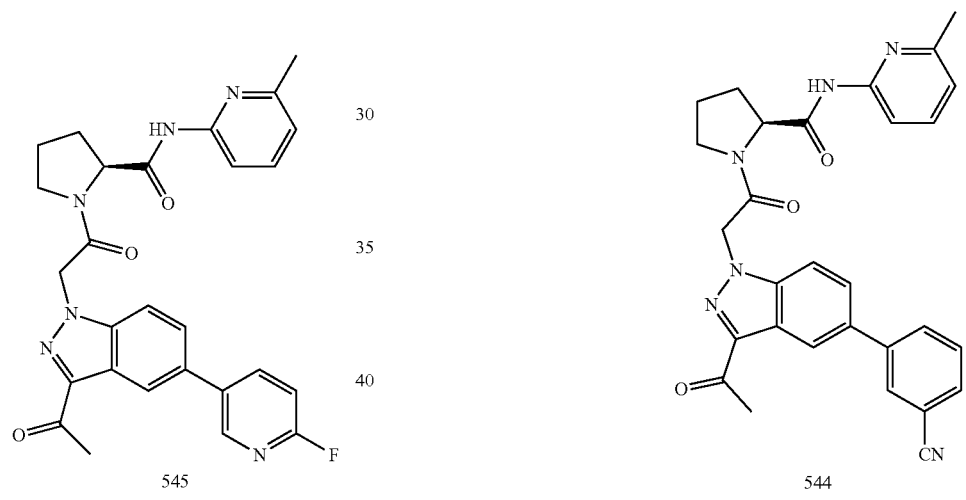

To a solution of 2-(3-acetyl-5-(6-fluoropyridin-3-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give the title compound.

$^1$H NMR (400 MHz, DMSO-$d_6$) δ 10.45 (s, 1H), 8.56 (s, 1H), 8.37-8.29 (m, 2H), 7.85-7.82 (m, 3H), 7.64-7.60 (m, 1H), 7.30 (dd, J=8.0 Hz, 2.8 Hz, 1H), 6.93 (d, J=7.2 Hz, 1H), 5.69-5.67 (m, 2H), 4.61-4.57 (m, 1H), 3.85-3.77 (m, 2H), 2.66 (s, 3H), 2.32 (s, 3H), 2.20-1.92 (m, 4H).

To a solution of 2-(3-acetyl-5-(3-cyanophenyl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 544.

$^1$H NMR (400 MHz, DMSO-$d_6$) δ 10.45 (s, 1H), 8.41 (s, 1H), 8.19 (s, 1H), 8.05 (d, J=8.4 Hz, 1H), 7.87-7.60 (m, 6H), 6.93 (d, J=7.2 Hz, 1H), 5.65-5.64 (m, 2H), 4.61-4.58 (m, 1H), 3.85-3.77 (m, 2H), 2.66 (s, 3H), 2.41 (s, 3H), 2.20-1.93 (m, 4H).

451
(S)-1-(2-(3-Acetyl-5-(quinolin-7-yl)-1H-indazol-1-yl)acetyl)-N-(6-methylpyridin-2-yl)pyrrolidine-2-carboxamide (589)

452
(S)-1-(2-(3-Acetyl-5-(naphthalen-2-yl)-1H-indazol-1-yl)acetyl)-N-(6-methylpyridin-2-yl)pyrrolidine-2-carboxamide (585)

Scheme 165

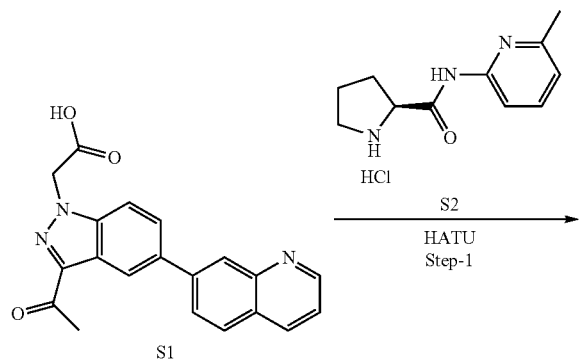

Scheme 166

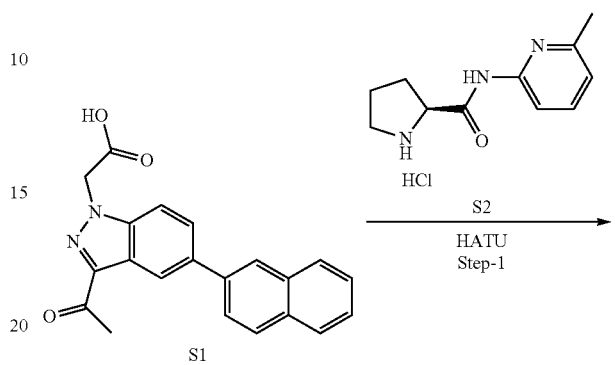

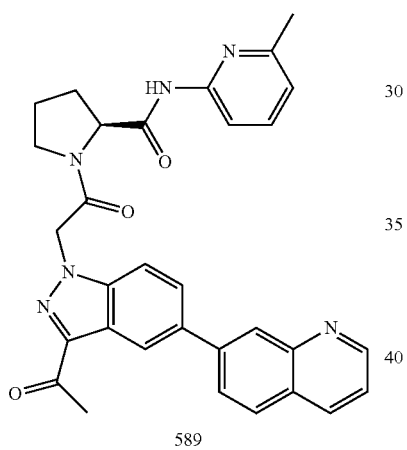

589

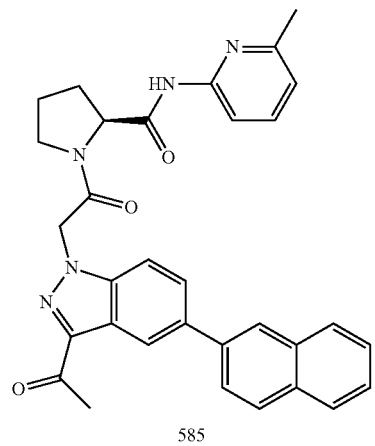

585

To a solution of 2-(3-acetyl-5-(quinolin-7-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 589.

$^1$H NMR (400 MHz, DMSO-$d_6$) δ 10.49 (s, 1H), 8.97 (s, 1H), 8.56 (s, 1H), 8.44-8.42 (s, 1H), 8.31 (d, J=3.1 Hz, 1H), 8.13-8.11 (m, 1H), 8.03-7.86 (m, 4H), 7.65-7.56 (m, 2H), 6.96-6.93 (m, 1H), 5.72-5.71 (m, 2H), 4.62-4.61 (m, 1H), 3.92-3.75 (m, 2H), 2.66 (s, 3H), 2.43 (s, 3H), 2.25-1.98 (m, 4H).

To a solution of 2-(3-acetyl-5-(naphthalen-2-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 585.

$^1$H NMR (400 MHz, DMSO-$d_6$) δ 10.47 (s, 1H), 8.52 (s, 1H), 8.26 (s, 1H), 8.06-8.04 (m, 2H), 7.98-7.84 (m, 5H), 7.65-7.54 (m, 3H), 6.94 (d, J=7.2 Hz, 1H), 5.69-5.68 (m, 2H), 4.62-4.61 (m, 1H), 3.86-3.81 (m, 2H), 2.67 (s, 3H), 2.42 (s, 3H), 2.21-1.95 (m, 4H).

453

(S)-1-(2-(3-Acetyl-5-(2,3-dihydro-1H-inden-5-yl)-1H-indazol-1-yl)acetyl)-N-(6-methylpyridin-2-yl)pyrrolidine-2-carboxamide (572)

Scheme 167

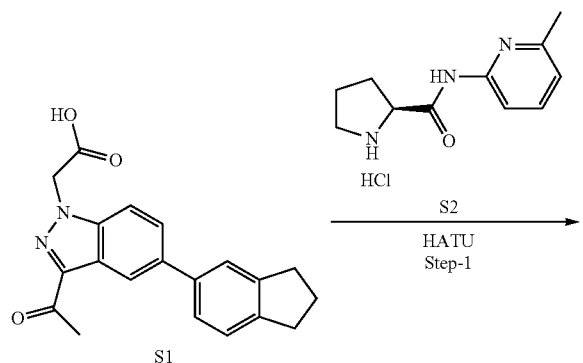

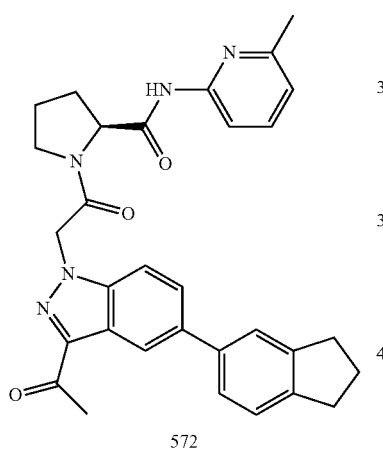

To a solution of 2-(3-acetyl-5-(2,3-dihydro-1H-inden-5-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 572.

$^1$H NMR (400 MHz, $CD_3OD$) δ 8.45 (s, 1H), 7.92-7.88 (s, 1H), 7.72-7.65 (s, 3H), 7.49 (s, 1H), 7.40 (d, J=8.0 Hz, 1H), 7.29 (d, J=7.6 Hz, 1H), 7.16 (d, J=7.6 Hz, 1H), 5.58-5.57 (m, 2H), 4.68-4.64 (m, 1H), 3.94-3.88 (m, 2H), 3.00-2.93 (m, 5H), 2.68 (s, 3H), 2.53 (s, 3H), 2.39-2.11 (m, 5H).

454

(S)-1-(2-(3-Acetyl-5-(imidazo[1,2-a]pyrimidin-3-yl)-1H-indazol-1-yl)acetyl)-N-(6-methylpyridin-2-yl)pyrrolidine-2-carboxamide (708)

Scheme 168

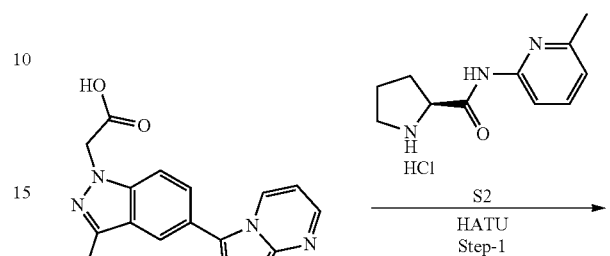

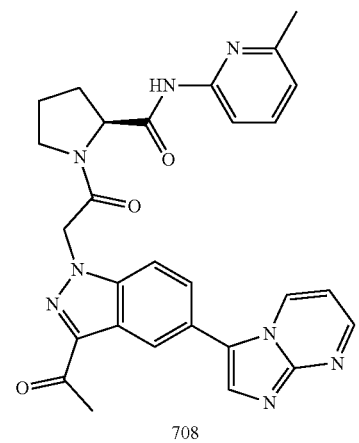

To a solution of 2-(3-acetyl-5-(imidazo[1,2-a]pyrimidin-3-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to afford compound 708.

$^1$H NMR (400 MHz, DMSO-$d_6$) δ 10.47 (s, 1H), 8.97 (d, J=5.6 Hz, 1H), 8.61 (s, 1H), 8.38 (s, 1H), 7.99-7.67 (m, 5H), 7.14-7.12 (m, 1H), 6.94 (d, J=7.0 Hz, 1H), 5.72-5.71 (m, 2H), 4.61-4.60 (m, 1H), 3.87-3.77 (m, 2H), 2.65 (s, 3H), 2.37 (s, 3H), 2.21-1.93 (m, 4H).

455
(S)-1-(2-(3-Acetyl-5-(5,6,7,8-tetrahydroimidazo[1,2-a]pyridin-3-yl)-1H-indazol-1-yl)acetyl)-N-(6-methylpyridin-2-yl)pyrrolidine-2-carboxamide (700)

456
(S)-1-(2-(3-Acetyl-5-(2-methylpyrimidin-5-yl)-1H-indazol-1-yl)acetyl)-N-(6-bromopyridin-2-yl)piperidine-2-carboxamide (593) & (R)-1-(2-(3-acetyl-5-(2-methylpyrimidin-5-yl)-1H-indazol-1-yl)acetyl)-N-(6-bromopyridin-2-yl)piperidine-2-carboxamide (592)

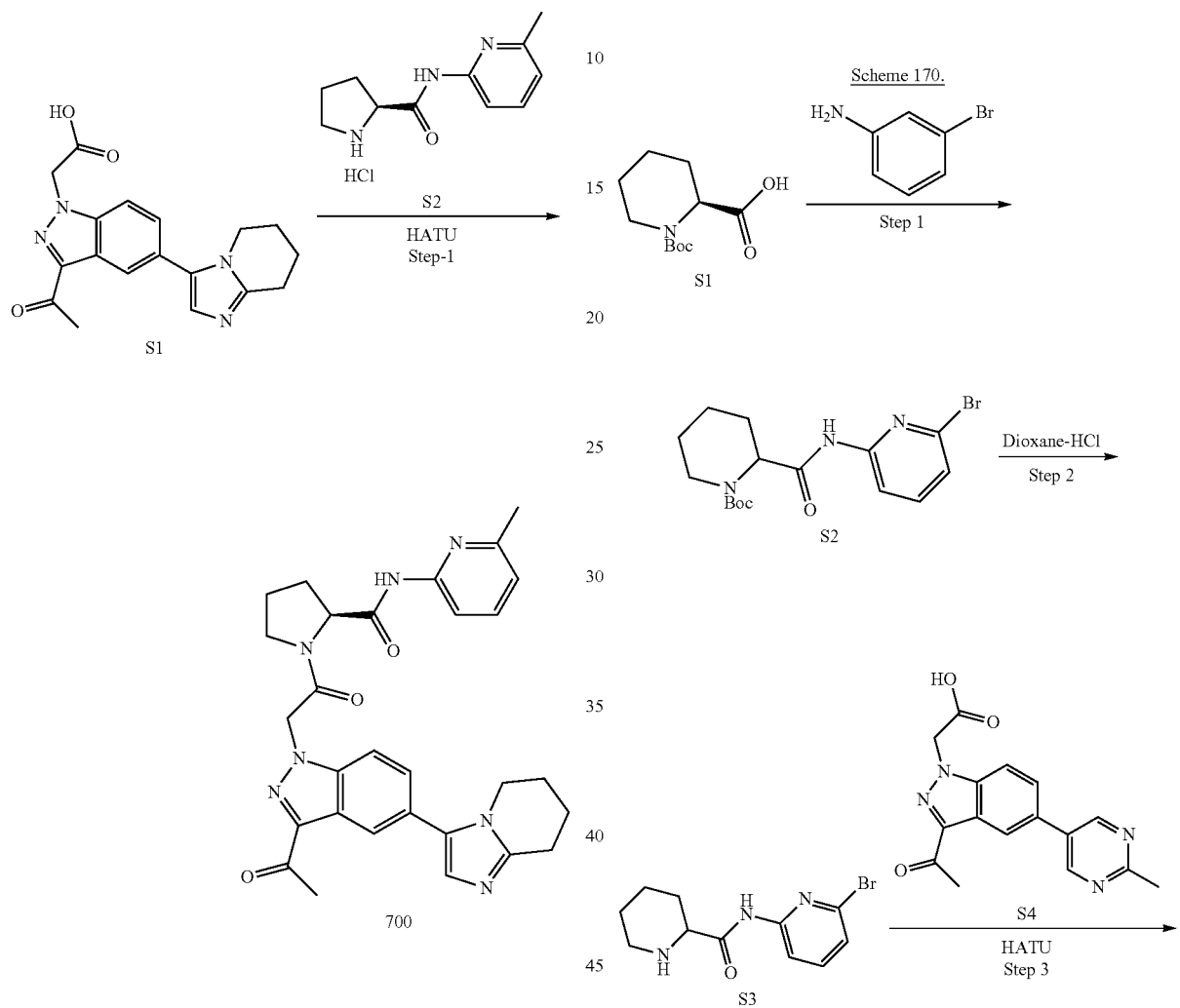

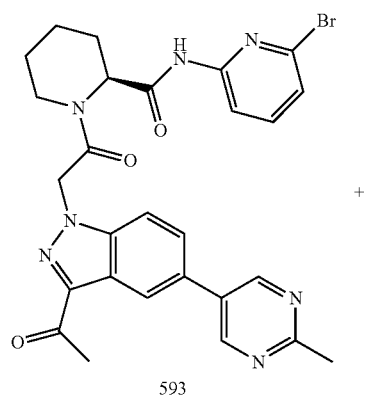

To a solution of 2-(3-acetyl-5-(5,6,7,8-tetrahydroimidazo[1,2-a]pyridin-3-yl)-1H-indazol-1-yl)acetic acid (1 equiv) in DMF (10 vol) at 0° C. under nitrogen atmosphere was added S2 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give compound 700.

$^1$H NMR (400 MHz, $CD_3OD$) δ 8.44 (s, 1H), 7.87-7.76 (m, 3H), 7.63-7.57 (m, 2H), 7.12 (d, J=7.6 Hz, 1H), 5.68 (s, 2H), 4.69-4.66 (m, 1H), 4.09-4.08 (m, 2H), 3.97-3.89 (m, 2H), 3.13-3.12 (m, 2H), 2.70 (s, 3H), 2.51 (s, 3H), 2.42-2.16 (m, 4H), 2.08-2.05 (m, 4H).

457

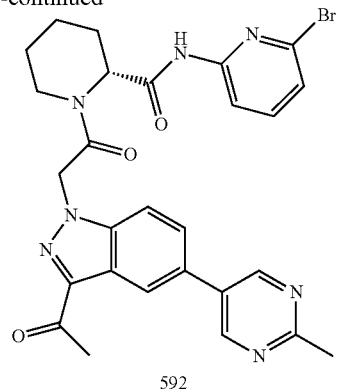
592

Step-1: tert-butyl 2-((6-bromopyridin-2-yl)carbamoyl)piperidine-1-carboxylate (S2)

To a solution of (S)-1-(tert-butoxycarbonyl)piperidine-2-carboxylic acid (1 equiv) in DMF (10 vol) at 0° C. under nitrogen atmosphere was added 6-bromopyridin-2-amine (1.2 equiv), EEDQ (1.5 equiv) and DIPEA (3 equiv). The reaction mixture was stirred at 80° C. for 16 h. After completion of the reaction, the reaction mixture was concentrated and the residue was extracted with ethyl acetate. The organic layer was separated, dried over anhydrous $Na_2SO_4$, filtered and then concentrated. The residue was purified by column chromatography on silica gel using Hexane/EtOAc to give compound S2.

Step 2: N-(6-bromopyridin-2-yl)piperidine-2-carboxamide hydrochloride (S3)

To a solution of compound 2 (1 equiv) in 1,4-dioxane (3 vol) at 0° C. under nitrogen atmosphere was added 4 N HCl in 1,4-dioxane (10 vol) and stirred at room temperature for 3 h. The reaction mixture was concentrated to give compound S3.

Step-3: (S)-1-(2-(3-Acetyl-5-(2-methylpyrimidin-5-yl)-1H-indazol-1-yl)acetyl)-N-(6-bromopyridin-2-yl)piperidine-2-carboxamide (593) & (R)-1-(2-(3-acetyl-5-(2-methylpyrimidin-5-yl)-1H-indazol-1-yl)acetyl)-N-(6-bromopyridin-2-yl)piperidine-2-carboxamide (592)

To a solution of compound S3 (1 equiv) in DMF (10 vol) at 0° C. under nitrogen atmosphere was added S4 (1.2 equiv), HATU (1.5 equiv) and DIPEA (3 equiv). The reaction mixture was stirred at room temperature for 16 h. After completion of the reaction, the reaction mixture was quenched with water. The resulting mixture was extracted with DCM. The organic layer was washed with brine, dried over anhydrous $Na_2SO_4$, filtered and then concentrated. The residue was purified by column chromatography on silica gel using DCM/MeOH to give racemic product. This racemic product was purified by SFC to give compound 593 as one isomer and compound 592 was another isomer.

593: $^1$H NMR (400 MHz, DMSO-$d_6$) δ 10.85 (s, 1H), 9.03 (s, 2H), 8.42 (s, 1H), 8.05 (d, J=8.1 Hz, 1H), 7.87-7.72 (m, 3H), 7.34 (d, J=7.6 Hz, 1H), 5.89-5.85 (m, 1H), 5.75-5.69 (m, 1H), 5.08-5.07 (m, 1H), 3.97-3.94 (m, 1H), 3.68-

458

3.61 (m, 1H), 2.68 (s, 3H), 2.61 (s, 3H), 2.17-2.13 (m, 1H), 1.76-1.59 (m, 4H), 1.47-1.32 (m, 1H).

592: $^1$H NMR (400 MHz, DMSO-$d_6$) δ 10.87 (s, 1H), 9.05 (s, 2H), 8.43 (s, 1H), 8.06 (d, J=8.1 Hz, 1H), 7.88-7.73 (m, 3H), 7.35 (d, J=7.6 Hz, 1H), 5.91-5.87 (m, 1H), 5.76-5.70 (m, 1H), 5.09-5.08 (m, 1H), 3.98-3.95 (m, 1H), 3.72-3.58 (m, 1H), 2.69 (s, 3H), 2.65 (s, 3H), 2.18-2.14 (m, 1H), 1.80-1.72 (m, 4H), 1.45-1.32 (m, 1H).

(2S,4R)-1-(2-(3-Acetyl-6-((dimethylamino)methyl)-5-(2-methylpyrimidin-5-yl)-1H-indazol-1-yl)acetyl)-N-(6-bromopyridin-2-yl)-4-fluoropyrrolidine-2-carboxamide (387)

Scheme 172

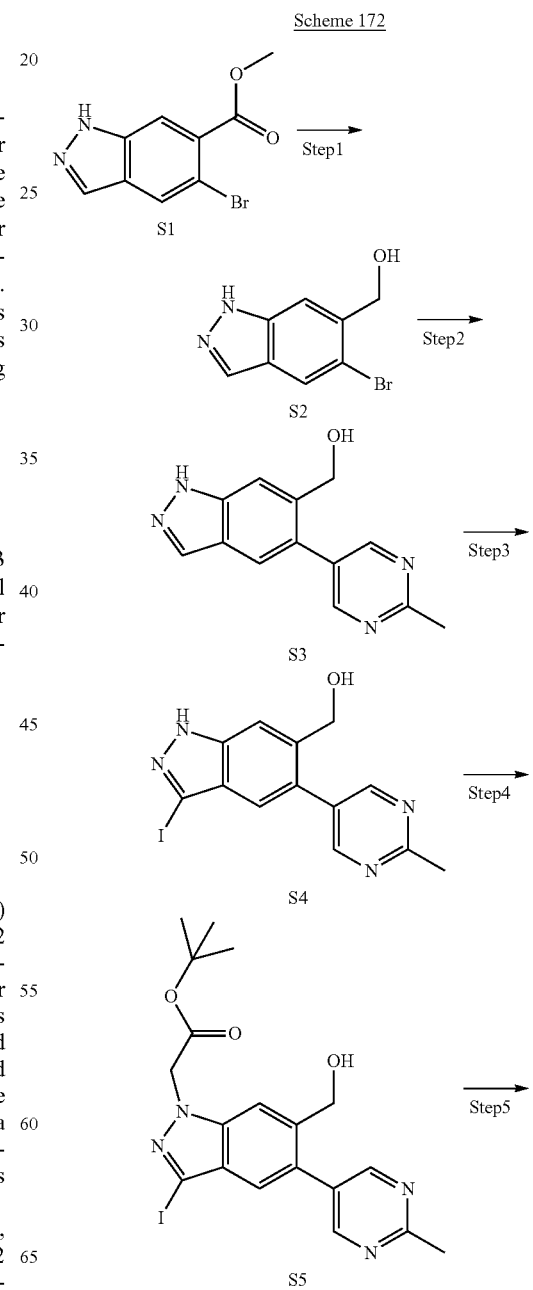

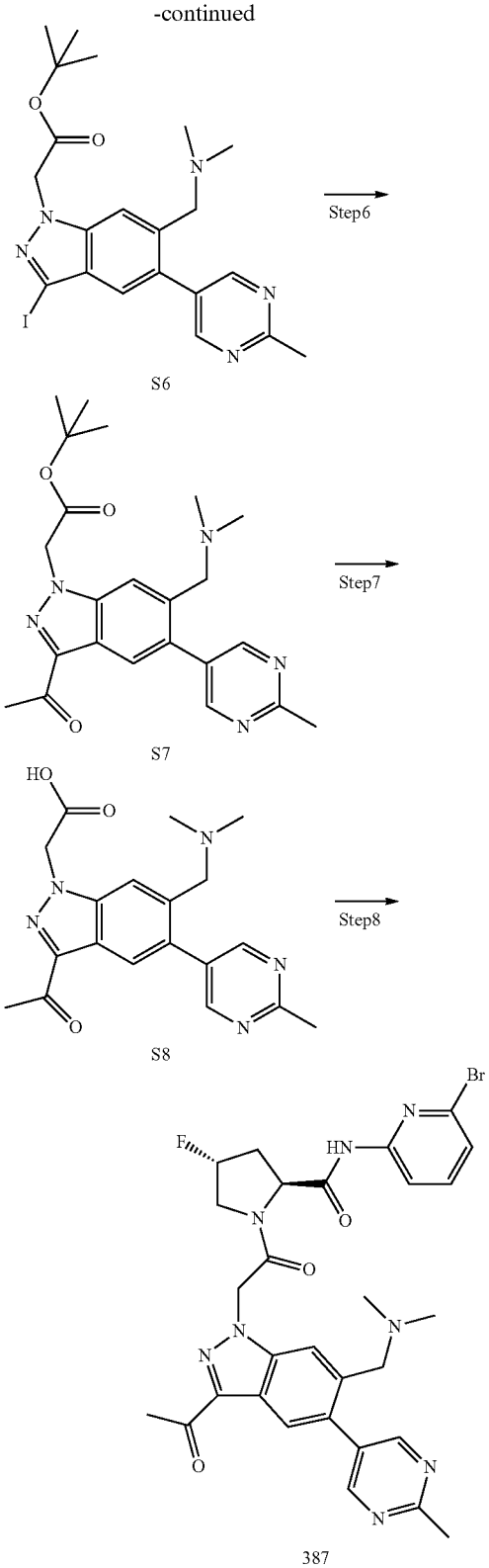

Step 1: (5-Bromo-1H-indazol-6-yl)methanol (S2)

To the solution of methyl 5-bromo-1H-indazole-6-carboxylate (1.02 g, 4.0 mmol) in anhydrous THF (8.0 mL) at 0° C., the solution of LAH in THF (1M, 7.0 mL) was added dropwise under Ar. After completion of addition, the cloudy mixture was stirred for 1 hr at 0° C., and then additional 2 hrs at room temperature. The mixture was cooled in an ice bath and quenched carefully with water. The mixture was filtered through a short pad of celite, and the cake was rinsed with THF-MeOH (1:1, 50 mL). The combined filtrate was dried over $MgSO_4$, and then concentrated. The remaining material was used for next step without further purification.

Step 2: (5-(2-Methylpyrimidin-5-yl)-1H-indazol-6-yl)methanol (S3)

A mixture of (5-bromo-1H-indazol-6-yl)methanol (0.72 g, 3.17 mmol), 2-methyl-5-(4,4,5,5-tetramethyl-1,3,2-dioxaborolan-2-yl)pyrimidine (698 mg, 3.17 mmol), $K_3PO_4$ (2.02 g, 9.51 mmol) and $Pd(dppf)_2Cl_2$ (252 mg, 0.31 mmol) in co-solvent of dioxane-$H_2O$ (dioxane 15.0 mL, $H_2O$ 3.0 mL) was purged with argon in a pressure vessel for 5 min and stirred at 100° C. overnight. The reaction mixture was cooled to rt. The volatiles are removed under reduced pressure and the residue was co-evaporated with toluene (30 mL) twice. The remaining solid was used for next step without further purification.

Step 3: (3-iodo-5-(2-Methylpyrimidin-5-yl)-1H-indazol-6-yl)methanol (S4)

The residue from above step was dissolved in anhydrous methanol (15.0 ml), sodium methoxide (25% in methanol) (2.0 mL) was added, followed by addition of iodine (885 mg, 3.49 mmol) in one portion. The mixture was stirred for 30 min, and quenched with water (1 mL). The volatiles are removed, and the residue was mixed with ethyl acetate (50 mL) and water (30 mL). The organic phase was collected and the aqueous phase was extracted twice with ethyl acetate. The combined organic solution was dried over $MgSO_4$ and further concentrated. The filtrate was concentrated and the residue was used for next step use.

Step 4: tert-Butyl 2-(6-(hydroxymethyl)-3-iodo-5-(2-methylpyrimidin-5-yl)-1H-indazol-1-yl)acetate (S5)

The residue from above step was dissolved in $CH_3CN$ (15 mL). To the solution, tert-butyl 2-bromoacetate (618 mg, 0.47 mL, 3.17 mmol) and solid $K_2CO_3$ (1.31 g, 9.5 mmol) are added. The mixture was stirred at room temperature overnight. The reaction was filtered. The cake was rinsed with additional $CH_3CN$. The combined solution was concentrated, and the resulting residue was purified to afford 547 mg of title product.

Step 5: tert-Butyl 2-(6-(((dimethylamino)methyl)-3-iodo-5-(2-methylpyrimidin-5-yl)-1H-indazol-1-yl)acetate (S6)

To the solution of tert-butyl 2-(6-(hydroxymethyl)-3-iodo-5-(2-methylpyrimidin-5-yl)-1H-indazol-1-yl)acetate (246 mg, 0.51 mmol) in DCM (10 mL), MsCl (88 mg, 0.77 mmol) was added at −78° C. The mixture was stirred for 1 hr at the temperature and then warmed up to room temperature. To the reaction mixture, the solution of dimethylamine in THF (2M, 3 mL) was added. The mixture was stirred for 2 hr at room temperature and then quenched with saturated aqueous $NaHCO_3$ (10 mL). The DCM layer was collected and the aqueous phase was extracted with DCM (10 mL×2).

461

The combined organic phase was washed with water, brine and dried over MgSO$_4$. The solution was filtered. The filtrate was concentrated and the residue was purified to afford 207 mg of title product.

Step 6: tert-Butyl 2-(3-acetyl-6-((dimethylamino)methyl)-5-(2-methylpyrimidin-5-yl)-1H-indazol-1-yl)acetate (S7)

To the degassed solution of tert-butyl 2-(6-((dimethylamino)methyl)-3-iodo-5-(2-methylpyrimidin-5-yl)-1H-indazol-1-yl)acetate (207 mg, 0.41 mmol) in DMF (6.0 mL), tributyl(1-ethoxyvinyl)stannane (0.21 mL, 0.61 mmol) and Pd(PPh$_3$)$_4$ (0.1 eq) are added under argon. The mixture was heated at 100° C. for 5 hrs and then cooled to room temperature. To the solution, aqueous HCl (1N, 15 mL) was added, and the mixture was stirred for 30 minutes at room temperature. The volatiles are removed, and the residue was mixed with ethyl acetate and water. The organic layer was separated from aqueous phase, and washed with brine. The organic phase was dried over MgSO$_4$. The solution was filtered through a short pad of silica gel. The filtrate was concentrated and the residue was purified to provide 137 mg of title product.

Step 7: 2-(3-Acetyl-6-((dimethylamino)methyl)-5-(2-methylpyrimidin-5-yl)-1H-indazol-1-yl)acetic acid (S8)

Tert-butyl 2-(3-acetyl-6-((dimethylamino)methyl)-5-(2-methylpyrimidin-5-yl)-1H-indazol-1-yl)acetate (137 mg, 0.32 mmol) was taken in 4N HCl dioxane (5.0 mL) and the resulting reaction mixture was stirred at room temperature overnight. After completion of the reaction monitored by HPLC, the solvent was removed under reduced pressure. The remaining residue was used directly without further purification.

Step 8: (2S,4R)-1-(2-(3-Acetyl-6-((dimethylamino)methyl)-5-(2-methylpyrimidin-5-yl)-1H-indazol-1-yl)acetyl)-N-(6-bromopyridin-2-yl)-4-fluoropyrrolidine-2-carboxamide (387)

To the solution of (2S,4R)—N-(6-bromopyridin-2-yl)-4-fluoropyrrolidine-2-carboxamide hydrochloride (104 mg, 0.32 mmol), 2-(3-acetyl-6-((dimethylamino)methyl)-5-(2-methylpyrimidin-5-yl)-1H-indazol-1-yl)acetic acid (0.32 mmol) from above step in DMF (1.0 mL), HATU (1.5 eq) was added, followed by dropwise addition of DIEA (4.0 eq) at room temperature. The mixture was stirred for 1 h at room temperature and the solution was purified by preparative HPLC to afford 58.3 mg of the title compound. $^1$H NMR (400 MHz, DMSO-d$_6$): (major rotamer) δ2.07-2.18 (m, 1H), 2.47-2.61 (m, 1H), 2.43 (s, 3H), 2.55 (s, 3H), 2.62 (s, 3H), 3.23 (s, 3H), 3.91-4.02 (m, 1H), 4.13-4.22 (m, 1H), 4.61 (t, J=8.4 Hz, 1H), 5.51 (d, J=52.4 Hz, 1H), 5.55-5.79 (m, 2H), 7.24 (d, J=7.6 Hz, 1H), 7.63 (t, J=8.0 Hz, 1H), 8.09 (s, 1H), 8.10 (d, J=8.4 Hz, 1H), 8.68 (s, 2H), 10.92 (s, 1H) ppm. $^{19}$F NMR (376 MHz, DMSO-d$_6$): (major rotamer) δ −175.55; LC (method A): t$_R$=1.24 min. LC/MS (EI) m/z: [M+H]$^+$ 639.21

1-(2-((2S,4R)-2-((6-Bromopyridin-2-yl)carbamoyl)-4-fluoropyrrolidin-1-yl)-2-oxoethyl)-N-methyl-5-(2-methylpyrimidin-5-yl)-1H-indazole-3-carboxamide (424)

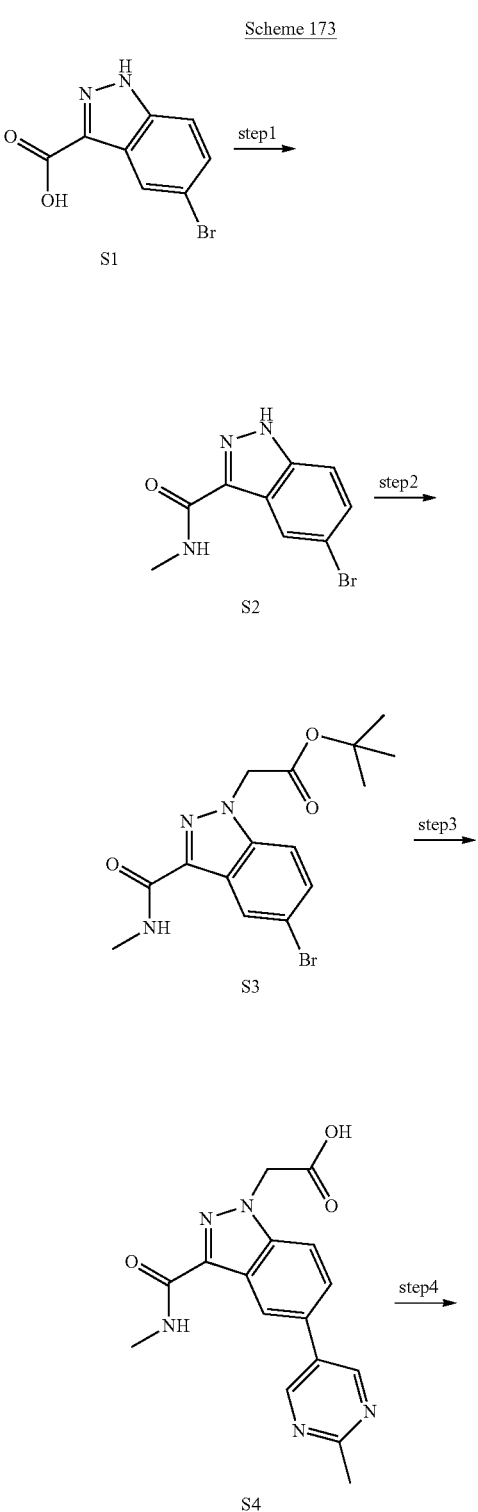

Scheme 173

-continued

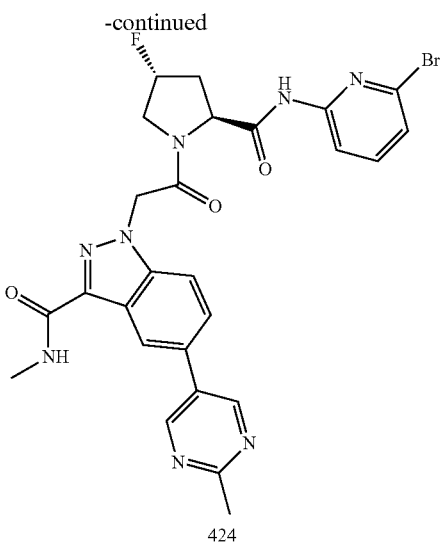

424

Step 1:
5-Bromo-N-methyl-1H-indazole-3-carboxamide (S2)

To the solution of 5-bromo-1H-indazole-3-carboxylic acid (723 mg, 3.0 mmol), methylamine.HCl (243 mg, 3.6 mmol) in DMF (10.0 mL), HATU (1.37 g, 3.6 mmol) was added, followed by dropwise addition of DIEA (1.57 mL, 9.0 mmol) at 0° C. The mixture was stirred for additional 1.5 hours and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The resulting residue was used for next step without further purification.

Step 2: tert-Butyl 2-(5-bromo-3-(methylcarbamoyl)-1H-indazol-1-yl)acetate (S3)

The residue from step 1 was dissolved in CH$_3$CN. To the solution, tert-butyl 2-bromoacetate (644 mg, 0.48 mL, 3.3 mmol) and solid K$_2$CO$_3$ (622 mg, 4.5 mmol) are added. The mixture was heated at 80° C. for 2 hr. The reaction was cooled to room temperature and filtered. The cake was rinsed with additional CH$_3$CN. The combined solution was concentrated, and the resulting residue was purified to afford 565 mg of title product.

Step 3: 2-(3-(Methylcarbamoyl)-5-(2-methylpyrimidin-5-yl)-1H-indazol-1-yl)acetic acid (S4)

A mixture of tert-butyl 2-(5-bromo-3-(methylcarbamoyl)-1H-indazol-1-yl)acetate (565 mg), 2-methyl-5-(4,4,5,5-tetramethyl-1,3,2-dioxaborolan-2-yl)pyrimidine (405 mg, 1.2 eq), K$_3$PO$_4$ (975 mg) and Pd(dppf)$_2$Cl$_2$ (0.1 eq) in co-solvent (dioxane 15 mL, H$_2$O 4.0 mL) was purged with argon in a pressure vessel for 5 min and stirred for 15 h at 100° C. The volatiles are removed under reduced pressure and the residue was washed with ethyl acetate twice. The remaining solid was then quenched with citric acid (10%) and the resulting precipitate was collected and dried for next step use without further purification.

Step 4: 1-(2-((2S,4R)-2-((6-Bromopyridin-2-yl)carbamoyl)-4-fluoropyrrolidin-1-yl)-2-oxoethyl)-N-methyl-5-(2-methylpyrimidin-5-yl)-1H-indazole-3-carboxamide (424)

To the solution of (2S,4R)—N-(6-bromopyridin-2-yl)-4-fluoropyrrolidine-2-carboxamide hydrochloride (0.3 mmol), 2-(3-(methylcarbamoyl)-5-(2-methylpyrimidin-5-yl)-1H-indazol-1-yl)acetic acid (98 mg, 0.3 mmol) in DMF (3.0 mL), HATU (1.3 eq) was added, followed by dropwise addition of DIEA (4.0 eq) at room temperature. The mixture was stirred for 1 h at room temperature and the solution was purified by preparative HPLC to afford 96.8 mg of the title compound. $^1$H NMR (400 MHz, DMSO-d$_6$): (major rotamer) δ1.99-2.17 (m, 1H), 2.48-2.53 (m, 1H), 2.61 (s, 3H), 2.75 (d, J=4.8 Hz, 3H), 3.83-3.95 (m, 1H), 4.11-4.20 (m, 1H), 4.60 (t, J=8.4 Hz, 1H), 5.37-5.66 (m, 3H), 7.32 (d, J=7.6 Hz, 1H), 7.71 (t, J=7.6 Hz, 1H), 7.91 (s, 2H), 8.08 (d, J=8.4 Hz, 1H), 8.27 (d, J=4.8 Hz, 1H), 8.37 (s, 1H), 8.96 (s, 2H), 10.92 (s, 1H) ppm. $^{19}$F NMR (376 MHz, DMSO-d$_6$): (major) δ −175.68 ppm. LC (method A): t$_R$=1.42 min. LC/MS (EI) m/z: [M+H]$^+$ 597.06.

(2S,4R)—N-(6-bromopyridin-2-yl)-4-fluoro-1-(2-(3-(2-hydroxyacetyl)-5-(2-methylpyrimidin-5-yl)-1H-indazol-1-yl)acetyl)pyrrolidine-2-carboxamide (440)

Scheme 174

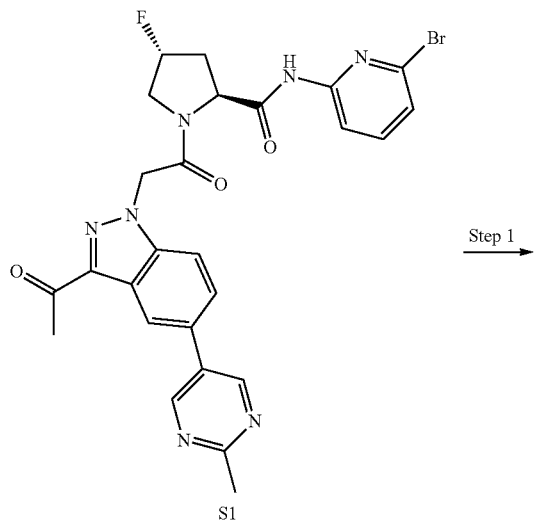

S1

-continued

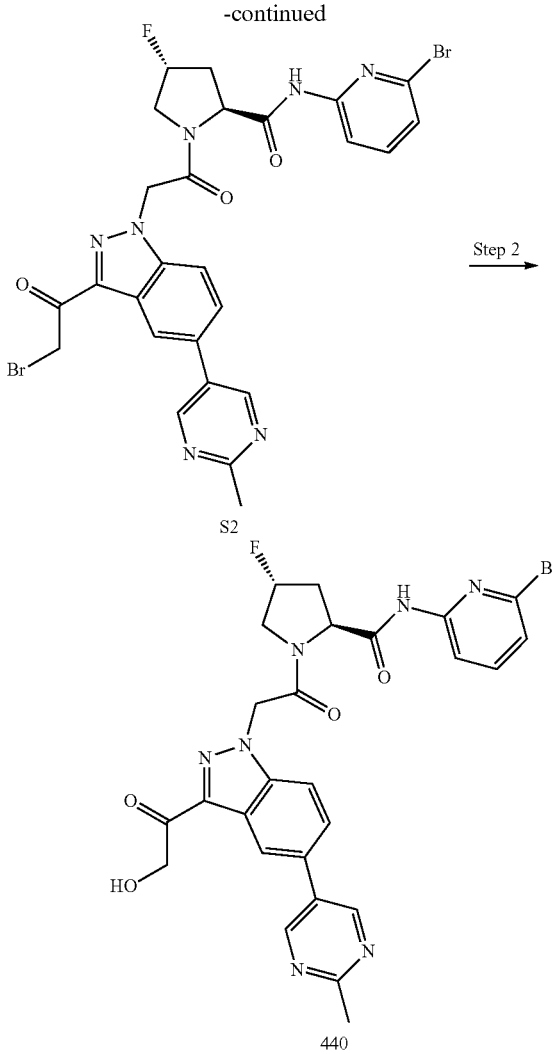

Step-1: (2S,4R)-1-(2-(3-(2-Bromoacetyl)-5-(2-methylpyrimidin-5-yl)-1H-indazol-1-yl)acetyl)-N-(6-bromopyridin-2-yl)-4-fluoropyrrolidine-2-carboxamide (S2)

The mixture of (2S,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide (498 mg, 0.858 mmol) and trimethylphenylammonium tribromide (483 mg, 1.3 mmol) in THF (12 mL) was heated in oil bath (60° C.) for 30 hours. The reaction was cooled to room temperature and the volatiles are evaporated. The residue was purified to give desire product (120 mg).

Step-2: (2S,4R)—N-(6-Bromopyridin-2-yl)-4-fluoro-1-(2-(3-(2-hydroxyacetyl)-5-(2-methylpyrimidin-5-yl)-1H-indazol-1-yl)acetyl)pyrrolidine-2-carboxamide (440)

The solution of (2S,4R)-1-(2-(3-(2-bromoacetyl)-5-(2-methylpyrimidin-5-yl)-1H-indazol-1-yl)acetyl)-N-(6-bromopyridin-2-yl)-4-fluoropyrrolidine-2-carboxamide (40 mg, 0.06 mmol) and sodium formate (62 mg, 0.91 mmol) in ethyl alcohol (4 mL)-H₂O (1 mL) was heated at 95° C. for 25 minutes using microwave. The reaction mixture was purified by preparative HPLC to afford 16.8 mg of desire product. $^1$H NMR (400 MHz, DMSO-$d_6$): (major rotamer) δ: 2.00-2.17 (m, 1H), 2.47-2.54 (m, 1H), 2.62 (s, 3H), 3.89-4.02 (m, 1H), 4.11-4.20 (m, 1H), 4.60 (t, J=8.4 Hz, 1H), 4.79 (s, 2H), 5.41-5.78 (m, 4H), 7.24 (d, J=7.6 Hz, 1H), 7.63 (t, J=8.0 Hz, 1H), 7.82 (s, 2H), 7.95 (d, J=8.0 Hz, 1H), 8.36 (s, 1H), 8.98 (s, 2H), 10.91 (s, 1H) ppm; $^{19}$F NMR (376 MHz, DMSO-$d_6$): (major rotamer) δ −175.69; LC (method A): $t_R$=1.37 min. LC/MS (EI) m/z: [M+H]$^+$ 595.94, 597.97.

(2S,4R)—N-(6-Bromopyridin-2-yl)-4-fluoro-1-(2-(3-(1-fluoroethyl)-5-(2-methylpyrimidin-5-yl)-1H-indazol-1-yl)acetyl)pyrrolidine-2-carboxamide (456)

Scheme 175

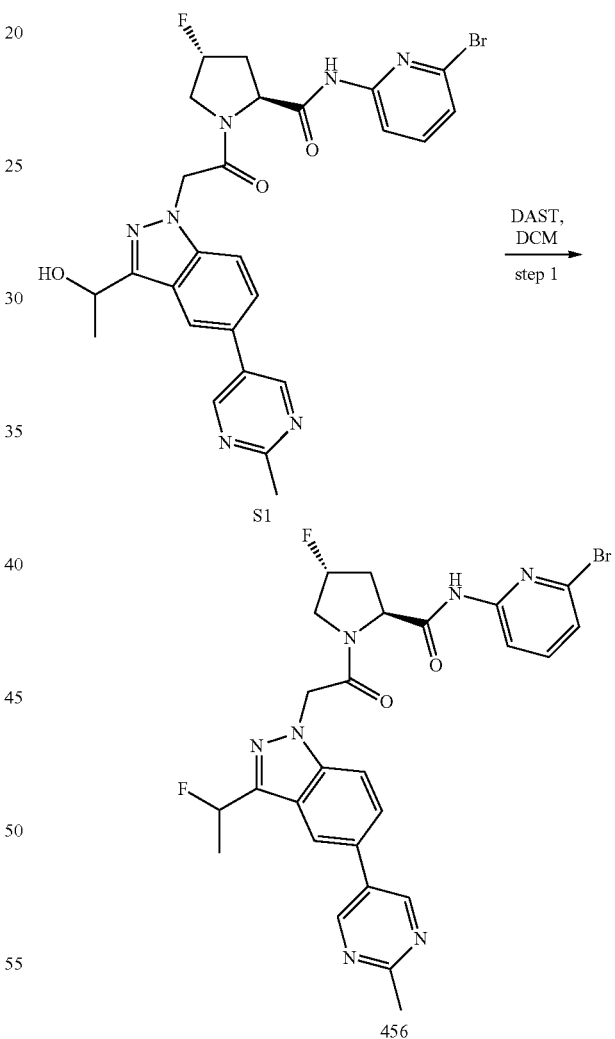

To the solution of (2S,4R)—N-(6-bromopyridin-2-yl)-4-fluoro-1-(2-(3-(1-hydroxyethyl)-5-(2-methylpyrimidin-5-yl)-1H-indazol-1-yl)acetyl)pyrrolidine-2-carboxamide (100 mg) in DCM (3 mL), DAST (1.5 eq) was added. The mixture was stirred overnight. The reaction was quenched with saturated NaHCO₃. The organic layer was collected and the aqueous phase was extracted with DCM (15 mL) twice. The combined DCM solution was dried over MgSO₄. The solution was filtered and the filtrate was concentrated, and the residue was purified to afford 35.5 mg of title product. 1H NMR (400 MHz, DMSO-$d_6$): (major rotamer) δ: 1.78 (dd, J=6.8, 23.6 Hz, 3H), 1.99-2.15 (m, 1H), 2.47-2.54 (m, 1H), 2.60 (s, 3H), 3.86-3.97 (m, 1H), 4.08-4.17 (m, 1H), 4.58 (t, J=8.4 Hz, 1H), 5.35-5.60 (m, 3H), 6.02-6.16 (m, 1H), 7.24 (d, J=7.6 Hz, 1H), 7.63 (t, J=8.0 Hz, 2H), 7.73 (d, J=9.2 Hz, 1H), 7.96 (d, J=8.4 Hz, 1H), 8.15 (s, 1H), 8.99 (s, 2H), 10.91 (s, 1H) ppm; 19F NMR (376 MHz, DMSO-$d_6$): (major rotamer) δ −162.55, −175.67; LC (method A): $t_R$=1.79 min. LC/MS (EI) m/z: [M+H]$^+$ 584.04.

2-(3-acetyl-5-(2-Methylpyrimidin-5-yl)-1H-indazol-1-yl)-1-((2S,4R)-2-(4-(6-bromopyridin-2-yl)-1H-imidazol-2-yl)-4-fluoropyrrolidin-1-yl)ethan-1-one (469)

The mixture was stirred for 1 h at room temperature and the solution was purified by preparative HPLC to afford 106.8 mg of the title compound. $^1$H NMR (400 MHz, DMSO-$d_6$): (major rotamer) δ 2.21-2.47 (m, 1H), 2.55 (s, 3H), 2.62 (s, 3H), 2.64-2.81 (m, 1H), 3.95-4.16 (m, 1H), 4.22-4.34 (m, 1H), 5.22 (t, J=9.6 Hz, 1H), 5.44-5.83 (m, 3H), 7.56 (d, J=7.6 Hz, 1H), 7.71-7.88 (m, 4H), 8.14 (s, 1H), 8.33 (s, 1H), 8.92 (s, 2H), ppm. $^{19}$F NMR (376 MHz, DMSO-$d_6$): (major) δ −176.89 ppm. LC (method A): $t_R$=1.45 min. LC/MS (EI) m/z: [M+H]$^+$ 605.11.

(3S,4S)-2-(2-(3-Acetyl-5-(2-methylpyrimidin-5-yl)-1H-indazol-1-yl)acetyl)-N-(6-bromopyridin-2-yl)-2-azabicyclo[2.2.1]heptane-3-carboxamide (475)

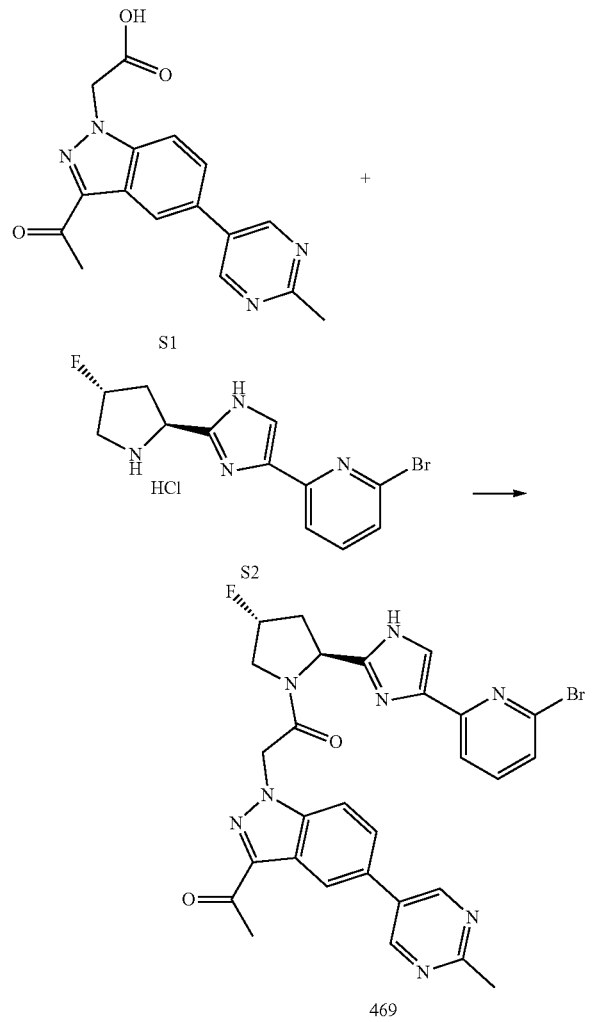

Scheme 176

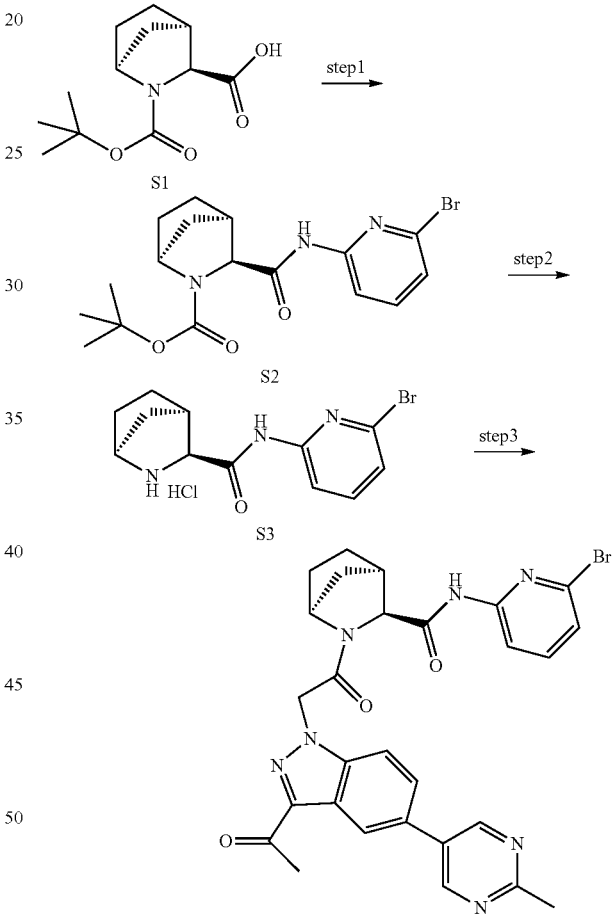

Scheme 177

Step 1: tert-Butyl (3S,4S)-3-((6-bromopyridin-2-yl)carbamoyl)-2-azabicyclo[2.2.1]heptane-2-carboxylate (S2)

To the solution of 2-bromo-6-(2-((2S,4R)-4-fluoropyrrolidin-2-yl)-1H-imidazol-4-yl)pyridine hydrochloride (125 mg, 0.36 mmol), 2-(3-acetyl-5-(2-methylpyrimidin-5-yl)-1H-indazol-1-yl)acetic acid (112 mg, 0.36 mmol) in DMF (3.0 mL), HATU (205 mg, 0.54 mmol) was added, followed by dropwise addition of DIEA (4.0 eq) at room temperature.

To an ice-cold solution of (3S,4S)-2-(tert-butoxycarbonyl)-2-azabicyclo[2.2.1]heptane-3-carboxylic acid (251 mg, 1.04 mmol) in 10 mL of CH$_2$Cl$_2$, 1-chloro-N,N,2-trimethyl-1-propenylamine (0.15 mL, 1.1 equiv) was added with stirring. The stirring was continued for 2.0 h at this temperature, then solid 6-bromopyridin-2-amine (198 mg, 1.14 mmol) was added, followed by iPr₂Net (3.0 eq). The cooling bath was removed and the reaction mixture was stirred overnight at rt. After completion of the reaction monitored by HPLC, the reaction mixture was added to water (20 mL) and extracted with DCM (2×20 mL). The organic layer was washed successively with an aqueous solution of NaHCO₃ (20 mL), water (20 mL), and brine (20 mL), then dried over Na₂SO₄ and concentrated under reduced pressure. The remaining residue was purified by flash column chromatography (ISCO eluted with Hexanes/EtOAC) to give 228 mg of desire title compound.

Step 2: (3S,4S)—N-(6-Bromopyridin-2-yl)-2-azabicyclo[2.2.1]heptane-3-carboxamide.TFA (S3)

The residue (228 mg) was dissolved in DCM (4 mL) and treated with TFA (2 mL) at room temperature. The mixture was stirred overnight. The volatiles are evaporated and the resulting residue was co-evaporated with toluene (10 mL) twice. The residue was further dried via vacuum and used for next step.

Step 3: (3S,4S)-2-(2-(3-Acetyl-5-(2-methylpyrimidin-5-yl)-1H-indazol-1-yl)acetyl)-N-(6-bromopyridin-2-yl)-2-azabicyclo[2.2.1]heptane-3-carboxamide (475)

To the solution of (3S,4S)—N-(6-bromopyridin-2-yl)-2-azabicyclo[2.2.1]heptane-3-carboxamide.TFA (79 mg, 0.2 mmol), 2-(3-acetyl-5-(2-methylpyrimidin-5-yl)-1H-indazol-1-yl)acetic acid (62 mg, 0.20 mmol) in DMF (3.0 mL), HATU (1.3 eq) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO₄. The solution was filtered and the solvent was removed. The residue was purified to afford 53.8 mg of the title compound. ¹H NMR (400 MHz, DMSO-d₆): (major rotamer) δ1.50-1.57 (m, 2H), 1.62-1.64 (m, 1H), 1.71-1.86 (m, 3H), 2.66 (s, 3H), 2.71 (s, 3H), 2.85 (s, 1H), 4.44 (s, 1H), 4.60 (s, 1H), 5.52-5.79 (m, 2H), 7.38 (d, J=8.4 Hz, 1H), 7.70 (t, J=7.6 Hz, 1H), 7.78-7.89 (m, 2H), 8.04 (d, J=8.4 Hz, 1H), 8.42 (s, 1H), 9.05 (s, 2H), 10.88 (br, s, 1H) ppm. LC (method A): t$_R$=1.87 min. LC/MS (EI) m/z: [M+H]⁺ 590.06.

(2S,4R)-1-(2-(3-Acetyl-5-(2-methylpyrimidin-5-yl)-1H-indazol-1-yl)acetyl)-N-((6-bromopyridin-2-yl)methyl)-4-fluoropyrrolidine-2-carboxamide (483)

Scheme 178

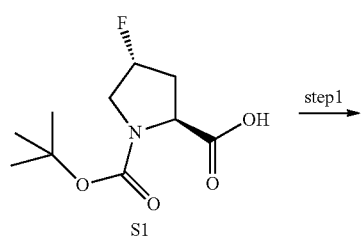

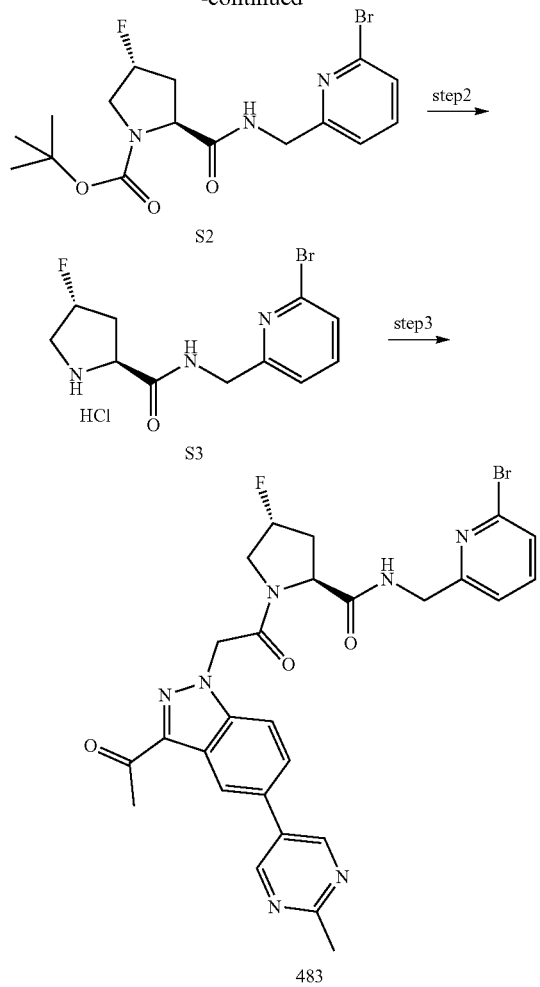

Step 1: tert-Butyl (2S,4R)-2-(((6-bromopyridin-2-yl)methyl)carbamoyl)-4-fluoropyrrolidine-1-carboxylate (S2)

To the mixture of (2S,4R)-1-(tert-butoxycarbonyl)-4-fluoropyrrolidine-2-carboxylic acid (233 mg, 1.0 mmol), (6-bromopyridin-2-yl)methanamine (205 mg, 1.1 mmol) in CH₃CN (10.0 mL), EDCI (1.3 eq) was added, followed by dropwise addition of DIEA (4.0 eq) at room temperature. The mixture was stirred for 3 h at room temperature and the volatiles are evaporated. The residue was diluted with 50 mL of 10% sodium carbonate and extracted with ethyl acetate. The combined organic solution was successively washed with water, brine and dried over MgSO₄. The solution was filtered and the solvent was removed. The residue was purified to afford 101 mg of the title compound.

Step 2: (2S,4R)—N-((6-Bromopyridin-2-yl)methyl)-4-fluoropyrrolidine-2-carboxamide hydrochloride (S3)

Tert-butyl (2S,4R)-2-(((6-bromopyridin-2-yl)methyl)carbamoyl)-4-fluoropyrrolidine-1-carboxylate (100 mg) was taken in 4N HCl dioxane (3.0 mL) and the resulting reaction mixture was stirred at room temperature for 2 h. After completion of the reaction monitored by HPLC, the solvent was removed under reduced pressure. The remaining residue was used directly without further purification.

Step 3: (2S,4R)-1-(2-(3-Acetyl-5-(2-methylpyrimidin-5-yl)-1H-indazol-1-yl)acetyl)-N-((6-bromopyridin-2-yl)methyl)-4-fluoropyrrolidine-2-carboxamide (483)

To the solution of (2S,4R)—N-((6-bromopyridin-2-yl)methyl)-4-fluoropyrrolidine-2-carboxamide hydrochloride (0.24 mmol), 2-(3-acetyl-5-(2-methylpyrimidin-5-yl)-1H-indazol-1-yl)acetic acid (62 mg, 0.20 mmol) in DMF (3.0 mL), HATU (1.3 eq) was added, followed by dropwise addition of DIEA (4.0 eq) at room temperature. The mixture was stirred for 1 h at room temperature and the solution was purified by preparative HPLC to afford 77.9 mg of the title compound. $^1$H NMR (400 MHz, DMSO-$d_6$): (major rotamer) δ2.00-2.16 (m, 1H), 2.47-2.53 (m, 1H), 2.57 (s, 3H), 2.62 (s, 3H), 3.84-3.97 (m, 1H), 4.12-4.23 (m, 1H), 4.25 (t, J=5.6 Hz, 1H), 4.39-4.44 (m, 1H), 5.40-5.78 (m, 3H), 7.16-7.187.23 (m, 1H), 7.34-7.39 (m, 2H), 7.75 (s, 2H), 8.38 (s, 1H), 8.99 (s, 2H), ppm. $^{19}$F NMR (376 MHz, DMSO-$d_6$): (major) δ −176.35 ppm. LC (method A): $t_R$=1.37 min. LC/MS (EI) m/z: [M+H]$^+$ 594.12.

(2S,4R)-1-(2-(3-Acetyl-5-(2-methylpyrimidin-5-yl)-1H-indazol-1-yl)acetyl)-4-fluoro-N-(6-(pentyloxy)pyridin-2-yl)pyrrolidine-2-carboxamide (519)

Scheme 179

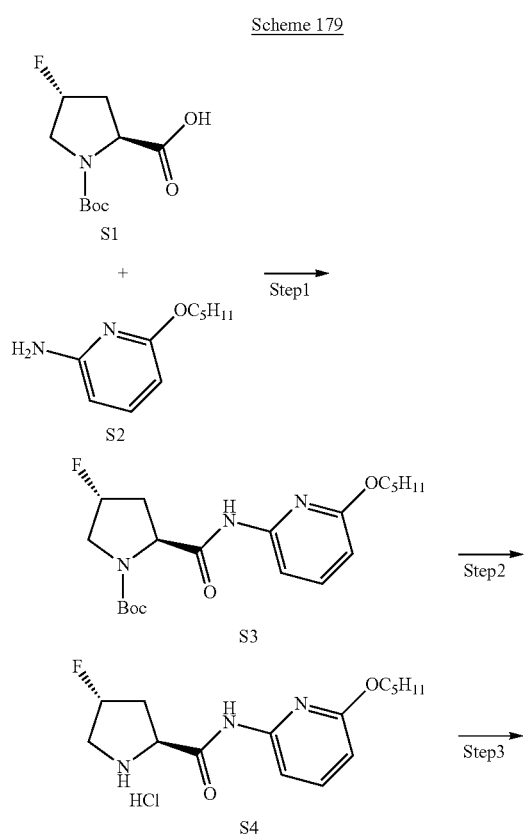

-continued

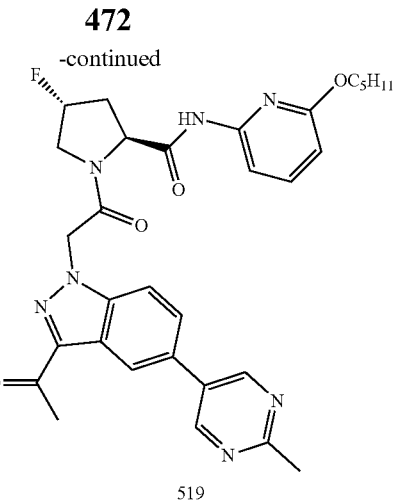

519

Step-1: tert-Butyl (2S,4R)-4-fluoro-2-((6-(pentyloxy)pyridin-2-yl)carbamoyl)pyrrolidine-1-carboxylate (S3)

In a pre-dried flask, (2S,4R)-1-(tert-butoxycarbonyl)-4-fluoropyrrolidine-2-carboxylic acid (583 mg, 2.50 mmol), 6-(pentyloxy)pyridin-2-amine (450 mg, 2.50 mmol) are placed, and then anhydrous DCM (12.0 mL) was added. The flask was placed in an ice bath. To the solution, dry pyridine (0.61 mL, 7.5 mmol) was added in one portion, followed by addition of POCl$_3$ (0.48 mL, 5.0 mmol). After completion of addition, the mixture was stirred for 1 hour at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 904 mg of desire product.

Step-2: (2S,4R)-4-Fluoro-N-(6-(pentyloxy)pyridin-2-yl)pyrrolidine-2-carboxamide hydrochloride (S4)

Tert-butyl (2S,4R)-4-fluoro-2-((6-(pentyloxy)pyridin-2-yl)carbamoyl)pyrrolidine-1-carboxylate (904 mg) from step 1 was taken in 4N HCl dioxane (8.0 mL) and the resulting reaction mixture was stirred at room temperature for 2 h. After completion of the reaction monitored by HPLC, the solvent was removed under reduced pressure. The remaining residue was used directly without further purification.

Step-3: (2S,4R)-1-(2-(3-Acetyl-5-(2-methylpyrimidin-5-yl)-1H-indazol-1-yl)acetyl)-4-fluoro-N-(6-(pentyloxy)pyridin-2-yl)pyrrolidine-2-carboxamide (519)

In a pre-dried flask, 2-(5-(2-methylpyrimidin-5-yl)-3-((methylsulfonyl)carbamoyl)-1H-indazol-1-yl)acetic acid (217 mg, 0.70 mmol), (2S,4R)-4-fluoro-N-(6-(pentyloxy)pyridin-2-yl)pyrrolidine-2-carboxamide hydrochloride (308 mg, 0.84 mmol) are placed, and then anhydrous DCM (6.0 mL) was added. The flask was placed in an ice bath. To the solution, dry pyridine (0.23 mL, 2.80 mmol) was added in one portion, followed by addition of POCl$_3$ (70 μL, 0.70 mmol). After completion of addition, the mixture was stirred for 1 hour at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 228 mg of desire product. $^1$H NMR (400 MHz, DMSO-d$_6$): (major rotamer) δ 0.78 (t, J=6.8 Hz, 3H), 1.22-1.27 (m, 4H), 1.56-1.62 (m, 2H), 2.01-2.18 (m, 1H), 2.43-2.52 (m, 1H), 2.57 (s, 3H), 2.61 (s, 3H), 3.97-4.00 (m, 1H), 4.09 (t, J=6.4 Hz, 2H), 4.13-4.21 (m, 1H), 4.69 (t, J=8.0 Hz, 1H), 5.50 (d, J=52.4 Hz, 1H), 5.55-5.78 (m, 2H), 6.38 (d, J=8.0 Hz, 1H), 7.52-7.55 (m, 2H), 7.77 (s, 2H), 8.35 (s, 1H), 8.95 (s, 2H), 10.31 (s, 1H) ppm. $^{19}$F NMR (376 MHz, DMSO-d$_6$): (major rotamer) δ -175.67; LC (method A): t$_R$=2.34 min. LC/MS (EI) m/z: [M+H]$^+$ 588.24.

(2S,5S)-1-(2-(3-Acetyl-5-(2-methylpyrimidin-5-yl)-1H-indazol-1-yl)acetyl)-N-(6-bromopyridin-2-yl)-5-methylpyrrolidine-2-carboxamide (530)

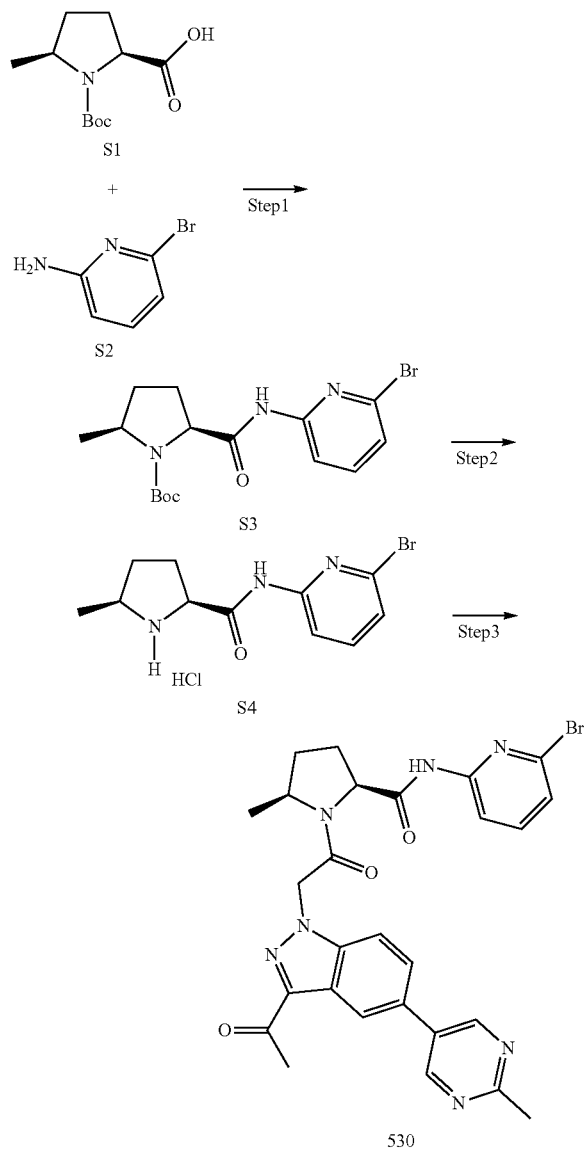

Step 1: tert-Butyl (2S,5S)-2-((6-bromopyridin-2-yl)carbamoyl)-5-methylpyrrolidine-1-carboxylate (S3)

In a pre-dried flask, (2S,5S)-1-(tert-butoxycarbonyl)-4-methylpyrrolidine-2-carboxylic acid (purchased from Aldrich) (522 mg, 2.28 mmol), 6-bromopyridin-2-amine (394 mg, 2.28 mmol) are placed, and then anhydrous DCM (15 mL) was added. The flask was placed in an ice bath. To the solution, dry pyridine (0.37 mL, 4.56 mmol) was added in one portion, followed by addition of POCl$_3$ (220 µL, 2.28 mmol). After completion of addition, the mixture was stirred for 4 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 737 mg of pure product.

Step 2: (2S,5S)—N-(6-Bromopyridin-2-yl)-5-methylpyrrolidine-2-carboxamide hydrochloride (S4)

Tert-butyl (2S,5S)-2-((6-bromopyridin-2-yl)carbamoyl)-5-methylpyrrolidine-1-carboxylate (737 mg) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (2S,5S)-1-(2-(3-Acetyl-5-(2-methylpyrimidin-5-yl)-1H-indazol-1-yl)acetyl)-N-(6-bromopyridin-2-yl)-5-methylpyrrolidine-2-carboxamide (530)

To the solution of (2S,5S)—N-(6-bromopyridin-2-yl)-5-methylpyrrolidine-2-carboxamide hydrochloride from above step, 2-(5-(2-methylpyrimidin-5-yl)-3-((methylsulfonyl)carbamoyl)-1H-indazol-1-yl)acetic acid (279 mg, 0.90 mmol) in DMF (5.0 mL), HATU (1.1 eq) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 208 mg of the title compound. $^1$H NMR (400 MHz, DMSO-d$_6$): (major rotamer) δ 1.36 (d, J=6.4 Hz, 3H), 1.69-1.74 (m, 1H), 1.84-1.92 (m, 1H), 2.01-2.10 (m, 1H), 2.18-2.25 (m, 1H), 2.57 (s, 3H), 2.62 (s, 3H), 4.38-4.50 (m, 2H), 5.42-5.74 (m, 2H), 7.20 (d, J=8.0 Hz, 1H), 7.61 (t, J=8.0 Hz, 1H), 7.75-7.80 (m, 2H), 7.97 (d, J=8.4 Hz, 1H), 8.35 (s, 1H), 8.98 (s, 2H), 10.82 (s, 1H) ppm. LC (method A): t$_R$=1.90 min. LC/MS (EI) m/z: [M+H]$^+$ 576.06, 578.09

(2S,4R)-1-(2-(3-Acetyl-5-(2-methylpyrimidin-5-yl)-1H-indazol-1-yl)acetyl)-N-(6-acetylpyridin-2-yl)-4-fluoropyrrolidine-2-carboxamide (584)

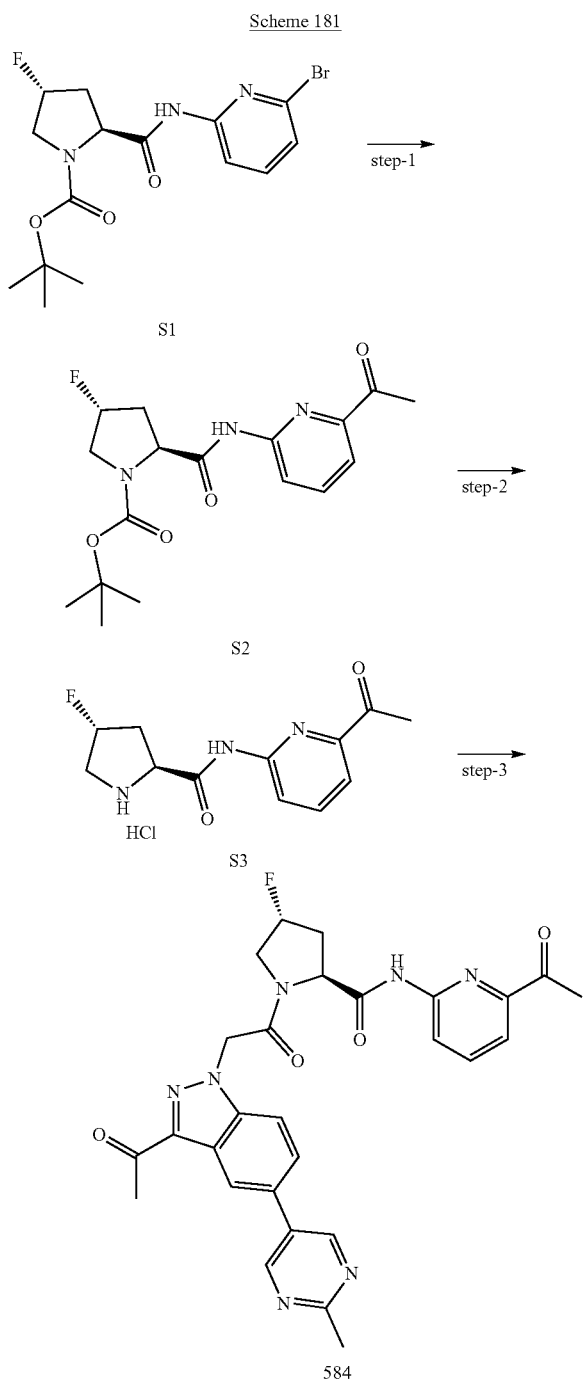

Step 1: tert-Butyl (2S,4R)-2-((6-acetylpyridin-2-yl)carbamoyl)-4-fluoropyrrolidine-1-carboxylate (S2)

To the degassed solution of tert-butyl (2S,4R)-2-((6-bromopyridin-2-yl)carbamoyl)-4-fluoropyrrolidine-1-carboxylate (1.24 g, 3.12 mmol) in DMF (10 mL), tributyl(1-ethoxyvinyl)stannane (1.30 g, 1.21 mL, 3.59 mmol) and Pd(PPh$_3$)$_4$ (0.1 eq) are added under argon. The mixture was heated at 100° C. overnight and then cooled to room temperature. To the solution, aqueous HCl (1N, 15 mL) was added, and the mixture was stirred for 60 minutes at room temperature. The volatiles are removed, and the residue was mixed with ethyl acetate and water. The organic layer was separated from aqueous phase, and washed with brine. The organic phase was dried over MgSO$_4$. The solution was filtered through a short pad of silica gel. The filtrate was concentrated and the residue was purified to provide 925 mg of title product.

Step 2: (2S,4R)—N-(6-Acetylpyridin-2-yl)-4-fluoropyrrolidine-2-carboxamide hydrochloride (S3)

Tert-butyl (2S,4R)-2-((6-acetylpyridin-2-yl)carbamoyl)-4-fluoropyrrolidine-1-carboxylate (109 mg, 0.31 mmol) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (2S,4R)-1-(2-(3-Acetyl-5-(2-methylpyrimidin-5-yl)-1H-indazol-1-yl)acetyl)-N-(6-acetylpyridin-2-yl)-4-fluoropyrrolidine-2-carboxamide (584)

To the solution of (2S,4R)—N-(6-acetylpyridin-2-yl)-4-fluoropyrrolidine-2-carboxamide hydrochloride (0.31 mmol), 2-(5-(2-methylpyrimidin-5-yl)-3-((methylsulfonyl)carbamoyl)-1H-indazol-1-yl)acetic acid (96 mg, 0.31 mmol) in DMF (2.0 mL), HATU (1.3 eq) was added, followed by dropwise addition of DIEA (4.0 eq) at room temperature. The mixture was stirred for 1 h at room temperature and the solution was purified by preparative HPLC to afford 95.3 mg of the title compound. $^1$H NMR (400 MHz, DMSO-d$_6$): (major rotamer) δ 2.04-2.22 (m, 1H), 2.48-2.65 (m, 1H), 2.51 (s, 3H), 2.57 (s, 3H), 2.61 (s, 3H), 3.89-4.02 (m, 1H), 4.14-4.23 (m, 1H), 4.74 (t, J=8.0 Hz, 1H), 5.50 (d, J=52.4 Hz, 1H), 5.57-5.80 (m, 2H), 7.56 (d, J=7.6 Hz, 1H), 7.78 (s, 1H), 7.87 (t, J=8.0 Hz, 1H), 8.17 (d, J=8.0 Hz, 1H), 8.35 (s, 1H), 8.95 (s, 1H), 10.76 (s, 1H) ppm. $^{19}$F NMR (376 MHz, DMSO-d$_6$): (major rotamer) δ −175.66; LC (method A): t$_R$=1.43 min. LC/MS (EI) m/z: [M+H]$^+$ 544.14.

(2S,4R)-1-(2-(3-Acetyl-5-(2-methylpyrimidin-5-yl)-1H-indazol-1-yl)acetyl)-4-fluoro-N-(6-(oxazol-2-yl)pyridin-2-yl)pyrrolidine-2-carboxamide (600)

Scheme 182

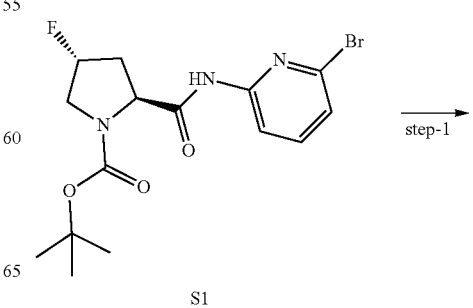

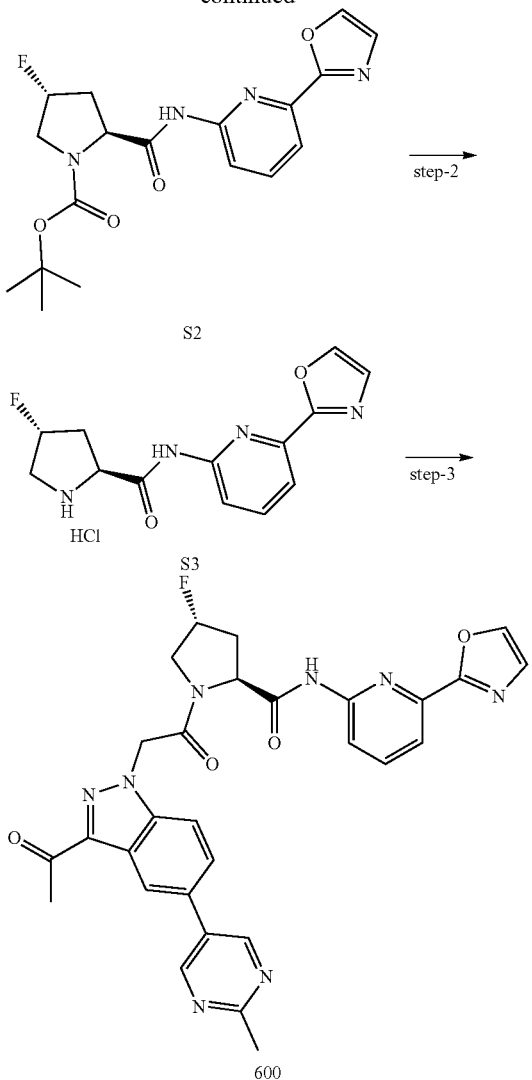

Step 1: tert-Butyl (2S,4R)-4-fluoro-2-((6-(oxazol-2-yl)pyridin-2-yl)carbamoyl)pyrrolidine-1-carboxylate (S2)

To the degassed solution of tert-butyl (2S,4R)-2-((6-bromopyridin-2-yl)carbamoyl)-4-fluoropyrrolidine-1-carboxylate (400 mg, 1.03 mmol) in DMF (10 mL), 2-(tributylstannyl)oxazole (406 mg, 1.15 mmol) and Pd(PPh$_3$)$_4$ (0.1 eq) are added under argon. The mixture was heated at 100° C. overnight and then cooled to room temperature. The volatiles are removed, and the residue was mixed with ethyl acetate and water. The organic layer was separated from aqueous phase, and washed with brine. The organic phase was dried over MgSO$_4$. The solution was filtered through a short pad of silica gel. The filtrate was concentrated and the residue was purified to provide 337 mg of title product.

Step 2: (2S,4R)-4-Fluoro-N-(6-(oxazol-2-yl)pyridin-2-yl)pyrrolidine-2-carboxamide hydrochloride (S3)

Tert-butyl (2S,4R)-4-fluoro-2-((6-(oxazol-2-yl)pyridin-2-yl)carbamoyl)pyrrolidine-1-carboxylate (337 mg) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (2S,4R)-1-(2-(3-Acetyl-5-(2-methylpyrimidin-5-yl)-1H-indazol-1-yl)acetyl)-4-fluoro-N-(6-(oxazol-2-yl)pyridin-2-yl)pyrrolidine-2-carboxamide (600)

To the solution of (2S,4R)-4-fluoro-N-(6-(oxazol-2-yl)pyridin-2-yl)pyrrolidine-2-carboxamide hydrochloride (200 mg, 0.64 mmol), 2-(5-(2-methylpyrimidin-5-yl)-3-((methylsulfonyl)carbamoyl)-1H-indazol-1-yl)acetic acid (0.64 mmol) in DMF (2.0 mL), HATU (292 mg, 0.77 mmol) was added, followed by dropwise addition of DIEA (4.0 eq) at room temperature. The mixture was stirred for 1 h at room temperature and the solution was purified by preparative HPLC to afford 65.5 mg of the title compound. $^1$H NMR (400 MHz, DMSO-d$_6$): (major rotamer) δ 2.11-2.29 (m, 1H), 2.53-2.63 (m, 1H), 2.65 (s, 3H), 2.69 (s, 3H), 3.98-4.11 (m, 1H), 4.21-4.30 (m, 1H), 4.80 (t, J=8.0 Hz, 1H), 5.57 (d, J=52.4 Hz, 1H), 5.64-5.87 (m, 2H), 7.43 (s, 1H), 7.78-7.88 (m, 3H), 7.93 (t, J=8.0 Hz, 1H), 8.16 (d, J=8.0 Hz, 1H), 8.27 (s, 1H), 8.43 (s, 1H), 9.03 (s, 2H), 11.00 (s, 1H) ppm. $^{19}$F NMR (376 MHz, DMSO-d$_6$): (major rotamer) δ −175.60; LC (method A): t$_R$=1.39 min. LC/MS (EI) m/z: [M+H]$^+$ 569.27.

(3S,4S)-2-(2-(3-Acetyl-5-(2-methylpyrimidin-5-yl)-1H-indazol-1-yl)acetyl)-N-(6-bromo-3-methylpyridin-2-yl)-2-azabicyclo[2.2.1]heptane-3-carboxamide (617)

Scheme 183

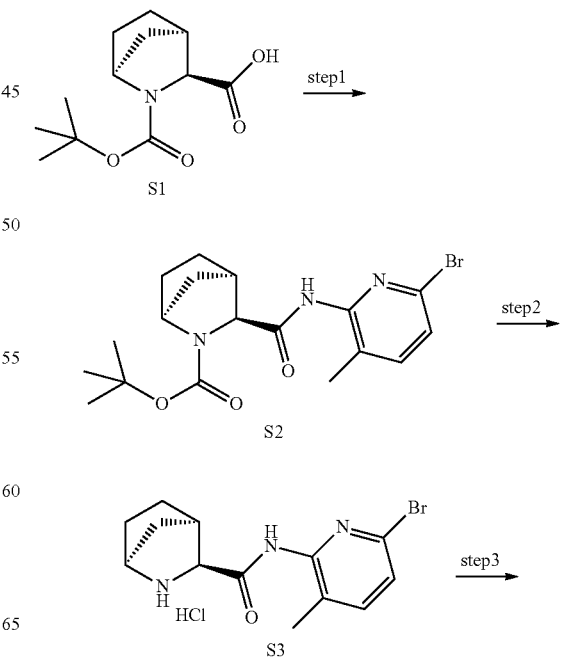

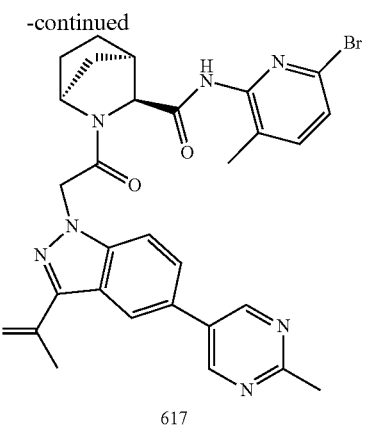

617

Step 1: tert-Butyl (3S,4S)-3-((6-bromo-3-methyl-pyridin-2-yl)carbamoyl)-2-azabicyclo[2.2.1]heptane-2-carboxylate (S2)

In a pre-dried flask, (3S,4S)-2-(tert-butoxycarbonyl)-2-azabicyclo[2.2.1]heptane-3-carboxylic acid (48 mg, 0.2 mmol), 6-bromo-3-methylpyridin-2-amine (37 mg, 0.2 mmol) are placed, and then anhydrous DCM (5 mL) was added. The flask was placed in an ice bath. To the solution, dry pyridine (50 μL, 0.6 mmol) was added in one portion, followed by addition of POCl₃ (20 μL, 0.2 mmol). After completion of addition, the mixture was stirred overnight at room temperature, and then the reaction was quenched with water (5 mL). The DCM layer was collected and the aqueous phase was extracted with DCM (10 mL×2). The combined DCM solution was washed with brine, and dried over MgSO₄. The solution was filtered and concentrated; the resulting residue was used for next step without further purification.

Step 2: (3S,4S)—N-(6-Bromo-3-methylpyridin-2-yl)-2-azabicyclo[2.2.1]heptane-3-carboxamide hydrochloride (S3)

tert-butyl (3S,4S)-3-((6-bromo-3-methylpyridin-2-yl)carbamoyl)-2-azabicyclo[2.2.1]heptane-2-carboxylate boxylate from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (3S,4S)-2-(2-(3-Acetyl-5-(2-methylpyrimidin-5-yl)-1H-indazol-1-yl)acetyl)-N-(6-bromo-3-methylpyridin-2-yl)-2-azabicyclo[2.2.1]heptane-3-carboxamide (617)

To the solution of (3S,4S)—N-(6-bromo-3-methylpyridin-2-yl)-2-azabicyclo[2.2.1]heptane-3-carboxamide hydrochloride (0.2 mmol), 2-(5-(2-methylpyrimidin-5-yl)-3-((methylsulfonyl)carbamoyl)-1H-indazol-1-yl)acetic acid (47 mg, 0.15 mmol) in DMF (3.0 mL), HATU (1.3 eq) was added, followed by dropwise addition of DIEA (4.0 eq) at room temperature. The mixture was stirred for 1 h at room temperature and the solution was purified by preparative HPLC to afford 32.4 mg of the title compound. ¹H NMR (400 MHz, DMSO-d₆): (major rotamer) δ1.53-1.64 (m, 3H), 1.74-1.85 (m, 2H), 1.88-1.91 (m, 1H), 2.06 (s, 3H), 2.65 (s, 3H), 2.69 (s, 3H), 2.88 (s, 1H), 4.39 (s, 1H), 4.64 (s, 1H), 5.50-5.80 (m, 2H), 7.42 (d, J=7.6 Hz, 1H), 7.61 (d, J=7.6 Hz, 1H), 7.81-7.86 (m, 2H), 8.43 (s, 1H), 9.05 (s, 2H), 10.23 (s, 1H) ppm. LC (method A): $t_R$=1.67 min. LC/MS (EI) m/z: [M+H]⁺ 604.27.

6-((2S,4R)-1-(2-(3-Acetyl-5-(2-methylpyrimidin-5-yl)-1H-indazol-1-yl)acetyl)-4-fluoropyrrolidine-2-carboxamido)-N,N-dimethylpicolinamide (618)

Scheme 184

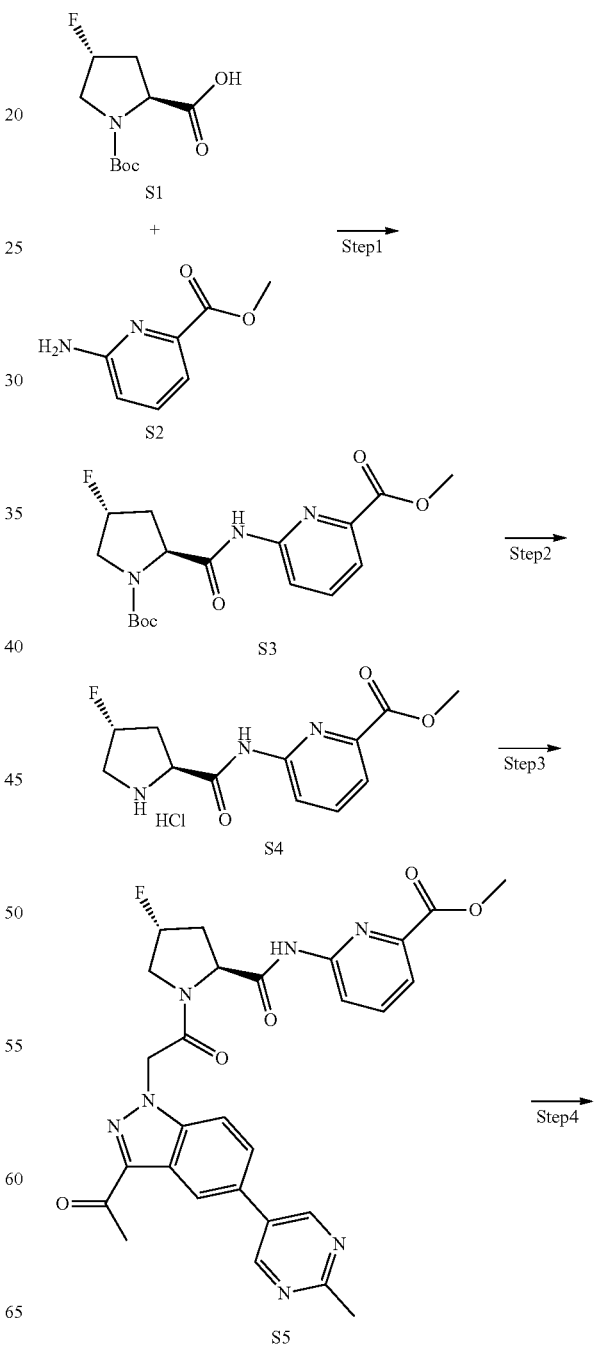

-continued

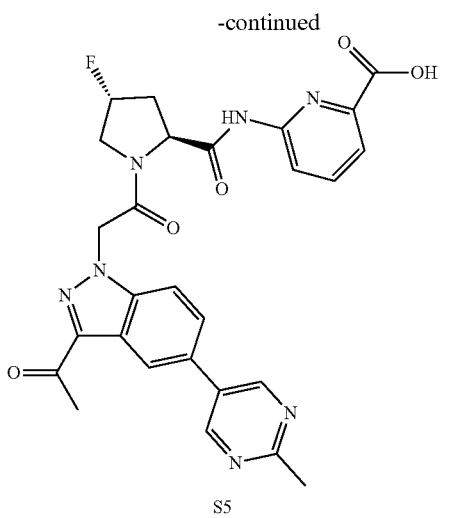

S5

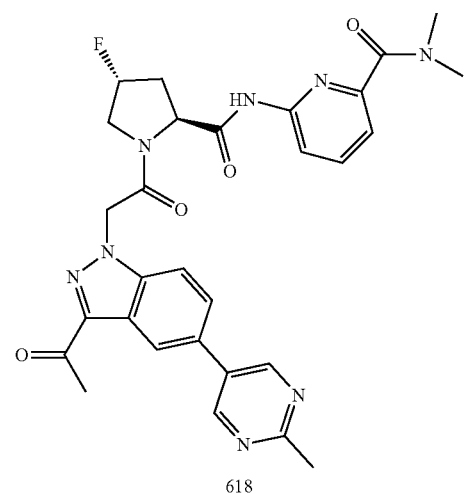

618

Step-1: Methyl 6-((2S,4R)-1-(tert-butoxycarbonyl)-4-fluoropyrrolidine-2-carboxamido)picolinate (S3)

In a pre-dried flask, (2S,4R)-1-(tert-butoxycarbonyl)-4-fluoropyrrolidine-2-carboxylic acid (1.17 g, 5.0 mmol), methyl 6-aminopicolinate (837 mg, 5.5 mmol) are placed, and then anhydrous DCM (20 mL) was added. The flask was placed in an ice bath. To the solution, dry pyridine (0.81 mL, 10.0 mmol) was added in one portion, followed by addition of POCl$_3$ (0.48 mL, 5.0 mmol). After completion of addition, the mixture was stirred for 1 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 1.65 g desire product.

Step-2: Methyl 6-((2S,4R)-4-fluoropyrrolidine-2-carboxamido)picolinate hydrochloride (S4)

Methyl 6-((2S,4R)-1-(tert-butoxycarbonyl)-4-fluoropyrrolidine-2-carboxamido)picolinate (1.65 g) from step 1 was taken in 4N HCl dioxane (8.0 mL) and the resulting reaction mixture was stirred at room temperature for 2 h. After completion of the reaction monitored by HPLC, the solvent was removed under reduced pressure. The remaining residue was used directly without further purification.

Step-3: Methyl 6-((2S,4R)-1-(2-(3-acetyl-5-(2-methylpyrimidin-5-yl)-1H-indazol-1-yl)acetyl)-4-fluoropyrrolidine-2-carboxamido)picolinate (S5)

To the solution of methyl 6-((2S,4R)-4-fluoropyrrolidine-2-carboxamido)picolinate hydrochloride (1.06 g, 3.50 mmol), 2-(3-acetyl-5-(2-methylpyrimidin-5-yl)-1H-indazol-1-yl)acetic acid (1.08 g, 3.50 mmol) in DMF (10.0 mL), HATU (1.52 g, 4.0 mmol) was added, followed by dropwise addition of DIEA (1.81 g, 2.50 mL) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 1.75 g of the title compound.

Step-4: 6-((2S,4R)-1-(2-(3-Acetyl-5-(2-methylpyrimidin-5-yl)-1H-indazol-1-yl)acetyl)-4-fluoropyrrolidine-2-carboxamido)picolinic acid (S6)

Methyl 6-((2S,4R)-1-(2-(3-acetyl-5-(2-methylpyrimidin-5-yl)-1H-indazol-1-yl)acetyl)-4-fluoropyrrolidine-2-carboxamido)picolinate (1.75 g, 3.13 mmol) was dissolved in a mixture of CH$_3$OH-THF-H$_2$O (5 mL-5 mL-5 mL) and treated with LiOH (225 mg, 9.4 mmol). The reaction mixture was stirred overnight at rt. The volatiles are evaporated under reduce pressure and the remaining residue was acidified with 10% citric acid (10 mL). The solid was collected, washed with water, and dried for use in the next step.

Step-5: 6-((2S,4R)-1-(2-(3-Acetyl-5-(2-methylpyrimidin-5-yl)-1H-indazol-1-yl)acetyl)-4-fluoropyrrolidine-2-carboxamido)-N,N-dimethylpicolinamide (618)

To the solution of 6-((2S,4R)-1-(2-(3-acetyl-5-(2-methylpyrimidin-5-yl)-1H-indazol-1-yl)acetyl)-4-fluoropyrrolidine-2-carboxamido)picolinic acid (134 mg, 0.25 mmol), dimethylamine hydrochloride (41 mg, 0.50 mmol) in DMF (3.0 mL), HATU (114 mg, 0.30 mmol) was added, followed by dropwise addition of DIEA (4.0 eq) at room temperature. The mixture was stirred for 1 h at room temperature and the solution was purified by preparative HPLC to afford 104.4 mg of the title compound. $^1$H NMR (400 MHz, DMSO-d$_6$): (major rotamer) δ 2.10-2.27 (m, 1H), 2.50-2.61 (m, 1H), 2.65 (s, 3H), 2.69 (s, 3H), 2.85 (s, 3H), 2.96 (s, 3H), 3.98-4.11 (m, 1H), 4.20-4.29 (m, 1H), 4.70 (t, J=8.0 Hz, 1H), 5.59 (d, J=52.4 Hz, 1H), 5.67-5.87 (m, 2H), 7.17 (d, J=7.6 Hz, 1H), 7.79-7.88 (m, 3H), 8.07 (d, J=8.4 Hz, 1H), 8.43 (s, 1H), 9.06 (s, 2H), 10.87 (s, 1H) ppm. $^{19}$F NMR (376 MHz, DMSO-d$_6$): (major rotamer) δ −175.70; LC (method A): t$_R$=1.20 min. LC/MS (EI) m/z: [M+H]$^+$ 573.33

483
6-((2S,4R)-1-(2-(3-Acetyl-5-(2-methylpyrimidin-5-yl)-1H-indazol-1-yl)acetyl)-4-fluoropyrrolidine-2-carboxamido)-N-methylpicolinamide (619)

484
(2S,4R)-1-(2-(3-Acetyl-5-(2-methylpyrimidin-5-yl)-1H-pyrazolo[3,4-c]pyridin-1-yl)acetyl)-N-(6-bromopyridin-2-yl)-4-fluoropyrrolidine-2-carboxamide (633)

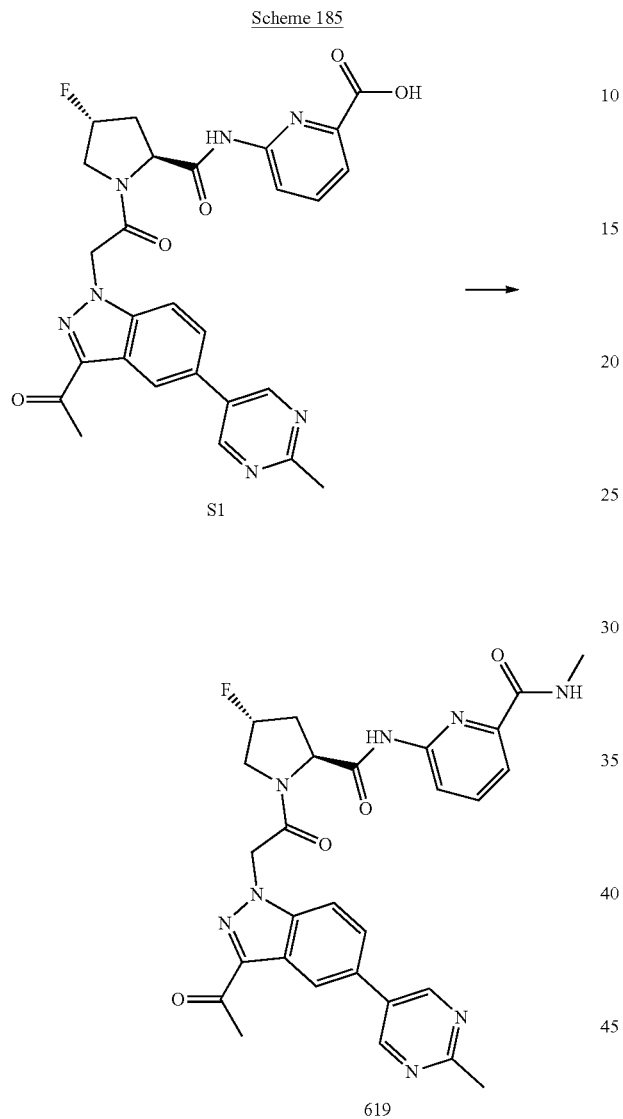

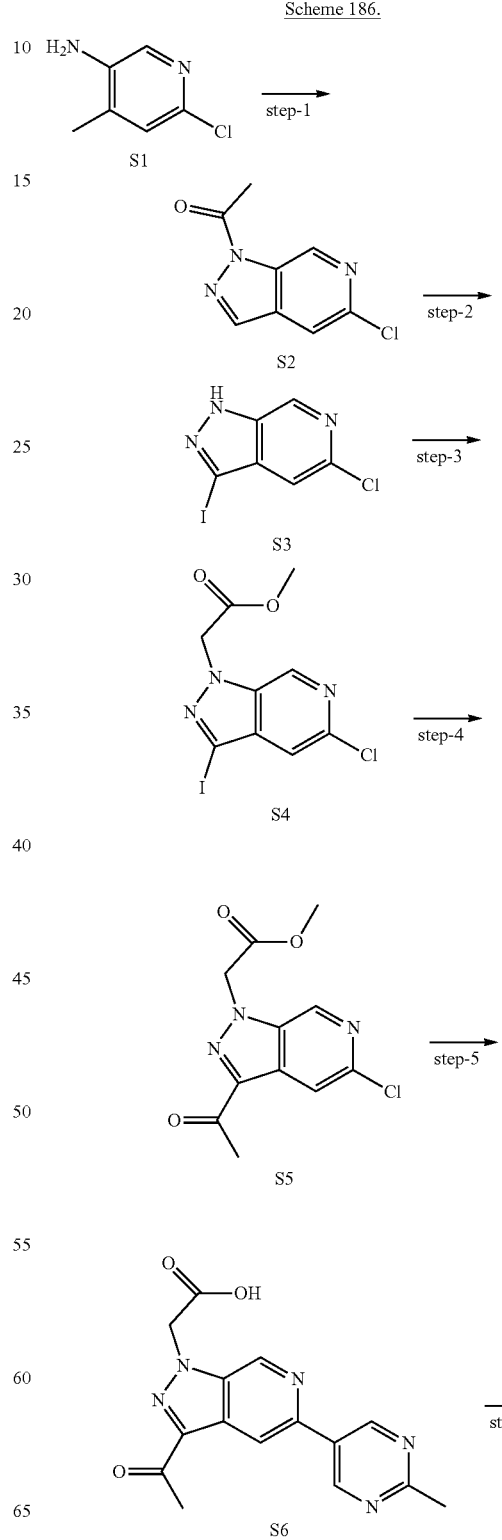

To the solution of 6-((2S,4R)-1-(2-(3-acetyl-5-(2-methylpyrimidin-5-yl)-1H-indazol-1-yl)acetyl)-4-fluoropyrrolidine-2-carboxamido)picolinic acid (134 mg, 0.25 mmol), methylamine hydrochloride (34 mg, 0.50 mmol) in DMF (3.0 mL), HATU (114 mg, 0.30 mmol) was added, followed by dropwise addition of DIEA (4.0 eq) at room temperature. The mixture was stirred for 1 h at room temperature and the solution was purified by preparative HPLC to afford 104.4 mg of the title compound. $^1$H NMR (400 MHz, DMSO-$d_6$): (major rotamer) δ 2.13-2.30 (m, 1H), 2.50-2.60 (m, 1H), 2.65 (s, 3H), 2.69 (s, 3H), 2.82 (d, J=4.8 Hz, 3H), 3.97-4.10 (m, 1H), 4.22-4.31 (m, 1H), 4.74 (t, J=8.0 Hz, 1H), 5.58 (d, J=52.4 Hz, 1H), 5.68-5.87 (m, 2H), 7.67 (d, J=7.6 Hz, 1H), 7.85 (s, 2H), 7.93 (t, J=8.0 Hz, 1H), 8.15 (d, J=8.4 Hz, 1H), 8.43 (s, 1H), 9.06 (s, 2H), 10.74 (s, 1H) ppm. $^{19}$F NMR (376 MHz, DMSO-$d_6$): (major rotamer) δ −175.65; LC (method A): $t_R$=1.21 min. LC/MS (EI) m/z: [M+H]$^+$ 559.33

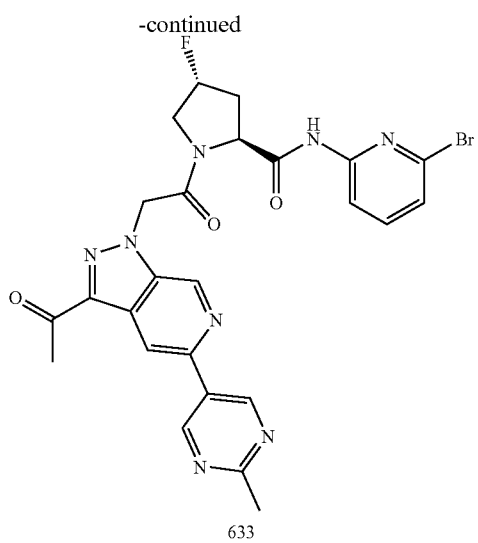

633

Step 1: 1-(5-Chloro-1H-pyrazolo[3,4-c]pyridin-1-yl)ethan-1-one (S2)

To the suspension of 6-chloro-4-methylpyridin-3-amine (10.0 g, 70 mmol) in toluene (110 mL), KOAc (8.2 g, 84.0 mmol) was added in one portion, followed by addition of Ac$_2$O (84 mmol). The mixture was heated at 70° C. overnight. Then, to the mixture, isoamyl nitrite (10.4 mL, 77 mmol) was added. The mixture was heated at 95° C. for 30 hr under Ar. The reaction was cooled to room temperature and filtered through a short pad of celite, and the residue was rinsed with ethyl acetate. The combined solution was concentrated and the resulting residue was purified to afford title compound.

Step 2: 5-Chloro-3-iodo-1H-pyrazolo[3,4-c]pyridine (S3)

To the solution of 1-(5-chloro-1H-pyrazolo[3,4-c]pyridin-1-yl)ethan-1-one (2.12 g, 10.83 mmol) in anhydrous methanol (30.0 ml), sodium methoxide (25% in methanol) (5.0 mL) was added. The mixture was stirred at room temperature for 20 minutes, and then iodine (3.30 g) was added in one portion. The mixture was stirred for additional 2 hr. The volatiles are removed, and the residue was mixed with ethyl acetate and filtered through a short pad of silica gel. The filtrate was concentrated and the resulting solid was used for next step without further purification.

Step 3: Methyl 2-(5-chloro-3-iodo-1H-pyrazolo[3,4-c]pyridin-1-yl)acetate (S4)

To the solution of 5-chloro-3-iodo-1H-pyrazolo[3,4-c]pyridine obtained from above step in CH$_3$CN (30 mL), methyl 2-bromoacetate (2.0 g, 1.23 mL, 13.0 mmol) and solid potassium carbonate (4.50 g, 33.0 mmol) are added. The mixture was refluxed in an oil bath overnight under Ar. The reaction was cooled to room temperature and filtered through a pad of celite. The solid cake was washed with additional CH$_3$CN (20 mL), and the combined solution was concentrated. The residue was purified to afford 1.83 g of desire product.

Step 4: Methyl 2-(3-acetyl-5-chloro-1H-pyrazolo[3,4-c]pyridin-1-yl)acetate (S5)

To the degassed solution of methyl 2-(5-chloro-3-iodo-1H-pyrazolo[3,4-c]pyridin-1-yl)acetate (1.83 g, 5.2 mmol) in DMF (20 mL), tributyl(1-ethoxyvinyl)stannane (1.93 mL, 5.72 mmol) and Pd(PPh$_3$)$_4$ (500 mg) are added under argon. The mixture was heated at 100° C. overnight and then cooled to room temperature. To the solution, aqueous HCl (1N, 15 mL) was added, and the mixture was stirred for 30 minutes at room temperature. The volatiles are removed, and the residue was mixed with ethyl acetate and water. The organic layer was separated from aqueous phase, and washed with brine. The organic phase was dried over MgSO$_4$. The solution was filtered through a short pad of silica gel. The filtrate was concentrated and the residue was purified to provide 987 mg of title product.

Step 5: 2-(3-Acetyl-5-(2-methylpyrimidin-5-yl)-1H-pyrazolo[3,4-c]pyridin-1-yl)acetic acid (S6)

Methyl 2-(3-acetyl-5-chloro-1H-pyrazolo[3,4-c]pyridin-1-yl)acetate (670 mg, 2.50 mmol), 2-methyl-5-(4,4,5,5-tetramethyl-1,3,2-dioxaborolan-2-yl)pyrimidine (609 mg, 2.76 mmol) and K$_3$PO$_4$ (1.60 g, 7.50 mmol) are mixed in co-solvent of dioxane (16 ml) and +H$_2$O (4 ml). The mixture was degassed and refilled with argon. To the mixture, Pd(PPh$_3$)$_4$ (0.1 eq) was added under Ar. The reaction was heated in an oil bath (125° C.) for 30 hrs. The reaction was cooled to room temperature and the volatiles are evaporated. The remaining materials are purified to afford 240 mg of title product.

Step 6: (2S,4R)-1-(2-(3-Acetyl-5-(2-methylpyrimidin-5-yl)-1H-pyrazolo[3,4-c]pyridin-1-yl)acetyl)-N-(6-bromopyridin-2-yl)-4-fluoropyrrolidine-2-carboxamide (633)

To the solution of (2S,4R)—N-(6-bromopyridin-2-yl)-4-fluoropyrrolidine-2-carboxamide hydrochloride (117 mg, 0.32 mmol), 2-(3-acetyl-5-(2-methylpyrimidin-5-yl)-1H-pyrazolo[3,4-c]pyridin-1-yl)acetic acid (0.32 mmol) in DMF (3.0 mL), HATU (146 mg, 0.38 mmol) was added, followed by dropwise addition of DIEA (4.0 eq) at room temperature. The mixture was stirred for 1 h at room temperature and the solution was purified by preparative HPLC to afford 118.4 mg of the title compound. $^1$H NMR (400 MHz, DMSO-d$_6$): (major rotamer) δ2.10-2.27 (m, 1H), 2.54-2.65 (m, 1H), 2.68 (s, 3H), 2.70 (s, 3H), 4.00-4.13 (m, 1H), 4.20-4.28 (m, 1H), 4.71 (t, J=8.4 Hz, 1H), 5.55 (d, J=52.4 Hz, 1H), 5.78-6.00 (m, 2H), 7.30 (d, J=7.6 Hz, 1H), 7.70 (t, J=8.0 Hz, 1H), 8.02 (d, J=8.0 Hz, 1H), 8.58 (s, 1H), 9.28 (s, 1H), 9.35 (s, 1H), 11.02 (s, 1H) ppm; $^{19}$F NMR (376 MHz, DMSO-d$_6$): (major rotamer) δ −175.65; LC (method A): $t_R$=1.57 min. LC/MS (EI) m/z: [M+H]$^+$ 581.24, 583.27

487

(2S,4S)-1-(2-(3-Acetyl-5-(2-methylpyrimidin-5-yl)-1H-indazol-1-yl)acetyl)-N-(6-bromo-3-methylpyridin-2-yl)-4-methylpyrrolidine-2-carboxamide (643)

Scheme 187

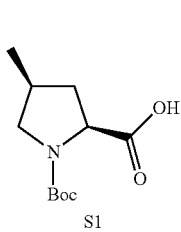
S1

+

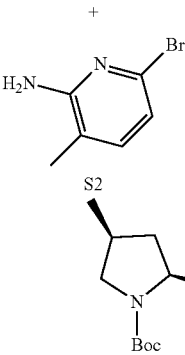
S2

Step1 →

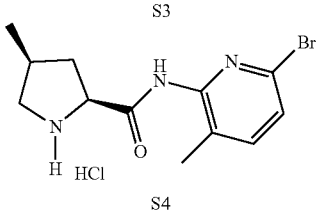
S3

Step2 →

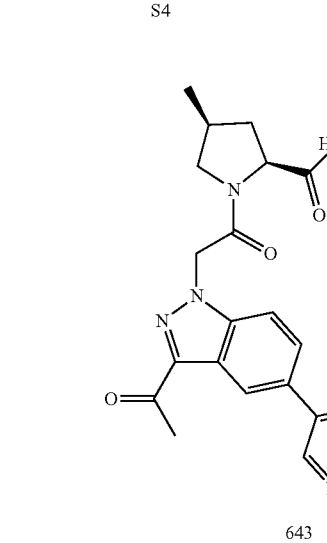
S4

Step3 →

643

Step 1: tert-Butyl (2S,4S)-2-((6-bromo-3-methylpyridin-2-yl)carbamoyl)-4-methylpyrrolidine-1-carboxylate (S3)

In a pre-dried flask, (2S,4S)-1-(tert-butoxycarbonyl)-4-methylpyrrolidine-2-carboxylic acid (purchased from Aldrich) (230 mg, 1.0 mmol), 6-bromo-3-methylpyridin-2-amine (188 mg, 1.0 mmol) are placed, and then anhydrous DCM (15 mL) was added. The flask was placed in an ice bath. To the solution, dry pyridine (0.25 mL, 3.0 mmol) was added in one portion, followed by addition of POCl$_3$ (100 µL, 1.0 mmol). After completion of addition, the mixture was stirred for 4 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 194 mg pure product. $^1$H NMR (400 MHz, DMSO-d$_6$): (major rotamer) δ 1.06 (d, J=6.4 Hz, 3H), 1.35 (s, 9H), 1.38-1.49 (m, 1H), 2.11 (s, 3H), 2.15-2.25 (m, 1H), 2.42-2.50 (m, 1H), 2.84-2.90 (m, 1H), 3.61-3.65 (m, 1H), 4.28 (t, J=8.0 Hz, 1H), 7.43 (d, J=7.6 Hz, 1H), 7.63 (t, J=7.6 Hz, 1H), 10.25 ppm. LC (method A): t$_R$=2.00 min. LC/MS (EI) m/z: [M+H]$^+$ 398.25

Step 2: (2S,4S)-N-(6-Bromo-3-methylpyridin-2-yl)-4-methylpyrrolidine-2-carboxamide hydrochloride (S4)

Tert-butyl (2S,4S)-2-((6-bromo-3-methylpyridin-2-yl)carbamoyl)-4-methylpyrrolidine-1-carboxylate (182 mg, 0.456 mmol) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (2S,4S)-1-(2-(3-Acetyl-5-(2-methylpyrimidin-5-yl)-1H-indazol-1-yl)acetyl)-N-(6-bromo-3-methylpyridin-2-yl)-4-methylpyrrolidine-2-carboxamide (643)

To the solution of (2S,4S)-N-(6-bromo-3-methylpyridin-2-yl)-4-methylpyrrolidine-2-carboxamide hydrochloride (0.456 mmol) from above step, 2-(5-(2-methylpyrimidin-5-yl)-3-((methylsulfonyl)carbamoyl)-1H-indazol-1-yl)acetic acid (140 mg, 0.45 mmol) in DMF (3.0 mL), HATU (190 mg) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 186.2 mg of the title compound. $^1$H NMR (400 MHz, DMSO-d$_6$): (major rotamer) δ 1.14 (d, J=6.4 Hz, 3H), 1.50-1.59 (m, 1H), 2.00 (s, 3H), 2.39-2.48 (m, 2H), 2.64 (s, 3H), 2.69 (s, 3H), 3.26-3.33 (m, 1H), 4.07 (t, J=7.6 Hz, 1H), 4.44 (t, J=8.0 Hz, 1H), 5.53-5.75 (m, 2H), 7.42 (d, J=8.0 Hz, 1H), 7.52 (d, J=7.6 Hz, 1H), 7.83 (s, 2H), 8.43 (s, 1H), 9.04 (s, 2H), 10.34 (s, 1H) ppm. LC (method A): t$_R$=1.67 min. LC/MS (EI) m/z: [M+H]$^+$ 590.34, 592.30

(2S,4R)-1-(2-(3-Acetyl-5-(2-methylpyrimidin-5-yl)-1H-indazol-1-yl)acetyl)-N-(6-bromo-3-methylpyridin-2-yl)-4-methylpyrrolidine-2-carboxamide (644)

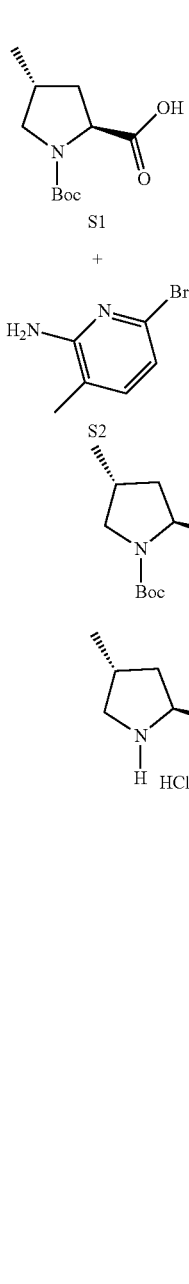

Scheme 188

644

Step 1: tert-Butyl (2S,4R)-2-((6-bromo-3-methylpyridin-2-yl)carbamoyl)-4-methylpyrrolidine-1-carboxylate (S3)

In a pre-dried flask, (2S,4R)-1-(tert-butoxycarbonyl)-4-methylpyrrolidine-2-carboxylic acid (purchased from Synthonix) (230 mg, 1.0 mmol), 6-bromo-3-methylpyridin-2-amine (188 mg, 1.0 mmol) are placed, and then anhydrous DCM (15 mL) was added. The flask was placed in an ice bath. To the solution, dry pyridine (0.25 mL, 3.0 mmol) was added in one portion, followed by addition of POCl$_3$ (100 µL, 1.0 mmol). After completion of addition, the mixture was stirred for 4 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 227 mg of pure product. $^1$H NMR (400 MHz, DMSO-d$_6$): (major rotamer) δ 0.99 (d, J=6.4 Hz, 3H), 1.36 (s, 9H), 1.82-1.93 (m, 1H), 2.02-2.06 (m, 1H), 2.11 (s, 3H), 2.30-2.37 (m, 1H), 2.86 (t, J=8.0 Hz, 1H), 3.57-3.61 (m, 1H), 4.35 (t, J=8.0 Hz, 1H), 7.43 (d, J=7.6 Hz, 1H), 7.63 (t, J=7.6 Hz, 1H), 10.25 ppm. LC (method A): t$_R$=2.04 min. LC/MS (EI) m/z: [M+H]$^+$ 398.25

Step 2: (2S,4R)—N-(6-Bromo-3-methylpyridin-2-yl)-4-methylpyrrolidine-2-carboxamide hydrochloride (S4)

Tert-butyl (2S,4R)-2-((6-bromo-3-methylpyridin-2-yl)carbamoyl)-4-methylpyrrolidine-1-carboxylate (227 mg, 0.57 mmol) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification. LC (method A): t$_R$=0.63 min. LC/MS (EI) m/z: [M+H]$^+$ 298.14

Step 3: (2S,4R)-1-(2-(3-Acetyl-5-(2-methylpyrimidin-5-yl)-1H-indazol-1-yl)acetyl)-N-(6-bromo-3-methylpyridin-2-yl)-4-methylpyrrolidine-2-carboxamide (644)

To the solution of (2S,4R)—N-(6-bromo-3-methylpyridin-2-yl)-4-methylpyrrolidine-2-carboxamide hydrochloride (0.456 mmol) from above step, 2-(5-(2-methylpyrimidin-5-yl)-3-((methylsulfonyl)carbamoyl)-1H-indazol-1-yl)acetic acid (177 mg, 0.57 mmol) in DMF (3.0 mL), HATU (217 mg) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 270.4 mg of the title compound. $^1$H NMR (400 MHz, DMSO-d$_6$): (major rotamer) δ 1.12 (d, J=6.4 Hz, 3H), 1.87-1.92 (m, 1H), 2.01 (s, 3H), 2.10-2.15 (m, 1H), 2.52-2.58 (m, 1H), 2.65 (s, 3H), 2.67 (s, 3H), 3.31-3.37 (m, 1H), 4.04 (t, J=7.6 Hz, 1H), 4.55 (d, J=7.6 Hz, 1H), 5.60-5.80 (m, 2H), 7.44 (d, J=8.0 Hz, 1H), 7.62 (d, J=7.6 Hz, 1H), 7.83 (s, 2H), 8.43 (s, 1H), 9.04 (s, 2H), 10.28 (s, 1H) ppm. LC (method A): t$_R$=1.70 min. LC/MS (EI) m/z: [M+H]$^+$ 590.27, 592.30

(2S,5S)-1-(2-(3-Acetyl-5-(2-methylpyrimidin-5-yl)-1H-indazol-1-yl)acetyl)-N-(6-bromo-3-methylpyridin-2-yl)-5-methylpyrrolidine-2-carboxamide (646)

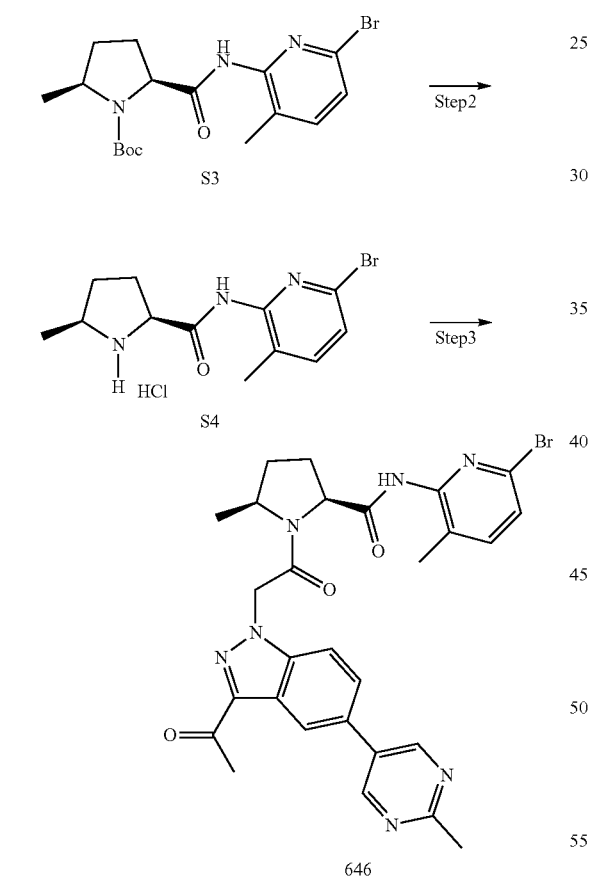

Step 1: tert-Butyl (2S,5S)-2-((6-bromo-3-methyl-pyridin-2-yl)carbamoyl)-5-methylpyrrolidine-1-carboxylate (S3)

In a pre-dried flask, (2S,5S)-1-(tert-butoxycarbonyl)-5-methylpyrrolidine-2-carboxylic acid (purchased from Aldrich) (230 mg, 1.0 mmol), 6-bromo-3-methylpyridin-2-amine (188 mg, 1.0 mmol) are placed, and then anhydrous DCM (15 mL) was added. The flask was placed in an ice bath. To the solution, dry pyridine (0.25 mL, 3.0 mmol) was added in one portion, followed by addition of POCl$_3$ (100 µL, 1.0 mmol). After completion of addition, the mixture was stirred for 4 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 310.0 mg pure product. $^1$H NMR (400 MHz, DMSO-d$_6$): (major rotamer) δ 1.21 (d, J=6.4 Hz, 3H), 1.37 (s, 9H), 1.97-2.00 (m, 2H), 1.57 (s, 1H), 2.11 (s, 3H), 2.15-2.22 (m, 1H), 3.88 (s, 1H), 4.35 (t, J=8.0 Hz, 1H), 7.43 (d, J=7.6 Hz, 1H), 7.63 (t, J=7.6 Hz, 1H), 10.23 ppm. LC (method A): t$_R$=2.11 min. LC/MS (EI) m/z: [M+H]$^+$ 398.25

Step 2: (2S,5S)—N-(6-Bromo-3-methylpyridin-2-yl)-5-methylpyrrolidine-2-carboxamide hydrochloride (S4)

Tert-butyl (2S,5S)-2-((6-bromo-3-methylpyridin-2-yl)carbamoyl)-5-methylpyrrolidine-1-carboxylate (310 mg, 0.78 mmol) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification. LC (method A): t$_R$=0.51 min. LC/MS (EI) m/z: [M+H]$^+$ 298.14

Step 3: (2S,5S)-1-(2-(3-Acetyl-5-(2-methylpyrimidin-5-yl)-1H-indazol-1-yl)acetyl)-N-(6-bromo-3-methylpyridin-2-yl)-5-methylpyrrolidine-2-carboxamide (646)

To the solution of (2S,5S)—N-(6-bromo-3-methylpyridin-2-yl)-5-methylpyrrolidine-2-carboxamide hydrochloride (0.456 mmol) from above step, 2-(5-(2-methylpyrimidin-5-yl)-3-((methylsulfonyl)carbamoyl)-1H-indazol-1-yl)acetic acid (140 mg, 0.45 mmol) in DMF (3.0 mL), HATU (190 mg) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 300.7 mg of the title compound. $^1$H NMR (400 MHz, DMSO-d$_6$): (major rotamer) δ 1.42 (d, J=6.4 Hz, 3H), 1.78-1.80 (m, 1H), 1.97-2.04 (m, 1H), 2.03 (s, 3H), 2.08-2.13 (m, 1H), 2.27-2.34 (m, 1H), 2.65 (s, 3H), 2.69 (s, 3H), 4.48-4.52 (m, 2H), 5.50-5.83 (m, 2H), 7.51 (d, J=7.6 Hz, 1H), 7.59 (d, J=7.6 Hz, 1H), 7.80-7.89 (m, 2H), 8.43 (s, 1H), 9.04 (s, 2H), 10.33 (s, 1H) ppm. LC (method A): t$_R$=1.70 min. LC/MS (EI) m/z: [M+H]$^+$ 590.34, 592.30

(1S,3S,5S)-2-(2-(3-Acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (647)

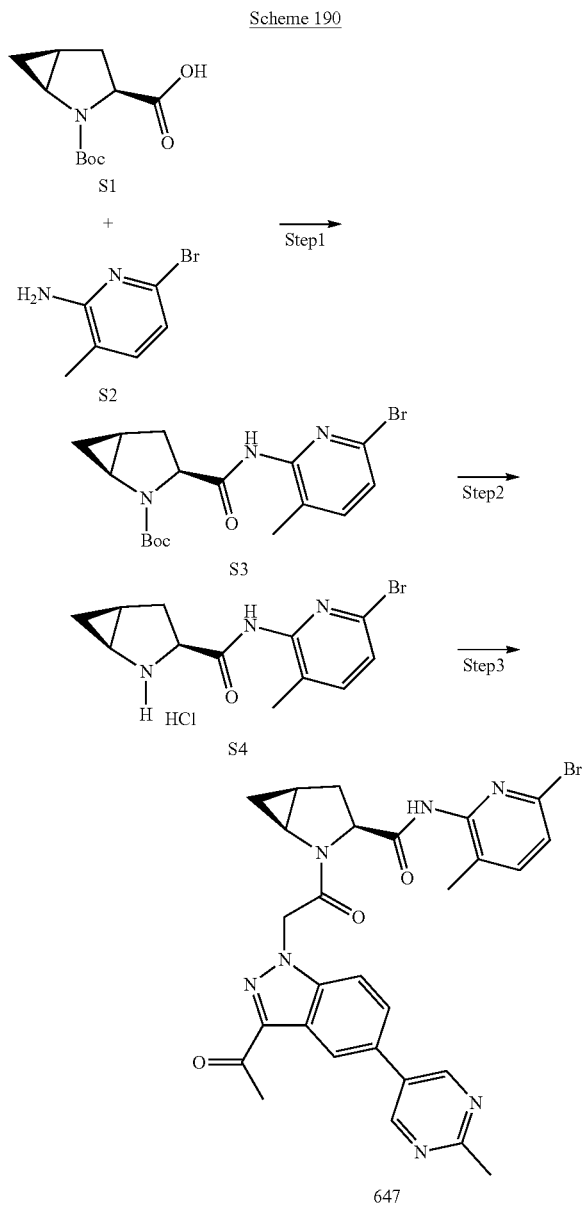

Scheme 190

Step 1: tert-Butyl (1S,3S,5S)-3-((6-bromo-3-methylpyridin-2-yl)carbamoyl)-2-azabicyclo[3.1.0]hexane-2-carboxylate (S3)

In a pre-dried flask, (1S,3S,5S)-2-(tert-butoxycarbonyl)-2-azabicyclo[3.1.0]hexane-3-carboxylic acid (228 mg, 1.0 mmol), 6-bromo-3-methylpyridin-2-amine (188 mg, 1.0 mmol) are placed, and then anhydrous DCM (15 mL) was added. The flask was placed in an ice bath. To the solution, dry pyridine (0.25 mL, 3.0 mmol) was added in one portion, followed by addition of POCl$_3$ (100 μL, 1.0 mmol). After completion of addition, the mixture was stirred for 4 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 302.0 mg pure product. $^1$H NMR (400 MHz, DMSO-d$_6$): (major rotamer) δ 0.62-0.64 (m, 1H), 0.97 (s, br, 1H), 1.34 (s, 9H), 1.49-1.58 (m, 1H), 1.90-1.96 (m, 1H), 2.10 (s, 3H), 2.54-2.69 (m, 1H), 3.37-3.41 (m, 1H), 4.66 (t, J=11.2 Hz, 1H), 7.43 (d, J=7.6 Hz, 1H), 7.63 (t, J=7.6 Hz, 1H), 10.31 ppm. LC (method A): t$_R$=2.01 min. LC/MS (EI) m/z: [M+H]$^+$ 396.15, 398.25

Step 2: (1S,3S,5S)—N-(6-Bromo-3-methylpyridin-2-yl)-2-azabicyclo[3.1.0]hexane-3-carboxamide hydrochloride (S4)

Tert-butyl (1S,3S,5S)-3-((6-bromo-3-methylpyridin-2-yl)carbamoyl)-2-azabicyclo[3.1.0]hexane-2-carboxylate (302 mg, 0.762 mmol) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (1S,3S,5S)-2-(2-(3-Acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (647)

To the solution of (1S,3S,5S)—N-(6-bromo-3-methylpyridin-2-yl)-2-azabicyclo[3.1.0]hexane-3-carboxamide hydrochloride (225 mg, 0.61 mmol) from above step, 2-(5-(2-methylpyrimidin-5-yl)-3-((methylsulfonyl)carbamoyl)-1H-indazol-1-yl)acetic acid (189 mg, 0.61 mmol) in DMF (3.0 mL), HATU (255 mg, 0.67 mmol) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 230.5 mg of the title compound. $^1$H NMR (400 MHz, DMSO-d$_6$): (major rotamer) δ 0.89-0.94 (m, 1H), 1.10-1.24 (m, 1H), 1.81-1.87 (m, 1H), 1.97-2.04 (m, 1H), 2.01 (s, 3H), 2.65 (s, 3H), 2.69 (s, 3H), 2.67-2.69 (m, 1H), 3.86-3.88 (m, 1H), 4.90 (d, J=11.2 Hz, 1H), 5.59-6.03 (m, 2H), 7.41 (d, J=7.6 Hz, 1H), 7.59 (d, J=7.6 Hz, 1H), 7.79-7.87 (m, 2H), 8.43 (s, 1H), 9.04 (s, 2H), 10.37 (s, 1H) ppm. LC (method A): t$_R$=1.67 min. LC/MS (EI) m/z: [M+H]$^+$ 590.20

495

(2S,5R)-1-(2-(3-Acetyl-5-(2-methylpyrimidin-5-yl)-1H-indazol-1-yl)acetyl)-N-(6-bromo-3-methylpyridin-2-yl)-5-methylpyrrolidine-2-carboxamide (731)

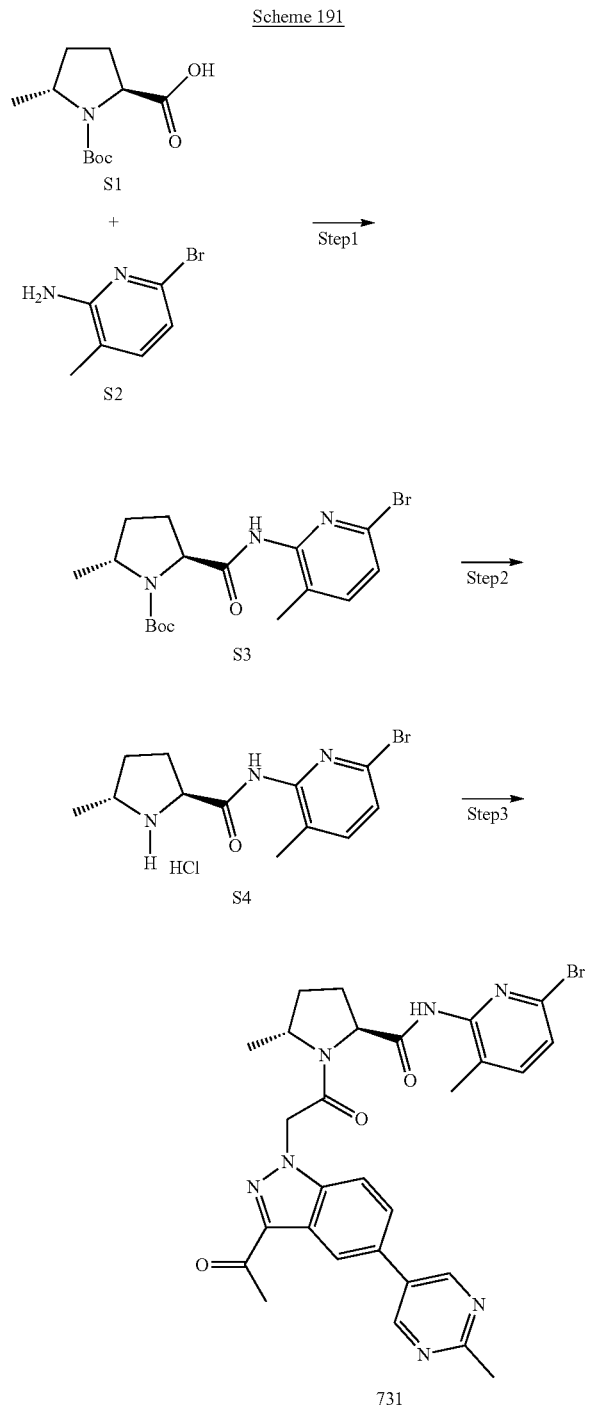

Step 1: tert-Butyl (2S,5R)-2-((6-bromo-3-methylpyridin-2-yl)carbamoyl)-5-methylpyrrolidine-1-carboxylate (S3)

In a pre-dried flask, (2S,5S)-1-(tert-butoxycarbonyl)-4-methylpyrrolidine-2-carboxylic acid (230 mg, 1.0 mmol), 6-bromo-3-methylpyridin-2-amine (188 mg, 1.0 mmol) are placed, and then anhydrous DCM (15 mL) was added. The flask was placed in an ice bath. To the solution, dry pyridine (0.25 mL, 3.0 mmol) was added in one portion, followed by addition of POCl$_3$ (100 μL, 1.0 mmol). After completion of addition, the mixture was stirred for 4 hours at 0° C., and then the reaction was quenched with water (15 mL). The DCM layer was collected and the aqueous phase was extracted with DCM (15 mL×2). The combined DCM solution was washed with brine, and dried over MgSO$_4$. The solution was filtered and concentrated; the resulting residue was purified to give 188 mg pure product. $^1$H NMR (400 MHz, DMSO-d$_6$): (major rotamer) δ 1.12 (t, J=8.8 Hz, 3H), 1.34 (s, 9H), 1.46-1.55 (m, 1H), 1.84-1.91 (m, 1H), 2.02-2.08 (m, 1H), 2.11 (s, 3H), 2.28-2.37 (m, 1H), 3.95-4.02 (m, 1H), 4.35 (t, J=8.8 Hz, 1H), 7.43 (d, J=7.6 Hz, 1H), 7.62 (t, J=7.6 Hz, 1H), 10.26 ppm. LC (method A): t$_R$=2.10 min. LC/MS (EI) m/z: [M+H]$^+$ 398.25

Step 2: (2S,5R)—N-(6-Bromo-3-methylpyridin-2-yl)-5-methylpyrrolidine-2-carboxamide hydrochloride (S4)

Tert-butyl (2S,5R)-2-((6-bromo-3-methylpyridin-2-yl)carbamoyl)-4-methylpyrrolidine-1-carboxylate (310 mg, 0.78 mmol) from step 1 was taken in 4N HCl dioxane (2.0 mL) and the resulting reaction mixture was stirred at room temperature for 2 h. After completion of the reaction monitored by HPLC, the solvent was removed under reduced pressure. The remaining residue was used directly without further purification.

Step 3: (2S,5R)-1-(2-(3-Acetyl-5-(2-methylpyrimidin-5-yl)-1H-indazol-1-yl)acetyl)-N-(6-bromo-3-methylpyridin-2-yl)-5-methylpyrrolidine-2-carboxamide (731)

To the solution of (2S,5R)—N-(6-bromo-3-methylpyridin-2-yl)-4-methylpyrrolidine-2-carboxamide hydrochloride (0.47 mmol) from above step, 2-(5-(2-methylpyrimidin-5-yl)-3-((methylsulfonyl)carbamoyl)-1H-indazol-1-yl)acetic acid (146 mg, 0.47 mmol) in DMF (3.0 mL), HATU (215 mg) was added, followed by dropwise addition of DIEA (4.0 eq) at room temperature. The mixture was stirred for 1 h at room temperature and the volatiles are evaporated. The residue was diluted with 50 mL of 10% sodium carbonate and extracted with ethyl acetate. The combined organic solution was successively washed with water, brine and dried over MgSO$_4$. The solution was filtered and the solvent was removed. The residue was purified to afford 77.8 mg of the title compound. $^1$H NMR (400 MHz, DMSO-d$_6$): (major rotamer) δ 1.40 (d, J=6.4 Hz, 3H), 1.73-1.79 (m, 1H), 1.92-2.06 (m, 1H), 1.97 (s, 3H), 2.22-2.32 (m, 1H), 2.41-2.45 (m, 1H), 2.64 (s, 3H), 2.68 (s, 3H), 4.52 (d, J=8.4 Hz, 1H), 4.59 (t, J=6.8 hz, 1H), 5.57-5.83 (m, 2H), 7.41 (d, J=7.6 Hz, 1H), 7.59 (d, J=7.6 Hz, 1H), 7.70-7.87 (m, 2H), 8.43 (s, 1H), 9.03 (s, 2H), 10.29 (s, 1H) ppm. LC (method A): t$_R$=1.64 min. LC/MS (EI) m/z: [M+H]$^+$ 590.34, 592.30.

497

(2S,4R)—N-(6-Bromopyridin-2-yl)-4-fluoro-1-(2-(3-((S)-1-hydroxyethyl)-5-(2-methylpyrimidin-5-yl)-1H-indazol-1-yl)acetyl)pyrrolidine-2-carboxamide (425) and (2S,4R)—N-(6-Bromopyridin-2-yl)-4-fluoro-1-(2-(3-((R)-1-hydroxyethyl)-5-(2-methylpyrimidin-5-yl)-1H-indazol-1-yl)acetyl)pyrrolidine-2-carboxamide (426)

Scheme 192

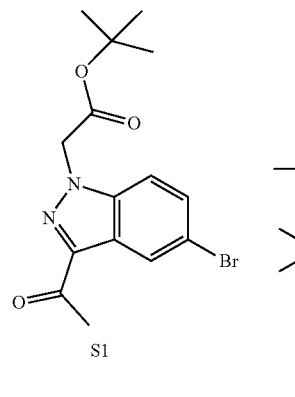

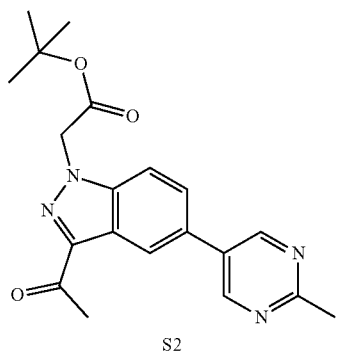

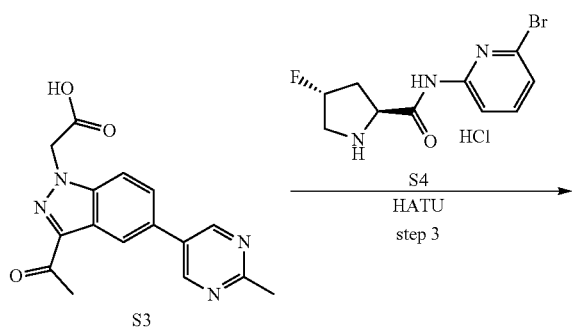

-continued

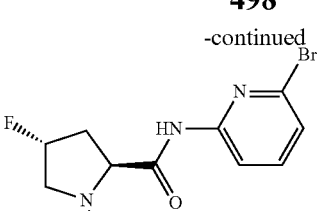

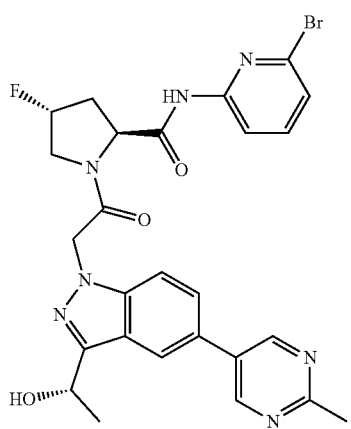

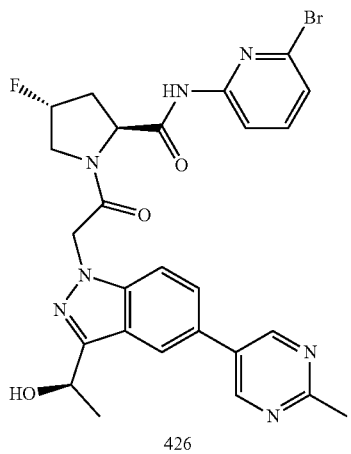

Step 1: tert-Butyl 2-(3-acetyl-5-(2-methylpyrimidin-5-yl)-1H-indazol-1-yl)acetate (S2)

A mixture of tert-butyl 2-(3-acetyl-5-bromo-1H-indazol-1-yl)acetate (353 mg), 2-methyl-5-(4,4,5,5-tetramethyl-1,3,2-dioxaborolan-2-yl)pyrimidine (242 mg), cesium carbonate (652 mg), DMF (4.5 mL), and water (0.5 mL) was purged with argon in a pressure vessel for 5 min. Tetrakis(triphenylphosphine)palladium (0) (20 mg) was then added under argon and the pressure vessel was sealed and heated at 100° C. overnight. The reaction mixture was cooled to room temperature and the solvent was removed under reduced pressure. The solvent was removed under reduced pressure and the remaining material was purified by silicagel chromatography to afford 360 mg.

Step 2: 2-(3-Acetyl-5-(2-methylpyrimidin-5-yl)-1H-indazol-1-yl)acetic acid (S3)

tert-butyl 2-(3-acetyl-5-(2-methylpyrimidin-5-yl)-1H-indazol-1-yl)acetate was dissolved in DCM (5 mL) and TFA (1 mL) was added. The reaction mixture was stirred overnight at room temperature and then the solvent was removed under reduced pressure. The remaining material was used directly in the next step.

Step 3 (2S,4R)-1-(2-(3-Acetyl-5-(2-methylpyrimidin-5-yl)-1H-indazol-1-yl)acetyl)-N-(6-bromopyridin-2-yl)-4-fluoropyrrolidine-2-carboxamide (S5)

To a solution of 2-(3-acetyl-5-(2-methylpyrimidin-5-yl)-1H-indazol-1-yl)acetic acid DMF (5 mL) was added DIEA (0.17 mL) followed by (2S,4R)—N-(6-bromopyridin-2-yl)-4-fluoropyrrolidine-2-carboxamide (102 mg). HATU (120 mg) was then added slowly and the reaction mixture was stirred for 18 h at rt. The reaction mixture was then added to water (10 mL) and extracted with EtOAc (2×15 mL). The organic layer was washed successively with an aq solution of NaHCO$_3$ (10 mL), water (10 mL), and brine (10 mL), then dried over Na$_2$SO$_4$ and concentrated under reduced pressure. The remaining residue was purified by HPLC to give the title compound.

Step 4 (2S,4R)—N-(6-Bromopyridin-2-yl)-4-fluoro-1-(2-(3-((S)-1-hydroxyethyl)-5-(2-methylpyrimidin-5-yl)-1H-indazol-1-yl)acetyl)pyrrolidine-2-carboxamide (425) and (2S,4R)—N-(6-Bromopyridin-2-yl)-4-fluoro-1-(2-(3-((R)-1-hydroxyethyl)-5-(2-methylpyrimidin-5-yl)-1H-indazol-1-yl)acetyl)pyrrolidine-2-carboxamide (426)

To a solution of (2S,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide (580 mg) in MeOH (20 mL) was added NaBH4 (38 mg) and stirred for 3 hr at room temperature. The reaction mixture was added acetone 1 mL and stirred for 1 h. Then removed solvent. The residue was separated isomer by chiral HPLC to obtained compound 425 and 426.

425: $^1$H NMR (400 MHz, DMSO-d$_6$) δ 1.58 (d, J=6.6 Hz, 3H), 2.03-2.25 (m, 1H), 2.57 (m, 1H), 2.68 (s, 3H), 3.92-4.01 (m, 1H), 4.20 (m, 1H), 4.61-4.70 (m, 1H), 5.09-5.20 (m, 1H), 5.28-5.49 (m, 2H), 5.50-5.63 (m, 2H), 7.33 (d, J=7.7 Hz, 1H), 7.63 (d, J=8.8 Hz, 1H), 7.67-7.86 (m, 2H), 8.04 (d, J=8.2 Hz, 1H), 8.25 (d, J=1.5 Hz, 1H), 9.03 (s, 2H), 10.99 (s, 1H); $^{19}$F NMR (376 MHz, DMSO) δ −175.67. LC (method A): t$_R$=1.40 min. LC/MS (EI) m/z: [M+H]$^+$ 582.

426: $^1$H NMR (400 MHz, DMSO-d$_6$) δ 1.58 (d, J=6.6 Hz, 3H), 2.03-2.25 (m, 1H), 2.57 (m, 1H), 2.68 (s, 3H), 3.92-4.01 (m, 1H), 4.20 (m, 1H), 4.61-4.70 (m, 1H), 5.09-5.20 (m, 1H), 5.28-5.49 (m, 2H), 5.50-5.63 (m, 2H), 7.33 (d, J=7.7 Hz, 1H), 7.63 (d, J=8.8 Hz, 1H), 7.67-7.86 (m, 2H), 8.04 (d, J=8.2 Hz, 1H), 8.25 (d, J=1.5 Hz, 1H), 9.03 (s, 2H), 10.99 (s, 1H); $^{19}$F NMR (376 MHz, DMSO) δ −175.64. LC (method A): t$_R$=1.40 min. LC/MS (EI) m/z: [M+H]$^+$ 582.

(1R,3S,5R)—N-(6-Bromopyridin-2-yl)-2-(2-(3-((S)-1-hydroxyethyl)-5-(2-methylpyrimidin-5-yl)-1H-indazol-1-yl)acetyl)-2-azabicyclo[3.1.0]hexane-3-carboxamide (409)

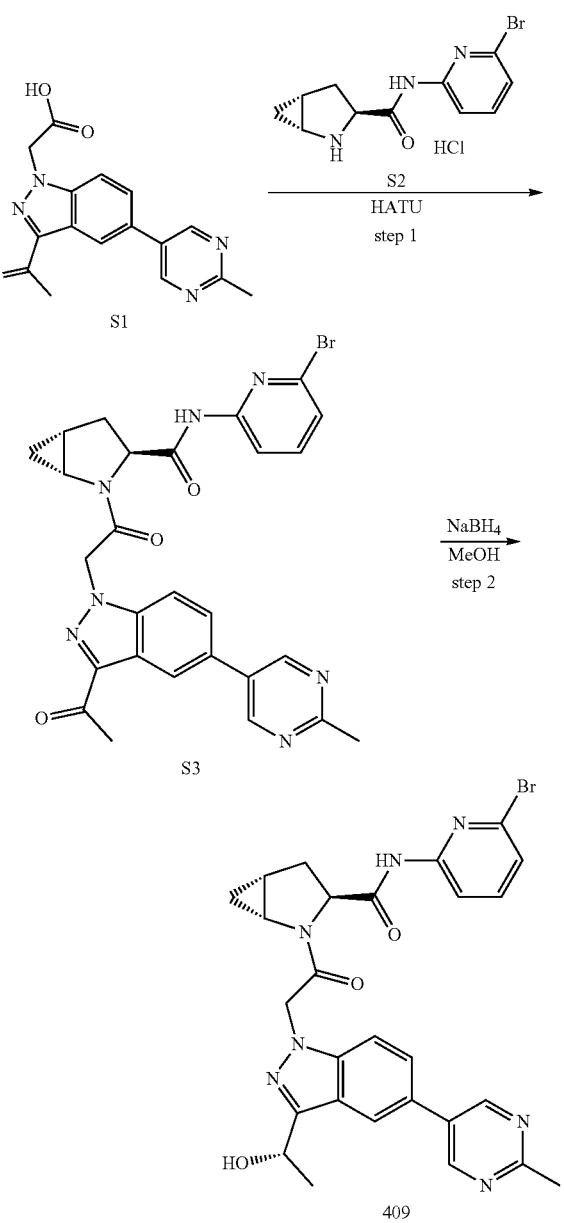

Scheme 194

Step 1 (1R,3S,5R)-2-(2-(3-Acetyl-5-(2-methylpyrimidin-5-yl)-1H-indazol-1-yl)acetyl)-N-(6-bromopyridin-2-yl)-2-azabicyclo[3.1.0]hexane-3-carboxamide (S3)

To a solution of 2-(3-acetyl-5-(2-methylpyrimidin-5-yl)-1H-indazol-1-yl)acetic acid (310 mg) DMF (5 mL) was added DIEA (0.17 mL) followed by (1R,3S,5R)—N-(6-bromopyridin-2-yl)-2-azabicyclo[3.1.0]hexane-3-carboxamide hydrochloride (320 mg). HATU (120 mg) was then added slowly and the reaction mixture was stirred for 18 h at rt. The reaction mixture was then added to water (10 mL) and extracted with EtOAc (2×15 mL). The organic layer was washed successively with an aq solution of $NaHCO_3$ (10 mL), water (10 mL), and brine (10 mL), then dried over $Na_2SO_4$ and concentrated under reduced pressure. The remaining residue was purified by HPLC to give the title compound.

Step 2 (1R,3S,5R)—N-(6-Bromopyridin-2-yl)-2-(2-(3-((S)-1-hydroxyethyl)-5-(2-methylpyrimidin-5-yl)-1H-indazol-1-yl)acetyl)-2-azabicyclo[3.1.0]hexane-3-carboxamide (409)

To a solution of (1R,3S,5R)-2-(2-(3-acetyl-5-(2-methyl-pyrimidin-5-yl)-1H-indazol-1-yl)acetyl)-N-(6-bromopyridin-2-yl)-2-azabicyclo[3.1.0]hexane-3-carboxamide (574 mg) in MeOH (5 mL) was added $NaBH_4$ (40 mg) then stirred for 3 hr at room temperature. The reaction mixture was then added AcOH and removed all solvent. The remaining residue was purified by HPLC to give the title compound. $^1$H NMR (400 MHz, DMSO) δ 0.72 (m, 1H), 0.98 (m, 1H), 1.24 (s, 1H), 1.59 (d, J=6.6 Hz, 3H), 1.83-1.94 (m, 1H), 2.20 (m, 1H), 2.31 (m, 1H), 2.68 (s, 3H), 3.76-3.83 (m, 1H), 4.40-4.49 (m, 1H), 5.16 (m, 1H), 5.34-5.46 (m, 2H), 5.70 (d, J=17.3 Hz, 1H), 7.33 (d, J=7.7 Hz, 1H), 7.58-7.79 (m, 2H), 8.04 (d, J=8.2 Hz, 1H), 8.22-8.30 (m, 1H), 9.03 (s, 2H), 10.75 (s, 1H). LC (method A): $t_R$=1.53 min. LC/MS (EI) m/z: [M+H]$^+$ 576.

(2S,4R)-1-(2-(3-Acetyl-5-(2-methylpyrimidin-5-yl)-1H-indazol-1-yl)acetyl)-4-fluoro-N-(2-methylpyridin-4-yl)pyrrolidine-2-carboxamide I (565)

To a solution of 2-(3-acetyl-5-(2-methylpyrimidin-5-yl)-1H-indazol-1-yl)acetic acid (310 mg) DMF (5 mL) was added DIEA (0.17 mL) followed by (2S,4R)-4-fluoro-N-(2-methylpyridin-4-yl)pyrrolidine-2-carboxamide hydrochloride (320 mg). HATU (120 mg) was then added slowly and the reaction mixture was stirred for 18 h at rt. The reaction mixture was then added to water (10 mL) and extracted with EtOAc (2×15 mL). The organic layer was washed successively with an aq solution of $NaHCO_3$ (10 mL), water (10 mL), and brine (10 mL), then dried over $Na_2SO_4$ and concentrated under reduced pressure. The remaining residue was purified by HPLC to give the title compound.

$^1$H NMR (400 MHz, DMSO) δ 2.18 (m, 1H), 2.38 (s, 3H), 2.51 (m, 3H), 2.65 (s, 3H), 3.98 (m, 1H), 4.07 (m, 1H), 4.25 (m, 1H), 4.55 (m, 1H), 5.52 (s, 1H), 5.62-5.80 (m, 2H), 5.86 (d, J=17.3 Hz, 1H), 7.30 (m, 1H), 7.39 (d, J=1.9 Hz, 1H), 7.75-7.92 (m, 1H), 8.26 (d, J=5.6 Hz, 1H), 8.43 (d, J=1.4 Hz, 1H), 9.04 (s, 2H), 10.42 (s, 1H). $^{19}$F NMR (376 MHz, DMSO-$d_6$): (major rotamer) δ −176.01. LC (method A): $t_R$=1.02 min. LC/MS (EI) m/z: [M+H]$^+$ 516.

2-Bromo-6-isocyanatopyridine

Scheme 196

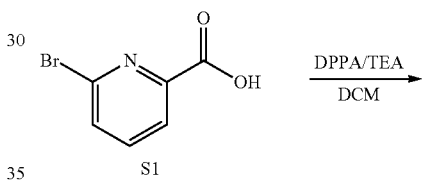

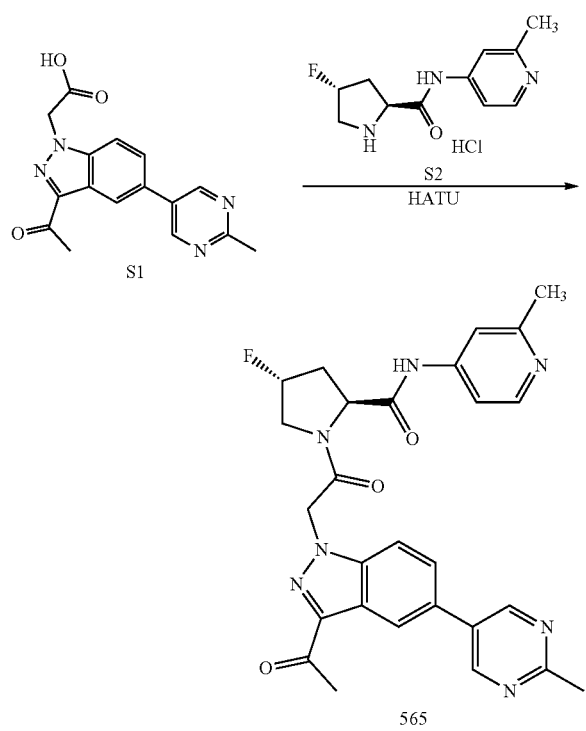

Step 1: 6-Bromopicolinoyl azide (S2)

Into a suspension of 6-bromopicolinic acid (0.294 g, 1.45 mmol) in DCM (10 mL), TEA (0.306 mL, 1.89 mmol) followed by DPPA (0.376, 1.75 mmol) was added at room temperature with stirring. After 1 hr, solvent was evaporated, and the crude was purified on ISCO with AcOEt in hexane (0-20%) as eluent to give 6-bromopicolinoyl azide (0.203 g) as white solid.

Step 2: 2-Bromo-6-isocyanatopyridine (S3)

6-bromopicolinoyl azide (0.203 g, 0.89 mmol) was dissolved in toluene (10 mL) and heated at 80° C. with stirring for 2 hr. Solvent was evaporated under reduced pressure to give 2-bromo-6-isocyanatopyridine (0.187 g)

503

(2R,4S))-2-(2-(3-Acetyl-5-(2-methylpyrimidin-5-yl)-1H-indazol-1-yl)acetyl)-N-(6-bromopyridin-2-yl)-4-fluoropyrrolidine-1-carboxamide (476) and (2S,4S)-2-(2-(3-acetyl-5-(2-methylpyrimidin-5-yl)-1H-indazol-1-yl)acetyl)-N-(6-bromopyridin-2-yl)-4-fluoropyrrolidine-1-carboxamide (477)

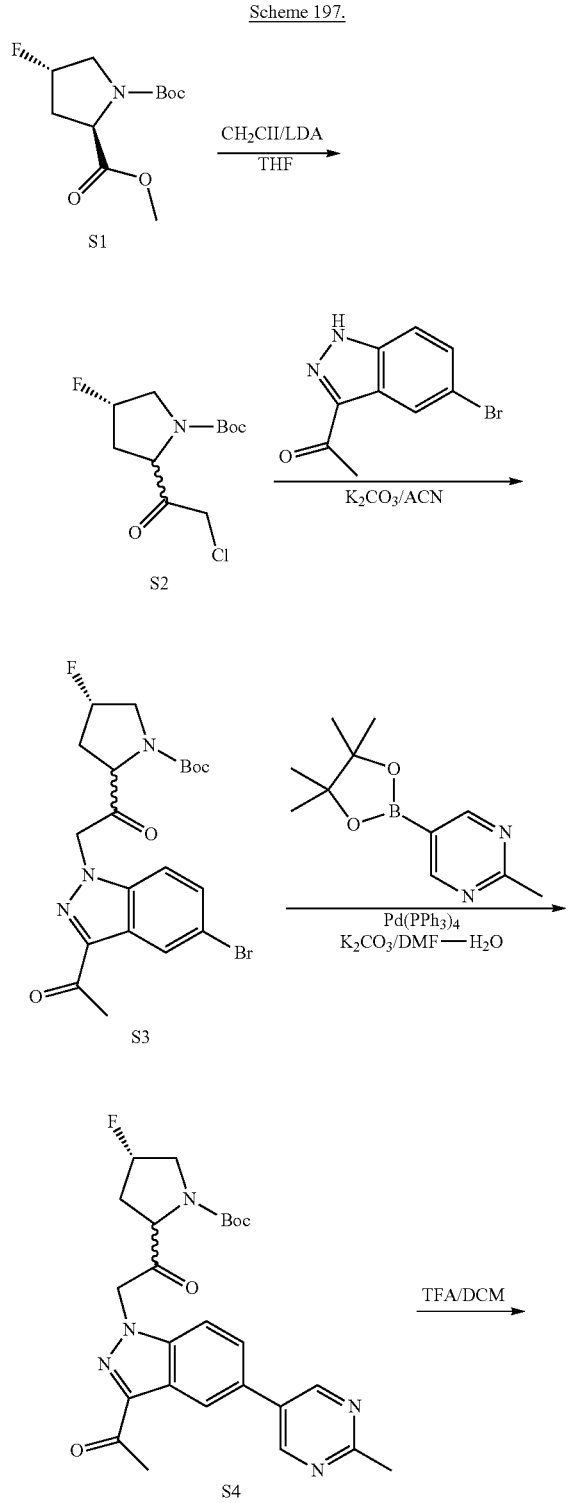

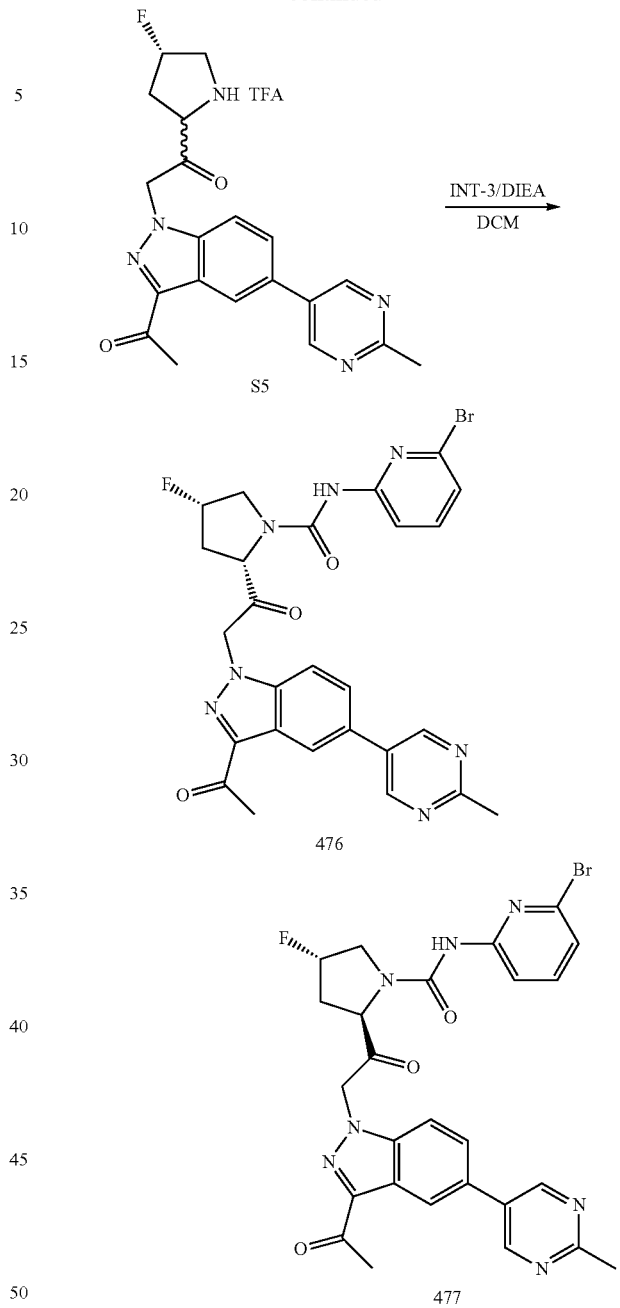

Step 1: tert-Butyl (2R, 4S) and (2S, 4S)-2-(2-chloroacetyl)-4-fluoropyrrolidine-1-carboxylate (S2)

Into a mixture of 1-(tert-butyl) 2-methyl (2R,4S)-4-fluoropyrrolidine-1,2-dicarboxylate (0.263 g, 1.06 mmol) and chloroiodomethane (0.31 mL, 4.26 mmol) in THF (5 mL), LDA (1 M in THF, 5.33 mL, 5.33 mmol) was added slowly at −78° C. under Ar with stirring. After 45 min, AcOH (1.5 mL) was added slowly to the mixture, and raise temperature to rt. Water was added and the mixture was extracted with AcOEt. The organic layer was washed with NaHCO$_3$ aq, brine, and dried over anhydrous Na$_2$SO$_4$. Solvent was evaporated under reduced pressure to give diastereomeric mixture of tert-butyl (2R, 4S) and (2S, 4S)-2-(2-chloroacetyl)-4-fluoropyrrolidine-1-carboxylate as brown oil for next step.

Step 2: tert-Butyl (2R, 4S) and (2S, 4S)-2-(2-(3-acetyl-5-bromo-1H-indazol-1-yl)acetyl)-4-fluoropyrrolidine-1-carboxylate (S3)

Diastereomeric mixture of tert-butyl (2R, 4S) and (2S, 4S)-2-(2-chloroacetyl)-4-fluoropyrrolidine-1-carboxylate was treated with 1-(5-bromo-1H-indazol-3-yl)ethan-1-one (0.239 g, 1.0 mmol), and K₂CO₃ (0.69 g, 5 mmol) in acetonitrile at 80° C. overnight. Solid was filtered and the solvent was evaporated. Residue was purified on ISCO with AcOEt in hexane (0-50%) as eluent to give diastereomeric mixture of (2R, 4S) and (2S, 4S)-2-(2-(3-acetyl-5-bromo-1H-indazol-1-yl)acetyl)-4-fluoropyrrolidine-1-carboxylate (0.23 g) as brown oil.

Step 3: tert-Butyl (2R, 4S) and (2S, 4S)-2-(2-(3-acetyl-5-(2-methylpyrimidin-5-yl)-1H-indazol-1-yl)acetyl)-4-fluoropyrrolidine-1-carboxylate (S4)

Into a mixture of diastereomeric mixture of (2R, 4S) and (2S, 4S)-2-(2-(3-acetyl-5-bromo-1H-indazol-1-yl)acetyl)-4-fluoropyrrolidine-1-carboxylate (0.23 g, 0.49 mmol), 2-methyl-5-(4,4,5,5-tetramethyl-1,3,2-dioxaborolan-2-yl) pyrimidine (0.129 g, 0.589 mmol), and K₂CO₃ in DMF-water (5-0.5 mL), add Pd(PPh₃)₄ (29 mg, 0.025 mmol). The mixture was heated at 80° C. under Ar for 4 hr. Cool down to rt, water was added and the mixture was extracted with AcOEt. After washed with brine and dried over anhydrous Na₂SO₄, solvent was removed by evaporation. The residue was purified on ISCO with MeOH in DCM (0-10%) as eluent to give diastereomeric mixture of tert-butyl (2R, 4S) and (2S, 4S)-2-(2-(3-acetyl-5-(2-methylpyrimidin-5-yl)-1H-indazol-1-yl)acetyl)-4-fluoropyrrolidine-1-carboxylate (0.211 g).

Step 4: 2-(3-Acetyl-5-(2-methylpyrimidin-5-yl)-1H-indazol-1-yl)-1-((2R, 4S) and (2S, 4S)-4-fluoropyrrolidin-2-yl)ethan-1-one TFA Salt (S5)

A diastereomeric mixture of tert-butyl (2R, 4S) and (2S, 4S)-2-(2-(3-acetyl-5-(2-methylpyrimidin-5-yl)-1H-indazol-1-yl)acetyl)-4-fluoropyrrolidine-1-carboxylate (0.211 g, 0.44 mmol) was treated with TFA (2 mL) in DCM (4 mL) for 2 hr at rt. Volatiles were evaporated to give diastereomeric mixture of 2-(3-acetyl-5-(2-methylpyrimidin-5-yl)-1H-indazol-1-yl)-1-((2R, 4S) and (2S, 4S)-4-fluoropyrrolidin-2-yl)ethan-1-one TFA salt.

Step 5: (2R,4S))-2-(2-(3-acetyl-5-(2-methylpyrimidin-5-yl)-1H-indazol-1-yl)acetyl)-N-(6-bromopyridin-2-yl)-4-fluoropyrrolidine-1-carboxamide (476) and (2S, 4S)-2-(2-(3-acetyl-5-(2-Methylpyrimidin-5-yl)-1H-indazol-1-yl)acetyl)-N-(6-bromopyridin-2-yl)-4-fluoropyrrolidine-1-carboxamide (477)

Diastereomeric mixture of 2-(3-acetyl-5-(2-methylpyrimidin-5-yl)-1H-indazol-1-yl)-1-((2R, 4S) and (2S, 4S)-4-fluoropyrrolidin-2-yl)ethan-1-one TFA salt (0.22 mmol) was dissolved in DCM (3 mL) and DIEA (0.174 mL, 1 mmol). 2-bromo-6-isocyanatopyridine (INT-3) (42 mg) was added and stirred at room temperature for 15 min. Solvent was removed by evaporation, and the residue was purified with ptlc with AcOEt as eluent to give (2R,4S), and (2S, 4S)-2-(2-(3-acetyl-5-(2-methylpyrimidin-5-yl)-1H-indazol-1-yl)acetyl)-N-(6-bromopyridin-2-yl)-4-fluoropyrrolidine-1-carboxamide. The absolute stereochemistry of diastereoisomers was tentatively assigned.

¹H NMR (400 MHz, Chloroform-d) δ 8.90 (s, 2H), 8.55 (dd, J=0.9, 1.6 Hz, 1H), 7.98 (dd, J=0.7, 8.3 Hz, 1H), 7.76-7.42 (m, 24H), 7.22 (dd, J=0.7, 7.8 Hz, 1H), 6.65 (s, 1H), 5.40 (t, J=4.4 Hz, 1H), 5.32-5.18 (m, 2H), 5.03 (d, J=14.5 Hz, 1H), 4.75 (dd, J=5.5, 10.8 Hz, 1H), 4.01 (ddd, J=4.7, 13.7, 32.0 Hz, 1H), 3.41 (dd, J=13.7, 28.0 Hz, 1H), 2.80 (s, 3H), 2.66 (s, 3H), 2.24-1.93 (m, 2H). LC (method A): tR=1.99 min. LC/MS (EI) m/z: [M+H]⁺ 580.

¹H NMR (400 MHz, Chloroform-d) δ 8.90 (s, 2H), 8.54 (dd, J=0.9, 1.7 Hz, 1H), 8.03 (dd, J=0.7, 8.3 Hz, 1H), 7.67-7.57 (m, 3H), 7.28-7.24 (m, 1H), 6.64 (s, 1H), 5.32-5.23 (m, 1H), 5.16 (dd, J=2.7, 5.8 Hz, 1H), 5.00 (d, J=14.5 Hz, 1H), 4.59 (dd, J=5.2, 9.3 Hz, 1H), 4.22 (ddd, J=2.1, 13.8, 19.2 Hz, 1H), 3.14 (ddd, J=3.4, 13.8, 34.0 Hz, 1H), 2.81 (s, 3H), 2.66 (s, 3H), 2.63-2.51 (m, 1H), 2.24-2.04 (m, 1H). LC (method A): tR=2.15 min. LC/MS (EI) m/z: [M+H]⁺ 580.

(1R,3S,5R)-3-(2-(3-Acetyl-5-(2-methylpyrimidin-5-yl)-1H-indazol-1-yl)acetyl)-N-(6-bromopyridin-2-yl)-2-azabicyclo[3.1.0]hexane-2-carboxamide (478)

Scheme 198

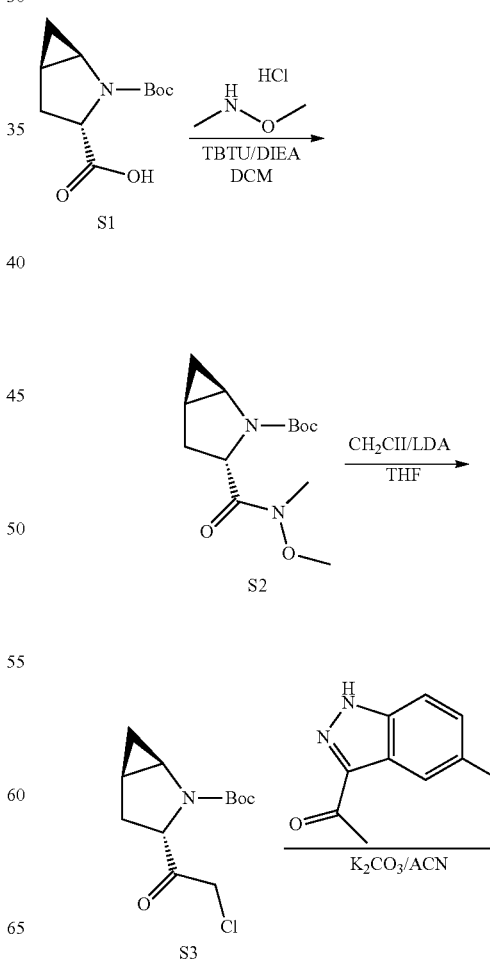

-continued

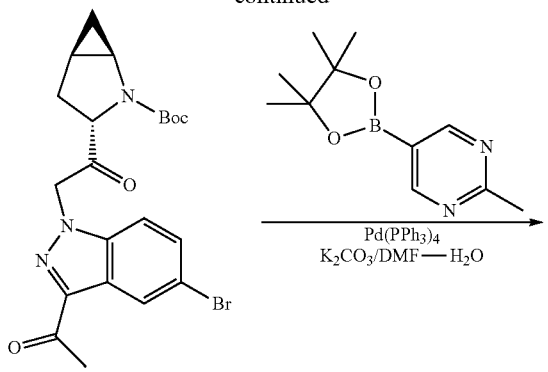

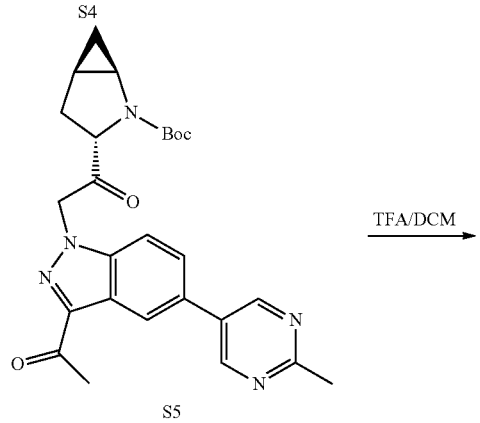

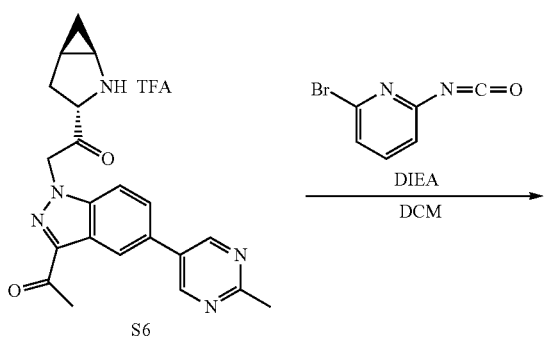

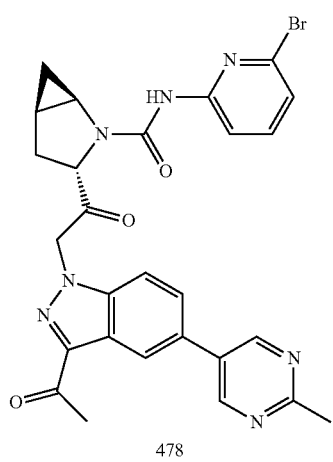

Step 1: tert-Butyl (1R,3S,5R)-3-(methoxy(methyl) carbamoyl)-2-azabicyclo[3.1.0]hexane-2-carboxylate (S2)

TBTU (2.12 g, 6.61 mmol) was added to (1R,3S,5R)-2-(tert-butoxycarbonyl)-2-azabicyclo[3.1.0]hexane-3-carboxylic acid (1.0 g, 4.41 mmol) in DCM (20 mL) with stirring. After 5 min, N,O-dimethylhydroxylamine hydrochloride (0.52 g, 5.29 mmol) followed by DIEA (1.92 mL, 11 mmol) was added. The mixture was stirred at room temperature for 2 hr and then subjected to aq workup with AcOEt extraction. Crude material was purified on ISCO with AcOEt in hexane (0-100%) as eluent to give tert-butyl (1R,3S,5R)-3-(methoxy(methyl)carbamoyl)-2-azabicyclo[3.1.0]hexane-2-carboxylate as white solid.

Step 2: tert-Butyl (1R,3S,5R)-3-(2-chloroacetyl)-2-azabicyclo[3.1.0]hexane-2-carboxylate (S3)

Into a mixture of tert-butyl (1R,3S,5R)-3-(methoxy(methyl)carbamoyl)-2-azabicyclo[3.1.0]hexane-2-carboxylate (0.53 g, 1.96 mmol) and chloroiodomethane (0.57 mL, 7.85 mmol) in THF (10 mL), LDA (1 M in THF, 9.8 mL, 9.8 mmol) was added in 15 min at −78° C. under Ar with stirring. After 30 min, AcOH (0.75 mL) in THF (1 mL) was added slowly to the mixture, and raise temperature to rt. Water was added and the mixture was extracted with AcOEt. The organic layer was washed with NaHCO$_3$ aq, brine, and dried over anhydrous Na$_2$SO$_4$. The solution was passed through a short column of silica gel and the solvent was evaporated under reduced pressure to give tert-butyl (1R,3S,5R)-3-(2-chloroacetyl)-2-azabicyclo[3.1.0]hexane-2-carboxylate (0.86 g) as brown syrup.

Step 3: tert-Butyl (1R,3S,5R)-3-(2-(3-acetyl-5-bromo-1H-indazol-1-yl)acetyl)-2-azabicyclo[3.1.0]hexane-2-carboxylate (S4)

tert-butyl (1R,3S,5R)-3-(2-chloroacetyl)-2-azabicyclo[3.1.0]hexane-2-carboxylate (0.86 g) was treated with 1-(5-bromo-1H-indazol-3-yl)ethan-1-one (0.456 g, 1.9 mmol), and K$_2$CO$_3$ (1.38 g, 10 mmol) in acetonitrile at 80° C. 1 hr. Solid was filtered and the solvent was evaporated. Residue was purified on ISCO with AcOEt in hexane (0-50%) as eluent to give tert-butyl (1R,3S,5R)-3-(2-(3-acetyl-5-bromo-1H-indazol-1-yl)acetyl)-2-azabicyclo[3.1.0]hexane-2-carboxylate (0.32 g) as brown foam.

Step 4: tert-Butyl (1R,3S,5R)-3-(2-(3-acetyl-5-(2-methylpyrimidin-5-yl)-1H-indazol-1-yl)acetyl)-2-azabicyclo[3.1.0]hexane-2-carboxylate (S5)

Into a mixture of tert-butyl (1R,3S,5R)-3-(2-(3-acetyl-5-bromo-1H-indazol-1-yl)acetyl)-2-azabicyclo[3.1.0]hexane-2-carboxylate (0.32 g, 0.69 mmol), 2-methyl-5-(4,4,5,5-tetramethyl-1,3,2-dioxaborolan-2-yl)pyrimidine (0.182 g, 0.83 mmol), and Cs$_2$CO$_3$ (0.45 g, 1.38 mmol) in DMF-water (7-0.7 mL), add Pd(PPh$_3$)$_4$ (40 mg, 0.035 mmol). The mixture was heated at 80° C. under Ar for 4 hr. Cool down to rt, water was added and the mixture was extracted with AcOEt. After washed with brine and dried over anhydrous Na$_2$SO$_4$, solvent was removed by evaporation. The residue was purified on ISCO with MeOH in DCM (0-10%) as eluent to give tert-butyl (1R,3S,5R)-3-(2-(3-acetyl-5-(2-methylpyrimidin-5-yl)-1H-indazol-1-yl)acetyl)-2-azabicyclo[3.1.0]hexane-2-carboxylate (0.225 g) as brown syrup.

Step 5: 2-(3-Acetyl-5-(2-methylpyrimidin-5-yl)-1H-indazol-1-yl)-1-((1R,3S,5R)-2-azabicyclo[3.1.0]hexan-3-yl)ethan-1-one TFA Salt (S6)

tert-butyl (1R,3S,5R)-3-(2-(3-acetyl-5-(2-methylpyrimidin-5-yl)-1H-indazol-1-yl)acetyl)-2-azabicyclo[3.1.0]hexane-2-carboxylate (54 mg, 0.114 mmol) was treated with TFA (1 mL) in DCM (2 mL) for 1 hr at rt. Volatiles were evaporated and the residue was coevaporated with toluene (5 mL) to give 2-(3-acetyl-5-(2-methylpyrimidin-5-yl)-1H-indazol-1-yl)-1-((1R,3S,5R)-2-azabicyclo[3.1.0]hexan-3-yl)ethan-1-one TFA salt.

Step 6: (1R,3S,5R)-3-(2-(3-Acetyl-5-(2-methylpyrimidin-5-yl)-1H-indazol-1-yl)acetyl)-N-(6-bromopyridin-2-yl)-2-azabicyclo[3.1.0]hexane-2-carboxamide (478)

2-(3-acetyl-5-(2-methylpyrimidin-5-yl)-1H-indazol-1-yl)-1-((1R,3S,5R)-2-azabicyclo[3.1.0]hexan-3-yl)ethan-1-one TFA salt was dissolved in DCM (2 mL) and DIEA (0.080 mL, 0.57 mmol). 2-bromo-6-isocyanatopyridine (0.030 g) was added and stirred at room temperature for 15 min. Solvent was removed by evaporation, and the residue was purified on ISCO with AcOEt as eluent to give (1R,3S,5R)-3-(2-(3-acetyl-5-(2-methylpyrimidin-5-yl)-1H-indazol-1-yl)acetyl)-N-(6-bromopyridin-2-yl)-2-azabicyclo[3.1.0]hexane-2-carboxamide (24 mg) as pale yellow solid.

$^1$H NMR (400 MHz, Chloroform-d) δ 8.89 (s, 2H), 8.53 (dd, J=1.0, 1.6 Hz, 1H), 8.04 (dd, J=0.7, 8.4 Hz, 1H), 7.67 (ddd, J=1.4, 8.3, 12.0 Hz, 2H), 7.60-7.52 (m, 4H), 7.50-7.43 (m, 2H), 7.20 (dd, J=0.7, 7.7 Hz, 1H), 6.69 (s, 1H), 5.15 (d, J=14.4 Hz, 1H), 4.97 (d, J=14.5 Hz, 1H), 4.19-4.08 (m, 2H), 3.72 (ddd, J=2.7, 5.5, 7.1 Hz, 1H), 2.80 (s, 4H), 2.74-2.68 (m, 1H), 2.65 (s, 3H), 2.29-2.18 (m, 1H), 1.87 (dd, J=7.5, 13.0 Hz, 1H), 1.50 (dq, J=5.1, 8.6 Hz, 1H), 0.76 (dtd, J=1.0, 7.0, 8.0 Hz, 1H), 0.63 (ddd, J=2.7, 4.8, 7.2 Hz, 1H). LC (method A): $t_R$=1.49 min. LC/MS (EI) m/z: [M+H]$^+$ 574.

2-(2-(3-Acetyl-5-(2-methylpyrazolo[1,5-a]pyrimidin-6-yl)-1H-indazol-1-yl)acetyl)-N-(6-bromopyridin-2-yl)-2-azabicyclo[2.1.1]hexane-1-carboxamide (689)

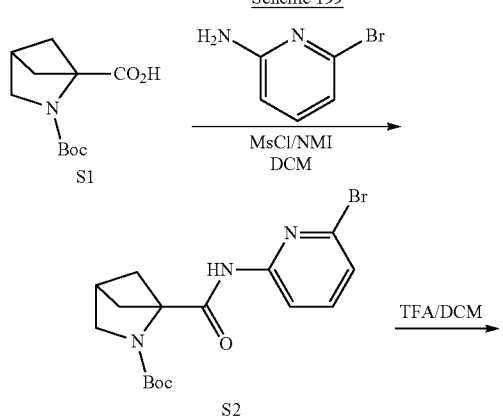

Scheme 199

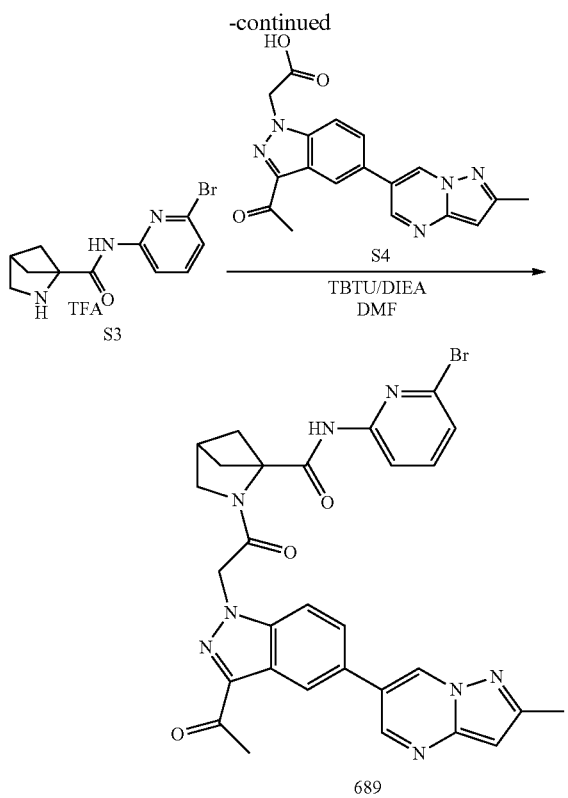

Step 1: tert-Butyl 1-((6-bromopyridin-2-yl)carbamoyl)-2-azabicyclo[2.1.1]hexane-2-carboxylate (S2)

Into a solution of 2-(tert-butoxycarbonyl)-2-azabicyclo[2.1.1]hexane-1-carboxylic acid (0.092 g, 0.405 mmol) in DCM (3 mL), N-methyl imidazole (0.081 mL, 2.65 mmol) followed by MsCl (0.035 mL, 0.45 mmol) was added at 0° C. with stirring. After 30 min, 6-bromopyridin-2-amine (0.07 g, 0.405 mmol) was added, and the mixture was stirred at room temperature overnight. Water was added and the mixture was extracted with AcOEt. After washed with brine and dried over anhydrous $Na_2SO_4$, solvent was removed by evaporation, and the residue was purified on ISCO with AcOEt in hexane (0-30%) as eluent to give tert-butyl 1-((6-bromopyridin-2-yl)carbamoyl)-2-azabicyclo[2.1.1]hexane-2-carboxylate (0.094 g).

Step 2: N-(6-Bromopyridin-2-yl)-2-azabicyclo[2.1.1]hexane-1-carboxamide TFA Salt (S3)

tert-butyl-1-((6-bromopyridin-2-yl)carbamoyl)-2-azabicyclo[2.1.1]hexane-2-carboxylate (0.094 g, 0.25 mmol) was treated with TFA (2 mL) in DCM (4 mL) at room temperature for 1 hr. Volatiles were removed under reduced pressure and the residue was co evaporated with toluene (5 mL) to give N-(6-bromopyridin-2-yl)-2-azabicyclo[2.1.1]hexane-1-carboxamide TFA salt for next step.

Step 3: 2-(2-(3-Acetyl-5-(2-methylpyrazolo[1,5-a]pyrimidin-6-yl)-1H-indazol-1-yl)acetyl)-N-(6-bromopyridin-2-yl)-2-azabicyclo[2.1.1]hexane-1-carboxamide (689)

Into a mixture of N-(6-bromopyridin-2-yl)-2-azabicyclo[2.1.1]hexane-1-carboxamide TFA salt (0.12 mmol) and 2-(3-acetyl-5-(2-methylpyrazolo[1,5-a]pyrimidin-6-yl)-1H-indazol-1-yl)acetic acid (0.12 mmol) in DMF (2 mL), TBTU (58 mg, 0.18 mmol) followed by DIEA (0.105 mL, 0.6 mmol) was added at room temperature with stirring. After 30 min, NaHCO₃ aq was added, and the solid formed was collected by filtration and purified on ISCO with MeOH in DCM (0-10%) as eluent to give 2-(2-(3-acetyl-5-(2-methylpyrazolo[1,5-a]pyrimidin-6-yl)-1H-indazol-1-yl)acetyl)-N-(6-bromopyridin-2-yl)-2-azabicyclo[2.1.1]hexane-1-carboxamide (64.5 mg)

$^1$H NMR (400 MHz, Chloroform-d) δ 8.78-8.69 (m, 2H), 8.52 (d, J=1.6 Hz, 1H), 8.15 (d, J=8.2 Hz, 1H), 8.08 (s, 1H), 7.65-7.55 (m, 2H), 7.48 (t, J=7.9 Hz, 1H), 7.15 (d, J=7.7 Hz, 1H), 6.51 (s, 1H), 5.28 (d, J=8.9 Hz, 2H), 3.72 (s, 2H), 2.99 (d, J=3.3 Hz, 1H), 2.70 (s, 3H), 2.54 (s, 3H), 2.28 (dt, J=2.4, 4.8 Hz, 2H), 1.84 (dd, J=1.9, 5.0 Hz, 2H). LC (method A): $t_R$=1.94 min. LC/MS (EI) m/z: [M+H]⁺ 613.

2-(2-(3-acetyl-5-(2-Methylpyrimidin-5-yl)-1H-indazol-1-yl)acetyl)-N-(6-bromopyridin-2-yl)-2-azabicyclo[2.1.1]hexane-1-carboxamide (462)

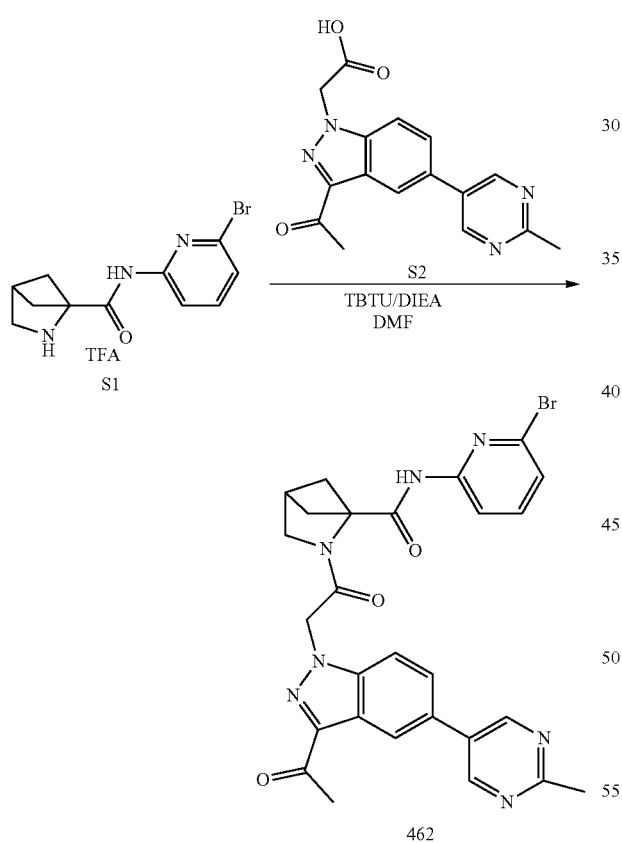

Scheme 200

462

Into a mixture of N-(6-bromopyridin-2-yl)-2-azabicyclo[2.1.1]hexane-1-carboxamide TFA salt (0.12 mmol) and 2-(3-acetyl-5-(2-methylpyrimidin-5-yl)-1H-indazol-1-yl)acetic acid (0.12 mmol) in DMF (2 mL), TBTU (58 mg, 0.18 mmol) followed by DIEA (0.105 mL, 0.6 mmol) was added at room temperature with stirring. After 30 min, NaHCO₃ aq was added, and the mixture was extracted with AcOEt. The solvent was removed by evaporation and the residue was purified on ISCO with MeOH in DCM (0-10%) as eluent to give 2-(2-(3-acetyl-5-(2-methylpyrimidin-5-yl)-1H-indazol-1-yl)acetyl)-N-(6-bromopyridin-2-yl)-2-azabicyclo[2.1.1]hexane-1-carboxamide (61 mg).

$^1$H NMR (400 MHz, Chloroform-d) δ 8.89 (s, 2H), 8.53 (dd, J=0.9, 1.7 Hz, 1H), 8.16 (dd, J=0.7, 8.2 Hz, 1H), 8.04 (s, 1H), 7.69-7.56 (m, 2H), 7.50 (t, J=7.9 Hz, 1H), 7.16 (dd, J=0.7, 7.7 Hz, 1H), 5.28 (s, 2H), 3.71 (s, 2H), 2.98 (t, J=3.2 Hz, 1H), 2.80 (s, 3H), 2.71 (s, 3H), 2.28 (ddd, J=1.9, 3.2, 5.2 Hz, 2H), 1.83 (dd, J=2.0, 4.9 Hz, 2H). LC (method A): $t_R$=1.67 min. LC/MS (EI) m/z: [M+H]⁺ 574.

(2S,4R)-1-(2-(1-Acetyl-6-(2-methylpyrimidin-5-yl)-1H-indol-3-yl)acetyl)-N-(2'-chloro-2-fluoro-[1,1'-biphenyl]-3-yl)-4-fluoropyrrolidine-2-carboxamide (710)

Scheme 201

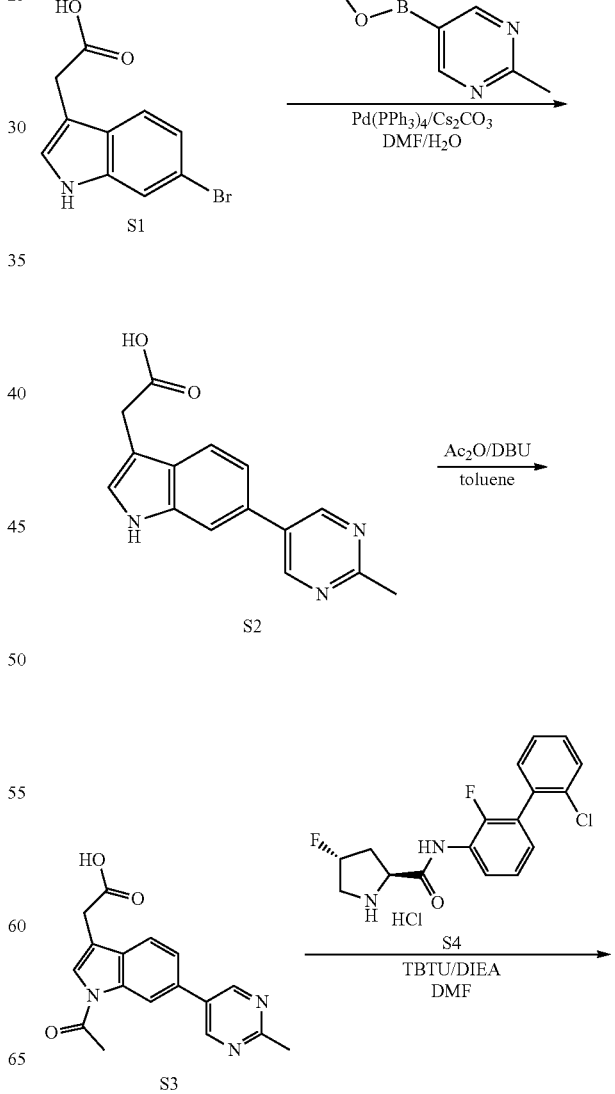

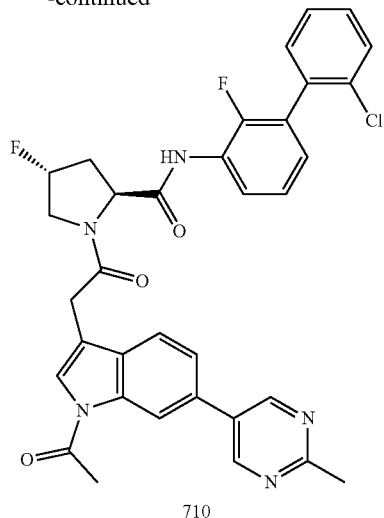

710

Step 1: 2-(6-(2-Methylpyrimidin-5-yl)-1H-indol-3-yl)acetic acid (S2)

Into a mixture of 2-(6-bromo-1H-indol-3-yl)acetic acid (0.11 g, 0.43 mmol), 2-methyl-5-(4,4,5,5-tetramethyl-1,3,2-dioxaborolan-2-yl)pyrimidine (0.114 g, 0.52 mmol), and $Cs_2CO_3$ (0.423 g, 1.30 mmol) in DMF-water (5-0.5 mL), add $Pd(PPh_3)_4$ (25 mg, 0.022 mmol). The mixture was heated at 90° C. under Ar for 2 hr. Cool down to rt, filter and concentrated under reduced pressure. The residue was purified on ISCO with MeOH in DCM (0-20%) as eluent to give 2-(6-(2-methylpyrimidin-5-yl)-1H-indol-3-yl)acetic acid (0.107 g) as yellow solid.

Step 2: 2-(1-Acetyl-6-(2-methylpyrimidin-5-yl)-1H-indol-3-yl)acetic acid (S3)

Into a suspension of 2-(6-(2-methylpyrimidin-5-yl)-1H-indol-3-yl)acetic acid (0.107 g, 0.4 mmol) in toluene (5 mL), add DBU (0.36 mL, 2.4 mmol) followed by $Ac_2O$. The mixture was heated at 90° C. 1 hr. Solvent was removed by evaporation, and the residue was subject to aq work up with AcOEt extraction. Crude was purified on ISCO with MeOH in DCM (0-15%) as eluent to give 2-(1-acetyl-6-(2-methylpyrimidin-5-yl)-1H-indol-3-yl)acetic acid (0.052 g) as yellow solid.

Step 3: (2S,4R)-1-(2-(1-Acetyl-6-(2-methylpyrimidin-5-yl)-1H-indol-3-yl)acetyl)-N-(2'-chloro-2-fluoro-[1,1'-biphenyl]-3-yl)-4-fluoropyrrolidine-2-carboxamide (710)

Into a mixture of 2-(1-acetyl-6-(2-methylpyrimidin-5-yl)-1H-indol-3-yl)acetic acid (26 mg, 0.084 mmol) and (2S,4R)—N-(2'-chloro-2-fluoro-[1,1'-biphenyl]-3-yl)-4-fluoropyrrolidine-2-carboxamide hydrochloride (34.5 g, 0.09 mmol) in DMF (1 mL), TBTU (40 mg, 0.126 mmol) followed by DIEA (0.073 mL, 0.42 mmol) was added at room temperature with stirring. After 15 min, $NaHCO_3$ aq was added to form precipitation. Solid was collected by filtration and purified with ptlc with MeOH in DCM (5%) as eluent to give (2S,4R)-1-(2-(1-acetyl-6-(2-methylpyrimidin-5-yl)-1H-indol-3-yl)acetyl)-N-(2'-chloro-2-fluoro-[1,1'-biphenyl]-3-yl)-4-fluoropyrrolidine-2-carboxamide (18.7 mg)

$^1$H NMR (400 MHz, Chloroform-d) δ 9.39 (d, J=3.0 Hz, 1H), 8.86 (s, 2H), 8.68 (d, J=1.6 Hz, 1H), 8.26 (ddd, J=1.7, 7.3, 8.7 Hz, 1H), 7.58 (dd, J=0.7, 8.1 Hz, 1H), 7.52 (d, J=1.2 Hz, 1H), 7.48-7.44 (m, 1H), 7.39-7.27 (m, 3H), 7.18 (td, J=1.1, 8.0 Hz, 1H), 7.04 (ddd, J=1.7, 6.8, 7.7 Hz, 1H), 5.36 (ddt, J=1.9, 4.6, 53.0 Hz, 1H), 5.06 (dd, J=7.0, 8.4 Hz, 1H), 4.03 (ddt, J=1.7, 12.4, 19.4 Hz, 1H), 3.84 (d, J=1.3 Hz, 2H), 3.69 (ddd, J=3.4, 12.4, 32.9 Hz, 1H), 3.01-2.82 (m, 1H), 2.80 (s, 3H), 2.50 (s, 4H), 1.75 (s, 1H). LC (method A): $t_R$=2.02 min. LC/MS (EI) m/z: [M+H]$^+$ 628.

(2S,4R)-1-(2-(1-Acetyl-6-(2-methylpyrimidin-5-yl)-1H-indol-3-yl)acetyl)-N-(6-bromopyridin-2-yl)-4-fluoropyrrolidine-2-carboxamide (711)

Scheme 202

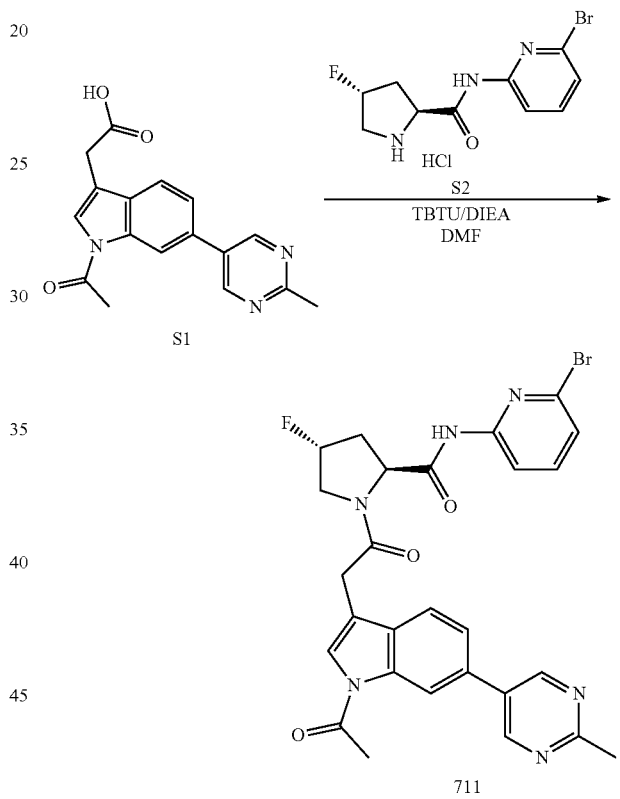

711

Into a mixture of 2-(1-acetyl-6-(2-methylpyrimidin-5-yl)-1H-indol-3-yl)acetic acid (26 mg, 0.084 mmol) and (2S,4R)—N-(6-bromopyridin-2-yl)-4-fluoropyrrolidine-2-carboxamide hydrochloride (29 mg, 0.09 mmol) in DMF (1 mL), TBTU (40 mg, 0.126 mmol) followed by DIEA (0.073 mL, 0.42 mmol) was added at room temperature with stirring. After 15 min, $NaHCO_3$ aq was added to form precipitation. Solid was collected by filtration and purified with ptlc with MeOH in DCM (5%) as eluent to give (2S,4R)-1-(2-(1-acetyl-6-(2-methylpyrimidin-5-yl)-1H-indol-3-yl)acetyl)-N-(6-bromopyridin-2-yl)-4-fluoropyrrolidine-2-carboxamide (15.6 mg).

$^1$H NMR (400 MHz, Chloroform-d) δ 9.29 (s, 1H), 8.89 (s, 2H), 8.70 (d, J=1.5 Hz, 1H), 8.08 (d, J=8.1 Hz, 1H), 7.61 (dd, J=0.7, 8.1 Hz, 1H), 7.57 (d, J=1.3 Hz, 1H), 7.52 (t, J=7.9 Hz, 1H), 7.46 (dd, J=1.7, 8.1 Hz, 1H), 7.20 (dd, J=0.7, 7.8 Hz, 1H), 5.33 (dt, J=3.7, 52.8 Hz, 1H), 4.91 (t, J=7.9 Hz, 1H), 4.07-3.92 (m, 1H), 3.91-3.63 (m, 3H), 2.80 (s, 3H), 2.63 (s, 3H), 2.62-2.44 (m, 2H), 1.79 (s, 1H). LC (method A): $t_R$=1.69 min. LC/MS (EI) m/z: [M+H]$^+$ 579.

(2S,4R)—N1-(1-Acetyl-6-(2-methylpyrimidin-5-yl)-1H-indol-3-yl)-N2-(6-bromopyridin-2-yl)-4-fluoro-pyrrolidine-1,2-dicarboxamide (203)

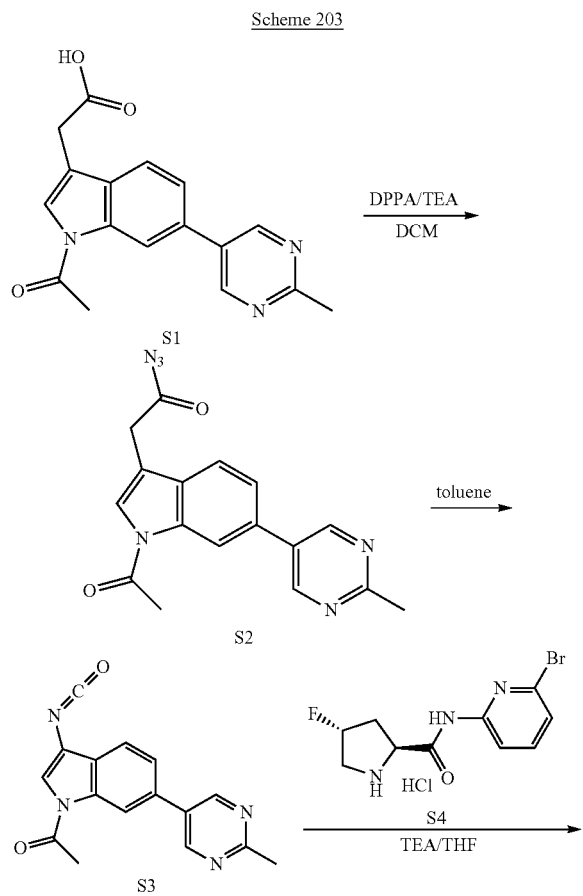

Step 1: 2-(1-Acetyl-6-(2-methylpyrimidin-5-yl)-1H-indol-3-yl)acetyl azide (S2)

2-(1-Acetyl-6-(2-methylpyrimidin-5-yl)-1H-indol-3-yl) acetic acid (0.26 g, 0.88 mmol) in DCM (10 mL) was treated with DPPA (0.4 mL, 1.8 mmol)) in the presence of TEA (0.4 mL, 2.2 mmol) for 2 hr at rt. Solvent was evaporated, and the residue was purified on ISCO with AcOEt in Hexane (0-100%) to give 2-(1-acetyl-6-(2-methylpyrimidin-5-yl)-1H-indol-3-yl)acetyl azide (0.216 g) as white solid.

Step 2: 1-(3-Isocyanato-6-(2-methylpyrimidin-5-yl)-1H-indol-1-yl)ethan-1-one (S3)

2-(1-Acetyl-6-(2-methylpyrimidin-5-yl)-1H-indol-3-yl) acetyl azide (0.216 g, 0.675 mmol) was heated in toluene at 100° C. for 1 hr. Solvent was evaporated under reduced pressure to give 1-(3-isocyanato-6-(2-methylpyrimidin-5-yl)-1H-indol-1-yl)ethan-1-one (0.2 g) as yellow solid.

Step 3: (2S,4R)—N1-(1-Acetyl-6-(2-methylpyrimidin-5-yl)-1H-indol-3-yl)-N2-(6-bromopyridin-2-yl)-4-fluoropyrrolidine-1,2-dicarboxamide (203)

Into (2S,4R)—N-(6-bromopyridin-2-yl)-4-fluoropyrrolidine-2-carboxamide hydrochloride (32.5 mg, 0.1 mmol) in THF (1 mL), TEA (0.042 mL, 0.3 mmol) followed by 1-(3-isocyanato-6-(2-methylpyrimidin-5-yl)-1H-indol-1-yl) ethan-1-one (0.031 g, 0.105 mmol) was added at room temperature with stirring. After 1 hr, AcOEt was added to dilute the mixture and was washed by NaHCO$_3$ aq, brine, and dried over anhydrous Na$_2$SO$_4$. Crude was purified with on ISCO with MeOH in DCM (0-10%) as eluent to give (2S,4R)—N1-(1-acetyl-6-(2-methylpyrimidin-5-yl)-1H-indol-3-yl)-N2-(6-bromopyridin-2-yl)-4-fluoropyrrolidine-1,2-dicarboxamide (40 mg).

$^1$H NMR (400 MHz, Chloroform-d) δ 9.33-9.26 (m, 1H), 8.81 (d, J=0.9 Hz, 2H), 8.56 (s, 1H), 8.14 (d, J=8.2 Hz, 1H), 7.70 (d, J=1.4 Hz, 1H), 7.53 (t, J=8.0 Hz, 1H), 7.39-7.29 (m, 2H), 7.21 (dd, J=0.7, 7.7 Hz, 1H), 6.84 (d, J=1.9 Hz, 1H), 5.40 (d, J=52.6 Hz, 1H), 4.90 (t, J=8.1 Hz, 1H), 4.06-3.81 (m, 2H), 2.86-2.59 (m, 4H), 2.57-2.36 (m, 4H). LC (method A): $t_R$=1.69 min. LC/MS (EI) m/z: [M+H]$^+$ 580.

(2S,4R)-1-(2-(1-Acetyl-6-(2-methylpyrimidin-5-yl)-1H-indol-3-yl)acetyl)-N-(2'-chloro-2-fluoro-[1,1'-biphenyl]-3-yl)-4-fluoropyrrolidine-2-carboxamide (293)

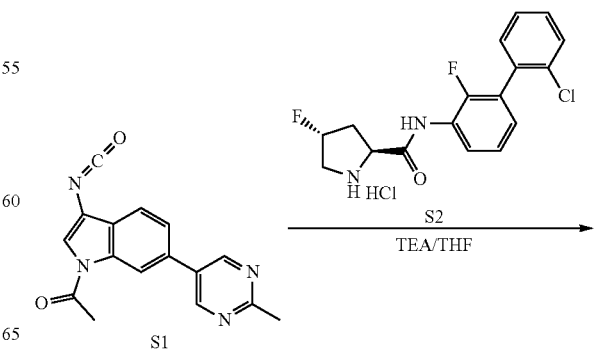

517

-continued

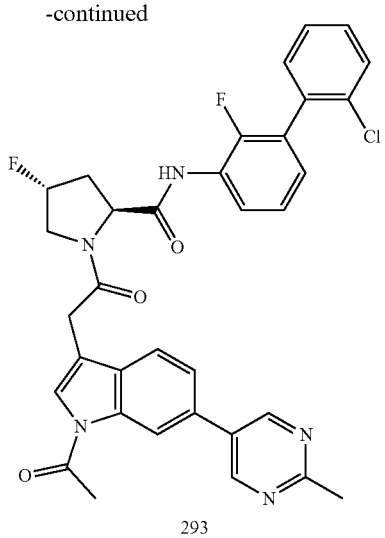

293

Into and (2S,4R)—N-(2-chloro-2-fluoro-[1,1'-biphenyl]-3-yl)-4-fluoropyrrolidine-2-carboxamide hydrochloride

518

(37.3 mg, 0.1 mmol) in THF (1 mL), TEA (0.028 mL, 0.2 mmol) followed by 1-(3-isocyanato-6-(2-methylpyrimidin-5-yl)-1H-indol-1-yl)ethan-1-one (0.031 g, 0.105 mmol) added at room temperature with stirring. After 1 hr, AcOEt added to dilute the mixture and washed by NaHCO₃ aq, brine, and dried over anhydrous Na₂SO₄. Crude purified with on ISCO with MeOH in DCM (0-10%) as eluent to give (2S,4R)-1-(2-(1-acetyl-6-(2-methylpyrimidin-5-yl)-1H-indol-3-yl)acetyl)-N-(2'-chloro-2-fluoro-[1,1'-biphenyl]-3-yl)-4-fluoropyrrolidine-2-carboxamide (44 mg).

$^1$H NMR (400 MHz, Chloroform-d) δ 9.23 (d, J=2.9 Hz, 1H), 8.78 (s, 2H), 8.56 (d, J=1.6 Hz, 1H), 8.29 (ddd, J=1.7, 7.4, 8.8 Hz, 1H), 7.71 (s, 1H), 7.49-7.37 (m, 2H), 7.36-7.24 (m, 4H), 7.17 (td, J=1.1, 8.0 Hz, 1H), 7.04 (ddd, J=1.7, 6.8, 7.7 Hz, 1H), 6.90 (s, 1H), 5.49-5.29 (m, 1H), 4.95 (t, J=7.9 Hz, 1H), 3.97 (dd, J=11.5, 21.4 Hz, 1H), 3.82 (ddd, J=3.6, 11.4, 32.5 Hz, 1H), 2.82-2.49 (m, 5H), 2.42 (s, 3H). LC (method A): $t_R$=2.18 min. LC/MS (EI) m/z: [M+H]⁺ 629.

(2S,4R)-1-(2-(3-Acetyl-5-(2-methylimidazo[1,2-a]pyridin-6-yl)-1H-indazol-1-yl)acetyl)-N-(6-bromopyrazin-2-yl)-4-fluoropyrrolidine-2-carboxamide (654)

Scheme 205

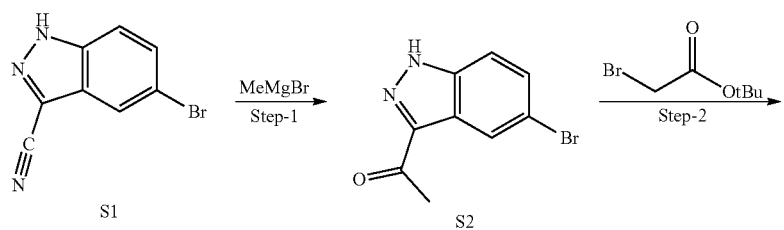

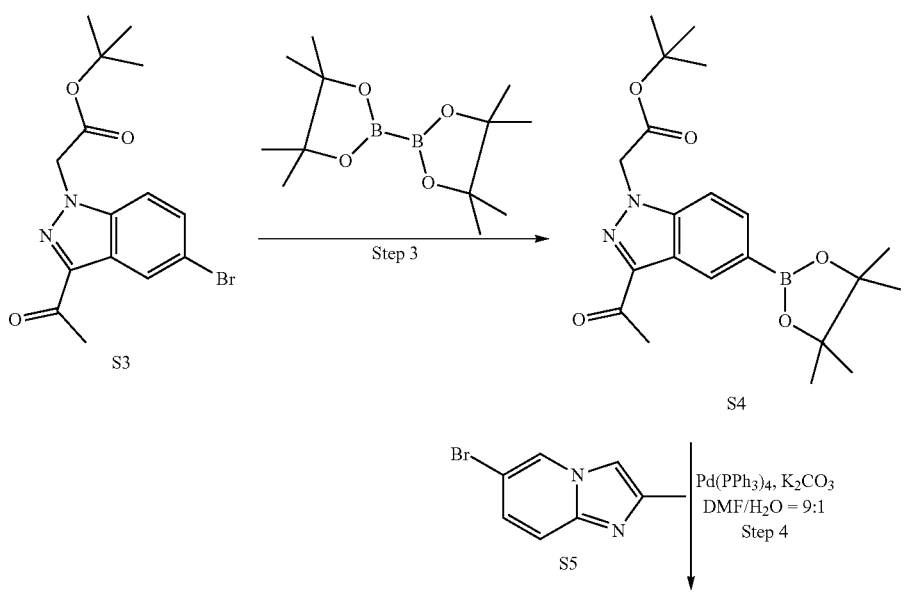

-continued

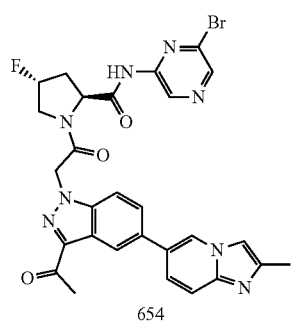 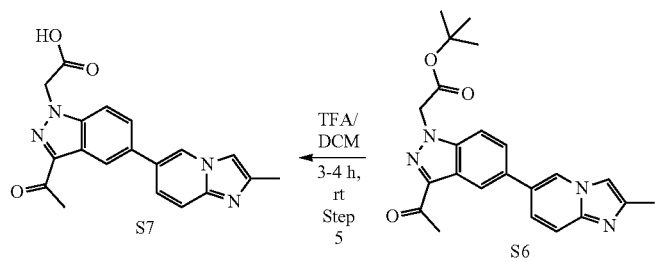

Step 1: 1-(5-Bromo-1H-indazol-3-yl)ethan-1-one (S2)

To an ice-cold solution of 5-bromo-1H-indazole-3-carbonitrile (110 g) in a mixture of 1.1 L THF and 3.3 L diethyl ether, methyl magnesium bromide (1 M in THF, 1.48 L, 3 equiv) was added dropwise. After completion of addition, the reaction mixture was brought to room temperature and stirred for 3 h. Then the reaction was cooled to 0° C. and the pH was adjusted to 5 using 1.5 N HCl (pH z 5). Then the reaction mass was stirred at room temperature for another 30 min. The reaction mixture was diluted with EtOAc and the layers were separated. The aqueous layer was again extracted with EtOAc. The combined organic layer was washed with water, washed with brine, dried over $Na_2SO_4$, and concentrated. The crude residue was recrystallized with a mixture of DCM:hexane (1:2, total 10 volume based on crude weight) to afford brown solid (100 g).

Step 2: tert-Butyl 2-(3-acetyl-5-bromo-1H-indazol-1-yl)acetate (S3)

To 1-(5-bromo-1H-indazol-3-yl)ethan-1-one (155 g, 1 equiv) and potassium carbonate (225.6 g, 2.5 equiv) in DMF (1.6 L) was added tert-butyl bromoacetate (136 mL, 1.2 equiv) dropwise at rt. The resulting mixture was stirred at 50° C. for 3 h. Then the reaction mixture was poured into water (16 L) and the precipitated solid was collected by filtration and dried to afford 186 g of the title product. The obtained material was used in the next step without further purification.

Step 3: tert-Butyl 2-(3-acetyl-5-(4,4,5,5-tetramethyl-1,3,2-dioxaborolan-2-yl)-1H-indazol-1-yl)acetate (S4)

A mixture of tert-butyl 2-(3-acetyl-5-bromo-1H-indazol-1-yl)acetate (1 equiv), 4,4,4'4',5,5,5',5'-octamethyl-2,2'-bi(1,3,2dioxabolane (1.1 equiv), and potassium acetate (3 equiv) in DMF (10 vol) was purged with argon for 5 min. 1,1'-Bis(diphenylphosphino)ferrocenedichloropalladium(II) (0.06 equiv) was then added under argon and the reaction mixture was heated at 90° C. overnight. The reaction mixture was cooled to room temperature and diluted with EtOAc and water. The organic layer was then separated, washed with brine, dried, and the solvent was removed under reduced pressure. The residue was purified by column chromatography on silica gel (MeOH/DCM) to give compound S4.

Step 4: tert-Butyl 2-(3-acetyl-5-(2-methylimidazo[1,2-a]pyridin-6-yl)-1H-indazol-1-yl)acetate (S6)

To a solution of 6-bromo-2-methylimidazo[1,2-a]pyridine (5, 1 equiv) in DMF/$H_2O$ (9:1, 10 vol) was added compound S4 (1 equiv), $K_2CO_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S6.

Step 5: 2-(3-acetyl-5-(2-methylimidazo[1,2-a]pyridin-6-yl)-1H-indazol-1-yl)acetic acid (S7)

To a solution of compound S6 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 6: (2S,4R)-1-(2-(3-Acetyl-5-(2-methylimidazo[1,2-a]pyridin-6-yl)-1H-indazol-1-yl)acetyl)-N-(6-bromopyrazin-2-yl)-4-fluoropyrrolidine-2-carboxamide (654)

To a solution of compound S7 (1 equiv) in DMF (10 vol) at 0° C. under an atmosphere of nitrogen was added (2S,4R)—N-(6-bromopyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 654 $^1$H NMR (400 MHz, DMSO-$d_6$) δ 2.08-2.31 (m, 1H), 2.37 (s, 3H), 2.52-2.63 (m, 1H), 2.65 (s, 3H), 3.95-4.15 (m, 1H), 4.20-4.32 (m, 1H), 4.64-4.79 (m, 1H), 5.50-5.72 (m, 2H), 5.85 (d, J=17.3 Hz, 1H), 7.57 (s, 2H), 7.76 (s, 1H), 7.82 (d, J=1.2 Hz, 2H), 8.40 (s, 1H), 8.54 (s, 1H), 8.89 (s, 1H), 9.27 (s, 1H), 11.34 (s, 1H). $^{19}$F NMR (376 MHz, DMSO-$d_6$): δ −175.71. LC (method A): $t_R$=1.26 min. LC/MS (EI) m/z: [M+H]$^+$ 619.

(2S,4R)-1-(2-(3-Acetyl-5-(2-cyclopropylpyrazolo[1,5-a]pyrimidin-6-yl)-1H-indazol-1-yl)acetyl)-N-(6-bromopyrazin-2-yl)-4-fluoropyrrolidine-2-carboxamide (655)
Scheme 206
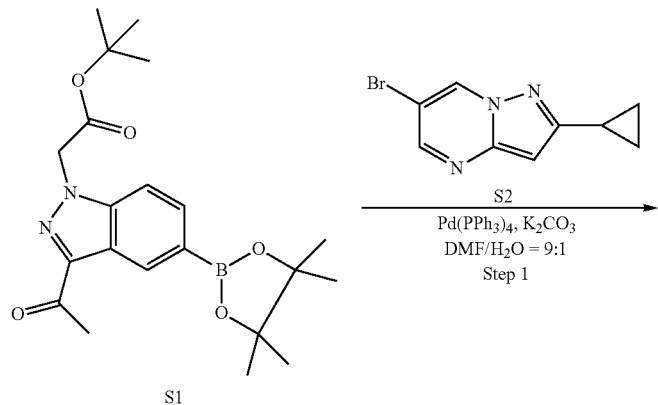
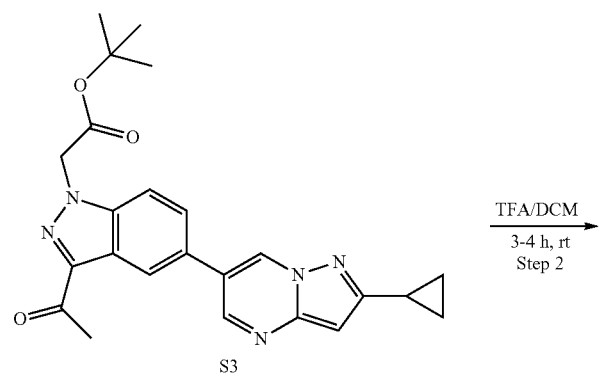
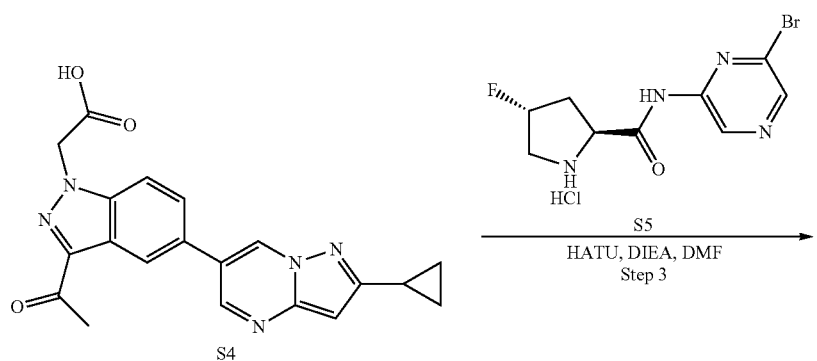

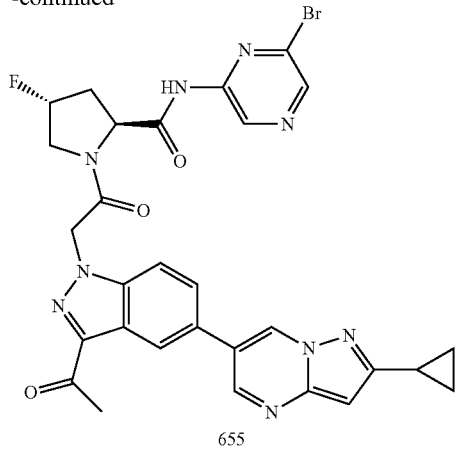

655

Step 1: tert-Butyl 2-(3-acetyl-5-(2-cyclopropylpyrazolo[1,5-a]pyrimidin-6-yl)-1H-indazol-1-yl)acetate (S3)

To a solution of 6-bromo-2-cyclopropypyrazolo[1,5-a] pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S3.

Step 2: 2-(3-Acetyl-5-(2-cyclopropylpyrazolo[1,5-a]pyrimidin-6-yl)-1H-indazol-1-acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (2S,4R)-1-(2-(3-Acetyl-5-(2-cyclopropylpyrazolo[1,5-a]pyrimidin-6-yl)-1H-indazol-1-yl)acetyl)-N-(6-bromopyrazin-2-yl)-4-fluoropyrrolidine-2-carboxamide (655)

To a solution of compound S4 (1 equiv) in DMF (10 vol) at 0° C. under an atmosphere of nitrogen was added (2S, 4R)—N-(6-bromopyrazin-2-yl)-4-fluoropyrrolidine-2-carboxamide hydrochloride (S5, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 655. $^1$H NMR (400 MHz, DMSO-d$_6$) δ 0.87-0.97 (m, 2H), 1.04-1.11 (m, 2H), 2.08-2.31 (m, 2H), 2.55-2.62 (m, 1H), 2.66 (s, 3H), 3.97-4.14 (m, 1H), 4.26 (dd, J=12.5, 22.3 Hz, 1H), 4.70 (t, J=7.5, 9.5 Hz, 1H), 5.49-5.71 (m, 2H), 5.85 (d, J=17.3 Hz, 1H), 6.52 (s, 1H), 7.82-7.94 (m, 2H), 8.45 (d, J=1.6 Hz, 1H), 8.54 (s, 1H), 8.83 (d, J=2.3 Hz, 1H), 9.27 (s, 1H), 9.33 (s, 1H), 11.34 (s, 1H). $^{19}$F NMR (376 MHz, DMSO-d$_6$): δ –175.72. LC (method A): t$_R$=2.00 min. LC/MS (EI) m/z: [M+H]$^+$ 646.

(1R,3S,5R)-2-(2-(3-Acetyl-5-(2-cyclopropylpyrazolo[1,5-a]pyrimidin-6-yl)-1H-indazol-1-yl)acetyl)-N-(6-bromopyrazin-2-yl)-2-azabicyclo[3.1.0]hexane-3-carboxamide (669)

Scheme 207

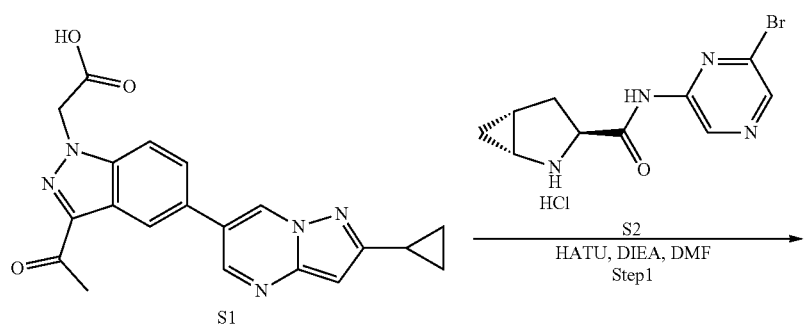

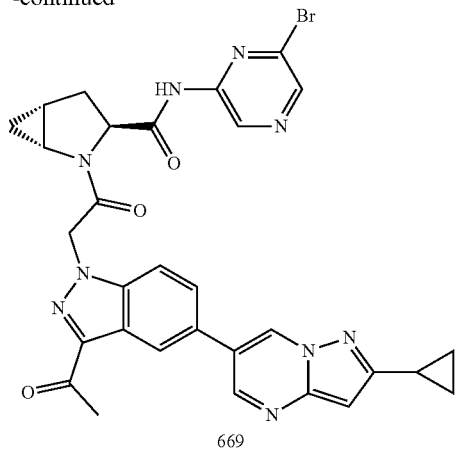

669

To a solution of compound S1 (1 equiv) in DMF (10 vol) at 0° C. under an atmosphere of nitrogen was added (1R,3S,5R)—N-(6-bromopyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 669. $^1$H NMR (400 MHz, DMSO-$d_6$) δ 0.85-0.94 (m, 3H), 0.99-1.11 (m, 3H), 1.88-1.98 (m, 1H), 2.09-2.19 (m, 1H), 2.23-2.42 (m, 2H), 2.67 (s, 3H), 3.84-3.93 (m, 1H), 4.50 (dd, J=5.5, 9.1 Hz, 1H), 5.64 (d, J=17.3 Hz, 1H), 6.00 (d, J=17.3 Hz, 1H), 6.53 (s, 1H), 7.83-7.97 (m, 2H), 8.46 (s, 1H), 8.54 (s, 1H), 8.84 (d, J=2.2 Hz, 1H), 9.27 (s, 1H), 9.34 (d, J=2.2 Hz, 1H), 11.12 (s, 1H). LC (method A): $t_R$=2.12 min. LC/MS (EI) m/z: [M+H]$^+$ 640.

(2S,4R)-1-(2-(3-Acetyl-5-(2-cyclopropylpyrazolo[1,5-a]pyrimidin-6-yl)-1H-indazol-1-yl)acetyl)-4-fluoro-N-(6-(trifluoromethoxy)pyridin-2-yl)pyrrolidine-2-carboxamide (672)

Scheme 208

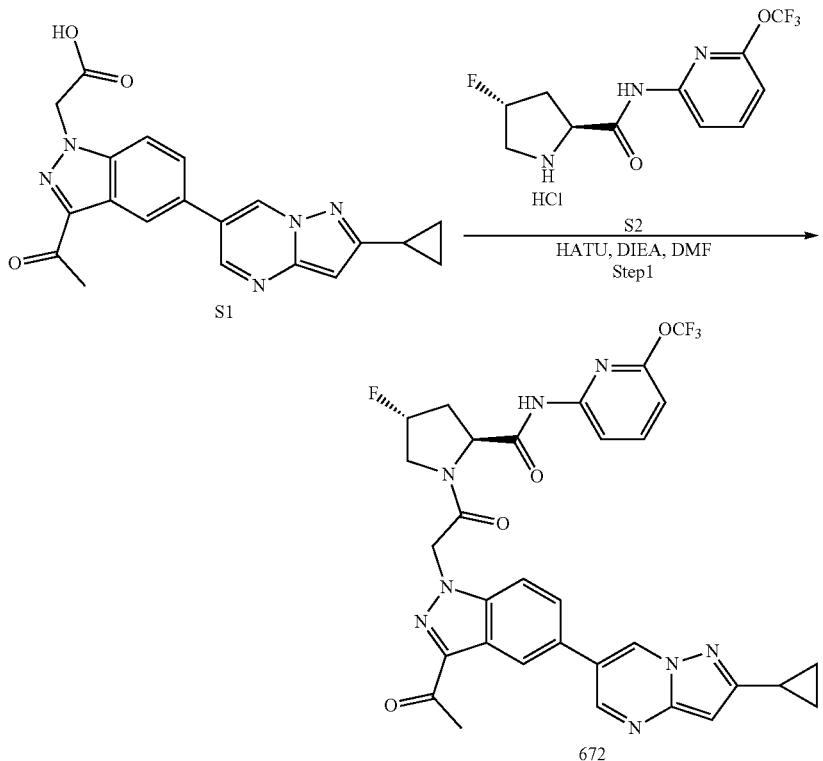

To a solution of compound S1 (1 equiv) in DMF (10 vol) at 0° C. under an atmosphere of nitrogen was added (2S, 4R)-4-fluoro-N-(6-(trifluoromethoxy)pyridin-2-yl)pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 672. $^1$H NMR (400 MHz, DMSO-$d_6$) δ 0.89-0.94 (m, 2H), 1.02-1.10 (m, 2H), 2.07-2.28 (m, 2H), 2.55-2.63 (m, 1H), 2.65 (s, 3H), 3.91-4.13 (m, 1H), 4.25 (dd, J=12.5, 22.2 Hz, 1H), 4.78 (t, J=8.5 Hz, 1H), 5.48-5.70 (m, 2H), 5.84 (d, J=17.3 Hz, 1H), 6.52 (s, 1H), 6.97 (d, J=7.8 Hz, 1H), 7.81-7.93 (m, 2H), 7.97 (t, J=8.0 Hz, 1H), 8.05 (d, J=8.3 Hz, 1H), 8.45 (t, J=1.2 Hz, 1H), 8.83 (d, J=2.2 Hz, 1H), 9.32 (d, J=2.2 Hz, 1H), 10.86 (s, 1H). $^{19}$F NMR (376 MHz, DMSO-$d_6$): δ −175.70, −55.15. LC (method A): $t_R$=2.35 min. LC/MS (EI) m/z: [M+H]$^+$ 651.

(1R,3S,5R)-2-(2-(3-Acetyl-5-(2-cyclopropylpyrazolo[1,5-a]pyrimidin-6-yl)-1H-indazol-1-yl)acetyl)-N-(6-bromopyridin-2-yl)-2-azabicyclo[3.1.0]hexane-3-carboxamide (673)

To a solution of compound S1 (1 equiv) in DMF (10 vol) at 0° C. under an atmosphere of nitrogen was added (1R,3S,5R)—N-(6-bromopyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 673. $^1$H NMR (400 MHz, DMSO-$d_6$) δ 0.85-0.90 (m, 1H), 0.94-0.99 (m, 2H), 1.05-1.16 (m, 3H), 1.88-2.03 (m, 1H), 2.14-2.23 (m, 1H), 2.25-2.32 (m, 1H), 2.36-2.45 (m, 1H), 2.71 (s, 3H), 3.87-3.97 (m, 1H), 4.46-4.60 (m, 1H), 5.67 (d, J=17.2 Hz, 1H), 6.04 (d, J=17.2 Hz, 1H), 6.57 (s, 1H), 7.37 (d, J=7.7 Hz, 1H), 7.76 (t, J=8.0 Hz, 1H), 7.88-7.97 (m, 2H), 8.08 (d, J=8.2 Hz, 1H), 8.51 (d, J=1.5 Hz, 1H), 8.88 (d, J=2.3 Hz, 1H), 9.37 (d, J=2.2 Hz, 1H), 10.80 (s, 1H). LC (method A): $t_R$=2.28 min. LC/MS (EI) m/z: [M+H]$^+$ 639.

Scheme 209

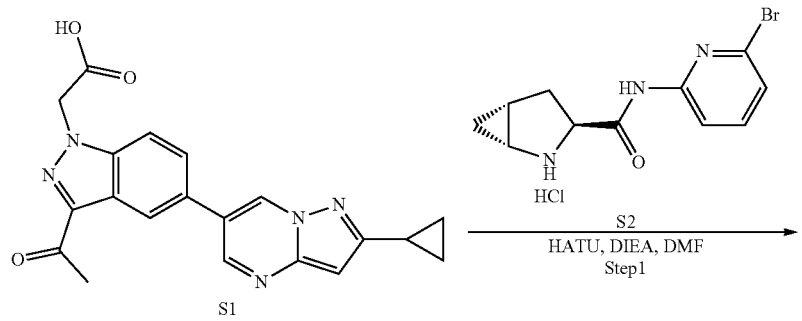

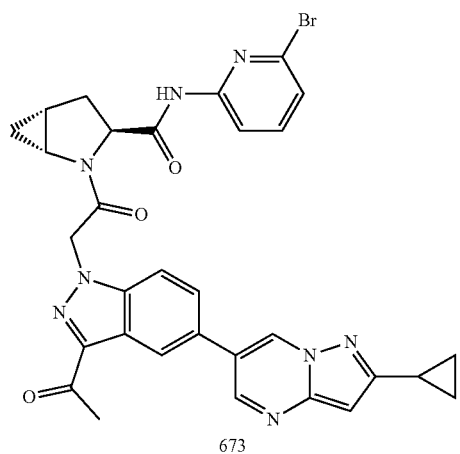

673

(2S,4R)-1-(2-(3-Acetyl-5-(2-cyclopropylpyrazolo[1,5-a]pyrimidin-6-yl)-1H-indazol-1-yl)acetyl)-N-(6-bromopyridin-2-yl)-4-fluoropyrrolidine-2-carboxamide (674)

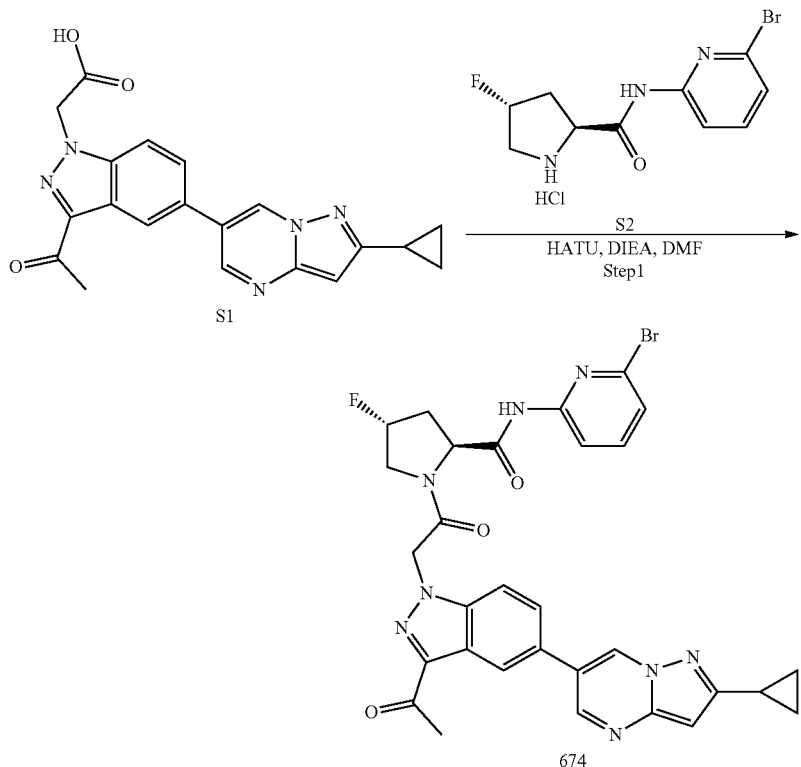

To a solution of compound S1 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 674. $^1$H NMR (400 MHz, DMSO-$d_6$) δ 0.89-0.96 (m, 2H), 1.04-1.11 (m, 2H), 2.09-2.28 (m, 2H), 2.60 (d, J=20.6 Hz, 1H), 2.66 (s, 3H), 3.96-4.14 (m, 1H), 4.24 (dd, J=12.6, 22.4 Hz, 1H), 4.69 (t, J=8.5 Hz, 1H), 5.47-5.70 (m, 2H), 5.84 (d, J=17.3 Hz, 1H), 6.52 (s, 1H), 7.32 (d, J=7.7 Hz, 1H), 7.72 (d, J=8.0 Hz, 1H), 7.83-7.92 (m, 2H), 8.03 (d, J=8.2 Hz, 1H), 8.45 (d, J=1.6 Hz, 1H), 8.83 (d, J=2.2 Hz, 1H), 9.32 (d, J=2.2 Hz, 1H), 11.00 (s, 1H). $^{19}$F NMR (376 MHz, DMSO-$d_6$): δ −175.66. LC (method A): $t_R$=2.16 min. LC/MS (EI) m/z: [M+H]$^+$ 645.

(2S,4R)-1-(2-(3-Acetyl-5-(2-cyclopropylpyrazolo[1,5-a]pyrimidin-6-yl)-1H-indazol-1-yl)acetyl)-N-(6-bromo-5-methylpyrazin-2-yl)-4-fluoropyrrolidine-2-carboxamide (675)

Scheme 211

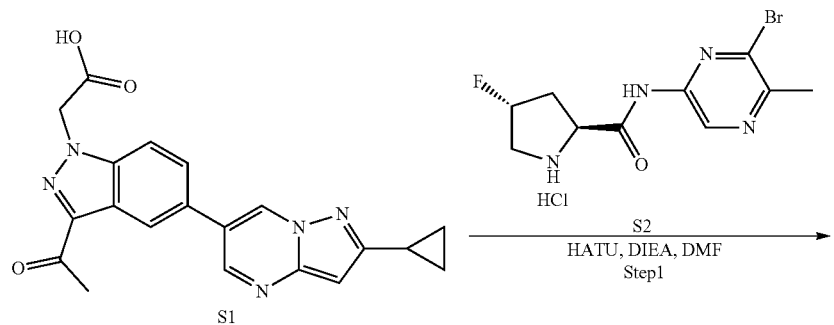

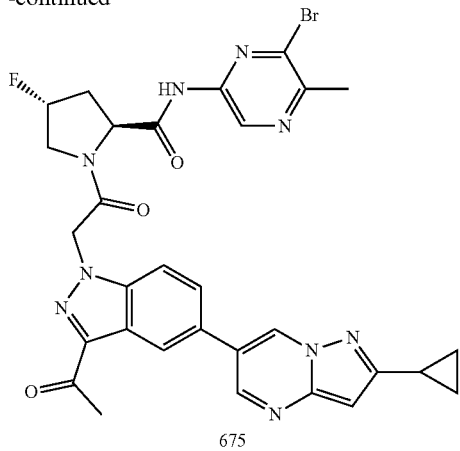

To a solution of compound S1 (1 equiv) in DMF (10 vol) at 0° C. under an atmosphere of nitrogen was added (2S,4R)—N-(6-bromo-5-methylpyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 675. $^1$H NMR (400 MHz, DMSO-$d_6$) δ 0.89-0.94 (m, 2H), 1.03-1.10 (m, 2H), 2.10-2.31 (m, 2H), 2.53 (s, 3H), 2.55-2.64 (m, 1H), 2.65 (s, 3H), 3.96-4.13 (m, 1H), 4.19-4.34 (m, 1H), 4.69 (t, J=7.5, 9.4 Hz, 1H), 5.48-5.70 (m, 2H), 5.85 (d, J=17.3 Hz, 1H), 6.52 (s, 1H), 7.78-7.96 (m, 2H), 8.45 (d, J=1.6 Hz, 1H), 8.83 (d, J=2.2 Hz, 1H), 9.13 (s, 1H), 9.32 (d, J=2.2 Hz, 1H), 11.22 (s, 1H). $^{19}$F NMR (376 MHz, DMSO-$d_6$): δ −175.72. LC (method A): $t_R$=2.11 min. LC/MS (EI) m/z: [M+H]$^+$ 660.

(2S,4R)-1-(2-(3-Acetyl-5-(2-methylpyrazolo[1,5-a]pyrimidin-6-yl)-1H-indol-1-yl)acetyl)-4-fluoro-N-(6-(trifluoromethoxy)pyridin-2-yl)pyrrolidine-2-carboxamide (656)

Scheme 212

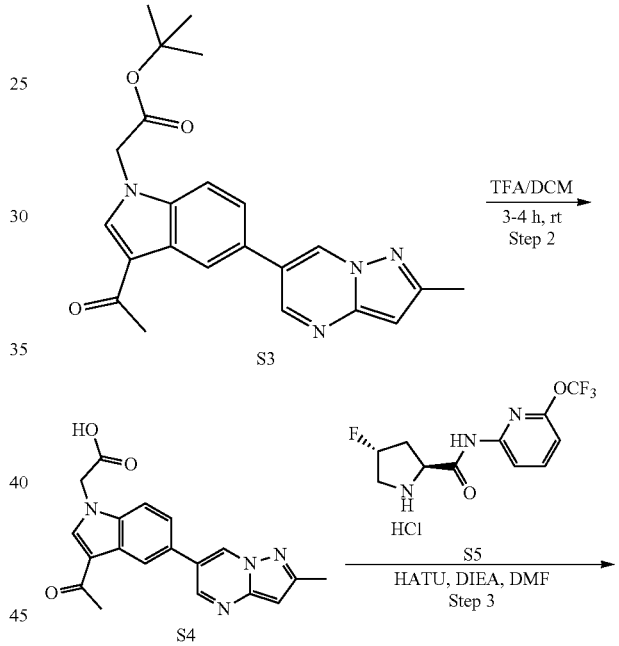

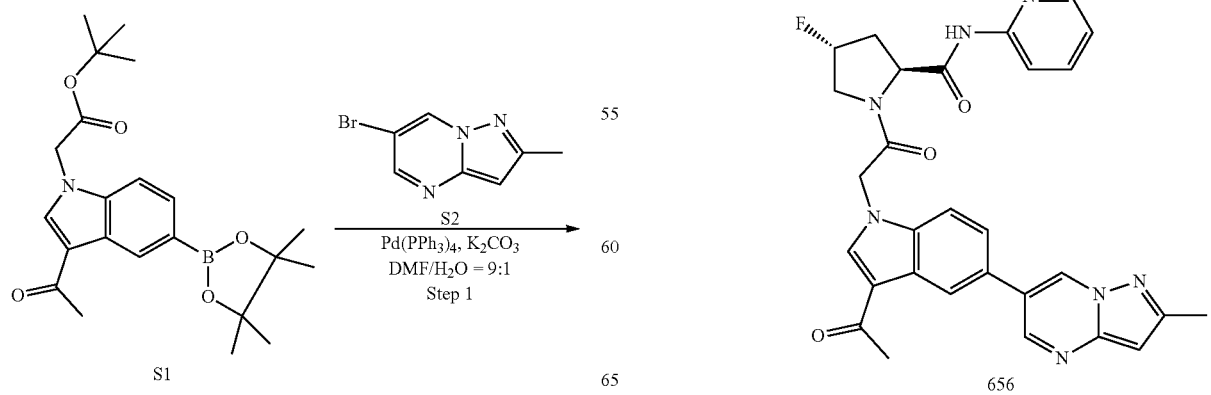

Step 1: tert-Butyl 2-(3-acetyl-5-(2-methylpyrazolo[1,5-a]pyrimidin-6-yl)-1H-indol-1-yl)acetate (S3)

To a solution of 6-bromo-2-methylpyrazolo[1,5-a]pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S3.

Step 2: 2-(3-Acetyl-5-(2-methylpyrazolo[1,5-a]pyrimidin-6-yl)-1H-indol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (2S,4R)-1-(2-(3-Acetyl-5-(2-methylpyrazolo[1,5-a]pyrimidin-6-yl)-1H-indol-1-yl)acetyl)-4-fluoro-N-(6-(trifluoromethoxy)pyridin-2-yl)pyrrolidine-2-carboxamide (656)

To a solution of compound S4 (1 equiv) in DMF (10 vol) at 0° C. under an atmosphere of nitrogen was added (2S,4R)-4-fluoro-N-(6-(trifluoromethoxy)pyridin-2-yl)pyrrolidine-2-carboxamide hydrochloride (S5, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 656. $^1$H NMR (400 MHz, DMSO-d$_6$) δ 2.08-2.27 (m, 1H), 2.48 (s, 3H), 2.51 (s, 3H), 2.53-2.65 (m, 1H), 3.92-4.09 (m, 1H), 4.17-4.29 (m, 1H), 4.80 (d, J=8.5 Hz, 1H), 5.31 (d, J=17.3 Hz, 1H), 5.45 (d, J=17.2 Hz, 1H), 5.49-5.66 (m, 1H), 6.56 (s, 1H), 6.97 (d, J=7.9 Hz, 1H), 7.57-7.68 (m, 2H), 7.97 (t, J=8.0 Hz, 1H), 8.08-8.03 (m, 1H), 8.32 (s, 1H), 8.46 (d, J=1.8 Hz, 1H), 8.81 (d, J=2.3 Hz, 1H), 9.23 (d, J=2.3 Hz, 1H), 10.87 (s, 1H). $^{19}$F NMR (376 MHz, DMSO-d$_6$): δ −175.65, −55.12. LC (method A): t$_R$=2.00 min. LC/MS (EI) m/z: [M+H]$^+$ 624.

(2S,4R)-1-(2-(3-Acetyl-5-(2-methylpyrazolo[1,5-a]pyrimidin-6-yl)-1H-indol-1-yl)acetyl)-N-(6-bromo-4-methylpyridin-2-yl)-4-fluoropyrrolidine-2-carboxamide (657)

Scheme 213

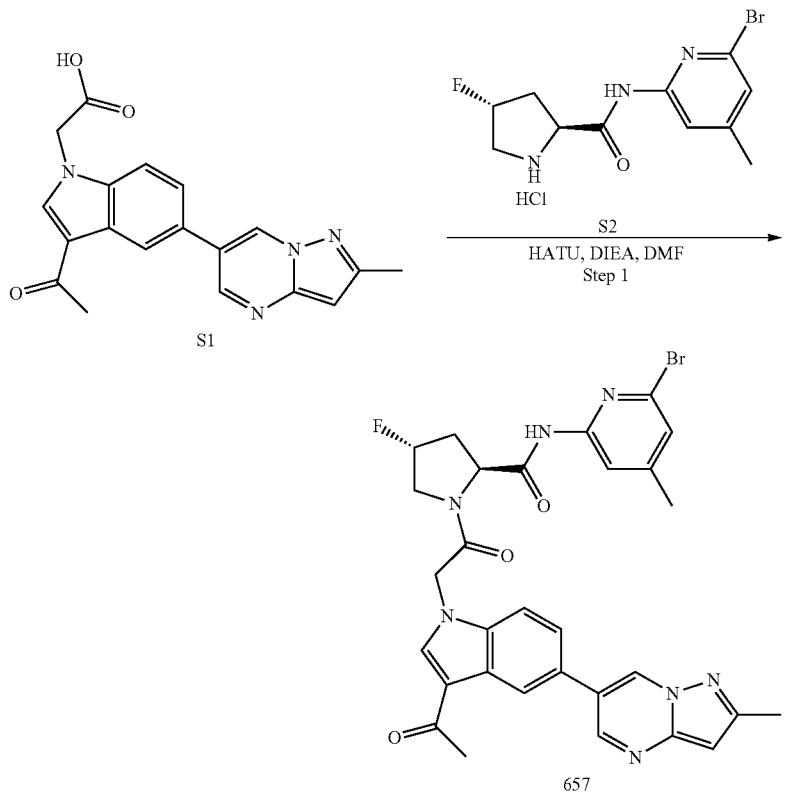

To a solution of compound S1 (1 equiv) in DMF (10 vol) at 0° C. under an atmosphere of nitrogen was added (2S,4R)—N-(6-bromo-4-methylpyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 657. $^1$H NMR (400 MHz, DMSO-$d_6$) δ 2.06-2.24 (m, 1H), 2.27 (s, 3H), 2.46 (s, 3H), 2.48 (s, 3H), 2.54-2.63 (m, 1H), 3.92-4.08 (m, 1H), 4.20 (dd, J=12.7, 21.9 Hz, 1H), 4.69 (t, J=8.5 Hz, 1H), 5.29 (d, J=17.3 Hz, 1H), 5.44 (d, J=17.2 Hz, 1H), 5.48-5.65 (m, 1H), 6.56 (s, 1H), 7.20 (s, 1H), 7.61-7.69 (m, 2H), 7.89 (s, 1H), 8.32 (s, 1H), 8.46 (d, J=1.7 Hz, 1H), 8.81 (s, 1H), 9.23 (d, J=2.3 Hz, 1H), 10.92 (s, 1H). $^{19}$F NMR (376 MHz, DMSO-$d_6$): δ −175.59. LC (method A): $t_R$=1.94 min. LC/MS (EI) m/z: [M+H]$^+$ 632.

(2S,4R)-1-(2-(3-Acetyl-5-(2-methylpyrazolo[1,5-a]pyrimidin-6-yl)-1H-indazol-1-yl)acetyl)-N-(6-(difluoromethoxy)pyridin-2-yl)-4-fluoropyrrolidine-2-carboxamide (658)

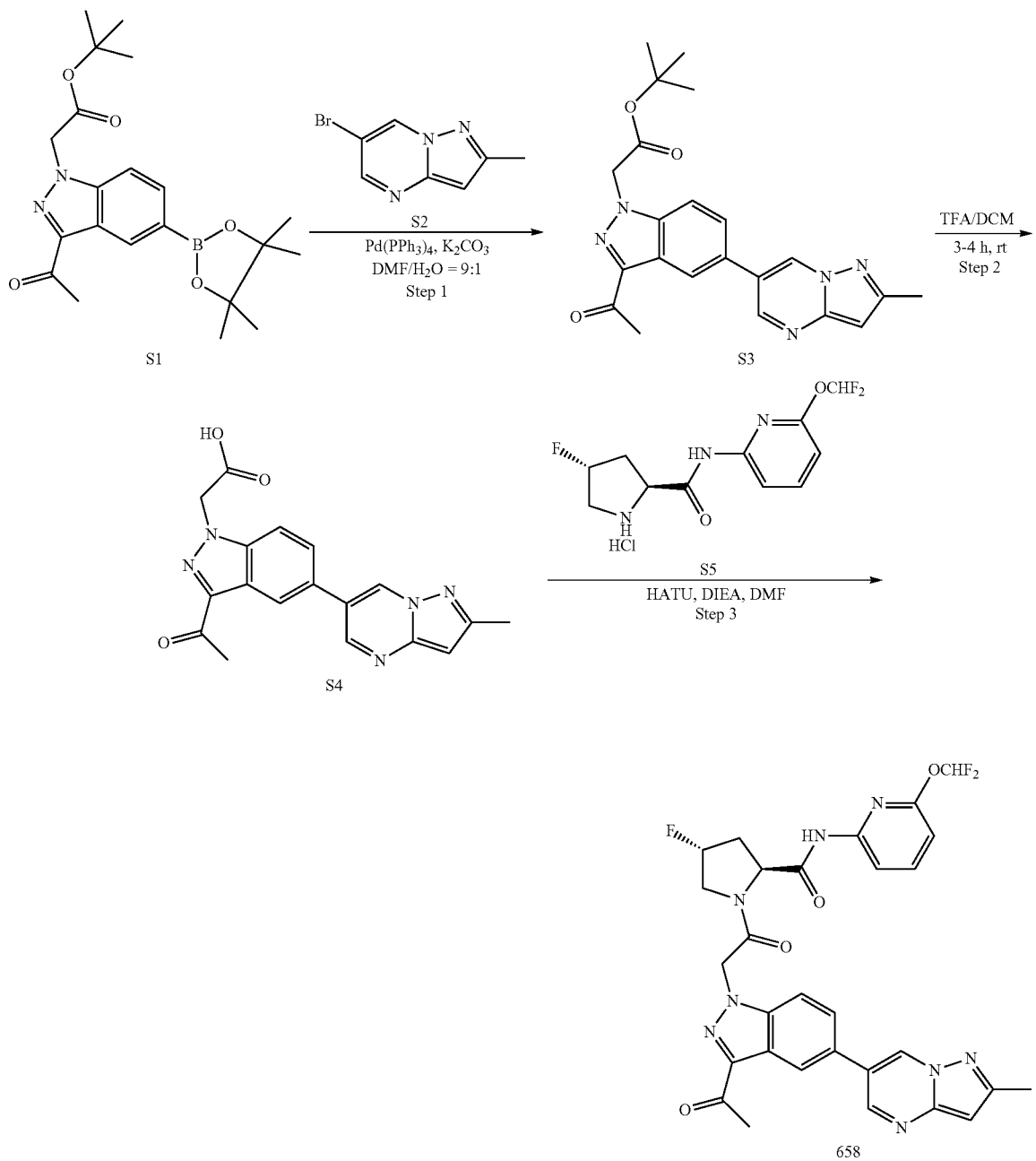

Scheme 214

Step 1: tert-Butyl 2-(3-acetyl-5-(2-methylpyrazolo[1,5-a]pyrimidin-6-yl)-1H-indazol-1-yl)acetate (S3)

To a solution of 6-bromo-2-methylpyrazolo[1,5-a]pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S3.

Step 2: 2-(3-Acetyl-5-(2-methylpyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 1: (2S,4R)-1-(2-(3-Acetyl-5-(2-methylpyrazolo[1,5-a]pyrimidin-6-yl)-1H-indazol-1-yl)acetyl)-N-(6-(difluoromethoxy)pyridin-2-yl)-4-fluoropyrrolidine-2-carboxamide (658)

To a solution of compound S1 (1 equiv) in DMF (10 vol) at 0° C. under an atmosphere of nitrogen was added (2S,4R)—N-(6-(difluoromethoxy)pyridin-2-yl)-4-fluoropyrrolidine-2-carboxamide hydrochloride (5, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 6. $^1$H NMR (400 MHz, DMSO-d$_6$) δ 2.07-2.28 (m, 1H), 2.47 (s, 3H), 2.54-2.63 (m, 1H), 2.66 (s, 3H), 3.95-4.11 (m, 1H), 4.25 (dd, J=12.2, 22.3 Hz, 1H), 4.77 (t, J=8.4 Hz, 1H), 5.50-5.70 (m, 2H), 5.84 (d, J=17.3 Hz, 1H), 6.58 (s, 1H), 6.73-6.79 (m, 1H), 7.72-7.31 (m, 1H), 7.83-7.94 (m, 4H), 8.46 (d, J=1.6 Hz, 1H), 8.85 (d, J=2.2 Hz, 1H), 9.34 (d, J=2.2 Hz, 1H), 10.72 (s, 1H). $^{19}$F NMR (376 MHz, DMSO-d$_6$): δ −175.67, −85.71. LC (method A): t$_R$=2.00 min. LC/MS (EI) m/z: [M+H]$^+$ 607.

(2S,4R)-1-(2-(3-Acetyl-5-(2-methylpyrazolo[1,5-a]pyrimidin-6-yl)-1H-indazol-1-yl)acetyl)-N-(6-bromo-5-methylpyrazin-2-yl)-4-fluoropyrrolidine-2-carboxamide (662)

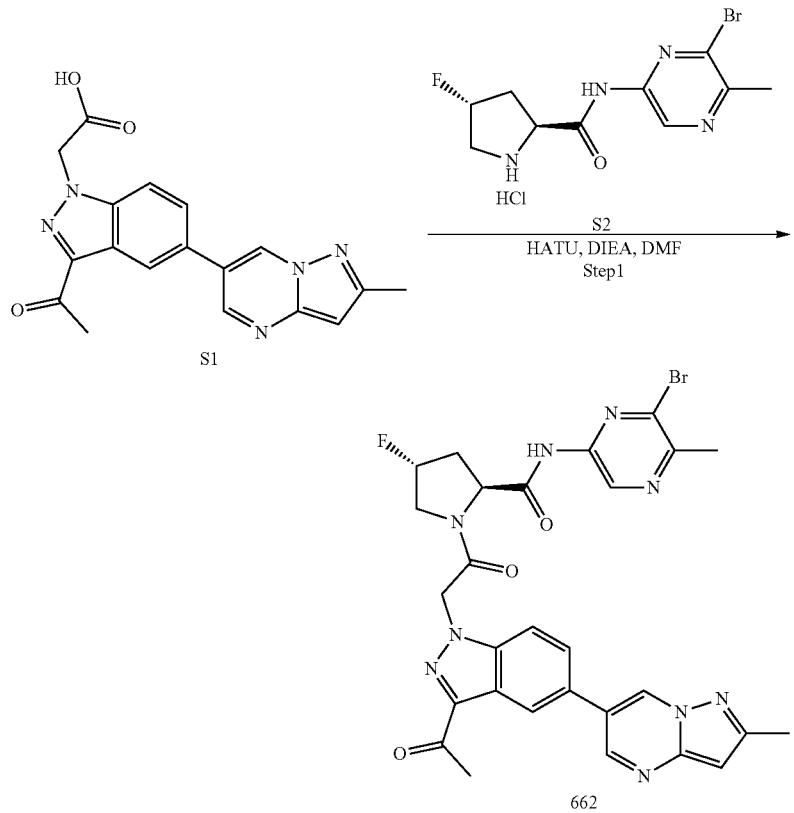

Scheme 215

To a solution of compound S1 (1 equiv) in DMF (10 vol) at 0° C. under an atmosphere of nitrogen was added (2S,4R)—N-(6-bromo-5-methylpyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 662. $^1$H NMR (400 MHz, DMSO-$d_6$) δ 2.10-2.34 (m, 1H), 2.47 (s, 3H), 2.52 (s, 3H), 2.55-2.62 (m, 1H), 2.65 (s, 3H), 3.97-4.14 (m, 1H), 4.20-4.33 (m, 1H), 4.66-4.75 (m, 1H), 5.49-5.71 (m, 2H), 5.85 (d, J=17.3 Hz, 1H), 6.57 (s, 1H), 7.75-7.97 (m, 2H), 8.46 (d, J=1.7 Hz, 1H), 8.84 (d, J=2.3 Hz, 1H), 9.13 (s, 1H), 9.34 (d, J=2.3 Hz, 1H), 11.22 (s, 1H). $^{19}$F NMR (376 MHz, DMSO-$d_6$): δ −175.72. LC (method A): $t_R$=1.86 min. LC/MS (EI) m/z: [M+H]$^+$ 634.

(1R,3S,5R)-2-(2-(3-Acetyl-5-(2-methylpyrazolo[1,5-a]pyrimidin-6-yl)-1H-indazol-1-yl)acetyl)-N-(6-bromo-5-methylpyrazin-2-yl)-2-azabicyclo[3.1.0]hexane-3-carboxamide (666)

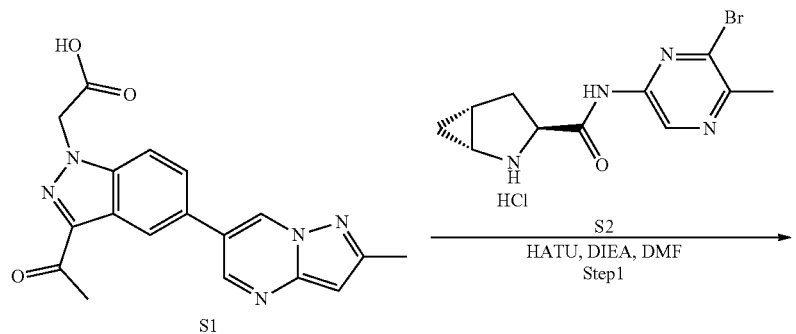

Scheme 216

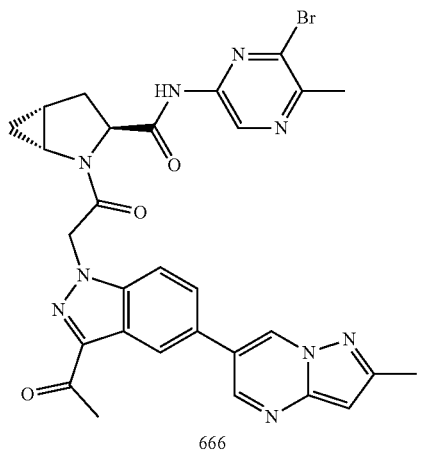

666

To a solution of compound S1 (1 equiv) in DMF (10 vol) at 0° C. under an atmosphere of nitrogen was added (1R,3S,5R)—N-(6-bromo-5-methylpyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 666. $^1$H NMR (400 MHz, DMSO-$d_6$) δ 0.82-0.90 (m, 1H), 1.01-1.07 (m, 1H), 1.87-1.98 (m, 1H), 2.22-2.41 (m, 2H), 2.47 (s, 3H), 2.54 (s, 3H), 2.67 (s, 3H), 3.85-3.91 (m, 1H), 4.49 (dd, J=5.4, 9.1 Hz, 1H), 5.63 (d, J=17.2 Hz, 1H), 6.00 (d, J=17.3 Hz, 1H), 6.58 (s, 1H), 7.86-7.95 (m, 2H), 8.47 (d, J=1.5 Hz, 1H), 8.86 (d, J=2.2 Hz, 1H), 9.14 (s, 1H), 9.35 (d, J=2.2 Hz, 1H), 11.00 (s, 1H). LC (method A): $t_R$=1.99 min. LC/MS (EI) m/z: [M+H]$^+$ 628.

(1R,3S,5R)-2-(2-(3-Acetyl-5-(2-methylpyrazolo[1,5-a]pyrimidin-6-yl)-1H-indazol-1-yl)acetyl)-N-(6-(trifluoromethoxy)pyridin-2-yl)-2-azabicyclo[3.1.0]hexane-3-carboxamide (670)

Scheme 217

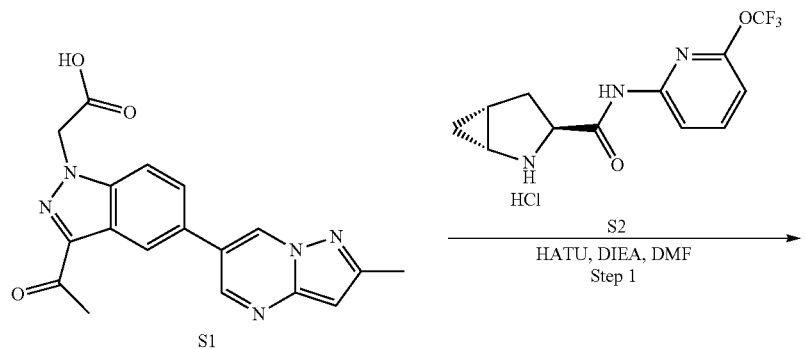

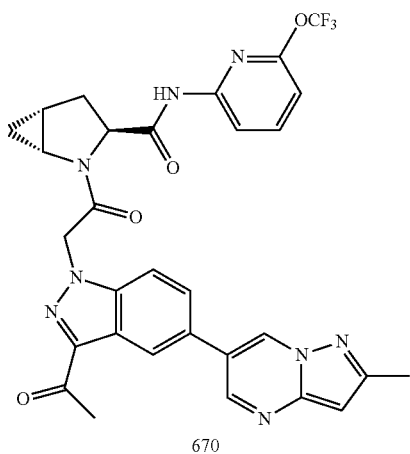

To a solution of compound S1 (1 equiv) in DMF (10 vol) at 0° C. under an atmosphere of nitrogen was added (1R,3S,5R)—N-(6-(trifluoromethoxy)pyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 670.

$^1$H NMR (400 MHz, DMSO-$d_6$) δ 0.79-0.85 (m, 1H), 0.99-1.11 (m, 1H), 1.87-1.96 (m, 1H), 2.20-2.29 (m, 1H), 2.30-2.39 (m, 1H), 2.47 (s, 3H), 2.66 (s, 3H), 3.85-3.95 (m, 1H), 4.55 (dd, J=5.5, 9.0 Hz, 1H), 5.63 (d, J=17.3 Hz, 1H), 6.00 (d, J=17.2 Hz, 1H), 6.58 (s, 1H), 6.97 (d, J=7.8 Hz, 1H), 7.85-7.93 (m, 2H), 7.98 (t, J=8.0 Hz, 1H), 8.05 (d, J=8.2 Hz, 1H), 8.47 (d, J=1.6 Hz, 1H), 8.85 (d, J=2.2 Hz, 1H), 9.34 (d, J=2.3 Hz, 1H), 10.63 (s, 1H). $^{19}$F NMR (376 MHz, DMSO-$d_6$): δ −55.11. LC (method A): $t_R$=2.23 min. LC/MS (EI) m/z: [M+H]$^+$ 619.

(1R,3S,5R)-2-(2-(3-Acetyl-5-(2-methyl-[1,2,4]triazolo[1,5-a]pyridin-6-yl)-1H-indazol-1-yl)acetyl)-N-(6-bromopyrazin-2-yl)-2-azabicyclo[3.1.0]hexane-3-carboxamide (659)

Scheme 218

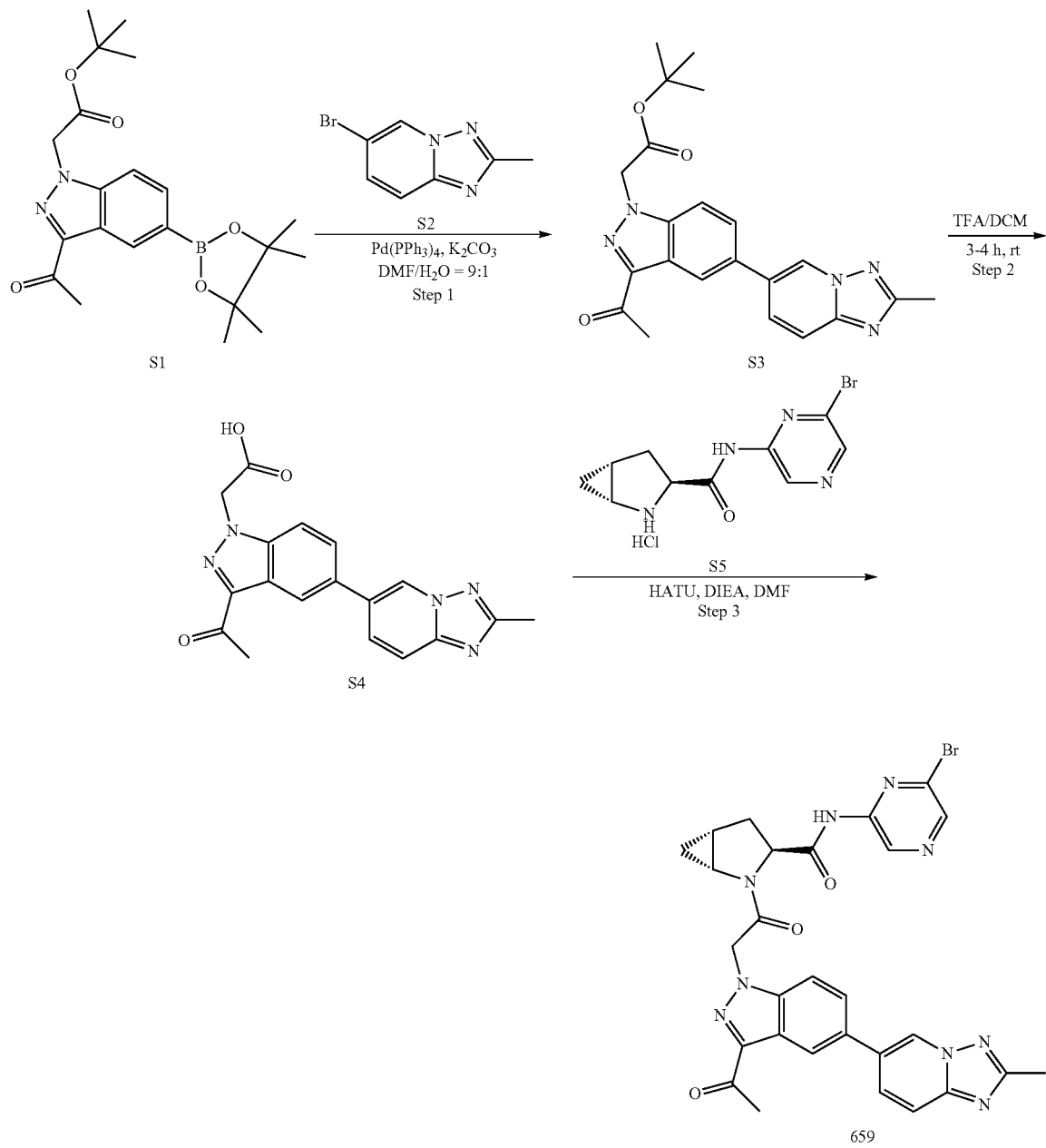

Step 1: tert-Butyl 2-(3-acetyl-5-(2-methyl-[1,2,4]triazolo[1,5-a]pyridin-6-yl)-1H-indazol-1-yl)acetate (3S)

To a solution of 6-bromo-2-methyl-[1,2,4]triazolo[1,5-a]pyridine (1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S3.

Step 2: 2-(3-Acetyl-5-(2-methyl-[1,2,4]triazol[1,5-a]pyridin-6-yl)-1H-indazol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (1R,3S,5R)-2-(2-(3-Acetyl-5-(2-methyl-[1,2,4]triazolo[1,5-a]pyridin-6-yl)-1H-indazol-1-yl)acetyl)-N-(6-bromopyrazin-2-yl)-2-azabicyclo[3.1.0]hexane-3-carboxamide (659)

To a solution of compound S4 (1 equiv) in DMF (10 vol) at 0° C. under an atmosphere of nitrogen was added (1R,3S,5R)—N-(6-bromopyrazin-2-yl)-2-azabicyclo[3.1.0]hexane-3-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 659. $^1$H NMR (400 MHz, DMSO-$d_6$) δ 0.84-0.88 (m, 1H), 1.02-1.10 (m, 1H), 1.87-1.97 (m, 1H), 2.25-2.40 (m, 2H), 2.49-2.53 (m, 3H), 2.67 (s, 3H), 3.84-3.92 (m, 1H), 4.47-4.55 (m, 1H), 5.64 (d, J=17.2 Hz, 1H), 6.00 (d, J=17.3 Hz, 1H), 7.81 (d, J=9.2 Hz, 1H), 7.85-7.94 (m, 2H), 7.97-8.01 (m, 1H), 8.44-8.48 (m, 1H), 8.54 (s, 1H), 9.19-9.23 (m, 1H), 9.27 (s, 1H), 11.13 (s, 1H). LC (method A): $t_R$=1.69 min. LC/MS (EI) m/z: [M+H]$^+$ 614.

(1R,3S,5R)-2-(2-(3-Acetyl-5-(2-methyl-[1,2,4]triazolo[1,5-a]pyridin-6-yl)-1H-indazol-1-yl)acetyl)-N-(6-bromopyridin-2-yl)-2-azabicyclo[3.1.0]hexane-3-carboxamide (660)

To a solution of compound S1 (1 equiv) in DMF (10 vol) at 0° C. under an atmosphere of nitrogen was added (1R,3S,5R)—N-(6-bromopyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 660. $^1$H NMR (400 MHz, DMSO-$d_6$) δ 0.75-0.88 (m, 1H), 1.03 (dd, J=5.0, 9.1 Hz, 1H), 1.88-1.96 (m, 1H), 2.17-2.28 (m, 1H), 2.31-2.40 (m, 1H), 2.51 (d, J=2.8 Hz, 3H), 2.67 (s, 3H), 3.80-3.92 (m, 1H), 4.48 (dd, J=5.4, 9.1 Hz, 1H), 5.63 (d, J=17.2 Hz, 1H), 6.00 (d, J=17.3 Hz, 1H), 7.33 (d, J=7.7 Hz, 1H), 7.72 (t, J=8.0 Hz, 1H), 7.81 (d, J=9.2 Hz, 1H), 7.85-7.93 (m, 2H), 7.97-8.06 (m, 2H), 8.45 (s, 1H), 9.20 (d, J=1.8 Hz, 1H), 10.76 (s, 1H). LC (method A): $t_R$=1.87 min. LC/MS (EI) m/z: [M+H]$^+$ 613.

Scheme 219

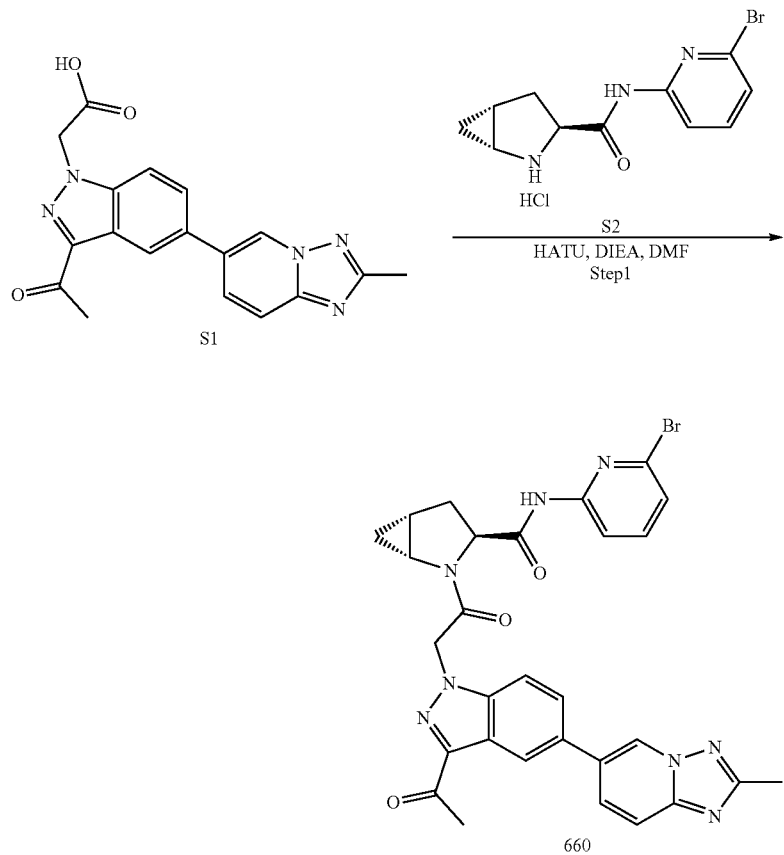

(2S,4R)-1-(2-(3-Acetyl-5-(2-methyl-[1,2,4]triazolo[1,5-a]pyridin-6-yl)-1H-indazol-1-yl)acetyl)-N-(6-bromopyridin-2-yl)-4-fluoropyrrolidine-2-carboxamide (661)

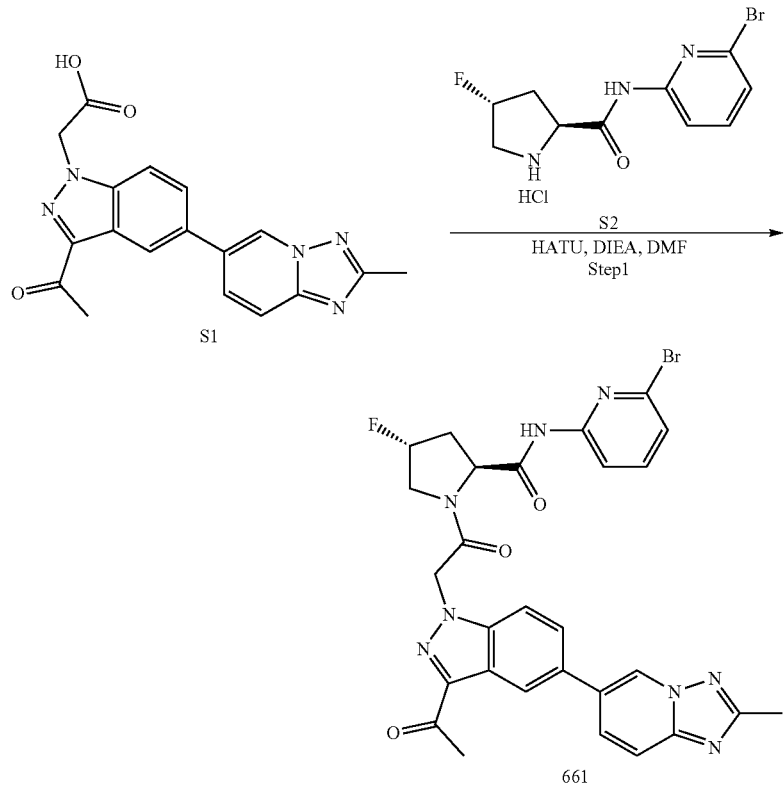

To a solution of compound S1 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 661. $^1$H NMR (400 MHz, DMSO-$d_6$) δ 2.05-2.30 (m, 1H), 2.50 (s, 3H), 2.55-2.63 (m, 1H), 2.66 (s, 3H), 3.97-4.13 (m, 1H), 4.18-4.34 (m, 1H), 4.69 (dd, J=7.6, 9.5 Hz, 1H), 5.49-5.70 (m, 2H), 5.85 (d, J=17.3 Hz, 1H), 7.32 (d, J=7.7 Hz, 1H), 7.48 (dd, J=1.9, 7.2 Hz, 1H), 7.71 (t, J=8.0 Hz, 1H), 7.85 (d, J=8.9 Hz, 1H), 7.93-8.07 (m, 3H), 8.51 (d, J=1.7 Hz, 1H), 8.89 (d, J=7.1 Hz, 1H), 11.00 (s, 1H). $^{19}$F NMR (376 MHz, DMSO-$d_6$): δ −175.66. LC (method A): $t_R$=1.70 min. LC/MS (EI) m/z: [M+H]$^+$ 619.

(2S,4R)-1-(2-(3-Acetyl-5-(2-methyl-[1,2,4]triazolo[1,5-a]pyridin-6-yl)-1H-indazol-1-yl)acetyl)-N-(6-bromo-5-methylpyrazin-2-yl)-4-fluoropyrrolidine-2-carboxamide (663)

Scheme 221

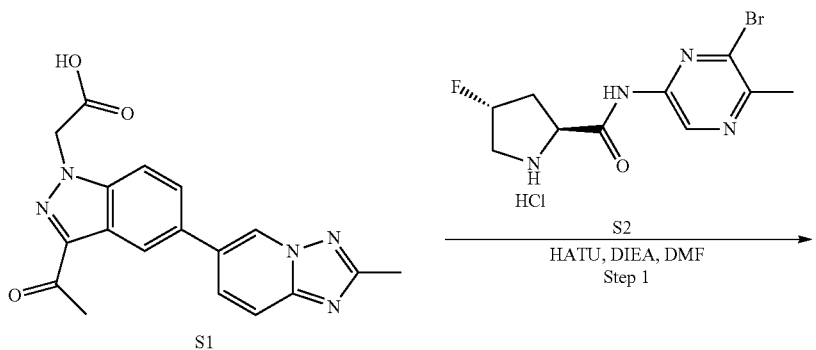

-continued

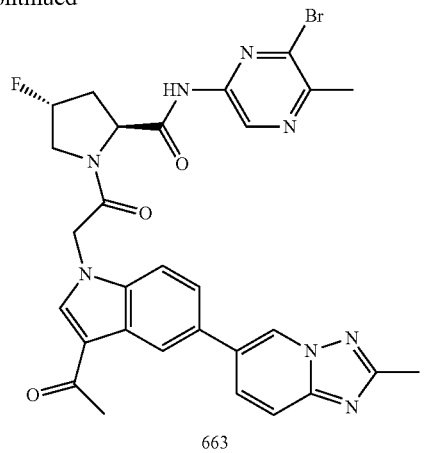

663

To a solution of compound S1 (1 equiv) in DMF (10 vol) at 0° C. under an atmosphere of nitrogen was added (2S,4R)—N-(6-bromo-5-methylpyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 663. $^1$H NMR (400 MHz, DMSO-$d_6$) δ 2.11-2.30 (m, 1H), 2.51 (s, 3H), 2.53 (s, 3H), 2.55-2.62 (m, 1H), 2.66 (s, 3H), 3.98-4.12 (m, 1H), 4.25 (dd, J=12.5, 22.2 Hz, 1H), 4.69 (t, J=8.5 Hz, 1H), 5.48-5.69 (m, 2H), 5.85 (d, J=17.3 Hz, 1H), 7.79-7.87 (m, 2H), 7.89-7.95 (m, 1H), 7.97-8.01 (m, 1H), 8.44 (d, J=1.5 Hz, 1H), 9.13 (s, 1H), 9.20 (d, J=1.6 Hz, 1H), 11.22 (s, 1H). $^{19}$F NMR (376 MHz, DMSO-$d_6$): δ −175.72. LC (method A): $t_R$=1.66 min. LC/MS (EI) m/z: [M+H]$^+$ 634.

(1R,3S,5R)-2-(2-(3-Acetyl-5-(pyrazolo[1,5-a]pyrimidin-6-yl)-1H-indazol-1-yl)acetyl)-N-(6-bromopyrazin-2-yl)-2-azabicyclo[3.1.0]hexane-3-carboxamide (664)

Scheme 222

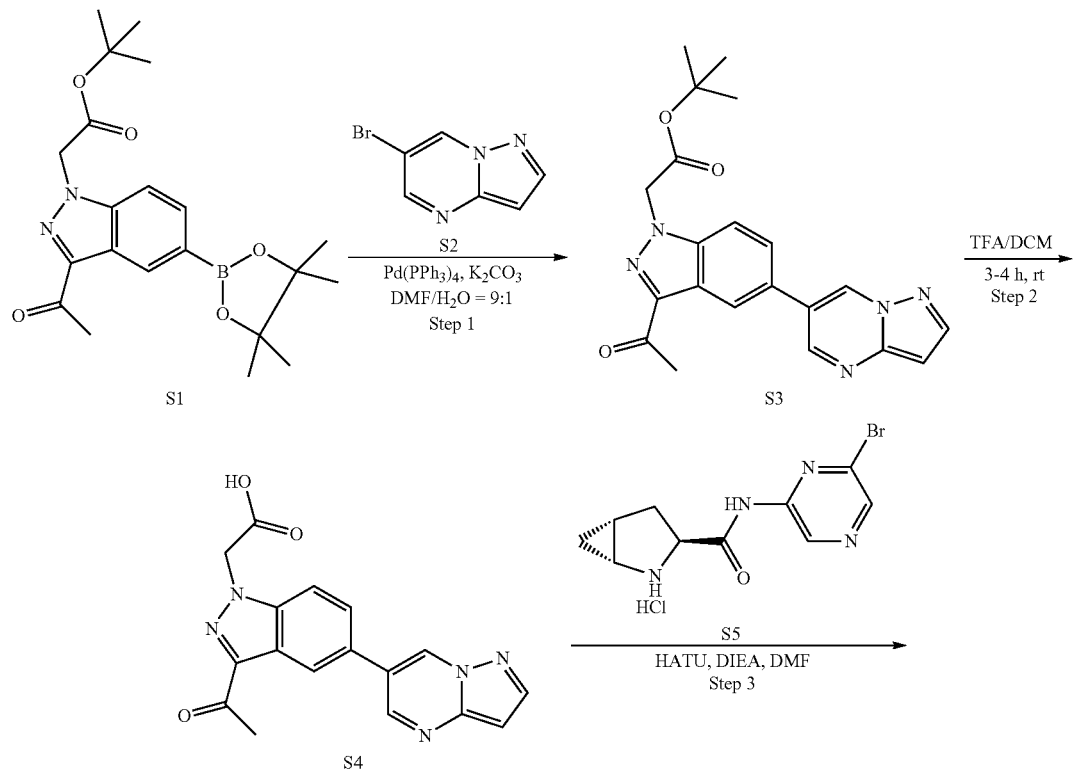

-continued

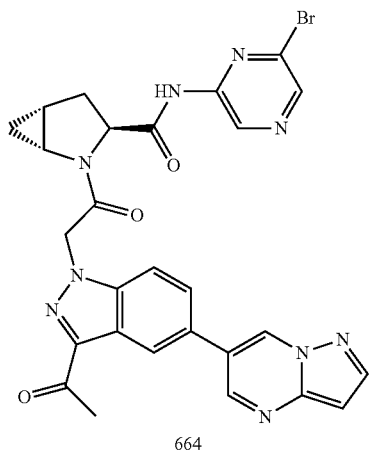

664

Step 1: tert-Butyl 2-(3-acetyl-5-(pyrazolo[1,5-a]pyrimidin-6-yl)-1H-indazol-1-yl)acetate (S3)

To a solution of 6-bromopyrazolo[1,5-a]pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated. The remaining residue was purified by column chromatography on silica gel to give compound S3.

Step 2: 2-(3-Acetyl-5-(pyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (10 vol). The reaction mixture was stirred at room temperature for 3 h and then concentrated. The remaining material was used directly in the next synthetic step.

Step 3: (1R,3S,5R)-2-(2-(3-Acetyl-5-(pyrazolo[1,5-a]pyrimidin-6-yl)-1H-indazol-1-yl)acetyl)-N-(6-bromopyrazin-2-yl)-2-azabicyclo[3.1.0]hexane-3-carboxamide (664)

To a solution of compound S4 (1 equiv) in DMF (10 vol) at 0° C. under an atmosphere of nitrogen was added (1R, 3S,5R)—N-(6-bromopyrazin-2-yl)-2-azabicyclo[3.1.0]hexane-3-carboxamide hydrochloride (5, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 664. $^1$H NMR (400 MHz, DMSO-d$_6$) δ 0.83-0.92 (m, 1H), 1.02-1.08 (m, 1H), 1.93 (p, J=6.7 Hz, 1H), 2.24-2.42 (m, 2H), 2.67 (s, 3H), 3.82-3.92 (m, 1H), 4.51 (dd, J=5.4, 9.1 Hz, 1H), 5.64 (d, J=17.2 Hz, 1H), 6.01 (d, J=17.3 Hz, 1H), 6.80 (d, J=2.3 Hz, 1H), 7.88-7.99 (m, 2H), 8.28 (d, J=2.3 Hz, 1H), 8.50-8.56 (m, 2H), 8.95 (d, J=2.3 Hz, 1H), 9.27 (s, 1H), 9.50 (d, J=2.2 Hz, 1H), 11.13 (s, 1H). LC (method A): t$_R$=1.77 min. LC/MS (EI) m/z: [M+H]$^+$ 600.

(2S,4R)-1-(2-(3-Acetyl-5-(pyrazolo[1,5-a]pyrimidin-6-yl)-1H-indazol-1-yl)acetyl)-N-(6-bromo-5-methylpyrazin-2-yl)-4-fluoropyrrolidine-2-carboxamide (665)

Scheme 223

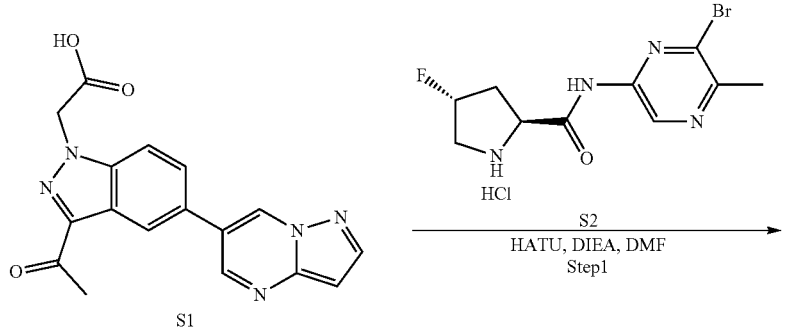

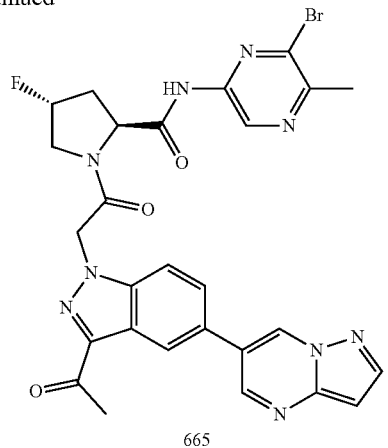

665

To a solution of compound S1 (1 equiv) in DMF (10 vol) at 0° C. under an atmosphere of nitrogen was added (2S, 4R)—N-(6-bromo-5-methylpyrazin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 665. $^1$H NMR (400 MHz, DMSO-$d_6$) δ 2.10-2.32 (m, 1H), 2.52 (s, 3H), 2.55-2.63 (m, 1H), 2.66 (s, 3H), 3.97-4.13 (m, 1H), 4.21-4.32 (m, 1H), 4.66-4.75 (m, 1H), 5.50-5.71 (m, 2H), 5.85 (d, J=17.3 Hz, 1H), 6.79 (d, J=2.3 Hz, 1H), 7.86 (d, J=8.8 Hz, 1H), 7.94 (dd, J=1.6, 8.9 Hz, 1H), 8.28 (d, J=2.3 Hz, 1H), 8.48-8.56 (m, 1H), 8.94 (d, J=2.2 Hz, 1H), 9.13 (s, 1H), 9.48 (d, J=2.4 Hz, 1H), 11.22 (s, 1H). $^{19}$F NMR (376 MHz, DMSO-$d_6$): δ −175.71. LC (method A): $t_R$=1.75 min. LC/MS (EI) m/z: [M+H]$^+$ 620.

(1R,3S,5R)-2-(2-(3-Acetyl-5-(pyrazolo[1,5-a]pyrimidin-6-yl)-1H-indazol-1-yl)acetyl)-N-(6-bromo-5-methylpyrazin-2-yl)-2-azabicyclo[3.1.0]hexane-3-carboxamide (667)

Scheme 224

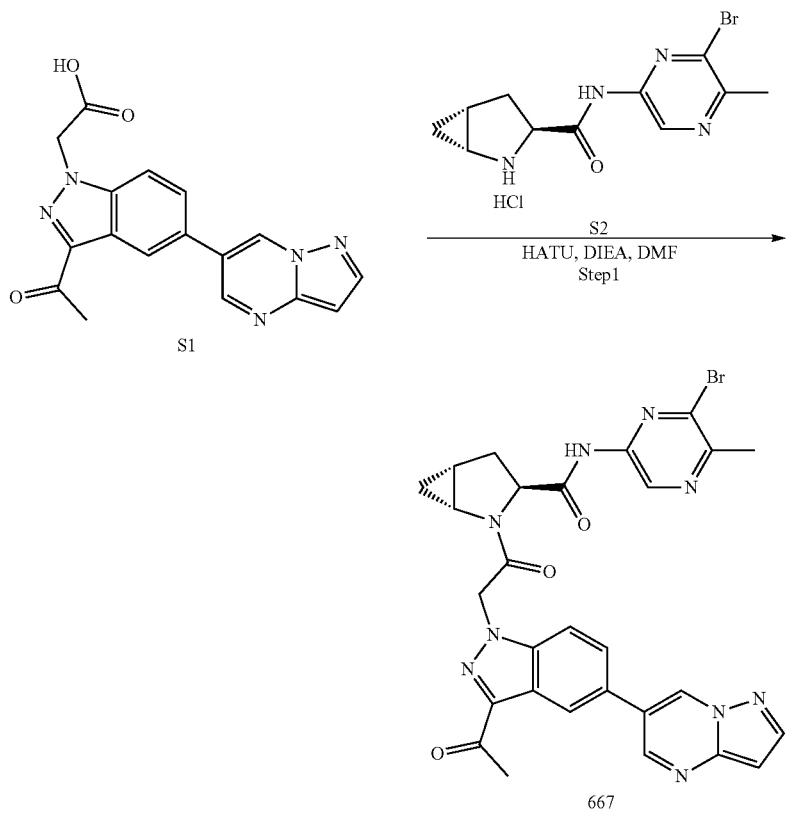

To a solution of compound S1 (1 equiv) in DMF (10 vol) at 0° C. under an atmosphere of nitrogen was added (1R, 3S,5R)—N-(6-bromo-5-methylpyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 667. $^1$H NMR (400 MHz, DMSO-$d_6$) δ 0.81-0.93 (m, 1H), 1.02-1.11 (m, 1H), 1.89-1.98 (m, 1H), 2.23-2.31 (m, 1H), 2.33-2.41 (m, 1H), 2.53 (s, 3H), 2.67 (s, 3H), 3.85-3.92 (m, 1H), 4.50 (dd, J=5.4, 9.1 Hz, 1H), 5.64 (d, J=17.2 Hz, 1H), 6.00 (d, J=17.3 Hz, 1H), 6.80 (d, J=2.3 Hz, 1H), 7.87-7.97 (m, 2H), 8.28 (d, J=2.3 Hz, 1H), 8.49-8.53 (m, 1H), 8.95 (d, J=2.3 Hz, 1H), 9.14 (s, 1H), 9.49 (d, J=2.2 Hz, 1H), 11.00 (s, 1H). LC (method A): $t_R$=1.88 min. LC/MS (EI) m/z: [M+H]$^+$ 614.

(2S,4R)-1-(2-(3-Acetyl-5-(pyrazolo[1,5-a]pyrimidin-6-yl)-1H-indazol-1-yl)acetyl)-4-fluoro-N-(6-(trifluoromethoxy)pyridin-2-yl)pyrrolidine-2-carboxamide (668)

To a solution of compound S1 (1 equiv) in DMF (10 vol) at 0° C. under an atmosphere of nitrogen was added (2S, 4R)-4-fluoro-N-(6-(trifluoromethoxy)pyridin-2-yl)pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 668. $^1$H NMR (400 MHz, DMSO-$d_6$) δ 2.09-2.28 (m, 1H), 2.58 (dd, J=6.4, 12.4 Hz, 1H), 2.66 (s, 3H), 3.94-4.13 (m, 1H), 4.20-4.33 (m, 1H), 4.78 (t, J=8.4 Hz, 1H), 5.49-5.71 (m, 2H), 5.85 (d, J=17.3 Hz, 1H), 6.80 (d, J=2.3 Hz, 1H), 6.97 (d, J=7.8 Hz, 1H), 7.87 (s, 1H), 7.92-8.01 (m, 2H), 8.05 (d, J=8.3 Hz, 1H), 8.28 (d, J=2.4 Hz, 1H), 8.50 (d, J=1.6 Hz, 1H), 8.94 (d, J=2.2 Hz, 1H), 9.47-9.50 (m, 1H), 10.87 (s, 1H). $^{19}$F NMR (376 MHz, DMSO-$d_6$): δ −175.69, −55.12. LC (method A): $t_R$=2.02 min. LC/MS (EI) m/z: [M+H]$^+$ 610.

Scheme 225

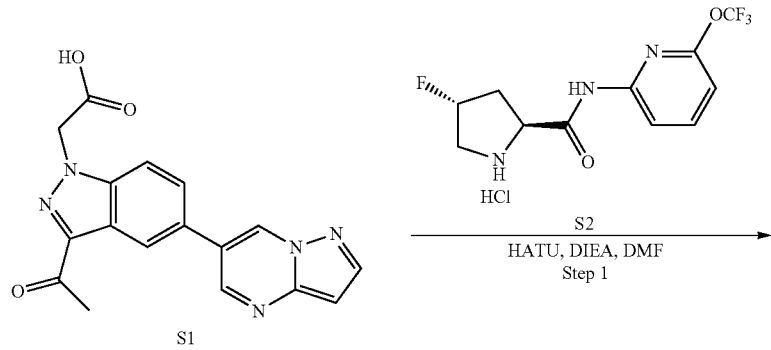

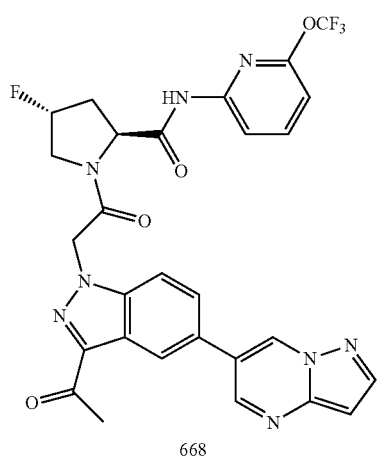

668

557

(1R,3S,5R)-2-(2-(3-Acetyl-5-(pyrazolo[1,5-a]pyrimidin-6-yl)-1H-indazol-1-yl)acetyl)-N-(6-(trifluoromethoxy)pyridin-2-yl)-2-azabicyclo[3.1.0]hexane-3-carboxamide (671)

558

(2S,4R)-1-(2-(3-Acetyl-5-(2-methylpyrimidin-5-yl)-1H-indazol-1-yl)acetyl)-4-fluoro-N-(6-(trifluoromethoxy)pyridin-2-yl)pyrrolidine-2-carboxamide (344)

Scheme 226

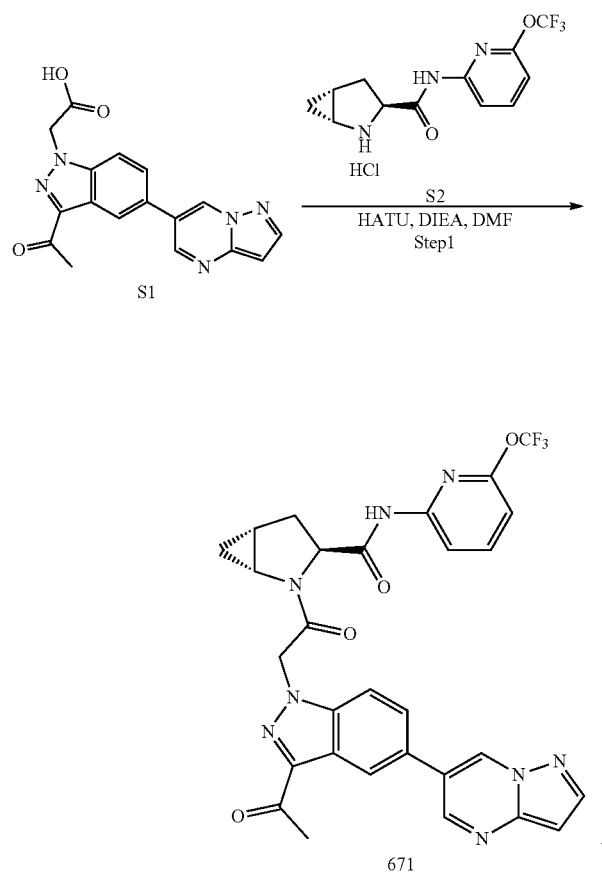

Scheme 227

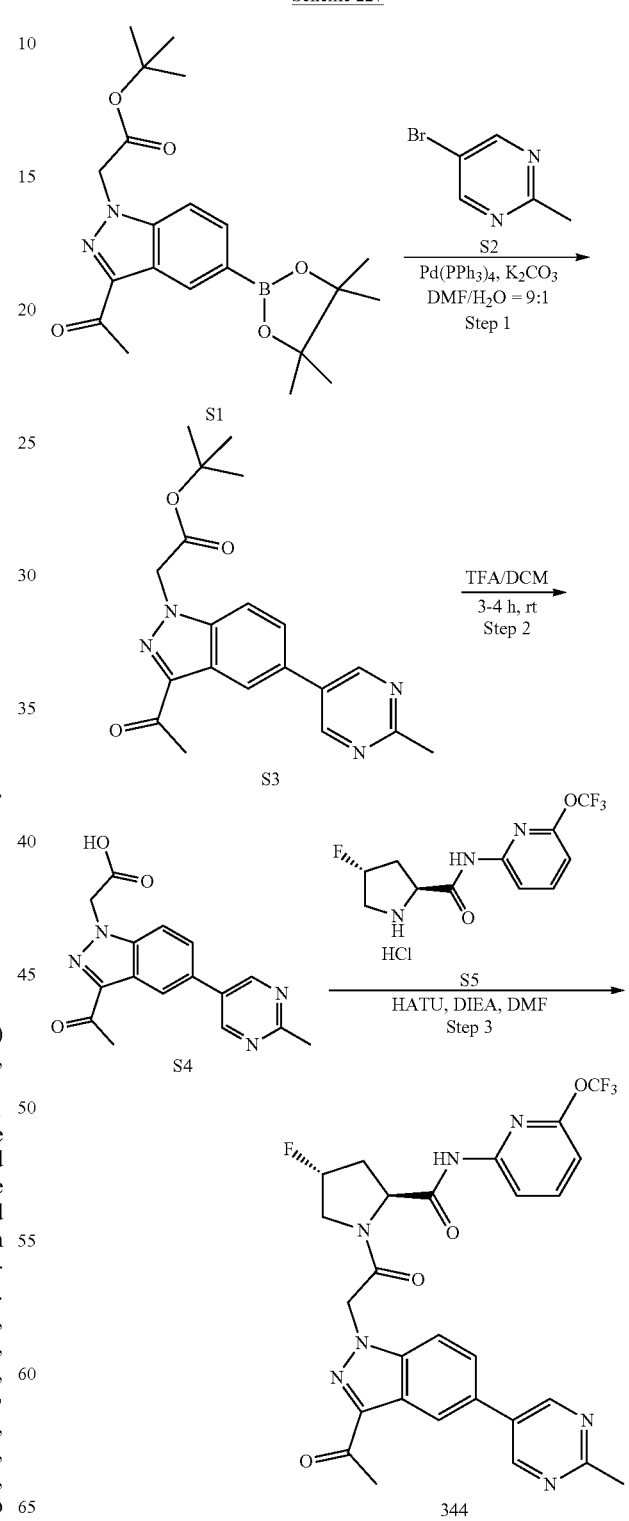

To a solution of compound S1 (1 equiv) in DMF (10 vol) at 0° C. under an atmosphere of nitrogen was added (1R,3S,5R)—N-(6-(trifluoromethoxy)pyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 671. $^1$H NMR (400 MHz, DMSO-$d_6$) δ 0.79-0.86 (m, 1H), 1.00-1.10 (m, 1H), 1.88-1.99 (m, 1H), 2.20-2.28 (m, 1H), 2.31-2.40 (m, 1H), 2.67 (s, 3H), 3.85-3.92 (m, 1H), 4.55 (dd, J=5.5, 9.0 Hz, 1H), 5.64 (d, J=17.2 Hz, 1H), 6.01 (d, J=17.3 Hz, 1H), 6.80 (d, J=2.3 Hz, 1H), 6.97 (d, J=7.8 Hz, 1H), 7.86-8.02 (m, 3H), 8.05 (d, J=8.2 Hz, 1H), 8.28 (d, J=2.3 Hz, 1H), 8.51 (s, 1H), 8.95 (d, J=2.2 Hz, 1H), 9.49 (d, J=2.2 Hz, 1H), 10.63 (s, 1H). $^{19}$F NMR (376 MHz, DMSO-$d_6$): δ −55.16. LC (method A): $t_R$=2.13 min. LC/MS (EI) m/z: [M+H]$^+$ 605.

Step 1: tert-Butyl 2-(3-acetyl-5-(2-methylpyrimidin-5-yl)-1H-indazol-1-yl)acetate (S3)

To a solution of 5-bromo-2-methylpyrimidine (S2, 1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-methylpyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-methylpyrimidin-5-yl)-1H-indazol-1-yl)acetyl)-4-fluoro-N-(6-(trifluoromethoxy)pyridin-2-yl)pyrrolidine-2-carboxamide (344)

To a solution of compound S4 (1 equiv) in DMF (10 vol) at 0° C. under an atmosphere of nitrogen was added (2S,4R)-4-fluoro-N-(6-(trifluoromethoxy)pyridin-2-yl)pyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 344. ¹H NMR (400 MHz, DMSO-d₆) δ 2.07-2.32 (m, 1H), 2.54-2.61 (m, 1H), 2.65 (s, 3H), 2.69 (s, 3H), 3.93-4.11 (m, 1H), 4.25 (dd, J=12.5, 22.1 Hz, 1H), 4.78 (t, J=8.5 Hz, 1H), 5.49-5.70 (m, 2H), 5.85 (d, J=17.3 Hz, 1H), 6.97 (d, J=7.8 Hz, 1H), 7.85 (s, 2H), 7.94-8.09 (m, 2H), 8.42 (d, J=1.5 Hz, 1H), 9.03 (s, 2H), 10.86 (s, 1H). ¹⁹F NMR (376 MHz, DMSO-d₆): δ −175.70, −55.14. LC (method A): $t_R$=1.88 min. LC/MS (EI) m/z: [M+H]⁺ 586.

(2S,4R)-1-(2-(3-Acetyl-5-(2-methylpyrimidin-5-yl)-1H-indazol-1-yl)acetyl)-N-(6-bromo-4-methylpyridin-2-yl)-4-fluoropyrrolidine-2-carboxamide (345)

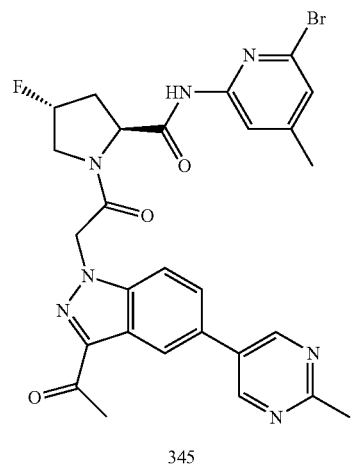

345

To a solution of compound S1 (1 equiv) in DMF (10 vol) at 0° C. under an atmosphere of nitrogen was added (2S,4R)—N-(6-bromo-4-methylpyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 345. ¹H NMR (400 MHz, DMSO-d₆) δ 2.06-2.24 (m, 1H), 2.27 (s, 3H), 2.54-2.61 (m, 1H), 2.65 (s, 3H), 2.69 (s, 3H), 3.94-4.15 (m, 1H), 4.24 (dd, J=12.5, 22.2 Hz, 1H), 4.67 (t, J=8.5 Hz, 1H), 5.47-5.67 (m, 2H), 5.84 (d, J=17.3 Hz, 1H), 7.20 (s, 1H), 7.87 (d, J=6.0 Hz, 3H), 8.43 (s, 1H), 9.04 (d, J=1.0 Hz, 2H), 10.90 (s, 1H). ¹⁹F NMR (376 MHz, DMSO-d₆): δ −175.66. LC (method A): $t_R$=1.81 min. LC/MS (EI) m/z: [M+H]⁺ 594.

(2S,4R)-1-(2-(3-Acetyl-5-(2-methylpyrimidin-5-yl)-1H-indazol-1-yl)acetyl)-N-(6-bromo-5-methylpyrazin-2-yl)-4-fluoropyrrolidine-2-carboxamide (349)

Scheme 228

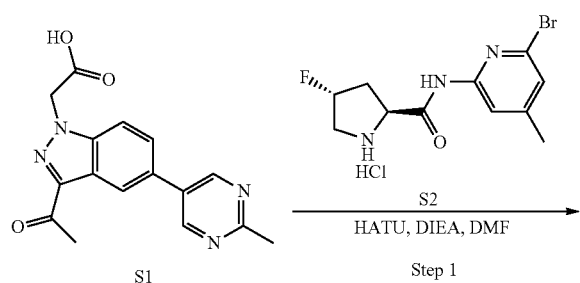

Scheme 229

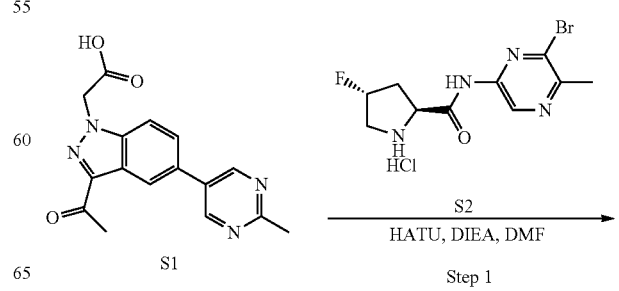

561
-continued

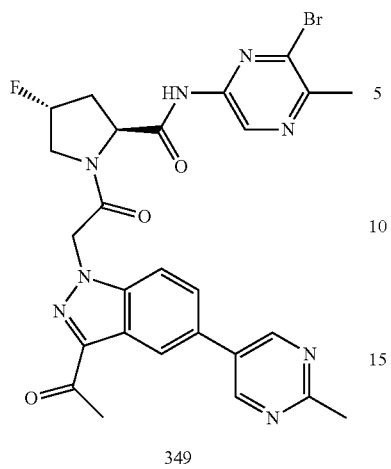

349

562
-continued

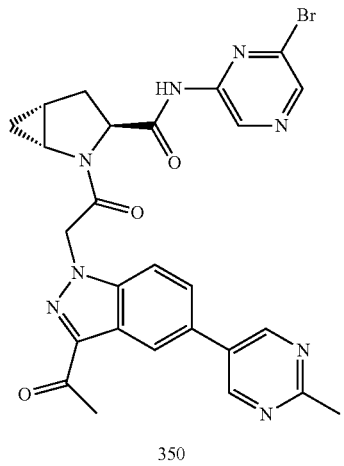

350

To a solution of compound S1 (1 equiv) in DMF (10 vol) at 0° C. under an atmosphere of nitrogen was added (2S, 4R)—N-(6-bromo-5-methylpyrazin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 349. $^1$H NMR (400 MHz, DMSO-$d_6$) δ 2.08-2.32 (m, 1H), 2.53 (s, 3H), 2.55-2.63 (m, 1H), 2.65 (s, 3H), 2.69 (s, 3H), 3.95-4.12 (m, 1H), 4.18-4.31 (m, 1H), 4.68 (dd, J=7.5, 9.5 Hz, 1H), 5.49-5.71 (m, 2H), 5.85 (d, J=17.3 Hz, 1H), 7.86 (d, J=1.4 Hz, 2H), 8.42 (d, J=1.3 Hz, 1H), 9.03 (s, 2H), 9.13 (s, 1H), 11.21 (s, 1H). $^{19}$F NMR (376 MHz, DMSO-$d_6$): δ −175.73. LC (method A): $t_R$=1.58 min. LC/MS (EI) m/z: [M+H]$^+$ 595.

(1R,3S,5R)-2-(2-(3-Acetyl-5-(2-methylpyrimidin-5-yl)-1H-indazol-1-yl)acetyl)-N-(6-bromopyrazin-2-yl)-2-azabicyclo[3.1.0]hexane-3-carboxamide (350)

To a solution of compound S1 (1 equiv) in DMF (10 vol) at 0° C. under an atmosphere of nitrogen was added (1R, 3S,5R)—N-(6-bromopyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 350. $^1$H NMR (400 MHz, DMSO-$d_6$) δ 0.82-0.89 (m, 1H), 1.01-1.10 (m, 1H), 1.89-1.97 (m, 1H), 2.18-2.43 (m, 2H), 2.66 (s, 3H), 2.69 (s, 3H), 3.84-3.94 (m, 1H), 4.50 (dd, J=5.5, 9.1 Hz, 1H), 5.64 (d, J=17.2 Hz, 1H), 6.00 (d, J=17.2 Hz, 1H), 7.88 (s, 2H), 8.44 (s, 1H), 8.54 (s, 1H), 9.04 (s, 2H), 9.27 (s, 1H), 11.12 (s, 1H). LC (method A): $t_R$=1.62 min. LC/MS (EI) m/z: [M+H]$^+$ 575.

(1R,3S,5R)-2-(2-(3-Acetyl-5-(2-methylpyrimidin-5-yl)-1H-indazol-1-yl)acetyl)-N-(6-bromo-5-methylpyrazin-2-yl)-2-azabicyclo[3.1.0]hexane-3-carboxamide (365)

Scheme 230

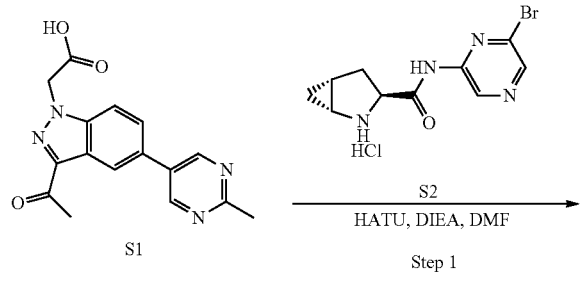

Scheme 231

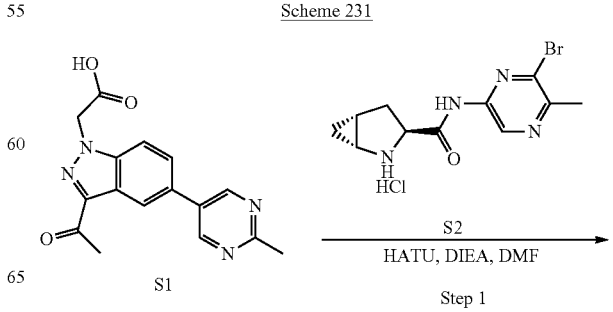

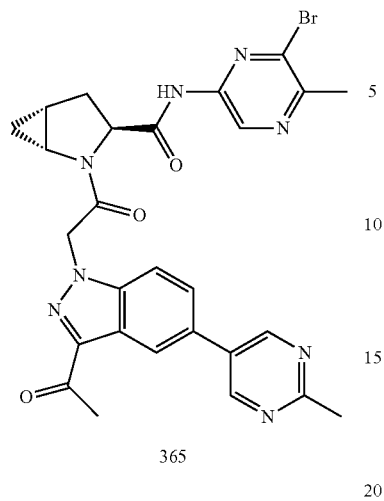

365

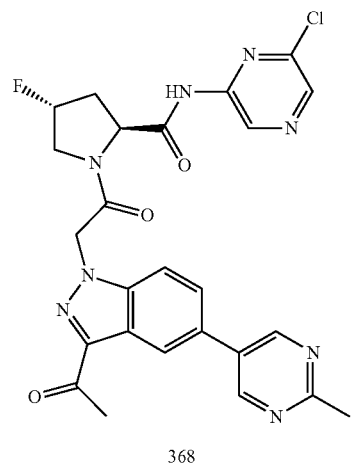

368

To a solution of compound S1 (1 equiv) in DMF (10 vol) at 0° C. under an atmosphere of nitrogen was added (1R, 3S,5R)—N-(6-bromo-5-methylpyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 365. $^1$H NMR (400 MHz, DMSO-$d_6$) δ 0.82-0.89 (m, 1H), 1.00-1.10 (m, 1H), 1.86-1.99 (m, 1H), 2.20-2.29 (m, 1H), 2.30-2.42 (m, 1H), 2.54 (s, 3H), 2.66 (s, 3H), 2.69 (s, 3H), 3.84-3.95 (m, 1H), 4.49 (dd, J=5.4, 9.1 Hz, 1H), 5.63 (d, J=17.3 Hz, 1H), 6.00 (d, J=17.3 Hz, 1H), 7.88 (d, J=2.0 Hz, 2H), 8.44 (t, J=1.2 Hz, 1H), 9.04 (s, 2H), 9.13 (s, 1H), 10.99 (s, 1H). LC (method A): $t_R$=1.73 min. LC/MS (EI) m/z: [M+H]$^+$ 589.

(2S,4R)-1-(2-(3-Acetyl-5-(2-methylpyrimidin-5-yl)-1H-indazol-1-yl)acetyl)-N-(6-chloropyrazin-2-yl)-4-fluoropyrrolidine-2-carboxamide (368)

To a solution of compound S1 (1 equiv) in DMF (10 vol) at 0° C. under an atmosphere of nitrogen was added (2S, 4R)—N-(6-chloropyrazin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 368. $^1$H NMR (400 MHz, DMSO-d6) δ 2.13-2.31 (m, 1H), 2.54-2.62 (m, 1H), 2.65 (s, 3H), 2.69 (s, 3H), 3.97-4.15 (m, 1H), 4.26 (dd, J=12.5, 22.2 Hz, 1H), 4.70 (dd, J=7.5, 9.6 Hz, 1H), 5.51-5.72 (m, 2H), 5.86 (d, J=17.3 Hz, 1H), 7.86 (s, 2H), 8.43 (d, J=1.3 Hz, 1H), 8.48 (s, 1H), 9.03 (s, 2H), 9.25 (s, 1H), 11.32 (s, 1H). $^{19}$F NMR (376 MHz, DMSO-$d_6$): δ −175.74. LC (method A): $t_R$=1.41 min. LC/MS (EI) m/z: [M+H]$^+$ 537.

(1R,3S,5R)-2-(2-(3-Acetyl-5-(2-methylpyrimidin-5-yl)-1H-indazol-1-yl)acetyl)-N-(6-chloropyrazin-2-yl)-2-azabicyclo[3.1.0]hexane-3-carboxamide (375)

Scheme 232

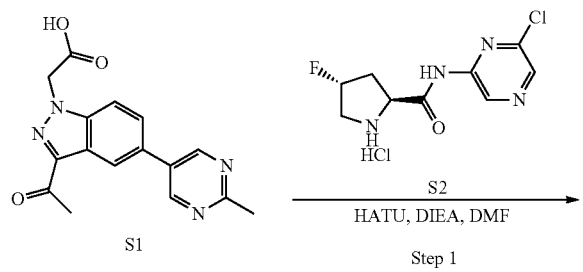

Step 1

Scheme 233

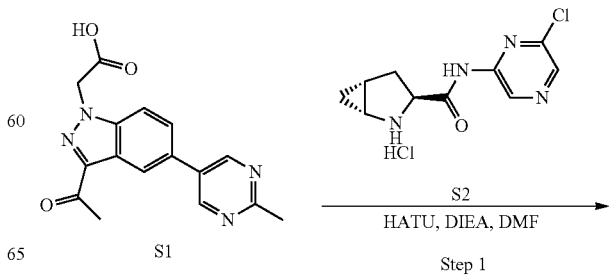

Step 1

-continued

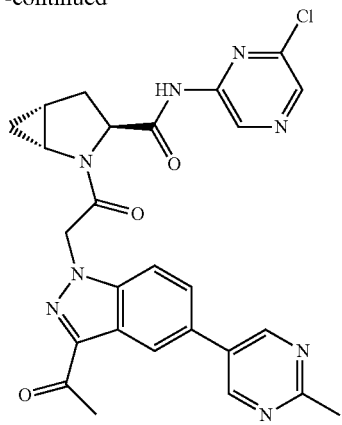

375

To a solution of compound S1 (1 equiv) in DMF (10 vol) at 0° C. under an atmosphere of nitrogen was added (1R,3S,5R)—N-(6-chloropyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 375. $^1$H NMR (400 MHz, DMSO-$d_6$) δ 0.83-0.88 (m, 1H), 1.00-1.10 (m, 1H), 1.87-2.00 (m, 1H), 2.24-2.31 (m, 1H), 2.32-2.41 (m, 1H), 2.66 (s, 3H), 2.69 (s, 3H), 3.82-3.93 (m, 1H), 4.50 (dd, J=5.4, 9.1 Hz, 1H), 5.64 (d, J=17.2 Hz, 1H), 6.00 (d, J=17.3 Hz, 1H), 7.88 (d, J=1.7 Hz, 2H), 8.44 (d, J=1.5 Hz, 1H), 8.48 (s, 1H), 9.04 (s, 2H), 9.26 (s, 1H), 11.10 (s, 1H). LC (method A): $t_R$=1.56 min. LC/MS (EI) m/z: [M+H]$^+$ 531.

(2S,4R)-1-(2-(3-Acetyl-5-(2-methylpyrimidin-5-yl)-1H-indazol-1-yl)acetyl)-4-fluoro-N-(6-(trifluoromethyl)pyrazin-2-yl)pyrrolidine-2-carboxamide (581)

Scheme 234

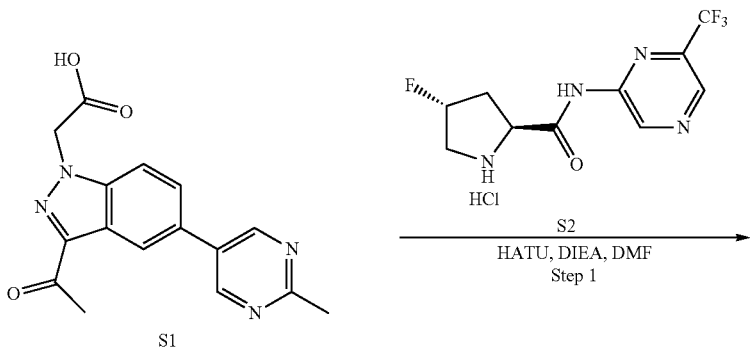

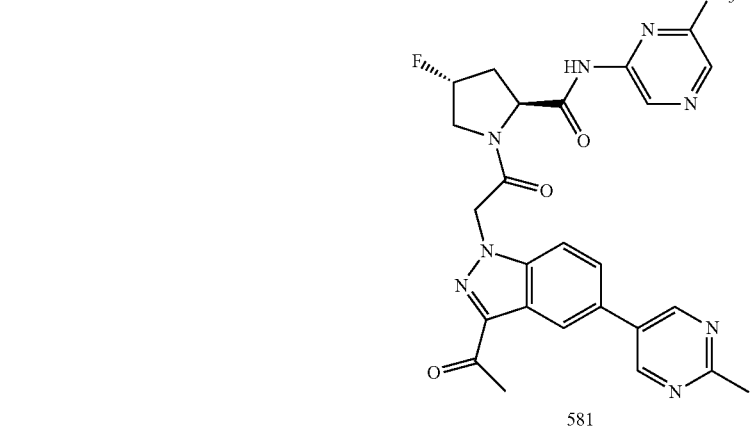

581

To a solution of compound S1 (1 equiv) in DMF (10 vol) at 0° C. under an atmosphere of nitrogen was added (2S, 4R)-4-fluoro-N-(6-(trifluoromethyl)pyrazin-2-yl)pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 581. $^1$H NMR (400 MHz, DMSO-$d_6$) δ 2.12-2.34 (m, 1H), 2.54-2.63 (m, 1H), 2.65 (s, 3H), 2.69 (s, 3H), 3.96-4.14 (m, 1H), 4.20-4.34 (m, 1H), 4.76 (t, J=8.5 Hz, 1H), 5.51-5.74 (m, 2H), 5.87 (d, J=17.3 Hz, 1H), 7.86 (d, J=1.3 Hz, 2H), 8.42 (d, J=1.5 Hz, 1H), 8.86 (s, 1H), 9.03 (s, 2H), 9.58 (s, 1H), 11.54 (s, 1H). $^{19}$F NMR (376 MHz, DMSO-$d_6$): δ −175.66, −66.42. LC (method A): $t_R$=1.64 min. LC/MS (EI) m/z: [M+H]$^+$ 571.

(2S,4R)-1-(2-(3-Acetyl-5-(2-methylpyrimidin-5-yl)-1H-indazol-1-yl)acetyl)-N-(6-(difluoromethoxy)pyridin-2-yl)-4-fluoropyrrolidine-2-carboxamide (582)

Scheme 235

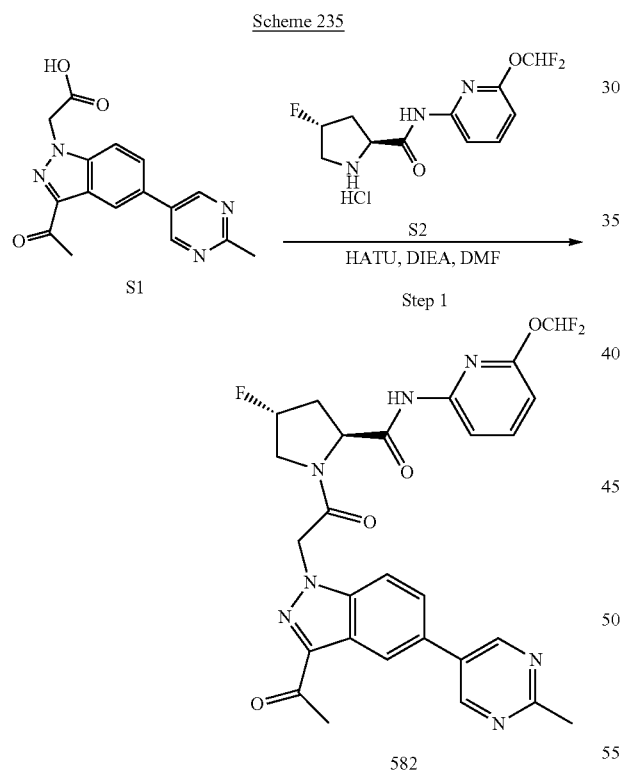

To a solution of compound S1 (1 equiv) in DMF (10 vol) at 0° C. under an atmosphere of nitrogen was added (2S, 4R)—N-(6-(difluoromethoxy)pyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 582. $^1$H NMR (400 MHz, DMSO-$d_6$) δ 2.07-2.28 (m, 1H), 2.59 (d, J=21.2 Hz, 1H), 2.65 (s, 3H), 2.69 (s, 3H), 3.93-4.11 (m, 1H), 4.25 (dd, J=12.4, 22.0 Hz, 1H), 4.76 (t, J=8.4 Hz, 1H), 5.48-5.71 (m, 2H), 5.85 (d, J=17.3 Hz, 1H), 6.72-6.77 (m, 1H), 7.52 (t, J=73.1 Hz, 1H), 7.81-7.92 (m, 4H), 8.43 (d, J=1.4 Hz, 1H), 9.04 (s, 2H), 10.74 (s, 1H). $^{19}$F NMR (376 MHz, DMSO-$d_6$): δ −175.68, −88.83−−83.99. LC (method A): $t_R$=1.77 min. LC/MS (EI) m/z: [M+H]$^+$ 568

(1R,3S,5R)-2-(2-(3-Acetyl-5-(2-aminopyrimidin-5-yl)-1H-indazol-1-yl)acetyl)-N-(6-bromopyrazin-2-yl)-2-azabicyclo[3.1.0]hexane-3-carboxamide (352)

Scheme 236

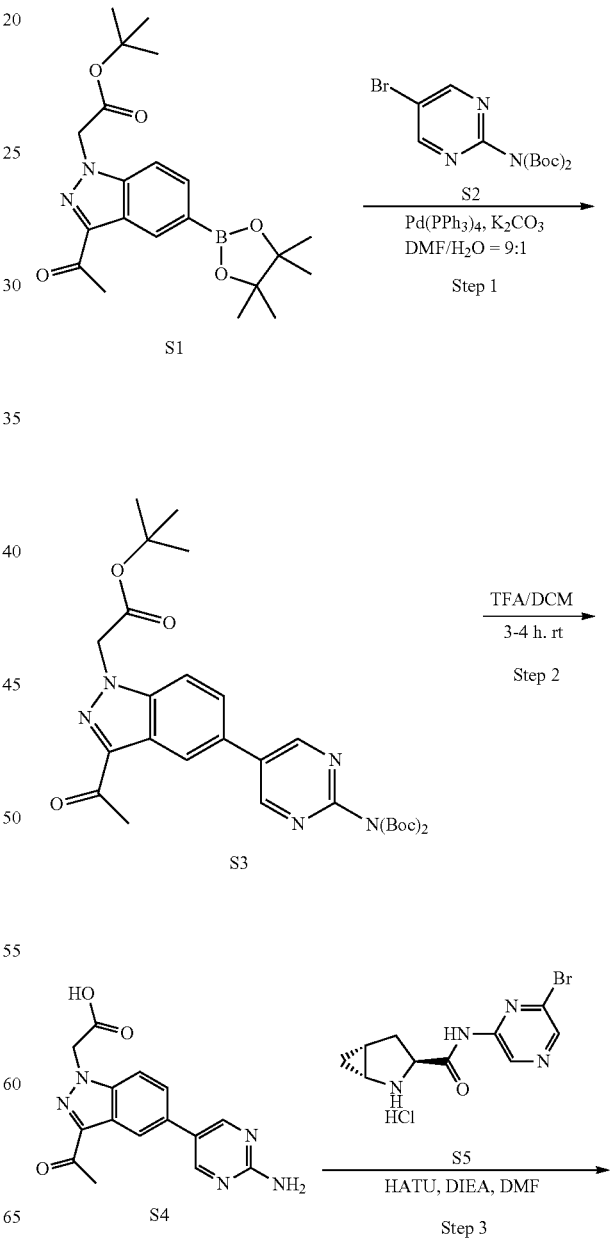

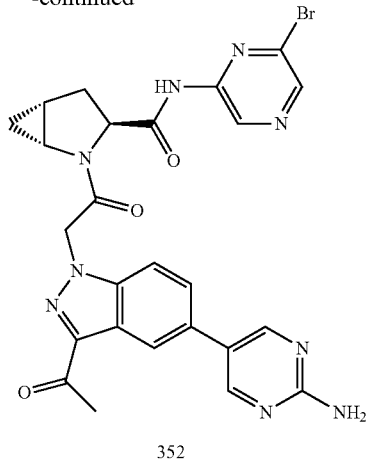

352

Step 1: tert-Butyl 2-(3-acetyl-5-(2-(Bis(tert-butoxy-carbonyl)amino)pyrimidin-5-yl)-1H-indazol-1-yl)acetate (S3)

To a solution of 2-[Bis(tert-Butoxycarbonyl)amino]-5-bromopyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-aminopyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (1R,3S,5R)-2-(2-(3-Acetyl-5-(2-aminopyrimidin-5-yl)-1H-indazol-1-yl)acetyl)-N-(6-bromopyrazin-2-yl)-2-azabicyclo[3.1.0]hexane-3-carboxamide (352)

To a solution of compound S4 (1 equiv) in DMF (10 vol) at 0° C. under an atmosphere of nitrogen was added (1R, 3S,5R)—N-(6-bromopyrazin-2-yl)-2-azabicyclo[3.1.0]hexane-3-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 352. $^1$H NMR (400 MHz, DMSO-d$_6$) δ 0.82-0.88 (m, 1H), 0.99-1.09 (m, 1H), 1.88-1.98 (m, 1H), 2.21-2.41 (m, 2H), 2.65 (s, 3H), 3.84-3.90 (m, 1H), 4.49 (dd, J=5.5, 9.1 Hz, 1H), 5.61 (d, J=17.2 Hz, 1H), 5.97 (d, J=17.3 Hz, 1H), 6.80 (s, 2H), 7.72-7.83 (m, 2H), 8.27 (d, J=1.6 Hz, 1H), 8.54 (s, 1H), 8.60 (s, 2H), 9.27 (s, 1H), 11.12 (s, 1H). LC (method A): t$_R$=1.42 min. LC/MS (EI) m/z: [M+H]$^+$ 576.

(2S,4R)-1-(2-(3-Acetyl-5-(2-aminopyrimidin-5-yl)-1H-indazol-1-yl)acetyl)-N-(6-bromopyrazin-2-yl)-4-fluoropyrrolidine-2-carboxamide (353)

Scheme 337

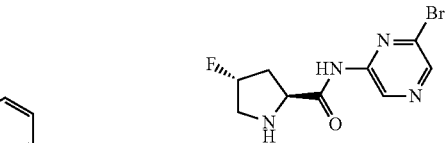

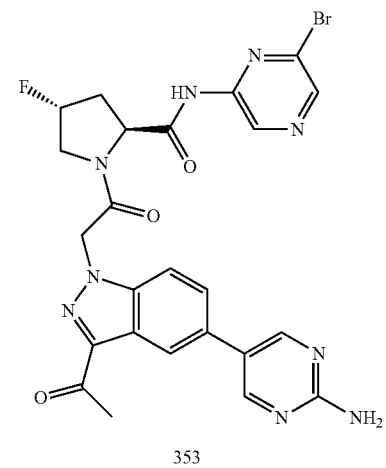

353

To a solution of compound S1 (1 equiv) in DMF (10 vol) at 0° C. under an atmosphere of nitrogen was added (2S, 4R)—N-(6-bromopyrazin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 353. $^1$H NMR (400 MHz, DMSO-d$_6$) δ 2.12-2.32 (m, 1H), 2.55-2.62 (m, 1H), 2.63 (s, 3H), 3.97-4.13 (m, 1H), 4.19-4.31 (m, 1H), 4.66-4.73 (m, 1H), 5.50-5.66 (m, 2H), 5.82 (d, J=17.3 Hz, 1H), 6.78 (s, 2H), 7.69-7.82 (m, 2H), 8.26 (s, 1H), 8.54 (s, 1H), 8.58 (s, 2H), 9.26 (s, 1H), 11.34 (s, 1H). $^{19}$F NMR (376 MHz, DMSO-d$_6$): δ −175.73. LC (method A): t$_R$=1.25 min. LC/MS (EI) m/z: [M+H]$^+$ 582.

571

(1R,3S,5R)-2-(2-(3-Acetyl-5-(2-aminopyrimidin-5-yl)-1H-indazol-1-yl)acetyl)-N-(6-bromopyridin-2-yl)-2-azabicyclo[3.1.0]hexane-3-carboxamide (364)

Scheme 238

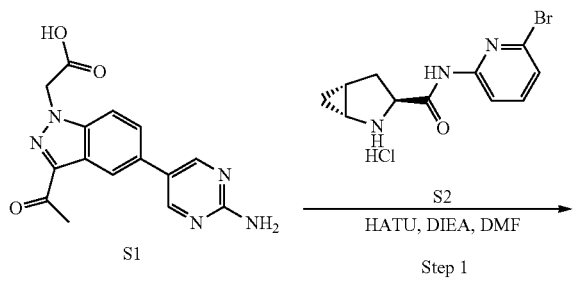

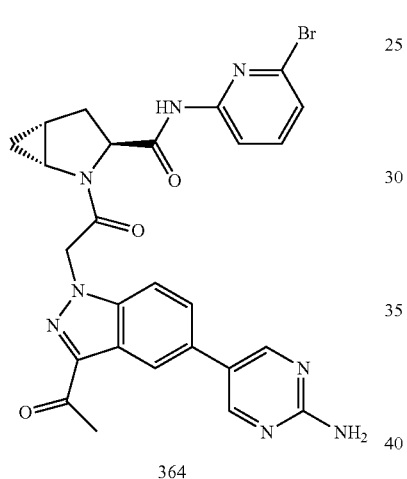

364

To a solution of compound S1 (1 equiv) in DMF (10 vol) at 0° C. under an atmosphere of nitrogen was added (1R,3S,5R)—N-(6-bromopyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 364. $^1$H NMR (400 MHz, DMSO-d$_6$) δ 0.78-0.84 (m, 1H), 0.98-1.08 (m, 1H), 1.82-1.97 (m, 1H), 2.19-2.29 (m, 1H), 2.30-2.40 (m, 1H), 2.65 (s, 3H), 3.82-3.91 (m, 1H), 4.38-4.54 (m, 1H), 5.60 (d, J=17.2 Hz, 1H), 5.96 (d, J=17.2 Hz, 1H), 6.78 (s, 2H), 7.33 (d, J=7.7 Hz, 1H), 7.68-7.77 (m, 2H), 7.80 (d, J=8.8 Hz, 1H), 8.03 (d, J=8.2 Hz, 1H), 8.24-8.31 (m, 1H), 8.59 (s, 2H), 10.75 (s, 1H). LC (method A): t$_R$=1.61 min. LC/MS (EI) m/z: [M+H]$^+$ 575.

572

(2S,4R)-1-(2-(3-Acetyl-5-(2-aminopyrimidin-5-yl)-1H-indazol-1-yl)acetyl)-N-(6-bromo-4-methoxypyridin-2-yl)-4-fluoropyrrolidine-2-carboxamide (432)

Scheme 239

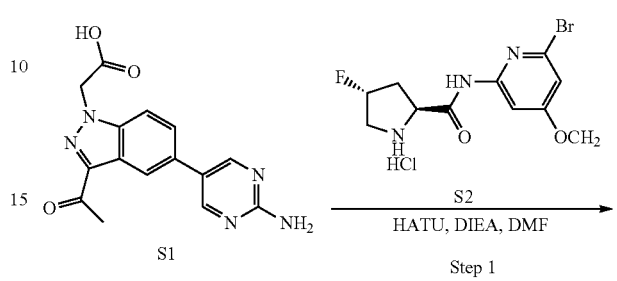

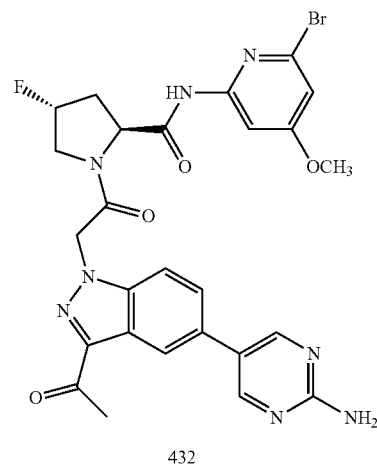

432

To a solution of compound S1 (1 equiv) in DMF (10 vol) at 0° C. under an atmosphere of nitrogen was added (2S,4R)—N-(6-bromo-4-methoxypyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 432. $^1$H NMR (400 MHz, DMSO-d$_6$) δ 2.05-2.29 (m, 1H), 2.54-2.61 (m, 1H), 2.64 (s, 3H), 3.82 (s, 3H), 3.93-4.11 (m, 1H), 4.18-4.31 (m, 1H), 4.67 (t, J=8.5 Hz, 1H), 5.47-5.65 (m, 2H), 5.81 (d, J=17.3 Hz, 1H), 6.78 (s, 2H), 6.96 (d, J=2.0 Hz, 1H), 7.64 (d, J=2.0 Hz, 1H), 7.71-7.81 (m, 2H), 8.26 (q, J=1.9, 2.7 Hz, 1H), 8.59 (s, 2H), 10.93 (s, 1H). $^{19}$F NMR (376 MHz, DMSO-d$_6$): δ −175.67. LC (method A): t$_R$=1.55 min. LC/MS (EI) m/z: [M+H]$^+$ 611.

573

(1R,3S,5R)-2-(2-(3-Acetyl-5-(2-aminopyrimidin-5-yl)-1H-indazol-1-yl)acetyl)-N-(6-bromo-4-methoxy-pyridin-2-yl)-2-azabicyclo[3.1.0]hexane-3-carboxamide (434)

574

(2S,4R)-1-(2-(3-Acetyl-5-(2-aminopyrimidin-5-yl)-1H-indazol-1-yl)acetyl)-N-(6-bromo-3-methylpyridin-2-yl)-4-fluoropyrrolidine-2-carboxamide (435)

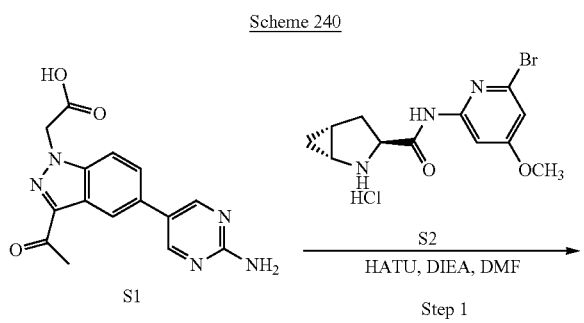

To a solution of compound S1 (1 equiv) in DMF (10 vol) at 0° C. under an atmosphere of nitrogen was added (1R,3S,5R)—N-(6-bromo-4-methoxypyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 434. $^1$H NMR (400 MHz, DMSO-$d_6$) δ 0.75-0.87 (m, 1H), 0.98-1.09 (m, 1H), 1.83-1.95 (m, 1H), 2.19-2.26 (m, 1H), 2.29-2.36 (m, 1H), 2.65 (s, 3H), 3.82-3.90 (m, 4H), 4.47 (dd, J=5.3, 9.1 Hz, 1H), 5.59 (d, J=17.2 Hz, 1H), 5.95 (d, J=17.2 Hz, 1H), 6.78 (s, 2H), 6.96 (d, J=2.1 Hz, 1H), 7.65 (d, J=2.0 Hz, 1H), 7.74 (dd, J=1.7, 8.8 Hz, 1H), 7.80 (d, J=8.8 Hz, 1H), 8.27 (d, J=1.3 Hz, 1H), 8.59 (s, 2H), 10.70 (s, 1H). LC (method A): $t_R$=1.72 min. LC/MS (EI) m/z: [M+H]$^+$ 605.

To a solution of compound S1 (1 equiv) in DMF (10 vol) at 0° C. under an atmosphere of nitrogen was added (2S,4R)—N-(6-bromo-3-methylpyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 435. $^1$H NMR (400 MHz, DMSO-$d_6$) δ 2.00 (s, 3H), 2.12-2.29 (m, 1H), 2.57-2.69 (m, 4H), 3.92-4.12 (m, 1H), 4.15-4.32 (m, 1H), 4.60 (t, J=8.5 Hz, 1H), 5.47-5.64 (m, 2H), 5.81 (d, J=17.3 Hz, 1H), 6.78 (s, 2H), 7.42 (d, J=7.9 Hz, 1H), 7.60 (d, J=7.9 Hz, 1H), 7.71-7.77 (m, 2H), 8.27 (s, 1H), 8.58 (s, 2H), 10.44 (s, 1H). $^{19}$F NMR (376 MHz, DMSO-$d_6$): δ −176.04. LC (method A): $t_R$=1.28 min. LC/MS (EI) m/z: [M+H]$^+$ 595.

575

(1R,3S,5R)-2-(2-(3-Acetyl-5-(2-aminopyrimidin-5-yl)-1H-indazol-1-yl)acetyl)-N-(6-bromo-3-methylpyridin-2-yl)-2-azabicyclo[3.1.0]hexane-3-carboxamide (446)

576

(2S,4R)-1-(2-(3-Acetyl-5-(2-aminopyrimidin-5-yl)-1H-indazol-1-yl)acetyl)-N-(6-bromo-5-fluoropyridin-2-yl)-4-fluoropyrrolidine-2-carboxamide (451)

Scheme 242

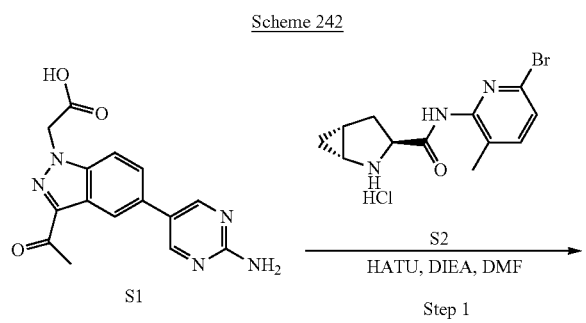

Scheme 243

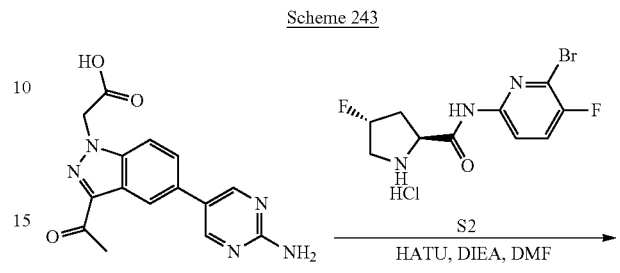

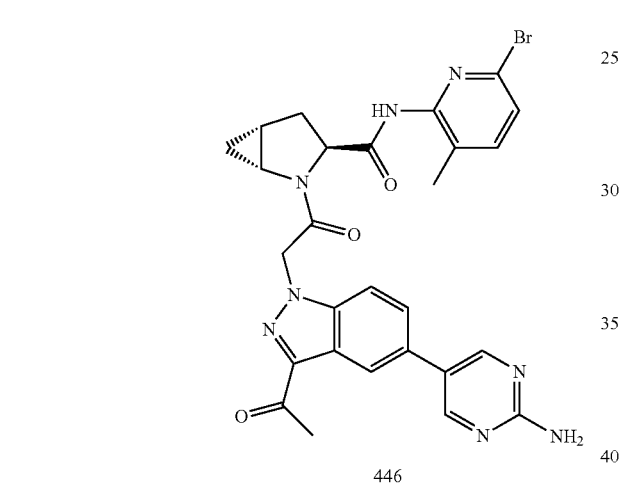

To a solution of compound S1 (1 equiv) in DMF (10 vol) at 0° C. under an atmosphere of nitrogen was added (1R,3S,5R)—N-(6-bromo-3-methylpyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 446. $^1$H NMR (400 MHz, DMSO-$d_6$) δ 0.83-0.90 (m, 1H), 1.01-1.09 (m, 1H), 1.85-1.97 (m, 1H), 2.03 (s, 3H), 2.24-2.32 (m, 1H), 2.34-2.46 (m, 1H), 2.64 (s, 3H), 3.75-3.86 (m, 1H), 4.42 (dd, J=5.0, 9.2 Hz, 1H), 5.59 (d, J=17.2 Hz, 1H), 5.91 (d, J=17.3 Hz, 1H), 6.78 (s, 2H), 7.44 (d, J=7.9 Hz, 1H), 7.62 (d, J=7.9 Hz, 1H), 7.71-7.80 (m, 2H), 8.28 (d, J=1.5 Hz, 1H), 8.59 (s, 2H), 10.23 (s, 1H). LC (method A): $t_R$=1.4 min. LC/MS (EI) m/z: [M+H]$^+$ 589.

To a solution of compound S1 (1 equiv) in DMF (10 vol) at 0° C. under an atmosphere of nitrogen was added (2S,4R)—N-(6-bromo-5-fluoropyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 451. $^1$H NMR (400 MHz, DMSO-$d_6$) δ 2.07-2.25 (m, 1H), 2.53-2.60 (m, 1H), 2.63 (s, 3H), 3.92-4.12 (m, 1H), 4.22 (dd, J=12.5, 22.3 Hz, 1H), 4.61-4.70 (m, 1H), 5.46-5.64 (m, 2H), 5.80 (d, J=17.3 Hz, 1H), 6.78 (s, 2H), 7.70-7.79 (m, 2H), 7.82-7.88 (m, 1H), 8.04 (dd, J=3.3, 8.9 Hz, 1H), 8.25-8.29 (m, 1H), 8.58 (s, 2H), 11.07 (s, 1H). $^{19}$F NMR (376 MHz, DMSO-$d_6$): δ −175.66, −120.38. LC (method A): $t_R$=1.56 min. LC/MS (EI) m/z: [M+H]$^+$ 599.

(1R,3S,5R)-2-(2-(3-Acetyl-5-(2-aminopyrimidin-5-yl)-1H-indazol-1-yl)acetyl)-N-(6-bromo-5-fluoropyridin-2-yl)-2-azabicyclo[3.1.0]hexane-3-carboxamide (458)

Scheme 244

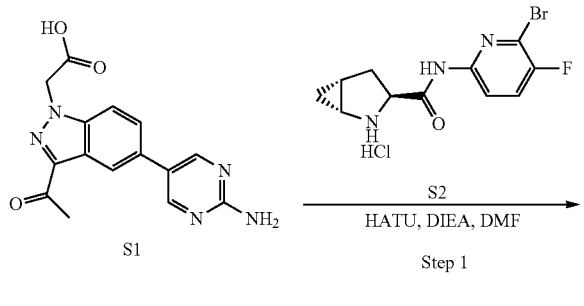

To a solution of compound S1 (1 equiv) in DMF (10 vol) at 0° C. under an atmosphere of nitrogen was added (1R,3S,5R)—N-(6-bromo-5-fluoropyridin-2-yl)-2-azabicyclo [3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 458. $^1$H NMR (400 MHz, DMSO-$d_6$) δ 0.77-0.86 (m, 1H), 0.99-1.07 (m, 1H), 1.84-1.97 (m, 1H), 2.19-2.28 (m, 1H), 2.33 (dd, J=9.2, 13.5 Hz, 1H), 2.64 (s, 3H), 3.75-3.92 (m, 1H), 4.38-4.51 (m, 1H), 5.59 (d, J=17.2 Hz, 1H), 5.95 (d, J=17.2 Hz, 1H), 6.78 (s, 2H), 7.71-7.81 (m, 2H), 7.83-7.88 (m, 1H), 8.05 (dd, J=3.3, 8.9 Hz, 1H), 8.27 (t, J=1.1 Hz, 1H), 8.58 (s, 2H), 10.83 (s, 1H). $^{19}$F NMR (376 MHz, DMSO-$d_6$): δ −120.93. LC (method A): $t_R$=1.71 min. LC/MS (EI) m/z: [M+H]$^+$ 593.

(2S,4R)-1-(2-(3-Acetyl-5-(2-aminopyrimidin-5-yl)-1H-indazol-1-yl)acetyl)-4-fluoro-N-(1-(S2,2,2-trifluoroethyl)-1H-pyrazol-3-yl)pyrrolidine-2-carboxamide (558)

Scheme 245

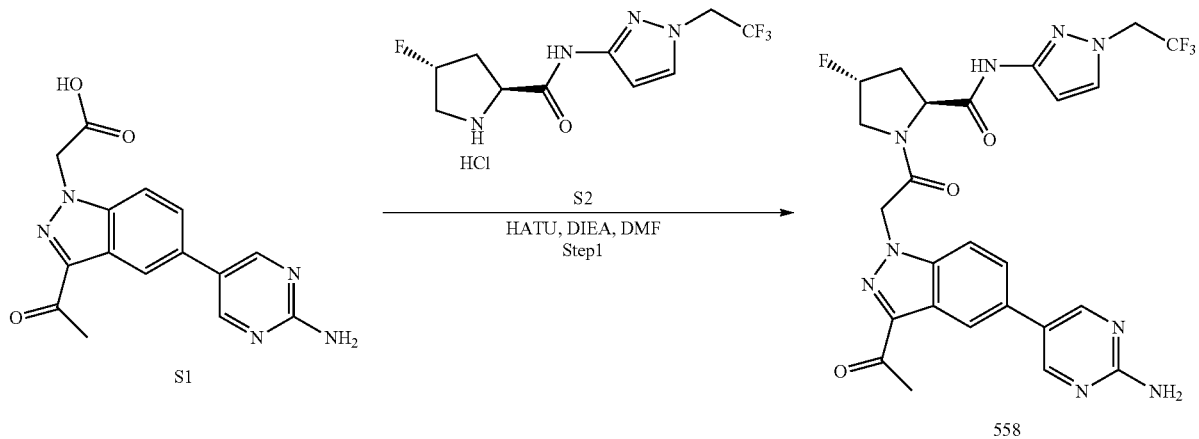

To a solution of compound S1 (1 equiv) in DMF (10 vol) at 0° C. under an atmosphere of nitrogen was added (2S,4R)-4-fluoro-N-(1-(S2,2,2-trifluoroethyl)-1H-pyrazol-3-yl) pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 558. $^1$H NMR (400 MHz, DMSO-$d_6$) δ 2.01-2.28 (m, 1H), 2.53-2.61 (m, 1H), 2.64 (s, 3H), 3.89-4.10 (m, 1H), 4.23 (dd, J=12.5, 22.0 Hz, 1H), 4.57 (t, J=8.5 Hz, 1H), 4.92-5.14 (m, 2H), 5.46-5.64 (m, 2H), 5.81 (d, J=17.3 Hz, 1H), 6.57 (d, J=2.4 Hz, 1H), 6.80 (s, 2H), 7.67-7.83 (m, 3H), 8.27 (d, J=1.2 Hz, 1H), 8.59 (d, J=2.8 Hz, 2H), 10.78 (s, 1H). $^{19}$F NMR (376 MHz, DMSO-$d_6$): δ −175.89, −70.29. LC (method A): $t_R$=1.23 min. LC/MS (EI) m/z: [M+H]$^+$ 574.

-continued

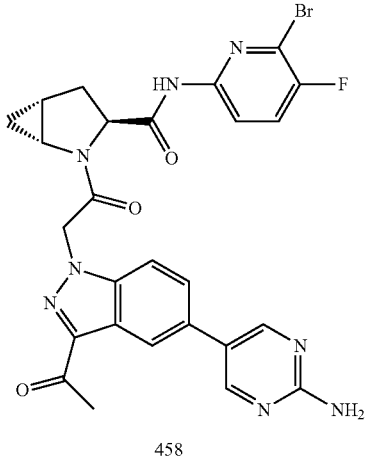

458

579

(2S,4R)-1-(2-(3-Acetyl-5-(2-aminopyrimidin-5-yl)-1H-indazol-1-yl)acetyl)-4-fluoro-N-(6-(trifluoromethoxy)pyridin-2-yl)pyrrolidine-2-carboxamide (559)

Scheme 246

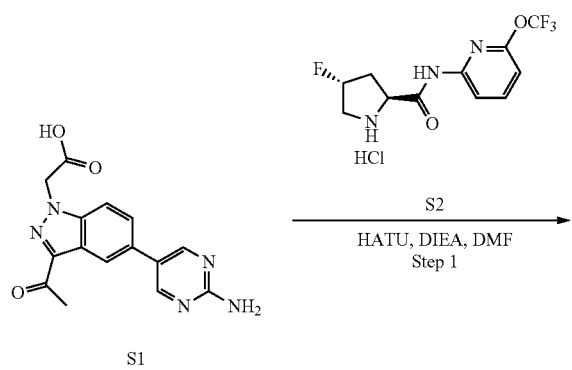

580

(2S,4R)-1-(2-(3-Acetyl-5-(2-aminopyrimidin-5-yl)-1H-indazol-1-yl)acetyl)-4-fluoro-N-(6-(trifluoromethyl)pyridin-2-yl)pyrrolidine-2-carboxamide (560)

Scheme 43

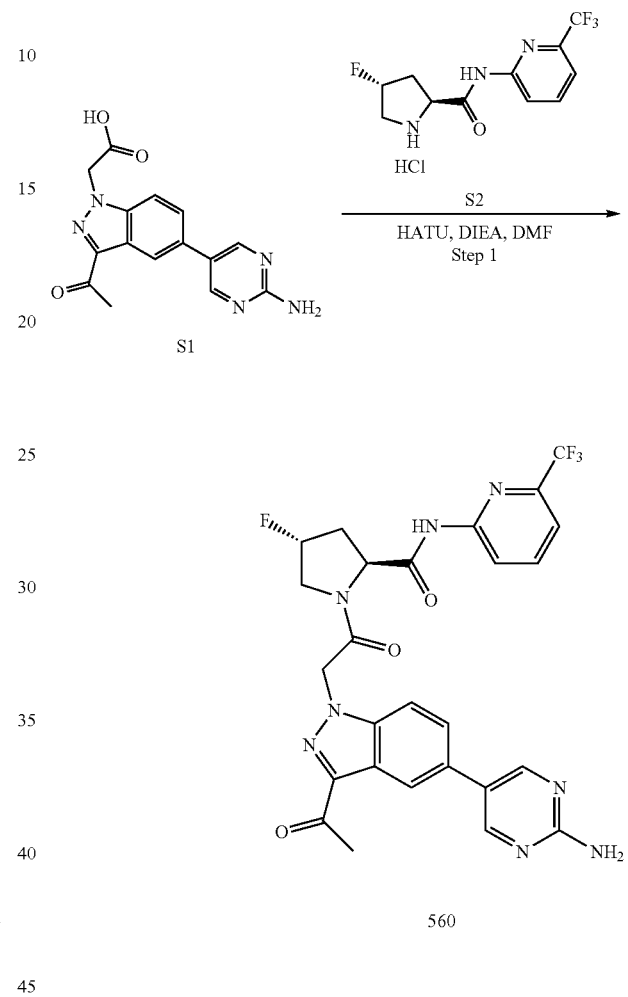

To a solution of compound S1 (1 equiv) in DMF (10 vol) at 0° C. under an atmosphere of nitrogen was added (2S,4R)-4-fluoro-N-(6-(trifluoromethoxy)pyridin-2-yl)pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 559. $^1$H NMR (400 MHz, DMSO-$d_6$) δ 2.07-2.27 (m, 1H), 2.54-2.61 (m, 1H), 2.63 (s, 3H), 3.94-4.10 (m, 1H), 4.18-4.30 (m, 1H), 4.76 (t, J=8.5 Hz, 1H), 5.47-5.68 (m, 2H), 5.81 (d, J=17.3 Hz, 1H), 6.80 (s, 2H), 6.97 (d, J=7.8 Hz, 1H), 7.70-7.79 (m, 2H), 7.93-8.07 (m, 2H), 8.26 (s, 1H), 8.58 (s, 2H), 10.87 (s, 1H). $^{19}$F NMR (376 MHz, DMSO-$d_6$): δ −175.70, −55.11. LC (method A): $t_R$=1.74 min. LC/MS (EI) m/z: [M+H]$^+$ 586.

To a solution of compound S1 (1 equiv) in DMF (10 vol) at 0° C. under an atmosphere of nitrogen was added (2S,4R)-4-fluoro-N-(6-(trifluoromethyl)pyridin-2-yl)pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 560. $^1$H NMR (400 MHz, DMSO-$d_6$) δ 2.07-2.29 (m, 1H), 2.54-2.60 (m, 1H), 2.63 (s, 3H), 3.93-4.12 (m, 1H), 4.24 (dd, J=12.5, 22.2 Hz, 1H), 4.74 (t, J=8.5 Hz, 1H), 5.47-5.66 (m, 2H), 5.81 (d, J=17.3 Hz, 1H), 6.80 (s, 2H), 7.58 (d, J=7.6 Hz, 1H), 7.68-7.81 (m, 2H), 8.06 (d, J=8.0 Hz, 1H), 8.25 (d, J=1.5 Hz, 1H), 8.30 (d, J=8.5 Hz, 1H), 8.57 (s, 2H), 11.14 (s, 1H). $^{19}$F NMR (376 MHz, DMSO-$d_6$): δ −175.60, −66.63. LC (method A): $t_R$=1.63 min. LC/MS (EI) m/z: [M+H]$^+$ 571.

581

(2S,4R)-1-(2-(3-Acetyl-5-(2-aminopyrimidin-5-yl)-1H-indazol-1-yl)acetyl)-4-fluoro-N-(2-fluoro-3-(trifluoromethoxy)phenyl)pyrrolidine-2-carboxamide (563)

582

(1R,3S,5R)-2-(2-(3-Acetyl-5-(2-aminopyrimidin-5-yl)-1H-indazol-1-yl)acetyl)-N-(6-bromo-3-methylpyridin-2-yl)-5-methyl-2-azabicyclo[3.1.0]hexane-3-carboxamide (620)

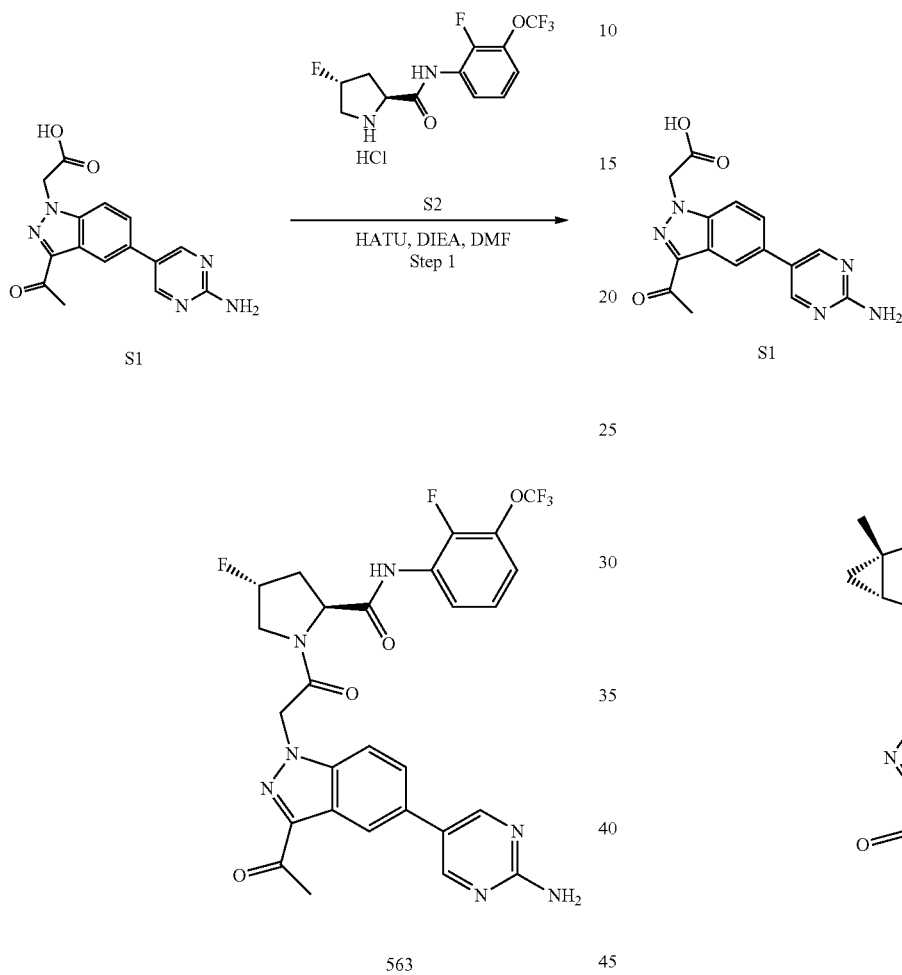

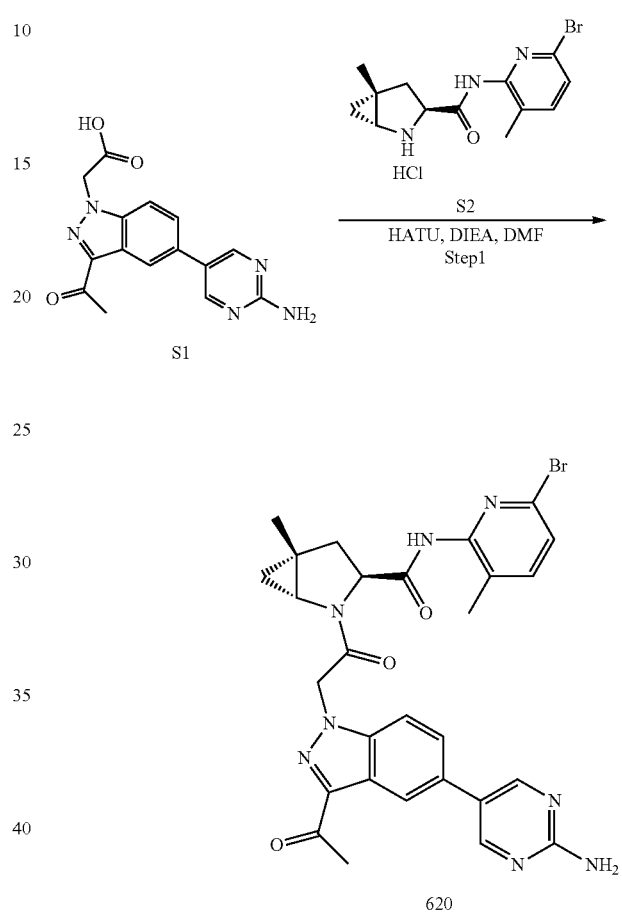

To a solution of compound S1 (1 equiv) in DMF (10 vol) at 0° C. under an atmosphere of nitrogen was added (2S,4R)-4-fluoro-N-(2-fluoro-3-(trifluoromethoxy)phenyl)pyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 563. $^1$H NMR (400 MHz, DMSO-$d_6$) δ 2.11-2.30 (m, 1H), 2.53-2.61 (m, 1H), 2.63 (s, 3H), 3.93-4.10 (m, 1H), 4.24 (dd, J=12.4, 22.2 Hz, 1H), 4.66-4.81 (m, 1H), 5.48-5.66 (m, 2H), 5.82 (d, J=17.3 Hz, 1H), 6.80 (s, 2H), 7.22-7.34 (m, 2H), 7.71-7.81 (m, 2H), 7.84-7.90 (m, 1H), 8.27 (s, 1H), 8.59 (s, 2H), 10.19 (s, 1H). $^{19}$F NMR (376 MHz, DMSO-$d_6$): δ −175.66, −140.58, −57.93. LC (method A): $t_R$=1.81 min. LC/MS (EI) m/z: [M+H]$^+$ 604.

To a solution of compound S1 (1 equiv) in DMF (10 vol) at 0° C. under an atmosphere of nitrogen was added (1R,3S,5R)—N-(6-bromo-3-methylpyridin-2-yl)-5-methyl-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 620. $^1$H NMR (400 MHz, DMSO-$d_6$) δ 0.98-1.06 (m, 2H), 1.23-1.29 (m, 2H), 1.33 (s, 3H), 2.05 (s, 3H), 2.65 (s, 3H), 3.55-3.64 (m, 1H), 4.41 (dd, J=5.1, 9.2 Hz, 1H), 5.55 (d, J=17.2 Hz, 1H), 5.89 (d, J=17.3 Hz, 1H), 6.81 (s, 2H), 7.45 (d, J=7.9 Hz, 1H), 7.63 (d, J=7.9 Hz, 1H), 7.72-7.81 (m, 2H), 8.28 (s, 1H), 8.60 (s, 2H), 10.28 (s, 1H). LC (method A): $t_R$=1.64 min. LC/MS (EI) m/z: [M+H]$^+$ 603.

583

(1R,2S,5S)-3-(2-(3-Acetyl-5-(2-aminopyrimidin-5-yl)-1H-indazol-1-yl)acetyl)-N-(6-bromo-3-methyl-pyridin-2-yl)-3-azabicyclo[3.1.0]hexane-2-carboxamide (635)

584

(2S,4R)-1-(2-(3-Acetyl-5-(2-cyclopropylpyrimidin-5-yl)-1H-indazol-1-yl)acetyl)-N-(6-bromopyrazin-2-yl)-4-fluoropyrrolidine-2-carboxamide (354)

Scheme 250

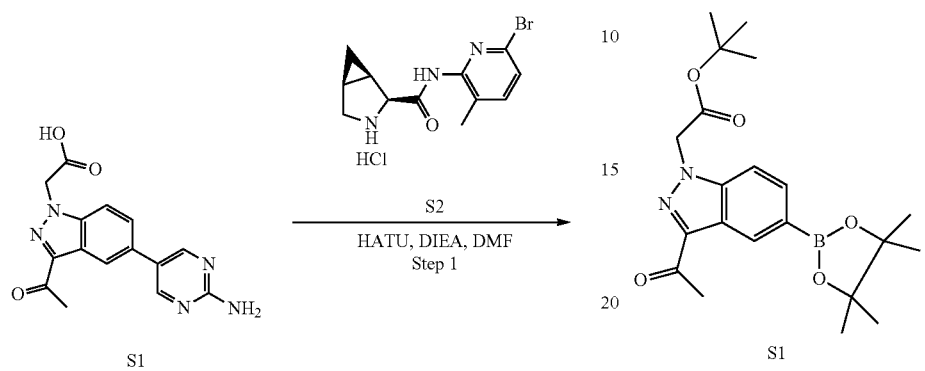

Scheme 251

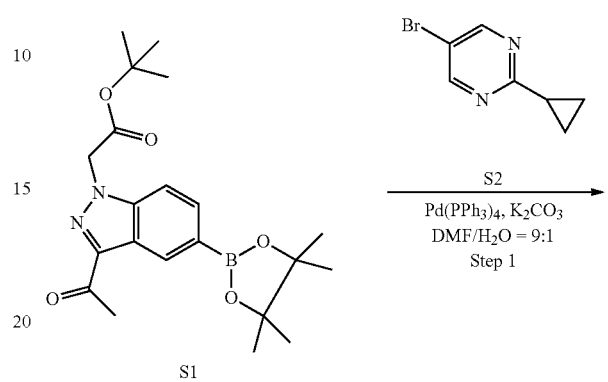

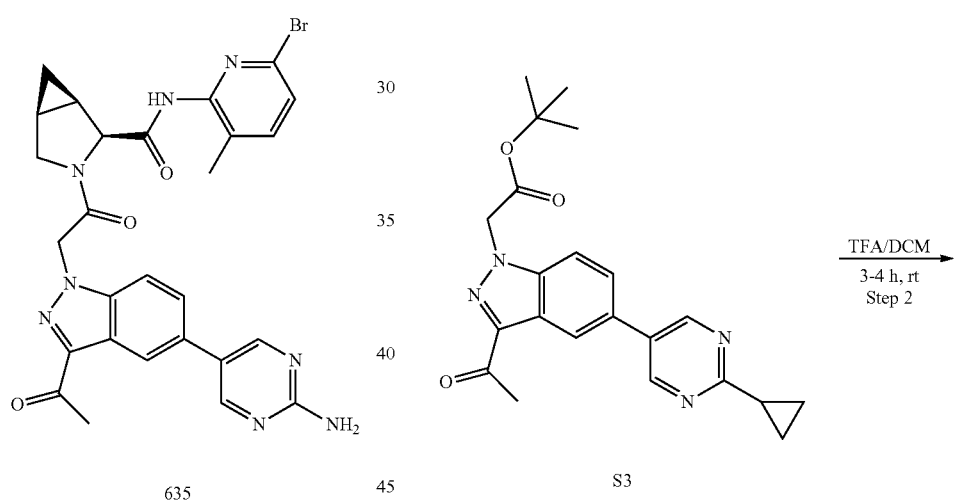

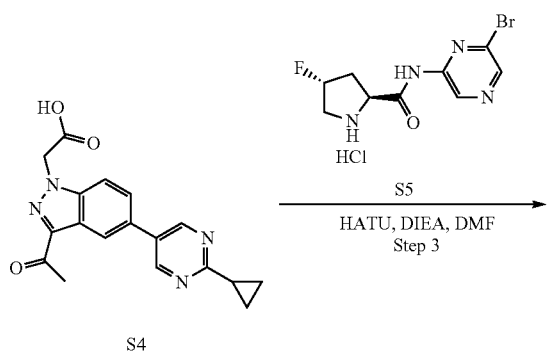

To a solution of compound S1 (1 equiv) in DMF (10 vol) at 0° C. under an atmosphere of nitrogen was added (1R,2S,5S)—N-(6-bromo-3-methylpyridin-2-yl)-3-azabicyclo[3.1.0]hexane-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 635. $^1$H NMR (400 MHz, DMSO-$d_6$) δ 0.74-0.91 (m, 2H), 1.84-1.93 (m, 1H), 2.01-2.13 (m, 4H), 2.63 (s, 3H), 3.89 (d, J=9.6 Hz, 1H), 4.03 (dd, J=5.2, 9.7 Hz, 1H), 4.59 (d, J=5.4 Hz, 1H), 5.49-5.69 (m, 2H), 6.81 (s, 2H), 7.42 (d, J=7.9 Hz, 1H), 7.60 (d, J=8.0 Hz, 1H), 7.70-7.78 (m, 2H), 8.27 (s, 1H), 8.59 (s, 2H), 10.29 (s, 1H). LC (method A): $t_R$=1.43 min. LC/MS (EI) m/z: [M+H]$^+$ 589.

-continued

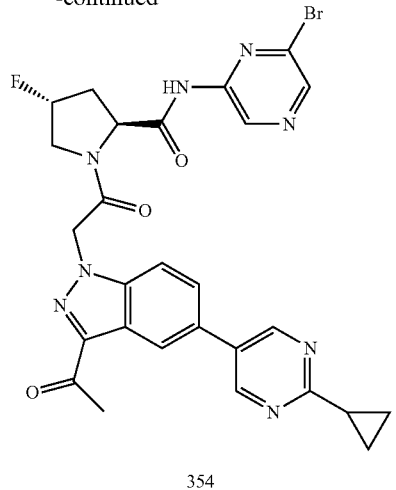

354

Step 1: tert-Butyl 2-(3-acetyl-5-(2-cyclopropylpyrimidin-5-yl)-1H-indazol-1-yl)acetate (S3)

To a solution of 5-bromo-2-cyclopropylpyrimidine (S2, 1 equiv) in DMF/H$_2$O (9:1, vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-cyclopropylpyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-cyclopropylpyrimidin-5-yl)-1H-indazol-1-yl)acetyl)-N-(6-bromopyrazin-2-yl)-4-fluoropyrrolidine-2-carboxamide (354)

To a solution of compound S4 (1 equiv) in DMF (10 vol) at 0° C. under an atmosphere of nitrogen was added (2S,4R)—N-(6-bromopyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 354. $^1$H NMR (400 MHz, DMSO-d$_6$) δ 1.02-1.13 (m, 4H), 2.08-2.31 (m, 2H), 2.55-2.62 (m, 1H), 2.65 (s, 3H), 3.97-4.14 (m, 1H), 4.25 (dd, J=12.5, 22.3 Hz, 1H), 4.69 (dd, J=7.5, 9.5 Hz, 1H), 5.50-5.72 (m, 2H), 5.85 (d, J=17.3 Hz, 1H), 7.84 (s, 2H), 8.40 (s, 1H), 8.54 (s, 1H), 8.96 (s, 2H), 9.26 (s, 1H), 11.33 (s, 1H). $^{19}$F NMR (376 MHz, DMSO-d$_6$): δ −175.73. LC (method A): t$_R$=1.87 min. LC/MS (EI) m/z: [M+H]$^+$ 607.

(1R,3S,5R)-2-(2-(3-Acetyl-5-(2-cyclopropylpyrimidin-5-yl)-1H-indazol-1-yl)acetyl)-N-(6-bromopyrazin-2-yl)-2-azabicyclo[3.1.0]hexane-3-carboxamide (536)

Scheme 252

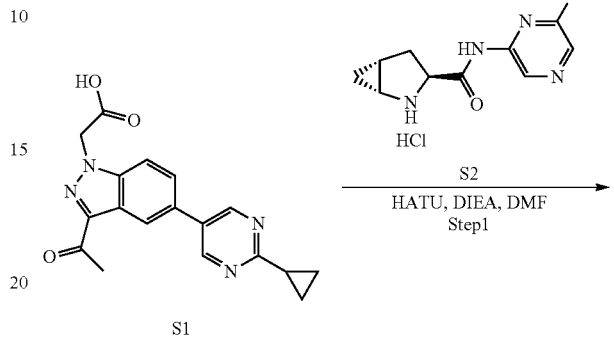

536

To a solution of compound S1 (1 equiv) in DMF (10 vol) at 0° C. under an atmosphere of nitrogen was added (1R,3S,5R)—N-(6-bromopyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 536. $^1$H NMR (400 MHz, DMSO-d$_6$) δ 0.83-0.90 (m, 1H), 1.01-1.13 (m, 5H), 1.89-2.00 (m, 1H), 2.20-2.42 (m, 3H), 2.66 (s, 3H), 3.82-3.92 (m, 1H), 4.49 (dd, J=5.5, 9.1 Hz, 1H), 5.63 (d, J=17.2 Hz, 1H), 6.00 (d, J=17.3 Hz, 1H), 7.81-7.91 (m, 2H), 8.41 (s, 1H), 8.54 (s, 1H), 8.97 (s, 2H), 9.27 (s, 1H), 11.12 (s, 1H). LC (method A): t$_R$=2.01 min. LC/MS (EI) m/z: [M+H]$^+$ 601.

587

(2S,4R)-1-(2-(3-Acetyl-5-(2-ethylpyrazolo[1,5-a]pyrimidin-6-yl)-1H-indazol-1-yl)acetyl)-N-(6-bromopyridin-2-yl)-4-fluoropyrrolidine-2-carboxamide (681)

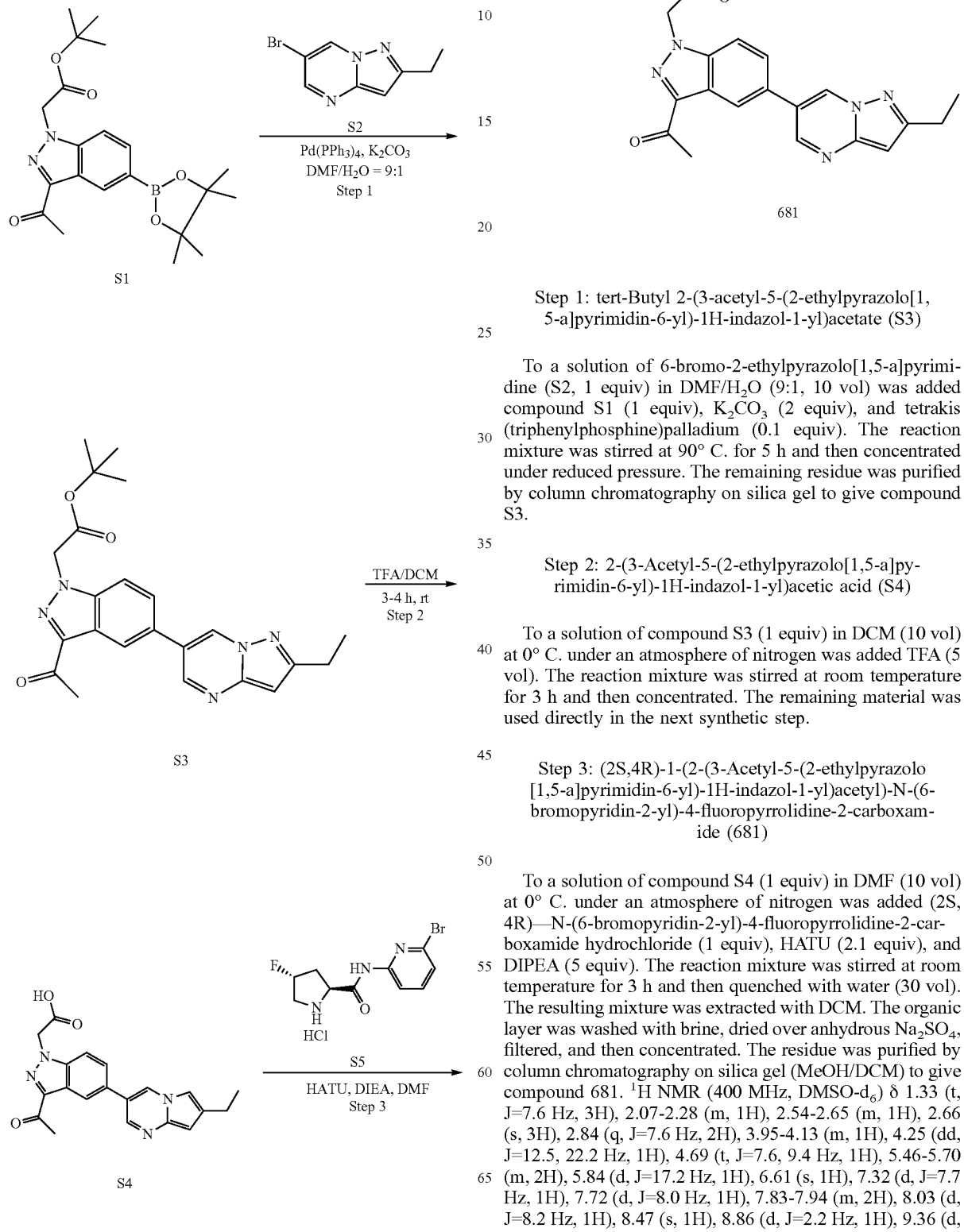

Step 1: tert-Butyl 2-(3-acetyl-5-(2-ethylpyrazolo[1,5-a]pyrimidin-6-yl)-1H-indazol-1-yl)acetate (S3)

To a solution of 6-bromo-2-ethylpyrazolo[1,5-a]pyrimidine (S2, 1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-ethylpyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-ethylpyrazolo[1,5-a]pyrimidin-6-yl)-1H-indazol-1-yl)acetyl)-N-(6-bromopyridin-2-yl)-4-fluoropyrrolidine-2-carboxamide (681)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 681. $^1$H NMR (400 MHz, DMSO-d$_6$) δ 1.33 (t, J=7.6 Hz, 3H), 2.07-2.28 (m, 1H), 2.54-2.65 (m, 1H), 2.66 (s, 3H), 2.84 (q, J=7.6 Hz, 2H), 3.95-4.13 (m, 1H), 4.25 (dd, J=12.5, 22.2 Hz, 1H), 4.69 (t, J=7.6, 9.4 Hz, 1H), 5.46-5.70 (m, 2H), 5.84 (d, J=17.2 Hz, 1H), 6.61 (s, 1H), 7.32 (d, J=7.7 Hz, 1H), 7.72 (d, J=8.0 Hz, 1H), 7.83-7.94 (m, 2H), 8.03 (d, J=8.2 Hz, 1H), 8.47 (s, 1H), 8.86 (d, J=2.2 Hz, 1H), 9.36 (d, J=2.2 Hz, 1H), 11.00 (s, 1H). $^{19}$F NMR (376 MHz, DMSO-d$_6$): δ −175.66. LC (method A): t$_R$=2.11 min. LC/MS (EI) m/z: [M+H]$^+$ 633.

(2S,4R)-1-(2-(3-Acetyl-5-(2-(tert-butyl)pyrazolo[1,5-a]pyrimidin-6-yl)-1H-indazol-1-yl)acetyl)-N-(6-bromopyridin-2-yl)-4-fluoropyrrolidine-2-carboxamide (682)

Scheme 254

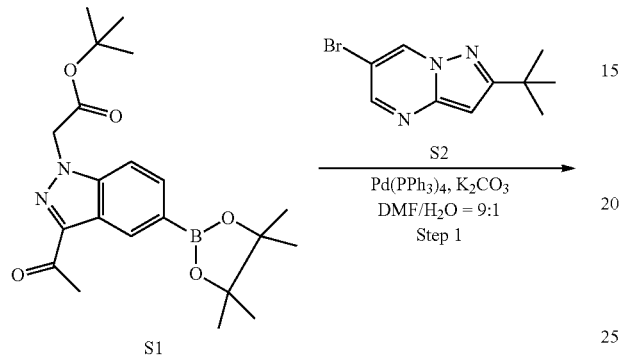

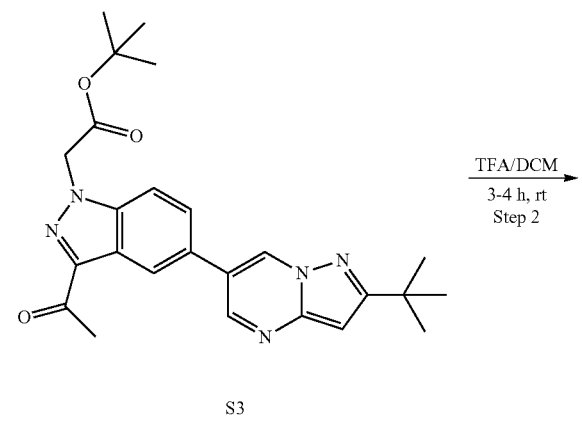

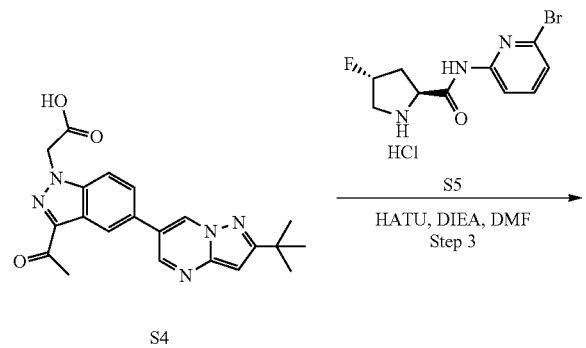

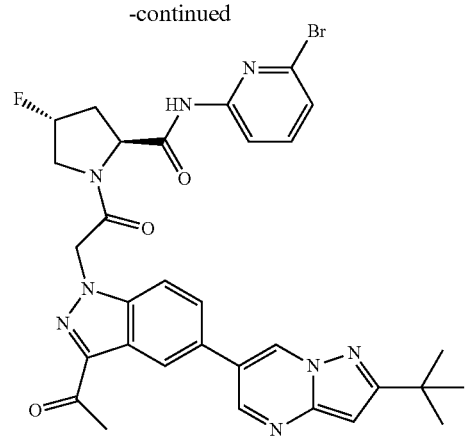

Step 1: tert-Butyl 2-(3-acetyl-5-(2-(tert-butyl)pyrazolo[1,5-a]pyrimidin-6-yl)-1H-indazol-1-yl)acetate (S3)

To a solution of 6-bromo-2-(tert-butyl)pyrazolo[1,5-a]pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-acetyl-5-(2-(tert-butyl)pyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(tert-butyl)pyrazolo[1,5-a]pyrimidin-6-yl)-1H-indazol-1-yl)acetyl)-N-(6-bromopyridin-2-yl)-4-fluoropyrrolidine-2-carboxamide (682)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 682. $^1$H NMR (400 MHz, DMSO-d$_6$) δ 1.41 (s, 9H), 2.07-2.28 (m, 1H), 2.57-2.63 (m, 1H), 2.68 (s, 3H), 3.95-4.11 (m, 1H), 4.25 (dd, J=12.5, 22.2 Hz, 1H), 4.69 (t, J=8.5 Hz, 1H), 5.47-5.70 (m, 2H), 5.84 (d, J=17.3 Hz, 1H), 6.68 (s, 1H), 7.32 (d, J=7.7 Hz, 1H), 7.69-7.74 (m, 1H), 7.84 (d, J=8.8 Hz, 1H), 7.92 (dd, J=1.7, 8.7 Hz, 1H), 8.03 (d, J=8.2 Hz, 1H), 8.47 (s, 1H), 8.86 (d, J=2.2 Hz, 1H), 9.41 (d, J=2.2 Hz, 1H), 11.00 (s, 1H). $^{19}$F NMR (376 MHz, DMSO-$d_6$): δ −175.66. LC (method A): $t_R$=2.49 min. LC/MS (EI) m/z: [M+H]$^+$ 661.

(2S,4R)-1-(2-(3-Acetyl-5-(2-(cyclopropylamino)pyrimidin-5-yl)-1H-indazol-1-yl)acetyl)-N-(6-bromopyridin-2-yl)-4-fluoropyrrolidine-2-carboxamide (367)

Scheme 255

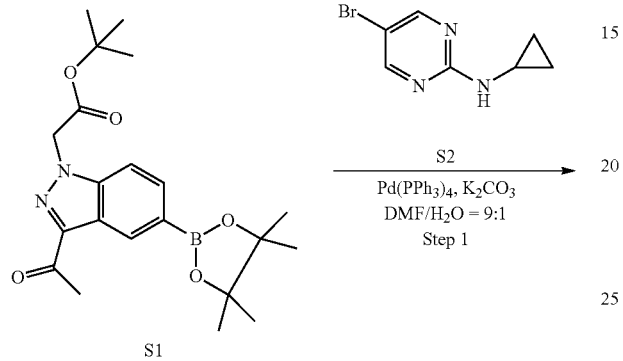

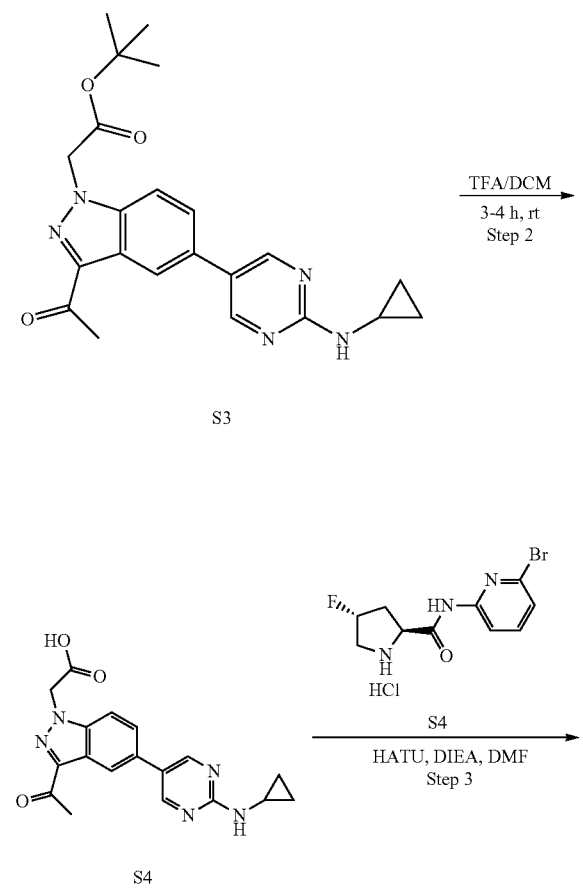

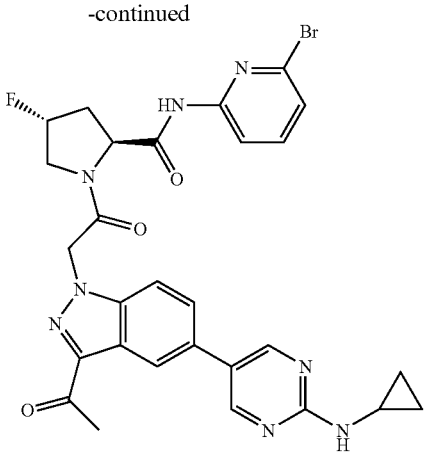

Step 1: tert-Butyl 2-(3-acetyl-5-(2-(cyclopropylamino)pyrimidin-5-yl)-1H-indazol-1-yl)acetate (S3)

To a solution of 5-bromo-N-cyclopropylpyrimidin-2-amine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(cyclopropylamino)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(cyclopropylamino)pyrimidin-5-yl)-1H-indazol-1-yl)acetyl)-N-(6-bromopyridin-2-yl)-4-fluoropyrrolidine-2-carboxamide (367)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 367. $^1$H NMR (400 MHz, DMSO-$d_6$) δ 0.49-0.55 (m, 2H), 0.68-0.77 (m, 2H), 2.08-2.28 (m, 1H), 2.54-2.61 (m, 1H), 2.64 (s, 3H), 2.73-2.81 (m, 1H), 3.96-4.14 (m, 1H), 4.15-4.32 (m, 1H), 4.61-4.76 (m, 1H), 5.47-5.65 (m, 2H), 5.81 (d, J=17.3 Hz, 1H), 7.33 (d, J=7.7 Hz, 1H), 7.55 (d, J=3.6 Hz, 1H), 7.69-7.82 (m, 3H), 8.03 (d, J=8.2 Hz, 1H), 8.28 (s, 1H), 8.65 (s, 2H), 10.99 (s, 1H). $^{19}$F NMR (376 MHz, DMSO-$d_6$): δ −175.68. LC (method A): $t_R$=1.77 min. LC/MS (EI) m/z: [M+H]$^+$ 621.

593

(1R,3S,5R)-2-(2-(3-Acetyl-5-(2-(cyclopropylamino)pyrimidin-5-yl)-1H-indazol-1-yl)acetyl)-N-(6-bromopyrazin-2-yl)-2-azabicyclo[3.1.0]hexane-3-carboxamide (380)

594

(2S,4R)-1-(2-(3-Acetyl-5-(2-(hydroxymethyl)pyrimidin-5-yl)-1H-indazol-1-yl)acetyl)-N-(6-bromopyridin-2-yl)-4-fluoropyrrolidine-2-carboxamide (374)

Scheme 256

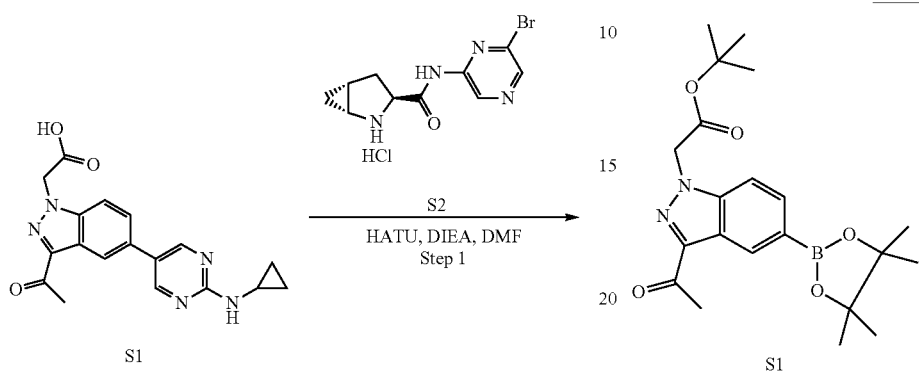

Scheme 257

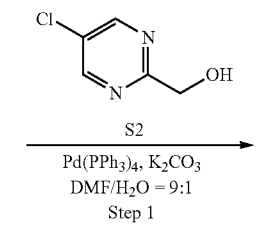

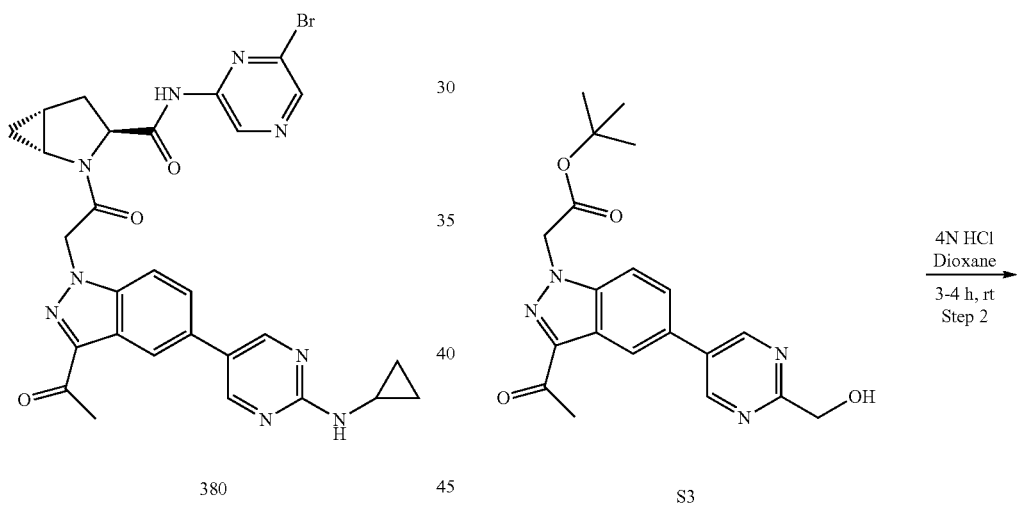

To a solution of compound S1 (1 equiv) in DMF (10 vol) at 0° C. under an atmosphere of nitrogen was added (1R, 3S,5R)—N-(6-bromopyrazin-2-yl)-2-azabicyclo[3.1.0] hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 380. $^1$H NMR (400 MHz, DMSO-$d_6$) δ 0.48-0.56 (m, 2H), 0.66-0.75 (m, 2H), 0.81-0.89 (m, 1H), 1.00-1.10 (m, 1H), 1.88-1.98 (m, 1H), 2.20-2.41 (m, 2H), 2.65 (s, 3H), 2.73-2.81 (m, 1H), 3.79-3.95 (m, 1H), 4.49 (dd, J=5.5, 9.1 Hz, 1H), 5.61 (d, J=17.2 Hz, 1H), 5.97 (d, J=17.3 Hz, 1H), 7.55 (d, J=3.6 Hz, 1H), 7.72-7.85 (m, 2H), 8.29 (d, J=1.4 Hz, 1H), 8.54 (s, 1H), 8.66 (s, 2H), 9.27 (s, 1H), 11.12 (s, 1H). LC (method A): $t_R$=1.75 min. LC/MS (EI) m/z: [M+H]$^+$ 616.

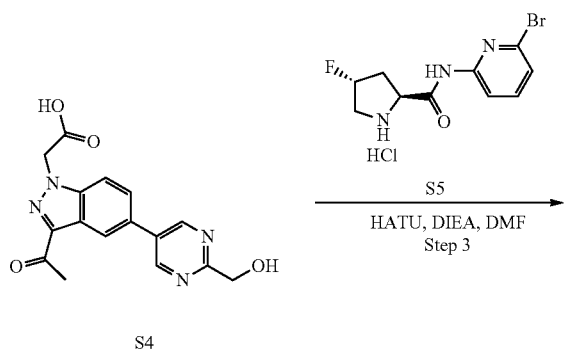

(2S,4R)-1-(2-(3-Acetyl-5-(2-(hydroxymethyl)pyrimidin-5-yl)-1H-indazol-1-yl)acetyl)-N-(6-bromopyrazin-2-yl)-4-fluoropyrrolidine-2-carboxamide (398)

Scheme 258

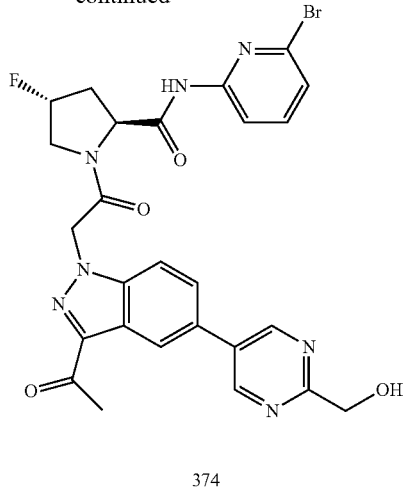

374

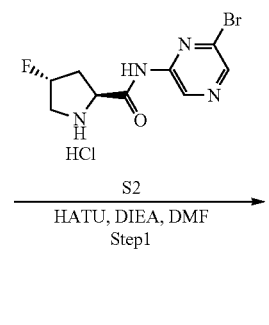

Step 1: tert-Butyl 2-(3-acetyl-5-(2-(hydroxymethyl)pyrimidin-5-yl)-1H-indazol-1-yl)acetate (S3)

To a solution of (5-chloropyrimidin-2-yl)methanol (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(hydroxymethyl)pyrimidin-5-yl)-1H-indazol-1-yl)acetic acid (S4)

To a solution of compound S3 (1 equiv) in under an atmosphere of nitrogen was added 4N dioxane HCl (10 vol). The reaction mixture was stirred at room temperature for 3 h and then concentrated. The remaining material was used directly in the next synthetic step.

Step 3: (2S,4R)-1-(2-(3-Acetyl-5-(2-(hydroxymethyl)pyrimidin-5-yl)-1H-indazol-1-yl)acetyl)-N-(6-bromopyridin-2-yl)-4-fluoropyrrolidine-2-carboxamide (374)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 374. $^1$H NMR (400 MHz, DMSO-d$_6$) δ 2.08-2.30 (m, 1H), 2.53-2.62 (m, 1H), 2.66 (s, 3H), 3.96-4.11 (m, 1H), 4.17-4.32 (m, 1H), 4.69 (d, J=6.2 Hz, 3H), 5.35 (d, J=6.4 Hz, 1H), 5.48-5.70 (m, 2H), 5.85 (d, J=17.3 Hz, 1H), 7.33 (d, J=7.7 Hz, 1H), 7.71 (t, J=8.0 Hz, 1H), 7.85-7.94 (m, 2H), 8.03 (d, J=8.2 Hz, 1H), 8.46 (s, 1H), 9.13 (s, 2H), 10.99 (s, 1H). $^{19}$F NMR (376 MHz, DMSO-d$_6$): δ −175.66. LC (method A): t$_R$=1.42 min. LC/MS (EI) m/z: [M+H]$^+$ 596.

To a solution of compound S1 (1 equiv) in DMF (10 vol) at 0° C. under an atmosphere of nitrogen was added (2S,4R)—N-(6-bromopyrazin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 398. $^1$H NMR (400 MHz, DMSO-d$_6$) δ 2.09-2.31 (m, 1H), 2.54-2.62 (m, 1H), 2.66 (s, 3H), 3.04-3.17 (m, 1H), 3.97-4.12 (m, 1H), 4.20-4.32 (m, 1H), 4.65-4.72 (m, 3H), 5.50-5.73 (m, 2H), 5.86 (d, J=17.3 Hz, 1H), 7.85-7.96 (m, 2H), 8.46 (s, 1H), 8.54 (s, 1H), 9.13 (s, 2H), 9.26 (s, 1H), 11.34 (s, 1H). $^{19}$F NMR (376 MHz, DMSO-d$_6$): δ −175.72. LC (method A): t$_R$=1.24 min. LC/MS (EI) m/z: [M+H]$^+$ 597.

597

(1R,3S,5R)-2-(2-(3-Acetyl-5-(2-(methylamino)pyrimidin-5-yl)-1H-indazol-1-yl)acetyl)-N-(6-bromopyrazin-2-yl)-2-azabicyclo[3.1.0]hexane-3-carboxamide (379)

Scheme 259

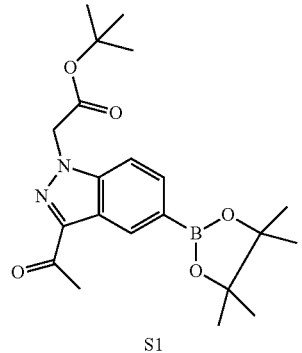
S1

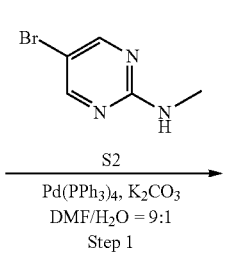
S2
Pd(PPh₃)₄, K₂CO₃
DMF/H₂O = 9:1
Step 1

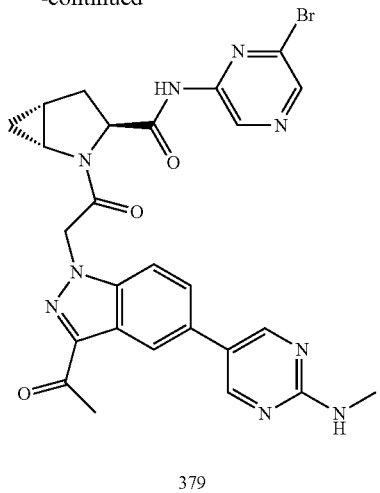
379

Step 1: tert-Butyl 2-(3-acetyl-5-(2-(methylamino)pyrimidin-5-yl)-1H-indazol-1-yl)acetate (S3)

To a solution of 5-bromo-N-methylpyrimidin-2-amine (S2, 1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(methylamino)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

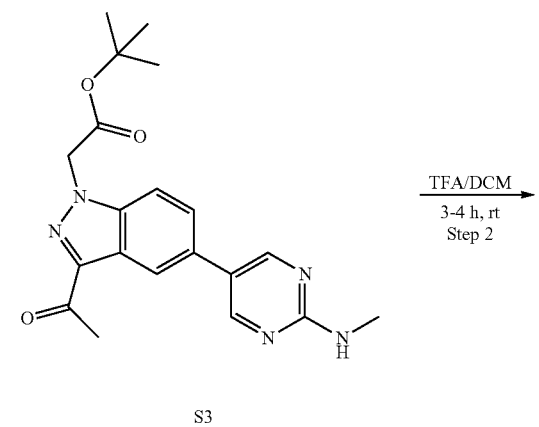
S3

TFA/DCM
3-4 h, rt
Step 2

Step 3: (1R,3S,5R)-2-(2-(3-Acetyl-5-(2-(methylamino)pyrimidin-5-yl)-1H-indazol-1-yl)acetyl)-N-(6-bromopyrazin-2-yl)-2-azabicyclo[3.1.0]hexane-3-carboxamide (379)

To a solution of compound S4 (1 equiv) in DMF (10 vol) at 0° C. under an atmosphere of nitrogen was added (1R,3S,5R)—N-(6-bromopyrazin-2-yl)-2-azabicyclo[3.1.0]hexane-3-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 379. ¹H NMR (400 MHz, DMSO-d₆) δ 0.80-0.87 (m, 1H), 0.99-1.07 (m, 1H), 1.84-1.97 (m, 1H), 2.21-2.42 (m, 2H), 2.65 (s, 3H), 2.87 (d, J=4.8 Hz, 3H), 3.81-3.94 (m, 1H), 4.49 (dd, J=5.5, 9.1 Hz, 1H), 5.61 (d, J=17.2 Hz, 1H), 5.96 (d, J=17.2 Hz, 1H), 7.21-7.28 (m, 1H), 7.70-7.84 (m, 2H), 8.27 (d, J=1.6 Hz, 1H), 8.54 (s, 1H), 8.64 (s, 2H), 9.27 (s, 1H), 11.12 (s, 1H). LC (method A): t$_R$=1.61 min. LC/MS (EI) m/z: [M+H]⁺ 590.

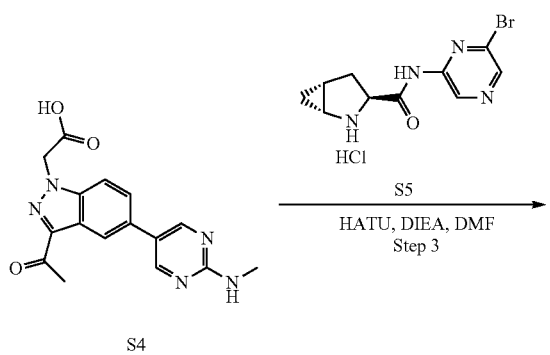
S4

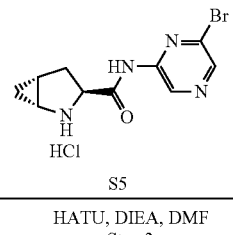
S5
HATU, DIEA, DMF
Step 3

599

(2S,4R)-1-(2-(3-Acetyl-5-(2-(methylamino)pyrimidin-5-yl)-1H-indazol-1-yl)acetyl)-N-(6-bromopyridin-2-yl)-4-fluoropyrrolidine-2-carboxamide (390)

Scheme 260

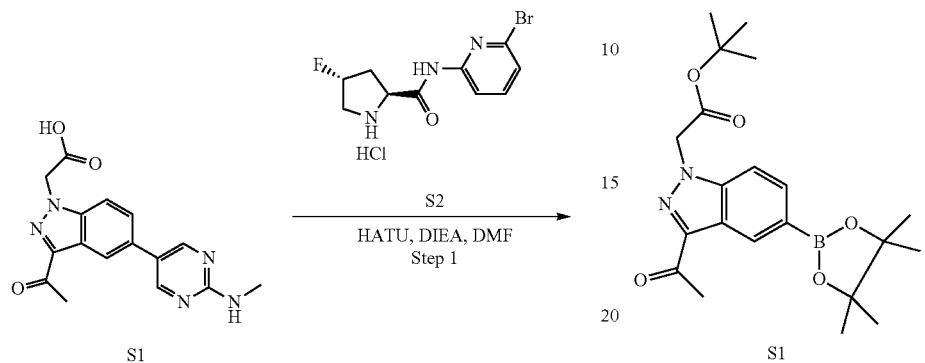

390

To a solution of compound S1 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 390. $^1$H NMR (400 MHz, DMSO-$d_6$) δ 2.06-2.27 (m, 1H), 2.54-2.59 (m, 1H), 2.64 (s, 3H), 2.87 (d, J=4.7 Hz, 3H), 3.94-4.12 (m, 1H), 4.17-4.32 (m, 1H), 4.67 (dd, J=7.6, 9.4 Hz, 1H), 5.46-5.66 (m, 2H), 5.81 (d, J=17.3 Hz, 1H), 7.22-7.28 (m, 1H), 7.33 (d, J=7.7 Hz, 1H), 7.69-7.80 (m, 3H), 8.03 (d, J=8.2 Hz, 1H), 8.26 (s, 1H), 8.63 (s, 2H), 10.99 (s, 1H). $^{19}$F NMR (376 MHz, DMSO-$d_6$): δ −175.68. LC (method A): $t_R$=1.64 min. LC/MS (EI) m/z: [M+H]$^+$ 595.

600

(2S,4R)-1-(2-(3-Acetyl-5-(2-methoxypyrimidin-5-yl)-1H-indazol-1-yl)acetyl)-N-(6-bromopyridin-2-yl)-4-fluoropyrrolidine-2-carboxamide (384)

Scheme 261

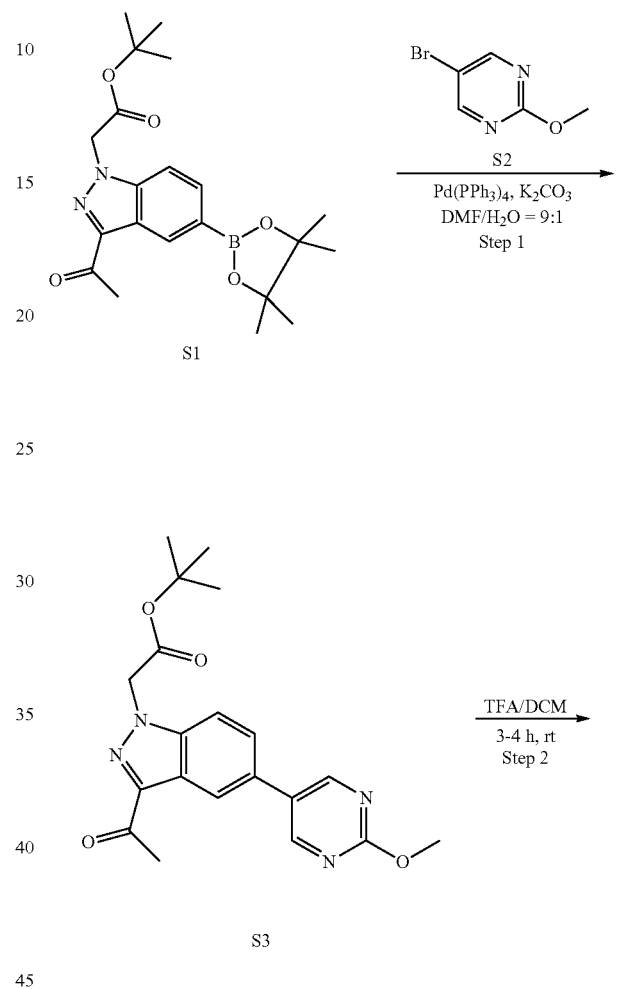

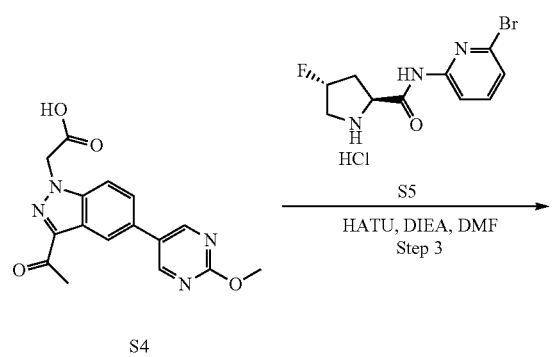

601
-continued

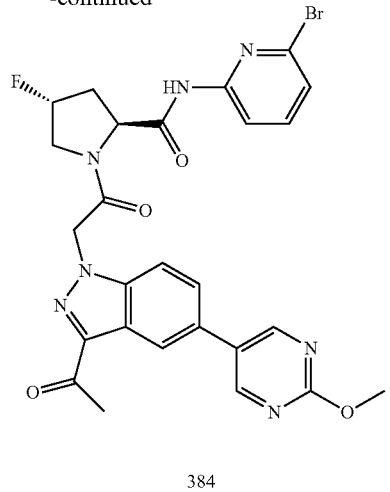

384

Step 1: tert-butyl 2-(3-Acetyl-5-(2-methoxypyrimidin-5-yl)-1H-indazol-1-yl)acetate (S3)

To a solution of 5-bromo-2-methoxypyrimidine (S2, 1 equiv) in DMF/$H_2O$ (9:1, 10 vol) was added compound S1 (1 equiv), $K_2CO_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-methoxypyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-methoxypyrimidin-5-yl)-1H-indazol-1-yl)acetyl)-N-(6-bromopyridin-2-yl)-4-fluoropyrrolidine-2-carboxamide (384)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 384. $^1$H NMR (400 MHz, DMSO-$d_6$) δ 2.07-2.27 (m, 1H), 2.54-2.61 (m, 1H), 2.65 (s, 3H), 3.99 (s, 4H), 4.18-4.32 (m, 1H), 4.68 (dd, J=7.6, 9.4 Hz, 1H), 5.47-5.69 (m, 2H), 5.83 (d, J=17.3 Hz, 1H), 7.32 (d, J=7.7 Hz, 1H), 7.71 (t, J=7.9 Hz, 1H), 7.82 (d, J=2.0 Hz, 1H), 8.03 (d, J=8.2 Hz, 1H), 8.38 (t, J=1.2 Hz, 1H), 8.94 (s, 2H), 10.99 (s, 1H). $^{19}$F NMR (376 MHz, DMSO-$d_6$): δ −175.67. LC (method A): $t_R$=1.84 min. LC/MS (EI) m/z: [M+H]$^+$ 596.

602

(1R,3S,5R)-2-(2-(3-Acetyl-5-(2-methoxypyrimidin-5-yl)-1H-indazol-1-yl)acetyl)-N-(6-bromopyrazin-2-yl)-2-azabicyclo[3.1.0]hexane-3-carboxamide (385)

Scheme 262

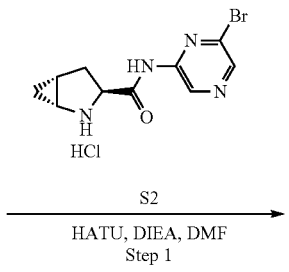

S1

HATU, DIEA, DMF
Step 1

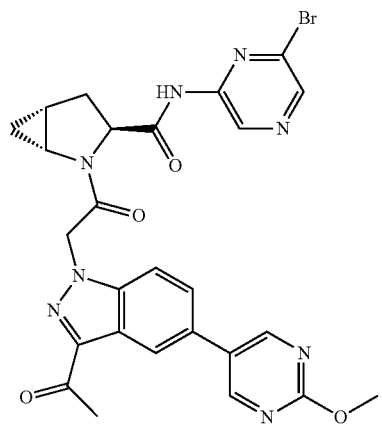

385

To a solution of compound S1 (1 equiv) in DMF (10 vol) at 0° C. under an atmosphere of nitrogen was added (1R,3S,5R)—N-(6-bromopyrazin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 385. $^1$H NMR (400 MHz, DMSO-$d_6$) δ 0.80-0.90 (m, 1H), 1.00-1.08 (m, 1H), 1.84-1.97 (m, 1H), 2.22-2.45 (m, 2H), 2.66 (s, 3H), 3.85-3.93 (m, 1H), 3.99 (s, 3H), 4.50 (dd, J=5.5, 9.1 Hz, 1H), 5.63 (d, J=17.2 Hz, 1H), 5.99 (d, J=17.3 Hz, 1H), 7.80-7.90 (m, 2H), 8.39 (s, 1H), 8.54 (s, 1H), 8.95 (s, 2H), 9.27 (s, 1H), 11.12 (s, 1H). LC (method A): $t_R$=1.8 min. LC/MS (EI) m/z: [M+H]$^+$ 591.

603

(2S,4R)-1-(2-(3-Acetyl-5-(2-methoxypyrimidin-5-yl)-1H-indazol-1-yl)acetyl)-N-(6-bromo-4-methoxy-pyridin-2-yl)-4-fluoropyrrolidine-2-carboxamide (431)

604

(1R,3S,5R)-2-(2-(3-Acetyl-5-(2-methoxypyrimidin-5-yl)-1H-indazol-1-yl)acetyl)-N-(6-bromo-4-methoxypyridin-2-yl)-2-azabicyclo[3.1.0]hexane-3-carboxamide (433)

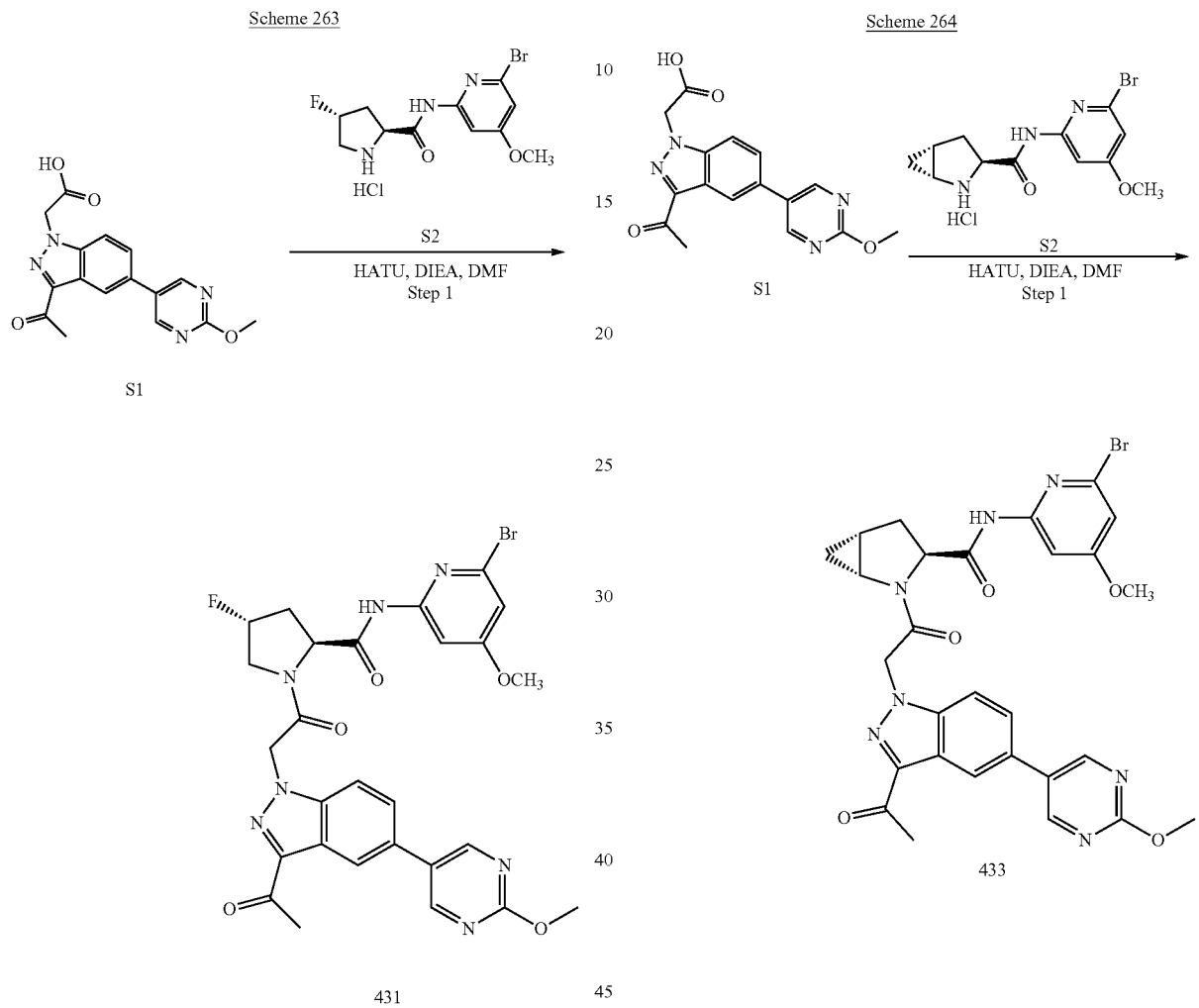

To a solution of compound S1 (1 equiv) in DMF (10 vol) at 0° C. under an atmosphere of nitrogen was added (2S,4R)—N-(6-bromo-4-methoxypyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 431. $^1$H NMR (400 MHz, DMSO-$d_6$) δ 2.07-2.26 (m, 1H), 2.53-2.64 (m, 1H), 2.65 (s, 3H), 3.82 (s, 3H), 3.99 (s, 4H), 4.16-4.34 (m, 1H), 4.64-4.71 (m, 1H), 5.47-5.66 (m, 2H), 5.83 (d, J=17.3 Hz, 1H), 6.96 (d, J=2.0 Hz, 1H), 7.64 (d, J=1.9 Hz, 1H), 7.78-7.85 (m, 2H), 8.38 (d, J=1.4 Hz, 1H), 8.94 (s, 2H), 10.94 (s, 1H). $^{19}$F NMR (376 MHz, DMSO-$d_6$): δ −175.67. LC (method A): $t_R$=1.93 min. LC/MS (EI) m/z: [M+H]$^+$ 626.

To a solution of compound S1 (1 equiv) in DMF (10 vol) at 0° C. under an atmosphere of nitrogen was added (1R,3S,5R)—N-(6-bromo-4-methoxypyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 433. $^1$H NMR (400 MHz, DMSO-$d_6$) δ 0.79-0.86 (m, 1H), 0.99-1.10 (m, 1H), 1.84-1.97 (m, 1H), 2.17-2.27 (m, 1H), 2.30-2.39 (m, 1H), 2.66 (s, 3H), 3.83 (s, 4H), 3.99 (s, 3H), 4.47 (dd, J=5.2, 9.1 Hz, 1H), 5.62 (d, J=17.2 Hz, 1H), 5.98 (d, J=17.2 Hz, 1H), 6.96 (d, J=2.0 Hz, 1H), 7.65 (d, J=2.0 Hz, 1H), 7.79-7.89 (m, 2H), 8.38-8.44 (m, 1H), 8.95 (s, 2H), 10.70 (s, 1H). LC (method A): $t_R$=2.08 min. LC/MS (EI) m/z: [M+H]$^+$ 620.

605

(2S,4R)-1-(2-(3-Acetyl-5-(2-methoxypyrimidin-5-yl)-1H-indazol-1-yl)acetyl)-N-(6-bromo-3-methyl-pyridin-2-yl)-4-fluoropyrrolidine-2-carboxamide (436)

Scheme 265

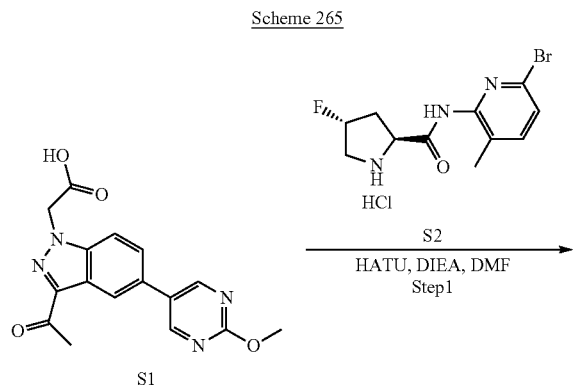

To a solution of compound S1 (1 equiv) in DMF (10 vol) at 0° C. under an atmosphere of nitrogen was added (2S, 4R)—N-(6-bromo-3-methylpyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 436. $^1$H NMR (400 MHz, DMSO-$d_6$) δ 2.00 (s, 3H), 2.11-2.30 (m, 1H), 2.64 (s, 4H), 3.99 (s, 4H), 4.19-4.33 (m, 1H), 4.61 (t, J=8.5 Hz, 1H), 5.47-5.67 (m, 2H), 5.84 (d, J=17.3 Hz, 1H), 7.42 (d, J=7.9 Hz, 1H), 7.60 (d, J=8.0 Hz, 1H), 7.80 (s, 2H), 8.38 (s, 1H), 8.94 (s, 2H), 10.44 (s, 1H). $^{19}$F NMR (376 MHz, DMSO-$d_6$): δ −176.04. LC (method A): $t_R$=1.67 min. LC/MS (EI) m/z: [M+H]$^+$ 610.

606

(1R,3S,5R)-2-(2-(3-Acetyl-5-(2-methoxypyrimidin-5-yl)-1H-indazol-1-yl)acetyl)-N-(6-bromo-3-methyl-pyridin-2-yl)-2-azabicyclo[3.1.0]hexane-3-carboxamide (445)

Scheme 266

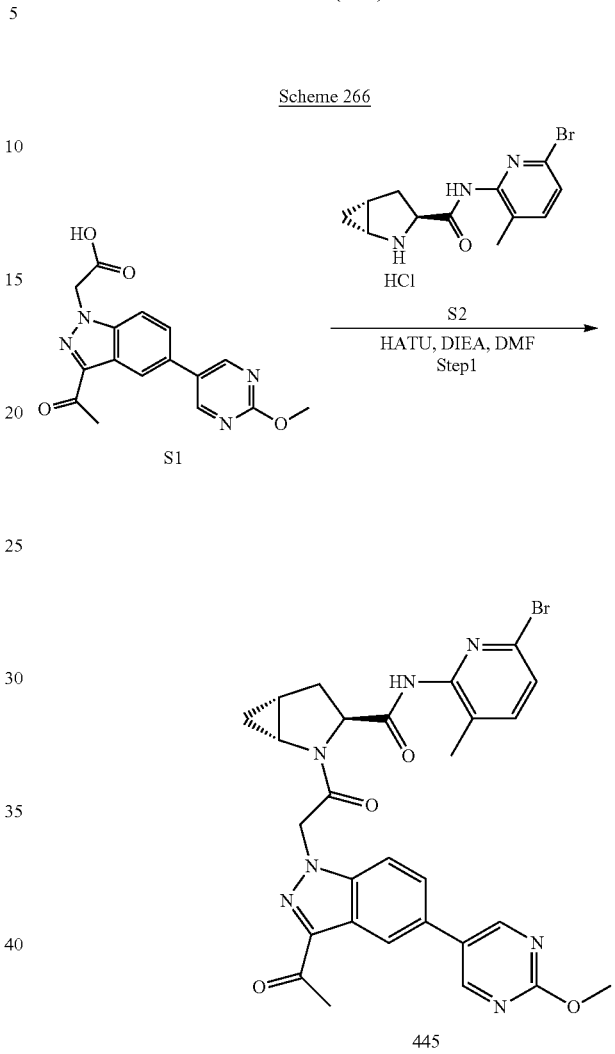

To a solution of compound S1 (1 equiv) in DMF (10 vol) at 0° C. under an atmosphere of nitrogen was added (1R, 3S,5R)—N-(6-bromo-3-methylpyridin-2-yl)-2-azabicyclo [3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 445. $^1$H NMR (400 MHz, DMSO-$d_6$) δ 0.82-0.93 (m, 1H), 1.03-1.09 (m, 1H), 1.89-1.98 (m, 1H), 2.03 (s, 3H), 2.21-2.32 (m, 1H), 2.36-2.43 (m, 1H), 2.65 (s, 3H), 3.75-3.86 (m, 1H), 3.99 (s, 3H), 4.43 (dd, J=5.0, 9.3 Hz, 1H), 5.62 (d, J=17.2 Hz, 1H), 5.94 (d, J=17.3 Hz, 1H), 7.44 (d, J=7.9 Hz, 1H), 7.62 (d, J=8.0 Hz, 1H), 7.79-7.88 (m, 2H), 8.39 (s, 1H), 8.95 (s, 2H), 10.23 (s, 1H). LC (method A): $t_R$=1.76 min. LC/MS (EI) m/z: [M+H]$^+$ 604.

607

(2S,4R)-1-(2-(3-Acetyl-5-(2-methoxypyrimidin-5-yl)-1H-indazol-1-yl)acetyl)-N-(6-bromo-5-fluoropyridin-2-yl)-4-fluoropyrrolidine-2-carboxamide (450)

Scheme 267

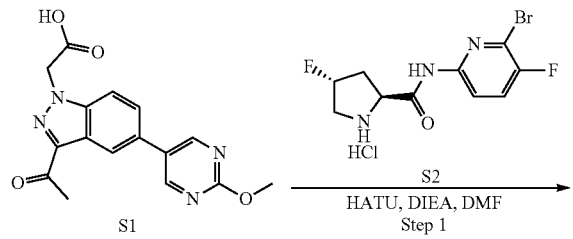

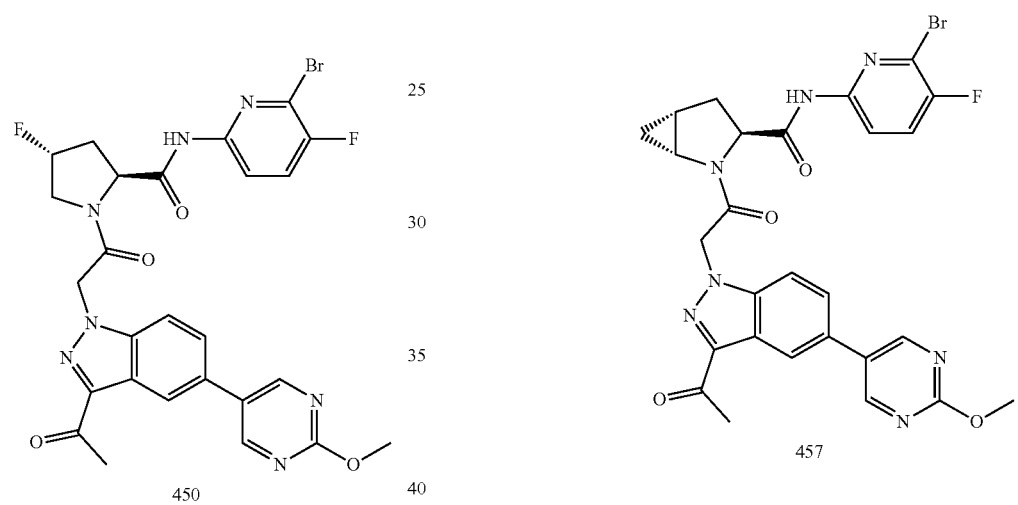

To a solution of compound S1 (1 equiv) in DMF (10 vol) at 0° C. under an atmosphere of nitrogen was added (2S, 4R)—N-(6-bromo-5-fluoropyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 450. $^1$H NMR (400 MHz, DMSO-$d_6$) δ 2.07-2.25 (m, 1H), 2.54-2.61 (m, 1H), 2.64 (s, 3H), 3.93-4.10 (m, 4H), 4.17-4.31 (m, 1H), 4.66 (dd, J=7.5, 9.5 Hz, 1H), 5.47-5.68 (m, 2H), 5.83 (d, J=17.3 Hz, 1H), 7.79-7.89 (m, 3H), 8.03-8.09 (m, 1H), 8.37 (t, J=1.2 Hz, 1H), 8.94 (s, 2H), 11.07 (s, 1H). $^{19}$F NMR (376 MHz, DMSO-$d_6$): δ −175.71, −120.37. LC (method A): $t_R$=1.91 min. LC/MS (EI) m/z: [M+H]$^+$ 614.

608

(1R,3S,5R)-2-(2-(3-Acetyl-5-(2-methoxypyrimidin-5-yl)-1H-indazol-1-yl)acetyl)-N-(6-bromo-5-fluoropyridin-2-yl)-2-azabicyclo[3.1.0]hexane-3-carboxamide (457)

Scheme 268

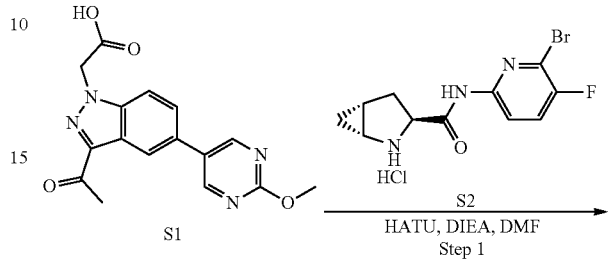

To a solution of compound S1 (1 equiv) in DMF (10 vol) at 0° C. under an atmosphere of nitrogen was added (1R, 3S,5R)—N-(6-bromo-5-fluoropyridin-2-yl)-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 457. $^1$H NMR (400 MHz, DMSO-$d_6$) δ 0.78-0.88 (m, 1H), 0.99-1.09 (m, 1H), 1.87-1.94 (m, 1H), 2.17-2.28 (m, 1H), 2.30-2.40 (m, 1H), 2.65 (s, 3H), 3.82-3.91 (m, 1H), 3.98 (s, 3H), 4.45 (dd, J=5.4, 9.1 Hz, 1H), 5.61 (d, J=17.2 Hz, 1H), 5.98 (d, J=17.3 Hz, 1H), 7.84 (td, J=7.4, 9.1, 9.6 Hz, 3H), 8.05 (dd, J=3.3, 8.9 Hz, 1H), 8.37-8.40 (m, 1H), 8.94 (s, 2H), 10.83 (s, 1H). $^{19}$F NMR (376 MHz, DMSO-$d_6$): δ −120.70. LC (method A): $t_R$=2.06 min. LC/MS (EI) m/z: [M+H]$^+$ 608.

609

(1R,3S,5R)-2-(2-(3-Acetyl-5-(2-methoxypyrimidin-5-yl)-1H-indazol-1-yl)acetyl)-N-(6-bromo-3-methyl-pyridin-2-yl)-5-methyl-2-azabicyclo[3.1.0]hexane-3-carboxamide (632)

610

(1R,2S,5S)-3-(2-(3-Acetyl-5-(2-methoxypyrimidin-5-yl)-1H-indazol-1-yl)acetyl)-N-(6-bromo-3-methyl-pyridin-2-yl)-3-azabicyclo[3.1.0]hexane-2-carboxamide (634)

Scheme 269

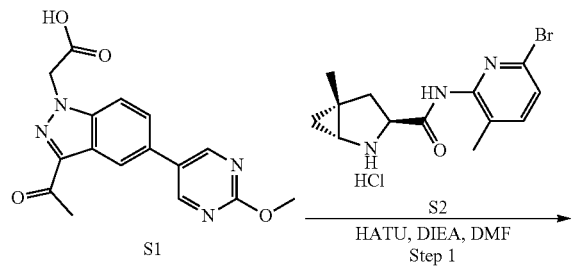

Scheme 270

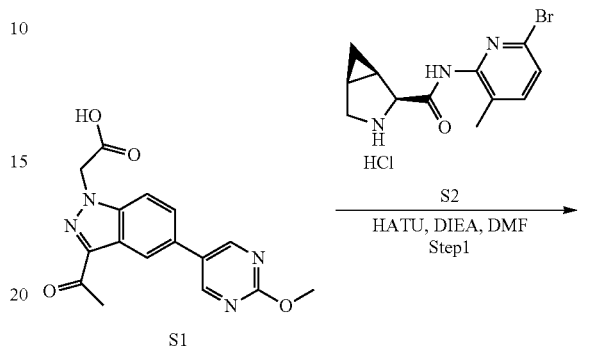

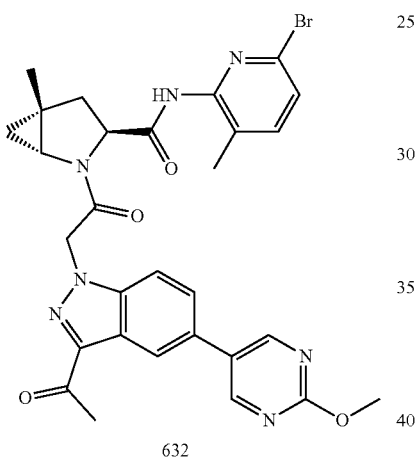

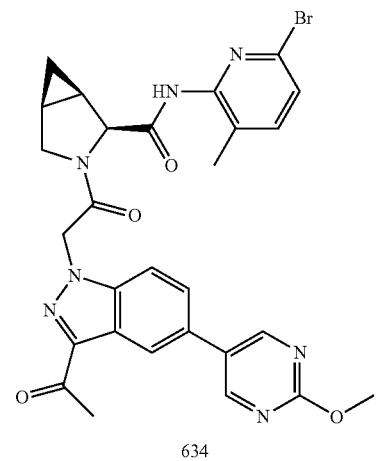

To a solution of compound S1 (1 equiv) in DMF (10 vol) at 0° C. under an atmosphere of nitrogen was added (1R,3S,5R)—N-(6-bromo-3-methylpyridin-2-yl)-5-methyl-2-azabicyclo[3.1.0]hexane-3-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 632. $^1$H NMR (400 MHz, DMSO-d$_6$) δ 0.97-1.09 (m, 2H), 1.33 (s, 3H), 2.05 (s, 4H), 2.53-2.60 (m, 1H), 2.66 (s, 3H), 3.57-3.64 (m, 1H), 3.99 (s, 3H), 4.37-4.49 (m, 1H), 5.57 (d, J=17.2 Hz, 1H), 5.92 (d, J=17.3 Hz, 1H), 7.45 (d, J=7.9 Hz, 1H), 7.63 (d, J=7.9 Hz, 1H), 7.82 (d, J=1.6 Hz, 2H), 8.39 (d, J=1.5 Hz, 1H), 8.96 (s, 2H), 10.28 (s, 1H). LC (method A): t$_R$=1.97 min. LC/MS (EI) m/z: [M+H]$^+$ 618.

To a solution of compound S1 (1 equiv) in DMF (10 vol) at 0° C. under an atmosphere of nitrogen was added (1R,2S,5S)—N-(6-bromo-3-methylpyridin-2-yl)-3-azabicyclo[3.1.0]hexane-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 634. 1H NMR (400 MHz, DMSO-d$_6$) δ 0.76-0.90 (m, 2H), 1.87-1.96 (m, 1H), 2.01-2.10 (m, 4H), 2.64 (s, 3H), 3.89 (d, J=9.6 Hz, 1H), 3.99 (s, 3H), 4.01-4.09 (m, 1H), 4.60 (d, J=5.4 Hz, 1H), 5.58 (d, J=4.7 Hz, 2H), 7.42 (d, J=7.9 Hz, 1H), 7.60 (d, J=7.9 Hz, 1H), 7.80 (d, J=2.0 Hz, 2H), 8.38 (s, 1H), 8.95 (s, 2H), 10.30 (s, 1H). LC (method A): t$_R$=1.75 min. LC/MS (EI) m/z: [M+H]$^+$ 604.

611

(1R,2S,5S)-3-(2-(3-Acetyl-5-(2-methoxypyrimidin-5-yl)-1H-indazol-1-yl)acetyl)-N-(6-bromo-3-cyclopropylpyridin-2-yl)-3-azabicyclo[3.1.0]hexane-2-carboxamide (641)

Scheme 271

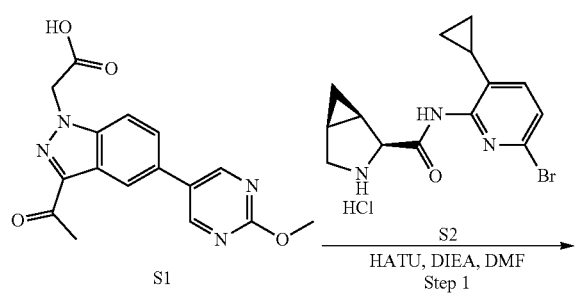

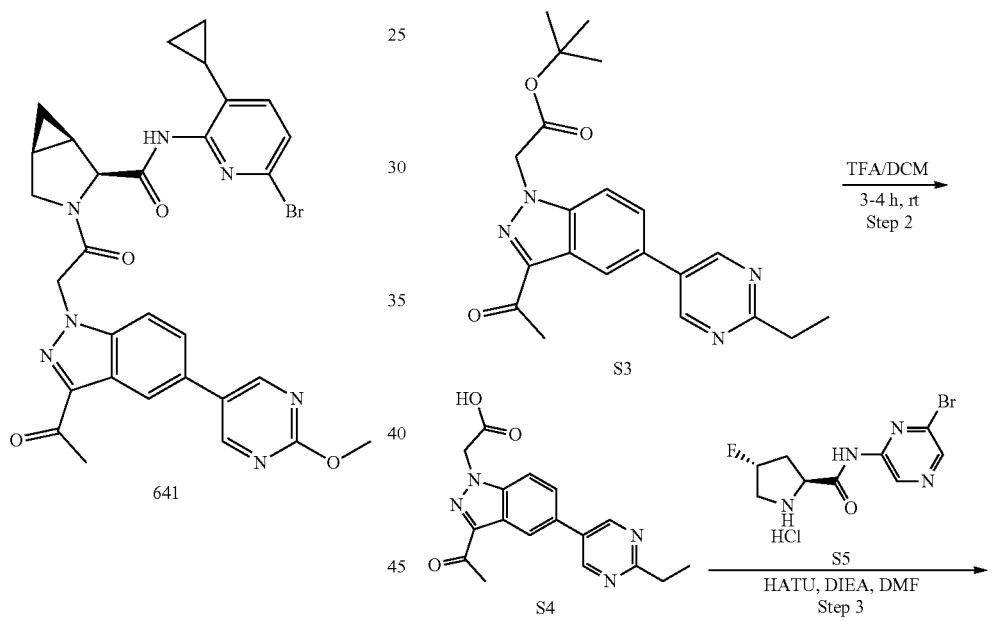

To a solution of compound S1 (1 equiv) in DMF (10 vol) at 0° C. under an atmosphere of nitrogen was added (1R, 2S,5S)—N-(6-bromo-3-cyclopropylpyridin-2-yl)-3-azabicyclo[3.1.0]hexane-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 641. $^1$H NMR (400 MHz, DMSO-$d_6$) δ 0.48-0.59 (m, 2H), 0.68-0.81 (m, 3H), 0.83-0.89 (m, 1H), 1.81-1.93 (m, 2H), 2.04 (d, J=6.2 Hz, 1H), 2.64 (s, 3H), 3.90 (d, J=9.7 Hz, 1H), 3.99 (s, 3H), 4.01-4.09 (m, 1H), 4.62 (d, J=5.5 Hz, 1H), 5.53-5.67 (m, 2H), 7.29 (d, J=8.1 Hz, 1H), 7.39 (d, J=8.1 Hz, 1H), 7.81 (s, 2H), 8.38 (s, 1H), 8.95 (s, 2H), 10.25 (s, 1H). LC (method A): $t_R$=1.92 min. LC/MS (EI) m/z: [M+H]$^+$ 630.

612

(2S,4R)-1-(2-(3-Acetyl-5-(2-ethylpyrimidin-5-yl)-1H-indazol-1-yl)acetyl)-N-(6-bromopyrazin-2-yl)-4-fluoropyrrolidine-2-carboxamide (388)

Scheme 272

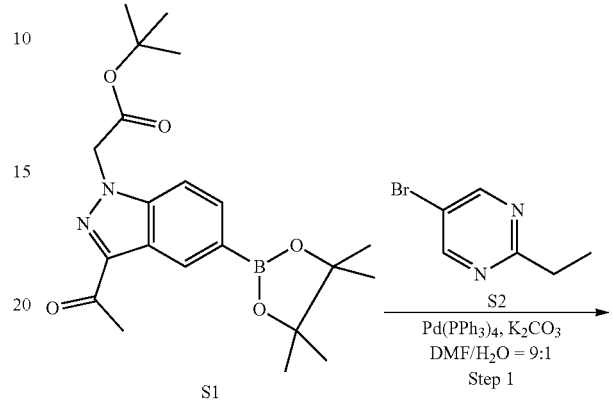

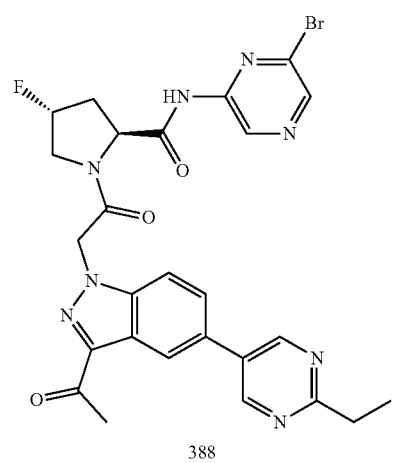

Step 1: tert-Butyl 2-(3-acetyl-5-(2-ethylpyrimidin-5-yl)-1H-indazol-1-yl)acetate (S3)

To a solution of 5-bromo-2-ethylpyrimidine (S2, 1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-ethylpyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-acetyl-5-(2-ethylpyrimidin-5-yl)-1H-indazol-1-yl)acetyl)-N-(6-bromopyrazin-2-yl)-4-fluoropyrrolidine-2-carboxamide (388)

To a solution of compound S4 (1 equiv) in DMF (10 vol) at 0° C. under an atmosphere of nitrogen was added (2S,4R)—N-(6-bromopyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 388. $^1$H NMR (400 MHz, DMSO-d₆) δ 1.34 (t, J=7.6 Hz, 3H), 2.12-2.33 (m, 1H), 2.55-2.63 (m, 1H), 2.65 (s, 3H), 2.97 (q, J=7.6 Hz, 2H), 3.98-4.13 (m, 1H), 4.26 (dd, J=12.5, 22.3 Hz, 1H), 4.64-4.74 (m, 1H), 5.49-5.70 (m, 2H), 5.86 (d, J=17.3 Hz, 1H), 7.81-7.88 (m, 2H), 8.43 (t, J=1.2 Hz, 1H), 8.54 (s, 1H), 9.06 (s, 2H), 9.26 (s, 1H), 11.34 (s, 1H). $^{19}$F NMR (376 MHz, DMSO-d₆): δ −175.73. LC (method A): t$_R$=1.7 min. LC/MS (EI) m/z: [M+H]$^+$ 595.

(2S,4R)-1-(2-(3-Acetyl-5-(2-ethylpyrimidin-5-yl)-1H-indazol-1-yl)acetyl)-N-(6-bromopyridin-2-yl)-4-fluoropyrrolidine-2-carboxamide (566)

Scheme 273

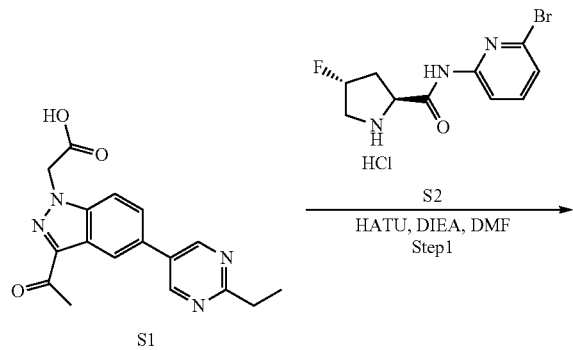

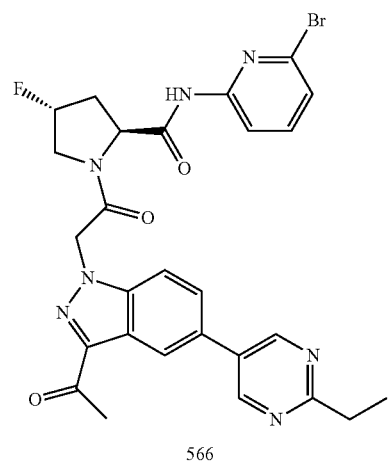

566

To a solution of compound S1 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 566. $^1$H NMR (400 MHz, DMSO-d₆) δ 1.33 (t, J=7.6 Hz, 3H), 2.05-2.26 (m, 1H), 2.54-2.61 (m, 1H), 2.65 (s, 3H), 2.96 (q, J=7.6 Hz, 2H), 3.95-4.13 (m, 1H), 4.24 (dd, J=22.4, 12.7 Hz, 1H), 4.67 (t, J=8.5 Hz, 1H), 5.47-5.70 (m, 2H), 5.85 (d, J=17.3 Hz, 1H), 7.32 (d, J=7.7 Hz, 1H), 7.71 (t, J=8.0 Hz, 1H), 7.86 (d, J=2.2 Hz, 2H), 8.03 (d, J=8.2 Hz, 1H), 8.42 (s, 1H), 9.06 (s, 2H), 11.01 (s, 1H). $^{19}$F NMR (376 MHz, DMSO-d₆): δ −175.66. LC (method A): t$_R$=1.9 min. LC/MS (EI) m/z: [M+H]$^+$ 594.

(2S,4R)-1-(2-(3-Acetyl-5-(2-isopropylpyrimidin-5-yl)-1H-indazol-1-yl)acetyl)-N-(6-bromopyrazin-2-yl)-4-fluoropyrrolidine-2-carboxamide (389)

Scheme 274

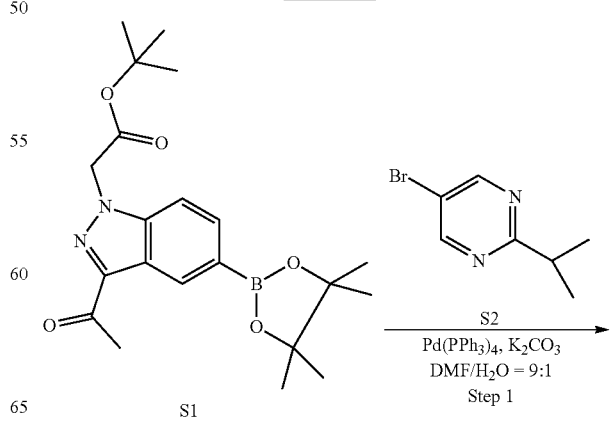

-continued

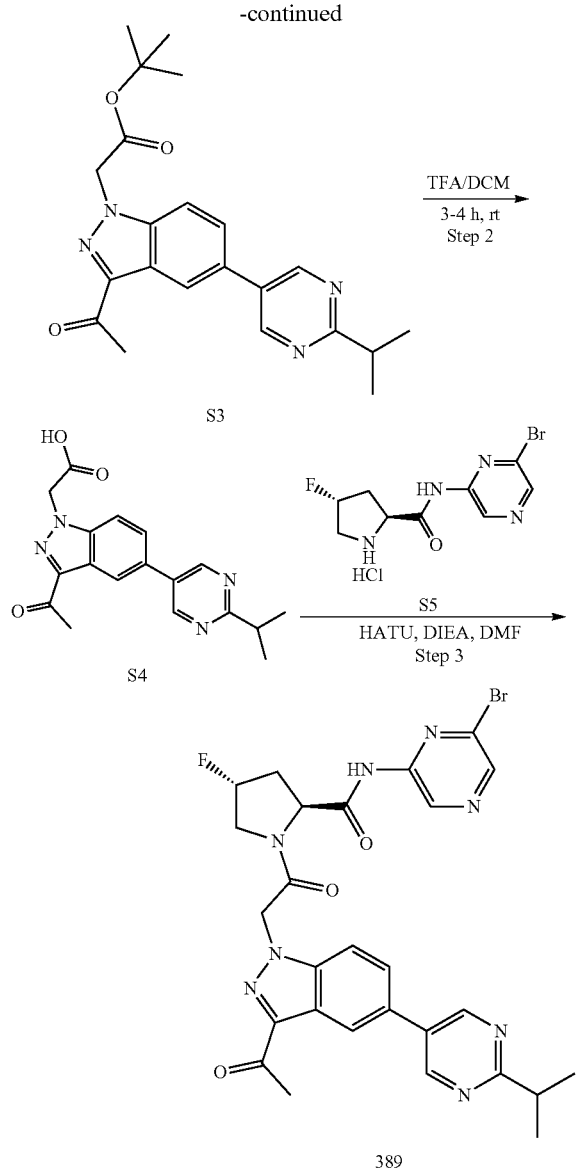

Step 1: tert-Butyl 2-(3-acetyl-5-(2-isopropylpyrimidin-5-yl)-1H-indazol-1-yl)acetate (S3)

To a solution of 5-bromo-2-isopropylpyrimidine (S2, 1 equiv) in DMF/H$_2$O (9:1, vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-isopropylpyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-isopropylpyrimidin-5-yl)-1H-indazol-1-yl)acetyl)-N-(6-bromopyrazin-2-yl)-4-fluoropyrrolidine-2-carboxamide (389)

To a solution of compound S4 (1 equiv) in DMF (10 vol) at 0° C. under an atmosphere of nitrogen was added (2S,4R)—N-(6-bromopyrazin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 389. $^1$H NMR (400 MHz, DMSO-d$_6$) δ 1.34 (d, J=6.9 Hz, 6H), 2.08-2.32 (m, 1H), 2.53-2.63 (m, 1H), 2.65 (s, 3H), 3.16-3.26 (m, 1H), 3.97-4.14 (m, 1H), 4.26 (dd, J=12.8, 21.9 Hz, 1H), 4.70 (dd, J=7.5, 9.5 Hz, 1H), 5.50-5.72 (m, 2H), 5.85 (d, J=17.3 Hz, 1H), 7.87 (t, J=1.3 Hz, 2H), 8.42 (d, J=1.3 Hz, 1H), 8.54 (s, 1H), 9.07 (s, 2H), 9.26 (s, 1H), 11.34 (s, 1H). $^{19}$F NMR (376 MHz, DMSO-d$_6$): δ −175.73. LC (method A): t$_R$=1.96 min. LC/MS (EI) m/z: [M+H]$^+$ 609.

(2S,4R)-1-(2-(3-Acetyl-5-(2-isopropylpyrimidin-5-yl)-1H-indazol-1-yl)acetyl)-N-(6-bromopyridin-2-yl)-4-fluoropyrrolidine-2-carboxamide (567)

Scheme 275

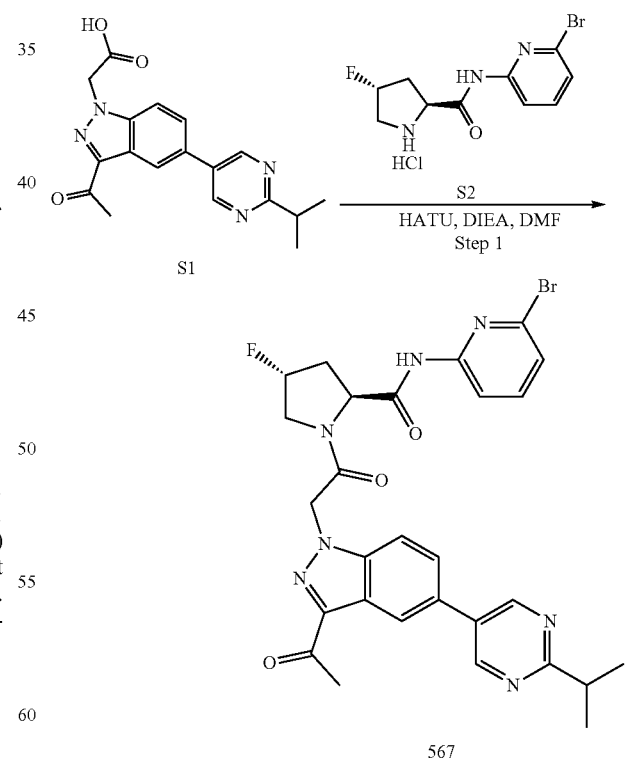

To a solution of compound S1 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 567. $^1$H NMR (400 MHz, DMSO-$d_6$) δ 1.33 (d, J=6.9 Hz, 6H), 2.05-2.27 (m, 1H), 2.55-2.63 (m, 1H), 2.65 (s, 3H), 3.17-3.26 (m, 1H), 3.95-4.13 (m, 1H), 4.19-4.31 (m, 1H), 4.62-4.73 (m, 1H), 5.48-5.69 (m, 2H), 5.85 (d, J=17.3 Hz, 1H), 7.32 (d, J=7.7 Hz, 1H), 7.71 (t, J=8.0 Hz, 1H), 7.86 (t, J=1.6 Hz, 2H), 8.03 (d, J=8.2 Hz, 1H), 8.42 (t, J=1.2 Hz, 1H), 9.06 (s, 2H), 11.01 (s, 1H). $^{19}$F NMR (376 MHz, DMSO-$d_6$): δ −175.66. LC (method A): $t_R$=2.15 min. LC/MS (EI) m/z: [M+H]$^+$ 608.

(2S,4R)-1-(2-(3-Acetyl-5-(2-(cyanomethyl)pyrimidin-5-yl)-1H-indazol-1-yl)acetyl)-N-(6-bromopyridin-2-yl)-4-fluoropyrrolidine-2-carboxamide (391)

Scheme 276

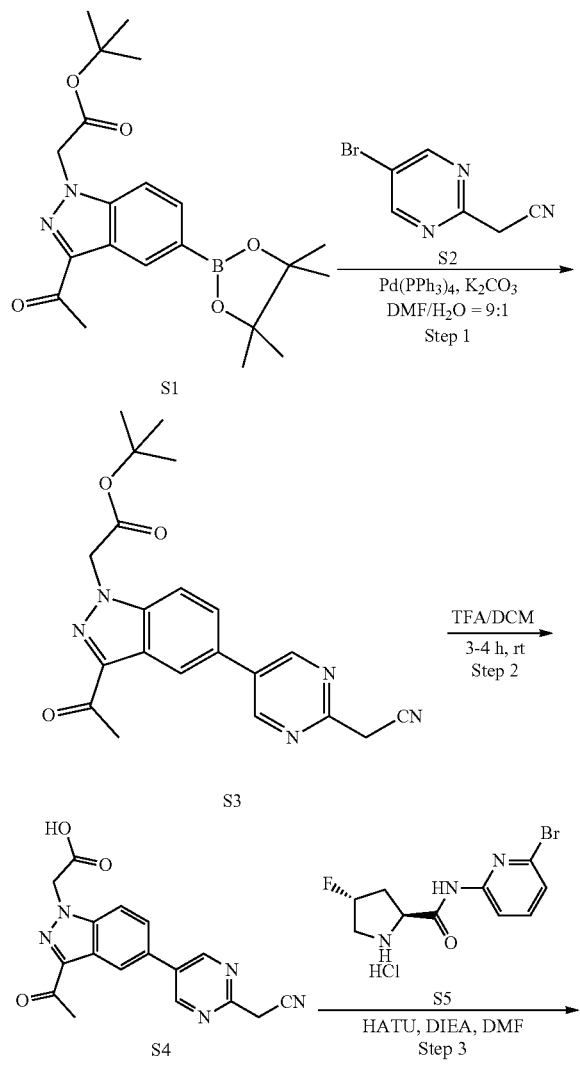

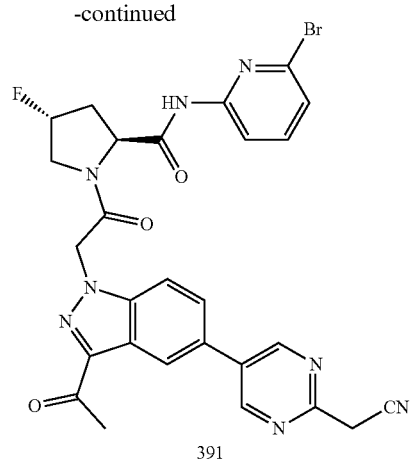

Step 1: tert-butyl 2-(3-Acetyl-5-(2-(cyanomethyl)pyrimidin-5-yl)-1H-indazol-1-yl)acetate (S3)

To a solution of 2-(5-bromopyrimidin-2-yl)acetonitrile (S2, 1 equiv) in DMF/$H_2O$ (9:1, 10 vol) was added compound S1 (1 equiv), $K_2CO_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(cyanomethyl)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(cyanomethyl)pyrimidin-5-yl)-1H-indazol-1-yl)acetyl)-N-(6-bromopyridin-2-yl)-4-fluoropyrrolidine-2-carboxamide (391)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 391. $^1$H NMR (400 MHz, DMSO-$d_6$) δ 2.07-2.27 (m, 1H), 2.57-2.65 (m, 1H), 2.66 (s, 3H), 3.96-4.12 (m, 1H), 4.24 (dd, J=12.5, 22.2 Hz, 1H), 4.49 (s, 2H), 4.65-4.75 (m, 1H), 5.48-5.72 (m, 2H), 5.85 (d, J=17.3 Hz, 1H), 7.35 (d, J=8.2 Hz, 1H), 7.71 (t, J=8.0 Hz, 1H), 7.90 (dd, J=6.0, 7.6 Hz, 2H), 8.03 (d, J=8.2 Hz, 1H), 8.48 (s, 1H), 9.18 (s, 2H), 10.99 (s, 1H). $^{19}$F NMR (376 MHz, DMSO-$d_6$): δ −175.68. LC (method A): $t_R$=1.73 min. LC/MS (EI) m/z: [M+H]$^+$ 605.

tert-butyl ((5-(3-Acetyl-1-(2-(((2S,4R)-2-((6-bromopyridin-2-yl)carbamoyl)-4-fluoropyrrolidin-1-yl)-2-oxoethyl)-1H-indazol-5-yl)pyrimidin-2-yl)methyl)carbamate (403)

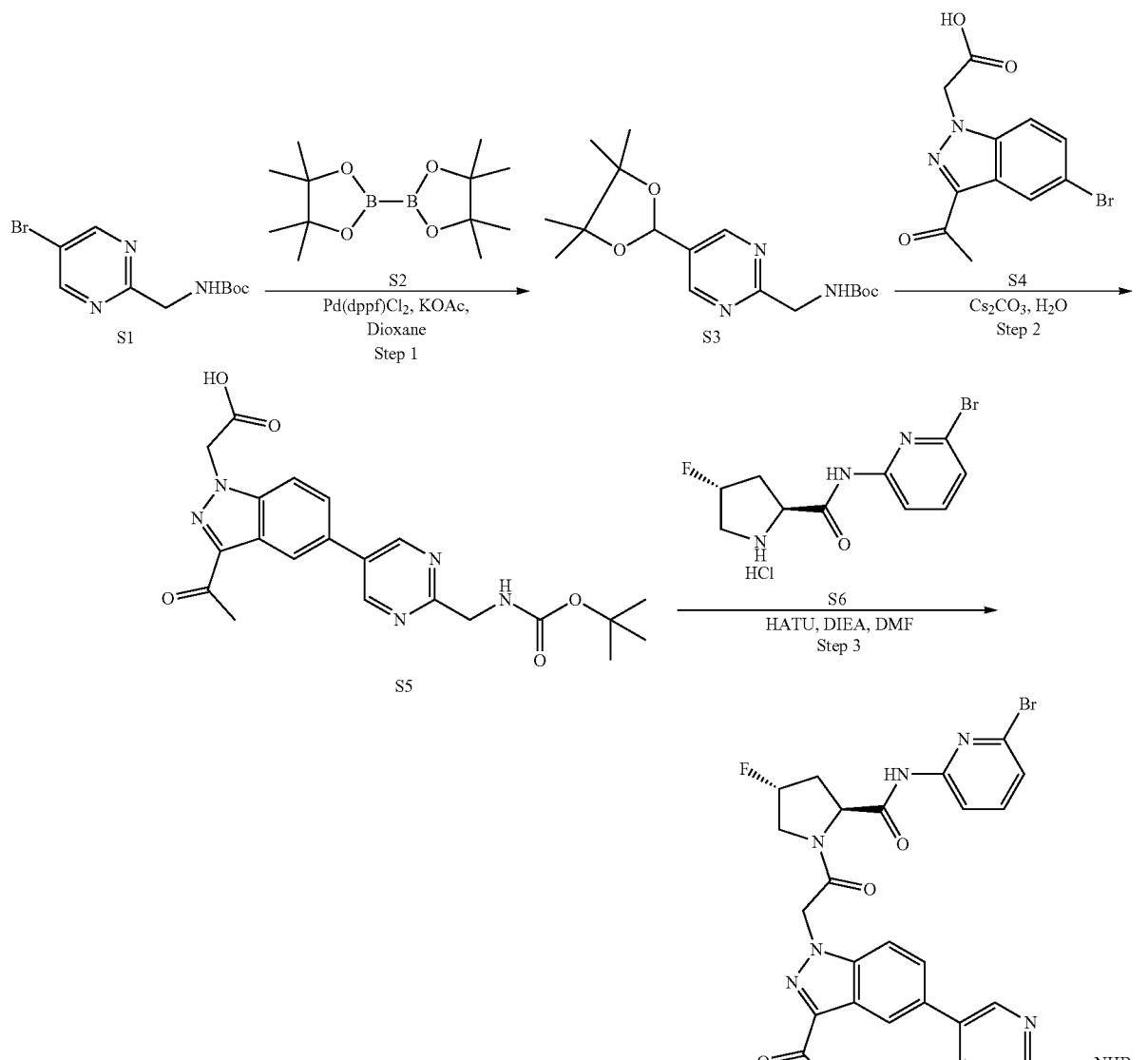

Scheme 277

Step 1: tert-Butyl ((5-(4,4,5,5-tetramethyl-1,3,2-dioxaborolan-2-yl)pyrimidin-2-yl)methyl)carbamate (S3)

To a mixture of compound S1 (1 equiv), AcOK (3 equiv), and compound 2 (1.2 equiv) in dioxane (10 vol) stirred at room temperature under nitrogen was added Pd(dppf)Cl$_2$ (0.05 equiv) in one portion. The resulting mixture was stirred at 90° C. under nitrogen for 3 h. After cooling the reaction mixture to room temperature and directly used in the next step.

Step 2: 2-(3-Acetyl-5-(2-(((tert-butoxycarbonyl)amino)methyl)pyrimidin-5-yl)-1H-indazol-1-yl)acetic acid (S5)

To a solution of compound S3 (1 equiv) in dioxane and water (9:1 vol) at room temperature under an atmosphere of nitrogen was added CS$_2$CO$_3$ (3 equiv) and compound S4. The resulting mixture was stirred at 90° C. under nitrogen for 3 h. After cooling the reaction mixture to room temperature, the mixture was filtered through Celite and washed with dioxane. The filtrate was concentrated under high vacuum and The residue was purified by column chromatography on silica gel (MeOH/DCM) to give compound S5.

Step 3: tert-Butyl ((5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)methyl)carbamate (403)

To a solution of compound S5 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 403. $^1$H NMR (400 MHz, DMSO-$d_6$) δ 1.42 (s, 9H), 2.08-2.31 (m, 1H), 2.54-2.62 (m, 1H), 2.65 (s, 3H), 3.97-4.13 (m, 1H), 4.18-4.31 (m, 1H), 4.40 (d, J=6.1 Hz, 2H), 4.68 (t, J=7.6, 9.5 Hz, 1H), 5.48-5.69 (m, 2H), 5.85 (d, J=17.3 Hz, 1H), 7.28 (t, J=6.1 Hz, 1H), 7.32 (d, J=7.7 Hz, 1H), 7.71 (t, J=8.0 Hz, 1H), 7.85-7.91 (m, 2H), 8.03 (d, J=8.2 Hz, 1H), 8.45 (s, 1H), 9.10 (s, 2H), 10.99 (s, 1H). 19F NMR (376 MHz, DMSO-$d_6$): δ -175.67. LC (method A): tR=2.09 min. LC/MS (EI) m/z: [M+H]+ 695.

(2S,4R)-1-(2-(3-Acetyl-5-(2-(aminomethyl)pyrimidin-5-yl)-1H-indazol-1-yl)acetyl)-N-(6-bromopyridin-2-yl)-4-fluoropyrrolidine-2-carboxamide hydrochloride (404)

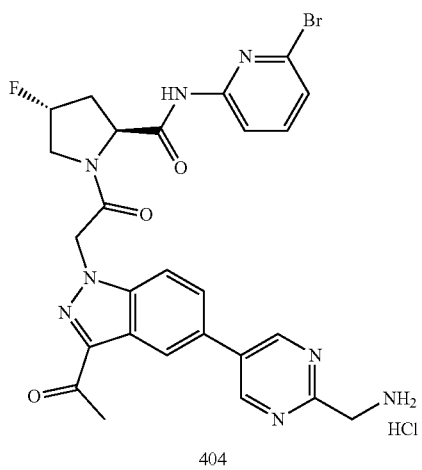

404

To a solution of compound 403 (1 equiv) under an atmosphere of nitrogen was added 4N HCl dioxane (10 vol). The reaction mixture was stirred at room temperature for 3 h and then concentrated to give compound 404. $^1$H NMR (400 MHz, DMSO-$d_6$) δ 2.07-2.29 (m, 1H), 2.55-2.63 (m, 1H), 2.66 (s, 3H), 3.98-4.13 (m, 1H), 4.25 (dd, J=12.5, 22.2 Hz, 1H), 4.36-4.45 (m, 2H), 4.68 (t, J=8.5 Hz, 1H), 5.49-5.73 (m, 2H), 5.87 (d, J=17.3 Hz, 1H), 7.33 (d, J=7.7 Hz, 1H), 7.71 (t, J=8.0 Hz, 1H), 7.88-7.96 (m, 2H), 8.03 (d, J=8.2 Hz, 1H), 8.48-8.61 (m, 3H), 9.26 (s, 2H), 11.00 (s, 1H). $^{19}$F NMR (376 MHz, DMSO-$d_6$): δ -175.68. LC (method A): $t_R$=1.16 min. LC/MS (EI) m/z: [M+H]$^+$ 595.

(2S,4R)-1-(2-(5-(2-(Acetamidomethyl)pyrimidin-5-yl)-3-acetyl-1H-indazol-1-yl)acetyl)-N-(6-bromopyridin-2-yl)-4-fluoropyrrolidine-2-carboxamide (406)

Scheme 278

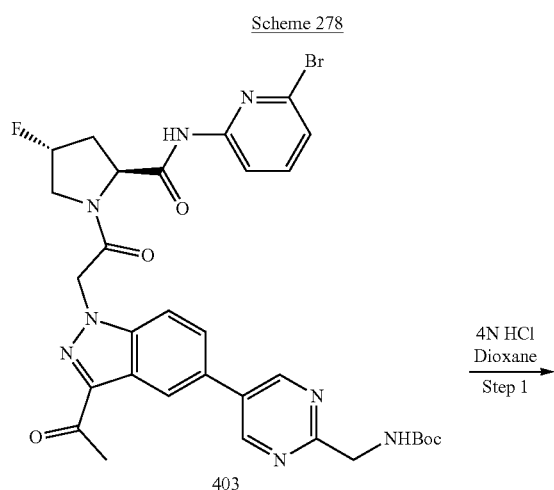

403

4N HCl Dioxane
Step 1

Scheme 279

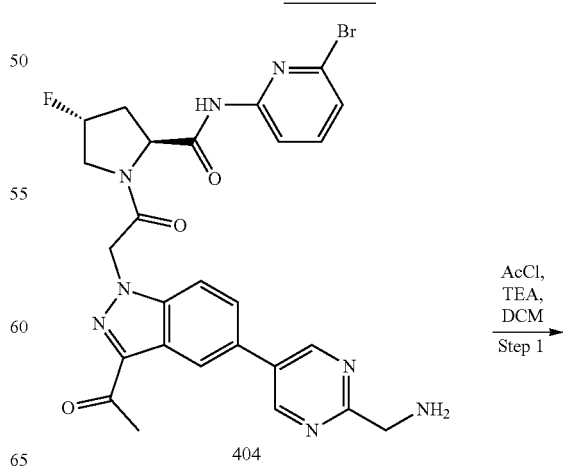

404

AcCl, TEA, DCM
Step 1

-continued

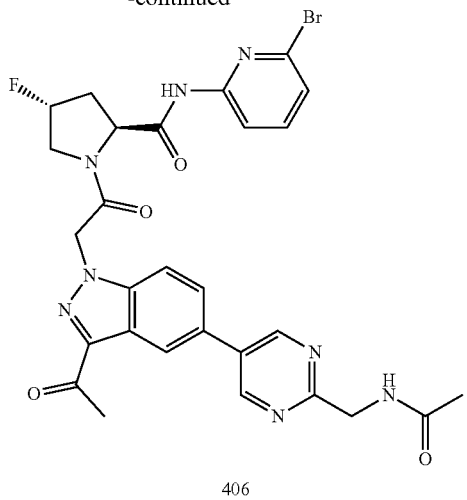

406

To a solution of compound 404 (1 equiv) in DCM (10 vol) at 0° C. under an atmosphere of nitrogen was added acetyl chloride (1.1 equiv), and TEA (3 equiv). The reaction mixture was stirred at room temperature for 1 h and then concentrated. The residue was purified by column chromatography on silica gel (MeOH/DCM) to give compound 406. $^1$H NMR (400 MHz, DMSO-$d_6$) δ 1.93 (s, 3H), 2.06-2.27 (m, 1H), 2.55-2.63 (m, 1H), 2.65 (s, 3H), 3.96-4.12 (m, 1H), 4.19-4.31 (m, 1H), 4.52 (d, J=5.9 Hz, 2H), 4.68 (t, J=8.5 Hz, 1H), 5.47-5.70 (m, 2H), 5.85 (d, J=17.3 Hz, 1H), 7.33 (d, J=7.7 Hz, 1H), 7.71 (t, J=8.0 Hz, 1H), 7.85-7.92 (m, 2H), 8.03 (d, J=8.2 Hz, 1H), 8.42-8.50 (m, 2H), 9.10 (s, 2H), 10.99 (s, 1H). $^{19}$F NMR (376 MHz, DMSO-$d_6$): δ −175.67. LC (method A): $t_R$=1.41 min. LC/MS (EI) m/z: [M+H]$^+$ 637.

(2S,4R)-1-(2-(3-Acetyl-5-(2-fluoropyrazolo[1,5-a]pyrimidin-6-yl)-1H-indazol-1-yl)acetyl)-N-(6-bromopyridin-2-yl)-4-fluoropyrrolidine-2-carboxamide (683)

Scheme 280

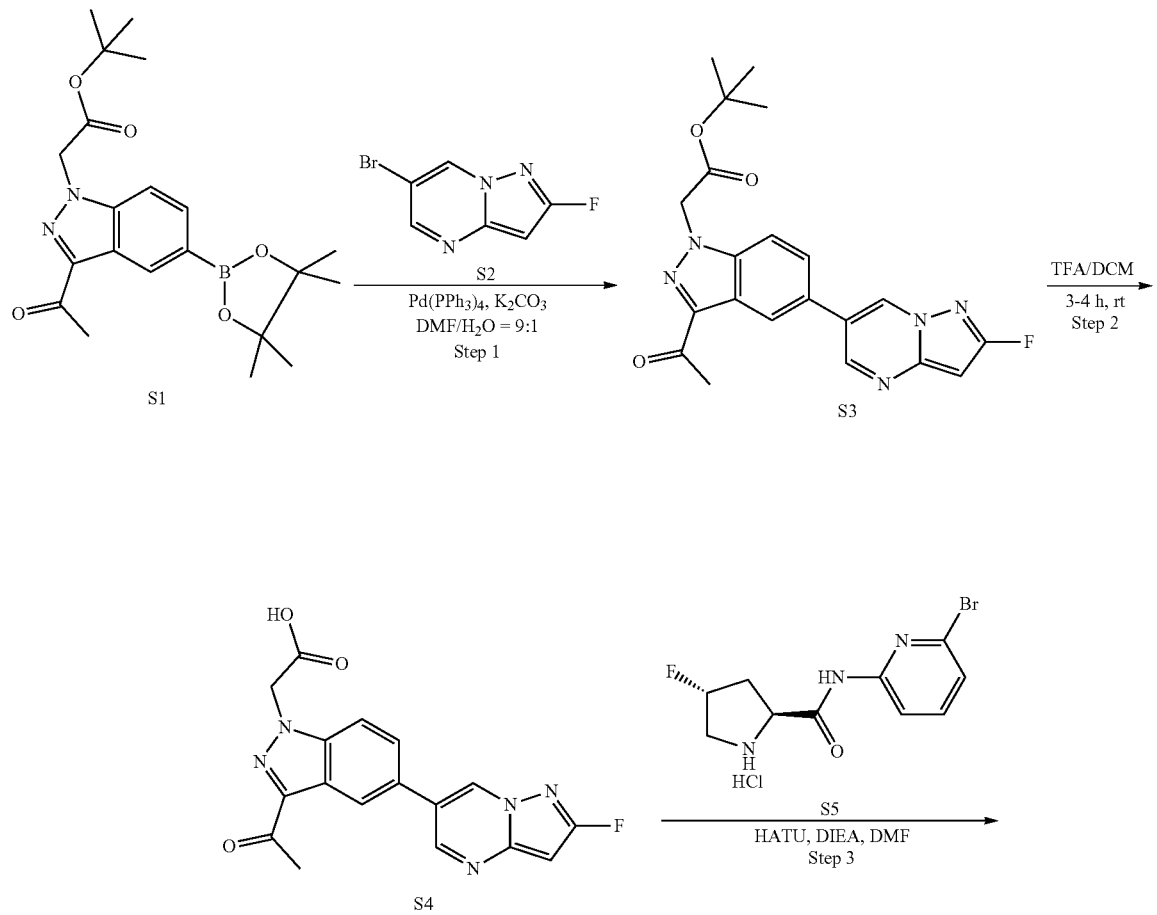

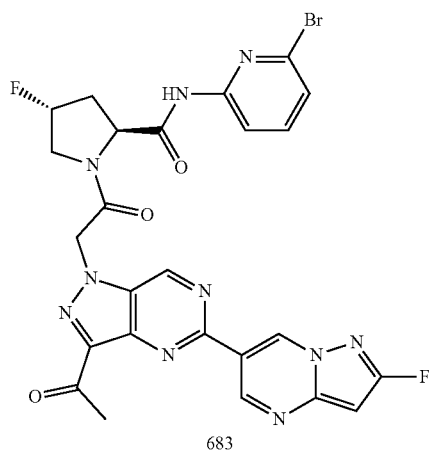

683

Step 1: tert-Butyl 2-(3-acetyl-5-(2-fluoropyrazolo[1,5-a]pyrimidin-6-yl)-1H-indazol-1-yl)acetate (S3)

To a solution of 6-bromo-2-fluoropyrazolo[1,5-a]pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-fluoropyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-fluoropyrazolo[1,5-a]pyrimidin-6-yl)-1H-indazol-1-yl)acetyl)-N-(6-bromopyridin-2-yl)-4-fluoropyrrolidine-2-carboxamide (683)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 683. $^1$H NMR (400 MHz, DMSO-d$_6$) δ 2.08-2.28 (m, 1H), 2.55-2.62 (m, 1H), 2.66 (s, 3H), 3.94-4.14 (m, 1H), 4.19-4.32 (m, 1H), 4.69 (t, J=8.5 Hz, 1H), 5.48-5.69 (m, 2H), 5.85 (d, J=17.3 Hz, 1H), 6.57 (d, J=4.9 Hz, 1H), 7.32 (d, J=7.7 Hz, 1H), 7.71 (t, J=8.0 Hz, 1H), 7.84-7.95 (m, 2H), 8.03 (d, J=8.2 Hz, 1H), 8.49 (d, J=1.5 Hz, 1H), 8.99 (d, J=2.3 Hz, 1H), 9.43 (d, J=2.2 Hz, 1H), 11.00 (s, 1H). $^{19}$F NMR (376 MHz, DMSO-d$_6$): δ −175.65, −120.78. LC (method A): t$_R$=2.09 min. LC/MS (EI) m/z: [M+H]$^+$ 623.

(2S,4R)-1-(2-(3-Acetyl-5-(2-(trifluoromethyl)pyrazolo[1,5-a]pyrimidin-6-yl)-1H-indazol-1-yl)acetyl)-N-(6-bromopyridin-2-yl)-4-fluoropyrrolidine-2-carboxamide (684)

Scheme 281

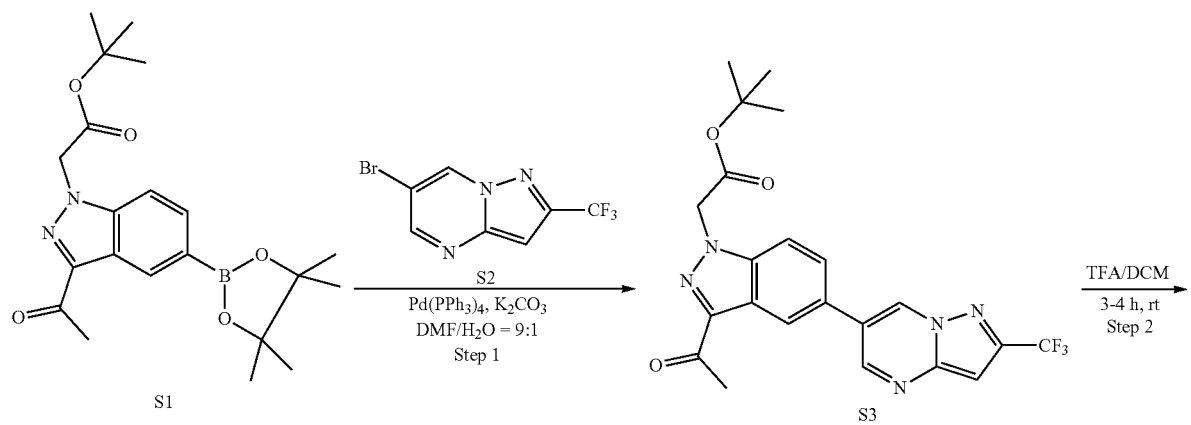

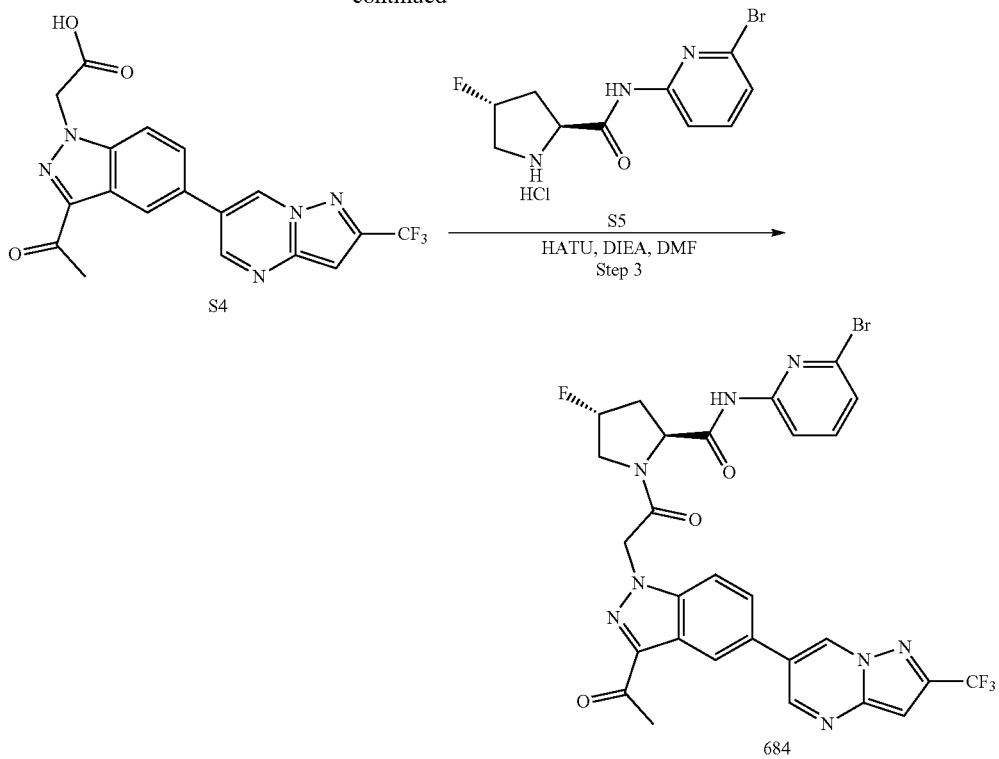

Step 1: tert-Butyl 2-(3-acetyl-5-(2-(trifluoromethyl)pyrazolo[1,5-a]pyrimidin-6-yl)-1H-indazol-1-yl)acetate (S3)

To a solution of 6-bromo-2-(trifluoromethyl)pyrazolo[1,5-a]pyrimidine (S2, 1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(trifluoromethyl)pyrazolo[1,5-a]pyrimidin-6-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(trifluoromethyl)pyrazolo[1,5-a]pyrimidin-6-yl)-1H-indazol-1-yl)acetyl)-N-(6-bromopyridin-2-yl)-4-fluoropyrrolidine-2-carboxamide (684)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 684. ¹H NMR (400 MHz, DMSO-d₆) δ 2.07-2.28 (m, 1H), 2.55-2.64 (m, 1H), 2.67 (s, 3H), 3.95-4.12 (m, 1H), 4.20-4.30 (m, 1H), 4.69 (dd, J=7.5, 9.4 Hz, 1H), 5.48-5.71 (m, 2H), 5.86 (d, J=17.3 Hz, 1H), 7.29-7.36 (m, 2H), 7.70 (d, J=8.0 Hz, 1H), 7.89 (d, J=8.8 Hz, 1H), 7.94-7.98 (m, 1H), 8.03 (d, J=8.2 Hz, 1H), 8.52-8.60 (m, 1H), 9.14 (d, J=2.2 Hz, 1H), 9.65 (d, J=2.1 Hz, 1H), 11.00 (s, 1H). ¹⁹F NMR (376 MHz, DMSO-d₆): δ −175.65, −60.94. LC (method A): $t_R$=2.43 min. LC/MS (EI) m/z: [M+H]⁺ 673.

(2S,4R)-1-(2-(3-Acetyl-5-(5-methylpyrazin-2-yl)-1H-indazol-1-yl)acetyl)-N-(6-bromopyridin-2-yl)-4-fluoropyrrolidine-2-carboxamide (465)

Scheme 282

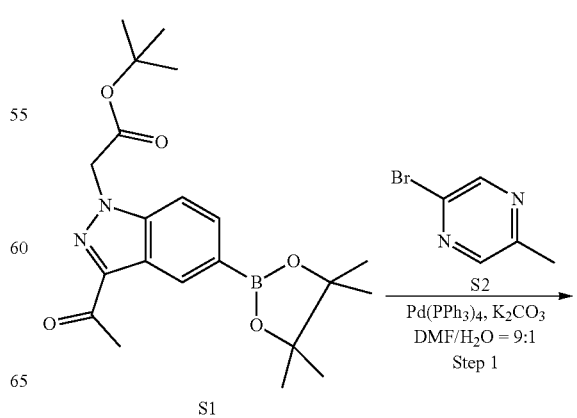

629

-continued

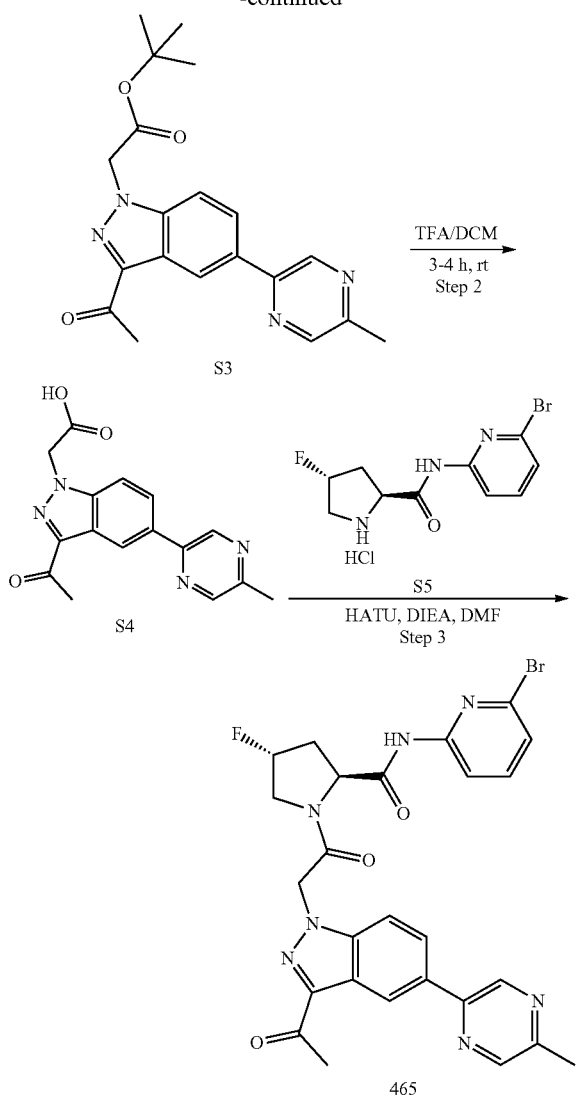

Step 1: tert-Butyl 2-(3-acetyl-5-(5-methylpyrazin-2-yl)-1H-indazol-1-yl)acetate (S3)

To a solution of 2-bromo-5-methylpyrazine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(5-methylpyrazin-2-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

630

Step 3: (2S,4R)-1-(2-(3-Acetyl-5-(5-methylpyrazin-2-yl)-1H-indazol-1-yl)acetyl)-N-(6-bromopyridin-2-yl)-4-fluoropyrrolidine-2-carboxamide (465)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 465. $^1$H NMR (400 MHz, DMSO-d$_6$) δ 2.04-2.27 (m, 1H), 2.55 (s, 3H), 2.57-2.62 (m, 1H), 2.65 (s, 3H), 3.96-4.15 (m, 1H), 4.17-4.33 (m, 1H), 4.63-4.74 (m, 1H), 5.48-5.68 (m, 2H), 5.83 (d, J=17.3 Hz, 1H), 7.31 (d, J=7.7 Hz, 1H), 7.71 (d, J=8.0 Hz, 1H), 7.82 (d, J=9.0 Hz, 1H), 8.02 (d, J=8.2 Hz, 1H), 8.22 (dd, J=1.7, 8.9 Hz, 1H), 8.63 (d, J=1.5 Hz, 1H), 8.87-8.92 (m, 1H), 9.14 (d, J=1.4 Hz, 1H), 10.99 (s, 1H). $^{19}$F NMR (376 MHz, DMSO-d$_6$): δ −175.66. LC (method A): t$_R$=1.86 min. LC/MS (EI) m/z: [M+H]$^+$ 580.

(2S,4R)-1-(2-(3-Acetyl-5-(5-methylpyrazin-2-yl)-1H-indazol-1-yl)acetyl)-N-(6-bromo-3-methylpyridin-2-yl)-4-fluoropyrrolidine-2-carboxamide (467)

Scheme 283

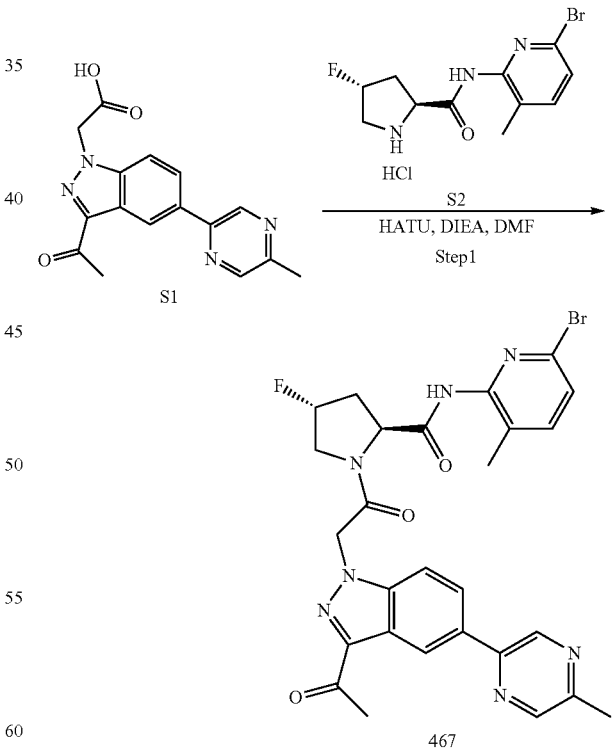

To a solution of compound S1 (1 equiv) in DMF (10 vol) at 0° C. under an atmosphere of nitrogen was added (2S, 4R)—N-(6-bromo-3-methylpyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 467. 1H NMR (400 MHz, DMSO-d₆) δ 2.00 (s, 3H), 2.12-2.30 (m, 1H), 2.55 (s, 3H), 2.58-2.70 (m, 4H), 3.93-4.12 (m, 1H), 4.25 (dd, J=12.5, 21.9 Hz, 1H), 4.61 (t, J=8.5 Hz, 1H), 5.48-5.66 (m, 2H), 5.84 (d, J=17.3 Hz, 1H), 7.42 (d, J=7.9 Hz, 1H), 7.60 (d, J=7.9 Hz, 1H), 7.79 (d, J=8.8 Hz, 1H), 8.21 (dd, J=1.6, 8.9 Hz, 1H), 8.64 (s, 1H), 8.90 (s, 1H), 9.15 (s, 1H), 10.45 (s, 1H). ¹⁹F NMR (376 MHz, DMSO-d₆): δ −176.03. LC (method A): t$_R$=1.69 min. LC/MS (EI) m/z: [M+H]⁺ 594.

(2S,4R)-1-(2-(3-Acetyl-5-(2-methylpyrimidin-4-yl)-1H-indazol-1-yl)acetyl)-N-(6-bromo-3-methylpyridin-2-yl)-4-fluoropyrrolidine-2-carboxamide (468)

Scheme 284

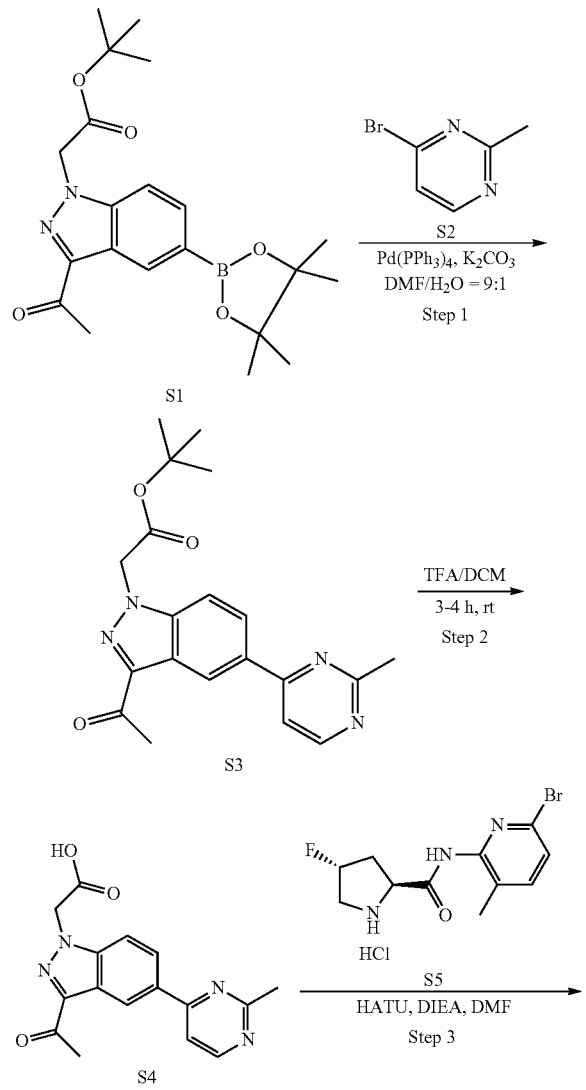

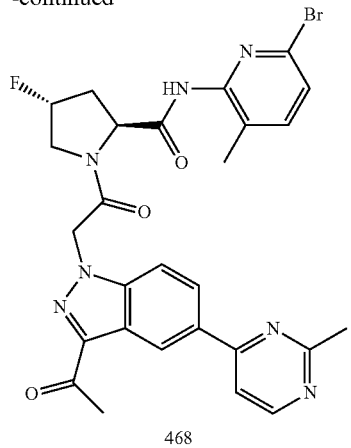

468

Step 1: tert-Butyl 2-(3-acetyl-5-(2-methylpyrimidin-4-yl)-1H-indazol-1-yl)acetate (S3)

To a solution of 4-bromo-2-methylpyrimidine (S2, 1 equiv) in DMF/H₂O (9:1, 10 vol) was added compound S1 (1 equiv), K₂CO₃ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-methylpyrimidin-4-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-methylpyrimidin-4-yl)-1H-indazol-1-yl)acetyl)-N-(6-bromo-3-methylpyridin-2-yl)-4-fluoropyrrolidine-2-carboxamide (468)

To a solution of compound S4 (1 equiv) in DMF (10 vol) at 0° C. under an atmosphere of nitrogen was added (2S,4R)—N-(6-bromo-3-methylpyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 468. ¹H NMR (400 MHz, DMSO-d₆) δ 2.00 (s, 3H), 2.12-2.30 (m, 1H), 2.58-2.70 (m, 4H), 2.72 (s, 3H), 3.93-4.12 (m, 1H), 4.18-4.32 (m, 1H), 4.61 (t, J=8.5 Hz, 1H), 5.48-5.66 (m, 2H), 5.85 (d, J=17.3 Hz, 1H), 7.42 (d, J=7.9 Hz, 1H), 7.60 (d, J=7.9 Hz, 1H), 7.81 (d, J=8.8 Hz, 1H), 7.92 (d, J=5.4 Hz, 1H), 8.26 (dd, J=1.6, 8.9 Hz, 1H), 8.75 (d, J=5.4 Hz, 1H), 9.01 (s, 1H), 10.45 (s, 1H). ¹⁹F NMR (376 MHz, DMSO-d₆): δ −176.01. LC (method A): t$_R$=1.57 min. LC/MS (EI) m/z: [M+H]⁺ 594.

633

(2S,4R)-1-(2-(3-Acetyl-5-(5,6-dihydro-4H-pyrrolo[1,2-b]pyrazol-3-yl)-1H-indazol-1-yl)acetyl)-N-(6-bromopyridin-2-yl)-4-fluoropyrrolidine-2-carboxamide (693)

Scheme 285

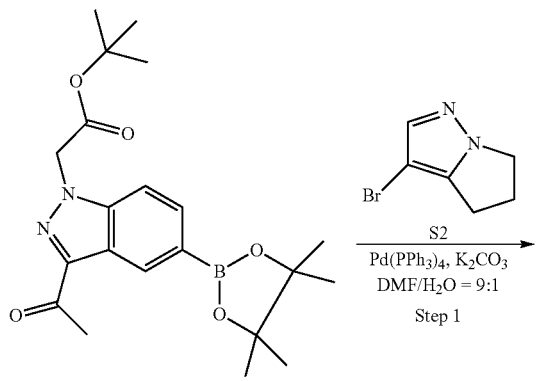

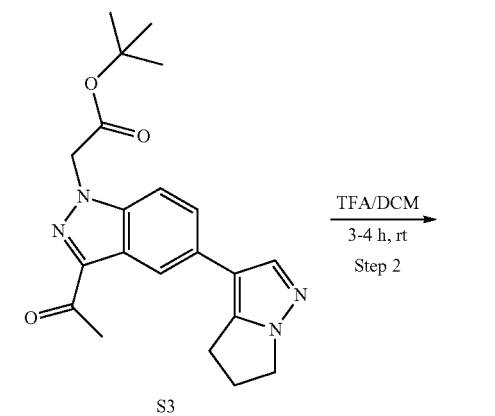

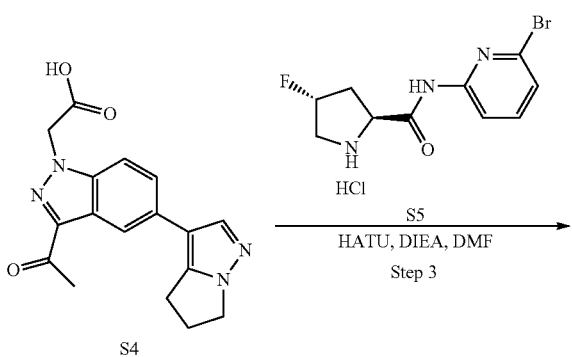

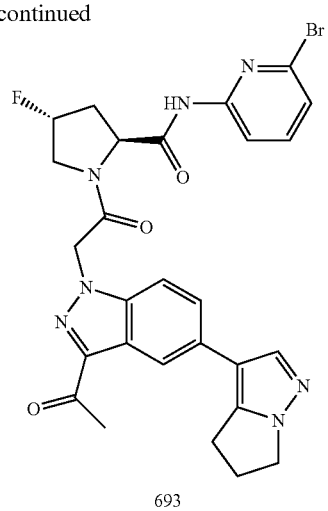

Step 1: tert-butyl 2-(3-acetyl-5-(5,6-dihydro-4H-pyrrolo[1,2-b]pyrazol-3-yl)-1H-indazol-1-yl)acetate (S3)

To a solution of 3-bromo-5,6-dihydro-4H-pyrrolo[1,2-b]pyrazole (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-acetyl-5-(5,6-dihydro-4H-pyrrolo[1,2-b]pyrazol-3-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(5,6-dihydro-4H-pyrrolo[1,2-b]pyrazol-3-yl)-1H-indazol-1-yl)acetyl)-N-(6-bromopyridin-2-yl)-4-fluoropyrrolidine-2-carboxamide (693)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 693. $^1$H NMR (400 MHz, DMSO-d$_6$) δ 2.05-2.26 (m, 1H), 2.54-2.70 (m, 6H), 3.11 (t, J=7.3 Hz, 2H), 3.94-4.14 (m, 3H), 4.22 (dd, J=12.5, 22.3 Hz, 1H), 4.67 (t, J=8.5 Hz, 1H), 5.46-5.65 (m, 2H), 5.77 (d, J=17.3 Hz, 1H), 7.33 (d, J=7.8 Hz, 1H), 7.62-7.75 (m, 3H), 7.90 (s, 1H), 8.03 (d, J=8.2 Hz, 1H), 8.20 (d, J=1.5 Hz, 1H), 10.99 (s, 1H). $^{19}$F NMR (376 MHz, DMSO-d$_6$): δ −175.70. LC (method A): t$_R$=1.81 min. LC/MS (EI) m/z: [M+H]$^+$ 594.

(2S,4R)-1-(2-(3-Acetyl-5-(quinazolin-6-yl)-1H-indazol-1-yl)acetyl)-N-(6-bromopyridin-2-yl)-4-fluoropyrrolidine-2-carboxamide (504)

Scheme 286

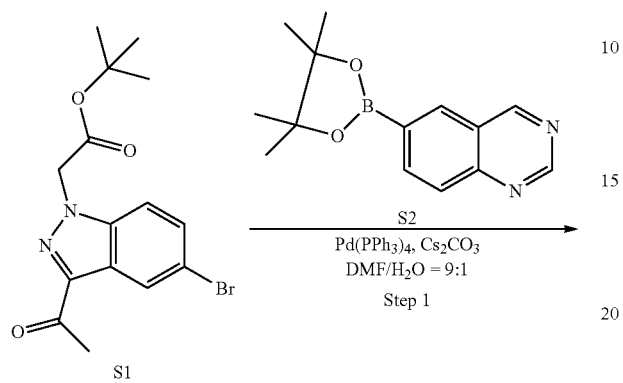

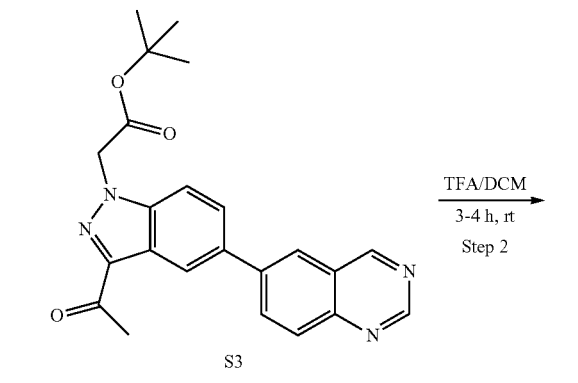

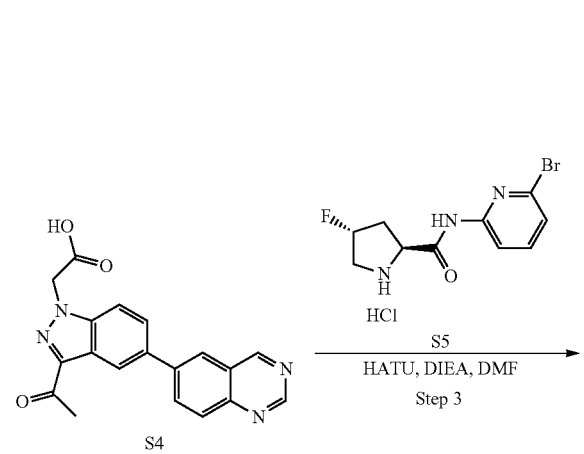

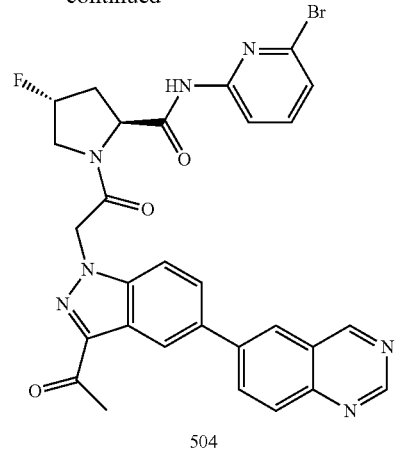

Step 1: tert-Butyl 2-(3-acetyl-5-(quinazolin-6-yl)-1H-indazol-1-yl)acetate (S3)

To a solution of 6-(4,4,5,5-tetramethyl-1,3,2-dioxaborolan-2-yl)quinazoline (S2, 1 equiv) in DMF/H$_2$O (9:1, 10 vol) was added compound S1 (1 equiv), Cs$_2$CO$_3$ (2 equiv), and tetrakis(triphenylphosphine)palladium (0.1 equiv). The reaction mixture was stirred at 90° C. for 3 h and then concentrated under reduced pressure. The remaining residue was purified by column chromatography on silica gel to give compound S3.

Step 2: 2-(3-Acetyl-5-(quinazolin-6-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(quinazolin-6-yl)-1H-indazol-1-yl)acetyl)-N-(6-bromopyridin-2-yl)-4-fluoropyrrolidine-2-carboxamide (504)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 504. $^1$H NMR (400 MHz, DMSO-d$_6$) δ 2.08-2.30 (m, 1H), 2.54-2.62 (m, 1H), 2.67 (s, 3H), 3.96-4.16 (m, 1H), 4.25 (dd, J=12.5, 22.4 Hz, 1H), 4.69 (dd, J=7.5, 9.5 Hz, 1H), 5.48-5.70 (m, 2H), 5.86 (d, J=17.3 Hz, 1H), 7.33 (d, J=7.7 Hz, 1H), 7.71 (t, J=8.0 Hz, 1H), 7.89 (d, J=8.8 Hz, 1H), 7.97-8.06 (m, 2H), 8.16 (s, 1H), 8.42 (dd, J=2.1, 8.8 Hz, 1H), 8.53 (d, J=2.2 Hz, 1H), 8.58 (d, J=1.7 Hz, 1H), 9.32 (s, 1H), 9.73 (s, 1H), 11.01 (s, 1H). $^{19}$F NMR (376 MHz, DMSO-d$_6$): δ −175.64. LC (method A): t$_R$=1.8 min. LC/MS (EI) m/z: [M+H]$^+$ 616.

(2S,4R)-1-(2-(3-Acetyl-5-(2-(S2,2,2-trifluoroethoxy)pyrimidin-5-yl)-1H-indazol-1-yl)acetyl)-N-(6-bromopyridin-2-yl)-4-fluoropyrrolidine-2-carboxamide (505)

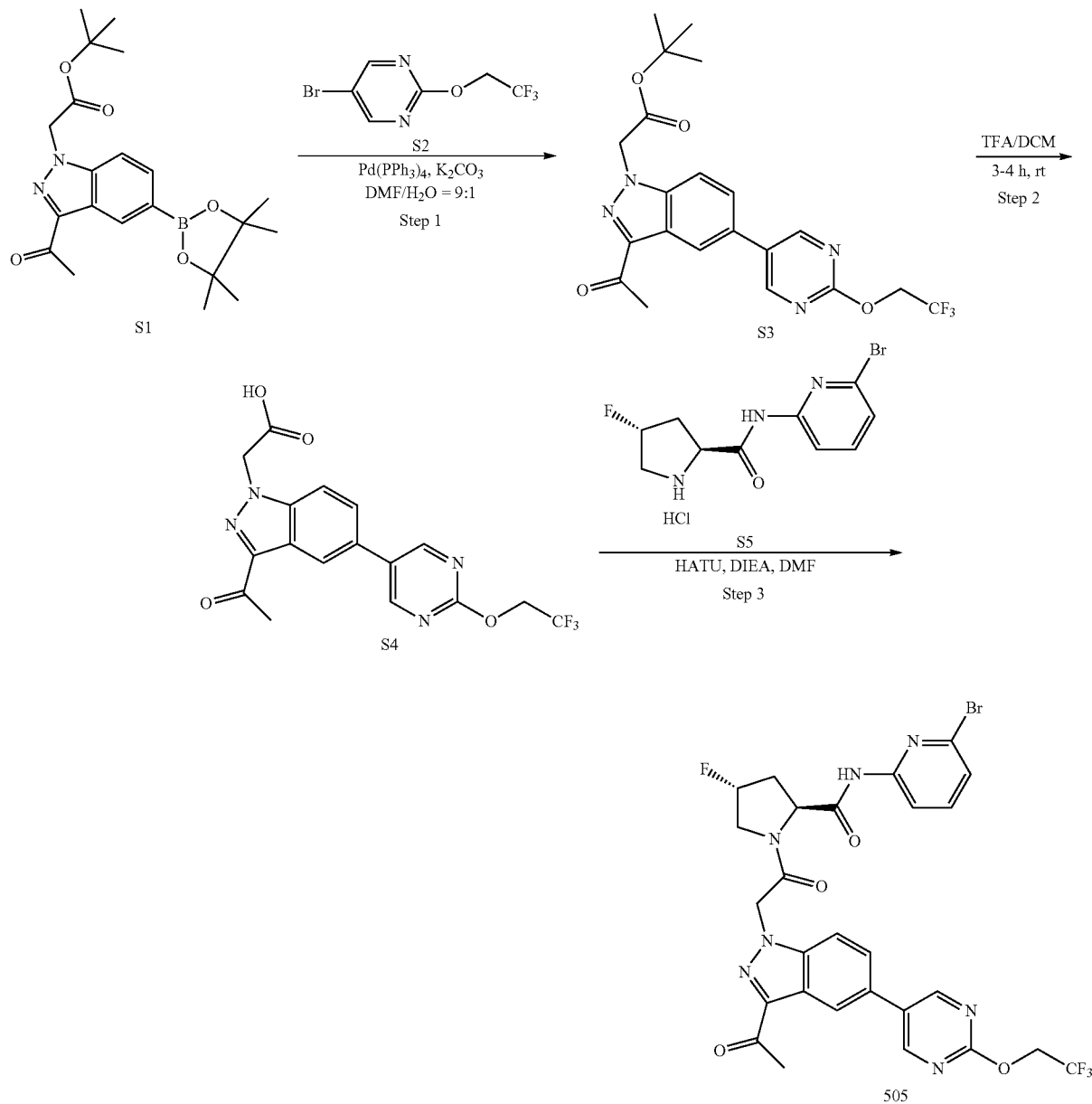

Step 1: tert-Butyl 2-(3-acetyl-5-(2-(S2,2,2-trifluoroethoxy)pyrimidin-5-yl)-1H-indazol-1-yl)acetate (S3)

To a solution of 5-bromo-2-(S2,2,2-trifluoroethoxy)pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(S2,2,2-trifluoroethoxy)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(S2,2,2-trifluoroethoxy)pyrimidin-5-yl)-1H-indazol-1-yl)acetyl)-N-(6-bromopyridin-2-yl)-4-fluoropyrrolidine-2-carboxamide (505)

To a solution of compound S4 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 505. $^1$H NMR (400 MHz, DMSO-$d_6$) δ 2.06-2.26 (m, 1H), 2.53-2.63 (m, 1H), 2.64 (s, 3H), 3.93-4.11 (m, 1H), 4.16-4.34 (m, 1H), 4.67 (t, J=8.5 Hz, 1H), 5.11 (q, J=8.9 Hz, 2H), 5.47-5.69 (m, 2H), 5.83 (d, J=17.3 Hz, 1H), 7.32 (d, J=7.7 Hz, 1H), 7.70 (t, J=8.0 Hz, 1H), 7.84 (d, J=1.2 Hz, 2H), 8.02 (d, J=8.2 Hz, 1H), 8.41 (s, 1H), 9.02 (s, 2H), 10.99 (s, 1H). $^{19}$F NMR (376 MHz, DMSO-$d_6$): δ -175.67, -72.42. LC (method A): $t_R$=2.3 min. LC/MS (EI) m/z: $[M+H]^+$ 664.

(2S,4R)-1-(2-(3-Acetyl-5-(2-(methylsulfonyl)pyrimidin-5-yl)-1H-indazol-1-yl)acetyl)-N-(6-bromopyridin-2-yl)-4-fluoropyrrolidine-2-carboxamide (521)

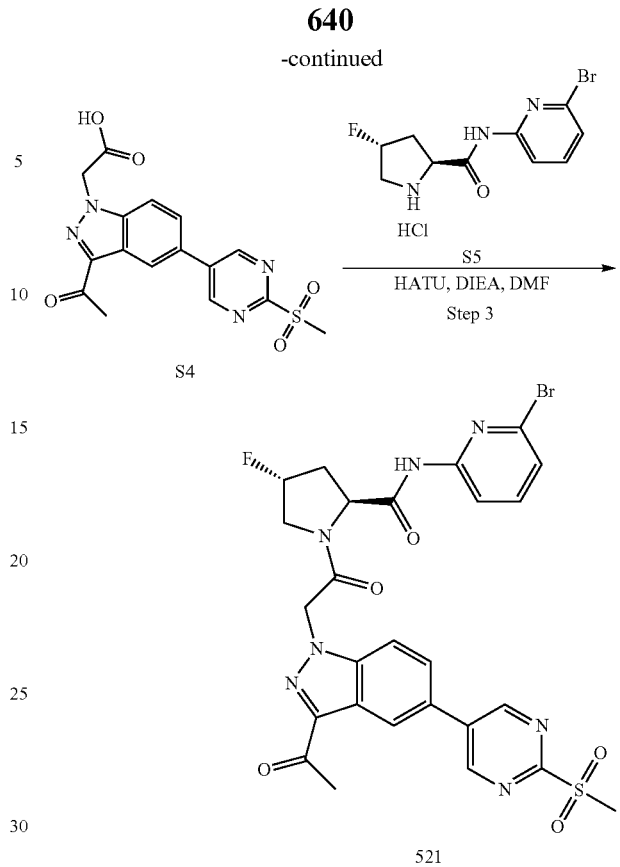

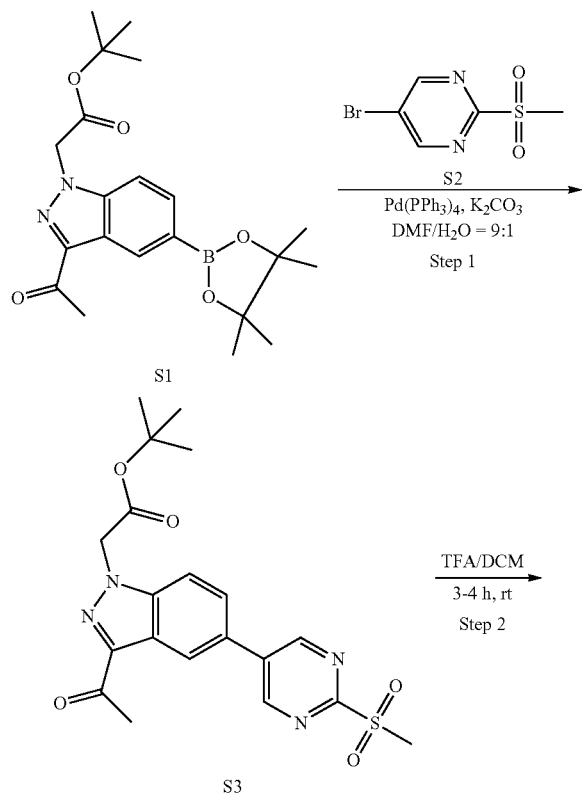

Scheme 208

Step 1: tert-Butyl 2-(3-acetyl-5-(2-(methylsulfonyl)pyrimidin-5-yl)-1H-indazol-1-yl)acetate (S3)

To a solution of 5-bromo-2-(methylsulfonyl)pyrimidine (S2, 1 equiv) in DMF/$H_2O$ (9:1, 10 vol) was added compound S1 (1 equiv), $K_2CO_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(methylsulfonyl)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(methylsulfonyl)pyrimidin-5-yl)-1H-indazol-1-yl)acetyl)-N-(6-bromopyridin-2-yl)-4-fluoropyrrolidine-2-carboxamide (521)

To a solution of compound S4 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 521. $^1$H NMR (400 MHz, DMSO-$d_6$) δ 2.05-2.29 (m, 1H), 2.60 (d, J=24.9 Hz, 1H), 2.66 (s, 3H), 3.45 (s, 3H), 3.95-4.11 (m, 1H), 4.24 (dd, J=12.5, 22.1 Hz, 1H), 4.68 (dd, J=7.5, 9.5 Hz, 1H), 5.47-5.73 (m, 2H), 5.86 (d, J=17.3 Hz, 1H), 7.32 (d, J=7.7 Hz, 1H), 7.70 (t, J=8.0 Hz, 1H), 7.90-8.09 (m, 3H), 8.54-8.64 (m, 1H), 9.43 (s, 2H), 10.99 (s, 1H). $^{19}$F NMR (376 MHz, DMSO-$d_6$): δ −175.66. LC (method A): $t_R$=1.71 min. LC/MS (EI) m/z: [M+H]$^+$ 644.

(2S,4R)-1-(2-(5-(2-(1H-Pyrazol-1-yl)pyrimidin-5-yl)-3-acetyl-1H-indazol-1-yl)acetyl)-N-(6-bromopyridin-2-yl)-4-fluoropyrrolidine-2-carboxamide (522)

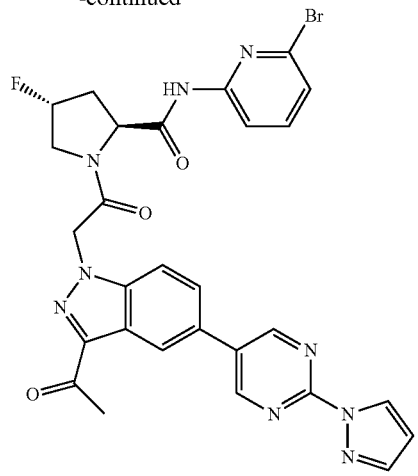

522

Scheme 289

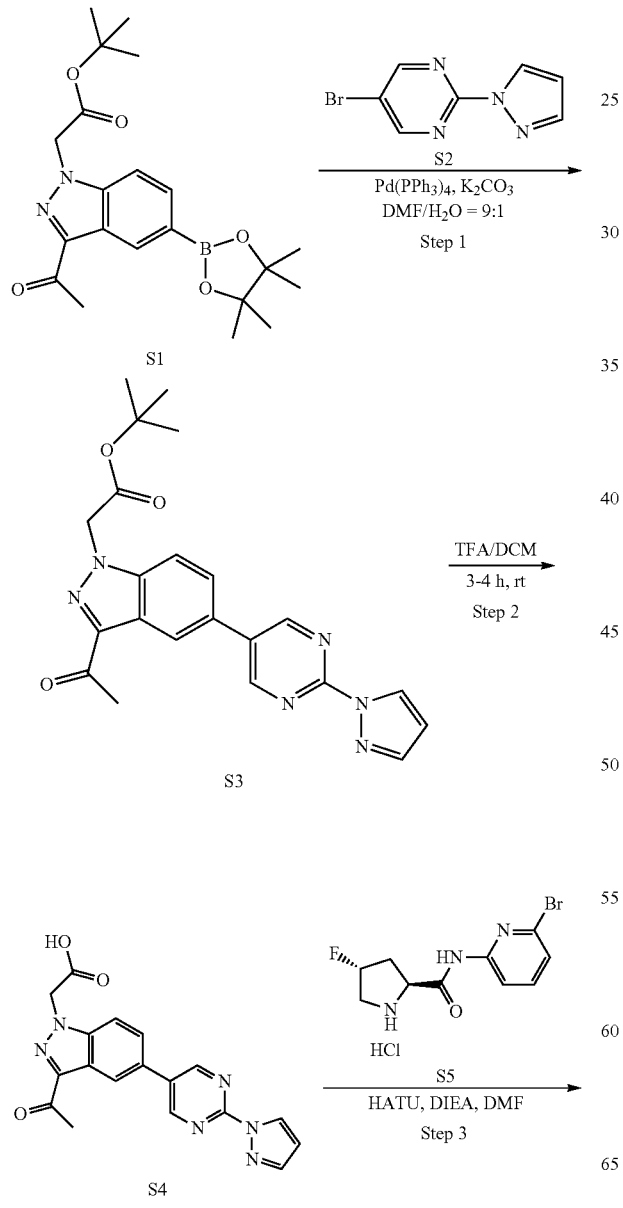

Step 1: tert-Butyl 2-(5-(2-(1H-pyrazol-1-yl)pyrimidin-5-yl)-3-acetyl-1H-indazol-1-yl)acetate (S3)

To a solution of 5-bromo-2-(1H-pyrazol-1-yl)pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(5-(2-(1H-Pyrazol-1-yl)pyrimidin-5-yl)-3-acetyl-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(5-(2-(1H-Pyrazol-1-yl)pyrimidin-5-yl)-3-acetyl-1H-indazol-1-yl)acetyl)-N-(6-bromopyridin-2-yl)-4-fluoropyrrolidine-2-carboxamide (522)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 522. $^1$H NMR (400 MHz, DMSO-$d_6$) δ 2.05-2.28 (m, 1H), 2.55-2.63 (m, 1H), 2.66 (s, 3H), 3.97-4.13 (m, 1H), 4.24 (dd, J=12.7, 22.0 Hz, 1H), 4.65-4.75 (m, 1H), 5.46-5.71 (m, 2H), 5.85 (d, J=17.3 Hz, 1H), 6.63-6.70 (m, 1H), 7.32 (d, J=7.7 Hz, 1H), 7.71 (t, J=8.0 Hz, 1H), 7.87-7.96 (m, 3H), 8.03 (d, J=8.2 Hz, 1H), 8.50 (d, J=1.6 Hz, 1H), 8.71 (d, J=2.6 Hz, 1H), 9.20 (s, 2H), 10.99 (s, 1H). $^{19}$F NMR (376 MHz, DMSO-$d_6$): δ −175.65. LC (method A): $t_R$=1.9 min. LC/MS (EI) m/z: [M+H]$^+$ 632.

(2S,4R)-1-(2-(3-Acetyl-5-(1-(pyrimidin-2-yl)-1H-pyrazol-4-yl)-1H-indazol-1-yl)acetyl)-N-(6-bromopyridin-2-yl)-4-fluoropyrrolidine-2-carboxamide (696)

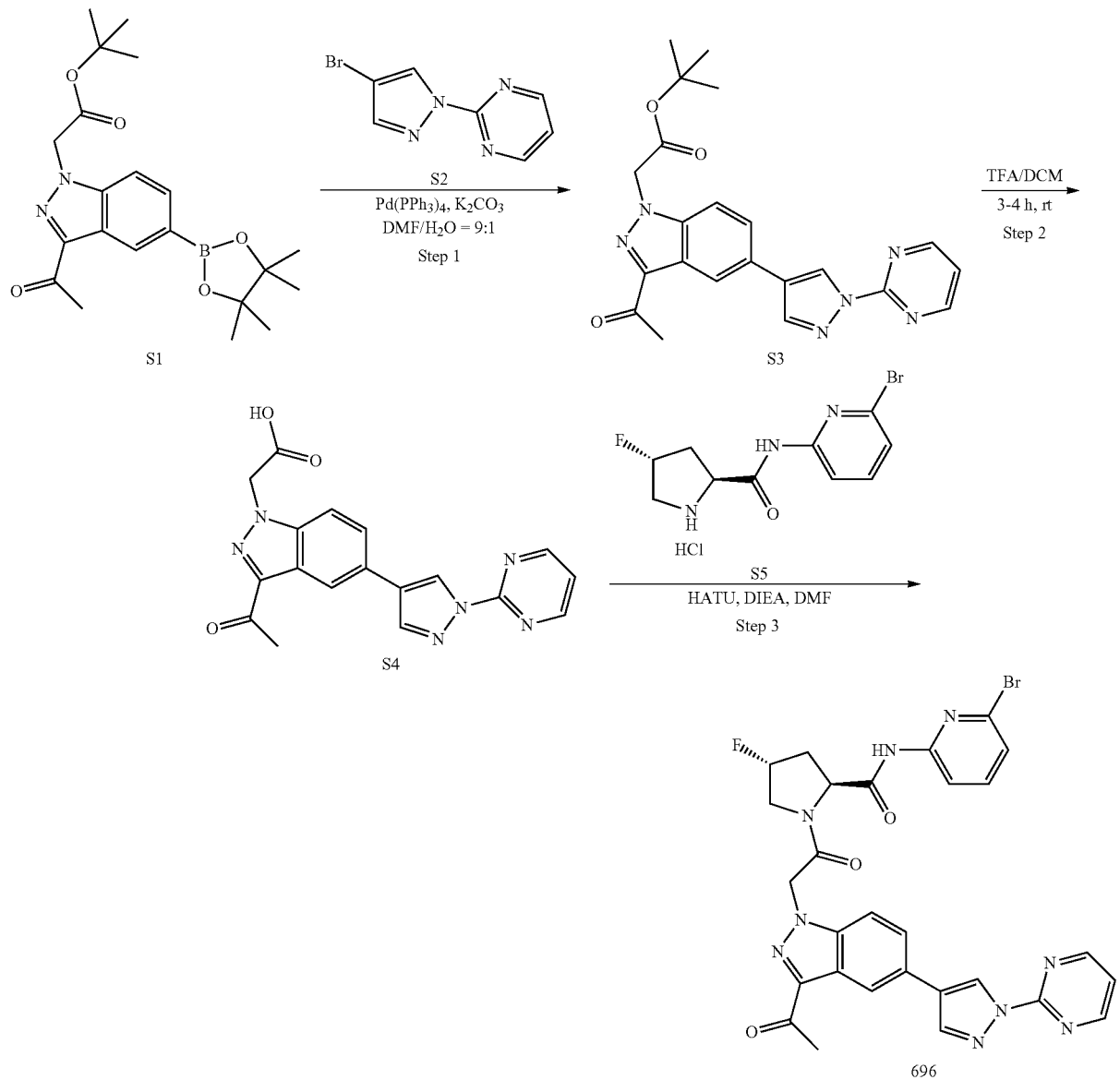

Step 1: tert-Butyl 2-(3-acetyl-5-(1-(pyrimidin-2-yl)-1H-pyrazol-4-yl)-1H-indazol-1-yl)acetate (S3)

To a solution of 2-(4-bromo-1H-pyrazol-1-yl)pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(1-(pyrimidin-2-yl)-1H-pyrazol-4-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(1-(pyrimidin-2-yl)-1H-pyrazol-4-yl)-1H-indazol-1-yl)acetyl)-N-(6-bromopyridin-2-yl)-4-fluoropyrrolidine-2-carboxamide (696)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 696. $^1$H NMR (400 MHz, DMSO-$d_6$) δ 1.96-2.26 (m, 1H), 2.54-2.62 (m, 1H), 2.64 (s, 3H), 3.95-4.13 (m, 1H), 4.15-4.32 (m, 1H), 4.68 (dd, J=7.5, 9.5 Hz, 1H), 5.45-5.65 (m, 2H), 5.80 (d, J=17.3 Hz, 1H), 7.32 (d, J=7.7 Hz, 1H), 7.51 (t, J=4.8 Hz, 1H), 7.67-7.78 (m, 2H), 7.94 (dd, J=1.6, 8.8 Hz, 1H), 8.03 (d, J=8.2 Hz, 1H), 8.36-8.48 (m, 2H), 8.91 (d, J=4.8 Hz, 2H), 9.12 (s, 1H), 10.99 (s, 1H). $^{19}$F NMR (376 MHz, DMSO-$d_6$): δ −175.65. LC (method A): $t_R$=1.76 min. LC/MS (EI) m/z: [M+H]$^+$ 632.

methyl 2-(5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate (540)

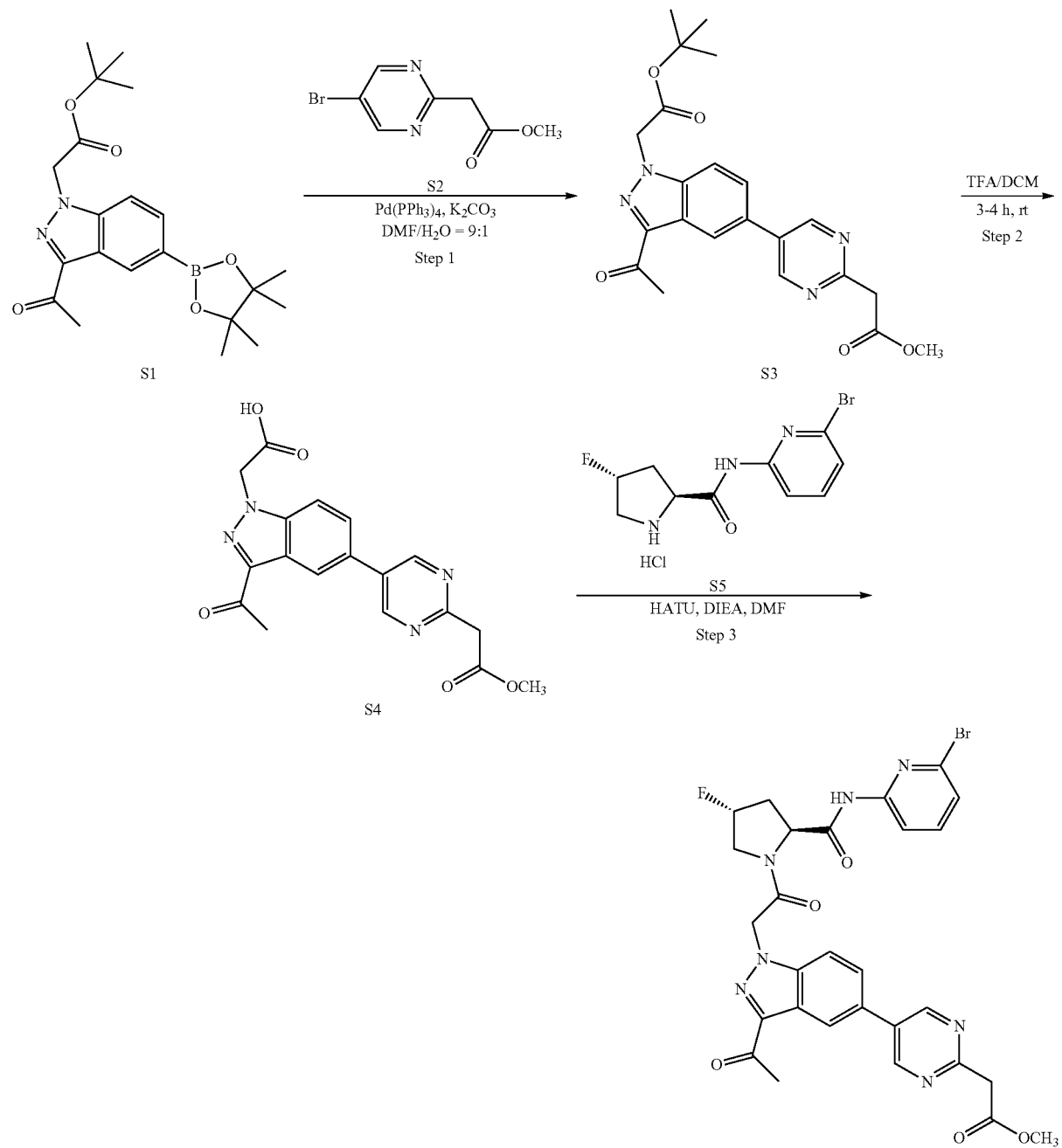

Scheme 291

Step 1: tert-Butyl 2-(3-acetyl-5-(2-(2-methoxy-2-oxoethyl)pyrimidin-5-yl)-1H-indazol-1-yl)acetate (S3)

To a solution of methyl 2-(5-bromopyrimidin-2-yl)acetate (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(2-methoxy-2-oxoethyl)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: Methyl 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate (540)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 540. $^1$H NMR (400 MHz, DMSO-d$_6$) δ 2.06-2.28 (m, 1H), 2.54-2.61 (m, 1H), 2.66 (s, 3H), 3.68 (s, 3H), 4.07 (s, 3H), 4.24 (dd, J=12.5, 22.1 Hz, 1H), 4.68 (dd, J=7.6, 9.4 Hz, 1H), 5.45-5.71 (m, 2H), 5.85 (d, J=17.3 Hz, 1H), 7.33 (d, J=7.7 Hz, 1H), 7.71 (t, J=8.0 Hz, 1H), 7.85-7.93 (m, 2H), 8.03 (d, J=8.2 Hz, 1H), 8.46 (t, J=1.2 Hz, 1H), 9.12 (s, 2H), 11.00 (s, 1H). $^{19}$F NMR (376 MHz, DMSO-d$_6$): δ −175.67. LC (method A): t$_R$=1.77 min. LC/MS (EI) m/z: [M+H]$^+$ 638.

(2S,4R)-1-(2-(3-Acetyl-5-(2-(methylthio)pyrimidin-5-yl)-1H-indazol-1-yl)acetyl)-N-(6-bromopyridin-2-yl)-4-fluoropyrrolidine-2-carboxamide (531)

Scheme 292

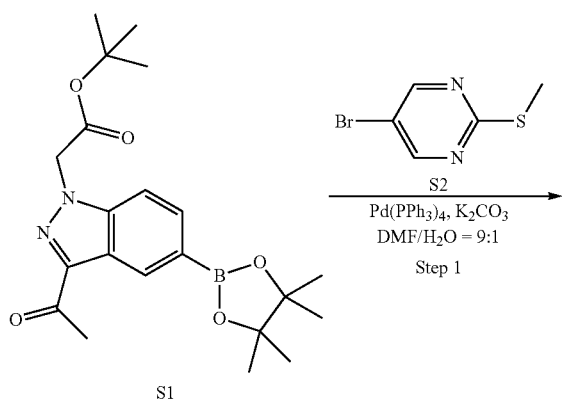

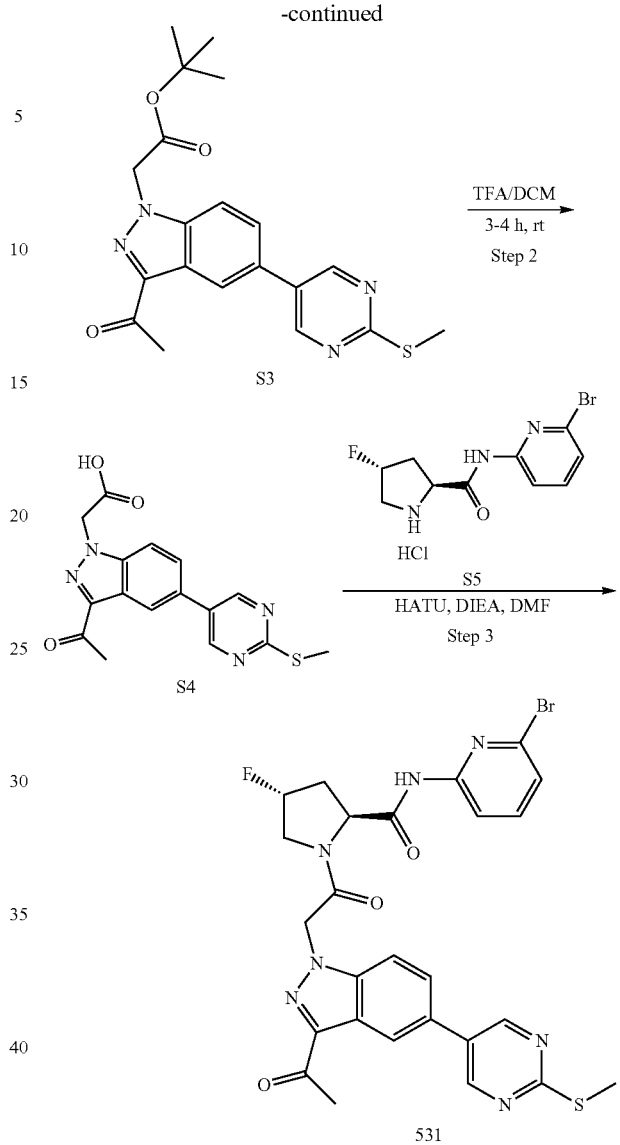

Step 1: tert-Butyl 2-(3-acetyl-5-(2-(methylthio)pyrimidin-5-yl)-1H-indazol-1-yl)acetate (S3)

To a solution of methyl 5-bromo-2-(methylthio)pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(methylthio)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

649

Step 3: (2S,4R)-1-(2-(3-Acetyl-5-(2-(methylthio) pyrimidin-5-yl)-1H-indazol-1-yl)acetyl)-N-(6-bromopyridin-2-yl)-4-fluoropyrrolidine-2-carboxamide (531)

To a solution of compound S4 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 531. $^1$H NMR (400 MHz, DMSO-$d_6$) δ 2.05-2.25 (m, 1H), 2.54-2.61 (m, 4H), 2.65 (s, 3H), 3.96-4.12 (m, 1H), 4.18-4.33 (m, 1H), 4.68 (dd, J=7.6, 9.4 Hz, 1H), 5.44-5.69 (m, 2H), 5.84 (d, J=17.3 Hz, 1H), 7.32 (d, J=7.6 Hz, 1H), 7.71 (t, J=8.0 Hz, 1H), 7.85 (d, J=1.2 Hz, 2H), 8.03 (d, J=8.2 Hz, 1H), 8.42 (d, J=1.3 Hz, 1H), 8.99 (s, 2H), 10.99 (s, 1H). $^{19}$F NMR (376 MHz, DMSO-$d_6$): δ −175.67. LC (method A): $t_R$=2.17 min. LC/MS (EI) m/z: [M+H]$^+$ 612.

2-(5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetic acid (533)

650

To a solution of methyl 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate (540, 1 equiv) in THF/$H_2O$ (3:1, 10 vol) was added LiOH (2.1 equiv) and the reaction mixture was stirred at room temperature for 5 h and then concentrated under reduced pressure. The remaining residue was neutralize using 2N HCl, solid was filtered and purified by column chromatography on silica gel to give compound 533. $^1$H NMR (400 MHz, DMSO-$d_6$) δ 2.07-2.27 (m, 1H), 2.56-2.63 (m, 1H), 2.66 (s, 3H), 3.93-4.14 (m, 3H), 4.24 (dd, J=12.6, 22.3 Hz, 1H), 4.64-4.75 (m, 1H), 5.47-5.71 (m, 2H), 5.85 (d, J=17.3 Hz, 1H), 7.33 (d, J=7.7 Hz, 1H), 7.71 (t, J=8.0 Hz, 1H), 7.85-7.94 (m, 2H), 8.03 (d, J=8.2 Hz, 1H), 8.43-8.48 (m, 1H), 9.11 (s, 2H), 11.00 (s, 1H), 12.57 (s, 1H). $^{19}$F NMR (376 MHz, DMSO-$d_6$): δ −175.67. LC (method A): $t_R$=1.5 min. LC/MS (EI) m/z: [M+H]$^+$ 624.

(2S,4R)-1-(2-(3-Acetyl-5-(2-(2-amino-2-oxoethyl) pyrimidin-5-yl)-1H-indazol-1-yl)acetyl)-N-(6-bromopyridin-2-yl)-4-fluoropyrrolidine-2-carboxamide (532)

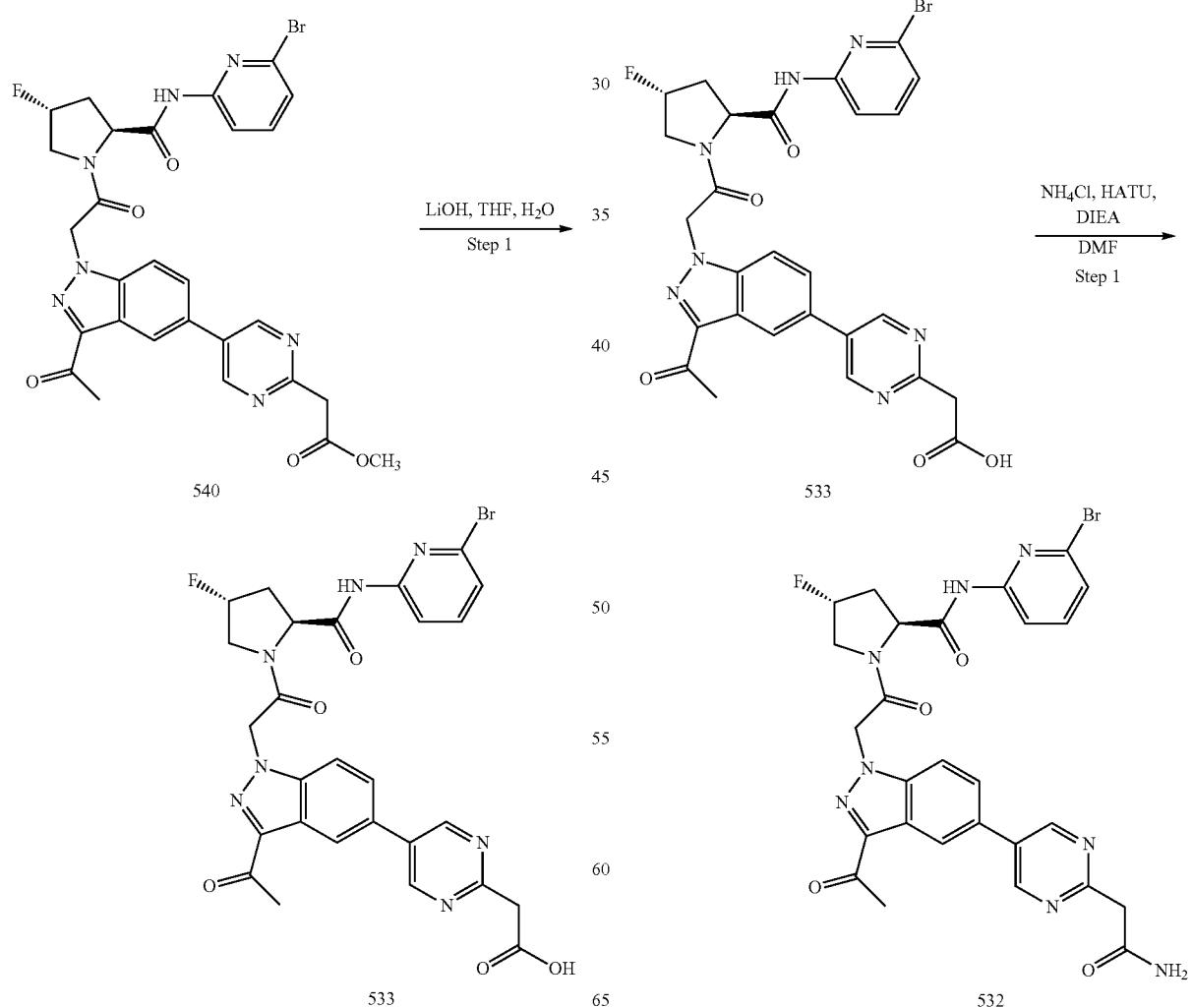

To a solution of compound 533 (1 equiv) in DMF (10 vol) at 0° C. under an atmosphere of nitrogen was added NH$_4$Cl (5 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 532. $^1$H NMR (400 MHz, DMSO-d$_6$) δ 1.97-2.19 (m, 1H), 2.47-2.57 (m, 1H), 2.58 (s, 3H), 3.73 (s, 2H), 3.86-4.07 (m, 1H), 4.16 (dd, J=12.5, 22.2 Hz, 1H), 4.60 (t, J=8.5 Hz, 1H), 5.40-5.63 (m, 2H), 5.77 (d, J=17.3 Hz, 1H), 6.96 (s, 1H), 7.25 (d, J=7.7 Hz, 1H), 7.46 (s, 1H), 7.63 (t, J=8.0 Hz, 1H), 7.78-7.84 (m, 2H), 7.95 (d, J=8.2 Hz, 1H), 8.37 (t, J=1.3 Hz, 1H), 9.00 (s, 2H), 10.92 (s, 1H). $^{19}$F NMR (376 MHz, DMSO-d$_6$): δ −175.67. LC (method A): t$_R$=1.36 min. LC/MS (EI) m/z: [M+H]$^+$ 623.

Ethyl 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate (537)

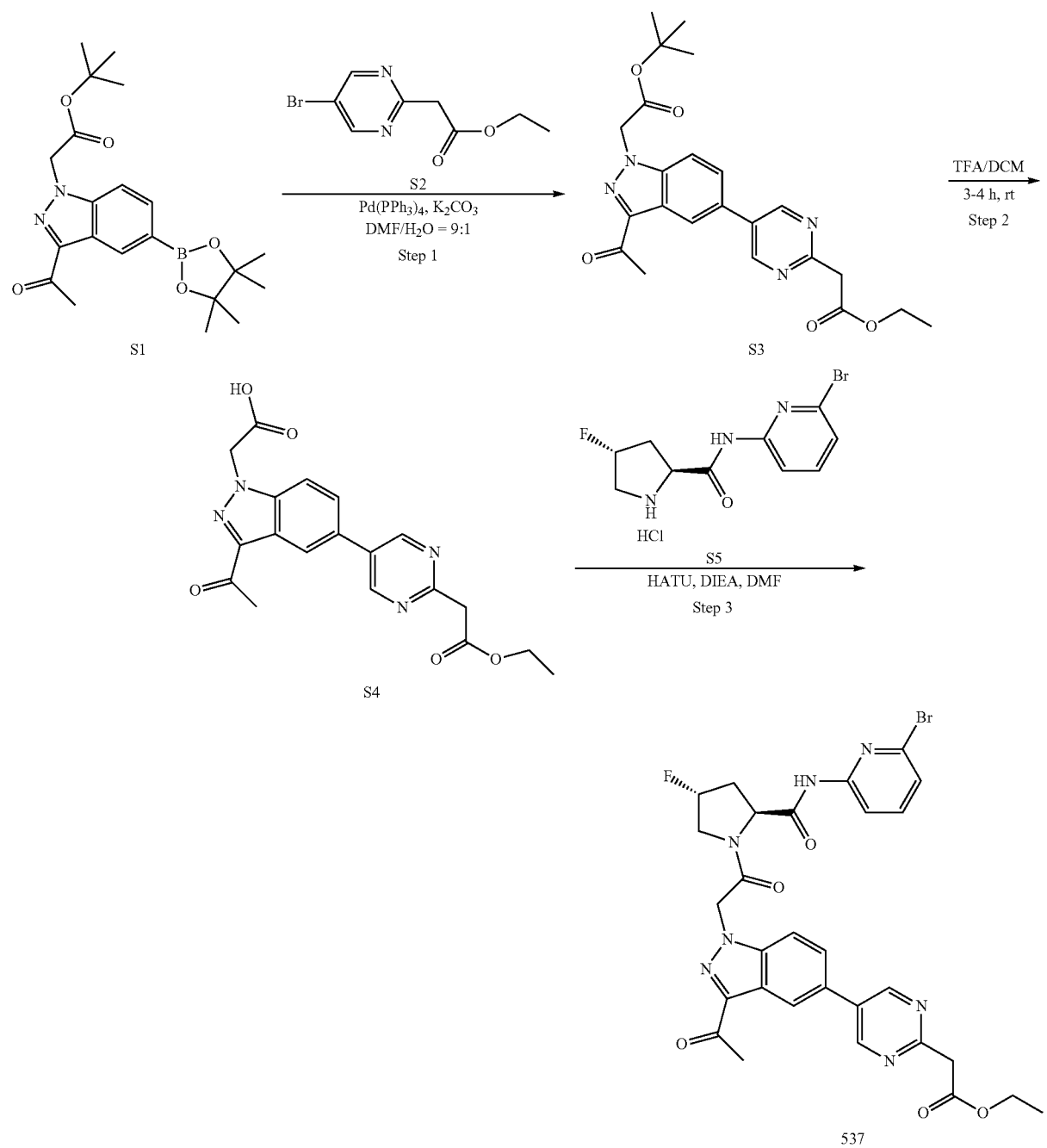

Scheme 295

Step 1: tert-Butyl 2-(3-acetyl-5-(2-(2-ethoxy-2-oxo-ethyl)pyrimidin-5-yl)-1H-indazol-1-yl)acetate (S3)

To a solution of ethyl 2-(5-bromopyrimidin-2-yl)acetate (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(2-ethoxy-2-oxoethyl)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: Ethyl 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate (537)

To a solution of compound S4 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 537. $^1$H NMR (400 MHz, DMSO-d$_6$) δ 1.21 (t, J=7.1 Hz, 3H), 2.07-2.30 (m, 1H), 2.54-2.63 (m, 1H), 2.65 (s, 3H), 3.93-4.30 (m, 6H), 4.68 (t, J=8.5 Hz, 1H), 5.47-5.70 (m, 2H), 5.84 (d, J=17.3 Hz, 1H), 7.32 (d, J=7.7 Hz, 1H), 7.70 (t, J=8.0 Hz, 1H), 7.79-7.93 (m, 2H), 8.02 (d, J=8.2 Hz, 1H), 8.45 (d, J=1.5 Hz, 1H), 9.12 (s, 2H), 10.99 (s, 1H). $^{19}$F NMR (376 MHz, DMSO-d$_6$): δ −175.66. LC (method A): t$_R$=1.93 min. LC/MS (EI) m/z: [M+H]$^+$ 652.

ethyl 2-(5-(3-Acetyl-1-(2-((2S,4R)-2-((6-bromo-5-fluoropyridin-2-yl)carbamoyl)-4-fluoropyrrolidin-1-yl)-2-oxoethyl)-1H-indazol-5-yl)pyrimidin-2-yl) acetate (539)

Scheme 296

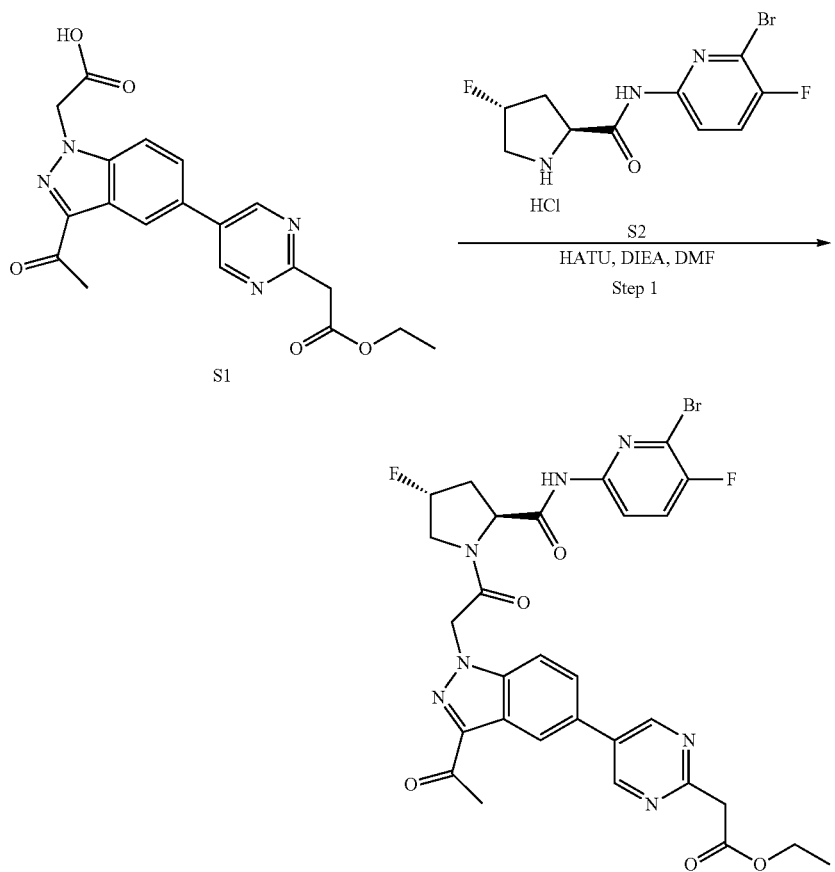

To a solution of compound S1 (1 equiv) in DMF (10 vol) at 0° C. under an atmosphere of nitrogen was added (2S,4R)—N-(6-bromo-5-fluoropyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 296. $^1$H NMR (400 MHz, DMSO-$d_6$) δ 1.21 (t, J=7.1 Hz, 3H), 2.06-2.27 (m, 1H), 2.53-2.63 (m, 1H), 2.65 (s, 3H), 3.95-4.28 (m, 6H), 4.66 (dd, J=7.5, 9.5 Hz, 1H), 5.46-5.69 (m, 2H), 5.84 (d, J=17.3 Hz, 1H), 7.92-7.81 (m, 3H), 8.04 (dd, J=3.3, 8.9 Hz, 1H), 8.45 (s, 1H), 9.12 (s, 2H), 11.07 (s, 1H). $^{19}$F NMR (376 MHz, DMSO-$d_6$): δ −175.70, −120.36. LC (method A): $t_R$=2.00 min. LC/MS (EI) m/z: [M+H]$^+$ 670.

To a solution of compound S1 (1 equiv) in DMF (10 vol) at 0° C. under an atmosphere of nitrogen was added (2S,4R)—N-(6-bromo-3-methylpyridin-2-yl)-4-fluoropyrrolidine-2-carboxamide hydrochloride (S2, 1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous $Na_2SO_4$, filtered, and then concentrated. The residue was purified by column chromatography on silica gel (MeOH/DCM) to give compound 540. $^1$H NMR (400 MHz, DMSO-$d_6$) δ 1.21 (t, J=7.1 Hz, 3H), 2.00 (s, 3H), 2.12-2.30 (m, 1H), 2.55-2.71 (m, 4H), 3.93-4.32 (m, 6H), 4.61 (t, J=8.5 Hz, 1H), 5.47-5.68 (m, 2H), 5.85 (d, J=17.3 Hz, 1H), 7.42 (d, J=7.9 Hz, 1H), 7.60 (d, J=8.0 Hz, 1H), 7.81-7.91 (m, 2H), 8.47 (d, J=1.6 Hz, 1H), 9.12 (s, 2H), 10.45 (s, 1H). $^{19}$F NMR (376 MHz, DMSO-$d_6$): δ −175.03. LC (method A): $t_R$=1.77 min. LC/MS (EI) m/z: [M+H]$^+$ 666.

Ethyl 2-(5-(3-acetyl-1-(2-((2S,4R)-2-((6-bromo-3-methylpyridin-2-yl)carbamoyl)-4-fluoropyrrolidin-1-yl)-2-oxoethyl)-1H-indazol-5-yl)pyrimidin-2-yl)acetate (540)

Scheme 297

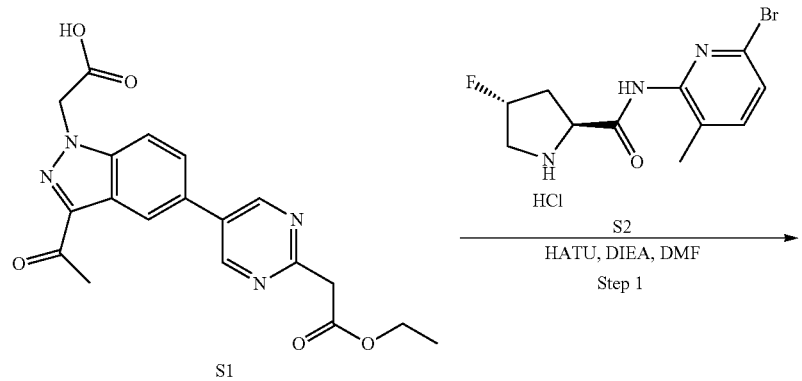

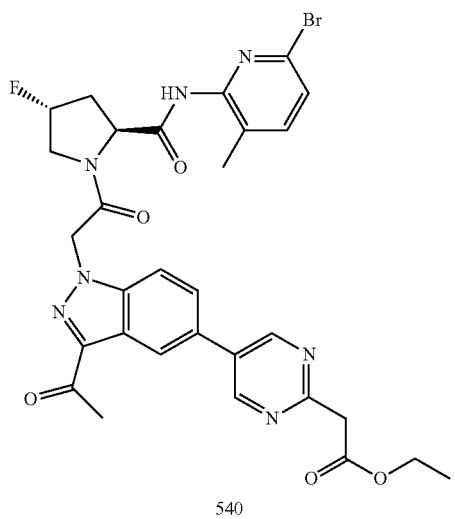

540

(2S,4R)-1-(2-(3-aAetyl-5-(2-(pyridin-4-yloxy)pyrimidin-5-yl)-1H-indazol-1-yl)acetyl)-N-(6-bromopyridin-2-yl)-4-fluoropyrrolidine-2-carboxamide (554)
Scheme 298
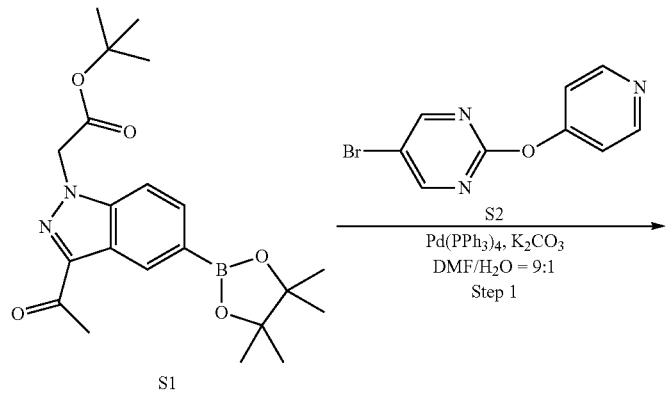
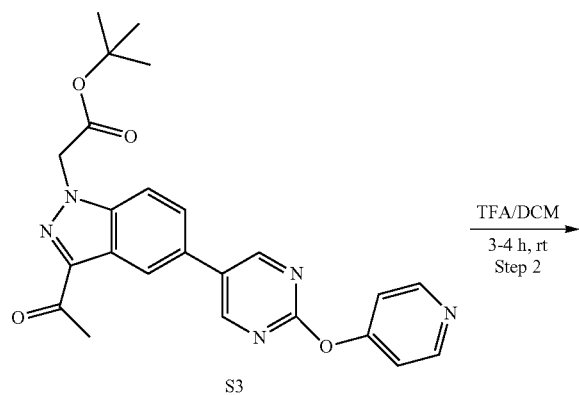
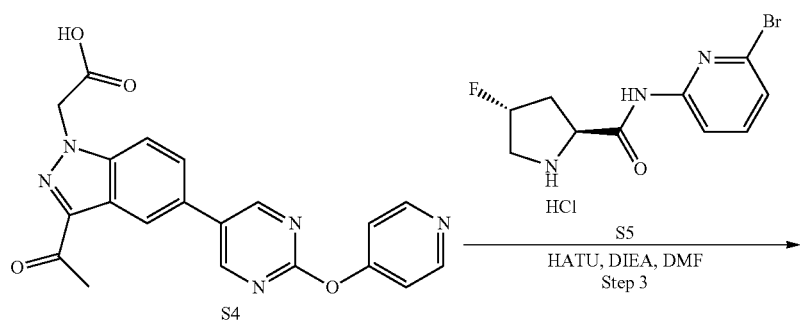

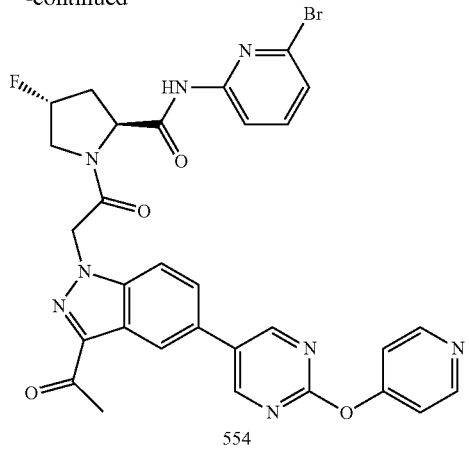

554

Step 1: tert-Butyl 2-(3-acetyl-5-(2-(pyridin-4-yloxy)pyrimidin-5-yl)-1H-indazol-1-yl)acetate (S3)

To a solution of 5-bromo-2-(pyridin-4-yloxy)pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(pyridin-4-yloxy)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-a=Acetyl-5-(2-(pyridin-4-yloxy)pyrimidin-5-yl)-1H-indazol-1-yl)acetyl)-N-(6-bromopyridin-2-yl)-4-fluoropyrrolidine-2-carboxamide (554)

To a solution of compound S4 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 554. $^1$H NMR (400 MHz, DMSO-d$_6$) δ 2.06-2.26 (m, 1H), 2.54-2.62 (m, 1H), 2.66 (s, 3H), 3.95-4.13 (m, 1H), 4.24 (dd, J=12.5, 22.2 Hz, 1H), 4.68 (dd, J=7.6, 9.5 Hz, 1H), 5.47-5.71 (m, 2H), 5.85 (d, J=17.3 Hz, 1H), 6.34-6.46 (m, 2H), 7.32 (d, J=7.7 Hz, 1H), 7.71 (t, J=8.0 Hz, 1H), 7.86-7.97 (m, 2H), 8.02 (d, J=8.2 Hz, 1H), 8.51 (d, J=1.6 Hz, 1H), 8.85-8.99 (m, 2H), 9.26 (s, 2H), 10.99 (s, 1H). $^{19}$F NMR (376 MHz, DMSO-d$_6$): δ −175.66. LC (method A): t$_R$=1.69 min. LC/MS (EI) m/z: [M+H]$^+$ 659.

(5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)methyl dimethylcarbamate (555)

Scheme 299

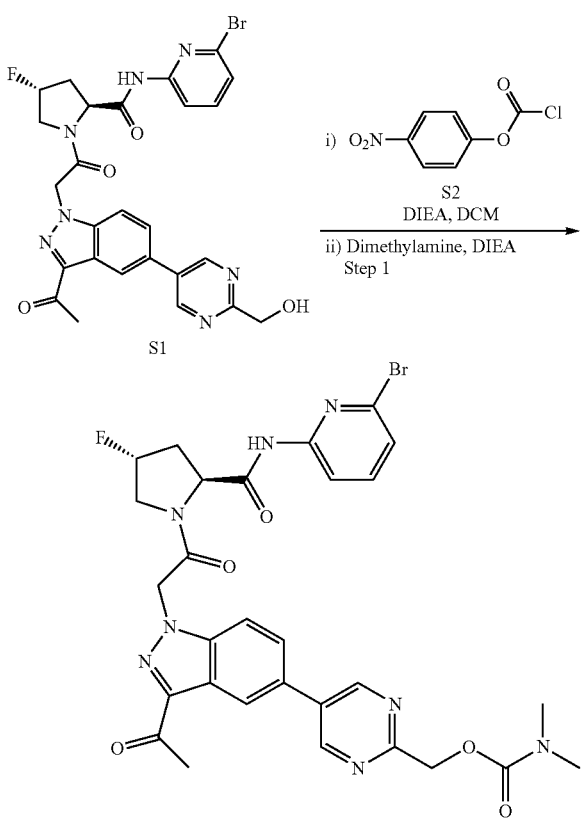

555

To a solution of compound S1 (1 equiv) in DCM (10 vol) at 0° C. under an atmosphere of nitrogen was added 4-nitrophenyl carbonochloridate (S2, 1.5 equiv), and DIPEA (3 equiv). The reaction mixture was stirred at room temperature for 1 h, then dimethylamine (1.5 equiv) and DIPEA were added, stirred the reaction mixture for 10 min and concentrated. The residue was purified by column chromatography on silica gel (MeOH/DCM) to give compound 555. $^1$H NMR (400 MHz, DMSO-$d_6$) δ 2.04-2.28 (m, 1H), 2.54-2.60 (m, 1H), 2.65 (s, 3H), 2.86 (s, 3H), 2.98 (s, 3H), 3.94-4.11 (m, 1H), 4.24 (dd, J=12.5, 22.2 Hz, 1H), 4.63-4.74 (m, 1H), 5.27 (s, 2H), 5.48-5.71 (m, 2H), 5.85 (d, J=17.3 Hz, 1H), 7.32 (d, J=7.7 Hz, 1H), 7.71 (t, J=8.0 Hz, 1H), 7.84-7.92 (m, 2H), 8.02 (d, J=8.2 Hz, 1H), 8.45 (d, J=1.5 Hz, 1H), 9.13 (s, 2H), 11.01 (s, 1H). $^{19}$F NMR (376 MHz, DMSO-$d_6$): δ −175.66. LC (method A): $t_R$=1.79 min. LC/MS (EI) m/z: [M+H]$^+$ 667.

(2S,4R)-1-(2-(3-Acetyl-5-(2-(methylsulfonamido)pyrimidin-5-yl)-1H-indazol-1-yl)acetyl)-N-(6-bromopyridin-2-yl)-4-fluoropyrrolidine-2-carboxamide (556)

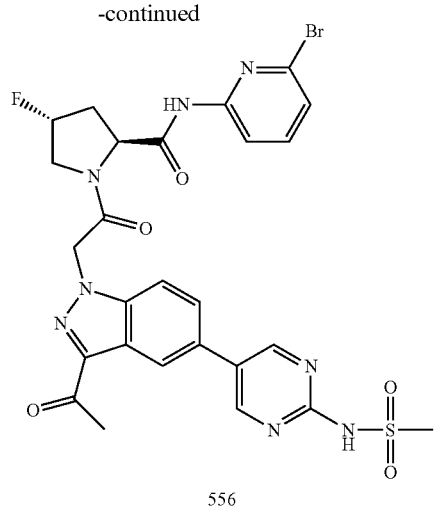

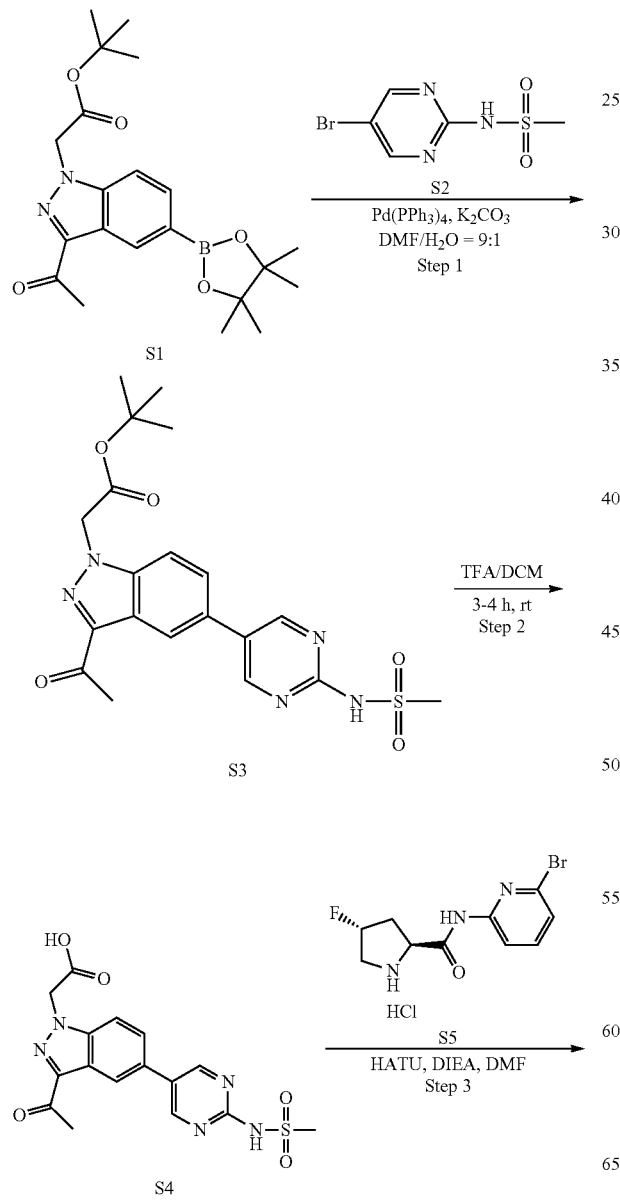

Step 1: tert-Butyl 2-(3-acetyl-5-(2-(methylsulfonamido)pyrimidin-5-yl)-1H-indazol-1-yl)acetate (S3)

To a solution of N-(5-bromopyrimidin-2-yl)methanesulfonamide (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(methylsulfonamido)pyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-(methylsulfonamido)pyrimidin-5-yl)-1H-indazol-1-yl)acetyl)-N-(6-bromopyridin-2-yl)-4-fluoropyrrolidine-2-carboxamide (556)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 556. $^1$H NMR (400 MHz, DMSO-$d_6$) δ 2.07-2.29 (m, 1H), 2.56-2.66 (m, 4H), 2.89 (d, J=2.4 Hz, 3H), 4.02 (dd, J=12.1, 37.8 Hz, 1H), 4.16-4.30 (m, 1H), 4.62-4.72 (m, 1H), 5.44-5.70 (m, 2H), 5.74-5.89 (m, 1H), 7.19-7.29 (m, 1H), 7.31-7.52 (m, 2H), 7.66-7.76 (m, 1H), 7.78-7.89 (m, 1H), 7.99-8.07 (m, 2H), 8.17-8.22 (m, 1H), 8.95-9.00 (m, 1H), 10.99-11.03 (m, 1H). $^{19}$F NMR (376 MHz, DMSO-d$_6$): δ −175.65. LC (method A): $t_R$=1.63 min. LC/MS (EI) m/z: [M+H]$^+$ 659.

(2S,4R)-1-(2-(3-Acetyl-5-(2-(methoxymethyl)pyrimidin-5-yl)-1H-indazol-1-yl)acetyl)-N-(6-bromopyridin-2-yl)-4-fluoropyrrolidine-2-carboxamide (737)

Scheme 301

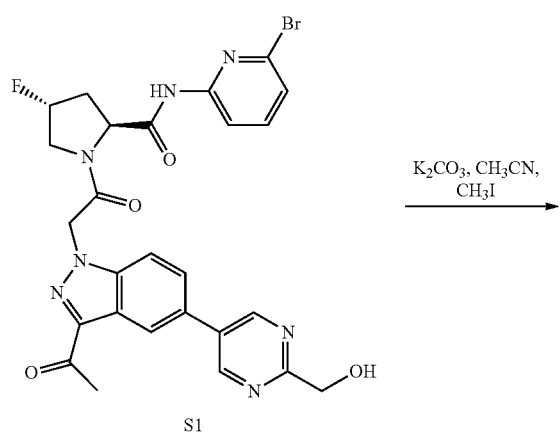

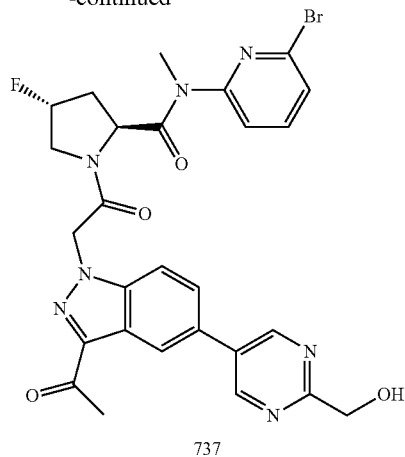

To a solution of compound S1 (1 equiv) in CH$_3$CN (10 vol) under an atmosphere of nitrogen was added K$_2$CO$_3$ (2 equiv), and CH$_3$I (1.1 equiv). The reaction mixture was stirred at room temperature for 48 h and then solvent was removed under reduced pressure. The residue was purified by column chromatography on silica gel (MeOH/DCM) to give compound S2. $^1$H NMR (400 MHz, DMSO-d$_6$) δ 2.16-2.36 (m, 1H), 2.60-2.72 (m, 4H), 3.23 (s, 3H), 3.91-4.08 (m, 1H), 4.23 (dd, J=12.6, 21.8 Hz, 1H), 4.62 (s, 1H), 4.68 (d, 2H), 5.37 (t, J=6.4 Hz, 1H), 5.48-5.67 (m, 2H), 5.80 (d, J=17.4 Hz, 1H), 7.46 (d, J=8.0 Hz, 1H), 7.55 (d, J=7.7 Hz, 1H), 7.81 (dd, J=6.9, 8.5 Hz, 2H), 7.91 (dd, J=6.3, 8.1 Hz, 1H), 8.46 (s, 1H), 9.14 (s, 2H). $^{19}$F NMR (376 MHz, DMSO-d$_6$): δ −175.18. LC (method A): $t_R$=1.48 min. LC/MS (EI) m/z: [M+H]$^+$ 610.

(2S,4R)-1-(2-(3-Acetyl-5-(1-(5-fluoropyrimidin-2-yl)-1H-pyrazol-4-yl)-1H-indazol-1-yl)acetyl)-N-(6-bromopyridin-2-yl)-4-fluoropyrrolidine-2-carboxamide (699)

Scheme 302

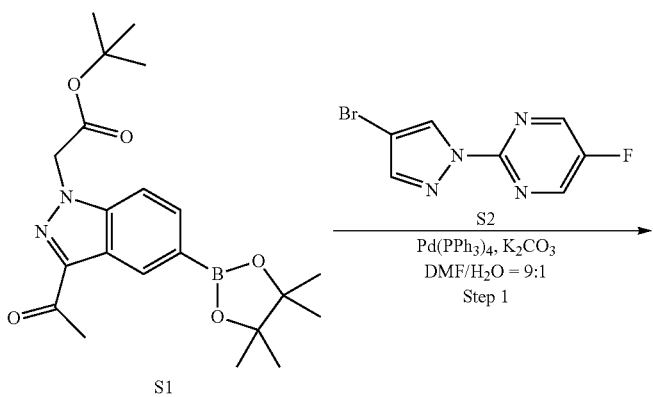

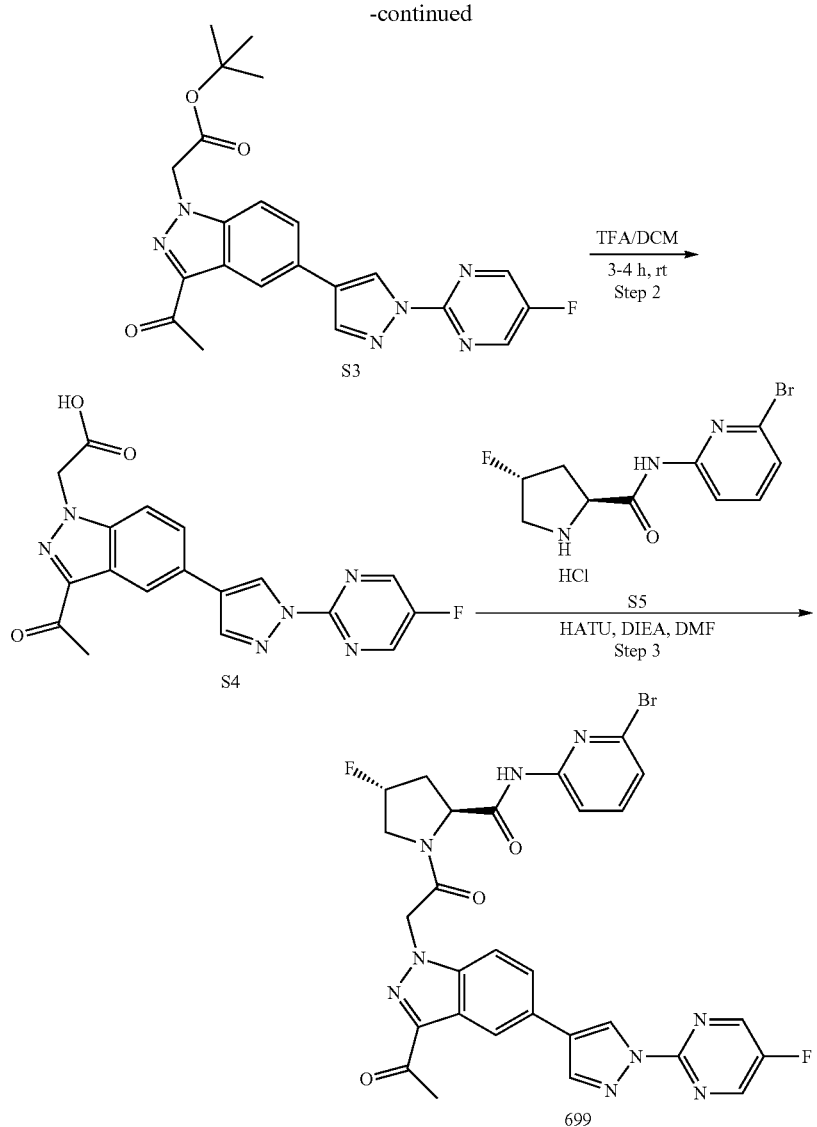

Step 1: tert-Butyl 2-(3-acetyl-5-(1-(5-fluoropyrimidin-2-yl)-1H-pyrazol-4-yl)-1H-indazol-1-yl)acetate (S3)

To a solution of 2-(4-bromo-1H-pyrazol-1-yl)-5-fluoropyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(1-(5-fluoropyrimidin-2-yl)-1H-pyrazol-4-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(1-(5-fluoropyrimidin-2-yl)-1H-pyrazol-4-yl)-1H-indazol-1-yl)acetyl)-N-(6-bromopyridin-2-yl)-4-fluoropyrrolidine-2-carboxamide (699)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 699. $^1$H NMR (400 MHz, DMSO-d$_6$) δ 2.04-2.26 (m, 1H), 2.54-2.62 (m, 1H), 2.64 (s, 3H), 3.94-4.12 (m, 1H), 4.23 (dd, J=12.5, 22.3 Hz, 1H), 4.64-4.74 (m, 1H), 5.46-5.65 (m, 2H), 5.80 (d, J=17.3 Hz, 1H), 7.32 (d, J=7.7 Hz, 1H), 7.67-7.78 (m, 2H), 7.94 (dd, J=1.6, 8.8 Hz, 1H), 8.03 (d, J=8.2 Hz, 1H), 8.41 (s, 1H), 8.44 (d, J=1.5 Hz, 1H), 9.00 (s, 2H), 9.08 (s, 1H), 11.01 (s, 1H). $^{19}$F NMR (376 MHz, DMSO-d$_6$): δ −175.64, −142.16. LC (method A): t$_R$=1.92 min. LC/MS (EI) m/z: [M+H]$^+$ 650.

(2S,4R)-1-(2-(3-Acetyl-5-(1-methyl-2-oxo-1,2-dihydropyrimidin-5-yl)-1H-indazol-1-yl)acetyl)-N-(6-bromopyridin-2-yl)-4-fluoropyrrolidine-2-carboxamide (702)

Scheme 303

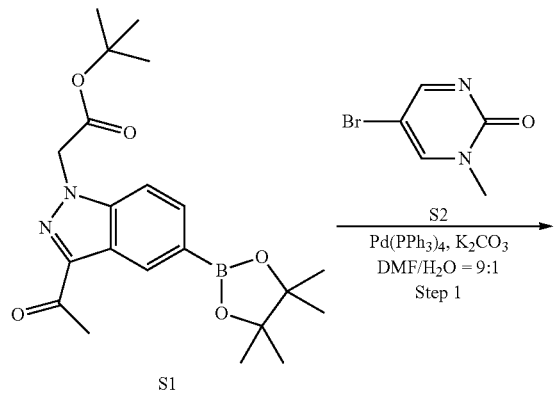

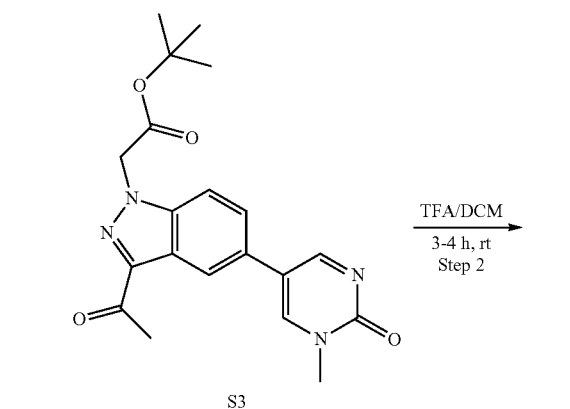

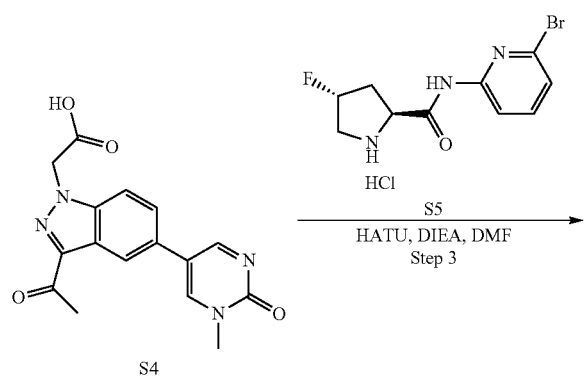

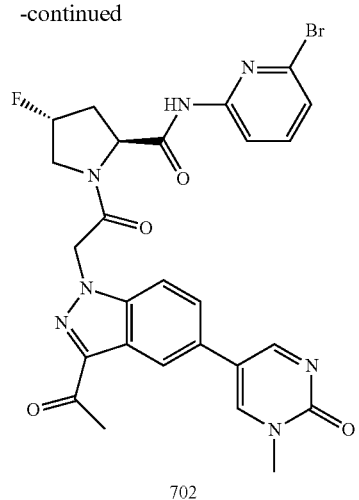

Step 1: tert-Butyl 2-(3-acetyl-5-(1-methyl-2-oxo-1,2-dihydropyrimidin-5-yl)-1H-indazol-1-yl)acetate (S3)

To a solution of 5-bromo-1-methylpyrimidin-2(1H)-one (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(1-methyl-2-oxo-1,2-dihydropyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(1-methyl-2-oxo-1,2-dihydropyrimidin-5-yl)-1H-indazol-1-yl)acetyl)-N-(6-bromopyridin-2-yl)-4-fluoropyrrolidine-2-carboxamide (702)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 702. $^1$H NMR (400 MHz, DMSO-d$_6$) δ 2.04-2.27 (m, 1H), 2.53-2.61 (m, 1H), 2.63 (s, 3H), 3.54 (s, 3H), 3.94-4.13 (m, 1H), 4.22 (dd, J=12.5, 22.3 Hz, 1H), 4.67 (t, J=8.5 Hz, 1H), 5.45-5.68 (m, 2H), 5.82 (d, J=17.3 Hz, 1H), 7.32 (d, J=7.7 Hz, 1H), 7.62-7.83 (m, 3H), 8.02 (d, J=8.2 Hz, 1H), 8.31 (d, J=1.5 Hz, 1H), 8.65 (d, J=3.3 Hz, 1H), 8.94 (d, J=3.3 Hz, 1H), 11.01 (s, 1H). $^{19}$F NMR (376 MHz, DMSO-d$_6$): δ −175.64. LC (method A): t$_R$=1.38 min. LC/MS (EI) m/z: [M+H]$^+$ 596.

669

(2S,4R)-1-(2-(3-Acetyl-5-(2-fluoropyrimidin-5-yl)-1H-indazol-1-yl)acetyl)-N-(6-bromopyridin-2-yl)-4-fluoropyrrolidine-2-carboxamide (583)

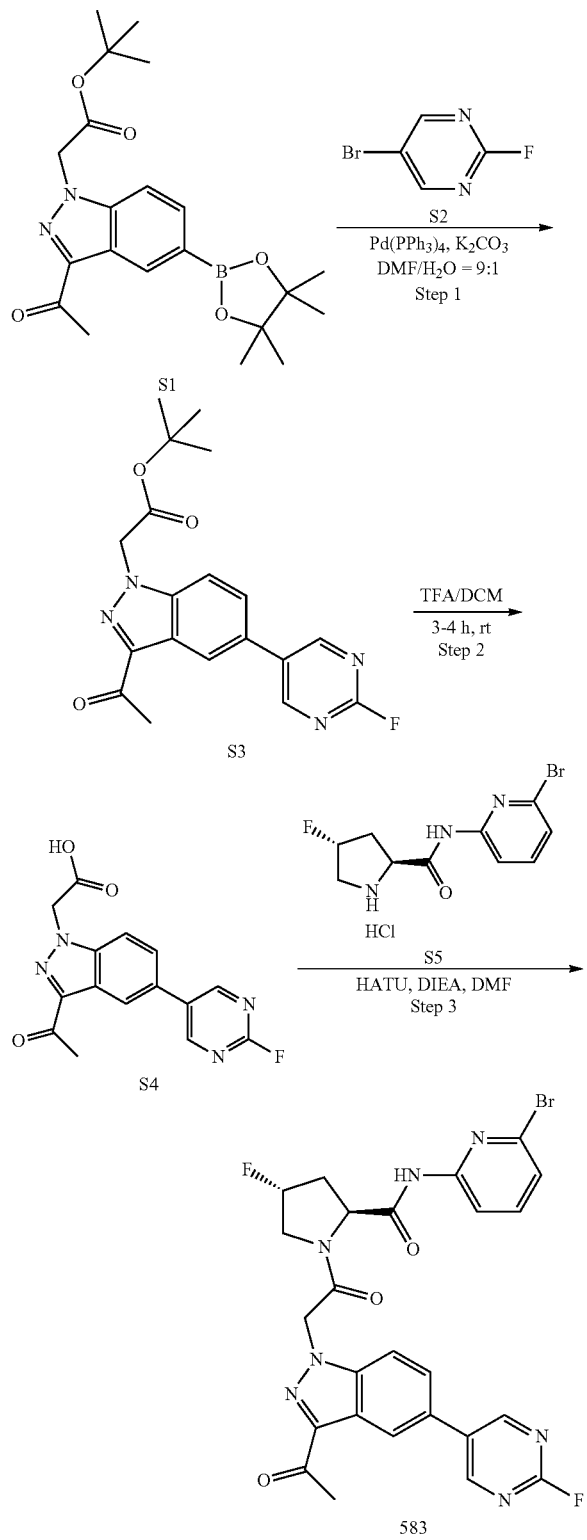

670

Step 1: tert-Butyl 2-(3-acetyl-5-(2-fluoropyrimidin-5-yl)-1H-indazol-1-yl)acetate (S3)

To a solution of 5-bromo-2-fluoropyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-fluoropyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-fluoropyrimidin-5-yl)-1H-indazol-1-yl)acetyl)-N-(6-bromopyridin-2-yl)-4-fluoropyrrolidine-2-carboxamide (583)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 583. $^1$H NMR (400 MHz, DMSO-d$_6$) δ 2.05-2.27 (m, 1H), 2.54-2.63 (m, 1H), 2.66 (s, 3H), 3.95-4.14 (m, 1H), 4.19-4.33 (m, 1H), 4.68 (dd, J=7.5, 9.5 Hz, 1H), 5.48-5.72 (m, 2H), 5.86 (d, J=17.3 Hz, 1H), 7.32 (d, J=7.7 Hz, 1H), 7.71 (t, J=8.0 Hz, 1H), 7.88 (s, 1H), 7.96 (s, 1H), 8.03 (d, J=8.2 Hz, 1H), 8.47 (d, J=1.3 Hz, 1H), 9.14 (d, J=1.4 Hz, 2H), 11.02 (s, 1H). $^{19}$F NMR (376 MHz, DMSO-d$_6$): δ −175.65, −49.66. LC (method A): t$_R$=1.94 min. LC/MS (EI) m/z: [M+H]$^+$ 584.

methyl 5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxylate (596)

Scheme 305

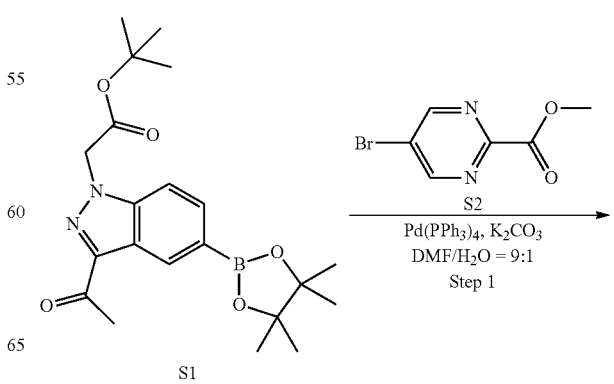

671

-continued

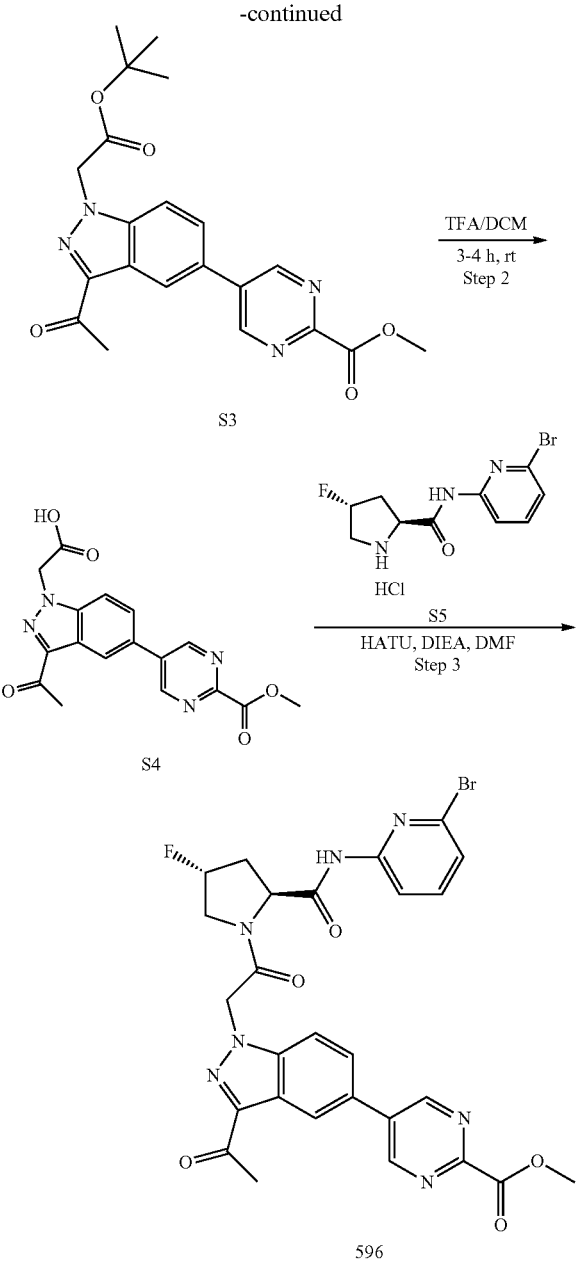

Step 1: Methyl 5-(3-acetyl-1-(2-(tert-butoxy)-2-oxoethyl)-1H-indazol-5-yl)pyrimidine-2-carboxylate (S3)

To a solution of methyl 5-bromopyrimidine-2-carboxylate (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-(methoxycarbonyl)pyrimidin-5-yl)-1H-indazol-1-yl)acetic acid (S4)

To a solution of compound S3 (1 equiv) in DCM (10 vol) at 0° C. under an atmosphere of nitrogen was added TFA (5

672 vol). The reaction mixture was stirred at room temperature for 3 h and then concentrated. The remaining material was used directly in the next synthetic step.

Step 3: Methyl 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxylate (596)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 596. $^1$H NMR (400 MHz, DMSO-d$_6$) δ 2.07-2.29 (m, 1H), 2.56-2.65 (m, 1H), 2.66 (s, 3H), 3.95 (s, 4H), 4.24 (dd, J=12.5, 22.2 Hz, 1H), 4.64-4.73 (m, 1H), 5.46-5.72 (m, 2H), 5.87 (d, J=17.3 Hz, 1H), 7.33 (d, J=7.7 Hz, 1H), 7.71 (t, J=8.0 Hz, 1H), 7.91 (d, J=8.8 Hz, 1H), 7.98-8.08 (m, 2H), 8.57 (d, J=1.7 Hz, 1H), 9.35 (s, 2H), 11.02 (s, 1H). $^{19}$F NMR (376 MHz, DMSO-d$_6$): δ −175.64. LC (method A): t$_R$=1.66 min. LC/MS (EI) m/z: [M+H]$^+$ 624.

(2S,4R)-1-(2-(5-(2-Acetamidopyrimidin-5-yl)-3-acetyl-1H-indazol-1-yl)acetyl)-N-(6-bromopyridin-2-yl)-4-fluoropyrrolidine-2-carboxamide (597)

Scheme 306

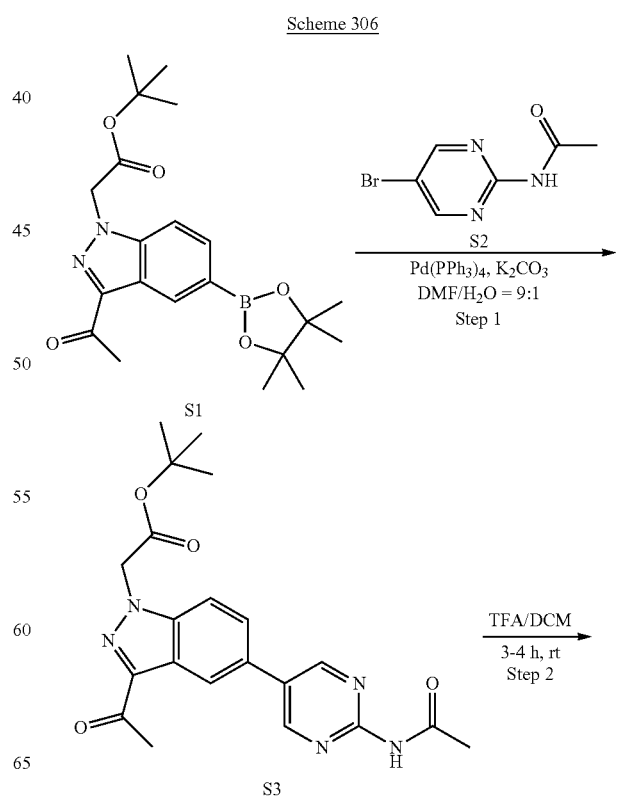

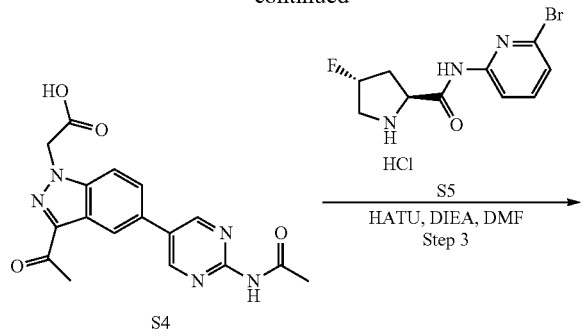

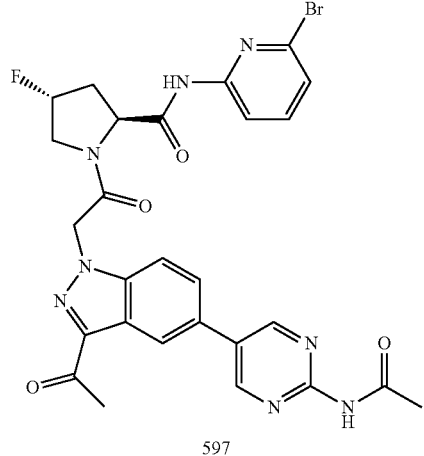

Step 1: tert-bBtyl 2-(5-(2-acetamidopyrimidin-5-yl)-3-acetyl-1H-indazol-1-yl)acetate (S3)

To a solution of N-(5-bromopyrimidin-2-yl)acetamide (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(5-(2-Acetamidopyrimidin-5-yl)-3-acetyl-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(5-(2-Acetamidopyrimidin-5-yl)-3-acetyl-1H-indazol-1-yl)acetyl)-N-(6-bromopyridin-2-yl)-4-fluoropyrrolidine-2-carboxamide (597)

To a solution of compound S4 (1 equiv) in DMF (10 vol) at 0° C. under an atmosphere of nitrogen was added (2S, 4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 597. $^1$H NMR (400 MHz, DMSO-d$_6$) δ 2.06-2.26 (m, 4H), 2.55-2.63 (m, 1H), 2.65 (s, 3H), 4.03 (dd, J=12.3, 37.1 Hz, 1H), 4.24 (dd, J=12.6, 22.2 Hz, 1H), 4.68 (t, J=8.5 Hz, 1H), 5.47-5.69 (m, 2H), 5.85 (d, J=17.3 Hz, 1H), 7.33 (d, J=7.8 Hz, 1H), 7.71 (t, J=8.0 Hz, 1H), 7.85 (d, J=2.8 Hz, 2H), 8.03 (d, J=8.2 Hz, 1H), 8.42 (s, 1H), 8.99 (s, 2H), 10.69 (s, 1H), 11.01 (s, 1H). $^{19}$F NMR (376 MHz, DMSO-d$_6$): δ −175.66. LC (method A): t$_R$=1.5 min. LC/MS (EI) m/z: [M+H]$^+$ 623.

5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxylic acid (598)

Scheme 307

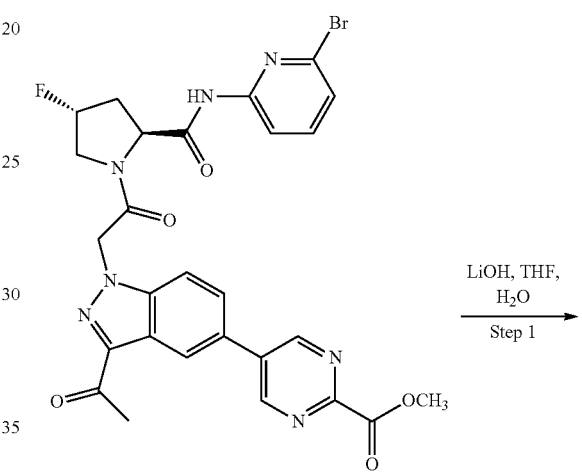

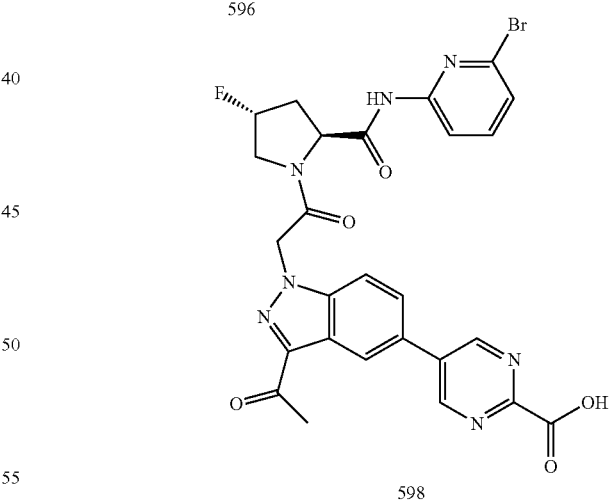

To a solution of methyl 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxylate (596, 1 equiv) in THF/H$_2$O (1:1, 10 vol) was added LiOH (3 equiv) and the reaction mixture was stirred at room temperature for 3 h and then concentrated under reduced pressure. The remaining residue was neutralize using 2N HCl, solid was filtered to give compound 598. $^1$H NMR (400 MHz, DMSO-d$_6$) δ 2.06-2.26 (m, 1H), 2.55-2.62 (m, 1H), 2.67 (d, J=3.0 Hz, 4H), 3.93-4.13 (m, 1H), 4.25 (dd, J=12.6, 22.0 Hz, 1H), 4.68 (t, J=8.5 Hz, 1H), 5.49-5.72 (m, 2H), 5.87 (d, J=17.3 Hz, 1H), 7.33 (d, J=7.7 Hz, 1H), 7.71 (t, J=8.0 Hz, 1H), 7.87-8.05 (m, 3H), 8.54 (d, J=1.6 Hz, 1H), 9.30 (d, J=7.0 Hz, 2H), 11.02 (s, 1H). $^{19}$F NMR (376 MHz, DMSO-$d_6$): δ −175.67. LC (method A): $t_R$=1.38 min. LC/MS (EI) m/z: [M+H]$^+$ 610.

5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxamide (599)

3H), 8.25 (s, 1H), 8.54 (s, 1H), 9.28 (s, 2H), 11.02 (s, 1H). $^{19}$F NMR (376 MHz, DMSO-$d_6$): δ −175.65. LC (method A): $t_R$=1.43 min. LC/MS (EI) m/z: [M+H]$^+$ 609.

(2S,4R)-1-(2-(3-Acetyl-5-(2-hydroxypyrimidin-5-yl)-1H-indazol-1-yl)acetyl)-N-(6-bromopyridin-2-yl)-4-fluoropyrrolidine-2-carboxamide (604)

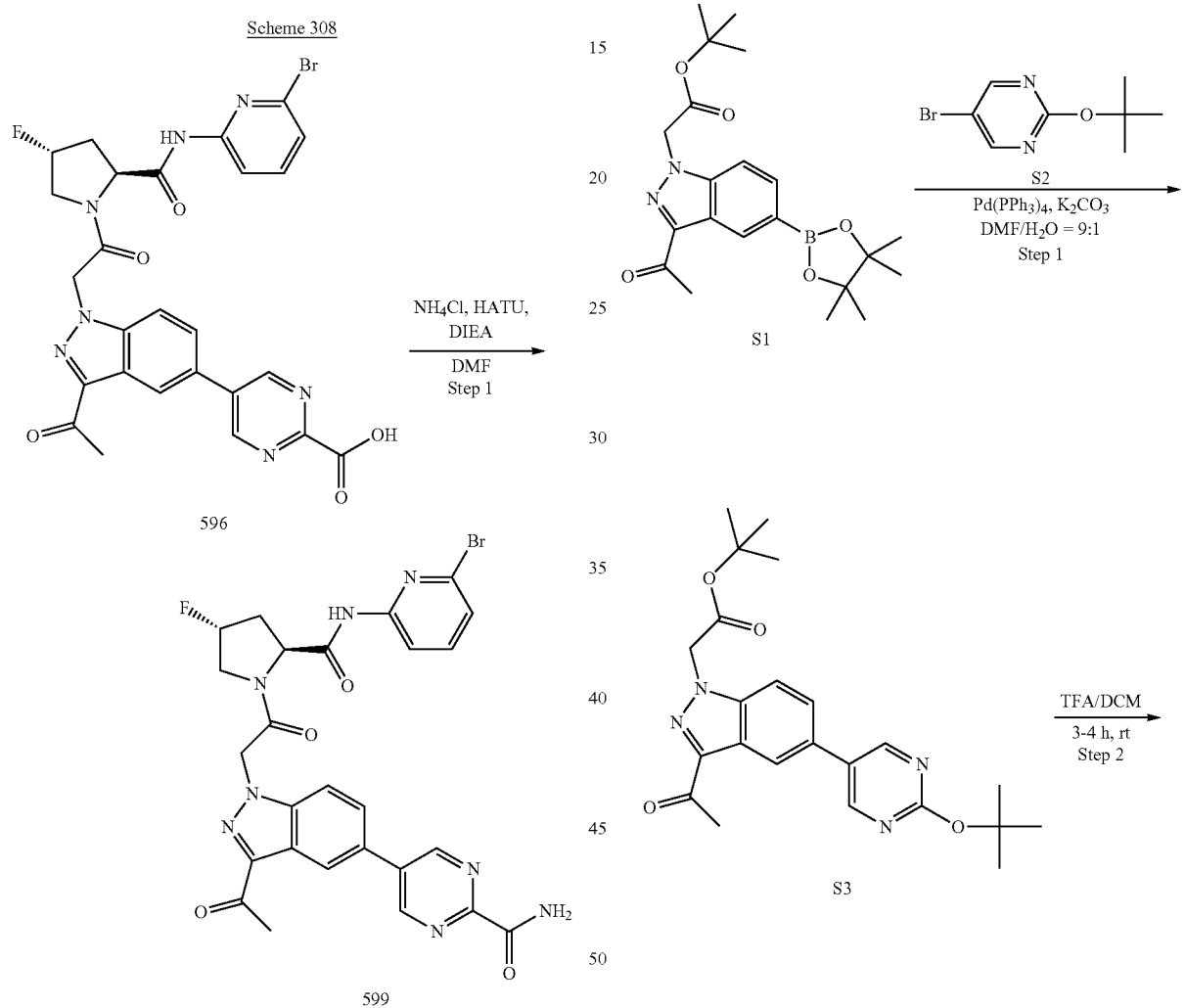

To a solution of compound 596 (1 equiv) in DMF (10 vol) at 0° C. under an atmosphere of nitrogen was added NH$_4$Cl (5 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 599. $^1$H NMR (400 MHz, DMSO-$d_6$) δ 2.08-2.27 (m, 1H), 2.53-2.64 (m, 1H), 2.66 (s, 3H), 4.04 (dd, J=12.0, 38.0 Hz, 1H), 4.25 (dd, J=12.5, 22.2 Hz, 1H), 4.68 (t, J=8.5 Hz, 1H), 5.48-5.73 (m, 2H), 5.87 (d, J=17.3 Hz, 1H), 7.33 (d, J=7.7 Hz, 1H), 7.71 (t, J=8.0 Hz, 1H), 7.84 (s, 1H), 7.88-8.07 (m,

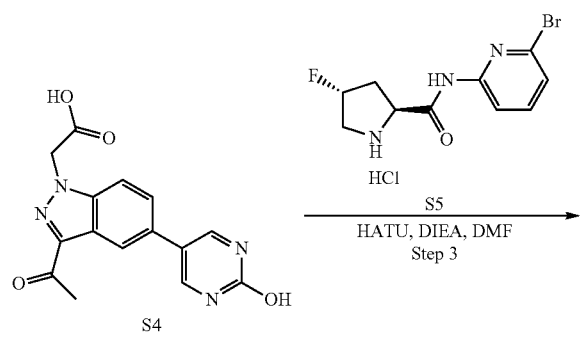

677
-continued

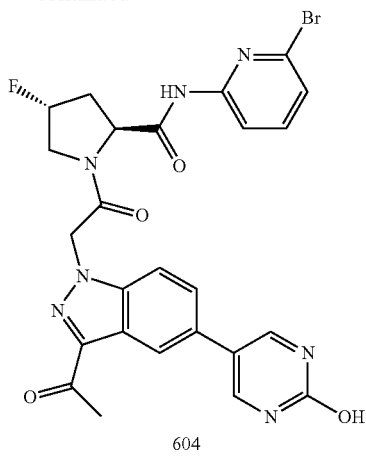

604

Step 1: tert-Butyl 2-(3-acetyl-5-(2-(tert-butoxy)pyrimidin-5-yl)-1H-indazol-1-yl)acetate (S3)

To a solution of 5-bromo-2-(tert-butoxy)pyrimidine (S2, 1 equiv) in DMF/H$_2$O (9:1, 10 vol) was added compound S1 (1 equiv), K$_2$CO$_3$ (2 equiv), and tetrakis(triphenylphosphine)palladium (0.1 equiv). The reaction mixture was stirred at 90° C. for 5 h and then concentrated under reduced pressure. The remaining residue was purified by column chromatography on silica gel to give compound S3.

Step 2: 2-(3-Acetyl-5-(2-hydroxypyrimidin-5-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(2-hydroxypyrimidin-5-yl)-1H-indazol-1-yl)acetyl)-N-(6-bromopyridin-2-yl)-4-fluoropyrrolidine-2-carboxamide (604)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na$_2$SO$_4$, filtered, and then concentrated. The residue was purified by column chromatography on silica gel (MeOH/DCM) to give compound 604. $^1$H NMR (400 MHz, DMSO-d$_6$) δ 2.03-2.25 (m, 1H), 2.54-2.63 (m, 1H), 2.64 (s, 3H), 4.02 (dd, J=12.1, 36.9 Hz, 1H), 4.23 (dd, J=12.5, 22.3 Hz, 1H), 4.67 (t, J=8.5 Hz, 1H), 5.47-5.67 (m, 2H), 5.82 (d, J=17.3 Hz, 1H), 7.33 (d, J=7.7 Hz, 1H), 7.69-7.83 (m, 3H), 8.03 (d, J=8.2 Hz, 1H), 8.27 (s, 1H), 8.51-8.74 (m, 2H), 11.01 (s, 1H), 12.24 (s, 1H). $^{19}$F NMR (376 MHz, DMSO-d$_6$): δ −175.66. LC (method A): t$_R$=1.28 min. LC/MS (EI) m/z: [M+H]$^+$ 582.

678

(2S,4R)-1-(2-(3-Acetyl-5-(1-cyclopropyl-1H-pyrazol-4-yl)-1H-indazol-1-yl)acetyl)-N-(6-bromopyridin-2-yl)-4-fluoropyrrolidine-2-carboxamide (706)

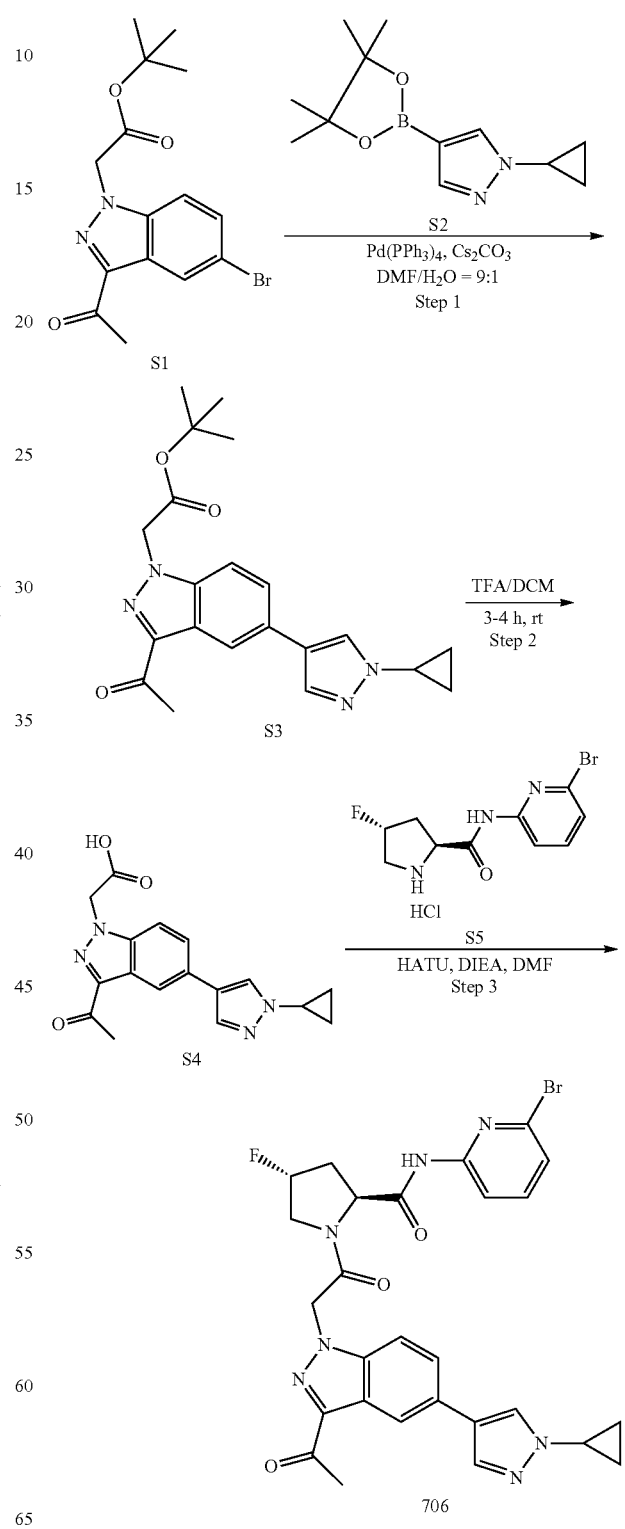

Step 1: tert-Butyl 2-(3-acetyl-5-(1-cyclopropyl-1H-pyrazol-4-yl)-1H-indazol-1-yl)acetate (S3)

To a solution of 1-cyclopropyl-4-(4,4,5,5-tetramethyl-1,3,2-dioxaborolan-2-yl)-1H-pyrazole (S2, 1 equiv) in DMF/H₂O (9:1, 10 vol) was added compound S1 (1 equiv), Cs₂CO₃ (2 equiv), and tetrakis(triphenylphosphine)palladium (0.1 equiv). The reaction mixture was stirred at 90° C. for 3 h and then concentrated under reduced pressure. The remaining residue was purified by column chromatography on silica gel to give compound S3.

Step 2: 2-(3-Acetyl-5-(1-cyclopropyl-1H-pyrazol-4-yl)-1H-indazol-1-yl)acetic acid (S4)

To a solution of compound S3 (1 equiv) in DCM (10 vol) at 0° C. under an atmosphere of nitrogen was added TFA (5 vol). The reaction mixture was stirred at room temperature for 3 h and then concentrated. The remaining material was used directly in the next synthetic step.

Step 3: (2S,4R)-1-(2-(3-Acetyl-5-(1-cyclopropyl-1H-pyrazol-4-yl)-1H-indazol-1-yl)acetyl)-N-(6-bromopyridin-2-yl)-4-fluoropyrrolidine-2-carboxamide (706)

To a solution of compound S4 (1 equiv) in DMF (10 vol) at 0° C. under an atmosphere of nitrogen was added (2S,4R)—N-(6-bromopyridin-2-yl)-4-fluoropyrrolidine-2-carboxamide hydrochloride (1 equiv), HATU (2.1 equiv), and DIPEA (5 equiv). The reaction mixture was stirred at room temperature for 3 h and then quenched with water (30 vol). The resulting mixture was extracted with DCM. The organic layer was washed with brine, dried over anhydrous Na₂SO₄, filtered, and then concentrated. The residue was purified by column chromatography on silica gel (MeOH/DCM) to give compound 706. ¹H NMR (400 MHz, DMSO-d₆) δ 0.95-1.04 (m, 2H), 1.10-1.16 (m, 2H), 2.08-2.26 (m, 1H), 2.54-2.58 (m, 1H), 2.62 (s, 3H), 3.72-3.83 (m, 1H), 3.95-4.10 (m, 1H), 4.22 (dd, J=12.5, 22.3 Hz, 1H), 4.64-4.73 (m, 1H), 5.46-5.67 (m, 2H), 5.77 (d, J=17.3 Hz, 1H), 7.33 (d, J=7.7 Hz, 1H), 7.67-7.76 (m, 3H), 7.88 (s, 1H), 8.03 (d, J=8.2 Hz, 1H), 8.27 (s, 1H), 8.31 (s, 1H), 11.01 (s, 1H). ¹⁹F NMR (376 MHz, DMSO-d₆): δ −175.65. LC (method A): t$_R$=1.94 min. LC/MS (EI) m/z: [M+H]⁺ 594.

(2S,4R)-1-(2-(3-Acetyl-5-(2-(methylsulfinyl)pyrimidin-5-yl)-1H-indazol-1-yl)acetyl)-N-(6-bromopyridin-2-yl)-4-fluoropyrrolidine-2-carboxamide (649)

Scheme 311

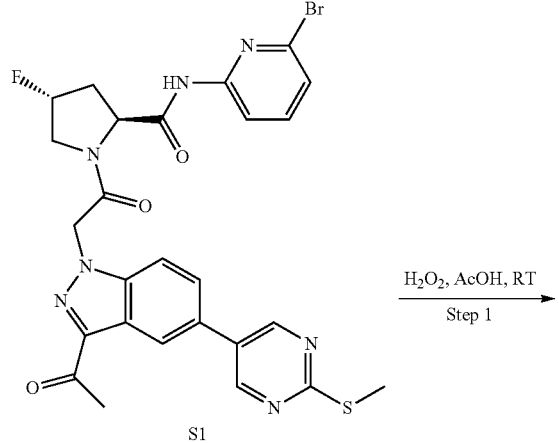

S1

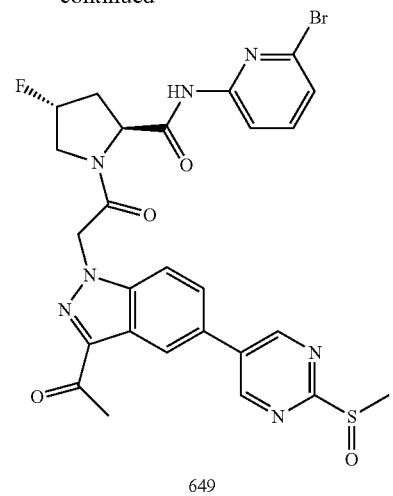

649

To a solution of compound S1 (1 equiv) in Acetic acid (10 vol) under an atmosphere of nitrogen was added 30% Aq H₂O₂ (4 equiv) The reaction mixture was stirred at room temperature for 24 h, then the reaction mixture was cooled in ice bath and adjusted to PH 8 with 4N aq NaOH, precipitated solid was filtered and purified by column chromatography on silica gel (MeOH/DCM) to give compound 649. ¹H NMR (400 MHz, DMSO-d₆) δ 2.05-2.30 (m, 1H), 2.55-2.66 (m, 1H), 2.66 (s, 3H), 2.94 (s, 3H), 3.94-4.14 (m, 1H), 4.25 (dd, J=12.5, 22.3 Hz, 1H), 4.68 (t, J=8.5 Hz, 1H), 5.50-5.72 (m, 2H), 5.87 (d, J=17.3 Hz, 1H), 7.33 (d, J=7.7 Hz, 1H), 7.71 (t, J=8.0 Hz, 1H), 7.87-7.99 (m, 2H), 8.03 (d, J=8.2 Hz, 1H), 8.54 (s, 1H), 9.36 (s, 2H), 11.02 (s, 1H). ¹⁹F NMR (376 MHz, DMSO-d₆): δ −175.64. LC (method A): t$_R$=1.51 min. LC/MS (EI) m/z: [M+H]⁺ 628.

tert-butyl ((5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)(methyl)(oxo)-16-sulfanylidene)carbamate (650)

Scheme 312

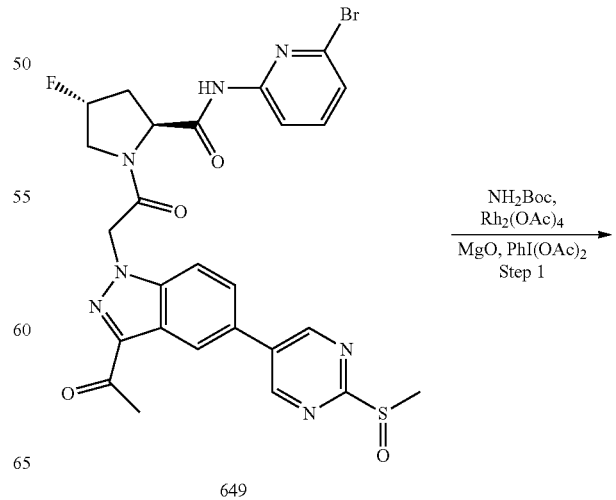

649

681
-continued

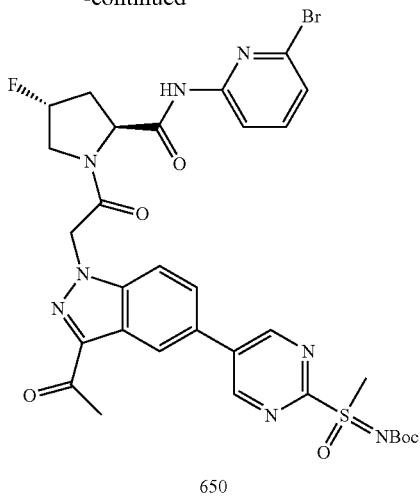
650

682
-continued

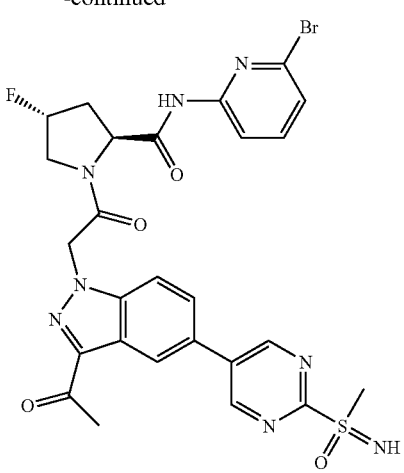
732

To a solution of compound 649 (1 equiv) in DCM (10 vol), tert-butyl carbamate (1.5 equiv), Rh₂(OAc)₄ (0.025 equiv) and MgO (4 equiv) under an atmosphere of nitrogen was added PhI(OAc)₂ (1.5 equiv) The reaction mixture was stirred at 40° C. for 8 h, The reaction mixture was filtered through celite and concentrated under reduced pressure. The remaining residue was purified by column chromatography on silica gel (MeOH/DCM) to give compound 650. $^1$H NMR (400 MHz, DMSO-d₆) δ 1.21-1.28 (m, 9H), 2.09-2.28 (m, 1H), 2.55-2.64 (m, 1H), 2.67 (s, 3H), 3.49 (s, 3H), 3.99-4.14 (m, 1H), 4.25 (dd, J=12.5, 22.3 Hz, 1H), 4.68 (t, J=8.5 Hz, 1H), 5.47-5.75 (m, 2H), 5.88 (d, J=17.4 Hz, 1H), 7.33 (d, J=7.7 Hz, 1H), 7.71 (t, J=8.0 Hz, 1H), 7.93 (d, J=8.8 Hz, 1H), 8.03 (dd, J=5.7, 8.6 Hz, 2H), 8.60 (s, 1H), 9.50 (s, 2H), 11.02 (s, 1H). $^{19}$F NMR (376 MHz, DMSO-d₆): δ −175.66. LC (method A): $t_R$=1.99 min. LC/MS (EI) m/z: [M+H]⁺ 743.

(2S,4R)-1-(2-(3-Acetyl-5-(2-(S-methylsulfonimidoyl)pyrimidin-5-yl)-1H-indazol-1-yl)acetyl)-N-(6-bromopyridin-2-yl)-4-fluoropyrrolidine-2-carboxamide (732)

To a solution of compound S1 (1 equiv) in DCM (10 vol) at 0° C. under an atmosphere of nitrogen was added TFA (5 vol). The reaction mixture was stirred at room temperature for 3 h and then concentrated. The remaining material was purified by HPLC to give compound 732. $^1$H NMR (400 MHz, DMSO-d₆) δ 2.01-2.19 (m, 1H), 2.47-2.58 (m, 1H), 2.59 (s, 3H), 3.31 (s, 3H), 3.86-4.04 (m, 2H), 4.17 (dd, J=12.5, 22.2 Hz, 1H), 4.61 (dd, J=7.4, 9.5 Hz, 1H), 5.40-5.66 (m, 2H), 5.79 (d, J=17.3 Hz, 1H), 7.25 (d, J=7.7 Hz, 1H), 7.63 (t, J=8.0 Hz, 1H), 7.82-7.99 (m, 3H), 8.49 (d, J=1.6 Hz, 1H), 9.30 (s, 2H), 10.92 (s, 1H). $^{19}$F NMR (376 MHz, DMSO-d₆): δ −175.66, −74.53. LC (method A): $t_R$=1.46 min. LC/MS (EI) m/z: [M+H]⁺ 643.

(2S,4R)-1-(2-(3-Acetyl-5-(2-chloropyrimidin-5-yl)-1H-indazol-1-yl)acetyl)-N-(6-bromopyridin-2-yl)-4-fluoropyrrolidine-2-carboxamide (651)

Scheme 313

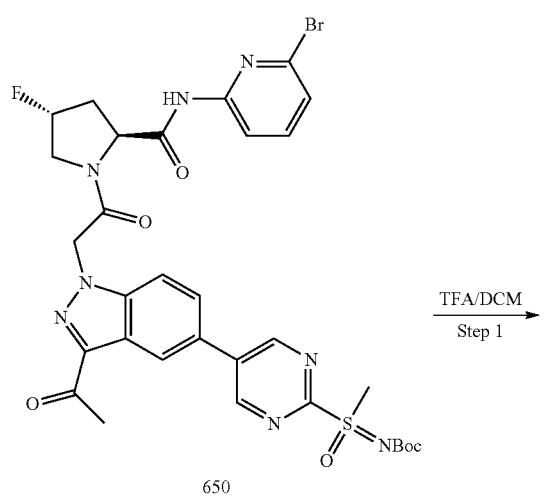
650

TFA/DCM
Step 1 →

Scheme 314

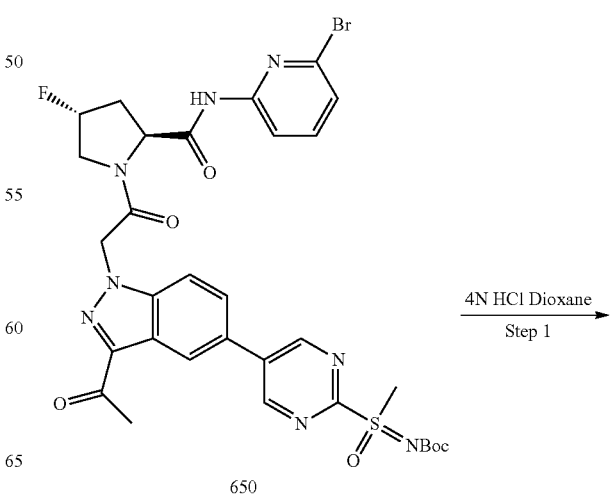
650

4N HCl Dioxane
Step 1 →

-continued

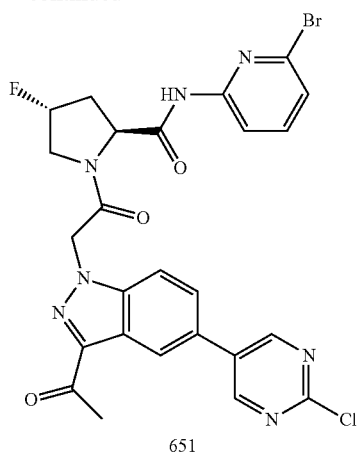

651

To a solution of compound S1 (1 equiv) under an atmosphere of nitrogen was added 4N HCl dioxane (10 vol). The reaction mixture was stirred at room temperature for 1 h and then concentrated to give compound 651. $^1$H NMR (400 MHz, DMSO-$d_6$) δ 2.08-2.26 (m, 1H), 2.54-2.62 (m, 1H), 2.66 (s, 3H), 3.97-4.13 (m, 1H), 4.24 (dd, J=12.5, 22.3 Hz, 1H), 4.63-4.72 (m, 1H), 5.48-5.73 (m, 2H), 5.86 (d, J=17.3 Hz, 1H), 7.30-7.35 (m, 1H), 7.71 (t, J=8.0 Hz, 1H), 7.88-7.94 (m, 2H), 8.03 (d, J=8.2 Hz, 1H), 8.49 (s, 1H), 9.15 (s, 2H), 11.02 (s, 1H). $^{19}$F NMR (376 MHz, DMSO-$d_6$): δ −175.65. LC (method A): $t_R$=2.05 min. LC/MS (EI) m/z: [M+H]$^+$ 600.

(2S,4S)-1-(2-(3-Acetyl-5-(2-methylpyrimidin-5-yl)-1H-indazol-1-yl)acetyl)-N-(6-bromopyridin-2-yl)-4-((dimethylamino)methyl)-4-fluoropyrrolidine-2-carboxamide (639)

Scheme 315

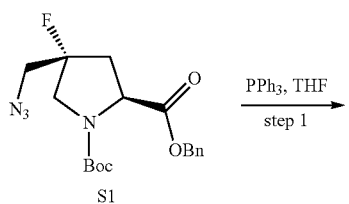

S1

PPh$_3$, THF
step 1

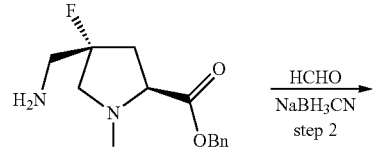

S2

HCHO
NaBH$_3$CN
step 2

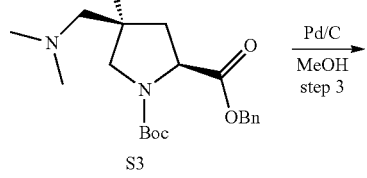

S3

Pd/C
MeOH
step 3

-continued

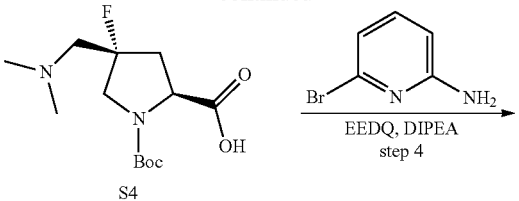

S4

EEDQ, DIPEA
step 4

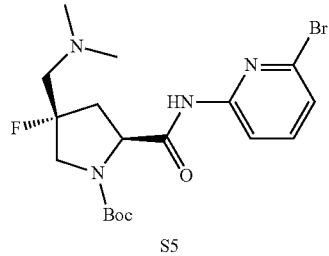

S5

TFA/DCM

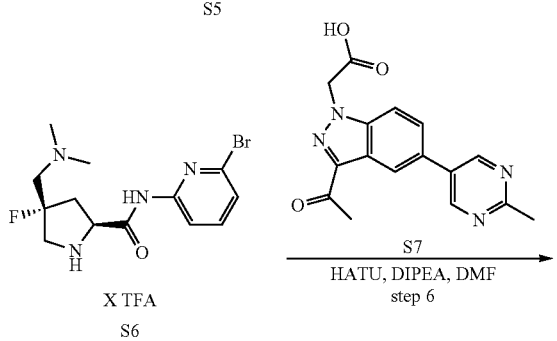

S6 · X TFA

S7

HATU, DIPEA, DMF
step 6

639

Step 1: (2S,4S)-2-Benzyl 1-tert-butyl 4-(aminomethyl)-4-fluoropyrrolidine-1,2-dicarboxylate (S2)

To a solution of (2S,4R)-2-benzyl 1-tert-butyl 4-(azidomethyl)-4-fluoropyrrolidine-1,2-dicarboxylate (300 mg, 0.79 mmol) in THF (5 mL) was added a solution of PPh$_3$ (250 mg, 0.95 mmol) in THF/water (2 mL/0.5 mL) at 0° C. The reaction was stirred at room temperature for 16 hrs. The mixture was partitioned with EtOAc and water and the organic layer was washed with brine, dried over anhydrous Na$_2$SO$_4$, filtered and concentrated under reduced pressure. The residue was purified by column chromatography on silica gel (DCM:MeOH=20:1) to give compound S2 (250 mg, 89.9% yield) as a yellow oil. LC/MS (ESI) m/z: 353 (M+H)$^+$.

Step 2: (2S,4S)-2-Benzyl 1-tert-butyl 4-((dimethyl-amino)methyl)-4-fluoropyrrolidine-1,2-dicarboxylate (S3)

To a mixture of (2S,4S)-2-benzyl 1-tert-butyl 4-(aminomethyl)-4-fluoropyrrolidine-1,2-dicarboxylate (250 mg, 0.71 mmol) and formaldehyde (213 mg, 7.1 mmol) in MeOH (6 mL) was added NaBH$_3$CN (147 mg, 2.3 mmol) and AcOH (84 mg, 1.4 mmol) at 0° C. The reaction mixture was stirred at room temperature overnight. The mixture was diluted with EtOAc and washed with 5% aq. NaHCO$_3$ solution and brine, dried over anhydrous Na$_2$SO$_4$ and concentrated under reduced pressure. The residue was purified by column chromatography on silica gel (PE:EtOAc=3:1 to 1:2) to give compound S3 (210 mg, 77.8% yield) as a light oil. LC/MS (ESI) m/z: 381 (M+H)$^+$.

Step 3: (2S,4S)-1-(tert-Butoxycarbonyl)-4-((dimethylamino)methyl)-4-fluoropyrrolidine-2-carboxylic acid (S4)

To a solution of (2S,4S)-2-benzyl 1-tert-butyl 4-((dimethylamino)methyl)-4-fluoropyrrolidine-1,2-dicarboxylate (210 mg, 0.55 mmol) in MeOH (3 mL) was added 10% Pd/C (21 mg). The mixture was degassed under N$_2$ for three times and stirred under a H$_2$ atmosphere for 3 hrs at room temperature. The mixture was filtered and the filtrate was evaporated under reduced pressure to give compound S4 (180 mg, 100% yield) as a yellow oil, which was directly used to the next reaction without further purification. LC/MS (ESI) m/z: 291 (M+H)$^+$.

Step 4: (2S,4S)-tert-Butyl 2-((6-bromopyridin-2-yl)carbamoyl)-4-((dimethylamino)methyl)-4-fluoropyrrolidine-1-carboxylate (S5)

To a mixture of (2S,4S)-1-(tert-butoxycarbonyl)-4-((dimethylamino)methyl)-4-fluoropyrrolidine-2-carboxylic acid (40 mg, 0.14 mmol), 6-bromopyridin-2-amine (26 mg, 0.15 mmol) and EEDQ (69 mg, 0.28 mmol) in DCE (3 mL) was added DIPEA (0.07 mL, 0.42 mmol). The reaction was stirred at 90° C. overnight. The mixture was evaporated under reduced pressure and the residue was purified by column chromatography on silica gel (PE:EtOAc=2:1 to 1:2) to give compound 5 (35 mg, 56.4% yield) as a light oil. LC/MS (ESI) m/z: 445 (M+H)$^+$.

Step 5: (2S,4R)—N-(6-Bromopyridin-2-yl)-4-((dimethylamino)methyl)-4-fluoropyrrolidine-2-carboxamide (S6)

To a solution of (2S,4S)-tert-butyl 2-((6-bromopyridin-2-yl)carbamoyl)-4-((dimethylamino) methyl)-4-fluoropyrrolidine-1-carboxylate (35 mg) in DCM (3 mL) was added TFA (1 mL) at 0° C. The reaction was stirred at room temperature for 1 hr. The mixture was evaporated under reduced pressure to give compound S6 (30 mg, 100% yield), which was used in the next step without further purification. LC/MS (ESI) m/z: 345 (M+H)$^+$.

Step 6: (2S,4S)-1-(2-(3-Acetyl-5-(2-methylpyrimidin-5-yl)-1H-indazol-1-yl)acetyl)-N-(6-bromopyridin-2-yl)-4-((dimethylamino)methyl)-4-fluoropyrrolidine-2-carboxamide (639)

To a mixture of compound S6 (30 mg, 0.09 mmol), 2-(3-acetyl-5-(2-methylpyrimidin-5-yl)-1H-indazol-1-yl) acetic acid (28.0 mg, 0.09 mmol) and HATU (51.3 mg, 0.14 mmol) in DMF was added DIPEA (0.04 mL, 0.27 mmol). The reaction mixture was stirred at room temperature overnight. The mixture was diluted with EtOAc and washed with 10% aq. LiCl solution and brine. The organic layer was dried over Na$_2$SO$_4$ and concentrated under reduced pressure. The residue was purified by prep HPLC to give 639 (8.0 mg, 13.9% yield) as a white solid. $^1$HNMR (400 MHz, DMSO-d$_6$) δ 10.99 (s, 1H), 9.03 (s, 2H), 8.42 (d, J=1.0 Hz, 1H), 8.02 (d, J=8.2 Hz, 1H), 7.88-7.82 (m, 2H), 7.70 (t, J=8.0 Hz, 1H), 7.32 (d, J=7.3 Hz, 1H), 5.85 (d, J=17.3 Hz, 1H), 5.63 (d, J=17.3 Hz, 1H), 4.70-4.63 (m, 1H), 4.24 (m, 1H), 4.01 (m, 1H), 2.77 (m, 2H), 2.68 (s, 3H), 2.63 (s, 3H), 2.35-2.25 (m, 6H), 2.23-2.05 (m, 2H). LC/MS (ESI) m/z: 637 (M+H)$^+$.

(2S,4S)-1-(2-(3-Acetyl-5-(2-methylpyrimidin-5-yl)-1H-indazol-1-yl)acetyl)-N-(6-bromo-3-methylpyridin-2-yl)-4-((dimethylamino)methyl)-4-fluoropyrrolidine-2-carboxamide (645)

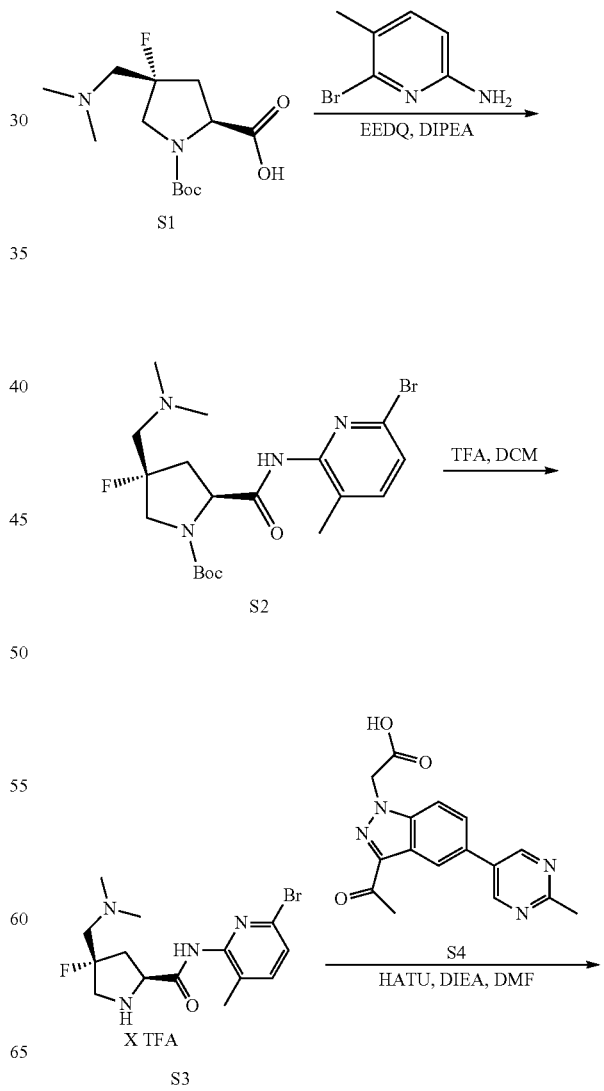

Scheme 316

-continued

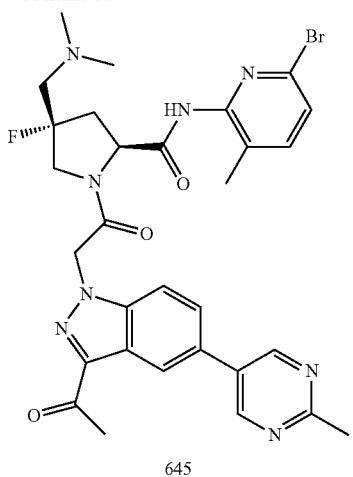 [SMILES: CC(=O)c1nn(CC(=O)N2C[C@@](F)(CN(C)C)C[C@H]2C(=O)Nc2cccc(Br)n2)c2ccc(-c3cnc(C)nc3)cc12]

645

The titled compound was prepared according to the procedure from Scheme 314 from appropriate starting materials. ¹HNMR (400 MHz, CD₃OD) δ 9.00 (s, 2H), 8.54 (s, 1H), 7.77 (s, 2H), 7.53 (d, J=8.0 Hz, 1H), 7.37 (d, J=8.0 Hz, 1H), 5.69 (d, J=17.0 Hz, 1H), 5.53 (d, J=17.1 Hz, 1H), 4.36-4.27 (m, 1H), 4.06-3.95 (m, 1H), 2.86 (m, 1H), 2.75 (s, 3H), 2.69 (s, 3H), 2.42 (s, 6H), 2.36-2.23 (m, 2H), 2.10 (s, 3H), 1.40-1.28 (m, 2H). LC/MS (ESI) m/z: 651 (M+H)⁺.

(2S,4S)-1-(2-(3-Acetyl-5-(2-methylpyrimidin-5-yl)-1H-indazol-1-yl)acetyl)-N-(6-bromo-3-cyclopropylpyridin-2-yl)-4-((dimethylamino)methyl)-4-fluoropyrrolidine-2-carboxamide (733)

Scheme 317

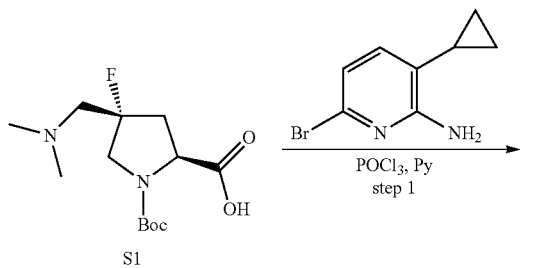

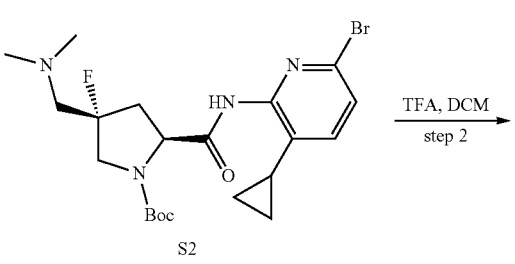

-continued

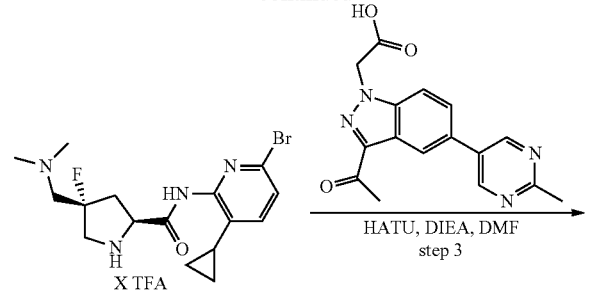

733

Step 1: (2S,4S)-tert-Butyl 2-((6-bromo-3-cyclopropylpyridin-2-yl)carbamoyl)-4-((dimethylamino)methyl)-4-fluoropyrrolidine-1-carboxylate (S2)

To a mixture of (2S,4S)-1-(tert-butoxycarbonyl)-4-((dimethylamino)methyl)-4-fluoropyrrolidine-2-carboxylic acid (90 mg, 0.31 mmol) and 6-bromo-3-cyclopropylpyridin-2-amine (66 mg, 0.31 mmol) in dry DCM (5 mL) was added pyridine (0.12 mL, 1.55 mmol) followed by drop-wise addition of POCl₃/DCM solution (0.03 mL in 1 mL of DCM) at 0° C. The reaction was stirred at room temperature for 30 min. The mixture was poured into ice water (10 mL) and extracted with DCM (2×5 mL). The combined organic layers are washed with brine, dried over anhydrous Na₂SO₄ and evaporated under reduced pressure. The residue was purified by column chromatography on silica gel (PE:EtOAc=5:1 to 1:1) to give compound 2 (40 mg, 26.7% yield) as a light oil. LC/MS (ESI) m/z: 485 (M+H)⁺.

Step 2: (2S,4R)—N-(6-Bromo-3-cyclopropylpyridin-2-yl)-4-((dimethylamino)methyl)-4-fluoropyrrolidine-2-carboxamide (S3)

To a solution of (2S,4S)-tert-butyl 2-((6-bromo-3-cyclopropylpyridin-2-yl)carbamoyl)-4-((dimethylamino)methyl)-4-fluoropyrrolidine-1-carboxylate (40 mg) in DCM (3 mL) was added TFA (1 mL) at 0° C. The reaction was stirred at room temperature for 1 hr. The mixture was concentrated to dryness to give compound 3 (35 mg, 100% yield) as a yellow solid, which was directly used to the next reaction without further purification. LC/MS (ESI) m/z: 385 (M+H)⁺.

Step 3: (2S,4S)-1-(2-(3-Acetyl-5-(2-methylpyrimidin-5-yl)-1H-indazol-1-yl)acetyl)-N-(6-bromo-3-cyclopropylpyridin-2-yl)-4-((dimethylamino)methyl)-4-fluoropyrrolidine-2-carboxamide (733)

The titled compound was prepared according to the procedure for Scheme 314 from appropriate starting materials. $^1$HNMR (400 MHz, DMSO-$d_6$) δ 10.41 (s, 1H), 9.04 (s, 2H), 8.43 (s, 1H), 7.90-7.79 (m, 2H), 7.39 (d, J=8.1 Hz, 1H), 7.29 (d, J=8.2 Hz, 1H), 5.85 (d, J=17.3 Hz, 1H), 5.60 (d, J=17.2 Hz, 1H), 4.64 (t, J=8.5 Hz, 1H), 4.26 (m, 1H), 4.06-3.94 (m, 1H), 2.84 (s, 2H), 2.69 (s, 3H), 2.64 (s, 3H), 2.31 (s, 6H), 2.24-2.11 (m, 1H), 1.80 (m, 1H), 0.74-0.65 (m, 2H), 0.58-0.43 (m, 2H). LC/MS (ESI) m/z: 677 (M+H)$^+$.

(1R,3S,4R)-2-(2-(3-Acetyl-5-(2-methylpyrimidin-5-yl)-1H-indazol-1-yl)acetyl)-N-(6-bromopyridin-2-yl)-2-azabicyclo[2.2.2]octane-3-carboxamide (734)

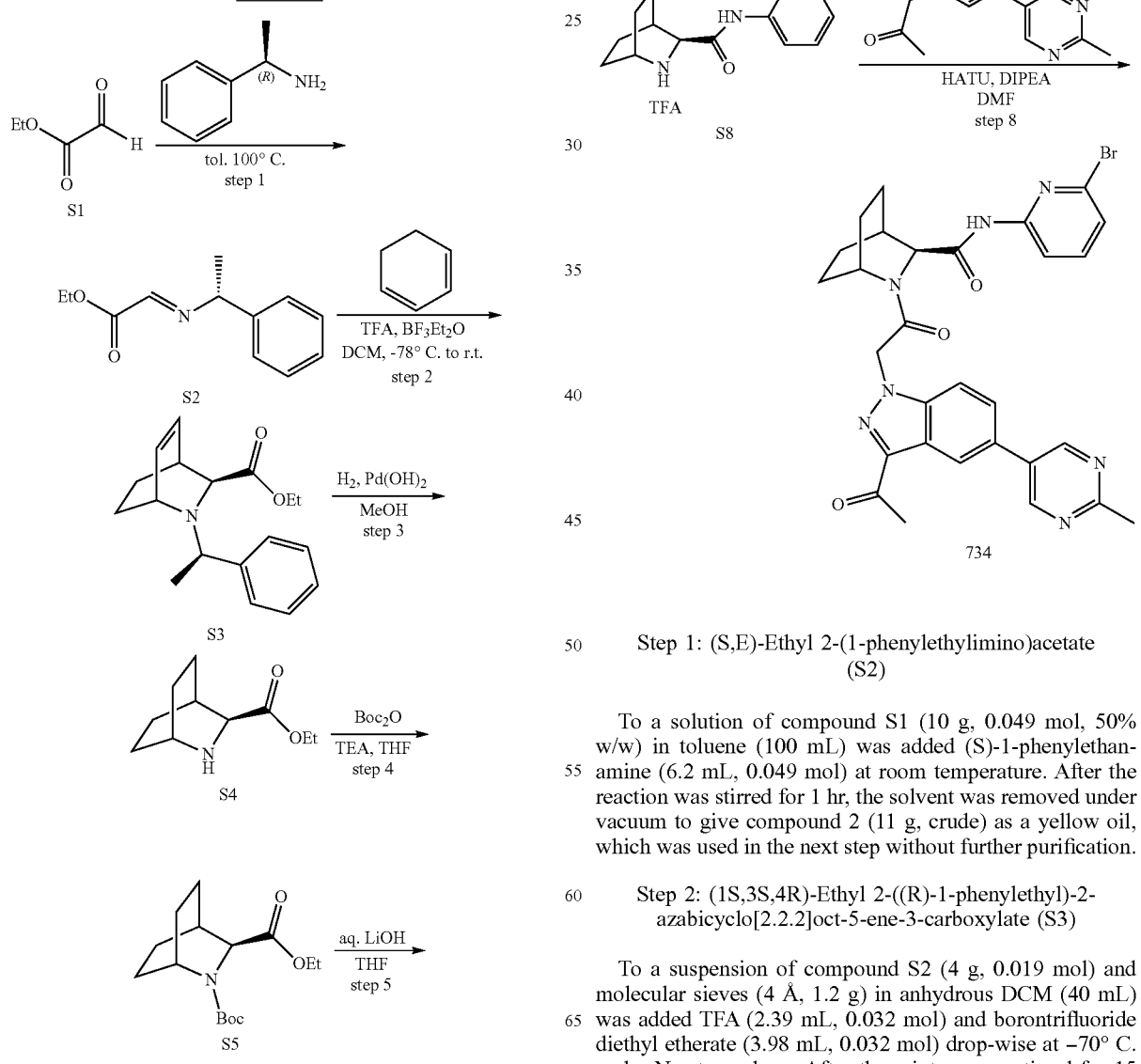

Step 1: (S,E)-Ethyl 2-(1-phenylethylimino)acetate (S2)

To a solution of compound S1 (10 g, 0.049 mol, 50% w/w) in toluene (100 mL) was added (S)-1-phenylethanamine (6.2 mL, 0.049 mol) at room temperature. After the reaction was stirred for 1 hr, the solvent was removed under vacuum to give compound 2 (11 g, crude) as a yellow oil, which was used in the next step without further purification.

Step 2: (1S,3S,4R)-Ethyl 2-((R)-1-phenylethyl)-2-azabicyclo[2.2.2]oct-5-ene-3-carboxylate (S3)

To a suspension of compound S2 (4 g, 0.019 mol) and molecular sieves (4 Å, 1.2 g) in anhydrous DCM (40 mL) was added TFA (2.39 mL, 0.032 mol) and borontrifluoride diethyl etherate (3.98 mL, 0.032 mol) drop-wise at −70° C. under $N_2$ atmosphere. After the mixture was stirred for 15 minutes, cyclohexadiene (3.07 mL, 0.032 mL) was added drop-wise. The reaction was stirred at room temperature overnight. The mixture was washed with saturated aqueous NaHCO$_3$ solution. The separated organic layer was extracted with 3N HCl. The combined aqueous layers are basified with saturated aqueous NaHCO$_3$, and then extracted with ethyl acetate. The combined organic layers are washed with brine, dried over anhydrous Na$_2$SO$_4$, filtered and concentrated. The residue was purified by silica gel column chromatography (PE/EtOAc=6/1) to give compound S3 (2 g, 35.9% yield) as a yellow oil.

Step 3: (S)-Ethyl 2-azabicyclo[2.2.2]octane-3-carboxylate (S4)

To a solution of compound 3 (1.2 g, 4.211 mmol) in EtOH (10 mL) was added Pd(OH)$_2$ (100 mg, 10% wt). The reaction was stirred at room temperature for 2 hrs under a H$_2$ atmosphere. The mixture was filtered and the filtrate was evaporated to dryness to give compound 4 (700 mg, 90.9% yield) as a colorless oil. LC/MS (ESI) m/z: 184 (M+H)$^+$.

Step 4: (S)-2-tert-Butyl 3-ethyl 2-azabicyclo[2.2.2]octane-2,3-dicarboxylate (S5)

To a solution of compound S4 (700 mg, 3.86 mmol) in DCM (10 mL) was added Et$_3$N (1.6 mL, 11.58 mmol), DMAP (47 mg, 0.386 mmol) and Boc$_2$O (1.26 g, 5.790 mmol). The reaction was stirred at room temperature overnight. The mixture was diluted with DCM and washed with brine, dried over anhydrous Na$_2$SO$_4$, filtered and concentrated to dryness. The residue was purified by column chromatography on silica gel (eluted with PE/EtOAc=100:1 to 50:1) to give compound 5 (600 mg, 55.0% yield) as a white solid. LC/MS (ESI) m/z: 284 (M+H)$^+$.

Step 5: (S)-2-(tert-Butoxycarbonyl)-2-azabicyclo[2.2.2]octane-3-carboxylic acid (S6)

To a solution of compound 5 (600 mg, 2.12 mmol) in THF (10 mL)/MeOH (5 mL)/water (5 mL) was added NaOH (153 mg, 6.36 mmol). The reaction was stirred at room temperature overnight. The mixture was concentrated and diluted with water, washed with ether twice. The aqueous layer was acidified with 1 N aq. HCl to pH-3 and extracted with EtOAc twice. The combined organic layers are washed with brine, dried over anhydrous Na$_2$SO$_4$, filtered and concentrated to give compound 6 (460 mg, 85.2% yield) as a colorless oil. LC/MS (ESI) m/z: 200 (M+H−56)$^+$.

Step 6: (S)-tert-Butyl 3-(6-bromopyridin-2-ylcarbamoyl)-2-azabicyclo[2.2.2]octane-2-carboxylate (S7)

To a solution of compound S6 (230 mg, 0.90 mmol) in DCE (5 mL) was added EEDQ (446 mg, 1.80 mmol), DIPEA (0.60 mL, 3.60 mmol) and 6-bromopyridin-2-amine (156 mg, 0.90 mmol). The reaction was stirred at 90° C. for 16 hrs and cooled to room temperature. The mixture was concentrated to dryness and the residue was purified by column chromatography on silica gel (eluted with petroleum ether:Ethyl acetate=30:1 to 20:1) to give compound 7 (67 mg, 18.2% yield) as a white solid. LC/MS (ESI) m/z: 410 (M+H)$^+$.

Step 7: (S)—N-(6-Bromopyridin-2-yl)-2-azabicyclo[2.2.2]octane-3-carboxamide (S8)

A solution of compound S7 (67 mg, 0.1638 mmol) in HCl/dioxane solution (1 mL, 1M) was stirred at room temperature for 1 hr. The reaction mixture was concentrated to give crude compound 8 (60 mg, 90.5% yield) as a yellow solid, which was used in the next step without purification. LC/MS (ESI) m/z: 310 (M+H)$^+$.

Step 8: (S)-2-(2-(3-Acetyl-5-(2-methylpyrimidin-5-yl)-1H-indazol-1-yl)acetyl)-N-(6-bromopyridin-2-yl)-2-azabicyclo[2.2.2]octane-3-carboxamide (734)

To a mixture of compound S8 (60 mg, 0.159 mmol) and 2-(3-acetyl-5-(2-methylpyrimidin-5-yl)-1H-indazol-1-yl)acetic acid (54 mg, 0.17 mmol) in DMF (3 mL) was added DIPEA (0.08 mL, 0.47 mmol) and HATU (90.6 mg, 0.24 mmol). The reaction was stirred at room temperature for 16 hrs. The mixture was diluted with EtOAc and washed with 10% aq. LiCl solution and brine. The organic layer was dried over anhydrous Na$_2$SO$_4$ and concentrated. The residue was purified by prep HPLC to give the titled compound (6.3 mg, 6.6% yield) as a white solid. $^1$HNMR (400 MHz, CDCl$_3$) δ 8.90 (s, 2H), 8.56 (s, 1H), 8.27 (s, 1H), 8.16 (d, J=8.2 Hz, 1H), 7.65 (d, J=1.1 Hz, 2H), 7.53 (t, J=7.9 Hz, 1H), 7.20 (d, J=7.6 Hz, 1H), 5.43 (q, J=16.0 Hz, 2H), 4.40 (s, 1H), 4.20 (s, 1H), 2.80 (s, 3H), 2.73 (s, 3H), 2.39 (s, 1H), 2.22 (m, 1H), 1.94-1.77 (m, 6H), 1.25 (s, 1H). LC/MS (ESI) m/z: 602 (M+H)$^+$.

(2S,4R)-1-(2-(3-Acetyl-5-(1H-benzo[d]imidazol-2-yl)-1H-indazol-1-yl)acetyl)-N-(6-bromopyridin-2-yl)-4-fluoropyrrolidine-2-carboxamide (735)

Scheme 319

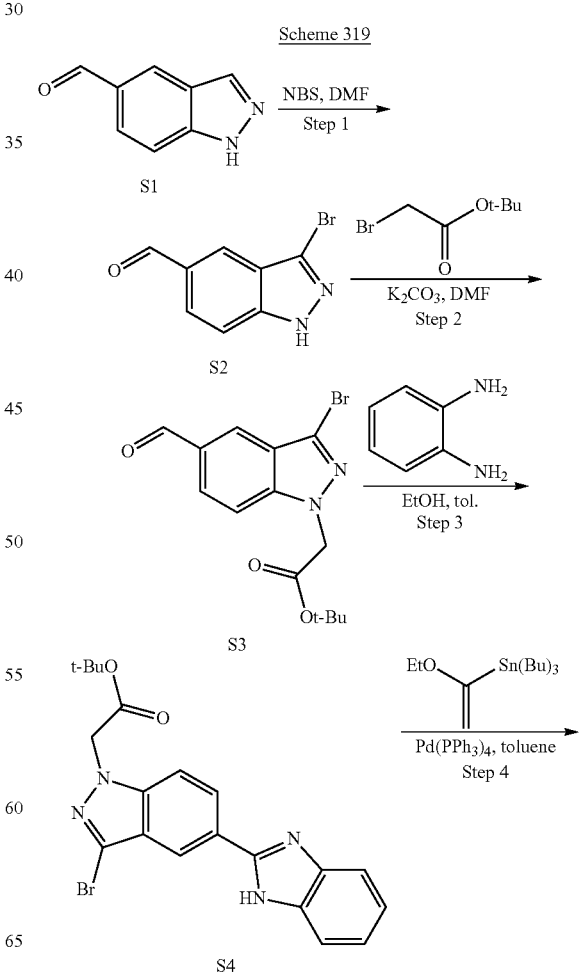

-continued

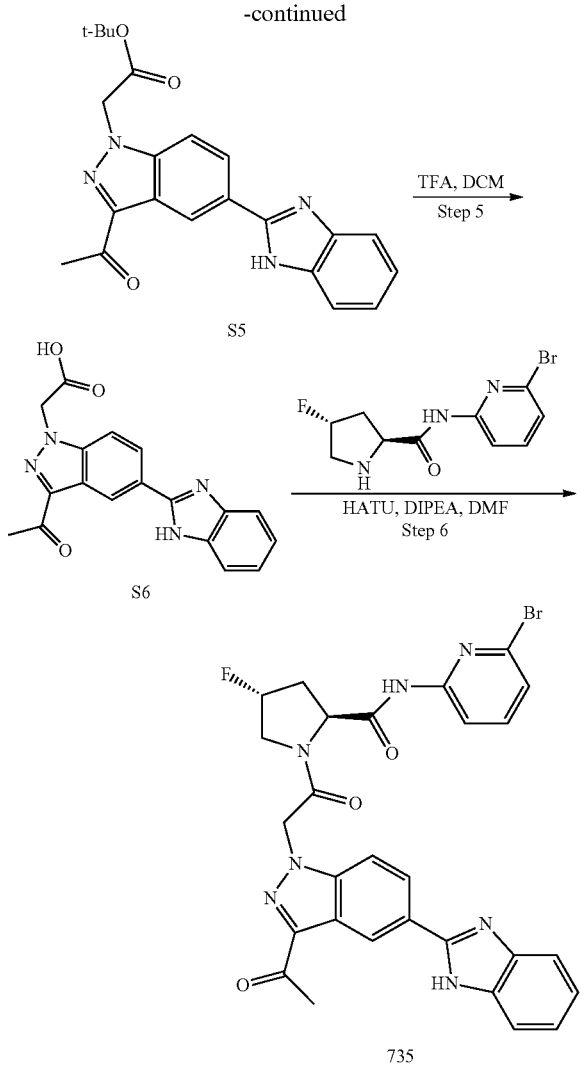

Step 1: 3-Bromo-1H-indazole-5-carbaldehyde (S2)

To a solution of 1H-indazole-5-carbaldehyde (1 g, 6.85 mmol) in toluene (15 mL) was added NBS (1.46 g, 8.22 mmol) at 0° C. After the reaction was stirred at room temperature overnight, the reaction mixture was cooled to 0° C. The solid precipitated was collected by filtration, washed with MeCN and water, and dried to afford compound S2 (1.3 g, 70.9% yield) as a white solid. LC/MS (ESI) m/z: 224 (M+H)$^+$.

Step 2: tert-Butyl 2-(3-bromo-5-formyl-1H-indazol-1-yl)acetate (S3)

To a solution of 3-bromo-1H-indazole-5-carbaldehyde (1.3 g, 5.83 mmol) in DMF (15 mL) was added K$_2$CO$_3$ (1.61 g, 11.66 mmol) and tert-butyl 2-bromoacetate (1.37 g, 7.00 mmol) at 0° C. The reaction was stirred at room temperature overnight. The mixture was diluted with EtOAc and washed with water and brine. The organic layer was dried over anhydrous Na$_2$SO$_4$, filtered and concentrated. The residue was purified by column chromatography on silica gel (eluted with Petroleum ether:Ethyl acetate=5:1) to give compound S3 (1.1 g, 55.83% yield) as a white solid. LC/MS (ESI) m/z: 339 (M+H)$^+$.

Step 3: tert-Butyl 2-(5-(1H-benzo[d]imidazol-2-yl)-3-bromo-1H-indazol-1-yl)acetate (S4)

To a solution of tert-butyl 2-(3-bromo-5-formyl-1H-indazol-1-yl)acetate (500 mg, 1.48 mmol) in EtOH (6 mL) and toluene (6 mL) was added benzene-1,2-diamine (799.2 mg, 7.4 mmol) at 0° C. The reaction was stirred at 100° C. overnight. The mixture was concentrated and diluted with EtOAc, washed with diluted aq. HCl and brine. The organic layer was dried over anhydrous Na$_2$SO$_4$, filtered and concentrated. The residue was purified by column chromatography on silica gel (eluted with Petroleum ether:Ethyl acetate=5:1) to afford compound S4 (260 mg, 40.1% yield) as a yellow solid. LC/MS (ESI) m/z: 427 (M+H)$^+$.

Step 4: tert-Butyl 2-(3-acetyl-5-(1H-benzo[d]imidazol-2-yl)-1H-indazol-1-yl)acetate (S5)

To a solution of tert-butyl 2-(5-(1H-benzo[d]imidazol-2-yl)-3-bromo-1H-indazol-1-yl)acetate (110 mg, 0.26 mmol) in toluene (6 mL) was added tributyl(1-ethoxyvinyl)stannane (140 mg, 0.39 mmol) and Pd(PPh$_3$)$_4$ (5 mg) at 0° C. The reaction was degassed under N$_2$ atmosphere and stirred at 100° C. overnight under N$_2$ atmosphere protection. The mixture was diluted with EtOAc and washed with 1 N aq. HCl twice. The organic phase was dried over anhydrous Na$_2$SO$_4$, filtered and concentrated. The residue was purified by column chromatography on silica gel (eluted with Petroleum ether:Ethyl acetate=3:1) to afford compound S5 (50 mg, 49.3% yield) as a yellow solid. LC/MS (ESI) m/z: 391 (M+H−56)$^+$.

Step 5: 2-(3-Acetyl-5-(1H-benzo[d]imidazol-2-yl)-1H-indazol-1-yl)acetic acid (S6)

To a solution of tert-butyl 2-(3-acetyl-5-(1H-benzo[d]imidazol-2-yl)-1H-indazol-1-yl)acetate (50 mg, 0.13 mmol) in DCM (3 mL) was added TFA (1 mL) at 0° C. The reaction was stirred at room temperature for 1 hr. The mixture was concentrated to dryness to give compound S6 (45 mg, 100% yield) as a brown solid, which was directly used to the next reaction without further purification. LC/MS (ESI) m/z: 335 (M+H)$^+$.

Step 6: (2S,4R)-1-(2-(3-Acetyl-5-(1H-benzo[d]imidazol-2-yl)-1H-indazol-1-yl)acetyl)-N-(6-bromopyridin-2-yl)-4-fluoropyrrolidine-2-carboxamide (735)

To a mixture of 2-(3-acetyl-5-(1H-benzo[d]imidazol-2-yl)-1H-indazol-1-yl)acetic acid (45 mg, 0.13 mmol), (2S,4R)—N-(6-bromopyridin-2-yl)-4-fluoropyrrolidine-2-carboxamide (37.3 mg, 0.13 mmol) and HATU (76 mg, 0.20 mmol) in DMF (2 mL) was added DIPEA (0.09 mL, 0.52 mmol) at 0° C. The reaction was stirred at room temperature overnight. The mixture was diluted with EtOAc and washed with 10% aq. LiCl solution and brine. The organic layer was dried over anhydrous Na$_2$SO$_4$, filtered and concentrate. The residue was purified by silica gel column chromatography (DCM:MeOH=40:1) to give the titled compound (8.0 mg, 13.9% yield) as a white solid. $^1$H NMR (400 MHz, DMSO-d$_6$) δ 9.01 (s, 1H), 8.34 (dd, J=8.9, 1.6 Hz, 1H), 8.03 (d, J=8.0 Hz, 1H), 7.85 (t, J=8.8 Hz, 1H), 7.61 (s, 2H), 7.32 (d, J=7.6 Hz, 1H), 7.21 (dd, J=5.8, 3.1 Hz, 2H), 5.85 (d, J=17.6 Hz, 1H), 5.65 (d, J=17.1 Hz, 1H), 4.64 (t, J=8.8, 1H), 4.22-4.28 (m, 1H), 4.09-3.96 (m, 1H), 3.14 (dd, J=7.5, 4.2

Hz, 1H), 2.67 (s, 3H), 2.32 (m, 1H), 2.21-2.08 (m, 1H), 0.85 (t, J=6.4 Hz, 1H). LC/MS (ESI) m/z: 604 (M+H)⁺.

(2S,4R)-1-(2-(3-Acetyl-5-(2-methylpyrimidin-5-yl)-1H-indazol-1-yl)acetyl-N-(6-bromo-4-methoxypyridine-2-yl)-4-fluoropyrrolidine-2-carboxamide (351)

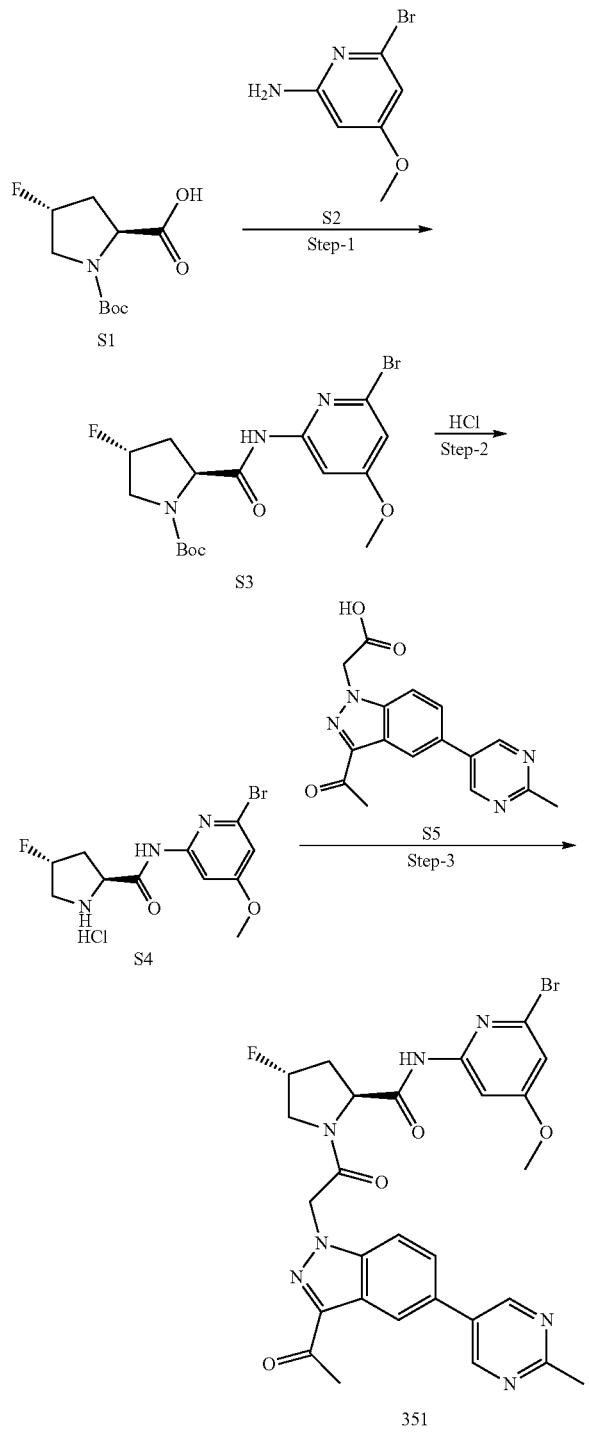

Scheme 320

351

Step-1: Tert-Butyl-(2S,4R)-2-((6-bromo-4-methoxypyridine-2-yl) carbamoyl-4-fluoropyrrolidine-1-carboxylate (S3)

To an ice cold solution of (2S, 4R)-1-(tert-butoxycarbonyl)-4-fluoropyrrolidine-2-carboxylic acid (250 mg, 1.1 mmole) in 6 mL of CH2Cl2, 1-chloro-N,N,2-trimethylprop-1-en-1-amine (0.15 mL, 1.1 equiv) was added drop-wise with stirring. The stirring was continued for 3 hours at the same temperature. Then 6-bromo-4-methoxypyridin-2-amine (239 mg, 1.0 equiv) was added, followed by 0.50 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 436 mg (97%) of tert-butyl-(2S,4R)-2-((6-bromo-4-methoxypyridine-2-yl) carbamoyl-4-fluoropyrrolidine-1-carboxylate as clear oil.

Step-2: (2S,4R)—N-(6-Bromo-4-methoxypyridine-2-yl)-4-fluoropyrrolidine-2-carboxamide (S4)

Tert-butyl-(2S,4R)-2-((6-bromo-4-methoxypyridine-2-yl) carbamoyl-4-fluoropyrrolidine-1-carboxylate was added dissolve in 10 ml of 4N HCl in Dioxane. The resulting solution was stirred at room temperature for a 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl-N-(6-bromo-4-methoxypyridine-2-yl)-4-fluoropyrrolidine-2-carboxamide (351)

To a stirred solution of (2S,4R)—N-(6-bromo-4-methoxypyridine-2-yl)-4-fluoropyrrolidine-2-carboxamide (HCl salt, 54 mg) in DMF (5 mL) was added S5 (47 mg), HATU (82 mg, 1.2 equiv), and DIEA (0.1 mL, 3 equiv). The reaction was stirred at room temperature for a couple of hours. It was then diluted with EtOAC (15 mL), and water (10 mL). The organic layer was washed with brine (3×15 mL), dried over Na₂SO₄ and concentrated in vacuum. The resulting oil was purified by ISCO (silica gel, eluted with 10% MeOH in DCM gradient) and yielded 50 mg (54%) of titled compound. ¹H NMR (400 MHz, DMSO-d₆): (major rotamer) δ 2.03-2.27 (m, 1H), 2.52-2.64 (m, 1H), 2.65 (s, 3H), 2.69 (s, 3H), 3.82 (s, 3H), 3.94-4.09 (m, 1H), 4.18-4.29 (m, 1H), 4.66 (t, 1H, J=8.56 Hz), 5.05-5.21 (m, 1H), 5.49-5.88 (m, 3H), 6.98 (s, 1H), 7.65 (s, 1H), 7.74-7.86 (m, 1H), 7.88 (s, 1H), 8.43 (s, 1H), 9.05 (s, 2H), 10.97 (s, 1H); ¹⁹F NMR (376 MHz, DMSO-d₆ 300K): (major rotamer) δ −175.7. LC (method A): t$_R$=1.74 min. LC/MS (EI) m/z: [M]+ 610.

(2S,4R)-1-(2-(3-Acetyl-5-(2-methylpyrimidin-5-yl)-1H-indazol-1-yl)acetyl)-4-fluoro-N-(4-(2,2,2-trifluoroethyl)thiazol-2-yl)pyrrolidine-2-carboxamide (355)

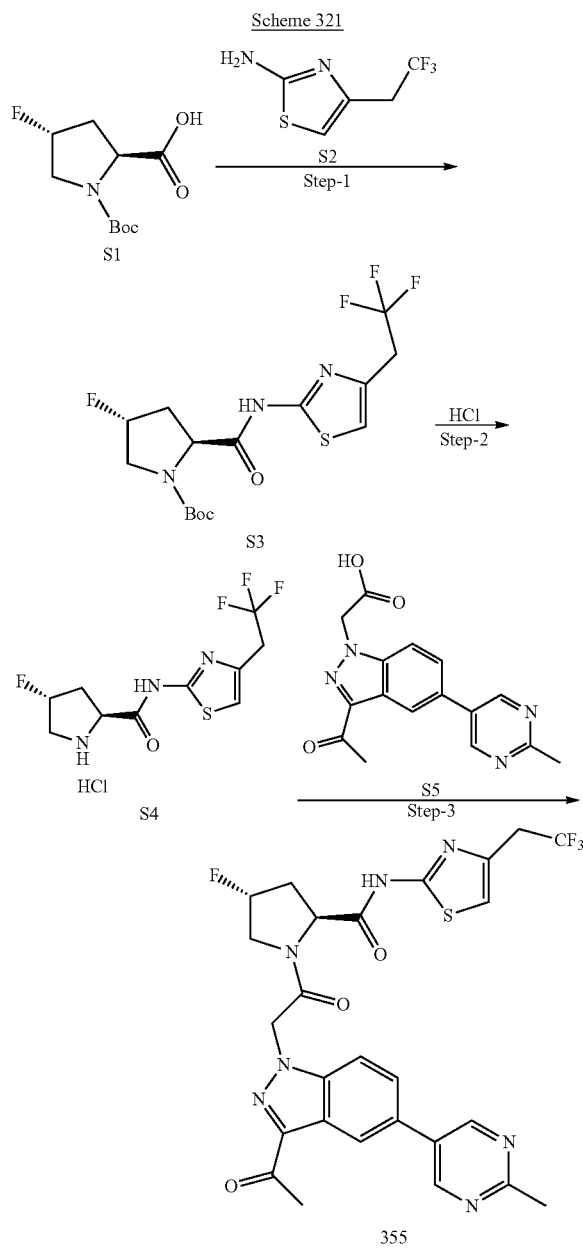

Step-1: tert-Butyl (2S,4R)-4-fluoro-2-((4-(2,2,2-trifluoroethyl)thiazol-2-yl)carbamoyl)pyrrolidine-1-carboxylate (S3)

To an ice cold solution of (2S, 4R)-1-(tert-butoxycarbonyl)-4-fluoropyrrolidine-2-carboxylic acid (250 mg, 1.1 mmole) in 6 mL of CH2Cl2, 1-chloro-N,N,2-trimethylprop-1-en-1-amine (0.15 mL, 1.1 equiv) was added drop-wise with stirring. The stirring was continued for 3 hours at the same temperature. Then 4-(2,2,2-trifluoroethyl)thiazol-2-amine (257 mg, 1.0 equiv) was added, followed by 0.50 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 357 mg of tert-butyl (2S,4R)-4-fluoro-2-((4-(2,2,2-trifluoroethyl)thiazol-2-yl)carbamoyl)pyrrolidine-1-carboxylate as yellow oil.

Step-2: (2S,4R)-4-Fluoro-N-(4-(2,2,2-trifluoroethyl)thiazol-2-yl)pyrrolidine-2-carboxamide (S4)

tert-butyl (2S,4R)-4-fluoro-2-((4-(2,2,2-trifluoroethyl)thiazol-2-yl)carbamoyl)pyrrolidine-1-carboxylate was added dissolve in 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(4-(2,2,2-trifluoroethyl)thiazol-2-yl)pyrrolidine-2-carboxamide (355)

To a stirred solution (2S,4R)-4-fluoro-N-(4-(2,2,2-trifluoroethyl)thiazol-2-yl)pyrrolidine-2-carboxamide (HCl salt, 80 mg) in DMF (10 mL) was added S5 (75 mg, 1 equiv.), HATU (109 mg, 1.2 equiv), and DIEA (0.21 mL, 5 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 79 mg (56%) of titled compound. $^1$H NMR (400 MHz, DMSO-d$_6$): (major rotamer) δ 2.09-2.27 (m, 1H), 2.52-2.64 (m, 1H), 2.65 (s, 3H), 2.69 (s, 3H), 3.62-3.73 (m, 2H), 3.97-4.13 (m, 1H), 4.20-4.31 (m, 1H), 4.64 (t, 1H, J=8.48 Hz), 5.48-5.88 (m, 3H), 7.15 (s, 1H), 7.88 (s, 2H), 8.43 (s, 1H), 9.04 (s, 2H), 12.41 (s, 1H); $^{19}$F NMR (376 MHz, DMSO-d$_6$300K): (major rotamer) δ −176.0 (1F), −63.7 (3F, CF3). LC (method A): t$_R$=1.66 min. LC/MS (EI) m/z: [M+H]$^+$ 590.

(2S,4R)-1-(2-(3-Acetyl-5-(2-methylpyrimidin-5-yl)-1H-indazol-1-yl)acetyl)-4-fluoro-N-(1-(2,2,2-trifluoroethyl)-1H-pyrazol-3-yl)pyrrolidine-2-carboxamide (357)

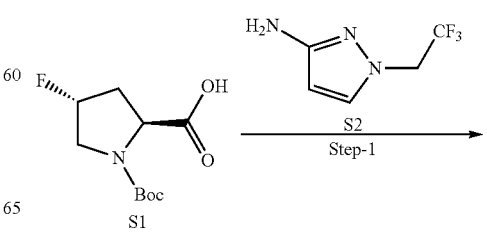

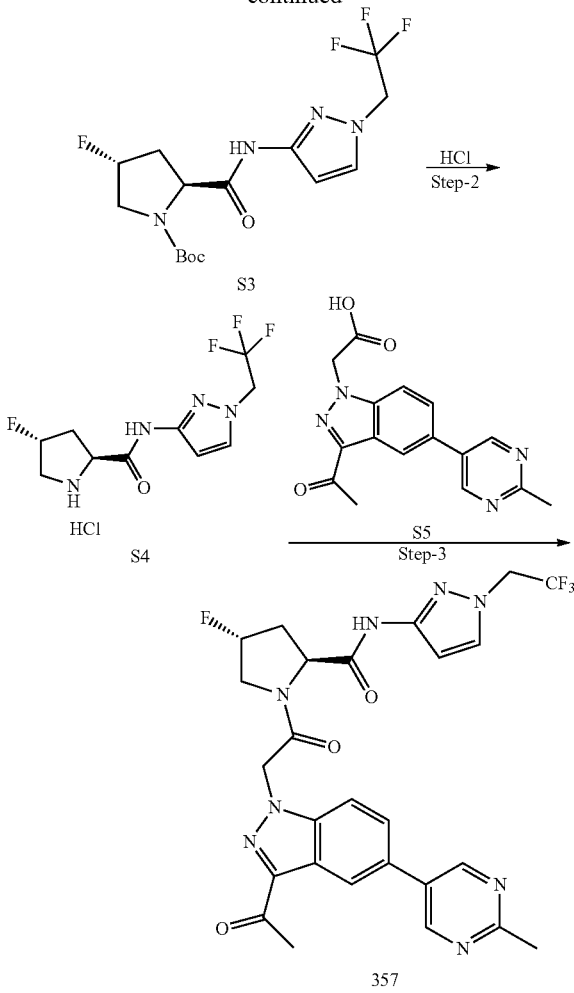

Step-1: tert-Butyl (2S,4R)-4-fluoro-2-((1-(2,2,2-trifluoroethyl)-1H-pyrazol-3-yl)carbamoyl)pyrrolidine-1-carboxylate (S3)

To an ice cold solution of (2S, 4R)-1-(tert-butoxycarbonyl)-4-fluoropyrrolidine-2-carboxylic acid (250 mg, 1.1 mmole) in 6 mL of CH2Cl2, 1-chloro-N,N,2-trimethylprop-1-en-1-amine (0.15 mL, 1.1 equiv) was added drop-wise with stirring. The stirring was continued for 3 hours at the same temperature. Then 1-(2,2,2-trifluoroethyl)-1H-pyrazol-3-amine (182 mg, 1.0 equiv) was added, followed by 0.50 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 350 mg of tert-butyl (2S,4R)-4-fluoro-2-((1-(2,2,2-trifluoroethyl)-1H-pyrazol-3-yl)carbamoyl)pyrrolidine-1-carboxylate as yellow oil.

Step-2: (2S,4R)-4-Fluoro-N-(1-(2,2,2-trifluoroethyl)-1H-pyrazol-3-yl)pyrrolidine-2-carboxamide (S4)

To tert-butyl (2S,4R)-4-fluoro-2-((1-(2,2,2-trifluoroethyl)-1H-pyrazol-3-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(1-(2,2,2-trifluoroethyl)-1H-pyrazol-3-yl)pyrrolidine-2-carboxamide (357)

To a stirred solution (2S,4R)-4-fluoro-N-(1-(2,2,2-trifluoroethyl)-1H-pyrazol-3-yl)pyrrolidine-2-carboxamide (HCl salt, 73 mg) in DMF (10 mL) was added S5 (71 mg, 1 equiv.), HATU (105 mg, 1.2 equiv), and DIEA (0.20 mL, 5 equiv). The reaction was stirred at room temperature for a couple of hours. It was then diluted with EtOAC (15 mL), and water (10 mL). The organic layer was washed with brine (3×15 mL), dried over $Na_2SO_4$ and concentrated in vacuuo. The resulting oil was purified by ISCO (silica gel, eluted with 10% MeOH in DCM gradient) and yielded 40 mg (31%) of titled compound. $^1$H NMR (400 MHz, DMSO-$d_6$): (major rotamer) δ 2.03-2.22 (m, 1H), 2.52-2.64 (m, 1H), 2.65 (s, 3H), 2.69 (s, 3H), 3.88-4.09 (m, 1H), 4.15-4.28 (m, 1H), 4.61 (t, 1H, J=8.7 Hz), 4.90-5.01 (m, 2H), 5.48-5.88 (m, 3H), 6.52 (s, 1H), 7.79 (s, 1H), 7.82 (s, 2H), 8.45 (s, 1H), 9.04 (s, 2H), 10.76 (s, 1H); $^{19}$F NMR (376 MHz, DMSO-$d_6$300K): (major rotamer) δ −175.9 (1F), −70.3 (3F, CF3). LC (method A): $t_R$=1.39 min. LC/MS (EI) m/z: [M+H]$^+$ 573.

(2S,4R)-1-(2-(3-Acetyl-5-(2-methylpyrimidin-5-yl)-1H-indazol-1-yl)acetyl)-N-(3-bromo-2-chlorophenyl)-4-fluoropyrrolidine-2-carboxamide (358)

Scheme 323

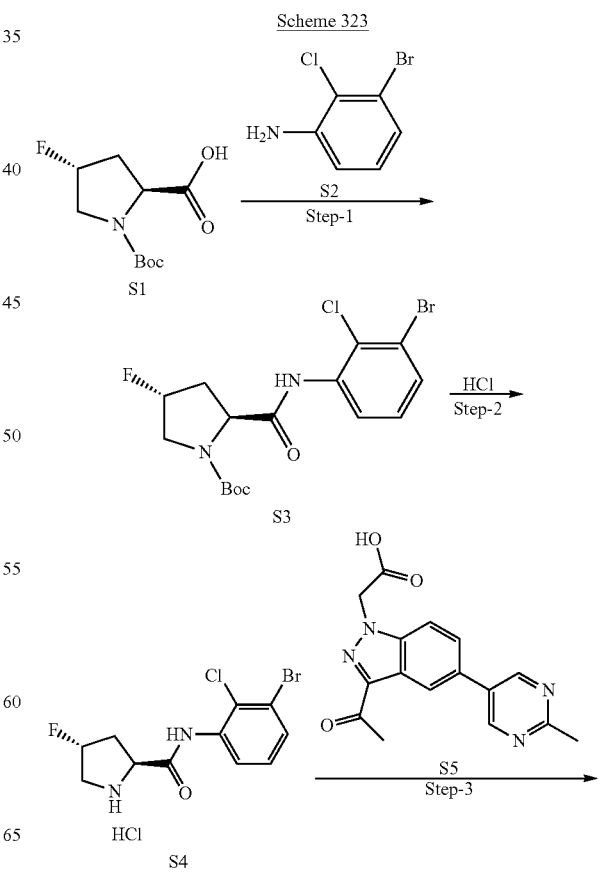

-continued

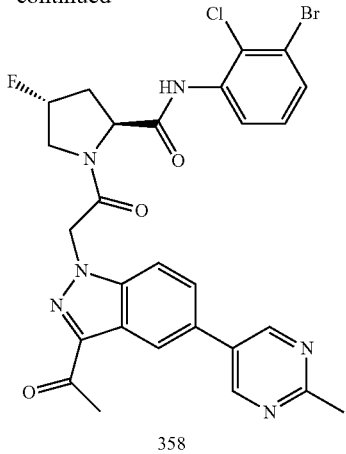

358

Step-1: tert-Butyl (2S,4R)-2-((3-bromo-2-chlorophenyl)carbamoyl)-4-fluoropyrrolidine-1-carboxylate (S3)

To an ice cold solution of (2S, 4R)-1-(tert-butoxycarbonyl)-4-fluoropyrrolidine-2-carboxylic acid (250 mg, 1.1 mmole) in 6 mL of CH2Cl2, 1-chloro-N,N,2-trimethylprop-1-en-1-amine (0.15 mL, 1.1 equiv) was added drop-wise with stirring. The stirring was continued for 3 hours at the same temperature. Then 3-bromo-2-chloroaniline (244 mg, 1.1 equiv) was added, followed by 0.50 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 301 mg of tert-butyl (2S,4R)-2-((3-bromo-2-chlorophenyl)carbamoyl)-4-fluoropyrrolidine-1-carboxylate as yellow solid.

Step-2: (2S,4R)—N-(3-Bromo-2-chlorophenyl)-4-fluoropyrrolidine-2-carboxamide (S4)

To tert-butyl (2S,4R)-2-((3-bromo-2-chlorophenyl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(3-bromo-2-chlorophenyl)-4-fluoropyrrolidine-2-carboxamide (358)

To a stirred solution (2S,4R)—N-(3-bromo-2-chlorophenyl)-4-fluoropyrrolidine-2-carboxamide (HCl salt, 79 mg) in DMF (10 mL) was added S4 (68 mg, 1 equiv.), HATU (100 mg, 1.2 equiv), and DIEA (0.13 mL, 5 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded (38 mg 28%) of titled compound. 1H NMR (400 MHz, DMSO-d$_6$): (major rotamer) δ 2.13-2.35 (m, 1H), 2.52-2.64 (m, 1H), 2.66 (s, 3H), 2.69 (s, 3H), 3.94-4.12 (m, 1H), 4.21-4.32 (m, 1H), 4.75 (t, 1H, J=8.6 Hz), 5.46-5.85 (m, 3H), 7.21-7.25 (m, 1H), 7.56-7.72 (m, 2H), 7.81-7.86 (m, 2H), 9.05 (s, 2H), 9.84 (s, 1H); 19F NMR (376 MHz, DMSO-d$_6$ 300K): (major rotamer) δ −176.0 (1F). LC (method A): tR=1.87 min. LC/MS (EI) m/z: [M]+ 613.

(2S,4R)-1-(2-(3-Acetyl-5-(2-methylpyrimidin-5-yl)-1H-indazol-1-yl)acetyl)-N-(6-bromo-4-chloropyridin-2-yl)-4-fluoropyrrolidine-2-carboxamide (359)

Scheme 324

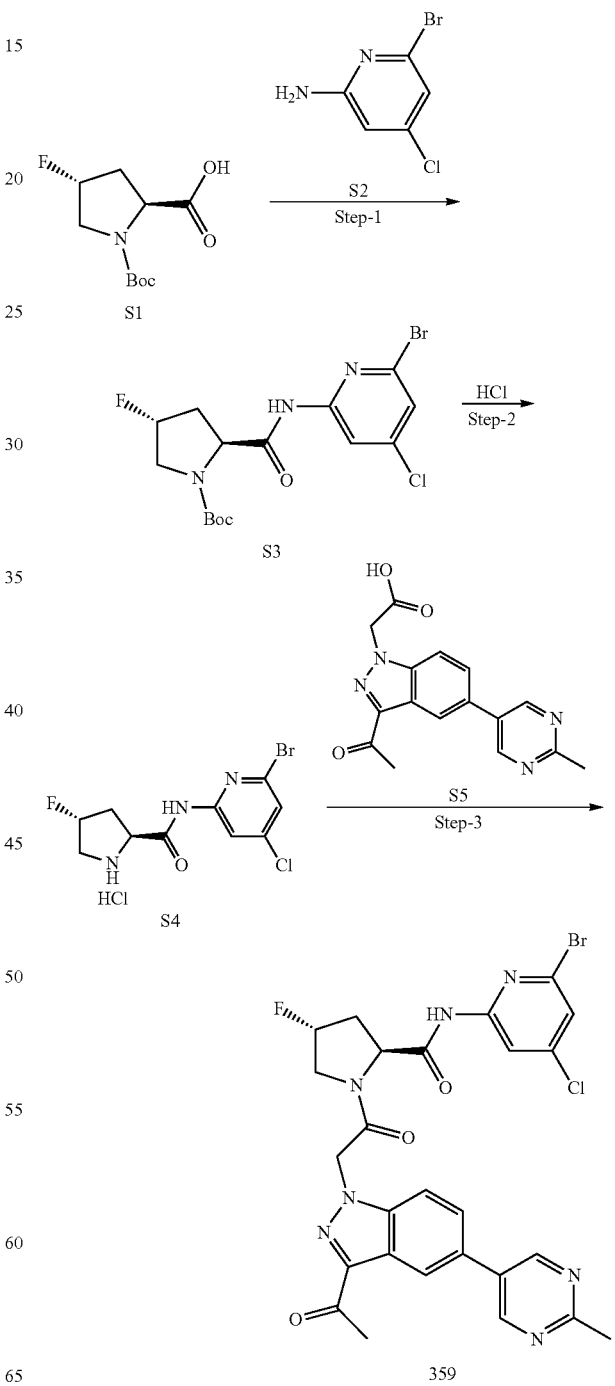

703

Step-1: tert-Butyl (2S,4R)-2-((6-bromo-4-chloro-pyridin-2-yl)carbamoyl)-4-fluoropyrrolidine-1-carboxylate (S3)

To an ice cold solution of (2S, 4R)-1-(tert-butoxycarbonyl)-4-fluoropyrrolidine-2-carboxylic acid (221 mg, 0.95 mmole) in 6 mL of $CH_2Cl_2$, 1-chloro-N,N,2-trimethylprop-1-en-1-amine (0.14 mL, 1.1 equiv) was added drop-wise with stirring. The stirring was continued for 3 hours at the same temperature. Then 6-bromo-4-chloropyridin-2-amine (217 mg, 1.1 equiv) was added, followed by 0.40 mL (3 equiv) Hunig's base. The cooling bath was removed and the reaction mixture was stirred at room temperature overnight. The solvent was co-evaporated with 5 mL of MeOH, and the residue was purified by ISCO (eluted with ethyl acetate in hexane, gradient) to obtain 286 mg of tert-butyl (2S,4R)-2-((6-bromo-4-chloropyridin-2-yl)carbamoyl)-4-fluoropyrrolidine-1-carboxylate as yellow solid.

Step-2: 2-(3-Acetyl-5-(2-methylpyrimidin-5-yl)-1H-indazol-1-yl)acetic acid (S4)

To tert-butyl (2S,4R)-2-((6-bromo-4-chloropyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-4-chloropyridin-2-yl)-4-fluoropyrrolidine-2-carboxamide (359)

To a stirred solution (2S,4R)—N-(6-bromo-4-chloropyridin-2-yl)-4-fluoropyrrolidine-2-carboxamide (HCl salt, 46 mg) in DMF (6 mL) was added S5 (45 mg, 1 equiv.), HATU (59 mg, 1.2 equiv), and DIEA (0.07 mL, 5 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and HPLC prepped, and yielded (45 mg 31%) of titled compound. 1H NMR (400 MHz, DMSO-$d_6$): (major rotamer) δ 2.13-2.35 (m, 1H), 2.52-2.64 (m, 1H), 2.66 (s, 3H), 2.69 (s, 3H), 3.94-4.12 (m, 1H), 4.21-4.32 (m, 1H), 4.75 (t, 1H, J=8.6 Hz), 5.46-5.85 (m, 3H), 7.21-7.25 (m, 1H), 7.56-7.72 (m, 2H), 7.81-7.86 (m, 2H), 9.06 (s, 2H), 10.22 (s, 1H); 19F NMR (376 MHz, DMSO-$d_6$ 300K): (major rotamer) δ −176.6 (1F). LC (method A): tR=1.96 min. LC/MS (EI) m/z: [M]+ 613.

704

(2S,4R)-1-(2-(3-Acetyl-5-(2-methylpyrimidin-5-yl)-1H-indazol-1-yl)acetyl)-N-(6-bromo-4-(trifluoromethyl)pyridin-2-yl)-4-fluoropyrrolidine-2-carboxamide (370)

Scheme 325

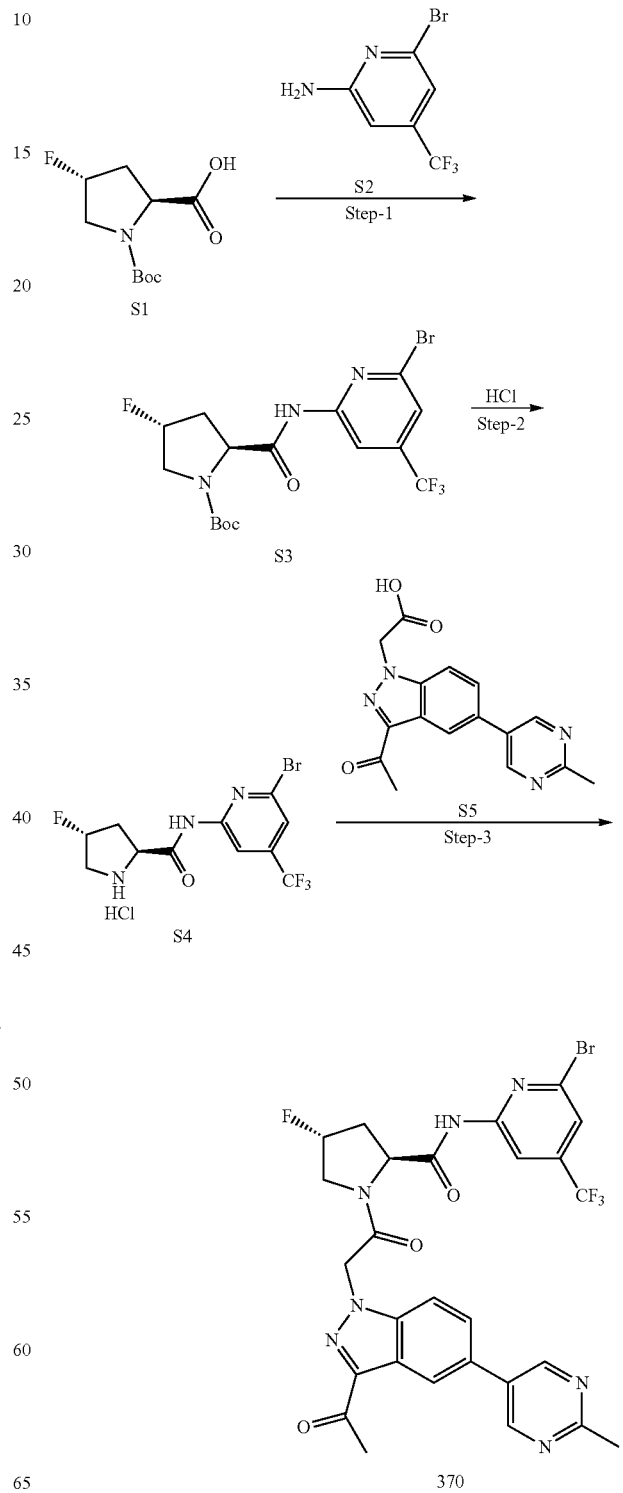

Step-1: tert-Butyl (2S,4R)-2-((6-bromo-4-(trifluoromethyl)pyridin-2-yl)carbamoyl)-4-fluoropyrrolidine-1-carboxylate (S3)

To an ice cold solution of (2S, 4R)-1-(tert-butoxycarbonyl)-4-fluoropyrrolidine-2-carboxylic acid (250 mg, 1.1 mmole) in 8 mL of CH2Cl2, 1-chloro-N,N,2-trimethylprop-1-en-1-amine (0.15 mL, 1.1 equiv) was added drop-wise with stirring. The stirring was continued for 3 hours at the same temperature. Then 6-bromo-4-(trifluoromethyl)pyridin-2-amine (284 mg, 1.1 equiv) was added, followed by 0.50 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 209 mg of tert-butyl (2S,4R)-2-((6-bromo-4-(trifluoromethyl)pyridin-2-yl)carbamoyl)-4-fluoropyrrolidine-1-carboxylate as yellow solid.

Step-2: 2-(3-Acetyl-5-(2-methylpyrimidin-5-yl)-1H-indazol-1-yl)acetic acid (S4)

To tert-butyl (2S,4R)-2-((6-bromo-4-(trifluoromethyl)pyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-4-(trifluoromethyl)pyridin-2-yl)-4-fluoropyrrolidine-2-carboxamide (370)

To a stirred solution (2S,4R)—N-(6-bromo-4-(trifluoromethyl)pyridin-2-yl)-4-fluoropyrrolidine-2-carboxamide (HCl salt, 87 mg) in DMF (10 mL) was added S5 (72 mg, 1.05 equiv.), HATU (105 mg, 1.2 equiv), and DIEA (0.14 mL, 3.5 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and HPLC prepped, and yielded (71 mg 50%) of titled compound. 1H NMR (400 MHz, DMSO-$d_6$): (major rotamer) δ 2.10-2.31 (m, 1H), 2.53-2.64 (m, 1H), 2.65 (s, 3H), 2.69 (s, 3H), 3.95-4.11 (m, 1H), 4.19-4.31 (m, 1H), 4.69 (t, 1H, J=8.4 Hz), 5.47-5.55 (m, 1H), 5.66 (d, d, 1H, J=17.7 Hz), 5.86 (d, 1H, J=17.7 Hz), 7.80 (s, 1H), 7.87 (s, 2H), 8.34 (s, 1H), 8.43 (s, 1H), 9.05 (s, 2H), 11.50 (s, 1H); 19F NMR (376 MHz, DMSO-$d_6$ 300K): (major rotamer) δ −63.58 (3F, CF3), −175.67 (1F). LC (method A): tR=2.09 min. LC/MS (EI) m/z: [M]+ 648

(2S,4R)-1-(2-(3-Acetyl-5-(2-methylpyrimidin-5-yl)-1H-indazol-1-yl)acetyl)-4-fluoro-N-(2-(2,2,2-trifluoroethoxy)pyrimidin-4-yl)pyrrolidine-2-carboxamide (377)

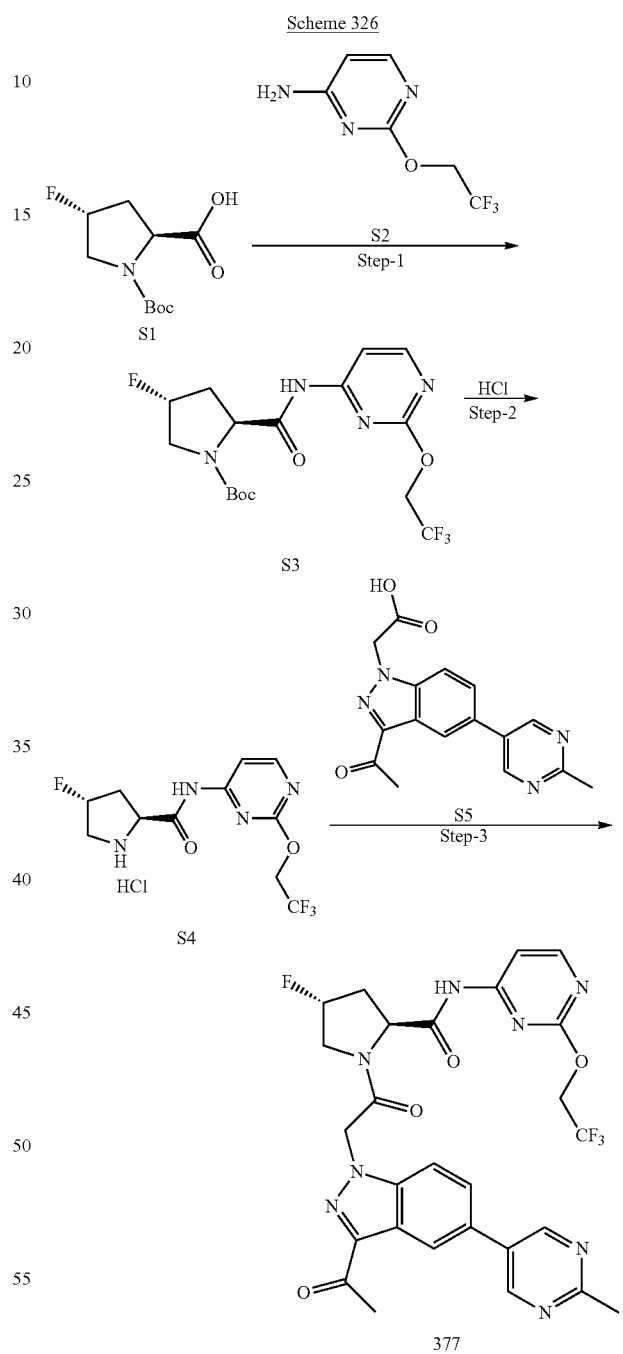

Scheme 326

Step-1: tert-Butyl (2S,4R)-4-fluoro-2-((2-(2,2,2-trifluoroethoxy)pyrimidin-4-yl)carbamoyl)pyrrolidine-1-carboxylate (S3)

To an ice cold solution of (2S, 4R)-1-(tert-butoxycarbonyl)-4-fluoropyrrolidine-2-carboxylic acid (250 mg, 1.1 mmole) in 8 mL of CH2Cl2, 1-chloro-N,N,2-trimethylprop- 1-en-1-amine (0.15 mL, 1.1 equiv) was added drop-wise with stirring. The stirring was continued for 3 hours at the same temperature. Then 2-(2,2,2-trifluoroethoxy)pyrimidin-4-amine (227 mg, 1.1 equiv) was added, followed by 0.50 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 390 mg of tert-butyl (2S,4R)-4-fluoro-2-((2-(2,2,2-trifluoroethoxy)pyrimidin-4-yl)carbamoyl)pyrrolidine-1-carboxylate as yellow oil.

Step-2: (2S,4R)-4-Fluoro-N-(2-(2,2,2-trifluoroethoxy)pyrimidin-4-yl)pyrrolidine-2-carboxamide (S4)

To tert-butyl (2S,4R)-4-fluoro-2-((2-(2,2,2-trifluoroethoxy)pyrimidin-4-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(2-(2,2,2-trifluoroethoxy)pyrimidin-4-yl)pyrrolidine-2-carboxamide (377)

To a stirred solution (2S,4R)-4-fluoro-N-(2-(2,2,2-trifluoroethoxy)pyrimidin-4-yl)pyrrolidine-2-carboxamide (HCl salt, 91 mg) in DMF (10 mL) was added S5 (81 mg, 1.05 equiv.), HATU (218 mg, 1.2 equiv), and DIEA (0.22 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and HPLC prepped, and yielded 90 mg (58%) of titled compound. 1H NMR (400 MHz, DMSO-$d_6$): (major rotamer) δ 2.07-2.29 (m, 1H), 2.53-2.63 (m, 1H), 2.65 (s, 3H), 2.69 (s, 3H), 3.97-4.11 (m, 1H), 4.19-4.30 (m, 1H), 4.69 (t, 1H, J=9 Hz), 4.94-5.05 (m, 2H), 5.49-5.89 (m, 3H), 7.75 (d, 1H, J=5.8 Hz), 7.86 (s, 2H), 8.43 (s, 1H), 8.50 (d, 1H, J=6.8 Hz), 9.04 (s, 2H), 11.20 (s, 1H); 19F NMR (376 MHz, DMSO-$d_6$300K): (major rotamer) δ −72.71 (3F, CF3), −175.76 (1F). LC (method A): tR=1.67 min. LC/MS (EI) m/z: [M+H]+ 601

(2S,4R)-1-(2-(3-Acetyl-5-(2-methylpyrimidin-5-yl)-1H-indazol-1-yl)acetyl)-4-fluoro-N-(1-(2,2,2-trifluoroethyl)-1H-1,2,4-triazol-3-yl)pyrrolidine-2-carboxamide (378)

Scheme 327

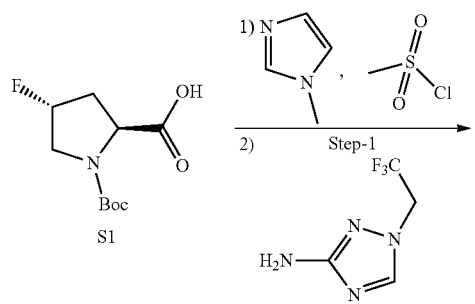

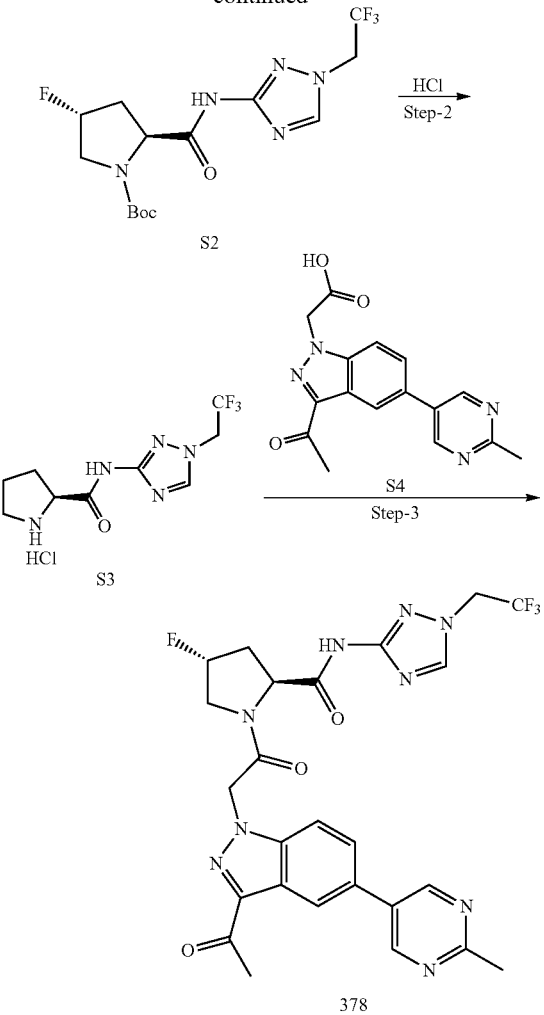

Step-1: tert-Butyl (2S,4R)-4-fluoro-2-((1-(2,2,2-trifluoroethyl)-1H-1,2,4-triazol-3-yl)carbamoyl)pyrrolidine-1-carboxylate (S2)

To a stirred solution of (2S, 4R)-1-(tert-butoxycarbonyl)-4-fluoropyrrolidine-2-carboxylic acid (250 mg, 1.1 mmole) in 8 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-5° C. Then 1-(2,2,2-trifluoroethyl)-1H-1,2,4-triazol-3-amine (178 mg, 1 equiv) was added, and stirred for 18 h at room temperature. Water (20 mL) was added to the reaction mixture, layers were separated and aqueous layer was extracted with DCM (3×10 mL). The combined organic layer was washed with 1N HCl (10 mL), followed by Sat NaHCO3 (10 mL) and with brine (10 mL). Combined organic layer was dried over Na2SO4, concentrated and ready to use in step-2.

Step-2: (2S,4R)-4-Fluoro-N-(1-(2,2,2-trifluoroethyl)-1H-1,2,4-triazol-3-yl)pyrrolidine-2-carboxamide (S3)

To tert-butyl (2S,4R)-4-fluoro-2-((1-(2,2,2-trifluoroethyl)-1H-1,2,4-triazol-3-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(1-(2,2,2-trifluoroethyl)-1H-1,2,4-triazol-3-yl)pyrrolidine-2-carboxamide (378)

To a stirred solution (2S,4R)-4-fluoro-N-(1-(2,2,2-trifluoroethyl)-1H-1,2,4-triazol-3-yl)pyrrolidine-2-carboxamide (HCl salt, 75 mg) in DMF (10 mL) was added S4 (74 mg, 1.05 equiv.), HATU (182 mg, 2 equiv), and DIEA (0.2 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 82 mg (60%) of titled compound. 1H NMR (400 MHz, DMSO-d$_6$): (major rotamer) δ 2.05-2.23 (m, 1H), 2.54-2.62 (m, 1H), 2.65 (s, 3H), 2.69 (s, 3H), 3.93-4.09 (m, 1H), 4.17-4.29 (m, 1H), 4.58 (t, 1H, J=7.8 Hz), 5.14-5.23 (m, 2H), 5.47-5.88 (m, 3H), 7.86 (s, 2H), 8.44 (s, 1H), 8.49 (s, 1H), 9.05 (s, 2H), 10.79 (s, 1H); 19F NMR (376 MHz, DMSO-d$_6$ 300K): (major rotamer) δ −69.99 (3F, CF3), −175.87 (1F). LC (method A): tR=1.14 min. LC/MS (EI) m/z: [M+H]+ 574

(2S,4R)-1-(2-(3-Acetyl-5-(2-methylpyrimidin-5-yl)-1H-indazol-1-yl)acetyl)-N-(5-bromo-1-methyl-1H-pyrazol-3-yl)-4-fluoropyrrolidine-2-carboxamide (381)

Scheme 328

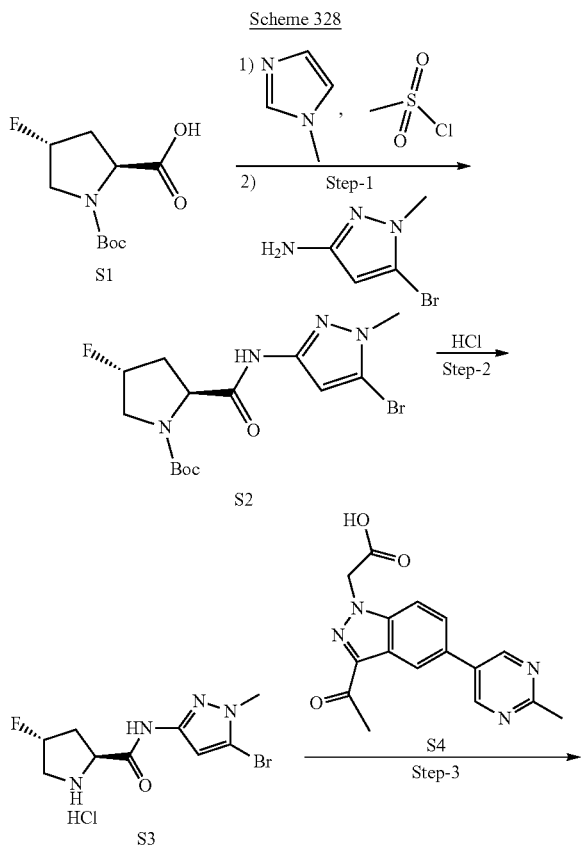

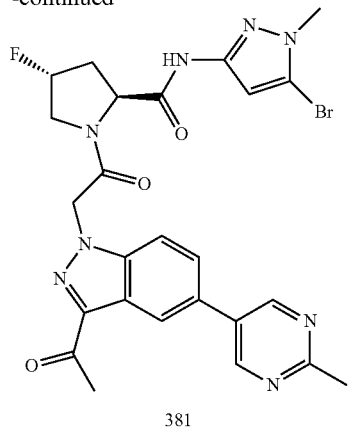

381

Step-1: tert-Butyl (2S,4R)-2-((5-bromo-1-methyl-1H-pyrazol-3-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (158 mg, 0.68 mmole) in 10 mL of CH2Cl2, was added 1-methyl imidazole (0.14 mL, 2.5 equiv.) at 0-5° C. under nitrogen atmosphere. The reaction mixture was stirred for 10 min at 0-5° C. and then added methane sulfonyl chloride (0.06 mL, 1.2 equiv) at the same temperature. It was stirred for 1 h at 0-50° C. Then 5-bromo-1-methyl-1H-pyrazol-3-amine (120 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and with brine (10 mL). Combined organic layer was dried over Na2SO4, concentrated and ready to use in step-2.

Step-2: (2S,4R)—N-(5-Bromo-1-methyl-1H-pyrazol-3-yl)-4-fluoropyrrolidine-2-carboxamide (S3)

To tert-butyl (2S,4R)-2-((5-bromo-1-methyl-1H-pyrazol-3-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(5-bromo-1-methyl-1H-pyrazol-3-yl)-4-fluoropyrrolidine-2-carboxamide (381)

To a stirred solution (2S,4R)—N-(5-bromo-1-methyl-1H-pyrazol-3-yl)-4-fluoropyrrolidine-2-carboxamide (HCl salt, 69 mg) in DMF (10 mL) was added S4 (65 mg, 1.05 equiv.), HATU (175 mg, 2.2 equiv), and DIEA (0.18 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 20 mg (16%) of titled compound. 1H NMR (400 MHz, DMSO-d$_6$): (major rotamer) δ 2.03-2.21 (m, 1H), 2.43-2.52 (m, 1H), 2.65 (s, 3H), 2.69 (s, 3H), 3.92-4.07 (m, 1H), 4.18-4.28 (m, 1H), 4.55 (t, 1H, J=9 Hz), 5.45-5.87 (m, 3H), 6.53 (s, 1H), 7.78-7.91 (m, 1H), 7.87 (s, 1H), 8.43 (s, 1H), 9.04 (s, 2H), 10.74 (s, 1H); 19F NMR (376 MHz, DMSO-$d_6$ 300K): (major rotamer) δ −175.94 (1F). LC (method A): tR=1.40 min. LC/MS (EI) m/z: [M]+ 583.

(2S,4R)-1-(2-(3-Acetyl-5-(2-methylpyrimidin-5-yl)-1H-indazol-1-yl)acetyl)-N-(6-bromo-3-methoxypyridin-2-yl)-4-fluoropyrrolidine-2-carboxamide (386)

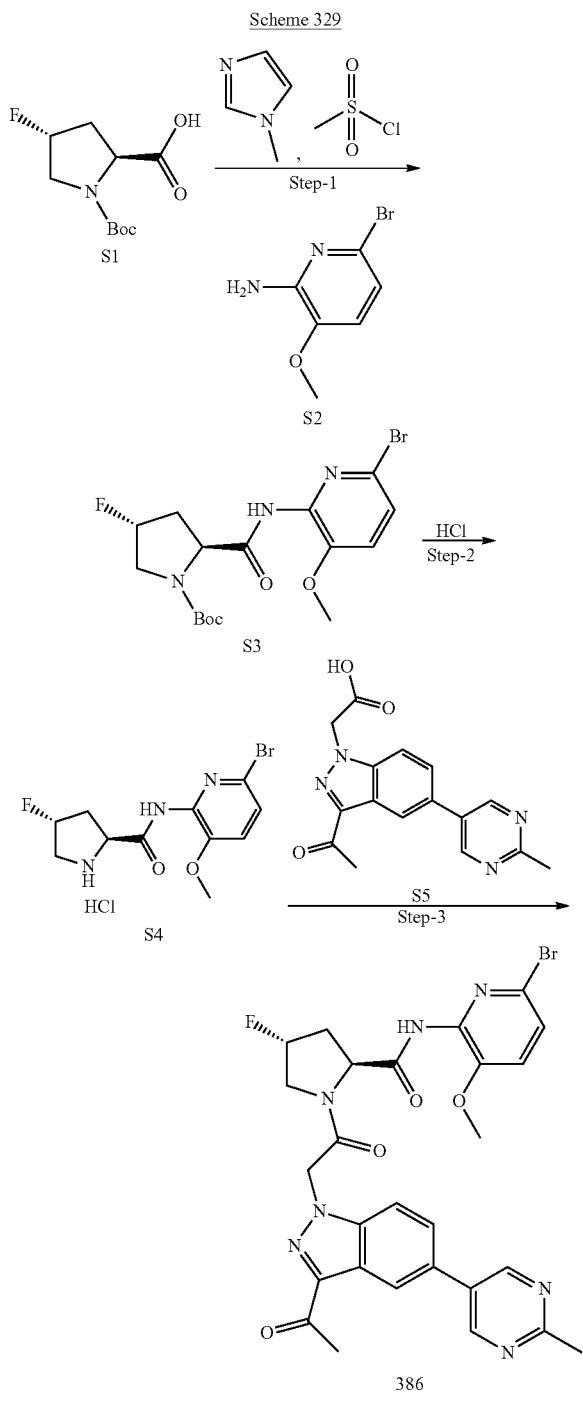

Scheme 329

Step-1: tert-Butyl (2S,4R)-2-((6-bromo-3-methoxypyridin-2-yl)carbamoyl)-4-fluoropyrrolidine-1-carboxylate (S3)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-5° C. Then 6-bromo-3-methoxypyridin-2-amine (217 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and purified by ISCO (SiO2, 5% MeOH in DCM gradient) to obtain titled compound 220 mg (50% yield).

Step-2: (2S,4R)—N-(6-Bromo-3-methoxypyridin-2-yl)-4-fluoropyrrolidine-2-carboxamide (S4)

To tert-butyl (2S,4R)-2-((6-bromo-3-methoxypyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-3-methoxypyridin-2-yl)-4-fluoropyrrolidine-2-carboxamide (386)

To a stirred solution (2S,4R)—N-(6-bromo-3-methoxypyridin-2-yl)-4-fluoropyrrolidine-2-carboxamide (HCl salt, 94 mg) in DMF (10 mL) was added S5 (82 mg, 1.05 equiv.), HATU (217 mg, 2.2 equiv), and DIEA (0.21 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 92 mg (59%) of 386. 1H NMR (400 MHz, DMSO-$d_6$): (major rotamer) δ 2.11-2.35 (m, 1H), 2.55-2.60 (m, 1H), 2.66 (s, 3H), 2.69 (s, 3H), 3.77 (s, 3H), 3.91-4.08 (m, 1H), 4.20-4.33 (m, 1H), 4.73 (t, 1H, J=7.3 Hz), 5.47-5.88 (m, 3H), 7.40-7.45 (m, 2H), 7.80-7.92 (m, 2H), 8.46 (s, 1H), 9.06 (s, 2H), 10.07 (s, 1H); 19F NMR (376 MHz, DMSO-$d_6$ 300K): (major rotamer) δ −175.81 (1F). LC (method A): tR=1.48 min. LC/MS (EI) m/z: [M]+ 610.

(2S,4R)-1-(2-(3-Acetyl-5-(2-methylpyrimidin-5-yl)-1H-indazol-1-yl)acetyl)-N-(6-bromo-5-methoxypyridin-2-yl)-4-fluoropyrrolidine-2-carboxamide (394)

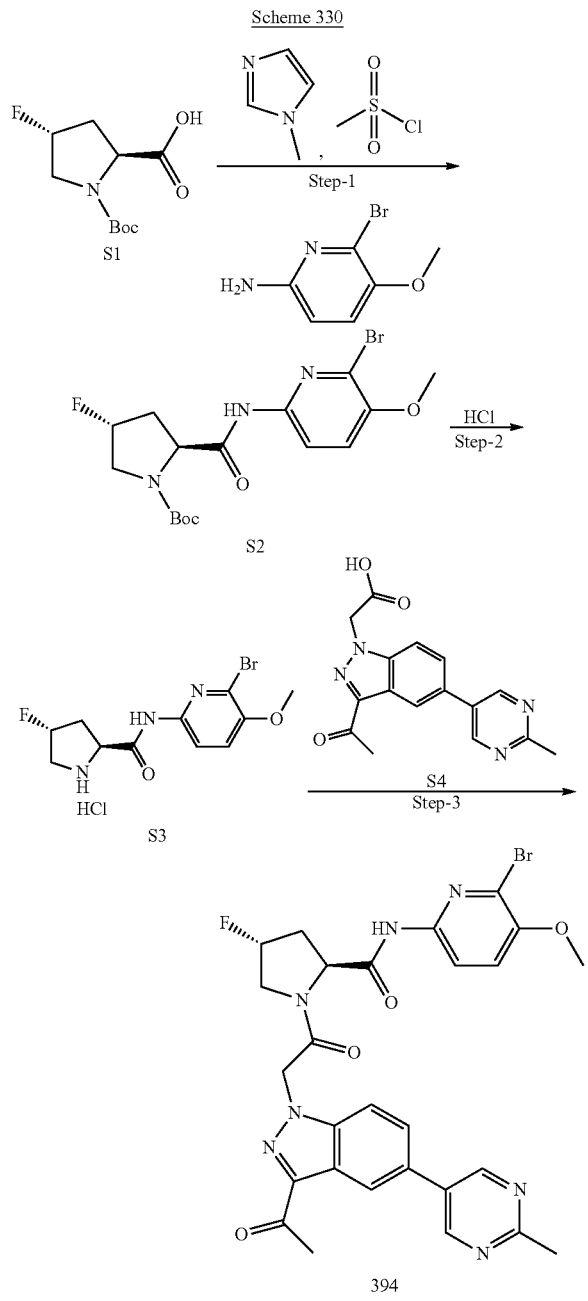

394

Step-1: tert-Butyl (2S,4R)-2-((6-bromo-5-methoxypyridin-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 6-bromo-5-methoxypyridin-2-amine (217 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and to obtain titled compound 390 mg (93% purity).

Step-2: (2S,4R)—N-(6-Bromo-5-methoxypyridin-2-yl)-4-fluoropyrrolidine-2-carboxamide (S3)

To tert-butyl (2S,4R)-2-((6-bromo-5-methoxypyridin-2-yl)carbamoyl)-4-fluoropyrrolidine-1-carboxylate (crude product from step 1) was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-5-methoxypyridin-2-yl)-4-fluoropyrrolidine-2-carboxamide (394)

To a stirred solution (2S,4R)—N-(6-bromo-5-methoxypyridin-2-yl)-4-fluoropyrrolidine-2-carboxamide (HCl salt, 83 mg) in DMF (10 mL) was added S4 (71 mg, 1.05 equiv.), HATU (105 mg, 1.2 equiv), and DIEA (0.20 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 80 mg (57%) of 394. 1H NMR (400 MHz, DMSO-d6): (major rotamer) δ 2.06-2.25 (m, 1H), 2.53-2.61 (m, 1H), 2.65 (s, 3H), 2.69 (s, 3H), 3.83 (s, 3H), 3.95-4.11 (m, 1H), 4.18-4.29 (m, 1H), 4.64 (t, 1H, J=8.3 Hz), 5.47-5.88 (m, 3H), 7.55 (d, 1H, J=8.8 Hz), 7.86 (s, br, 2H), 7.98 (d, 1H, J=8.8 Hz), 8.43 (s, br, 1H), 9.03 (s, 2H), 10.83 (s, 1H); 19F NMR (376 MHz, DMSO-d6 300K): (major rotamer) δ −175.70 (1F). LC (method A): tR=1.62 min. LC/MS (EI) m/z: [M]+ 610.

Methyl 2-((2S,4R)-1-(2-(3-Acetyl-5-(2-methylpyrimidin-5-yl)-1H-indazol-1-yl)acetyl)-4-fluoropyrrolidine-2-carboxamido)-6-chloroisonicotinate (396)

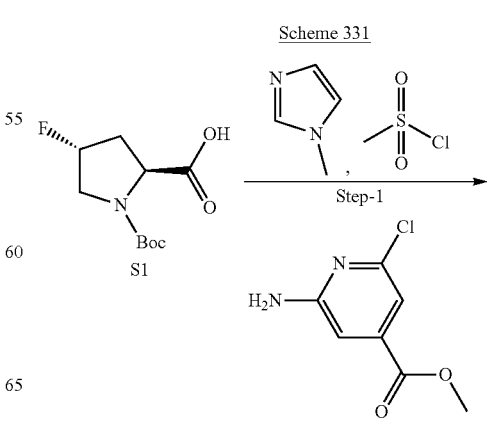

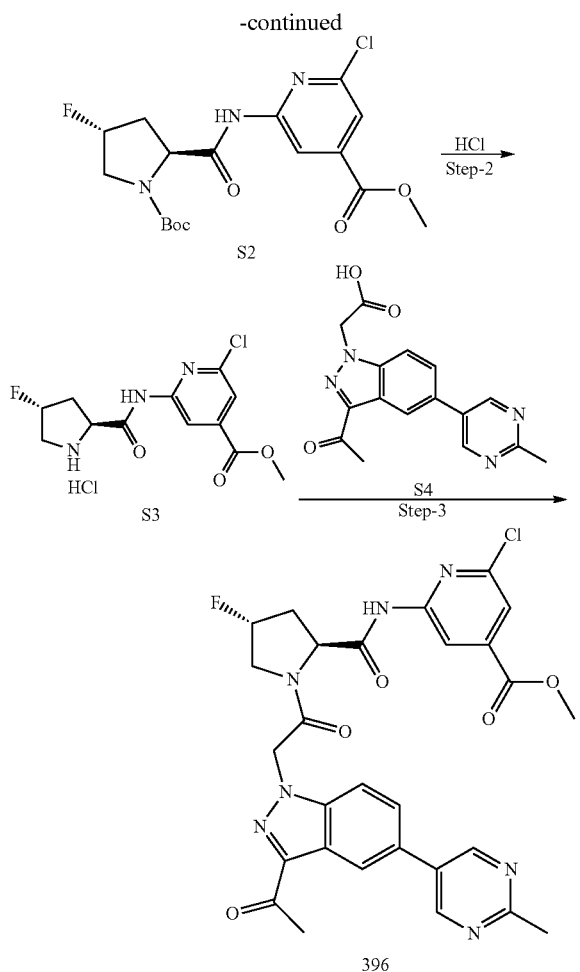

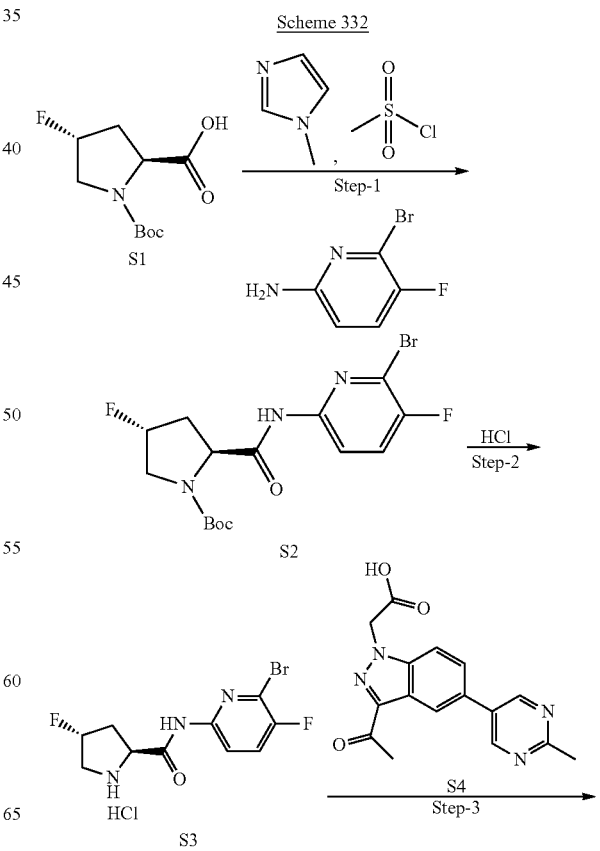

resulting solution was stirred at room temperature for 6 hours. Then, the reaction mixture was concentrated in vacuuo and used for the following step.

Step-3: Methyl 2-((2S,4R)-1-(2-(3-acetyl-5-(2-methylpyrimidin-5-yl)-1H-indazol-1-yl)acetyl)-4-fluoropyrrolidine-2-carboxamido)-6-chloroisonicotinate (396)

To a stirred solution of Methyl 2-chloro-6-((2S,4R)-4-fluoropyrrolidine-2-carboxamido)isonicotinate (HCl salt, 60 mg) in DMF (8 mL) was added S4 (56 mg, 1.05 equiv.), HATU (82 mg, 1.2 equiv), and DIEA (0.15 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 52 mg (49%) of 396. 1H NMR (400 MHz, DMSO-$d_6$): (major rotamer) δ 2.08-2.28 (m, 1H), 2.53-2.60 (m, 1H), 2.65 (s, 3H), 2.69 (s, 3H), 3.89 (s, 3H), 3.96-4.11 (m, 1H), 4.20-4.31 (m, 1H), 4.68 (t, 1H, J=8.9 Hz), 5.47-5.87 (m, 3H), 7.53 (s, 1H), 7.80-7.85 (m, 1H), 7.86 (s, 1H), 8.42 (s, 1H), 8.50 (s, 1H), 9.05 (s, 2H), 11.33 (s, 1H); 19F NMR (376 MHz, DMSO-$d_6$300K): (major rotamer) δ −175.68 (1F). LC (method A): tR=1.77 min. LC/MS (EI) m/z: [M]+ 594.

(2S,4R)-1-(2-(3-Acetyl-5-(2-methylpyrimidin-5-yl)-1H-indazol-1-yl)acetyl)-N-(6-bromo-5-fluoropyridin-2-yl)-4-fluoropyrrolidine-2-carboxamide (397)

Scheme 332

Step-1: Methyl 2-((2S,4R)-1-(tert-Butoxycarbonyl)-4-fluoropyrrolidine-2-carboxamido)-6-chloroisonicotinate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then methyl 2-amino-6-chloroisonicotinate (201 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and purified by ISCO (5% MeOH in DCM gradient) to obtain titled compound 130 mg (32% yield).

Step-2: Methyl 2-chloro-6-((2S,4R)-4-Fluoropyrrolidine-2-carboxamido)isonicotinate (S3)

To methyl 2-((2S,4R)-1-(tert-butoxycarbonyl)-4-fluoropyrrolidine-2-carboxamido)-6-chloroisonicotinate (product from step 1) was added 10 ml of 4N HCl in Dioxane. The

397.

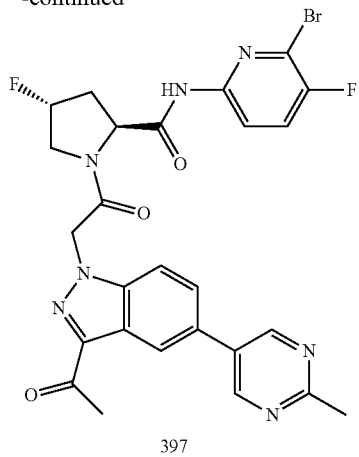

397

Step-1: tert-Butyl (2S,4R)-2-((6-bromo-5-fluoro-pyridin-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 6-bromo-5-fluoropyridin-2-amine (204 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and to obtain titled compound 400 mg (quantitative yield).

Step-2: (2S,4R)—N-(6-Bromo-5-fluoropyridin-2-yl)-4-fluoropyrrolidine-2-carboxamide (S3)

To tert-butyl (2S,4R)-2-((6-bromo-5-fluoropyridin-2-yl)carbamoyl)-4-fluoropyrrolidine-1-carboxylate (product from step 1) was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-5-fluoropyridin-2-yl)-4-fluoropyrrolidine-2-carboxamide (397)

To a stirred solution of (2S,4R)—N-(6-bromo-5-fluoropyridin-2-yl)-4-fluoropyrrolidine-2-carboxamide (HCl salt, 92 mg) in DMF (10 mL) was added S4 (83 mg, 1.05 equiv.), HATU (119 mg, 1.2 equiv), and DIEA (0.23 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 93 mg (60%) of 397. 1H NMR (400 MHz, DMSO-d$_6$): (major rotamer) δ 2.07-2.25 (m, 1H), 2.53-2.60 (m, 1H), 2.65 (s, 3H), 2.69 (s, 3H), 3.96-4.11 (m, 1H), 4.18-4.29 (m, 1H), 4.66 (t, 1H, J=8.8 Hz), 5.47-5.88 (m, 3H), 7.53 (s, 1H), 7.83-7.89 (m, 3H), 8.02-8.07 (m, 1H), 8.43 (s, 1H), 8.50 (s, 1H), 9.05 (s, 2H), 11.10 (s, 1H); 19F NMR (376 MHz, DMSO-d$_6$ 300K): (major rotamer) δ −120.83 (1F), −175.70 (1F). LC (method A): tR=1.74 min. LC/MS (EI) m/z: [M]+ 598.

(2S,4R)-1-(2-(3-Acetyl-5-(2-methylpyrimidin-5-yl)-1H-indazol-1-yl)acetyl)-N-(1-(2,2-difluoroethyl)-1H-pyrazol-3-yl)-4-fluoropyrrolidine-2-carboxamide (401)

Scheme 333

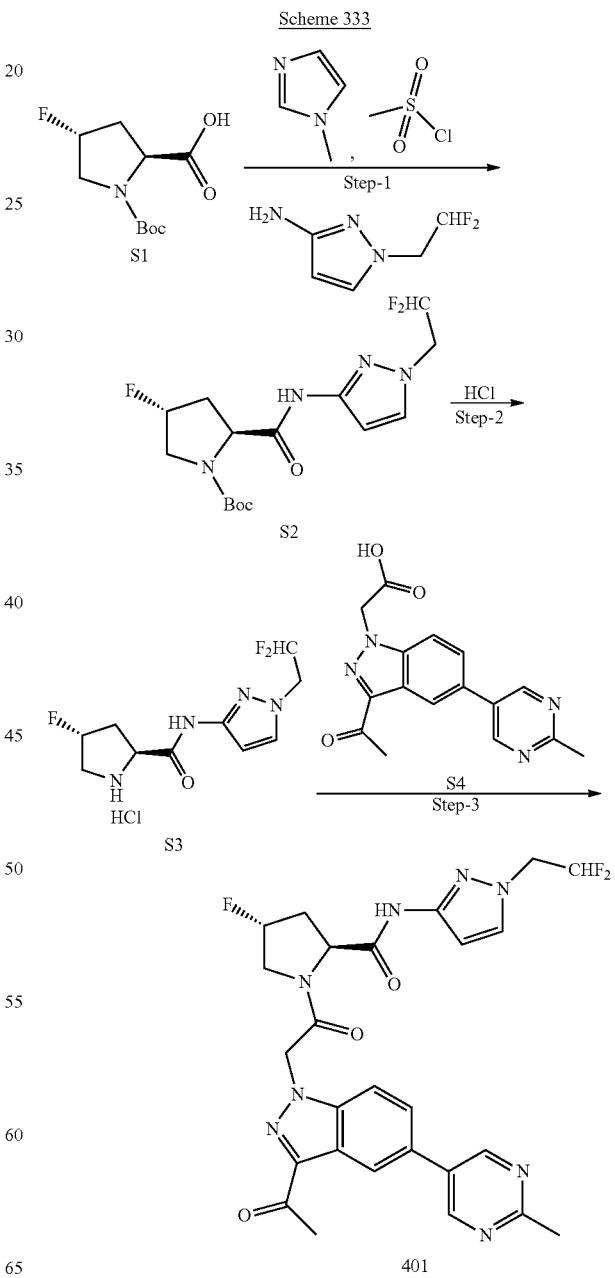

719

Step-1: tert-Butyl (2S,4R)-2-((1-(2,2-difluoroethyl)-1H-pyrazol-3-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 1-(2,2-difluoroethyl)-1H-pyrazol-3-amine (157 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and to obtain titled compound 386 mg as a white solid (quantitative yield).

Step-2: (2S,4R)—N-(1-(2,2-Difluoroethyl)-1H-pyrazol-3-yl)-4-fluoropyrrolidine-2-carboxamide (S3)

To tert-butyl (2S,4R)-2-((1-(2,2-difluoroethyl)-1H-pyrazol-3-yl)carbamoyl)-4-fluoropyrrolidine-1-carboxylate (product from step 1) was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(1-(2,2-difluoroethyl)-1H-pyrazol-3-yl)-4-fluoropyrrolidine-2-carboxamide (401)

To a stirred solution of (2S,4R)—N-(1-(2,2-difluoroethyl)-1H-pyrazol-3-yl)-4-fluoropyrrolidine-2-carboxamide (HCl salt, 100 mg) in DMF (10 mL) was added S4 (104 mg, 1.0 equiv.), HATU (151 mg, 1.2 equiv), and DIEA (0.3 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 101 mg (55%) of 401. 1H NMR (400 MHz, DMSO-d$_6$): (major rotamer) δ 2.05-2.26 (m, 1H), 2.55-2.61 (m, 1H), 2.65 (s, 3H), 2.69 (s, 3H), 3.93-4.17 (m, 1H), 4.18-4.28 (m, 1H), 4.44-4.60 (m, 3H), 5.29-5.85 (m, 3H), 6.05-6.35 (m, 1H), 6.51 (s, 1H), 7.64 (s, 1H), 7.86 (s, 2H), 8.43 (s, 1H), 9.04 (s, 2H), 10.68 (s, 1H); 19F NMR (376 MHz, DMSO-d$_6$300K): (major rotamer) δ −122.56 (2F), −175.90 (1F). LC (method A): tR=1.27 min. LC/MS (EI) m/z: [M+H]+ 555.

720

(2S,4R)-1-(2-(3-Acetyl-5-(2-methylpyrimidin-5-yl)-1H-indazol-1-yl)acetyl)-N-(6-bromo-5-methylpyridin-2-yl)-4-fluoropyrrolidine-2-carboxamide (402)

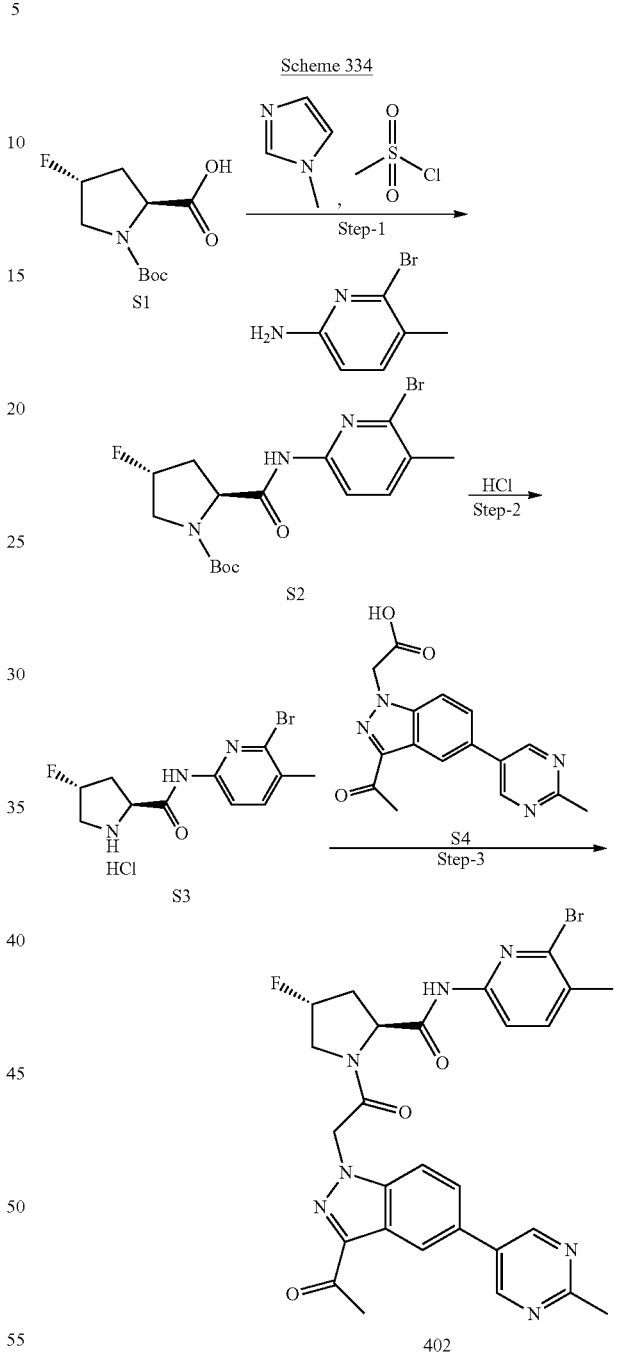

Scheme 334

Step-1: tert-Butyl (2S,4R)-2-((6-bromo-5-methylpyridin-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-5° C. Then 6-bromo-5-methylpyridin-2-amine (200 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and to obtain titled compound 404 mg (quantitative yield).

Step-2: (2S,4R)—N-(6-Bromo-5-methylpyridin-2-yl)-4-fluoropyrrolidine-2-carboxamide (S3)

To tert-butyl (2S,4R)-2-((6-bromo-5-methylpyridin-2-yl)carbamoyl)-4-fluoropyrrolidine-1-carboxylate (product from step 1) was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-5-methylpyridin-2-yl)-4-fluoropyrrolidine-2-carboxamide (402)

To a stirred solution of (2S,4R)—N-(6-bromo-5-methylpyridin-2-yl)-4-fluoropyrrolidine-2-carboxamide (HCl salt, 111 mg) in DMF (10 mL) was added S4 (102 mg, 1.05 equiv.), HATU (150 mg, 1.2 equiv), and DIEA (0.28 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 102 mg (52%) of 402. 1H NMR (400 MHz, DMSO-d$_6$): (major rotamer) δ 2.07-2.22 (m, 1H), 2.26 (s, 3H), 2.53-2.57 (m, 1H), 2.65 (s, 3H), 2.69 (s, 3H), 3.96-4.10 (m, 1H), 4.18-4.29 (m, 1H), 4.67 (t, 1H, J=8.6 Hz), 5.45-5.87 (m, 3H), 7.72 (d, 1H, J=8.2 Hz), 7.77-7.81 (m, 2H), 7.94 (d, 1H, J=8.2 Hz), 8.43 (s, 1H), 9.05 (s, 2H), 10.91 (s, 1H); 19F NMR (376 MHz, DMSO-d$_6$ 300K): (major rotamer) δ −175.67 (1F). LC (method A): tR=1.81 min. LC/MS (EI) m/z: [M]+ 594.

(2S,4R)-1-(2-(3-Acetyl-5-(2-methylpyrimidin-5-yl)-1H-indazol-1-yl)acetyl)-N-(6-bromo-3-methylpyridin-2-yl)-4-fluoropyrrolidine-2-carboxamide (405)

Scheme 335

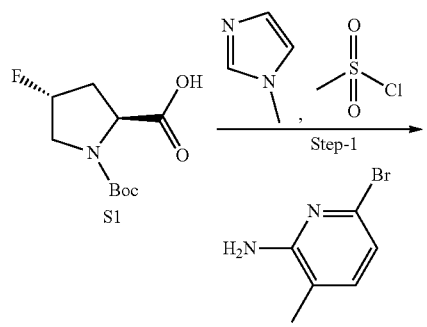

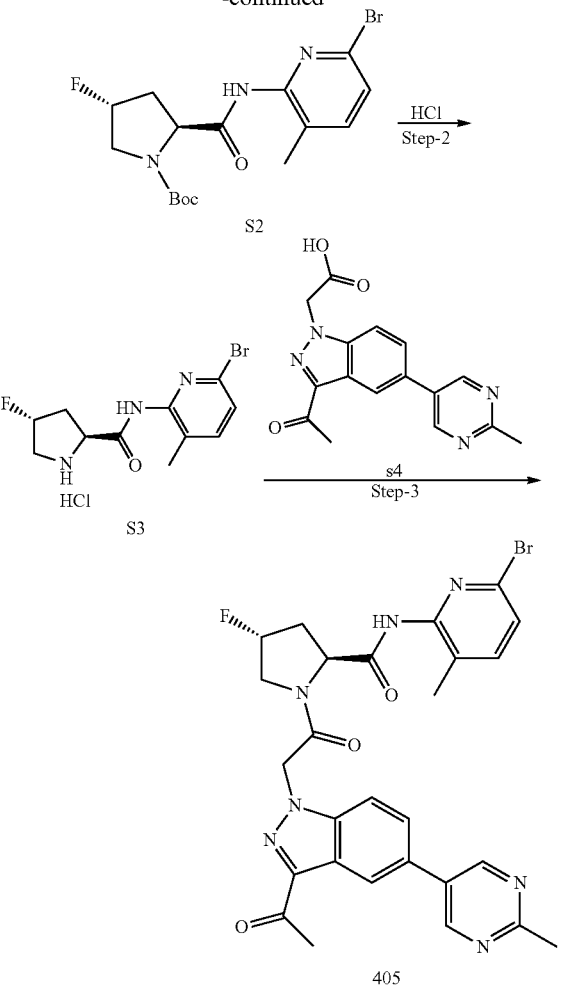

Step-1: tert-Butyl (2S, 4R)-2-((6-bromo-3-methylpyridin-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 6-bromo-3-methylpyridin-2-amine (200 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 430 mg (quantitative yield) of titled compound was obtained.

Step-2: (2S,4R)—N-(6-Bromo-3-methylpyridin-2-yl)-4-fluoropyrrolidine-2-carboxamide (S3)

To tert-butyl (2S,4R)-2-((6-bromo-3-methylpyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-3-methylpyridin-2-yl)-4-fluoropyrrolidine-2-carboxamide (405)

To a stirred solution of (2S,4R)—N-(6-bromo-3-methylpyridin-2-yl)-4-fluoropyrrolidine-2-carboxamide (HCl salt, 120 mg) in DMF (10 mL) was added S4 (109 mg, 1.0 equiv.), HATU (160 mg, 1.2 equiv), and DIEA (0.30 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 102 mg (51%) of 405. 1H NMR (400 MHz, DMSO-$d_6$): (major rotamer) δ 2.01 (s, 3H), 2.08-2.28 (m, 1H), 2.57-2.63 (m, 1H), 2.65 (s, 3H), 2.69 (s, 3H), 3.97-4.10 (m, 1H), 4.20-4.31 (m, 1H), 4.61 (t, 1H, J=8.2 Hz), 5.49-5.89 (m, 3H), 7.44 (d, 1H, J=8.0 Hz), 7.61 (d, 1H, J=8.0 Hz), 7.80-7.89 (m, 3H), 8.44 (s, 1H), 9.05 (s, 2H), 10.48 (s, 1H); 19F NMR (376 MHz, DMSO-$d_6$ 300K): (major rotamer) δ −176.04 (1F). LC (method A): tR=1.49 min. LC/MS (EI) m/z: [M]+ 594.

(2S,4R)-1-(2-(3-Acetyl-5-(2-methylpyrimidin-5-yl)-1H-indazol-1-yl)acetyl)-4-fluoro-N-(5-fluoropyridin-2-yl)pyrrolidine-2-carboxamide (407)

Scheme 336

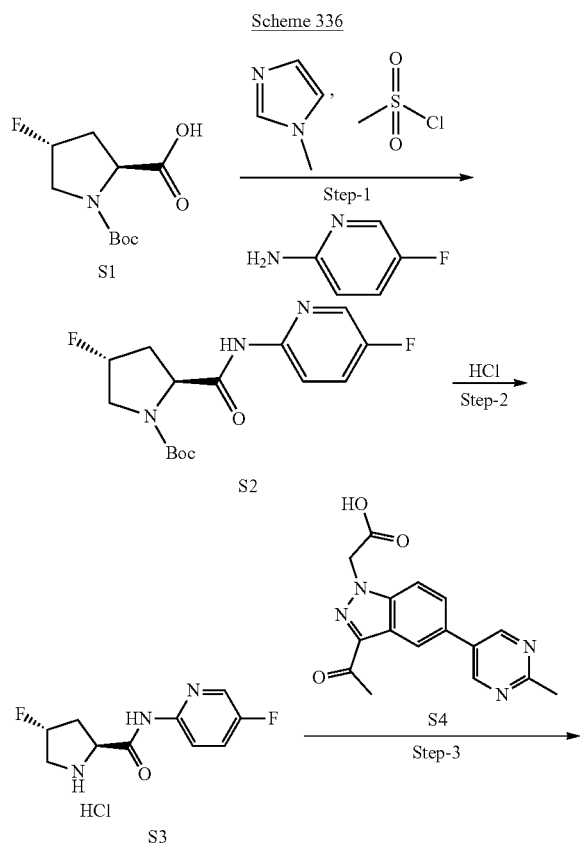

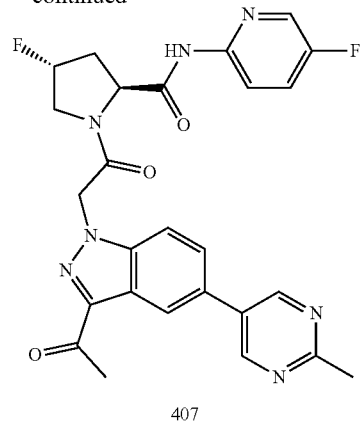

407

Step-1: tert-Butyl (2S,4R)-4-fluoro-2-((5-fluoropyridin-2-yl)carbamoyl)pyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 5-fluoropyridin-2-amine (200 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 430 mg (quantitative yield) of titled compound was obtained.

Step-2: (2S,4R)—N-(6-bromo-3-methylpyridin-2-yl)-4-fluoropyrrolidine-2-carboxamide (S3)

To tert-butyl (2S,4R)-4-fluoro-2-((5-fluoropyridin-2-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(5-fluoropyridin-2-yl)pyrrolidine-2-carboxamide (407)

To a stirred solution of (2S,4R)—N-(6-bromo-3-methylpyridin-2-yl)-4-fluoropyrrolidine-2-carboxamide (HCl salt, 120 mg) in DMF (10 mL) was added S4 (109 mg, 1.0 equiv.), HATU (160 mg, 1.2 equiv), and DIEA (0.30 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 102 mg (51%) of 407. 1H NMR (400 MHz, DMSO-$d_6$): (major rotamer) δ 2.08-2.26 (m, 1H), 2.53-2.61 (m, 1H), 2.65 (s, 3H), 2.69 (s, 3H), 3.95-4.10 (m, 1H), 4.18-4.31 (m, 1H), 4.70 (t, 1H, J=8.0 Hz), 5.44-5.89 (m, 3H), 7.68-7.44 (m, 1H), 7.81-7.90 (m, 2H), 8.04-8.11 (m, 1H), 8.32 (s, 1H), 8.42 (s, 1H), 9.04 (s, 2H), 10.79 (s, 1H); 19F NMR (376 MHz, DMSO-d$_6$300K): (major rotamer) δ −133.15 (1F), −175.76 (1F). LC (method A): tR=1.38 min. LC/MS (EI) m/z: [M+H]+ 520.

(2S,4R)-1-(2-(3-Acetyl-5-(2-methylpyrimidin-5-yl)-1H-indazol-1-yl)acetyl)-N-(3-bromo-5-fluoropyridin-2-yl)-4-fluoropyrrolidine-2-carboxamide (408)

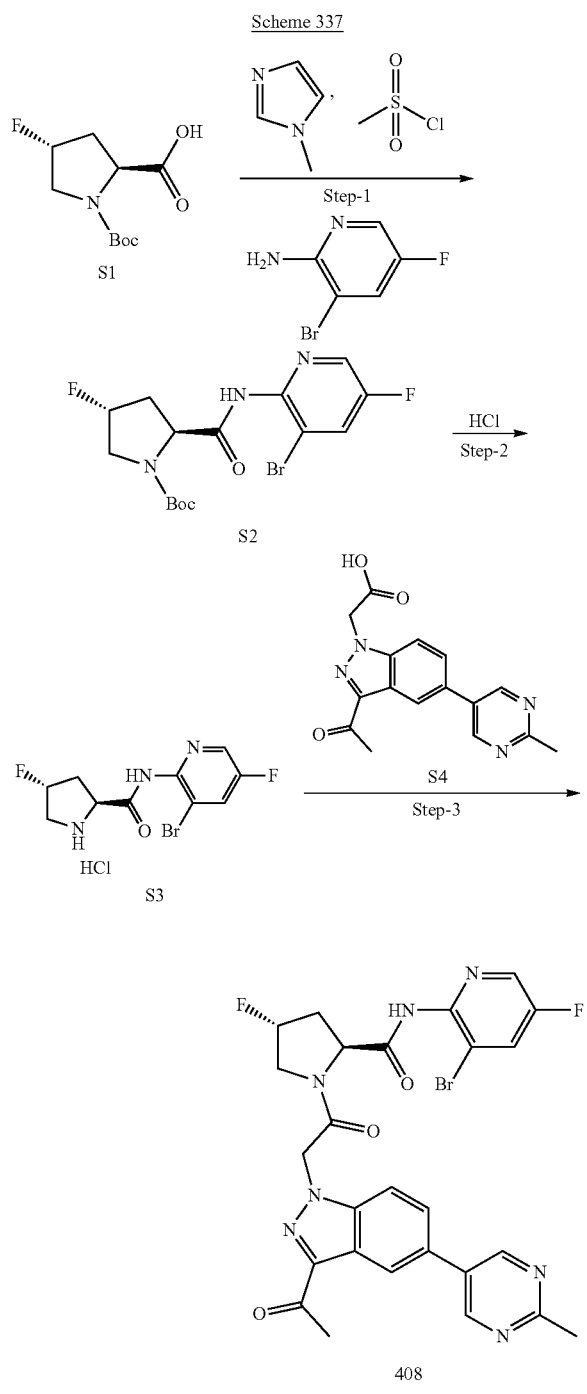

Step-1: tert-Butyl (2S,4R)-2-((3-bromo-5-fluoropyridin-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 3-bromo-5-fluoropyridin-2-amine (204 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 195 mg (48%) of titled compound was obtained.

Step-2: (2S,4R)—N-(3-Bromo-5-fluoropyridin-2-yl)-4-fluoropyrrolidine-2-carboxamide (S3)

To tert-butyl (2S,4R)-2-((3-bromo-5-fluoropyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(3-bromo-5-fluoropyridin-2-yl)-4-fluoropyrrolidine-2-carboxamide (408)

To a stirred solution of (2S,4R)—N-(3-bromo-5-fluoropyridin-2-yl)-4-fluoropyrrolidine-2-carboxamide (HCl salt, 72 mg) in DMF (8 mL) was added S4 (65 mg, 1.0 equiv.), HATU (74 mg, 1.2 equiv), and DIEA (0.18 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 75 mg (60%) of 408. 1H NMR (400 MHz, DMSO-d$_6$): (major rotamer) δ 2.19-2.35 (m, 1H), 2.53-2.61 (m, 1H), 2.65 (s, 3H), 2.69 (s, 3H), 3.94-4.09 (m, 1H), 4.21-4.31 (m, 1H), 4.65 (t, 1H, J=8.6 Hz), 5.47-5.91 (m, 3H), 7.79-7.91 (m, 2H), 8.25-8.29 (m, 1H), 8.43-8.48 (m, 2H), 9.05 (s, 2H), 10.42 (s, 1H); 19F NMR (376 MHz, DMSO-d$_6$300K): (major rotamer) δ −127.95 (1F), −176.08 (1F). LC (method A): tR=1.35 min. LC/MS (EI) m/z: [M]+ 598.

(2S,4R)-1-(2-(3-Acetyl-5-(2-methylpyrimidin-5-yl)-1H-indazol-1-yl)acetyl)-N-(4-bromo-1-(2,2,2-trifluoroethyl)-1H-pyrazol-3-yl)-4-fluoropyrrolidine-2-carboxamide (420)

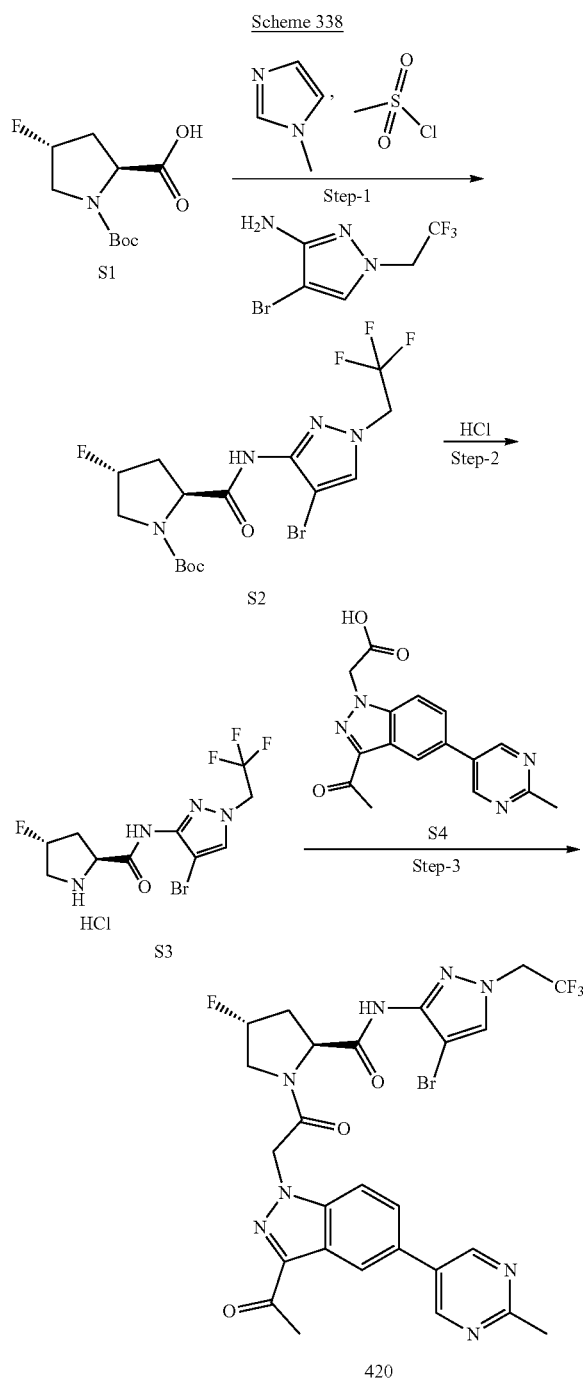

Step-1: tert-Butyl (2S,4R)-2-((4-bromo-1-(2,2,2-trifluoroethyl)-1H-pyrazol-3-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 4-bromo-1-(2,2,2-trifluoroethyl)-1H-pyrazol-3-amine (261 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 455 mg (98%, white solid) of titled compound was obtained.

Step-2: (2S,4R)—N-(4-Bromo-1-(2,2,2-trifluoroethyl)-1H-pyrazol-3-yl)-4-fluoropyrrolidine-2-carboxamide (S3)

To tert-butyl (2S,4R)-2-((4-bromo-1-(2,2,2-trifluoroethyl)-1H-pyrazol-3-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(4-bromo-1-(2,2,2-trifluoroethyl)-1H-pyrazol-3-yl)-4-fluoropyrrolidine-2-carboxamide (420)

To a stirred solution of (2S,4R)—N-(4-bromo-1-(2,2,2-trifluoroethyl)-1H-pyrazol-3-yl)-4-fluoropyrrolidine-2-carboxamide (HCl salt, 106 mg) in DMF (10 mL) was added S4 (83 mg, 1.0 equiv.), HATU (119 mg, 1.2 equiv), and DIEA (0.23 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 79 mg (47%) of 420. 1H NMR (400 MHz, CH3OH-d4): (major rotamer) δ 2.31-2.47 (m, 1H), 2.69-2.71 (m, 1H), 2.72 (s, 3H), 2.77 (s, 3H), 3.96-4.11 (m, 1H), 4.22-4.36 (m, 1H), 4.89-4.99 (m, 2H), 5.13 (t, 1H, J=8.4 Hz), 5.41-5.71 (m, 3H), 7.75-7.82 (m, 2H), 7.85 (s, 1H), 8.57 (s, 1H), 9.05 (s, 2H); 19F NMR (376 MHz, CH3OH-d4, 300K): (major rotamer) δ −74.15 (3F), −179.58 (1F). LC (method A): tR=1.50 min. LC/MS (EI) m/z: [M]+ 651.

(2S,4R)-1-(2-(3-Acetyl-5-(2-methylpyrimidin-5-yl)-1H-indazol-1-yl)acetyl)-N-(4-methyl-1-(2,2,2-trifluoroethyl)-1H-pyrazol-3-yl)-4-fluoropyrrolidine-2-carboxamide (422)

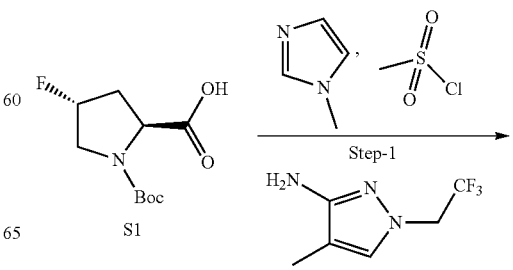

729
-continued

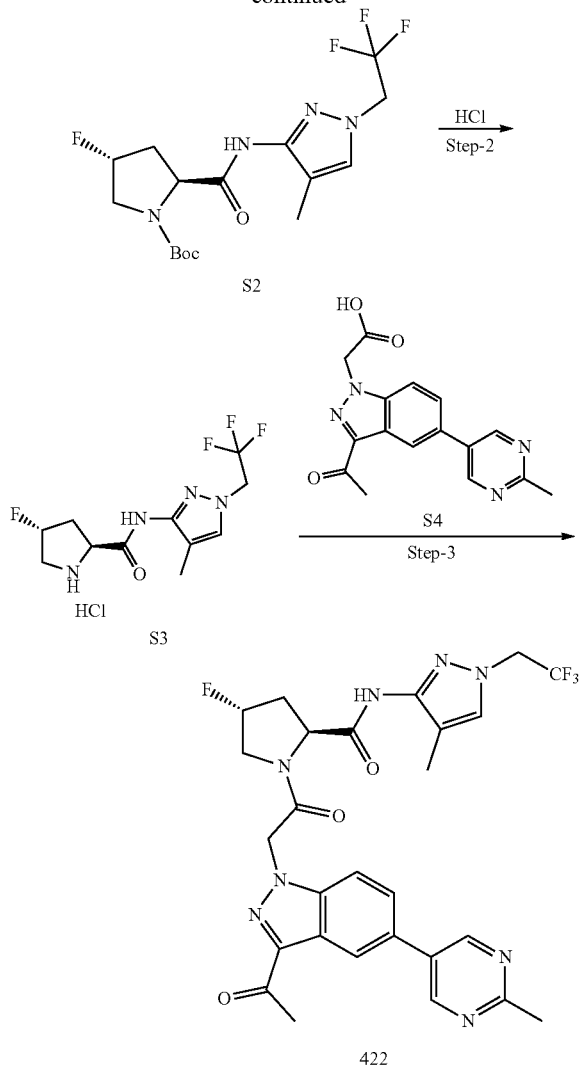

Step-1: tert-Butyl (2S,4R)-2-((4-methyl-1-(2,2,2-trifluoroethyl)-1H-pyrazol-3-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 4-methyl-1-(2,2,2-trifluoroethyl)-1H-pyrazol-3-amine (192 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 401 mg (quantitative yield) of titled compound was obtained.

730

Step-2: (2S,4R)—N-(4-Methyl-1-(2,2,2-trifluoroethyl)-1H-pyrazol-3-yl)-4-fluoropyrrolidine-2-carboxamide (S3)

To tert-butyl (2S,4R)-2-((4-methyl-1-(2,2,2-trifluoroethyl)-1H-pyrazol-3-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(4-methyl-1-(2,2,2-trifluoroethyl)-1H-pyrazol-3-yl)-4-fluoropyrrolidine-2-carboxamide (422)

To a stirred solution of (2S,4R)—N-(4-methyl-1-(2,2,2-trifluoroethyl)-1H-pyrazol-3-yl)-4-fluoropyrrolidine-2-carboxamide (HCl salt, 121 mg) in DMF (10 mL) was added S4 (113 mg, 1.0 equiv.), HATU (169 mg, 1.2 equiv), and DIEA (0.32 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 90 mg (41%) of 422. 1H NMR (400 MHz, DMSO-$d_6$): (major rotamer) δ 1.75 (s, 3H), 2.07-2.25 (m, 1H), 2.53-2.61 (m, 1H), 2.65 (s, 3H), 2.69 (s, 3H), 3.94-4.09 (m, 1H), 4.18-4.29 (m, 1H), 4.55 (t, 1H, J=8.8 Hz), 4.89-5.04 (m, 2H), 5.45-5.86 (m, 3H), 7.52 (s, 1H), 7.80-7.88 (m, 2H), 8.45 (s, 1H), 9.05 (s, 2H), 9.94 (s, 1H); 19F NMR (376 MHz, DMSO-$d_6$300K): (major rotamer) δ −70.28 (3F), −176.12 (1F). LC (method A): tR=1.41 min. LC/MS (EI) m/z: [M+H]+ 587.

(2S,4R)-1-(2-(3-Acetyl-5-(2-methylpyrimidin-5-yl)-1H-indazol-1-yl)acetyl)-N-(5-methyl-1-(2,2,2-trifluoroethyl)-1H-pyrazol-3-yl)-4-fluoropyrrolidine-2-carboxamide (429)

Scheme 340

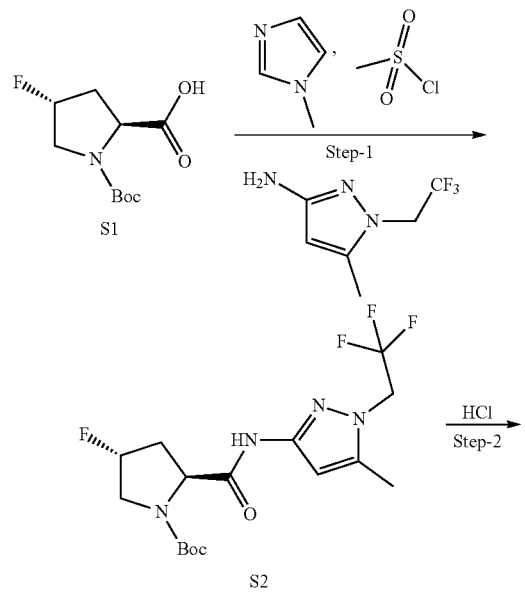

-continued

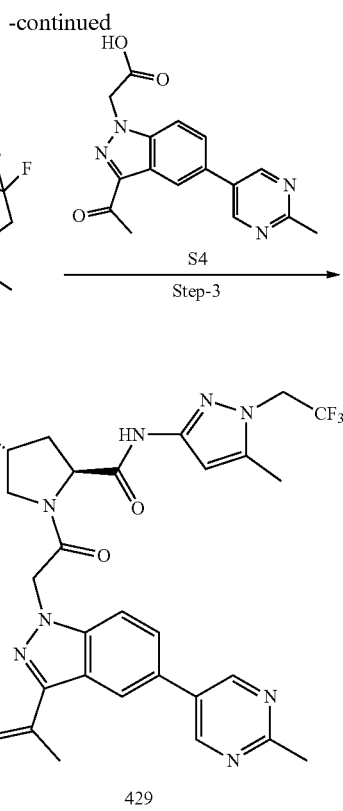

Step-1: tert-Butyl (2S,4R)-2-((5-methyl-1-(2,2,2-trifluoroethyl)-1H-pyrazol-3-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 5-methyl-1-(2,2,2-trifluoroethyl)-1H-pyrazol-3-amine (192 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 421 mg (quantitative yield) of titled compound was obtained.

Step-2: (2S,4R)—N-(5-Methyl-1-(2,2,2-trifluoroethyl)-1H-pyrazol-3-yl)-4-fluoropyrrolidine-2-carboxamide (S3)

To tert-butyl (2S,4R)-2-((5-methyl-1-(2,2,2-trifluoroethyl)-1H-pyrazol-3-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(5-methyl-1-(2,2,2-trifluoroethyl)-1H-pyrazol-3-yl)-4-fluoropyrrolidine-2-carboxamide (429)

To a stirred solution of (2S,4R)—N-(5-methyl-1-(2,2,2-trifluoroethyl)-1H-pyrazol-3-yl)-4-fluoropyrrolidine-2-carboxamide (HCl salt, 141 mg) in DMF (10 mL) was added S4 (132 mg, 1.0 equiv.), HATU (196 mg, 1.2 equiv), and DIEA (0.39 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 108 mg (43%) of 429. 1H NMR (400 MHz, DMSO-$d_6$): (major rotamer) δ 2.03-2.21 (m, 1H), 2.24 (s, 3H), 2.53-2.58 (m, 1H), 2.65 (s, 3H), 2.69 (s, 3H), 3.93-4.08 (m, 1H), 4.17-4.27 (m, 1H), 4.56 (t, 1H, J=8.3 Hz), 5.45-5.87 (m, 3H), 6.39 (s, 1H), 7.78-7.87 (m, 1H), 7.85 (s, 1H), 8.44 (s, 1H), 9.05 (s, 2H), 10.42 (s, 1H); 19F NMR (376 MHz, DMSO-$d_6$300K): (major rotamer) δ −69.62 (3F), −175.86 (1F). LC (method A): tR=1.50 min. LC/MS (EI) m/z: [M+H]+ 587.

(2S,4R)-1-(2-(3-Acetyl-5-(2-methylpyrimidin-5-yl)-1H-indazol-1-yl)acetyl)-N-(4-chloro-1-(2,2,2-trifluoroethyl)-1H-pyrazol-3-yl)-4-fluoropyrrolidine-2-carboxamide (430)

Scheme 341

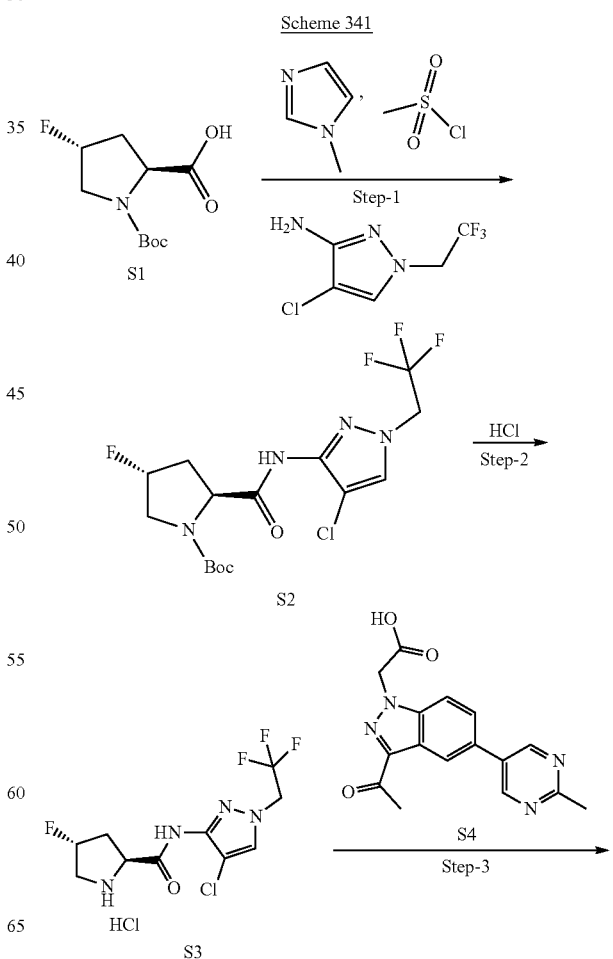

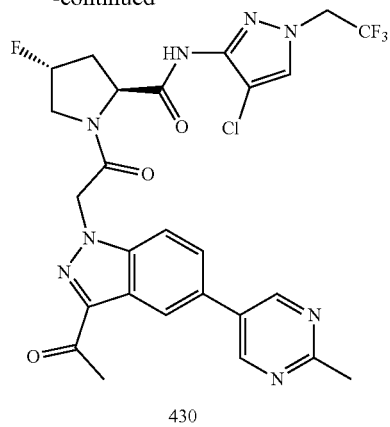

430

Step-1: tert-Butyl (2S, 4R)-2-((4-chloro-1-(2,2,2-trifluoroethyl)-1H-pyrazol-3-yl)carbamoyl)-4-fluoro-pyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 4-chloro-1-(2,2,2-trifluoroethyl)-1H-pyrazol-3-amine (214 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 390 mg of titled compound was obtained.

Step-2: (2S,4R)—N-(4-Chloro-1-(2,2,2-trifluoroethyl)-1H-pyrazol-3-yl)-4-fluoropyrrolidine-2-carboxamide (S3)

To tert-butyl (2S,4R)-2-((4-chloro-1-(2,2,2-trifluoroethyl)-1H-pyrazol-3-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(4-chloro-1-(2,2,2-trifluoroethyl)-1H-pyrazol-3-yl)-4-fluoropyrrolidine-2-carboxamide (430)

To a stirred solution of (2S,4R)—N-(4-chloro-1-(2,2,2-trifluoroethyl)-1H-pyrazol-3-yl)-4-fluoropyrrolidine-2-carboxamide (HCl salt, 139 mg) in DMF (10 mL) was added S4 (123 mg, 1.0 equiv.), HATU (182 mg, 1.2 equiv), and DIEA (0.45 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 118 mg (49%) of 430. 1H NMR (400 MHz, DMSO-d6): (major rotamer) δ 2.09-2.28 (m, 1H), 2.51-2.59 (m, 1H), 2.66 (s, 3H), 2.69 (s, 3H), 3.93-4.07 (m, 1H), 4.20-4.30 (m, 1H), 4.57 (t, 1H, J=8.1 Hz), 5.01-5.21 (m, 2H), 5.44-5.90 (m, 3H), 7.78-7.91 (m, 2H), 8.06 (s, 1H), 8.44 (s, 1H), 9.05 (s, 2H), 10.09 (s, 1H); 19F NMR (376 MHz, DMSO-d6 300K): (major rotamer) δ −70.23 (3F), −176.17 (1F). LC (method A): tR=1.47 min. LC/MS (EI) m/z: [M+H]+ 607.

(2S,4R)-1-(2-(3-Acetyl-5-(2-methylpyrimidin-5-yl)-1H-indazol-1-yl)acetyl)-4-fluoro-N-(1-(3,3,3-trifluoropropyl)-1H-pyrazol-3-yl)pyrrolidine-2-carboxamide (437)

Scheme 342

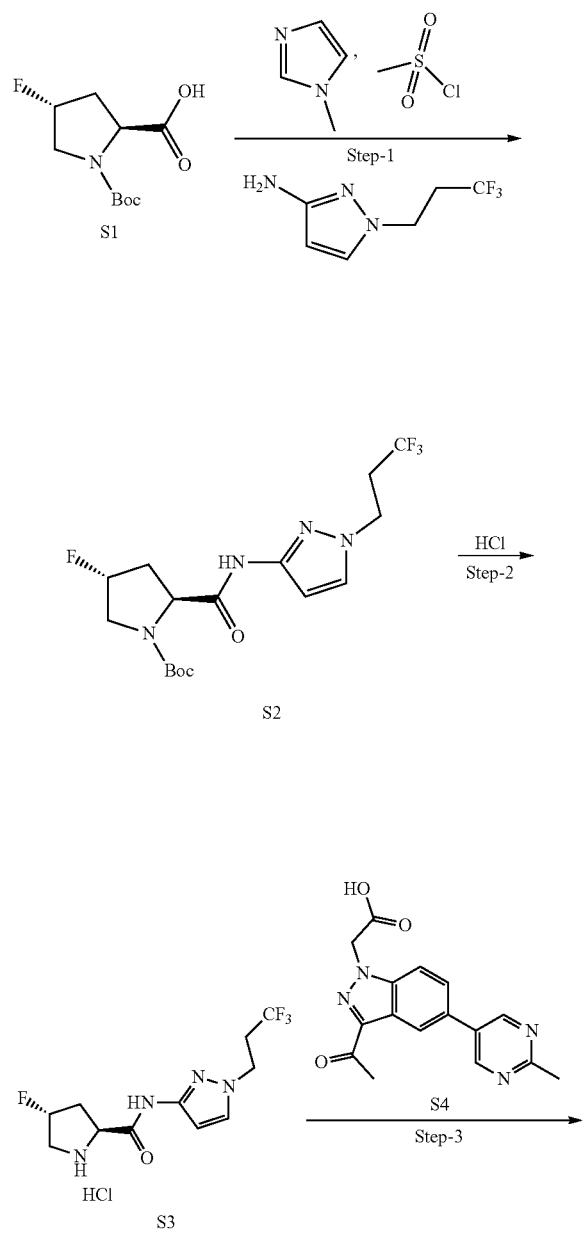

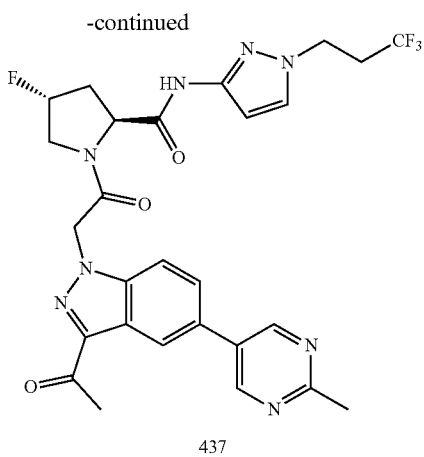

437

Step-1: tert-Butyl (2S,4R)-4-fluoro-2-((1-(3,3,3-trifluoropropyl)-1H-pyrazol-3-yl)carbamoyl)pyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 1-(3,3,3-trifluoropropyl)-1H-pyrazol-3-amine (192 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 395 mg of titled compound was obtained.

Step-2: (2S,4R)-4-Fluoro-N-(1-(3,3,3-trifluoropropyl)-1H-pyrazol-3-yl)pyrrolidine-2-carboxamide (S#)

To tert-butyl (2S,4R)-4-fluoro-2-((1-(3,3,3-trifluoropropyl)-1H-pyrazol-3-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(1-(3,3,3-trifluoropropyl)-1H-pyrazol-3-yl)pyrrolidine-2-carboxamide (437)

To a stirred solution of (2S,4R)-4-fluoro-N-(1-(3,3,3-trifluoropropyl)-1H-pyrazol-3-yl)pyrrolidine-2-carboxamide (HCl salt, 135 mg) in DMF (10 mL) was added S4 (127 mg, 1.0 equiv.), HATU (187 mg, 1.2 equiv), and DIEA (0.45 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 143 mg (60%) of 437. 1H NMR (400 MHz, DMSO-d6): (major rotamer) δ 2.01-2.21 (m, 1H), 2.52-2.58 (m, 1H), 2.65 (s, 3H), 2.69 (s, 3H), 2.71-2.82 (m, 2H), 3.93-4.06 (m, 1H), 4.19-4.33 (m, 3H), 4.57 (t, 1H, J=8.8 Hz), 5.41-5.85 (m, 3H), 6.43 (d, 1H, J=2.1 Hz), 7.64 (d, 1H, J=2.1 Hz), 7.82-7.89 (m, 1H), 7.86 (s, 1H), 8.44 (s, 1H), 9.03 (s, 2H), 10.63 (s, 1H); 19F NMR (376 MHz, DMSO-d6 300K): (major rotamer) δ −64.04 (3F), −175.88 (1F). LC (method A): tR=1.48 min. LC/MS (EI) m/z: [M+H]+ 587.

(2S,4R)-1-(2-(3-Acetyl-5-(2-methylpyrimidin-5-yl)-1H-indazol-1-yl)acetyl)-N-(5-bromo-2-fluoropyridin-4-yl)-4-fluoropyrrolidine-2-carboxamide (438)

Scheme 343

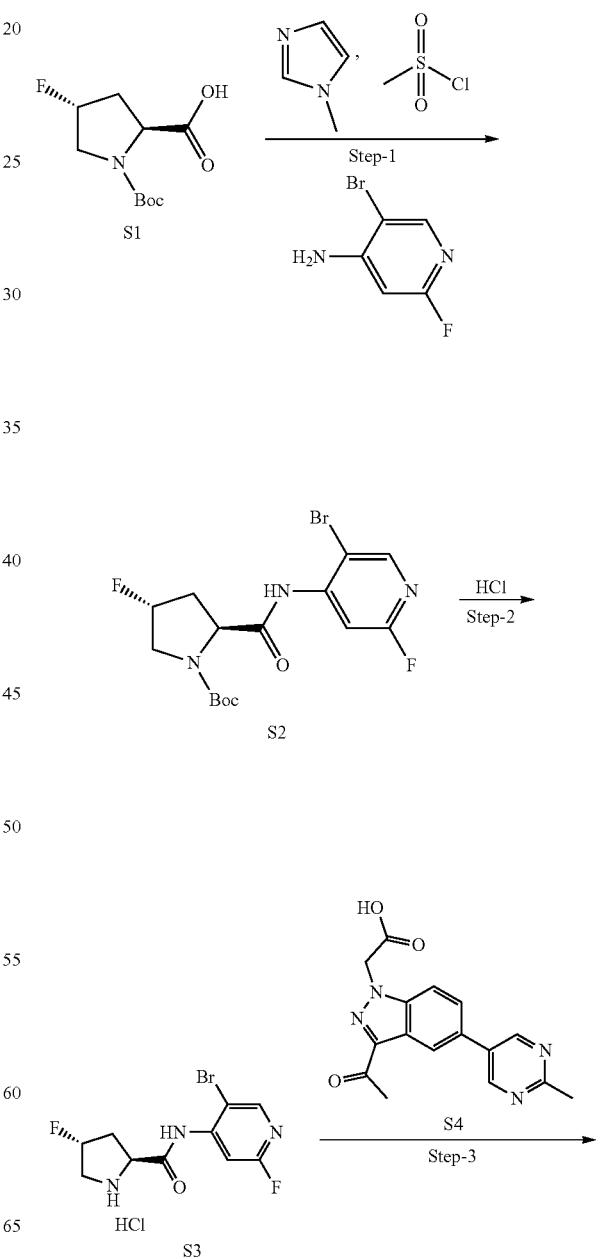

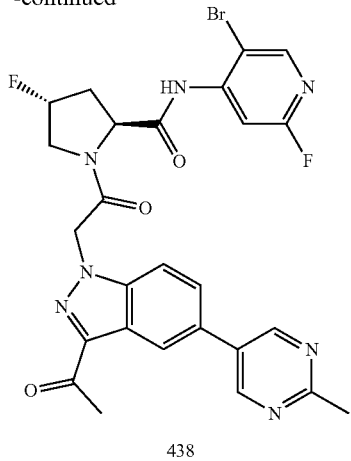

438

Step-1: tert-Butyl (2S,4R)-2-((5-bromo-2-fluoropyridin-4-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-5° C. Then 5-bromo-2-fluoropyridin-4-amine (189 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 365 mg (84%) of titled compound was obtained.

Step-2: (2S,4R)—N-(5-Bromo-2-fluoropyridin-4-yl)-4-fluoropyrrolidine-2-carboxamide (S3)

To tert-butyl (2S,4R)-2-((5-bromo-2-fluoropyridin-4-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(5-bromo-2-fluoropyridin-4-yl)-4-fluoropyrrolidine-2-carboxamide (438)

To a stirred solution of (2S,4R)—N-(5-bromo-2-fluoropyridin-4-yl)-4-fluoropyrrolidine-2-carboxamide (HCl salt, 124 mg) in DMF (10 mL) was added S4 (112 mg, 1.0 equiv.), HATU (164 mg, 1.2 equiv), and DIEA (0.3 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 72 mg (34%) of 438. 1H NMR (400 MHz, DMSO-d6): (major rotamer) δ 2.11-2.29 (m, 1H), 2.53-2.61 (m, 1H), 2.65 (s, 3H), 2.69 (s, 3H), 3.94-4.12 (m, 1H), 4.20-4.31 (m, 1H), 4.89 (t, 1H, J=8.6 Hz), 5.49-5.91 (m, 3H), 7.83-7.91 (m, 2H), 8.34-8.46 (m, 2H), 9.05 (s, 2H), 10.68 (s, 1H); 19F NMR (376 MHz, DMSO-d6 300K): (major rotamer) δ −142.91 (1F), −175.87 (1F). LC (method A): tR=1.55 min. LC/MS (EI) m/z: [M]+ 598.

(2S,4R)-1-(2-(3-Acetyl-5-(2-methylpyrimidin-5-yl)-1H-indazol-1-yl)acetyl)-4-fluoro-N-(1-methyl-1H-pyrazolo[3,4-b]pyridin-3-yl)pyrrolidine-2-carboxamide (439)

Scheme 344

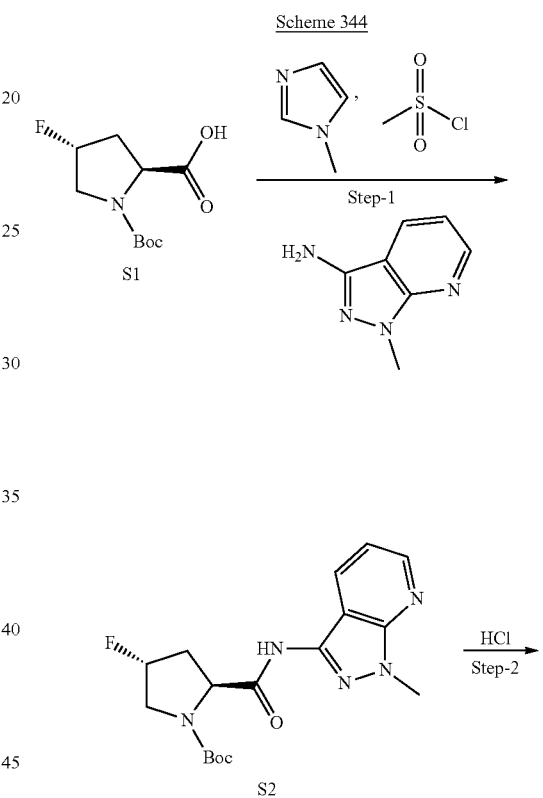

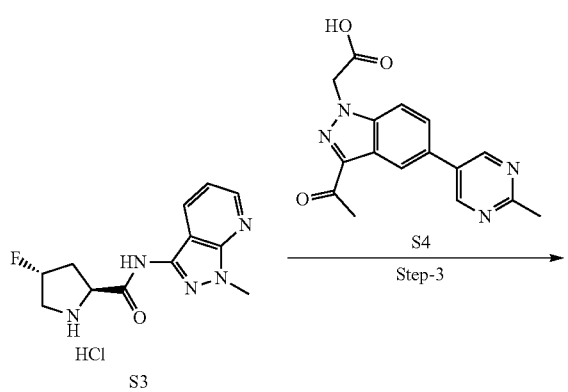

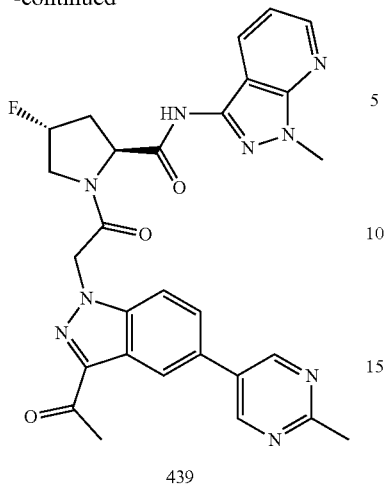

439

Step-1 tert-Butyl (2S,4R)-4-fluoro-2-((1-methyl-1H-pyrazolo[3,4-b]pyridin-3-yl)carbamoyl)pyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 1-methyl-1H-pyrazolo[3,4-b]pyridin-3-amine (159 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 259 mg (71%) of titled compound was obtained.

Step-2: (2S,4R)-4-Fluoro-N-(1-methyl-1H-pyrazolo[3,4-b]pyridin-3-yl)pyrrolidine-2-carboxamide (S3)

To tert-butyl (2S,4R)-4-fluoro-2-((1-methyl-1H-pyrazolo[3,4-b]pyridin-3-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(1-methyl-1H-pyrazolo[3,4-b]pyridin-3-yl)pyrrolidine-2-carboxamide (439)

To a stirred solution of (2S,4R)-4-fluoro-N-(1-methyl-1H-pyrazolo[3,4-b]pyridin-3-yl)pyrrolidine-2-carboxamide (HCl salt, 102 mg) in DMF (10 mL) was added S4 (106 mg, 1.0 equiv.), HATU (155 mg, 1.2 equiv), and DIEA (0.3 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 87 mg (46%) of 439. 1H NMR (400 MHz, DMSO-d6): (major rotamer) δ 2.16-2.30 (m, 1H), 2.53-2.61 (m, 1H), 2.65 (s, 3H), 2.69 (s, 3H), 3.96 (s, 3H), 3.98-4.13 (m, 1H), 4.21-4.33 (m, 1H), 4.69 (t, 1H, J=9.0 Hz), 5.52-5.91 (m, 3H), 7.05-7.09 (dd, 1H, J1=8.7 Hz, J2=4.9 Hz), 7.81-7.88 (m, 1H), 7.85 (s, 1H), 8.24 (d, 1H, J=8.7 Hz), 8.43 (s, 1H), 8.50 (d, 1H, J=4.9 Hz), 9.05 (s, 2H), 10.92 (s, 1H); 19F NMR (376 MHz, DMSO-d6 300K): (major rotamer) δ −175.91 (1F). LC (method A): tR=1.21 min. LC/MS (EI) m/z: [M+H]+ 556.

(2S,4R)-1-(2-(3-Acetyl-5-(2-methylpyrimidin-5-yl)-1H-indazol-1-yl)acetyl)-N-(4-bromothiazol-2-yl)-4-fluoropyrrolidine-2-carboxamide (448)

Scheme 345

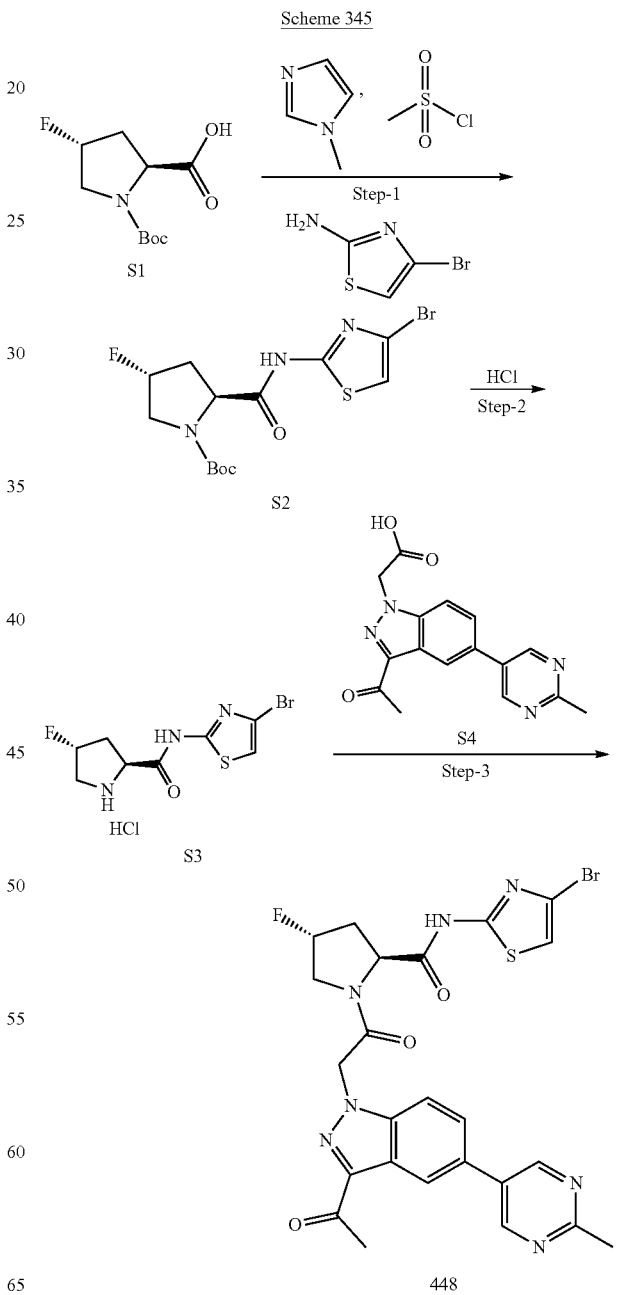

448

Step-1 tert-Butyl (2S,4R)-2-((4-bromothiazol-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 4-bromothiazol-2-amine (179 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 390 mg (97%) of titled compound was obtained.

Step-2: (2S,4R)—N-(4-Bromothiazol-2-yl)-4-fluoro-pyrrolidine-2-carboxamide (S3)

To tert-butyl (2S,4R)-2-((4-bromothiazol-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(4-bromothiazol-2-yl)-4-fluoropyrrolidine-2-carboxamide (448)

To a stirred solution of (2S,4R)—N-(4-bromothiazol-2-yl)-4-fluoropyrrolidine-2-carboxamide (HCl salt, 115 mg) in DMF (10 mL) was added S4 (107 mg, 1.0 equiv.), HATU (160 mg, 1.2 equiv), and DIEA (0.3 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 130 mg (63%) of 448. 1H NMR (400 MHz, DMSO-d$_6$): (major rotamer) δ 2.09-2.28 (m, 1H), 2.53-2.61 (m, 1H), 2.65 (s, 3H), 2.69 (s, 3H), 3.99-4.14 (m, 1H), 4.21-4.31 (m, 1H), 4.62 (t, 1H, J=7.9 Hz), 5.49-5.87 (m, 3H), 7.28 (s, 1H), 7.78-7.90 (m, 2H), 8.42 (s, 1H), 9.05 (s, 2H), 12.61 (s, 1H); 19F NMR (376 MHz, DMSO-d$_6$ 300K): (major rotamer) δ −176.05 (1F). LC (method A): tR=1.56 min. LC/MS (EI) m/z: [M]+ 586.

(2S,4R)-1-(2-(3-Acetyl-5-(2-methylpyrimidin-5-yl)-1H-indazol-1-yl)acetyl)-N-(4-bromo-5-methylthiazol-2-yl)-4-fluoropyrrolidine-2-carboxamide (449)

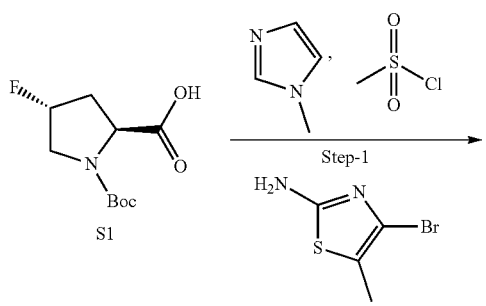

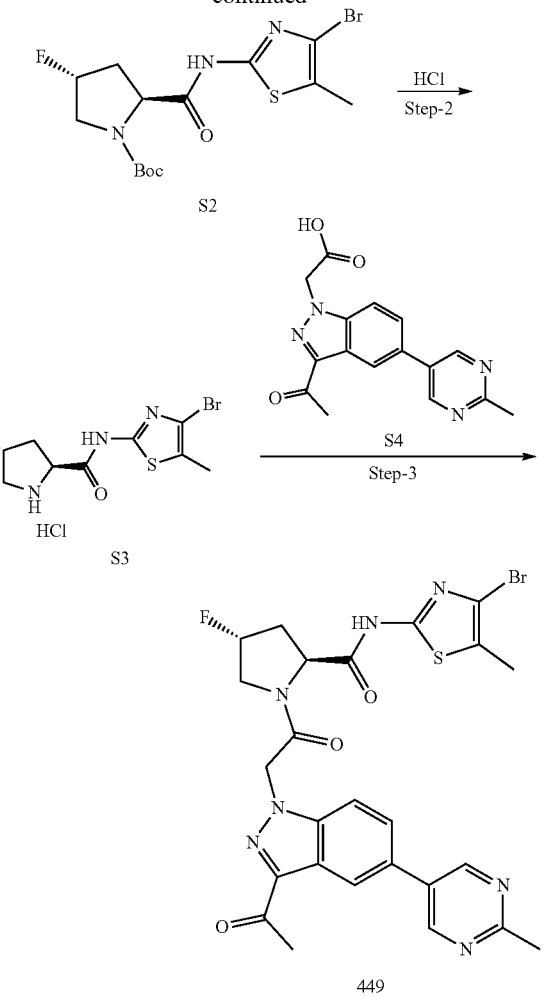

Step-1: tert-Butyl (2S,4R)-2-((4-bromo-5-methylthiazol-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-5° C. Then 4-bromo-5-methylthiazol-2-amine (207 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 409 mg (quantitative yield) of titled compound was obtained.

Step-2: (2S,4R)—N-(4-Bromo-5-methylthiazol-2-yl)-4-fluoropyrrolidine-2-carboxamide (S3)

To tert-butyl (2S,4R)-2-((4-bromo-5-methylthiazol-2-yl)carbamoyl)-4-fluoropyrrolidine-1-carboxylate was added 10

Step-3: (2S,4R)-1-(2-(3-Acetyl-5-(2-methylpyrimidin-5-yl)-1H-indazol-1-yl)acetyl)-N-(4-bromo-5-methylthiazol-2-yl)-4-fluoropyrrolidine-2-carboxamide (449)

To a stirred solution of (2S,4R)—N-(4-bromo-5-methylthiazol-2-yl)-4-fluoropyrrolidine-2-carboxamide (HCl salt, 121 mg) in DMF (10 mL) was added S4 (109 mg, 1.0 equiv.), HATU (160 mg, 1.2 equiv), and DIEA (0.3 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 88 mg (42%) of 449. 1H NMR (400 MHz, DMSO-d$_6$): (major rotamer) δ 2.09-2.20 (m, 1H), 2.24 (s, 3H), 2.53-2.61 (m, 1H), 2.65 (s, 3H), 2.69 (s, 3H), 3.98-4.13 (m, 1H), 4.19-4.33 (m, 1H), 4.59 (t, 1H, J=8.5 Hz), 5.48-5.89 (m, 3H), 7.77-7.91 (m, 1H), 7.86 (s, 1H), 8.43 (s, 1H), 9.04 (s, 2H), 12.44 (s, 1H); 19F NMR (376 MHz, DMSO-d$_6$300K): (major rotamer) δ −176.04 (1F). LC (method A): tR=1.73 min. LC/MS (EI) m/z: [M]+ 600.

(2S,4R)-1-(2-(3-Acetyl-5-(2-methylpyrimidin-5-yl)-1H-indazol-1-yl)acetyl)-N-(4-(2-chlorophenyl)thiazol-2-yl)-4-fluoropyrrolidine-2-carboxamide (453)

Scheme 347

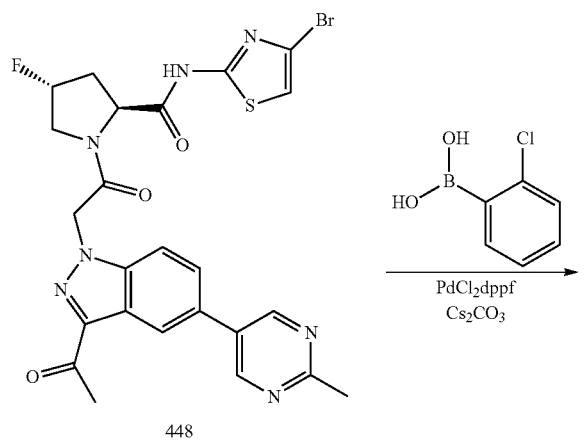

448

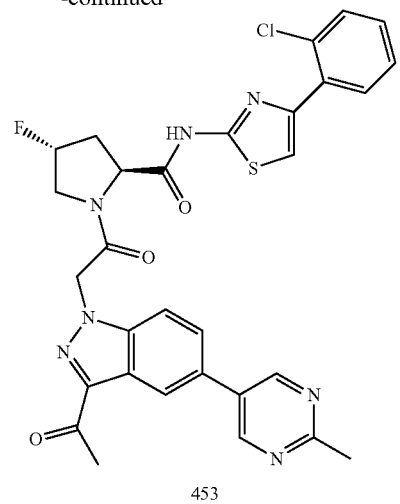

453

To a stirred solution of (2S,4R)-1-(2-(3-acetyl-5-(2-methylpyrimidin-5-yl)-1H-indazol-1-yl)acetyl)-N-(4-bromothiazol-2-yl)-4-fluoropyrrolidine-2-carboxamide (55 mg, 0.1 mmole) in DMF (10 mL) was added (2-chlorophenyl) boronic acid (37 mg, 2.2 equiv.), Cs$_2$CO$_3$ (61 mg, 2 equiv) under inert atmosphere. The reaction mixture was degassed for 5 min and then was added PdCl2dppf (5 mg, 6%). It was degassed again for 5 to 10 min and then heated at 90° C. for 18 hours. It was then cooled and diluted with EtOAC (20 mL). The organic layer was separated, washed with brine (3×15 mL), dried over Na2SO4 and concentrated in vacuuo. The resulting oil was purified by ISCO (silica gel, eluted with 10% MeOH in DCM gradient) and yielded 25 mg (43%) of 453. 1H NMR (400 MHz, DMSO-d$_6$): (major rotamer) δ 2.09-2.30 (m, 1H), 2.53-2.61 (m, 1H), 2.65 (s, 3H), 2.69 (s, 3H), 3.99-4.15 (m, 1H), 4.19-4.33 (m, 1H), 4.69 (t, 1H, J=8.4 Hz), 5.51-5.90 (m, 3H), 7.34-7.44 (m, 2H), 7.54 d, 1H, J=7.4 Hz), 7.58 (s, 1H), 7.76-7.89 (m, 3H), 8.43 (s, 1H), 9.03 (s, 2H), 12.53 (s, 1H); 19F NMR (376 MHz, DMSO-d$_6$300K): (major rotamer) δ −175.90 (1F). LC (method A): tR=2.06 min. LC/MS (EI) m/z: [M]+ 618.

(2S,4R)-1-(2-(3-Acetyl-5-(2-methylpyrimidin-5-yl)-1H-indazol-1-yl)acetyl)-N-(1-ethyl-1H-pyrazol-3-yl)-4-fluoropyrrolidine-2-carboxamide (463)

Scheme 348

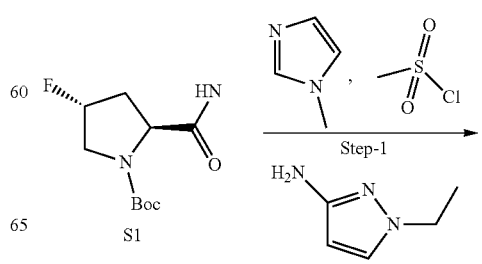

S1

745

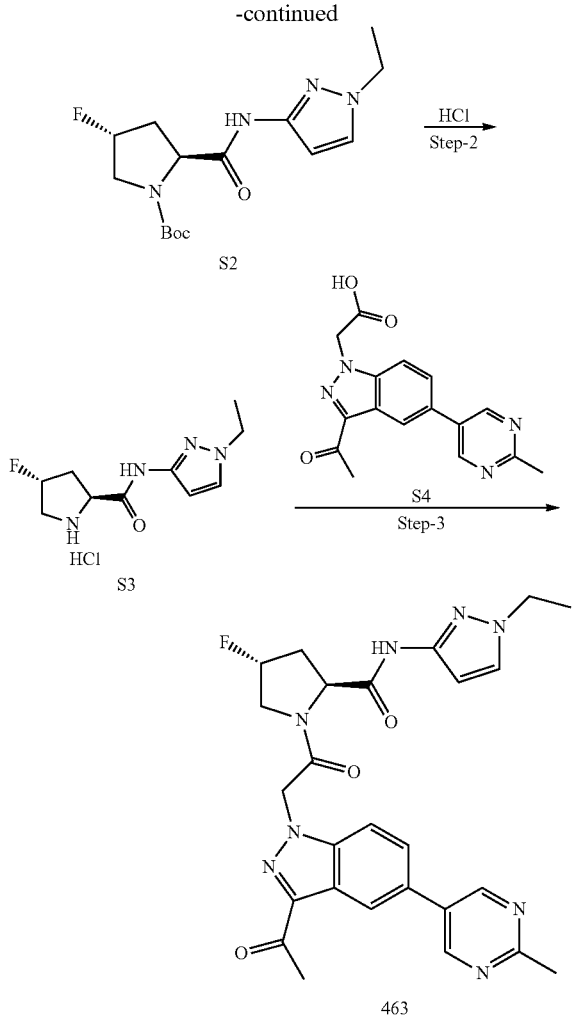

Step-1: tert-Butyl (2S,4R)-2-((1-ethyl-1H-pyrazol-3-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 1-ethyl-1H-pyrazol-3-amine (119 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 304 mg of titled compound was obtained.

Step-2: (2S,4R)—N-(1-ethyl-1H-pyrazol-3-yl)-4-fluoropyrrolidine-2-carboxamide (S3)

To tert-butyl (2S,4R)-2-((1-ethyl-1H-pyrazol-3-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(1-ethyl-1H-pyrazol-3-yl)-4-fluoropyrrolidine-2-carboxamide (463)

To a stirred solution of (2S,4R)—N-(1-ethyl-1H-pyrazol-3-yl)-4-fluoropyrrolidine-2-carboxamide (HCl salt, 100 mg) in DMF (10 mL) was added S4 (118 mg, 1.0 equiv.), HATU (173 mg, 1.2 equiv), and DIEA (0.33 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 93 mg (47%) of 463. 1H NMR (400 MHz, DMSO-$d_6$): (major rotamer) δ 1.23 (t, 3H, J=7.2 Hz), 2.04-2.22 (m, 1H), 2.52-2.58 (m, 1H), 2.65 (s, 3H), 2.69 (s, 3H), 3.92-4.08 (m, 3H), 4.19-4.33 (m, 3H), 4.57 (t, 1H, J=8.8 Hz), 5.46-5.85 (m, 3H), 6.38 (d, 1H, J=2.3 Hz), 7.56 (d, 1H, J=2.3 Hz), 7.79-7.89 (m, 1H), 7.86 (s, 1H), 8.44 (s, 1H), 9.05 (s, 2H), 10.60 (s, 1H); 19F NMR (376 MHz, DMSO-$d_6$ 300K): (major rotamer) δ −175.88 (1F). LC (method A): tR=1.22 min. LC/MS (EI) m/z: [M+H]+ 519.

(2S,4R)-1-(2-(3-Acetyl-5-(2-methylpyrimidin-5-yl)-1H-indazol-1-yl)acetyl)-N-(6-bromo-3-chloropyridin-2-yl)-4-fluoropyrrolidine-2-carboxamide (472)

Scheme 349

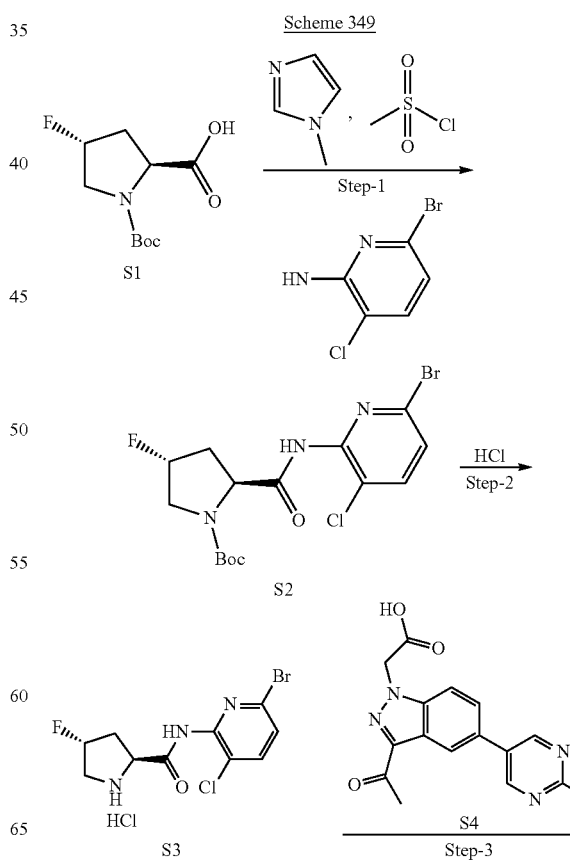

-continued

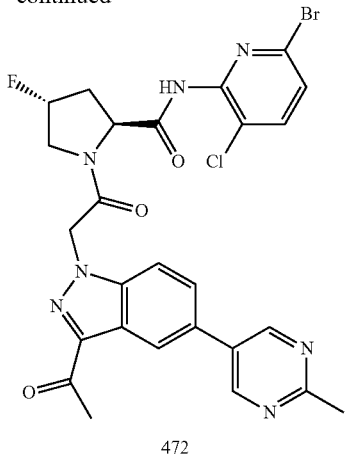

472

Step-1: tert-Butyl (2S,4R)-2-((6-bromo-3-chloro-pyridin-2-yl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 6-bromo-3-chloropyridin-2-amine (220 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and purified by ISCO (silica gel, eluted with 5% CH3OH in DCM gradient) 181 mg of titled compound was obtained.

Step-2: (2S,4R)—N-(6-Bromo-3-chloropyridin-2-yl)-4-fluoropyrrolidine-2-carboxamide (S3)

To tert-butyl (2S,4R)-2-((6-bromo-3-chloropyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(6-bromo-3-chloropyridin-2-yl)-4-fluoropyrrolidine-2-carboxamide (472)

To a stirred solution of (2S,4R)—N-(6-bromo-3-chloro-pyridin-2-yl)-4-fluoropyrrolidine-2-carboxamide (HCl salt, 120 mg) in DMF (10 mL) was added S4 (104 mg, 1.0 equiv.), HATU (137 mg, 1.2 equiv), and DIEA (0.30 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 124 mg (61%) of 472. 1H NMR (400 MHz, DMSO-$d_6$): (major rotamer) δ 2.20-2.39 (m, 1H), 2.57-2.63 (m, 1H), 2.65 (s, 3H), 2.69 (s, 3H), 3.93-4.10 (m, 1H), 4.20-4.31 (m, 1H), 4.67 (t, 1H, J=8.7 Hz), 5.49-5.91 (m, 3H), 7.36 (d, 1H, J=8.2 Hz), 7.79-7.90 (m, 2H), 8.17 (d, 1H, J=8.2 Hz), 8.45 (s, 1H), 9.05 (s, 2H), 10.58 (s, 1H); 19F NMR (376 MHz, DMSO-$d_6$ 300K): (major rotamer) δ −176.01 (1F). LC (method A): tR=1.52 min. LC/MS (EI) m/z: [M+H]+ 616.

(2S,4R)-1-(2-(3-acetyl-5-(2-Methylpyrimidin-5-yl)-1H-indazol-1-yl)acetyl)-4-fluoro-N-(1-(5-fluoropyridin-2-yl)-1H-pyrazol-3-yl)pyrrolidine-2-carboxamide (479)

Scheme 350

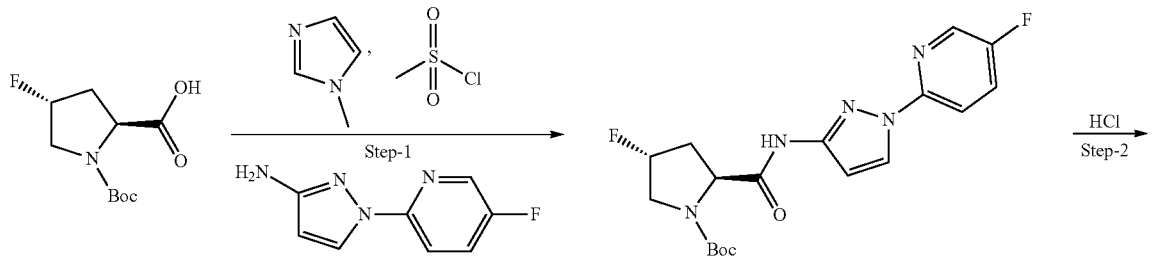

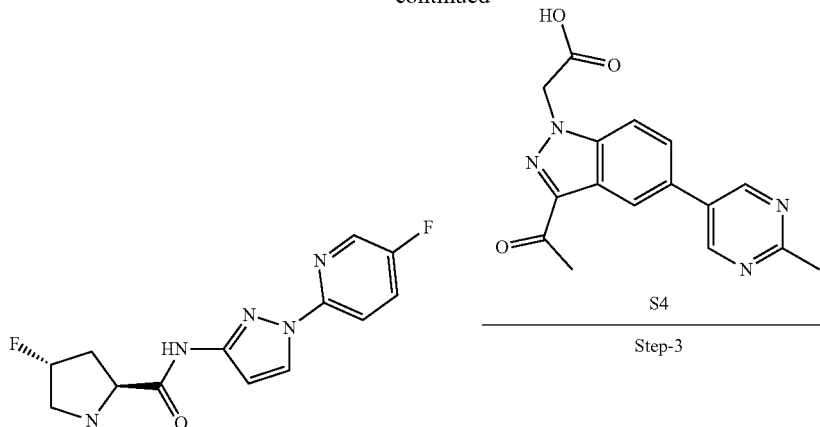

Step-1: tert-Butyl (2S,4R)-4-fluoro-2-((1-(5-fluoro-pyridin-2-yl)-1H-pyrazol-3-yl)carbamoyl)pyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 1-(5-fluoropyridin-2-yl)-1H-pyrazol-3-amine (191 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 395 mg (quantitative yield) of titled compound was obtained.

Step-2: (2S,4R)-4-Fluoro-N-(1-(5-fluoropyridin-2-yl)-1H-pyrazol-3-yl)pyrrolidine-2-carboxamide (S3)

To tert-butyl (2S,4R)-4-fluoro-2-((1-(5-fluoropyridin-2-yl)-1H-pyrazol-3-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(1-(5-fluoropyridin-2-yl)-1H-pyrazol-3-yl)pyrrolidine-2-carboxamide (479)

To a stirred solution of (2S,4R)-4-fluoro-N-(1-(5-fluoropyridin-2-yl)-1H-pyrazol-3-yl)pyrrolidine-2-carboxamide (HCl salt, 150 mg) in DMF (12 mL) was added S4 (141 mg, 1.0 equiv.), HATU (205 mg, 1.2 equiv), and DIEA (0.40 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 123 mg (47%) of 479. 1H NMR (400 MHz, DMSO-$d_6$): (major rotamer) δ 2.09-2.28 (m, 1H), 2.57-2.63 (m, 1H), 2.66 (s, 3H), 2.68 (s, 3H), 3.96-4.11 (m, 1H), 4.20-4.31 (m, 1H), 4.65 (t, 1H, J=8.9 Hz), 5.49-5.88 (m, 3H), 6.80 (d, 1H, J=2.8 Hz), 7.72-7.77 (m, 1H), 7.85-7.96 (m, 2H), 7.86 (s, 1H), 8.42-8.47 (m, 3H), 9.02 (s, 2H), 10.97 (s, 1H); 19F NMR (376 MHz, DMSO-$d_6$ 300K): (major rotamer) δ −131.81 (1F), −175.85 (1F). LC (method A): tR=1.62 min. LC/MS (EI) m/z: [M+H]+ 586.

(2S,4R)-1-(2-(3-Acetyl-5-(2-methylpyrimidin-5-yl)-1H-indazol-1-yl)acetyl)-N-(6-bromo-5-fluoro-3-methylpyridin-2-yl)-4-fluoropyrrolidine-2-carboxamide (520)

Scheme 351

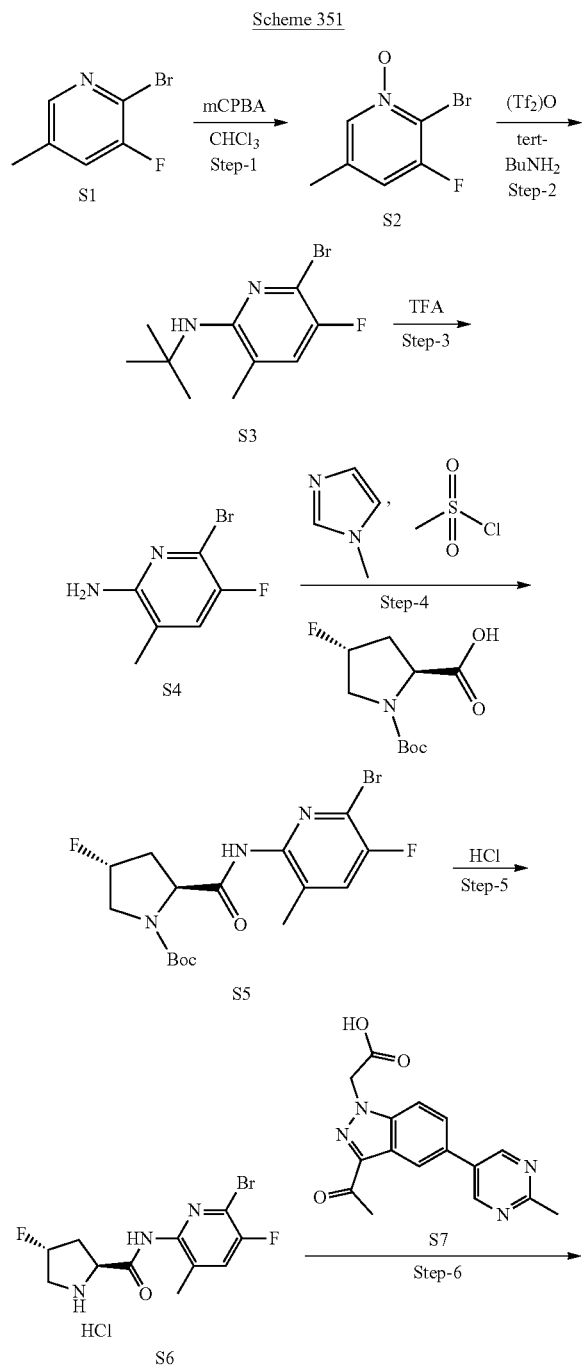

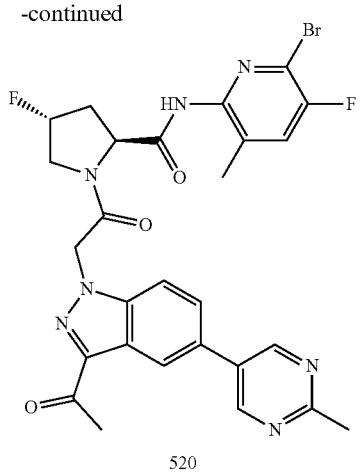

520

Step-1: 2-Bromo-3-fluoro-5-methyl-1-(1-oxidanyl)-pyridine (S2)

To a stirred solution of 2-bromo-3-fluoro-5-methylpyridine (284 mg) in CHCl3 (15 mL) was added mCPBA (0.4 g, 1.3 equiv). The reaction mixture was heated to 50° C. for 4 hours to complete the reaction. It was cooled and diluted with 20 mL DCM and washed with sat. NaHCO3 solution (5×15 mL) until no acid left in the organic layer. It was then dried by Na2SO4 and concentrated in vacuuo, which was ready for the next step.

Step-2: 6-Bromo-N-(tert-butyl)-5-fluoro-3-methyl-pyridin-2-amine (S3)

To a stirred solution of 2-Bromo-3-fluoro-5-methyl-1-(1-oxidanyl)-pyridine (200 mg, 0.97 mmole) in DCM (15 mL) was cooled to 0° C. (ice bath), added tert-Butyl amine (0.51 mL, 5 equiv), and trifluoroacidic anhydride (0.18 mL, 1.1 equiv). The reaction mixture was stirred at 0-5° C. for 1 h and added more reagents of both if the reaction was not completed. Then, it was added 15 mL of sat. NaHCO3 to neutralize. The organic layer was separated. It was washed again by 10 mL of sat. NaHCO3, brine (10 mL), dried and concentrated. The crude was purified by ISCO (silica gel, eluted by 30% EtOAc in Hexanes) to obtain 388 mg (40%) of title compound as a white solid.

Step-3: 6-Bromo-5-fluoro-3-methylpyridin-2-amine (S4)

To the solid of 6-Bromo-N-(tert-butyl)-5-fluoro-3-methylpyridin-2-amine was added 10 mL of TFA and the reaction mixture was heated at 50° C. until completion. Then it was concentrated, dissolved in DCM (15 mL), washed with sat. NaHCO3 to basic (PH=9). The organic layer was combined and dried with Na2SO4 and concentrated to be used for the next step.

Step-4: tert-Butyl (2S,4R)-2-((6-bromo-5-fluoro-3-methylpyridin-2-yl)carbamoyl)-4-fluoropyrrolidine-1-carboxylate (S5)

To a stirred solution of (2S, 4R)-1-(tert-butoxycarbonyl)-4-fluoropyrrolidine-2-carboxylic acid (464 mg, 2.0 mmole) in 20 mL of CH2Cl2, was added 1-methyl imidazole (0.40 mL, 2.5 equiv.) at 0-5° C. under nitrogen atmosphere. The reaction mixture was stirred for 10 min at 0-5° C. and then added methane sulfonyl chloride (0.2 mL, 1.2 equiv) at the same temperature. It was stirred for 1 h at 0-50° C. Then 6-bromo-5-fluoro-3-methylpyridin-2-amine (412 mg, 1 equiv) was added, and stirred for 18 h at room temperature. Water (15 mL) was added to the reaction mixture, layers were separated and aqueous layer was extracted with DCM (3×15 mL). The combined organic layer was washed with 1N HCl (15 mL), followed by Sat NaHCO3 (15 mL) and then with brine (10 mL). Combined organic layer was dried over Na2SO4, concentrated and purified by ISCO (silica gel, eluted by 5% MeOH in DCM gradient) to obtained 406 mg (48% yield) of titled compound as white foam solid.

Step-5: (2S,4R)—N-(6-Bromo-5-fluoro-3-methyl-pyridin-2-yl)-4-fluoropyrrolidine-2-carboxamide (S6)

To tert-butyl (2S,4R)-2-((6-bromo-5-fluoro-3-methylpyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-6: (2S,4R)-1-(2-(3-Acetyl-5-(2-methylpyrimidin-5-yl)-1H-indazol-1-yl)acetyl)-N-(6-bromo-5-fluoro-3-methylpyridin-2-yl)-4-fluoropyrrolidine-2-carboxamide (520)

To a stirred solution of (2S,4R)—N-(6-bromo-5-fluoro-3-methylpyridin-2-yl)-4-fluoropyrrolidine-2-carboxamide (HCl salt, 200 mg) in DMF (12 mL) was added S7 (143 mg, 1.0 equiv.), HATU (210 mg, 1.2 equiv), and DIEA (0.4 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 128 mg (47%) of 520. 1H NMR (400 MHz, DMSO-d$_6$): (major rotamer) δ 2.04 (s, 3H), 2.11-2.25 (m, 1H), 2.57-2.63 (m, 1H), 2.65 (s, 3H), 2.69 (s, 3H), 3.96-4.11 (m, 1H), 4.20-4.31 (m, 1H), 4.59 (t, 1H, J=8.4 Hz), 5.49-5.88 (m, 3H), 7.78-7.85 (m, 3H), 8.4 (s, 1H), 9.05 (s, 2H), 10.46 (s, 1H); 19F NMR (376 MHz, DMSO-d$_6$ 300K): (major rotamer) δ −119.06 (1F), −176.07 (1F). LC (method A): tR=1.58 min. LC/MS (EI) m/z: [M]+ 612.

(2S,4R)-1-(2-(3-Acetyl-5-(2-methylpyrimidin-5-yl)-1H-indazol-1-yl)acetyl)-N-(6-bromo-3-ethylpyridin-2-yl)-4-fluoropyrrolidine-2-carboxamide (534)

Scheme 352

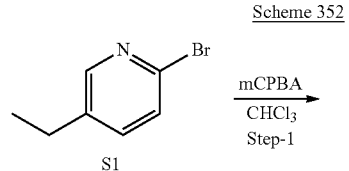

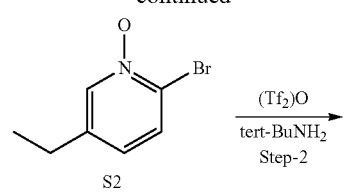

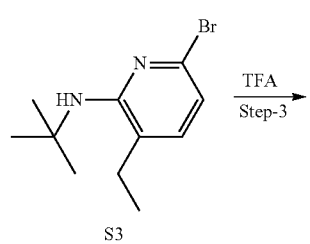

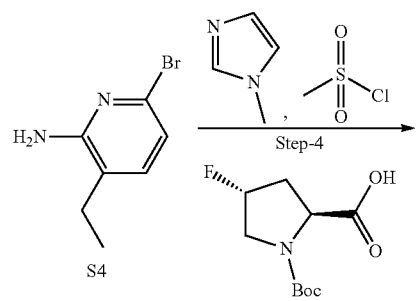

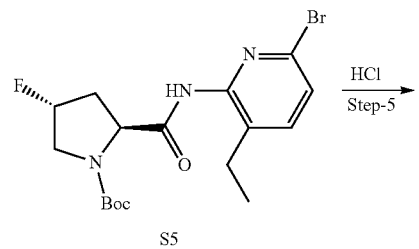

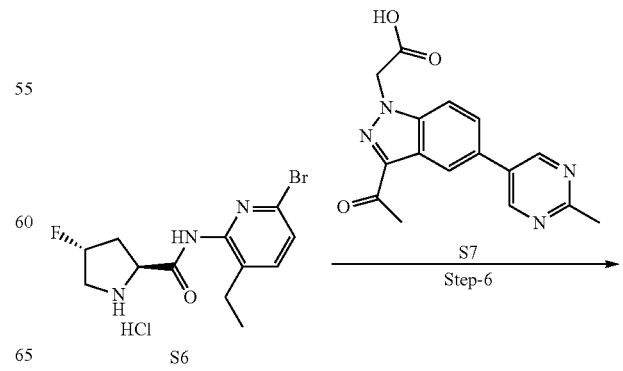

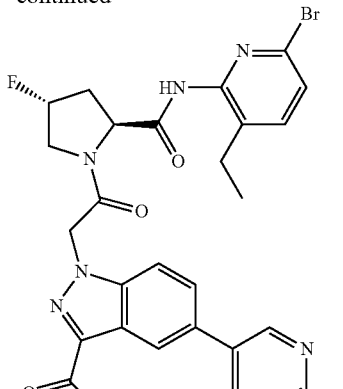

534

Step-1: 2-Bromo-5-ethyl-1-(1-oxidanyl)-pyridine (S2)

To a stirred solution of 2-bromo-5-ethylpyridine (1 g, 5 mmole) in CHCl3 (15 mL) was added mCPBA (1.7, 1.5 equiv). The reaction mixture was heated to 50° C. for 4 hours to complete the reaction. It was cooled and diluted with 20 mL DCM and washed with sat. NaHCO3 solution (5×15 mL) until no acid left in the organic layer. It was then dried by Na2SO4 and concentrated in vacuuo, which (1 g) was ready for the next step.

Step-2: 6-Bromo-N-(tert-butyl)-3-ethylpyridin-2-amine (S3)

To a stirred solution 2-Bromo-5-ethyl-1-(1-oxidanyl)-pyridine (1 g, 5 mmole) in DCM (15 mL) was cooled to 0° C. (ice bath), added tert-Butyl amine (2.6 mL, 5 equiv), and trifluoroacidic anhydride (1.54 mL, 1.1 equiv). The reaction mixture was stirred at 0-5° C. for 1 h and added more reagents of both if the reaction was not completed. Then, it was added 15 mL of sat. NaHCO3 to neutralize. The organic layer was separated. It was washed again by 10 mL of sat. NaHCO3, brine (10 mL), dried and concentrated. The crude was purified by ISCO (silica gel, eluted by 30% EtOAc in Hexanes) to obtain 369 mg (37%) of title compound as a white solid.

Step-3: 6-Bromo-3-ethylpyridin-2-amine (S4)

To the solid of 6-bromo-N-(tert-butyl)-3-ethylpyridin-2-amine was added 10 mL of TFA and the reaction mixture was heated at 50° C. until completion. Then it was concentrated, dissolved in DCM (15 mL), washed with sat. NaHCO3 to basic (PH=9). The organic layer was combined and dried with Na2SO4 and concentrated to be used for the next step.

Step-4: tert-Butyl (2S,4R)-2-((6-bromo-3-ethylpyridin-2-yl)carbamoyl)-4-fluoropyrrolidine-1-carboxylate (S5)

To a stirred solution of (2S, 4R)-1-(tert-butoxycarbonyl)-4-fluoropyrrolidine-2-carboxylic acid (125 mg, 0.54 mmole) in 8 mL of CH2Cl2, was added 1-methyl imidazole (0.11 mL, 2.5 equiv.) at 0-5° C. under nitrogen atmosphere. The reaction mixture was stirred for 10 min at 0-5° C. and then added methane sulfonyl chloride (0.05 mL, 1.2 equiv) at the same temperature. It was stirred for 1 h at 0-50° C. Then 6-bromo-3-ethylpyridin-2-amine (109 mg, 1 equiv) was added, and stirred for 18 h at room temperature. Water (15 mL) was added to the reaction mixture, layers were separated and aqueous layer was extracted with DCM (3×15 mL). The combined organic layer was washed with 1N HCl (15 mL), followed by Sat NaHCO3 (15 mL) and then with brine (10 mL). Combined organic layer was dried over Na2SO4, concentrated and purified by ISCO (silica gel, eluted by 5% MeOH in DCM gradient) to obtained 235 mg (quantitative yield) of titled compound as yellow solid.

Step-5: (2S,4R)—N-(6-Bromo-3-ethylpyridin-2-yl)-4-fluoropyrrolidine-2-carboxamide (S6)

To tert-butyl (2S,4R)-2-((6-bromo-3-ethylpyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-6: (2S,4R)-1-(2-(3-Acetyl-5-(2-methylpyrimidin-5-yl)-1H-indazol-1-yl)acetyl)-N-(6-bromo-3-ethylpyridin-2-yl)-4-fluoropyrrolidine-2-carboxamide (534)

To a stirred solution of (2S,4R)—N-(6-bromo-3-ethylpyridin-2-yl)-4-fluoropyrrolidine-2-carboxamide (HCl salt, 162 mg) in DMF (12 mL) was added S7 (167 mg, 1.0 equiv.), HATU (246 mg, 1.2 equiv), and DIEA (0.5 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 107 mg (32%) of 534. 1H NMR (400 MHz, DMSO-$d_6$): (major rotamer) δ 0.97 (t, 3H, J=7.7 Hz), 2.09-2.31 (m, 1H), 2.39 (q, 2H, J=7.7 Hz), 2.57-2.63 (m, 1H), 2.65 (s, 3H), 2.69 (s, 3H), 3.96-4.11 (m, 1H), 4.20-4.31 (m, 1H), 4.61 (t, 1H, J=8.3 Hz), 5.49-5.88 (m, 3H), 7.48 (d, 1H, J=8.0 Hz), 7.65 (d, 1H, J=8.0 Hz), 7.82-7.90 (m, 2H), 8.46 (s, 1H), 9.05 (s, 2H), 10.35 (s, 1H); 19F NMR (376 MHz, DMSO-$d_6$ 300K): (major rotamer) δ −176.07 (1F). LC (method A): tR=1.62 min. LC/MS (EI) m/z: [M]+ 612.

(2S,4R)-1-(2-(3-Acetyl-5-(2-methylpyrimidin-5-yl)-1H-indazol-1-yl)acetyl)-N-(6-bromo-3-cyclopropylpyridin-2-yl)-4-fluoropyrrolidine-2-carboxamide (538)

Scheme 353

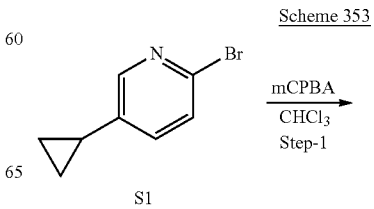

757
-continued

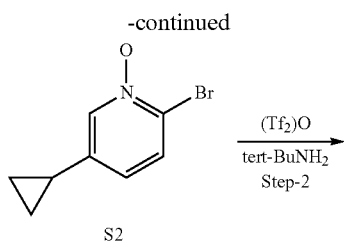

S2

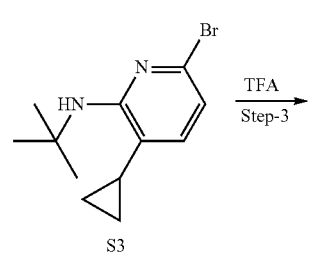

S3

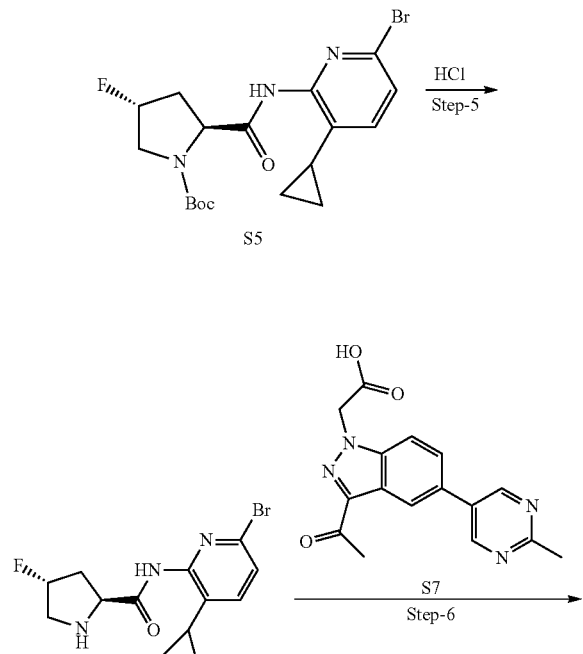

758
-continued

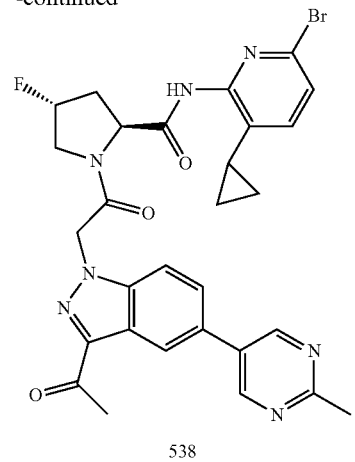

538

Step-1: 2-Bromo-5-cyclopropyl-1-(l1-oxidanyl)-l14-pyridine (S2)

To a stirred solution of 2-bromo-5-cyclopropylpyridine (1 g, 5 mmole) in CHCl3 (15 mL) was added mCPBA (1.7, 1.5 equiv). The reaction mixture was heated to 50° C. for 4 hours to complete the reaction. It was cooled and diluted with 20 mL DCM and washed with sat. NaHCO3 solution (5×15 mL) until no acid left in the organic layer. It was then dried by Na2SO4 and concentrated in vacuuo, which (1 g) was ready for the next step.

Step-2: 6-Bromo-N-(tert-butyl)-3-cyclopropylpyridin-2-amine (S3)

To a stirred solution 2-bromo-5-cyclopropyl-1-(l1-oxidanyl)-l14-pyridine (1 g, 5 mmole) in DCM (15 mL) was cooled to 0° C. (ice bath), added tert-Butyl amine (2.6 mL, 5 equiv), and trifluoroacidic anhydride (1.54 mL, 1.1 equiv). The reaction mixture was stirred at 0-5° C. for 1 h and added more reagents of both if the reaction was not completed. Then, it was added 15 mL of sat. NaHCO3 to neutralize. The organic layer was separated. It was washed again by 10 mL of sat. NaHCO3, brine (10 mL), dried and concentrated. The crude was purified by ISCO (silica gel, eluted by 30% EtOAc in Hexanes) to obtain 480 mg (36%) of title compound as a yellow solid.

Step-3: 6-Bromo-3-cyclopropylpyridin-2-amine (S4)

To the solid of 6-bromo-N-(tert-butyl)-3-cyclopropylpyridin-2-amine was added 10 mL of TFA and the reaction mixture was heated at 50° C. until completion. Then it was concentrated, dissolved in DCM (15 mL), washed with sat. NaHCO3 to basic (PH=9). The organic layer was combined and dried with Na2SO4 and concentrated to be used for the next step.

Step-4: tert-Butyl (2S,4R)-2-((6-bromo-3-cyclopropylpyridin-2-yl)carbamoyl)-4-fluoropyrrolidine-1-carboxylate (S5)

To a stirred solution of (2S, 4R)-1-(tert-butoxycarbonyl)-4-fluoropyrrolidine-2-carboxylic acid (125 mg, 0.54 mmole) in 8 mL of CH2Cl2, was added 1-methyl imidazole (0.11 mL, 2.5 equiv.) at 0-5° C. under nitrogen atmosphere. The reaction mixture was stirred for 10 min at 0-5° C. and then added methane sulfonyl chloride (0.05 mL, 1.2 equiv) at the same temperature. It was stirred for 1 h at 0-50° C. Then 6-bromo-3-cyclopropylpyridin-2-amine (115 mg, 1 equiv) was added, and stirred for 18 h at room temperature. Water (15 mL) was added to the reaction mixture, layers were separated and aqueous layer was extracted with DCM (3×15 mL). The combined organic layer was washed with 1N HCl (15 mL), followed by Sat NaHCO3 (15 mL) and then with brine (10 mL). Combined organic layer was dried over Na2SO4, concentrated and purified by ISCO (silica gel, eluted by 5% MeOH in DCM gradient) to obtained 180 mg (78%) of titled compound as a clear oil.

Step-5: (2S,4R)—N-(6-Bromo-3-cyclopropylpyridin-2-yl)-4-fluoropyrrolidine-2-carboxamide (S6)

To tert-butyl (2S,4R)-2-((6-bromo-3-cyclopropylpyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-6: (2S,4R)-1-(2-(3-acetyl-5-(2-methylpyrimidin-5-yl)-1H-indazol-1-yl)acetyl)-N-(6-bromo-3-cyclopropylpyridin-2-yl)-4-fluoropyrrolidine-2-carboxamide (538)

To a stirred solution of (2S,4R)—N-(6-bromo-3-cyclopropylpyridin-2-yl)-4-fluoropyrrolidine-2-carboxamide (HCl salt, 153 mg) in DMF (15 mL) was added S7 (130 mg, 1.0 equiv.), HATU (192 mg, 1.2 equiv), and DIEA (0.4 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 111 mg (43%) of 538. 1H NMR (400 MHz, DMSO-$d_6$): (major rotamer) δ 0.45-0.82 (m, 4H), 1.72-1.83 (m, 1H), 2.09-2.31 (m, 1H), 2.57-2.63 (m, 1H), 2.65 (s, 3H), 2.69 (s, 3H), 3.96-4.11 (m, 1H), 4.20-4.31 (m, 1H), 4.61 (t, 1H, J=8.3 Hz), 5.49-5.88 (m, 3H), 7.30 (d, 1H, J=8.0 Hz), 7.39 (d, 1H, J=8.0 Hz), 7.79-7.91 (m, 2H), 8.44 (s, 1H), 9.02 (s, 2H), 10.41 (s, 1H); 19F NMR (376 MHz, DMSO-$d_6$ 300K): (major rotamer) δ −176.01 (1F). LC (method A): tR=1.62 min. LC/MS (EI) m/z: [M]+ 620.

(2S,4R)-1-(2-(3-Acetyl-5-(2-methylpyrimidin-5-yl)-1H-indazol-1-yl)acetyl)-4-fluoro-N-(6-methylpyridin-2-yl)pyrrolidine-2-carboxamide (561)

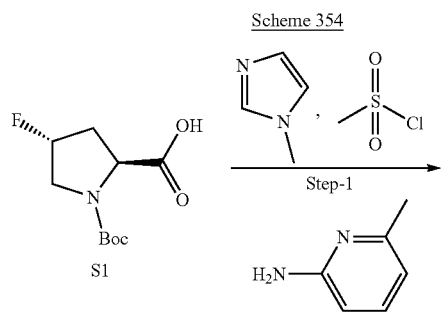

Scheme 354

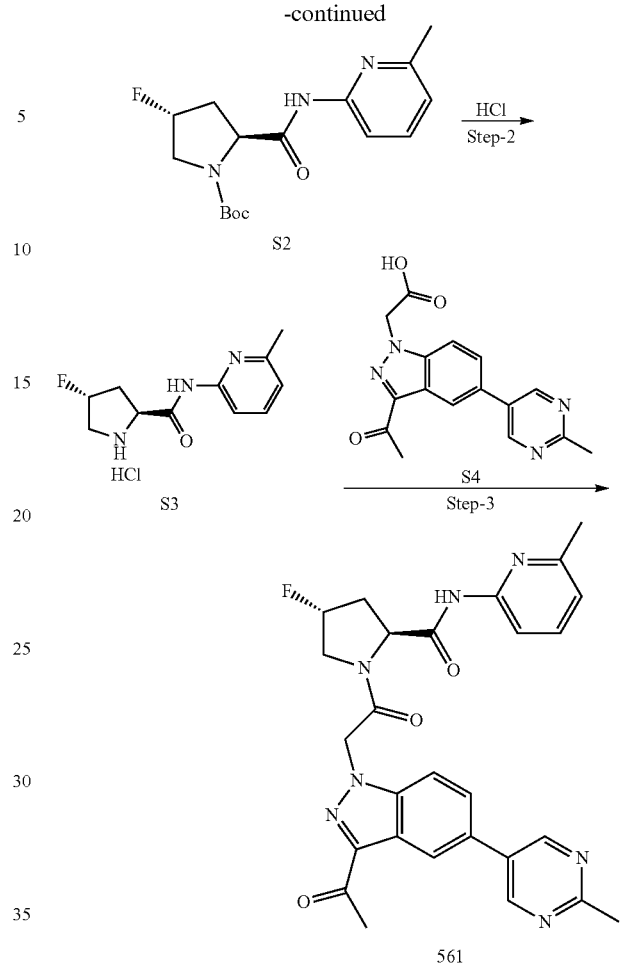

Step-1: tert-Butyl (2S,4R)-4-fluoro-2-((6-methylpyridin-2-yl)carbamoyl)pyrrolidine-1-carboxylate (S2)

To a stirred solution of (2S, 4R)-1-(tert-butoxycarbonyl)-4-fluoropyrrolidine-2-carboxylic acid (125 mg, 0.54 mmole) in 8 mL of CH2Cl2, was added 1-methyl imidazole (0.11 mL, 2.5 equiv.) at 0-5° C. under nitrogen atmosphere. The reaction mixture was stirred for 10 min at 0-5° C. and then added methane sulfonyl chloride (0.05 mL, 1.2 equiv) at the same temperature. It was stirred for 1 h at 0-50° C. Then 6-methylpyridin-2-amine (58 mg, 1 equiv) was added, and stirred for 18 h at room temperature. Water (15 mL) was added to the reaction mixture, layers were separated and aqueous layer was extracted with DCM (3×15 mL). The combined organic layer was washed with 1N HCl (15 mL), followed by Sat NaHCO3 (15 mL) and then with brine (10 mL). Combined organic layer was dried over Na2SO4, concentrated and purified by ISCO (silica gel, eluted by 5% MeOH in DCM gradient) to obtained 171 mg (99%) of titled compound as a clear oil.

Step-2: (2S,4R)-4-Fluoro-N-(6-methylpyridin-2-yl) pyrrolidine-2-carboxamide (S3)

To tert-butyl (2S,4R)-4-fluoro-2-((6-methylpyridin-2-yl) carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(6-methylpyridin-2-yl)pyrrolidine-2-carboxamide (561)

To a stirred solution of (2S,4R)-4-fluoro-N-(6-methylpyridin-2-yl)pyrrolidine-2-carboxamide (HCl salt, 139 mg) in DMF (15 mL) was added S4 (167 mg, 1.0 equiv.), HATU (246 mg, 1.2 equiv), and DIEA (0.5 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 149 mg (55%) of 561. 1H NMR (400 MHz, DMSO-d$_6$): (major rotamer) 2.09-2.25 (m, 1H), 2.32 (s, 3H), 2.57-2.63 (m, 1H), 2.65 (s, 3H), 2.69 (s, 3H), 3.96-4.11 (m, 1H), 4.20-4.31 (m, 1H), 4.61 (t, 1H, J=8.3 Hz), 5.49-5.88 (m, 3H), 6.94 (d, 1H, J=7.2 Hz), 7.56-7.59 (m, 1H), 7.76-7.91 (m, 3H), 8.43 (s, 1H), 9.03 (s, 2H), 10.58 (s, 1H); 19F NMR (376 MHz, DMSO-d$_6$300K): (major rotamer) δ −175.64 (1F). LC (method A): tR=1.35 min. LC/MS (EI) m/z: [M+H]+ 516.

(2S,4R)-1-(2-(3-Acetyl-5-(2-methylpyrimidin-5-yl)-1H-indazol-1-yl)acetyl)-4-fluoro-N-(6-(trifluoromethyl)pyridin-2-yl)pyrrolidine-2-carboxamide (562)

Scheme 355

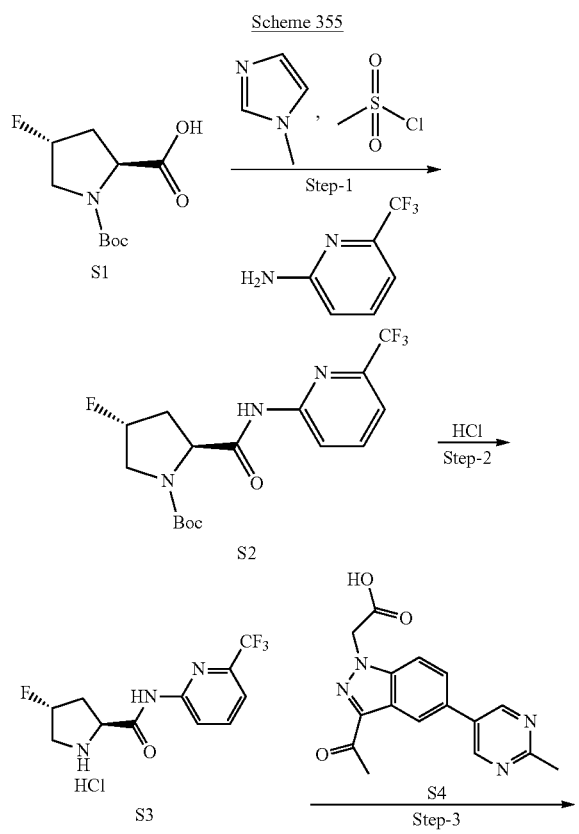

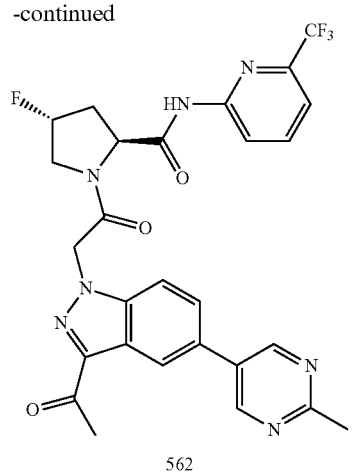

562

Step-1: tert-Butyl (2S,4R)-4-fluoro-2-((6-(trifluoromethyl)pyridin-2-yl)carbamoyl)pyrrolidine-1-carboxylate (S2)

To a stirred solution of (2S, 4R)-1-(tert-butoxycarbonyl)-4-fluoropyrrolidine-2-carboxylic acid (125 mg, 0.54 mmole) in 8 mL of CH2Cl2, was added 1-methyl imidazole (0.11 mL, 2.5 equiv.) at 0-5° C. under nitrogen atmosphere. The reaction mixture was stirred for 10 min at 0-5° C. and then added methane sulfonyl chloride (0.05 mL, 1.2 equiv) at the same temperature. It was stirred for 1 h at 0-50° C. Then 6-(trifluoromethyl)pyridin-2-amine (88 mg, 1 equiv) was added, and stirred for 18 h at room temperature. Water (15 mL) was added to the reaction mixture, layers were separated and aqueous layer was extracted with DCM (3×15 mL). The combined organic layer was washed with 1N HCl (15 mL), followed by Sat NaHCO3 (15 mL) and then with brine (10 mL). Combined organic layer was dried over Na2SO4, concentrated and purified by ISCO (silica gel, eluted by 5% MeOH in DCM gradient) to obtained 200 mg (99%) of titled compound as a clear oil.

Step-2: (2S,4R)-4-Fluoro-N-(6-(trifluoromethyl)pyridin-2-yl)pyrrolidine-2-carboxamide (S3)

To tert-butyl (2S,4R)-4-fluoro-2-((6-(trifluoromethyl)pyridin-2-yl)carbamoyl)pyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-4-fluoro-N-(6-(trifluoromethyl)pyridin-2-yl)pyrrolidine-2-carboxamide (562)

To a stirred solution of (2S,4R)-4-fluoro-N-(6-(trifluoromethyl)pyridin-2-yl)pyrrolidine-2-carboxamide (HCl salt, 169 mg) in DMF (15 mL) was added S4 (167 mg, 1.0 equiv.), HATU (246 mg, 1.2 equiv), and DIEA (0.5 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 154 mg (51%) of 562. 1H NMR (400 MHz, DMSO-$d_6$): (major rotamer) 2.09-2.29 (m, 1H), 2.57-2.63 (m, 1H), 2.65 (s, 3H), 2.69 (s, 3H), 3.96-4.11 (m, 1H), 4.20-4.31 (m, 1H), 4.61 (t, 1H, J=8.3 Hz), 5.49-5.88 (m, 3H), 7.58 (d, 1H, J=7.6 Hz), 7.76-7.88 (m, 2H), 8.02-8.09 (m, 1H), 8.29 (d, 1H, J=8.4 Hz), 8.44 (s, 1H), 9.03 (s, 2H), 11.12 (s, 1H); 19F NMR (376 MHz, DMSO-$d_6$ 300K): (major rotamer) δ −66.64 (3F), −175.61 (1F). LC (method A): tR=1.81 min. LC/MS (EI) m/z: [M+H]+ 570.

(2S,4R)-1-(2-(3-Acetyl-5-(2-methylpyrimidin-5-yl)-1H-indazol-1-yl)acetyl)-N-(6-bromo-3-(methoxymethyl)pyridin-2-yl)-4-fluoropyrrolidine-2-carboxamide (606)

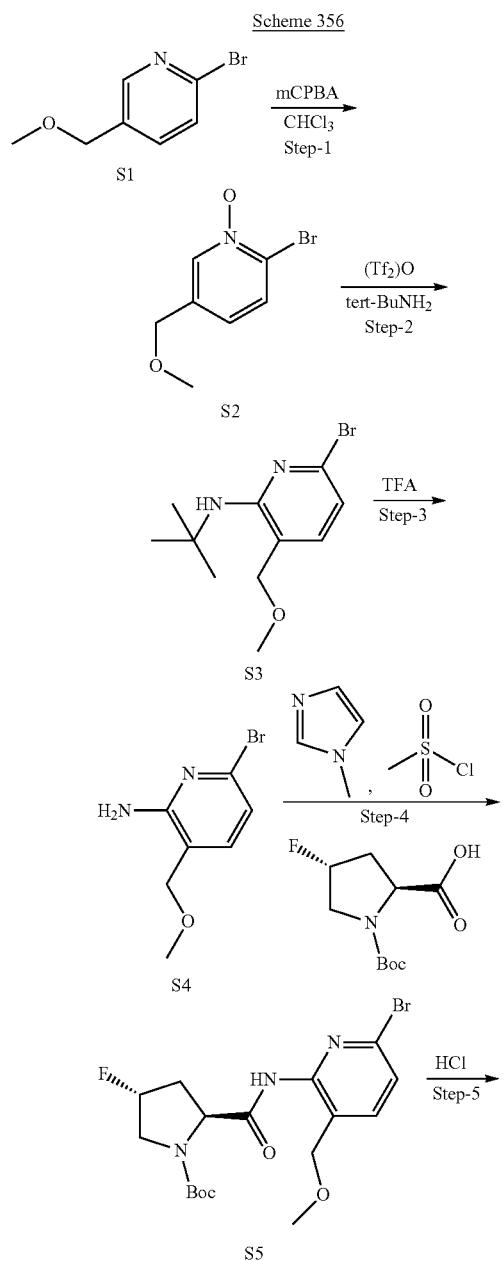

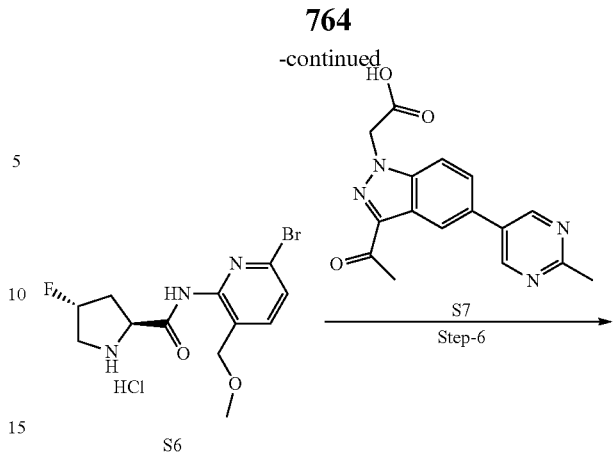

To a stirred solution of 2-bromo-5-(methoxymethyl)pyridine (2.4 g, 5 mmole) in CHCl3 (15 mL) was added mCPBA (5.3, 2.0 equiv). The reaction mixture was heated to 50° C. for 4 hours to complete the reaction. It was cooled and diluted with 20 mL DCM and washed with sat. NaHCO3 solution (5×15 mL) until no acid left in the organic layer. It was then dried by Na2SO4 and concentrated in vacuuo, which (1.3 g purified, pink color oil) was ready for the use next step.

Step-2: 6-Bromo-N-(tert-butyl)-3-methoxymethyl-pyridin-2-amine (S3)

To a stirred solution 2-bromo-5-(methoxymethyl)pyridine N-oxide (1.3 g, 6 mmole) in DCM (40 mL) was cooled to 0° C. (ice bath), added tert-Butyl amine (3.1 mL, 5 equiv), and trifluoroacidic anhydride (3 mL, 3 equiv). The reaction mixture was stirred at 0-5° C. for 1 h. It diluted with 20 mL DCM, and neutralized by 30 mL of sat. NaHCO3. The organic layer was separated. It was washed again by 30 mL of sat. NaHCO3, brine (10 mL), dried and concentrated. The crude was purified by ISCO (silica gel, eluted by 50% EtOAc in Hexanes) to obtain 799 mg (49%) of title compound as a yellow solid.

Step-3: 6-Bromo-3-cyclopropylpyridin-2-amine (S4)

To the solid of 6-bromo-N-(tert-butyl)-3-methoxymethyl-pyridin-2-amine was added 20 mL of TFA and the reaction mixture was heated at 50° C. until completion. Then it was concentrated, dissolved in DCM (15 mL), washed with sat.

NaHCO3 to basic (PH=9). The organic layer was combined and dried with Na2SO4 and concentrated to be used for the next step.

Step-4: tert-Butyl (2S,4R)-2-((6-bromo-3-(methoxymethyl)pyridin-2-yl)carbamoyl)-4-fluoro-pyrrolidine-1-carboxylate (S5)

To a stirred solution of (2S, 4R)-1-(tert-butoxycarbonyl)-4-fluoropyrrolidine-2-carboxylic acid (125 mg, 0.54 mmole) in 8 mL of CH2Cl2, was added 1-methyl imidazole (0.11 mL, 2.5 equiv.) at 0-5° C. under nitrogen atmosphere. The reaction mixture was stirred for 10 min at 0-5° C. and then added methane sulfonyl chloride (0.05 mL, 1.2 equiv) at the same temperature. It was stirred for 1 h at 0-50° C. Then 6-bromo-3-(methoxymethyl)pyridin-2-amine (116 mg, 1 equiv) was added, and stirred for 18 h at room temperature. Water (15 mL) was added to the reaction mixture, layers were separated and aqueous layer was extracted with DCM (3×15 mL). The combined organic layer was washed with 1N HCl (15 mL), followed by Sat NaHCO3 (15 mL) and then with brine (10 mL). Combined organic layer was dried over Na2SO4, concentrated and purified by ISCO (silica gel, eluted by 5% MeOH in DCM gradient) to obtained 201 mg (86%) of titled compound as yellow oil.

Step-5: (2S,4R)—N-(6-Bromo-3-(methoxymethyl)pyridin-2-yl)-4-fluoropyrrolidine-2-carboxamide (S6)

To tert-butyl (2S,4R)-2-((6-bromo-3-(methoxymethyl)pyridin-2-yl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-6: (2S,4R)-1-(2-(3-Acetyl-5-(2-methylpyrimidin-5-yl)-1H-indazol-1-yl)acetyl)-N-(6-bromo-3-(methoxymethyl)pyridin-2-yl)-4-fluoropyrrolidine-2-carboxamide (606)

To a stirred solution of (2S,4R)—N-(6-bromo-3-(methoxymethyl)pyridin-2-yl)-4-fluoropyrrolidine-2-carboxamide (HCl salt, 199 mg) in DMF (15 mL) was added S7 (167 mg, 1.0 equiv.), HATU (246 mg, 1.2 equiv), and DIEA (0.5 mL, 5.0 equiv). The reaction was stirred at room temperature for a couple of hours. It was then diluted with EtOAC (20 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 155 mg (46%) of 606. 1H NMR (400 MHz, DMSO-$d_6$): (major rotamer) δ 2.09-2.31 (m, 1H), 2.57-2.63 (m, 1H), 2.65 (s, 3H), 2.69 (s, 3H), 2.96 (s, 3H), 3.96-4.11 (m, 3H), 4.20-4.31 (m, 1H), 4.61 (t, 1H, J=8.3 Hz), 5.49-5.88 (m, 3H), 7.53 (d, 1H, J=8.0 Hz), 7.74 (d, 1H, J=8.0 Hz), 7.79-7.91 (m, 2H), 8.44 (s, 1H), 9.03 (s, 2H), 10.64 (s, 1H); 19F NMR (376 MHz, DMSO-$d_6$300K): (major rotamer) δ −175.95 (1F). LC (method A): tR=1.53 min. LC/MS (EI) m/z: [M]+ 624.

Methyl 2-((2S,4R)-1-(2-(3-Acetyl-5-(2-methylpyrimidin-5-yl)-1H-indazol-1-yl)acetyl)-4-fluoropyrrolidine-2-carboxamido)-6-bromonicotinate (607), 2-((2S,4R)-1-(2-(3-Acetyl-5-(2-methylpyrimidin-5-yl)-1H-indazol-1-yl)acetyl)-4-fluoropyrrolidine-2-carboxamido)-6-bromonicotinic acid (615) and 2-((2R,4R)-1-(2-(3-Acetyl-5-(2-methylpyrimidin-5-yl)-1H-indazol-1-yl)acetyl)-4-fluoropyrrolidine-2-carboxamido)-6-bromonicotinic acid (648)

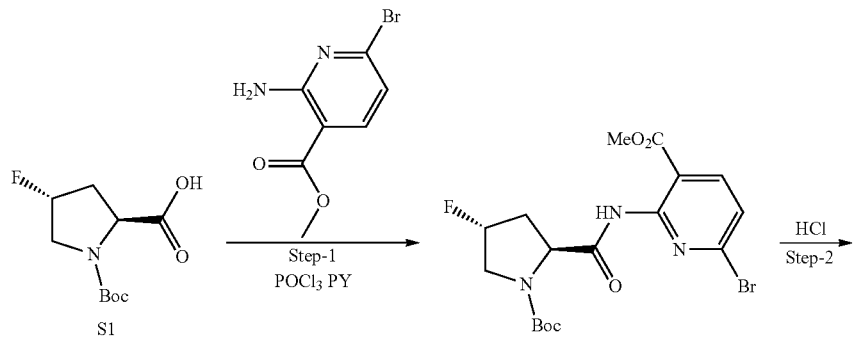

Scheme 357

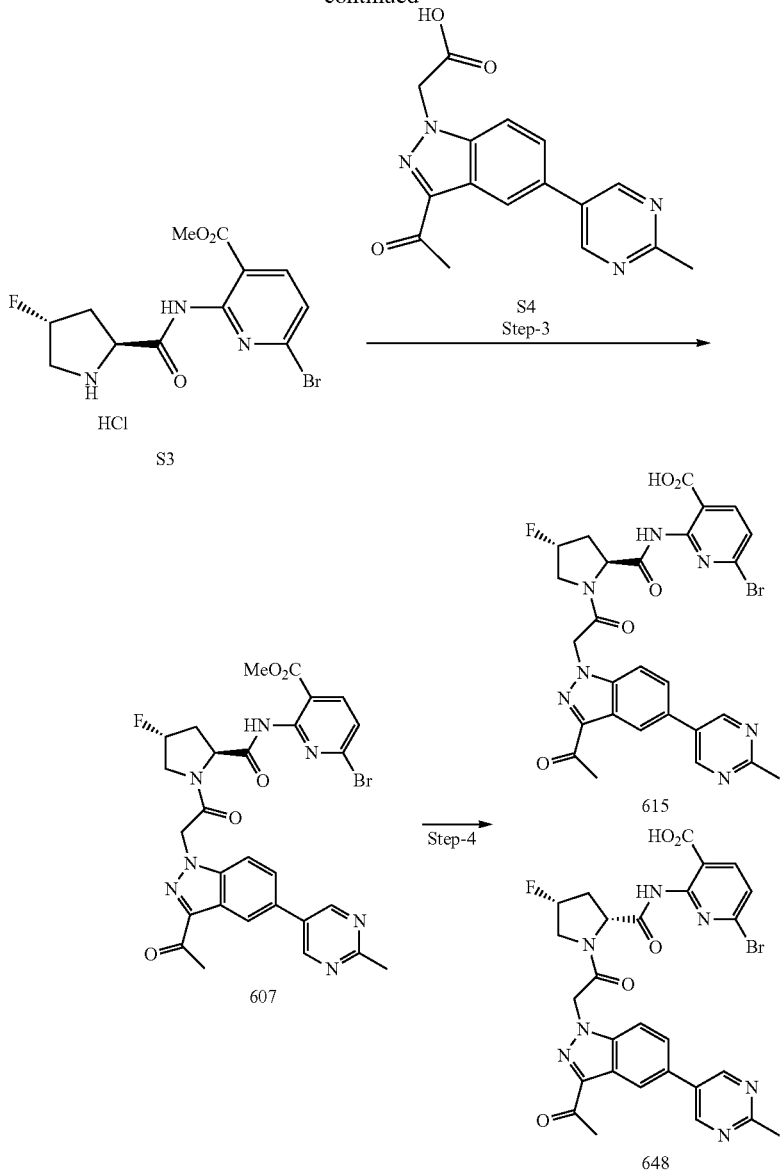

Step-1: Methyl 6-bromo-2-((2S,4R)-1-(tert-butoxycarbonyl)-4-fluoropyrrolidine-2-carboxamido)nicotinate (S2)

To a stirred solution of (2S, 4R)-1-(tert-butoxycarbonyl)-4-fluoropyrrolidine-2-carboxylic acid (128 mg, 0.55 mmole) and methyl 2-amino-6-bromonicotinate (126 mg, 1 equiv) in 10 mL of CH2Cl2, was added pyridine (0.22 mL, 5 equiv.), cooled to 0-5° C., added POCl3 drop wisely (0.051 mL, 1.0 equiv) at the same temperature under nitrogen. After addition, the reaction mixture was warmed up to room temperature and stirred until completion. It was diluted with 10 mL DCM, added Sat NaHCO3 solution and stirred for a while. Layers were separated and aqueous layer was extracted with DCM (1×15 mL). The combined organic layer was washed with brine (10 mL). Combined organic layer was dried over Na2SO4, concentrated and purified by ISCO (silica gel, eluted by 5% MeOH in DCM gradient) to obtained 74 mg (30%) of titled compound as yellow oil.

Step-2: Methyl 6-bromo-2-((2S,4R)-4-fluoropyrrolidine-2-carboxamido)nicotinate (S3)

To methyl 6-bromo-2-((2S,4R)-1-(tert-butoxycarbonyl)-4-fluoropyrrolidine-2-carboxamido)nicotinate was added 10 ml of 4N HCl in Dioxane. The resulting solution was stirred at room temperature for 6 hours. Then, the reaction mixture was concentrated in vacuuo and used for the following step.

Step-3: Methyl 2-((2S,4R)-1-(2-(3-acetyl-5-(2-methylpyrimidin-5-yl)-1H-indazol-1-yl)acetyl)-4-fluoropyrrolidine-2-carboxamido)-6-bromonicotinate (607)

To a stirred solution of methyl 6-bromo-2-((2S,4R)-4-fluoropyrrolidine-2-carboxamido)nicotinate (HCl salt, 63 mg) in DMF (8 mL) was added S4 (51 mg, 1.0 equiv.), HATU (73 mg, 1.2 equiv), and DIEA (0.14 mL, 5.0 equiv.). The reaction was stirred at room temperature for a couple of hours. It was then diluted with EtOAC (20 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 77 mg (69%, white solid) of 607. 1H NMR (400 MHz, DMSO-$d_6$): (major rotamer) δ 2.05-2.19 (m, 1H), 2.51-2.58 (m, 1H), 2.65 (s, 3H), 2.69 (s, 3H), 3.56 (s, 3H), 3.92-4.11 (m, 3H), 4.15-4.31 (m, 1H), 4.62 (t, 1H, J=8.2 Hz), 5.49-5.88 (m, 3H), 7.41 (d, 1H, J=8.0 Hz), 7.72-7.88 (m, 2H), 7.84 (d, 1H, J=8.0 Hz), 8.36 (s, 1H), 8.97 (s, 2H), 11.07 (s, 1H); 19F NMR (376 MHz, DMSO-$d_6$300K): (major rotamer) δ −175.85 (1F). LC (method A): tR=1.67 min. LC/MS (EI) m/z: [M]+ 638.

Step-4: 2-((2S,4R)-1-(2-(3-Acetyl-5-(2-methylpyrimidin-5-yl)-1H-indazol-1-yl)acetyl)-4-fluoropyrrolidine-2-carboxamido)-6-bromonicotinic acid (615) and 2-((2R,4R)-1-(2-(3-acetyl-5-(2-Methylpyrimidin-5-yl)-1H-indazol-1-yl)acetyl)-4-fluoropyrrolidine-2-carboxamido)-6-bromonicotinic acid (648)

To a stirred solution of methyl 2-((2S,4R)-1-(2-(3-acetyl-5-(2-methylpyrimidin-5-yl)-1H-indazol-1-yl)acetyl)-4-fluoropyrrolidine-2-carboxamido)-6-bromonicotinate in THF (1 mL) was added LiOH aqueous solution (4 mg LiOH, water 0.6 mL) and stirred at room temperature until completion. 2 peaks on LC/MS with same mass observed. Concentrated and purified by HPLC (C18, eluted with water/ACN) to obtain 615 (15 mg) and 648 (9 mg) 1H NMR-0145518 (400 MHz, DMSO-$d_6$): (major rotamer) δ 2.01-2.07 (m, 1H), 2.51-2.58 (m, 1H), 2.57 (s, 3H), 2.61 (s, 3H), 3.86-4.00 (m, 3H), 4.15-4.25 (m, 1H), 4.66 (m, 1H), 5.42-5.83 (m, 3H), 7.42 (d, 1H, J=7.9 Hz), 7.72-7.81 (m, 2H), 7.96 (d, 1H, J=7.9 Hz), 8.36 (s, 1H), 8.98 (s, 2H), 11.05 (s, 1H); 19F NMR (376 MHz, DMSO-$d_6$300K): (major rotamer) δ −175.73 (1F). LC (method A): tR=1.28 min. LC/MS (EI) m/z: [M]+ 624. 1H NMR-0145580 (400 MHz, DMSO-$d_6$): (major rotamer) δ 2.25-2.37 (m, 1H), 2.51-2.58 (m, 1H), 2.57 (s, 3H), 2.61 (s, 3H), 3.51-3.85 (m, 3H), 4.02-4.21 (m, 1H), 4.72 (d, 1H, J=10.7 Hz), 5.13-5.64 (m, 3H), 7.40 (d, 1H, J=8.1 Hz), 7.68-7.84 (m, 2H), 8.08 (d, 1H, J=8.1 Hz), 8.37 (s, 1H), 8.94 (s, 2H), 11.27 (s, 1H); 19F NMR (376 MHz, DMSO-$d_6$300K): (major rotamer) δ −171.32 (1F). LC (method A): tR=1.19 min. LC/MS (EI) m/z: [M]+624.

(1R,3S,5R)-2-(2-(3-Acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (421)

Scheme 358

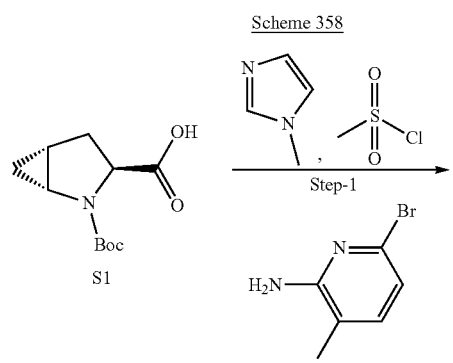

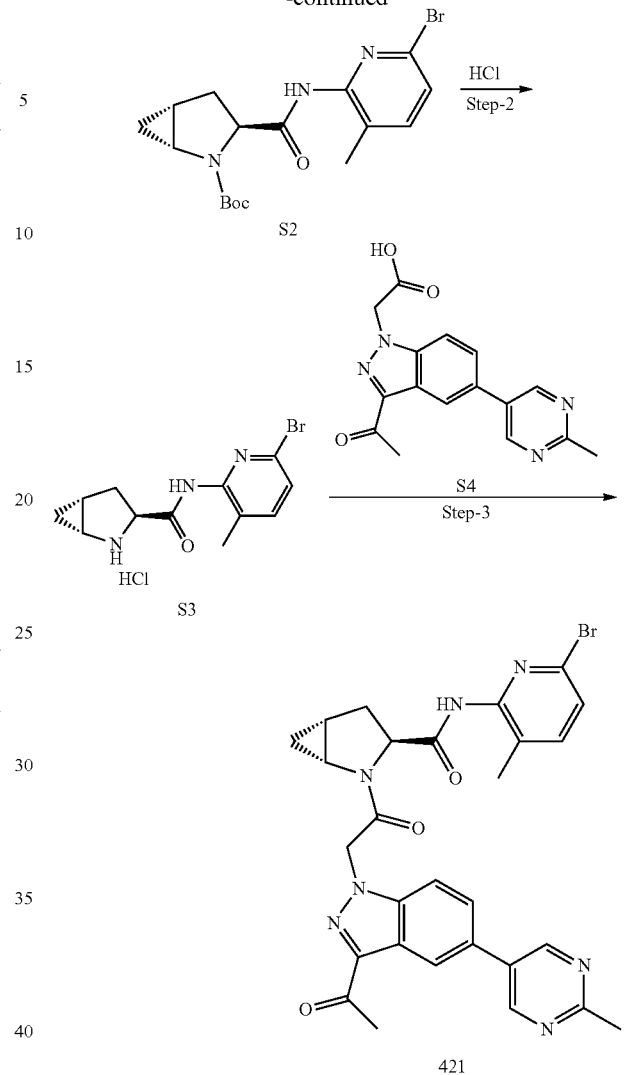

Step-1: tert-Butyl (1R,3S,5R)-3-((6-bromo-3-methylpyridin-2-yl)carbamoyl)-2-azabicyclo[3.1.0]hexane-2-carboxylate (S2)

To a stirred solution of (1R,3S,5R)-2-(tert-butoxycarbonyl)-2-azabicyclo[3.1.0]hexane-3-carboxylic acid (261 mg, 1.16 mmole) in 15 mL of CH2Cl2, was added 1-methyl imidazole (0.23 mL, 2.5 equiv.) at 0-5° C. under nitrogen atmosphere. The reaction mixture was stirred for 10 min at 0-5° C. and then added methane sulfonyl chloride (0.11 mL, 1.2 equiv) at the same temperature. It was stirred for 1 h at 0-50° C. Then 6-bromo-3-methylpyridin-2-amine (217 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and 371 mg (94% yield) of titled compound was obtained.

Step-2: (1R,3S,5R)—N-(6-Bromo-3-methylpyridin-2-yl)-2-azabicyclo[3.1.0]hexane-3-carboxamide (S3)

To tert-butyl (1R,3S,5R)-3-((6-bromo-3-methylpyridin-2-yl)carbamoyl)-2-azabicyclo[3.1.0]hexane-2-carboxylate was added 10 ml of 4N HCl in Dioxane. The resulting solution was stirred at room temperature for 6 hours. Then, the reaction mixture was concentrated in vacuuo and used for the following step.

Step-3: (1R,3S,5R)-2-(2-(3-Acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide (421)

To a stirred solution of (1R,3S,5R)—N-(6-bromo-3-methylpyridin-2-yl)-2-azabicyclo[3.1.0]hexane-3-carboxamide (HCl salt, 196 mg) in DMF (12 mL) was added S4 (182 mg, 1.0 equiv.), HATU (265 mg, 1.2 equiv), and DIEA (0.50 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 126 mg (37%) of 421. 1H NMR (400 MHz, DMSO-$d_6$): (major rotamer) δ 0.85-0.90 (m, 1H), 1.02-1.09 (m, 1H), 1.91-2.01 (m. 1H), 2.04 (s, 3H), 2.21-2.44 (m, 2H), 2.66 (s, 3H), 2.69 (s, 3H), 3.80-3.85 (m, 1H), 4.40-4.45 (m, 1H), 5.63 (d, 1H, J=17.22 Hz), 5.96 (d, 1H, J=17.22 Hz), 7.45 (d, 1H, J=8.2 Hz), 7.63 (d, 1H, J=8.2 Hz), 7.89 (s, 2H), 8.44 (s, 1H), 9.05 (s, 2H), 10.28 (s, 1H); LC (method A): tR=1.59 min. LC/MS (EI) m/z: [M]+589.

(1R,3S,5R)-2-(2-(3-Acetyl-5-(2-methylpyrimidin-5-yl)-1H-indazol-1-yl)acetyl)-N-(6-bromo-5-fluoropyridin-2-yl)-2-azabicyclo[3.1.0]hexane-3-carboxamide (447)

Scheme 359

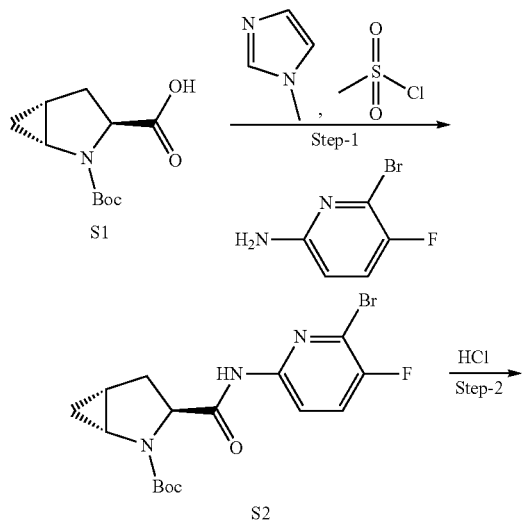

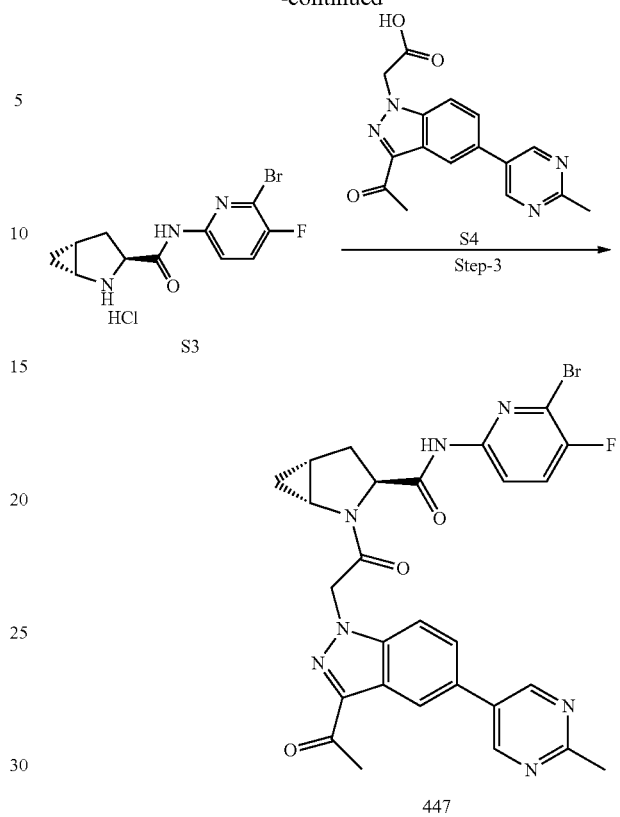

447

Step-1: tert-Butyl (1R,3S,5R)-3-((6-bromo-5-fluoropyridin-2-yl)carbamoyl)-2-azabicyclo[3.1.0]hexane-2-carboxylate (S2)

To a stirred solution of (1R,3S,5R)-2-(tert-butoxycarbonyl)-2-azabicyclo[3.1.0]hexane-3-carboxylic acid (257 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 6-bromo-5-fluoropyridin-2-amine (200 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and to obtain titled compound 395 mg (quantitative yield).

Step-2: (1R,3S,5R)—N-(6-Bromo-5-fluoropyridin-2-yl)-2-azabicyclo[3.1.0]hexane-3-carboxamide (S3)

To tert-butyl (1R,3S,5R)-3-((6-bromo-5-fluoropyridin-2-yl)carbamoyl)-2-azabicyclo[3.1.0]hexane-2-carboxylate (product from step 1) was added 10 ml of 4N HCl in Dioxane. The resulting solution was stirred at room temperature for 6 hours. Then, the reaction mixture was concentrated in vacuuo and used for the following step.

Step-3: (1R,3S,5R)-2-(2-(3-Acetyl-5-(2-methylpyrimidin-5-yl)-1H-indazol-1-yl)acetyl)-N-(6-bromo-5-fluoropyridin-2-yl)-2-azabicyclo[3.1.0]hexane-3-carboxamide (447)

To a stirred solution of (1R,3S,5R)—N-(6-bromo-5-fluoropyridin-2-yl)-2-azabicyclo[3.1.0]hexane-3-carboxamide (HCl salt, 64 mg) in DMF (10 mL) was added S4 (59 mg, 1.05 equiv.), HATU (87 mg, 1.2 equiv), and DIEA (0.16 mL, 5.0 equiv). The reaction was stirred at room temperature for a couple of hours. It was then diluted with EtOAC (10 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 42 mg (38%) of 447. 1H NMR (400 MHz, DMSO-$d_6$): (major rotamer) δ 0.75-0.84 (m, 1H), 1.02-1.09 (m, 1H), 1.82-1.94 (m, 1H), 2.18-2.35 (m, 1H), 2.65 (s, 3H), 2.69 (s, 3H), 3.85-3.95 (m, 1H), 4.41-4.48 (m, 1H), 5.61 (d, 1H, J=17.22 Hz), 5.97 (d, 1H, J=17.22 Hz), 7.75-7.83 (m, 3H), 8.06-8.09 (m, 1H), 8.43 (s, 1H), 9.04 (s, 2H), 10.82 (s, 1H); 19F NMR (376 MHz, DMSO-$d_6$ 300K): (major rotamer) δ −120.92 (1F) LC (method A): tR=1.88 min. LC/MS (EI) m/z: [M]+ 592.

(1R,3S,5R)-2-(2-(3-Acetyl-5-(2-methylpyrimidin-5-yl)-1H-indazol-1-yl)acetyl)-N-(6-bromo-3-cyclopropyl-pyridin-2-yl)-2-azabicyclo[3.1.0]hexane-3-carboxamide (603)

Scheme 360

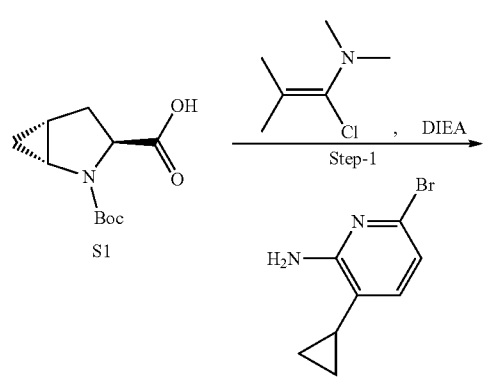

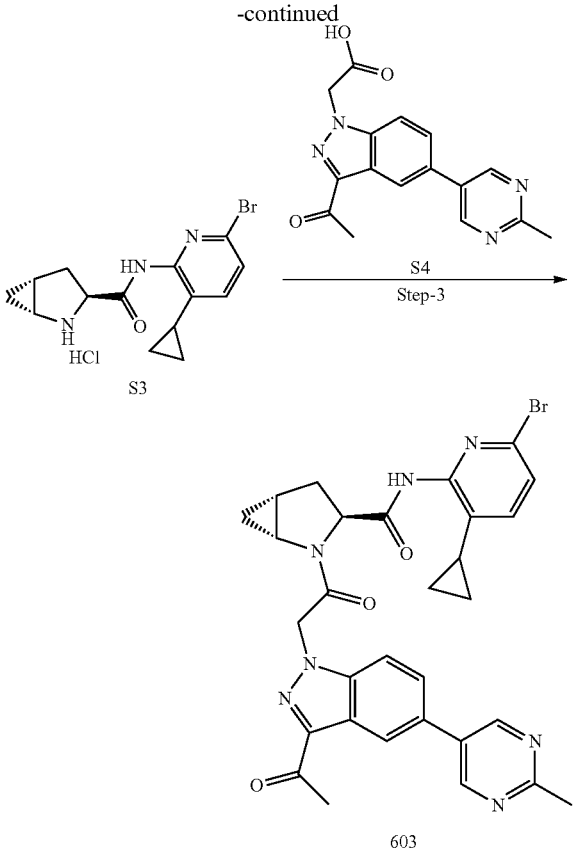

Step-1: tert-Butyl (1R,3S,5R)-3-((6-bromo-3-cyclopropylpyridin-2-yl)carbamoyl)-2-azabicyclo[3.1.0]hexane-2-carboxylate (S2)

To an ice cold solution of (1R,3S,5R)-2-(tert-butoxycarbonyl)-2-azabicyclo[3.1.0]hexane-3-carboxylic acid (128 mg, 1.1 mmole) in 6 mL of CH2Cl2, 1-chloro-N,N,2-trimethylprop-1-en-1-amine (0.07 mL, 1.1 equiv) was added drop-wise with stirring. The stirring was continued for 3 hours at the same temperature. Then 6-bromo-3-cyclopropylpyridin-2-amine (235 mg, 1.0 equiv) was added, followed by 0.30 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 230 mg (50%) of tert-Butyl (1R,3S,5R)-3-((6-bromo-3-cyclopropylpyridin-2-yl)carbamoyl)-2-azabicyclo[3.1.0]hexane-2-carboxylate.

Step-2: (1R,3S,5R)—N-(6-Bromo-3-cyclopropyl-pyridin-2-yl)-2-azabicyclo[3.1.0]hexane-3-carboxamide (S3)

To tert-butyl (1R,3S,5R)-3-((6-bromo-3-cyclopropylpyridin-2-yl)carbamoyl)-2-azabicyclo[3.1.0]hexane-2-carboxylate was added 10 ml of 4N HCl in Dioxane. The resulting solution was stirred at room temperature for 6 hours. Then, the reaction mixture was concentrated in vacuuo and used for the following step.

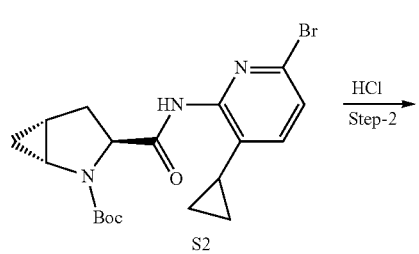

Step-3: (1R,3S,5R)-2-(2-(3-Acetyl-5-(2-methylpyrimidin-5-yl)-1H-indazol-1-yl)acetyl)-N-(6-bromo-3-cyclopropyl-pyridin-2-yl)-2-azabicyclo[3.1.0]hexane-3-carboxamide (603)

To a stirred solution of (1R,3S,5R)—N-(6-bromo-3-cyclopropyl-pyridin-2-yl)-2-azabicyclo[3.1.0]hexane-3-carboxamide (HCl salt, 173 mg) in DMF (5 mL) was added S4 (149 mg), HATU (219 mg, 1.2 equiv), and DIEA (0.43 mL, 3 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuum. The resulting oil was purified by ISCO (silica gel, eluted with 10% MeOH in DCM gradient) and yielded 129 mg (44%) of titled compound. 1H NMR (400 MHz, DMSO-$d_6$): (major rotamer) δ 0.75-0.84 (m, 4H), 1.05-1.11 (m, 2H), 1.82-1.94 (m, 2H), 2.22-2.41 (m, 2H), 2.65 (s, 3H), 2.69 (s, 3H), 3.85-3.95 (m, 1H), 4.41-4.48 (m, 1H), 5.58 (d, 1H, J=17.1 Hz), 5.89 (d, 1H, J=17.1 Hz), 7.32-7.45 (m, 2H), 7.92 (s, 2H), 8.45 (s, 1H), 9.05 (s, 2H), 10.19 (s, 1H); LC (method A): tR=1.78 min. LC/MS (EI) m/z: [M]+ 614.

(1R,3S,5R)-2-(2-(3-Acetyl-5-(2-methylpyrimidin-5-yl)-1H-indazol-1-yl)acetyl)-N-(6-bromo-3-cyclopropyl-pyridin-2-yl)-5-methyl-2-azabicyclo[3.1.0]hexane-3-carboxamide (616)

Scheme 361

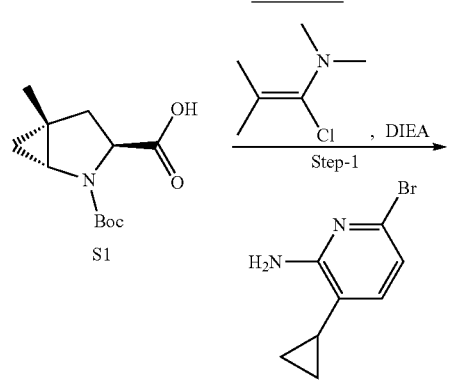

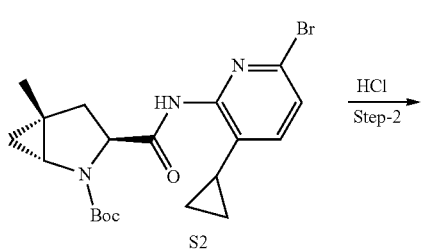

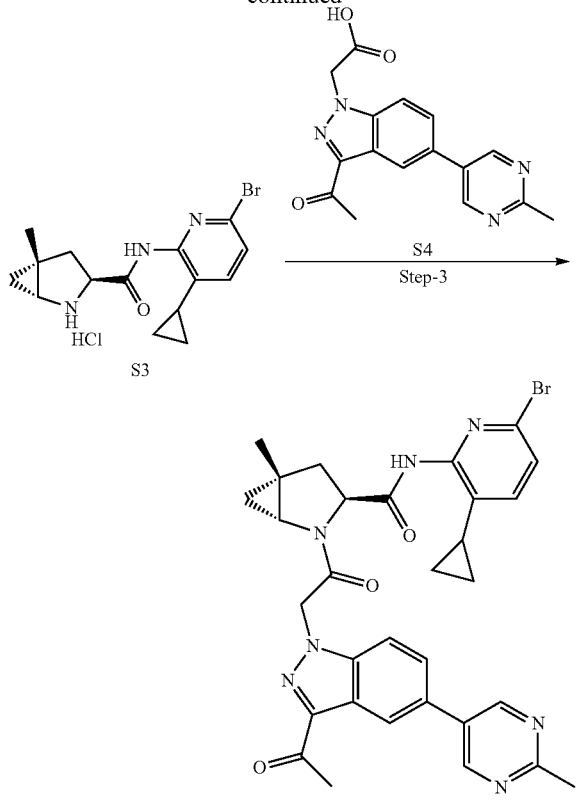

Step-1: tert-Butyl (1R,3S,5R)-3-((6-bromo-3-cyclopropylpyridin-2-yl)carbamoyl)-5-methyl-2-azabicyclo[3.1.0]hexane-2-carboxylate (S2)

To an ice cold solution of (1R,3S,5R)-2-(tert-butoxycarbonyl)-5-methyl-2-azabicyclo[3.1.0]hexane-3-carboxylic acid (128 mg, 0.42 mmole) in 6 mL of CH2Cl2, 1-chloro-N,N,2-trimethylprop-1-en-1-amine (0.03 mL, 1.1 equiv) was added drop-wise with stirring. The stirring was continued for 3 hours at the same temperature. Then 6-bromo-3-cyclopropylpyridin-2-amine (89 mg, 1.0 equiv) was added, followed by addition of 0.11 mL (3 equiv) Hunig's base. The cooling bath was removed and the reaction mixture was stirred at room temperature for overnight. The solvent was co-evaporated with 5 mL of MeOH, and the residue was purified by ISCO (eluted with ethyl acetate in hexane, gradient) to obtain 180 mg tert-butyl (1R,3S,5R)-3-((6-bromo-3-cyclopropylpyridin-2-yl)carbamoyl)-5-methyl-2-azabicyclo[3.1.0]hexane-2-carboxylate.

Step-2: (1R,3S,5R)—N-(6-Bromo-3-cyclopropyl-2-yl)-5-methyl-2-azabicyclo[3.1.0]hexane-3-carboxamide (S3)

To tert-butyl (1R,3S,5R)-3-((6-bromo-3-cyclopropylpyridin-2-yl)carbamoyl)-5-methyl-2-azabicyclo[3.1.0]hexane-2-carboxylate was added 10 ml of 4N HCl in Dioxane. The resulting solution was stirred at room temperature for 6 hours. Then, the reaction mixture was concentrated in vacuuo and used for the following step.

Step-3: (1R,3S,5R)-2-(2-(3-Acetyl-5-(2-methylpyrimidin-5-yl)-1H-indazol-1-yl)acetyl)-N-(6-bromo-3-cyclopropyl-pyridin-2-yl)-5-methyl-2-azabicyclo[3.1.0]hexane-3-carboxamide (616)

To a stirred solution of (1R,3S,5R)—N-(6-bromo-3-cyclopropyl-pyridin-2-yl)-5-methyl-2-azabicyclo[3.1.0]hexane-3-carboxamide (HCl salt, 180 mg) in DMF (5 mL) was added S4 (130 mg), HATU (192 mg, 1.2 equiv), and DIEA (0.36 mL, 3 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuum. The resulting oil was purified by ISCO (silica gel, eluted with 10% MeOH in DCM gradient) and yielded 152 mg (58%) of titled compound. 1H NMR (400 MHz, DMSO-$d_6$): (major rotamer) δ 0.52-0.60 (m, 2H), 0.73-0.79 (m, 2H), 1.01-1.08 (m, 2H), 1.32 (s, 3H), 1.74-1.85 (m, 1H), 2.02-2.13 (m, 1H), 2.55-2.59 (m, 1H), 2.65 (s, 3H), 2.69 (s, 3H), 3.61-3.66 (m, 1H), 4.44-4.51 (m, 1H), 5.55 (d, 1H, J=17.0 Hz), 5.85 (d, 1H, J=17.0 Hz), 7.32 (d, 1H, J=8.4), 7.42 (d, 1H, J=8.4 Hz), 8.45 (s, 1H), 9.05 (s, 2H), 10.20 (s, 1H); LC (method A): tR=1.97 min. LC/MS (EI) m/z: [M]+ 628.

1R,2S,5S)-3-(2-(3-Acetyl-5-(2-methylpyrimidin-5-yl)-1H-indazol-1-yl)acetyl)-N-(6-bromo-3-cyclopropylpyridin-2-yl)-3-azabicyclo[3.1.0]hexane-2-carboxamide (637)

Scheme 362

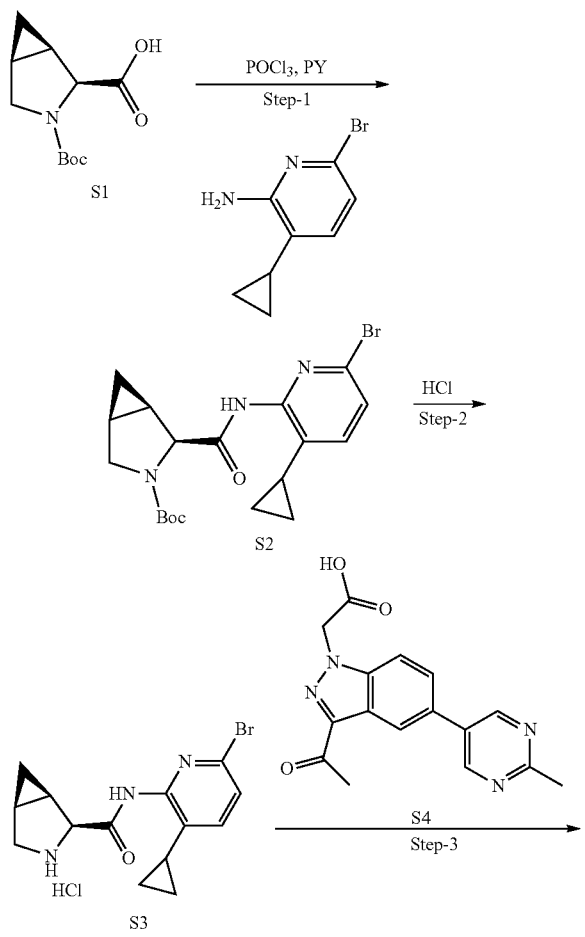

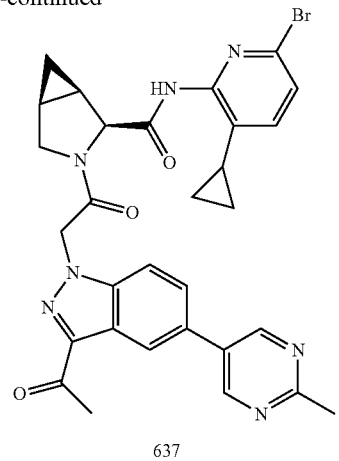

637

Step-1: tert-Butyl (1R,2S,5S)-2-((6-bromo-3-cyclopropylpyridin-2-yl)carbamoyl)-3-azabicyclo[3.1.0]hexane-3-carboxylate (S2)

To a stirred solution of (1R,2S,5S)-3-(tert-butoxycarbonyl)-3-azabicyclo[3.1.0]hexane-2-carboxylic acid (223 mg, 1.0 mmole) and 6-bromo-3-cyclopropylpyridin-2-amine (214 mg, 1 equiv) in 10 mL of CH2Cl2, was added pyridine (0.40 mL, 5 equiv.), cooled to 0-5° C., added POCl3 drop wisely (0.10 mL, 1.0 equiv) at the same temperature under nitrogen. After addition, the reaction mixture was warmed up to room temperature and stirred until completion. It was diluted with 10 mL DCM, added Sat NaHCO3 solution and stirred for a while. Layers were separated and aqueous layer was extracted with DCM (1×15 mL). The combined organic layer was washed with brine (10 mL). Combined organic layer was dried over Na2SO4, concentrated and purified by ISCO (silica gel, eluted by 5% MeOH in DCM gradient) to obtained 420 mg of titled compound as yellow oil.

Step-2: (1R,2S,5S)—N-(6-Bromo-3-cyclopropylpyridin-2-yl)-3-azabicyclo[3.1.0]hexane-2-carboxamide (S3)

To tert-butyl (1R,2S,5S)-2-((6-bromo-3-cyclopropylpyridin-2-yl)carbamoyl)-3-azabicyclo[3.1.0]hexane-3-carboxylate was added 10 ml of 4N HCl in Dioxane. The resulting solution was stirred at room temperature for 6 hours. Then, the reaction mixture was concentrated in vacuuo and used for the following step.

Step-3: (1R,2S,5S)-3-(2-(3-Acetyl-5-(2-methylpyrimidin-5-yl)-1H-indazol-1-yl)acetyl)-N-(6-bromo-3-cyclopropylpyridin-2-yl)-3-azabicyclo[3.1.0]hexane-2-carboxamide (637)

To a stirred solution of (1R,2S,5S)—N-(6-bromo-3-cyclopropylpyridin-2-yl)-3-azabicyclo[3.1.0]hexane-2-carboxamide (HCl salt, 80 mg) in DMF (5 mL) was added S4 (68 mg), HATU (100 mg, 1.2 equiv), and DIEA (0.19 mL, 3 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuum. The resulting oil was purified by ISCO (silica gel, eluted with 10% MeOH in DCM gradient) and yielded 80 mg (59%) of titled compound. 1H NMR (400 MHz, DMSO-$d_6$): (major rotamer) δ 0.49-0.90 (m, 6H), 1.82-2.08 (m, 3H), 2.64 (s, 3H), 2.69 (s, 3H), 3.90 (d, 1H, J=9.76 Hz), 4.03-4.07 (m, 1H), 4.63 (d, 1H, J=5.4 Hz), 5.54-5.64 (m, 2H), 7.29 (d, 1H, J=8.3), 7.39 (d, 1H, J=8.3 Hz), 8.43 (s, 1H), 9.05 (s, 2H), 10.23 (s, 1H); LC (method A): tR=1.76 min. LC/MS (EI) m/z: [M]+ 614.

(1R,2S,5S)-3-(2-(3-Acetyl-5-(2-methylpyrimidin-5-yl)-1H-indazol-1-yl)acetyl)-N-(1-(2,2,2-trifluoroethyl)-1H-pyrazol-3-yl)-3-azabicyclo[3.1.0]hexane-2-carboxamide (638)

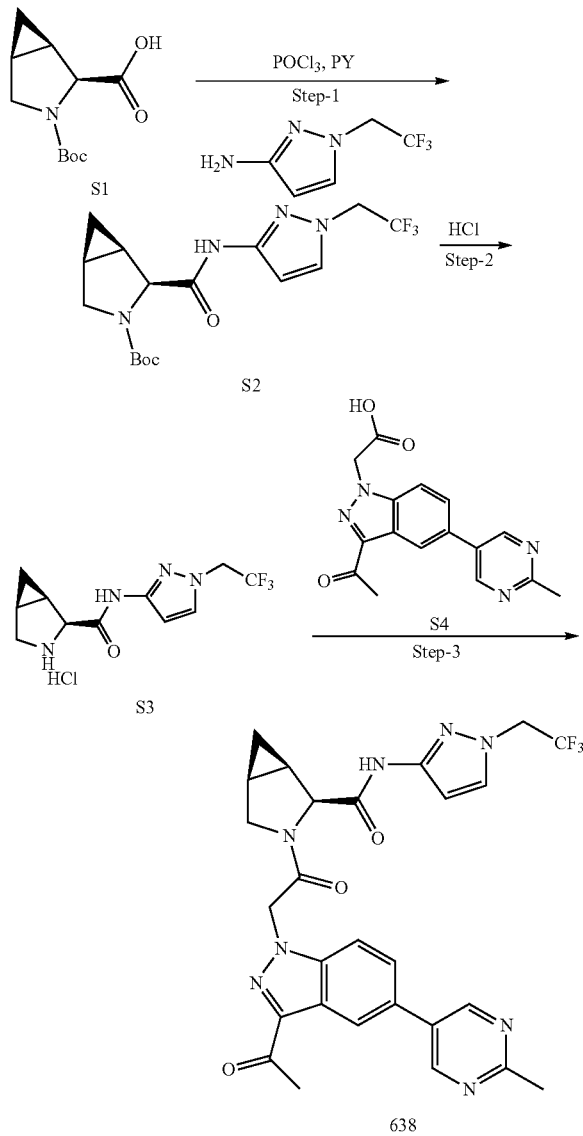

Step-1: tert-Butyl (1R,2S,5S)-2-((1-(2,2,2-trifluoroethyl)-1H-pyrazol-3-yl)carbamoyl)-3-azabicyclo [3.1.0]hexane-3-carboxylate (S2)

To a stirred solution of (1R,2S,5S)-3-(tert-butoxycarbonyl)-3-azabicyclo[3.1.0]hexane-2-carboxylic acid (223 mg, 1.0 mmole) and 6-bromo-3-cyclopropylpyridin-2-amine (165 mg, 1 equiv) in 10 mL of CH2Cl2, was added pyridine (0.40 mL, 5 equiv.), cooled to 0-5° C., added POCl3 drop wisely (0.10 mL, 1.0 equiv) at the same temperature under nitrogen. After addition, the reaction mixture was warmed up to room temperature and stirred until completion. It was diluted with 10 mL DCM, added Sat NaHCO3 solution and stirred for a while. Layers were separated and aqueous layer was extracted with DCM (1×15 mL). The combined organic layer was washed with brine (10 mL). Combined organic layer was dried over Na2SO4, concentrated and purified by ISCO (silica gel, eluted by 5% MeOH in DCM gradient) to obtained 369 mg of titled compound as yellow oil.

Step-2: (1R,2S,5S)—N-(1-(2,2,2-Trifluoroethyl)-1H-pyrazol-3-yl)-3-azabicyclo[3.1.0]hexane-2-carboxamide (S3)

To tert-butyl (1R,2S,5S)-2-((1-(2,2,2-trifluoroethyl)-1H-pyrazol-3-yl)carbamoyl)-3-azabicyclo[3.1.0]hexane-3-carboxylate was added 10 ml of 4N HCl in Dioxane. The resulting solution was stirred at room temperature for 6 hours. Then, the reaction mixture was concentrated in vacuuo and used for the following step.

Step-3: (1R,2S,5S)-3-(2-(3-Acetyl-5-(2-methylpyrimidin-5-yl)-1H-indazol-1-yl)acetyl)-N-(1-(2,2,2-trifluoroethyl)-1H-pyrazol-3-yl)-3-azabicyclo[3.1.0]hexane-2-carboxamide (638)

To a stirred solution of (1R,2S,5S)—N-(1-(2,2,2-trifluoroethyl)-1H-pyrazol-3-yl)-3-azabicyclo[3.1.0]hexane-2-carboxamide (HCl salt, 155 mg) in DMF (5 mL) was added S4 (155 mg), HATU (228 mg, 1.2 equiv), and DIEA (0.43 mL, 3 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuum. The resulting oil was purified by ISCO (silica gel, eluted with 10% MeOH in DCM gradient) and yielded 151 mg (53%) of titled compound. 1H NMR (400 MHz, DMSO-$d_6$): (major rotamer) δ 0.68-0.84 (m, 2H), 1.83-2.00 (m, 2H), 2.65 (s, 3H), 2.69 (s, 3H), 3.99-4.04 (m, 2H), 4.53 (m, 1H, J=2.4H), 4.96-5.07 (m, 2H), 5.59 (s, 2H), 6.54 (d, 1H, J=2.5 Hz), 7.69 (d, 1H, J=2.5 Hz), 7.83-7.89 (m, 2H), 8.44 (s, 1H), 9.07 (s, 2H), 10.59 (s, 1H); 19F NMR (376 MHz, DMSO-$d_6$ 300K): (major rotamer) δ −70.28 (3F). LC (method A): tR=1.49 min. LC/MS (EI) m/z: [M+H]+ 567.

(1S,2S,5R)-3-(2-(3-Acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide (605)

Scheme 364

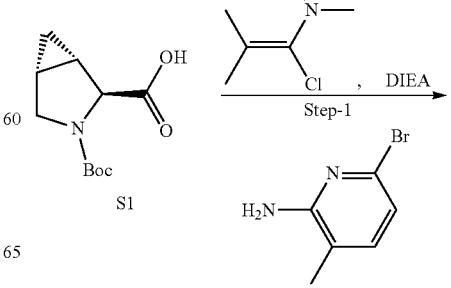

-continued

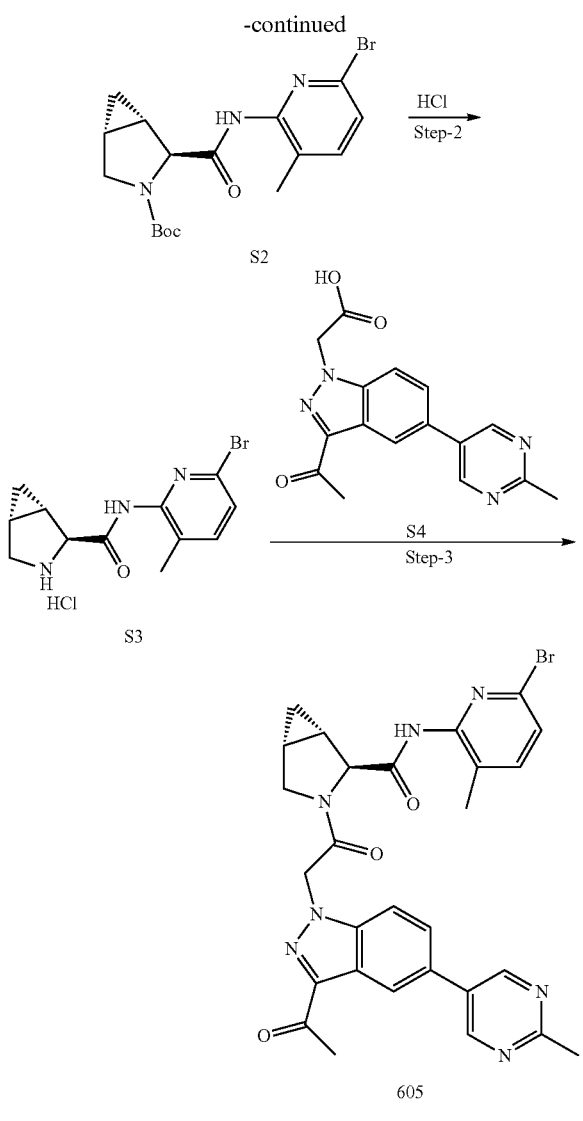

added 10 ml of 4N HCl in Dioxane. The resulting solution was stirred at room temperature for 6 hours. Then, the reaction mixture was concentrated in vacuuo and used for the following step.

Step-3: (1S,2S,5R)-3-(2-(3-Acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide (605)

To a stirred solution of (1S,2S,5R)—N-(6-bromo-3-methylpyridin-2-yl)-3-azabicyclo[3.1.0]hexane-2-carboxamide (HCl salt, 133 mg) in DMF (10 mL) was added S4 (124 mg), HATU (182 mg, 1.2 equiv), and DIEA (0.35 mL, 3 equiv). The reaction was stirred at room temperature for a couple of hours. It was then diluted with EtOAc (15 mL), and water (10 mL). The organic layer was washed with brine (3×15 mL), dried over $Na_2SO_4$ and concentrated in vacuum. The resulting oil was purified by ISCO (silica gel, eluted with 10% MeOH in DCM gradient) and yielded 161 mg (69%) of titled compound. 1H NMR (400 MHz, DMSO-$d_6$): (major rotamer) δ 0.42-0.45 (m, 1H), 0.81-0.93 (m, 2H), 1.81-1.92 (m, 2H), 2.05 (s, 3H) 2.65 (s, 3H), 2.69 (s, 3H), 3.88-4.01 (m, 2H), 5.50-5.81 (m, 2H), 6.46 (d, 1H, J=8.0 Hz), 7.65 (d, 1H, J=8.0 Hz), 7.75-7.87 (m, 2H), 8.44 (s, 1H), 9.04 (s, 2H), 10.42 (s, 1H); LC (method A): tR=1.62 min. LC/MS (EI) m/z: [M+H]+ 590.

2-(3-Acetyl-6-hydroxy-5-(2-methylpyrimidin-5-yl)-1H-indol-1-yl)acetic acid

Scheme 365

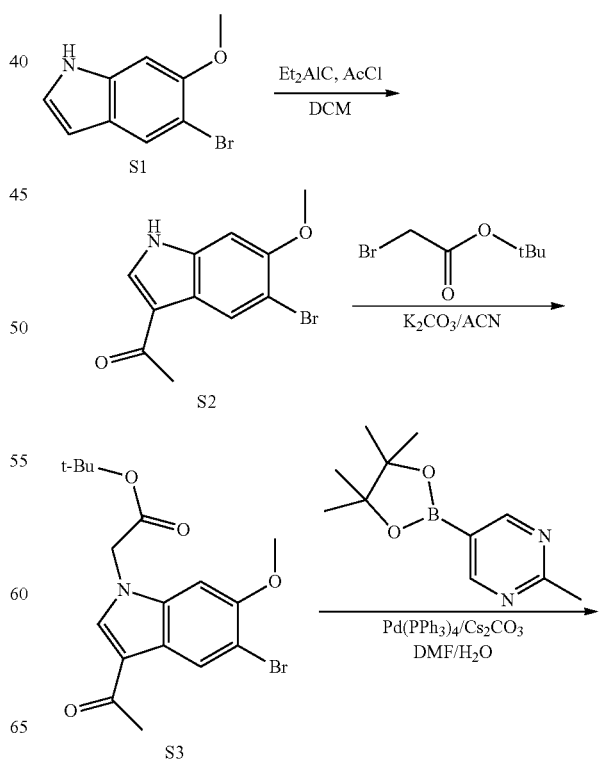

Step-1: tert-Butyl (1S,2S,5R)-2-((6-bromopyridin-2-yl)carbamoyl)-3-azabicyclo[3.1.0]hexane-3-carboxylate (S2)

To an ice cold solution of (1S,2S,5R)-3-(tert-butoxycarbonyl)-3-azabicyclo[3.1.0]hexane-2-carboxylic acid (103 mg, 0.45 mmole) in 6 mL of CH2Cl2, 1-chloro-N,N,2-trimethylprop-1-en-1-amine (0.07 mL, 1.1 equiv) was added drop-wise with stirring. The stirring was continued for 3 hours at the same temperature. Then 6-bromo-3-methylpyridin-2-amine (93 mg, 1.0 equiv) was added, followed by 0.23 mL (3 equiv) Hunig's base. The cooling bath was removed and the reaction mixture was stirred at room temperature for overnight. The solvent was co-evaporated with 5 mL of MeOH, and the residue was purified by ISCO (eluted 5% MeOH in DCM, gradient) to obtain 160 mg (90%) of title compound as yellow oil.

Step-2: (1S,2S,5R)—N-(6-Bromo-3-methylpyridin-2-yl)-3-azabicyclo[3.1.0]hexane-2-carboxamide (S3)

To tert-butyl (1S,2S,5R)-2-((6-bromopyridin-2-yl)carbamoyl)-3-azabicyclo[3.1.0]hexane-3-carboxylate was

783

-continued

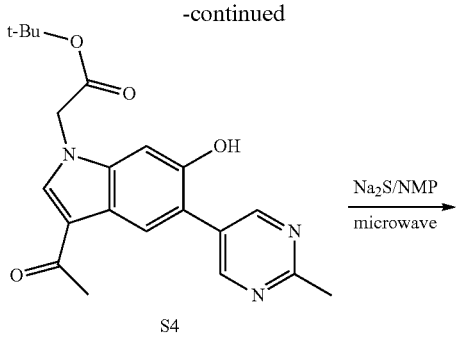

S4

→ Na₂S/NMP microwave

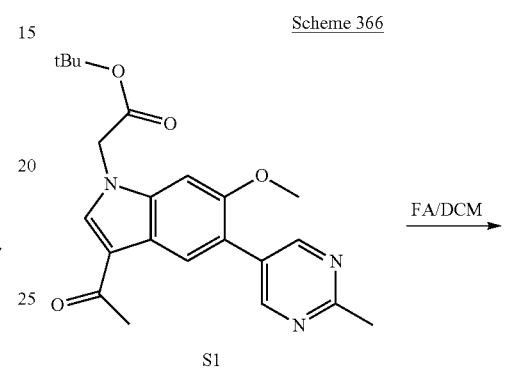

S5

1-(5-Bromo-6-methoxy-1H-indol-3-yl)ethan-1-one (S2)

Into a solution of 5-bromo-6-methoxy-1H-indole (1.01 g, 4.47 mmol) in DCM (20 mL) at 0° C. under Ar, Et₂AlCl in hexane (1.0M, 6.71 mL, 6.71 mmol) was added and the mixture was stirred for 10 min. AcCl (0.479 mL, 6.71 mmol) in DCM (20 mL) was then added and stirred at 0° C. for 1 hr. Citric acid (5% aq, 100 mL) was added to form precipitate. Solid was collected by filtration and dried to get 1-(5-bromo-6-methoxy-1H-indol-3-yl)ethan-1-one (2) (0.62 g) for next step.

tert-Butyl 2-(3-acetyl-5-bromo-6-methoxy-1H-indol-1-yl)acetate (S3)

The mixture of 1-(5-bromo-6-methoxy-1H-indol-3-yl)ethan-1-one (2) (0.62 g, 2.31 mmol) and tert-butyl 2-bromoacetate (0.375 mL, 2.54 mmol) was refluxed in acetonitrile (20 mL) in the presence of K₂CO₃ (0.35 g, 2.54 mmol) for 2 hr. After flirtation to remove solid, solution was concentrated to give tert-butyl 2-(3-acetyl-5-bromo-6-methoxy-1H-indol-1-yl)acetate (0.88 g) as solid for next step.

tert-Butyl 2-(3-acetyl-6-methoxy-5-(2-methylpyrimidin-5-yl)-1H-indol-1-yl)acetate (S4)

Into solution of tert-butyl 2-(3-acetyl-5-bromo-6-methoxy-1H-indol-1-yl)acetate (0.88 g, 2.3 mmol) and 2-methyl-5-(4,4,5,5-tetramethyl-1,3,2-dioxaborolan-2-yl)pyrimidine (0.61 g, 2.76 mmol) in DMF-H₂O (20 mL-2 mL), add Cs₂CO₃ (1.5 g, 4.6 mmol) and Pd(PPh₃)₄ (0.132 g, 0.115 mmol). The mixture was heated at 80 0° C. under Ar for 3 hr. DMF was evaporated under vacuum and residue was purified on ISCO with AcOEt in Hexane (50%-100%) as eluent to give tert-butyl 2-(3-acetyl-6-methoxy-5-(2-methylpyrimidin-5-yl)-1H-indol-1-yl)acetate (0.85 g) as yellow solid.

784

2-(3-Acetyl-6-hydroxy-5-(2-methylpyrimidin-5-yl)-1H-indol-1-yl)acetic acid (S5)

A mixture of tert-butyl 2-(3-acetyl-6-methoxy-5-(2-methylpyrimidin-5-yl)-1H-indol-1-yl)acetate (0.102 g, 0.258 mmol) and anhydrous Na₂S (0.1 g, 1.29 mmol) in NMP (2 mL) was heated at 145° C. in microwave reactor for 7 hr. HPLC separation to give 2-(3-acetyl-6-hydroxy-5-(2-methylpyrimidin-5-yl)-1H-indol-1-yl)acetic acid (0.064 g) as yellow powder.

2-(3-Acetyl-6-methoxy-5-(2-methylpyrimidin-5-yl)-1H-indol-1-yl)acetic acid

Scheme 366

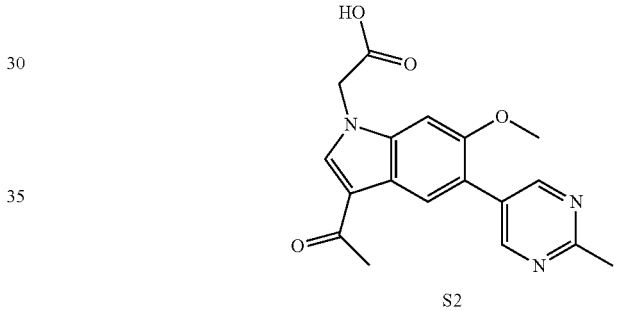

S1

→ FA/DCM

S2 tert-butyl 2-(3-acetyl-6-methoxy-5-(2-methylpyrimidin-5-yl)-1H-indol-1-yl)acetate (0.050 g, 0.127 mmol) was treated with TFA (1 mL) in DCM (1 mL) for 5 hr. After evaporation of volatiles, residue was co-evaporated with toluene (1 mL) and dried under vacuum to give 2-(3-acetyl-6-methoxy-5-(2-methylpyrimidin-5-yl)-1H-indol-1-yl)acetic acid.

(2S,4R)-1-(2-(3-Acetyl-6-methoxy-5-(2-methylpyrimidin-5-yl)-1H-indol-1-yl)acetyl)-N-(2'-chloro-2-fluoro-[1,1'-biphenyl]-3-yl)-4-fluoropyrrolidine-2-carboxamide (318)

Scheme 367

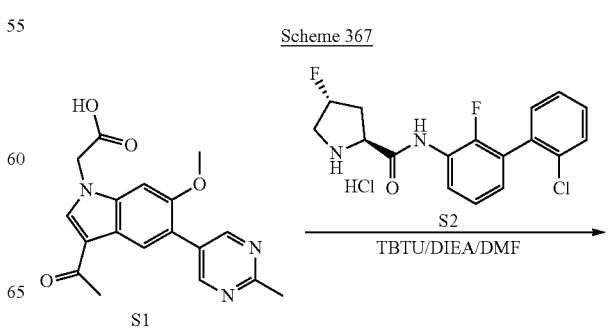

S1 + S2 → TBTU/DIEA/DMF

785

-continued

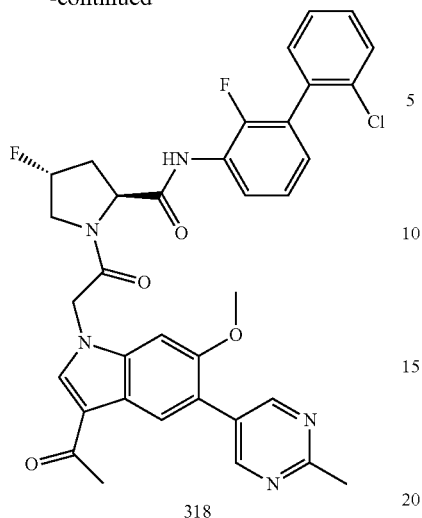

318

Into a mixture of 2-(3-acetyl-6-methoxy-5-(2-methylpyrimidin-5-yl)-1H-indol-1-yl)acetic acid (21.4 mg, 0.063 mmol) and (2S,4R)—N-(2-chloro-2-fluoro-[1,1'-biphenyl]-3-yl)-4-fluoropyrrolidine-2-carboxamide hydrochloride (23.5 g, 0.063 mmol) in DMF (2 mL), TBTU (32.1 mg, 0.1 mmol) followed by DIEA (0.066 mL, 0.36 mmol) was added at room temperature with stirring. After 1 hr, NaHCO₃ aq was added to form precipitation. Solid was collected by filtration and purified on ISCO with MeOH in DCM (5-10%) as eluent to give (2S,4R)-1-(2-(3-acetyl-6-hydroxy-5-(2-methylpyrimidin-5-yl)-1H-indol-1-yl)acetyl)-N-(2-chloro-2-fluoro-[1,1'-biphenyl]-3-yl)-4-fluoropyrrolidine-2-carboxamide (34.4 mg) as white powder.

¹H NMR (400 MHz, Chloroform-d) δ 8.78 (s, 2H), 8.28 (s, 1H), 8.17 (tdd, J=1.7, 4.0, 8.4 Hz, 1H), 7.67 (s, 1H), 7.48-7.41 (m, 1H), 7.35-7.27 (m, 2H), 7.26-7.21 (m, 1H), 7.14 (td, J=1.1, 7.9 Hz, 1H), 7.02 (ddd, J=1.7, 6.8, 7.9 Hz, 1H), 6.72 (s, 1H), 5.40 (d, J=52.5 Hz, 1H), 5.07-4.80 (m, 3H), 4.05-3.90 (m, 1H), 3.83-3.60 (m, 4H), 2.78 (s, 3H), 2.75-2.45 (m, 2H), 2.40 (s, 3H). LC (method A): tR=2.1 min. LC/MS (EI) m/z: [M+H]⁺ 658.

(2S,4R)-1-(2-(3-Acetyl-6-methoxy-5-(2-methylpyrimidin-5-yl)-1H-indol-1-yl)acetyl)-N-(6-bromopyridin-2-yl)-4-fluoropyrrolidine-2-carboxamide (319)

786

-continued

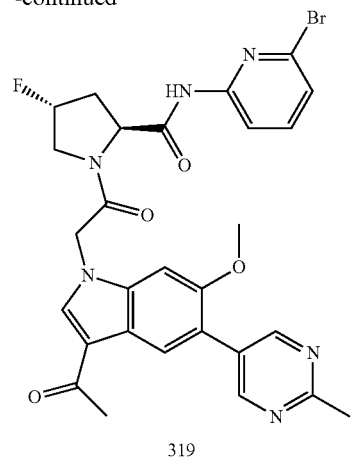

319

Into a mixture of 2-(3-acetyl-6-methoxy-5-(2-methylpyrimidin-5-yl)-1H-indol-1-yl)acetic acid (21.4 mg, 0.063 mmol) and (2S,4R)—N-(6-bromopyridin-2-yl)-4-fluoropyrrolidine-2-carboxamide hydrochloride (20.5 g, 0.063 mmol) in DMF (2 mL), TBTU (32.1 mg, 0.1 mmol) followed by DIEA (0.066 mL, 0.36 mmol) was added at room temperature with stirring. After 1 hr, NaHCO₃ (aq) was added to form precipitation. Solid was collected by filtration and purified on ISCO with MeOH in DCM (5-10%) as eluent to give (2S,4R)-1-(2-(3-acetyl-6-methoxy-5-(2-methylpyrimidin-5-yl)-1H-indol-1-yl)acetyl)-N-(6-bromopyridin-2-yl)-4-fluoropyrrolidine-2-carboxamide (31.2 mg) as white powder.

¹H NMR (400 MHz, Chloroform-d) δ 9.33 (s, 1H), 8.79 (s, 2H), 8.26 (s, 1H), 7.98 (d, J=8.1 Hz, 1H), 7.75 (s, 1H), 7.47 (t, J=7.9 Hz, 1H), 7.15 (dd, J=0.7, 7.7 Hz, 1H), 6.77 (s, 1H), 5.41-5.20 (m, 1H), 5.06-4.86 (m, 2H), 4.75 (t, J=7.8 Hz, 1H), 3.91-3.73 (m, 5H), 2.78 (s, 3H), 2.45 (s, 3H), 2.34-2.14 (m, 2H). LC (method A): tR=1.59 min. LC/MS (EI) m/z: [M+H]⁺ 609.

(2S,4R)-1-(2-(3-Acetyl-6-hydroxy-5-(2-methylpyrimidin-5-yl)-1H-indol-1-yl)acetyl)-N-(2-chloro-2-fluoro-[1,1'-biphenyl]-3-yl)-4-fluoropyrrolidine-2-carboxamide (320)

Scheme 368

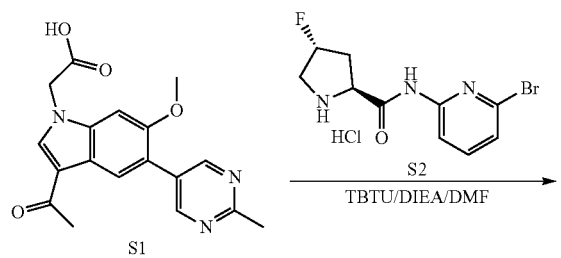

Scheme 369

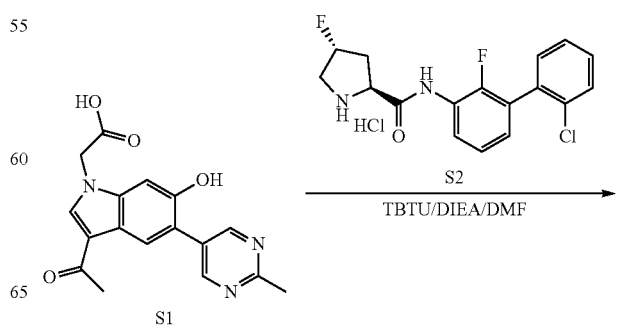

787

-continued

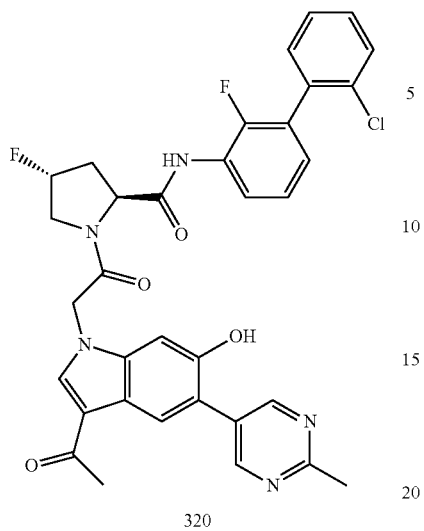

320

Into a mixture of 2-(3-acetyl-6-hydroxy-5-(2-methylpyrimidin-5-yl)-1H-indol-1-yl)acetic acid (30.6 mg, 0.094 mmol) and (2S,4R)—N-(2-chloro-2-fluoro-[1,1'-biphenyl]-3-yl)-4-fluoropyrrolidine-2-carboxamide hydrochloride (35 mg, 0.094 mmol) in DMF (1 mL), TBTU (45.3 mg, 0.141 mmol) followed by DIEA (0.082 mL, 0.47 mmol) was added at room temperature with stirring. After 1 hr, NaHCO$_3$ aq was added to form precipitation. Solid was collected by filtration and purified on ISCO with MeOH in DCM (5-10%) as eluent to give (2S,4R)-1-(2-(3-acetyl-6-hydroxy-5-(2-methylpyrimidin-5-yl)-1H-indol-1-yl)acetyl)-N-(2-chloro-2-fluoro-[1,1'-biphenyl]-3-yl)-4-fluoropyrrolidine-2-carboxamide (25.4 mg) as white powder.

$^1$H NMR (400 MHz, Chloroform-d) δ 8.81 (s, 2H), 8.20 (s, 1H), 7.99 (s, 1H), 7.85 (s, 1H), 7.62 (s, 1H), 7.43 (d, J=7.8 Hz, 1H), 7.16 (s, 1H), 7.02 (s, 2H), 6.64 (s, 1H), 5.38 (d, J=52.2 Hz, 1H), 4.85 (d, J=20.6 Hz, 3H), 3.82 (d, J=34.4 Hz, 2H), 3.44 (d, J=15.2 Hz, 0H), 2.96 (s, 2H), 2.88 (s, 2H), 2.78 (d, J=20.1 Hz, 4H), 2.55 (d, J=38.1 Hz, 0H), 2.40 (s, 3H). LC (method A): tR=1.89 min. LC/MS (EI) m/z: [M+H]$^+$ 644.

(2S,4R)-1-(2-(3-Acetyl-6-hydroxy-5-(2-methylpyrimidin-5-yl)-1H-indol-1-yl)acetyl)-N-(6-bromopyridin-2-yl)-4-fluoropyrrolidine-2-carboxamide (328)

Scheme 370

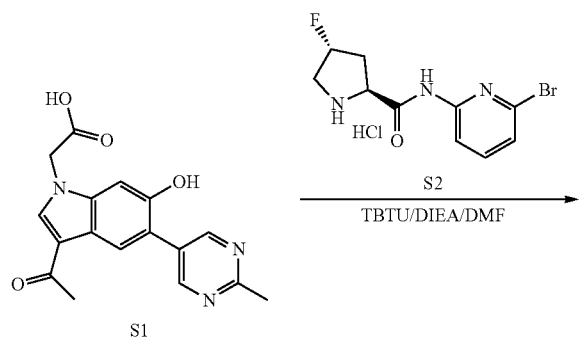

788

-continued

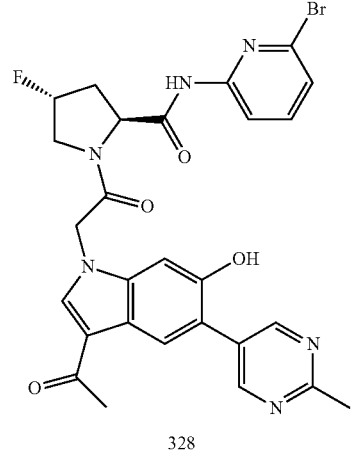

328

Into a mixture of 2-(3-acetyl-6-hydroxy-5-(2-methylpyrimidin-5-yl)-1H-indol-1-yl)acetic acid (0.101, 0.311 mmol) and (2S,4R)—N-(6-bromopyridin-2-yl)-4-fluoropyrrolidine-2-carboxamide hydrochloride (0.101 g, 0.311 mmol) in DMF (3 mL), TBTU (0.15 g, 0.466 mmol) followed by DIEA (0.324 mL, 1.87 mmol) was added at room temperature with stirring. After overnight, NaHCO$_3$ aq was added to form precipitation. Solid was collected by filtration and purified on ISCO with MeOH in DCM (5-10%) as eluent to give (2S,4R)-1-(2-(3-acetyl-6-hydroxy-5-(2-methylpyrimidin-5-yl)-1H-indol-1-yl)acetyl)-N-(6-bromopyridin-2-yl)-4-fluoropyrrolidine-2-carboxamide (99 mg) as gray powder.

$^1$H NMR (400 MHz, Chloroform-d) δ 9.04-8.84 (m, 2H), 8.23 (qd, J=5.2, 7.7, 9.4 Hz, 1H), 8.00 (s, 1H), 7.95-7.81 (m, 1H), 7.68-7.43 (m, 1H), 7.32-7.15 (m, 1H), 6.84 (qd, J=5.0, 7.6, 9.2 Hz, 1H), 5.43 (dd, J=12.5, 51.9 Hz, 1H), 5.03 (d, J=9.4 Hz, 2H), 4.77 (d, J=8.8 Hz, 1H), 4.11-3.74 (m, 3H), 3.53-3.32 (m, 1H), 2.86-2.72 (m, 3H), 2.64 (q, J=13.0, 15.7 Hz, 1H), 2.57-2.44 (m, 3H), 2.41-2.14 (m, 1H). LC (method A): tR=1.35 min. LC/MS (EI) m/z: [M+H]$^+$ 595.

(2S,4R)-1-(2-(3-Acetyl-6-methoxy-5-(2-methylpyrimidin-5-yl)-1H-indazol-1-yl)acetyl)-N-(6-bromopyridin-2-yl)-4-fluoropyrrolidine-2-carboxamide (373)

Scheme 371

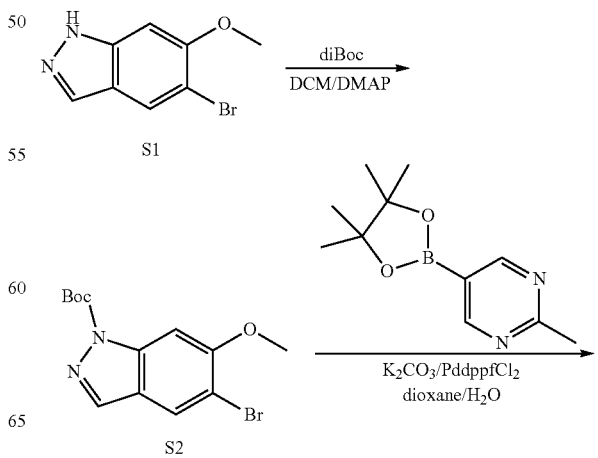

-continued

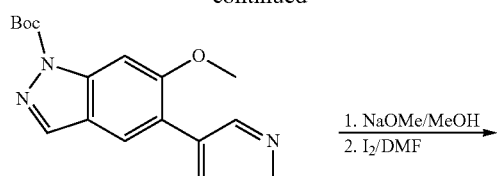

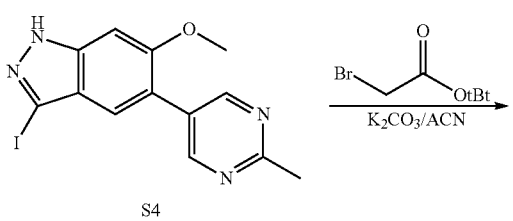

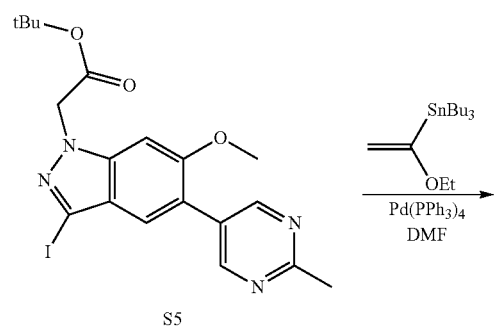

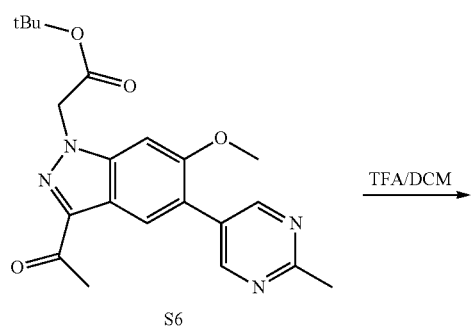

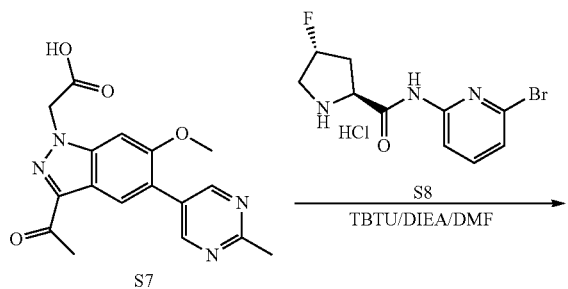

-continued

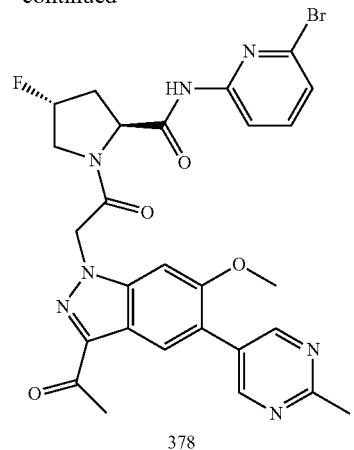

378

Step 1: tert-Butyl 5-bromo-6-methoxy-1H-indazole-1-carboxylate (S2)

5-bromo-6-methoxy-1H-indazole (0.892 g, 3.93 mmol) was treated with diBoc (0.95 mL, 4.12 mmol) at room temperature in DCM (30 mL) in the presence of catalytic amount of DMAP for 3 hr. Solvent was removed by evaporation and the tert-butyl 5-bromo-6-methoxy-1H-indazole-1-carboxylate was used for next step.

Step 2: tert-Butyl 6-methoxy-5-(2-methylpyrimidin-5-yl)-1H-indazole-1-carboxylate (S3)

Into solution of tert-butyl 5-bromo-6-methoxy-1H-indazole-1-carboxylate and 2-methyl-5-(4,4,5,5-tetramethyl-1,3,2-dioxaborolan-2-yl)pyrimidine (0.95 g, 4.32 mmol) in dioxane-$H_2O$ (20 mL-2 mL), $K_2CO_3$ (1.08 g, 7.86 mmol) and $PddppfCl_2$ (0.080 g, 0.098 mmol) were added. The mixture was heated to 90° C. under Ar for 2 hr. The reaction mixture was cooled to rt, filtered, and concentrated. Residue was dissolved in acetonitrile, filtered, and then concentrated to give tert-butyl 6-methoxy-5-(2-methylpyrimidin-5-yl)-1H-indazole-1-carboxylate for next step.

Step 3: 3-Iodo-6-methoxy-5-(2-methylpyrimidin-5-yl)-1H-indazole (S4)

tert-butyl 6-methoxy-5-(2-methylpyrimidin-5-yl)-1H-indazole-1-carboxylate in MeOH (20 mL) was treated with NaOMe (25% in MeOH, 2.6 mL, 12 mmol) at 60° C. for 30 min. The mixture was cooled to rt, and $I_2$ (1.22 g, 4.8 mmol) in DMF (2 mL) was added. After stirring at room temperature for 5 min, $Na_2SO_3$ (0.126 g) was added, and then pH of the mixture was adjusted to 6 with 1N HCl. The mixture was extracted with AcOEt. After washing with brine, and drying over anhydrous $Na_2SO_4$, the solvent was removed by evaporation to give 3-iodo-6-methoxy-5-(2-methylpyrimidin-5-yl)-1H-indazole (1.65 g) as brown solid.

Step 4: tert-Butyl 2-(3-iodo-6-methoxy-5-(2-methylpyrimidin-5-yl)-1H-indazol-1-yl)acetate (S5)

The mixture of 3-iodo-6-methoxy-5-(2-methylpyrimidin-5-yl)-1H-indazole (1.65 g) and tert-butyl 2-bromoacetate (0.638 mL, 4.32 mmol) was heated in DMF (20 mL) at 70° C. in the presence of $K_2CO_3$ (1.08 g, 7.86 mmol) for 1.5 hr. After flirtation to remove solid, water was added and extracted with AcOEt. Purification on ISCO with AcOEt in hexane (0-100%) as eluent gives tert-butyl 2-(3-iodo-6-methoxy-5-(2-methylpyrimidin-5-yl)-1H-indazol-1-yl)acetate (1.22 g) as yellow solid.

Step 5: tert-Butyl 2-(3-acetyl-6-methoxy-5-(2-methylpyrimidin-5-yl)-1H-indazol-1-yl)acetate (S6)

The mixture of tert-butyl 2-(3-iodo-6-methoxy-5-(2-methylpyrimidin-5-yl)-1H-indazol-1-yl)acetate (1.22 g, 2.54 mmol) and tributyl(1-ethoxyvinyl)stannane (1.29 mL, 3.8 mmol) in DMF (6 mL) was heated at 80° C. under Ar in the presence of Pd(PPh$_3$)$_4$ (0.29 mg, 0.254 mmol) overnight. After cooled down to rt, HCl aq (1N, 3 mL) was added and stirred for 1 hr. Water (30 mL) was added and extracted with AcOEt. Organic layer was washed with brine and dried over anhydrous Na$_2$SO$_4$. Solvent was removed under reduced pressure. Crude was purified on ISCO with AcOEt in hexane (0-100%) as eluent to give tert-butyl 2-(3-acetyl-6-methoxy-5-(2-methylpyrimidin-5-yl)-1H-indazol-1-yl)acetate (0.97 g) as pale yellow solid.

Step 6: 2-(3-Acetyl-6-methoxy-5-(2-methylpyrimidin-5-yl)-1H-indazol-1-yl)acetic acid (S7)

tert-butyl 2-(3-acetyl-6-methoxy-5-(2-methylpyrimidin-5-yl)-1H-indazol-1-yl)acetate (55 mg, 0.14 mmol) was treated with TFA (2 mL) in DCM (2 mL) for 3 hr. After evaporation of volatile, residue was co-evaporated with toluene (5 mL) and dried under vacuum to give 2-(3-acetyl-6-methoxy-5-(2-methylpyrimidin-5-yl)-1H-indazol-1-yl)acetic acid.

Step 7: (2S,4R)-1-(2-(3-Acetyl-6-methoxy-5-(2-methylpyrimidin-5-yl)-1H-indazol-1-yl)acetyl)-N-(6-bromopyridin-2-yl)-4-fluoropyrrolidine-2-carboxamide (378)

Into a mixture of 2-(3-acetyl-6-methoxy-5-(2-methylpyrimidin-5-yl)-1H-indazol-1-yl)acetic acid and (2S,4R)—N-(6-bromopyridin-2-yl)-4-fluoropyrrolidine-2-carboxamide hydrochloride (45.5 mg, 0.14 mmol) in DMF (1 mL), TBTU (67 mg, 0.21 mmol) followed by DIEA (0.122 mL, 0.7 mmol) was added at room temperature with stirring. After 1 hr, NaHCO$_3$ (aq) (10 mL) was added to form precipitation. Solid was collected by filtration, washed with water, and dried to give (2S,4R)-1-(2-(3-acetyl-6-methoxy-5-(2-methylpyrimidin-5-yl)-1H-indazol-1-yl)acetyl)-N-(6-bromopyridin-2-yl)-4-fluoropyrrolidine-2-carboxamide (63 mg) as white solid.

$^1$H NMR (400 MHz, Chloroform-d) δ 8.89 (s, 1H), 8.78 (s, 2H), 8.24 (s, 1H), 8.03 (d, J=8.2 Hz, 1H), 7.73-7.62 (m, 1H), 7.56-7.48 (m, 1H), 7.21 (dd, J=0.7, 7.7 Hz, 1H), 6.88 (s, 1H), 5.31 (s, 3H), 4.80 (t, J=8.1 Hz, 1H), 4.17 (dd, J=12.4, 19.8 Hz, 1H), 3.84 (s, 4H), 3.66 (ddd, J=3.2, 12.4, 34.6 Hz, 1H), 2.79 (s, 4H), 2.68 (s, 3H), 2.61-2.43 (m, 2H). LC (method A): tR=1.72 min. LC/MS (EI) m/z: [M+H]$^+$ 610.

1-(2-((2S,4R)-2-((2'-Chloro-2-fluoro-[1,1'-biphenyl]-3-yl)carbamoyl)-4-fluoropyrrolidin-1-yl)-2-oxoethyl)-5-(2-methylpyrimidin-5-yl)-1H-thieno[3,2-c]pyrazole-3-carboxamide (314)

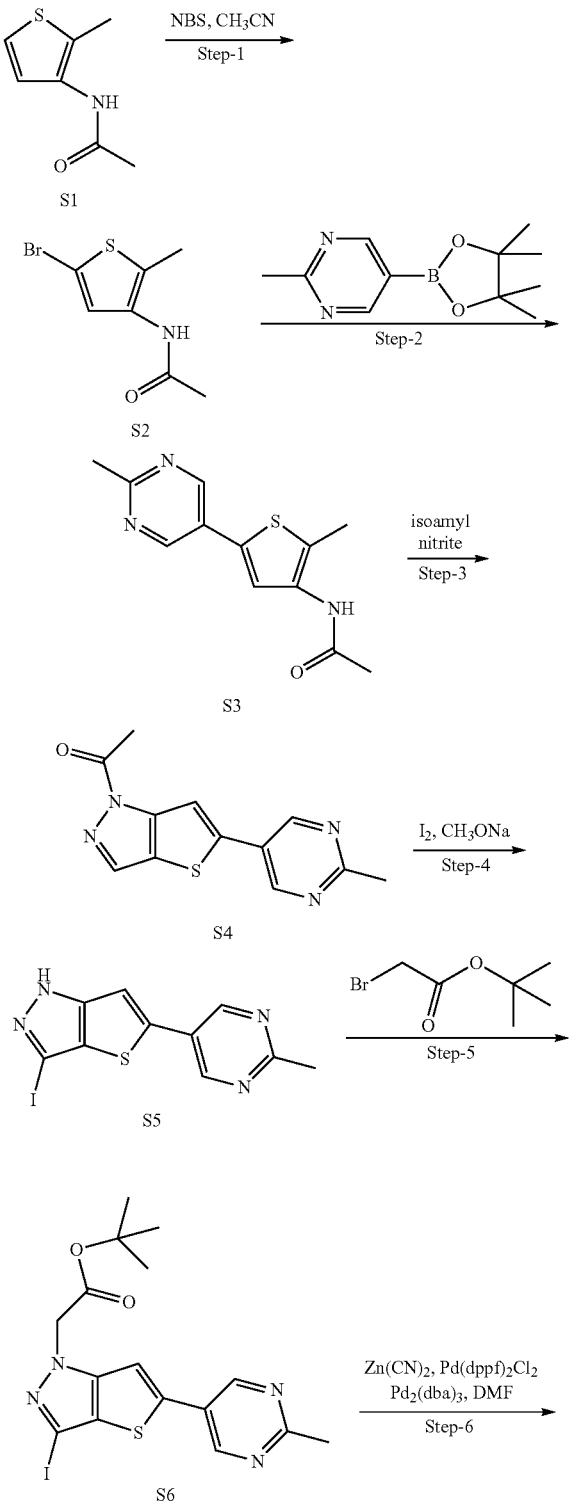

Scheme 372

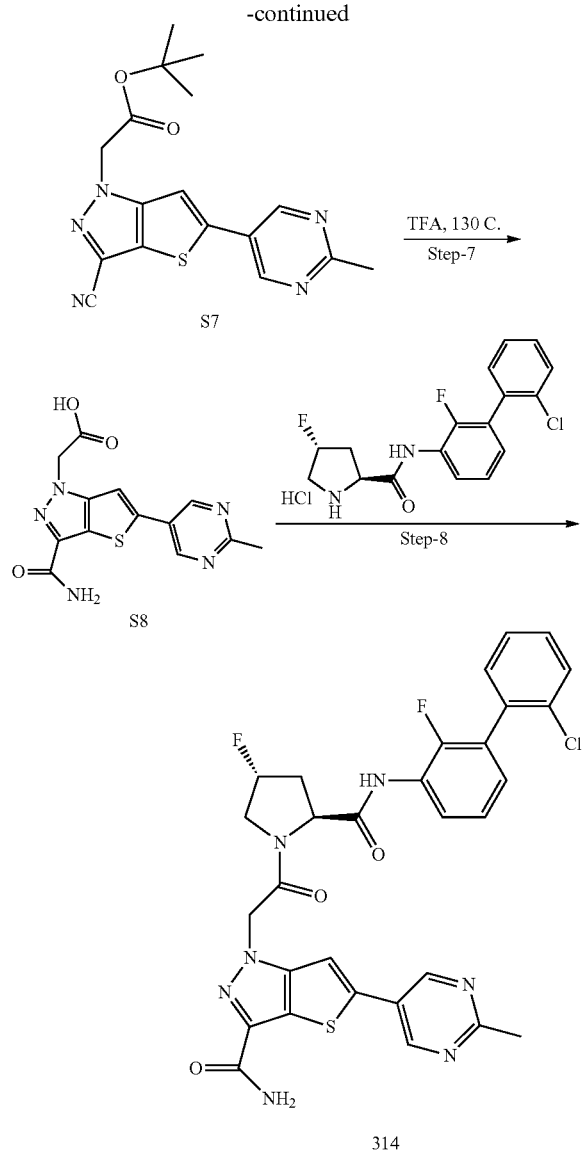

Step-1: N-(5-Bromo-2-methylthiophen-3-yl)acetamide (S2)

N-(2-methylthiophen-3-yl)acetamide (1.55 g, 10.0 mmol) in CH$_3$CN (85 mL) was treated with NBS (11 mmol) in portions at room temperature. The reaction was stirred for 4 hours at rt. The solvent was removed and the residue was purified to afford desired product (1.5 g). $^1$H NMR (400 MHz, CDCl$_3$) δ: 2.15 (s, 3H), 2.25 (s, 3H), 6.79 (br, s, 1H), 7.25 (s, 1H) ppm

Step-2: N-(2-Methyl-5-(2-methylpyrimidin-5-yl)thiophen-3-yl)acetamide (S3)

N-(5-bromo-2-methylthiophen-3-yl)acetamide (859 mg, 3.67 mmol), 2-methyl-5-(4,4,5,5-tetramethyl-1,3,2-dioxaborolan-2-yl)pyrimidine (888 mg, 4.0 mmol) and Cs$_2$CO$_3$ (1.8 g, 5.51 mmol) were mixed in co-solvent of DMF (16 ml) and H$_2$O (4 ml). The mixture was degassed and refilled with argon. To the mixture, Pd(PPh$_3$)$_4$ (0.1 eq) was added under Ar. The reaction was heated in an oil bath (95° C.) for 3 hrs. The reaction was cooled to room temperature and the volatiles were evaporated. The residue was treated with water and the resulting solid was collected, washed with water, and dried. The residue (702 mg) was used for next step without further purification. $^1$H NMR (400 MHz, DMSO-d$_6$) δ: 2.04 (s, 3H), 2.33 (s, 3H), 2.63 (s, 3H), 7.61 (s, 1H), 8.87 (s, 2H), 9.56 (s, 1H) ppm. LC (method A): t$_R$=0.76 min. LC/MS (EI) m/z: [M+H]$^+$ 248.15

Step-3: 1-(5-(2-Methylpyrimidin-5-yl)-1H-thieno[3,2-c]pyrazol-1-yl)ethan-1-one (S4)

N-(2-methyl-5-(2-methylpyrimidin-5-yl)thiophen-3-yl)acetamide (702 mg), KOAc (180 mg, 1.84 mmol) and Ac$_2$O (412 mg, 0.38 mL, 4.0 mmol) were mixed in dry toluene (35 mL). The mixture was heated in oil bath (80° C.) for 30 min. The reaction was cooled to room temperature and isoamyl nitrite (469 mg, 0.54 mL, 4.0 mmol) was added. The reaction mixture was heated at 125° C. for 5 hrs. The reaction was cooled to room temperature and filtered through Celite. The cake was washed with toluene (50 ml×2). The combined solution was concentrated and the resulting residue was purified to give desired product (435 mg). $^1$H NMR (400 MHz, CDCl$_3$) δ: 2.77 (s, 3H), 2.79 (s, 3H), 7.86 (s, 1H), 7.92 (s, 1H), 8.90 (s, 2H) ppm.

Step-4: 3-Iodo-5-(2-methylpyrimidin-5-yl)-1H-thieno[3,2-c]pyrazole (S5)

To the suspension of 1-(5-(2-methylpyrimidin-5-yl)-1H-thieno[3,2-c]pyrazol-1-yl)ethan-1-one (435 mg, 1.68 mmol) in anhydrous methanol (5.0 ml), sodium methoxide (25% in methanol) (1.0 mL) was added. The mixture was stirred at room temperature until the acetyl group was removed, and then iodine (510 mg, 2.02 mmol) was added in one portion at rt. The mixture was stirred for an additional 2 hr. The volatiles were removed, and the residue was mixed with ethyl acetate and filtered through a short pad of silica gel. The filtrate was concentrated and the resulting material was carried forward without further purification.

Step-5: tert-Butyl 2-(3-iodo-5-(2-methylpyrimidin-5-yl)-1H-thieno[3,2-c]pyrazol-1-yl)acetate (S6)

To the solution of 3-iodo-5-(2-methylpyrimidin-5-yl)-1H-thieno[3,2-c]pyrazole from Step-4 in CH$_3$CN (10 mL), tert-butyl 2-bromoacetate (1.85 mmol) and solid potassium carbonate (5.04 mmol) are added. The mixture was stirred overnight under Ar at rt. The reaction mixture was filtered through a pad of celite. The solid cake was washed with additional CH$_3$CN (20 mL), and the combined solution was concentrated. The residue was purified to afford pure tert-Butyl 2-(3-iodo-5-(2-methylpyrimidin-5-yl)-1H-thieno[3,2-c]pyrazol-1-yl)acetate (133 mg). $^1$H NMR (400 MHz, CDCl$_3$) δ: 1.48 (s, 9H), 2.79 (s, 3H), 4.98 (s, 2H), 7.21 (s, 1H), 8.85 (s, 2H) ppm.

Step-6: tert-butyl 2-(3-cyano-5-(2-methylpyrimidin-5-yl)-1H-thieno[3,2-c]pyrazol-1-yl)acetate (S7)

To the degassed solution of tert-butyl 2-(3-iodo-5-(2-methylpyrimidin-5-yl)-1H-thieno[3,2-c]pyrazol-1-yl)acetate (133 mg, 0.29 mmol) in the co-solvents DMF (3 mL) and water (0.3 mL), Zn(CN)$_2$ (41 mg, 0.35 mmol), Pd(dppf)$_2$Cl$_2$ and Pd$_2$(dba)$_3$ are added under Ar. The mixture was heated at 100° C. overnight. The reaction was cooled to rt, and the volatiles are evaporated under reduced pressure. The residue was diluted with ethyl acetate (15 mL) and filtered through a pad of Celite. The residue was washed with additional 30 mL of ethyl acetate. The combined organic solution was concentrated, and the residue was purified to afford 37 mg of the title compound. $^1$H NMR (400 MHz, CDCl$_3$) δ: 1.50 (s, 9H), 2.80 (s, 3H), 5.04 (s, 2H), 7.20 (s, 1H), 8.86 (s, 2H) ppm. LC (method A): $t_R$=2.48 min. LC/MS (EI) m/z: [M+H]$^+$ 235.26.

Step-7: 2-(3-Carbamoyl-5-(2-methylpyrimidin-5-yl)-1H-thieno[3,2-c]pyrazol-1-yl)acetic acid (S8)

A solution of tert-butyl 2-(3-cyano-5-(2-methylpyrimidin-5-yl)-1H-thieno[3,2-c]pyrazol-1-yl)acetate (37 mg, 0.104 mmol) in TFA (1.5 mL) and water (0.3 mL) was subjected to microwave irradiation at 140° C. for 60 min. The mixture was concentrated in vacuo, and the residue was co-evaporated with toluene (10 mL) twice. The compound was carried forward without further purification.

Step-8: 1-(2-((2S,4R)-2-((2'-Chloro-2-fluoro-[1,1'-biphenyl]-3-yl)carbamoyl)-4-fluoropyrrolidin-1-yl)-2-oxoethyl)-5-(2-methylpyrimidin-5-yl)-1H-thieno[3,2-c]pyrazole-3-carboxamide (314)

2-(3-Carbamoyl-5-(2-methylpyrimidin-5-yl)-1H-thieno[3,2-c]pyrazol-1-yl)acetic acid (0.1 mmol) from Step-7, HATU (0.15 mmol) and (2S,4R)—N-(2'-chloro-2-fluoro-[1,1'-biphenyl]-3-yl)-4-fluoropyrrolidine-2-carboxamide hydrochloride (0.1 mmol) were dissolved in DMF (1.2 mL). To the solution, DIEA (0.25 mL) was added dropwise at room temperature. The mixture was stirred for 1 h at room temperature and the volatiles were evaporated. The residue was partitioned between ethyl acetate and saturated aqueous NaHCO$_3$. The combined ethyl acetate solution was collected and washed with water, brine and dried over MgSO$_4$. The solution was concentrated and the remaining residue was purified to afford 11.4 mg of title compound. $^1$H NMR (400 MHz, DMSO-d$_6$): (major rotamer) δ: 2.03-2.20 (m, 1H), 2.43-2.56 (m, 1H), 2.60 (s, 3H), 3.78-3.91 (m, 1H), 4.04-4.12 (m, 1H), 4.72 (t, J=8.4 Hz, 1H), 5.27-5.34 (m, 3H), 6.98 (t, J=6.80 Hz, 1H), 7.11 (t, J=6.80 Hz, 1H), 7.24-7.41 (m, 4H), 7.49-7.51 (m, 1H), 7.65 (s, 1H), 7.70 (s, 1H), 7.91 (t, J=7.2 Hz, 1H), 8.93 (s, 2H), 9.98 (s, 1H) ppm. $^{19}$F NMR (376 MHz, DMSO-d$_6$300K): (major rotamer) δ −126.83, −175.64. LC (method A): $t_R$=1.87 min. LC/MS (EI) m/z: [M+H]$^+$ 636.39

(2S,4R)-1-(2-(3-Acetyl-5-(2-methylpyrimidin-5-yl)-1H-indazol-1-yl)acetyl)-N-(2-cyano-3-(trifluoromethoxy)phenyl)-4-fluoropyrrolidine-2-carboxamide (738)

Scheme 373

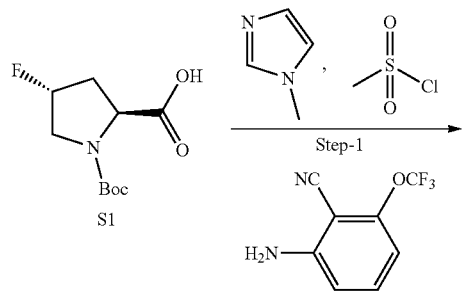

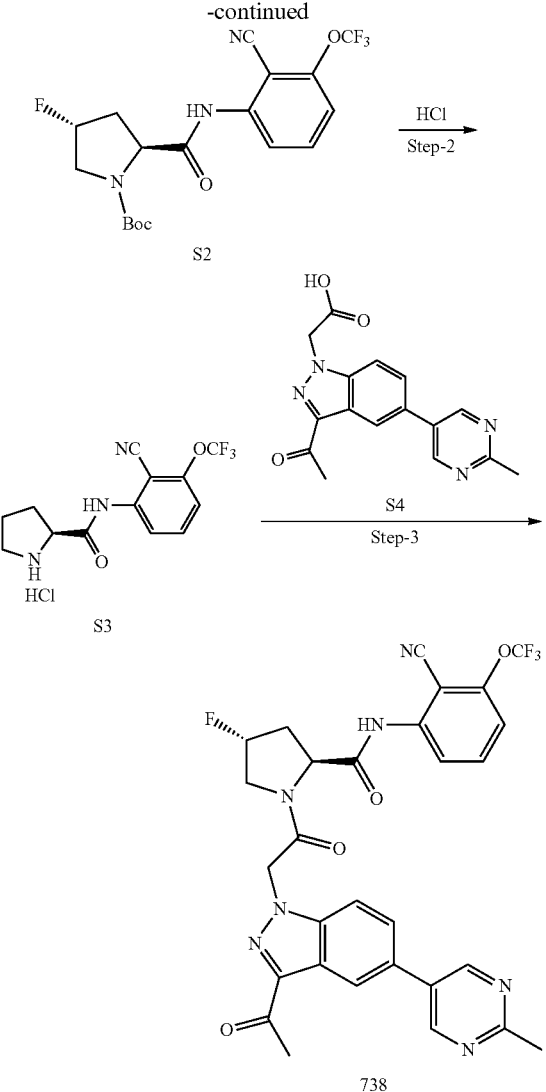

Step-1: tert-Butyl (2S,4R)-2-((2-cyano-3-(trifluoromethoxy)phenyl)carbamoyl)-4-fluoropyrrolidine-1-carboxylate (S2)

To a stirred solution of (2S, 4R)-1-(tert-butoxycarbonyl)-4-fluoropyrrolidine-2-carboxylic acid (250 mg, 1.07 mmole) in 10 mL of CH2Cl2, was added 1-methyl imidazole (0.21 mL, 2.5 equiv.) at 0-5° C. under nitrogen atmosphere. The reaction mixture was stirred for 10 min at 0-5° C. and then added methane sulfonyl chloride (0.1 mL, 1.2 equiv) at the same temperature. It was stirred for 1 h at 0-50° C. Then 2-amino-6-(trifluoromethoxy)benzonitrile (216 mg, 1 equiv) was added, and stirred for 18 h at room temperature. Water (10 mL) was added to the reaction mixture, layers were separated and aqueous layer was extracted with DCM (3×10 mL). The combined organic layer was washed with 1N HCl (10 mL), followed by Sat NaHCO3 (10 mL) and then with brine (10 mL). Combined organic layer was dried over Na2SO4, concentrated and purified by ISCO (silica gel, eluted by 5% MeOH in DCM gradient) to obtain titled compound 156 mg (37%).

Step-2: (2S,4R)—N-(2-Cyano-3-(trifluoromethoxy)phenyl)-4-fluoropyrrolidine-2-carboxamide (S3)

To Tert-butyl (2S,4R)-2-((2-cyano-3-(trifluoromethoxy)phenyl)carbamoyl)-4-fluoropyrrolidine-1-carboxylate was added 10 ml of 4N HCl in Dioxane. The resulting solution was stirred at room temperature for 6 hours. Then, the reaction mixture was concentrated in vacuuo and used for the following step.

Step-3: (2S,4R)-1-(2-(3-Acetyl-5-(2-methylpyrimidin-5-yl)-1H-indazol-1-yl)acetyl)-N-(2-cyano-3-(trifluoromethoxy)phenyl)-4-fluoropyrrolidine-2-carboxamide (738)

To a stirred solution of (2S,4R)—N-(2-cyano-3-(trifluoromethoxy)phenyl)-4-fluoropyrrolidine-2-carboxamide (HCl salt, 81 mg) in DMF (10 mL) was added 2-(3-acetyl-5-(2-methylpyrimidin-5-yl)-1H-indazol-1-yl)acetic acid (71 mg, 1.05 equiv.), HATU (100 mg, 1.2 equiv), and DIEA (0.19 mL, 5.0 equiv). The reaction was stirred at room temperature for a couple of hours. It was then diluted with EtOAC (15 mL), and water (10 mL). The organic layer was washed with brine (3×15 mL), dried over Na2SO4 and concentrated in vacuuo. The resulting oil was purified by ISCO (silica gel, eluted with 10% MeOH in DCM gradient) and yielded 88 mg (65%) of compound 738. 1H NMR (400 MHz, DMSO-$d_6$): (major rotamer) δ 2.14-2.32 (m, 1H), 2.56-2.59 (m, 1H), 2.65 (s, 3H), 2.69 (s, 3H), 3.99-4.11 (m, 1H), 4.22-4.33 (m, 1H), 4.66 (t, 1H, J=8.1 Hz), 5.53-5.90 (m, 3H), 7.46-7.55 (m, 1H), 7.75-7.92 (m, 3H), 8.45 (s, 1H), 9.05 (s, 2H), 10.67 (s, 1H); 19F NMR (376 MHz, DMSO-$d_6$300K): (major rotamer) δ −57.12 (3F), −176.10 (1F). LC (method A): tR=1.83 min. LC/MS (EI) m/z: [M+H]+ 610.

5-(3-acetyl-1-(2-((2S,4R)-2-((6-Bromopyridin-2-yl)carbamoyl)-4-fluoropyrrolidin-1-yl)-2-oxoethyl)-1H-indazol-5-yl)-2-aminopyrimidine 1-oxide (741)

Scheme 374

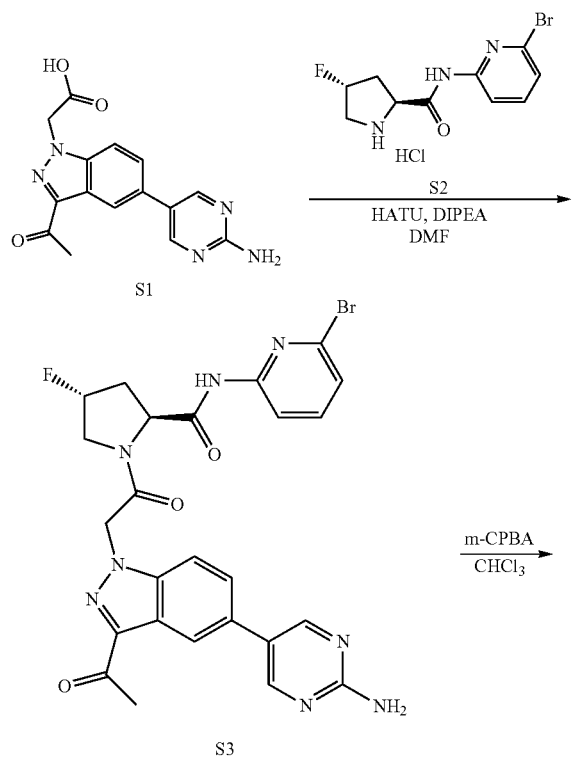

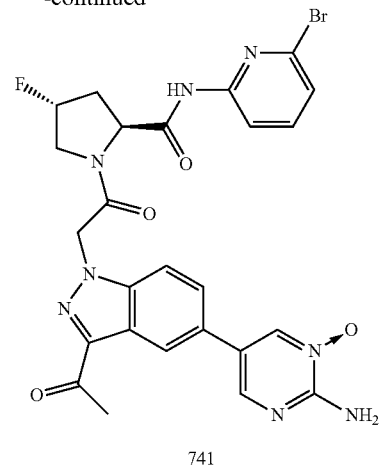

741

Step 1: (2S,4R)-1-(2-(3-Acetyl-5-(2-aminopyrimidin-5-yl)-1H-indazol-1-yl)acetyl)-N-(6-bromopyridin-2-yl)-4-fluoropyrrolidine-2-carboxamide (S3)

To a mixture of compound S1 (50 mg, 0.16 mmol) and compound 2 (52.1 mg, 0.16 mmol) in DMF (2 mL) was added DIPEA (82.7 mg, 0.64 mmol) and HATU (91.2 mg, 0.24 mmol) at 0° C. The reaction was stirred at room temperature overnight. The mixture was diluted with EtOAc and washed with 10% aq. LiCl solution and brine. The organic layer was dried over anhydrous $Na_2SO_4$ and concentrated to give a crude product, which was purified by silica gel column chromatography (eluted with DCM:MeOH=50:1 to 15:1) to give compound S2 (71 mg, 76.3% yield) as a white solid. LC/MS (ESI) m/z: 581 (M+H)+.

Step 2: 5-(3-Acetyl-1-(2-((2S,4R)-2-(6-bromopyridin-2-ylcarbamoyl)-4-fluoropyrrolidin-1-yl)-2-oxoethyl)-1H-indazol-5-yl)-2-aminopyrimidine 1-oxide (741)

To a solution of compound S3 (35 mg, 0.06 mol) in $CHCl_3$ (3 mL) was added m-CPBA (15.6 mg, 0.09 mol) and the mixture was stirred at room temperature for 16 hrs. The mixture was diluted with DCM and washed with 5% aq. $NaHCO_3$ solution and brine, dried over anhydrous $Na_2SO_4$, filtered and concentrated to give a crude product, which was purified by prep. HPLC to give 741 (13.6 mg, 37.9% yield) as a white solid. 1H NMR (400 MHz, DMSO-$d_6$) δ 11.05 (s, 1H), 8.78 (d, J=2.4 Hz, 1H), 8.32 (s, 1H), 8.22-8.23 (d, J=2.0 Hz, 1H), 8.02-8.04 (d, J=8.0 Hz, 1H), 7.69-7.81 (m, 5H), 7.31-7.33 (d, J=7.2 Hz, 1H), 5.80-5.84 (d, J=17.2 Hz, 1H), 5.60-5.64 (d, J=16.8 Hz, 1H), 5.48-5.62 (dm, 1H), 4.65-4.69 (t, 1H), 4.18-4.27 (m, 1H), 3.99-4.08 (m, 1H), 2.64 (s, 3H), 1.97-2.24 (m, 2H). LC/MS (ESI) m/z: 597 (M+H)+.

5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)-2-methylpyrimidine 1-oxide (742)

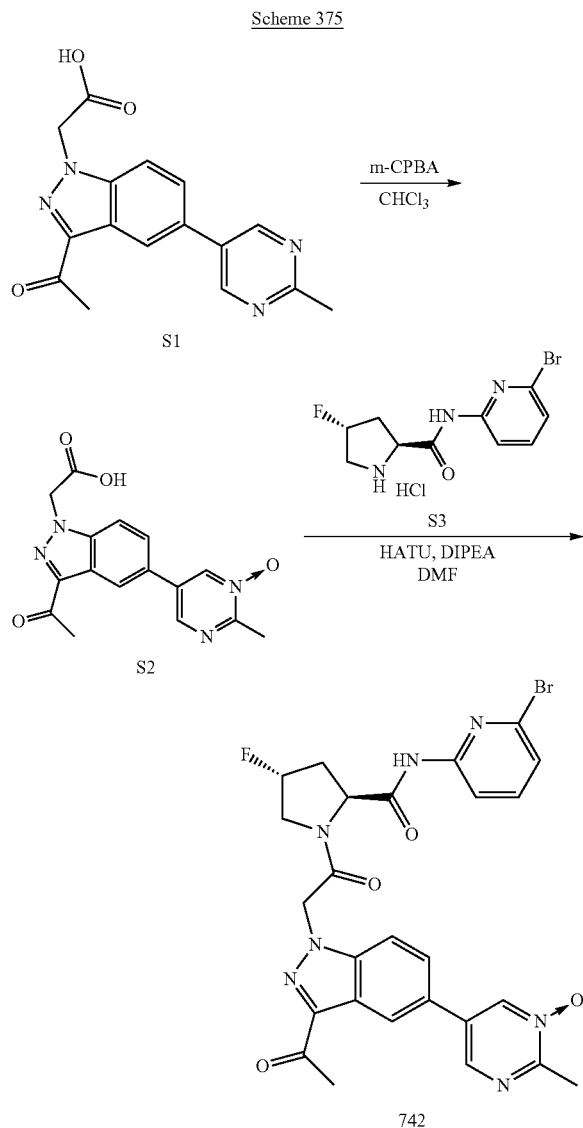

Step 1: 5-(3-Acetyl-1-(carboxymethyl)-1H-indazol-5-yl)-2-methylpyrimidine 1-oxide (S2)

To a solution of compound S1 (150 mg, 0.484 mmol) in CHCl$_3$ (3 mL) was added m-CPBA (125 mg, 0.725 mmol). The resulting mixture was stirred at room temperature overnight. The mixture was concentrated to dryness and the residue was purified by prep-HPLC to give compound 2 (40 mg, 25.4% yield) as a white solid. LC/MS (ESI) m/z: 327 (M+H)$^+$.

Step 2: 5-(3-Acetyl-1-(2-((2S,4R)-2-((6-bromopyridin-2-yl)carbamoyl)-4-fluoropyrrolidin-1-yl)-2-oxoethyl)-1H-indazol-5-yl)-2-methylpyrimidine 1-oxide (742)

To a mixture of compound S2 (40 mg, 0.123 mmol) and compound S3 (36 mg, 0.123 mmol) in DMF (1 mL) was added DIPEA (48 mg, 0.369 mmol) and HATU (93 mg, 0.246 mmol) at 0° C. The reaction was stirred at room temperature overnight. The mixture was diluted with EtOAc and washed with 10% aq. LiCl solution and brine. The organic layer was dried over anhydrous Na$_2$SO$_4$ and concentrated to give a crude product, which was purified by prep. HPLC to give 742 (11 mg, 14.9% yield) as a white solid. $^1$H NMR (400 MHz, DMSO-d$_6$) δ 11.01 (s, 1H), 8.98 (d, J=1.9 Hz, 1H), 8.57 (d, J=2.0 Hz, 1H), 8.46 (s, 1H), 8.02 (d, J=8.2 Hz, 1H), 7.89-7.82 (m, 2H), 7.71 (t, J=8.0 Hz, 1H), 7.32 (d, J=7.8 Hz, 1H), 5.85 (d, J=17.3 Hz, 1H), 5.65 (d, J=17.2 Hz, 1H), 5.49 (s, 1H), 4.69-4.64 (m, 1H), 4.27-4.18 (m, 1H), 4.02 (d, J=28.4 Hz, 1H), 2.65 (s, 3H), 2.61 (s, 3H), 2.25-2.16 (m, 1H), 2.15-2.06 (m, 1H). LC/MS (ESI) m/z: 596 (M+H)$^+$.

2-((2S,4R)-1-(2-(3-Acetyl-5-(2-methylpyrimidin-5-yl)-1H-indazol-1-yl)acetyl)-4-fluoropyrrolidine-2-carboxamido)-6-bromopyridine 1-oxide (743)

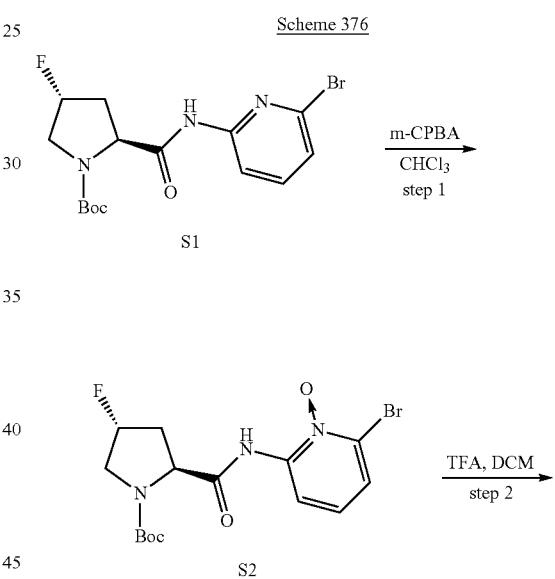

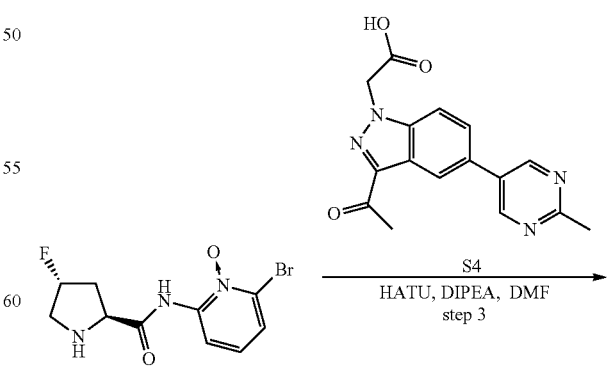

-continued

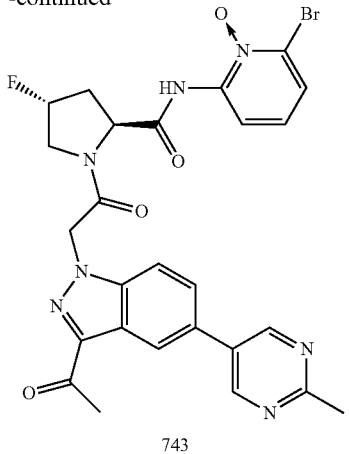

743

Step 1: 2-Bromo-6-((2S,4R)-1-(tert-butoxycarbonyl)-4-fluoropyrrolidine-2-carboxamido)pyridine 1-oxide (S2)

To a solution of (2S,4R)-tert-butyl 2-((6-bromopyridin-2-yl)carbamoyl)-4-fluoropyrrolidine-1-carboxylate (300 mg, 0.77 mmol) in CHCl$_3$ (10 mL) was added m-CPBA (133 mg, 0.77 mmol) at 0° C. The reaction was stirred at room temperature overnight. The mixture was diluted with DCM and washed with 5% aq. NaHCO$_3$ solution and brine. The organic layer was dried over anhydrous Na$_2$SO$_4$, filtered and concentrated to dryness. The residue was purified by silica gel column chromatography eluted with (DCM:MeOH=100:1) to give compound S2 (150 mg, 48.2% yield) as a brown solid. LC/MS (ESI) m/z: 404 (M+H)$^+$.

Step 2: 2-Bromo-6-((2S,4R)-4-fluoropyrrolidine-2-carboxamido)pyridine 1-oxide (S3)

To a solution of 2-bromo-6-((2S,4R)-1-(tert-butoxycarbonyl)-4-fluoropyrrolidine-2-carboxamido)pyridine 1-oxide (50 mg, 0.12 mmol) in DCM (2 mL) was added TFA (1 mL). The reaction was stirred at room temperature for 2 hrs. The mixture was concentrated to give compound 3 (48 mg, 100% yield) as a brown solid. LC/MS (ESI) m/z: 304 (M+H)$^+$.

Step 3: 2-((2S,4R)-1-(2-(3-Acetyl-5-(2-methylpyrimidin-5-yl)-1H-indazol-1-yl)acetyl)-4-fluoropyrrolidine-2-carboxamido)-6-bromopyridine 1-oxide (743)

To a mixture of 2-bromo-6-((2S,4R)-4-fluoropyrrolidine-2-carboxamido)pyridine 1-oxide (45 mg, 0.12 mmol), 2-(3-acetyl-5-(2-methylpyrimidin-5-yl)-1H-indazol-1-yl)acetic acid (37.2 mg, 0.12 mmol) and HATU (73 mg, 0.19 mmol) in DMF (2 mL) was added DIPEA (0.083 mL, 0.48 mmol) at 0° C. The reaction was stirred at room temperature overnight. The mixture was diluted with EtOAc and washed with 10% aq. LiCl solution and brine. The organic layer was dried over anhydrous Na$_2$SO$_4$ and concentrated to give a crude product, which was purified by prep. HPLC to give 743 (15 mg, 20.9% yield) as a white solid. $^1$HNMR (400 MHz, DMSO-d$_6$) δ 10.94 (s, 1H), 9.03 (s, 2H), 8.42 (d, J=0.8 Hz, 1H), 8.24 (dd, J=1.0, 0.8 Hz, 1H), 7.87 (d, J=0.8 Hz, 2H), 7.63 (dd, J=0.8, 1.8 Hz, 1H), 7.29 (t, J=8.4 Hz, 1H), 5.78 (dd, J=17.6, 17.3 Hz, 2H), 5.50-5.71 (m, 1H), 5.02 (t, J=8.5 Hz, 1H), 4.32-4.23 (m, 1H), 4.14-3.93 (m, 1H), 2.68 (d, J=3.5 Hz, 3H), 2.65 (s, 3H), 2.62 (s, 1H), 2.36-2.14 (m, 1H). LC/MS (ESI) m/z: 596 (M+H)$^+$.

5-(3-Acetyl-1-(2-((2S,4R)-2-((6-bromo-1-oxidopyridin-2-yl)carbamoyl)-4-fluoropyrrolidin-1-yl)-2-oxoethyl)-1H-indazol-5-yl)-2-methylpyrimidine 1-oxide (744)

Scheme 377

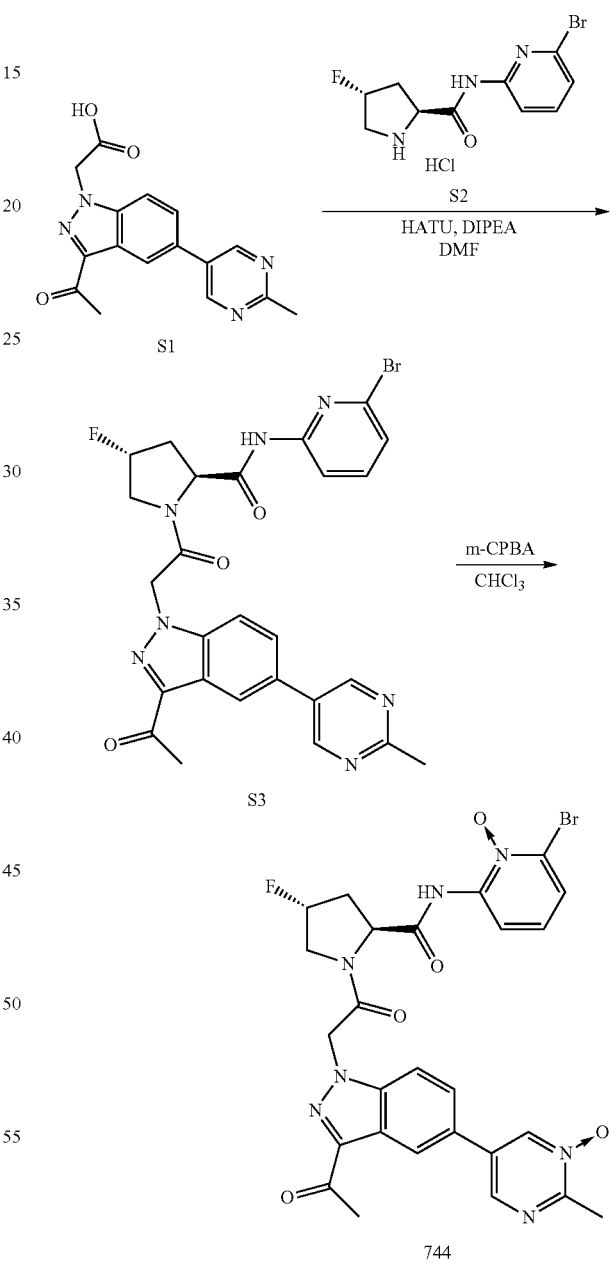

To a mixture of (4R)—N-(6-bromopyridin-2-yl)-4-fluoropyrrolidine-2-carboxamide (170 mg, 0.59 mmol) and 2-(3-acetyl-5-(2-methylpyrimidin-5-yl)-1H-indazol-1-yl) acetic acid (184 mg, 0.59 mmol) and DIPEA (382 mg, 2.96 mmol) in DMF (2 mL) was added HATU (495 mg, 1.30 mmol). The reaction was stirred at room temperature for 1.5 hrs. The mixture was diluted with EtOAc and washed with 10% aq. LiCl solution and brine. The organic layer was dried and concentrated to dryness. The residue was purified by column chromatography on silica gel eluted with DCM/MeOH (100:1 to 30:1) to give compound 3 (0.28 g, 81.6% yield) as a white solid. LC/MS (ESI) m/z: 580 (M+H)+.

Step 2: 5-(3-Acetyl-1-(2-((2S, 4R)-2-(6-bromo-1-oxidopyridin-2-ylcarbamoyl)-4-fluoropyrrolidin-1-yl)-2-oxoethyl)-1H-indazol-5-yl)-2-methylpyrimidine 1-oxide (744)

To a solution of (2S, 4R)-1-(2-(3-acetyl-5-(2-methylpyrimidin-5-yl)-1H-indazol-1-yl) acetyl)-N-(6-bromopyridin-2-yl)-4-fluoropyrrolidine-2-carboxamide (50 mg, 0.086 mmol) in CHCl₃ (3 mL) was added m-CPBA (45 mg, 0.26 mmol). The reaction was stirred at room temperature overnight. The mixture was diluted with DCM and washed with 5% aq. NaHCO₃ solution and brine. The organic layer was dried over anhydrous Na₂SO₄ and concentrated to dryness. The residue was purified by prep HPLC to give 744 (6.5 mg, 12.3% yield) as a white solid. ¹H NMR (400 MHz, DMSO-d₆) δ 10.93 (s, 1H), 8.98 (d, J=2.0 Hz, 1H), 8.56 (d, J=2.0 Hz, 1H), 8.48-8.36 (m, 1H), 8.24 (dd, J=8.4, 1.6 Hz, 1H), 7.87 (d, J=1.2 Hz, 2H), 7.62 (dd, J=8.4, 2.0 Hz, 1H), 7.28 (t, J=8.4 Hz, 1H), 5.93-5.45 (m, 3H), 5.02 (t, J=8.4 Hz, 1H), 4.26 (dd, J=22.0, 10.8 Hz, 1H), 4.02 (dd, J=36.8, 9.6 Hz, 1H), 2.68-2.55 (m, 7H), 2.29-2.14 (m, 1H). LC/MS (ESI) m/z: 612 (M+H)+.

tert-Butyl 2-(3-Acetyl-7-methyl-5-(2-methylpyrimidin-5-yl)-1H-indazol-1-yl)acetate Scheme 378

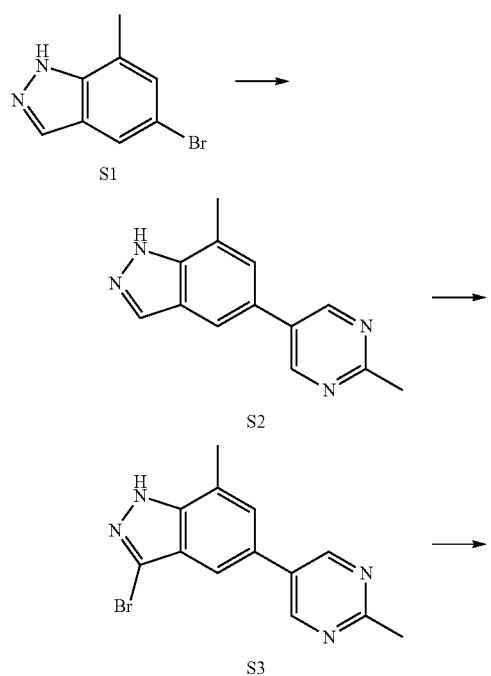

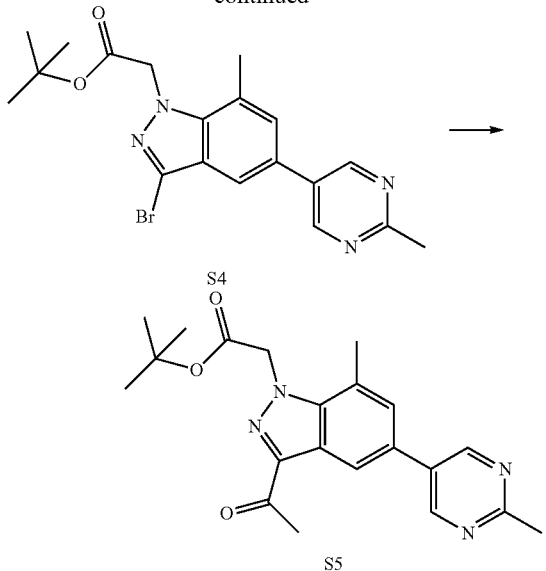

7-Methyl-5-(2-methylpyrimidin-5-yl)-1H-indazole (S2)

A mixture of 0.5 g of bromoindazole (1 equiv), 2-methyl-5-(4,4,5,5-tetramethyl-1,3,2-dioxaborolan-2-yl)pyrimidine (0.782 g, 1.5 equiv), cesium carbonate (2.315 g, 3 equiv) in dioxane (10 mL) and water (1.o mL) was purged with argon in a pressure vessel for 5 min. Tetrakis(triphenylphosphine) palladium (0) (0.550 g, 0.2 equiv) was then added under argon and the pressure vessel was sealed and heated at 90° C. overnight. The reaction mixture was cooled to room temperature and the solvent was removed under reduced pressure. The crude product was purified by ISCO (eluent: 0-3% MeOH in CH₂Cl₂) to get 0.395 g of the product as white solid.

3-Bromo-7-methyl-5-(2-methylpyrimidin-5-yl)-1H-indazole (S3)

To a stirred solution of indazole (1.75 g) in DMF (20 mL) NBS (1.05 g) was added. The reaction mixture was stirred at room temperature for 2 h. Then 0.209 g of additional NBS was added and the reaction mixture was stirred for 30 min at RT. The reaction mixture was then poured into water and the precipitate was isolated by filtration, dried and purified by ISCO (eluent: 0-5% MeOH in CH₂Cl₂) to get the desired product as white solid.

tert-Butyl 2-(3-bromo-7-methyl-5-(2-methylpyrimidin-5-yl)-1H-indazol-1-yl)acetate (S4)

A mixture of 0.215 g of 3-bromo-7-methyl-5-(2-methylpyrimidin-5-yl)-1H-indazole, 115 μL of tert-butyl bromoacetate and 0.196 g of potassium carbonate in anhydrous acetonitrile (10 mL) was refluxed for 4 h. The reaction mixture was then cooled to room temperature and the solvent was removed under reduced pressure. The residue was purified by ISCO (eluent: 0-1% MeOH in CH₂Cl₂) to get the product as white foam.

tert-Butyl 2-(3-acetyl-7-methyl-5-(2-methylpyrimidin-5-yl)-1H-indazol-1-yl)acetate (S5)

A solution of tert-butyl 2-(3-bromo-7-methyl-5-(2-methylpyrimidin-5-yl)-1H-indazol-1-yl)acetate (0.170 g 1 equiv), tri-butyl(1-ethoxyvinyl)tin 0.249 g, 2 equiv) and PdCl$_2$(PPh$_3$)$_2$ (28 mg, 0.1 equiv) in DMF (3 mL) was heated at 80° C. overnight under argon atmosphere. Then concentrated under reduced pressure and diluted with CH$_2$Cl$_2$ and washed with cold aq. HCl (2N). The organic layer was dried (Na$_2$SO$_4$), filtered and concentrated. The residue was purified by ISCO (eluent: 0-1% MeOH in CH$_2$Cl$_2$) to get a yellow solid.

(2S,4R)-1-(2-(3-Acetyl-7-methyl-5-(2-methylpyrimidin-5-yl)-1H-indazol-1-yl)acetyl)-N-(6-bromopyridin-2-yl)-4-fluoropyrrolidine-2-carboxamide (608)

(2S,4R)-tert-Butyl 2-((6-bromopyridin-2-yl)carbamoyl)-4-fluoropyrrolidine-1-carboxylate To an ice cold solution of trans-fluoroproline (0.23 g) in 5 mL of CH$_2$Cl$_2$, Ghosez's reagent (0.146 mL) was added drop-wise with stirring. The stirring was continued for 3 h. at same temperature. Then aminobromopyridine (0.191 g) was added, followed by 0.522 mL of Hünig's base (3 equiv.). The cooling bath was removed and the reaction mixture was stirred overnight at RT. The solvent was co-evaporated with 2 mL of MeOH. The crude product was purified by ISCO (0-0.1% MeOH in CH$_2$Cl$_2$) to get 0.2 g of the product as white solid.

Scheme 379

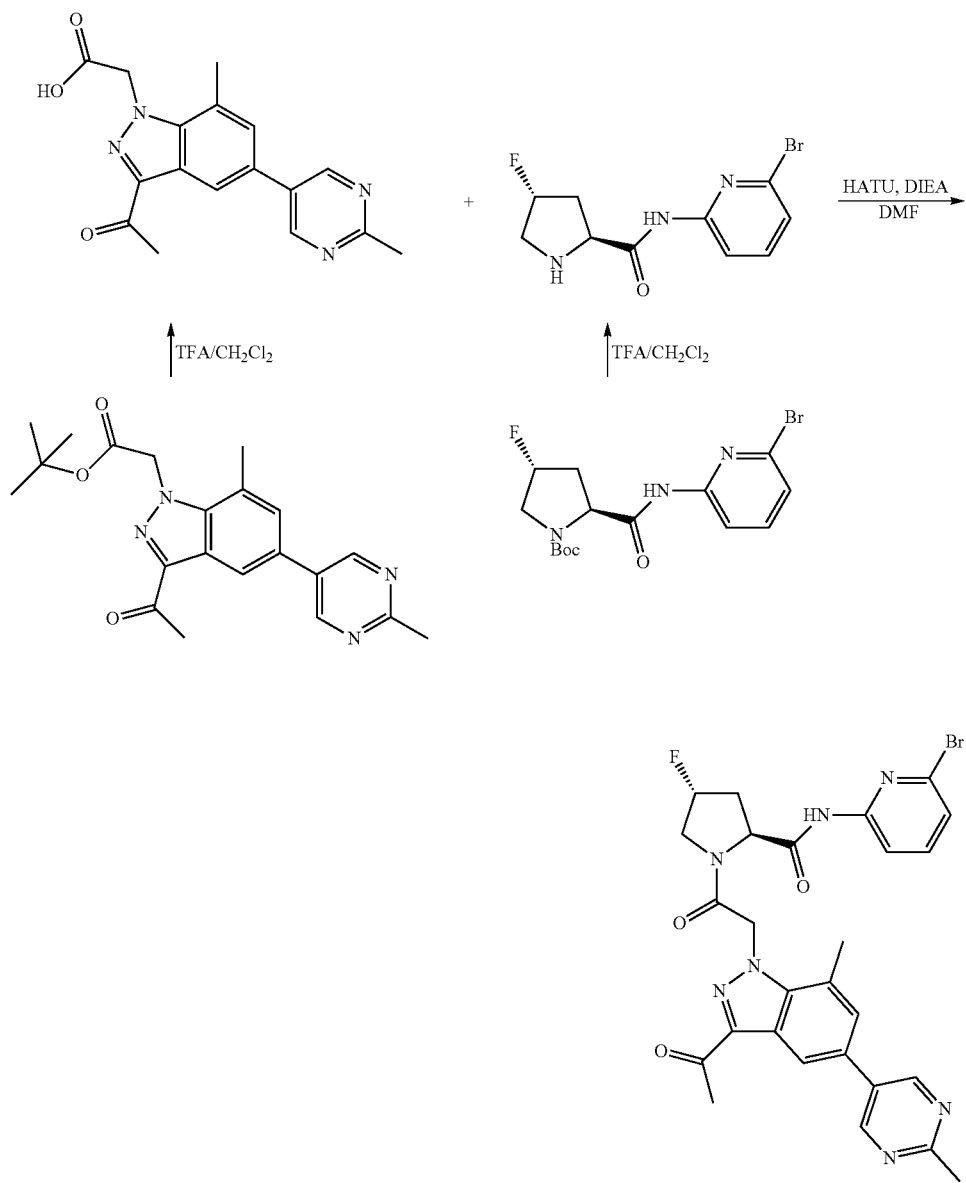

608

807

(2S,4R)—N-(6-Bromopyridin-2-yl)-4-fluoropyrroli-dine-2-carboxamide TFA salt

0.146 g of fluoropyridine was stirred in CH$_2$Cl$_2$ (1.0 mL) and TFA (1.0 mL) for 30 min. Then the volatiles are removed under reduced pressure. The residue was used as such for the next step.

(2S,4R)-1-(2-(3-Acetyl-7-methyl-5-(2-methylpy-rimidin-5-yl)-1H-indazol-1-yl)acetyl)-N-(6-bro-mopyridin-2-yl)-4-fluoropyrrolidine-2-carboxamide (608)

tert-Butyl 2-(3-acetyl-7-methyl-5-(2-methylpyrimidin-5-yl)-1H-indazol-1-yl)acetate (0.13 g) was stirred in CH$_2$Cl$_2$ (1 mL) and TFA (2 mL). After completion of the reaction (monitored by HPLC), the solvent was removed under reduced pressure. The remaining residue was dissolved in DMF (1 mL) and iPr$_2$NEt (0.297 mL, 5 equiv) was added, which was followed by the addition of the TFA salt from above reaction at 5° C. HATU (0.156 g, 1.2 equiv) was then added slowly at this same temperature and the reaction mixture was stirred for 30 min at RT. Then the reaction mixture was poured into water and the precipitate was isolated by filtration. The solid was dried and purified by ISCO (eluent: 0-2.5% MeOH in CH$_2$Cl$_2$) to get the desired product as cream colored solid. $^1$H-NMR (DMSO-d$_6$) (major rotamer): δ 2.07-2.24 (m, 1H), 2.54-2.59 (m, 1H), 2.64 (s, 3H), 2.67 (s, 3H), 2.69 (s, 3H), 3.91-4.03 (m, 1H), 4.27 (dd, J=21.6, 12.8 Hz, 1H), 4.70 (t, J=8.8 Hz, 1H), 5.54 (d, J=52 Hz, 1H), 5.76 (d, J=17.6 Hz, 1H), 5.92 (d, J=17.6 Hz, 1H), 7.32 (d, J=7.6 Hz, 1H), 7.59 (s, 1H), 7.71 (t, J=8 Hz, 1H), 8.01 (d, J=8 Hz, 1H), 8.29 (s, 2H), 11.02 (s, 1H). $^{19}$F-NMR (DMSO-d$_6$) (major rotamer): δ -176.2.

(2S,4R)-1-(2-(3-Acetyl-6-methyl-5-(2-methylpy-rimidin-5-yl)-1H-indazol-1-yl)acetyl)-N-(6-bro-mopyridin-2-yl)-4-fluoropyrrolidine-2-carboxamide (609)

Scheme 380

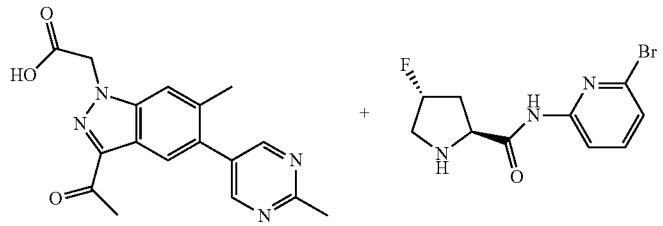

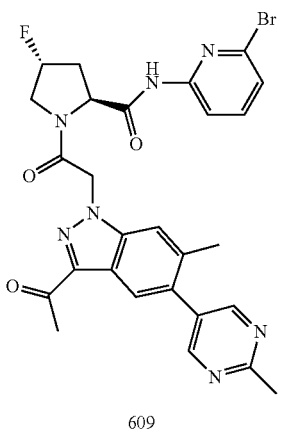

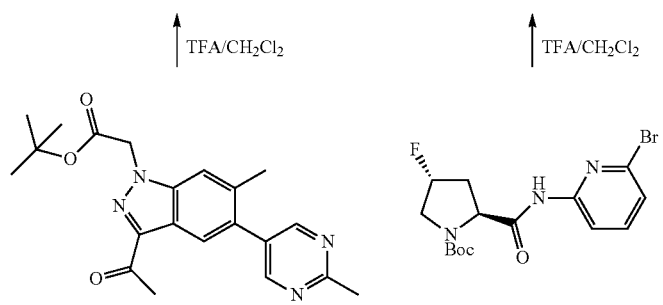

Compound 609 was prepared following the same procedure as for the synthesis of (2S,4R)-1-(2-(3-acetyl-7-methyl-5-(2-methylpyrimidin-5-yl)-1H-indazol-1-yl)acetyl)-N-(6-bromopyridin-2-yl)-4-fluoropyrrolidine-2-carboxamide was followed except that the starting material used was 5-bromo-6-methyl-1H-indazole. $^1$H-NMR (DMSO-d$_6$) (major rotamer): δ 2.08-2.25 (m, 1H), 2.33 (s, 3H), 2.54-2.58 (m, 1H), 2.61 (s, 3H), 2.69 (s, 3H), 3.97-4.09 (m, 1H), 4.22 (dd, J=22, 11.6 Hz, 1H), 4.68 (t, J=8.8 Hz, 1H), 5.55 (d, J=52.4 Hz, 1H), 5.58 (d, J=17.2 Hz, 1H), 5.78 (d, J=17.2 Hz, 1H), 7.32 (d, J=7.6 Hz, 1H), 7.66 (s, 1H), 7.71 (t, J=8 Hz, 1H), 7.97 (s, 1H), 8.03 (d, J=8 Hz, 1H), 8.74 (s, 2H), 11.00 (s, 1H). $^{19}$F-NMR (DMSO-d$_6$) (major rotamer): δ-175.6.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (636)

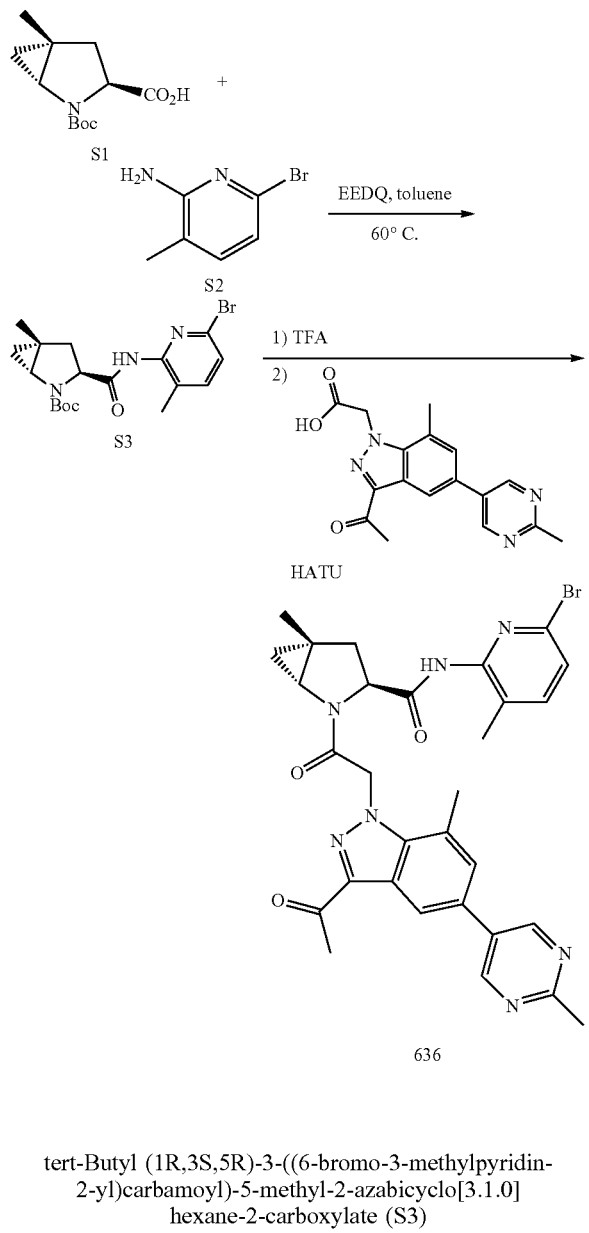

tert-Butyl (1R,3S,5R)-3-((6-bromo-3-methylpyridin-2-yl)carbamoyl)-5-methyl-2-azabicyclo[3.1.0]hexane-2-carboxylate (S3)

A mixture of (1R,3S,5R)-2-(tert-butoxycarbonyl)-5-methyl-2-azabicyclo[3.1.0]hexane-3-carboxylic acid (2 g), 6-bromo-3-methylpyridin-2-amine (1.707 g) and EEDQ (2.052 g) in toluene (50 mL) was heated at 60° C. for 8 h. An additional 0.410 g of EEDQ was added and the reaction mixture was stirred overnight at 60° C. Then 0.205 g of EEDQ was added and stirring was continued at 60° C. for 1 more hour. Finally, solvent was removed under reduced pressure and the residue was dissolved in CH₂Cl₂. This organic layer was washed with cold 1N aq. HCl, water and sat. aq. NaHCO₃ solution. The dichloromethane layer was dried (Na₂SO₄), filtered and concentrated. The residue was purified by ISCO (eluent: 0-2.5% MeOH in CH₂Cl₂) to get the desired product.

(1R,3S,5R)-2-(2-(3-Acetyl-7-methyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide (636)

tert-Butyl (1R,3S,5R)-3-((6-bromo-3-methylpyridin-2-yl)carbamoyl)-5-methyl-2-azabicyclo[3.1.0]hexane-2-carboxylate (89 mg) was dissolved in CH₂Cl₂ (1 mL) and equal volume of TFA was added. The mixture was stirred for 30 min at rt. Then the volatiles are removed under reduced pressure. The residue was dissolved in DMF (1.0 mL) and $^i$Pr₂NEt (172 μL) was added, followed by the sequential addition of 2-(3-acetyl-7-methyl-5-(2-methylpyrimidin-5-yl)-1H-indazol-1-yl)acetic acid [obtained by stirring 75 mg of tert-butyl 2-(3-acetyl-7-methyl-5-(2-methylpyrimidin-5-yl)-1H-indazol-1-yl)acetate with 1 mL of CH₂Cl₂ and 1.5 mL of TFA for 2 h at room temperature and evaporation of the volatiles] and HATU (90 mg) slowly at 5° C. The reaction mixture was then stirred for 30 min at RT, poured into water (10 mL) and the solid was isolated by filtration, washed with water and dried in vacuo. The solid was then purified by ISCO (eluent: 0-2.5% MeOH in CH₂Cl₂) to get a white solid. ¹H NMR (400 MHz, DMSO) (major rotamer) δ 0.83-0.97 (m, 1H), 1.02 (t, J=5.4 Hz, 1H), 1.32 (s, 3H), 2.02-2.04 (m, 1H)), 2.04 (s, 3H), 2.58 (dd, J=4.8, 14.0 Hz, 1H), 2.63 (s, 3H), 2.66 (s, 6H), 3.59 (dd, J=2.3, 5.6 Hz, 1H), 4.41 (dd, J=5.4, 9.3 Hz, 1H), 5.68 (d, J=17.8 Hz, 1H), 6.03 (d, J=17.8 Hz, 1H), 7.43 (d, J=7.9 Hz, 1H), 7.62 (d, J=7.8 Hz, 2H), 8.32 (d, J=1.6 Hz, 1H), 9.02 (s, 2H), 10.29 (s, 1H).

(1R,2S,5S)-3-(2-(3-Acetyl-7-methyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide (652)

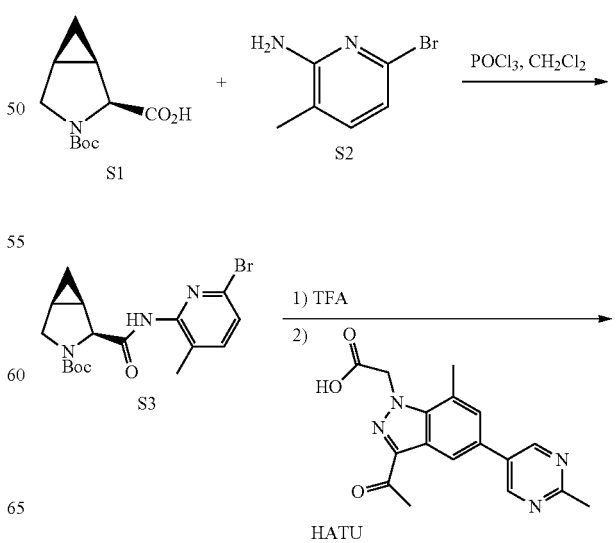

-continued

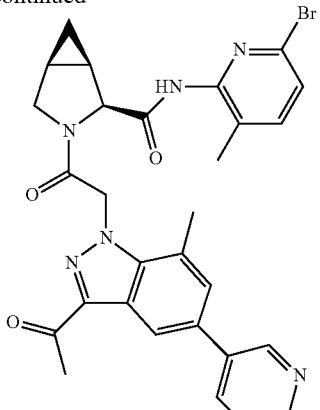

652 tert-Butyl (1R,2S,5S)-2-((6-bromo-3-methylpyridin-2-yl)carbamoyl)-3-azabicyclo[3.1.0]hexane-3-carboxylate (S3)

To an ice cooled solution of (1R,2S,5S)-3-(tert-butoxycarbonyl)-3-azabicyclo[3.1.0]hexane-2-carboxylic acid (5.0 g) and 6-bromo-3-methylpyridin-2-amine (4.12 g) in $CH_2Cl_2$ (100 ml) pyridine (8.9 mL) was added followed by the slow dropwise addition of $POCl_3$ (1 equiv. of carboxylic acid) at 5° C. The reaction mixture was stirred for 4 hr at 5° C. Saturated aqeuous $NaHCO_3$ solution was added and stirred for 1 h at room temperature. The organic layer was then extracted with DCM, washed with water and brine, dried with ($Na_2SO_4$), filtered and concentrated. The residue was purified by ISCO to afford tert-butyl (1R,2S,5S)-2-((6-bromo-3-methylpyridin-2-yl)carbamoyl)-3-azabicyclo[3.1.0]hexane-3-carboxylate.

(1R,2S,5S)-3-(2-(3-Acetyl-7-methyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide (652)

tert-Butyl (1R,2S,5S)-2-((6-bromo-3-methylpyridin-2-yl)carbamoyl)-3-azabicyclo[3.1.0]hexane-3-carboxylate (86 mg) was dissolved in $CH_2Cl_2$ (1 mL) and an equal volume of TFA was added. The mixture was stirred for 30 min at room temperature. Then the volatiles were removed under reduced pressure. The residue was dissolved in DMF (1.0 mL) and $^iPr_2NEt$ (172 μL) was added, followed by the sequential addition of 2-(3-acetyl-7-methyl-5-(2-methylpyrimidin-5-yl)-1H-indazol-1-yl)acetic acid [obtained by stirring 75 mg of tert-butyl 2-(3-acetyl-7-methyl-5-(2-methylpyrimidin-5-yl)-1H-indazol-1-yl)acetate with 1 mL of $CH_2Cl_2$ and 1.5 mL of TFA for 2 h at room temperature and evaporation of the volatiles] and HATU (90 mg) slowly at 5° C. The reaction mixture was then stirred for 30 min at RT, poured into water (10 mL) and the solid was isolated by filtration, washed with water and dried in vacuo. The solid was then purified by ISCO (eluent: 0-3% MeOH in $CH_2Cl_2$) to get a white solid. $^1H$ NMR (400 MHz, DMSO) (major rotamer) δ 0.73-0.85 (m, 2H), 2.03 (s, 3H), 2.03-2.09 (m, 1H), 2.63 (s, 3H), 2.67 (s, 3H), 2.68 (s, 3H), 3.87 (d, J=9.8 Hz, 1H), 4.02 (dd, J=5.1, 9.9 Hz, 1H), 4.63 (d, J=5.4 Hz, 1H), 5.65 (d, J=17.8 Hz, 1H), 5.75 (d, J=17.9 Hz, 1H), 7.41 (d, J=7.9 Hz, 1H), 7.49-7.65 (m, 2H), 8.30 (d, J=1.5 Hz, 1H), 9.01 (s, 2H), 10.39 (s, 1H).

(2S,4R)-1-(2-(3-Acetyl-5-(2-methylpyrimidin-5-yl)-1H-indazol-1-yl)acetyl)-4-fluoro-N-(3-methyl-6-(2,2,2-trifluoroethoxy)pyridin-2-yl)pyrrolidine-2-carboxamide (601)

Scheme 383

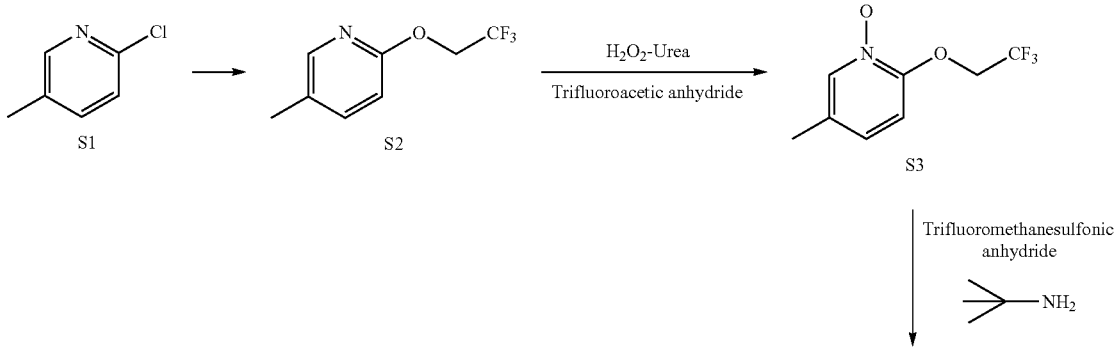

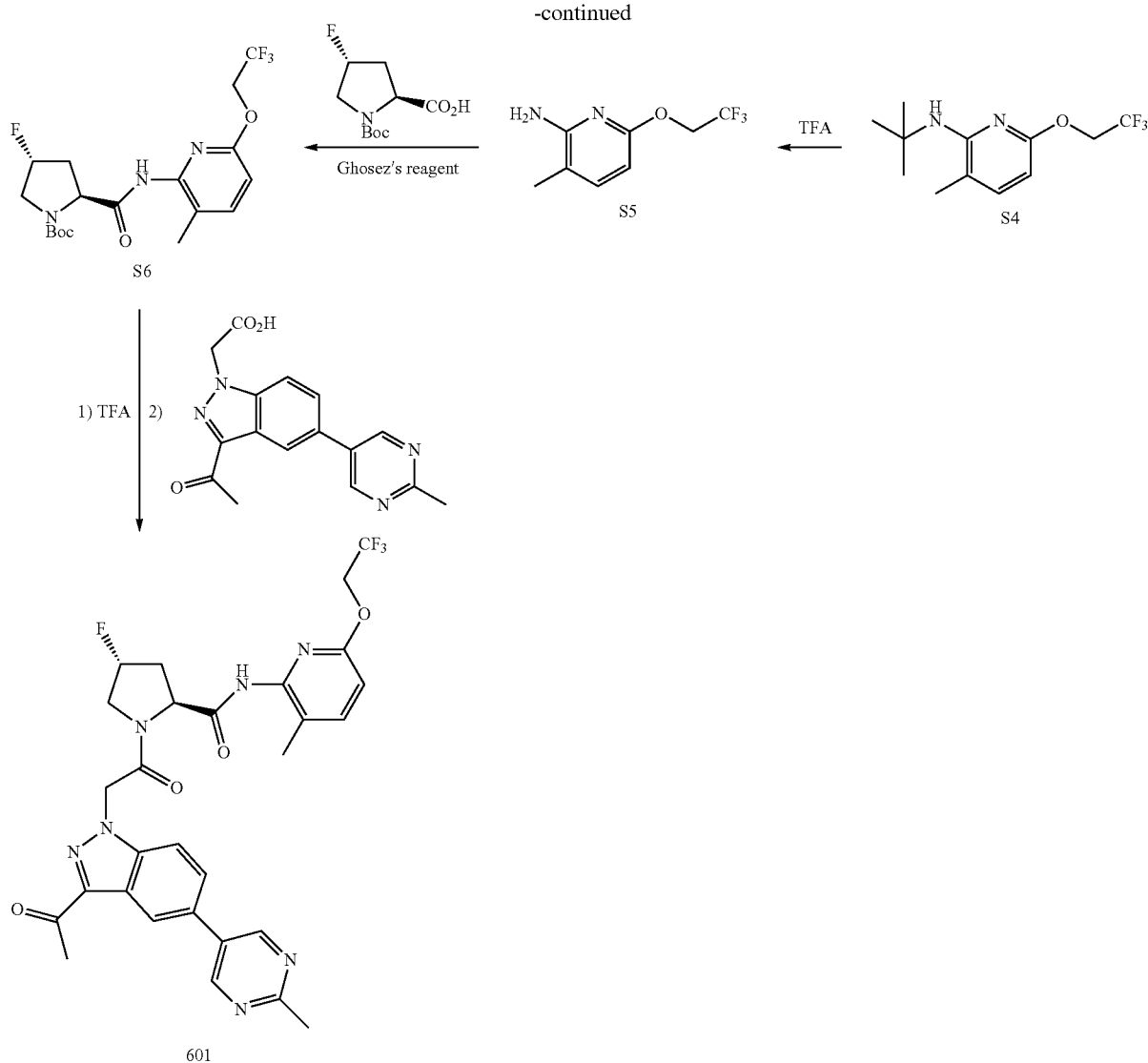

5-Methyl-2-(2,2,2-trifluoroethoxy)pyridine (S2)

Compound S2 was prepared according to the procedure from Yamaguchi, T. et al. PCT Int. Appl. 2012053186.

5-Methyl-1-($\lambda^1$-oxidanyl)-2-(2,2,2-trifluoroethoxy)-1$\lambda^4$-pyridine (S3)

To an ice cold a solution of 5-methyl-2-(2,2,2-trifluoroethoxy)pyridine (2.9 g) in CH$_2$Cl$_2$ (60 mL), solid hydrogen peroxide urea complex (2.2 g) was added. Then trifluoroacetic anhydride (5.3 mL) was added dropwise. After the addition was complete, the cooling bath was removed and the reaction mixture was stirred overnight at room temperature. The reaction mixture was diluted with CH$_2$Cl$_2$. The organic layer was washed with water, saturated aqeuous sodium metabisulfite solution and dried (Na$_2$SO$_4$). The organic layer was filtered and concentrated to afford 2.1 g of solid. The title compound was carried forward without further purification.

N-(tert-Butyl)-3-methyl-6-(2,2,2-trifluoroethoxy)pyridin-2-amine (S4)

To a solution of 5-methyl-1-($\lambda^1$-oxidanyl)-2-(2,2,2-trifluoroethoxy)-1$\lambda^4$-pyridine (2.1 g) at −20° C. in CH$_2$Cl$_2$ (50 mL), tert-butylamine (5.33 mL) was added followed by the dropwise addition of trifluoromethanesulfonic anhydride (5.7 mL). After being stirred for 1 h at −20° C., the reaction mixture was quenched with water. The layers were separated and the organic layer was washed with sat. K$_2$CO$_3$ solution. The organic layer was dried and concentrated and the residue was purified by ISCO (eluent: 0-0.5% EtOAc in hexanes) to get 0.46 g of colorless liquid.

3-Methyl-6-(2,2,2-trifluoroethoxy)pyridin-2-amine TFA Salt (S5)

A solution of N-(tert-butyl)-3-methyl-6-(2,2,2-trifluoroethoxy)pyridin-2-amine (0.456 g) in TFA (4.5 mL) was stirred at room temperature for 4 h. Then 0.5 mL of TFA was added and the mixture was stirred for 30 min. The volatiles were removed under reduced pressure and the residue was triturated with a 1:1 mixture of ether and heptane to afford 0.3 g of white solid.

tert-Butyl (2S,4R)-4-fluoro-2-((3-methyl-6-(2,2,2-trifluoroethoxy)pyridin-2-yl)carbamoyl)pyrrolidine-1-carboxylate (S6)

To an ice cold solution of trans-fluoroproline (0.208 g) in 5 mL of $CH_2Cl_2$, Ghosez's reagent (0.128 mL) was added dropwise with stirring. The stirring was continued for 3 hours at same temperature. Then 3-methyl-6-(2,2,2-trifluoroethoxy)pyridin-2-amine TFA salt (0.26 g) was added followed by 0.560 mL of Hünig's base (3 equiv.). The cooling bath was removed and the reaction mixture was stirred overnight at room temperature. The solvent was co-evaporated with 2 mL of MeOH and the crude product was purified by ISCO (0-0.1% MeOH in $CH_2Cl_2$) to afford 0.36 g of the product as light yellow solid.

(2S,4R)-1-(2-(3-Acetyl-5-(2-methylpyrimidin-5-yl)-1H-indazol-1-yl)acetyl)-4-fluoro-N-(3-methyl-6-(2,2,2-trifluoroethoxy)pyridin-2-yl)pyrrolidine-2-carboxamide (601)

tert-Butyl (2S,4R)-4-fluoro-2-((3-methyl-6-(2,2,2-trifluoroethoxy)pyridin-2-yl)carbamoyl)pyrrolidine-1-carboxylate (0.2 g) was dissolved in $CH_2Cl_2$ (2 mL) and an equal volume of TFA was added. The mixture was stirred for 30 min at rt. Then the volatiles were removed under reduced pressure. The residue was dissolved in DMF (1 mL) and $^iPr_2NEt$ (414 µL) was added, followed by the sequential addition of 2-(3-acetyl-5-(2-methylpyrimidin-5-yl)-1H-indazol-1-yl)acetic acid (0.147 g) and HATU (0.116 g, 1.2 equiv) slowly at 5° C. The reaction mixture was then stirred for 30 min at room temperature and poured into water (10 mL). The resulting solid was isolated by filtration, washed with water, and dried in vacuo. The solid was then purified by ISCO (eluent: 0-2.5% MeOH in $CH_2Cl_2$) to afford a white solid.
$^1$H-NMR (DMSO-$d_6$) (major rotamer): δ 1.99 (s, 3H), 2.11-2.28 (m, 1H), 2.57-2.64 (m, 1H), 2.64 (s, 3H), 2.69 (s, 3H), 3.95-4.07 (m, 1H), 4.25 (dd, J=22, 12.4 Hz, 1H), 4.67 (t, J=8.4 Hz, 1H), 4.82-4.92 (m, 2H), 5.56 (d, J=53.2 Hz, 1H), 5.62 (d, J=17.2 Hz, 1H), 5.84 (d, J=17.2 Hz, 1H), 6.77 (d, J=8.4 Hz, 1H), 7.64 (d, J=8.4 Hz, 1H), 7.81-7.86 (m, 2H), 8.43 (s, 1H), 9.04 (s, 2H), 11.12 (s, 1H). $^{19}$F-NMR (DMSO-$d_6$) (major rotamer): δ −176.1, −72.5.

(2S,4R)-1-(2-(3-Acetyl-5-(2-methylpyrimidin-5-yl)-1H-indazol-1-yl)acetyl)-N-(6-(1,1-difluoroethyl)-3-methylpyridin-2-yl)-4-fluoropyrrolidine-2-carboxamide (602)

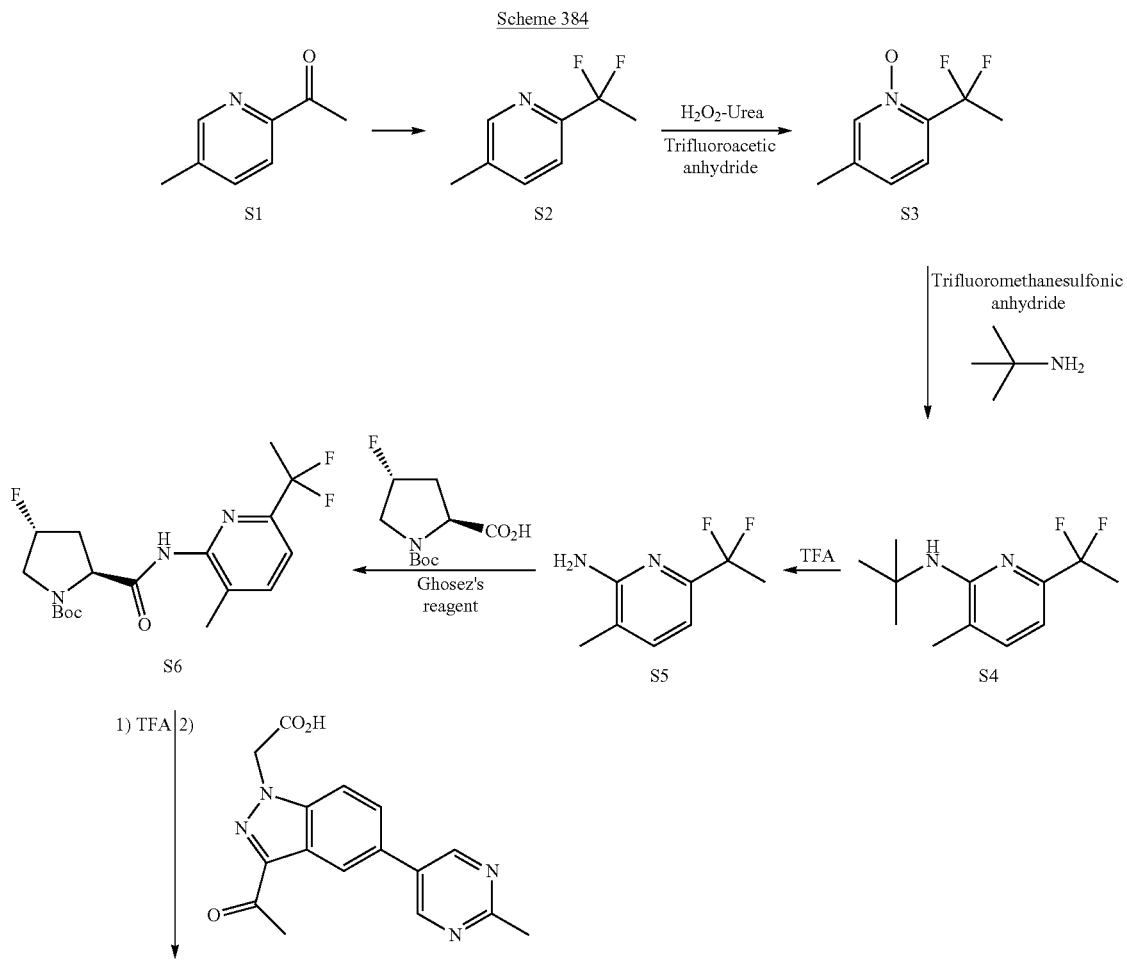

Scheme 384

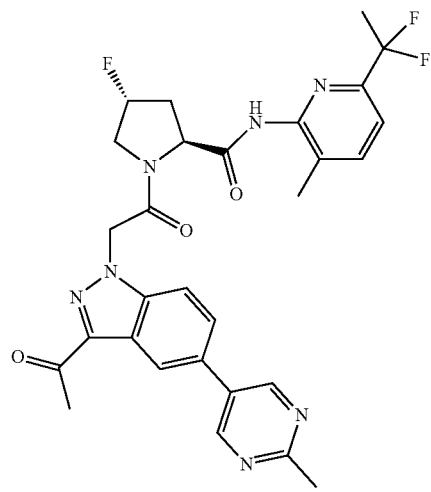

602

2-(1,1-Difluoroethyl)-5-methylpyridine

Compound S2 was prepared following the procedure from Los, M. R. et al U. S., 8288422, 16 Oct. 2012.

2-(1,1-difluoroethyl)-5-methyl-1((λ¹-oxidanyl)-1λ⁴-pyridine (S3)

Compound S3 was prepared following the same procedure as for the synthesis of 5-methyl-1-(λ¹-oxidanyl)-2-(2,2,2-trifluoroethoxy)-1λ⁴-pyridine (Scheme 383 compound S3) to afford light brownish oil.

N-(tert-Butyl)-6-(1,1-difluoroethyl)-3-methylpyridin-2-amine (S4)

Compound S4 was prepared following the procedure for N-(tert-Butyl)-3-methyl-6-(2,2,2-trifluoroethoxy)pyridin-2-amine (Scheme 383 compound S4). Crude product was purified by ISCO (eluent: hexanes) to afford the product as a colorless oil.

6-(1,1-Difluoroethyl)-3-methylpyridin-2-amine TFA Salt (S5)

Compound S5 was deprotected following the procedure for the deprotection of 3-methyl-6-(2,2,2-trifluoroethoxy)pyridin-2-amine TFA salt (Scheme 383 compound S5)

tert-Butyl (2S,4R)-2-((6-(1,1-difluoroethyl)-3-methylpyridin-2-yl)carbamoyl)-4-fluoropyrrolidine-1-carboxylate (S6)

The title compound was prepared according to the procedure described for the synthesis of tert-butyl (2S,4R)-4-fluoro-2-((3-methyl-6-(2,2,2-trifluoroethoxy)pyridin-2-yl)carbamoyl)pyrrolidine-1-carboxylate (Scheme 383 compound S6). The crude product was purified by ISCO (eluent: $CH_2Cl_2$) to afford the title compound as white foam.

(2S,4R)-1-(2-(3-Acetyl-5-(2-methylpyrimidin-5-yl)-1H-indazol-1-yl)acetyl)-N-(6-(1,1-difluoroethyl)-3-methylpyridin-2-yl)-4-fluoropyrrolidine-2-carboxamide (602)

The title compound was prepared according to the procedure described for the synthesis of (2S,4R)-1-(2-(3-acetyl-5-(2-methylpyrimidin-5-yl)-1H-indazol-1-yl)acetyl)-4-fluoro-N-(3-methyl-6-(2,2,2-trifluoroethoxy)pyridin-2-yl)pyrrolidine-2-carboxamide (601). Crude product was purified by ISCO (eluent: 0-2% MeOH in $CH_2Cl_2$) to get the desired product as cream colored solid. $^1$H-NMR (DMSO-$d_6$) (major rotamer): δ 1.91 (t, J=18.8 Hz, 3H), 2.09 (s, 3H), 2.13-2.31 (m, 1H), 2.60-2.69 (m, 1H), 2.64 (s, 3H), 2.69 (s, 3H), 4.02 (dd, J=37.6, 10.8 Hz, 1H), 4.25 (dd, J=22, 12.8 Hz, 1H), 4.68 (t, J=8 Hz, 1H), 5.57 (d, J=56.4 Hz, 1H), 5.62 (d, J=17.2 Hz, 1H), 5.84 (d, J=17.2 Hz, 1H), 7.47 (d, J=8 Hz, 1H), 7.79-7.85 (m, 3H), 8.43 (s, 1H), 9.03 (s, 2H), 10.42 (brs, 1H). $^{19}$F-NMR (DMSO-$d_6$) (major rotamer): δ −176.1, −88.3.

(1R,3S,5R)-2-(2-(3-Acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (541) and (1R,3S,5R)-2-(2-(3-Acetyl-5-(2-methylpyrimidin-5-yl)-1H-indazol-1-yl)acetyl)-N—((Z)-2-fluoro-3-phenylbut-2-en-1-yl)-2-azabicyclo[3.1.0]hexane-3-carboxamide (557)
Scheme 385
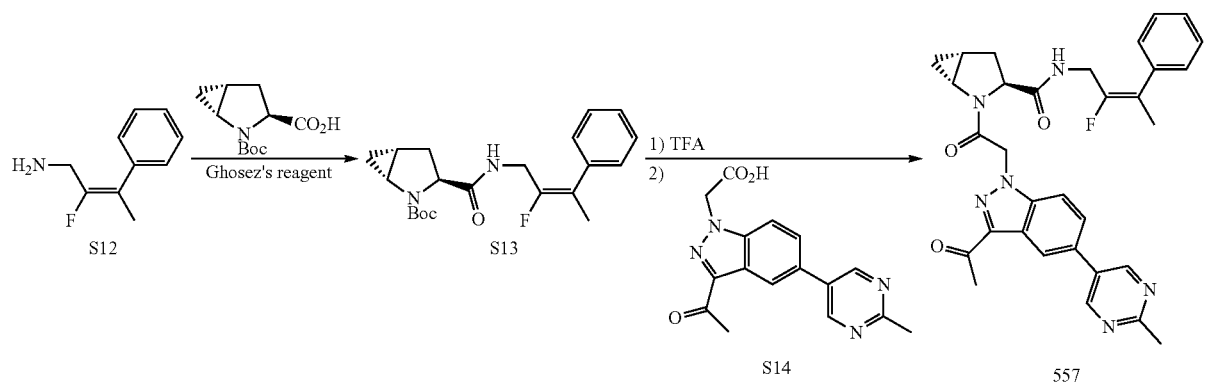
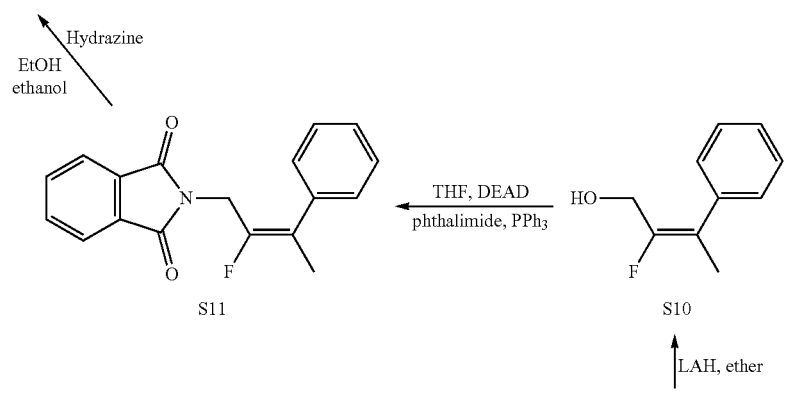
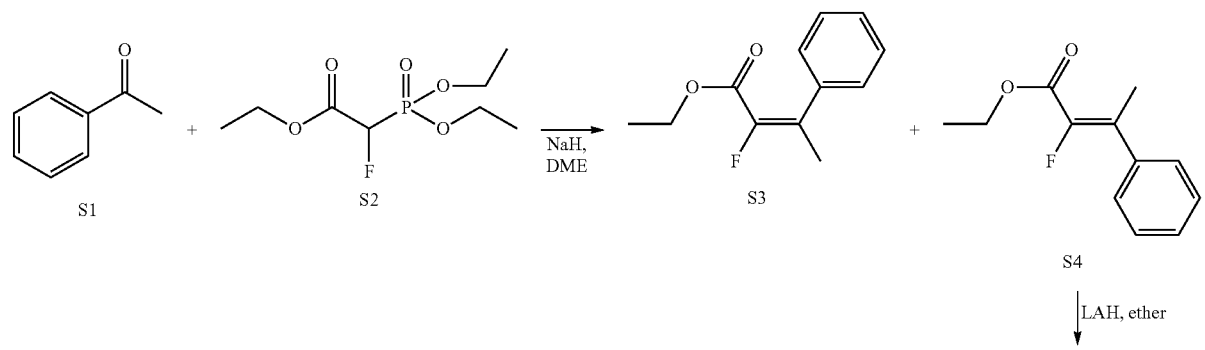

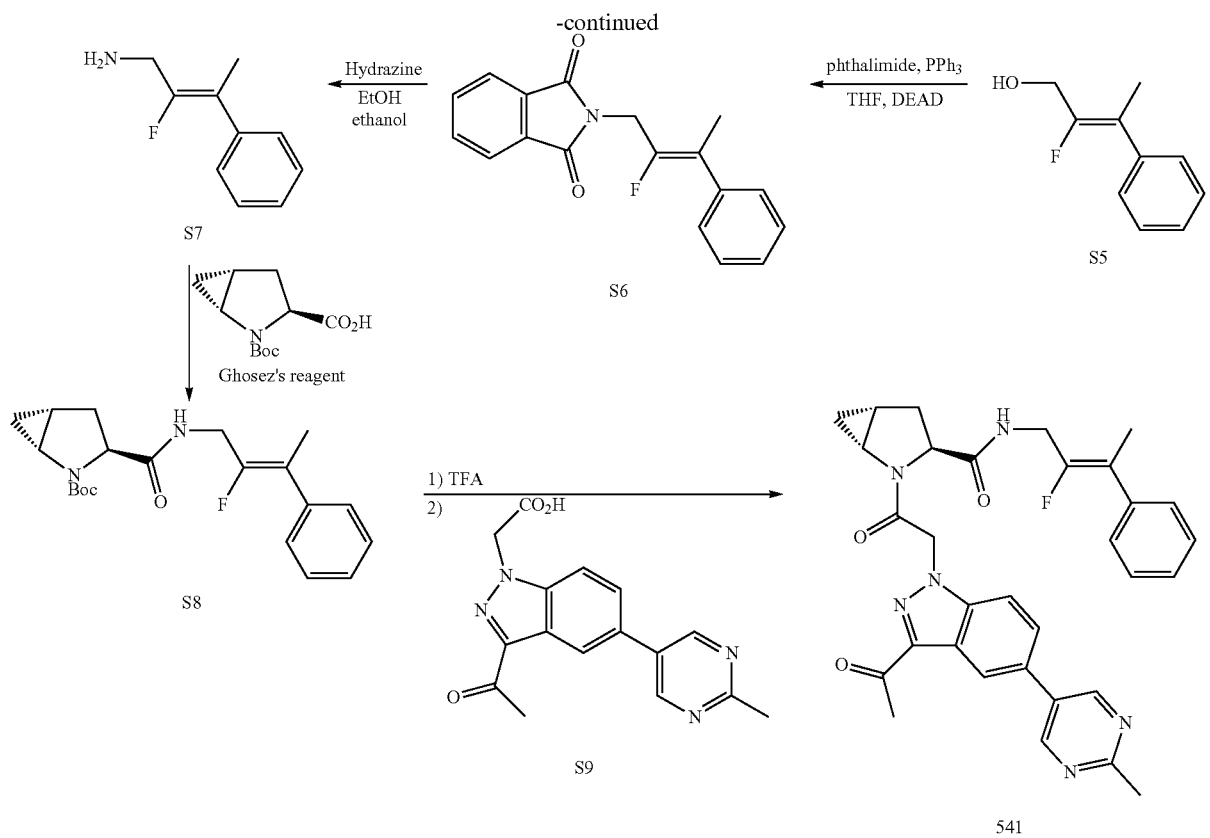

Ethyl (E)-2-fluoro-3-phenylbut-2-enoate and ethyl (Z)-2-fluoro-3-phenylbut-2-enoate (S3) and ethyl (Z)-2-fluoro-3-phenylbut-2-enoate (S4)

To a stirred solution of NaH (0.9 g, 60% in mineral oil) in DME (50 mL) at 0° C., ethyl 2-(diethoxyphosphoryl)-2-fluoroacetate (5 g) was added dropwise. Then the cooling bath was removed and the reaction mixture was stirred at room temperature for 1 h. Benzaldehyde (3.6 mL) was added at room temperature and the reaction mixture was stirred at 90° C. overnight. The reaction mixture was cooled to room temperature, diluted with ether, washed with water, dried ($Na_2SO_4$) and concentrated. The resultant residue was purified by ISCO (eluent: 0-0.5% EtOAc in hexanes. Ethyl (Z)-2-fluoro-3-phenylbut-2-enoate (S3) eluted first as a colorless liquid (0.37 g) and ethyl (E)-2-fluoro-3-phenylbut-2-enoate (S4) eluted later as light yellow liquid (1.3 g). (Ref. WO 2014/002052 and *J. Org. Chem.* 2009, 74, 4124-4131)

(E)-2-Fluoro-3-phenylbut-2-en-1-ol (S5)

To a stirred solution of LAH (0.221 g) in ether (20 mL) at room temperature, ethyl (E)-2-fluoro-3-phenylbut-2-enoate (1.3 g) (S4) in ether (10 mL) was added dropwise. The reaction mixture was stirred at room temperature for 1 hour and quenched by the careful addition of saturated aq. $NH_4Cl$ solution. This heterogeneous mixture was then extracted with ether. The organic layer was washed with water, brine and dried ($Na_2SO_4$). Upon concentration of the organic layer, the residue was carried forward without further purification.

(E)-2-(2-Fluoro-3-phenylbut-2-en-1-yl)isoindoline-1,3-dione (S6)

Phthalimide (1.06 g) and triphenylphosphine (2.4 g) in THF (20 mL) was added to a stirred solution of (E)-2-fluoro-3-phenylbut-2-en-1-ol (1 g) (S5). DEAD (1.52 mL) and the reaction was stirred for 16 hours at room temperature. The reaction mixture was concentrated under reduced pressure. The residue obtained was purified by ISCO (eluent: 0-2.5% EtOAc in hexanes) to afford 1.5 g of white solid.

(E)-2-Fluoro-3-phenylbut-2-en-1-amine hydrochloride (S7)

Hydrazine hydrate (0.74 mL) was added to heterogeneous solution of (E)-2-(2-fluoro-3-phenylbut-2-en-1-yl)isoindoline-1,3-dione (S6) (1.7 g) in EtOH (30 mL) and stirred at room temperature overnight. The precipitate was filtered off and the filtrate was concentrated. The residue was triturated with 4N HCl in dioxane (10 mL). Then the volatiles were removed under reduced pressure. The resulting white solid was dried under high vacuum to afford the title compound.

tert-Butyl (1R,3S,5R)-3-(((E)-2-fluoro-3-phenylbut-2-en-1-yl)carbamoyl)-2-azabicyclo[3.1.0]hexane-2-carboxylate (S8)

To an ice cold solution of (1R,3S,5R)-2-(tert-butoxycarbonyl)-2-azabicyclo[3.1.0]hexane-3-carboxylic acid (0.25 g) in 6 mL of $CH_2Cl_2$, 1-chloro-N,N,2-trimethyl-1-propenylamine (0.16 mL, 1.1 equiv.) was added dropwise with stirring. The stirring was continued for 3 hours at same temperature. Then solid (E)-2-fluoro-3-phenylbut-2-en-1- amine hydrochloride (0.2 g, 1.0 equiv.) (S7) was added followed by 0.7 mL of Hünig's base (4 equiv.). The cooling bath was removed and the reaction mixture was stirred overnight at room temperature. The solvent was co-evaporated with MeOH (1 mL) and the crude product was purified by ISCO (eluent: 0-0.5% MeOH in CH$_2$Cl$_2$) to afford 0.18 g of colorless resin.

(1R,3S,5R)-2-(2-(3-Acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (541)

tert-Butyl (1R,3S,5R)-3-(((E)-2-fluoro-3-phenylbut-2-en-1-yl)carbamoyl)-2-azabicyclo[3.1.0]hexane-2-carboxylate (0.1 g) (S9) was dissolved in CH$_2$Cl$_2$ (1 mL) and an equal volume of TFA was added. The mixture was stirred for 30 min at room temperature. Then the volatiles were removed under reduced pressure. The residue were dissolved in DMF (1 mL) and $^i$Pr$_2$NEt (232 µL) was added, followed by the sequential addition of 2-(3-acetyl-5-(2-methylpyrimidin-5-yl)-1H-indazol-1-yl)acetic acid (0.083 g) and HATU (0.122 g, 1.2 equiv) slowly at 5° C. The reaction mixture was then stirred for 30 min at room temperature, poured into water (10 mL) and the solid was isolated by filtration. The solid was washed with water, dried in vacuo, and purified by ISCO (eluent: 0-2% MeOH in CH$_2$Cl$_2$) to afford a white solid.

$^1$H-NMR (DMSO-d$_6$) (major rotamer): δ 0.78 (m, 1H), 0.996-1.04 (m, 1H), 1.83-1.87 (m, 1H), 1.94 (d, J=2.8 Hz, 3H), 2.07-2.13 (m, 1H), 2.21-2.26 (m, 1H), 2.65 (s, 3H), 2.69 (s, 3H), 3.73-3.75 (m, 1H), 3.80 (t, J=5.2 Hz, 1H), 3.85 (t, J=4.8 Hz, 1H), 4.24 (dd, J=8.8, 4.8 Hz, 1H), 5.58 (d, J=17.2 Hz, 1H), 5.91 (d, J=17.2 Hz, 1H), 7.24-7.38 (m, 5H), 7.85 (s, 2H), 8.16 (t, J=4.8 Hz, 1H), 8.44 (s, 1H), 9.04 (s, 2H). $^{19}$F-NMR (DMSO-d$_6$) (major rotamer): δ −113.3.

(Z)-2-Fluoro-3-phenylbut-2-en-1-ol (S10)

Compound S10 was prepared according to the procedure described for the synthesis of (E)-2-fluoro-3-phenylbut-2-en-1-ol (S5). The title compound was used in the next step without any purification.

(Z)-2-(2-Fluoro-3-phenylbut-2-en-1-yl)isoindoline-1,3-dione (S11)

(Z)-2-Fluoro-3-phenylbut-2-en-1-ol (S10) was converted to compound S11 as described for the synthesis of (E)-2-(2-Fluoro-3-phenylbut-2-en-1-yl)isoindoline-1,3-dione (S6). The crude product was purified by ISCO (eluent: 0-2.5% EtOAc in hexanes) to afford the product as white solid.

(Z)-2-Fluoro-3-phenylbut-2-en-1-amine hydrochloride (S12)

Compound S12 was prepared according to the procedure described for the synthesis of (E)-2-fluoro-3-phenylbut-2-en-1-amine hydrochloride (S7).

tert-Butyl (1R,3S,5R)-3-(((Z)-2-fluoro-3-phenylbut-2-en-1-yl)carbamoyl)-2-azabicyclo[3.1.0]hexane-2-carboxylate (S13)

Compound S13 was prepared according to the procedure described for the synthesis of tert-butyl (1R,3S,5R)-3-(((E)-2-fluoro-3-phenylbut-2-en-1-yl)carbamoyl)-2-azabicyclo[3.1.0]hexane-2-carboxylate (S8). The crude product was purified by ISCO (eluent: 0-0.5% MeOH in CH$_2$Cl$_2$) to get light yellow solid.

(1R,3S,5R)-2-(2-(3-Acetyl-5-(2-methylpyrimidin-5-yl)-1H-indazol-1-yl)acetyl)-N—((Z)-2-fluoro-3-phenylbut-2-en-1-yl)-2-azabicyclo[3.1.0]hexane-3-carboxamide (557)

The title compound was prepared according to the procedure described for the synthesis of (1R,3S,5R)-2-(2-(3-Acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (541). Compound 557 was purified by ISCO (eluent: 0-2.5% MeOH in CH$_2$Cl$_2$) to afford the title compound as white solid. $^1$H-NMR (DMSO-d$_6$) (major rotamer): δ 0.80-0.81 (m, 1H), 1.02-1.05 (m, 1H), 1.85-1.88 (m, 1H), 1.98 (d, J=2.8 Hz, 3H), 2.07-2.17 (m, 1H), 2.23-2.33 (m, 1H), 2.65 (s, 3H), 2.69 (s, 3H), 3.73-3.77 (m, 1H), 4.00-4.12 (m, 2H), 4.27 (dd, J=9.2, 4.8 Hz, 1H), 5.59 (d, J=17.2 Hz, 1H), 5.91 (d, J=17.2 Hz, 1H), 7.20-7.32 (m, 5H), 7.79 (dd, J=8.8, 1.6 Hz, 1H), 7.86 (d, J=8.8 Hz, 1H), 8.29 (t, J=5.6 Hz, 1H), 8.44 (s, 1H), 9.02 (s, 2H). $^{19}$F-NMR (DMSO-d$_6$) (major rotamer): δ −112.2

(1R,3S,5R)-2-(2-(3-Acetyl-5-(2-methylpyrimidin-5-yl)-1H-indazol-1-yl)acetyl)-N-((E)-3-(2-chlorophenyl)-2-fluorobut-2-en-1-yl)-2-azabicyclo[3.1.0]hexane-3-carboxamide (523)

Scheme 386

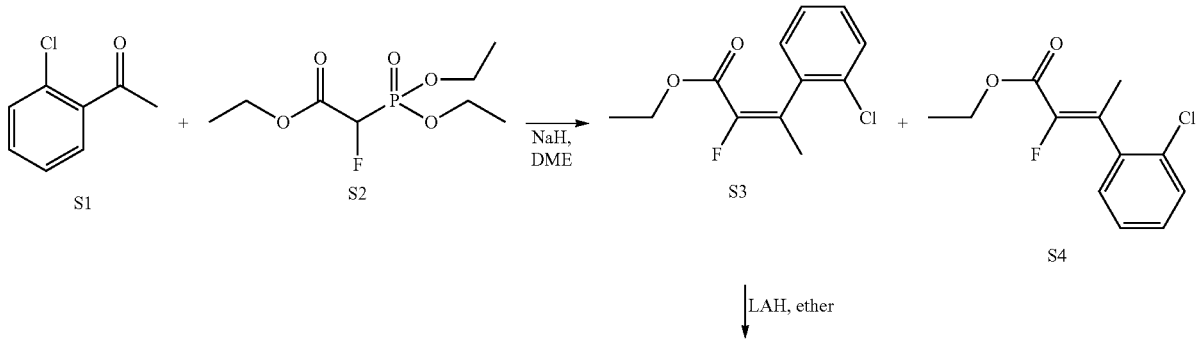

825 826

-continued

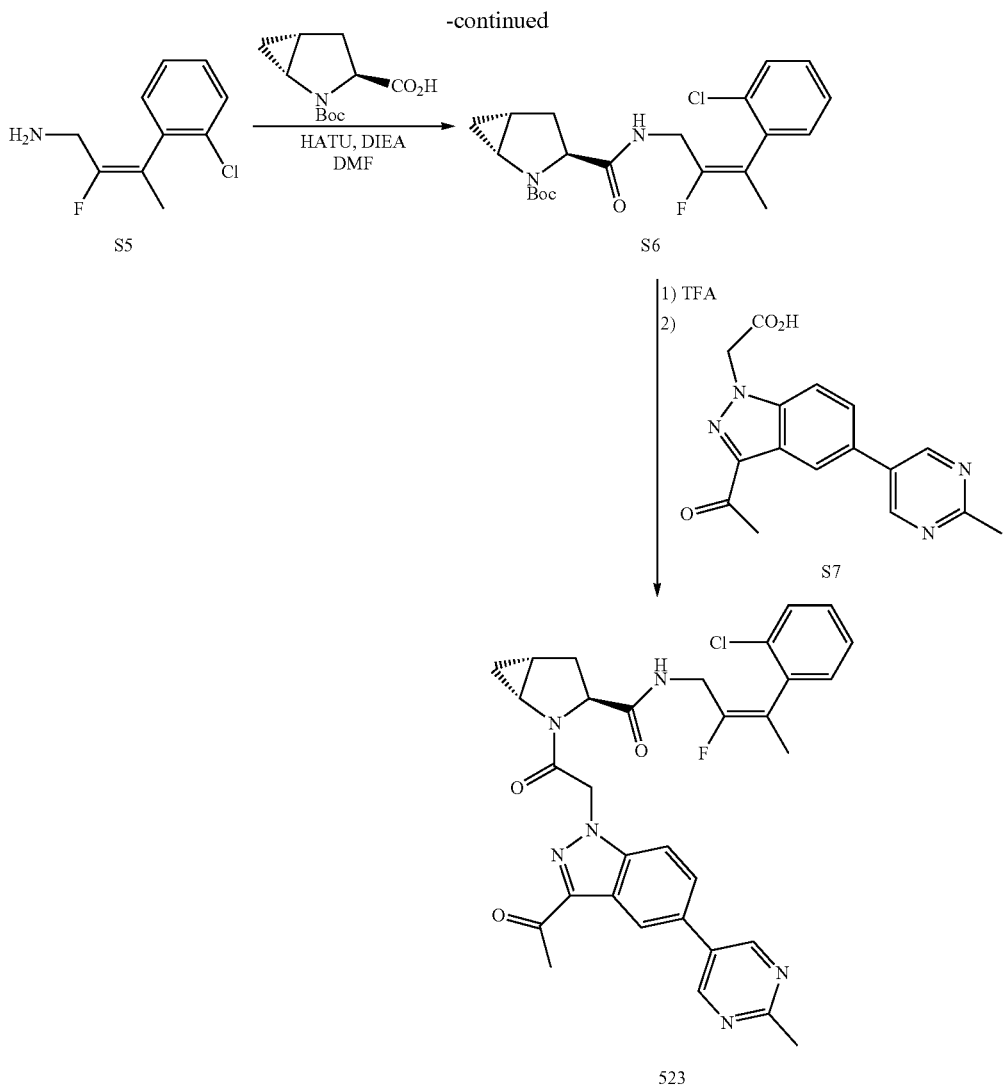

Ethyl (E)-3-(2-chlorophenyl)-2-fluorobut-2-enoate (S4) and Ethyl (Z)-3-(2-chlorophenyl)-2-fluorobut-2-enoate (S3)

Ethyl (E)-3-(2-chlorophenyl)-2-fluorobut-2-enoate (S4) and ethyl (Z)-3-(2-chlorophenyl)-2-fluorobut-2-enoate (S3) were prepared following the same procedure as for the synthesis of ethyl (Z)-2-fluoro-3-phenylbut-2-enoate (scheme 385 compound S3) and ethyl (Z)-2-fluoro-3-phenylbut-2-enoate (scheme 385 compound S4). The crude product was purified by ISCO (0-0.3% EtOAc in hexanes). Ethyl (Z)-3-(2-chlorophenyl)-2-fluorobut-2-enoate (S3) eluted first as a light yellow liquid followed by ethyl (E)-3-(2-chlorophenyl)-2-fluorobut-2-enoate (S4).

(E)-3-(2-Chlorophenyl)-2-fluorobut-2-en-1-amine hydrochloride (S5)

(E)-3-(2-Chlorophenyl)-2-fluorobut-2-en-1-amine hydrochloride (S5) was prepared following the same reaction procedures as those used for the synthesis of (E)-2-fluoro-3-phenylbut-2-en-1-amine hydrochloride (scheme 385 compound S12).

tert-Butyl (1R,3S,5R)-3-(((E)-3-(2-chlorophenyl)-2-fluorobut-2-en-1-yl)carbamoyl)-2-azabicyclo[3.1.0]hexane-2-carboxylate (S6)

Compound S6 was prepared following the same procedure as for the synthesis of tert-butyl (1R,3S,5R)-3-(((E)-2-fluoro-3-phenylbut-2-en-1-yl)carbamoyl)-2-azabicyclo[3.1.0]hexane-2-carboxylate (scheme 385 compound S13) to afford a yellow oil.

(1R,3S,5R)-2-(2-(3-Acetyl-5-(2-methylpyrimidin-5-yl)-1H-indazol-1-yl)acetyl)-N-((E)-3-(2-chlorophenyl)-2-fluorobut-2-en-1-yl)-2-azabicyclo[3.1.0]hexane-3-carboxamide (523)

tert-Butyl (1R,3S,5R)-3-(((E)-3-(2-chlorophenyl)-2-fluorobut-2-en-1-yl)carbamoyl)-2-azabicyclo[3.1.0]hexane-2-carboxylate (0.2 g) (S7) was dissolved in $CH_2Cl_2$ (2 mL) and an equal volume of TFA was added. The mixture was stirred for 30 min at room temperature. Then the volatiles were removed under reduced pressure. The residue was dissolved in DMF (1.5 mL) and $^iPr_2NEt$ (427 µL) was added followed by the sequential addition of 2-(3-acetyl-5-(2-methylpyrimidin-5-yl)-1H-indazol-1-yl)acetic acid (0.152 g) and HATU (0.224 g) slowly at 5° C. The reaction mixture was then stirred for 30 min at room temperature, poured into water (10 mL) and the solid was isolated by filtration, washed with water, and dried in vacuo. The solid was then purified by ISCO (eluent: 0-2.5% MeOH in $CH_2Cl_2$) to get a white solid.

$^1$H-NMR (DMSO-$d_6$) (major rotamer): δ 0.77 (1H), 1.00-1.03 (m, 1H), 1.80-1.87 (m, 1H), 1.87 (d, J=2.8 Hz, 3H), 2.05-2.11 (m, 1H), 2.18-2.24 (m, 1H), 2.65 (s, 3H), 2.69 (s, 3H), 3.59-3.72 (m, 3H), 4.22 (dd, J=9.2, 4.8 Hz, 1H), 5.57 (d, J=17.2 Hz, 1H), 5.90 (d, J=17.2 Hz, 1H), 7.33 (brs, 3H), 7.48 (d, J=7.6 Hz, 1H), 7.85 (s, 2H), 8.08 (brs, 1H), 8.44 (s, 1H), 9.04 (s, 2H). $^{19}$F-NMR (DMSO-$d_6$) (major rotamer): δ −114.9.

(1R,3S,5R)-2-(2-(3-Acetyl-5-(2-methylpyrimidin-5-yl)-1H-indazol-1-yl)acetyl)-N-((E)-3-(3-chlorophenyl)-2-fluorobut-2-en-1-yl)-2-azabicyclo[3.1.0]hexane-3-carboxamide (506) and (1R,3S,5R)-2-(2-(3-Acetyl-5-(2-methylpyrimidin-5-yl)-1H-indazol-1-yl)acetyl)-N—((Z)-3-(3-chlorophenyl)-2-fluorobut-2-en-1-yl)-2-azabicyclo[3.1.0]hexane-3-carboxamide (516)

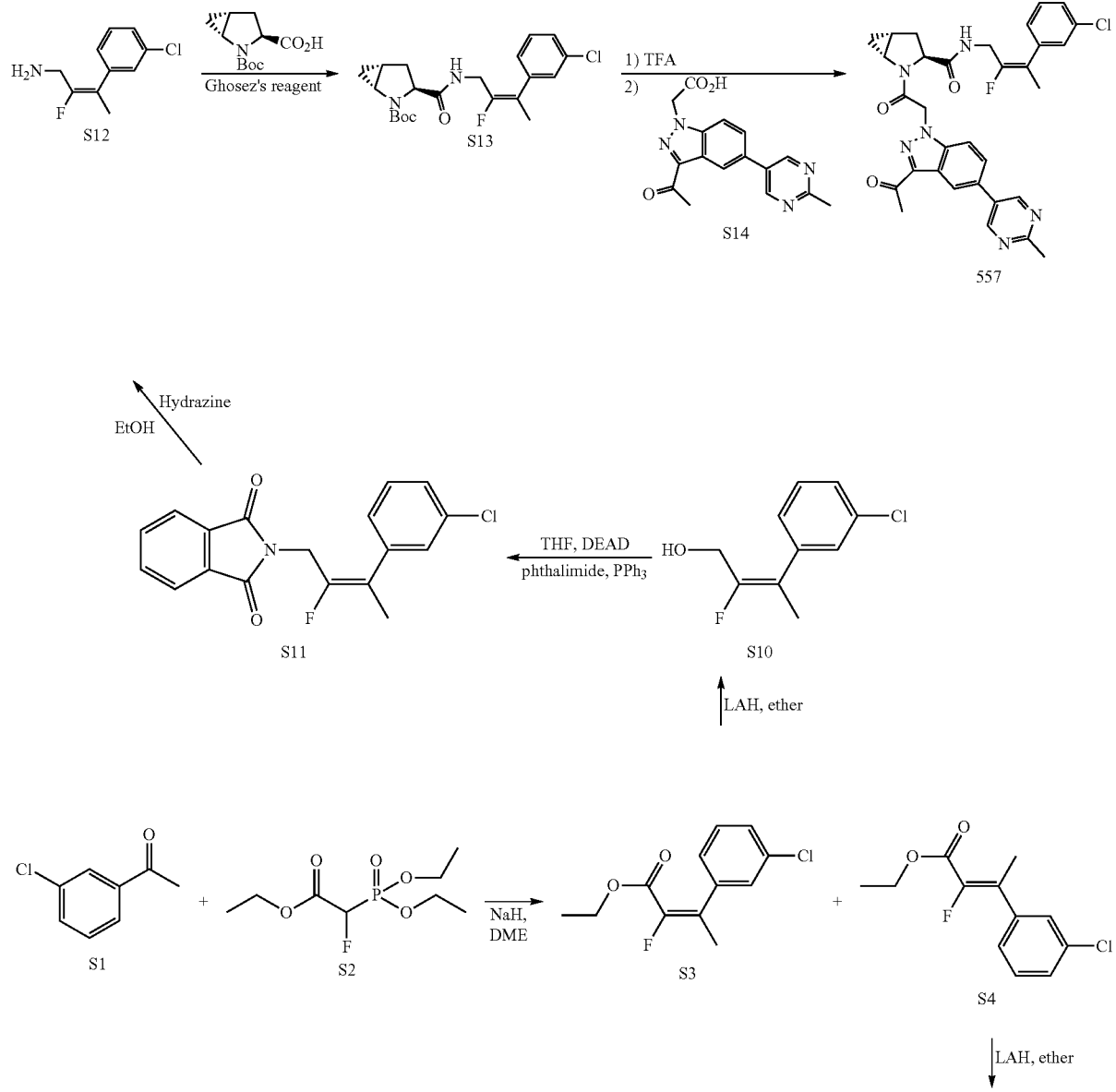

Scheme 387

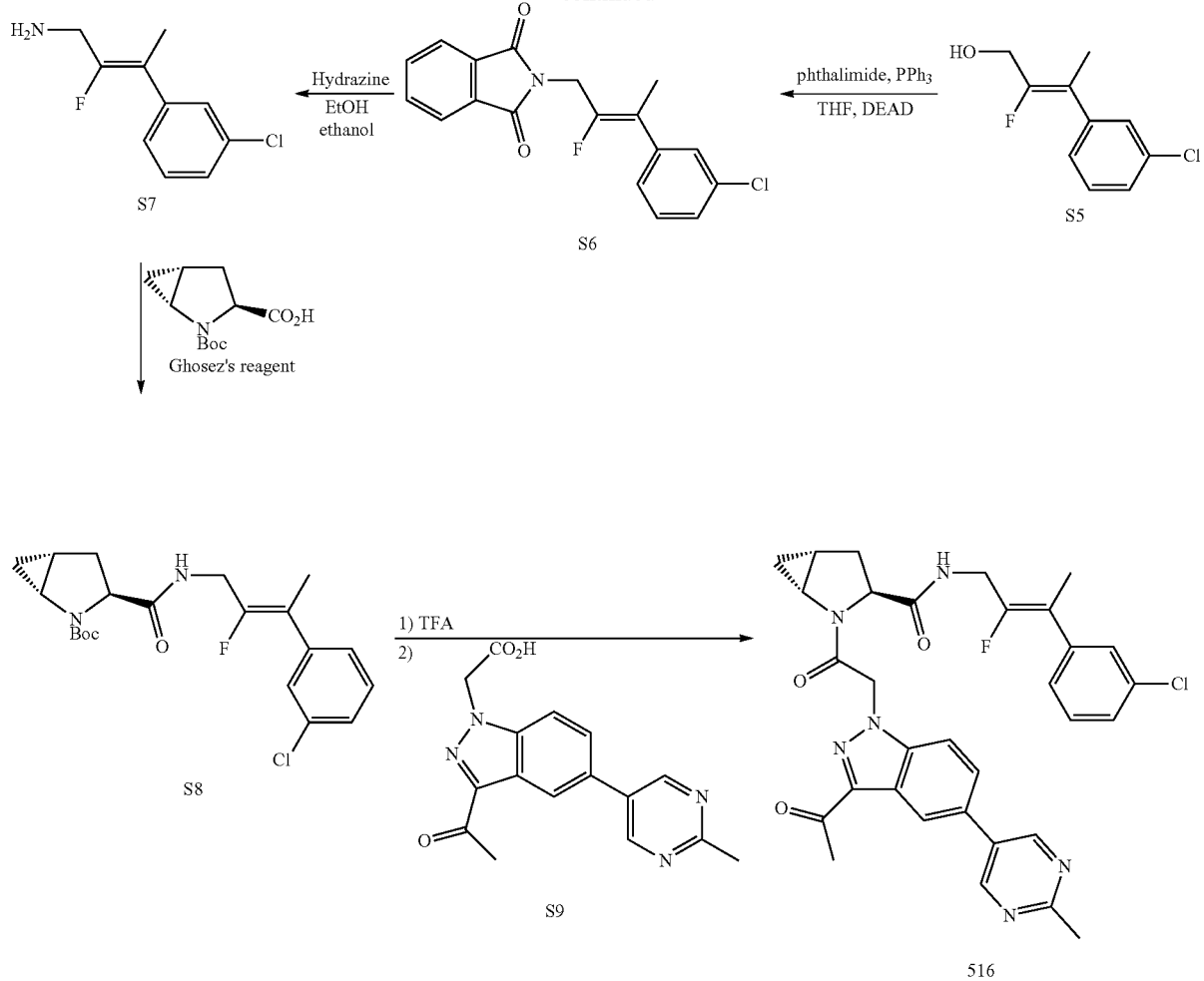

(1R,3S,5R)-2-(2-(3-Acetyl-5-(2-methylpyrimidin-5-yl)-1H-indazol-1-yl)acetyl)-N-((E)-3-(3-chlorophenyl)-2-fluorobut-2-en-1-yl)-2-azabicyclo[3.1.0]hexane-3-carboxamide (506)

The title compound was prepared following the same procedure as described for the synthesis of (1R,3S,5R)-2-(2-(3-acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide from (E)-2-fluoro-3-phenylbut-2-enoate (514) from ethyl (E)-3-(3-chlorophenyl)-2-fluorobut-2-enoate as the starting material. The crude product was purified by ISCO (eluent: 0-2.5% MeOH in CH$_2$Cl$_2$) to get white solid. $^1$H-NMR (DMSO-d$_6$) (major rotamer): δ 0.77 (1H), 1.00-1.03 (m, 1H), 1.80-1.87 (m, 1H), 1.87 (d, J=2.8 Hz, 3H), 2.05-2.11 (m, 1H), 2.18-2.24 (m, 1H), 2.65 (s, 3H), 2.69 (s, 3H), 3.59-3.72 (m, 3H), 4.22 (dd, J=9.2, 4.8 Hz, 1H), 5.57 (d, J=17.2 Hz, 1H), 5.90 (d, J=17.2 Hz, 1H), 7.33 (brs, 3H), 7.48 (d, J=7.6 Hz, 1H), 7.85 (s, 2H), 8.08 (brs, 1H), 8.44 (s, 1H), 9.04 (s, 2H). $^{19}$F-NMR (DMSO-d$_6$) (major rotamer): δ −114.9.

(1R,3S,5R)-2-(2-(3-Acetyl-5-(2-methylpyrimidin-5-yl)-1H-indazol-1-yl)acetyl)-N—((Z)-3-(3-chlorophenyl)-2-fluorobut-2-en-1-yl)-2-azabicyclo[3.1.0]hexane-3-carboxamide (516)

The title compound was prepared as described for the synthesis of (1R,3S,5R)-2-(2-(3-acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (557) from ethyl (Z)-3-(3-chlorophenyl)-2-fluorobut-2-enoate. The crude product was purified by ISCO (eluent: 0-2.5% MeOH in CH$_2$Cl$_2$) to get a white solid. $^1$H-NMR (DMSO-d$_6$) (major rotamer): δ 0.81 (m, 1H), 1.01-1.06 (m, 1H), 1.85-1.88 (m, 1H), 1.98 (d, J=2.8 Hz, 3H), 2.11-2.17 (m, 1H), 2.24-2.33 (m, 1H), 2.65 (s, 3H), 2.69 (s, 3H), 3.74 (t, J=5.2 Hz, 1H), 3.99-4.12 (m, 2H), 4.27 (dd, J=9.2, 4.8 Hz, 1H), 5.59 (d, J=17.2 Hz, 1H), 5.91 (d, J=17.2 Hz, 1H), 7.24-7.35 (m, 4H), 7.78 (d, J=8.4 Hz, 1H), (7.86, J=8.8 Hz, 1H), 8.30 (t, J=5.6 Hz, 1H), 8.43 (s, 1H), 9.01 (s, 2H). $^{19}$F-NMR (DMSO-d$_6$) (major rotamer): 6-110.7.

(1R,3S,5R)-2-(2-(3-Acetyl-5-(2-methylpyrimidin-5-yl)-1H-indazol-1-yl)acetyl)-N—((Z)-3-(2-chlorophenyl)-2-fluorobut-2-en-1-yl)-2-azabicyclo[3.1.0]hexane-3-carboxamide (528)

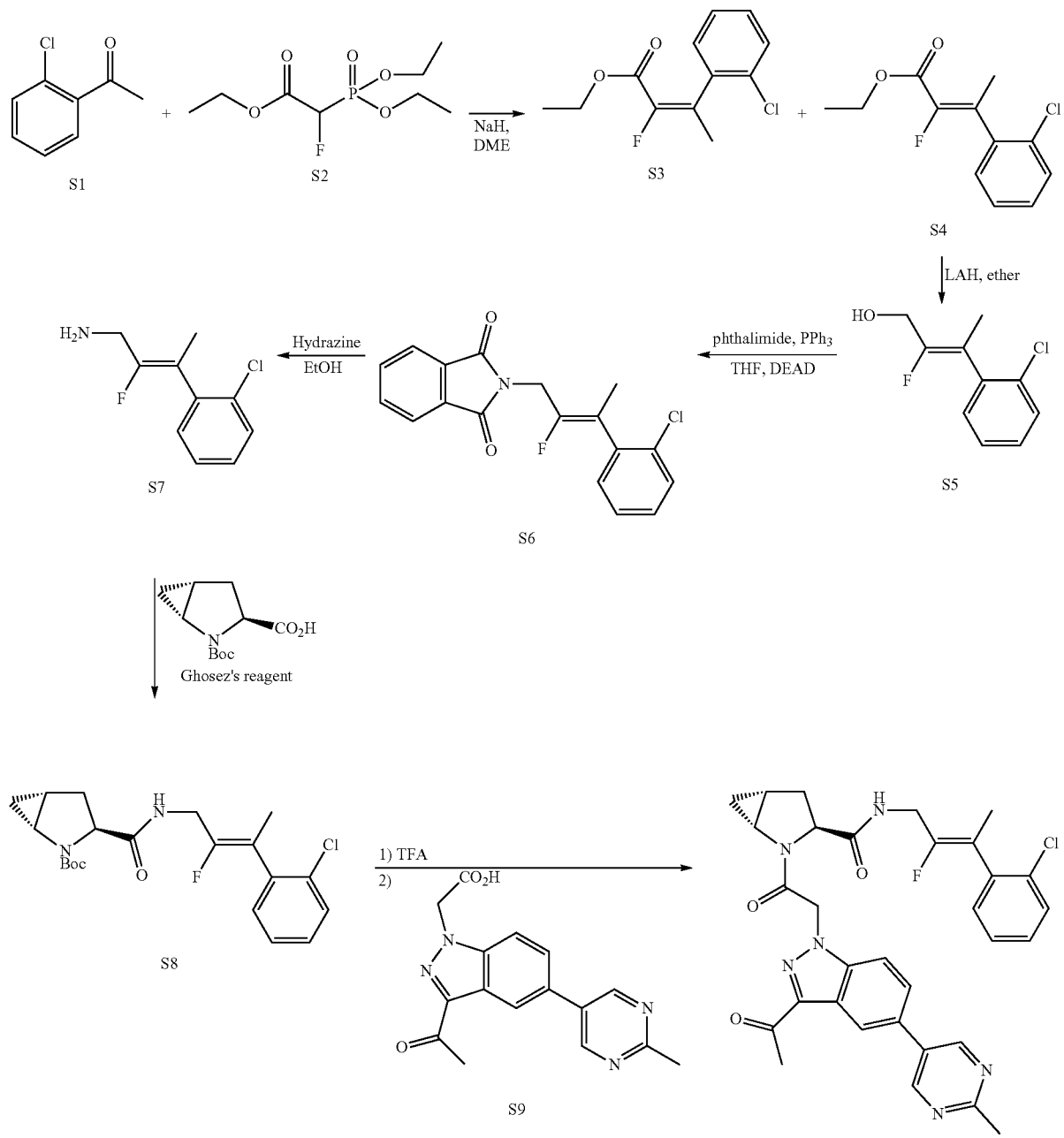

Scheme 388

Compound 528 was prepared following the same reaction procedures as those used for the synthesis of (1R,3S,5R)-2-(2-(3-Acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (541) using ethyl (Z)-3-(2-chlorophenyl)-2-fluorobut-2-enoate as the starting material.

(1R,3S,5R)-2-(2-(3-Acetyl-5-(2-methylpyrimidin-5-yl)-1H-indazol-1-yl)acetyl)-N-((E)-2-fluoro-3-phenylallyl)-2-azabicyclo[3.1.0]hexane-3-carboxamide (575)
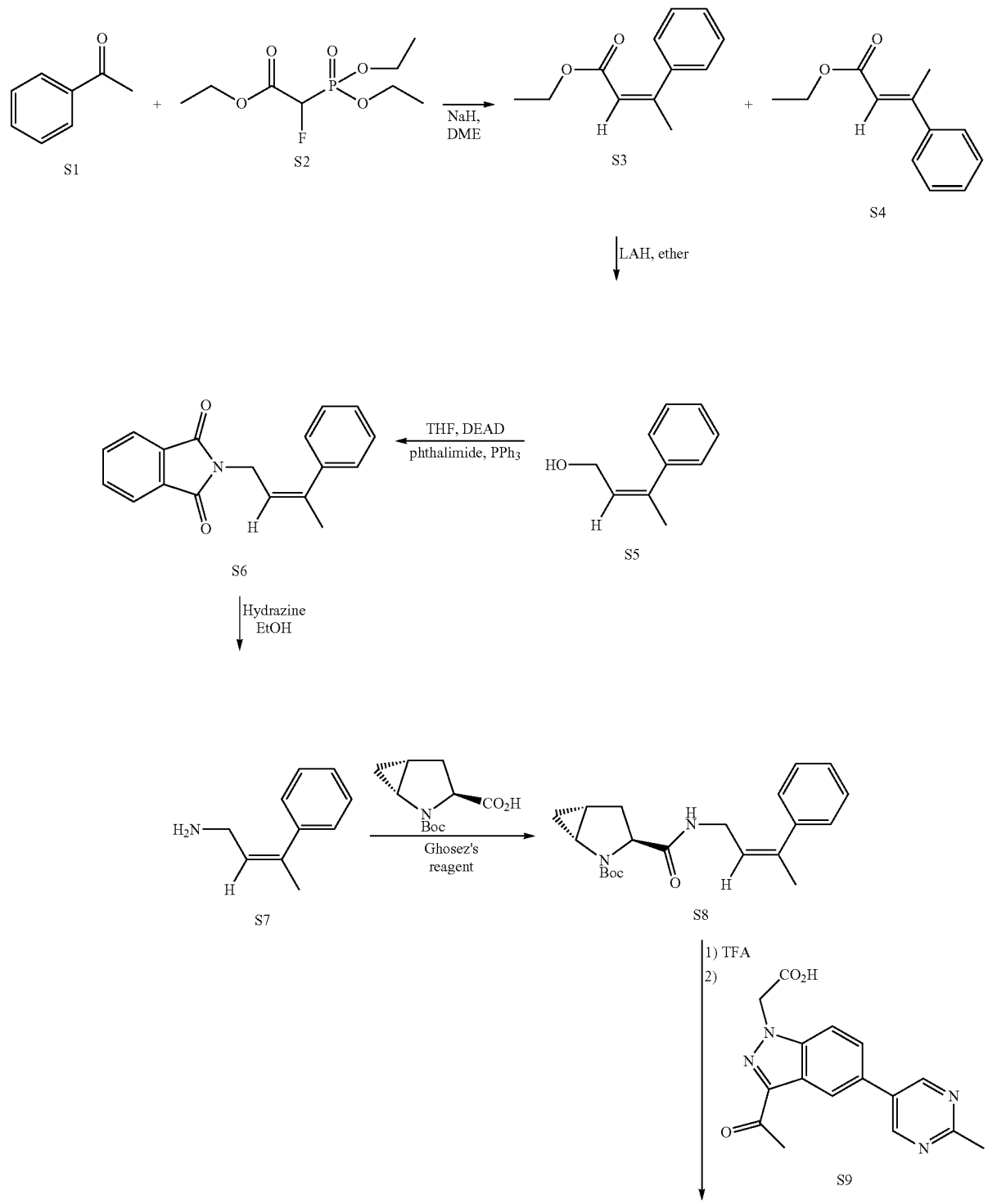

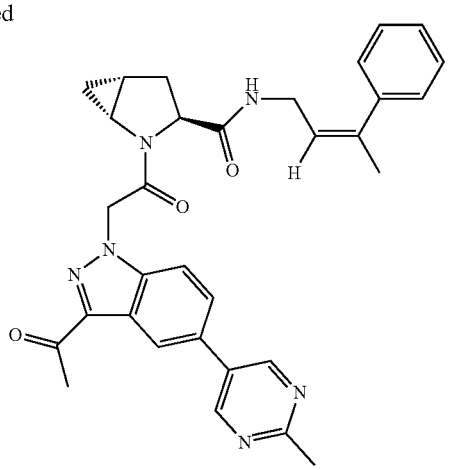

575

(1R,3S,5R)-2-(2-(3-Acetyl-5-(2-methylpyrimidin-5-yl)-1H-indazol-1-yl)acetyl)-N-((E)-2-fluoro-3-phenylallyl)-2-azabicyclo[3.1.0]hexane-3-carboxamide (575)

Compound 575 was prepared following the same reaction procedures as those used for the synthesis of (1R,3S,5R)-2-(2-(3-Acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide (541) starting from (E)-2-fluoro-3-phenylprop-2-en-1-ol. $^{1}$H-NMR (DMSO-$d_6$) (major rotamer): δ 0.80-0.81 (m, 1H), 1.00-1.05 (m, 1H), 1.84-1.87 (m, 1H), 2.07-2.15 (m, 1H), 2.22-2.28 (m, 1H), 2.65 (s, 3H), 2.69 (s, 3H), 3.72-3.75 (m, 1H), 4.06 (t, J=4.8 Hz, 1H), 4.11 (t, J=4.8 Hz, 1H), 4.27 (dd, J=9.2, 4.8 Hz, 1H), 5.59 (d, J=17.2 Hz, 1H), 5.90 (d, J=17.2 Hz, 1H), 6.39 (d, J=21.6 Hz, 1H), 7.23-7.41 (m, 5H), 7.85 (s, 2H), 8.32 (t, J=5.6 Hz, 1H), 8.44 (s, 1H), 9.04 (s, 2H). $^{19}$F-NMR (DMSO-$d_6$) (major rotamer): δ −104.5.

(2S,4R)-1-(2-(3-Acetyl-5-(2-methylpyrimidin-5-yl)-1H-indazol-1-yl)acetyl)-N-(2,5'-difluoro-2'-(methylsulfonyl)-[1,1'-biphenyl]-3-yl)-4-fluoropyrrolidine-2-carboxamide: (305)

Scheme 390

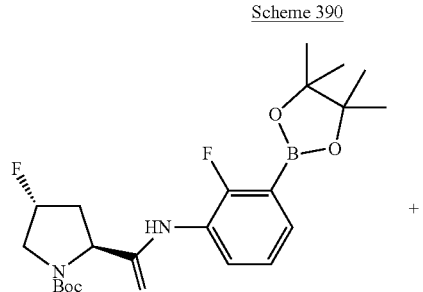

S1

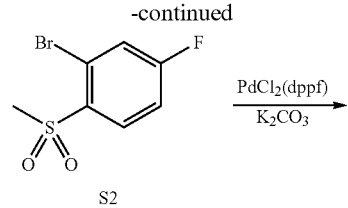

S2

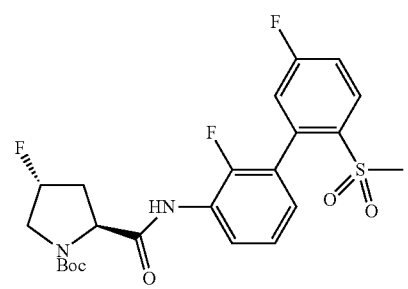

S3

1) TFA  2) 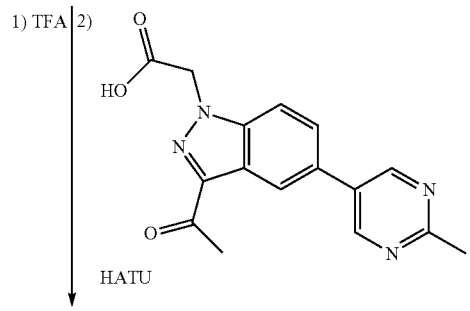

HATU

-continued

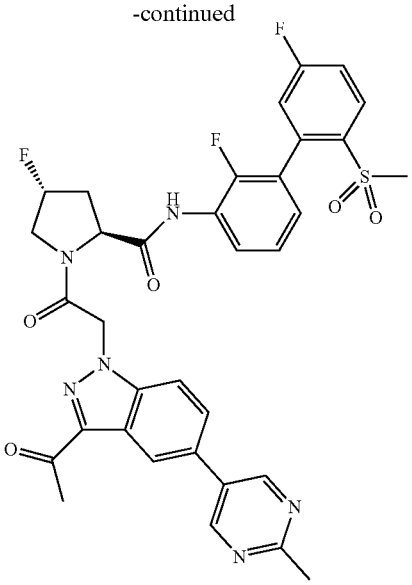

305 tert-Butyl (2S,4R)-2-((2,5'-difluoro-2'-(methylsulfonyl)-[1,1'-biphenyl]-3-yl)carbamoyl)-4-fluoropyrrolidine-1-carboxylate (S3)

tert-Butyl (2S,4R)-4-fluoro-2-((2-fluoro-3-(4,4,5,5-tetramethyl-1,3,2-dioxaborolan-2-yl)phenyl)carbamoyl)pyrrolidine-1-carboxylate (0.107 g), 2-bromo-4-fluoro-1-(methylsulfonyl)benzene (0.05 g), Pd(dppf)Cl₂ (32 mg) and potassium carbonate (0.136 g) were taken in a pressure tube under argon. To this mixture, 4 mL of dioxane and 1 mL of water were added. The mixture was bubbled with argon for 5 min and the vial stoppered and subjected to microwave irradiation at 100° C. for 45 min. The volatiles were removed under reduced pressure and the residue was purified by ISCO (0-0.7% MeOH in CH₂Cl₂) to afford the desired product.

(2S,4R)-1-(2-(3-Acetyl-5-(2-methylpyrimidin-5-yl)-1H-indazol-1-yl)acetyl)-N-(2,5'-difluoro-2'-(methylsulfonyl)-[1,1'-biphenyl]-3-yl)-4-fluoropyrrolidine-2-carboxamide: (305)

tert-Butyl (2S,4R)-2-((2,5'-difluoro-2'-(methylsulfonyl)-[1,1'-biphenyl]-3-yl)carbamoyl)-4-fluoropyrrolidine-1-carboxylate (0.05 g) was dissolved in CH₂Cl₂ (0.5 mL) and an equal volume of TFA was added. The mixture was stirred for 30 min at rt. Then the volatiles were removed under reduced pressure. The residue was dissolved in DMF (0.5 mL) and $^i$Pr₂NEt (87 µL) was added, followed by the sequential addition of 2-(3-acetyl-5-(2-methylpyrimidin-5-yl)-1H-indazol-1-yl)acetic acid (31 mg) and HATU (46 mg) slowly at 5° C. The reaction mixture was then stirred for 30 min at room temperature, poured into water (10 mL) and the solid was isolated by filtration, washed with water and dried in vacuo. The solid was then purified by ISCO (eluent: 0-2.5% MeOH in CH₂Cl₂) to get a white solid. ¹H NMR (400 MHz, CDCl₃) (major rotamer) δ 2.43-2.61 (m, 1H), 2.68 (s, 3H), 2.72-2.81 (m, 1H), 2.79 (s, 3H), 2.81 (s, 3H), 3.70-3.83 (m, 1H), 4.11-4.21 (m, 1H), 4.90 (t, J=7.8 Hz, 1H), 5.26-5.59 (m, 3H), 6.99-7.02 (m, 2H), 7.19 (t, J=8.0 Hz, 1H), 7.21-7.27 (m, 1H), 7.52-7.59 (m, 2H), 8.19-8.29 (m, 2H), 8.54 (d, J=4.0 Hz, 1H), 8.80 (s, 1H), 8.87 (s, 1H), 9.18 (s, 1H). ¹⁹F-NMR (DMSO-d₆) (major rotamer): δ −103.9, −126.5, −176.3.

(2S,4R)-1-(2-(3-Acetyl-5-(2-methylpyrimidin-5-yl)-1H-indazol-1-yl)acetyl)-N-(2'-chloro-2-fluoro-5'-sulfamoyl-[1,1'-biphenyl]-3-yl)-4-fluoropyrrolidine-2-carboxamide (341)

Scheme 391

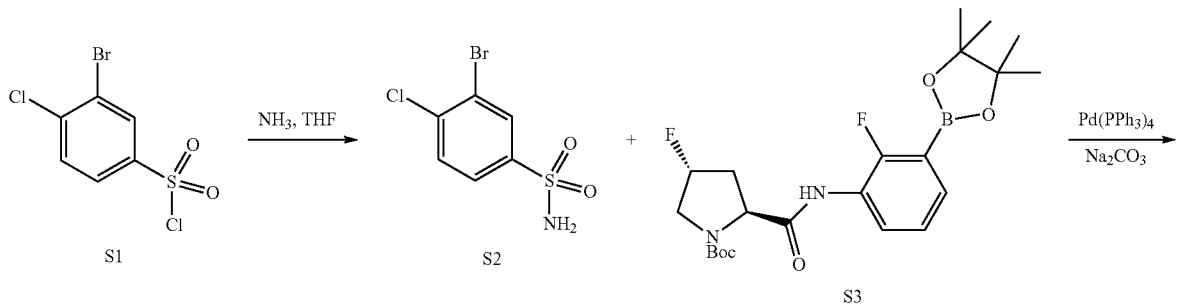

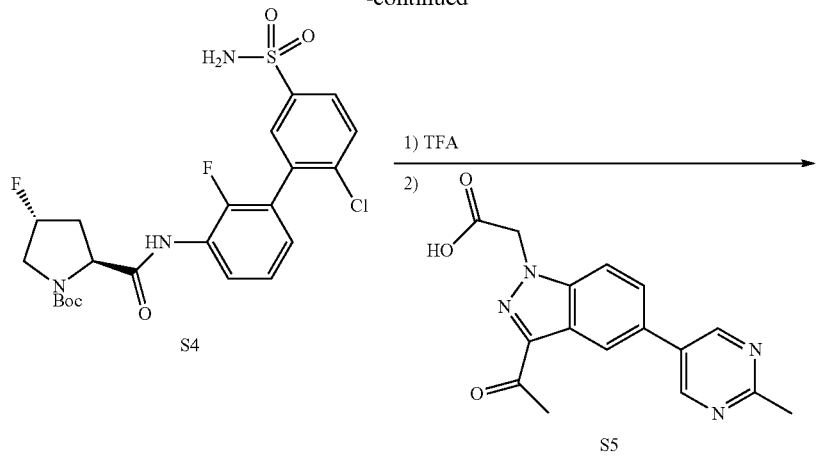

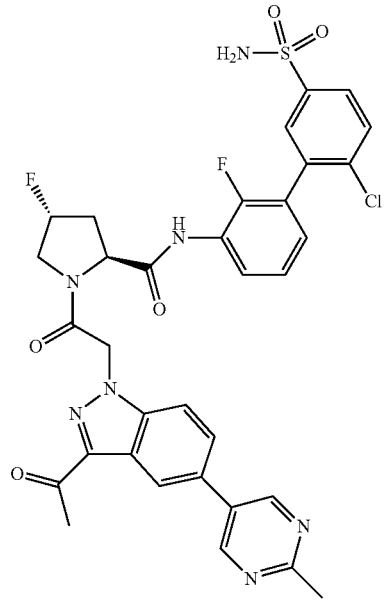

3-Bromo-4-chlorobenzenesulfonamide (S2)

A cooled solution of 3-bromo-4-chlorobenzenesulfonyl chloride (0.175 g) in THF (3 mL) was treated dropwise with 2.0 M ammonia in EtOH (0.66 mL) and stirred at 0° C. for 30 min. The solvents were removed under reduced pressure. The residue was used as such for the next step. (Procedure from *J. Med. Chem.* 2011, 54, 7299-7317).

tert-Butyl (2S,4R)-2-((2'-chloro-2-fluoro-5'-sulfamoyl-[1,1'-biphenyl]-3-yl)carbamoyl)-4-fluoropyrrolidine-1-carboxylate (S4)

tert-Butyl (2S,4R)-4-fluoro-2-((2-fluoro-3-(4,4,5,5-tetramethyl-1,3,2-dioxaborolan-2-yl)phenyl)carbamoyl)pyrrolidine-1-carboxylate (0.100 g), 3-bromo-4-chlorobenzenesulfonamide (0.05 g), Pd(PPh$_3$)$_4$ (42 mg) and sodium carbonate (97 mg) were taken in a pressure tube under argon. To this mixture, 4 mL of dioxane and 1 mL of water were added. The mixture was bubbled with argon for 5 min and the vial stoppered and subjected to microwave irradiation at 100° C. for 45 min. The volatiles were removed under reduced pressure and the residue was purified by ISCO (0-1.5% MeOH in CH$_2$Cl$_2$) to afford the desired product.

(2S,4R)-1-(2-(3-Acetyl-5-(2-methylpyrimidin-5-yl)-1H-indazol-1-yl)acetyl)-N-(2'-chloro-2-fluoro-5'-sulfamoyl-[1,1'-biphenyl]-3-yl)-4-fluoropyrrolidine-2-carboxamide (341)

tert-Butyl (2S,4R)-2-((2'-chloro-2-fluoro-5'-sulfamoyl-[1,1'-biphenyl]-3-yl)carbamoyl)-4-fluoropyrrolidine-1-carboxylate (79 mg) was dissolved in CH$_2$Cl$_2$ (1 mL) and an equal volume of TFA was added. The mixture was stirred for 30 min at rt. Then the volatiles were removed under reduced pressure. The residue was dissolved in DMF (1.5 mL) and $^i$Pr$_2$NEt (133 µL) was added, followed by the sequential addition of 2-(3-acetyl-5-(2-methylpyrimidin-5-yl)-1H-indazol-1-yl)acetic acid (47 mg) and HATU (70 mg) slowly at 5° C. The reaction mixture was then stirred for 30 min at RT, poured into water (10 mL) and the solid was isolated by filtration, washed with water and dried in vacuo. The solid was then purified by ISCO (eluent: 0-3.5% MeOH in CH$_2$Cl$_2$) to get a white solid. $^1$H NMR (400 MHz, Methanol-d$_4$) (major rotamer): δ 2.29-2.46 (m, 1H), 2.71 (s, 3H), 2.77 (s, 3H), 2.68-2.78 (m, 1H), 4.00-4.13 (m, 1H), 4.31 (dd, J=12.3, 20.6 Hz, 1H), 4.88 (t, J=8.4 Hz, 1H), 5.46-5.63 (m, 2H), 5.72 (d, J=17.1 Hz, 1H), 7.13 (t, J=7.1 Hz, 1H), 7.25 (t, J=7.9 Hz, 1H), 7.52 (dd, J=4.3, 8.4 Hz, 2H), 7.66-7.96 (m, 5H), 8.01 (t, J=7.5 Hz, 1H), 8.42 (d, J=8.4 Hz, 2H), 8.56 (s, 1H), 8.74 (s, 2H), 9.01 (s, 2H). $^{19}$F-NMR (DMSO-d$_6$) (major rotamer): δ −128.2, −178.6.

(2S,4R)-1-(2-(3-Acetyl-5-(2-methylpyrimidin-5-yl)-1H-indazol-1-yl)acetyl)-N-(2'-chloro-2-fluoro-5'-(N-methylsulfamoyl)-[1,1'-biphenyl]-3-yl)-4-fluoropyrrolidine-2-carboxamide: (342)

Scheme 392

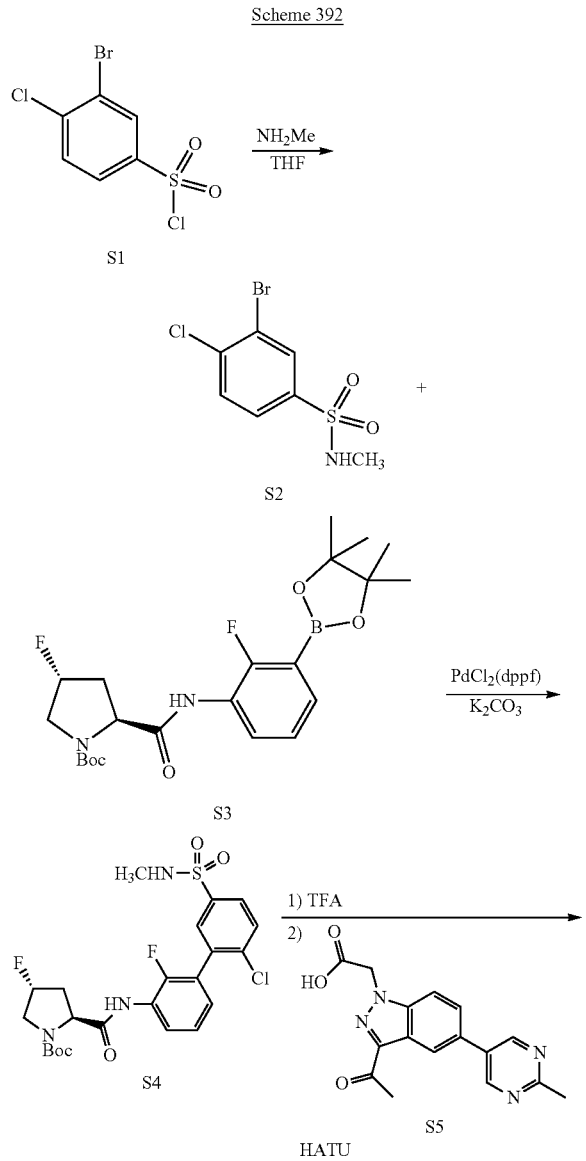

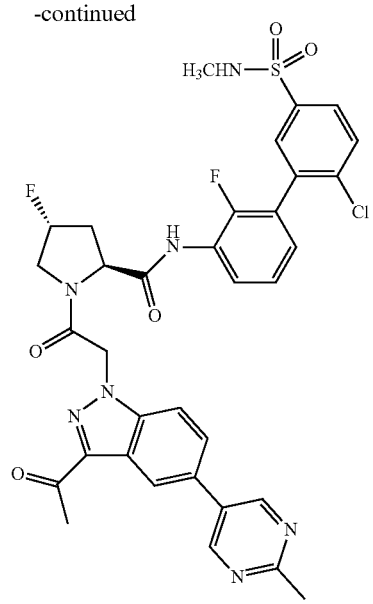

3-Bromo-4-chloro-N-methylbenzenesulfonamide (S2)

Compound S2 was prepared according to the procedure followed for the synthesis of 3-bromo-4-chlorobenzenesulfonamide (scheme 391 compound S2). The crude product obtained was used as such for the next step.

tert-Butyl (2S,4R)-2-((2'-chloro-2-fluoro-5'-(N-methylsulfamoyl)-[1,1'-biphenyl]-3-yl)carbamoyl)-4-fluoropyrrolidine-1-carboxylate (S4)

Compound S4 was prepared following the same procedure followed for the synthesis of tert-butyl (2S,4R)-2-((2'-chloro-2-fluoro-5'-sulfamoyl-[1,1'-biphenyl]-3-yl)carbamoyl)-4-fluoropyrrolidine-1-carboxylate (scheme 391 compound S3) The crude product was purified by ISCO (eluent: 0-1% MeOH in CH$_2$Cl$_2$) to afford a white solid.

(2S,4R)-1-(2-(3-Acetyl-5-(2-methylpyrimidin-5-yl)-1H-indazol-1-yl)acetyl)-N-(2'-chloro-2-fluoro-5'-(N-methylsulfamoyl)-[1,1'-biphenyl]-3-yl)-4-fluoropyrrolidine-2-carboxamide: (342)

tert-Butyl (2S,4R)-2-((2'-chloro-2-fluoro-5'-(N-methylsulfamoyl)-[1,1'-biphenyl]-3-yl)carbamoyl)-4-fluoropyrrolidine-1-carboxylate (70 mg) was dissolved in CH$_2$Cl$_2$ (1 mL) and an equal volume of TFA was added. The mixture was stirred for 30 min at rt. Then the volatiles were removed under reduced pressure. The residue was dissolved in DMF (1.0 mL) and $^i$Pr$_2$NEt (135 µL) was added, followed by the sequential addition of 2-(3-acetyl-5-(2-methylpyrimidin-5-yl)-1H-indazol-1-yl)acetic acid (40 mg) and HATU (60 mg) slowly at 5° C. The reaction mixture was then stirred for 30 min at room temperature, poured into water (10 mL) and the solid was isolated by filtration, washed with water and dried in vacuo. The solid was then purified by ISCO (eluent: 0-3.0% MeOH in CH$_2$Cl$_2$) to afford a white solid. $^1$H NMR (400 MHz, MeOD) (major rotamer): δ 2.26-2.48 (m, 1H), 2.55 (s, 3H), 2.69 (s, 3H), 2.72-2.77 (m, 1H), 2.77 (s, 3H), 4.00-4.13 (m, 1H), 4.29 (dd, J=20.8, 12.4 Hz, 1H), 4.88 (t, J=8.4 Hz, 1H), 5.53 (d, J=51.6 Hz, 1H), 5.57 (d, J=17.2 Hz, 1H), 5.70 (d, J=17.1 Hz, 1H), 7.13 (t, J=7.1 Hz, 1H), 7.23 (t, J=7.8 Hz, 1H), 7.71-7.91 (m, 5H), 7.99 (t, J=7.6 Hz, 1H), 8.53 (s, 1H), 8.99 (s, 2H). $^{19}$F-NMR (DMSO-d$_6$) (major rotamer): δ-128.2, −178.6.

(2S,4R)-1-(2-(3-Acetyl-5-(2-methylpyrimidin-5-yl)-1H-indazol-1-yl)acetyl)-N-(2'-chloro-5'-(N,N-dimethylsulfamoyl)-2-fluoro-[1,1'-biphenyl]-3-yl)-4-fluoropyrrolidine-2-carboxamide (343)
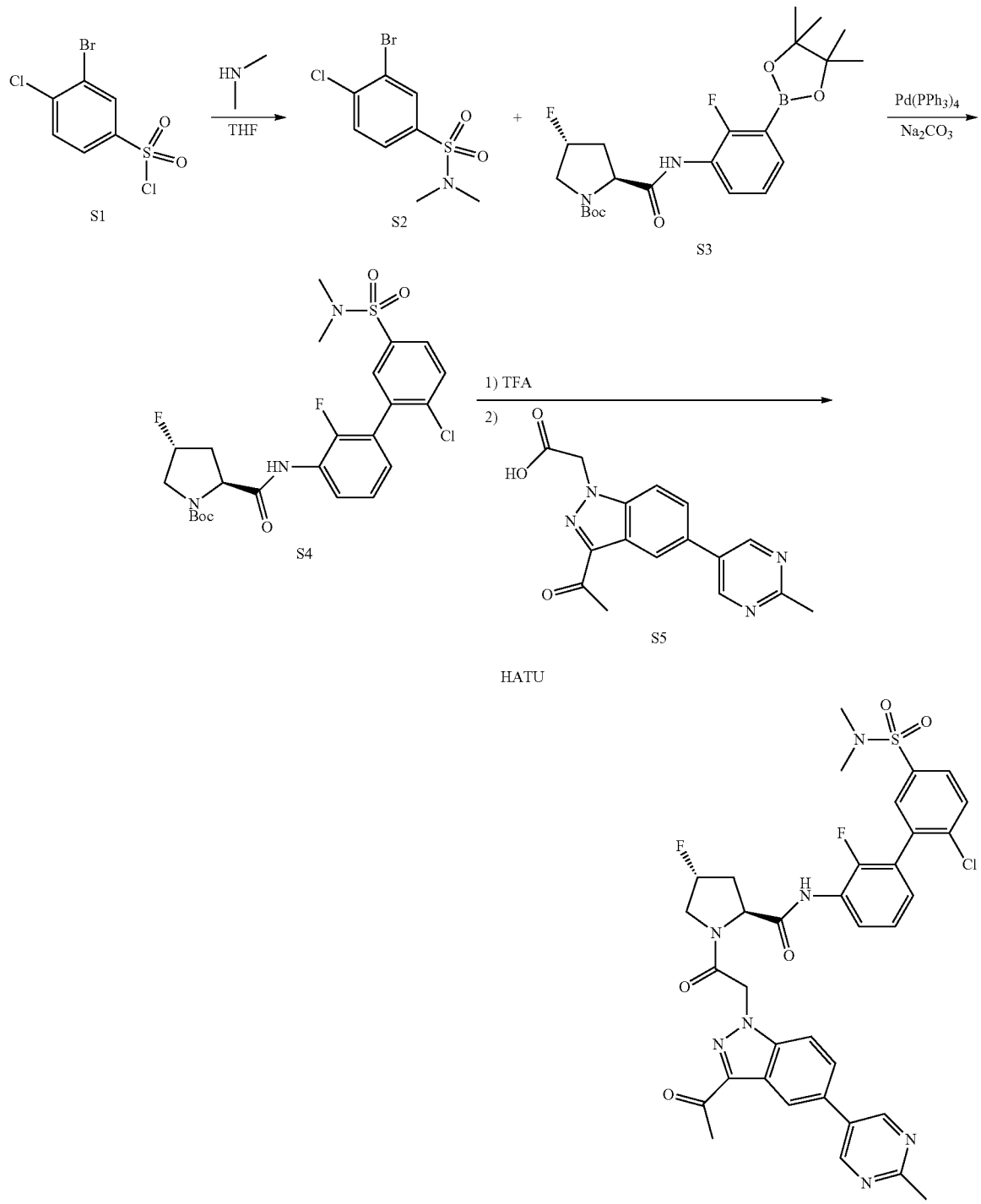

3-Bromo-4-chloro-N,N-dimethylbenzenesulfonamide (S3)

Compound S2 was prepared according to the procedure followed for the synthesis of 3-bromo-4-chlorobenzenesulfonamide (scheme 391 compound S2). The crude product obtained was used as such for the next step.

tert-Butyl (2S,4R)-2-((2'-chloro-5'-(N,N-dimethylsulfamoyl)-2-fluoro-[1,1'-biphenyl]-3-yl)carbamoyl)-4-fluoropyrrolidine-1-carboxylate (S4)

Compound S4 was prepared following the same procedure followed for the synthesis of tert-butyl (2S,4R)-2-((2'-chloro-2-fluoro-5'-sulfamoyl-[1,1'-biphenyl]-3-yl)carbamoyl)-4-fluoropyrrolidine-1-carboxylate (scheme 391 compound S3) The crude product was purified by ISCO (eluent: 0-1% MeOH in CH$_2$Cl$_2$) to afford a white solid.

2S,4R)-1-(2-(3-Acetyl-5-(2-methylpyrimidin-5-yl)-1H-indazol-1-yl)acetyl)-N-(2'-chloro-5'-(N,N-dimethylsulfamoyl)-2-fluoro-[1,1'-biphenyl]-3-yl)-4-fluoropyrrolidine-2-carboxamide (343)

tert-Butyl (2S,4R)-2-((2'-chloro-5'-(N,N-dimethylsulfamoyl)-2-fluoro-[1,1'-biphenyl]-3-yl)carbamoyl)-4-fluoropyrrolidine-1-carboxylate (0.1 g) was dissolved in CH$_2$Cl$_2$ (1 mL) and an equal volume of TFA was added. The mixture was stirred for 30 min at rt. Then the volatiles were removed under reduced pressure. The residue was dissolved in DMF (1.0 mL) and $^i$Pr$_2$NEt (160 μL) was added, followed by the sequential addition of 2-(3-acetyl-5-(2-methylpyrimidin-5-yl)-1H-indazol-1-yl)acetic acid (47 mg) and HATU (84 mg) slowly at 5° C. The reaction mixture was then stirred for 30 min at RT, poured into water (10 mL) and the solid was isolated by filtration, washed with water and dried in vacuo. The solid was then purified by ISCO (eluent: 0-2.5% MeOH in CH$_2$Cl$_2$) to get a white solid. $^1$H NMR (400 MHz, CDCl$_3$) (major rotamer) δ 2.45-2.57 (m, 1H), 2.67 (s, 3H), 2.71 (s, 6H), 2.75-2.96 (m, 1H), 2.81 (s, 3H), 3.64-3.76 (m, 1H), 4.18 (dd, J=12.4, 19.1 Hz, 1H), 4.96 (t, J=7.8 Hz, 1H), 5.31-5.50 (m, 3H), 7.04 (t, J=6.8 Hz, 1H), 7.21 (t, J=8.0 Hz, 1H), 7.54 (s, 2H), 7.63 (d, J=8.4 Hz, 1H), 7.66-7.76 (m, 2H), 8.28 (t, J=7.6 Hz, 1H), 8.54 (s, 1H), 8.86 (s, 2H), 8.93 (s, 1H). $^{19}$F-NMR (DMSO-d$_6$) (major rotamer): 6-129.9, −176.2.

(2S,4R)-1-(2-(3-Acetyl-5-(2-methylpyrimidin-5-yl)-1H-indazol-1-yl)acetyl)-N-(2'-chloro-5'-(N-cyclopropylsulfamoyl)-2-fluoro-[1,1'-biphenyl]-3-yl)-4-fluoropyrrolidine-2-carboxamide (745)

Scheme 394

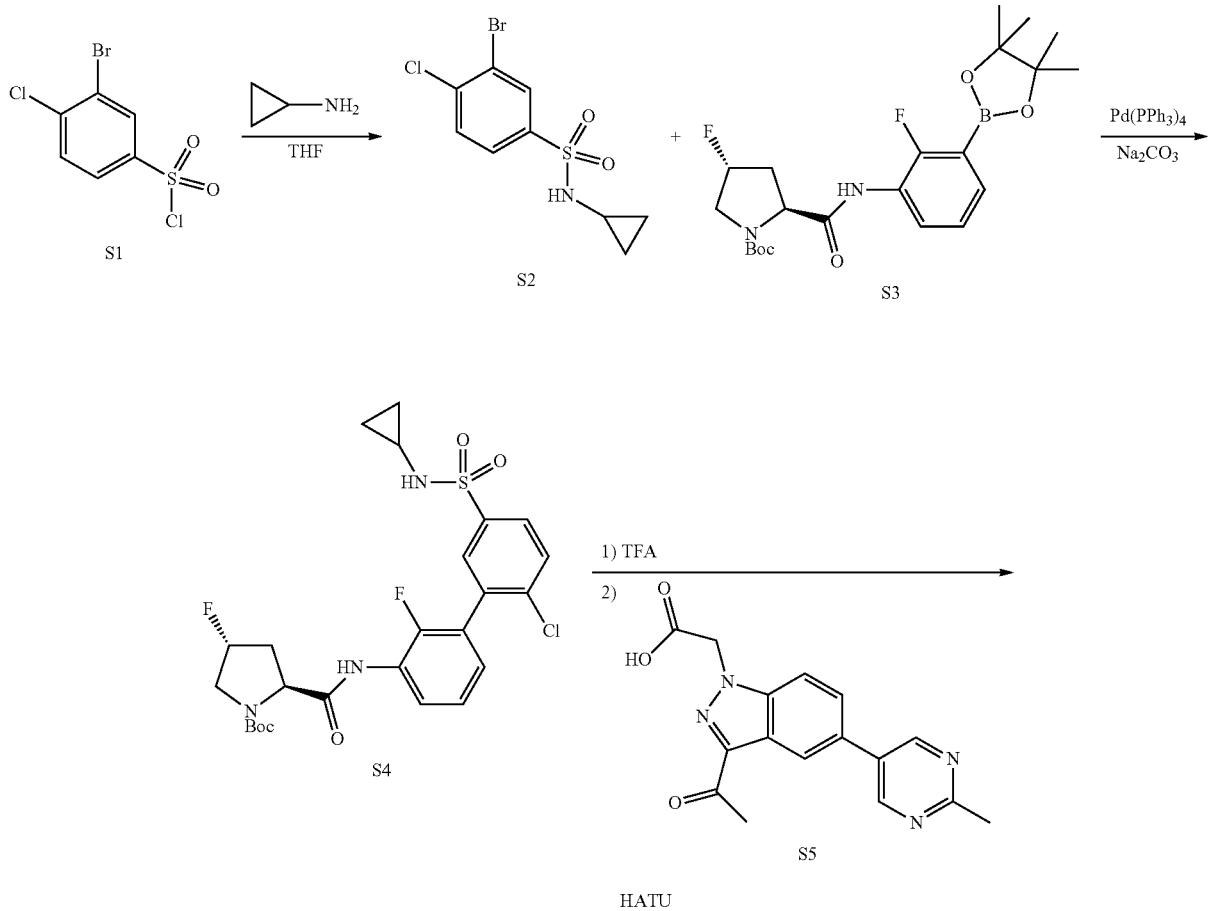

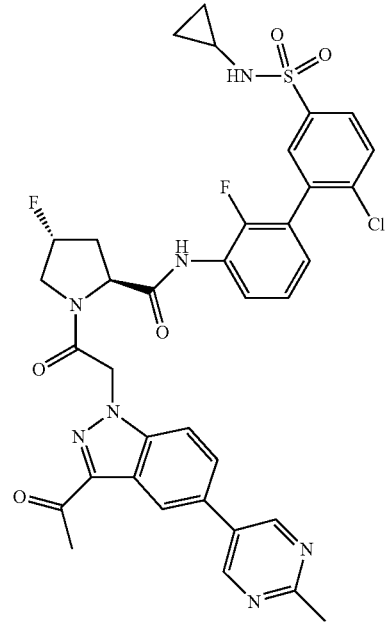

745

3-Bromo-4-chloro-N-cyclopropylbenzenesulfonamide (S2)

Compound S2 was prepared according to the procedure followed for the synthesis of 3-bromo-4-chlorobenzenesulfonamide (scheme 391 compound S2). The crude product obtained was used as such for the next step.

tert-Butyl (2S,4R)-2-((2'-chloro-5'-(N-cyclopropylsulfamoyl)-2-fluoro-[1,1'-biphenyl]-3-yl)carbamoyl)-4-fluoropyrrolidine-1-carboxylate (S4)

Compound S4 was prepared following the same procedure followed for the synthesis of tert-butyl (2S,4R)-2-((2'-chloro-2-fluoro-5'-sulfamoyl-[1,1'-biphenyl]-3-yl)carbamoyl)-4-fluoropyrrolidine-1-carboxylate (scheme 391 compound S3) The crude product was purified by ISCO (eluent: 0-1% MeOH in CH$_2$Cl$_2$) to afford a white solid.

(2S,4R)-1-(2-(3-Acetyl-5-(2-methylpyrimidin-5-yl)-1H-indazol-1-yl)acetyl)-N-(2'-chloro-5'-(N-cyclopropylsulfamoyl)-2-fluoro-[1,1'-biphenyl]-3-yl)-4-fluoropyrrolidine-2-carboxamide (745)

tert-Butyl (2S,4R)-2-((2'-chloro-5'-(N-cyclopropylsulfamoyl)-2-fluoro-[1,1'-biphenyl]-3-yl)carbamoyl)-4-fluoropyrrolidine-1-carboxylate (70 mg) was dissolved in CH$_2$Cl$_2$ (1 mL) and an equal volume of TFA was added. The mixture was stirred for 30 min at room temperature. Then the volatiles were removed under reduced pressure. The residue was dissolved in DMF (0.5 mL) and $^i$Pr$_2$NEt (110 μL) was added. This was followed by the sequential addition of 2-(3-acetyl-5-(2-methylpyrimidin-5-yl)-1H-indazol-1-yl) acetic acid (35 mg) and HATU (58 mg) slowly at 5° C. The reaction mixture was then stirred for 30 min at RT, poured into water (5 mL) and the solid was isolated by filtration, washed with water and dried in vacuo. The solid was then purified by ISCO (eluent: 0-3% MeOH in CH$_2$Cl$_2$) to get a white solid. $^1$H NMR (400 MHz, CDCl$_3$) (major rotamer): δ 0.56-0.59 (m, 4H), 2.20-2.25 (m, 1H), 2.38-2.49 (m, 1H), 2.64 (s, 3H), 2.72-2.78 (m, 1H), 2.79 (s, 3H), 3.76-3.85 (m, 1H), 4.14 (dd, J=19.2, 12.4 Hz, 1H), 4.92 (t, J=8 Hz, 1H), 5.32-5.49 (m, 3H), 5.96 (s, 1H), 6.99 (t, J=6.4 Hz, 1H), 7.07 (t, J=7.6 Hz, 1H), 7.38 (d, J=8.8 Hz, 1H), 7.51 (d, J=8.4 Hz, 1H), 7.58 (d, J=8.4 Hz, 1H), 7.81 (s, 1H), 7.84 (dd, J=8.4, 2 Hz, 1H), 8.10 (t, J=7.2 Hz, 1H), 8.48 (s, 1H), 8.79 (s, 1H), 9.09 (s, 1H). $^{19}$F NMR (376 MHz, CDCl$_3$) (major rotamer): δ −128.8, −176.1.

(2S,4R)-1-(2-(3-Acetyl-5-(2-methylpyrimidin-5-yl)-1H-indazol-1-yl)acetyl)-4-fluoro-N-(2-fluoro-3'-(methylsulfonyl)-[1,1'-biphenyl]-3-yl)pyrrolidine-2-carboxamide (295)

Scheme 395

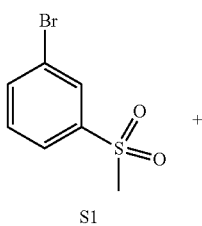

S1

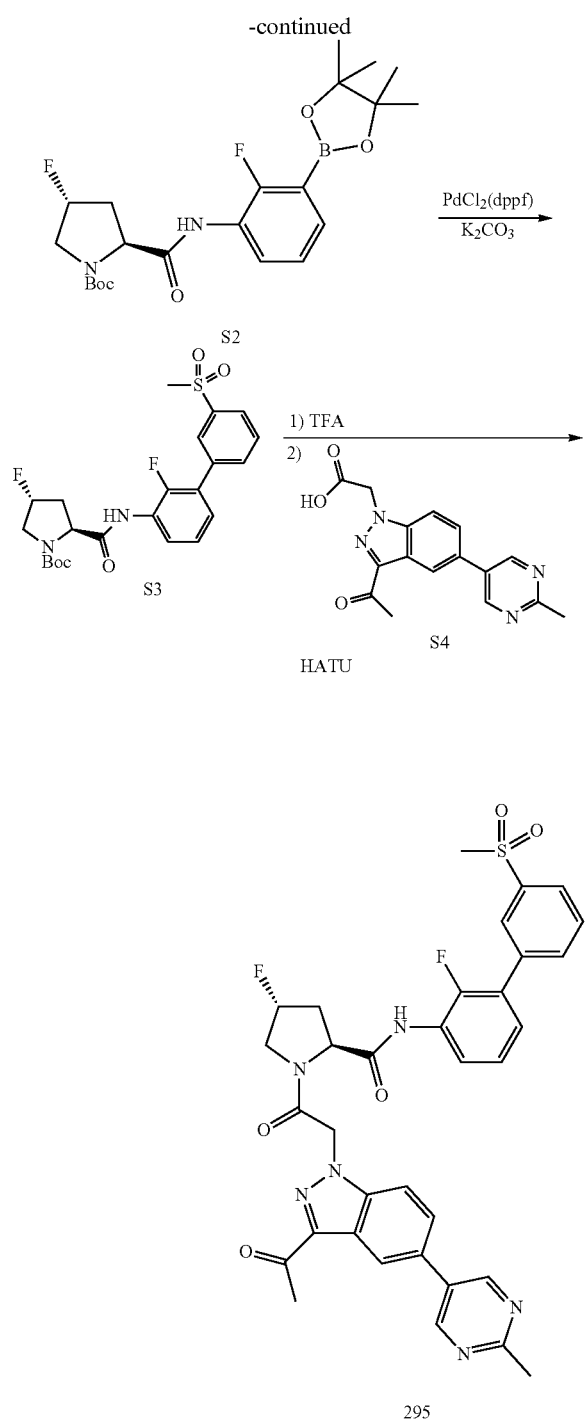

tert-Butyl (2S,4R)-4-Fluoro-2-((2-fluoro-3'-(methylsulfonyl)-[1,1'-biphenyl]-3-yl)carbamoyl)pyrrolidine-1-carboxylate (S3)

Compound S3 was prepared following the same procedure followed for the synthesis of tert-butyl (2S,4R)-2-((2'-chloro-2-fluoro-5'-sulfamoyl-[1,1'-biphenyl]-3-yl)carbamoyl)-4-fluoropyrrolidine-1-carboxylate (scheme 391 compound S3) The crude product was purified by ISCO (eluent: 0-1% MeOH in CH$_2$Cl$_2$) to afford a white solid.

(2S,4R)-1-(2-(3-Acetyl-5-(2-methylpyrimidin-5-yl)-1H-indazol-1-yl)acetyl)-4-fluoro-N-(2-fluoro-3'-(methylsulfonyl)-[1,1'-biphenyl]-3-yl)pyrrolidine-2-carboxamide (295)

tert-Butyl (2S,4R)-4-fluoro-2-((2-fluoro-3'-(methylsulfonyl)-[1,1'-biphenyl]-3-yl)carbamoyl)pyrrolidine-1-carboxylate (100 mg) was dissolved in CH$_2$Cl$_2$ (1 mL) and an equal volume of TFA was added. The mixture was stirred for 30 min at room temperature. Then the volatiles were removed under reduced pressure. The residue was dissolved in DMF (1.5 mL) and $^i$Pr$_2$NEt (205 µL) was added. This was followed by the sequential addition of 2-(3-acetyl-5-(2-methylpyrimidin-5-yl)-1H-indazol-1-yl)acetic acid (76 mg) and HATU (112 mg) slowly at 5° C. The reaction mixture was then stirred for 30 min at RT, poured into water (15 mL) and the solid was isolated by filtration, washed with water and dried in vacuo. The solid was then purified by ISCO (eluent: 0-2.5% MeOH in CH$_2$Cl$_2$) to get a white solid. $^1$H NMR (400 MHz, CDCl$_3$) (major rotamer): δ 2.47-2.59 (m, 1H), 2.65 (s, 3H), 2.72-2.88 (m, 1H), 2.79 (s, 3H), 3.09 (s, 3H), 3.69-3.81 (m, 1H), 4.19 (dd, J=19.6, 12.8 Hz, 1H), 4.96 (t, J=7.6 Hz, 1H), 5.32-5.50 (m, 3H), 7.15 (d, J=6 Hz, 2H), 7.48 (d, J=8.8 Hz, 1H), 7.54-7.61 (m, 2H), 7.71 (d, J=7.6 Hz, 1H), 8.05 (s, 1H), 8.13-8.18 (m, 1H), 8.52 (s, 1H), 8.82 (s, 1H), 8.99 (s, 1H). $^{19}$F NMR (376 MHz, CDCl$_3$) (major rotamer): δ −133.7, −176.1.

(2S,4R)-1-(2-(3-Acetyl-5-(2-methylpyrimidin-5-yl)-1H-indazol-1-yl)acetyl)-N-(6-cyclopropylpyridin-2-yl)-4-fluoropyrrolidine-2-carboxamide (576)

Scheme 395

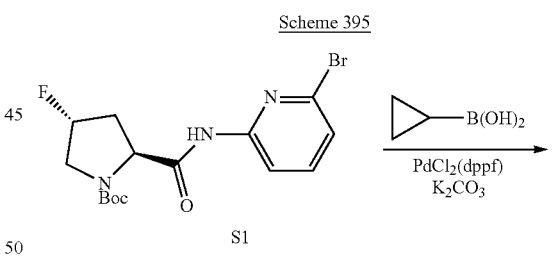

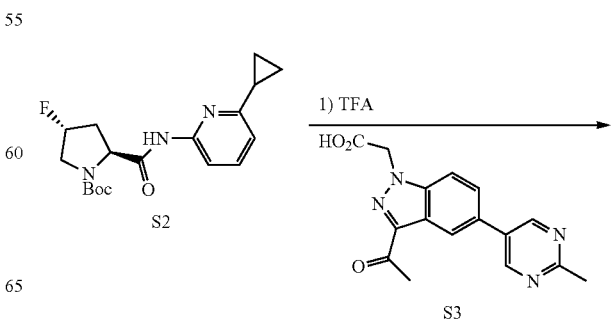

851

-continued

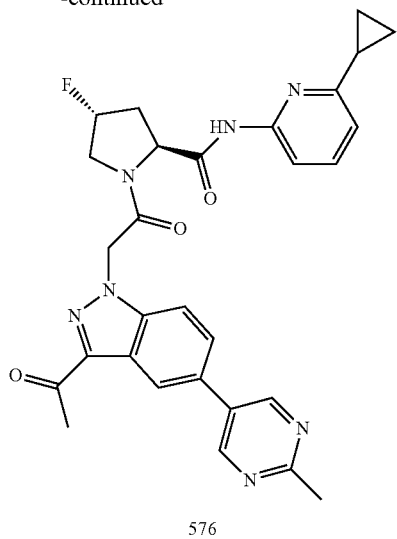

576 tert-Butyl (2S,4R)-2-((6-Cyclopropylpyridin-2-yl)carbamoyl)-4-fluoropyrrolidine-1-carboxylate (S2)

tert-Butyl (2S,4R)-2-((6-bromopyridin-2-yl)carbamoyl)-4-fluoropyrrolidine-1-carboxylate (0.5 g), cyclopropylboronic acid (0.7 g), Pd(dppf)Cl$_2$ (0.3 g) and potassium carbonate (0.889 g) were taken up in a pressure tube under argon. To this mixture, 20 mL of dioxane was added. The mixture was bubbled with argon for 5 min and the vial stoppered and heated at 100° C. overnight. The reaction mixture was filtered through Celite and the filtrate was concentrated under reduced pressure. The residue was purified by ISCO (0-0.5% MeOH in CH$_2$Cl$_2$) to afford the desired product.

(2S,4R)-1-(2-(3-Acetyl-5-(2-methylpyrimidin-5-yl)-1H-indazol-1-yl)acetyl)-N-(6-cyclopropylpyridin-2-yl)-4-fluoropyrrolidine-2-carboxamide (576)

tert-Butyl (2S,4R)-2-((6-cyclopropylpyridin-2-yl)carbamoyl)-4-fluoropyrrolidine-1-carboxylate (0.232 g) was dissolved in CH$_2$Cl$_2$ (3 mL) and equal volume of TFA was added. The mixture was stirred for 30 min at room temperature. Then the volatiles were removed under reduced pressure. The residue was dissolved in DMF (1.5 mL) and $^i$Pr$_2$NEt (0.581 mL) was added, followed by the sequential addition of 2-(3-acetyl-5-(2-methylpyrimidin-5-yl)-1H-indazol-1-yl)acetic acid (0.227 g) and HATU (0.304 g, 1.2 equiv) slowly at 5° C. The reaction mixture was then stirred for 30 min at room temperature, poured into water (10 mL) and the solid was isolated by filtration, washed with water and dried in vacuo. The solid was then purified by ISCO (eluent: 0-2.5% MeOH in CH$_2$Cl$_2$) to afford a white solid. $^1$H-NMR (DMSO-d$_6$) (major rotamer): δ 0.82-0.94 (m, 4H), 1.96-2.03 (m, 1H), 2.10-2.24 (m, 1H), 2.54-2.61 (m, 1H), 2.64 (s, 3H), 2.68 (s, 3H), 3.93-4.07 (m, 1H), 4.23 (dd, J=21.6, 12 Hz, 1H), 4.75 (t, J=8.4 Hz, 1H), 5.55 (d, J=54 Hz, 1H), 5.64 (d, J=17.2 Hz, 1H), 5.83 (d, J=17.2 Hz, 1H), 6.95 (d, J=7.6 Hz, 1H), 7.57 (t, J=7.6 Hz, 1H), 7.77 (d, J=8.4 Hz, 1H), 7.82-7.87 (m, 2H), 8.42 (s, 1H), 9.03 (s, 2H), 10.38 (s, 1H). $^{19}$F-NMR (DMSO-d$_6$) (major rotamer): δ −175.6.

852

(2S,4R)-1-(2-(3-Acetyl-5-(2-methylpyrimidin-5-yl)-1H-indazol-1-yl)acetyl)-4-fluoro-N-(6-methoxypyridin-2-yl)pyrrolidine-2-carboxamide (580)

Scheme 396

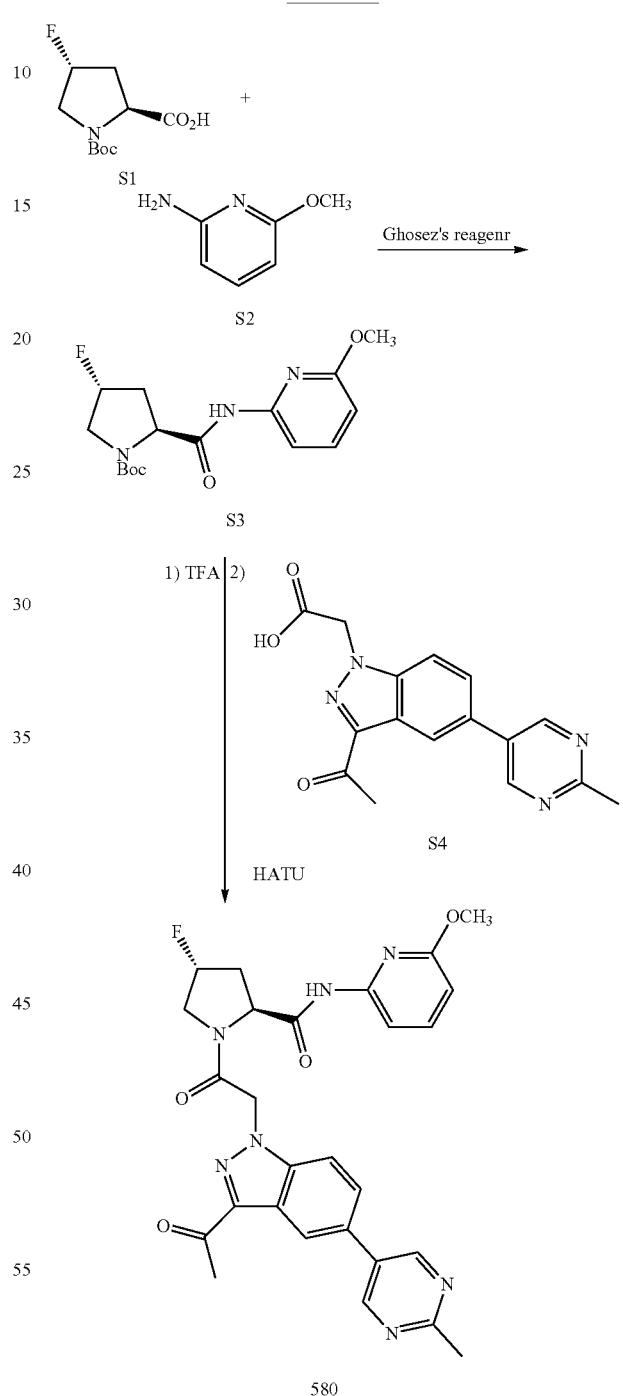

tert-Butyl (2S,4R)-4-fluoro-2-((6-methoxypyridin-2-yl)carbamoyl)pyrrolidine-1-carboxylate (S3)

To an ice cold solution of (2S,4R)-1-(tert-butoxycarbonyl)-4-fluoropyrrolidine-2-carboxylic acid (0.3 g) in 6 mL of CH$_2$Cl$_2$, 1-chloro-N,N,2-trimethyl-1-propenylamine (204 µL.) was added dropwise with stirring. The stirring was continued for 3 hours at same temperature. Then, 6-methoxypyridin-2-amine (0.145 g) was added followed by 672 µL of Hünig's base. The cooling bath was removed and the reaction mixture was stirred overnight at room temperature. The solvent was co-evaporated with MeOH (2 mL) and the residue was purified by ISCO (eluent: 0-0.5% MeOH in CH$_2$Cl$_2$).

(2S,4R)-1-(2-(3-Acetyl-5-(2-methylpyrimidin-5-yl)-1H-indazol-1-yl)acetyl)-4-fluoro-N-(6-methoxypyridin-2-yl)pyrrolidine-2-carboxamide (580)

tert-Butyl (2S,4R)-4-fluoro-2-((6-methoxypyridin-2-yl)carbamoyl)pyrrolidine-1-carboxylate (0.220 g) was dissolved in CH$_2$Cl$_2$ (2 mL) and an equal volume of TFA was added. The mixture was stirred for 30 min at room temperature. Then the volatiles were removed under reduced pressure. The residue was dissolved in DMF (2 mL), and $^i$Pr$_2$NEt (565 µL) was added. This was followed by the sequential addition of 2-(3-acetyl-5-(2-methylpyrimidin-5-yl)-1H-indazol-1-yl)acetic acid (0.220 g) and HATU (0.296 g) slowly at 5° C. The reaction mixture was then stirred for 30 min at RT, poured into water (10 mL) and the solid was isolated by filtration, washed with water and dried in vacuo. The solid was purified by ISCO (eluent: 0-2.5% MeOH in CH$_2$Cl$_2$) to afford a white solid. $^1$H NMR (400 MHz, DMSO) δ 2.01-2.45 (m, 1H), 2.56-2.59 (m, 1H), 2.65 (s, 3H), 2.68 (s, 3H), 3.80 (s, 3H), 3.96-4.07 (m, 1H), 4.17-4.31 (m, 1H), 4.76 (t, J=8.4 Hz, 1H), 5.56 (d, J=53.6 Hz, 1H), 5.65 (d, J=17.3 Hz, 1H), 5.83 (d, J=17.3 Hz, 1H), 6.49 (d, J=8.4 Hz, 1H), 7.57-7.68 (m, 2H), 7.70-7.87 (m, 2H), 8.42 (s, 1H), 9.03 (s, 2H), 10.43 (s, 1H). $^{19}$F NMR (376 MHz, DMSO) (major rotamer): δ -175.6.

(2S,4R)-1-(2-(3-Acetyl-5-(2-methylpyrimidin-5-yl)-1H-indazol-1-yl)acetyl)-4-fluoro-N-(6-methoxypyridin-2-yl)pyrrolidine-2-carboxamide (753)

Scheme 8-38

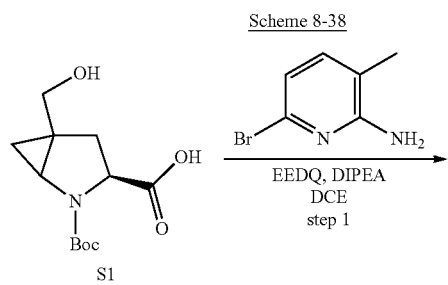

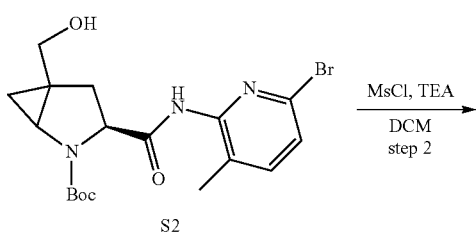

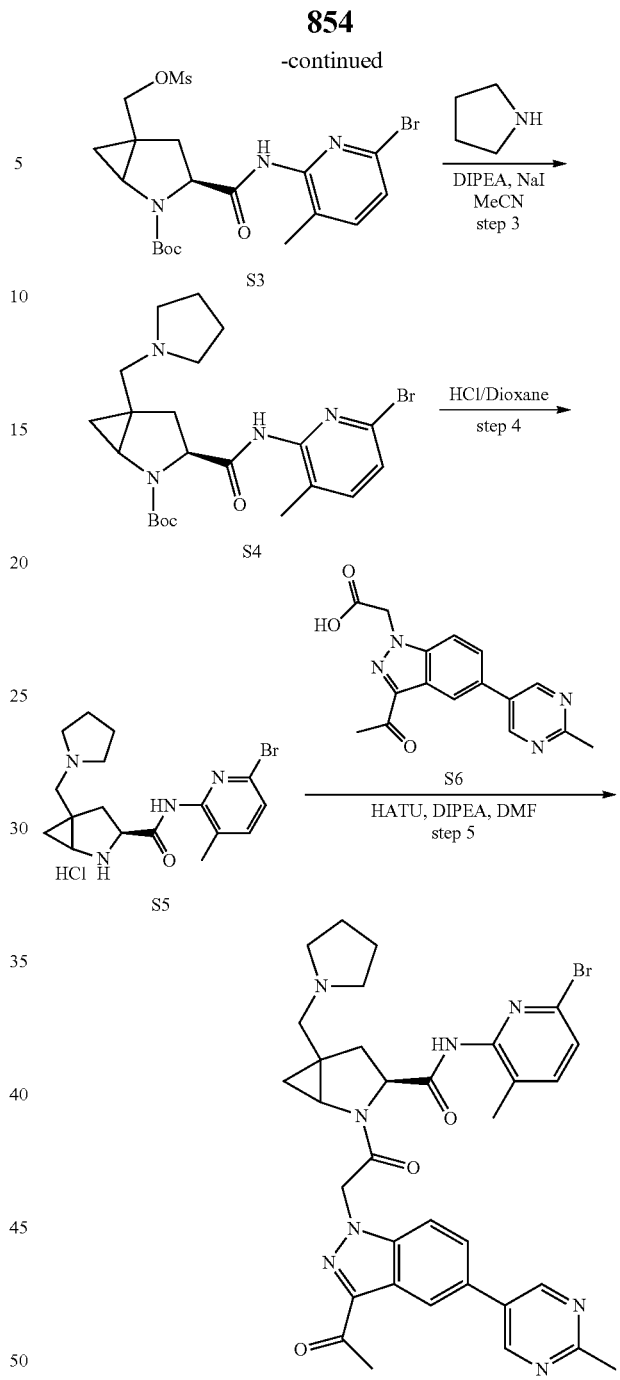

Step 1: (3S)-tert-Butyl 3-(6-bromo-3-methylpyridin-2-ylcarbamoyl)-5-(hydroxymethyl)-2-azabicyclo[3.1.0]hexane-2-carboxylate (S2)

To a solution of scheme 8-38 compound S1 (1 g, 3.89 mmol) and 6-bromo-3-methylpyridin-2-amine (870 mg, 4.67 mmol) in DCE (10 ml) was added DIPEA (2.56 mL, 15.56 mmol) and EEDQ (1.92 g, 7.78 mmol). The reaction was stirred at 90° C. overnight. The solvent was removed under vacuum. The residue was purified by column chromatography on silica gel (petroleum ether:ethyl acetate=2:1) to afford compound 2 (710 mg, 43.0% yield) as a white solid. LC/MS (ESI) m/z: 426 (M+H)$^+$.

Step 2: (3S)-tert-Butyl 3-(6-bromo-3-methylpyridin-2-ylcarbamoyl)-5-((methylsulfonyloxy)methyl)-2-azabicyclo[3.1.0]hexane-2-carboxylate (S3)

Methanesulfonyl chloride (0.08 mL, 1.05 mmol) was added to a solution of scheme 8-38 compound S2 (300 mg, 0.70 mmol) and triethylamine (0.19 mL, 1.41 mmol) in DCM (6 mL) dropwise at 0° C. After the addition was complete, the reaction was stirred at 0° C. for 2 hours. The mixture was poured into ice-water. The organic layer was separated, washed with brine, dried over anhydrous $Na_2SO_4$ and filtered. The filtrate was concentrated to afford the crude scheme 8-38 compound S3 (320 mg, 90.2% yield) as a yellow solid. The compound was carried forward without any further purification.

Step 3: (3S)-tert-Butyl 3-((6-bromo-3-methylpyridin-2-yl)carbamoyl)-5-(pyrrolidin-1-ylmethyl)-2-azabicyclo[3.1.0]hexane-2-carboxylate (S4)

To a mixture of (1R,3S,5S)-tert-butyl 3-((6-bromo-3-methylpyridin-2-yl)carbamoyl)-5-(((methylsulfonyl)oxy)methyl)-2-azabicyclo[3.1.0]hexane-2-carboxylate (25 mg, 0.05 mmol) in $CH_3CN$ (2 mL) was added DIPEA (0.035 mL, 0.2 mmol) and pyrrolidine (4 mg, 0.055 mmol). The reaction mixture was stirred at room temperature for 3 hours. The mixture was diluted with DCM and washed with water and brine. The organic layer was dried over anhydrous $Na_2SO_4$, filtered and concentrated to afford scheme 8-38 compound S4 (15 mg, 62.6% yield) as a brown solid. LC/MS (ESI) m/z: 479 (M+H)⁺.

Step 4: (3S)—N-(6-Bromo-3-methylpyridin-2-yl)-5-(pyrrolidin-1-ylmethyl)-2-azabicyclo[3.1.0]hexane-3-carboxamide (S5)

To a solution of (3S)-tert-butyl 3-((6-bromo-3-methylpyridin-2-yl)carbamoyl)-5-(pyrrolidin-1-ylmethyl)-2-azabicyclo[3.1.0]hexane-2-carboxylate (15 mg, 0.03 mmol) in dioxane (1 mL) was added HCl/dioxane (1 mL) at 0° C. The reaction was stirred at room temperature for 1 hour. The mixture was concentrated to afford scheme 8-38 compound S5 (17 mg, yield 100%) as a brown solid, which was directly used to the next reaction without further purification. LC/MS (ESI) m/z: 379 (M+H)⁺.

Step 5: (3S)-2-(2-(3-Acetyl-5-(2-methylpyrimidin-5-yl)-1H-indazol-1-yl)acetyl)-N-(6-bromo-3-methylpyridin-2-yl)-5-(pyrrolidin-1-ylmethyl)-2-azabicyclo[3.1.0]hexane-3-carboxamide (753)

To a mixture of 2-(3-acetyl-5-(1H-benzo[d]imidazol-2-yl)-1H-indazol-1-yl)acetic acid (17 mg, 0.03 mmol), 2-(3-acetyl-5-(2-methylpyrimidin-5-yl)-1H-indazol-1-yl)acetic acid (9.3 mg, 0.03 mmol) and HATU (22.8 mg, 0.06 mmol) in DMF (1 mL) was added DIPEA (0.09 mL, 0.02 mmol) at 0° C. The reaction mixture was stirred at room temperature overnight. The mixture was diluted with EtOAc and washed with 10% aqueous LiCl solution and brine. The organic layer was dried over anhydrous $Na_2SO_4$, filtered and concentrated. The residue was purified by prep HPLC to afford compound 753 (2.2 mg, 10.9% yield) as a white solid. ¹H-NMR (400 MHz, $CD_3OD$) δ 9.02 (s, 2H), 8.56 (s, 1H), 7.83 (d, J=3.7 Hz, 2H), 7.58 (d, J=7.8 Hz, 1H), 7.41 (d, J=8.0 Hz, 1H), 7.23 (s, 1H), 5.86 (d, J=17.3 Hz, 1H), 5.70 (s, 1H), 5.34 (t, J=4.7 Hz, 3H), 2.76 (s, 3H), 2.70 (d, J=3.3 Hz, 3H), 2.23-2.17 (m, 3H), 2.13 (s, 5H), 2.03 (s, 4H), 1.60 (s, 4H), 0.91 (s, 2H). LC/MS (ESI) m/z: 671 (M+H)⁺.

Example 7. Non-Limiting Examples of Compounds of Formula I

Table 1 shows illustrative compounds of Formula I with characterizing data. The compounds of Table 1 are described in PCT Patent Application No. PCT/US2015/017593 and U.S. patent application Ser. No. 14/631,625 titled "Aryl, Heteroaryl, and Heterocyclic Compounds for Treatment of Complement Mediated Disorders." The assay of Example 8 was used to determine the $IC_{50}$'s of the compounds. Other standard Factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 1

Non-limiting Examples of Compounds of Formula I

| Cmp No. | Structure | Name | $IC_{50}$ | RT min (Method A or B) | MS (M + 1) |
|---|---|---|---|---|---|
| 1 | 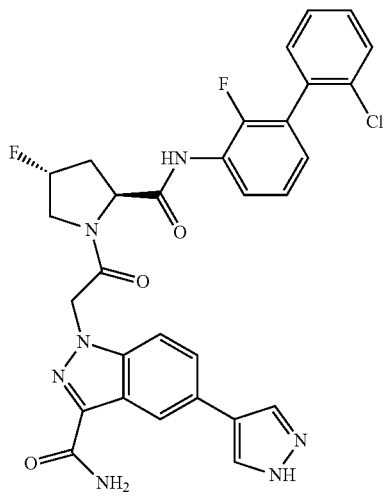 [SMILES: NC(=O)c1nn(CC(=O)N2C[C@H](F)C[C@H]2C(=O)Nc2cccc(-c3ccccc3Cl)c2F)c2ccc(-c3cn[nH]c3)cc12] | 1-(2-((2S,4R)-2-(2'-chloro-2-fluorobiphenyl-3-ylcarbamoyl)-4-fluoropyrrolidin-1-yl)-2-oxoethyl)-5-(1H-pyrazol-4-yl)-1H-indazole-3-carboxamide | *** | 1.79 (A) | 604 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 2 | 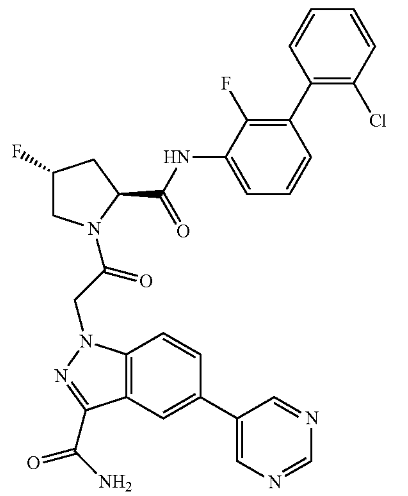 [SMILES: NC(=O)c1nn(CC(=O)N2C[C@H](F)C[C@H]2C(=O)Nc2cccc(-c3ccccc3Cl)c2F)c2ccc(-c3cncnc3)cc12] | 1-(2-((2S,4R)-2-(2'-chloro-2-fluorobiphenyl-3-ylcarbamoyl)-4-fluoropyrrolidin-1-yl)-2-oxoethyl)-5-(pyrimidin-5-yl)-1H-indazole-3-carboxamide | *** | 1.82 (A) | 616 |
| 3 | 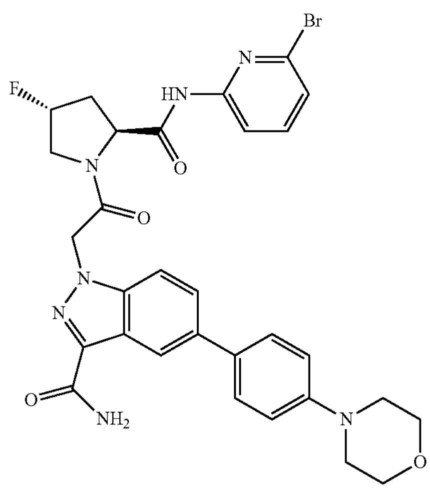 [SMILES: NC(=O)c1nn(CC(=O)N2C[C@H](F)C[C@H]2C(=O)Nc2cccc(Br)n2)c2ccc(-c3ccc(N4CCOCC4)cc3)cc12] | 1-(2-((2S,4R)-2-(6-bromopyridin-2-ylcarbamoyl)-4-fluoropyrrolidin-1-yl)-2-oxoethyl)-5-(4-morpholinophenyl)-1H-indazole-3-carboxamide | *** | 1.82 (A) | 650 |
| 4 | 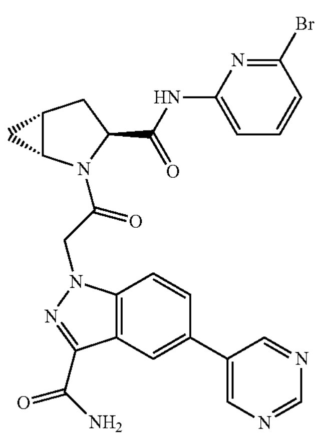 [SMILES: NC(=O)c1nn(CC(=O)N2[C@@H]3C[C@@H]3C[C@H]2C(=O)Nc2cccc(Br)n2)c2ccc(-c3cncnc3)cc12] | 1-(2-((1R,3S,5R)-3-(6-bromopyridin-2-ylcarbamoyl)-2-azabicyclo[3.1.0]hexan-2-yl)-2-oxoethyl)-5-(pyrimidin-5-yl)-1H-indazole-3-carboxamide | *** | 1.42 (A) | 561 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 5 | 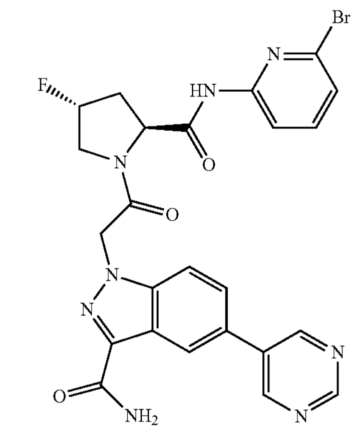 | 1-(2-((2S,4R)-2-(6-bromopyridin-2-ylcarbamoyl)-4-fluoropyrrolidin-1-yl)-2-oxoethyl)-5-(pyrimidin-5-yl)-1H-indazole-3-carboxamide | *** | 1.30 (A) | 567 |
| 6 | 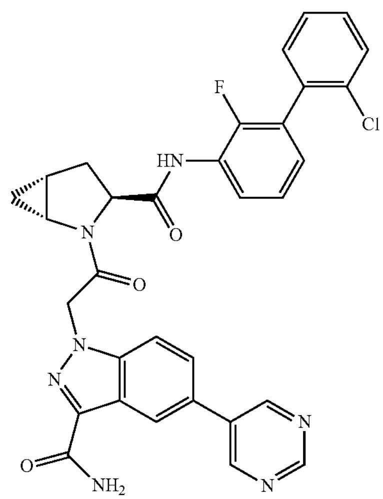 [SMILES: NC(=O)c1nn(CC(=O)N2[C@@H]3C[C@@H]3C[C@H]2C(=O)Nc2cccc(-c3ccccc3Cl)c2F)c2ccc(-c3cncnc3)cc12] | 1-(2-((1R,3S,5R)-3-(2'-chloro-2-fluorobiphenyl-3-ylcarbamoyl)-2-azabicyclo[3.1.0]hexan-2-yl)-2-oxoethyl)-5-(pyrimidin-5-yl)-1H-indazole-3-carboxamide | *** | 1.96 (A) | 610 |
| 7 | 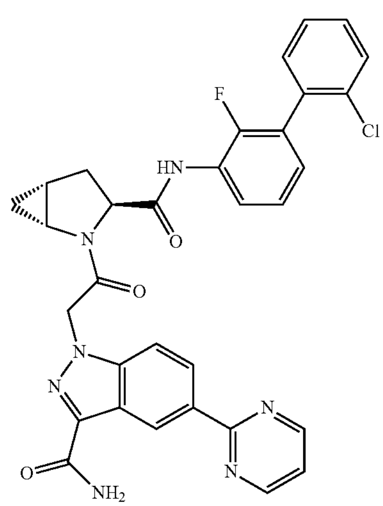 [SMILES: NC(=O)c1nn(CC(=O)N2[C@@H]3C[C@@H]3C[C@H]2C(=O)Nc2cccc(-c3ccccc3Cl)c2F)c2ccc(-c3ncccn3)cc12] | 1-(2-((1R,3S,5R)-3-(2'-chloro-2-fluorobiphenyl-3-ylcarbamoyl)-2-azabicyclo[3.1.0]hexan-2-yl)-2-oxoethyl)-5-(pyrimidin-2-yl)-1H-indazole-3-carboxamide | *** | 2.15 (A) | 610 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 8 | 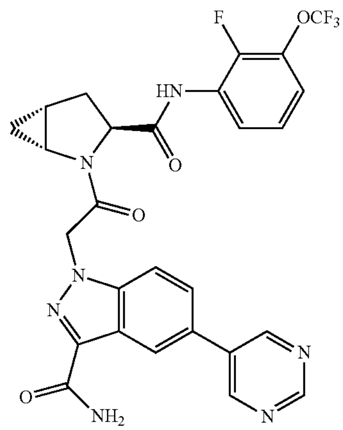 [SMILES: NC(=O)c1nn(CC(=O)N2[C@@H]3C[C@@H]3C[C@H]2C(=O)Nc2cccc(OC(F)(F)F)c2F)c2ccc(-c3cncnc3)cc12] | 1-(2-((1R,3S,5R)-3-(2-fluoro-3-(trifluoromethoxy)phenylcarbamoyl)-2-azabicyclo[3.1.0]hexan-2-yl)-2-oxoethyl)-5-(pyrimidin-5-yl)-1H-indazole-3-carboxamide | *** | 1.74 (A) | 584 |
| 9 | 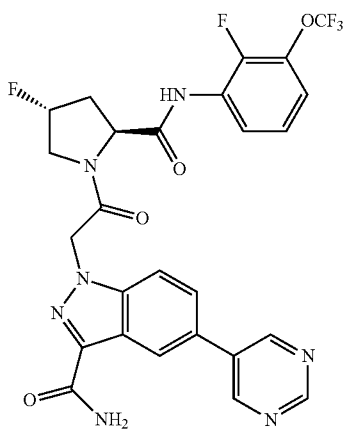 [SMILES: NC(=O)c1nn(CC(=O)N2C[C@H](F)C[C@H]2C(=O)Nc2cccc(OC(F)(F)F)c2F)c2ccc(-c3cncnc3)cc12] | 1-(2-((2S,4R)-4-fluoro-2-(2-fluoro-3-(trifluoromethoxy)phenylcarbamoyl)pyrrolidin-1-yl)-2-oxoethyl)-5-(pyrimidin-5-yl)-1H-indazole-3-carboxamide | *** | 1.64 (A) | 590 |
| 10 | 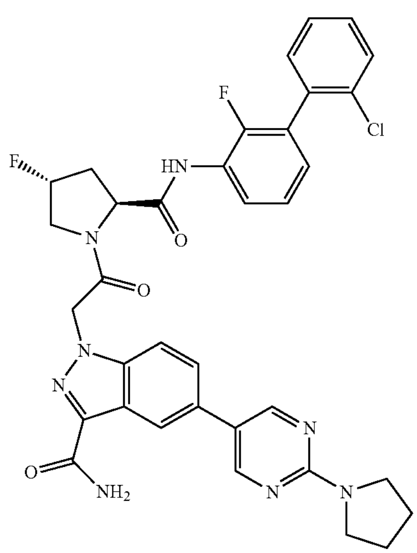 [SMILES: NC(=O)c1nn(CC(=O)N2C[C@H](F)C[C@H]2C(=O)Nc2cccc(-c3ccccc3Cl)c2F)c2ccc(-c3cnc(N4CCCC4)nc3)cc12] | 1-(2-((2S,4R)-2-(2'-chloro-2-fluorobiphenyl-3-ylcarbamoyl)-4-fluoropyrrolidin-1-yl)-2-oxoethyl)-5-(2-(pyrrolidin-1-yl)pyrimidin-5-yl)-1H-indazole-3-carboxamide | *** | 2.33 (A) | 685 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 11 | 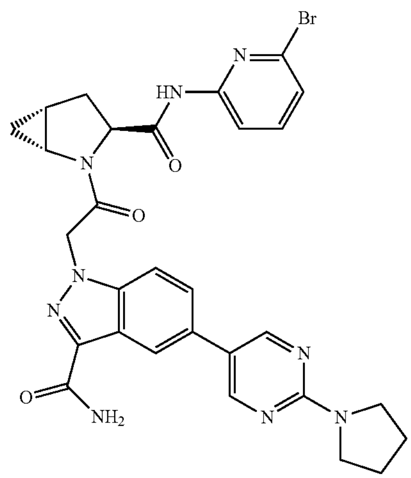 [SMILES: NC(=O)c1nn(CC(=O)N2[C@@H]3C[C@@H]3C[C@H]2C(=O)Nc2cccc(Br)n2)c2ccc(-c3cnc(N4CCCC4)nc3)cc12] | 1-(2-(((1R,3S,5R)-3-(6-bromopyridin-2-ylcarbamoyl)-2-azabicyclo[3.1.0]hexan-2-yl)-2-oxoethyl)-5-(2-(pyrrolidin-1-yl)pyrimidin-5-yl)-1H-indazole-3-carboxamide | *** | 1.82 (A) | 630 |
| 12 | 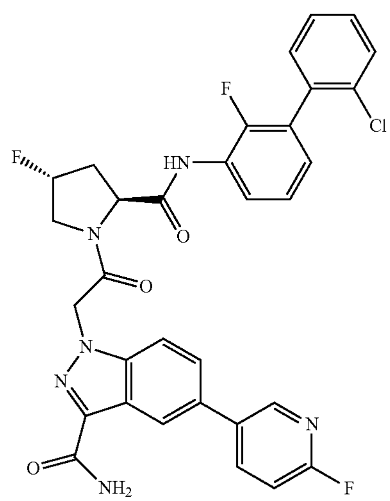 [SMILES: NC(=O)c1nn(CC(=O)N2C[C@H](F)C[C@H]2C(=O)Nc2cccc(-c3ccccc3Cl)c2F)c2ccc(-c3ccc(F)nc3)cc12] | 1-(2-((2S,4R)-2-(2'-chloro-2-fluorobiphenyl-3-ylcarbamoyl)-4-fluoropyrrolidin-1-yl)-2-oxoethyl)-5-(6-fluoropyridin-3-yl)-1H-indazole-3-carboxamide | *** | 2.43 (A) | 633 |
| 13 | 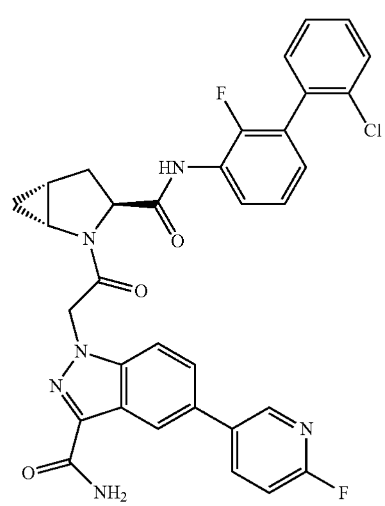 [SMILES: NC(=O)c1nn(CC(=O)N2[C@@H]3C[C@@H]3C[C@H]2C(=O)Nc2cccc(-c3ccccc3Cl)c2F)c2ccc(-c3ccc(F)nc3)cc12] | 1-(2-(((1R,3S,5R)-3-(2'-chloro-2-fluorobiphenyl-3-ylcarbamoyl)-2-azabicyclo[3.1.0]hexan-2-yl)-2-oxoethyl)-5-(6-fluoropyridin-3-yl)-1H-indazole-3-carboxamide | *** | 2.53 (A) | 627 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 14 | 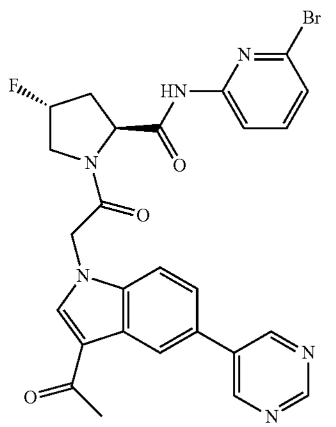 [SMILES: CC(=O)c1cn(CC(=O)N2C[C@H](F)C[C@H]2C(=O)Nc2cccc(Br)n2)c2ccc(-c3cncnc3)cc12] | (2S,4R)-1-(2-(3-acetyl-5-(pyrimidin-5-yl)-1H-indol-1-yl)acetyl)-N-(6-bromopyridin-2-yl)-4-fluoropyrrolidine-2-carboxamide | *** | 2.04 (A) | 565 |
| 15 | 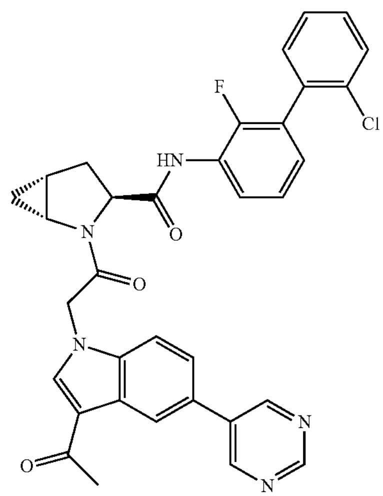 [SMILES: CC(=O)c1cn(CC(=O)N2[C@@H]3C[C@@H]3C[C@H]2C(=O)Nc2cccc(-c3ccccc3Cl)c2F)c2ccc(-c3cncnc3)cc12] | (1R,3S,5R)-2-(2-(3-acetyl-5-(pyrimidin-5-yl)-1H-indol-1-yl)acetyl)-N-(2'-chloro-2-fluorobiphenyl-3-yl)-2-azabicyclo[3.1.0]hexane-3-carboxamide | *** | 2.63 (A) | 608 |
| 16 | 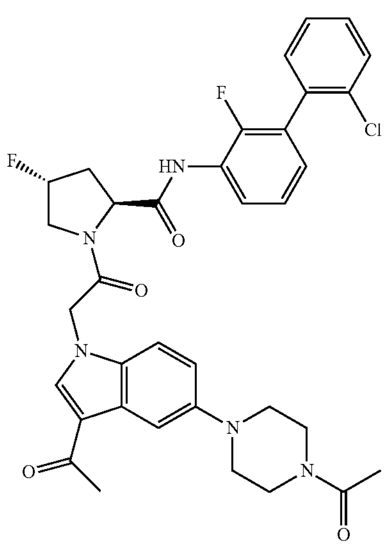 [SMILES: CC(=O)c1cn(CC(=O)N2C[C@H](F)C[C@H]2C(=O)Nc2cccc(-c3ccccc3Cl)c2F)c2ccc(N3CCN(C(C)=O)CC3)cc12] | (2S,4R)-1-(2-(3-acetyl-5-(4-acetylpiperazin-1-yl)-1H-indol-1-yl)acetyl)-N-(2'-chloro-2-fluorobiphenyl-3-yl)-4-fluoropyrrolidine-2-carboxamide | *** | 2.30 (A) | 664 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 17 | 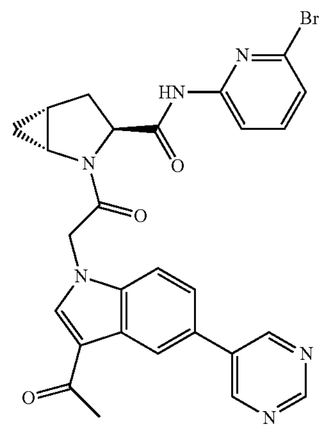 [SMILES: CC(=O)c1cn(CC(=O)N2[C@@H]3C[C@@H]3C[C@H]2C(=O)Nc2cccc(Br)n2)c2ccc(-c3cncnc3)cc12] | (1R,3S,5R)-2-(2-(3-acetyl-5-(pyrimidin-5-yl)-1H-indol-1-yl)acetyl)-N-(6-bromopyridin-2-yl)2-azabicyclo[3.1.0]hexane-3-carboxamide | *** | 2.44 (A) | 559 |
| 18 | 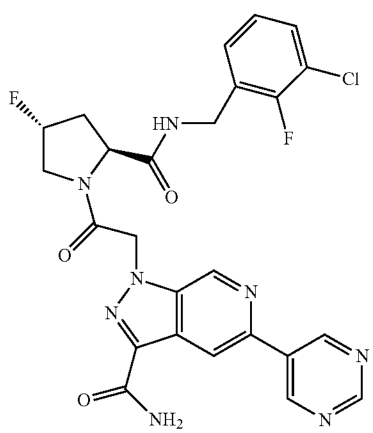 [SMILES: NC(=O)c1nn(CC(=O)N2C[C@H](F)C[C@H]2C(=O)NCc2cccc(Cl)c2F)c2cnc(-c3cncnc3)cc12] | 1-(2-((2S,4R)-2-(3-chloro-2-fluorobenzyl-carbamoyl)-4-fluoropyrrolidin-1-yl)-2-oxoethyl)-5-(pyrimidin-5-yl)-1H-pyrazolo[3,4-c]pyridine-3-carboxamide | *** | 1.75 (A) | 555 |
| 19 | 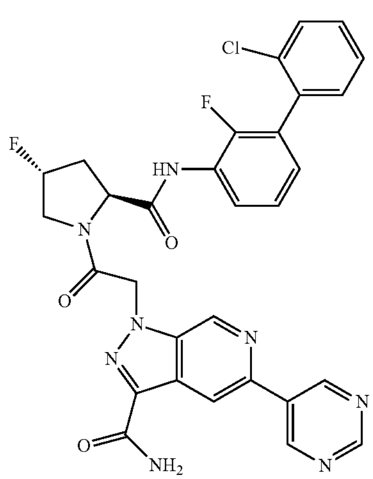 [SMILES: NC(=O)c1nn(CC(=O)N2C[C@H](F)C[C@H]2C(=O)Nc2cccc(-c3ccccc3Cl)c2F)c2cnc(-c3cncnc3)cc12] | 1-(2-((2S,4R)-2-(2'-chloro-2-fluorobiphenyl-3-ylcarbamoyl)-4-fluoropyrrolidin-1-yl)-2-oxoethyl)-5-(pyrimidin-5-yl)-1H-pyrazolo[3,4-c]pyridine-3-carboxamide | *** | 2.47 (A) | 617 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 20 | 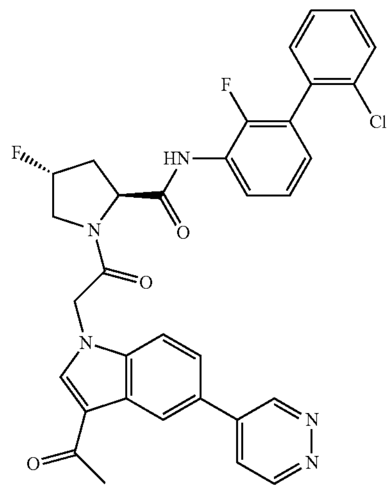 [SMILES: CC(=O)c1cn(CC(=O)N2C[C@H](F)C[C@H]2C(=O)Nc2cccc(-c3ccccc3Cl)c2F)c2ccc(-c3ccnnc3)cc12] | (2S,4R)-1-(2-(3-acetyl-5-(pyridazin-4-yl)-1H-indol-1-yl)acetyl)-N-(2'-chloro-2-fluorobiphenyl-3-yl)-4-fluoropyrrolidine-2-carboxamide | *** | 2.58 (A) | 614 |
| 21 | 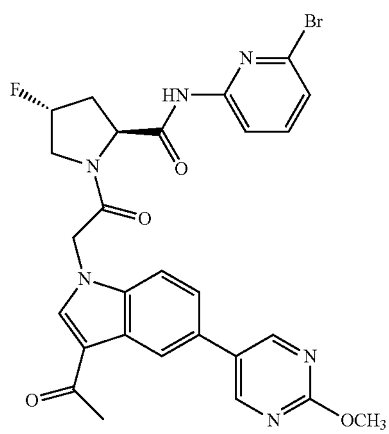 [SMILES: COc1ncc(-c2ccc3c(c2)c(C(C)=O)cn3CC(=O)N2C[C@H](F)C[C@H]2C(=O)Nc2cccc(Br)n2)cn1] | (2S,4R)-1-(2-(3-acetyl-5-(2-methoxypyrimidin-5-yl)-1H-indol-1-yl)acetyl)-N-(6-bromopyridin-2-yl)-4-fluoropyrrolidine-2-carboxamide | *** | 2.05 (A) | 595 |
| 22 | 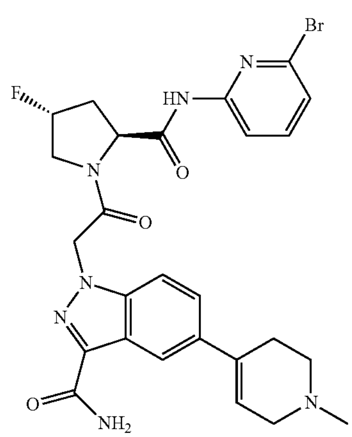 | 1-(2-((2S,4R)-2-(6-bromopyridin-2-ylcarbamoyl)-4-fluoropyrrolidin-1-yl)-2-oxoethyl)-5-(1-methyl-1,2,3,6-tetrahydropyridin-4-yl)-1H-indazole-3-carboxamide | *** | 1.19 (A) | 586 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 23 | 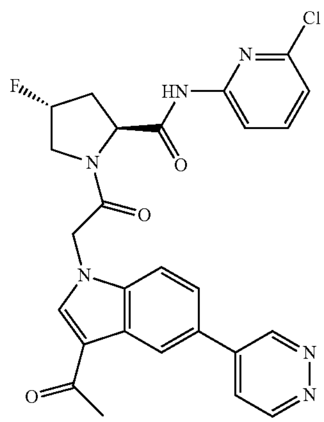 [SMILES: CC(=O)c1cn(CC(=O)N2C[C@H](F)C[C@H]2C(=O)Nc2cccc(Cl)n2)c2ccc(-c3ccnnc3)cc12] | (2S,4R)-1-(2-(3-acetyl-5-(pyridazin-4-yl)-1H-indol-1-yl)acetyl)-N-(6-chloropyridin-2-yl)-4-fluoropyrrolidine-2-carboxamide | *** | 2.24 (A) | 520 |
| 24 | 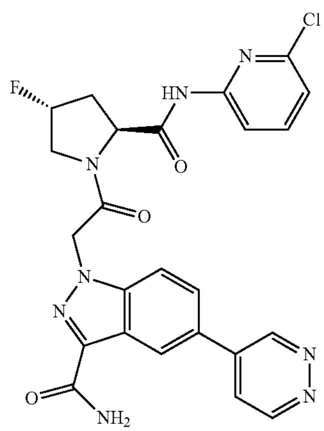 [SMILES: NC(=O)c1nn(CC(=O)N2C[C@H](F)C[C@H]2C(=O)Nc2cccc(Cl)n2)c2ccc(-c3ccnnc3)cc12] | 1-(2-((2S,4R)-2-(6-chloropyridin-2-ylcarbamoyl)-4-fluoropyrrolidin-1-yl)-2-oxoethyl)-5-(pyridazin-4-yl)-1H-indazole-3-carboxamide | *** | 2.23 (A) | 522 |
| 25 | 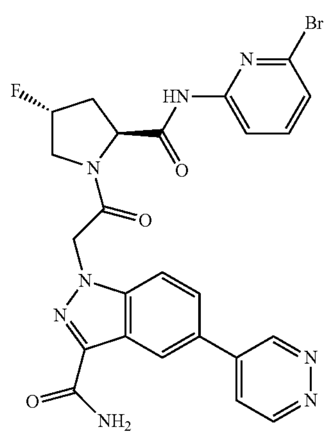 [SMILES: NC(=O)c1nn(CC(=O)N2C[C@H](F)C[C@H]2C(=O)Nc2cccc(Br)n2)c2ccc(-c3ccnnc3)cc12] | 1-(2-((2S,4R)-2-(6-bromopyridin-2-ylcarbamoyl)-4-fluoropyrrolidin-1-yl)-2-oxoethyl)-5-(pyridazin-4-yl)-1H-indazole-3-carboxamide | *** | 1.60 (A) | 567 |

TABLE 1-continued
Non-limiting Examples of Compounds of Formula I
| Cmp No. | Structure | Name | IC$_{50}$ | RT min (Method A or B) | MS (M + 1) |
|---|---|---|---|---|---|
| 26 | 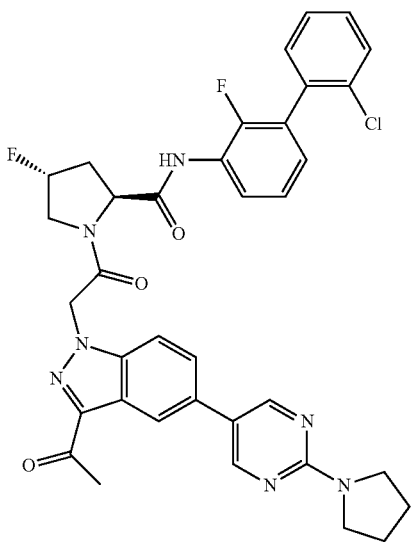 [SMILES: CC(=O)c1nn(CC(=O)N2C[C@H](F)C[C@H]2C(=O)Nc2cccc(-c3ccccc3Cl)c2F)c2ccc(-c3cnc(N4CCCC4)nc3)cc12] | (2S,4R)-1-(2-(3-acetyl-5-(2-(pyrrolidin-1-yl)pyrimidin-5-yl)-1H-indol-1-yl)acetyl)-N-(2'-chloro-2-fluorobiphenyl-3-yl)-4-fluoropyrrolidine-2-carboxamide | *** | 2.42 (A) | 683 |
| 27 | 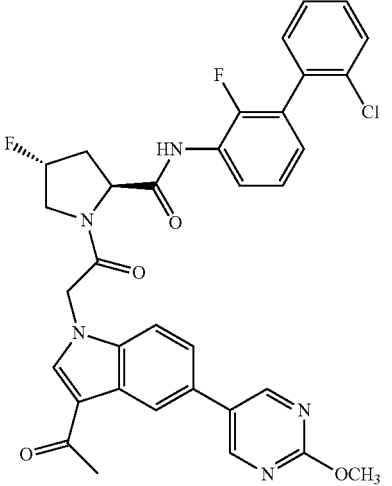 | (2S,4R)-1-(2-(3-acetyl-5-(2-methoxypyrimidin-5-yl)-1H-indol-1-yl)acetyl)-N-(2'-chloro-2-fluorobiphenyl-3-yl)-4-fluoropyrrolidine-2-carboxamide | *** | 2.16 (A) | 644 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 28 | 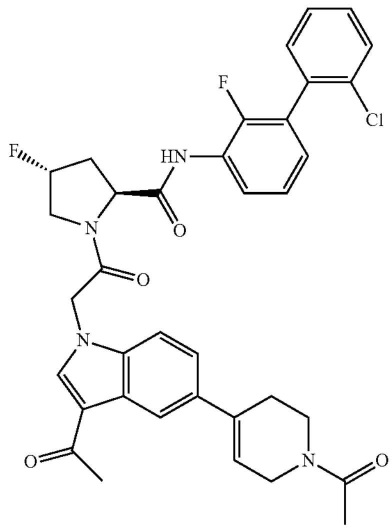 [SMILES: CC(=O)c1cn(CC(=O)N2C[C@H](F)C[C@H]2C(=O)Nc2cccc(-c3ccccc3Cl)c2F)c2ccc(C3=CCN(C(C)=O)CC3)cc12] | (2S,4R)-1-(2-(3-acetyl-5-(1-acetyl-1,2,3,6-tetrahydropyridin-4-yl)-1H-indol-1-yl)acetyl)-N-(2'-chloro-2-fluorobiphenyl-3-yl)-4-fluoropyrrolidine-2-carboxamide | *** | 2.07 (A) | 659 |
| 29 | 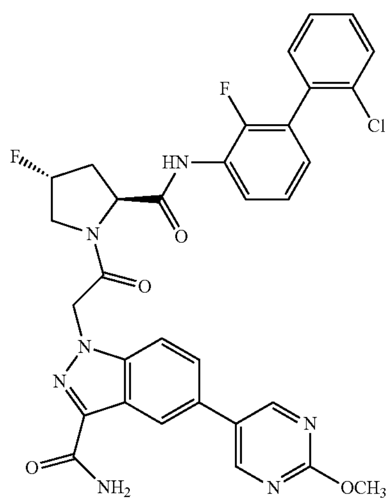 [SMILES: COc1ncc(-c2ccc3c(c2)c(C(N)=O)nn3CC(=O)N2C[C@H](F)C[C@H]2C(=O)Nc2cccc(-c3ccccc3Cl)c2F)cn1] | 1-(2-((2S,4R)-2-(2'-chloro-2-fluorobiphenyl-3-ylcarbamoyl)-4-fluoropyrrolidin-1-yl)-2-oxoethyl)-5-(2-methoxypyrimidin-5-yl)-1H-indazole-3-carboxamide | *** | 2.01 (A) | 646 |
| 30 | 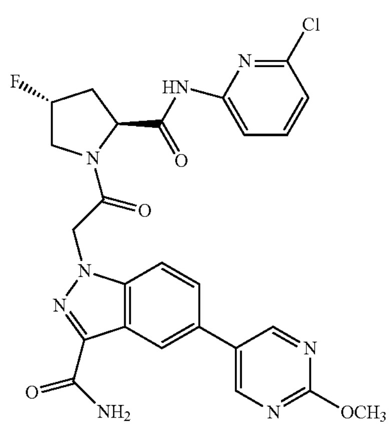 [SMILES: COc1ncc(-c2ccc3c(c2)c(C(N)=O)nn3CC(=O)N2C[C@H](F)C[C@H]2C(=O)Nc2cccc(Cl)n2)cn1] | 1-(2-((2S,4R)-2-(6-chloropyridin-2-ylcarbamoyl)-4-fluoropyrrolidin-1-yl)-2-oxoethyl)-5-(2-methoxypyrimidin-5-yl)-1H-indazole-3-carboxamide | *** | 1.43 (A) | 553 |

TABLE 1-continued
Non-limiting Examples of Compounds of Formula I
| Cmp No. | Structure | Name | IC$_{50}$ | RT min (Method A or B) | MS (M + 1) |
|---|---|---|---|---|---|
| 31 | 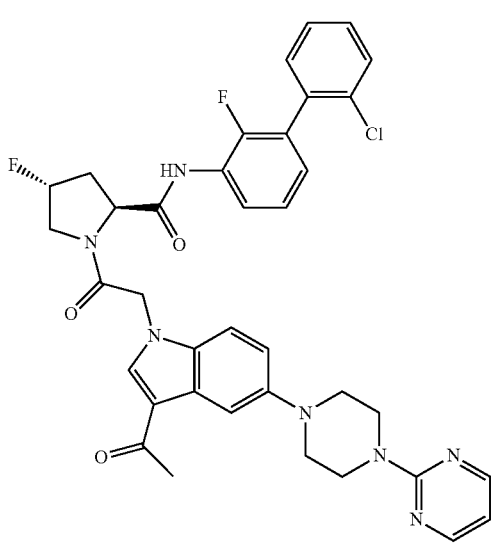 [SMILES: CC(=O)c1cn(CC(=O)N2C[C@H](F)C[C@H]2C(=O)Nc2cccc(-c3ccccc3Cl)c2F)c2ccc(N3CCN(c4ncccn4)CC3)cc12] | (2S,4R)-1-(2-(3-acetyl-5-(4-(pyrimidin-2-yl)piperazin-1-yl)-1H-indol-1-yl)acetyl)-N-(2'-chloro-2-fluorobiphenyl-3-yl)-4-fluoropyrrolidine-2-carboxamide | *** | 2.21 (A) | 698 |
| 32 | 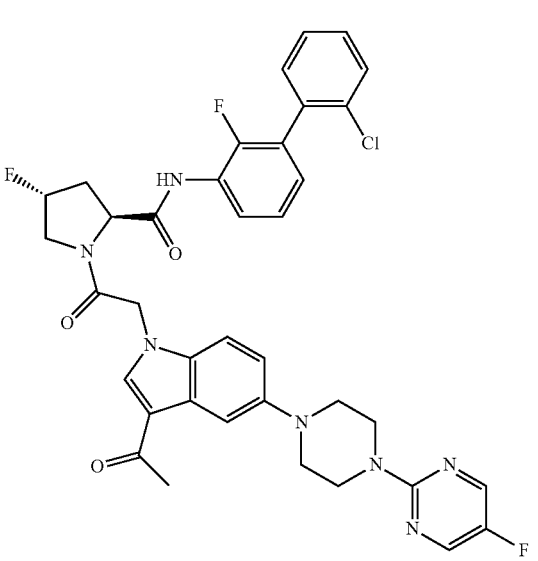 [SMILES: CC(=O)c1cn(CC(=O)N2C[C@H](F)C[C@H]2C(=O)Nc2cccc(-c3ccccc3Cl)c2F)c2ccc(N3CCN(c4ncc(F)cn4)CC3)cc12] | (2S,4R)-1-(2-(3-acetyl-5-(4-(5-fluoropyrimidin-2-yl)piperazin-1-yl)-1H-indol-1-yl)acetyl)-N-(2'-chloro-2-fluorobiphenyl-3-yl)-4-fluoropyrrolidine-2-carboxamide | *** | 2.43 (A) | 716 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 33 | 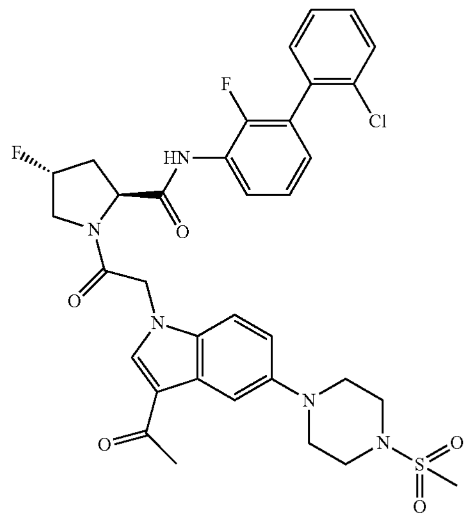 [SMILES: CC(=O)c1cn(CC(=O)N2C[C@H](F)C[C@H]2C(=O)Nc2cccc(-c3ccccc3Cl)c2F)c2ccc(N3CCN(S(C)(=O)=O)CC3)cc12] | (2S,4R)-1-(2-(3-acetyl-5-(4-(methylsulfonyl)piperazin-1-yl)-1H-indol-1-yl)acetyl)-N-(2'-chloro-2-fluorobiphenyl-3-yl)-4-fluoropyrrolidine-2-carboxamide | *** | 2.09 (A) | 698 |
| 34 | 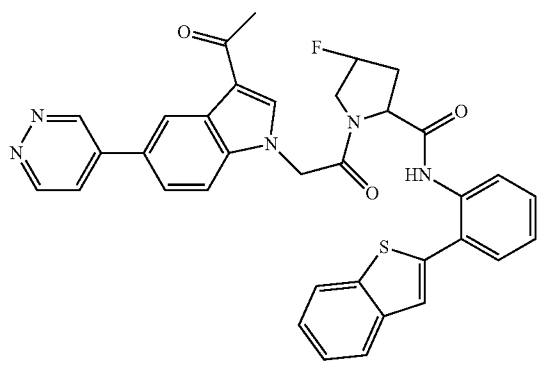 [SMILES: CC(=O)c1cn(CC(=O)N2CC(F)CC2C(=O)Nc2ccccc2-c2cc3ccccc3s2)c2ccc(-c3ccnnc3)cc12] | (2S,4R)-1-(2-(3-acetyl-5-(pyridazin-4-yl)-1H-indol-1-yl)acetyl)-N-(2-(benzo[d]thiazol-2-yl)phenyl)-4-fluoropyrrolidine-2-carboxamide | * | 3.91 (B) | 619 |
| 35 | 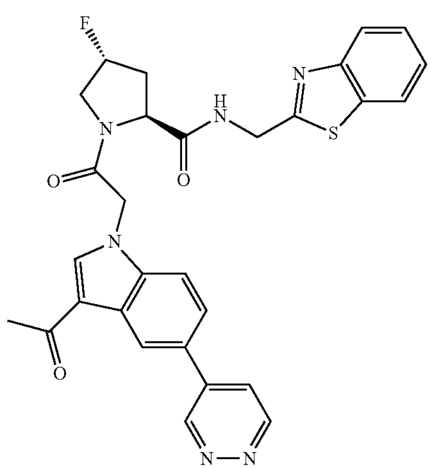 [SMILES: CC(=O)c1cn(CC(=O)N2C[C@H](F)C[C@H]2C(=O)NCc2nc3ccccc3s2)c2ccc(-c3ccnnc3)cc12] | (2S,4R)-1-(2-(3-acetyl-5-(pyridazin-4-yl)-1H-indol-1-yl)acetyl)-N-(benzo[d]thiazol-2-ylmethyl)-4-fluoropyrrolidine-2-carboxamide | ** | 2.33 (B) | 557 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 36 | 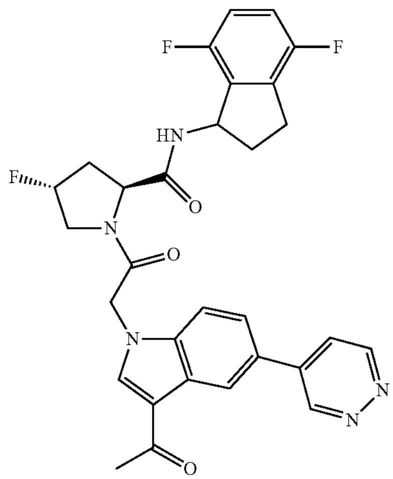 [SMILES: CC(=O)c1cn(CC(=O)N2C[C@H](F)C[C@H]2C(=O)NC2CCc3c(F)ccc(F)c32)c2ccc(-c3ccnnc3)cc12] | (2S,4R)-1-(2-(3-acetyl-5-(pyridazin-4-yl)-1H-indol-1-yl)acetyl)-N-(4,7-difluoro-2,3-dihydro-1H-inden-1-yl)-4-fluoropyrrolidine-2-carboxamide | ** | 2.89 (B) | 562 |
| 37 | 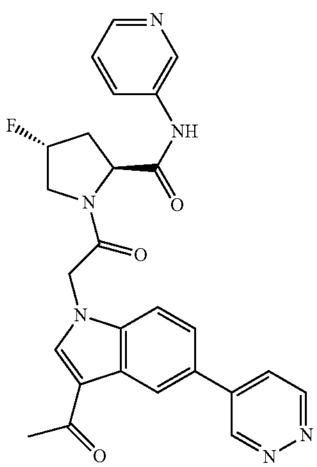 [SMILES: CC(=O)c1cn(CC(=O)N2C[C@H](F)C[C@H]2C(=O)Nc2cccnc2)c2ccc(-c3ccnnc3)cc12] | (2S,4R)-1-(2-(3-acetyl-5-(pyridazin-4-yl)-1H-indol-1-yl)acetyl)-4-fluoro-N-(pyridin-3-yl)pyrrolidine-2-carboxamide | ** | 2.08 (B) | 487 |
| 38 | 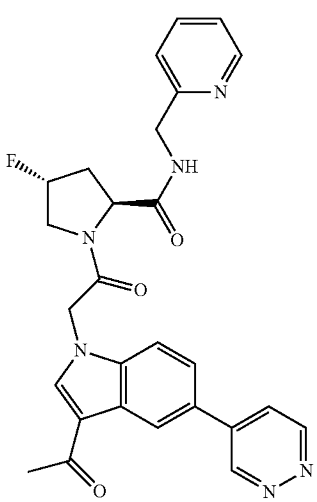 [SMILES: CC(=O)c1cn(CC(=O)N2C[C@H](F)C[C@H]2C(=O)NCc2ccccn2)c2ccc(-c3ccnnc3)cc12] | (2S,4R)-1-(2-(3-acetyl-5-(pyridazin-4-yl)-1H-indol-1-yl)acetyl)-4-fluoro-N-(pyridin-2-ylmethyl)pyrrolidine-2-carboxamide | *** | 2.03 (B) | 501 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 39 | 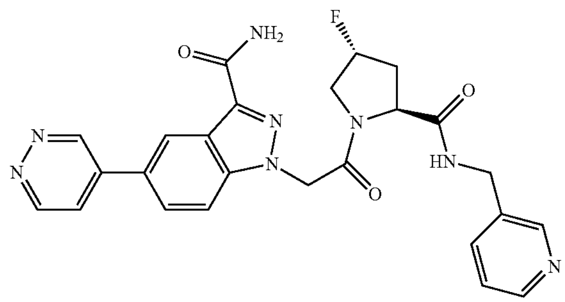 [SMILES: NC(=O)c1nn(CC(=O)N2C[C@H](F)C[C@H]2C(=O)NCc2cccnc2)c2ccc(-c3ccnnc3)cc12] | 1-(2-((2S,4R)-4-fluoro-2-(pyridin-3-ylmethylcarbamoyl)pyrrolidin-1-yl)-2-oxoethyl)-5-(pyridazin-4-yl)-1H-indazole-3-carboxamide | ** | 2.77 (B) | 503 |
| 40 | 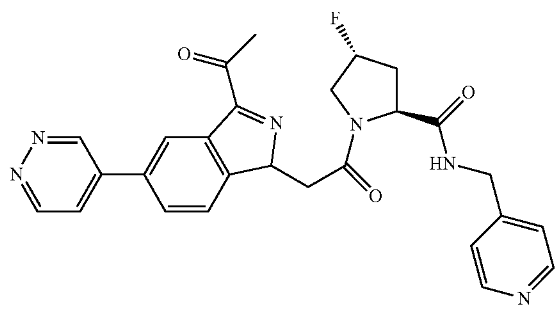 [SMILES: CC(=O)C1=NC(CC(=O)N2C[C@H](F)C[C@H]2C(=O)NCc2ccncc2)c2ccc(-c3ccnnc3)cc21] | (2S,4R)-1-(2-(3-acetyl-5-(pyridazin-4-yl)-1H-indol-1-yl)acetyl)-4-fluoro-N-(pyridin-4-ylmethyl)pyrrolidine-2-carboxamide | ** | 0.58 (B) | 501 |
| 41 | 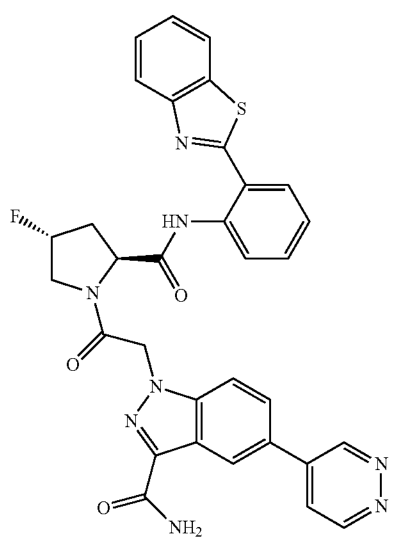 [SMILES: NC(=O)c1nn(CC(=O)N2C[C@H](F)C[C@H]2C(=O)Nc2ccccc2-c2nc3ccccc3s2)c2ccc(-c3ccnnc3)cc12] | 1-(2-((2S,4R)-2-(2-(benzo[d]thiazol-2-yl)phenylcarbamoyl)-4-fluoropyrrolidin-1-yl)-2-oxoethyl)-5-(pyridazin-4-yl)-1H-indazole-3-carboxamide | * | 3.49 (B) | 621 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 42 | 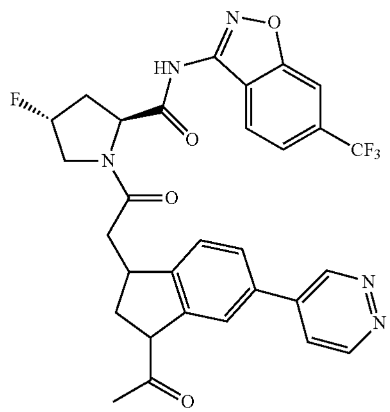 [SMILES: CC(=O)C1CC(CC(=O)N2C[C@H](F)C[C@H]2C(=O)Nc2noc3cc(C(F)(F)F)ccc23)c2ccc(-c3ccnnc3)cc21] | (2S,4R)-1-(2-(3-acetyl-5-(pyridazin-4-yl)-1H-indol-1-yl)acetyl)-4-fluoro-N-(6-(trifluoromethyl)benzo[d]isoxazol-3-yl)pyrrolidine-2-carboxamide | * | 3.24 (B) | 595 |
| 43 | 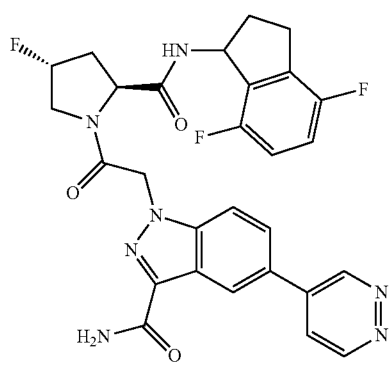 [SMILES: NC(=O)c1nn(CC(=O)N2C[C@H](F)C[C@H]2C(=O)NC2CCc3c(F)ccc(F)c32)c2ccc(-c3ccnnc3)cc12] | 1-(2-((2S,4R)-2-(4,7-difluoro-2,3-dihydro-1H-inden-1-ylcarbamoyl)-4-fluoropyrrolidin-1-yl)-2-oxoethyl)-5-(pyridazin-4-yl)-1H-indazole-3-carboxamide | ** | 2.69 (B) | 564 |
| 44 | 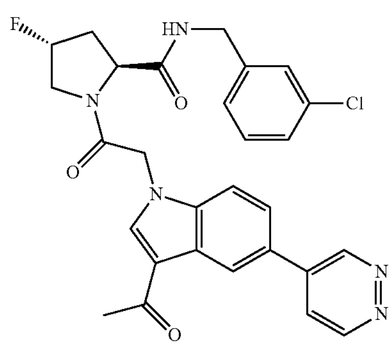 [SMILES: CC(=O)c1cn(CC(=O)N2C[C@H](F)C[C@H]2C(=O)NCc2cccc(Cl)c2)c2ccc(-c3ccnnc3)cc12] | (2S,4R)-1-(2-(3-acetyl-5-(pyridazin-4-yl)-1H-indol-1-yl)acetyl)-N-(3-chlorobenzyl)-4-fluoropyrrolidine-2-carboxamide | *** | 2.78 (B) | 534 |
| 45 | 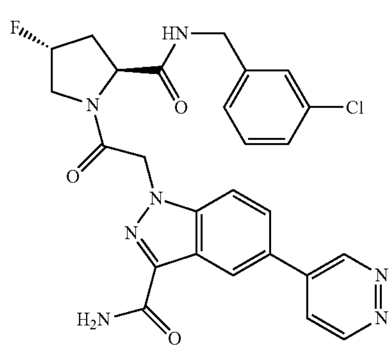 [SMILES: NC(=O)c1nn(CC(=O)N2C[C@H](F)C[C@H]2C(=O)NCc2cccc(Cl)c2)c2ccc(-c3ccnnc3)cc12] | 1-(2-((2S,4R)-2-(3-chlorobenzyl carbamoyl)-4-fluoropyrrolidin-1-yl)-2-oxoethyl)-5-(pyridazin-4-yl)-1H-indazole-3-carboxamide | *** | 2.48 (B) | 536 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 46 | 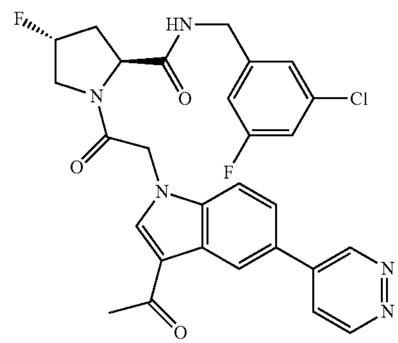 [SMILES: CC(=O)c1cn(CC(=O)N2C[C@H](F)C[C@H]2C(=O)NCc2cc(F)cc(Cl)c2)c2ccc(-c3ccnnc3)cc12] | (2S,4R)-1-(2-(3-acetyl-5-(pyridazin-4-yl)-1H-indol-1-yl)acetyl)-N-(3-chloro-5-fluorobenzyl)-4-fluoropyrrolidine-2-carboxamide | *** | 2.98 (B) | 552 |
| 47 | 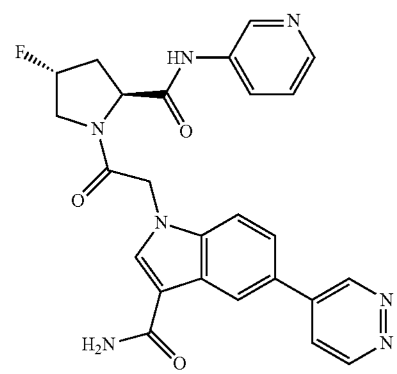 [SMILES: NC(=O)c1cn(CC(=O)N2C[C@H](F)C[C@H]2C(=O)Nc2cccnc2)c2ccc(-c3ccnnc3)cc12] | 1-(2-((2S,4R)-4-fluoro-2-(pyridin-3-ylcarbamoyl)pyrrolidin-1-yl)-2-oxoethyl)-5-(pyridazin-4-yl)-1H-indazole-3-carboxamide | * | 3.34 (B) | 489 |
| 48 | 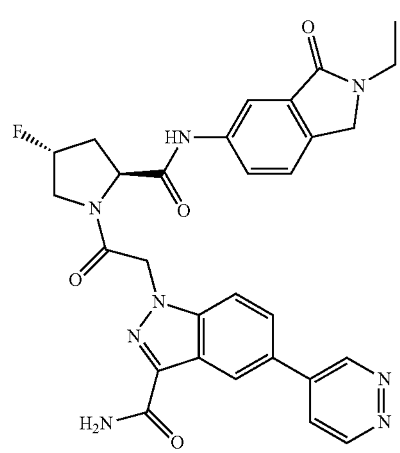 [SMILES: CCN1Cc2ccc(NC(=O)[C@@H]3C[C@@H](F)CN3C(=O)Cn3nc(C(N)=O)c4cc(-c5ccnnc5)ccc43)cc2C1=O] | 1-(2-((2S,4R)-2-(2-ethyl-3-oxoisoindolin-5-ylcarbamoyl)-4-fluoropyrrolidin-1-yl)-2-oxoethyl)-5-(pyridazin-4-yl)-1H-indazole-3-carboxamide | * | 1.97 (B) | 571 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 49 | 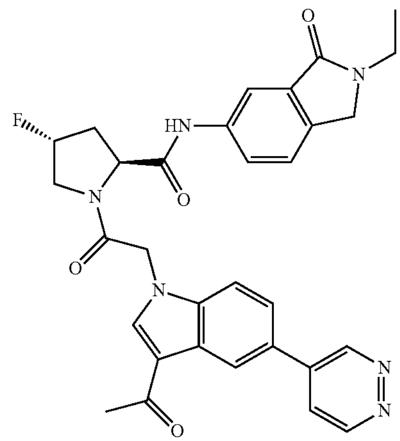 [SMILES: CCN1Cc2ccc(NC(=O)[C@@H]3C[C@@H](F)CN3C(=O)Cn3cc(C(C)=O)c4cc(-c5ccnnc5)ccc43)cc2C1=O] | (2S,4R)-1-(2-(3-acetyl-5-(pyridazin-4-yl)-1H-indol-1-yl)acetyl)-N-(2-ethyl-3-oxoisoindolin-5-yl)-4-fluoropyrrolidine-2-carboxamide | ** | 2.49 (B) | 569 |
| 50 | 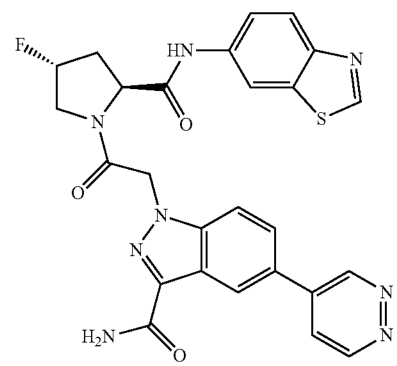 [SMILES: NC(=O)c1nn(CC(=O)N2C[C@H](F)C[C@H]2C(=O)Nc2ccc3ncsc3c2)c2ccc(-c3ccnnc3)cc12] | 1-(2-((2S,4R)-2-(benzo[d]thiazol-6-ylcarbamoyl)-4-fluoropyrrolidin-1-yl)-2-oxoethyl)-5-(pyridazin-4-yl)-1H-indazole-3-carboxamide | * | 2.03 (B) | 545 |
| 51 | 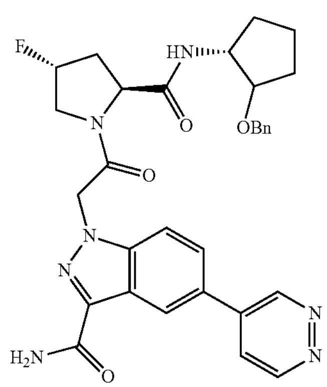 [SMILES: NC(=O)c1nn(CC(=O)N2C[C@H](F)C[C@H]2C(=O)N[C@@H]2CCCC2OCc2ccccc2)c2ccc(-c3ccnnc3)cc12] | 1-(2-((2S,4R)-2-((1R,2S)-2-(benzyloxy)cyclopentylcarbamoyl)-4-fluoropyrrolidin-1-yl)-2-oxoethyl)-5-(pyridazin-4-yl)-1H-indazole-3-carboxamide | * | 2.81 (B) | 586 |
| 52 | 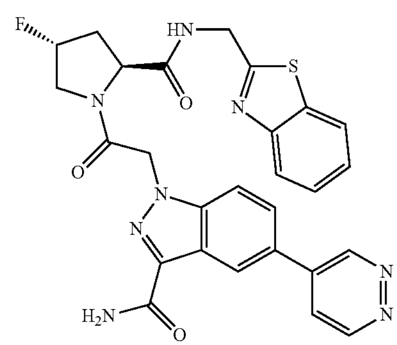 [SMILES: NC(=O)c1nn(CC(=O)N2C[C@H](F)C[C@H]2C(=O)NCc2nc3ccccc3s2)c2ccc(-c3ccnnc3)cc12] | 1-(2-((2S,4R)-2-(benzo[d]thiazol-2-ylmethylcarbamoyl)-4-fluoropyrrolidin-1-yl)-2-oxoethyl)-5-(pyridazin-4-yl)-1H-indazole-3-carboxamide | * | 2.15 (B) | 559 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 53 | 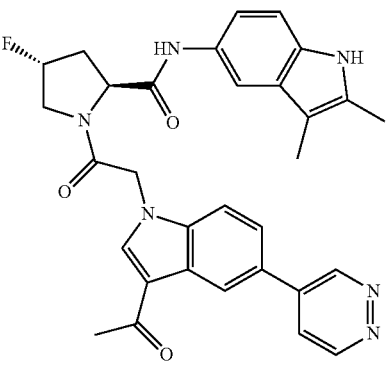 [SMILES: CC(=O)c1cn(CC(=O)N2C[C@H](F)C[C@H]2C(=O)Nc2ccc3[nH]c(C)c(C)c3c2)c2ccc(-c3ccnnc3)cc12] | (2S,4R)-1-(2-(3-acetyl-5-(pyridazin-4-yl)-1H-indol-1-yl)acetyl)-N-(2,3-dimethyl-1H-indol-5-yl)-4-fluoropyrrolidine-2-carboxamide | ** | 2.91 (B) | 553 |
| 54 | 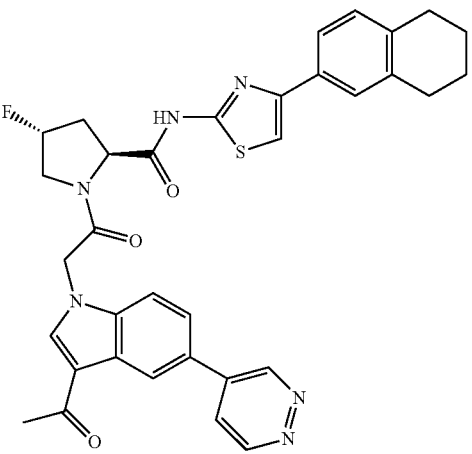 [SMILES: CC(=O)c1cn(CC(=O)N2C[C@H](F)C[C@H]2C(=O)Nc2nc(-c3ccc4c(c3)CCCC4)cs2)c2ccc(-c3ccnnc3)cc12] | (2S,4R)-1-(2-(3-acetyl-5-(pyridazin-4-yl)-1H-indol-1-yl)acetyl)-4-fluoro-N-(4-(5,6,7,8-tetrahydro-naphthalen-2-yl)thiazol-2-yl)pyrrolidine-2-carboxamide | * | 4.15 (B) | 623 |
| 55 | 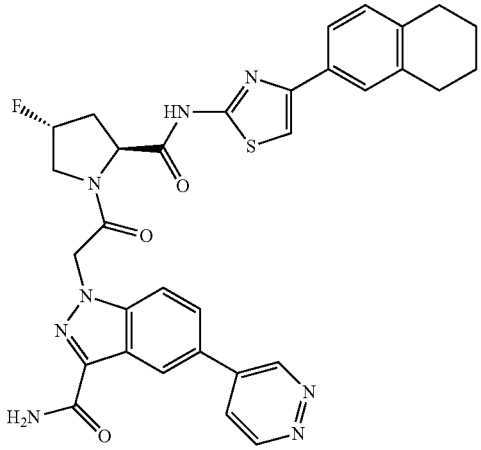 [SMILES: NC(=O)c1nn(CC(=O)N2C[C@H](F)C[C@H]2C(=O)Nc2nc(-c3ccc4c(c3)CCCC4)cs2)c2ccc(-c3ccnnc3)cc12] | 1-(2-((2S,4R)-4-fluoro-2-(4-(5,6,7,8-tetrahydro-naphthalen-2-yl)thiazol-2-ylcarbamoyl)pyrrolidin-1-yl)-2-oxoethyl)-5-(pyridazin-4-yl)-1H-indazole-3-carboxamide | * | 3.88 (B) | 625 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 56 | 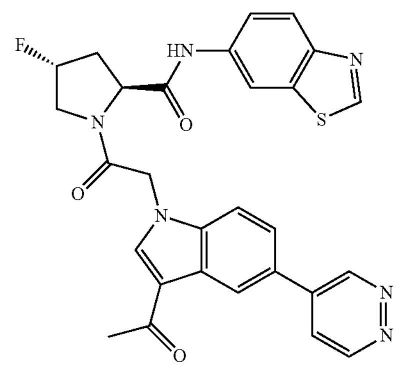 [SMILES: CC(=O)c1cn(CC(=O)N2C[C@H](F)C[C@H]2C(=O)Nc2ccc3ncsc3c2)c2ccc(-c3ccnnc3)cc12] | (2S,4R)-1-(2-(3-acetyl-5-(pyridazin-4-yl)-1H-indol-1-yl)acetyl)-N-(benzo[d]thiazol-6-yl)-4-fluoropyrrolidine-2-carboxamide | ** | 2.41 (B) | 543 |
| 57 | 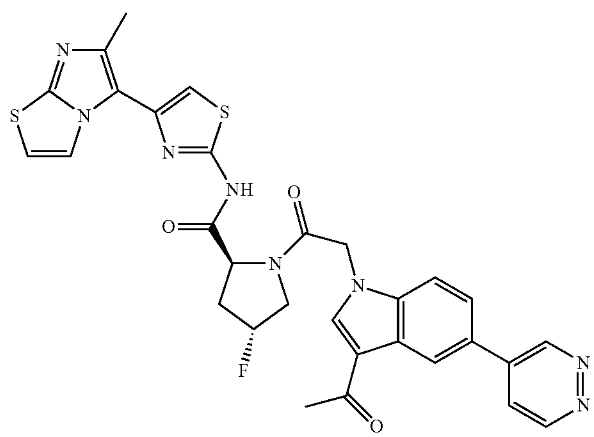 [SMILES: CC(=O)c1cn(CC(=O)N2C[C@H](F)C[C@H]2C(=O)Nc2nc(-c3c(C)nc4sccn34)cs2)c2ccc(-c3ccnnc3)cc12] | (2S,4R)-1-(2-(3-acetyl-5-(pyridazin-4-yl)-1H-indol-1-yl)acetyl)-4-fluoro-methylimidazo[2,1-b]thiazol-5-yl)thiazol-2-yl)pyrrolidine-2-carboxamide | * | 2.25 (B) | 629 |
| 58 | 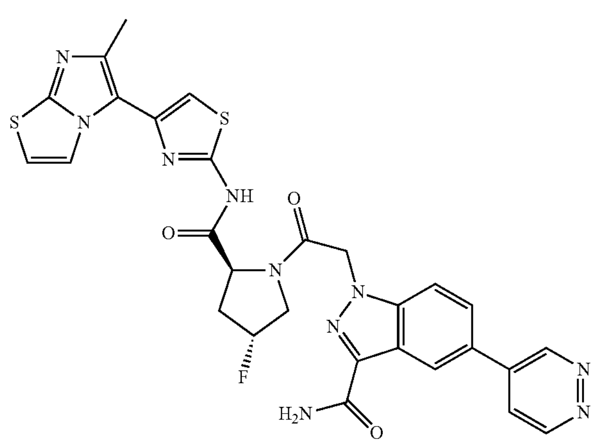 [SMILES: Cc1nc2sccn2c1-c1csc(NC(=O)[C@@H]2C[C@@H](F)CN2C(=O)Cn2nc(C(N)=O)c3cc(-c4ccnnc4)ccc32)n1] | 1-(2-((2S,4R)-4-fluoro-2-(4-(6-methylimidazo[2,1-b]thiazol-5-yl)thiazol-2-ylcarbamoyl)pyrrolidin-1-yl)-2-oxoethyl)-5-(pyridazin-4-yl)-1H-indazole-3-carboxamide | * | 1.83 (B) | 631 |

TABLE 1-continued
Non-limiting Examples of Compounds of Formula I
| Cmp No. | Structure | Name | IC$_{50}$ | RT min (Method A or B) | MS (M + 1) |
|---|---|---|---|---|---|
| 59 | 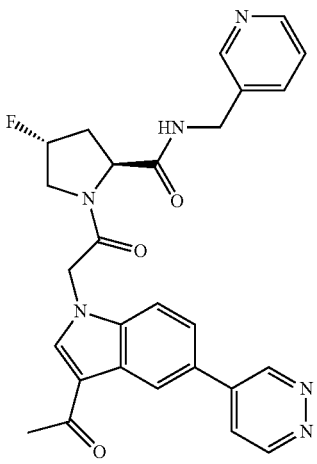 [SMILES: CC(=O)c1cn(CC(=O)N2C[C@H](F)C[C@H]2C(=O)NCc2cccnc2)c2ccc(-c3ccnnc3)cc12] | (2S,4R)-1-(2-(3-acetyl-5-(pyridazin-4-yl)-1H-indol-1-yl)acetyl)-4-fluoro-N-(pyridin-3-ylmethyl)pyrrolidine-2-carboxamide | ** | 0.62 (B) | 501 |
| 60 | 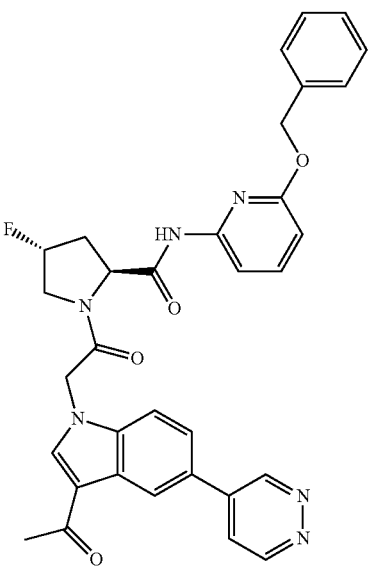 [SMILES: CC(=O)c1cn(CC(=O)N2C[C@H](F)C[C@H]2C(=O)Nc2cccc(OCc3ccccc3)n2)c2ccc(-c3ccnnc3)cc12] | (2s,4R)-1-(2-(3-acetyl-5-(pyridazin-4-yl)-1H-indol-1-yl)acetyl)-N-(6-(benzyloxy)pyridin-2-yl)-4-fluoropyrrolidine-2-carboxamide | ** | 3.63 (B) | 593 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 61 | 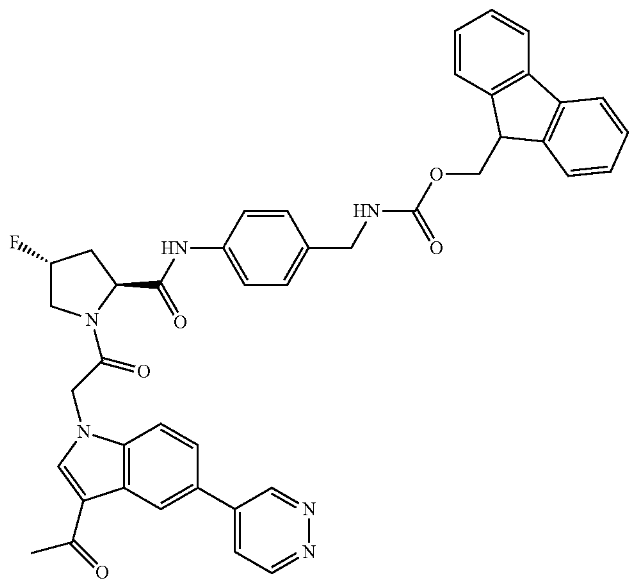 [SMILES: CC(=O)c1cn(CC(=O)N2C[C@H](F)C[C@H]2C(=O)Nc2ccc(CNC(=O)OCC3c4ccccc4-c4ccccc43)cc2)c2ccc(-c3ccnnc3)cc12] | (9H-fluoren-9-yl)methyl acetyl-5-(pyridazin-4-yl)-1H-indol-1-yl)acetyl)-4-fluoropyrrolidine-2-carboxamido)benzylcarbamate | * | 3.81 (B) | 737 |
| 62 | 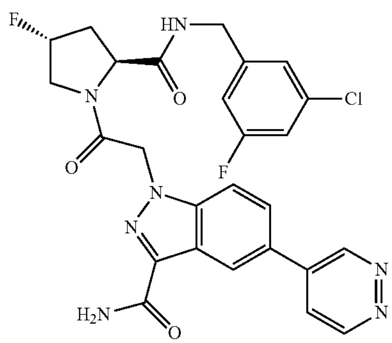 [SMILES: NC(=O)c1nn(CC(=O)N2C[C@H](F)C[C@H]2C(=O)NCc2cc(F)cc(Cl)c2)c2ccc(-c3ccnnc3)cc12] | 1-(2-((2S,4R)-2-(3-chloro-5-fluorobenzyl-carbamoyl)-4-fluoropyrrolidin-1-yl)-2-oxoethyl)-5-(pyridazin-4-yl)-1H-indazole-3-carboxamide | *** | 2.61 (B) | 554 |
| 63 | 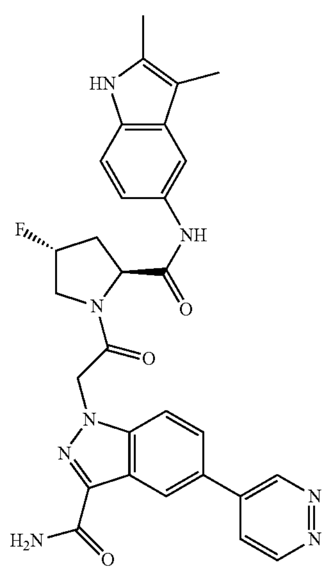 [SMILES: Cc1[nH]c2ccc(NC(=O)[C@@H]3C[C@@H](F)CN3C(=O)Cn3nc(C(N)=O)c4cc(-c5ccnnc5)ccc43)cc2c1C] | 1-(2-((2S,4R)-2-(2,3-dimethyl-1H-indol-5-ylcarbamoyl)-4-fluoropyrrolidin-1-yl)-2-oxoethyl)-5-(pyridazin-4-yl)-1H-indazole-3-carboxamide | ** | 2.55 (B) | 555 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 64 | 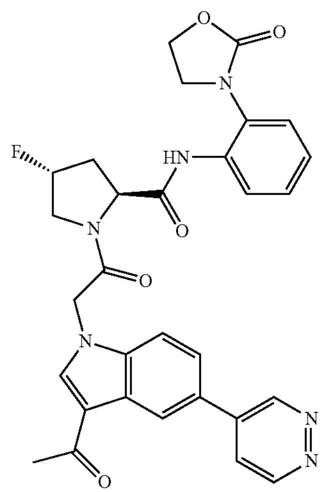 [SMILES: CC(=O)c1cn(CC(=O)N2C[C@H](F)C[C@H]2C(=O)Nc2ccccc2N2CCOC2=O)c2ccc(-c3ccnnc3)cc12] | (2S,4R)-1-(2-(3-acetyl-5-(pyridazin-4-yl)-1H-indol-1-yl)acetyl)-4-fluoro-N-(2-(2-oxooxazolidin-3-yl)phenyl) pyrrolidine-2-carboxamide | * | 2.29 (B) | 571 |
| 65 | 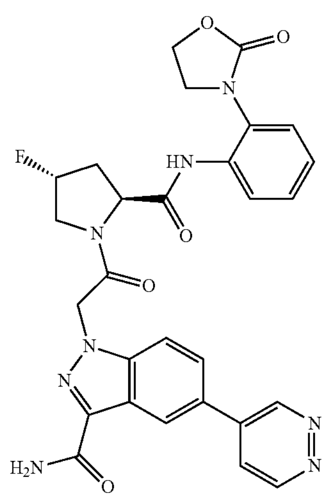 [SMILES: NC(=O)c1nn(CC(=O)N2C[C@H](F)C[C@H]2C(=O)Nc2ccccc2N2CCOC2=O)c2ccc(-c3ccnnc3)cc12] | 1-(2-((2S,4R)-4-fluoro-2-(2-(2-oxooxazolidin-3-yl)phenylcarbamoyl) pyrrolidin-1-yl)-2-oxoethyl)-5-(pyridazin-4-yl)-1H-indazole-3-carboxamide | * | 1.63 (B) | 573 |
| 66 | 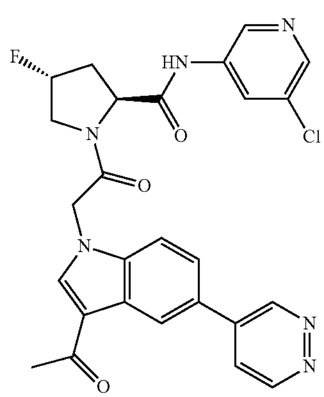 [SMILES: CC(=O)c1cn(CC(=O)N2C[C@H](F)C[C@H]2C(=O)Nc2cncc(Cl)c2)c2ccc(-c3ccnnc3)cc12] | (2S,4R)-1-(2-(3-acetyl-5-(pyridazin-4-yl)-1H-indol-1-yl)acetyl)-N-(5-chloropyridin-3-yl)-4-fluoropyrrolidine-2-carboxamide | *** | 2.63 (B) | 521 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 67 | 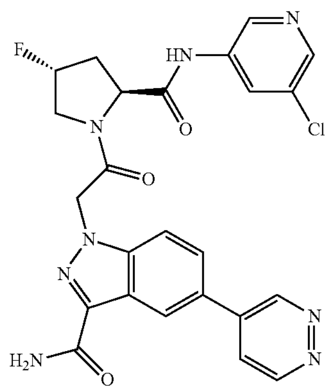 | 1-(2-((2S,4R)-2-(5-chloropyridin-3-ylcarbamoyl)-4-fluoropyrrolidin-1-yl)-2-oxoethyl)-5-(pyridazin-4-yl)-1H-indazole-3-carboxamide | ** | 2.34 (B) | 523 |
| 68 | 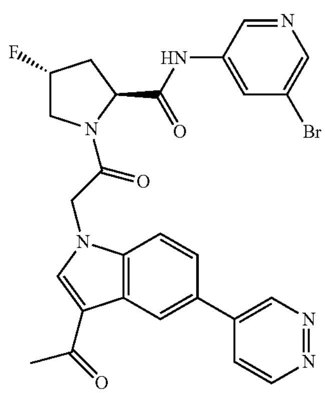 [SMILES: CC(=O)c1cn(CC(=O)N2C[C@H](F)C[C@H]2C(=O)Nc2cncc(Br)c2)c2ccc(-c3ccnnc3)cc12] | (2S,4R)-1-(2-(3-acetyl-5-(pyridazin-4-yl)-1H-indol-1-yl)acetyl)-N-(5-bromopyridin-3-yl)-4-fluoropyrrolidine-2-carboxamide | *** | 2.79 (B) | 565 |
| 69 | 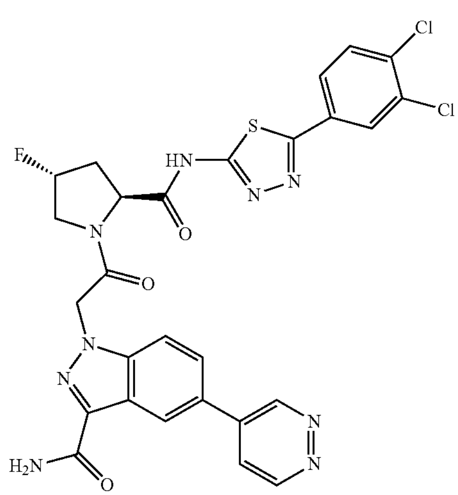 [SMILES: NC(=O)c1nn(CC(=O)N2C[C@H](F)C[C@H]2C(=O)Nc2nnc(-c3ccc(Cl)c(Cl)c3)s2)c2ccc(-c3ccnnc3)cc12] | 1-(2-((2S,4R)-2-(5-(3,4-dichlorophenyl)-1,3,4-thiadiazol-2-ylcarbamoyl)-4-fluoropyrrolidin-1-yl)-2-oxoethyl)-5-(pyridazin-4-yl)-1H-indazole-3-carboxamide | * | 3.61 (B) | 640 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 70 | 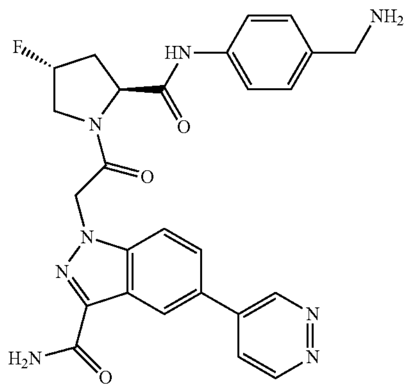 [SMILES: NCc1ccc(NC(=O)[C@@H]2C[C@@H](F)CN2C(=O)Cn2nc(C(N)=O)c3cc(-c4ccnnc4)ccc32)cc1] | 1-(2-((2S,4R)-2-(4-(aminomethyl)phenylcarbamoyl)-4-fluoropyrrolidin-1-yl)-2-oxoethyl)-5-(pyridazin-4-yl)-1H-indazole-3-carboxamide | * | 0.42 (B) | 517 |
| 71 | 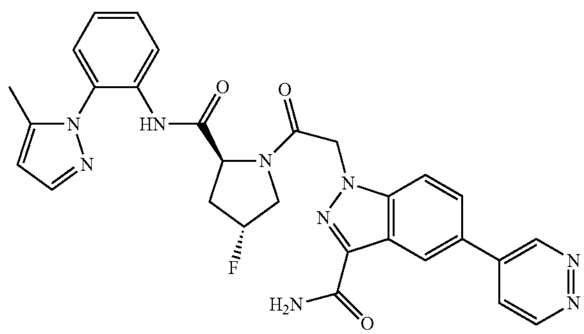 [SMILES: Cc1ccnn1-c1ccccc1NC(=O)[C@@H]1C[C@@H](F)CN1C(=O)Cn1nc(C(N)=O)c2cc(-c3ccnnc3)ccc21] | 1-(2-((2S,4R)-4-fluoro-2-(2-(5-methyl-1H-pyrazol-1-yl)phenylcarbamoyl)pyrrolidin-1-yl)-2-oxoethyl)-5-(pyridazin-4-yl)-1H-indazole-3-carboxamide | * | 2.54 (B) | 568 |
| 72 | 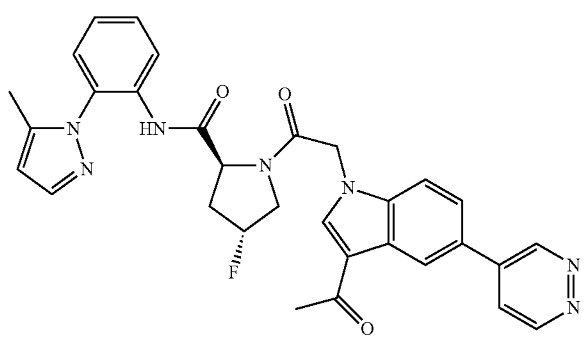 [SMILES: CC(=O)c1cn(CC(=O)N2C[C@H](F)C[C@H]2C(=O)Nc2ccccc2-n2nccc2C)c2ccc(-c3ccnnc3)cc12] | (2S,4R)-1-(2-(3-acetyl-5-(pyridazin-4-yl)-1H-indol-1-yl)acetyl)-4-fluoro-N-(2-(5-methyl-1H-pyrazol-1-yl)phenyl)pyrrolidine-2-carboxamide | * | 2.84 (B) | 566 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 73 | 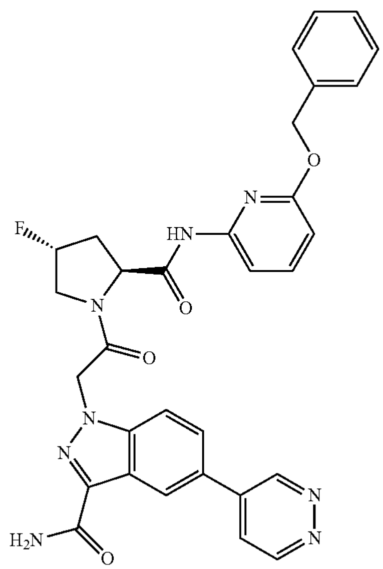 [SMILES: NC(=O)c1nn(CC(=O)N2C[C@H](F)C[C@H]2C(=O)Nc2cccc(OCc3ccccc3)n2)c2ccc(-c3ccnnc3)cc12] | 1-(2-((2S,4R)-2-(6-(benzyloxy)pyridin-2-ylcarbamoyl)-4-fluoropyrrolidin-1-yl)-2-oxoethyl)-5-(pyridazin-4-yl)-1H-indazole-3-carboxamide | * | 3.43 (B) | 595 |
| 74 | 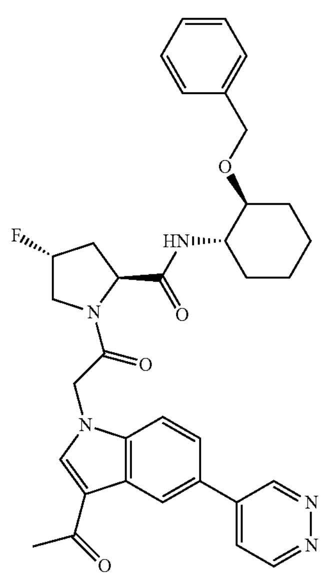 [SMILES: CC(=O)c1cn(CC(=O)N2C[C@H](F)C[C@H]2C(=O)N[C@H]2CCCC[C@@H]2OCc2ccccc2)c2ccc(-c3ccnnc3)cc12] | (2S,4R)-1-(2-(3-acetyl-5-(pyridazin-4-yl)-1H-indol-1-yl)acetyl)-N-((1S,2S)-2-(benzyloxy)cyclohexyl)-4-fluoropyrrolidine-2-carboxamide | * | 3.53 (B) | 598 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 75 | 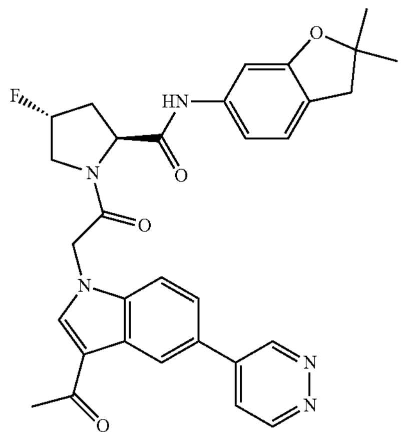 [SMILES: CC(=O)c1cn(CC(=O)N2C[C@H](F)C[C@H]2C(=O)Nc2ccc3c(c2)OC(C)(C)C3)c2ccc(-c3ccnnc3)cc12] | (2S,4R)-1-(2-(3-acetyl-5-(pyridazin-4-yl)-1H-indol-1-yl)acetyl)-N-(2,2-dimethyl-2,3-dihydrobenzofuran-6-yl)-4-fluoropyrrolidine-2-carboxamide | *** | 3.14 (B) | 556 |
| 76 | 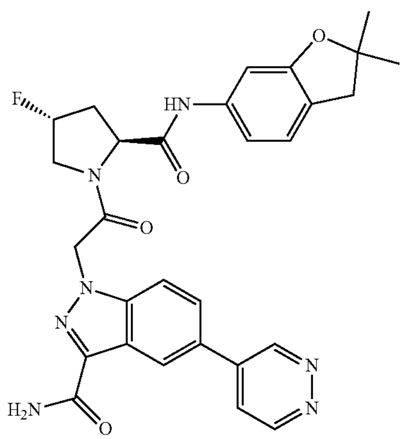 [SMILES: CC1(C)Cc2ccc(NC(=O)[C@@H]3C[C@@H](F)CN3C(=O)Cn3nc(C(N)=O)c4cc(-c5ccnnc5)ccc43)cc2O1] | 1-(2-((2S,4R)-2-(2,2-dimethyl-2,3-dihydrobenzofuran-6-ylcarbamoyl)-4-fluoropyrrolidin-1-yl)-2-oxoethyl)-5-(pyridazin-4-yl)-1H-indazole-3-carboxamide | *** | 2.92 (B) | 558 |
| 77 | 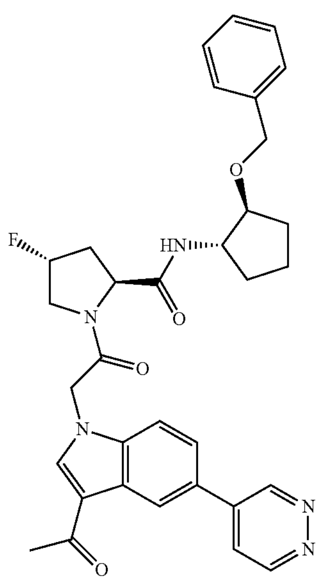 [SMILES: CC(=O)c1cn(CC(=O)N2C[C@H](F)C[C@H]2C(=O)N[C@H]2CCC[C@@H]2OCc2ccccc2)c2ccc(-c3ccnnc3)cc12] | (2S,4R)-1-(2-(3-acetyl-5-(pyridazin-4-yl)-1H-indol-1-yl)acetyl)-N-((1S,2S)-2-(benzyloxy)cyclopentyl)-4-fluoropyrrolidine-2-carboxamide | * | 3.33 (B) | 584 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 78 | 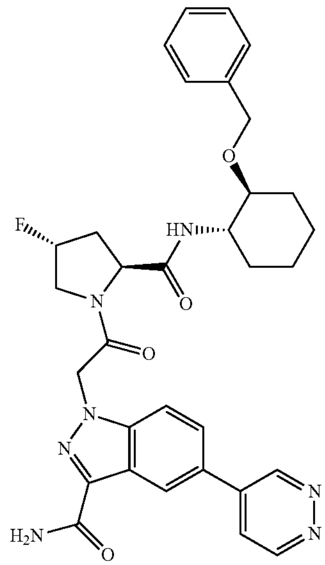 [SMILES: NC(=O)c1nn(CC(=O)N2C[C@H](F)C[C@H]2C(=O)N[C@H]2CCCC[C@@H]2OCc2ccccc2)c2ccc(-c3ccnnc3)cc12] | 1-(2-((2S,4R)-2-((1S,2S)-2-(benzyloxy)cyclohexyl-carbamoyl)-4-fluoropyrrolidin-1-yl)-2-oxoethyl)-5-(pyridazin-4-yl)-1H-indazole-3-carboxamide | * | 3.38 (B) | 600 |
| 79 | 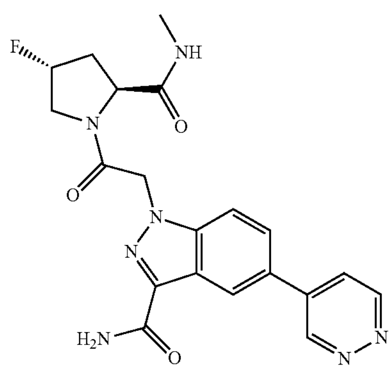 [SMILES: CNC(=O)[C@@H]1C[C@@H](F)CN1C(=O)Cn1nc(C(N)=O)c2cc(-c3ccnnc3)ccc21] | 1-(2-((2S,4R)-4-fluoro-2-(methylcarbamoyl)pyrrolidin-1-yl)-2-oxoethyl)-5-(pyridazin-4-yl)-1H-indazole-3-carboxamide | * | 2.10 (B) | 426 |
| 80 | 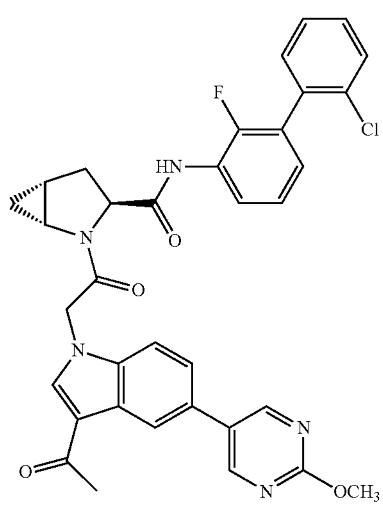 [SMILES: COc1ncc(-c2ccc3c(c2)c(C(C)=O)cn3CC(=O)N2[C@@H]3C[C@@H]3C[C@H]2C(=O)Nc2cccc(-c3ccccc3Cl)c2F)cn1] | (1R,3S,5R)-2-(2-(3-acetyl-5-(2-methoxypyrimidin-5-yl)-1H-indol-1-yl)acetyl)-N-(2'-chloro-2-fluorobiphenyl-3-yl)-2-azabicyclo[3.1.0]hexane-3-carboxamide | *** | 2.36 (A) | 638 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 81 | 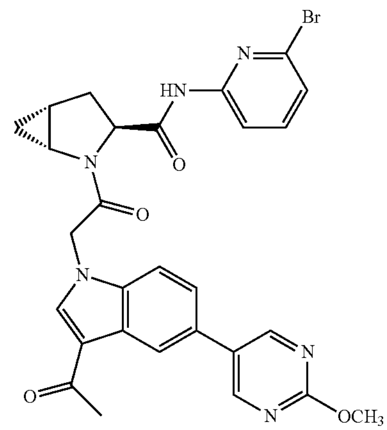 [SMILES: COc1ncc(-c2ccc3c(c2)c(C(C)=O)cn3CC(=O)N2[C@@H]3C[C@@H]3C[C@H]2C(=O)Nc2cccc(Br)n2)cn1] | (1R,3S,5R)-2-(2-(3-acetyl-5-(2-methoxypyrimidin-5-yl)-1H-indol-1-yl)acetyl)-N-(6-bromopyridin-2-yl)-2-azabicyclo[3.1.0]hexane-3-carboxamide | *** | 1.91 (A) | 591 |
| 82 | 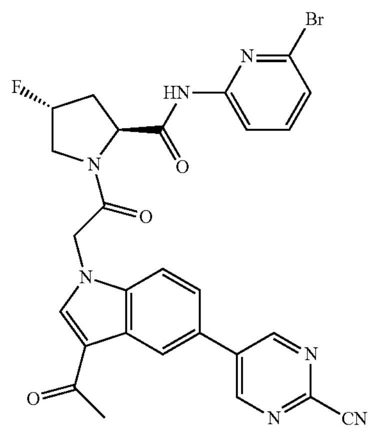 [SMILES: CC(=O)c1cn(CC(=O)N2C[C@H](F)C[C@H]2C(=O)Nc2cccc(Br)n2)c2ccc(-c3cnc(C#N)nc3)cc12] | (2S,4R)-1-(2-(3-acetyl-5-(2-cyanopyrimidin-5-yl)-1H-indol-1-yl)acetyl)-N-(6-bromopyridin-2-yl)-4-fluoropyrrolidine-2-carboxamide | *** | 1.97 (A) | 592 |
| 83 | 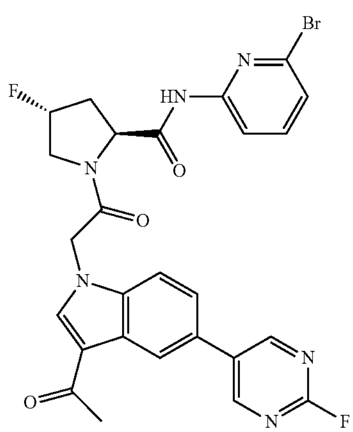 [SMILES: CC(=O)c1cn(CC(=O)N2C[C@H](F)C[C@H]2C(=O)Nc2cccc(Br)n2)c2ccc(-c3cnc(F)nc3)cc12] | (2S,4R)-1-(2-(3-acetyl-5-(2-fluoropyrimidin-5-yl)-1H-indol-1-yl)acetyl)-N-(6-bromopyridin-2-yl)-4-fluoropyrrolidine-2-carboxamide | *** | 1.86 (A) | 585 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 84 | 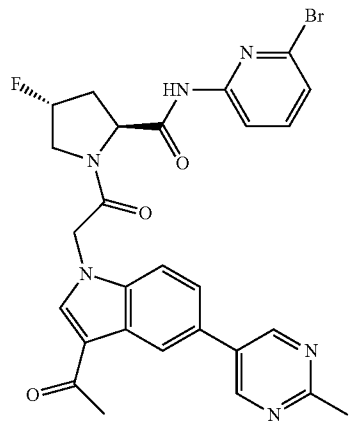 | (2S,4R)-1-(2-(3-acetyl-5-(2-methylpyrimidin-5-yl)-1H-indol-1-yl)acetyl)-N-(6-bromopyridin-2-yl)-4-fluoropyrrolidine-2-carboxamide | *** | 1.58 (A) | 581 |
| 85 | 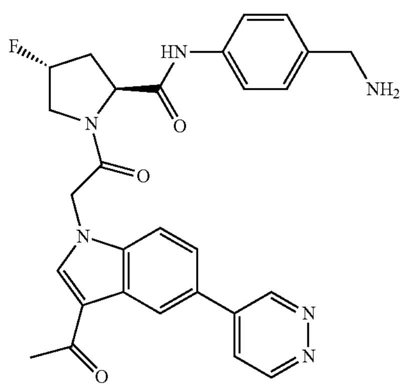 [SMILES: CC(=O)c1cn(CC(=O)N2C[C@H](F)C[C@H]2C(=O)Nc2ccc(CN)cc2)c2ccc(-c3ccnnc3)cc12] | (2S,4R)-1-(2-(3-acetyl-5-(pyridazin-4-yl)-1H-indol-1-yl)acetyl)-N-(4-(aminomethyl)phenyl)-4-fluoropyrrolidine-2-carboxamide | * | 0.69 (B) | 515 |
| 86 | 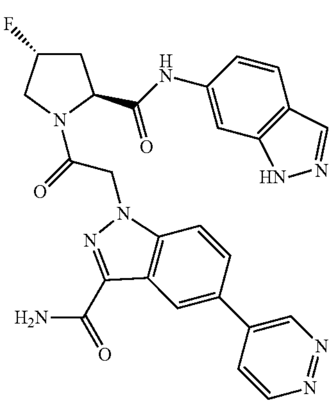 [SMILES: NC(=O)c1nn(CC(=O)N2C[C@H](F)C[C@H]2C(=O)Nc2ccc3cn[nH]c3c2)c2ccc(-c3ccnnc3)cc12] | 1-(2-((2S,4R)-2-(1H-indazol-6-ylcarbamoyl)-4-fluoropyrrolidin-1-yl)-2-oxoethyl)-5-(pyridazin-4-yl)-1H-indazole-3-carboxamide | * | 2.04 (B) | 528 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 87 | 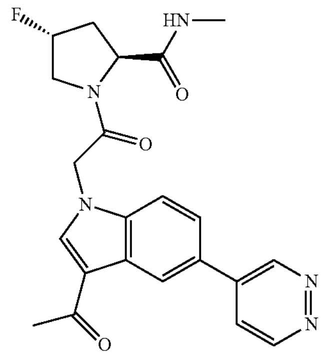 [SMILES: CNC(=O)[C@@H]1C[C@@H](F)CN1C(=O)Cn1cc(C(C)=O)c2cc(-c3ccnnc3)ccc21] | (2S,4R)-1-(2-(3-acetyl-5-(pyridazin-4-yl)-1H-indol-1-yl)acetyl)-4-fluoro-N-methylpyrrolidine-2-carboxamide | ** | 1.83 (B) | 424 |
| 88 | 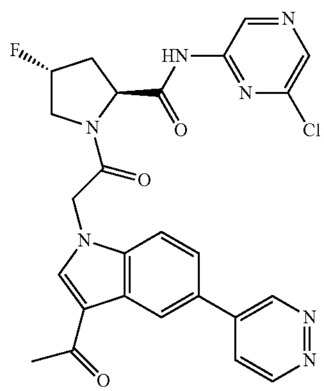 [SMILES: CC(=O)c1cn(CC(=O)N2C[C@H](F)C[C@H]2C(=O)Nc2cncc(Cl)n2)c2ccc(-c3ccnnc3)cc12] | (2S,4R)-1-(2-(3-acetyl-5-(pyridazin-4-yl)-1H-indol-1-yl)acetyl)-N-(6-chloropyrazin-2-yl)-4-fluoropyrrolidine-2-carboxamide | *** | 2.56 (B) | 522 |
| 89 | 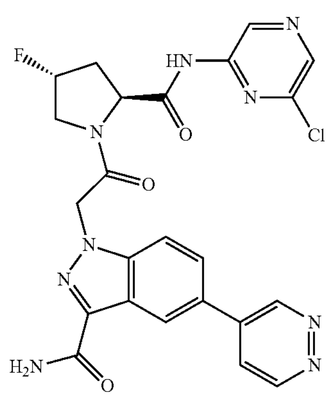 [SMILES: NC(=O)c1nn(CC(=O)N2C[C@H](F)C[C@H]2C(=O)Nc2cncc(Cl)n2)c2ccc(-c3ccnnc3)cc12] | 1-(2-((2S,4R)-2-(6-chloropyrazin-2-ylcarbamoyl)-4-fluoropyrrolidin-1-yl)-2-oxoethyl)-5-(pyridazin-4-yl)-1H-indazole-3-carboxamide | *** | 2.43 (B) | 524 |
| 90 | 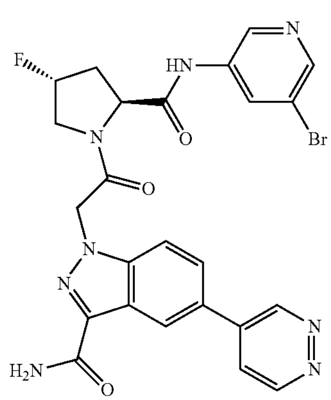 [SMILES: NC(=O)c1nn(CC(=O)N2C[C@H](F)C[C@H]2C(=O)Nc2cncc(Br)c2)c2ccc(-c3ccnnc3)cc12] | 1-(2-((2S,4R)-2-(5-bromopyridin-3-ylcarbamoyl)-4-fluoropyrrolidin-1-yl)-2-oxoethyl)-5-(pyridazin-4-yl)-1H-indazole-3-carboxamide | ** | 2.40 (B) | 567 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 91 | 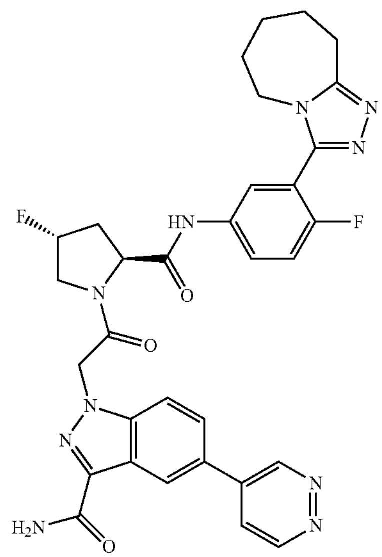 [SMILES: NC(=O)c1nn(CC(=O)N2C[C@H](F)C[C@H]2C(=O)Nc2ccc(F)c(-c3nnc4n3CCCCC4)c2)c2ccc(-c3ccnnc3)cc12] | 1-(2-((2S,4R)-4-fluoro-2-(4-fluoro-3-(6,7,8,9-tetrahydro-5H-[1,2,4]triazolo[4,3-a]azepin-3-yl)phenylcarbamoyl)pyrrolidin-1-yl)-2-oxoethyl)-5-(pyridazin-4-yl)-1H-indazole-3-carboxamide | * | 2.59 (B) | 641 |
| 92 | 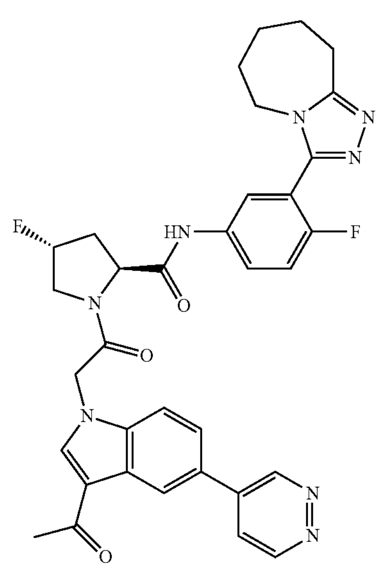 [SMILES: CC(=O)c1cn(CC(=O)N2C[C@H](F)C[C@H]2C(=O)Nc2ccc(F)c(-c3nnc4n3CCCCC4)c2)c2ccc(-c3ccnnc3)cc12] | (2S,4R)-1-(2-(3-acetyl-5-(pyridazin-4-yl)-1H-indol-1-yl)acetyl)-4-fluoro-N-(4-fluoro-3-(6,7,8,9-tetrahydro-5H-[1,2,4]triazolo[4,3-a]azepin-3-yl)phenyl)pyrrolidine-2-carboxamide | *** | 2.78 (B) | 639 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 93 | 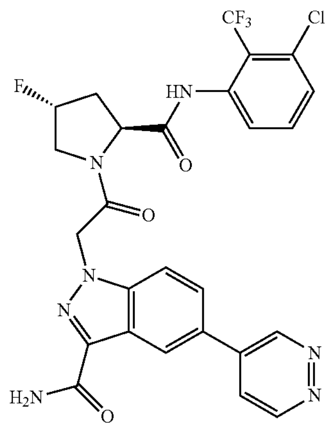 [SMILES: NC(=O)c1nn(CC(=O)N2C[C@H](F)C[C@H]2C(=O)Nc2cccc(Cl)c2C(F)(F)F)c2ccc(-c3ccnnc3)cc12] | 1-(2-((2S,4R)-2-(3-chloro-2-(trifluoromethyl)phenylcarbamoyl)-4-fluoropyrrolidin-1-yl)-2-oxoethyl)-5-(pyridazin-4-yl)-1H-indazole-3-carboxamide | * | 3.24 (B) | 590 |
| 94 | 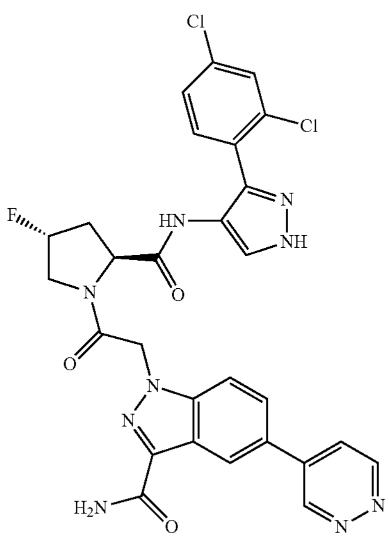 [SMILES: NC(=O)c1nn(CC(=O)N2C[C@H](F)C[C@H]2C(=O)Nc2c[nH]nc2-c2ccc(Cl)cc2Cl)c2ccc(-c3ccnnc3)cc12] | 1-(2-((2S,4R)-2-(3-(2,4-dichlorophenyl)-1H-pyrazol-4-ylcarbamoyl)-4-fluoropyrrolidin-1-yl)-2-oxoethyl)-5-(pyridazin-4-yl)-1H-indazole-3-carboxamide | * | 2.62 (B) | 622 |
| 95 | 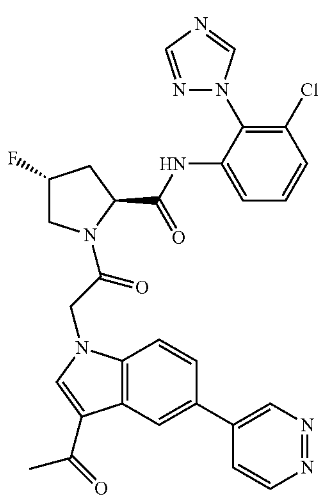 [SMILES: CC(=O)c1cn(CC(=O)N2C[C@H](F)C[C@H]2C(=O)Nc2cccc(Cl)c2-n2cncn2)c2ccc(-c3ccnnc3)cc12] | (2S,4R)-1-(2-(3-acetyl-5-(pyridazin-4-yl)-1H-indol-1-yl)acetyl)-N-(3-chloro-2-(1H-1,2,4-triazol-1-yl)phenyl)-4-fluoropyrrolidine-2-carboxamide | * | 2.31 (B) | 587 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 96 | 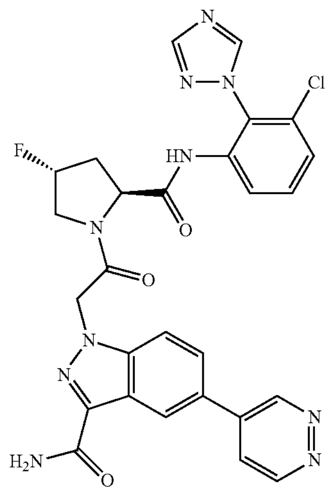 [SMILES: NC(=O)c1nn(CC(=O)N2C[C@H](F)C[C@H]2C(=O)Nc2cccc(Cl)c2-n2cncn2)c2ccc(-c3ccnnc3)cc12] | 1-(2-((2S,4R)-2-(3-chloro-2-(1H-1,2,4-triazol-1-yl)phenylcarbamoyl)-4-fluoropyrrolidin-1-yl)-2-oxoethyl)-5-(pyridazin-4-yl)-1H-indazole-3-carboxamide | * | 1.94 (B) | 589 |
| 97 | 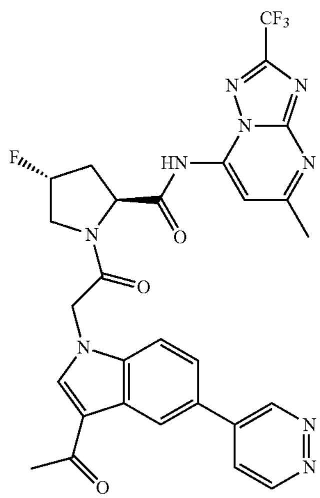 [SMILES: CC(=O)c1cn(CC(=O)N2C[C@H](F)C[C@H]2C(=O)Nc2cc(C)nc3nc(C(F)(F)F)nn23)c2ccc(-c3ccnnc3)cc12] | (2S,4R)-1-(2-(3-acetyl-5-(pyridazin-4-yl)-1H-indol-1-yl)acetyl)-4-fluoro-N-(5-methyl-2-(trifluoromethyl)-[1,2,4]triazolo[1,5-a]pyrimidin-7-yl)pyrrolidine-2-carboxamide | * | 2.46 (B) | 610 |
| 98 | 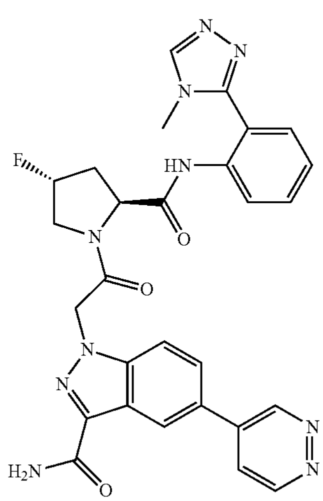 [SMILES: Cn1cnnc1-c1ccccc1NC(=O)[C@@H]1C[C@@H](F)CN1C(=O)Cn1nc(C(N)=O)c2cc(-c3ccnnc3)ccc21] | 1-(2-((2S,4R)-4-fluoro-2-(2-(4-methyl-4H-1,2,4-triazol-3-yl)phenylcarbamoyl)pyrrolidin-1-yl)-2-oxoethyl)-5-(pyridazin-4-yl)-1H-indazole-3-carboxamide | * | 2.42 (B) | 569 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 99 | 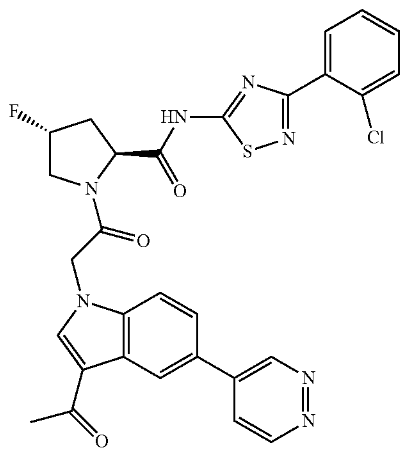 [SMILES: CC(=O)c1cn(CC(=O)N2C[C@H](F)C[C@H]2C(=O)Nc2nc(-c3ccccc3Cl)ns2)c2ccc(-c3ccnnc3)cc12] | (2S,4R)-1-(2-(3-acetyl-5-(pyridazin-4-yl)-1H-indol-1-yl)acetyl)-N-(3-(2-chlorophenyl)-1,2,4-thiadiazol-5-yl)-4-fluoropyrrolidine-2-carboxamide | *** | 3.29 (B) | 604 |
| 100 | 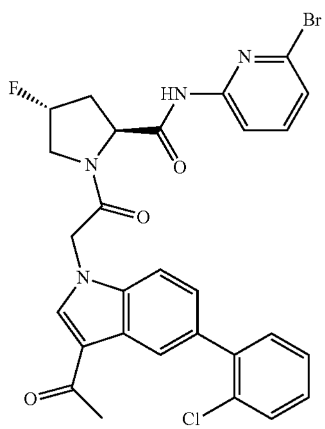 [SMILES: CC(=O)c1cn(CC(=O)N2C[C@H](F)C[C@H]2C(=O)Nc2cccc(Br)n2)c2ccc(-c3ccccc3Cl)cc12] | (2S,4R)-1-(2-(3-acetyl-5-(2-chlorophenyl)-1H-indol-1-yl)acetyl)-N-(6-bromopyridin-2-yl)-4-fluoropyrrolidine-2-carboxamide | *** | 2.45 (A) | 599 |
| 101 | 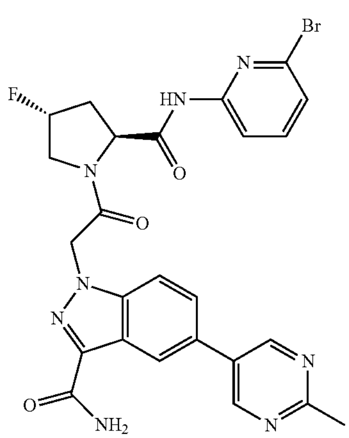 | 1-(2-((2S,4R)-2-(6-bromopyridin-2-ylcarbamoyl)-4-fluoropyrrolidin-1-yl)-2-oxoethyl)-5-(2-methylpyrimidin-5-yl)-1H-indazole-3-carboxamide | *** | 1.40 (A) | 583 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 102 | 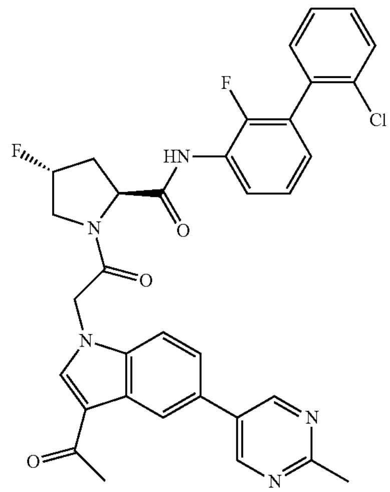 [SMILES: CC(=O)c1cn(CC(=O)N2C[C@H](F)C[C@H]2C(=O)Nc2cccc(-c3ccccc3Cl)c2F)c2ccc(-c3cnc(C)nc3)cc12] | (2S,4R)-1-(2-(3-acetyl-5-(2-methylpyrimidin-5-yl)-1H-indol-1-yl)acetyl)-N-(2'-chloro-2-fluorobiphenyl-3-yl)-4-fluoropyrrolidine-2-carboxamide | *** | 2.10 (A) | 628 |
| 103 | 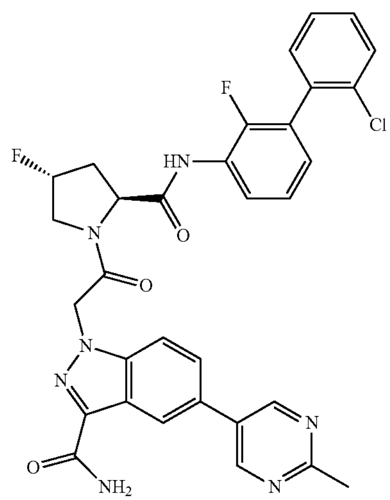 | 1-(2-((2S,4R)-2-(2'-chloro-2-fluorobiphenyl-3-ylcarbamoyl)-4-fluoropyrrolidin-1-yl)-2-oxoethyl)-5-2-methylpyrimidin-5-yl)-1H-indazole-3-carboxamide | *** | 1.91 (A) | 630 |
| 104 | 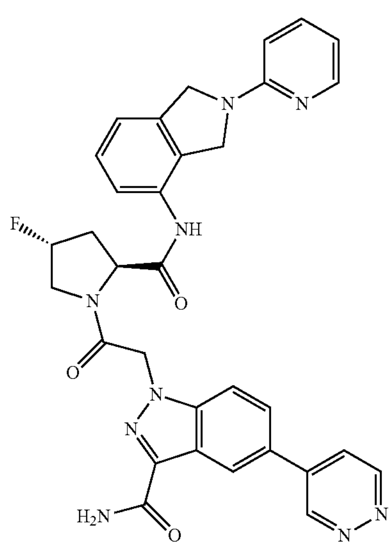 [SMILES: NC(=O)c1nn(CC(=O)N2C[C@H](F)C[C@H]2C(=O)Nc2cccc3c2CN(c2ccccn2)C3)c2ccc(-c3ccnnc3)cc12] | 1-(2-((2S,4R)-4-fluoro-2-(2-(pyridin-2-yl)isoindolin-4-ylcarbamoyl)pyrrolidin-1-yl)-2-oxoethyl)-5-(pyridazin-4-yl)-1H-indazole-3-carboxamide | * | 1.91 (B) | 606 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 105 | 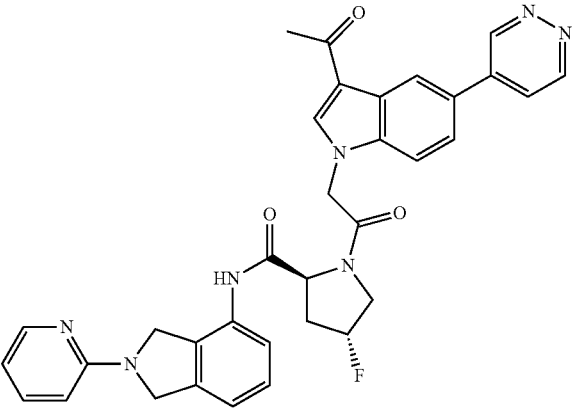 [SMILES: CC(=O)c1cn(CC(=O)N2C[C@H](F)C[C@H]2C(=O)Nc2cccc3c2CN(c2ccccn2)C3)c2ccc(-c3ccnnc3)cc12] | (2S,4R)-1-(2-(3-acetyl-5-(pyridazin-4-yl)-1H-indol-1-yl)acetyl)-4-fluoro-N-(2-(pyridin-2-yl)isoindolin-4-yl)pyrrolidine-2-carboxamide | * | 1.97 (B) | 604 |
| 106 | 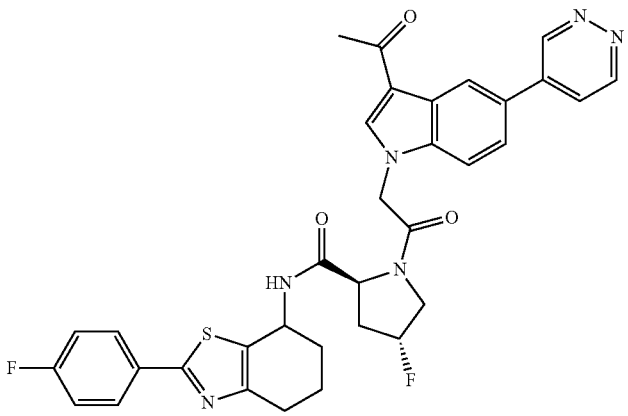 [SMILES: CC(=O)c1cn(CC(=O)N2C[C@H](F)C[C@H]2C(=O)NC2CCCc3nc(-c4ccc(F)cc4)sc32)c2ccc(-c3ccnnc3)cc12] | (2S,4R)-1-(2-(3-acetyl-5-(pyridazin-4-yl)-1H-indol-1-yl)acetyl)-4-fluoro-N-(2-(4-fluorophenyl)-4,5,6,7-tetrahydrobenzo[d]thiazol-7-yl)pyrrolidine-2-carboxamide | * | 2.94 (B) | 641 |
| 107 | 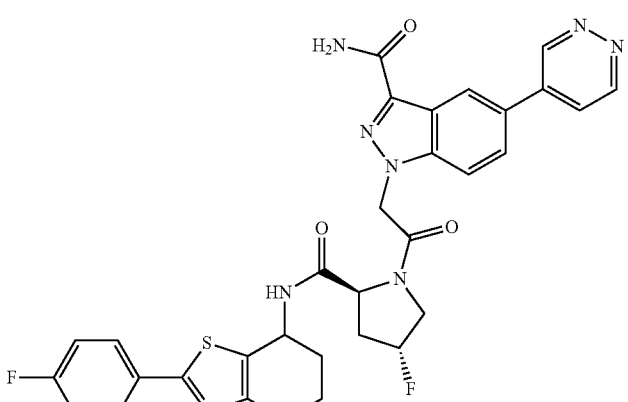 | 1-(2-((2S,4R)-4-fluoro-2-(2-(4-fluorophenyl)-4,5,6,7-tetrahydrobenzo[d]thiazol-7-ylcarbamoyl)pyrrolidin-1-yl)-2-oxoethyl)-5-(pyridazin-4-yl)-1H-indazole-3-carboxamide | * | 2.97 (B) | 643 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 108 | 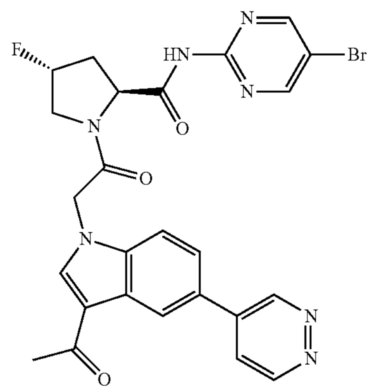 [SMILES: CC(=O)c1cn(CC(=O)N2C[C@H](F)C[C@H]2C(=O)Nc2ncc(Br)cn2)c2ccc(-c3ccnnc3)cc12] | (2S,4R)-1-(2-(3-acetyl-5-(pyridazin-4-yl)-1H-indol-1-yl)acetyl)-N-(5-bromopyrimidin-2-yl)-4-fluoropyrrolidine-2-carboxamide | ** | 1.85 (B) | 566 |
| 109 | 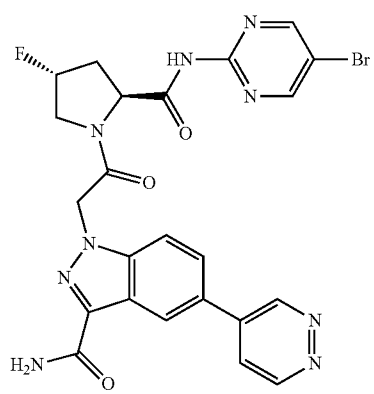 [SMILES: NC(=O)c1nn(CC(=O)N2C[C@H](F)C[C@H]2C(=O)Nc2ncc(Br)cn2)c2ccc(-c3ccnnc3)cc12] | 1-(2-((2S,4R)-2-(5-bromopyrimidin-2-ylcarbamoyl)-4-fluoropyrrolidin-1-yl)-2-oxoethyl)-5-(pyridazin-4-yl)-1H-indazole-3-carboxamide | ** | 1.86 (B) | 568 |
| 110 | 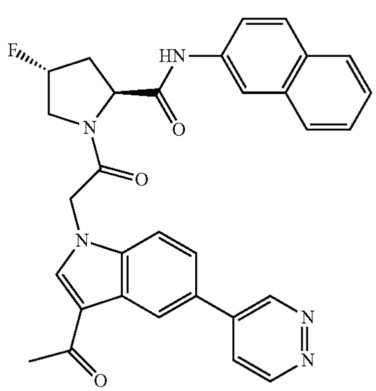 [SMILES: CC(=O)c1cn(CC(=O)N2C[C@H](F)C[C@H]2C(=O)Nc2ccc3ccccc3c2)c2ccc(-c3ccnnc3)cc12] | (2S,4R)-1-(2-(3-acetyl-5-(pyridazin-4-yl)-1H-indol-1-yl)acetyl)-4-fluoro-N-(naphthalen-2-yl)pyrrolidine-2-carboxamide | * | 3.14 (B) | 536 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 111 | 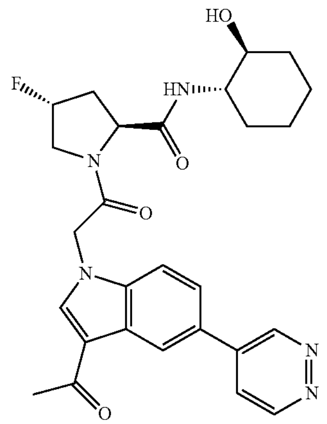 [SMILES: CC(=O)c1cn(CC(=O)N2C[C@H](F)C[C@H]2C(=O)N[C@H]2CCCC[C@@H]2O)c2ccc(-c3ccnnc3)cc12] | (2S,4R)-1-(2-(3-acetyl-5-(pyridazin-4-yl)-1H-indol-1-yl)acetyl)-4-fluoro-N-((1S,2S)-2-hydroxycyclohexyl)pyrrolidine-2-carboxamide | ** | 1.75 (B) | 508 |
| 112 | 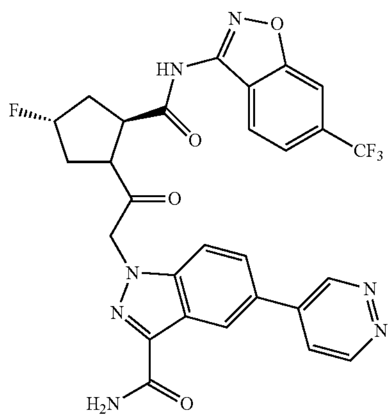 [SMILES: NC(=O)c1nn(CC(=O)C2C[C@H](F)C[C@H]2C(=O)Nc2noc3cc(C(F)(F)F)ccc23)c2ccc(-c3ccnnc3)cc12] | 1-(2-((2S,4R)-4-fluoro-2-(6-(trifluoromethyl)benzo[d]isoxazol-3-ylcarbamoyl)pyrrolidin-1-yl)-2-oxoethyl)-5-(pyridazin-4-yl)-1H-indazole-3-carboxamide | * | 2.95 (B) | 597 |
| 113 | 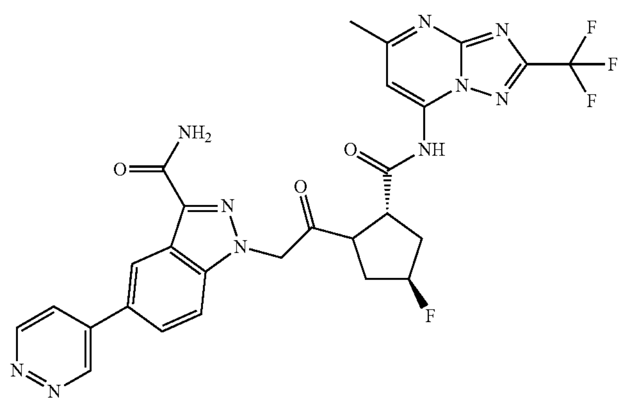 [SMILES: Cc1cc(NC(=O)[C@@H]2C[C@@H](F)CC2C(=O)Cn2nc(C(N)=O)c3cc(-c4ccnnc4)ccc32)n2nc(C(F)(F)F)nc2n1] | 1-(2-((2S,4R)-4-fluoro-2-(5-methyl-2-(trifluoromethyl)-[1,2,4]triazolo[1,5-a]pyrimidin-7-ylcarbamoyl)pyrrolidin-1-yl)-2-oxoethyl)-5-(pyridazin-4-yl)-1H-indazole-3-carboxamide | * | 2.07 (B) | 612 |
| 114 | 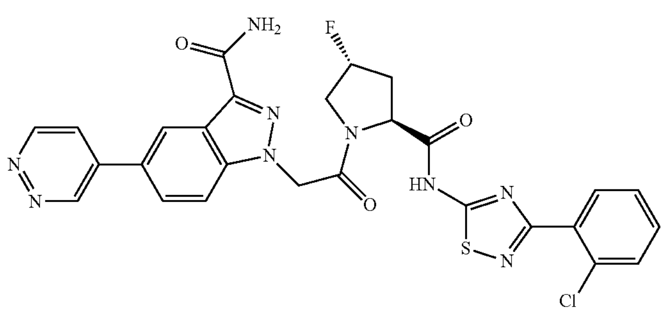 [SMILES: NC(=O)c1nn(CC(=O)N2C[C@H](F)C[C@H]2C(=O)Nc2nc(-c3ccccc3Cl)ns2)c2ccc(-c3ccnnc3)cc12] | 1-(2-((2S,4R)-2-(3-(2-chlorophenyl)-1,2,4-thiadiazol-5-ylcarbamoyl)-4-fluoropyrrolidin-1-yl)-2-oxoethyl)-5-(pyridazin-4-yl)-1H-indazole-3-carboxamide | ** | 2.89 (B) | 606 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 115 | 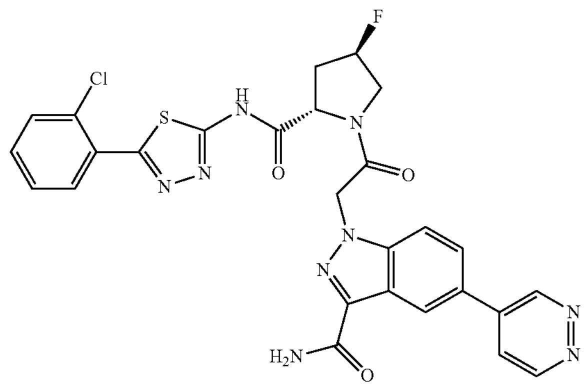 [SMILES: NC(=O)c1nn(CC(=O)N2C[C@H](F)C[C@H]2C(=O)Nc2nnc(-c3ccccc3Cl)s2)c2ccc(-c3ccnnc3)cc12] | 1-(2-((2S,4R)-2-(5-(2-chlorophenyl)-1,3,4-thiadiazol-2-ylcarbamoyl)-4-fluoropyrrolidin-1-yl)-2-oxoethyl)-5-(pyridazin-4-yl)-1H-indazole-3-carboxamide | * | 2.67 (B) | 606 |
| 116 | 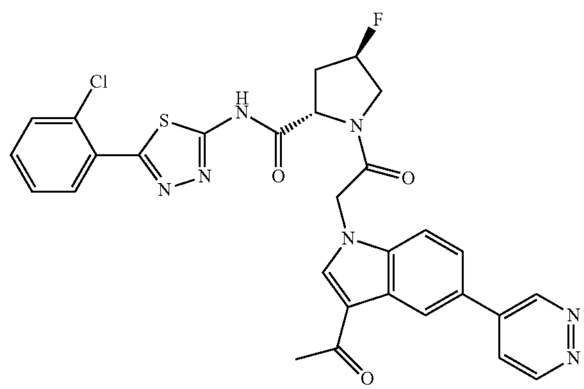 [SMILES: CC(=O)c1cn(CC(=O)N2C[C@H](F)C[C@H]2C(=O)Nc2nnc(-c3ccccc3Cl)s2)c2ccc(-c3ccnnc3)cc12] | (2S,4R)-1-(2-(3-acetyl-5-(pyridazin-4-yl)-1H-indol-1-yl)acetyl)-N-(5-(2-chlorophenyl)-1,3,4-thiadiazol-2-yl)-4-fluoropyrrolidine-2-carboxamide | ** | 3.30 (B) | 604 |
| 117 | 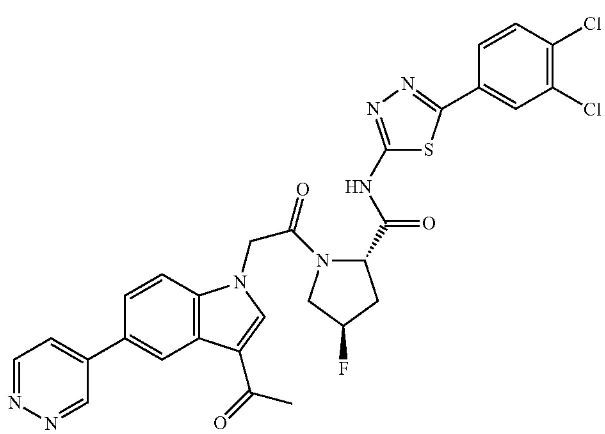 [SMILES: CC(=O)c1cn(CC(=O)N2C[C@H](F)C[C@H]2C(=O)Nc2nnc(-c3ccc(Cl)c(Cl)c3)s2)c2ccc(-c3ccnnc3)cc12] | (2S,4R)-1-(2-(3-acetyl-5-(pyridazin-4-yl)-1H-indol-1-yl)acetyl)-N-(5-(3,4-dichlorophenyl)-1,3,4-thiadiazol-2-yl)-4-fluoropyrrolidine-2-carboxamide | * | 3.73 (B) | 638 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 118 | 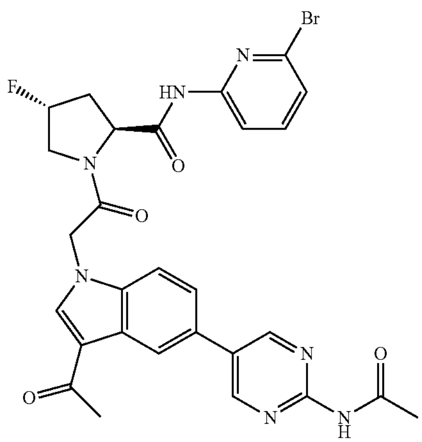 [SMILES: CC(=O)Nc1ncc(-c2ccc3c(c2)c(C(C)=O)cn3CC(=O)N2C[C@H](F)C[C@H]2C(=O)Nc2cccc(Br)n2)cn1] | (2S,4R)-1-(2-(5-(2-acetamidopyrimidin-5-yl)-3-acetyl-1H-indol-1-yl)acetyl)-N-(6-bromopyridin-2-yl)-4-fluoropyrrolidine-2-carboxamide | *** | 1.44 (A) | 622 |
| 119 | 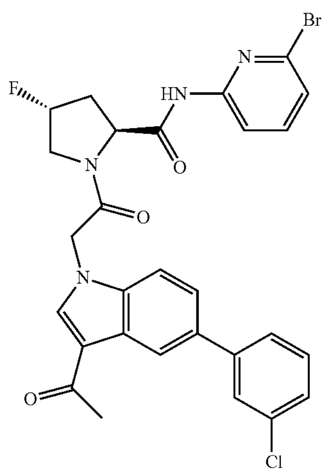 [SMILES: CC(=O)c1cn(CC(=O)N2C[C@H](F)C[C@H]2C(=O)Nc2cccc(Br)n2)c2ccc(-c3cccc(Cl)c3)cc12] | (2S,4R)-1-(2-(3-acetyl-5-(3-chlorophenyl)-1H-indol-1-yl)acetyl)-N-(6-bromopyridin-2-yl)-4-fluoropyrrolidine-2-carboxamide | *** | 2.54 (A) | 599 |
| 120 | 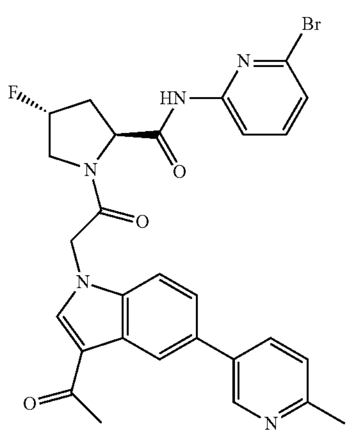 | (2S,4R)-1-(2-(3-acetyl-5-(6-methylpyridin-3-yl)-1H-indol-1-yl)acetyl)-N-(6-bromopyridin-2-yl)-4-fluoropyrrolidine-2-carboxamide | *** | 1.34 (A) | 578 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 121 | 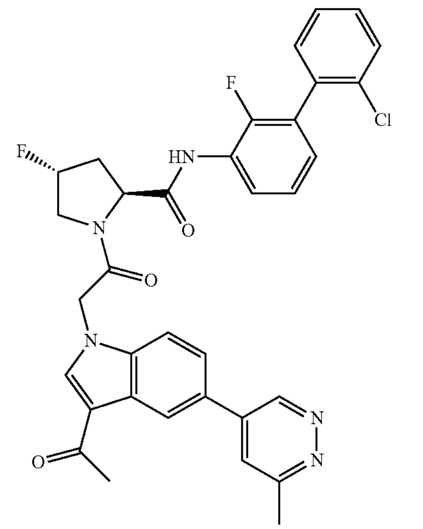 [SMILES: CC(=O)c1cn(CC(=O)N2C[C@H](F)C[C@H]2C(=O)Nc2cccc(-c3ccccc3Cl)c2F)c2ccc(-c3cnnc(C)c3)cc12] | (2S,4R)-1-(2-(3-acetyl-5-(6-methylpyridazin-4-yl)-1H-indol-1-yl)acetyl)-N-(2'-chloro-2-fluorobiphenyl-3-yl)-4-fluoropyrrolidine-2-carboxamide | *** | 1.96 (A) | 628 |
| 122 | 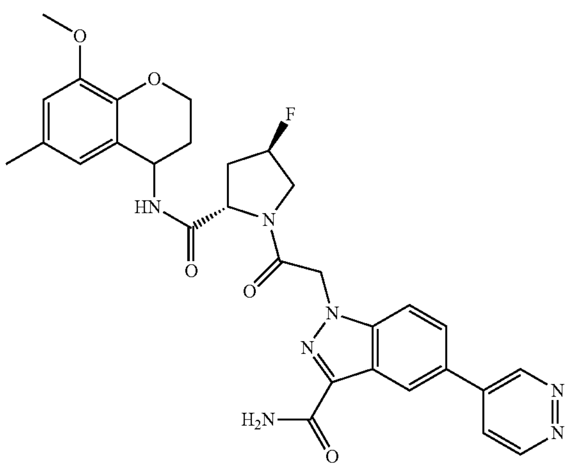 [SMILES: COc1cc(C)cc2c1OCCC2NC(=O)[C@@H]1C[C@@H](F)CN1C(=O)Cn1nc(C(N)=O)c2cc(-c3ccnnc3)ccc21] | 1-(2-((2S,4R)-4-fluoro-2-(8-methoxy-6-methylchroman-4-ylcarbamoyl)pyrrolidin-1-yl)-2-oxoethyl)-5-(pyridazin-4-yl)-1H-indazole-3-carboxamide | * | 2.38 (B) | 588 |
| 123 | 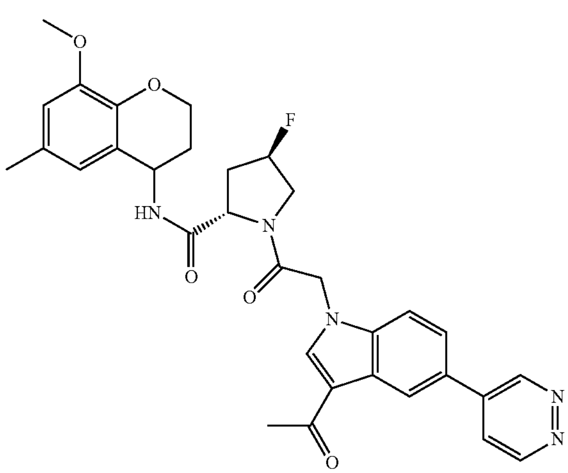 [SMILES: COc1cc(C)cc2c1OCCC2NC(=O)[C@@H]1C[C@@H](F)CN1C(=O)Cn1cc(C(C)=O)c2cc(-c3ccnnc3)ccc21] | (2S,4R)-1-(2-(3-acetyl-5-(pyridazin-4-yl)-1H-indol-1-yl)acetyl)-4-fluoro-N-(8-methoxy-6-methylchroman-4-yl)pyrrolidine-2-carboxamide | * | 2.58/2.73 (B) | 586 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 124 | 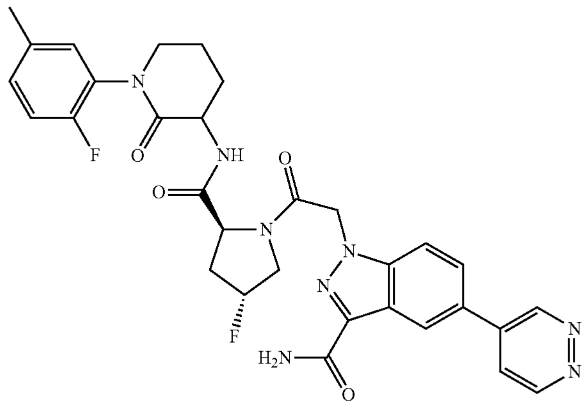 [SMILES: Cc1ccc(F)c(N2CCCC(NC(=O)[C@@H]3C[C@@H](F)CN3C(=O)Cn3nc(C(N)=O)c4cc(-c5ccnnc5)ccc43)C2=O)c1] | 1-(2-((2S,4R)-4-fluoro-2-(1-(2-fluoro-5-methylphenyl)-2-oxopiperidin-3-ylcarbamoyl)pyrrolidin-1-yl)-2-oxoethyl)-5-(pyridazin-4-yl)-1H-indazole-3-carboxamide | ** | 2.61 (B) | 617 |
| 125 | 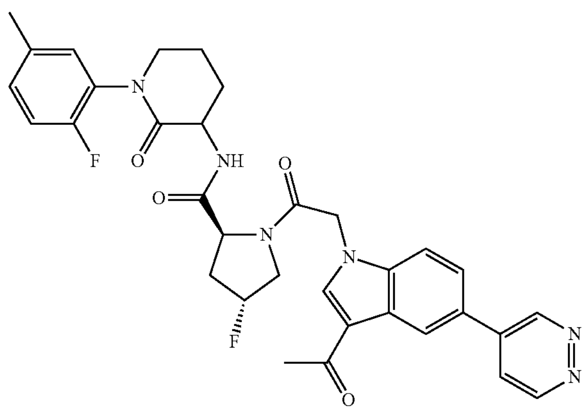 [SMILES: CC(=O)c1cn(CC(=O)N2C[C@H](F)C[C@H]2C(=O)NC2CCCN(c3cc(C)ccc3F)C2=O)c2ccc(-c3ccnnc3)cc12] | (2S,4R)-1-(2-(3-acetyl-5-(pyridazin-4-yl)-1H-indol-1-yl)acetyl)-4-fluoro-N-(1-(2-fluoro-5-methylphenyl)-2-oxopiperidin-3-yl)pyrrolidine-2-carboxamide | ** | 2.92 (B) | 615 |
| 126 | 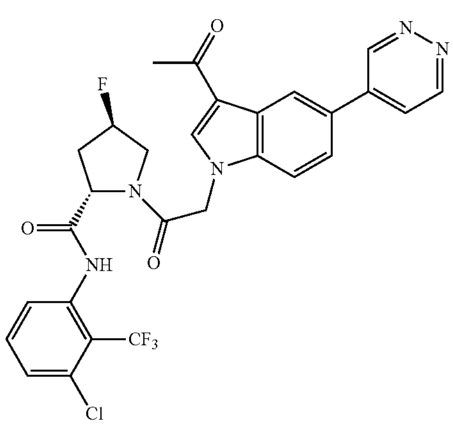 [SMILES: CC(=O)c1cn(CC(=O)N2C[C@H](F)C[C@H]2C(=O)Nc2cccc(Cl)c2C(F)(F)F)c2ccc(-c3ccnnc3)cc12] | (2S,4R)-1-(2-(3-acetyl-5-(pyridazin-4-yl)-1H-indol-1-yl)acetyl)-N-(3-chloro-2-(trifluoromethyl)phenyl)-4-fluoropyrrolidine-2-carboxamide | * | 3.09 (B) | 588 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 127 | 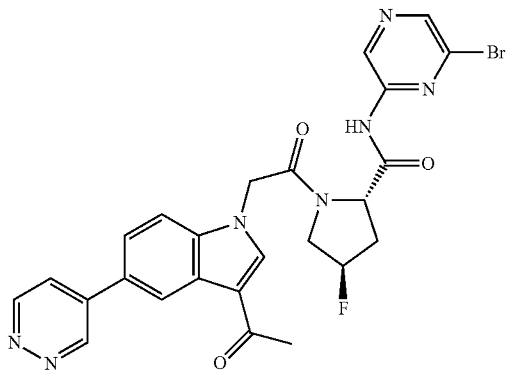 [SMILES: CC(=O)c1cn(CC(=O)N2C[C@H](F)C[C@H]2C(=O)Nc2cncc(Br)n2)c2ccc(-c3ccnnc3)cc12] | (2S,4R)-1-(2-(3-acetyl-5-(pyridazin-4-yl)-1H-indol-1-yl)acetyl)-N-(6-bromopyrazin-2-yl)-4-fluoropyrrolidine-2-carboxamide | *** | 2.47 (B) | 566 |
| 128 | 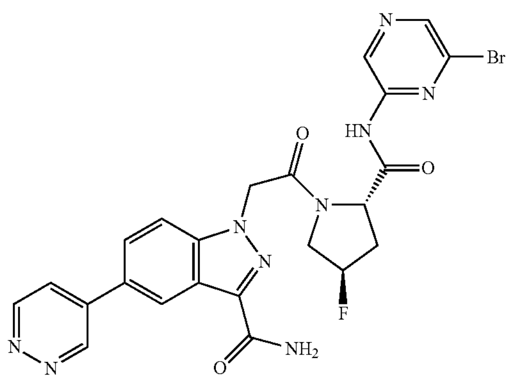 [SMILES: NC(=O)c1nn(CC(=O)N2C[C@H](F)C[C@H]2C(=O)Nc2cncc(Br)n2)c2ccc(-c3ccnnc3)cc12] | 1-(2-((2S,4R)-2-(6-bromopyrazin-2-ylcarbamoyl)-4-fluoropyrrolidin-1-yl)-2-oxoethyl)-5-(pyridazin-4-yl)-1H-indazole-3-carboxamide | *** | 2.22 (B) | 568 |
| 129 | 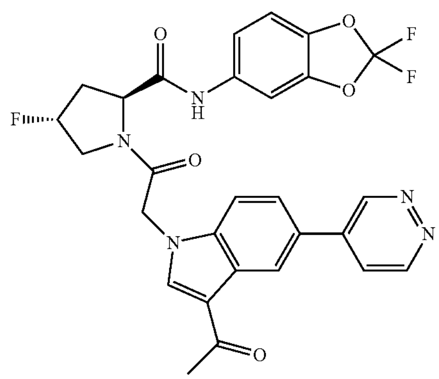 [SMILES: CC(=O)c1cn(CC(=O)N2C[C@H](F)C[C@H]2C(=O)Nc2ccc3c(c2)OC(F)(F)O3)c2ccc(-c3ccnnc3)cc12] | (2S,4R)-1-(2-(3-acetyl-5-(pyridazin-4-yl)-1H-indol-1-yl)acetyl)-4-fluoro-N-(2,2,6-trifluorobenzo[d][1,3]dioxol-5-yl)pyrrolidine-2-carboxamide | ** | 3.19 (B) | 584 |
| 130 | 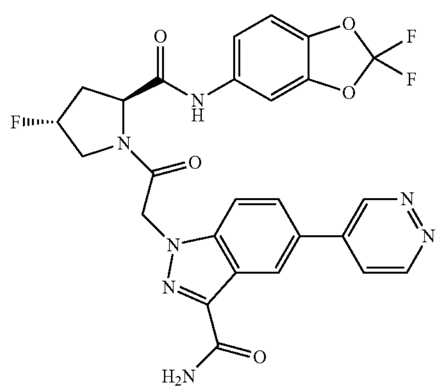 [SMILES: NC(=O)c1nn(CC(=O)N2C[C@H](F)C[C@H]2C(=O)Nc2ccc3c(c2)OC(F)(F)O3)c2ccc(-c3ccnnc3)cc12] | 1-(2-((2S,4R)-4-fluoro-2-(2,2,6-trifluorobenzo[d][1,3]dioxol-5-ylcarbamoyl)pyrrolidin-1-yl)-2-oxoethyl)-5-(pyridazin-4-yl)-1H-indazole-3-carboxamide | ** | 2.86 (B) | 586 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 131 | 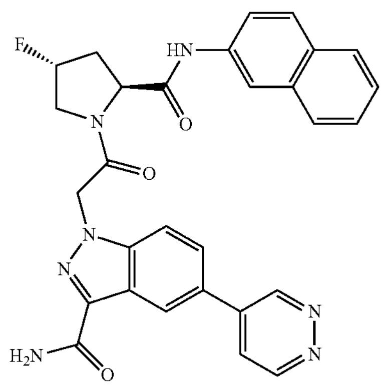 [SMILES: NC(=O)c1nn(CC(=O)N2C[C@H](F)C[C@H]2C(=O)Nc2ccc3ccccc3c2)c2ccc(-c3ccnnc3)cc12] | 1-(2-((2S,4R)-4-fluoro-2-(naphthalen-2-ylcarbamoyl)pyrrolidin-1-yl)-2-oxoethyl)-5-(pyridazin-4-yl)-1H-indazole-3-carboxamide | * | 2.77 (B) | 538 |
| 132 | 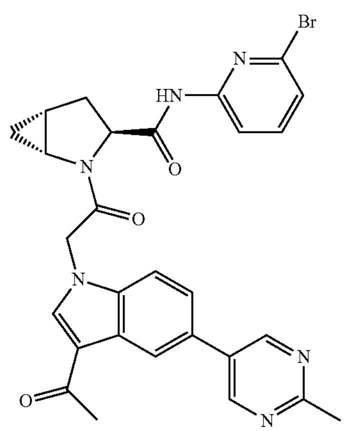 [SMILES: CC(=O)c1cn(CC(=O)N2[C@@H]3C[C@@H]3C[C@H]2C(=O)Nc2cccc(Br)n2)c2ccc(-c3cnc(C)nc3)cc12] | (1R,3S,5R)-2-(2-(3-acetyl-5-(2-methylpyrimidin-5-yl)-1H-indol-1-yl)acetyl)-N-(6-bromopyridin-2-yl)-2-azabicyclo[3.1.0]hexane-3-carboxamide | *** | 1.74 (A) | 573 |
| 133 | 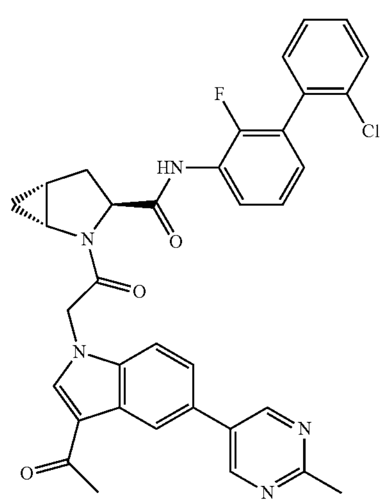 [SMILES: CC(=O)c1cn(CC(=O)N2[C@@H]3C[C@@H]3C[C@H]2C(=O)Nc2cccc(-c3ccccc3Cl)c2F)c2ccc(-c3cnc(C)nc3)cc12] | (1R,3S,5R)-2-(2-(3-acetyl-5-(2-methylpyrimidin-5-yl)-1H-indol-1-yl)acetyl)-N-(2'-chloro-2-fluorobiphenyl-3-yl)-2-azabicyclo[3.1.0]hexane-3-carboxamide | *** | 2.21 (A) | 622 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 134 | 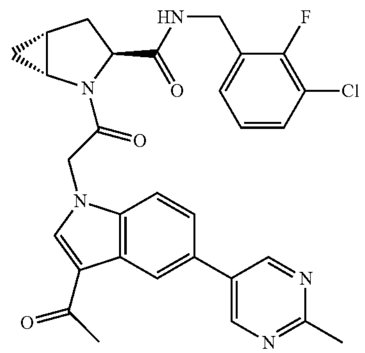 [SMILES: CC(=O)c1cn(CC(=O)N2[C@@H]3C[C@@H]3C[C@H]2C(=O)NCc2cccc(Cl)c2F)c2ccc(-c3cnc(C)nc3)cc12] | (1R,3S,5R)-2-(2-(3-acetyl-5-(2-methylpyrimidin-5-yl)-1H-indol-1-yl)acetyl)-N-(3-chloro-2-fluorobenzyl)-2-azabicyclo[3.1.0]hexane-3-carboxamide | *** | 1.71 (A) | 560 |
| 135 | 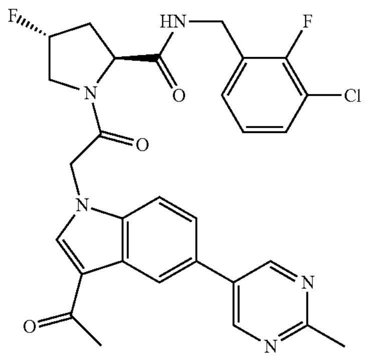 [SMILES: CC(=O)c1cn(CC(=O)N2C[C@H](F)C[C@H]2C(=O)NCc2cccc(Cl)c2F)c2ccc(-c3cnc(C)nc3)cc12] | (2S,4R)-1-(2-(3-acetyl-5-(2-methylpyrimidin-5-yl)-1H-indol-1-yl)acetyl)-N-(3-chloro-2-fluorobenzyl)-4-fluoropyrrolidine-2-carboxamide | *** | 1.64 (A) | 566 |
| 136 | 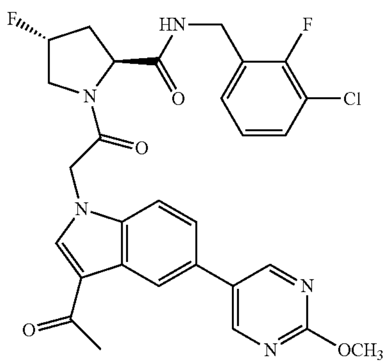 [SMILES: COc1ncc(-c2ccc3c(c2)c(C(C)=O)cn3CC(=O)N2C[C@H](F)C[C@H]2C(=O)NCc2cccc(Cl)c2F)cn1] | (2S,4R)-1-(2-(3-acetyl-5-(2-methoxypyrimidin-5-yl)-1H-indol-1-yl)acetyl)-N-(3-chloro-2-fluorobenzyl)-4-fluoropyrrolidine-2-carboxamide | *** | 1.80 (A) | 582 |
| 137 | 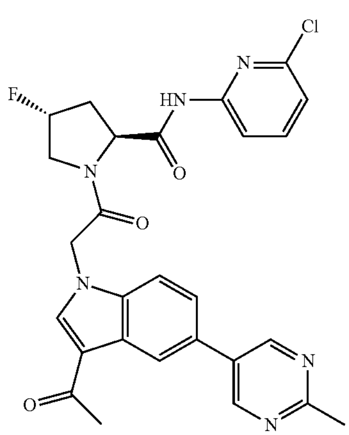 | (2S,4R)-1-(2-(3-acetyl-5-(2-methylpyrimidin-5-yl)-1H-indol-1-yl)acetyl)-N-(6-chloropyridin-2-yl)-4-fluoropyrrolidine-2-carboxamide | *** | 1.53 (A) | 535 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 138 | 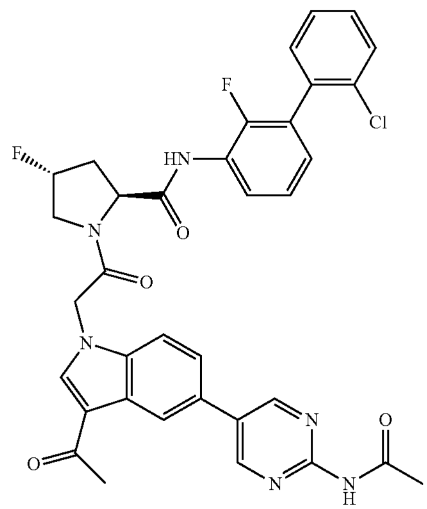 [SMILES: CC(=O)Nc1ncc(-c2ccc3c(c2)c(C(C)=O)cn3CC(=O)N2C[C@H](F)C[C@H]2C(=O)Nc2cccc(-c3ccccc3Cl)c2F)cn1] | (2S,4R)-1-(2-(5-(2-acetamidopyrimidin-5-yl)-3-acetyl-1H-indol-1-yl)acetyl)-N-(2'-chloro-2-fluorobiphenyl-3-yl)-4-fluoropyrrolidine-2-carboxamide | *** | 1.95 (A) | 671 |
| 139 | 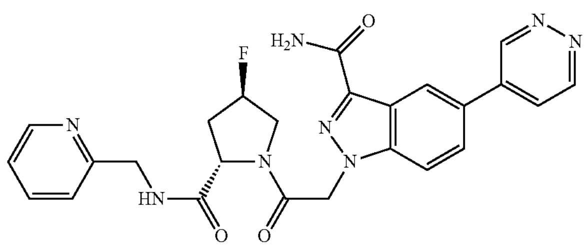 [SMILES: NC(=O)c1nn(CC(=O)N2C[C@H](F)C[C@H]2C(=O)NCc2ccccn2)c2ccc(-c3ccnnc3)cc12] | 1-(2-((2S,4R)-4-fluoro-2-(pyridin-2-ylmethylcarbamoyl)pyrrolidin-1-yl)-2-oxoethyl)-5-(pyridazin-4-yl)-1H-indazole-3-carboxamide | ** | 3.38 (B) | 503 |
| 140 | 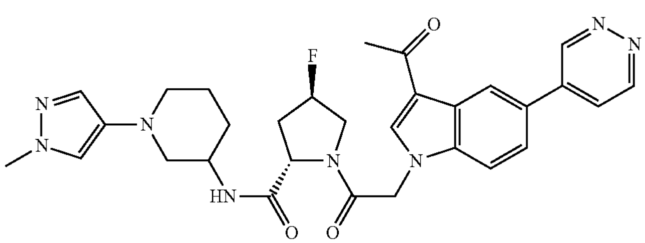 [SMILES: CC(=O)c1cn(CC(=O)N2C[C@H](F)C[C@H]2C(=O)NC2CCCN(c3cnn(C)c3)C2)c2ccc(-c3ccnnc3)cc12] | (2S,4R)-1-(2-(3-acetyl-5-(pyridazin-4-yl)-1H-indol-1-yl)acetyl)-4-fluoro-N-(1-(1-methyl-1H-pyrazol-4-yl)piperidin-3-yl)pyrrolidine-2-carboxamide | ** | 1.51 (B) | 573 |
| 141 | 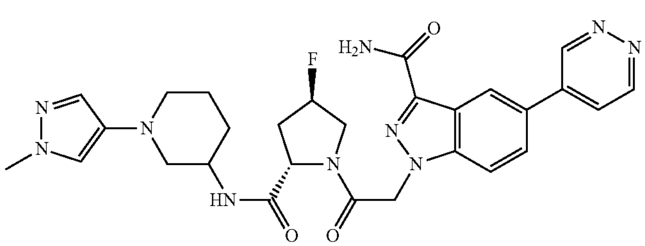 [SMILES: Cn1cc(N2CCCC(NC(=O)[C@@H]3C[C@@H](F)CN3C(=O)Cn3nc(C(N)=O)c4cc(-c5ccnnc5)ccc43)C2)cn1] | 1-(2-((2S,4R)-4-fluoro-2-(1-(1-methyl-1H-pyrazol-4-yl)piperidin-3-ylcarbamoyl)pyrrolidin-1-yl)-2-oxoethyl)-5-(pyridazin-4-yl)-1H-indazole-3-carboxamide | * | 2.37 (B) | 575 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 142 | 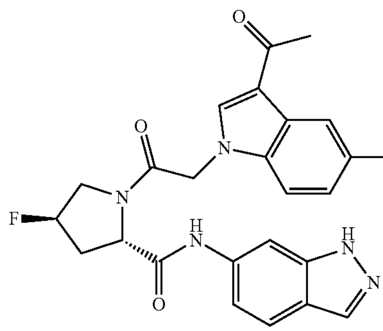 | (2S,4R)-1-(2-(3-acetyl-5-(pyridazin-4-yl)-1H-indol-1-yl)acetyl)-4-fluoro-N-(1H-indazol-6-yl)pyrrolidine-2-carboxamide | ** | 2.10 (B) | 526 |
| 143 | 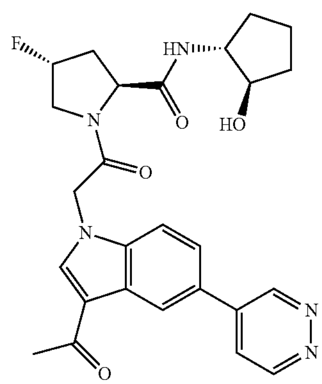 [SMILES: CC(=O)c1cn(CC(=O)N2C[C@H](F)C[C@H]2C(=O)N[C@@H]2CCC[C@H]2O)c2ccc(-c3ccnnc3)cc12] | (2S,4R)-1-(2-(3-acetyl-5-(pyridazin-4-yl)-1H-indol-1-yl)acetyl)-4-fluoro-N-((1R,2R)-2-hydroxycyclopentyl)pyrrolidine-2-carboxamide | * | 1.59 (B) | 494 |
| 144 | 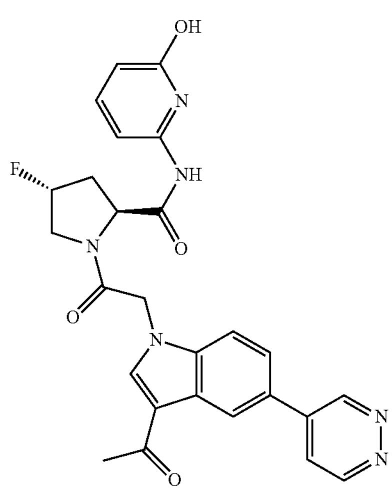 [SMILES: CC(=O)c1cn(CC(=O)N2C[C@H](F)C[C@H]2C(=O)Nc2cccc(O)n2)c2ccc(-c3ccnnc3)cc12] | (2S,4R)-1-(2-(3-acetyl-5-(pyridazin-4-yl)-1H-indol-1-yl)acetyl)-4-fluoro-N-(6-hydroxypyridin-2-yl)pyrrolidine-2-carboxamide | * | 1.43 (B) | 503 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 145 | 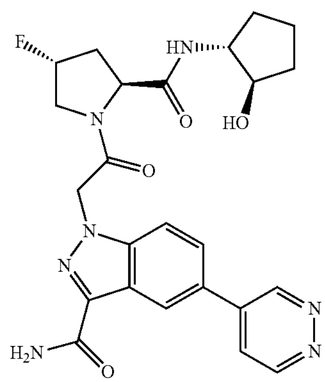 [SMILES: NC(=O)c1nn(CC(=O)N2C[C@H](F)C[C@H]2C(=O)N[C@@H]2CCC[C@H]2O)c2ccc(-c3ccnnc3)cc12] | 1-(2-((2S,4R)-4-fluoro-2-((1R,2R)-2-hydroxycyclopentyl carbamoyl)pyrrolidin-1-yl)-2-oxoethyl)-5-(pyridazin-4-yl)-1H-indazole-3-carboxamide | * | 1.66 (B) | 496 |
| 146 | 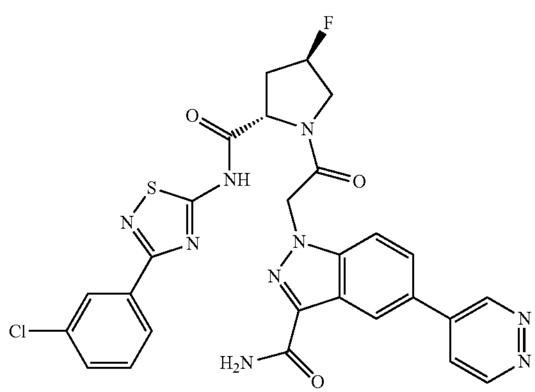 [SMILES: NC(=O)c1nn(CC(=O)N2C[C@H](F)C[C@H]2C(=O)Nc2nc(-c3cccc(Cl)c3)ns2)c2ccc(-c3ccnnc3)cc12] | 1-(2-((2S,4R)-2-(3-(3-chlorophenyl)-1,2,4-thiadiazol-5-ylcarbamoyl)-4-fluoropyrrolidin-1-yl)-2-oxoethyl)-5-(pyridazin-4-yl)-1H-indazole-3-carboxamide | * | 3.47 (B) | 606 |
| 147 | 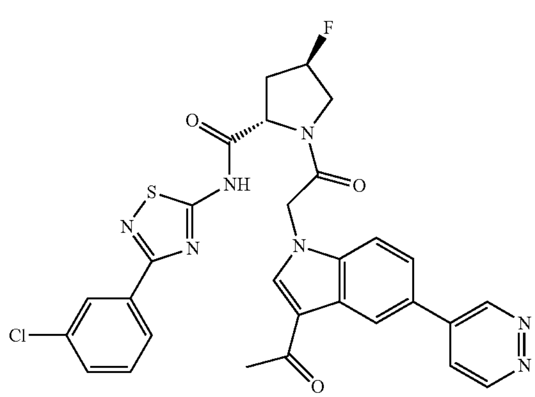 [SMILES: CC(=O)c1cn(CC(=O)N2C[C@H](F)C[C@H]2C(=O)Nc2nc(-c3cccc(Cl)c3)ns2)c2ccc(-c3ccnnc3)cc12] | (2S,4R)-1-(2-(3-acetyl-5-(pyridazin-4-yl)-1H-indol-1-yl)acetyl)-N-(3-(3-chlorophenyl)-1,2,4-thiadiazol-5-yl)-4-fluoropyrrolidine-2-carboxamide | * | 3.67 (B) | 604 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 148 | 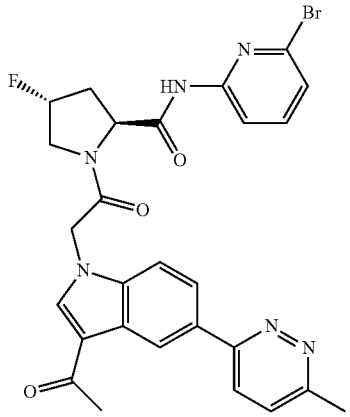 [SMILES: CC(=O)c1cn(CC(=O)N2C[C@H](F)C[C@H]2C(=O)Nc2cccc(Br)n2)c2ccc(-c3ccc(C)nn3)cc12] | (2S,4R)-1-(2-(3-acetyl-5-(6-methylpyridazin-3-yl)-1H-indol-1-yl)acetyl)-N-(6-bromopyridin-2-yl)-4-fluoropyrrolidine-2-carboxamide | *** | 1.49 (A) | 580 |
| 149 | 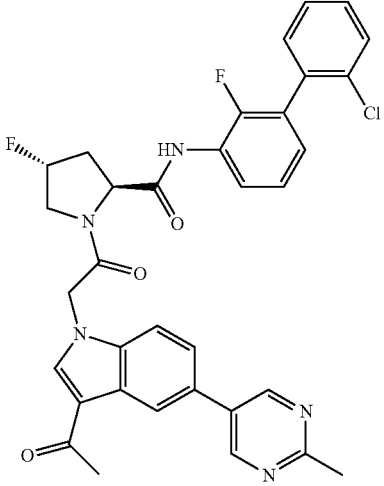 | (2S,4R)-1-(2-(3-acetyl-5-(2-methylpyrimidin-5-yl)-1H-indol-1-yl)acetyl)-N-(2,2'-dichlorobiphenyl-3-yl)-4-fluoropyrrolidine-2-carboxamide | *** | 2.17 (A) | 644 |
| 150 | 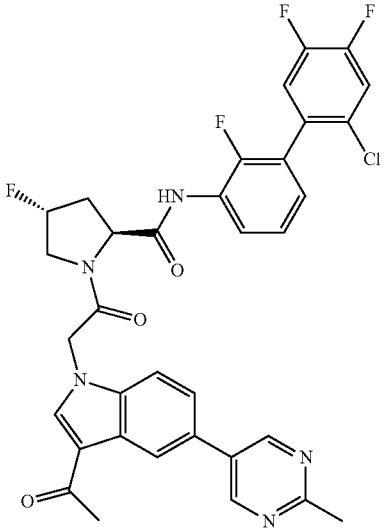 [SMILES: CC(=O)c1cn(CC(=O)N2C[C@H](F)C[C@H]2C(=O)Nc2cccc(-c3cc(F)c(F)cc3Cl)c2F)c2ccc(-c3cnc(C)nc3)cc12] | (2S,4R)-1-(2-(3-acetyl-5-(2-methylpyrimidin-5-yl)-1H-indol-1-yl)acetyl)-N-(2'-chloro-2,4',5'-trifluorobiphenyl-3-yl)-4-fluoropyrrolidine-2-carboxamide | *** | 2.22 (A) | 664 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 151 | 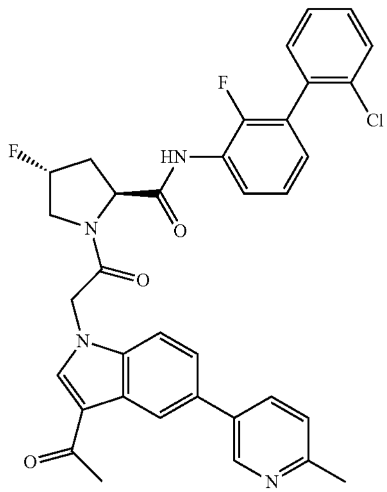 [SMILES: CC(=O)c1cn(CC(=O)N2C[C@H](F)C[C@H]2C(=O)Nc2cccc(-c3ccccc3Cl)c2F)c2ccc(-c3ccc(C)nc3)cc12] | (2S,4R)-1-(2-(3-acetyl-5-(6-methylpyridin-3-yl)-1H-indol-1-yl)acetyl)-N-(2'-chloro-2-fluorobiphenyl-3-yl)-4-fluoropyrrolidine-2-carboxamide | *** | 1.91 (A) | 627 |
| 152 | 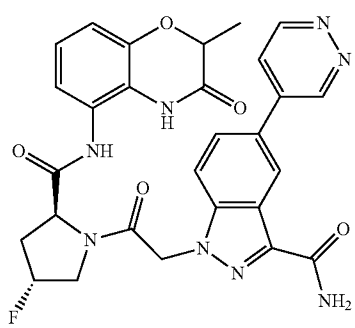 [SMILES: CC1Oc2cccc(NC(=O)[C@@H]3C[C@@H](F)CN3C(=O)Cn3nc(C(N)=O)c4cc(-c5ccnnc5)ccc43)c2NC1=O] | 1-(2-((2S,4R)-4-fluoro-2-(2-methyl-3-oxo-3,4-dihydro-2H-benzo[b][1,4]oxazin-5-ylcarbamoyl)pyrrolidin-1-yl)-2-oxoethyl)-5-(pyridazin-4-yl)-1H-indazole-3-carboxamide | * | 1.97 (B) | 573 |
| 153 | 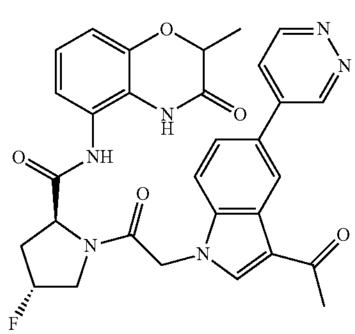 [SMILES: CC(=O)c1cn(CC(=O)N2C[C@H](F)C[C@H]2C(=O)Nc2cccc3c2NC(=O)C(C)O3)c2ccc(-c3ccnnc3)cc12] | (2S,4R)-1-(2-(3-acetyl-5-(pyridazin-4-yl)-1H-indol-1-yl)acetyl)-4-fluoro-N-(2-methyl-3-oxo-3,4-dihydro-2H-benzo[b][1,4]oxazin-5-yl)pyrrolidine-2-carboxamide | * | 2.31 (B) | 571 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 154 | 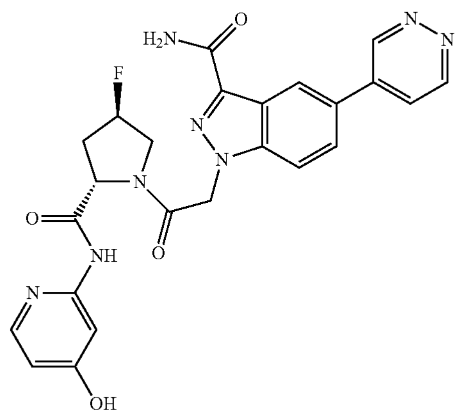 [SMILES: NC(=O)c1nn(CC(=O)N2C[C@H](F)C[C@H]2C(=O)Nc2cc(O)ccn2)c2ccc(-c3ccnnc3)cc12] | 1-(2-((2S,4R)-4-fluoro-2-(4-hydroxypyridin-2-ylcarbamoyl)pyrrolidin-1-yl)-2-oxoethyl)-5-(pyridazin-4-yl)-1H-indazole-3-carboxamide | * | 2.17 (B) | 505 |
| 155 | 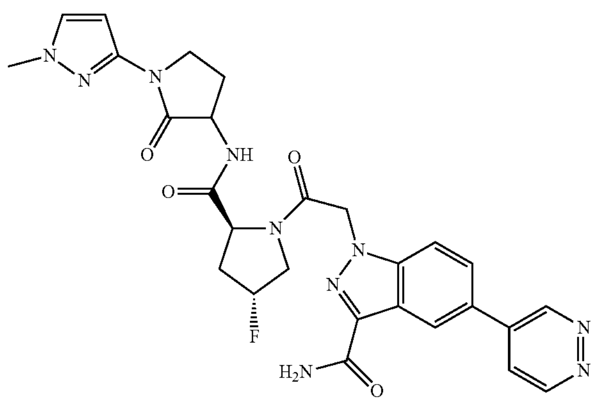 [SMILES: Cn1ccc(N2CCC(NC(=O)[C@@H]3C[C@@H](F)CN3C(=O)Cn3nc(C(N)=O)c4cc(-c5ccnnc5)ccc43)C2=O)n1] | 1-(2-((2S,4R)-4-fluoro-2-(1-(1-methyl-1H-pyrazol-3-yl)-2-oxopyrrolidin-3-ylcarbamoyl)pyrrolidin-1-yl)-2-oxoethyl)-5-(pyridazin-4-yl)-1H-indazole-3-carboxamide | * | 1.19 (B) | 575 |
| 156 | 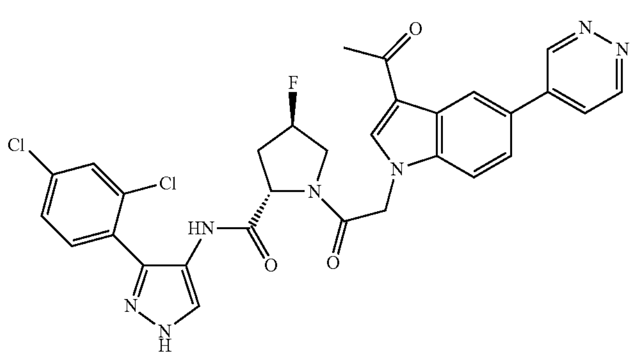 [SMILES: CC(=O)c1cn(CC(=O)N2C[C@H](F)C[C@H]2C(=O)Nc2c[nH]nc2-c2ccc(Cl)cc2Cl)c2ccc(-c3ccnnc3)cc12] | (2S,4R)-1-(2-(3-acetyl-5-(pyridazin-4-yl)-1H-indol-1-yl)acetyl)-N-(3-(2,4-dichlorophenyl)-1H-pyrazol-4-yl)-4-fluoropyrrolidine-2-carboxamide | * | 2.98 (B) | 620 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 157 | 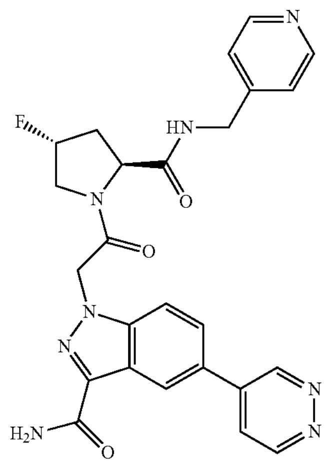 [SMILES: NC(=O)c1nn(CC(=O)N2C[C@H](F)C[C@H]2C(=O)NCc2ccncc2)c2ccc(-c3ccnnc3)cc12] | 1-(2-((2S,4R)-4-fluoro-2-(pyridin-4-ylmethylcarbamoyl)pyrrolidin-1-yl)-2-oxoethyl)-5-(pyridazin-4-yl)-1H-indazole-3-carboxamide | * | 0.37 (B) | 503 |
| 158 | 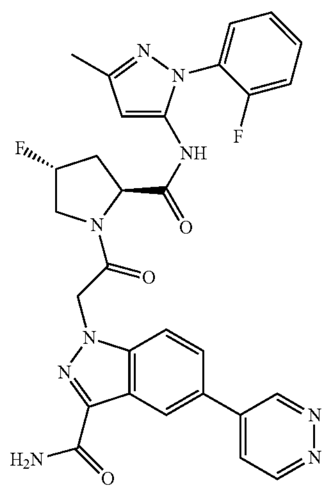 [SMILES: Cc1cc(NC(=O)[C@@H]2C[C@@H](F)CN2C(=O)Cn2nc(C(N)=O)c3cc(-c4ccnnc4)ccc32)n(-c2ccccc2F)n1] | 1-(2-((2S,4R)-4-fluoro-2-(1-(2-fluorophenyl)-3-methyl-1H-pyrazol-5-ylcarbamoyl)pyrrolidin-1-yl)-2-oxoethyl)-5-(pyridazin-4-yl)-1H-indazole-3-carboxamide | * | 2.49 (B) | 586 |
| 159 | 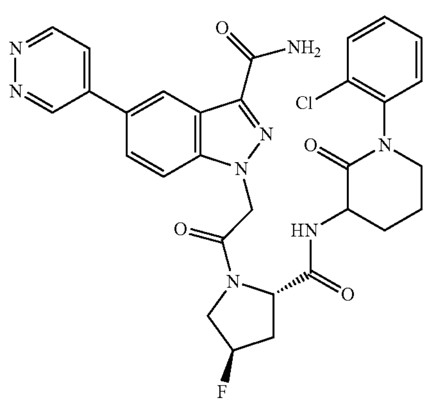 [SMILES: NC(=O)c1nn(CC(=O)N2C[C@H](F)C[C@H]2C(=O)NC2CCCN(c3ccccc3Cl)C2=O)c2ccc(-c3ccnnc3)cc12] | 1-(2-((2S,4R)-2-(1-(2-chlorophenyl)-2-oxopiperidin-3-ylcarbamoyl)-4-fluoropyrrolidin-1-yl)-2-oxoethyl)-5-(pyridazin-4-yl)-1H-indazole-3-carboxamide | ** | 2.46 (B) | 619 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 160 | 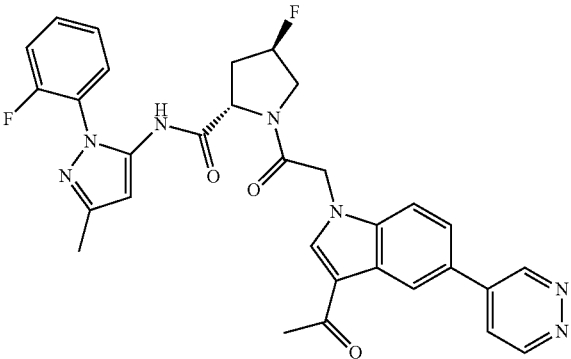 [SMILES: CC(=O)c1cn(CC(=O)N2C[C@H](F)C[C@H]2C(=O)Nc2cc(C)nn2-c2ccccc2F)c2ccc(-c3ccnnc3)cc12] | (2S,4R)-1-(2-(3-acetyl-5-(pyridazin-4-yl)-1H-indol-1-yl)acetyl)-4-fluoro-N-(1-(2-fluorophenyl)-3-methyl-1H-pyrazol-5-yl)pyrrolidine-2-carboxamide | ** | 2.36 (B) | 584 |
| 161 | 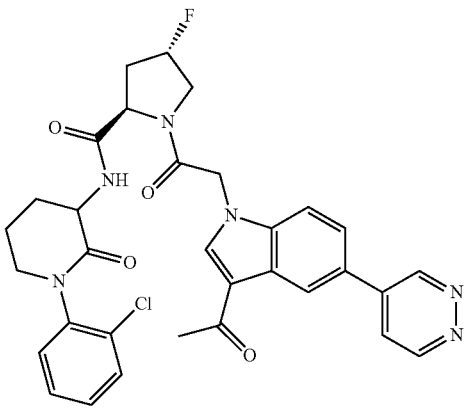 [SMILES: CC(=O)c1cn(CC(=O)N2C[C@@H](F)C[C@@H]2C(=O)NC2CCCN(c3ccccc3Cl)C2=O)c2ccc(-c3ccnnc3)cc12] | (2R,4S)-1-(2-(3-acetyl-5-(pyridazin-4-yl)-1H-indol-1-yl)acetyl)-N-(1-(2-chlorophenyl)-2-oxopiperidin-3-yl)-4-fluoropyrrolidine-2-carboxamide | *** | 2.85 (B) | 617 |
| 162 | 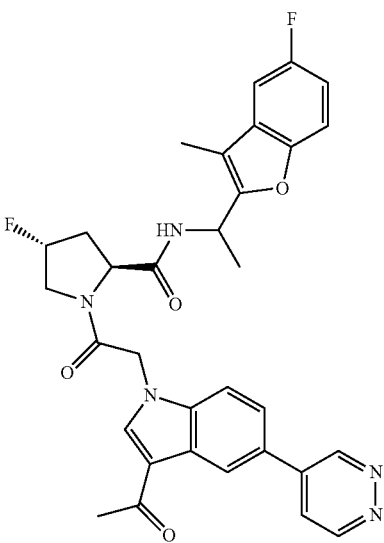 [SMILES: CC(=O)c1cn(CC(=O)N2C[C@H](F)C[C@H]2C(=O)NC(C)c2oc3ccc(F)cc3c2C)c2ccc(-c3ccnnc3)cc12] | (2S,4R)-1-(2-(3-acetyl-5-(pyridazin-4-yl)-1H-indol-1-yl)acetyl)-4-fluoro-N-(1-(5-fluoro-3-methylbenzofuran-2-yl)ethyl)pyrrolidine-2-carboxamide | ** | 3.52 (B) | 586 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 163 | 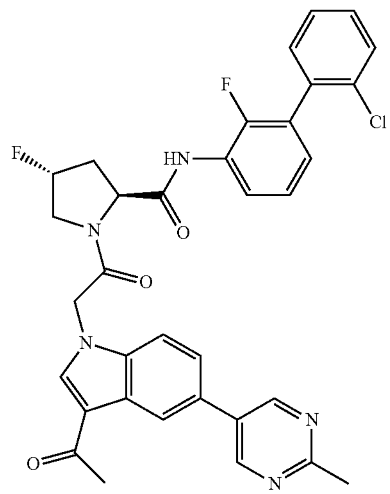 [SMILES: CC(=O)c1cn(CC(=O)N2C[C@H](F)C[C@H]2C(=O)Nc2cccc(-c3ccccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2'-chloro-2-fluorobiphenyl-3-yl)-4-fluoropyrrolidine-2-carboxamide | *** | 2.23 (A) | 629 |
| 164 | 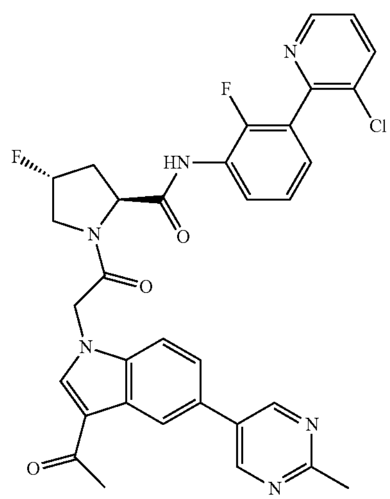 [SMILES: CC(=O)c1cn(CC(=O)N2C[C@H](F)C[C@H]2C(=O)Nc2cccc(-c3ncccc3Cl)c2F)c2ccc(-c3cnc(C)nc3)cc12] | (2S,4R)-1-(2-(3-acetyl-5-(2-methylpyrimidin-5-yl)-1H-indol-1-yl)acetyl)-N-(3-(3-chloropyridin-2-yl)-2-fluorophenyl)-4-fluoropyrrolidine-2-carboxamide | *** | 1.65 (A) | 629 |
| 165 | 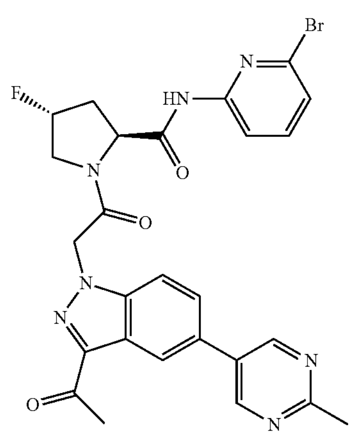 | (2S,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide | *** | 1.75 (A) | 580 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 166 | 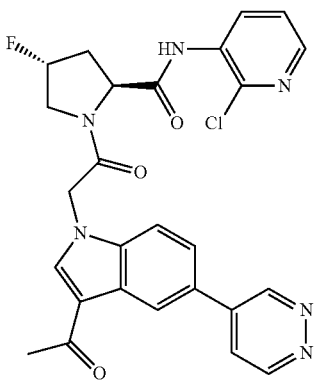 [SMILES: CC(=O)c1cn(CC(=O)N2C[C@H](F)C[C@H]2C(=O)Nc2cccnc2Cl)c2ccc(-c3ccnnc3)cc12] | (2S,4R)-1-(2-(3-acetyl-5-(pyridazin-4-yl)-1H-indol-1-yl)acetyl)-N-(2-chloropyridin-3-yl)-4-fluoropyrrolidine-2-carboxamide | ** | 2.26 (B) | 521 |
| 167 | 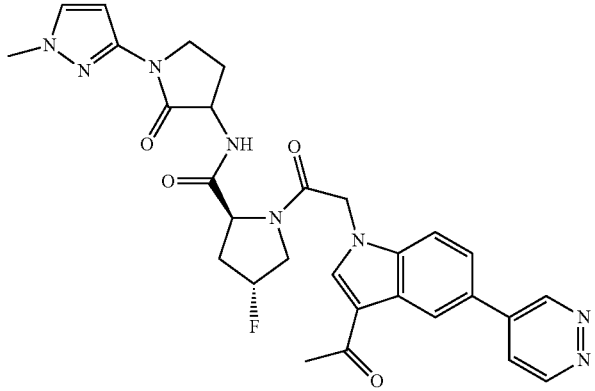 [SMILES: CC(=O)c1cn(CC(=O)N2C[C@H](F)C[C@H]2C(=O)NC2CCN(c3ccn(C)n3)C2=O)c2ccc(-c3ccnnc3)cc12] | (2S,4R)-1-(2-(3-acetyl-5-(pyridazin-4-yl)-1H-indol-1-yl)acetyl)-4-fluoro-N-(1-(1-methyl-1H-pyrazol-3-yl)-2-oxopyrrolidin-3-yl)pyrrolidine-2-carboxamide | ** | 2.15 (B) | 573 |
| 168 | 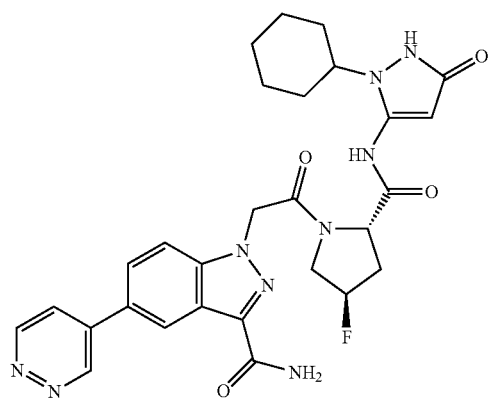 [SMILES: NC(=O)c1nn(CC(=O)N2C[C@H](F)C[C@H]2C(=O)Nc2cc(=O)[nH]n2C2CCCCC2)c2ccc(-c3ccnnc3)cc12] | 1-(2-((2S,4R)-2-(2-cyclohexyl-5-oxo-2,5-dihydro-1H-pyrazol-3-ylcarbamoyl)-4-fluoropyrrolidin-1-yl)-2-oxoethyl)-5-(pyridazin-4-yl)-1H-indazole-3-carboxamide | * | 2.20 (B) | 576 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 169 | 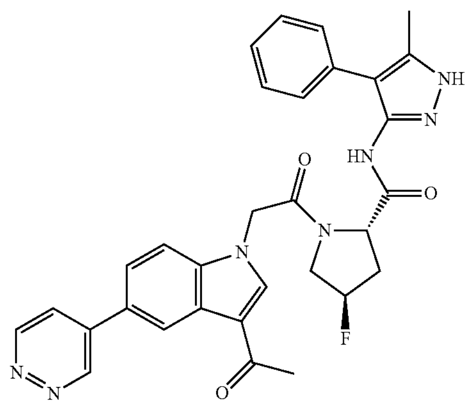 [SMILES: CC(=O)c1cn(CC(=O)N2C[C@H](F)C[C@H]2C(=O)Nc2n[nH]c(C)c2-c2ccccc2)c2ccc(-c3ccnnc3)cc12] | (2S,4R)-1-(2-(3-acetyl-5-(pyridazin-4-yl)-1H-indol-1-yl)acetyl)-4-fluoro-N-(5-methyl-4-phenyl-1H-pyrazol-3-yl)pyrrolidine-2-carboxamide | *** | 2.88 (B) | 566 |
| 170 | 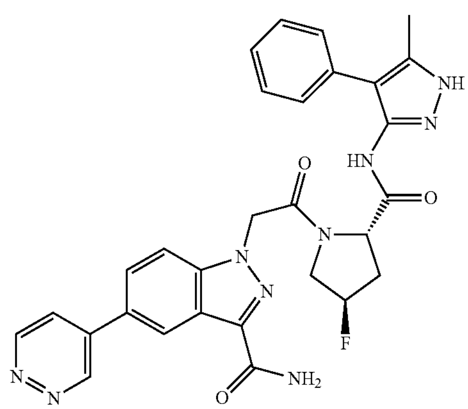 [SMILES: Cc1[nH]nc(NC(=O)[C@@H]2C[C@@H](F)CN2C(=O)Cn2nc(C(N)=O)c3cc(-c4ccnnc4)ccc32)c1-c1ccccc1] | 1-(2-((2S,4R)-4-fluoro-2-(5-methyl-4-phenyl-1H-pyrazol-3-ylcarbamoyl)pyrrolidin-1-yl)-2-oxoethyl)-5-(pyridazin-4-yl)-1H-indazole-3-carboxamide | ** | 2.58 (B) | 568 |
| 171 | 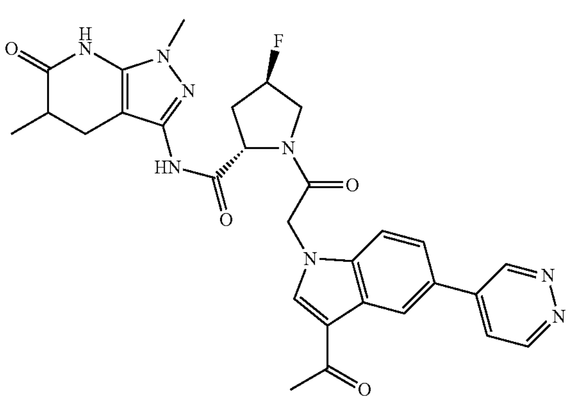 [SMILES: CC(=O)c1cn(CC(=O)N2C[C@H](F)C[C@H]2C(=O)Nc2nn(C)c3c2CC(C)C(=O)N3)c2ccc(-c3ccnnc3)cc12] | (2S,4R)-1-(2-(3-acetyl-5-(pyridazin-4-yl)-1H-indol-1-yl)acetyl)-N-(1,5-dimethyl-6-oxo-4,5,6,7-tetrahydro-1H-pyrazolo[3,4-b]pyridin-3-yl)-4-fluoropyrrolidine-2-carboxamide | ** | 1.26 (B) | 573 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 172 | 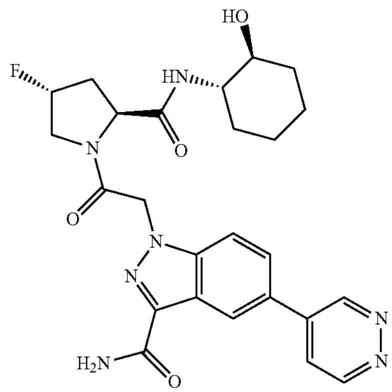 [SMILES: NC(=O)c1nn(CC(=O)N2C[C@H](F)C[C@H]2C(=O)N[C@H]2CCCC[C@@H]2O)c2ccc(-c3ccnnc3)cc12] | 1-(2-((2S,4R)-4-fluoro-2-((1S,2S)-2-hydroxycyclohexyl carbamoyl) pyrrolidin-1-yl)-2-oxoethyl)-5-(pyridazin-4-yl)-1H-indazole-3-carboxamide | * | 1.54 (B) | 510 |
| 173 | 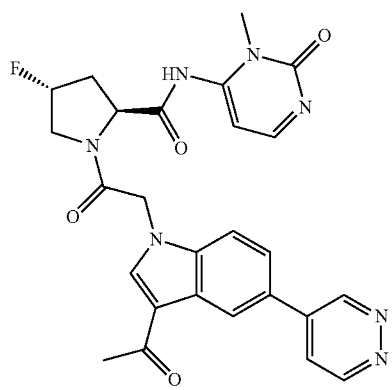 [SMILES: CC(=O)c1cn(CC(=O)N2C[C@H](F)C[C@H]2C(=O)Nc2ccnc(=O)n2C)c2ccc(-c3ccnnc3)cc12] | (2S,4R)-1-(2-(3-acetyl-5-(pyridazin-4-yl)-1H-indol-1-yl)acetyl)-4-fluoro-N-(3-methyl-2-oxo-2,3-dihydropyrimidin-4-yl)pyrrolidine-2-carboxamide | * | 2.17 (B) | 518 |
| 174 | 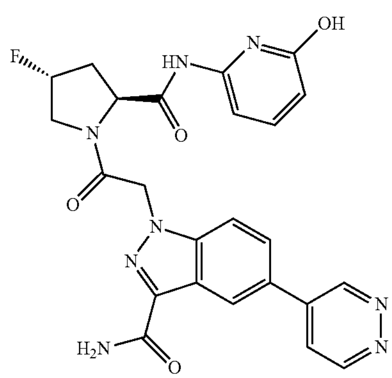 [SMILES: NC(=O)c1nn(CC(=O)N2C[C@H](F)C[C@H]2C(=O)Nc2cccc(O)n2)c2ccc(-c3ccnnc3)cc12] | 1-(2-((2S,4R)-4-fluoro-2-(6-hydroxypyridin-2-ylcarbamoyl) pyrrolidin-1-yl)-2-oxoethyl)-5-(pyridazin-4-yl)-1H-indazole-3-carboxamide | * | 1.71 (B) | 505 |
| 175 | 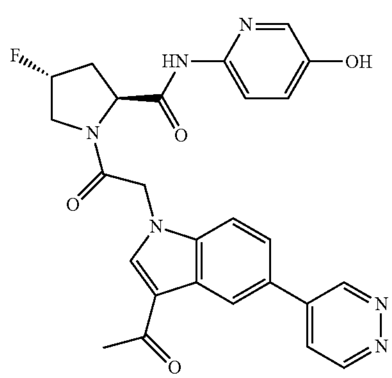 [SMILES: CC(=O)c1cn(CC(=O)N2C[C@H](F)C[C@H]2C(=O)Nc2ccc(O)cn2)c2ccc(-c3ccnnc3)cc12] | (2S,4R)-1-(2-(3-acetyl-5-(pyridazin-4-yl)-1H-indol-1-yl)acetyl)-4-fluoro-N-(5-hydroxypyridin-2-yl)pyrrolidine-2-carboxamide | * | 2.25 (B) | 503 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 176 | 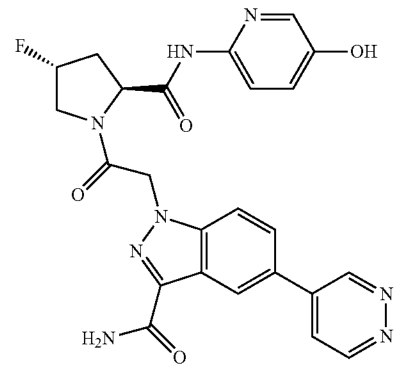 [SMILES: NC(=O)c1nn(CC(=O)N2C[C@H](F)C[C@H]2C(=O)Nc2ccc(O)cn2)c2ccc(-c3ccnnc3)cc12] | 1-(2-((2S,4R)-4-fluoro-2-(5-hydroxypyridin-2-ylcarbamoyl)pyrrolidin-1-yl)-2-oxoethyl)-5-(pyridazin-4-yl)-1H-indazole-3-carboxamide | * | 1.06 (B) | 505 |
| 177 | 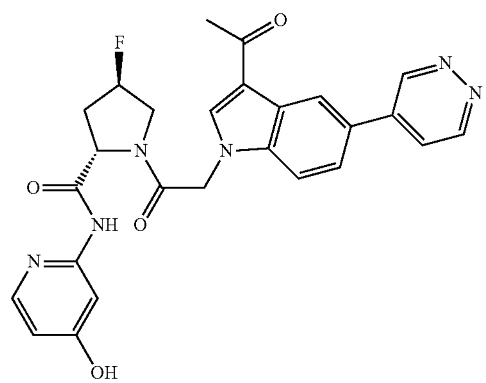 [SMILES: CC(=O)c1cn(CC(=O)N2C[C@H](F)C[C@H]2C(=O)Nc2cc(O)ccn2)c2ccc(-c3ccnnc3)cc12] | (2S,4R)-1-(2-(3-acetyl-5-(pyridazin-4-yl)-1H-indol-1-yl)acetyl)-4-fluoro-N-(4-hydroxypyridin-2-yl)pyrrolidine-2-carboxamide | ** | 2.08 (B) | 503 |
| 178 | 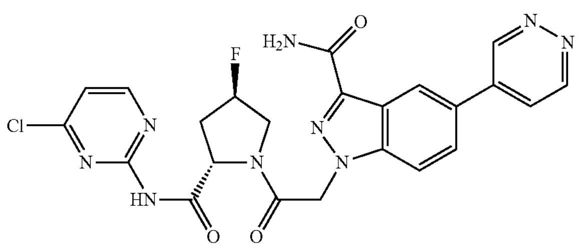 [SMILES: NC(=O)c1nn(CC(=O)N2C[C@H](F)C[C@H]2C(=O)Nc2nccc(Cl)n2)c2ccc(-c3ccnnc3)cc12] | 1-(2-((2S,4R)-2-(4-chloropyrimidin-2-ylcarbamoyl)-4-fluoropyrrolidin-1-yl)-2-oxoethyl)-5-(pyridazin-4-yl)-1H-indazole-3-carboxamide | * | 3.26 (B) | 524 |
| 179 | 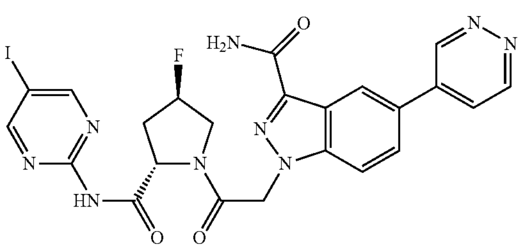 [SMILES: NC(=O)c1nn(CC(=O)N2C[C@H](F)C[C@H]2C(=O)Nc2ncc(I)cn2)c2ccc(-c3ccnnc3)cc12] | 1-(2-((2S,4R)-4-fluoro-2-(5-iodopyrimidin-2-ylcarbamoyl)pyrrolidin-1-yl)-2-oxoethyl)-5-(pyridazin-4-yl)-1H-indazole-3-carboxamide | ** | 2.78 (B) | 616 |
| 180 | 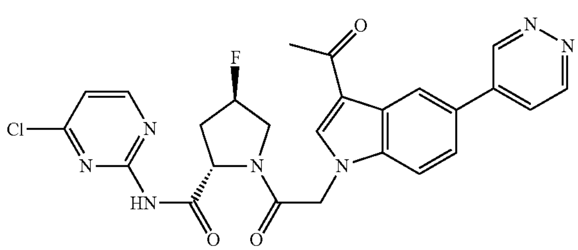 [SMILES: CC(=O)c1cn(CC(=O)N2C[C@H](F)C[C@H]2C(=O)Nc2nccc(Cl)n2)c2ccc(-c3ccnnc3)cc12] | (2S,4R)-1-(2-(3-acetyl-5-(pyridazin-4-yl)-1H-indol-1-yl)acetyl)-N-(4-chloropyrimidin-2-yl)-4-fluoropyrrolidine-2-carboxamide | * | 3.57 (B) | 522 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 181 | 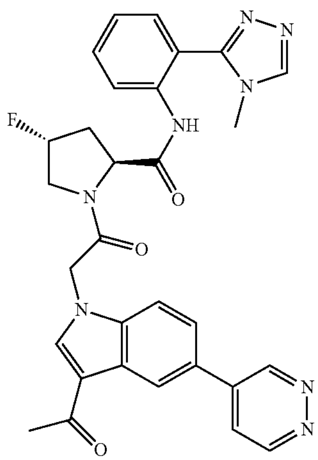 [SMILES: CC(=O)c1cn(CC(=O)N2C[C@H](F)C[C@H]2C(=O)Nc2ccccc2-c2nncn2C)c2ccc(-c3ccnnc3)cc12] | (2S,4R)-1-(2-(3-acetyl-5-(pyridazin-4-yl)-1H-indol-1-yl)acetyl)-4-fluoro-N-(2-(4-methyl-4H-1,2,4-triazol-3-yl)phenyl)pyrrolidine-2-carboxamide | * | 3.16 (B) | 567 |
| 182 | 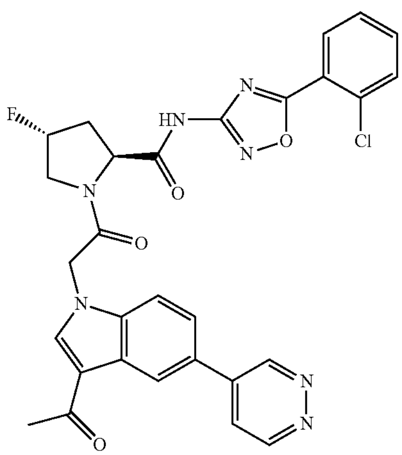 [SMILES: CC(=O)c1cn(CC(=O)N2C[C@H](F)C[C@H]2C(=O)Nc2noc(-c3ccccc3Cl)n2)c2ccc(-c3ccnnc3)cc12] | (2S,4R)-1-(2-(3-acetyl-5-(pyridazin-4-yl)-1H-indol-1-yl)acetyl)-N-(5-(2-chlorophenyl)-1,2,4-oxadiazol-3-yl)-4-fluoropyrrolidine-2-carboxamide | *** | 3.45 (B) | 588 |
| 183 | 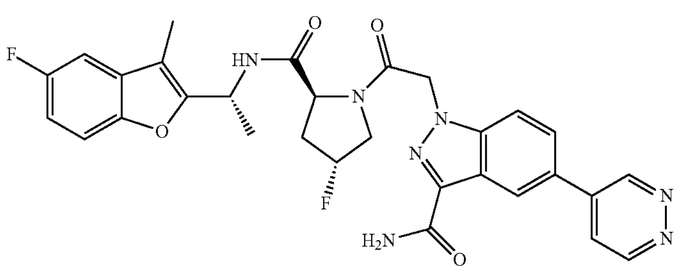 [SMILES: Cc1c([C@@H](C)NC(=O)[C@@H]2C[C@@H](F)CN2C(=O)Cn2nc(C(N)=O)c3cc(-c4ccnnc4)ccc32)oc2ccc(F)cc12] | 1-(2-((2S,4R)-4-fluoro-2-((R)-1-(5-fluoro-3-methylbenzofuran-2-yl)ethylcarbamoyl)pyrrolidin-1-yl)-2-oxoethyl)-5-(pyridazin-4-yl)-1H-indazole-3-carboxamide | * | 3.02 (B) | 588 |
| 184 | 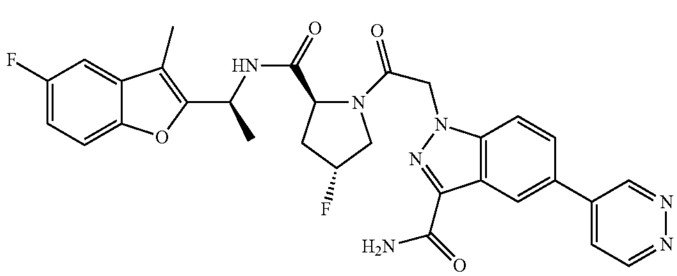 [SMILES: Cc1c([C@H](C)NC(=O)[C@@H]2C[C@@H](F)CN2C(=O)Cn2nc(C(N)=O)c3cc(-c4ccnnc4)ccc32)oc2ccc(F)cc12] | 1-(2-((2S,4R)-4-fluoro-2-((S)-1-(5-fluoro-3-methylbenzofuran-2-yl)ethylcarbamoyl)pyrrolidin-1-yl)-2-oxoethyl)-5-(pyridazin-4-yl)-1H-indazole-3-carboxamide | ** | 3.30 (B) | 588 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 185 | 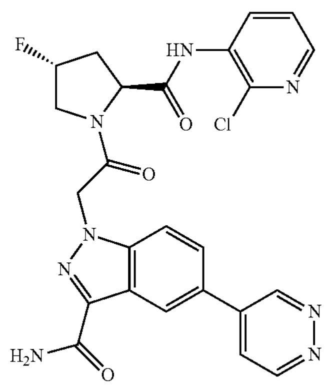 [SMILES: NC(=O)c1nn(CC(=O)N2C[C@H](F)C[C@H]2C(=O)Nc2cccnc2Cl)c2ccc(-c3ccnnc3)cc12] | 1-(2-((2S,4R)-2-(2-chloropyridin-3-ylcarbamoyl)-4-fluoropyrrolidin-1-yl)-2-oxoethyl)-5-(pyridazin-4-yl)-1H-indazole-3-carboxamide | ** | 1.70 (B) | 523 |
| 186 | 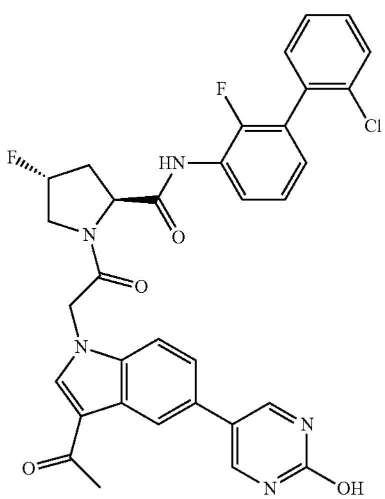 [SMILES: CC(=O)c1cn(CC(=O)N2C[C@H](F)C[C@H]2C(=O)Nc2cccc(-c3ccccc3Cl)c2F)c2ccc(-c3cnc(O)nc3)cc12] | (2S,4R)-1-(2-(3-acetyl-5-(2-hydroxypyrimidin-5-yl)-1H-indol-1-yl)acetyl)-N-(2'-chloro-2-fluorobiphenyl-3-yl)-4-fluoropyrrolidine-2-carboxamide | *** | 1.79 (A) | 630 |
| 187 | 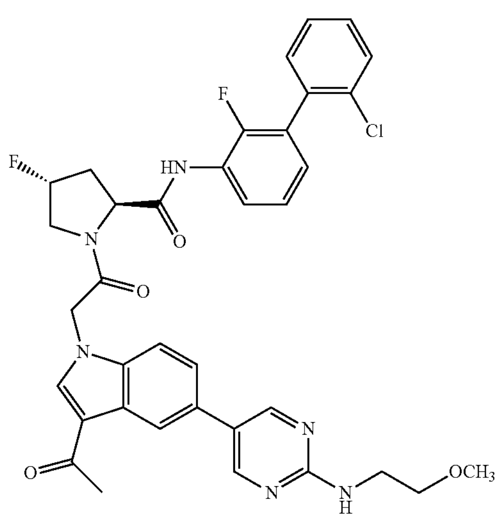 [SMILES: COCCNc1ncc(-c2ccc3c(c2)c(C(C)=O)cn3CC(=O)N2C[C@H](F)C[C@H]2C(=O)Nc2cccc(-c3ccccc3Cl)c2F)cn1] | (2S,4R)-1-(2-(3-acetyl-5-(2-(2-methoxyethylamino)pyrimidin-5-yl)-1H-indol-1-yl)acetyl)-N-(2'-chloro-2-fluorobiphenyl-3-yl)-4-fluoropyrrolidine-2-carboxamide | *** | 2.16 (A) | 687 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 188 | 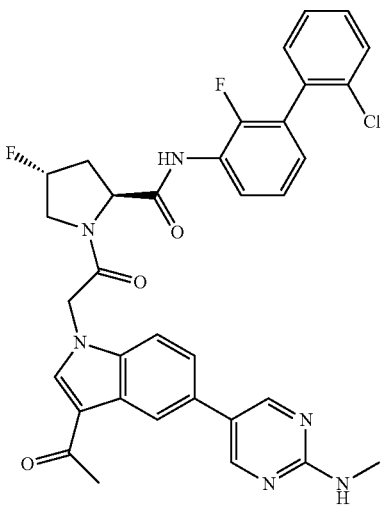 [SMILES: CNc1ncc(-c2ccc3c(c2)c(C(C)=O)cn3CC(=O)N2C[C@H](F)C[C@H]2C(=O)Nc2cccc(-c3ccccc3Cl)c2F)cn1] | (2S,4R)-1-(2-(3-acetyl-5-(2-(methylamino)pyrimidin-5-yl)-1H-indol-1-yl)acetyl)-N-(2'-chloro-2-fluorobiphenyl-3-yl)-4-fluoropyrrolidine-2-carboxamide | *** | 2.08 (A) | 643 |
| 189 | 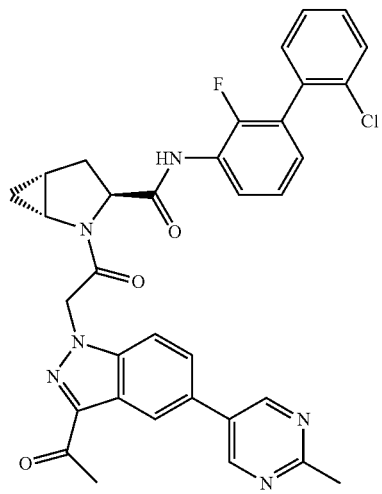 [SMILES: CC(=O)c1nn(CC(=O)N2[C@@H]3C[C@@H]3C[C@H]2C(=O)Nc2cccc(-c3ccccc3Cl)c2F)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(2'-chloro-2-fluorobiphenyl-3-yl)-2-azabicyclo[3.1.0]hexane-3-carboxamide | *** | 2.37 (A) | 623 |
| 190 | 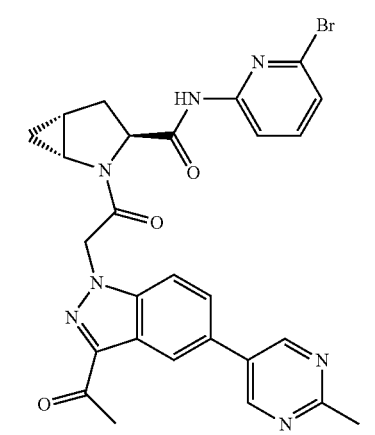 [SMILES: CC(=O)c1nn(CC(=O)N2[C@@H]3C[C@@H]3C[C@H]2C(=O)Nc2cccc(Br)n2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromopyridin-2-yl)-2-azabicyclo[3.1.0]hexane-3-carboxamide | *** | 1.90 (A) | 574 |

TABLE 1-continued

Non-limiting Examples of Compounds of Formula I

| Cmp No. | Structure | Name | IC$_{50}$ | RT min (Method A or B) | MS (M + 1) |
|---|---|---|---|---|---|
| 191 | 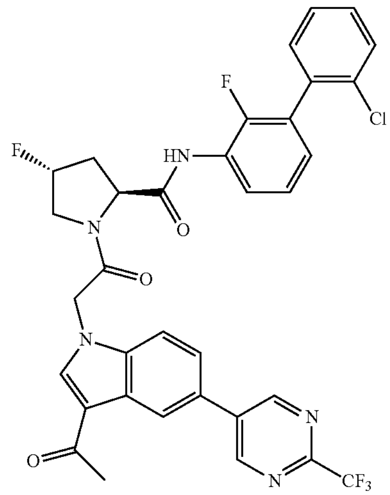 [SMILES: CC(=O)c1cn(CC(=O)N2C[C@H](F)C[C@H]2C(=O)Nc2cccc(-c3ccccc3Cl)c2F)c2ccc(-c3cnc(C(F)(F)F)nc3)cc12] | (2S,4R)-1-(2-(3-acetyl-5-(2-(trifluoromethyl)pyrimidin-5-yl)-1H-indol-1-yl)acetyl)-N-(2'-chloro-2-fluorobiphenyl-3-yl)-4-fluoropyrrolidine-2-carboxamide | *** | 2.64 (A) | 682 |

Table 2 provides additional compounds within the scope of the present invention. The assay of Example 8 was used to determine the IC$_{50}$'s of the compounds. Other standard Factor D inhibition assays are also available. Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

TABLE 2

Additional Compounds of the Present Invention

| Cmp No. | Structure | Name | IC$_{50}$ | RT min (Method A or B) | MS (M + 1) |
|---|---|---|---|---|---|
| 192 | 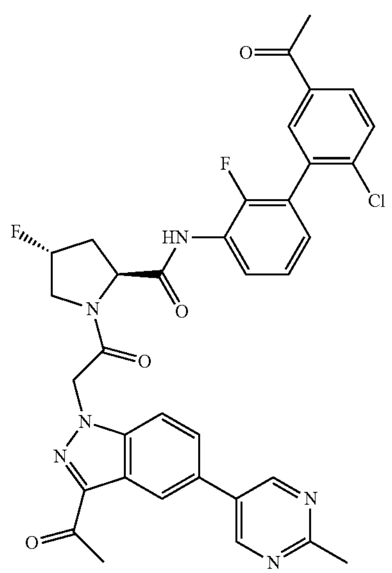 [SMILES: CC(=O)c1ccc(Cl)c(-c2cccc(NC(=O)[C@@H]3C[C@@H](F)CN3C(=O)Cn3nc(C(C)=O)c4cc(-c5cnc(C)nc5)ccc43)c2F)c1] | (2S,4R)-N-(5'-acetyl-2'-chloro-2-fluorobiphenyl-3-yl)-1-(2-(3-acetyl-5-(2-methylpyrimidin-5-yl)-1H-indazol-1-yl)acetyl)-4-fluoropyrrolidine-2-carboxamide | *** | 2.08 (A) | 671 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 193 | 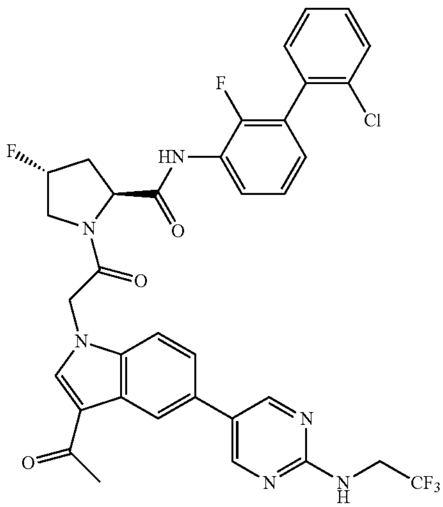 [SMILES: CC(=O)c1cn(CC(=O)N2C[C@H](F)C[C@H]2C(=O)Nc2cccc(-c3ccccc3Cl)c2F)c2ccc(-c3cnc(NCC(F)(F)F)nc3)cc12] | (2S,4R)-1-(2-(3-acetyl-5-(2-(2,2,2-trifluoroethylamino)pyrimidin-5-yl)-1H-indol-1-yl)acetyl)-N-(2'-chloro-2-fluorobiphenyl-3-yl)-4-fluoropyrrolidine-2-carboxamide | *** | 2.45 (A) | 711 |
| 194 | 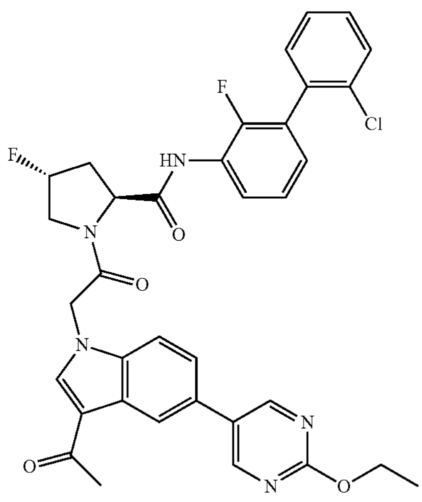 [SMILES: CCOc1ncc(-c2ccc3c(c2)c(C(C)=O)cn3CC(=O)N2C[C@H](F)C[C@H]2C(=O)Nc2cccc(-c3ccccc3Cl)c2F)cn1] | (2S,4R)-1-(2-(3-acetyl-5-(2-ethoxypyrimidin-5-yl)-1H-indol-1-yl)acetyl)-N-(2'-chloro-2-fluorobiphenyl-3-yl)-4-fluoropyrrolidine-2-carboxamide | *** | 2.40 (A) | 658 |
| 195 | 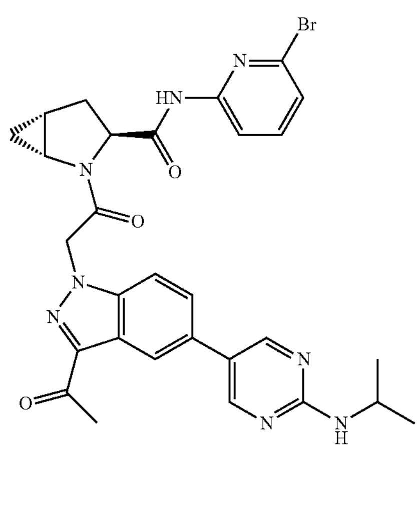 [SMILES: CC(=O)c1nn(CC(=O)N2[C@@H]3C[C@@H]3C[C@H]2C(=O)Nc2cccc(Br)n2)c2ccc(-c3cnc(NC(C)C)nc3)cc12] | (1R,3S,5R)-2-(2-(3-acetyl-5-(2-(isopropylamino)pyrimidin-5-yl)-1H-indazol-1-yl)acetyl)-N-(6-bromopyridin-2-yl)-2-azabicyclo[3.1.0]hexane-3-carboxamide | *** | 2.25 (A) | 618 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 196 | 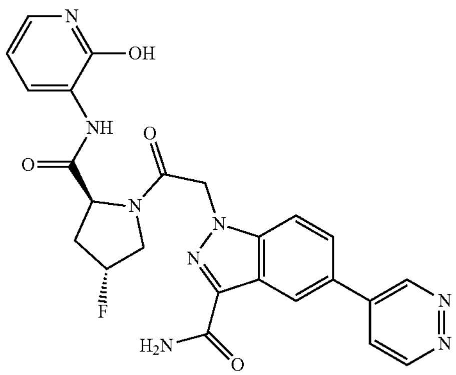 [SMILES: NC(=O)c1nn(CC(=O)N2C[C@H](F)C[C@H]2C(=O)Nc2cccnc2O)c2ccc(-c3ccnnc3)cc12] | 1-(2-((2S,4R)-4-fluoro-2-(2-hydroxypyridin-3-ylcarbamoyl)pyrrolidin-1-yl)-2-oxoethyl)-5-(pyridazin-4-yl)-1H-indazole-3-carboxamide | * | 0.67 (B) | 505 |
| 197 | 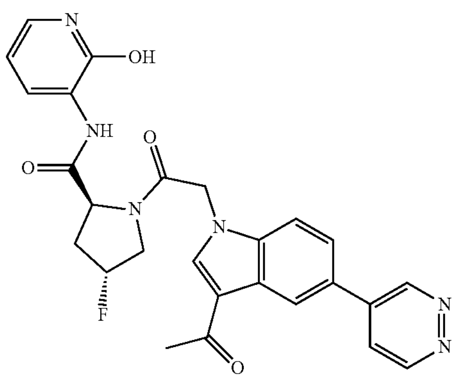 [SMILES: CC(=O)c1cn(CC(=O)N2C[C@H](F)C[C@H]2C(=O)Nc2cccnc2O)c2ccc(-c3ccnnc3)cc12] | (2S,4R)-1-(2-(3-acetyl-5-(pyridazin-4-yl)-1H-indol-1-yl)acetyl)-4-fluoro-N-(2-hydroxypyridin-3-yl)pyrrolidine-2-carboxamide | * | 1.31 (B) | 503 |
| 198 | 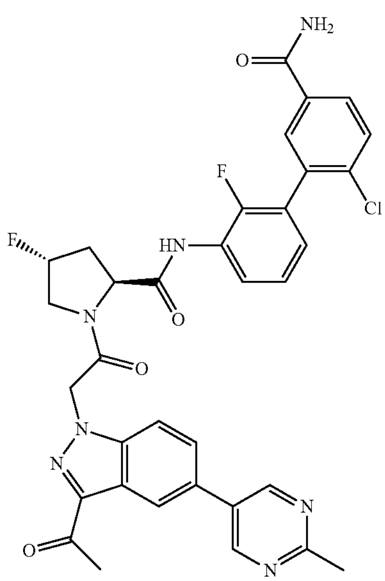 [SMILES: CC(=O)c1nn(CC(=O)N2C[C@H](F)C[C@H]2C(=O)Nc2cccc(-c3cc(C(N)=O)ccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(5'-carbamoyl-2'-chloro-2-fluorobiphenyl-3-yl)-4-fluoropyrrolidine-2-carboxamide | *** | 1.68 (A) | 672 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 199 | 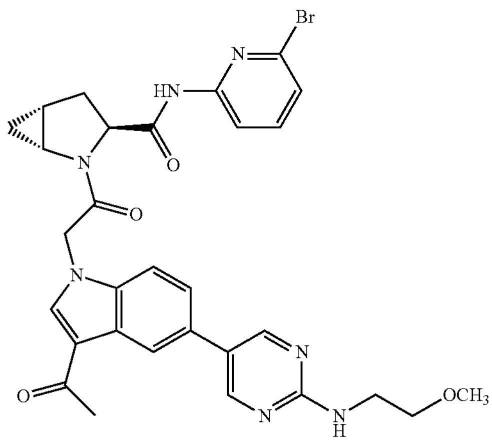 [SMILES: COCCNc1ncc(-c2ccc3c(c2)c(C(C)=O)cn3CC(=O)N2[C@@H]3C[C@@H]3C[C@H]2C(=O)Nc2cccc(Br)n2)cn1] | (1R,3S,5R)-2-(2-(3-acetyl-5-(2-(2-methoxyethylamino)pyrimidin-5-yl)-1H-indol-1-yl)acetyl)-N-(6-bromopyridin-2-yl)-2-azabicyclo[3.1.0]hexane-3-carboxamide | *** | 1.84 (A) | 633 |
| 200 | 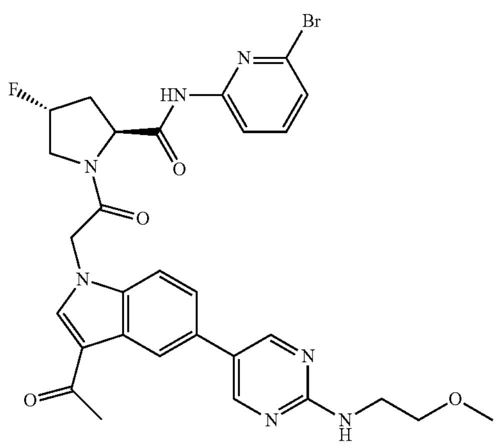 [SMILES: COCCNc1ncc(-c2ccc3c(c2)c(C(C)=O)cn3CC(=O)N2C[C@H](F)C[C@H]2C(=O)Nc2cccc(Br)n2)cn1] | (2S,4R)-1-(2-(3-acetyl-5-(2-(2-methoxyethylamino)pyrimidin-5-yl)-1H-indol-1-yl)acetyl)-N-(6-bromopyridin-2-yl)-4-fluoropyrrolidine-2-carboxamide | *** | 1.70 (A) | 639 |
| 201 | 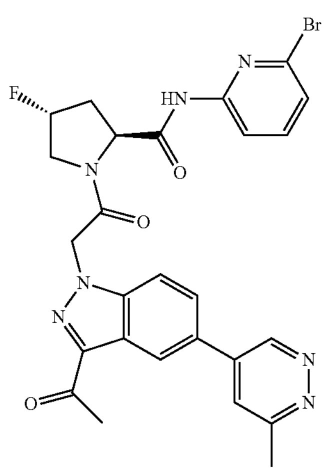 [SMILES: CC(=O)c1nn(CC(=O)N2C[C@H](F)C[C@H]2C(=O)Nc2cccc(Br)n2)c2ccc(-c3cnnc(C)c3)cc12] | (2S,4R)-1-(2-(3-acetyl-5-(6-methylpyridazin-4-yl)-1H-indazol-1-yl)acetyl)-N-(6-bromopyridin-2-yl)-4-fluoropyrrolidine-2-carboxamide | *** | 1.62 (A) | 581 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 202 | 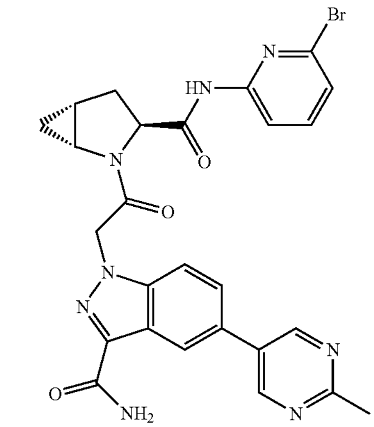 [SMILES: Cc1ncc(-c2ccc3c(c2)c(C(N)=O)nn3CC(=O)N2[C@@H]3C[C@@H]3C[C@H]2C(=O)Nc2cccc(Br)n2)cn1] | 1-(2-((1R,3S,5R)-3-(6-bromopyridin-2-ylcarbamoyl)-2-azabicyclo[3.1.0]hexan-2-yl)-2-oxoethyl)-5-(2-methylpyrimidin-5-yl)-1H-indazole-3-carboxamide | *** | 1.52 (A) | 577 |
| 203 | 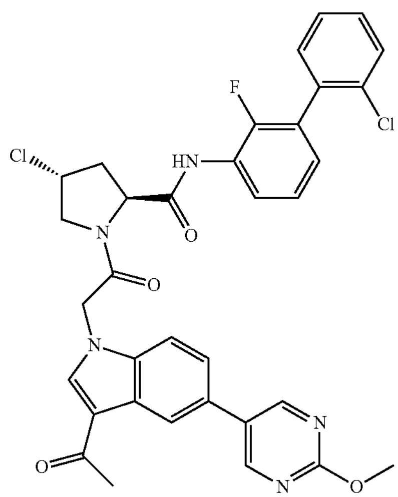 [SMILES: COc1ncc(-c2ccc3c(c2)c(C(C)=O)cn3CC(=O)N2C[C@H](Cl)C[C@H]2C(=O)Nc2cccc(-c3ccccc3Cl)c2F)cn1] | (2S,4R)-1-(2-(3-acetyl-5-(2-methoxypyrimidin-5-yl)-1H-indol-1-yl)acetyl)-4-chloro-N-(2'-chloro-2-fluorobiphenyl-3-yl)pyrrolidine-2-carboxamide | *** | 2.41 (A) | 660 |
| 204 | 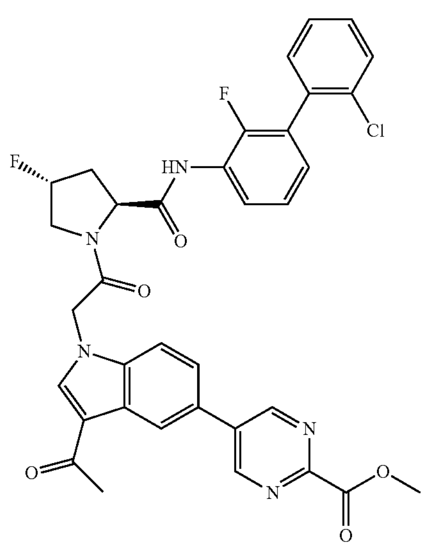 [SMILES: COC(=O)c1ncc(-c2ccc3c(c2)c(C(C)=O)cn3CC(=O)N2C[C@H](F)C[C@H]2C(=O)Nc2cccc(-c3ccccc3Cl)c2F)cn1] | methyl 5-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)pyrimidine-2-carboxylate | *** | 2.10 (A) | 672 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 205 | 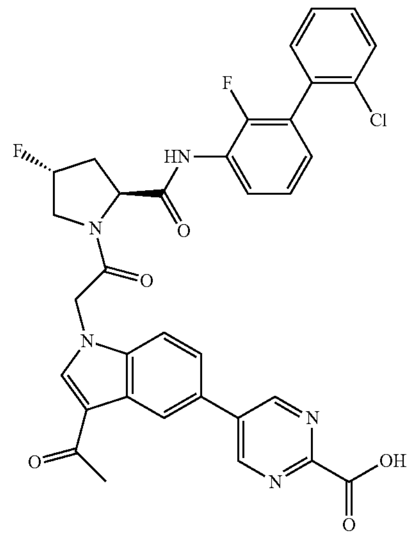 [SMILES: CC(=O)c1cn(CC(=O)N2C[C@H](F)C[C@H]2C(=O)Nc2cccc(-c3ccccc3Cl)c2F)c2ccc(-c3cnc(C(=O)O)nc3)cc12] | 5-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)pyrimidine-2-carboxylic acid | *** | 1.88 (A) | 658 |
| 206 | 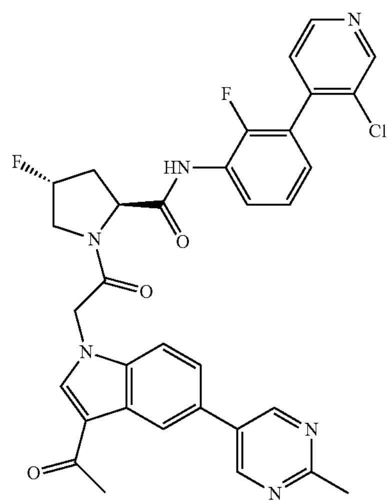 [SMILES: CC(=O)c1cn(CC(=O)N2C[C@H](F)C[C@H]2C(=O)Nc2cccc(-c3ccncc3Cl)c2F)c2ccc(-c3cnc(C)nc3)cc12] | (2S,4R)-1-(2-(3-acetyl-5-(2-methylpyrimidin-5-yl)-1H-indol-1-yl)acetyl)-N-(3-(3-chloropyridin-4-yl)-2-fluorophenyl)-4-fluoropyrrolidine-2-carboxamide | *** | 1.65 (A) | 629 |
| 207 | 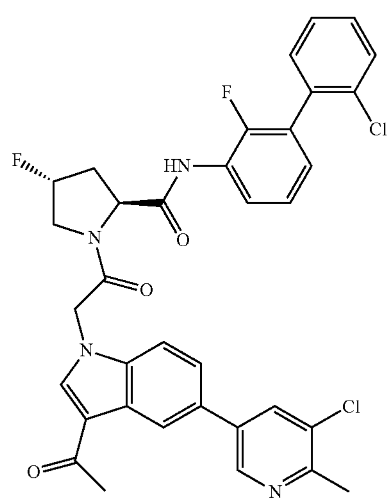 [SMILES: CC(=O)c1cn(CC(=O)N2C[C@H](F)C[C@H]2C(=O)Nc2cccc(-c3ccccc3Cl)c2F)c2ccc(-c3cnc(C)c(Cl)c3)cc12] | (2S,4R)-1-(2-(3-acetyl-5-(5-chloro-6-methylpyridin-3-yl)-1H-indol-1-yl)acetyl)-N-(2'-chloro-2-fluorobiphenyl-3-yl)-4-fluoropyrrolidine-2-carboxamide | *** | 2.61 (A) | 661 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 208 | 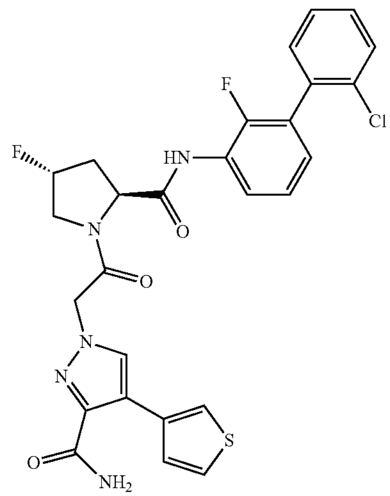 [SMILES: NC(=O)c1nn(CC(=O)N2C[C@H](F)C[C@H]2C(=O)Nc2cccc(-c3ccccc3Cl)c2F)cc1-c1ccsc1] | 1-(2-((2S,4R)-2-(2'-chloro-2-fluorobiphenyl-3-ylcarbamoyl)-4-fluoropyrrolidin-1-yl)-2-oxoethyl)-4-(thiophen-3-yl)-1H-pyrazole-3-carboxamide | ** | 2.17 (A) | 570 |
| 209 | 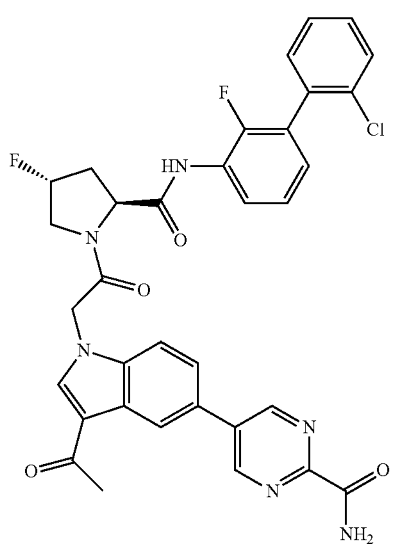 [SMILES: CC(=O)c1cn(CC(=O)N2C[C@H](F)C[C@H]2C(=O)Nc2cccc(-c3ccccc3Cl)c2F)c2ccc(-c3cnc(C(N)=O)nc3)cc12] | 5-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)pyrimidine-2-carboxamide | *** | 1.90 (A) | 657 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 210 | 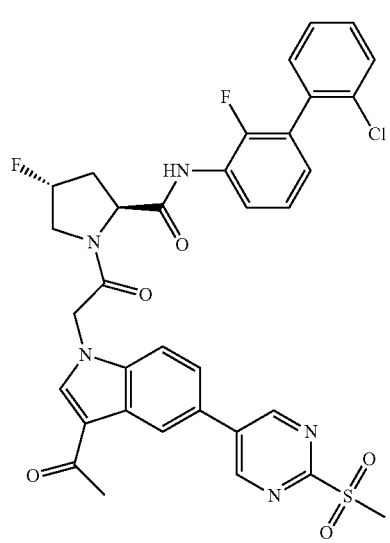 [SMILES: CC(=O)c1cn(CC(=O)N2C[C@H](F)C[C@H]2C(=O)Nc2cccc(-c3ccccc3Cl)c2F)c2ccc(-c3cnc(S(C)(=O)=O)nc3)cc12] | (2S,4R)-1-(2-(3-acetyl-5-(2-(methylsulfonyl)pyrimidin-5-yl)-1H-indol-1-yl)acetyl)-N-(2'-chloro-2-fluorobiphenyl-3-yl)-4-fluoropyrrolidine-2-carboxamide | *** | 2.18 (A) | 692 |
| 211 | 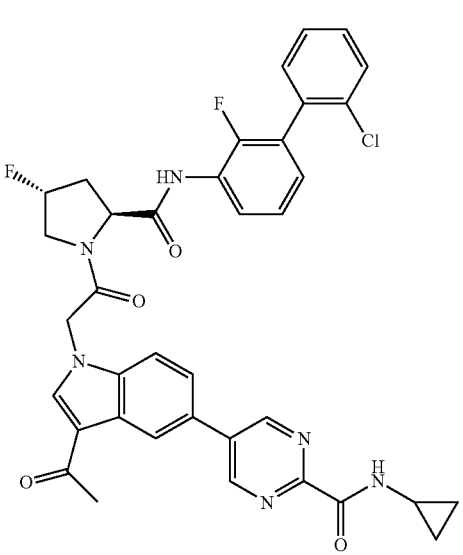 [SMILES: CC(=O)c1cn(CC(=O)N2C[C@H](F)C[C@H]2C(=O)Nc2cccc(-c3ccccc3Cl)c2F)c2ccc(-c3cnc(C(=O)NC4CC4)nc3)cc12] | 5-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)-N-cyclopropylpyrimidine-2-carboxamide | *** | 2.14 (A) | 697 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 212 | 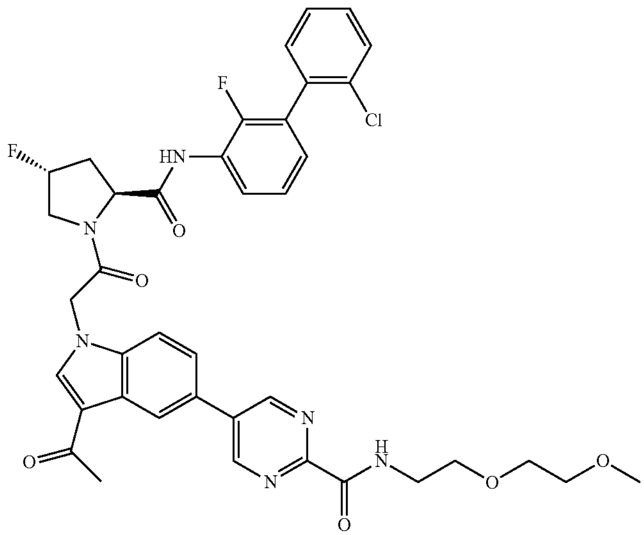 [SMILES: COCCOCCNC(=O)c1ncc(-c2ccc3c(c2)c(C(C)=O)cn3CC(=O)N2C[C@H](F)C[C@H]2C(=O)Nc2cccc(-c3ccccc3Cl)c2F)cn1] | 5-(3-acetyl-1-(2-((2S,4R)-2-(2'-chloro-2-fluorobiphenyl-3-ylcarbamoyl)-4-fluoropyrrolidin-1-yl)-2-oxoethyl)-1H-indol-5-yl)-N-(2-(2-methoxyethoxy)ethyl)pyrimidine-2-carboxamide | *** | 2.07 (A) | 759 |
| 213 | 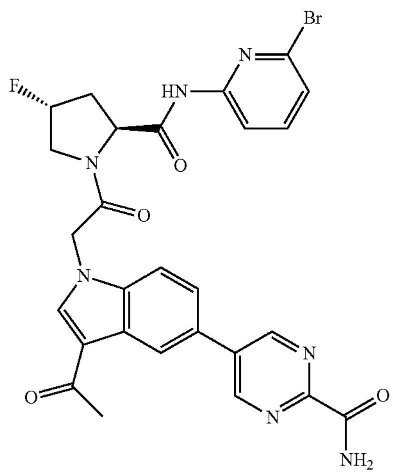 [SMILES: CC(=O)c1cn(CC(=O)N2C[C@H](F)C[C@H]2C(=O)Nc2cccc(Br)n2)c2ccc(-c3cnc(C(N)=O)nc3)cc12] | 5-(3-acetyl-1-(2-((2S,4R)-2-(6-bromopyridin-2-ylcarbamoyl)-4-fluoropyrrolidin-1-yl)-2-oxoethyl)-1H-indol-5-yl)pyrimidine-2-carboxamide | *** | 1.42 (A) | 608 |
| 214 | 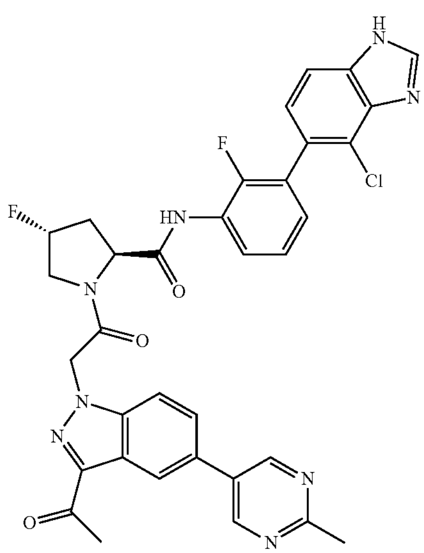 [SMILES: CC(=O)c1nn(CC(=O)N2C[C@H](F)C[C@H]2C(=O)Nc2cccc(-c3ccc4[nH]cnc4c3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-(4-chloro-1H-benzo[d]imidazol-5-yl)-2-fluorophenyl)-4-fluoropyrrolidine-2-carboxamide | *** | 1.51 (A) | 669 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 215 | 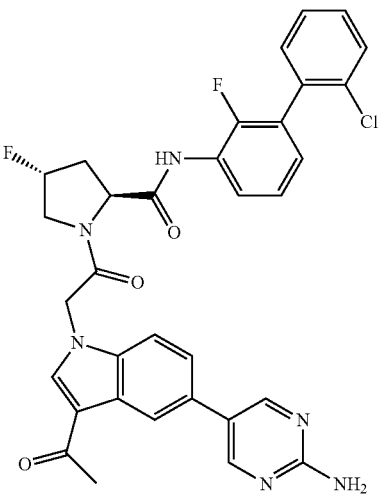 [SMILES: CC(=O)c1cn(CC(=O)N2C[C@H](F)C[C@H]2C(=O)Nc2cccc(-c3ccccc3Cl)c2F)c2ccc(-c3cnc(N)nc3)cc12] | (2S,4R)-1-(2-(3-acetyl-5-(2-aminopyrimidin-5-yl)-1H-indol-1-yl)acetyl)-N-(2'-chloro-2-fluorobiphenyl-3-yl)-4-fluoropyrrolidine-2-carboxamide | *** | 1.98 (A) | 629 |
| 216 | 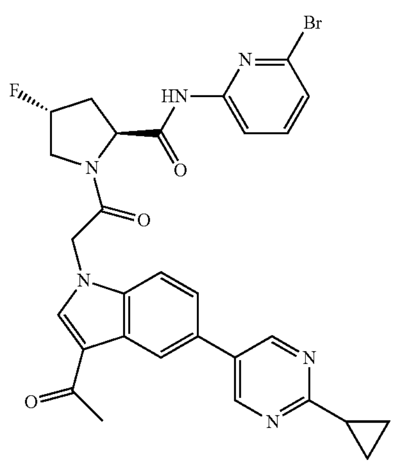 [SMILES: CC(=O)c1cn(CC(=O)N2C[C@H](F)C[C@H]2C(=O)Nc2cccc(Br)n2)c2ccc(-c3cnc(C4CC4)nc3)cc12] | (2S,4R)-1-(2-(3-acetyl-5-(2-cyclopropylpyrimidin-5-yl)-1H-indol-1-yl)acetyl)-N-(6-bromopyridin-2-yl)-4-fluoropyrrolidine-2-carboxamide | *** | 1.98 (A) | 605 |
| 217 | 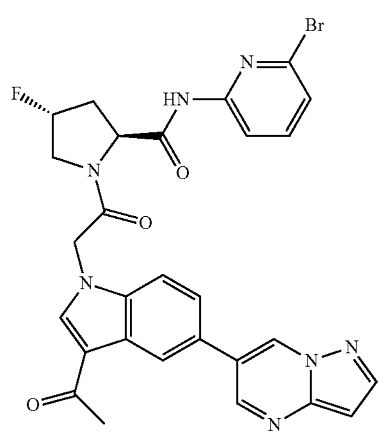 | (2S,4R)-1-(2-(3-acetyl-5-(pyrazolo[1,5-a]pyrimidin-6-yl)-1H-indol-1-yl)acetyl)-N-(6-bromopyridin-2-yl)-4-fluoropyrrolidine-2-carboxamide | *** | 1.78 (A) | 605 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 218 | 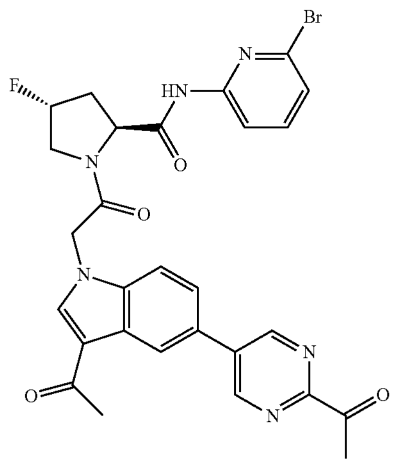 [SMILES: CC(=O)c1ncc(-c2ccc3c(c2)c(C(C)=O)cn3CC(=O)N2C[C@H](F)C[C@H]2C(=O)Nc2cccc(Br)n2)cn1] | (2S,4R)-1-(2-(3-acetyl-5-(2-acetylpyrimidin-5-yl)-1H-indol-1-yl)acetyl)-N-(6-bromopyridin-2-yl)-4-fluoropyrrolidine-2-carboxamide | *** | 1.71 (A) | 607 |
| 219 | 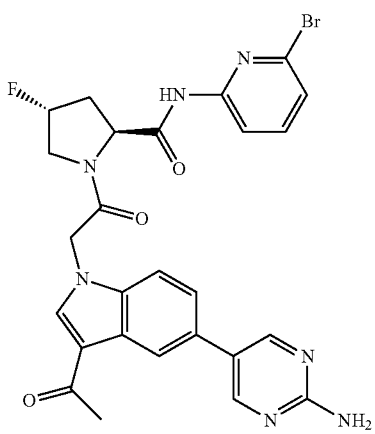 [SMILES: CC(=O)c1cn(CC(=O)N2C[C@H](F)C[C@H]2C(=O)Nc2cccc(Br)n2)c2ccc(-c3cnc(N)nc3)cc12] | (2S,4R)-1-(2-(3-acetyl-5-(2-aminopyrimidin-5-yl)-1H-indol-1-yl)acetyl)-N-(6-bromopyridin-2-yl)-4-fluoropyrrolidine-2-carboxamide | *** | 1.41 (A) | 580 |
| 220 | 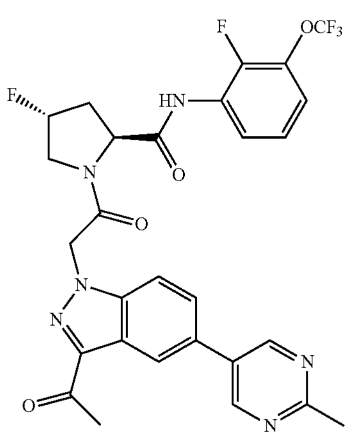 [SMILES: CC(=O)c1nn(CC(=O)N2C[C@H](F)C[C@H]2C(=O)Nc2cccc(OC(F)(F)F)c2F)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2-fluoro-3-(trifluoromethoxy)phenyl)pyrrolidine-2-carboxamide | *** | 2.02 (A) | 603 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 221 | 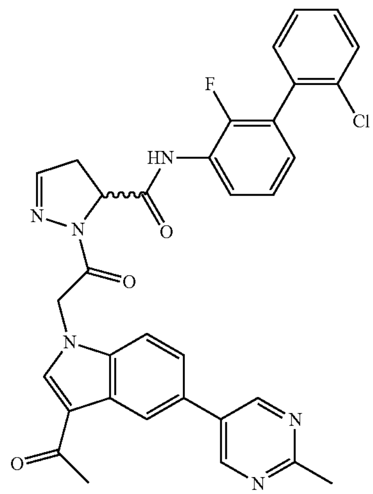 [SMILES: CC(=O)c1cn(CC(=O)N2N=CCC2C(=O)Nc2cccc(-c3ccccc3Cl)c2F)c2ccc(-c3cnc(C)nc3)cc12] | 1-(2-(3-acetyl-5-(2-methylpyrimidin-5-yl)-1H-indol-1-yl)acetyl)-N-(2'-chloro-2-fluorobiphenyl-3-yl)-4,5-dihydro-1H-pyrazole-5-carboxamide | *** | 2.14 (A) | 609 |
| 222 | 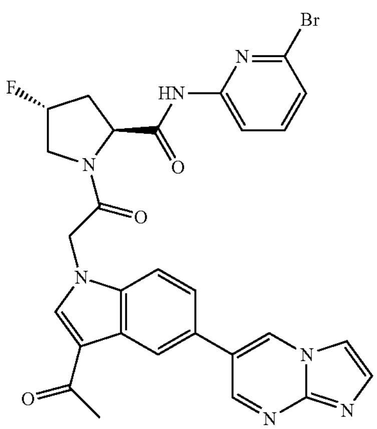 [SMILES: CC(=O)c1cn(CC(=O)N2C[C@H](F)C[C@H]2C(=O)Nc2cccc(Br)n2)c2ccc(-c3cnc4nccn4c3)cc12] | (2S,4R)-1-(2-(3-acetyl-5-(imidazo[1,2-a]pyrimidin-6-yl)-1H-indol-1-yl)acetyl)-N-(6-bromopyridin-2-yl)-4-fluoropyrrolidine-2-carboxamide | *** | 1.35 (A) | 604 |
| 223 | 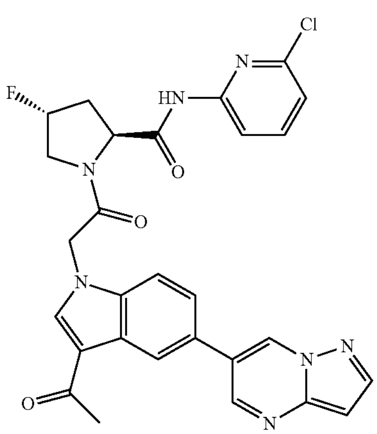 [SMILES: CC(=O)c1cn(CC(=O)N2C[C@H](F)C[C@H]2C(=O)Nc2cccc(Cl)n2)c2ccc(-c3cnc4ccnn4c3)cc12] | (2S,4R)-1-(2-(3-acetyl-5-(pyrazolo[1,5-a]pyrimidin-6-yl)-1H-indol-1-yl)acetyl)-N-(6-chloropyridin-2-yl)-4-fluoropyrrolidine-2-carboxamide | *** | 1.72 (A) | 560 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 224 | 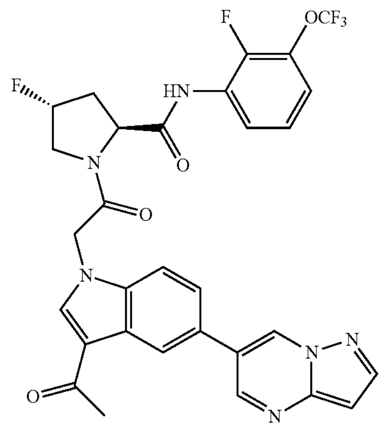 [SMILES: CC(=O)c1cn(CC(=O)N2C[C@H](F)C[C@H]2C(=O)Nc2cccc(OC(F)(F)F)c2F)c2ccc(-c3cnc4ccnn4c3)cc12] | (2S,4R)-1-(2-(3-acetyl-5-(pyrazolo[1,5-a]pyrimidin-6-yl)-1H-indol-1-yl)acetyl)-4-fluoro-N-(2-fluoro-3-(trifluoromethoxy)phenyl)pyrrolidine-2-carboxamide | *** | 2.04 (A) | 627 |
| 225 | 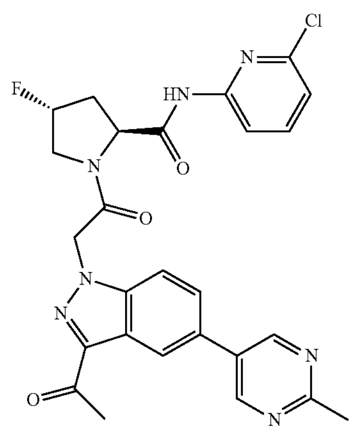 [SMILES: CC(=O)c1nn(CC(=O)N2C[C@H](F)C[C@H]2C(=O)Nc2cccc(Cl)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-chloropyridin-2-yl)-4-fluoropyrrolidine-2-carboxamide | *** | 1.67 (A) | 536 |
| 226 | 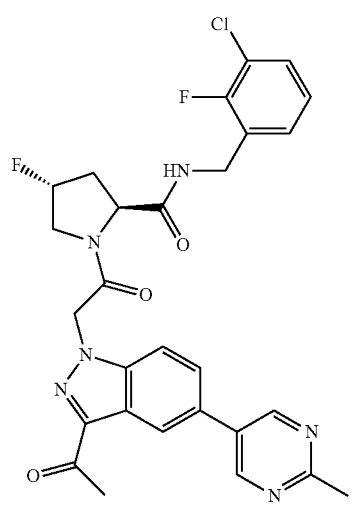 [SMILES: CC(=O)c1nn(CC(=O)N2C[C@H](F)C[C@H]2C(=O)NCc2cccc(Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-chloro-2-fluorobenzyl)-4-fluoropyrrolidine-2-carboxamide | *** | 1.76 (A) | 567 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 227 | 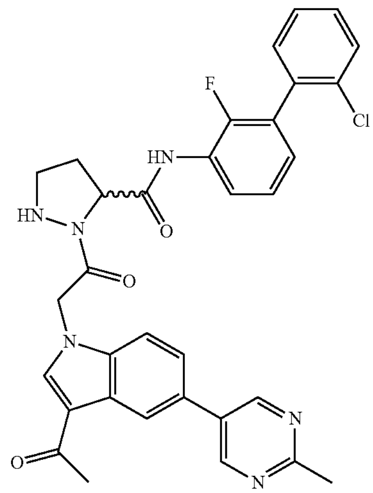 [SMILES: CC(=O)c1cn(CC(=O)N2NCCC2C(=O)Nc2cccc(-c3ccccc3Cl)c2F)c2ccc(-c3cnc(C)nc3)cc12] | 2-(2-(3-acetyl-5-(2-methylpyrimidin-5-yl)-1H-indol-1-yl)acetyl)-N-(2'-chloro-2-fluorobiphenyl-3-yl)pyrazolidine-3-carboxamide | *** | 1.93 (A) | 611 |
| 228 | 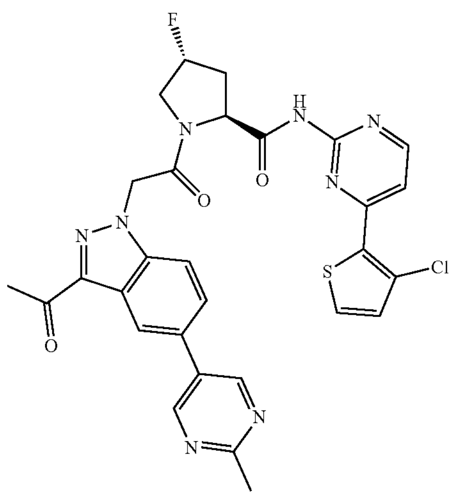 [SMILES: CC(=O)c1nn(CC(=O)N2C[C@H](F)C[C@H]2C(=O)Nc2nccc(-c3sccc3Cl)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(4-(3-chlorothiophen-2-yl)pyrimidin-2-yl)-4-fluoropyrrolidine-2-carboxamide | *** | 1.81 (A) | 619 |
| 229 | 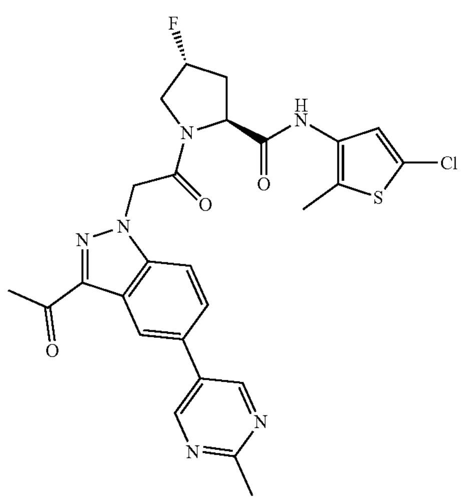 [SMILES: CC(=O)c1nn(CC(=O)N2C[C@H](F)C[C@H]2C(=O)Nc2cc(Cl)sc2C)c2ccc(-c3cnc(C)nc3)cc12] | (2S,4R)-1-(2-(3-acetyl-5-(2-methylpyrimidin-5-yl)-1H-indazol-1-yl)acetyl)-N-(5-chloro-2-methylthiophen-3-yl)-4-fluoropyrrolidine-2-carboxamide | *** | 1.88 (A) | 555 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 230 | 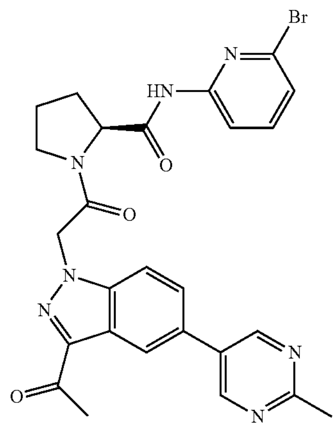 [SMILES: CC(=O)c1nn(CC(=O)N2CCC[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)pyrrolidine-2-carboxamide | *** | 3.42 (B) | 562 |
| 231 | 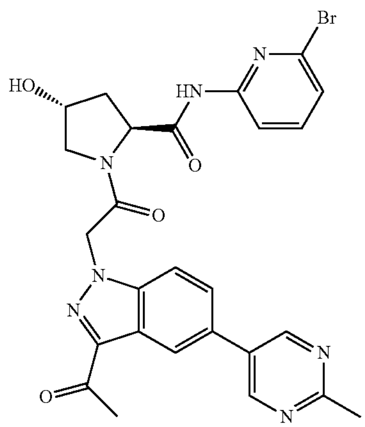 [SMILES: CC(=O)c1nn(CC(=O)N2C[C@H](O)C[C@H]2C(=O)Nc2cccc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromopyridin-2-yl)-4-hydroxypyrrolidine-2-carboxamide | *** | 3.31 (B) | 578 |
| 232 | 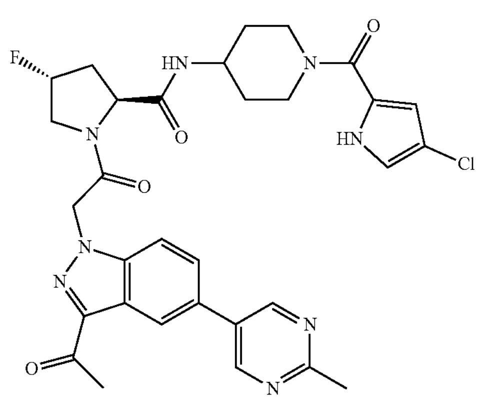 [SMILES: CC(=O)c1nn(CC(=O)N2C[C@H](F)C[C@H]2C(=O)NC2CCN(C(=O)c3cc(Cl)c[nH]3)CC2)c2ccc(-c3cnc(C)nc3)cc12] | (2S,4R)-1-(2-(3-acetyl-5-(2-methylpyrimidin-5-yl)-1H-indazol-1-yl)acetyl)-N-(1-(4-chloro-1H-pyrrole-2-carbonyl)piperidin-4-yl)-4-fluoropyrrolidine-2-carboxamide | *** | 3.16 (B) | 635 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 233 | 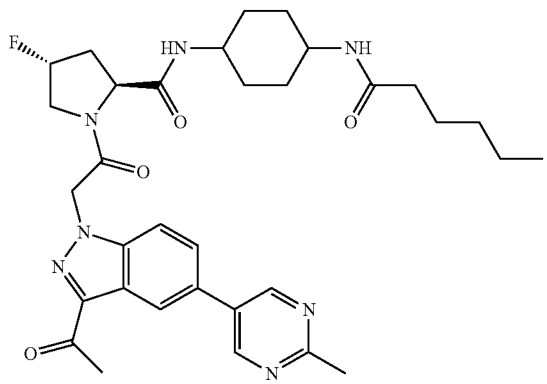 [SMILES: CCCCCC(=O)NC1CCC(NC(=O)[C@@H]2C[C@@H](F)CN2C(=O)Cn2nc(C(C)=O)c3cc(-c4cnc(C)nc4)ccc32)CC1] | (2S,4R)-1-(2-(3-acetyl-5-(2-methylpyrimidin-5-yl)-1H-indazol-1-yl)acetyl)-4-fluoro-N-(4-hexanamidocyclohexyl)pyrrolidine-2-carboxamide | ** | 3.55 (B) | 620 |
| 234 | 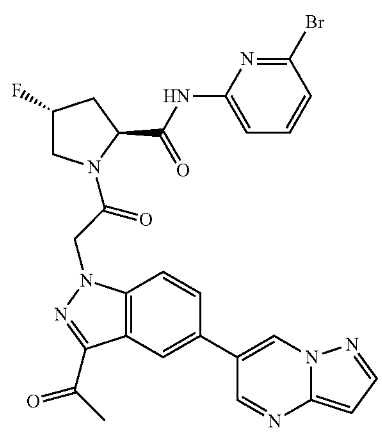 | (2S,4R)-1-(2-(3-acetyl-5-(pyrazolo[1,5-a]pyrimidin-6-yl)-1H-indazol-1-yl)acetyl)-N-(6-bromopyridin-2-yl)-4-fluoropyrrolidine-2-carboxamide | *** | 2.10 (A) | 605 |
| 235 | 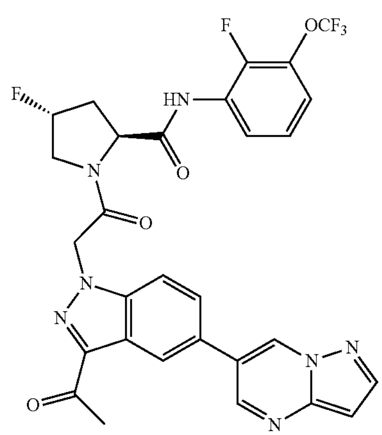 [SMILES: CC(=O)c1nn(CC(=O)N2C[C@H](F)C[C@H]2C(=O)Nc2cccc(OC(F)(F)F)c2F)c2ccc(-c3cnc4ccnn4c3)cc12] | (2S,4R)-1-(2-(3-acetyl-5-(pyrazolo[1,5-a]pyrimidin-6-yl)-1H-indazol-1-yl)acetyl)-4-fluoro-N-(2-fluoro-3-(trifluoromethoxy)phenyl)pyrrolidine-2-carboxamide | *** | 2.35 (A) | 628 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 236 | 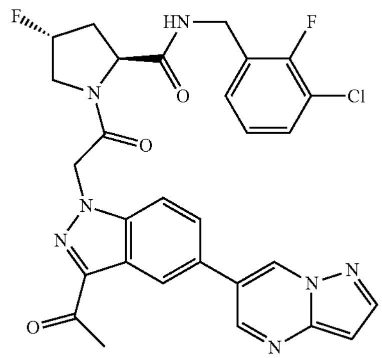 [SMILES: CC(=O)c1nn(CC(=O)N2C[C@H](F)C[C@H]2C(=O)NCc2cccc(Cl)c2F)c2ccc(-c3cnc4ccnn4c3)cc12] | (2S,4R)-1-(2-(3-acetyl-5-(pyrazolo[1,5-a]pyrimidin-6-yl)-1H-indazol-1-yl)acetyl)-N-(3-chloro-2-fluorobenzyl)-4-fluoropyrrolidine-2-carboxamide | *** | 2.11 (A) | 592 |
| 237 | 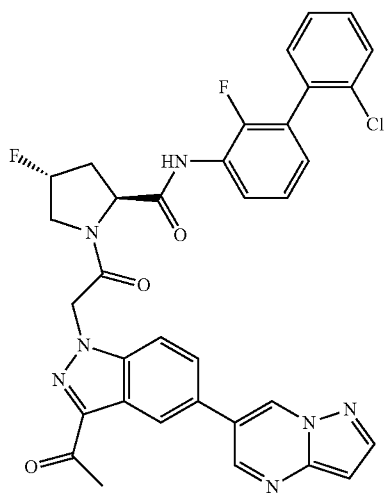 [SMILES: CC(=O)c1nn(CC(=O)N2C[C@H](F)C[C@H]2C(=O)Nc2cccc(-c3ccccc3Cl)c2F)c2ccc(-c3cnc4ccnn4c3)cc12] | (2S,4R)-1-(2-(3-acetyl-5-(pyrazolo[1,5-a]pyrimidin-6-yl)-1H-indazol-1-yl)acetyl)-N-(2'-chloro-2-fluorobiphenyl-3-yl)-4-fluoropyrrolidine-2-carboxamide | *** | 2.52 (A) | 654 |
| 238 | 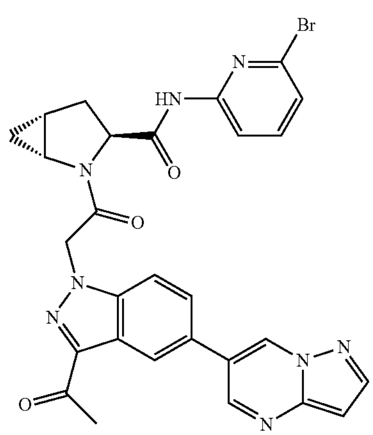 | (1R,3S,5R)-2-(2-(3-acetyl-5-(pyrazolo[1,5-a]pyrimidin-6-yl)-1H-indazol-1-yl)acetyl)-N-(6-bromopyridin-2-yl)-2-azabicyclo[3.1.0]hexane-3-carboxamide | *** | 2.30 (A) | 599 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 239 | 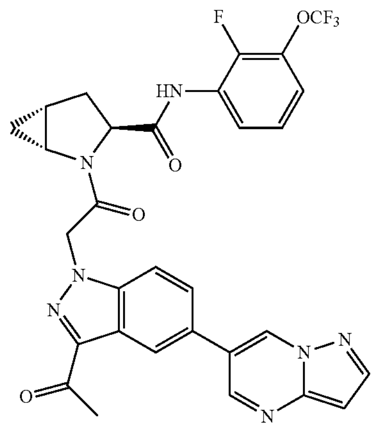 [SMILES: CC(=O)c1nn(CC(=O)N2[C@@H]3C[C@@H]3C[C@H]2C(=O)Nc2cccc(OC(F)(F)F)c2F)c2ccc(-c3cnc4ccnn4c3)cc12] | (1R,3S,5R)-2-(2-(3-acetyl-5-(pyrazolo[1,5-a]pyrimidin-6-yl)-1H-indazol-1-yl)acetyl)-N-(2-fluoro-3-(trifluoromethoxy)phenyl)-2-azabicyclo[3.1.0]hexane-3-carboxamide | *** | 2.52 (A) | 622 |
| 240 | 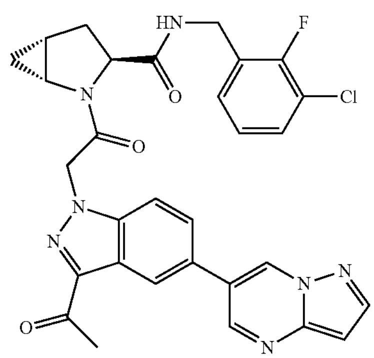 [SMILES: CC(=O)c1nn(CC(=O)N2[C@@H]3C[C@@H]3C[C@H]2C(=O)NCc2cccc(Cl)c2F)c2ccc(-c3cnc4ccnn4c3)cc12] | (1R,3S,5R)-2-(2-(3-acetyl-5-(pyrazolo[1,5-a]pyrimidin-6-yl)-1H-indazol-1-yl)acetyl)-N-(3-chloro-2-fluorobenzyl)-2-azabicyclo[3.1.0]hexane-3-carboxamide | *** | 2.21 (A) | 586 |
| 241 | 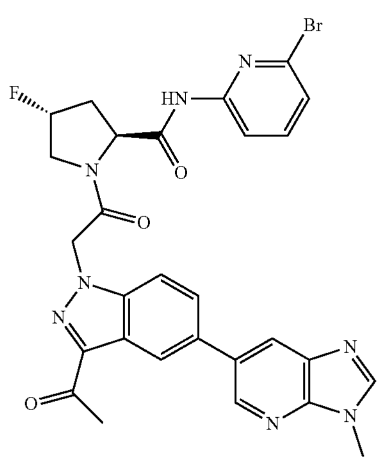 [SMILES: CC(=O)c1nn(CC(=O)N2C[C@H](F)C[C@H]2C(=O)Nc2cccc(Br)n2)c2ccc(-c3cnc4c(c3)ncn4C)cc12] | (2S,4R)-1-(2-(3-acetyl-5-(3-methyl-3H-imidazo[4,5-b]pyridin-6-yl)-1H-indazol-1-yl)acetyl)-N-(6-bromopyridin-2-yl)-4-fluoropyrrolidine-2-carboxamide | *** | 1.95 (A) | 619 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 242 | 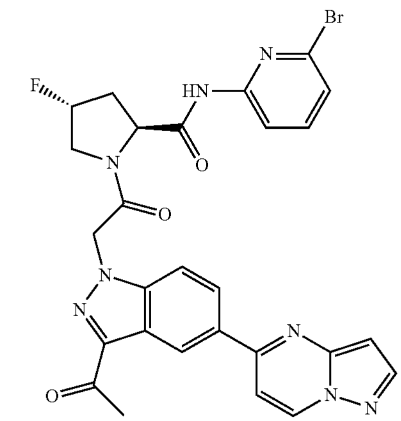 [SMILES: CC(=O)c1nn(CC(=O)N2C[C@H](F)C[C@H]2C(=O)Nc2cccc(Br)n2)c2ccc(-c3ccn4nccc4n3)cc12] | (2S,4R)-1-(2-(3-acetyl-5-(pyrazolo[1,5-a]pyrimidin-5-yl)-1H-indazol-1-yl)acetyl)-N-(6-bromopyridin-2-yl)-4-fluoropyrrolidine-2-carboxamide | *** | 2.24 (A) | 605 |
| 243 | 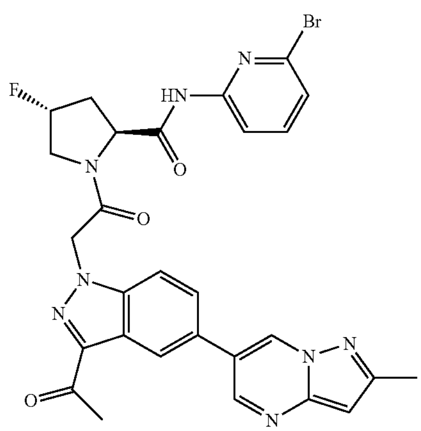 | (2S,4R)-1-(2-(3-acetyl-5-(2-methylpyrazolo[1,5-a]pyrimidin-6-yl)-1H-indazol-1-yl)acetyl)-N-(6-bromopyridin-2-yl)-4-fluoropyrrolidine-2-carboxamide | *** | 2.29 (A) | 619 |
| 244 | 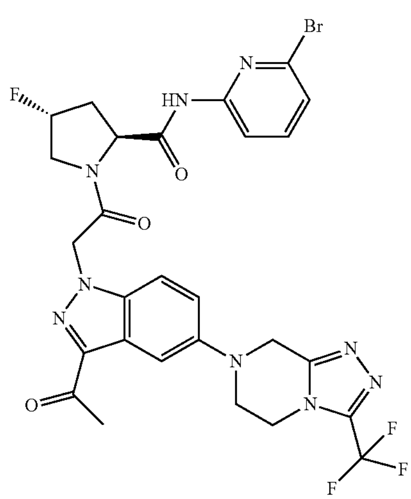 [SMILES: CC(=O)c1nn(CC(=O)N2C[C@H](F)C[C@H]2C(=O)Nc2cccc(Br)n2)c2ccc(N3CCn4c(nnc4C(F)(F)F)C3)cc12] | (2S,4R)-1-(2-(3-acetyl-5-(3-(trifluoromethyl)-5,6-dihydro-[1,2,4]triazolo[4,3-a]pyrazin-7(8H)-yl)-1H-indazol-1-yl)acetyl)-N-(6-bromopyridin-2-yl)-4-fluoropyrrolidine-2-carboxamide | *** | 2.35 (A) | 678 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 245 | 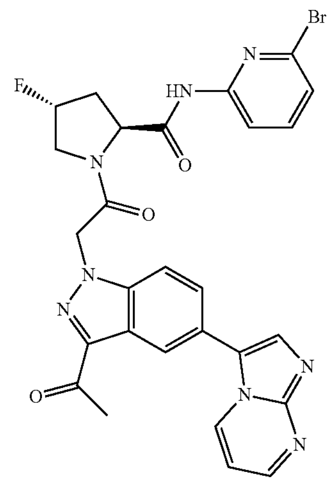 | (2S,4R)-1-(2-(3-acetyl-5-(imidazo[1,2-a]pyrimidin-3-yl)-1H-indazol-1-yl)acetyl)-N-(6-bromopyridin-2-yl)-4-fluoropyrrolidine-2-carboxamide | *** | 2.47 (A) | 605 |
| 246 | 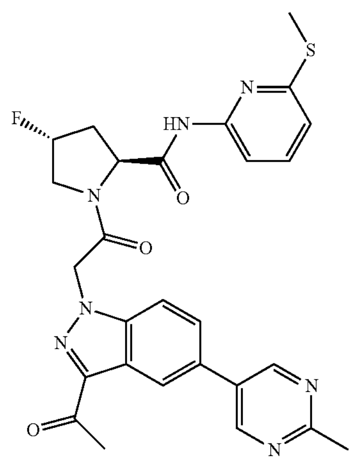 [SMILES: CSc1cccc(NC(=O)[C@@H]2C[C@@H](F)CN2C(=O)Cn2nc(C(C)=O)c3cc(-c4cnc(C)nc4)ccc32)n1] | (2S,4R)-1-(2-(3-acetyl-5-(2-methylpyrimidin-5-yl)-1H-indazol-1-yl)acetyl)-4-fluoro-N-(6-(methylthio)pyridin-2-yl)pyrrolidine-2-carboxamide | *** | 2.68 (A) | 548 |
| 247 | 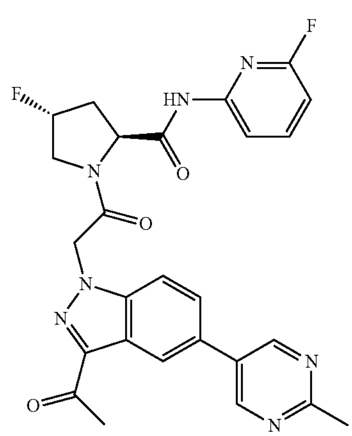 [SMILES: CC(=O)c1nn(CC(=O)N2C[C@H](F)C[C@H]2C(=O)Nc2cccc(F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-fluoropyridin-2-yl)pyrrolidine-2-carboxamide | *** | 2.60 (A) | 520 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 248 | 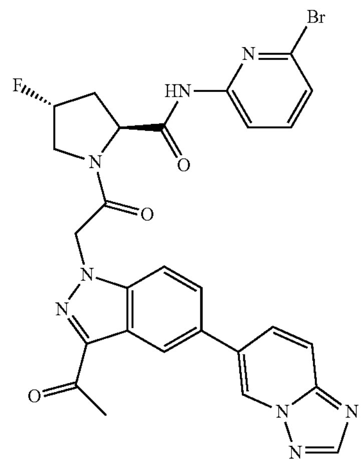 [SMILES: CC(=O)c1nn(CC(=O)N2C[C@H](F)C[C@H]2C(=O)Nc2cccc(Br)n2)c2ccc(-c3ccc4ncnn4c3)cc12] | (2S,4R)-1-(2-(5-([1,2,4]triazolo[1,5-a]pyridin-6-yl)-3-acetyl-1H-indazol-1-yl)acetyl)-N-(6-bromopyridin-2-yl)-4-fluoropyrrolidine-2-carboxamide | *** | | |
| 249 | 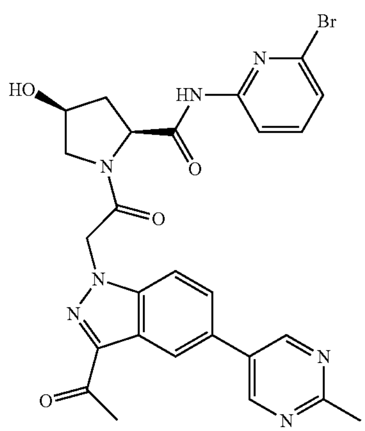 [SMILES: CC(=O)c1nn(CC(=O)N2C[C@@H](O)C[C@H]2C(=O)Nc2cccc(Br)n2)c2ccc(-c3cnc(C)nc3)cc12] | (2S,4S)-1-(2-(3-acetyl-5-(2-methylpyrimidin-5-yl)-1H-indazol-1-yl)acetyl)-N-(6-bromopyridin-2-yl)-4-hydroxypyrrolidine-2-carboxamide | *** | 3.07 (B) | 578 |
| 250 | 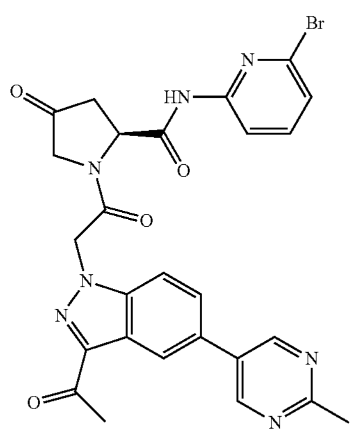 [SMILES: CC(=O)c1nn(CC(=O)N2CC(=O)C[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)-4-oxopyrrolidine-2-carboxamide | *** | 3.24 (B) | 576 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 251 | 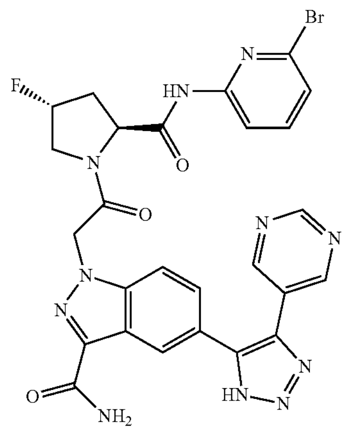 [SMILES: NC(=O)c1nn(CC(=O)N2C[C@H](F)C[C@H]2C(=O)Nc2cccc(Br)n2)c2ccc(-c3[nH]nnc3-c3cncnc3)cc12] | 1-(2-((2S,4R)-2-(6-bromopyridin-2-ylcarbamoyl)-4-fluoropyrrolidin-1-yl)-2-oxoethyl)-5-(4-(pyrimidin-5-yl)-1H-1,2,3-triazol-5-yl)-1H-indazole-3-carboxamide | *** | 1.19 (A) | 636 |
| 252 | 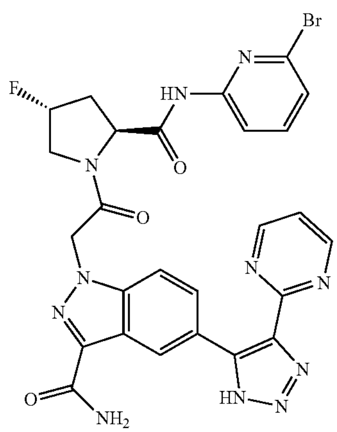 [SMILES: NC(=O)c1nn(CC(=O)N2C[C@H](F)C[C@H]2C(=O)Nc2cccc(Br)n2)c2ccc(-c3[nH]nnc3-c3ncccn3)cc12] | 1-(2-((2S,4R)-2-(6-bromopyridin-2-ylcarbamoyl)-4-fluoropyrrolidin-1-yl)-2-oxoethyl)-5-(4-(pyrimidin-2-yl)-1H-1,2,3-triazol-5-yl)-1H-indazole-3-carboxamide | ** | 1.18 (A) | 636 |
| 253 | 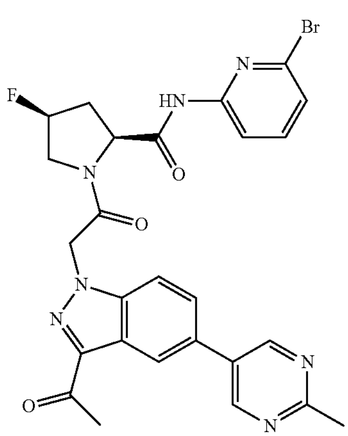 [SMILES: CC(=O)c1nn(CC(=O)N2C[C@@H](F)C[C@H]2C(=O)Nc2cccc(Br)n2)c2ccc(-c3cnc(C)nc3)cc12] | (2S,4S)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide | *** | 3.28 (B) | 580 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 254 | 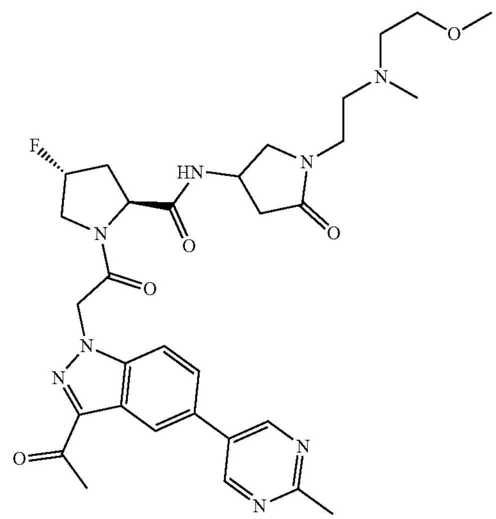 [SMILES: COCCN(C)CCN1CC(NC(=O)[C@@H]2C[C@@H](F)CN2C(=O)Cn2nc(C(C)=O)c3cc(-c4cnc(C)nc4)ccc32)CC1=O] | (2S,4R)-1-(2-(3-acetyl-5-(2-methylpyrimidin-5-yl)-1H-indazol-1-yl)acetyl)-4-fluoro-N-(1-(2-((2-methoxyethyl)(methyl)amino)ethyl)-5-oxopyrrolidin-3-yl)pyrrolidine-2-carboxamide | * | 2.63 (B) | 623 |
| 255 | 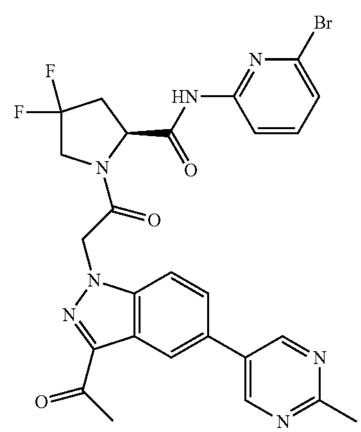 [SMILES: CC(=O)c1nn(CC(=O)N2CC(F)(F)C[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)-4,4-difluoropyrrolidine-2-carboxamide | *** | 3.70 (B) | 598 |
| 256 | 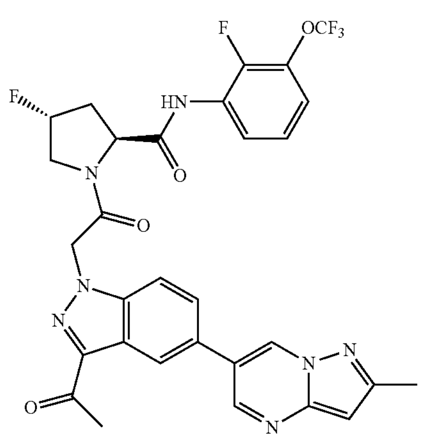 | (2S,4R)-1-(2-(3-acetyl-5-(2-methylpyrazolo[1,5-a]pyrimidin-6-yl)-1H-indazol-1-yl)acetyl)-4-fluoro-N-(2-fluoro-3-(trifluoromethoxy)phenyl)pyrrolidine-2-carboxamide | *** | 2.19 (A) | 642 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 257 | 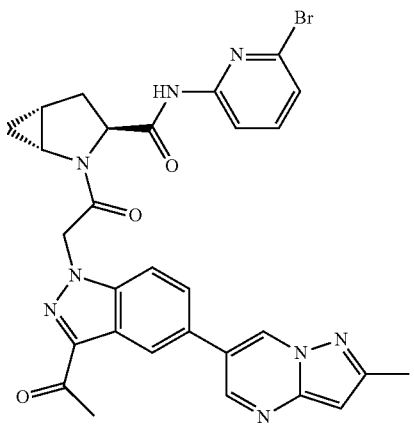 | (1R,3S,5R)-2-(2-(3-acetyl-5-(2-methylpyrazolo[1,5-a]pyrimidin-6-yl)-1H-indazol-1-yl)acetyl)-N-(6-bromopyridin-2-yl)-2-azabicyclo[3.1.0]hexane-3-carboxamide | *** | 2.07 (A) | 613 |
| 258 | 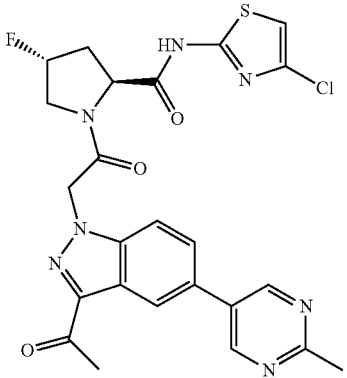 [SMILES: CC(=O)c1nn(CC(=O)N2C[C@H](F)C[C@H]2C(=O)Nc2nc(Cl)cs2)c2ccc(-c3cnc(C)nc3)cc12] | (2S,4R)-1-(2-(3-acetyl-5-(2-methylpyrimidin-5-yl)-1H-indazol-1-yl)acetyl)-N-(4-chlorothiazol-2-yl)-4-fluoropyrrolidine-2-carboxamide | *** | 1.52 (A) | 542 |
| 259 | 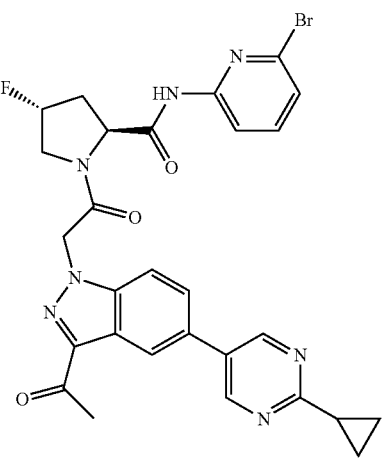 | (2S,4R)-1-(2-(3-acetyl-5-(2-cyclopropylpyrimidin-5-yl)-1H-indazol-1-yl)acetyl)-N-(6-bromopyridin-2-yl)-4-fluoropyrrolidine-2-carboxamide | *** | 2.06 (A) | 606 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 260 | 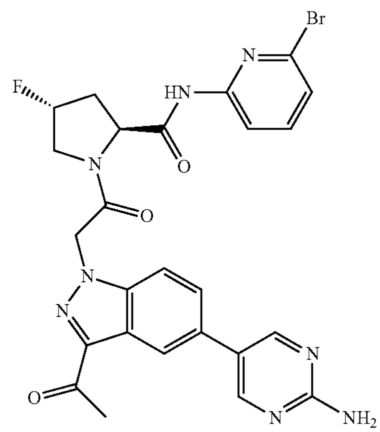 [SMILES: CC(=O)c1nn(CC(=O)N2C[C@H](F)C[C@H]2C(=O)Nc2cccc(Br)n2)c2ccc(-c3cnc(N)nc3)cc12] | (2S,4R)-1-(2-(3-acetyl-5-(2-aminopyrimidin-5-yl)-1H-indazol-1-yl)acetyl)-N-(6-bromopyridin-2-yl)-4-fluoropyrrolidine-2-carboxamide | *** | 1.48 (A) | 581 |
| 261 | 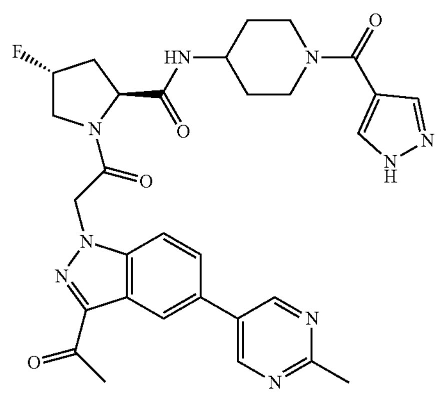 [SMILES: CC(=O)c1nn(CC(=O)N2C[C@H](F)C[C@H]2C(=O)NC2CCN(C(=O)c3cn[nH]c3)CC2)c2ccc(-c3cnc(C)nc3)cc12] | (2S,4R)-N-(1-(1H-pyrazole-4-carbonyl)piperidin-4-yl)-1-(2-(3-acetyl-5-(2-methylpyrimidin-5-yl)-1H-indazol-1-yl)acetyl)-4-fluoropyrrolidine-2-carboxamide | ** | 2.54 (B) | 602 |
| 262 | 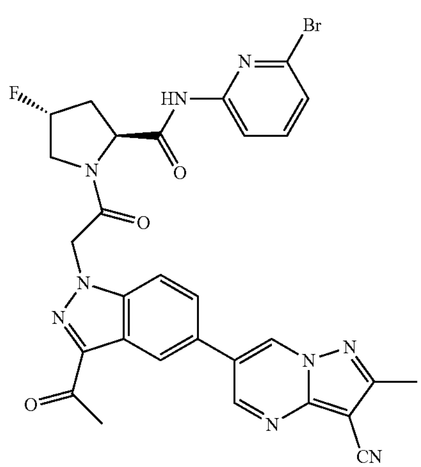 [SMILES: CC(=O)c1nn(CC(=O)N2C[C@H](F)C[C@H]2C(=O)Nc2cccc(Br)n2)c2ccc(-c3cnc4c(C#N)c(C)nn4c3)cc12] | (2S,4R)-1-(2-(3-acetyl-5-(3-cyano-2-methylpyrazolo[1,5-a]pyrimidin-6-yl)-1H-indazol-1-yl)acetyl)-N-(6-bromopyridin-2-yl)-4-fluoropyrrolidine-2-carboxamide | *** | 2.07 (A) | 644 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 263 | 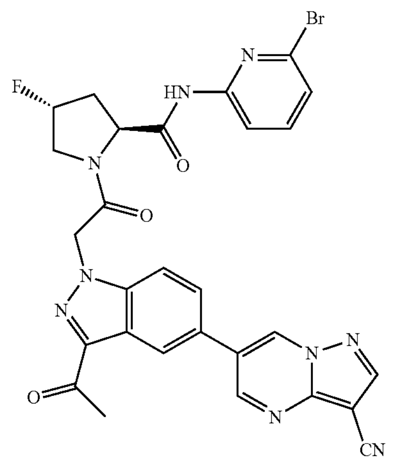 [SMILES: CC(=O)c1nn(CC(=O)N2C[C@H](F)C[C@H]2C(=O)Nc2cccc(Br)n2)c2ccc(-c3cnc4c(C#N)cnn4c3)cc12] | (2S,4R)-1-(2-(3-acetyl-5-(3-cyanopyrazolo[1,5-a]pyrimidin-6-yl)-1H-indazol-1-yl)acetyl)-N-(6-bromopyridin-2-yl)-4-fluoropyrrolidine-2-carboxamide | *** | 1.94 (A) | 630 |
| 264 | 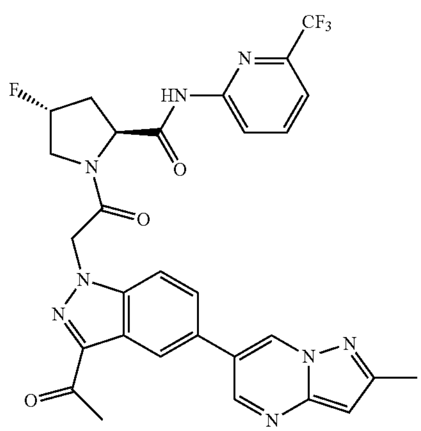 [SMILES: CC(=O)c1nn(CC(=O)N2C[C@H](F)C[C@H]2C(=O)Nc2cccc(C(F)(F)F)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-4-fluoro-N-(6-(trifluoromethyl)pyridin-2-yl)pyrrolidine-2-carboxamide | *** | 2.07 (A) | 609 |
| 265 | 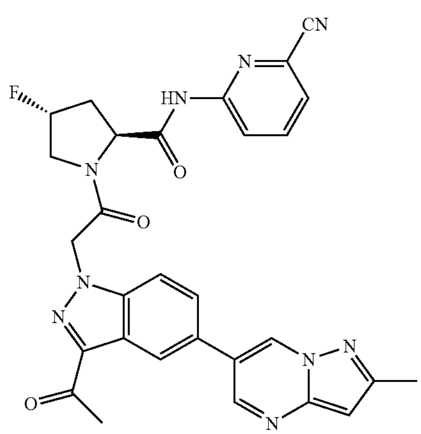 | (2S,4R)-1-(2-(3-acetyl-5-(2-methylpyrazolo[1,5-a]pyrimidin-6-yl)-1H-indazol-1-yl)acetyl)-N-(6-cyanopyridin-2-yl)-4-fluoropyrrolidine-2-carboxamide | *** | 1.70 (A) | 566 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 266 | 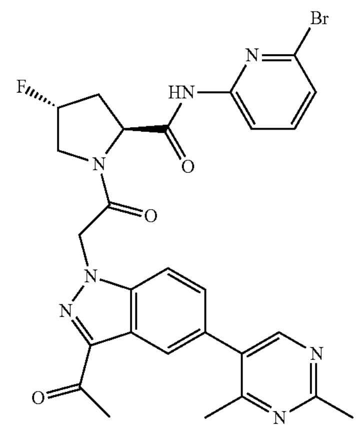 [SMILES: CC(=O)c1nn(CC(=O)N2C[C@H](F)C[C@H]2C(=O)Nc2cccc(Br)n2)c2ccc(-c3cnc(C)nc3C)cc12] | (2S,4R)-1-(2-(3-acetyl-5-(2,4-dimethylpyrimidin-5-yl)-1H-indazol-1-yl)acetyl)-N-(6-bromopyridin-2-yl)-4-fluoropyrrolidine-2-carboxamide | *** | 1.69 (A) | 594 |
| 267 | 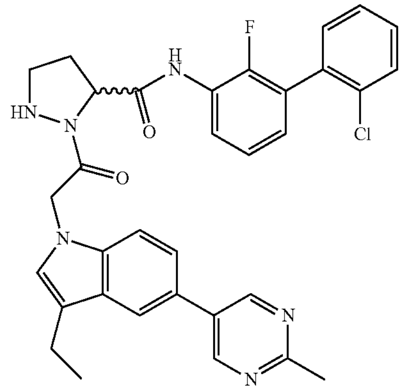 [SMILES: CCc1cn(CC(=O)N2NCCC2C(=O)Nc2cccc(-c3ccccc3Cl)c2F)c2ccc(-c3cnc(C)nc3)cc12] | N-(2'-chloro-2-fluorobiphenyl-3-yl)-2-(2-(3-ethyl-5-(2-methylpyrimidin-5-yl)-1H-indol-1-yl)acetyl)pyrazolidine-3-carboxamide | ** | 2.43 (A) | 597 |
| 268 | 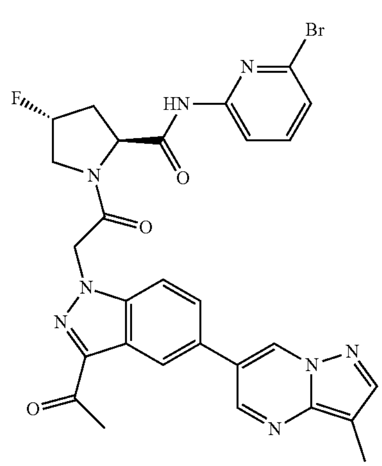 [SMILES: CC(=O)c1nn(CC(=O)N2C[C@H](F)C[C@H]2C(=O)Nc2cccc(Br)n2)c2ccc(-c3cnc4c(C)cnn4c3)cc12] | (2S,4R)-1-(2-(3-acetyl-5-(3-methylpyrazolo[1,5-a]pyrimidin-6-yl)-1H-indazol-1-yl)acetyl)-N-(6-bromopyridin-2-yl)-4-fluoropyrrolidine-2-carboxamide | *** | 2.02 (A) | 619 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 269 | 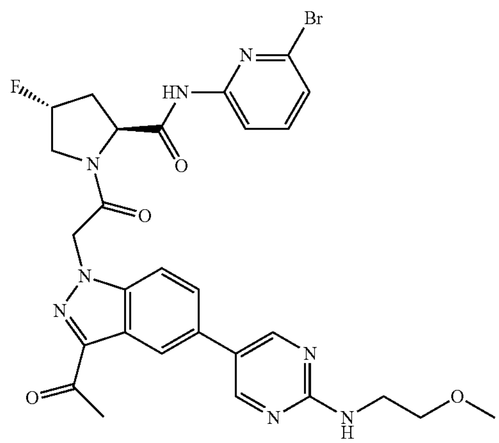 [SMILES: COCCNc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(3-acetyl-5-(2-(2-methoxyethylamino)pyrimidin-5-yl)-1H-indazol-1-yl)acetyl)-N-(6-bromopyridin-2-yl)-4-fluoropyrrolidine-2-carboxamide | *** | 1.79 (A) | 639 |
| 270 | 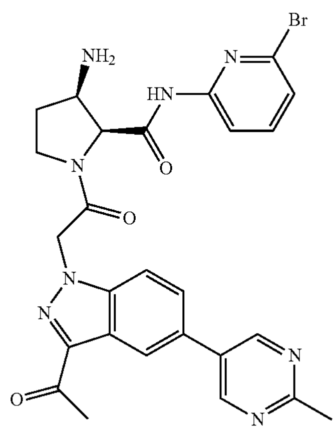 [SMILES: CC(=O)c1nn(CC(=O)N2CC[C@@H](N)[C@H]2C(=O)Nc2cccc(Br)n2)c2ccc(-c3cnc(C)nc3)cc12] | (2S,3R)-1-(2-(3-acetyl-5-(2-methylpyrimidin-5-yl)-1H-indazol-1-yl)acetyl)-3-amino-N-(6-bromopyridin-2-yl)pyrrolidine-2-carboxamide | *** | 2.66 (B) | 577 |
| 271 | 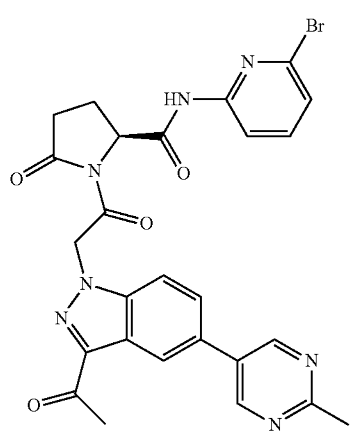 [SMILES: CC(=O)c1nn(CC(=O)N2C(=O)CC[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)-5-oxopyrrolidine-2-carboxamide | *** | 3.51 (B) | 576 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 272 | 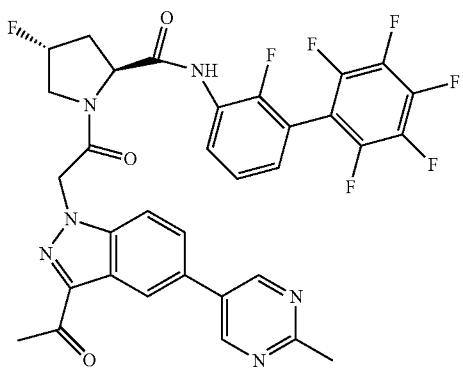 [SMILES: CC(=O)c1nn(CC(=O)N2C[C@H](F)C[C@H]2C(=O)Nc2cccc(-c3c(F)c(F)c(F)c(F)c3F)c2F)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2,2',3',4',5',6'-hexafluorobiphenyl-3-yl)pyrrolidine-2-carboxamide | *** | | |
| 273 | 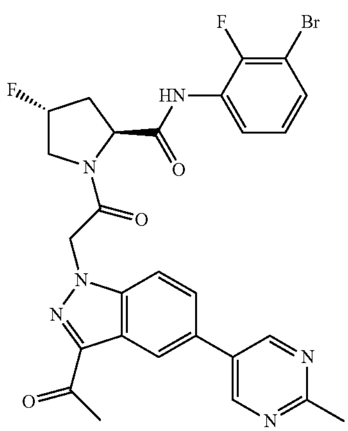 [SMILES: CC(=O)c1nn(CC(=O)N2C[C@H](F)C[C@H]2C(=O)Nc2cccc(Br)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-bromo-2-fluorophenyl)-4-fluoropyrrolidine-2-carboxamide | *** | | |
| 274 | 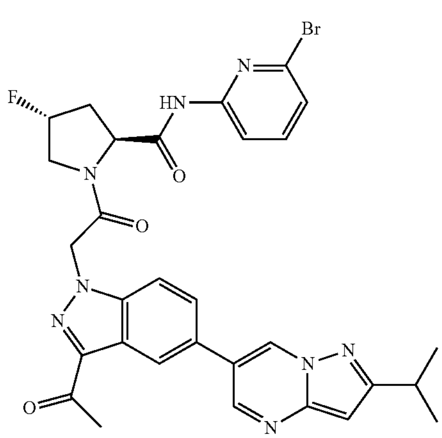 [SMILES: CC(=O)c1nn(CC(=O)N2C[C@H](F)C[C@H]2C(=O)Nc2cccc(Br)n2)c2ccc(-c3cnc4cc(C(C)C)nn4c3)cc12] | (2S,4R)-1-(2-(3-acetyl-5-(2-isopropylpyrazolo[1,5-a]pyrimidin-6-yl)-1H-indazol-1-yl)acetyl)-N-(6-bromopyridin-2-yl)-4-fluoropyrrolidine-2-carboxamide | *** | 2.34 (A) | 647 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 275 | 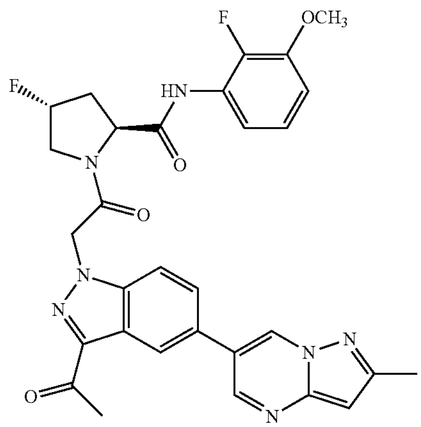 [SMILES: COc1cccc(NC(=O)[C@@H]2C[C@@H](F)CN2C(=O)Cn2nc(C(C)=O)c3cc(-c4cnc5cc(C)nn5c4)ccc32)c1F] | (2S,4R)-1-(2-(3-acetyl-5-(2-methylpyrazolo[1,5-a]pyrimidin-6-yl)-1H-indazol-1-yl)acetyl)-4-fluoro-N-(2-fluoro-3-methoxyphenyl)pyrrolidine-2-carboxamide | *** | 1.80 (A) | 588 |
| 276 | 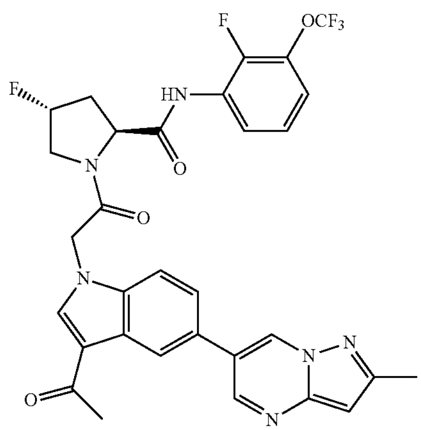 [SMILES: CC(=O)c1cn(CC(=O)N2C[C@H](F)C[C@H]2C(=O)Nc2cccc(OC(F)(F)F)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-4-fluoro-N-(2-fluoro-3-(trifluoromethoxy)phenyl)pyrrolidine-2-carboxamide | *** | 2.09 (A) | 641 |
| 277 | 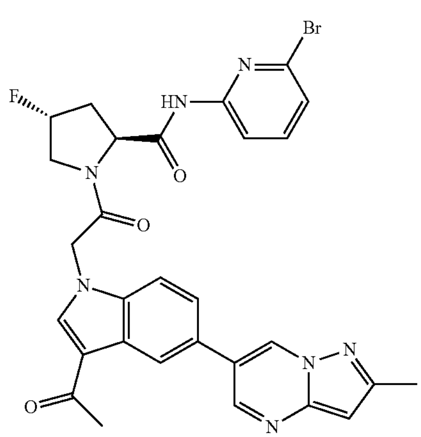 [SMILES: CC(=O)c1cn(CC(=O)N2C[C@H](F)C[C@H]2C(=O)Nc2cccc(Br)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-N-(6-bromopyridin-2-yl)-4-fluoropyrrolidine-2-carboxamide | *** | 1.82 (A) | 618 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 278 | 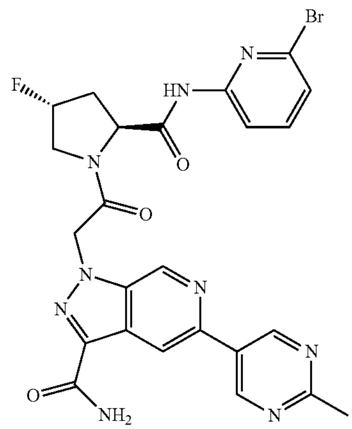 [SMILES: Cc1ncc(-c2cc3c(C(N)=O)nn(CC(=O)N4C[C@H](F)C[C@H]4C(=O)Nc4cccc(Br)n4)c3cn2)cn1] | 1-(2-((2S,4R)-2-(6-bromopyridin-2-ylcarbamoyl)-4-fluoropyrrolidin-1-yl)-2-oxoethyl)-5-(2-methylpyrimidin-5-yl)-1H-pyrazolo[3,4-c]pyridine-3-carboxamide | *** | 1.18 (A) | 582 |
| 279 | 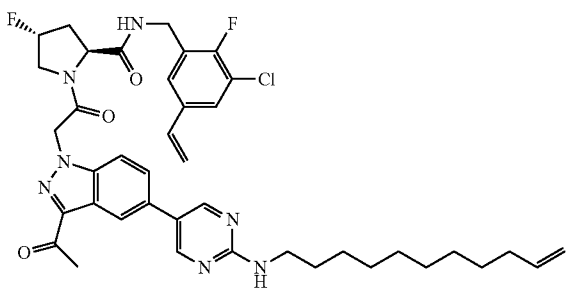 [SMILES: C=CCCCCCCCCCNc1ncc(-c2ccc3c(c2)c(C(C)=O)nn3CC(=O)N2C[C@H](F)C[C@H]2C(=O)NCc2cc(C=C)cc(Cl)c2F)cn1] | (2S,4R)-1-(2-(3-acetyl-5-(2-(undec-10-enylamino)pyrimidin-5-yl)-1H-indazol-1-yl)acetyl)-N-(3-chloro-2-fluoro-5-vinylbenzyl)-4-fluoropyrrolidine-2-carboxamide | * | 4.83 (B) | 746 |
| 280 | 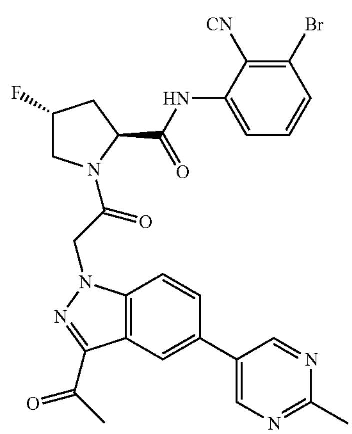 | (2S,4R)-1-(2-(3-acetyl-5-(2-methylpyrimidin-5-yl)-1H-indazol-1-yl)acetyl)-N-(3-bromo-2-cyanophenyl)-4-fluoropyrrolidine-2-carboxamide | ** | 1.66 (A) | 606 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 281 | 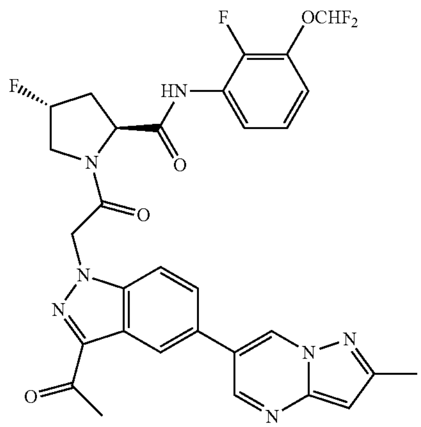 [SMILES: CC(=O)c1nn(CC(=O)N2C[C@H](F)C[C@H]2C(=O)Nc2cccc(OC(F)F)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-N-(3-(difluoromethoxy)-2-fluorophenyl)-4-fluoropyrrolidine-2-carboxamide | *** | 1.99 (A) | 624 |
| 282 | 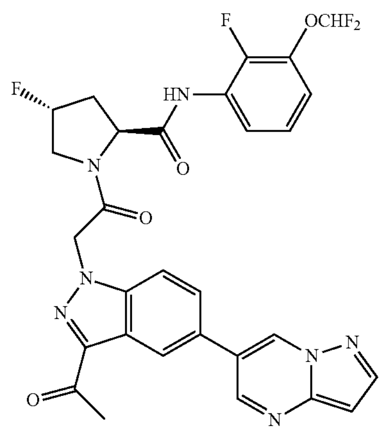 [SMILES: CC(=O)c1nn(CC(=O)N2C[C@H](F)C[C@H]2C(=O)Nc2cccc(OC(F)F)c2F)c2ccc(-c3cnc4ccnn4c3)cc12] | (2S,4R)-1-(2-(3-acetyl-5-(pyrazolo[1,5-a]pyrimidin-6-yl)-1H-indazol-1-yl)acetyl)-N-(3-(difluoromethoxy)-2-fluorophenyl)-4-fluoropyrrolidine-2-carboxamide | *** | 1.90 (A) | 610 |
| 283 | 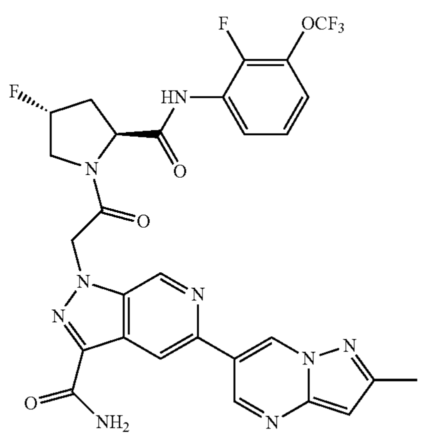 [SMILES: Cc1cc2ncc(-c3cc4c(C(N)=O)nn(CC(=O)N5C[C@H](F)C[C@H]5C(=O)Nc5cccc(OC(F)(F)F)c5F)c4cn3)cn2n1] | 1-(2-((2S,4R)-4-fluoro-2-(2-fluoro-3-(trifluoromethoxy)phenylcarbamoyl)pyrrolidin-1-yl)-2-oxoethyl)-5-(2-methylpyrazolo[1,5-a]pyrimidin-6-yl)-1H-pyrazolo[3,4-c]pyridine-3-carboxamide | *** | 1.79 (A) | 644 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 284 | 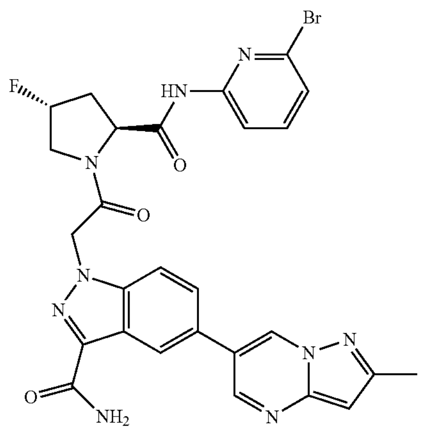 [SMILES: Cc1cc2ncc(-c3ccc4c(c3)c(C(N)=O)nn4CC(=O)N3C[C@H](F)C[C@H]3C(=O)Nc3cccc(Br)n3)cn2n1] | 1-(2-((2S,4R)-2-(6-bromopyridin-2-ylcarbamoyl)-4-fluoropyrrolidin-1-yl)-2-oxoethyl)-5-(2-methylpyrazolo[1,5-a]pyrimidin-6-yl)-1H-indazole-3-carboxamide | *** | 1.60 (A) | 620 |
| 285 | 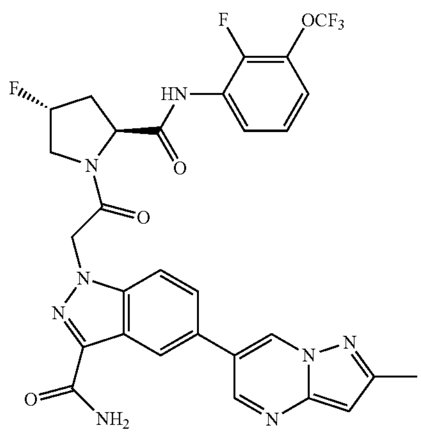 [SMILES: Cc1cc2ncc(-c3ccc4c(c3)c(C(N)=O)nn4CC(=O)N3C[C@H](F)C[C@H]3C(=O)Nc3cccc(OC(F)(F)F)c3F)cn2n1] | 1-(2-((2S,4R)-4-fluoro-2-(2-fluoro-3-(trifluoromethoxy)phenylcarbamoyl)pyrrolidin-1-yl)-2-oxoethyl)-5-(2-methylpyrazolo[1,5-a]pyrimidin-6-yl)-1H-indazole-3-carboxamide | *** | 1.88 (A) | 620 |
| 286 | 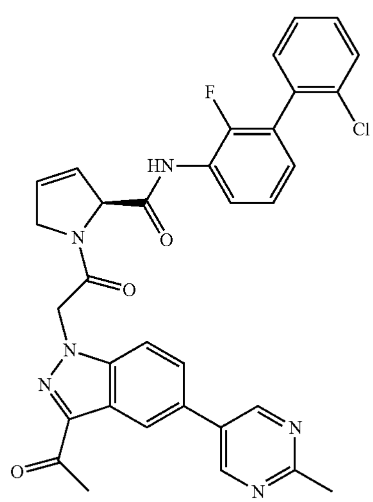 [SMILES: CC(=O)c1nn(CC(=O)N2CC=C[C@H]2C(=O)Nc2cccc(-c3ccccc3Cl)c2F)c2ccc(-c3cnc(C)nc3)cc12] | (S)-1-(2-(3-acetyl-5-(2-methylpyrimidin-5-yl)-1H-indazol-1-yl)acetyl)-N-(2'-chloro-2-fluorobiphenyl-3-yl)-2,5-dihydro-1H-pyrrole-2-carboxamide | *** | 3.60 (B) | 607 (M − 1) |

TABLE 2-continued

Additional Compounds of the Present Invention

| Cmp No. | Structure | Name | IC$_{50}$ | RT min (Method A or B) | MS (M + 1) |
|---|---|---|---|---|---|
| 287 | 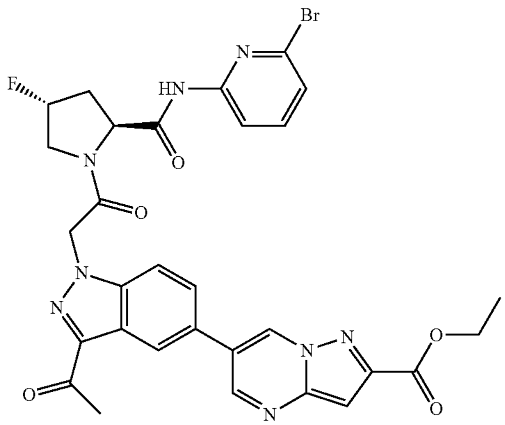 [SMILES: CCOC(=O)c1cc2ncc(-c3ccc4c(c3)c(C(C)=O)nn4CC(=O)N3C[C@H](F)C[C@H]3C(=O)Nc3cccc(Br)n3)cn2n1] | ethyl 6-(3-acetyl-1-(2-((2S,4R)-2-(6-bromopyridin-2-ylcarbamoyl)-4-fluoropyrrolidin-1-yl)-2-oxoethyl)-1H-indazol-5-yl)pyrazolo[1,5-a]pyrimidine-2-carboxylate | *** | 2.14 (A) | 677 |
| 288 | 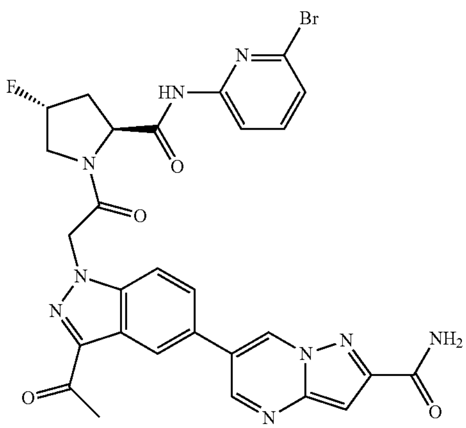 [SMILES: CC(=O)c1nn(CC(=O)N2C[C@H](F)C[C@H]2C(=O)Nc2cccc(Br)n2)c2ccc(-c3cnc4cc(C(N)=O)nn4c3)cc12] | 6-(3-acetyl-1-(2-((2S,4R)-2-(6-bromopyridin-2-ylcarbamoyl)-4-fluoropyrrolidin-1-yl)-2-oxoethyl)-1H-indazol-5-yl)pyrazolo[1,5-a]pyrimidine-2-carboxamide | *** | 1.55 (A) | 648 |
| 289 | 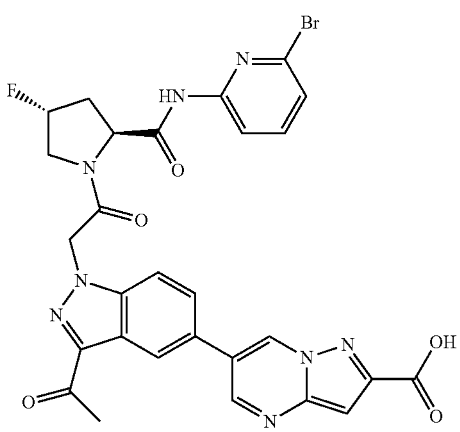 [SMILES: CC(=O)c1nn(CC(=O)N2C[C@H](F)C[C@H]2C(=O)Nc2cccc(Br)n2)c2ccc(-c3cnc4cc(C(=O)O)nn4c3)cc12] | 6-(3-acetyl-1-(2-((2S,4R)-2-(6-bromopyridin-2-ylcarbamoyl)-4-fluoropyrrolidin-1-yl)-2-oxoethyl)-1H-indazol-5-yl)pyrazolo[1,5-a]pyrimidine-2-carboxylic acid | *** | 1.62 (A) | 649 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 290 | 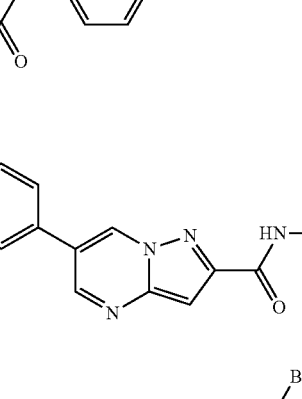 | 6-(3-acetyl-1-(2-((2S,4R)-2-(6-bromopyridin-2-ylcarbamoyl)-4-fluoropyrrolidin-1-yl)-2-oxoethyl)-1H-indazol-5-yl)-N-(2-(2-methoxyethoxy)ethyl)pyrazolo[1,5-a]pyrimidine-2-carboxamide | *** | 1.75 (A) | 750 |
| 291 | 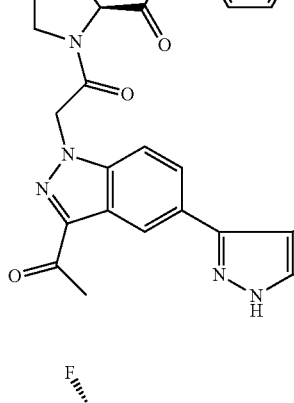 | (2S,4R)-1-(2-(3-acetyl-5-(1H-thieno[3,2-c]pyrazol-3-yl)-1H-indazol-1-yl)acetyl)-N-(6-bromopyridin-2-yl)-4-fluoropyrrolidine-2-carboxamide | *** | 1.95 (A) | 610 |
| 292 | 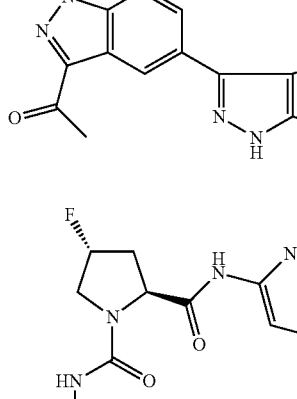 | (2S,4R)-N1-(1-acetyl-6-(2-methylpyrimidin-5-yl)-1H-indol-3-yl)-N2-(6-bromopyridin-2-yl)-4-fluoropyrrolidine-1,2-dicarboxamide | *** | 1.69 (A) | 580 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 293 | 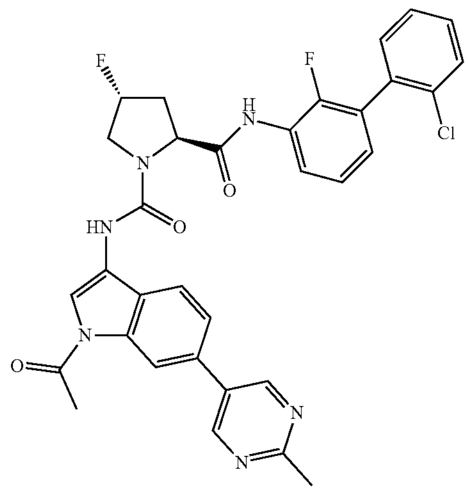 [SMILES: CC(=O)n1cc(NC(=O)N2C[C@H](F)C[C@H]2C(=O)Nc2cccc(-c3ccccc3Cl)c2F)c2ccc(-c3cnc(C)nc3)cc21] | (2S,4R)-N1-(1-acetyl-6-(2-methylpyrimidin-5-yl)-1H-indol-3-yl)-N2-(2'-chloro-2-fluorobiphenyl-3-yl)-4-fluoropyrrolidine-1,2-dicarboxamide | *** | 2.18 (A) | 629 |
| 294 | 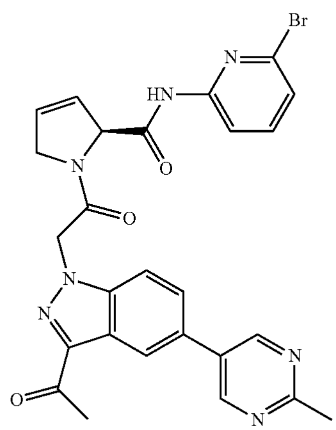 [SMILES: CC(=O)c1nn(CC(=O)N2CC=C[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)-2,5-dihydro-1H-pyrrole-2-carboxamide | *** | 3.02 (B) | 560 |
| 295 | 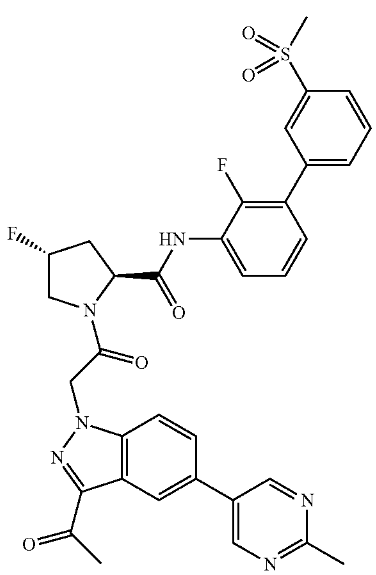 [SMILES: CC(=O)c1nn(CC(=O)N2C[C@H](F)C[C@H]2C(=O)Nc2cccc(-c3cccc(S(C)(=O)=O)c3)c2F)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2-fluoro-3'-(methylsulfonyl)biphenyl-3-yl)pyrrolidine-2-carboxamide | *** | 1.67 (A) | 673 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 296 | 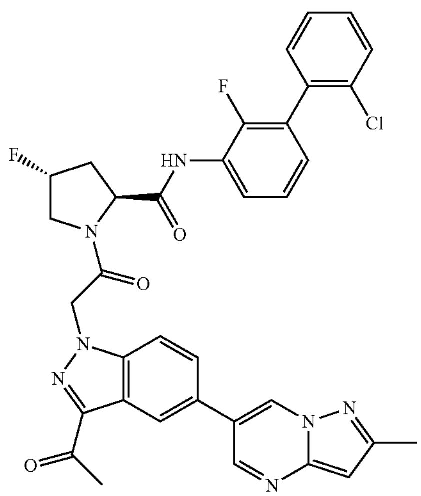 [SMILES: CC(=O)c1nn(CC(=O)N2C[C@H](F)C[C@H]2C(=O)Nc2cccc(-c3ccccc3Cl)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-N-(2'-chloro-2-fluorobiphenyl-3-yl)-4-fluoropyrrolidine-2-carboxamide | *** | 2.39 (A) | 668 |
| 297 | 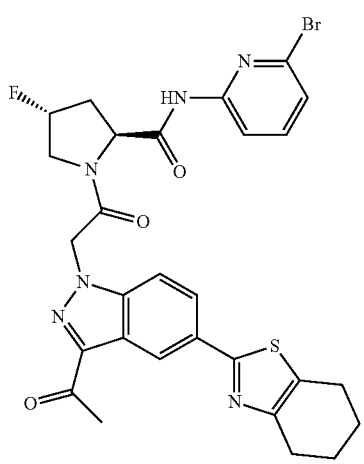 [SMILES: CC(=O)c1nn(CC(=O)N2C[C@H](F)C[C@H]2C(=O)Nc2cccc(Br)n2)c2ccc(-c3nc4c(s3)CCCC4)cc12] | (2S,4R)-1-(2-(3-acetyl-5-(4,5,6,7-tetrahydrobenzo[d]thiazol-2-yl)-1H-indazol-1-yl)acetyl)-N-(6-bromopyridin-2-yl)-4-fluoropyrrolidine-2-carboxamide | * | 2.57 (A) | 625 |
| 298 | 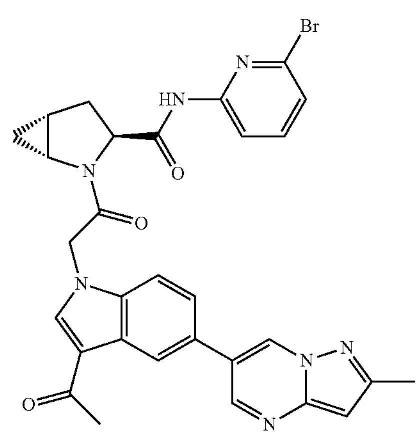 [SMILES: CC(=O)c1cn(CC(=O)N2[C@@H]3C[C@@H]3C[C@H]2C(=O)Nc2cccc(Br)n2)c2ccc(-c3cnc4cc(C)nn4c3)cc12] | (1R,3S,5R)-2-(2-(3-acetyl-5-(2-methylpyrazolo[1,5-a]pyrimidin-6-yl)-1H-indol-1-yl)acetyl)-N-(6-bromopyridin-2-yl)-2-azabicyclo[3.1.0]hexane-3-carboxamide | *** | 1.95 (A) | 612 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 299 | 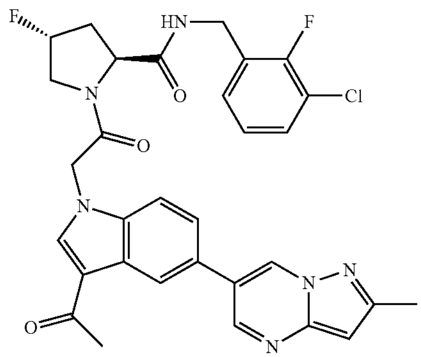 [SMILES: CC(=O)c1cn(CC(=O)N2C[C@H](F)C[C@H]2C(=O)NCc2cccc(Cl)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-N-(3-chloro-2-fluorobenzyl)-4-fluoropyrrolidine-2-carboxamide | *** | 1.85 (A) | 605 |
| 300 | 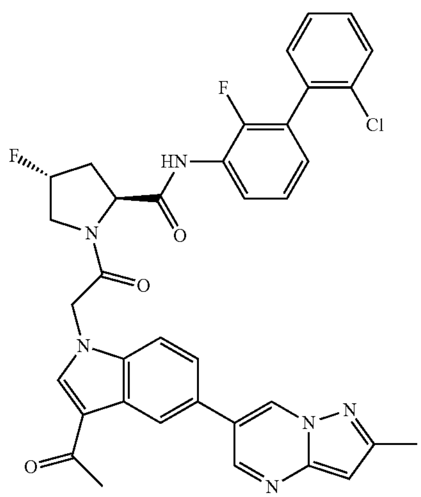 [SMILES: CC(=O)c1cn(CC(=O)N2C[C@H](F)C[C@H]2C(=O)Nc2cccc(-c3ccccc3Cl)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-N-(2'-chloro-2-fluorobiphenyl-3-yl)-4-fluoropyrrolidine-2-carboxamide | *** | 2.26 (A) | 667 |
| 301 | 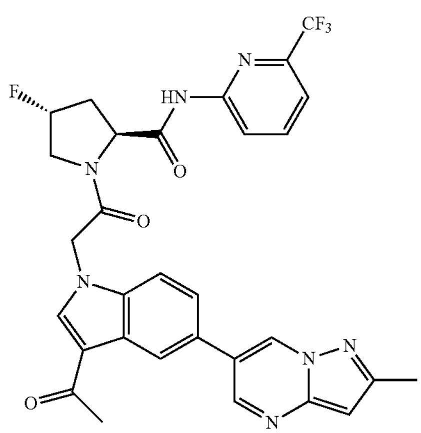 | (2S,4R)-1-(2-(3-acetyl-5-(2-methylpyrazolo[1,5-a]pyrimidin-6-yl)-1H-indol-1-yl)acetyl)-4-fluoro-N-(6-(trifluoromethyl)pyridin-2-yl)pyrrolidine-2-carboxamide | *** | 1.93 (A) | 608 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 302 | 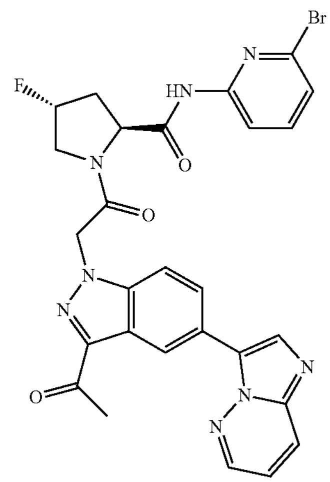 [SMILES: CC(=O)c1nn(CC(=O)N2C[C@H](F)C[C@H]2C(=O)Nc2cccc(Br)n2)c2ccc(-c3cnc4cccnn34)cc12] | (2S,4R)-1-(2-(3-acetyl-5-(imidazo[1,2-b]pyridazin-3-yl)-1H-indazol-1-yl)acetyl)-N-(6-bromopyridin-2-yl)-4-fluoropyrrolidine-2-carboxamide | *** | 1.60 (A) | 605 |
| 303 | 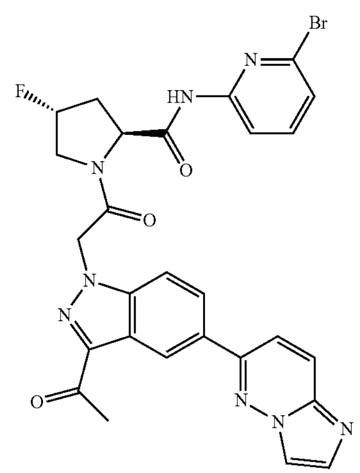 [SMILES: CC(=O)c1nn(CC(=O)N2C[C@H](F)C[C@H]2C(=O)Nc2cccc(Br)n2)c2ccc(-c3ccc4nccn4n3)cc12] | (2S,4R)-1-(2-(3-acetyl-5-(imidazo[1,2-b]pyridazin-6-yl)-1H-indazol-1-yl)acetyl)-N-(6-bromopyridin-2-yl)-4-fluoropyrrolidine-2-carboxamide | *** | 1.50 (A) | 605 |
| 304 | 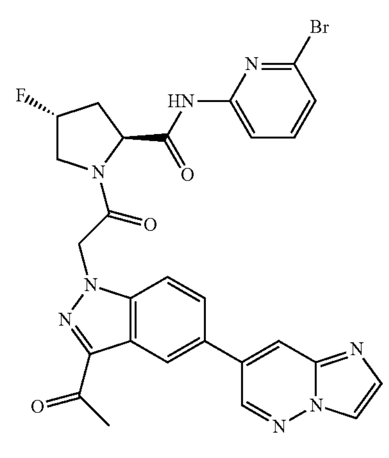 [SMILES: CC(=O)c1nn(CC(=O)N2C[C@H](F)C[C@H]2C(=O)Nc2cccc(Br)n2)c2ccc(-c3cnn4ccnc4c3)cc12] | (2S,4R)-1-(2-(3-acetyl-5-(imidazo[1,2-b]pyridazin-7-yl)-1H-indazol-1-yl)acetyl)-N-(6-bromopyridin-2-yl)-4-fluoropyrrolidine-2-carboxamide | *** | 1.49 (A) | 605 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 305 | 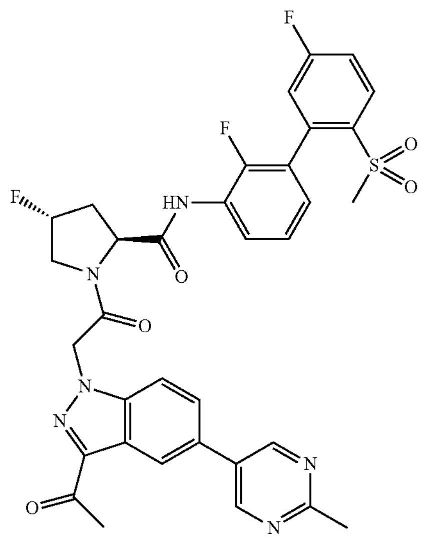 [SMILES: CC(=O)c1nn(CC(=O)N2C[C@H](F)C[C@H]2C(=O)Nc2cccc(-c3cc(F)ccc3S(C)(=O)=O)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2,5'-difluoro-2'-(methylsulfonyl)biphenyl-3-yl)-4-fluoropyrrolidine-2-carboxamide | *** | 1.74 (A) | 691 |
| 306 | 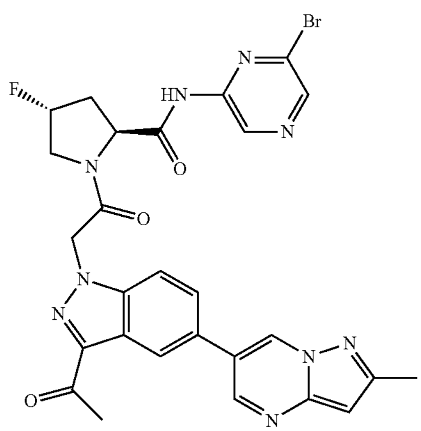 [SMILES: CC(=O)c1nn(CC(=O)N2C[C@H](F)C[C@H]2C(=O)Nc2cncc(Br)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-N-(6-bromopyrazin-2-yl)-4-fluoropyrrolidine-2-carboxamide | *** | 1.77 (A) | 620 |
| 307 | 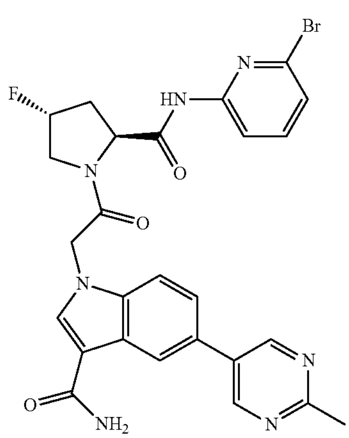 [SMILES: Cc1ncc(-c2ccc3c(c2)c(C(N)=O)cn3CC(=O)N2C[C@H](F)C[C@H]2C(=O)Nc2cccc(Br)n2)cn1] | 1-(2-((2S,4R)-2-(6-bromopyridin-2-ylcarbamoyl)-4-fluoropyrrolidin-1-yl)-2-oxoethyl)-5-(2-methylpyrimidin-5-yl)-1H-indole-3-carboxamide | *** | 1.30 (A) | 580 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 308 | 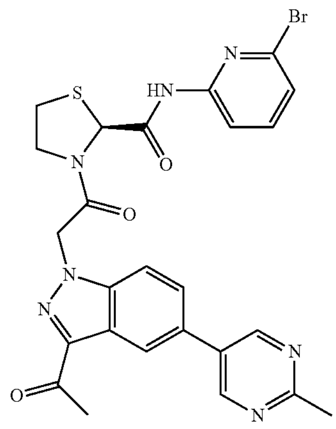 | (S)-3-(2-(3-acetyl-5-(2-methylpyrimidin-5-yl)-1H-indazol-1-yl)acetyl)-N-(6-bromopyridin-2-yl)thiazolidine-2-carboxamide | *** | 1.77 (A) | 580 |
| 309 | 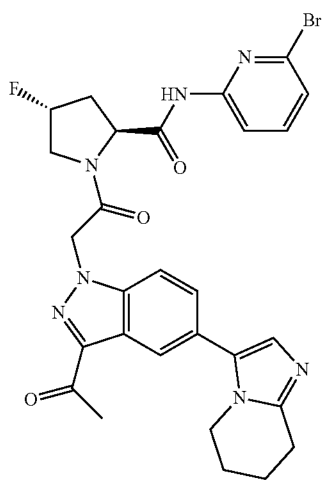 [SMILES: CC(=O)c1nn(CC(=O)N2C[C@H](F)C[C@H]2C(=O)Nc2cccc(Br)n2)c2ccc(-c3cnc4n3CCCC4)cc12] | (2S,4R)-1-(2-(3-acetyl-5-(5,6,7,8-tetrahydroimidazo[1,2-a]pyridin-3-yl)-1H-indazol-1-yl)acetyl)-N-(6-bromopyridin-2-yl)-4-fluoropyrrolidine-2-carboxamide | *** | 1.47 (A) | 608 |
| 310 | 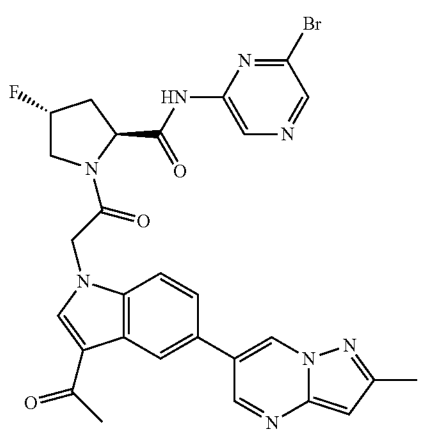 [SMILES: CC(=O)c1cn(CC(=O)N2C[C@H](F)C[C@H]2C(=O)Nc2cncc(Br)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-N-(6-bromopyrazin-2-yl)-4-fluoropyrrolidine-2-carboxamide | *** | 1.64 (A) | 619 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 311 | 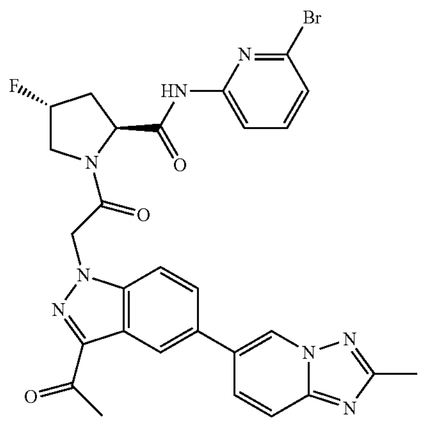 [SMILES: CC(=O)c1nn(CC(=O)N2C[C@H](F)C[C@H]2C(=O)Nc2cccc(Br)n2)c2ccc(-c3ccc4nc(C)nn4c3)cc12] | (2S,4R)-1-(2-(3-acetyl-5-(2-methyl-[1,2,4]triazolo[1,5-a]pyridin-6-yl)-1H-indazol-1-yl)acetyl)-N-(6-bromopyridin-2-yl)-4-fluoropyrrolidine-2-carboxamide | *** | 1.74 (A) | 619 |
| 312 | 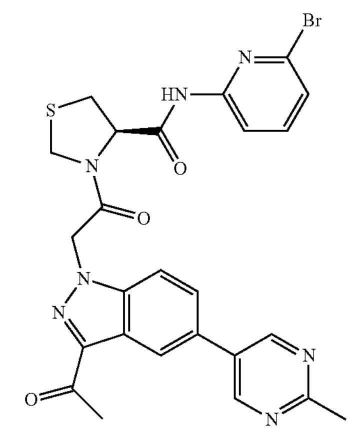 [SMILES: CC(=O)c1nn(CC(=O)N2CSC[C@H]2C(=O)Nc2cccc(Br)n2)c2ccc(-c3cnc(C)nc3)cc12] | (R)-3-(2-(3-acetyl-5-(2-methylpyrimidin-5-yl)-1H-indazol-1-yl)acetyl)-N-(6-bromopyridin-2-yl)thiazolidine-4-carboxamide | *** | 1.78 (A) | 580 |
| 313 | 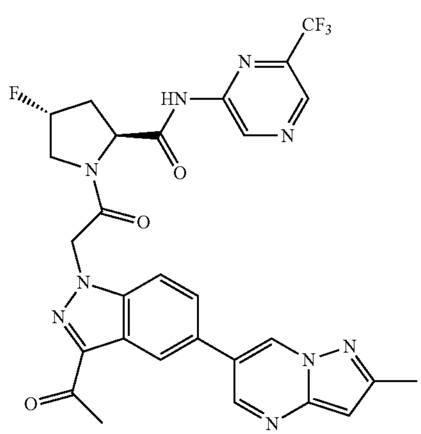 | (2S,4R)-1-(2-(3-acetyl-5-(2-methylpyrazolo[1,5-a]pyrimidin-6-yl)-1H-indazol-1-yl)acetyl)-4-fluoro-N-(6-(trifluoromethyl)pyrazin-2-yl)pyrrolidine-2-carboxamide | *** | 1.91 (A) | 610 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 314 | 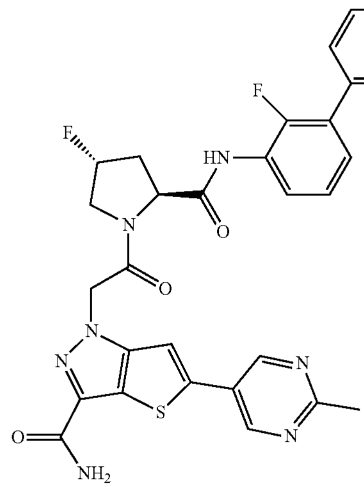 | 1-(2-((2S,4R)-2-(2'-chloro-2-fluorobiphenyl-3-ylcarbamoyl)-4-fluoropyrrolidin-1-yl)-2-oxoethyl)-5-(2-methylpyrimidin-5-yl)-1H-thieno[3,2-c]pyrazole-3-carboxamide | *** | 1.87 (A) | 636 |
| 315 | 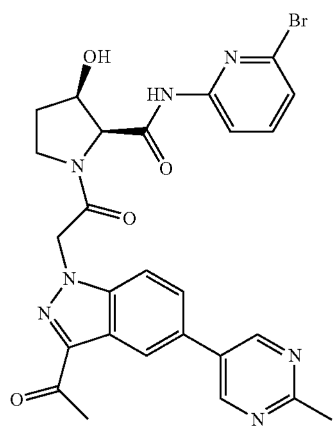 [SMILES: CC(=O)c1nn(CC(=O)N2CC[C@@H](O)[C@H]2C(=O)Nc2cccc(Br)n2)c2ccc(-c3cnc(C)nc3)cc12] | (2S,3R)-1-(2-(3-acetyl-5-(2-methylpyrimidin-5-yl)-1H-indazol-1-yl)acetyl)-N-(6-bromopyridin-2-yl)-3-hydroxypyrrolidine-2-carboxamide | *** | 3.73 (B) | 578 |
| 316 | 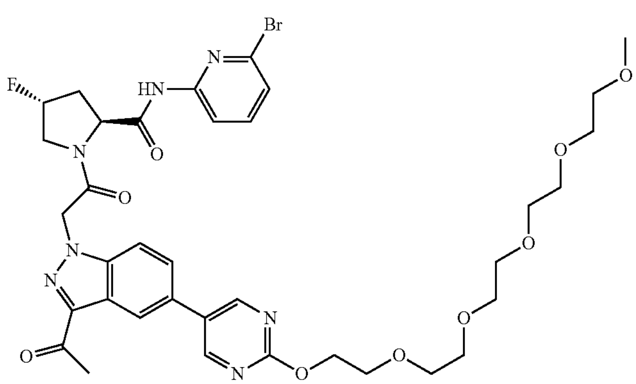 [SMILES: COCCOCCOCCOCCOCCOc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(5-(2-(2,5,8,11,14-pentaoxahexadecan-16-yloxy)pyrimidin-5-yl)-3-acetyl-1H-indazol-1-yl)acetyl)-N-(6-bromopyridin-2-yl)-4-fluoropyrrolidine-2-carboxamide | *** | 1.96 (A) | 816 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 317 | 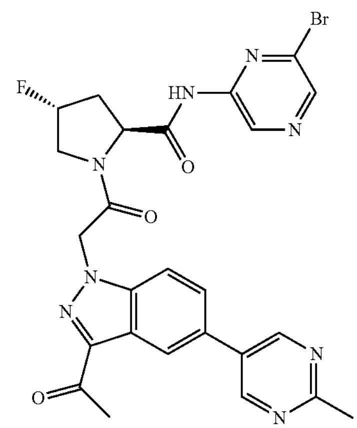 [SMILES: CC(=O)c1nn(CC(=O)N2C[C@H](F)C[C@H]2C(=O)Nc2cncc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromopyrazin-2-yl)-4-fluoropyrrolidine-2-carboxamide | *** | 1.50 (A) | 581 |
| 318 | 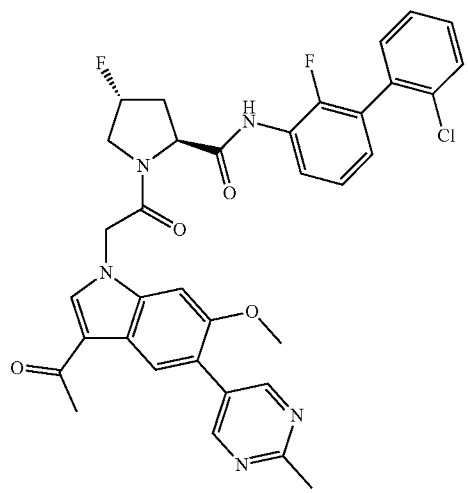 [SMILES: COc1cc2c(cc1-c1cnc(C)nc1)c(C(C)=O)cn2CC(=O)N1C[C@H](F)C[C@H]1C(=O)Nc1cccc(-c2ccccc2Cl)c1F] | (2S,4R)-1-(2-(3-acetyl-6-methoxy-5-(2-methylpyrimidin-5-yl)-1H-indol-1-yl)acetyl)-N-(2'-chloro-2-fluorobiphenyl-3-yl)-4-fluoropyrrolidine-2-carboxamide | *** | 2.10 (A) | 658 |
| 319 | 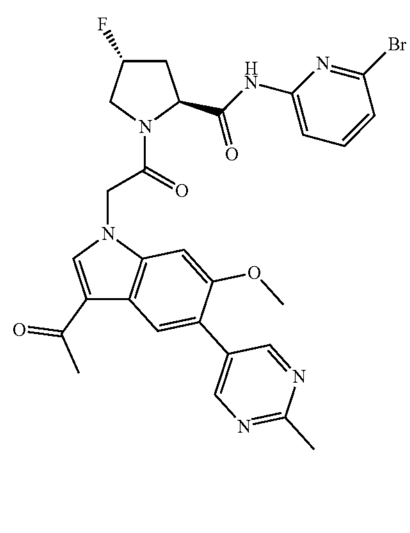 [SMILES: COc1cc2c(cc1-c1cnc(C)nc1)c(C(C)=O)cn2CC(=O)N1C[C@H](F)C[C@H]1C(=O)Nc1cccc(Br)n1] | (2S,4R)-1-(2-(3-acetyl-6-methoxy-5-(2-methylpyrimidin-5-yl)-1H-indol-1-yl)acetyl)-N-(6-bromopyridin-2-yl)-4-fluoropyrrolidine-2-carboxamide | *** | 1.59 (A) | 609 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 320 | 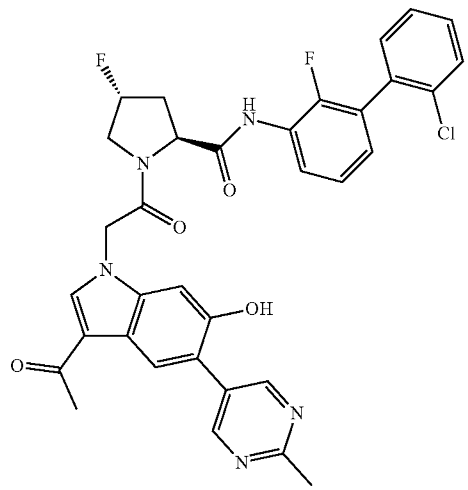 [SMILES: CC(=O)c1cn(CC(=O)N2C[C@H](F)C[C@H]2C(=O)Nc2cccc(-c3ccccc3Cl)c2F)c2cc(O)c(-c3cnc(C)nc3)cc12] | (2S,4R)-1-(2-(3-acetyl-6-hydroxy-5-(2-methylpyrimidin-5-yl)-1H-indol-1-yl)acetyl)-N-(2'-chloro-2-fluorobiphenyl-3-yl)-4-fluoropyrrolidine-2-carboxamide | *** | 1.89 (A) | 644 |
| 321 | 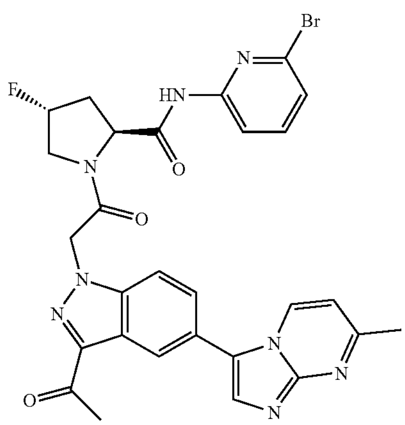 [SMILES: CC(=O)c1nn(CC(=O)N2C[C@H](F)C[C@H]2C(=O)Nc2cccc(Br)n2)c2ccc(-c3cnc4nc(C)ccn34)cc12] | (2S,4R)-1-(2-(3-acetyl-5-(7-methylimidazo[1,2-a]pyrimidin-3-yl)-1H-indazol-1-yl)acetyl)-N-(6-bromopyridin-2-yl)-4-fluoropyrrolidine-2-carboxamide | *** | 1.38 (A) | 619 |
| 322 | 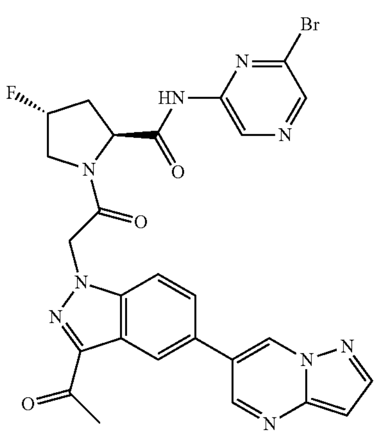 [SMILES: CC(=O)c1nn(CC(=O)N2C[C@H](F)C[C@H]2C(=O)Nc2cncc(Br)n2)c2ccc(-c3cnc4ccnn4c3)cc12] | (2S,4R)-1-(2-(3-acetyl-5-(pyrazolo[1,5-a]pyrimidin-6-yl)-1H-indazol-1-yl)acetyl)-N-(6-bromopyrazin-2-yl)-4-fluoropyrrolidine-2-carboxamide | *** | 1.63 (A) | 606 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 323 | 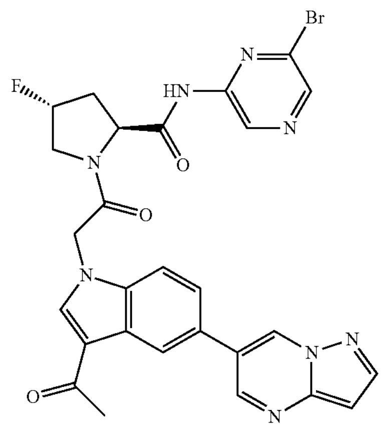 [SMILES: CC(=O)c1cn(CC(=O)N2C[C@H](F)C[C@H]2C(=O)Nc2cncc(Br)n2)c2ccc(-c3cnc4ccnn4c3)cc12] | (2S,4R)-1-(2-(3-acetyl-5-(pyrazolo[1,5-a]pyrimidin-6-yl)-1H-indol-1-yl)acetyl)-N-(6-bromopyrazin-2-yl)-4-fluoropyrrolidine-2-carboxamide | *** | 1.50 (A) | 605 |
| 324 | 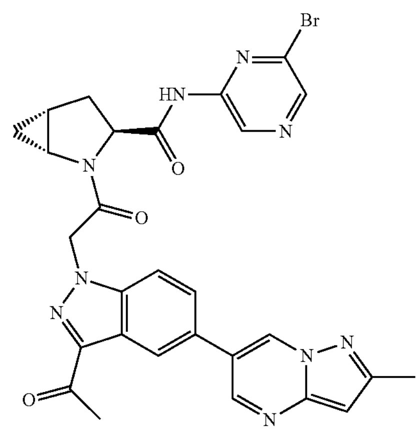 [SMILES: CC(=O)c1nn(CC(=O)N2[C@@H]3C[C@@H]3C[C@H]2C(=O)Nc2cncc(Br)n2)c2ccc(-c3cnc4cc(C)nn4c3)cc12] | (1R,3S,5R)-2-(2-(3-acetyl-5-(2-methylpyrazolo[1,5-a]pyrimidin-6-yl)-1H-indazol-1-yl)acetyl)-N-(6-bromopyrazin-2-yl)-2-azabicyclo[3.1.0]hexane-3-carboxamide | *** | 1.88 (A) | 614 |
| 325 | 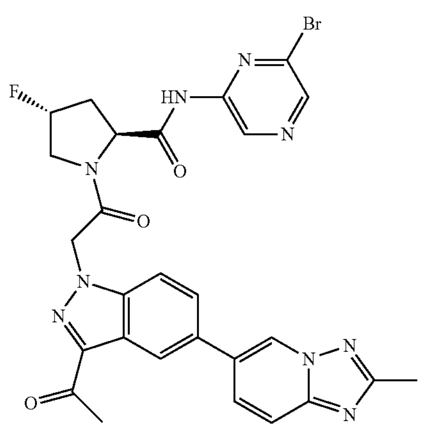 [SMILES: CC(=O)c1nn(CC(=O)N2C[C@H](F)C[C@H]2C(=O)Nc2cncc(Br)n2)c2ccc(-c3ccc4nc(C)nn4c3)cc12] | (2S,4R)-1-(2-(3-acetyl-5-(2-methyl-[1,2,4]triazolo[1,5-a]pyridin-6-yl)-1H-indazol-1-yl)acetyl)-N-(6-bromopyrazin-2-yl)-4-fluoropyrrolidine-2-carboxamide | *** | 1.54 (A) | 620 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 326 | 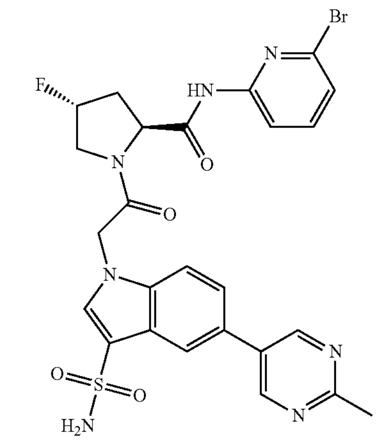 [SMILES: Cc1ncc(-c2ccc3c(c2)c(S(N)(=O)=O)cn3CC(=O)N2C[C@H](F)C[C@H]2C(=O)Nc2cccc(Br)n2)cn1] | (2S,4R)-N-(6-bromopyridin-2-yl)-4-fluoro-1-(2-(5-(2-methylpyrimidin-5-yl)-3-sulfamoyl-1H-indol-1-yl)acetyl)pyrrolidine-2-carboxamide | ND | | |
| 327 | 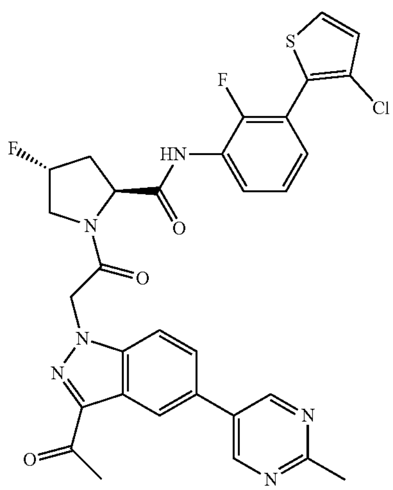 [SMILES: CC(=O)c1nn(CC(=O)N2C[C@H](F)C[C@H]2C(=O)Nc2cccc(-c3sccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-(3-chlorothiophen-2-yl)-2-fluorophenyl)-4-fluoropyrrolidine-2-carboxamide | *** | 2.11 (A) | 635 |
| 328 | 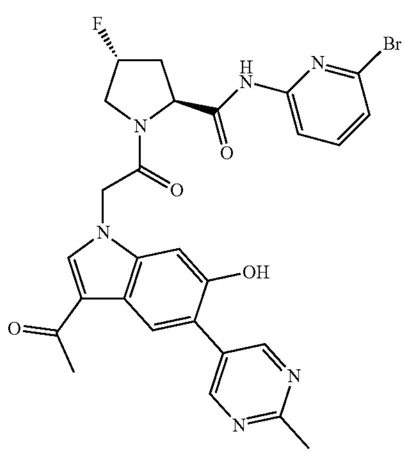 [SMILES: CC(=O)c1cn(CC(=O)N2C[C@H](F)C[C@H]2C(=O)Nc2cccc(Br)n2)c2cc(O)c(-c3cnc(C)nc3)cc12] | (2S,4R)-1-(2-(3-acetyl-6-hydroxy-5-(2-methylpyrimidin-5-yl)-1H-indol-1-yl)acetyl)-N-(6-bromopyridin-2-yl)-4-fluoropyrrolidine-2-carboxamide | *** | 1.35 (A) | 595 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 329 | 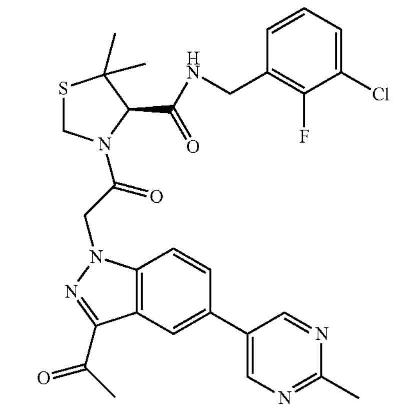 [SMILES: CC(=O)c1nn(CC(=O)N2CSC(C)(C)[C@H]2C(=O)NCc2cccc(Cl)c2F)c2ccc(-c3cnc(C)nc3)cc12] | (R)-3-(2-(3-acetyl-5-(2-methylpyrimidin-5-yl)-1H-indazol-1-yl)acetyl)-N-(3-chloro-2-fluorobenzyl)-5,5-dimethylthiazolidine-4-carboxamide | ** | 2.00 (A) | 596 |
| 330 | 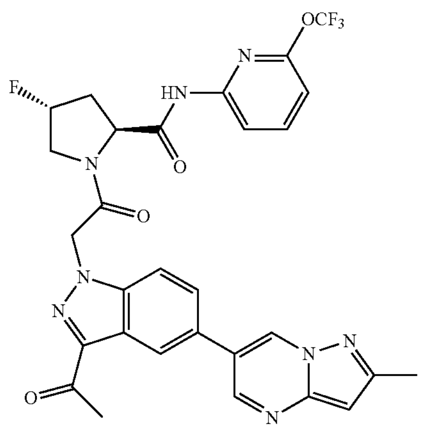 [SMILES: CC(=O)c1nn(CC(=O)N2C[C@H](F)C[C@H]2C(=O)Nc2cccc(OC(F)(F)F)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-4-fluoro-N-(6-(trifluoromethoxy)pyridin-2-yl)pyrrolidine-2-carboxamide | *** | 2.13 (A) | 625 |
| 331 | 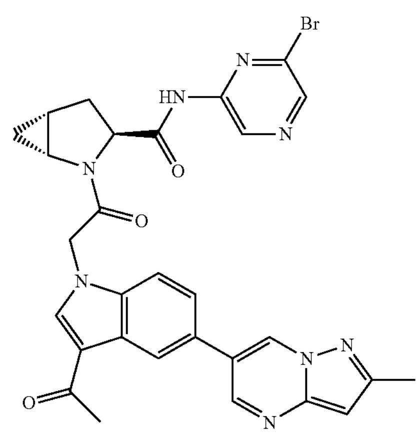 [SMILES: CC(=O)c1cn(CC(=O)N2[C@@H]3C[C@@H]3C[C@H]2C(=O)Nc2cncc(Br)n2)c2ccc(-c3cnc4cc(C)nn4c3)cc12] | (1R,3S,5R)-2-(2-(3-acetyl-5-(2-methylpyrazolo[1,5-a]pyrimidin-6-yl)-1H-indol-1-yl)acetyl)-N-(6-bromopyrazin-2-yl)-2-azabicyclo[3.1.0]hexane-3-carboxamide | *** | 1.76 (A) | 613 |

TABLE 2-continued

Additional Compounds of the Present Invention

| Cmp No. | Structure | Name | IC$_{50}$ | RT min (Method A or B) | MS (M + 1) |
|---|---|---|---|---|---|
| 332 | 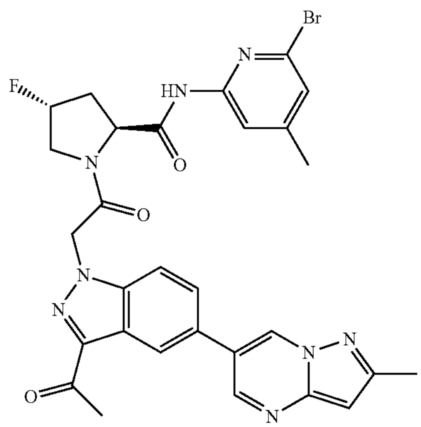 [SMILES: CC(=O)c1nn(CC(=O)N2C[C@H](F)C[C@H]2C(=O)Nc2cc(C)cc(Br)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-N-(6-bromo-4-methylpyridin-2-yl)-4-fluoropyrrolidine-2-carboxamide | *** | 2.07 (A) | 633 |

TABLE 3

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 333 | 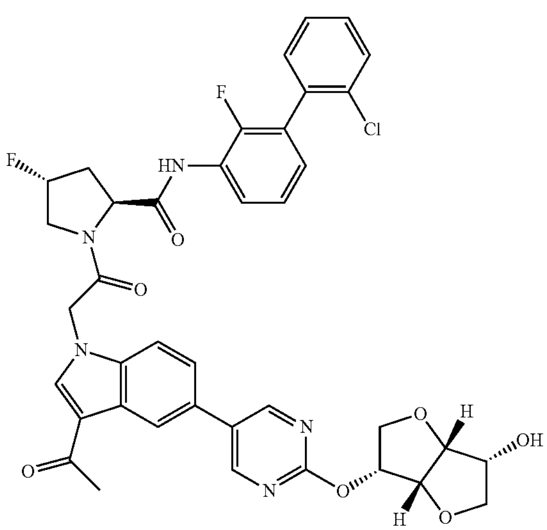 [SMILES: CC(=O)c1cn(CC(=O)N2C[C@H](F)C[C@H]2C(=O)Nc2cccc(-c3ccccc3Cl)c2F)c2ccc(-c3cnc(O[C@@H]4CO[C@H]5[C@@H]4OC[C@H]5O)nc3)cc12] | (2S,4R)-1-(2-(3-acetyl-5-(2-(((3R,3aR,6R,6aR)-6-hydroxyhexahydrofuro[3,2-b]furan-3-yl)oxy)pyrimidin-5-yl)-1H-indol-1-yl)acetyl)-N-(2'-chloro-2-fluoro-[1,1'-biphenyl]-3-yl)-4-fluoropyrrolidine-2-carboxamide | *** | 3.42 (B) | 758 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 334 | 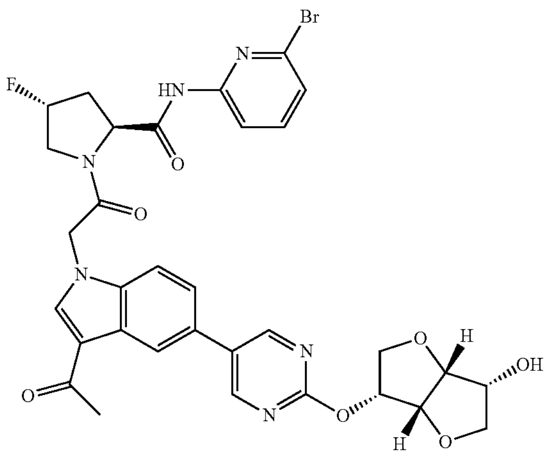 [SMILES: CC(=O)c1cn(CC(=O)N2C[C@H](F)C[C@H]2C(=O)Nc2cccc(Br)n2)c2ccc(-c3cnc(O[C@@H]4CO[C@H]5[C@@H]4OC[C@H]5O)nc3)cc12] | (2S,4R)-1-(2-(3-acetyl-5-(2-(((3R,3aR,6R,6aR)-6-hydroxyhexahydrofuro[3,2-b]furan-3-yl)oxy)pyrimidin-5-yl)-1H-indol-1-yl)acetyl)-N-(6-bromopyridin-2-yl)-4-fluoropyrrolidine-2-carboxamide | *** | 2.94 (B) | 709 |
| 335 | 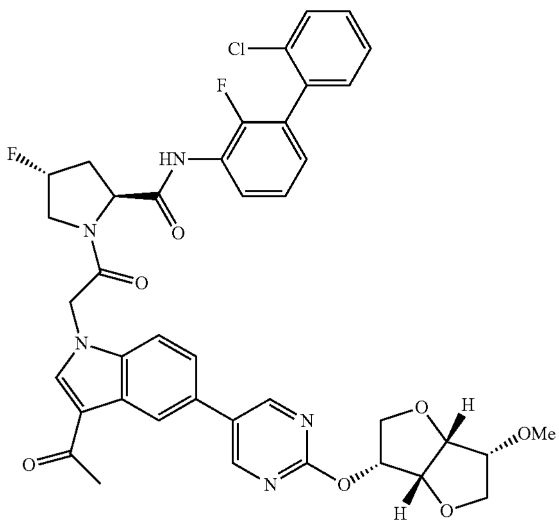 [SMILES: CO[C@@H]1CO[C@H]2[C@@H]1OC[C@H]2Oc1ncc(-c2ccc3c(c2)c(C(C)=O)cn3CC(=O)N2C[C@H](F)C[C@H]2C(=O)Nc2cccc(-c3ccccc3Cl)c2F)cn1] | (2S,4R)-1-(2-(3-acetyl-5-(2-(((3R,3aR,6R,6aR)-6-methoxyhexahydrofuro[3,2-b]furan-3-yl)oxy)pyrimidin-5-yl)-1H-indol-1-yl)acetyl)-N-(2'-chloro-2-fluoro-[1,1'-biphenyl]-3-yl)-4-fluoropyrrolidine-2-carboxamide | *** | 3.63 (B) | 772 |
| 337 | 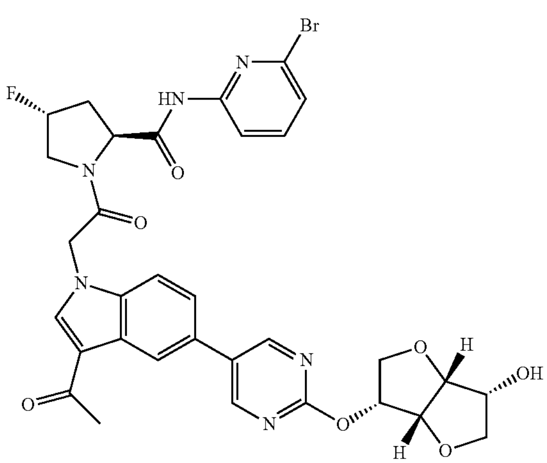 [SMILES: CC(=O)c1cn(CC(=O)N2C[C@H](F)C[C@H]2C(=O)Nc2cccc(Br)n2)c2ccc(-c3cnc(O[C@@H]4CO[C@H]5[C@@H]4OC[C@H]5O)nc3)cc12] | (2S,4R)-1-(2-(3-acetyl-5-(2-(((3R,3aR,6R,6aR)-6-methoxyhexahydrofuro[3,2-b]furan-3-yl)oxy)pyrimidin-5-yl)-1H-indol-1-yl)acetyl)-N-(6-bromopyridin-2-yl)-4-fluoropyrrolidine-2-carboxamide | *** | 3.14 (B) | 723 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 339 | 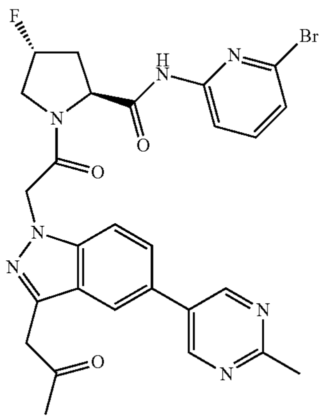 [SMILES: CC(=O)Cc1nn(CC(=O)N2C[C@H](F)C[C@H]2C(=O)Nc2cccc(Br)n2)c2ccc(-c3cnc(C)nc3)cc12] | (2S,4R)-N-(6-bromopyridin-2-yl)-4-fluoro-1-(2-(5-(2-methylpyrimidin-5-yl)-3-(2-oxopropyl)-1H-indazol-1-yl)acetyl)pyrrolidine-2-carboxamide | | 1.53 (A) | 594 |
| 340 | 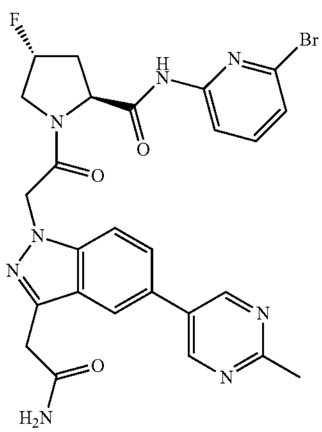 [SMILES: Cc1ncc(-c2ccc3c(c2)c(CC(N)=O)nn3CC(=O)N2C[C@H](F)C[C@H]2C(=O)Nc2cccc(Br)n2)cn1] | (2S,4R)-1-(2-(3-(2-amino-2-oxoethyl)-5-(2-methylpyrimidin-5-yl)-1H-indazol-1-yl)acetyl)-N-(6-bromopyridin-2-yl)-4-fluoropyrrolidine-2-carboxamide | ** | 1.25 (A) | 595 |
| 341 | 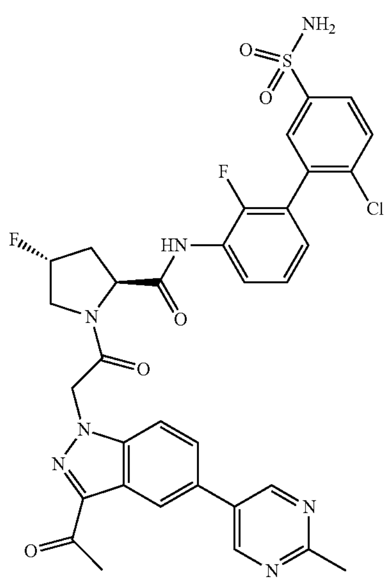 [SMILES: CC(=O)c1nn(CC(=O)N2C[C@H](F)C[C@H]2C(=O)Nc2cccc(-c3cc(S(N)(=O)=O)ccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2'-chloro-2-fluoro-5'-sulfamoyl-[1,1'-biphenyl]-3-yl)-4-fluoropyrrolidine-2-carboxamide | *** | 1.68 (A) | 708 |

| Comp No. | Structure | Name | IC$_5$ (Stars) | RT min (Method A,B,C or D) | MS (M + 1) |
|---|---|---|---|---|---|
| 342 | 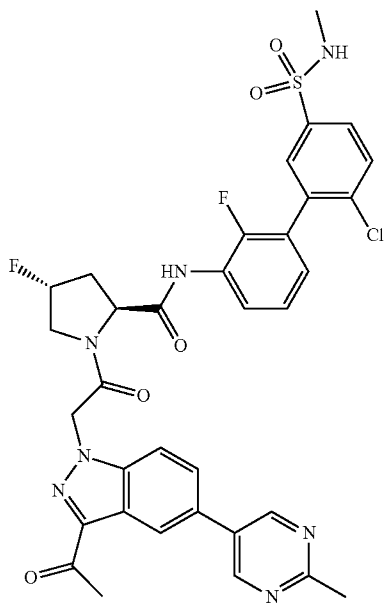 [SMILES: CNS(=O)(=O)c1ccc(Cl)c(-c2cccc(NC(=O)[C@@H]3C[C@@H](F)CN3C(=O)Cn3nc(C(C)=O)c4cc(-c5cnc(C)nc5)ccc43)c2F)c1] | (2S,4R)-1-(2-(3-acetyl-5-(2-methylpyrimidin-5-yl)-1H-indazol-1-yl)acetyl)-N-(2'-chloro-2-fluoro-5'-(N-methylsulfamoyl)-[1,1'-biphenyl]-3-yl)-4-fluoropyrrolidine-2-carboxamide | *** | 1.86 (A) | 722 |
| 343 | 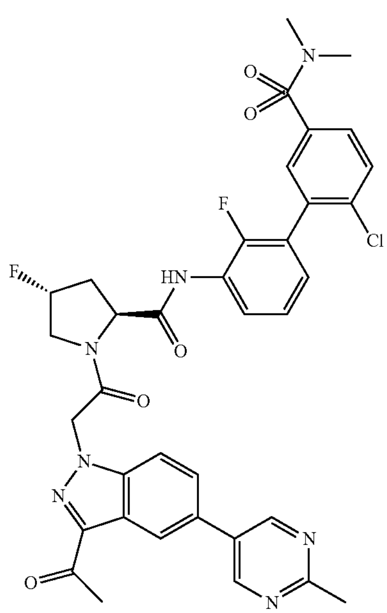 | (2S,4R)-1-(2-(3-acetyl-5-(2-methylpyrimidin-5-yl)-1H-indazol-1-yl)acetyl)-N-(2'-chloro-5'-(N,N-dimethylsulfamoyl)-2-fluoro-[1,1'-biphenyl]-3-yl)-4-fluoropyrrolidine-2-carboxamide | *** | 2.03 (A) | 736 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 344 | 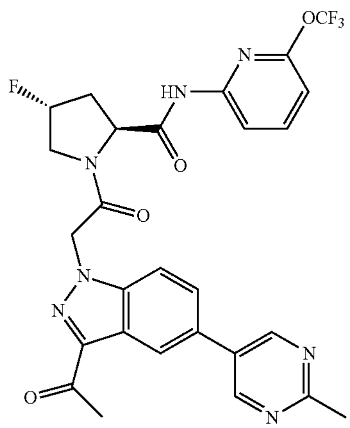 [SMILES: CC(=O)c1nn(CC(=O)N2C[C@H](F)C[C@H]2C(=O)Nc2cccc(OC(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-(trifluoromethoxy)pyridin-2-yl)pyrrolidine-2-carboxamide | *** | 1.88 (A) | 586 |
| 345 | 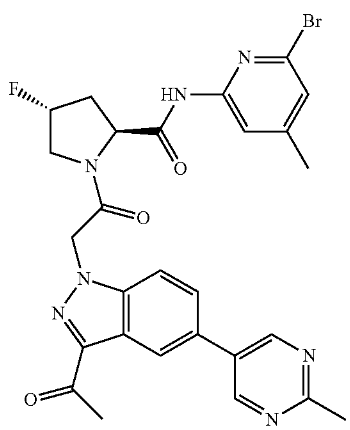 [SMILES: CC(=O)c1nn(CC(=O)N2C[C@H](F)C[C@H]2C(=O)Nc2cc(C)cc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-4-methylpyridin-2-yl)-4-fluoropyrrolidine-2-carboxamide | *** | 1.81 (A) | 594 |
| 346 | 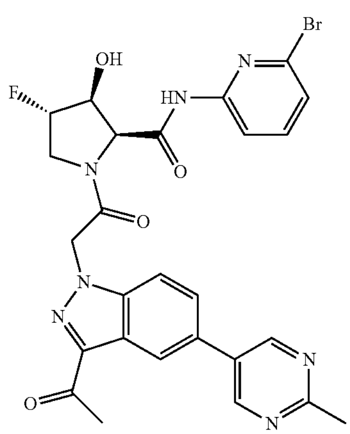 [SMILES: CC(=O)c1nn(CC(=O)N2C[C@H](F)[C@@H](O)[C@H]2C(=O)Nc2cccc(Br)n2)c2ccc(-c3cnc(C)nc3)cc12] | (2S,3S,4S)-1-(2-(3-acetyl-5-(2-methylpyrimidin-5-yl)-1H-indazol-1-yl)acetyl)-N-(6-bromopyridin-2-yl)-4-fluoro-3-hydroxypyrrolidine-2-carboxamide | *** | 3.39 (B) | 598 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 347 | 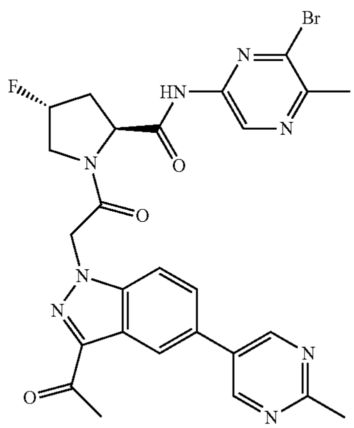 [SMILES: CC(=O)c1nn(CC(=O)N2C[C@H](F)C[C@H]2C(=O)Nc2cnc(C)c(Br)n2)c2ccc(-c3cnc(C)nc3)cc12] | (2S,4R)-1-(2-(3-acetyl-5-(2-methyl-3H-imidazo[4,5-b]pyridin-6-yl)-1H-indazol-1-yl)acetyl)-N-(6-bromopyridin-2-yl)-4-fluoropyrrolidine-2-carboxamide | *** | 1.35 (A) | 619 |
| 349 | 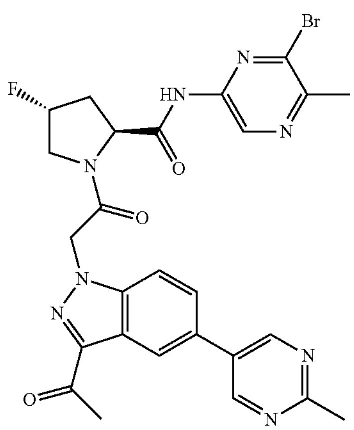 [SMILES: CC(=O)c1nn(CC(=O)N2C[C@H](F)C[C@H]2C(=O)Nc2cnc(C)c(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-5-methylpyrazin-2-yl)-4-fluoropyrrolidine-2-carboxamide | *** | 1.58 (A) | 595 |
| 350 | 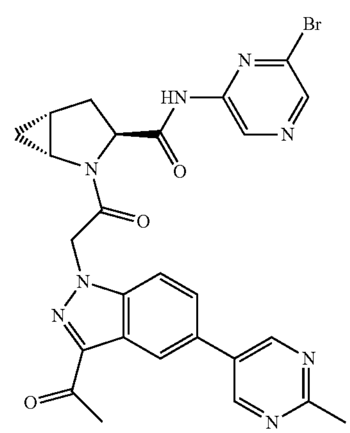 [SMILES: CC(=O)c1nn(CC(=O)N2[C@@H]3C[C@@H]3C[C@H]2C(=O)Nc2cncc(Br)n2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromopyrazin-2-yl)-2-azabicyclo[3.1.0]hexane-3-carboxamide | *** | 1.62 (A) | 575 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 351 | 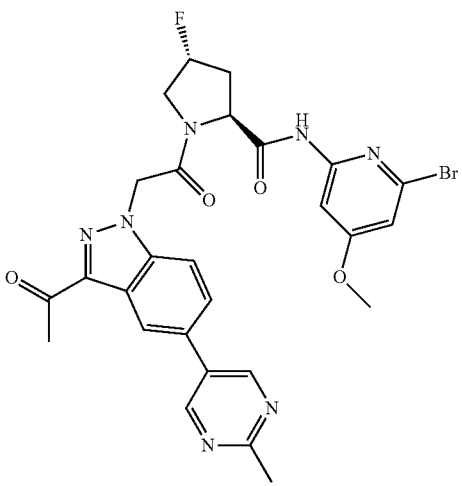 [SMILES: COc1cc(Br)nc(NC(=O)[C@@H]2C[C@@H](F)CN2C(=O)Cn2nc(C(C)=O)c3cc(-c4cnc(C)nc4)ccc32)c1] | (2S,4R)-1-(2-(3-acetyl-5-(2-methylpyrimidin-5-yl)-1H-indazol-1-yl)acetyl)-N-(6-bromo-4-methoxypyridin-2-yl)-4-fluoropyrrolidine-2-carboxamide | *** | 1.74 (A) | 610 |
| 352 | 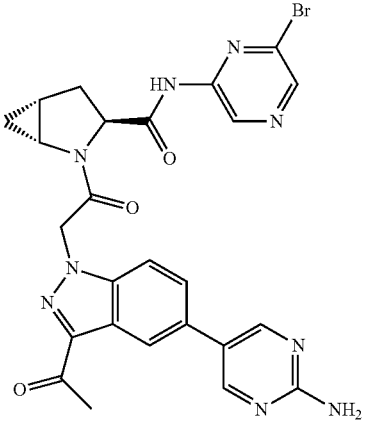 [SMILES: CC(=O)c1nn(CC(=O)N2[C@@H]3C[C@@H]3C[C@H]2C(=O)Nc2cncc(Br)n2)c2ccc(-c3cnc(N)nc3)cc12] | (1R,3S,5R)-2-(2-(3-acetyl-5-(2-aminopyrimidin-5-yl)-1H-indazol-1-yl)acetyl)-N-(6-bromopyrazin-2-yl)-2-azabicyclo[3.1.0]hexane-3-carboxamide | *** | 1.42 (A) | 576 |
| 353 | 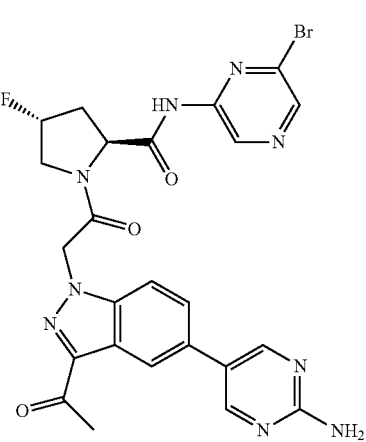 [SMILES: CC(=O)c1nn(CC(=O)N2C[C@H](F)C[C@H]2C(=O)Nc2cncc(Br)n2)c2ccc(-c3cnc(N)nc3)cc12] | (2S,4R)-1-(2-(3-acetyl-5-(2-aminopyrimidin-5-yl)-1H-indazol-1-yl)acetyl)-N-(6-bromopyrazin-2-yl)-4-fluoropyrrolidine-2-carboxamide | *** | 1.25 (A) | 582 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 354 | 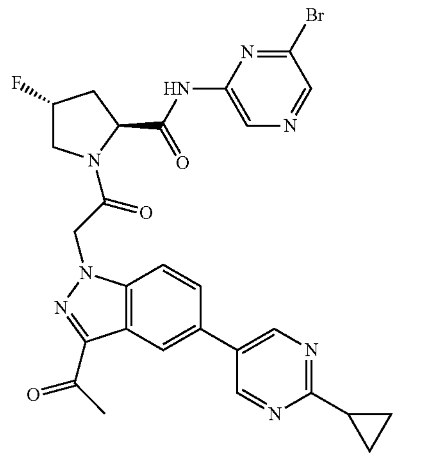 [SMILES: CC(=O)c1nn(CC(=O)N2C[C@H](F)C[C@H]2C(=O)Nc2cncc(Br)n2)c2ccc(-c3cnc(C4CC4)nc3)cc12] | (2S,4R)-1-(2-(3-acetyl-5-(2-cyclopropylpyrimidin-5-yl)-1H-indazol-1-yl)acetyl)-N-(6-bromopyrazin-2-yl)-4-fluoropyrrolidine-2-carboxamide | *** | 1.87 (A) | 607 |
| 355 | 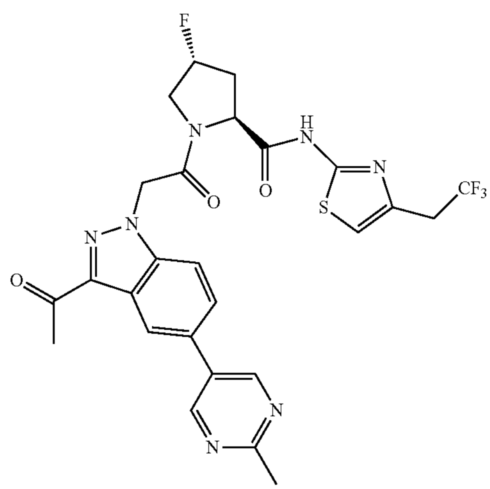 [SMILES: CC(=O)c1nn(CC(=O)N2C[C@H](F)C[C@H]2C(=O)Nc2nc(CC(F)(F)F)cs2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(4-(2,2,2-trifluoroethyl)thiazol-2-yl)pyrrolidine-2-carboxamide | *** | 1.66 (A) | 590 |
| 356 | 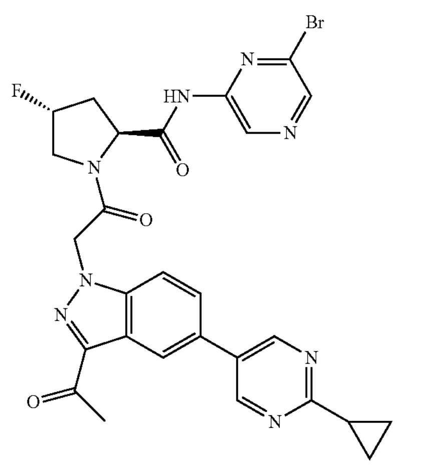 [SMILES: CC(=O)c1nn(CC(=O)N2C[C@H](F)C[C@H]2C(=O)Nc2cncc(Br)n2)c2ccc(-c3cnc(C4CC4)nc3)cc12] | (1R,3S,5R)-2-(2-(3-acetyl-5-(2-cyclopropylpyrimidin-5-yl)-1H-indazol-1-yl)acetyl)-N-(6-bromopyrazin-2-yl)-2-azabicyclo[3.1.0]hexane-3-carboxamide | *** | 2.01 (A) | 601 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 357 | 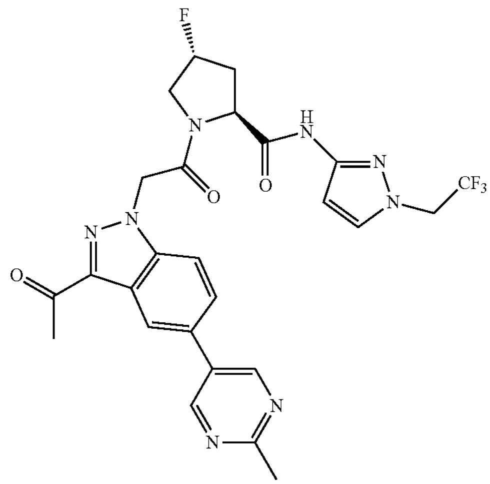 [SMILES: CC(=O)c1nn(CC(=O)N2C[C@H](F)C[C@H]2C(=O)Nc2ccn(CC(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(1-(2,2,2-trifluoroethyl)-1H-pyrazol-3-yl)pyrrolidine-2-carboxamide | *** | 1.39 (A) | 573 |
| 358 | 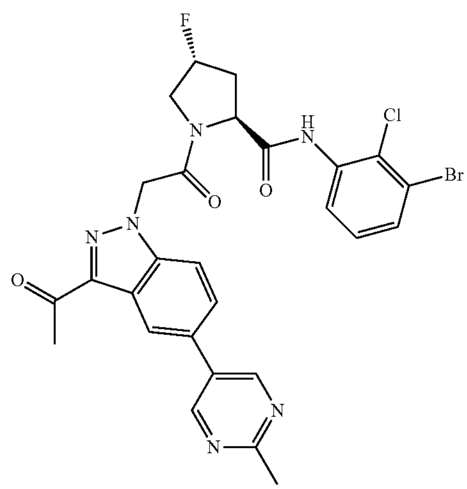 [SMILES: CC(=O)c1nn(CC(=O)N2C[C@H](F)C[C@H]2C(=O)Nc2cccc(Br)c2Cl)c2ccc(-c3cnc(C)nc3)cc12] | (2S,4R)-1-(2-(3-acetyl-5-(2-methylpyrimidin-5-yl)-1H-indazol-1-yl)acetyl)-N-(3-bromo-2-chlorophenyl)-4-fluoropyrrolidine-2-carboxamide | *** | | |
| 359 | 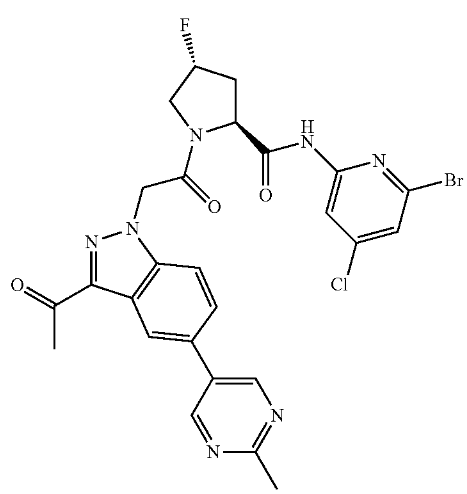 [SMILES: CC(=O)c1nn(CC(=O)N2C[C@H](F)C[C@H]2C(=O)Nc2cc(Cl)cc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-4-chloropyridin-2-yl)-4-fluoropyrrolidine-2-carboxamide | *** | 1.96 (A) | 616 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 360 | 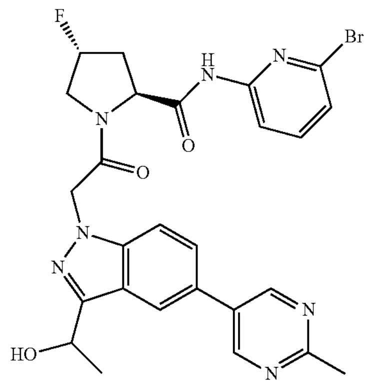 [SMILES: Cc1ncc(-c2ccc3c(c2)c(C(C)O)nn3CC(=O)N2C[C@H](F)C[C@H]2C(=O)Nc2cccc(Br)n2)cn1] | (2S,4R)-N-(6-bromopyridin-2-yl)-4-fluoro-1-(2-(3-(1-hydroxyethyl)-5-(2-methylpyrimidin-5-yl)-1H-indazol-1-yl)acetyl)pyrrolidine-2-carboxamide | ** | | |
| 361 | 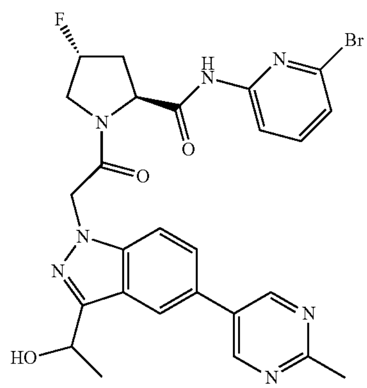 [SMILES: Cc1ncc(-c2ccc3c(c2)c(C(C)O)nn3CC(=O)N2C[C@H](F)C[C@H]2C(=O)Nc2cccc(Br)n2)cn1] | (2S,4R)-N-(6-bromopyridin-2-yl)-4-fluoro-1-(2-(3-(1-hydroxyethyl)-5-(2-methylpyrimidin-5-yl)-1H-indazol-1-yl)acetyl)pyrrolidine-2-carboxamide | ** | | |
| 362 | 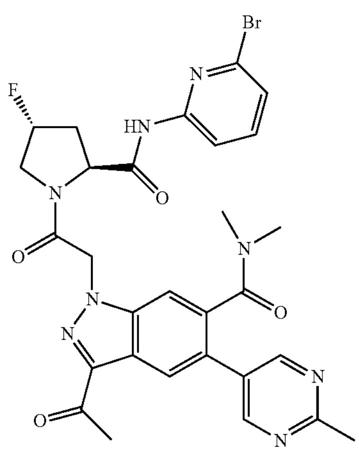 [SMILES: CC(=O)c1nn(CC(=O)N2C[C@H](F)C[C@H]2C(=O)Nc2cccc(Br)n2)c2cc(C(=O)N(C)C)c(-c3cnc(C)nc3)cc12] | 3-acetyl-1-(2-((2S,4R)-2-((6-bromopyridin-2-yl)carbamoyl)-4-fluoropyrrolidin-1-yl)-2-oxoethyl)-N,N-dimethyl-5-(2-methylpyrimidin-5-yl)-1H-indazole-6-carboxamide | *** | 1.48 (A) | 651 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 363 | 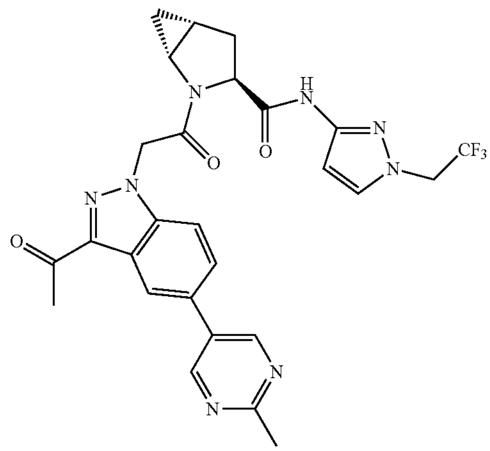 [SMILES: CC(=O)c1nn(CC(=O)N2[C@@H]3C[C@@H]3C[C@H]2C(=O)Nc2ccn(CC(F)(F)F)n2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(1-(2,2,2-trifluoroethyl)-1H-pyrazol-3-yl)-2-azabicyclo[3.1.0]hexane-3-carboxamide | *** | 1.52 (A) | 567 |
| 364 | 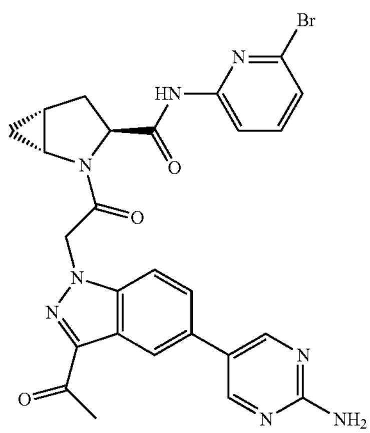 [SMILES: CC(=O)c1nn(CC(=O)N2[C@@H]3C[C@@H]3C[C@H]2C(=O)Nc2cccc(Br)n2)c2ccc(-c3cnc(N)nc3)cc12] | (1R,3S,5R)-2-(2-(3-acetyl-5-(2-aminopyrimidin-5-yl)-1H-indazol-1-yl)acetyl)-N-(6-bromopyridin-2-yl)-2-azabicyclo[3.1.0]hexane-3-carboxamide | *** | 1.61 (A) | 575 |
| 365 | 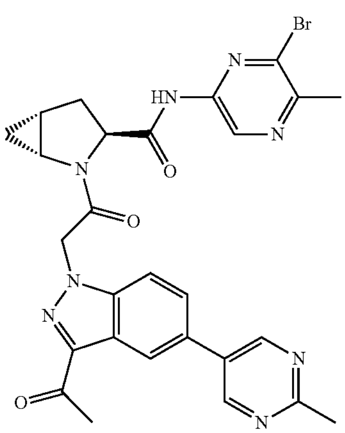 [SMILES: CC(=O)c1nn(CC(=O)N2[C@@H]3C[C@@H]3C[C@H]2C(=O)Nc2cnc(C)c(Br)n2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-5-methylpyrazin-2-yl)-2-azabicyclo[3.1.0]hexane-3-carboxamide | *** | 1.73 (A) | 589 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 366 | 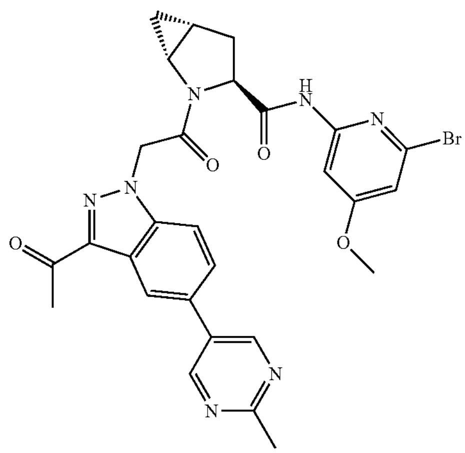 [SMILES: COc1cc(Br)nc(NC(=O)[C@@H]2C[C@H]3C[C@H]3N2C(=O)Cn2nc(C(C)=O)c3cc(-c4cnc(C)nc4)ccc32)c1] | (1R,3S,5R)-2-(2-(3-acetyl-5-(2-methylpyrimidin-5-yl)-1H-indazol-1-yl)acetyl)-N-(6-bromo-4-methoxypyridin-azabicyclo[3.1.0]hexane-3-carboxamide | *** | 1.89 (A) | 604 |
| 367 | 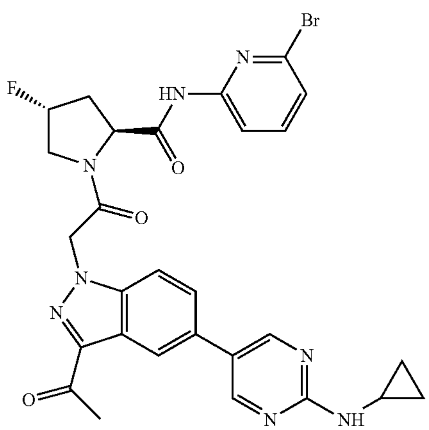 [SMILES: CC(=O)c1nn(CC(=O)N2C[C@H](F)C[C@H]2C(=O)Nc2cccc(Br)n2)c2ccc(-c3cnc(NC4CC4)nc3)cc12] | (2S,4R)-1-(2-(3-acetyl-5-(2-(cyclopropylamino)pyrimidin-5-yl)-1H-indazol-1-yl)acetyl)-N-(6-bromopyridin-2-yl)-4-fluoropyrrolidine-2-carboxamide | *** | 1.77 (A) | 621 |
| 368 | 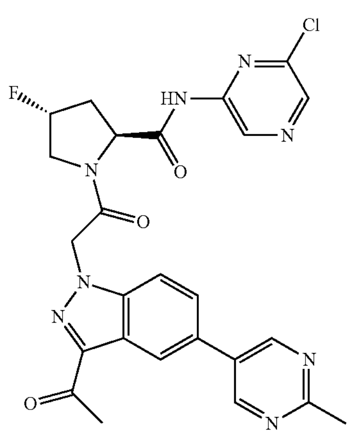 | (2S,4R)-1-(2-(3-acetyl-5-(2-methylpyrimidin-5-yl)-1H-indazol-1-yl)acetyl)-N-(6-chloropyrazin-2-yl)-4-fluoropyrrolidine-2-carboxamide | *** | 1.41 (A) | 537 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 369 | 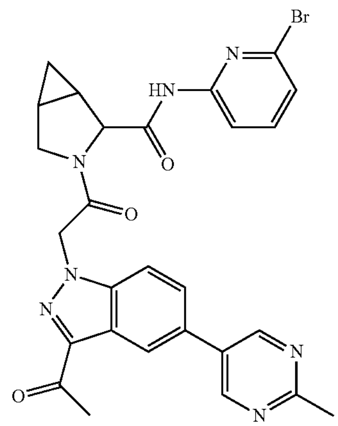 [SMILES: CC(=O)c1nn(CC(=O)N2CC3CC3C2C(=O)Nc2cccc(Br)n2)c2ccc(-c3cnc(C)nc3)cc12] | 3-(2-(3-acetyl-5-(2-methylpyrimidin-5-yl)-1H-indazol-1-yl)acetyl)-N-(6-bromopyridin-2-yl)-3-azabicyclo[3.1.0]hexane-2-carboxamide | *** | 2.85 (B) | 574 |
| 370 | 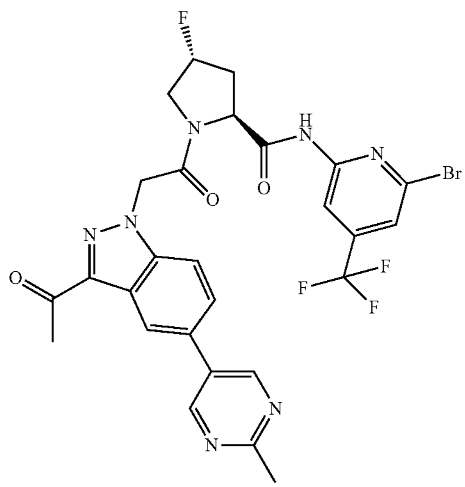 [SMILES: CC(=O)c1nn(CC(=O)N2C[C@H](F)C[C@H]2C(=O)Nc2cc(C(F)(F)F)cc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-4-(trifluoromethyl)pyridin-2-yl)-4-fluoropyrrolidine-2-carboxamide | *** | 8.18 (A) | 648 |
| 371 | 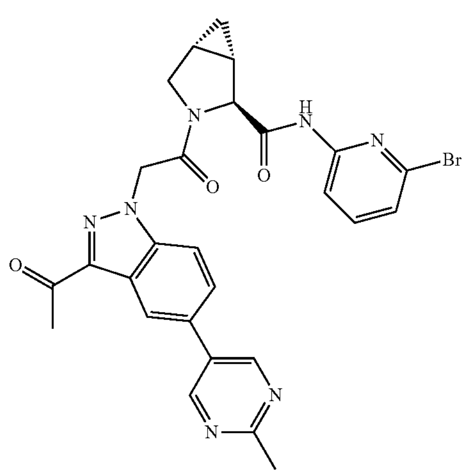 [SMILES: CC(=O)c1nn(CC(=O)N2C[C@@H]3C[C@@H]3[C@H]2C(=O)Nc2cccc(Br)n2)c2ccc(-c3cnc(C)nc3)cc12] | (1S,2S,5R)-3-(2-(3-acetyl-5-(2-methylpyrimidin-5-yl)-1H-indazol-1-yl)acetyl)-N-(6-bromopyridin-2-yl)-3-azabicyclo[3.1.0]hexane-2-carboxamide | *** | 1.79 (A) | 574 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 372 | 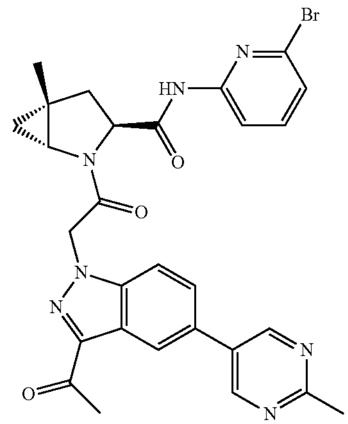 [SMILES: CC(=O)c1nn(CC(=O)N2[C@H](C(=O)Nc3cccc(Br)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide | *** | 3.48 (B) | 588 |
| 373 | 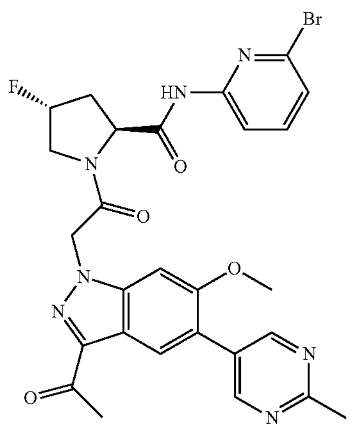 [SMILES: COc1cc2c(cc1-c1cnc(C)nc1)c(C(C)=O)nn2CC(=O)N1C[C@H](F)C[C@H]1C(=O)Nc1cccc(Br)n1] | (2S,4R)-1-(2-(3-acetyl-6-methoxy-5-(2-methylpyrimidin-5-yl)-1H-indazol-1-yl)acetyl)-N-(6-bromopyridin-2-yl)-4-fluoropyrrolidine-2-carboxamide | *** | 1.72 (A) | 612 |
| 374 | 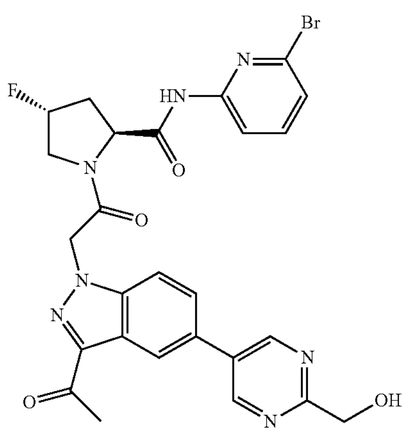 [SMILES: CC(=O)c1nn(CC(=O)N2C[C@H](F)C[C@H]2C(=O)Nc2cccc(Br)n2)c2ccc(-c3cnc(CO)nc3)cc12] | (2S,4R)-1-(2-(3-acetyl-5-(2-(hydroxymethyl)pyrimidin-5-yl)-1H-indazol-1-yl)acetyl)-N-(6-bromopyridin-2-yl)-4-fluoropyrrolidine-2-carboxamide | *** | 1.43 (A) | 596 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 375 | 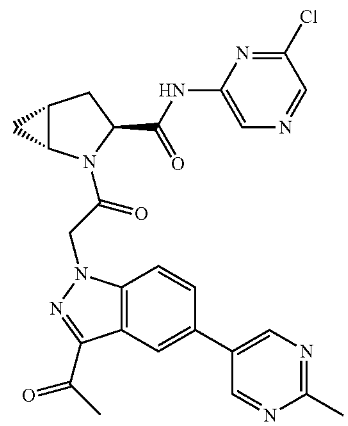 | (1R,3S,5R)-2-(2-(3-acetyl-5-(2-methylpyrimidin-5-yl)-1H-indazol-1-yl)acetyl)-N-(6-chloropyrazin-2-yl)-2-azabicyclo[3.1.0]hexane-3-carboxamide | *** | 1.56 (A) | 531 |
| 376 | 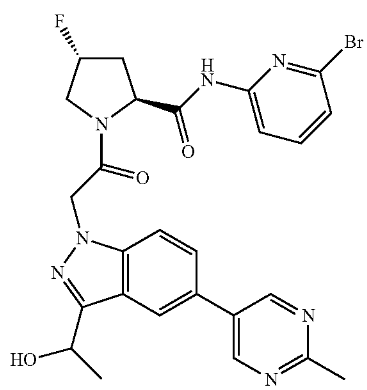 [SMILES: Cc1ncc(-c2ccc3c(c2)c(C(C)O)nn3CC(=O)N2C[C@H](F)C[C@H]2C(=O)Nc2cccc(Br)n2)cn1] | (2S,4R)-N-(6-bromopyridin-2-yl)-4-fluoro-1-(2-(3-(1-hydroxyethyl)-5-(2-methylpyrimidin-5-yl)-1H-indazol-1-yl)acetyl)pyrrolidine-2-carboxamide | ** | 1.39 (A) | 582 |
| 377 | 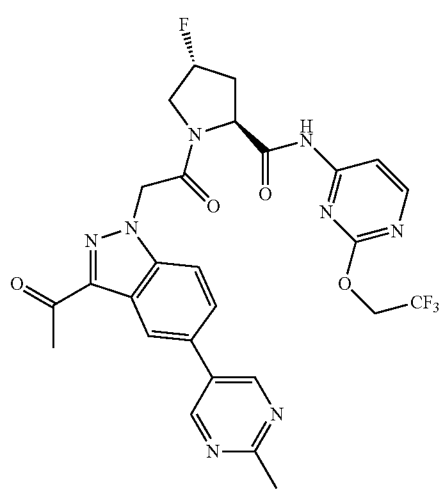 [SMILES: CC(=O)c1nn(CC(=O)N2C[C@H](F)C[C@H]2C(=O)Nc2ccnc(OCC(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2-(2,2,2-trifluoroethoxy)pyrimidin-4-yl)pyrrolidine-2-carboxamide | *** | 1.67 (A) | 601 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 378 | 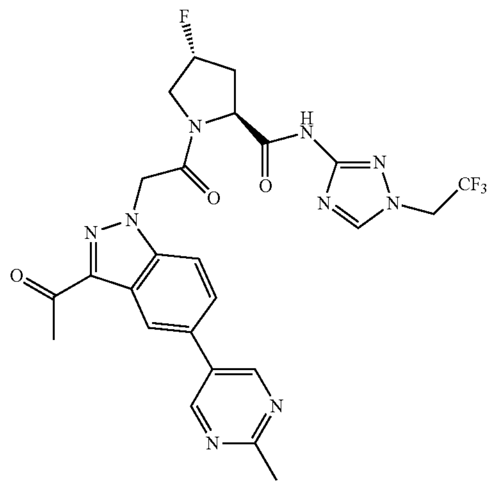 [SMILES: CC(=O)c1nn(CC(=O)N2C[C@H](F)C[C@H]2C(=O)Nc2ncn(CC(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(1-(2,2,2-trifluoroethyl)-1H-1,2,4-triazol-3-yl)pyrrolidine-2-carboxamide | *** | 1.14 (A) | 574 |
| 379 | 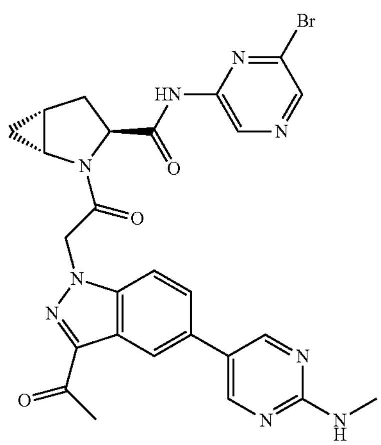 [SMILES: CNc1ncc(-c2ccc3c(c2)c(C(C)=O)nn3CC(=O)N2[C@@H]3C[C@@H]3C[C@H]2C(=O)Nc2cncc(Br)n2)cn1] | (1R,3S,5R)-2-(2-(3-acetyl-5-(2-(methylamino)pyrimidin-5-yl)-1H-indazol-1-yl)acetyl)-N-(6-bromopyrazin-2-yl)-2-azabicyclo[3.1.0]hexane-3-carboxamide | *** | 1.61 (A) | 590 |
| 380 | 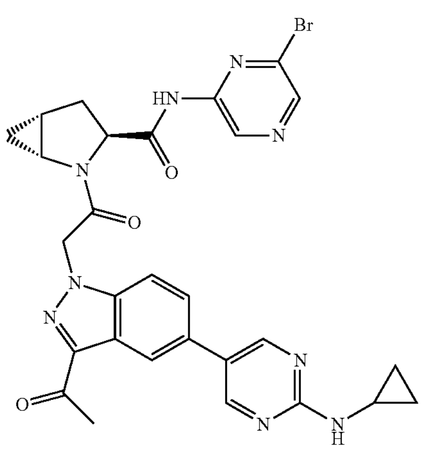 [SMILES: CC(=O)c1nn(CC(=O)N2[C@@H]3C[C@@H]3C[C@H]2C(=O)Nc2cncc(Br)n2)c2ccc(-c3cnc(NC4CC4)nc3)cc12] | (1R,3S,5R)-2-(2-(3-acetyl-5-(2-(cyclopropylamino)pyrimidin-5-yl)-1H-indazol-1-yl)acetyl)-N-(6-bromopyrazin-2-yl)-2-azabicyclo[3.1.0]hexane-3-carboxamide | *** | 1.75 (A) | 616 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 381 | 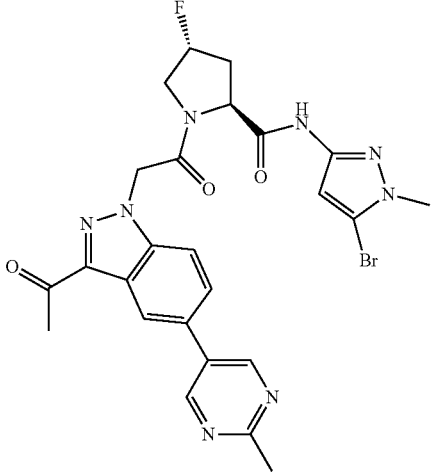 [SMILES: CC(=O)c1nn(CC(=O)N2C[C@H](F)C[C@H]2C(=O)Nc2cc(Br)n(C)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(5-bromo-1-methyl-1H-pyrazol-3-yl)-4-fluoropyrrolidine-2-carboxamide | *** | 1.40 (A) | 583 |
| 382 | 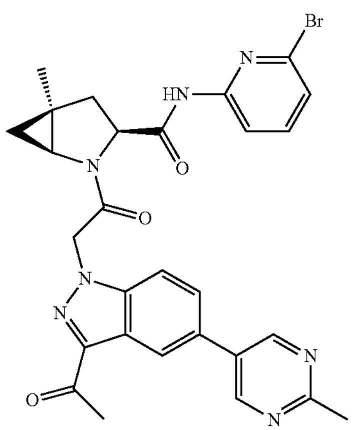 [SMILES: CC(=O)c1nn(CC(=O)N2[C@H]3C[C@@]3(C)C[C@H]2C(=O)Nc2cccc(Br)n2)c2ccc(-c3cnc(C)nc3)cc12] | (1S,3S,5S)-2-(2-(3-acetyl-5-(2-methylpyrimidin-5-yl)-1H-indazol-1-yl)acetyl)-N-(6-bromopyridin-2-yl)-5-methyl-2-azabicyclo[3.1.0]hexane-3-carboxamide | *** | 3.51 (B) | 588 |
| 383 | 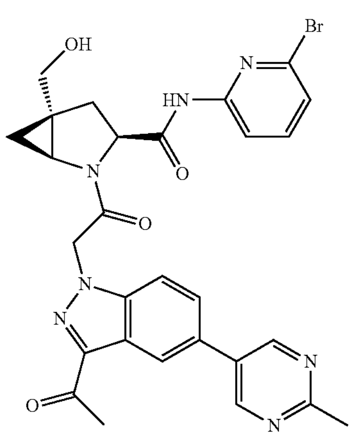 [SMILES: CC(=O)c1nn(CC(=O)N2[C@H]3C[C@@]3(CO)C[C@H]2C(=O)Nc2cccc(Br)n2)c2ccc(-c3cnc(C)nc3)cc12] | (1S,3S,5R)-2-(2-(3-acetyl-5-(2-methylpyrimidin-5-yl)-1H-indazol-1-yl)acetyl)-N-(6-bromopyridin-2-yl)-5-(hydroxymethyl)-2-azabicyclo[3.1.0]hexane-3-carboxamide | *** | 3.39 (B) | 604 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 384 | 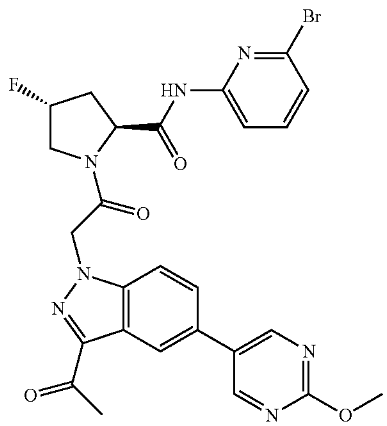 [SMILES: COc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(3-acetyl-5-(2-methoxypyrimidin-5-yl)-1H-indazol-1-yl)acetyl)-N-(6-bromopyridin-2-yl)-4-fluoropyrrolidine-2-carboxamide | *** | 1.84 (A) | 596 |
| 385 | 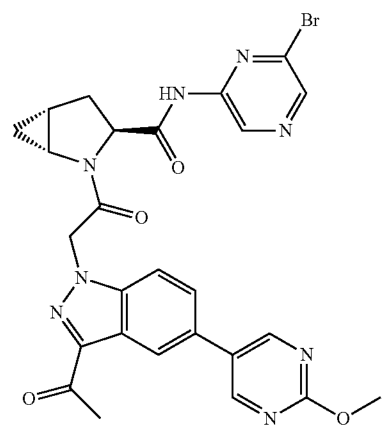 [SMILES: COc1ncc(-c2ccc3c(c2)c(C(C)=O)nn3CC(=O)N2[C@@H]3C[C@@H]3C[C@H]2C(=O)Nc2cncc(Br)n2)cn1] | (1R,3S,5R)-2-(2-(3-acetyl-5-(2-methoxypyrimidin-5-yl)-1H-indazol-1-yl)acetyl)-N-(6-bromopyrazin-2-yl)-2-azabicyclo[3.1.0]hexane-3-carboxamide | *** | 1.80 (A) | 591 |
| 386 | 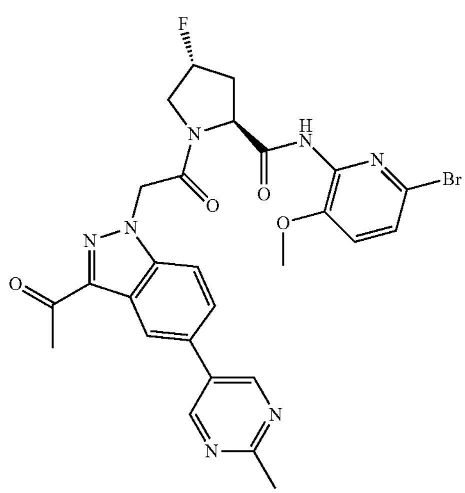 [SMILES: COc1ccc(Br)nc1NC(=O)[C@@H]1C[C@@H](F)CN1C(=O)Cn1nc(C(C)=O)c2cc(-c3cnc(C)nc3)ccc21] | (2S,4R)-1-(2-(3-acetyl-5-(2-methylpyrimidin-5-yl)-1H-indazol-1-yl)acetyl)-N-(6-bromo-3-methoxypyridin-2-yl)-4-fluoropyrrolidine-2-carboxamide | *** | 1.48 (A) | 611 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 387 | 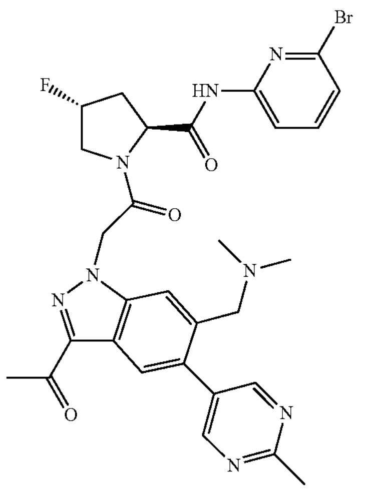 [SMILES: CC(=O)c1nn(CC(=O)N2C[C@H](F)C[C@H]2C(=O)Nc2cccc(Br)n2)c2cc(CN(C)C)c(-c3cnc(C)nc3)cc12] | (2S,4R)-1-(2-(3-acetyl-6-((dimethylamino)methyl)-5-(2-methylpyrimidin-5-yl)-1H-indazol-1-yl)acetyl)-N-(6-bromopyridin-2-yl)-4-fluoropyrrolidine-2-carboxamide | *** | 1.24 (A) | 639 |
| 388 | 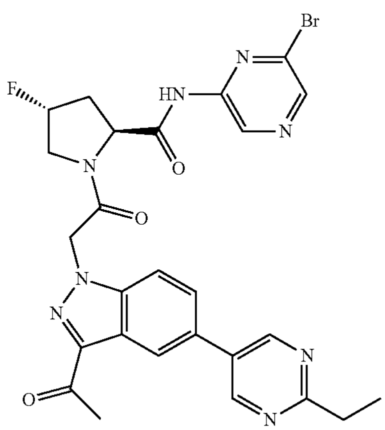 [SMILES: CCc1ncc(-c2ccc3c(c2)c(C(C)=O)nn3CC(=O)N2C[C@H](F)C[C@H]2C(=O)Nc2cncc(Br)n2)cn1] | (2S,4R)-1-(2-(3-acetyl-5-(2-ethylpyrimidin-5-yl)-1H-indazol-1-yl)acetyl)-N-(6-bromopyrazin-2-yl)-4-fluoropyrrolidine-2-carboxamide | *** | 1.70 (A) | 595 |
| 389 | 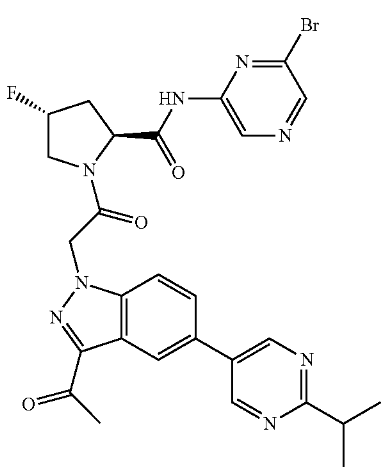 [SMILES: CC(=O)c1nn(CC(=O)N2C[C@H](F)C[C@H]2C(=O)Nc2cncc(Br)n2)c2ccc(-c3cnc(C(C)C)nc3)cc12] | (2S,4R)-1-(2-(3-acetyl-5-(2-isopropylpyrimidin-5-yl)-1H-indazol-1-yl)acetyl)-N-(6-bromopyrazin-2-yl)-4-fluoropyrrolidine-2-carboxamide | *** | 1.96 (A) | 609 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 390 | 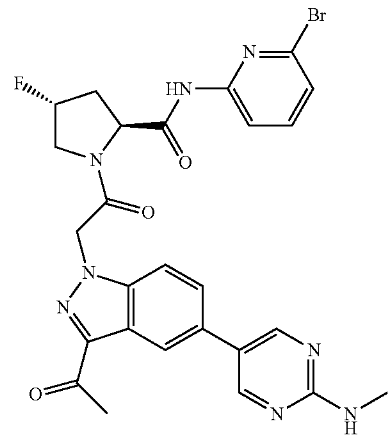 [SMILES: CNc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(3-acetyl-5-(2-(methylamino)pyrimidin-5-yl)-1H-indazol-1-yl)acetyl)-N-(6-bromopyridin-2-yl)-4-fluoropyrrolidine-2-carboxamide | *** | 1.64 (A) | 595 |
| 391 | 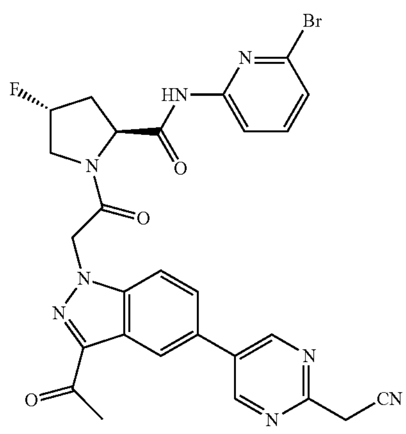 [SMILES: CC(=O)c1nn(CC(=O)N2C[C@H](F)C[C@H]2C(=O)Nc2cccc(Br)n2)c2ccc(-c3cnc(CC#N)nc3)cc12] | (2S,4R)-1-(2-(3-acetyl-5-(2-(cyanomethyl)pyrimidin-5-yl)-1H-indazol-1-yl)acetyl)-N-(6-bromopyridin-2-yl)-4-fluoropyrrolidine-2-carboxamide | *** | 1.73 (A) | 605 |
| 392 | 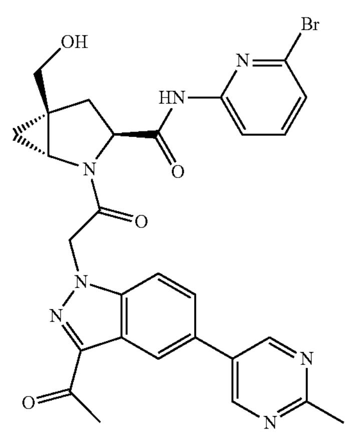 [SMILES: CC(=O)c1nn(CC(=O)N2[C@H](C(=O)Nc3cccc(Br)n3)C[C@@]3(CO)C[C@@H]23)c2ccc(-c3cnc(C)nc3)cc12] | (1R,3S,5S)-2-(2-(3-acetyl-5-(2-methylpyrimidin-5-yl)-1H-indazol-1-yl)acetyl)-N-(6-bromopyridin-2-yl)-5-(hydroxymethyl)-2-azabicyclo[3.1.0]hexane-3-carboxamide | *** | 2.68 (B) | 604 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 393 | 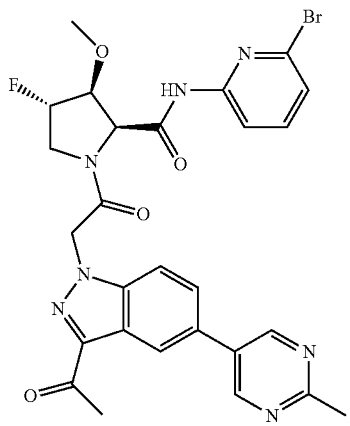 [SMILES: CO[C@H]1[C@@H](C(=O)Nc2cccc(Br)n2)N(C(=O)Cn2nc(C(C)=O)c3cc(-c4cnc(C)nc4)ccc32)C[C@@H]1F] | (2S,3S,4S)-1-(2-(3-acetyl-5-(2-methylpyrimidin-5-yl)-1H-indazol-1-yl)acetyl)-N-(6-bromopyridin-2-yl)-4-fluoro-3-methoxypyrrolidine-2-carboxamide | *** | 3.27 (B) | 610 |
| 394 | 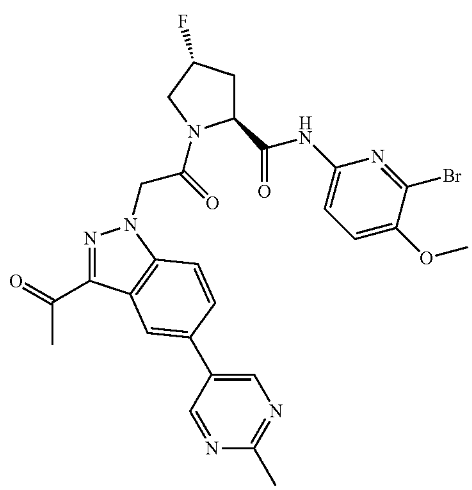 [SMILES: COc1ccc(NC(=O)[C@@H]2C[C@@H](F)CN2C(=O)Cn2nc(C(C)=O)c3cc(-c4cnc(C)nc4)ccc32)nc1Br] | (2S,4R)-1-(2-(3-acetyl-5-(2-methylpyrimidin-5-yl)-1H-indazol-1-yl)acetyl)-N-(6-bromo-5-methoxypyridin-2-yl)-4-fluoropyrrolidine-2-carboxamide | *** | 1.62 (A) | 612 |
| 395 | 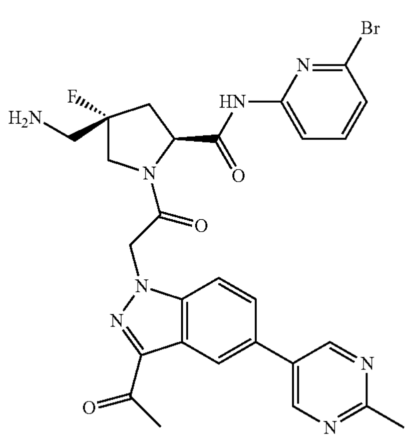 [SMILES: CC(=O)c1nn(CC(=O)N2C[C@@](F)(CN)C[C@H]2C(=O)Nc2cccc(Br)n2)c2ccc(-c3cnc(C)nc3)cc12] | (2S,4S)-1-(2-(3-acetyl-5-(2-methylpyrimidin-5-yl)-1H-indazol-1-yl)acetyl)-4-(aminomethyl)-N-(6-bromopyridin-2-yl)-4-fluoropyrrolidine-2-carboxamide | *** | 2.56 (B) | 609 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 396 | 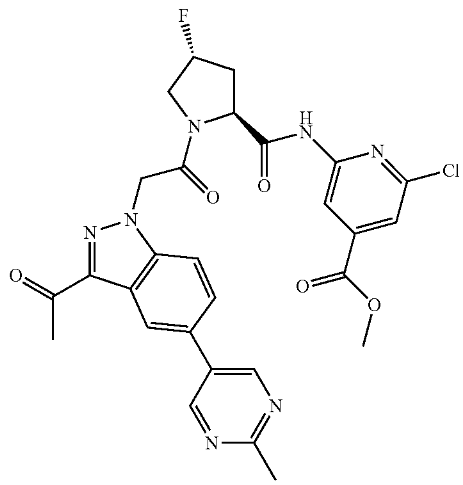 [SMILES: COC(=O)c1cc(Cl)nc(NC(=O)[C@@H]2C[C@@H](F)CN2C(=O)Cn2nc(C(C)=O)c3cc(-c4cnc(C)nc4)ccc32)c1] | methyl 2-((2S,4R)-1-(2-(3-acetyl-5-(2-methylpyrimidin-5-yl)-1H-indazol-1-yl)acetyl)-4-fluoropyrrolidine-2-carboxamido)-6-chloroisonicotinate | *** | 1.77 (A) | 594 |
| 397 | 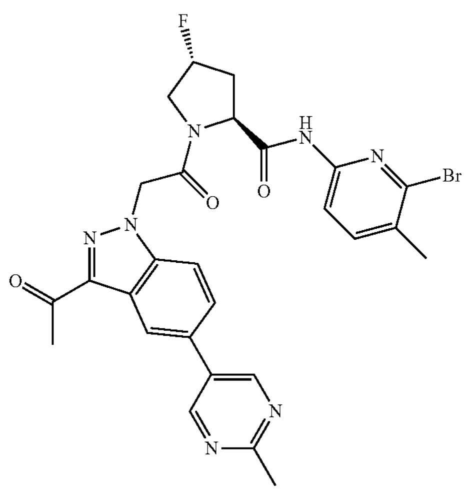 [SMILES: CC(=O)c1nn(CC(=O)N2C[C@H](F)C[C@H]2C(=O)Nc2ccc(C)c(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-5-fluoropyridin-2-yl)-4-fluoropyrrolidine-2-carboxamide | *** | 1.73 (A) | 598 |
| 398 | 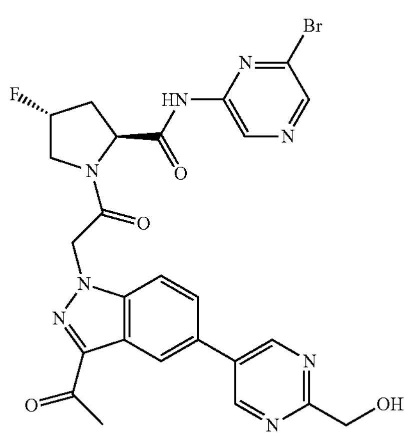 [SMILES: CC(=O)c1nn(CC(=O)N2C[C@H](F)C[C@H]2C(=O)Nc2cncc(Br)n2)c2ccc(-c3cnc(CO)nc3)cc12] | (2S,4R)-1-(2-(3-acetyl-5-(2-(hydroxymethyl)pyrimidin-5-yl)-1H-indazol-1-yl)acetyl)-N-(6-bromopyrazin-2-yl)-4-fluoropyrrolidine-2-carboxamide | *** | 1.24 (A) | 597 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 399 | 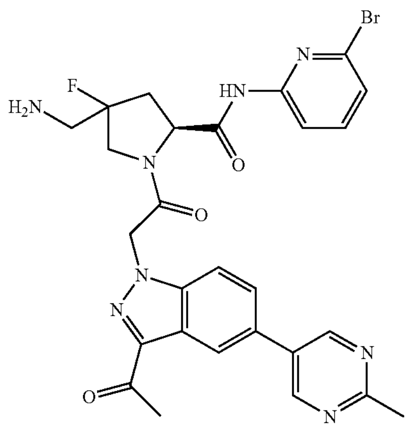 [SMILES: CC(=O)c1nn(CC(=O)N2CC(F)(CN)C[C@H]2C(=O)Nc2cccc(Br)n2)c2ccc(-c3cnc(C)nc3)cc12] | (2S)-1-(2-(3-acetyl-5-(2-methylpyrimidin-5-yl)-1H-indazol-1-yl)acetyl)-4-(aminomethyl)-N-(6-bromopyridin-2-yl)-4-fluoropyrrolidine-2-carboxamide | *** | 2.38 (B) | 609 |
| 400 | 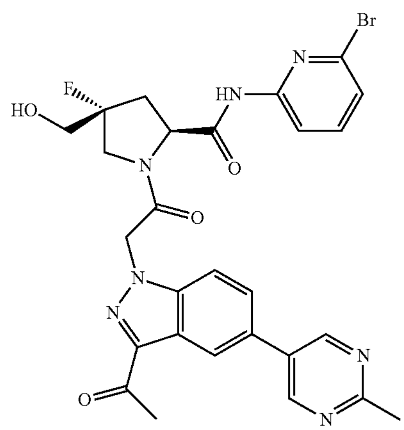 [SMILES: CC(=O)c1nn(CC(=O)N2C[C@@](F)(CO)C[C@H]2C(=O)Nc2cccc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromopyridin-2-yl)-4-fluoro-4-(hydroxymethyl)pyrrolidine-2-carboxamide | *** | 2.46 (B) | 608 |
| 401 | 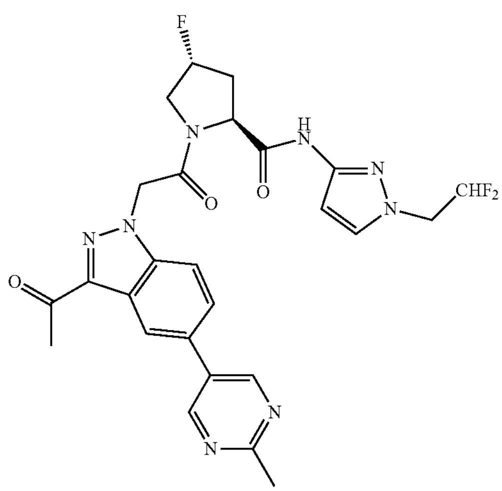 [SMILES: CC(=O)c1nn(CC(=O)N2C[C@H](F)C[C@H]2C(=O)Nc2ccn(CC(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(1-(2,2-difluoroethyl)-1H-pyrazol-3-yl)-4-fluoropyrrolidine-2-carboxamide | *** | 1.27 (A) | 555 |

TABLE 3-continued

Additional Non-limiting Examples of Compounds of Formula I

| Comp No | Structure | Name | IC₅ (Stars) | RT min (Method A,B,C or D) | MS (M + 1) |
|---|---|---|---|---|---|
| 402 | 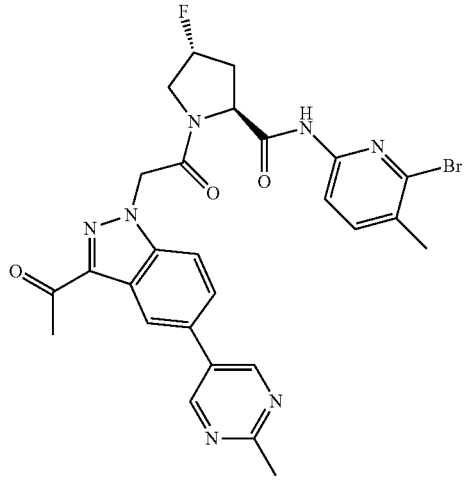 [SMILES: CC(=O)c1nn(CC(=O)N2C[C@H](F)C[C@H]2C(=O)Nc2ccc(C)c(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-5-methylpyridin-2-yl)-4-fluoropyrrolidine-2-carboxamide | *** | 1.81 (A) | 594 |
| 403 | 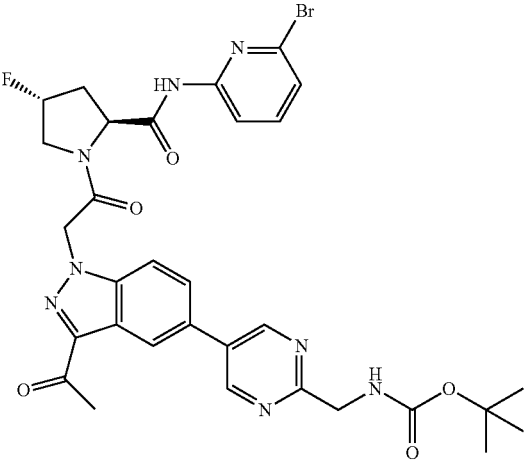 [SMILES: CC(=O)c1nn(CC(=O)N2C[C@H](F)C[C@H]2C(=O)Nc2cccc(Br)n2)c2ccc(-c3cnc(CNC(=O)OC(C)(C)C)nc3)cc12] | tert-butyl ((5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)methyl)carbamate | *** | 2.09 (A) | 695 |
| 404 | 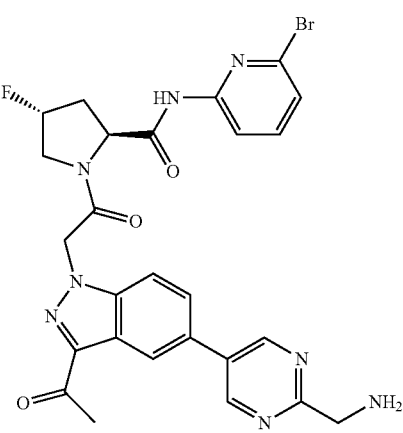 [SMILES: CC(=O)c1nn(CC(=O)N2C[C@H](F)C[C@H]2C(=O)Nc2cccc(Br)n2)c2ccc(-c3cnc(CN)nc3)cc12] | (2S,4R)-1-(2-(3-acetyl-5-(2-(aminomethyl)pyrimidin-5-yl)-1H-indazol-1-yl)acetyl)-N-(6-bromopyridin-2-yl)-4-fluoropyrrolidine-2-carboxamide | *** | 1.16 (A) | 595 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 405 | 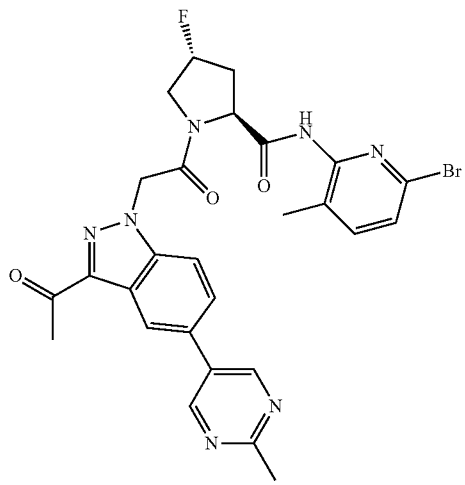 [SMILES: CC(=O)c1nn(CC(=O)N2C[C@H](F)C[C@H]2C(=O)Nc2nc(Br)ccc2C)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-methylpyridin-2-yl)-4-fluoropyrrolidine-2-carboxamide | *** | 1.49 (A) | 594 |
| 406 | 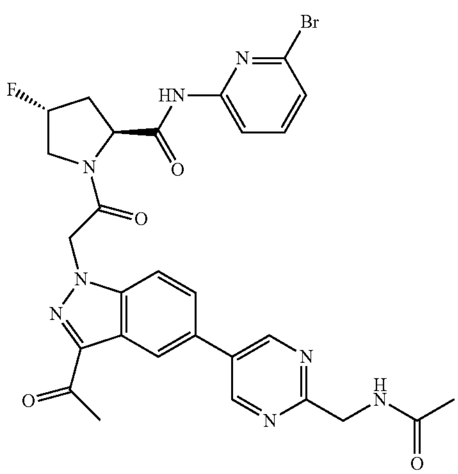 [SMILES: CC(=O)NCc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(5-(2-(acetamidomethyl)pyrimidin-5-yl)-3-acetyl-1H-indazol-1-yl)acetyl)-N-(6-bromopyridin-2-yl)-4-fluoropyrrolidine-2-carboxamide | *** | 1.41 (A) | 637 |
| 407 | 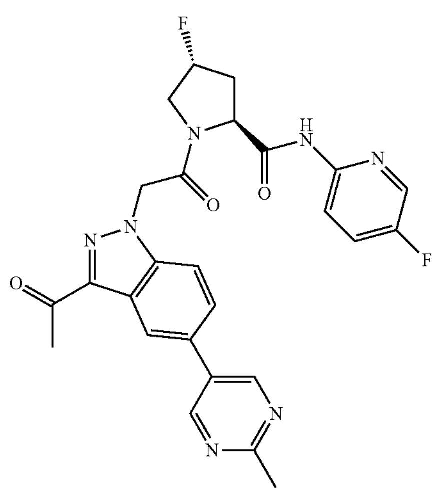 [SMILES: CC(=O)c1nn(CC(=O)N2C[C@H](F)C[C@H]2C(=O)Nc2ccc(F)cn2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(5-fluoropyridin-2-yl)pyrrolidine-2-carboxamide | *** | 1.38 (A) | 520 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 408 | 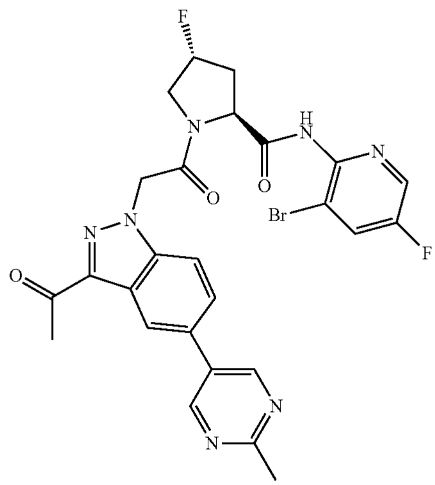 [SMILES: CC(=O)c1nn(CC(=O)N2C[C@H](F)C[C@H]2C(=O)Nc2ncc(F)cc2Br)c2ccc(-c3cnc(C)nc3)cc12] | (2S,4R)-1-(2-(3-acetyl-5-(2-methylpyrimidin-5-yl)-1H-indazol-1-yl)acetyl)-N-(3-bromo-5-fluoropyridin-2-yl)-4-fluoropyrrolidine-2-carboxamide | *** | 1.35 (A) | 598 |
| 409 | 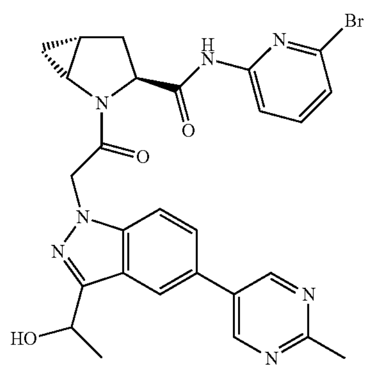 | (1R,3S,5R)-N-(6-bromopyridin-2-yl)-2-(2-(3-(1-hydroxyethyl)-5-(2-methylpyrimidin-5-yl)-1H-indazol-1-yl)acetyl)-2-azabicyclo[3.1.0]hexane-3-carboxamide | *** | 1.53 (A) | 576 |
| 411 | 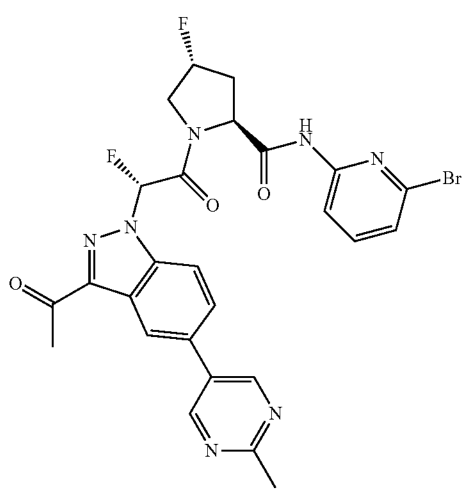 [SMILES: CC(=O)c1nn([C@H](F)C(=O)N2C[C@H](F)C[C@H]2C(=O)Nc2cccc(Br)n2)c2ccc(-c3cnc(C)nc3)cc12] | (2S,4R)-1-((R)-2-(3-acetyl-5-(2-methylpyrimidin-5-yl)-1H-indazol-1-yl)-2-fluoroacetyl)-N-(6-bromopyridin-2-yl)-4-fluoropyrrolidine-2-carboxamide | ** | 1.88 (A) | 598 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 412 | 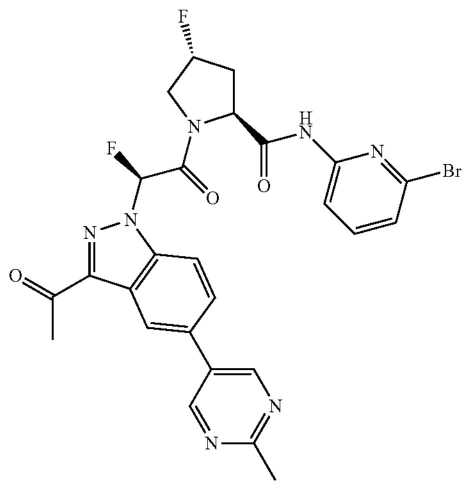 [SMILES: CC(=O)c1nn([C@@H](F)C(=O)N2C[C@H](F)C[C@H]2C(=O)Nc2cccc(Br)n2)c2ccc(-c3cnc(C)nc3)cc12] | (2S,4R)-1-((S)-2-(3-acetyl-5-(2-methylpyrimidin-5-yl)-1H-indazol-1-yl)-2-fluoroacetyl)-N-(6-bromopyridin-2-yl)-4-fluoropyrrolidine-2-carboxamide | *** | 1.73 (A) | 598 |
| 413 | 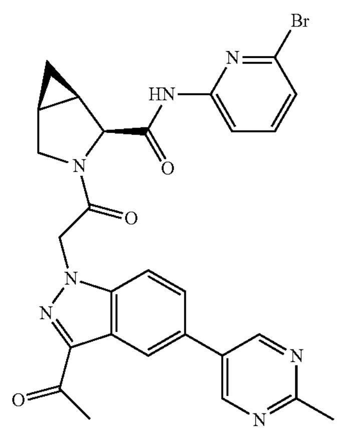 [SMILES: CC(=O)c1nn(CC(=O)N2C[C@H]3C[C@H]3[C@H]2C(=O)Nc2cccc(Br)n2)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(6-bromopyridin-2-yl)-3-azabicyclo[3.1.0]hexane-2-carboxamide | *** | 3.21 (B) | 574 |
| 414 | 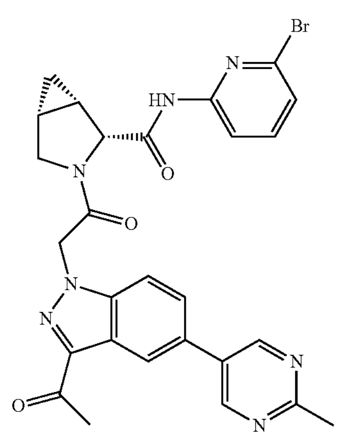 [SMILES: CC(=O)c1nn(CC(=O)N2C[C@@H]3C[C@@H]3[C@@H]2C(=O)Nc2cccc(Br)n2)c2ccc(-c3cnc(C)nc3)cc12] | (1S,2R,5R)-3-(2-(3-acetyl-5-(2-methylpyrimidin-5-yl)-1H-indazol-1-yl)acetyl)-N-(6-bromopyridin-2-yl)-3-azabicyclo[3.1.0]hexane-2-carboxamide | ** | 3.21 (B) | 574 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 415 | 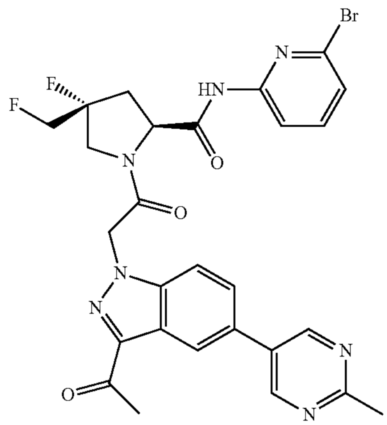 [SMILES: CC(=O)c1nn(CC(=O)N2C[C@@](F)(CF)C[C@H]2C(=O)Nc2cccc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromopyridin-2-yl)-4-fluoro-4-(fluoromethyl)pyrrolidine-2-carboxamide | *** | 2.84 (B) | 612 |
| 416 | 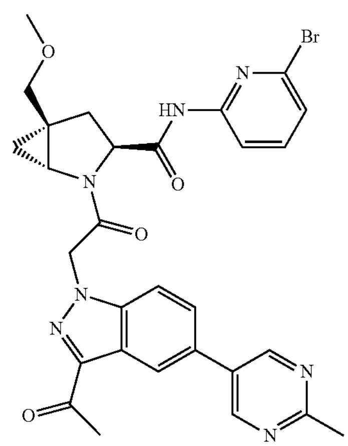 [SMILES: COC[C@@]12C[C@@H](C(=O)Nc3cccc(Br)n3)N(C(=O)Cn3nc(C(C)=O)c4cc(-c5cnc(C)nc5)ccc43)[C@@H]1C2] | (1R,3S,5S)-2-(2-(3-acetyl-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide | *** | 3.02 (B) | 618 |
| 417 | 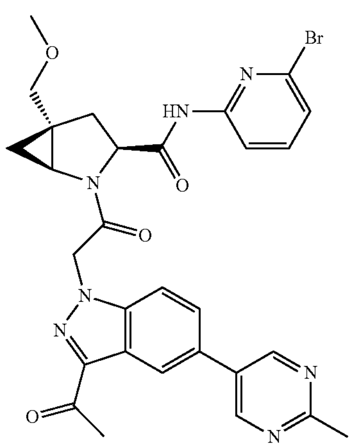 [SMILES: COC[C@@]12C[C@@H]1N(C(=O)Cn1nc(C(C)=O)c3cc(-c4cnc(C)nc4)ccc31)[C@H](C(=O)Nc1cccc(Br)n1)C2] | (1S,3S,5R)-2-(2-(3-acetyl-5-(2-methylpyrimidin-5-yl)-1H-indazol-1-yl)acetyl)-N-(6-bromopyridin-2-yl)-5-(methoxymethyl)-2-azabicyclo[3.1.0]hexane-3-carboxamide | *** | 3.32 (B) | 618 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 418 | 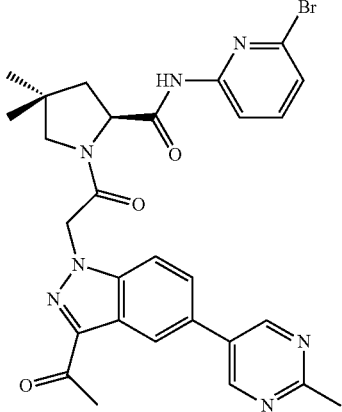 | (2S,4R)-1-(2-(3-acetyl-5-(2-methylpyrimidin-5-yl)-1H-indazol-1-yl)acetyl)-N-(6-bromopyridin-2-yl)-4-fluoro-4-methylpyrrolidine-2-carboxamide | *** | 3.08 (B) | 594 |
| 419 | 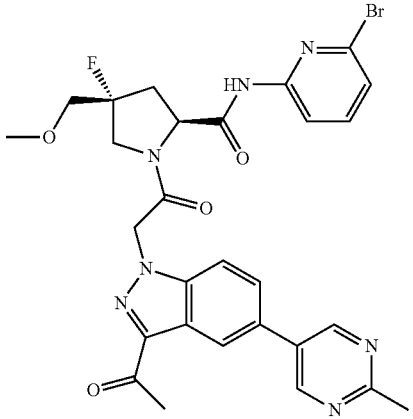 | (2S,4R)-1-(2-(3-acetyl-5-(2-methylpyrimidin-5-yl)-1H-indazol-1-yl)acetyl)-N-(6-bromopyridin-2-yl)-4-fluoro-4-(methoxymethyl)pyrrolidine-2-carboxamide | *** | 2.79 (B) | 624 |
| 420 | 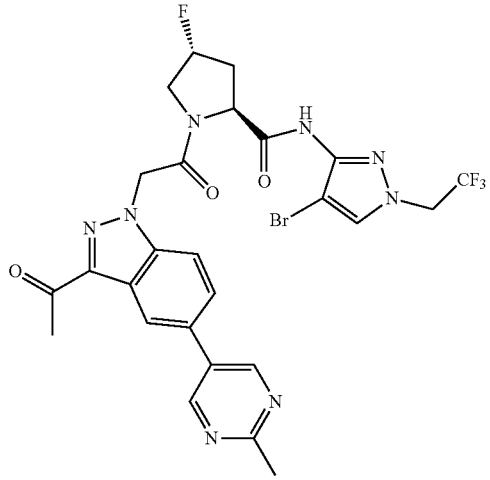 | (2S,4R)-1-(2-(3-acetyl-5-(2-methylpyrimidin-5-yl)-1H-indazol-1-yl)acetyl)-N-(4-bromo-1-(2,2,2-trifluoroethyl)-1H-pyrazol-3-yl)-4-fluoropyrrolidine-2-carboxamide | *** | 1.50 (A) | 651 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 421 | 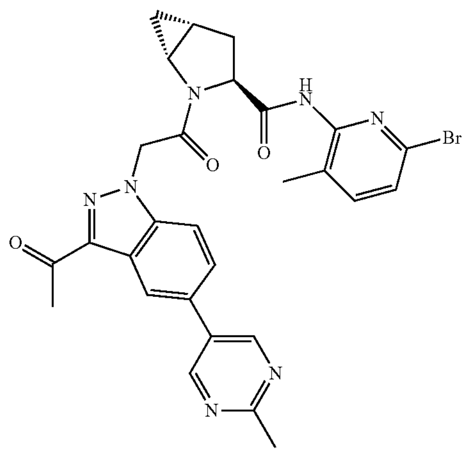 [SMILES: CC(=O)c1nn(CC(=O)N2[C@@H]3C[C@@H]3C[C@H]2C(=O)Nc2nc(Br)ccc2C)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 1.59 (A) | 589 |
| 422 | 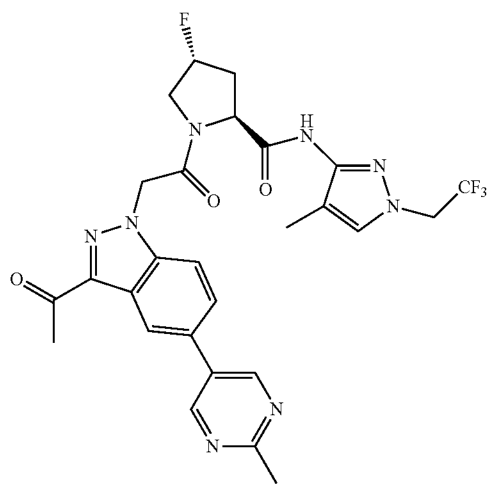 [SMILES: CC(=O)c1nn(CC(=O)N2C[C@H](F)C[C@H]2C(=O)Nc2nn(CC(F)(F)F)cc2C)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(4-methyl-1-(2,2,2-trifluoroethyl)-1H-pyrazol-3-yl)pyrrolidine-2-carboxamide | *** | 1.41 (A) | 586 |
| 424 | 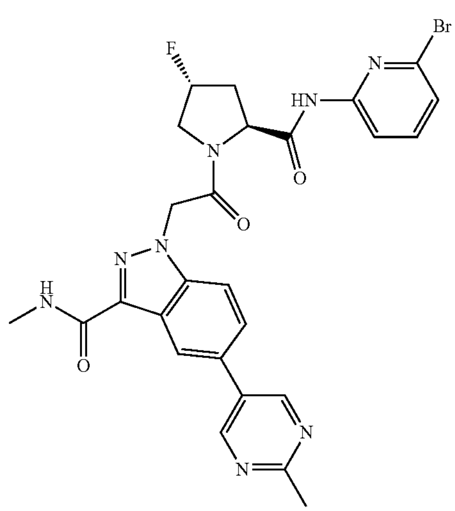 [SMILES: CNC(=O)c1nn(CC(=O)N2C[C@H](F)C[C@H]2C(=O)Nc2cccc(Br)n2)c2ccc(-c3cnc(C)nc3)cc12] | 1-(2-((2S,4R)-2-((6-bromopyridin-2-yl)carbamoyl)-4-fluoropyrrolidin-1-yl)-2-oxoethyl)-N-methyl-5-(2-methylpyrimidin-5-yl)-1H-indazole-3-carboxamide | *** | 1.42 (A) | 597 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 425 | 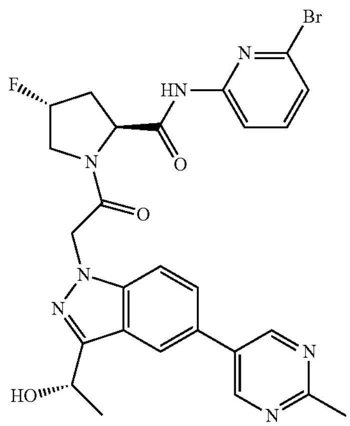 | (2S,4R)-N-(6-bromopyridin-2-yl)-4-fluoro-1-(2-(3-((S)-1-hydroxyethyl)-5-(2-methylpyrimidin-5-yl)-1H-indazol-1-yl)acetyl)pyrrolidine-2-carboxamide | ** | | |
| 426 | 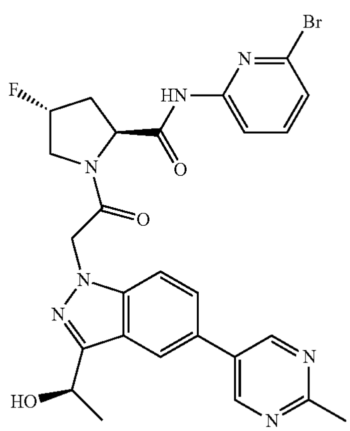 | (2S,4R)-N-(6-bromopyridin-2-yl)-4-fluoro-1-(2-(3-((R)-1-hydroxyethyl)-5-(2-methylpyrimidin-5-yl)-1H-indazol-1-yl)acetyl)pyrrolidine-2-carboxamide | ** | | |
| 427 | 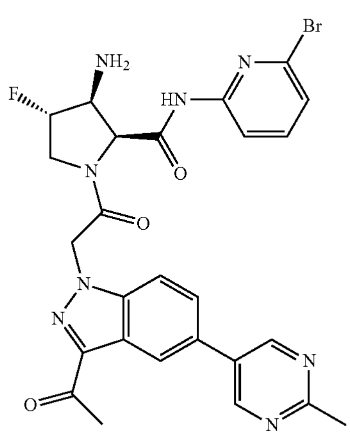 [SMILES: CC(=O)c1nn(CC(=O)N2C[C@H](F)[C@@H](N)[C@H]2C(=O)Nc2cccc(Br)n2)c2ccc(-c3cnc(C)nc3)cc12] | (2S,3S,4S)-1-(2-(3-acetyl-5-(2-methylpyrimidin-5-yl)-1H-indazol-1-yl)acetyl)-3-amino-N-(6-bromopyridin-2-yl)-4-fluoropyrrolidine-2-carboxamide | *** | 2.37 (B) | 595 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 428 | 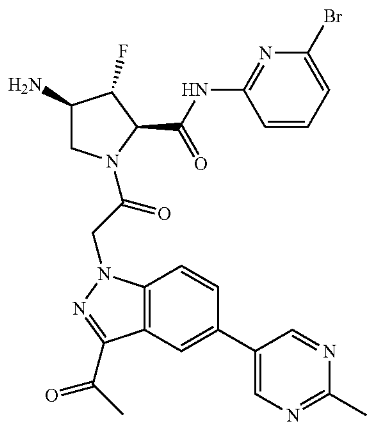 [SMILES: CC(=O)c1nn(CC(=O)N2C[C@@H](N)[C@H](F)[C@H]2C(=O)Nc2cccc(Br)n2)c2ccc(-c3cnc(C)nc3)cc12] | (2R,3S,4R)-1-(2-(3-acetyl-5-(2-methylpyrimidin-5-yl)-1H-indazol-1-yl)acetyl)-4-amino-N-(6-bromopyridin-2-yl)-3-fluoropyrrolidine-2-carboxamide | * | 2.54 (B) | 595 |
| 429 | 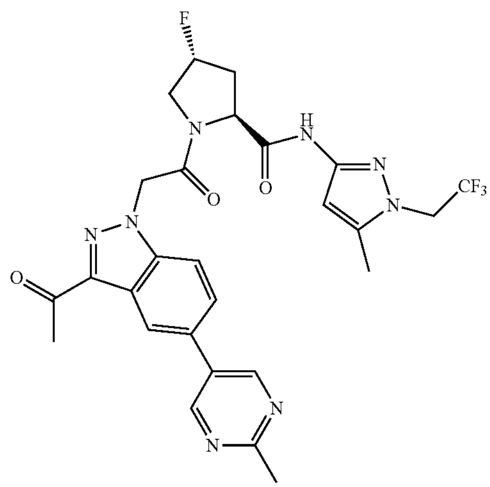 [SMILES: CC(=O)c1nn(CC(=O)N2C[C@H](F)C[C@H]2C(=O)Nc2cc(C)n(CC(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(5-methyl-1-(2,2,2-trifluoroethyl)-1H-pyrazol-3-yl)pyrrolidine-2-carboxamide | *** | 1.50 (A) | 587 |
| 430 | 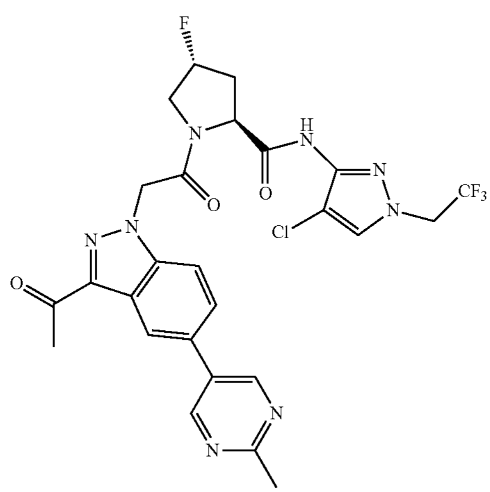 [SMILES: CC(=O)c1nn(CC(=O)N2C[C@H](F)C[C@H]2C(=O)Nc2nn(CC(F)(F)F)cc2Cl)c2ccc(-c3cnc(C)nc3)cc12] | (2S,4R)-1-(2-(3-acetyl-5-(2-methylpyrimidin-5-yl)-1H-indazol-1-yl)acetyl)-N-(4-chloro-1-(2,2,2-trifluoroethyl)-1H-pyrazol-3-yl)-4-fluoropyrrolidine-2-carboxamide | *** | 1.47 (A) | 607 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 431 | 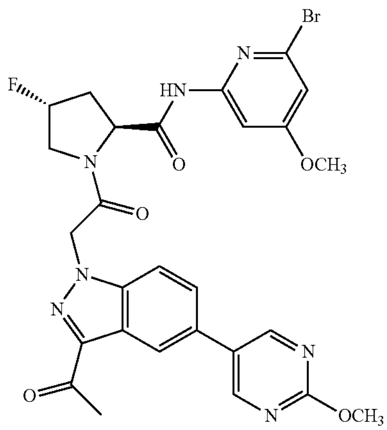 [SMILES: COc1cc(Br)nc(NC(=O)[C@@H]2C[C@@H](F)CN2C(=O)Cn2nc(C(C)=O)c3cc(-c4cnc(OC)nc4)ccc32)c1] | (2S,4R)-1-(2-(3-acetyl-5-(2-methoxypyrimidin-5-yl)-1H-indazol-1-yl)acetyl)-N-(6-bromo-4-methoxypyridin-2-yl)-4-fluoropyrrolidine-2-carboxamide | *** | 1.93 (A) | 626 |
| 432 | 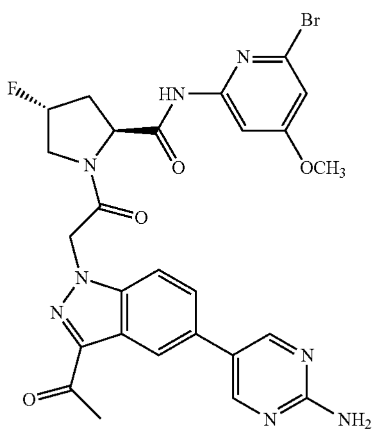 [SMILES: COc1cc(Br)nc(NC(=O)[C@@H]2C[C@@H](F)CN2C(=O)Cn2nc(C(C)=O)c3cc(-c4cnc(N)nc4)ccc32)c1] | (2S,4R)-1-(2-(3-acetyl-5-(2-aminopyrimidin-5-yl)-1H-indazol-1-yl)acetyl)-N-(6-bromo-4-methoxypyridin-2-yl)-4-fluoropyrrolidine-2-carboxamide | *** | 1.55 (A) | 611 |
| 433 | 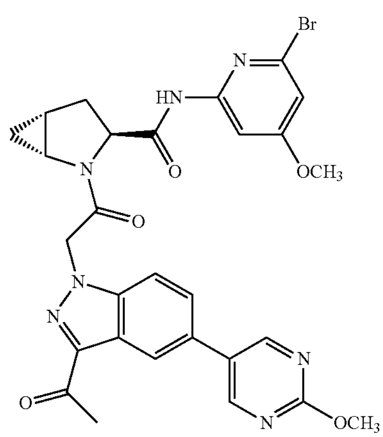 [SMILES: COc1cc(Br)nc(NC(=O)[C@@H]2C[C@H]3C[C@H]3N2C(=O)Cn2nc(C(C)=O)c3cc(-c4cnc(OC)nc4)ccc32)c1] | (1R,3S,5R)-2-(2-(3-acetyl-5-(2-methoxypyrimidin-5-yl)-1H-indazol-1-yl)acetyl)-N-(6-bromo-4-methoxypyridin-2-yl)-2-azabicyclo[3.1.0]hexane-3-carboxamide | *** | 2.08 (A) | 620 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 434 | 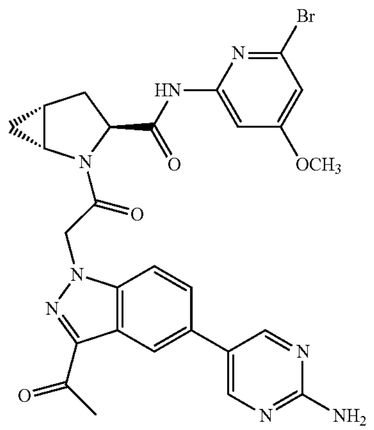 [SMILES: COc1cc(Br)nc(NC(=O)[C@@H]2C[C@H]3C[C@H]3N2C(=O)Cn2nc(C(C)=O)c3cc(-c4cnc(N)nc4)ccc32)c1] | (1R,3S,5R)-2-(2-(3-acetyl-5-(2-aminopyrimidin-5-yl)-1H-indazol-1-yl)acetyl)-N-(6-bromo-4-methoxypyridin-2-yl)-2-azabicyclo[3.1.0]hexane-3-carboxamide | *** | 1.72 (A) | 605 |
| 435 | 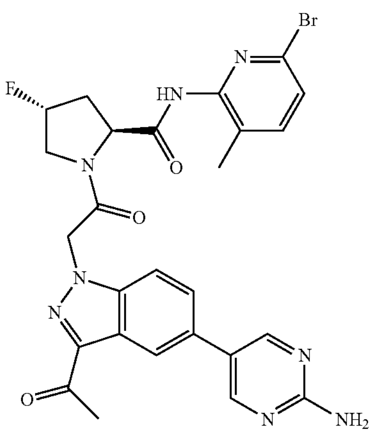 [SMILES: CC(=O)c1nn(CC(=O)N2C[C@H](F)C[C@H]2C(=O)Nc2nc(Br)ccc2C)c2ccc(-c3cnc(N)nc3)cc12] | (2S,4R)-1-(2-(3-acetyl-5-(2-aminopyrimidin-5-yl)-1H-indazol-1-yl)acetyl)-N-(6-bromo-3-methylpyridin-2-yl)-4-fluoropyrrolidine-2-carboxamide | *** | 1.28 (A) | 595 |
| 436 | 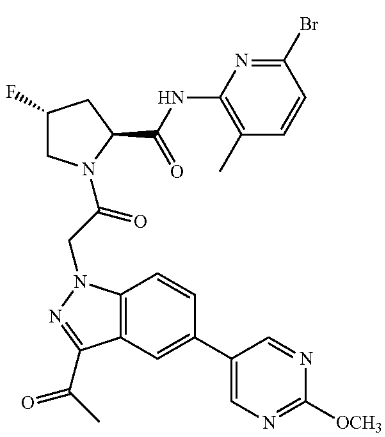 [SMILES: COc1ncc(-c2ccc3c(c2)c(C(C)=O)nn3CC(=O)N2C[C@H](F)C[C@H]2C(=O)Nc2nc(Br)ccc2C)cn1] | (2S,4R)-1-(2-(3-acetyl-5-(2-methoxypyrimidin-5-yl)-1H-indazol-1-yl)acetyl)-N-(6-bromo-3-methylpyridin-2-yl)-4-fluoropyrrolidine-2-carboxamide | *** | 1.67 (A) | 610 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 437 | 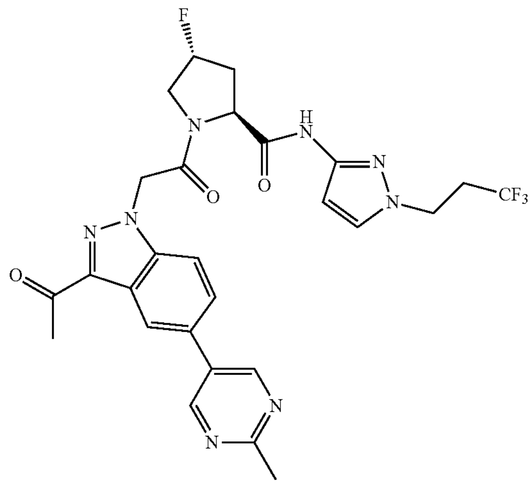 [SMILES: CC(=O)c1nn(CC(=O)N2C[C@H](F)C[C@H]2C(=O)Nc2ccn(CCC(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(1-(3,3,3-trifluoropropyl)-1H-pyrazol-3-yl)pyrrolidine-2-carboxamide | *** | 1.48 (A) | 586 |
| 438 | 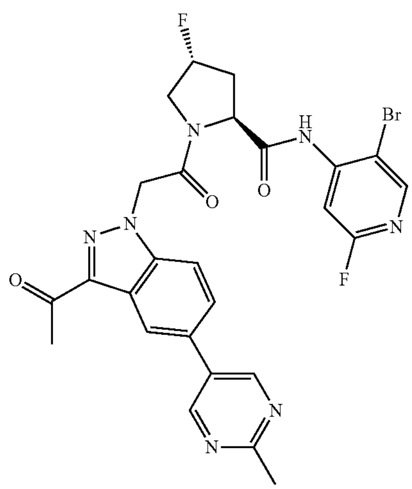 [SMILES: CC(=O)c1nn(CC(=O)N2C[C@H](F)C[C@H]2C(=O)Nc2cc(F)ncc2Br)c2ccc(-c3cnc(C)nc3)cc12] | (2S,4R)-1-(2-(3-acetyl-5-(2-methylpyrimidin-5-yl)-1H-indazol-1-yl)acetyl)-N-(5-bromo-2-fluoropyridin-4-yl)-4-fluoropyrrolidine-2-carboxamide | *** | 1.55 (A) | 598 |
| 439 | 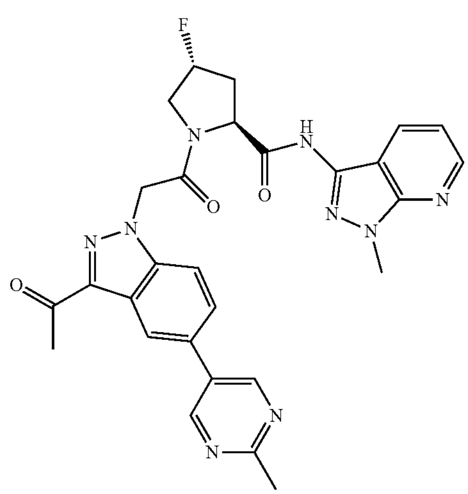 [SMILES: CC(=O)c1nn(CC(=O)N2C[C@H](F)C[C@H]2C(=O)Nc2nn(C)c3ncccc23)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(1-methyl-1H-pyrazolo[3,4-b]pyridin-3-yl)pyrrolidine-2-carboxamide | *** | 1.21 (A) | 556 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 440 | 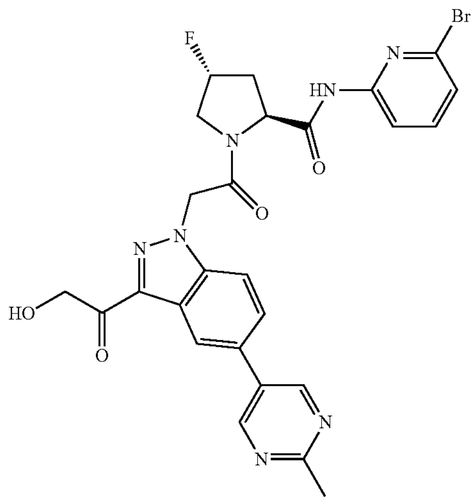 [SMILES: Cc1ncc(-c2ccc3c(c2)c(C(=O)CO)nn3CC(=O)N2C[C@H](F)C[C@H]2C(=O)Nc2cccc(Br)n2)cn1] | (2S,4R)-N-(6-bromopyridin-2-yl)-4-fluoro-1-(2-(3-(2-hydroxyacetyl)-5-(2-methylpyrimidin-5-yl)-1H-indazol-1-yl)acetyl)pyrrolidine-2-carboxamide | *** | 1.37 (A) | 598 |
| 442 | 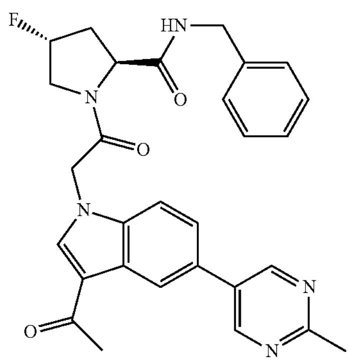 [SMILES: CC(=O)c1cn(CC(=O)N2C[C@H](F)C[C@H]2C(=O)NCc2ccccc2)c2ccc(-c3cnc(C)nc3)cc12] | (2S,4R)-1-(2-(3-acetyl-5-(2-methylpyrimidin-5-yl)-1H-indol-1-yl)acetyl)-N-benzyl-4-fluoropyrrolidine-2-carboxamide | *** | 8.97 (D) | 514 |
| 443 | 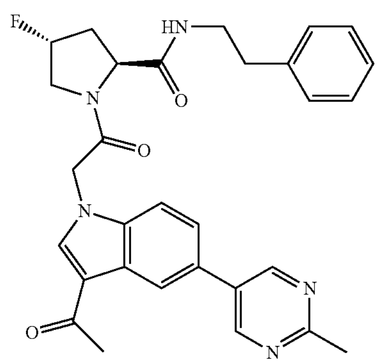 [SMILES: CC(=O)c1cn(CC(=O)N2C[C@H](F)C[C@H]2C(=O)NCCc2ccccc2)c2ccc(-c3cnc(C)nc3)cc12] | (2S,4R)-1-(2-(3-acetyl-5-(2-methylpyrimidin-5-yl)-1H-indol-1-yl)acetyl)-4-fluoro-N-phenethylpyrrolidine-2-carboxamide | *** | 9.42 (D) | 528 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 444 | 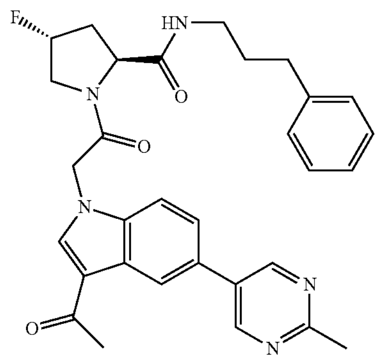 [SMILES: CC(=O)c1cn(CC(=O)N2C[C@H](F)C[C@H]2C(=O)NCCCc2ccccc2)c2ccc(-c3cnc(C)nc3)cc12] | (2S,4R)-1-(2-(3-acetyl-5-(2-methylpyrimidin-5-yl)-1H-indol-1-yl)acetyl)-4-fluoro-N-(3-phenylpropyl) pyrrolidine-2-carboxamide | *** | 9.79 (D) | 542 |
| 445 | 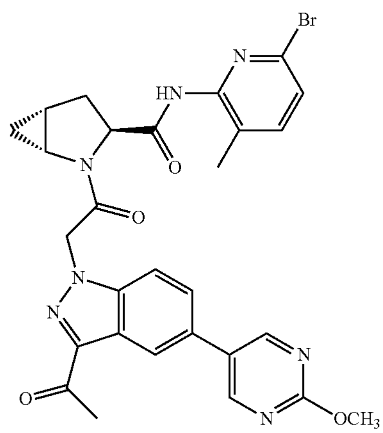 [SMILES: COc1ncc(-c2ccc3c(c2)c(C(C)=O)nn3CC(=O)N2[C@@H]3C[C@@H]3C[C@H]2C(=O)Nc2nc(Br)ccc2C)cn1] | (1R,3S,5R)-2-(2-(3-acetyl-5-(2-methoxypyrimidin-5-yl)-1H-indazol-1-yl)acetyl)-N-(6-bromo-3-methylpyridin-2-yl)-2-azabicyclo[3.1.0] hexane-3-carboxamide | *** | 1.76 (A) | 604 |
| 446 | 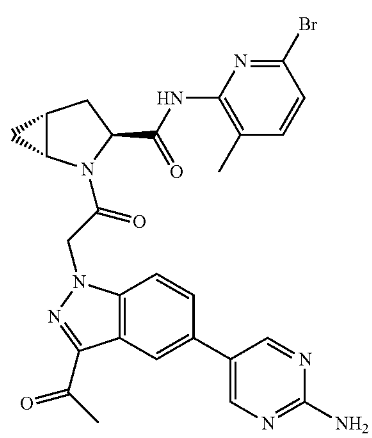 [SMILES: CC(=O)c1nn(CC(=O)N2[C@@H]3C[C@@H]3C[C@H]2C(=O)Nc2nc(Br)ccc2C)c2ccc(-c3cnc(N)nc3)cc12] | (1R,3S,5R)-2-(2-(3-acetyl-5-(2-aminopyrimidin-5-yl)-1H-indazol-1-yl)acetyl)-N-(6-bromo-3-methylpyridin-2-yl)-2-azabicyclo[3.1.0] hexane-3-carboxamide | *** | 1.40 (A) | 589 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 447 | 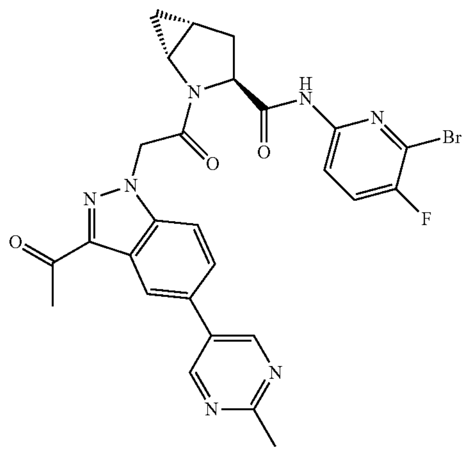 [SMILES: CC(=O)c1nn(CC(=O)N2[C@@H]3C[C@@H]3C[C@H]2C(=O)Nc2ccc(F)c(Br)n2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-5-fluoropyridin-2-yl)-2-azabicyclo[3.1.0]hexane-3-carboxamide | *** | 1.88 (A) | 592 |
| 448 | 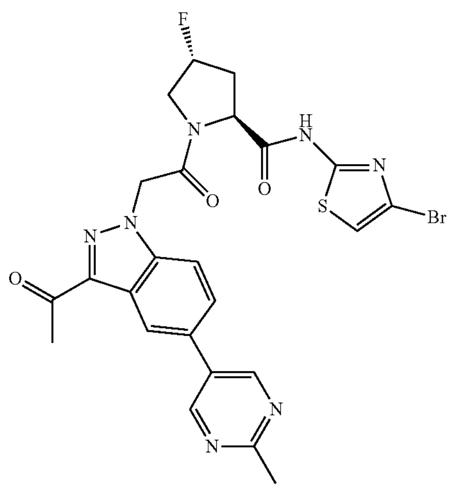 [SMILES: CC(=O)c1nn(CC(=O)N2C[C@H](F)C[C@H]2C(=O)Nc2nc(Br)cs2)c2ccc(-c3cnc(C)nc3)cc12] | (2S,4R)-1-(2-(3-acetyl-5-(2-methylpyrimidin-5-yl)-1H-indazol-1-yl)acetyl)-N-(4-bromothiazol-2-yl)-4-fluoropyrrolidine-2-carboxamide | *** | 1.56 (A) | 586 |
| 449 | 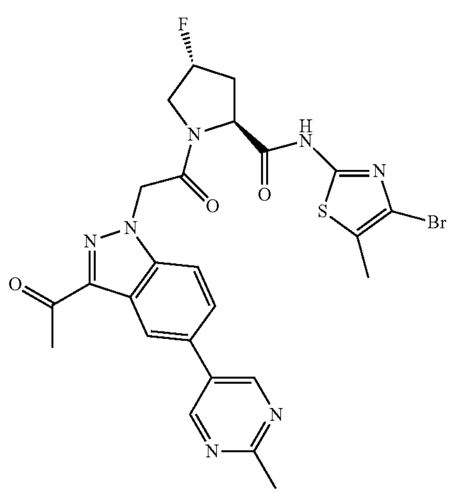 [SMILES: CC(=O)c1nn(CC(=O)N2C[C@H](F)C[C@H]2C(=O)Nc2nc(Br)c(C)s2)c2ccc(-c3cnc(C)nc3)cc12] | (2S,4R)-1-(2-(3-acetyl-5-(2-methylpyrimidin-5-yl)-1H-indazol-1-yl)acetyl)-N-(4-bromo-5-methylthiazol-2-yl)-4-fluoropyrrolidine-2-carboxamide | *** | 1.73 (A) | 600 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 450 | 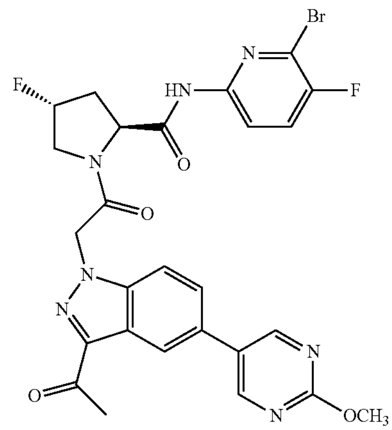 [SMILES: COc1ncc(-c2ccc3c(c2)c(C(C)=O)nn3CC(=O)N2C[C@H](F)C[C@H]2C(=O)Nc2ccc(F)c(Br)n2)cn1] | (2S,4R)-1-(2-(3-acetyl-5-(2-methoxypyrimidin-5-yl)-1H-indazol-1-yl)acetyl)-N-(6-bromo-5-fluoropyridin-2-yl)-4-fluoropyrrolidine-2-carboxamide | *** | 1.91 (A) | 614 |
| 451 | 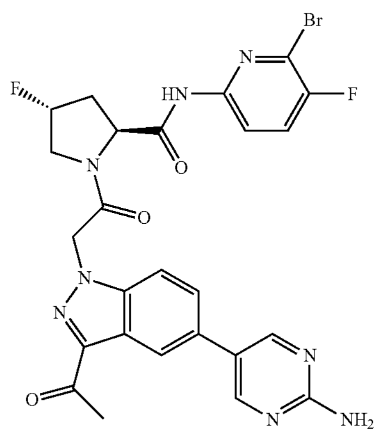 [SMILES: CC(=O)c1nn(CC(=O)N2C[C@H](F)C[C@H]2C(=O)Nc2ccc(F)c(Br)n2)c2ccc(-c3cnc(N)nc3)cc12] | (2S,4R)-1-(2-(3-acetyl-5-(2-aminopyrimidin-5-yl)-1H-indazol-1-yl)acetyl)-N-(6-bromo-5-fluoropyridin-2-yl)-4-fluoropyrrolidine-2-carboxamide | *** | 1.56 (A) | 599 |
| 452 | 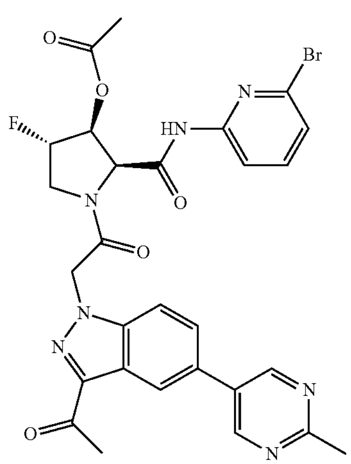 [SMILES: CC(=O)O[C@H]1[C@@H](C(=O)Nc2cccc(Br)n2)N(C(=O)Cn2nc(C(C)=O)c3cc(-c4cnc(C)nc4)ccc32)C[C@@H]1F] | (2S,3S,4S)-1-(2-(3-acetyl-5-(2-methylpyrimidin-5-yl)-1H-indazol-1-yl)acetyl)-2-((6-bromopyridin-2-yl)carbamoyl)-4-fluoropyrrolidin-3-yl acetate | *** | 2.81 (B) | 638 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 453 | 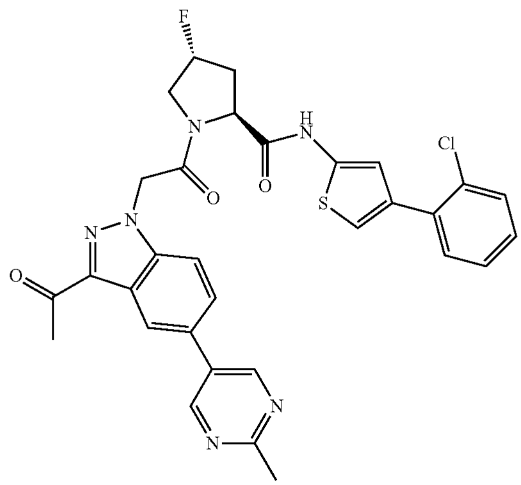 [SMILES: CC(=O)c1nn(CC(=O)N2C[C@H](F)C[C@H]2C(=O)Nc2cc(-c3ccccc3Cl)cs2)c2ccc(-c3cnc(C)nc3)cc12] | (2S,4R)-1-(2-(3-acetyl-5-(2-methylpyrimidin-5-yl)-1H-indazol-1-yl)acetyl)-N-(4-(2-chlorophenyl)thiazol-2-yl)-4-fluoropyrrolidine-2-carboxamide | * | 2.06 (A) | 618 |
| 454 | 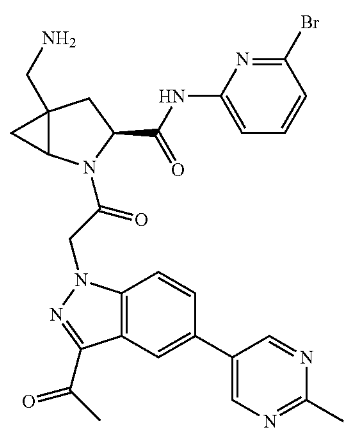 [SMILES: CC(=O)c1nn(CC(=O)N2C3CC3(CN)C[C@H]2C(=O)Nc2cccc(Br)n2)c2ccc(-c3cnc(C)nc3)cc12] | (3S)-2-(2-(3-acetyl-5-(2-methylpyrimidin-5-yl)-1H-indazol-1-yl)acetyl)-5-(aminomethyl)-N-(6-bromopyridin-2-yl)-2-azabicyclo[3.1.0]hexane-3-carboxamide | *** | 2.70 (B) | 603 |
| 455 | 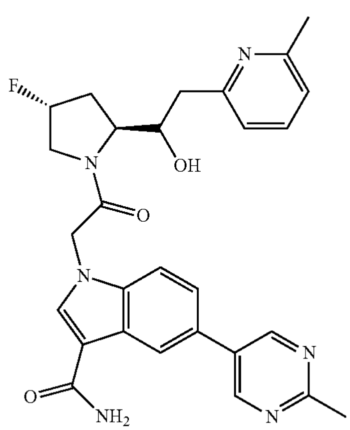 [SMILES: Cc1cccc(CC(O)[C@@H]2C[C@@H](F)CN2C(=O)Cn2cc(C(N)=O)c3cc(-c4cnc(C)nc4)ccc32)n1] | 1-(2-((2S,4R)-4-fluoro-2-((S)-1-hydroxy-2-(6-methylpyridin-2-yl)ethyl)pyrrolidin-1-yl)-2-oxoethyl)-5-(2-methylpyrimidin-5-yl)-1H-indole-3-carboxamide | * | 1.33 (B) | 517 |

TABLE 3-continued

Additional Non-limiting Examples of Compounds of Formula I

| Comp No. | Structure | Name | IC5 (Stars) | RT min (Method A,B,C or D) | MS (M + 1) |
|---|---|---|---|---|---|
| 456 | 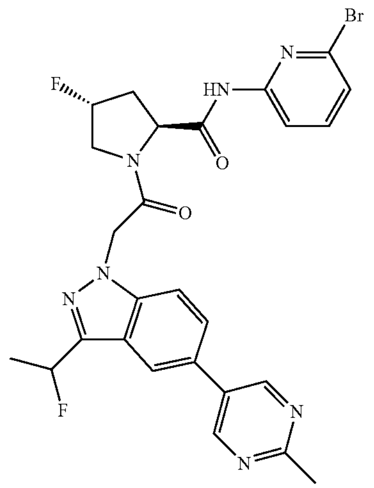 [SMILES: Cc1ncc(-c2ccc3c(c2)c(C(C)F)nn3CC(=O)N2C[C@H](F)C[C@H]2C(=O)Nc2cccc(Br)n2)cn1] | (2S,4R)-N-(6-bromopyridin-2-yl)-4-fluoro-1-(2-(3-(1-fluoroethyl)-5-(2-methylpyrimidin-5-yl)-1H-indazol-1-yl)acetyl)pyrrolidine-2-carboxamide | *** | 1.79 (A) | 584 |
| 457 | 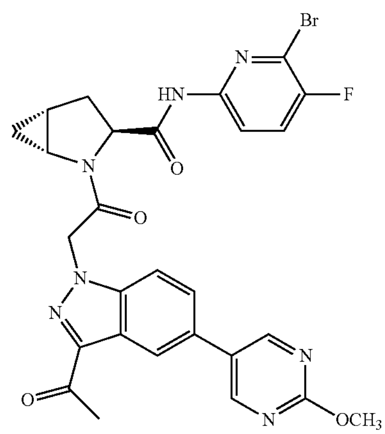 [SMILES: COc1ncc(-c2ccc3c(c2)c(C(C)=O)nn3CC(=O)N2[C@@H]3C[C@@H]3C[C@H]2C(=O)Nc2ccc(F)c(Br)n2)cn1] | (1R,3S,5R)-2-(2-(3-acetyl-5-(2-methoxypyrimidin-5-yl)-1H-indazol-1-yl)acetyl)-N-(6-bromo-5-fluoropyridin-2-yl)-2-azabicyclo[3.1.0]hexane-3-carboxamide | *** | 2.06 (A) | 608 |
| 458 | 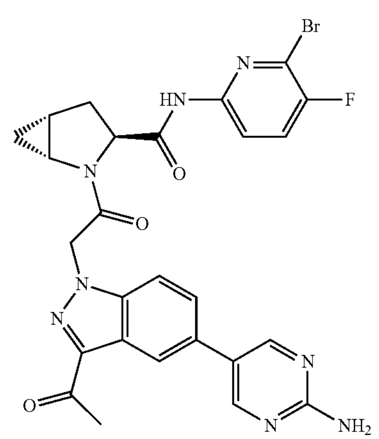 [SMILES: CC(=O)c1nn(CC(=O)N2[C@@H]3C[C@@H]3C[C@H]2C(=O)Nc2ccc(F)c(Br)n2)c2ccc(-c3cnc(N)nc3)cc12] | (1R,3S,5R)-2-(2-(3-acetyl-5-(2-aminopyrimidin-5-yl)-1H-indazol-1-yl)acetyl)-N-(6-bromo-5-fluoropyridin-2-yl)-2-azabicyclo[3.1.0]hexane-3-carboxamide | *** | 1.71 (A) | 593 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 459 | 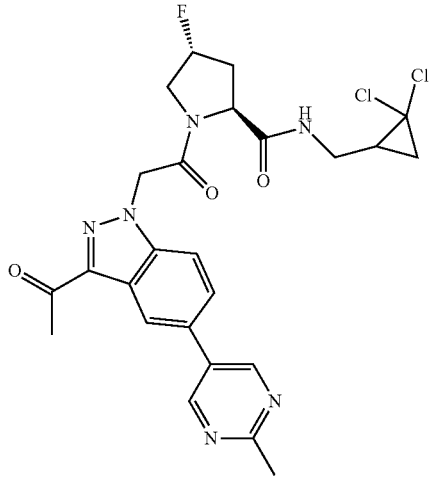 [SMILES: CC(=O)c1nn(CC(=O)N2C[C@H](F)C[C@H]2C(=O)NCC2CC2(Cl)Cl)c2ccc(-c3cnc(C)nc3)cc12] | (2S,4R)-1-(2-(3-acetyl-5-(2-methylpyrimidin-5-yl)-1H-indazol-1-yl)acetyl)-N-((2,2-dichlorocyclopropyl)methyl)-4-fluoropyrrolidine-2-carboxamide | *** | 1.52 (A) | 547 |
| 460 | 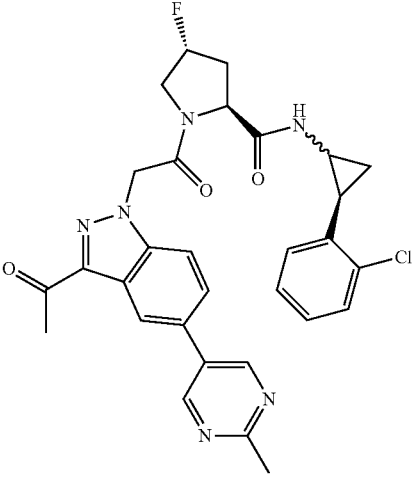 [SMILES: CC(=O)c1nn(CC(=O)N2C[C@H](F)C[C@H]2C(=O)NC2C[C@H]2c2ccccc2Cl)c2ccc(-c3cnc(C)nc3)cc12] | (2S,4R)-1-(2-(3-acetyl-5-(2-methylpyrimidin-5-yl)-1H-indazol-1-yl)acetyl)-N-((2S)-2-(2-chlorophenyl)cyclopropyl)-4-fluoropyrrolidine-2-carboxamide | *** | 1.77 (A) | 575 |
| 461 | 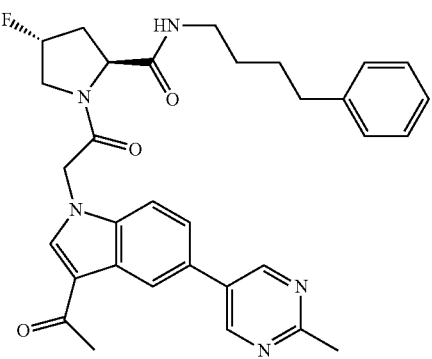 [SMILES: CC(=O)c1cn(CC(=O)N2C[C@H](F)C[C@H]2C(=O)NCCCCc2ccccc2)c2ccc(-c3cnc(C)nc3)cc12] | (2S,4R)-1-(2-(3-acetyl-5-(2-methylpyrimidin-5-yl)-1H-indol-1-yl)acetyl)-4-fluoro-N-(4-phenylbutyl)pyrrolidine-2-carboxamide | *** | 10.45 (D) | 556 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 462 | 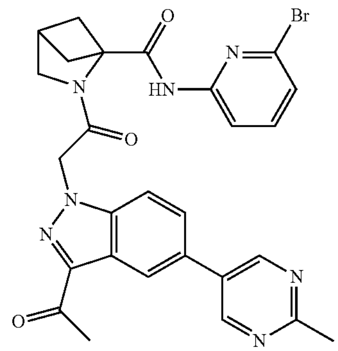 [SMILES: CC(=O)c1nn(CC(=O)N2CC3CC2(C(=O)Nc2cccc(Br)n2)C3)c2ccc(-c3cnc(C)nc3)cc12] | 2-(2-(3-acetyl-5-(2-methylpyrimidin-5-yl)-1H-indazol-1-yl)acetyl)-N-(6-bromopyridin-2-yl)-2-azabicyclo[2.1.1]hexane-1-carboxamide | *** | 1.67 (A) | 574 |
| 463 | 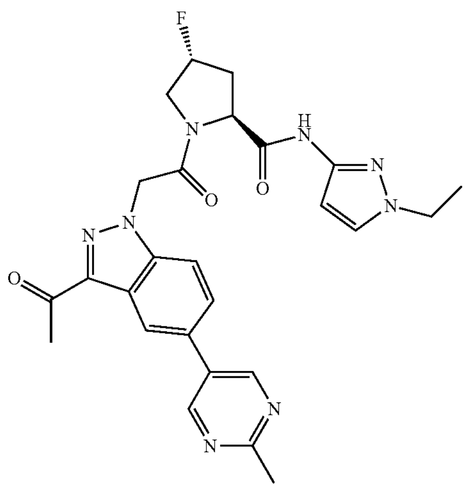 [SMILES: CCn1ccc(NC(=O)[C@@H]2C[C@@H](F)CN2C(=O)Cn2nc(C(C)=O)c3cc(-c4cnc(C)nc4)ccc32)n1] | (2S,4R)-1-(2-(3-acetyl-5-(2-methylpyrimidin-5-yl)-1H-indazol-1-yl)acetyl)-N-(1-ethyl-1H-pyrazol-3-yl)-4-fluoropyrrolidine-2-carboxamide | *** | 1.22 (A) | 518 |
| 464 | 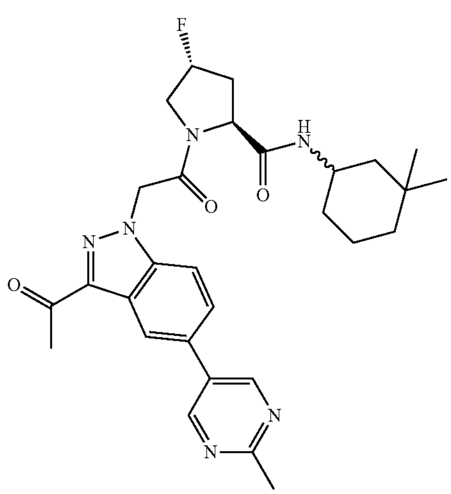 [SMILES: CC(=O)c1nn(CC(=O)N2C[C@H](F)C[C@H]2C(=O)NC2CCCC(C)(C)C2)c2ccc(-c3cnc(C)nc3)cc12] | (2S,4R)-1-(2-(3-acetyl-5-(2-methylpyrimidin-5-yl)-1H-indazol-1-yl)acetyl)-N-(3,3-dimethylcyclohexyl)-4-fluoropyrrolidine-2-carboxamide | *** | 1.86 (A) | 535 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 465 | 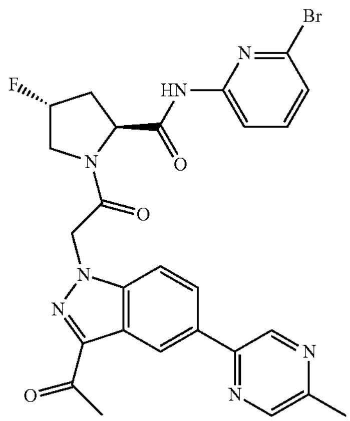 [SMILES: CC(=O)c1nn(CC(=O)N2C[C@H](F)C[C@H]2C(=O)Nc2cccc(Br)n2)c2ccc(-c3cnc(C)cn3)cc12] | (2S,4R)-1-(2-(3-acetyl-5-(5-methylpyrazin-2-yl)-1H-indazol-1-yl)acetyl)-N-(6-bromopyridin-2-yl)-4-fluoropyrrolidine-2-carboxamide | *** | 1.86 (A) | 580 |
| 467 | 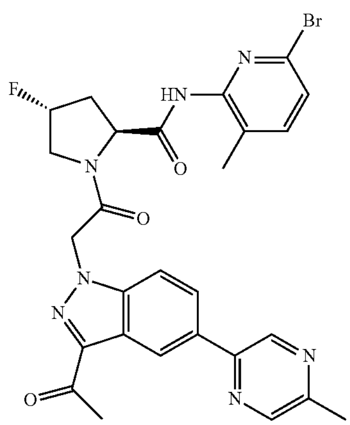 [SMILES: CC(=O)c1nn(CC(=O)N2C[C@H](F)C[C@H]2C(=O)Nc2nc(Br)ccc2C)c2ccc(-c3cnc(C)cn3)cc12] | (2S,4R)-1-(2-(3-acetyl-5-(5-methylpyrazin-2-yl)-1H-indazol-1-yl)acetyl)-N-(6-bromo-3-methylpyridin-2-yl)-4-fluoropyrrolidine-2-carboxamide | *** | 1.69 (A) | 594 |
| 468 | 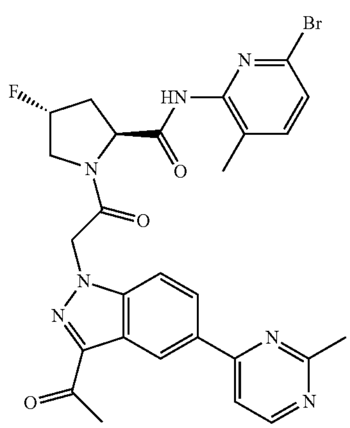 [SMILES: CC(=O)c1nn(CC(=O)N2C[C@H](F)C[C@H]2C(=O)Nc2nc(Br)ccc2C)c2ccc(-c3ccnc(C)n3)cc12] | (2S,4R)-1-(2-(3-acetyl-5-(2-methylpyrimidin-4-yl)-1H-indazol-1-yl)acetyl)-N-(6-bromo-3-methylpyridin-2-yl)-4-fluoropyrrolidine-2-carboxamide | *** | 1.57 (A) | 594 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 469 | 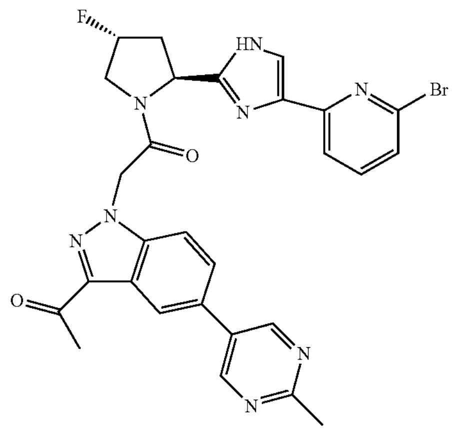 [SMILES: CC(=O)c1nn(CC(=O)N2C[C@H](F)C[C@H]2c2nc(-c3cccc(Br)n3)c[nH]2)c2ccc(-c3cnc(C)nc3)cc12] | 2-(3-acetyl-5-(2-methylpyrimidin-5-yl)-1H-indazol-1-yl)-1-((2S,4R)-2-(4-(6-bromopyridin-2-yl)-1H-imidazol-2-yl)-4-fluoropyrrolidin-1-yl)ethan-1-one | *** | 1.45 (A) | 605 |
| 472 | 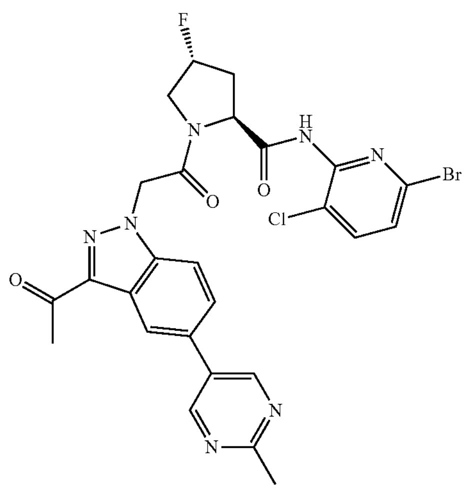 [SMILES: CC(=O)c1nn(CC(=O)N2C[C@H](F)C[C@H]2C(=O)Nc2nc(Br)ccc2Cl)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-chloropyridin-2-yl)-4-fluoropyrrolidine-2-carboxamide | *** | 1.52 (A) | 615 |
| 473 | 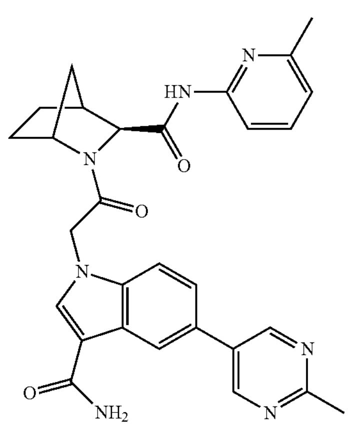 [SMILES: Cc1cccc(NC(=O)[C@@H]2C3CCC(C3)N2C(=O)Cn2cc(C(N)=O)c3cc(-c4cnc(C)nc4)ccc32)n1] | 1-(2-((1R,3S,4S)-3-((6-methylpyridin-2-yl)carbamoyl)-2-azabicyclo[2.2.1]heptan-2-yl)-2-oxoethyl)-5-(2-methylpyrimidin-5-yl)-1H-indole-3-carboxamide | * | 2.31 (B) | 524 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 474 | 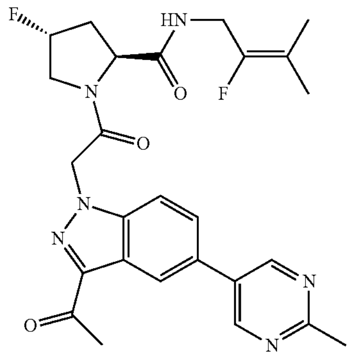 [SMILES: CC(=O)c1nn(CC(=O)N2C[C@H](F)C[C@H]2C(=O)NCC(F)=C(C)C)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2-fluoro-3-methylbut-2-en-1-yl)pyrrolidine-2-carboxamide | *** | 9.55 (D) | 511 |
| 475 | 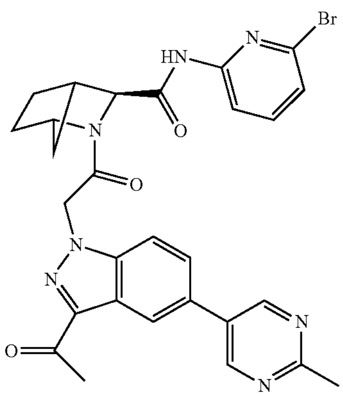 [SMILES: CC(=O)c1nn(CC(=O)N2C3CCC(C3)[C@H]2C(=O)Nc2cccc(Br)n2)c2ccc(-c3cnc(C)nc3)cc12] | (3S,4S)-2-(2-(3-acetyl-5-(2-methylpyrimidin-5-yl)-1H-indazol-1-yl)acetyl)-N-(6-bromopyridin-2-yl)-2-azabicyclo[2.2.1]heptane-3-carboxamide | *** | 1.87 (A) | 590 |
| 476 | 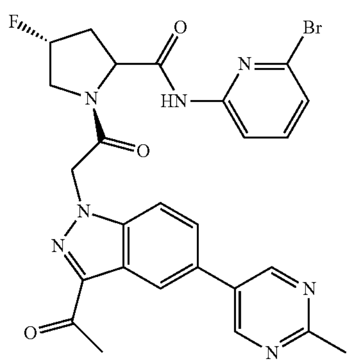 | (2R,4S)-2-(2-(3-acetyl-5-(2-methylpyrimidin-5-yl)-1H-indazol-1-yl)acetyl)-N-(6-bromopyridin-2-yl)-4-fluoropyrrolidine-1-carboxamide | * | 1.99 (A) | 582 |
| 477 | 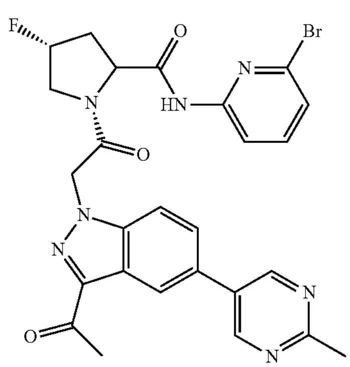 | (2S,4S)-2-(2-(3-acetyl-5-(2-methylpyrimidin-5-yl)-1H-indazol-1-yl)acetyl)-N-(6-bromopyridin-2-yl)-4-fluoropyrrolidine-1-carboxamide | * | 2.15 (A) | 575 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 478 | 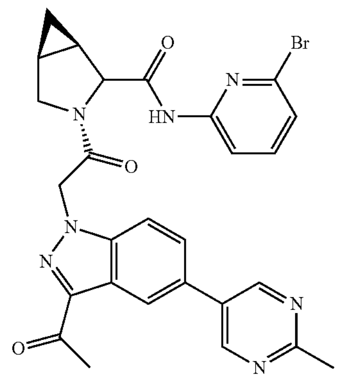 | (1R,3S,5R)-3-(2-(3-acetyl-5-(2-methylpyrimidin-5-yl)-1H-indazol-1-yl)acetyl)-N-(6-bromopyridin-2-yl)-2-azabicyclo[3.1.0]hexane-2-carboxamide | * | 2.15 (A) | 575 |
| 479 | 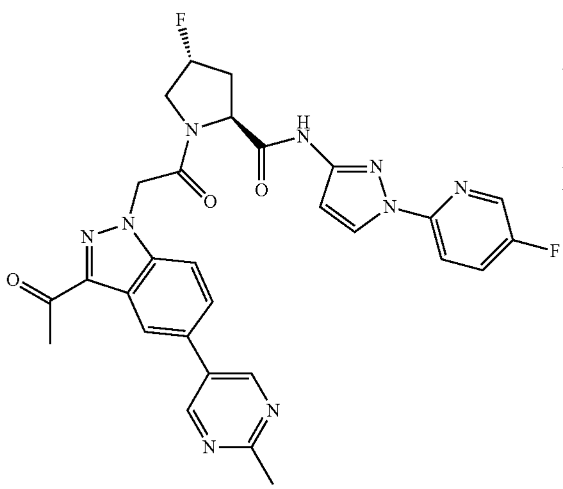 [SMILES: CC(=O)c1nn(CC(=O)N2C[C@H](F)C[C@H]2C(=O)Nc2ccn(-c3ccc(F)cn3)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(1-(5-fluoropyridin-2-yl)-1H-pyrazol-3-yl)pyrrolidine-2-carboxamide | *** | 1.62 (A) | 586 |
| 480 | 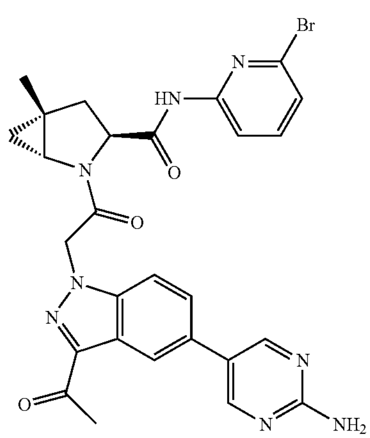 [SMILES: CC(=O)c1nn(CC(=O)N2[C@H](C(=O)Nc3cccc(Br)n3)C[C@@]3(C)C[C@@H]23)c2ccc(-c3cnc(N)nc3)cc12] | (1R,3S,5R)-2-(2-(3-acetyl-5-(2-aminopyrimidin-5-yl)-1H-indazol-1-yl)acetyl)-N-(6-bromopyridin-2-yl)-5-methyl-2-azabicyclo[3.1.0]hexane-3-carboxamide | *** | 3.17 (B) | 589 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 481 | 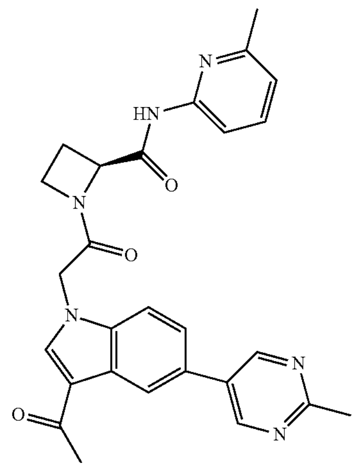 [SMILES: CC(=O)c1cn(CC(=O)N2CC[C@H]2C(=O)Nc2cccc(C)n2)c2ccc(-c3cnc(C)nc3)cc12] | (S)-1-(2-(3-acetyl-5-(2-methylpyrimidin-5-yl)-1H-indol-1-yl)acetyl)-N-(6-methylpyridin-2-yl)azetidine-2-carboxamide | * | 9.30 (C) | 483 |
| 482 | 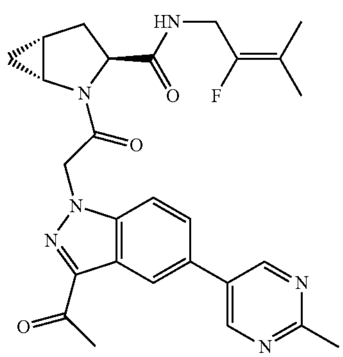 [SMILES: CC(=O)c1nn(CC(=O)N2[C@@H]3C[C@@H]3C[C@H]2C(=O)NCC(F)=C(C)C)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(2-fluoro-3-methylbut-2-en-1-yl)-2-azabicyclo[3.1.0]hexane-3-carboxamide | *** | 11.88 (C) | 505 |
| 483 | 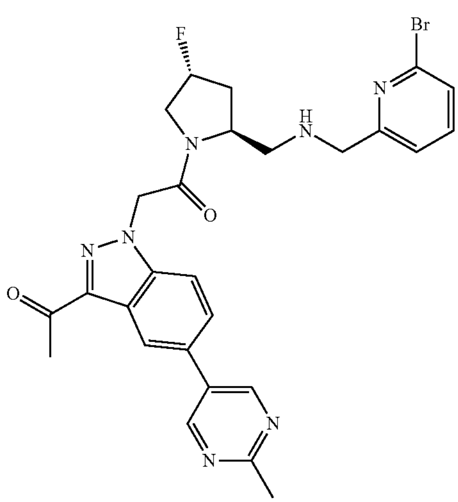 [SMILES: CC(=O)c1nn(CC(=O)N2C[C@H](F)C[C@H]2CNCc2cccc(Br)n2)c2ccc(-c3cnc(C)nc3)cc12] | (2S,4R)-1-(2-(3-acetyl-5-(2-methylpyrimidin-5-yl)-1H-indazol-1-yl)acetyl)-N-((6-bromopyridin-2-yl)methyl)-4-fluoropyrrolidine-2-carboxamide | *** | 1.37 (A) | 594 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 484 | 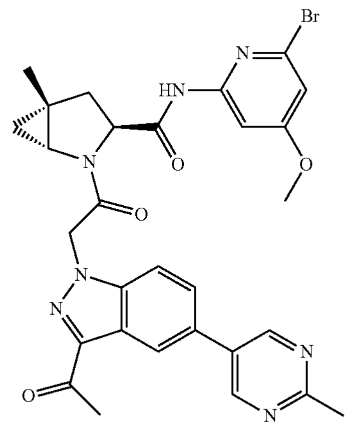 [SMILES: COc1cc(Br)nc(NC(=O)[C@@H]2C[C@@]3(C)C[C@H]3N2C(=O)Cn2nc(C(C)=O)c3cc(-c4cnc(C)nc4)ccc32)c1] | (1R,3S,5R)-2-(2-(3-acetyl-5-(2-methylpyrimidin-5-yl)-1H-indazol-1-yl)acetyl)-N-(6-bromo-4-methoxypyridin-2-yl)-5-methyl-2-azabicyclo[3.1.0]hexane-3-carboxamide | *** | 3.81 (B) | 618 |
| 485 | 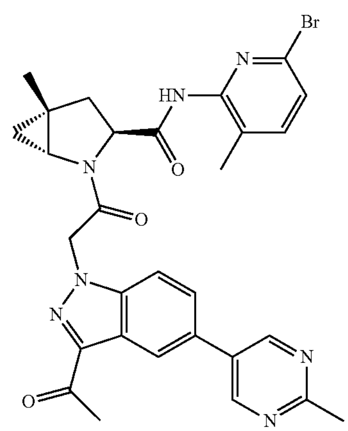 [SMILES: CC(=O)c1nn(CC(=O)N2[C@H](C(=O)Nc3nc(Br)ccc3C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 3.04 (B) | 602 |
| 486 | 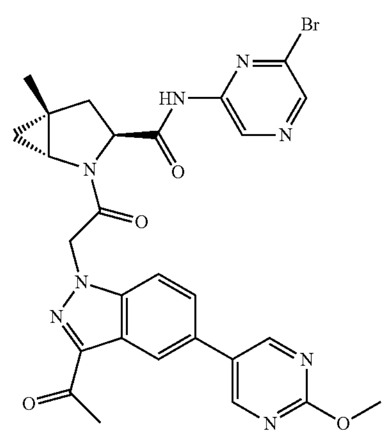 [SMILES: COc1ncc(-c2ccc3c(c2)c(C(C)=O)nn3CC(=O)N2[C@H](C(=O)Nc3cncc(Br)n3)C[C@@]3(C)C[C@@H]23)cn1] | (1R,3S,5R)-2-(2-(3-acetyl-5-(2-methoxypyrimidin-5-yl)-1H-indazol-1-yl)acetyl)-N-(6-bromopyrazin-2-yl)-5-methyl-2-azabicyclo[3.1.0]hexane-3-carboxamide | *** | 3.62 (B) | 605 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 488 | 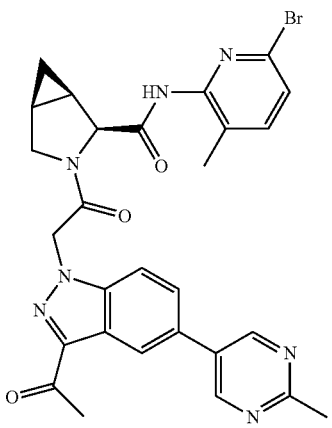 [SMILES: CC(=O)c1nn(CC(=O)N2C[C@H]3C[C@H]3[C@H]2C(=O)Nc2nc(Br)ccc2C)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide | *** | 9.89 (D) | 590 (M + 2) |
| 489 | 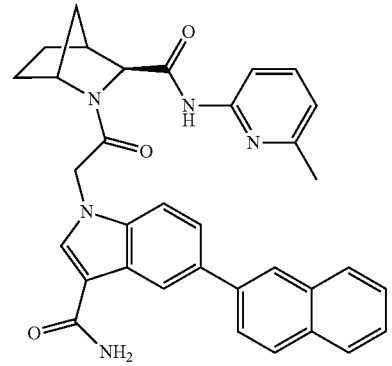 [SMILES: Cc1cccc(NC(=O)[C@@H]2C3CCC(C3)N2C(=O)Cn2cc(C(N)=O)c3cc(-c4ccc5ccccc5c4)ccc32)n1] | 1-(2-((1R,3S,4S)-3-((6-methylpyridin-2-yl)carbamoyl)-2-azabicyclo[2.2.1]heptan-2-yl)-2-oxoethyl)-5-(naphthalen-2-yl)-1H-indole-3-carboxamide | * | 3.49 (B) | 558 |
| 490 | 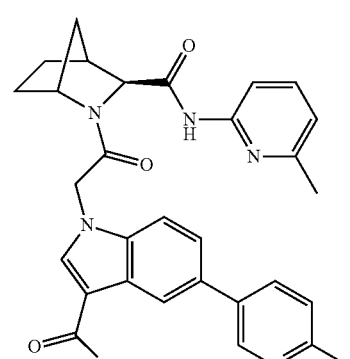 | 1-(2-((1R,3S,4S)-3-((6-methylpyridin-2-yl)carbamoyl)-2-azabicyclo[2.2.1]heptan-2-yl)-2-oxoethyl)-5-(6-methylpyridin-3-yl)-1H-indole-3-carboxamide | * | 1.12 (B) | 523 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 491 | 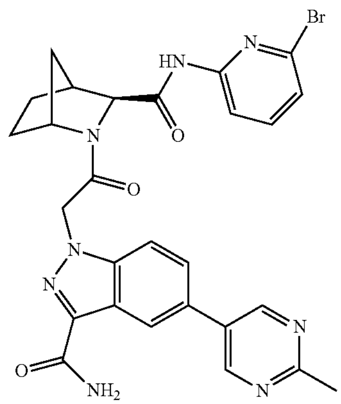 [SMILES: Cc1ncc(-c2ccc3c(c2)c(C(N)=O)nn3CC(=O)N2C3CCC(C3)[C@H]2C(=O)Nc2cccc(Br)n2)cn1] | (1R,3S,4S)-2-(2-(3-acetyl-5-(2-methylpyrimidin-5-yl)-1H-indazol-1-yl)acetyl)-N-(6-bromopyridin-2-yl)-2-azabicyclo[2.2.1]heptane-3-carboxamide | *** | 1.89 (A) | 588 |
| 494 | 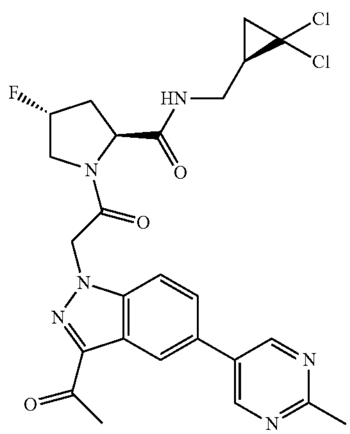 [SMILES: CC(=O)c1nn(CC(=O)N2C[C@H](F)C[C@H]2C(=O)NC[C@H]2CC2(Cl)Cl)c2ccc(-c3cnc(C)nc3)cc12] | (2S,4R)-1-(2-(3-acetyl-5-(2-methylpyrimidin-5-yl)-1H-indazol-1-yl)acetyl)-N-(((R)-2,2-dichlorocyclopropyl)methyl)-4-fluoropyrrolidine-2-carboxamide | *** | 9.91 (D) | 548 |
| 495 | 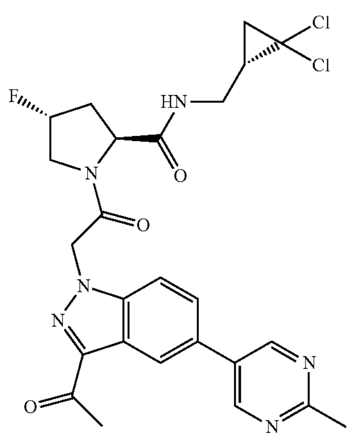 [SMILES: CC(=O)c1nn(CC(=O)N2C[C@H](F)C[C@H]2C(=O)NC[C@@H]2CC2(Cl)Cl)c2ccc(-c3cnc(C)nc3)cc12] | (2S,4R)-1-(2-(3-acetyl-5-(2-methylpyrimidin-5-yl)-1H-indazol-1-yl)acetyl)-N-(((S)-2,2-dichlorocyclopropyl)methyl)-4-fluoropyrrolidine-2-carboxamide | *** | 9.67 (D) | 548 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 496 | 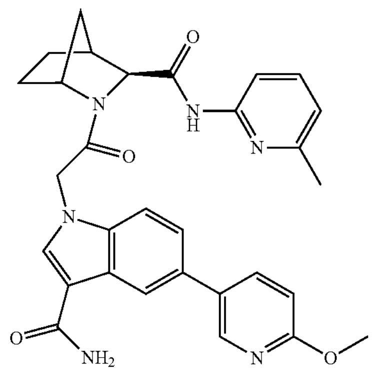 [SMILES: COc1ccc(-c2ccc3c(c2)c(C(N)=O)cn3CC(=O)N2C3CCC(C3)[C@H]2C(=O)Nc2cccc(C)n2)cn1] | 5-(6-methoxypyridin-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 2.34 (B) | 539 |
| 497 | 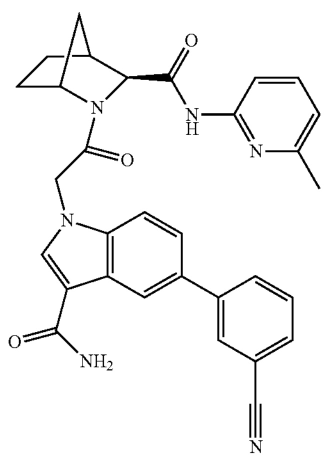 [SMILES: Cc1cccc(NC(=O)[C@@H]2C3CCC(C3)N2C(=O)Cn2cc(C(N)=O)c3cc(-c4cccc(C#N)c4)ccc32)n1] | 5-(3-cyanophenyl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 2.82 (B) | 533 |
| 498 | 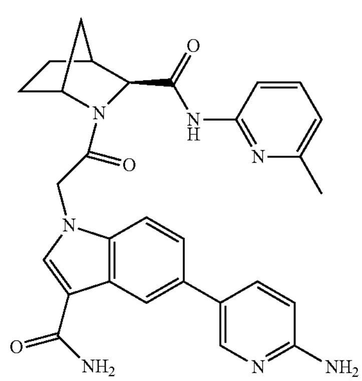 [SMILES: Cc1cccc(NC(=O)[C@@H]2C3CCC(C3)N2C(=O)Cn2cc(C(N)=O)c3cc(-c4ccc(N)nc4)ccc32)n1] | 5-(6-aminopyridin-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 2.60 (B) | 524 |

TABLE 3-continued

Additional Non-limiting Examples of Compounds of Formula I

| Comp No. | Structure | Name | IC5 (Stars) | RT min (Method A,B,C or D) | MS (M + 1) |
|---|---|---|---|---|---|
| 499 | 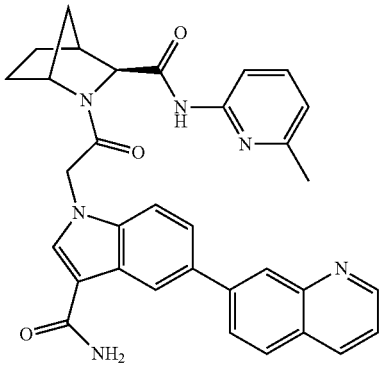 [SMILES: Cc1cccc(NC(=O)[C@@H]2C3CCC(C3)N2C(=O)Cn2cc(C(N)=O)c3cc(-c4ccc5cccnc5c4)ccc32)n1] | 1-(2-((1R,3S,4S)-3-((6-methylpyridin-2-yl)carbamoyl)-2-azabicyclo[2.2.1]heptan-2-yl)-2-oxoethyl)-5-(quinolin-7-yl)-1H-indole-3-carboxamide | ** | 2.02 (B) | 559 |
| 500 | 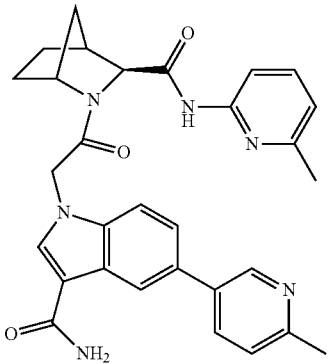 [SMILES: Cc1ccc(-c2ccc3c(c2)c(C(N)=O)cn3CC(=O)N2C3CCC(C3)[C@H]2C(=O)Nc2cccc(C)n2)cn1] | 5-(6-fluoropyridin-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 2.61 (B) | 527 |
| 501 | 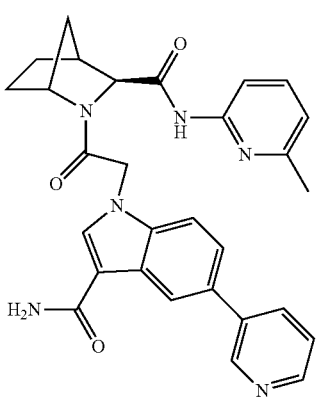 [SMILES: Cc1cccc(NC(=O)[C@@H]2C3CCC(C3)N2C(=O)Cn2cc(C(N)=O)c3cc(-c4cccnc4)ccc32)n1] | 1-(2-((1R,3S,4S)-3-((6-methylpyridin-2-yl)carbamoyl)-2-azabicyclo[2.2.1]heptan-2-yl)-2-oxoethyl)-5-(pyridin-3-yl)-1H-indole-3-carboxamide | * | 3.38 (B) | 509 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 503 | 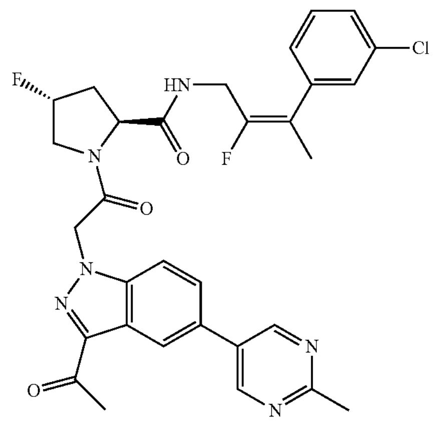 [SMILES: CC(=O)c1nn(CC(=O)N2C[C@H](F)C[C@H]2C(=O)NC/C(F)=C(/C)c2cccc(Cl)c2)c2ccc(-c3cnc(C)nc3)cc12] | (2S,4R)-1-(2-(3-acetyl-5-(2-methylpyrimidin-5-yl)-1H-indazol-1-yl)acetyl)-N-((E)-3-(3-chlorophenyl)-2-fluorobut-2-en-1-yl)-4-fluoropyrrolidine-2-carboxamide | *** | 2.07 (A) | 607 |
| 504 | 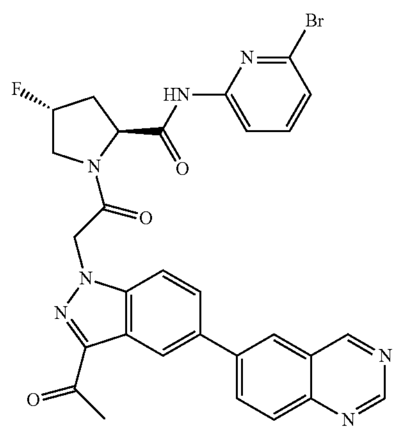 [SMILES: CC(=O)c1nn(CC(=O)N2C[C@H](F)C[C@H]2C(=O)Nc2cccc(Br)n2)c2ccc(-c3ccc4ncncc4c3)cc12] | (2S,4R)-1-(2-(3-acetyl-5-(quinazolin-6-yl)-1H-indazol-1-yl)acetyl)-N-(6-bromopyridin-2-yl)-4-fluoropyrrolidine-2-carboxamide | *** | 1.80 (A) | 616 |
| 505 | 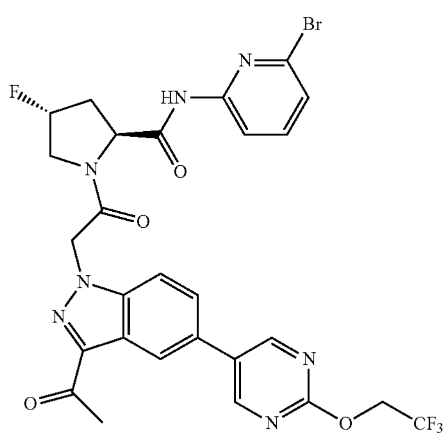 [SMILES: CC(=O)c1nn(CC(=O)N2C[C@H](F)C[C@H]2C(=O)Nc2cccc(Br)n2)c2ccc(-c3cnc(OCC(F)(F)F)nc3)cc12] | (2S,4R)-1-(2-(3-acetyl-5-(2-(2,2,2-trifluoroethoxy)pyrimidin-5-yl)-1H-indazol-1-yl)acetyl)-N-(6-bromopyridin-2-yl)-4-fluoropyrrolidine-2-carboxamide | *** | 2.30 (A) | 664 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 506 | 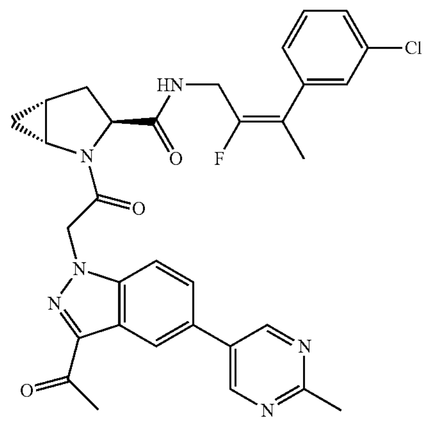 [SMILES: CC(=O)c1nn(CC(=O)N2[C@@H]3C[C@@H]3C[C@H]2C(=O)NC/C(F)=C(/C)c2cccc(Cl)c2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((E)-3-(3-chlorophenyl)-2-fluorobut-2-en-1-yl)-2-azabicyclo[3.1.0]hexane-3-carboxamide | *** | 2.15 (A) | 601 |
| 507 | 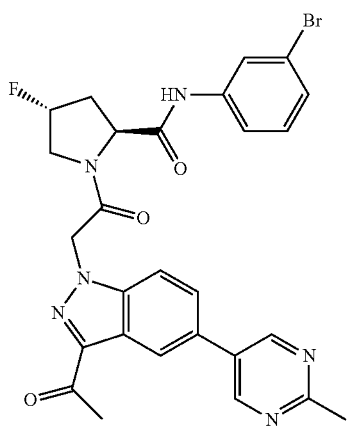 | (2S,4R)-1-(2-(3-acetyl-5-(2-methylpyrimidin-5-yl)-1H-indazol-1-yl)acetyl)-N-(3-bromophenyl)-4-fluoropyrrolidine-2-carboxamide | *** | 10.79 (D) | 577 (M − 2) |
| 508 | 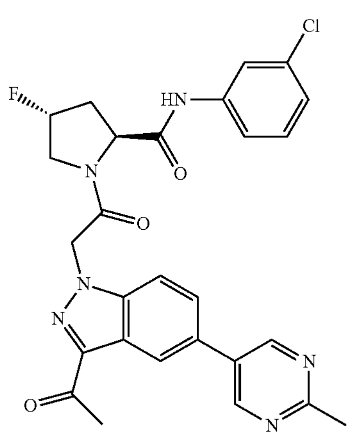 | (2S,4R)-1-(2-(3-acetyl-5-(2-methylpyrimidin-5-yl)-1H-indazol-1-yl)acetyl)-N-(3-chlorophenyl)-4-fluoropyrrolidine-2-carboxamide | *** | 10.95 (D) | 535 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 509 | 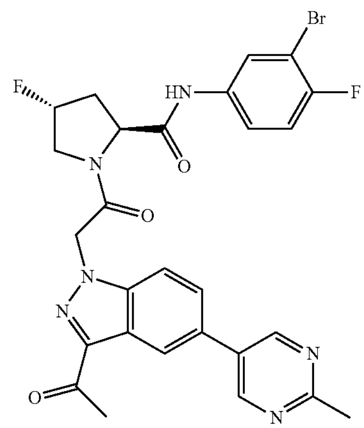 [SMILES: CC(=O)c1nn(CC(=O)N2C[C@H](F)C[C@H]2C(=O)Nc2ccc(F)c(Br)c2)c2ccc(-c3cnc(C)nc3)cc12] | (2S,4R)-1-(2-(3-acetyl-5-(2-methylpyrimidin-5-yl)-1H-indazol-1-yl)acetyl)-N-(3-bromo-4-fluorophenyl)-4-fluoropyrrolidine-2-carboxamide | *** | 11.04 (D) | 599 (M + 2) |
| 510 | 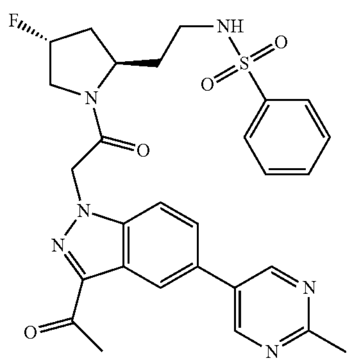 [SMILES: CC(=O)c1nn(CC(=O)N2C[C@H](F)C[C@H]2CCNS(=O)(=O)c2ccccc2)c2ccc(-c3cnc(C)nc3)cc12] | N-(2-((2R,4R)-1-(2-(3-acetyl-5-(2-methylpyrimidin-5-yl)-1H-indol-1-yl)acetyl)-4-fluoropyrrolidin-2-yl)ethyl)benzenesulfonamide | ** | 9.55 (D) | 564 |
| 511 | 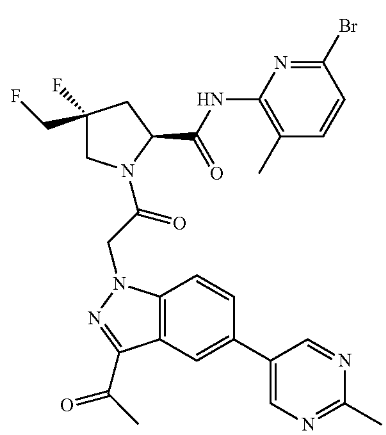 [SMILES: CC(=O)c1nn(CC(=O)N2C[C@@](F)(CF)C[C@H]2C(=O)Nc2nc(Br)ccc2C)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-methylpyridin-2-yl)-4-fluoro-4-(fluoromethyl)pyrrolidine-2-carboxamide | *** | 3.11 (B) | 626 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 512 | 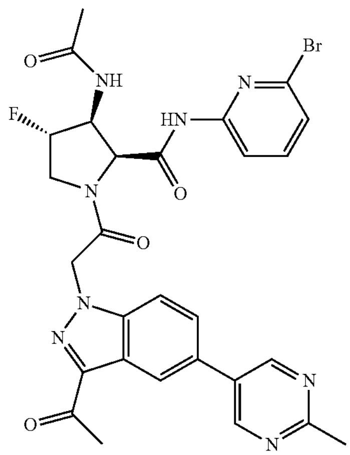 [SMILES: CC(=O)N[C@H]1[C@@H](C(=O)Nc2cccc(Br)n2)N(C(=O)Cn2nc(C(C)=O)c3cc(-c4cnc(C)nc4)ccc32)C[C@@H]1F] | (2S,3S,4S)-3-acetamido-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide | *** | 2.66 (B) | 637 |
| 513 | 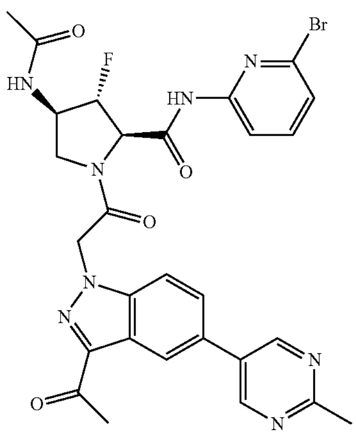 [SMILES: CC(=O)N[C@@H]1CN(C(=O)Cn2nc(C(C)=O)c3cc(-c4cnc(C)nc4)ccc32)[C@H](C(=O)Nc2cccc(Br)n2)[C@H]1F] | (2R,3S,4R)-4-acetamido-1-(2-(3-acetyl-5-(2-methylpyrimidin-5-yl)-1H-indazol-1-yl)acetyl)-N-(6-bromopyridin-2-yl)-3-fluoropyrrolidine-2-carboxamide | *** | 2.77 (B) | 637 |
| 514 | 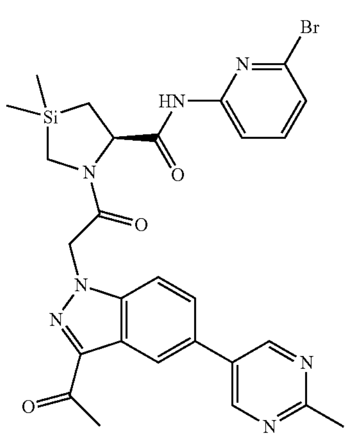 | (R)-1-(2-(3-acetyl-5-(2-methylpyrimidin-5-yl)-1H-indazol-1-yl)acetyl)-N-(6-bromopyridin-2-yl)-3,3-dimethyl-1,3-azasilolidine-5-carboxamide | ** | 3.49 (B) | 606 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 515 | 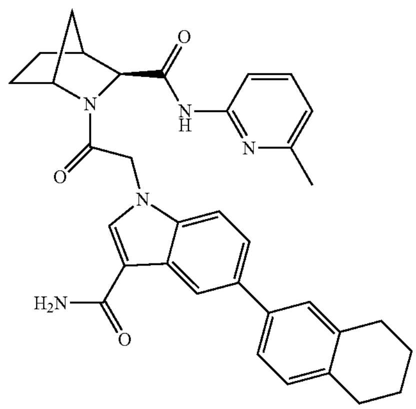 [SMILES: Cc1cccc(NC(=O)[C@@H]2C3CCC(C3)N2C(=O)Cn2cc(C(N)=O)c3cc(-c4ccc5c(c4)CCCC5)ccc32)n1] | 1-(2-((1R,3S,4S)-3-((6-methylpyridin-2-yl)carbamoyl)-2-azabicyclo[2.2.1]heptan-2-yl)-2-oxoethyl)-5-(5,6,7,8-tetrahydronaphthalen-2-yl)-1H-indole-3-carboxamide | * | 3.72 (B) | 562 |
| 516 | 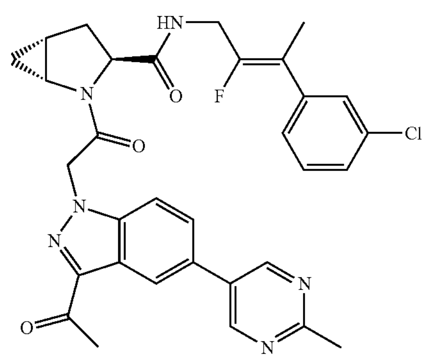 [SMILES: CC(=O)c1nn(CC(=O)N2[C@@H]3C[C@@H]3C[C@H]2C(=O)NC/C(F)=C(\C)c2cccc(Cl)c2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((Z)-3-(3-chlorophenyl)-2-fluorobut-2-en-1-yl)-2-azabicyclo[3.1.0]hexane-3-carboxamide | *** | 2.07 (A) | 601 |
| 517 | 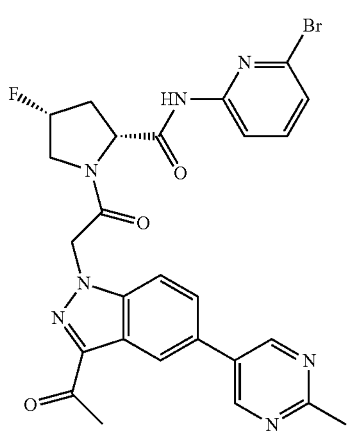 [SMILES: CC(=O)c1nn(CC(=O)N2C[C@H](F)C[C@@H]2C(=O)Nc2cccc(Br)n2)c2ccc(-c3cnc(C)nc3)cc12] | (2R,4R)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide | * | | |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 518 | 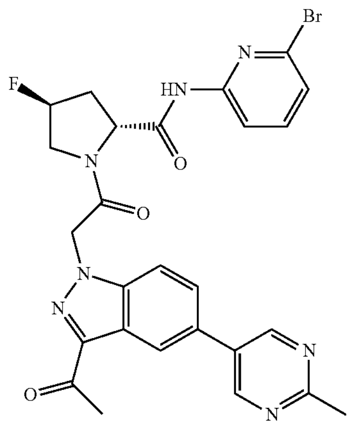 [SMILES: CC(=O)c1nn(CC(=O)N2C[C@@H](F)C[C@@H]2C(=O)Nc2cccc(Br)n2)c2ccc(-c3cnc(C)nc3)cc12] | (2R,4S)-1-(2-(3-acetyl-5-(2-methylpyrimidin-5-yl)-1H-indazol-1-yl)acetyl)-N-(6-bromopyridin-2-yl)-4-fluoropyrrolidine-2-carboxamide | * | | |
| 519 | 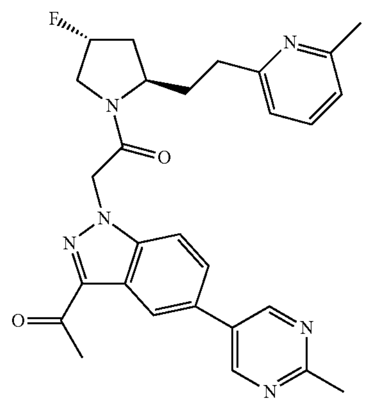 [SMILES: CC(=O)c1nn(CC(=O)N2C[C@H](F)C[C@H]2CCc2cccc(C)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-(pentyloxy)pyridin-2-yl)pyrrolidine-2-carboxamide | ** | 2.34 (A) | 588 |
| 520 | 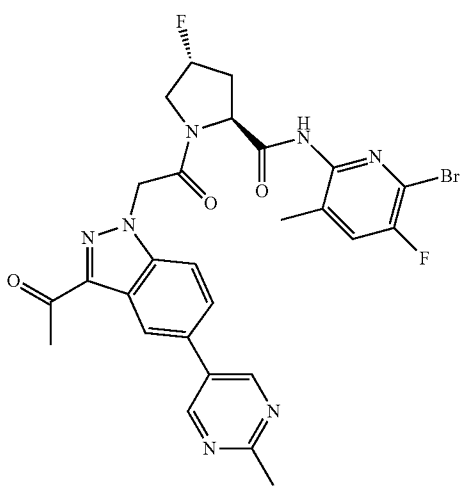 [SMILES: CC(=O)c1nn(CC(=O)N2C[C@H](F)C[C@H]2C(=O)Nc2nc(Br)c(F)cc2C)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-5-fluoro-3-methylpyridin-2-yl)-4-fluoropyrrolidine-2-carboxamide | *** | 1.58 (A) | 612 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 521 | 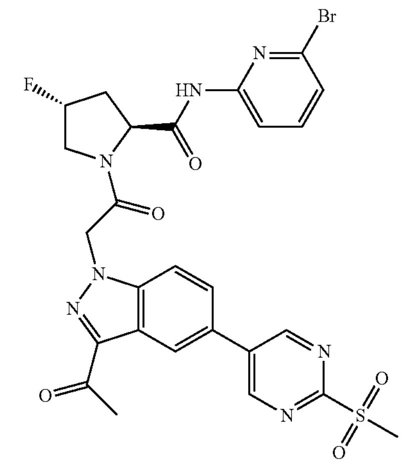 [SMILES: CC(=O)c1nn(CC(=O)N2C[C@H](F)C[C@H]2C(=O)Nc2cccc(Br)n2)c2ccc(-c3cnc(S(C)(=O)=O)nc3)cc12] | (2S,4R)-1-(2-(3-acetyl-5-(2-(methylsulfonyl)pyrimidin-5-yl)-1H-indazol-1-yl)acetyl)-N-(6-bromopyridin-2-yl)-4-fluoropyrrolidine-2-carboxamide | *** | 1.71 (A) | 644 |
| 522 | 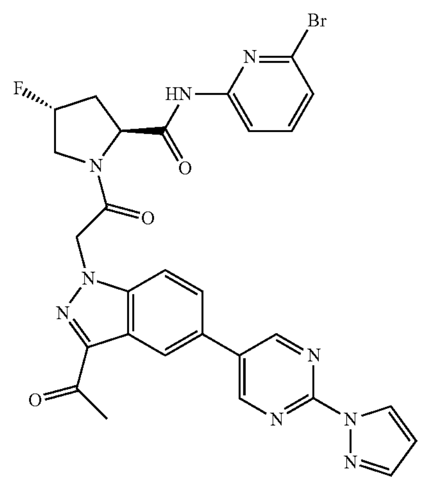 [SMILES: CC(=O)c1nn(CC(=O)N2C[C@H](F)C[C@H]2C(=O)Nc2cccc(Br)n2)c2ccc(-c3cnc(-n4cccn4)nc3)cc12] | (2S,4R)-1-(2-(5-(2-(1H-pyrazol-1-yl)pyrimidin-5-yl)-3-acetyl-1H-indazol-1-yl)acetyl)-N-(6-bromopyridin-2-yl)-4-fluoropyrrolidine-2-carboxamide | *** | 1.90 (A) | 632 |
| 523 | 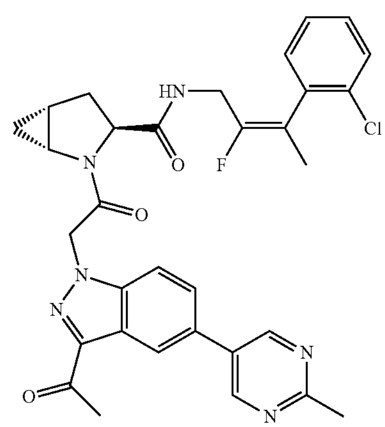 [SMILES: CC(=O)c1nn(CC(=O)N2[C@@H]3C[C@@H]3C[C@H]2C(=O)NC/C(F)=C(/C)c2ccccc2Cl)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((E)-3-(2-chlorophenyl)-2-fluorobut-2-en-1-yl)-2-azabicyclo[3.1.0]hexane-3-carboxamide | *** | 2.11 (A) | 601 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 524 | 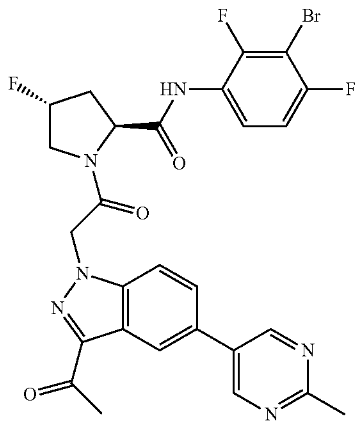 [SMILES: CC(=O)c1nn(CC(=O)N2C[C@H](F)C[C@H]2C(=O)Nc2ccc(F)c(Br)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(3-bromo-2,4-difluorophenyl)-4-fluoropyrrolidine-2-carboxamide | *** | 10.88 (D) | 616 |
| 525 | 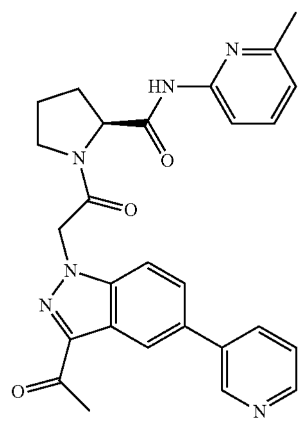 [SMILES: CC(=O)c1nn(CC(=O)N2CCC[C@H]2C(=O)Nc2cccc(C)n2)c2ccc(-c3cccnc3)cc12] | (S)-1-(2-(3-acetyl-5-(pyridin-3-yl)-1H-indazol-1-yl)acetyl)-N-(6-methylpyridin-2-yl)pyrrolidine-2-carboxamide | ** | 8.39 (C) | 483 |
| 526 | 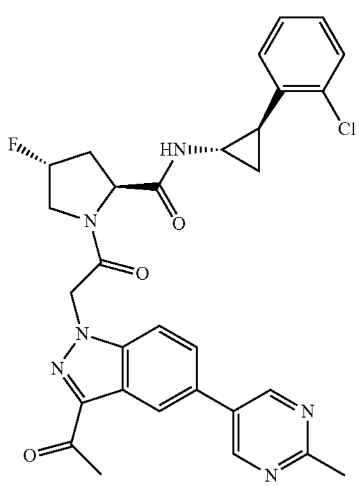 [SMILES: CC(=O)c1nn(CC(=O)N2C[C@H](F)C[C@H]2C(=O)N[C@H]2C[C@@H]2c2ccccc2Cl)c2ccc(-c3cnc(C)nc3)cc12] | (2S,4R)-1-(2-(3-acetyl-5-(2-methylpyrimidin-5-yl)-1H-indazol-1-yl)acetyl)-N-((1S,2R)-2-(2-chlorophenyl)cyclopropyl)-4-fluoropyrrolidine-2-carboxamide | *** | 10.75 (D) | 576 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 527 | 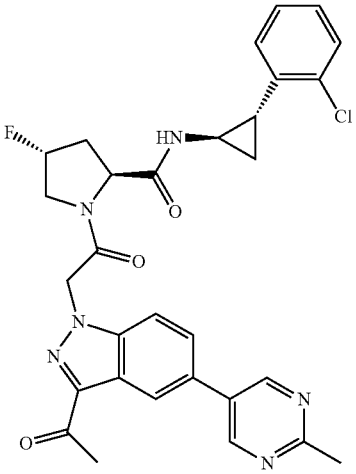 [SMILES: CC(=O)c1nn(CC(=O)N2C[C@H](F)C[C@H]2C(=O)N[C@@H]2C[C@H]2c2ccccc2Cl)c2ccc(-c3cnc(C)nc3)cc12] | (2S,4R)-1-(2-(3-acetyl-5-(2-methylpyrimidin-5-yl)-1H-indazol-1-yl)acetyl)-N-((1R,2S)-2-(2-chlorophenyl)cyclopropyl)-4-fluoropyrrolidine-2-carboxamide | *** | 10.57 (D) | 576 |
| 528 | 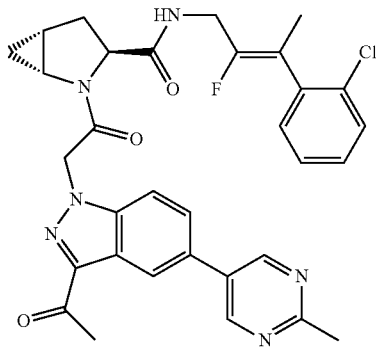 [SMILES: CC(=O)c1nn(CC(=O)N2[C@@H]3C[C@@H]3C[C@H]2C(=O)NC/C(F)=C(\C)c2ccccc2Cl)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((Z)-3-(2-chlorophenyl)-2-fluorobut-2-en-1-yl)-2-azabicyclo[3.1.0]hexane-3-carboxamide | *** | 2.01 (A) | 601 |
| 529 | 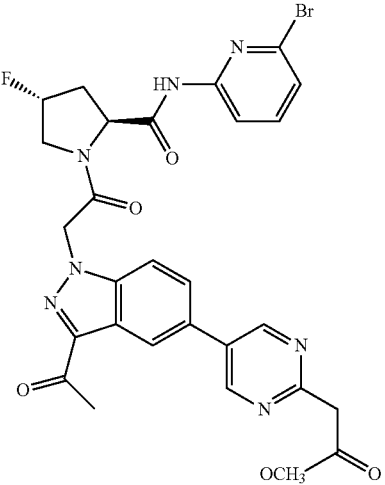 [SMILES: COC(=O)Cc1ncc(-c2ccc3c(c2)c(C(C)=O)nn3CC(=O)N2C[C@H](F)C[C@H]2C(=O)Nc2cccc(Br)n2)cn1] | methyl 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate | *** | 1.77 (A) | 638 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 530 | 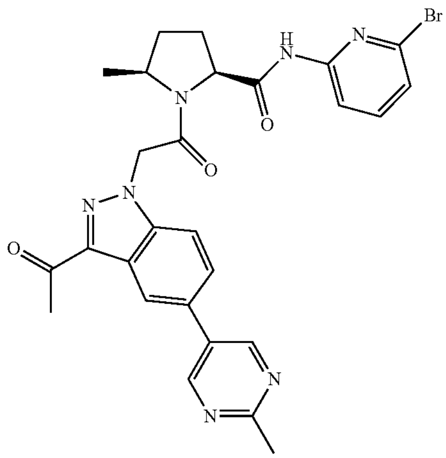 [SMILES: CC(=O)c1nn(CC(=O)N2[C@@H](C)CC[C@H]2C(=O)Nc2cccc(Br)n2)c2ccc(-c3cnc(C)nc3)cc12] | (2S,5S)-1-(2-(3-acetyl-5-(2-methylpyrimidin-5-yl)-1H-indazol-1-yl)acetyl)-N-(6-bromopyridin-2-yl)-5-methylpyrrolidine-2-carboxamide | *** | 1.90 (A) | 576 |
| 531 | 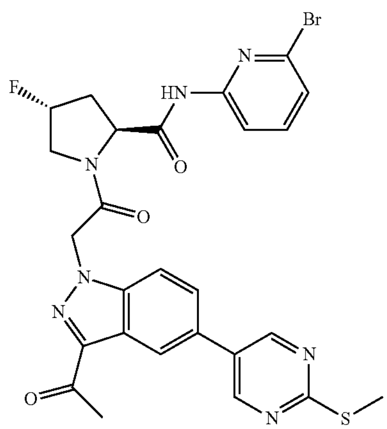 [SMILES: CSc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(3-acetyl-5-(2-(methylthio)pyrimidin-5-yl)-1H-indazol-1-yl)acetyl)-N-(6-bromopyridin-2-yl)-4-fluoropyrrolidine-2-carboxamide | *** | 2.17 (A) | 612 |
| 532 | 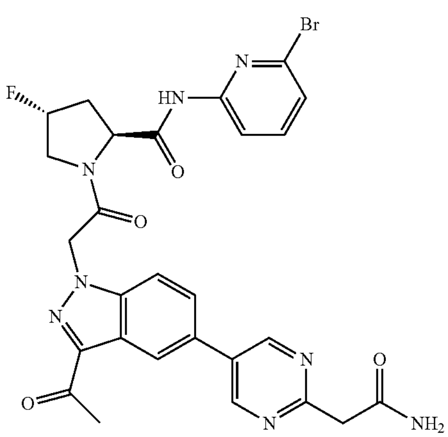 [SMILES: CC(=O)c1nn(CC(=O)N2C[C@H](F)C[C@H]2C(=O)Nc2cccc(Br)n2)c2ccc(-c3cnc(CC(N)=O)nc3)cc12] | (2S,4R)-1-(2-(3-acetyl-5-(2-(2-amino-2-oxoethyl)pyrimidin-5-yl)-1H-indazol-1-yl)acetyl)-N-(6-bromopyridin-2-yl)-4-fluoropyrrolidine-2-carboxamide | *** | 1.36 (A) | 623 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 533 | 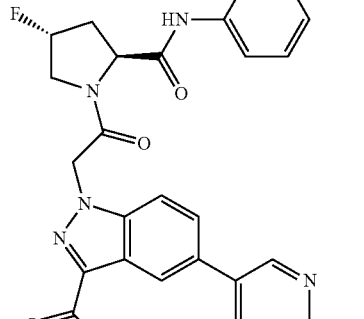 | 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetic acid | *** | 1.50 (A) | 624 |
| 534 | 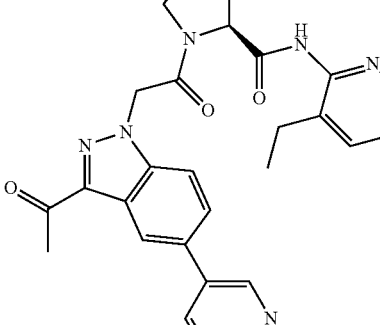 | (2S,4R)-1-(2-(3-acetyl-5-(2-methylpyrimidin-5-yl)-1H-indazol-1-yl)acetyl)-N-(6-bromo-3-ethylpyridin-2-yl)-4-fluoropyrrolidine-2-carboxamide | *** | 1.62 (A) | 608 |
| 535 | 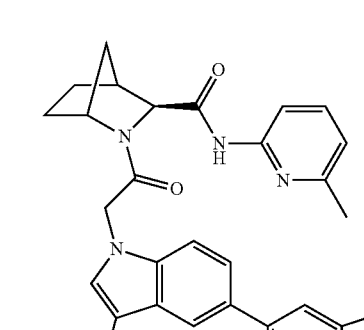 | 5-(6,7-dihydro-5H-cyclopenta[b]pyridin-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 3.55 (B) | 549 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 536 | 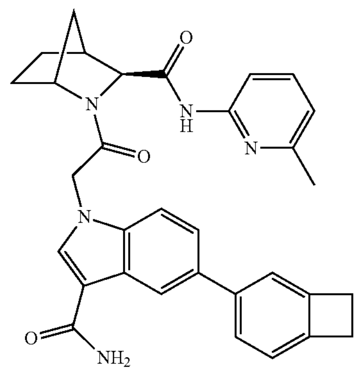 [SMILES: Cc1cccc(NC(=O)[C@@H]2C3CCC(C3)N2C(=O)Cn2cc(C(N)=O)c3cc(-c4ccc5c(c4)CC5)ccc32)n1] | 5-(bicyclo[4.2.0]octa-1,3,5-trien-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 3.53 (B) | 534 |
| 537 | 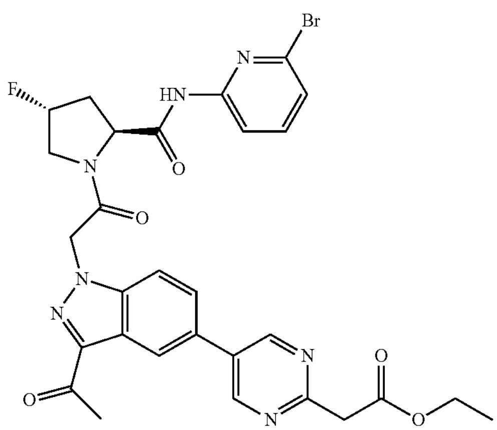 [SMILES: CCOC(=O)Cc1ncc(-c2ccc3c(c2)c(C(C)=O)nn3CC(=O)N2C[C@H](F)C[C@H]2C(=O)Nc2cccc(Br)n2)cn1] | ethyl 2-(5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)acetate | *** | 1.93 (A) | 652 |
| 538 | 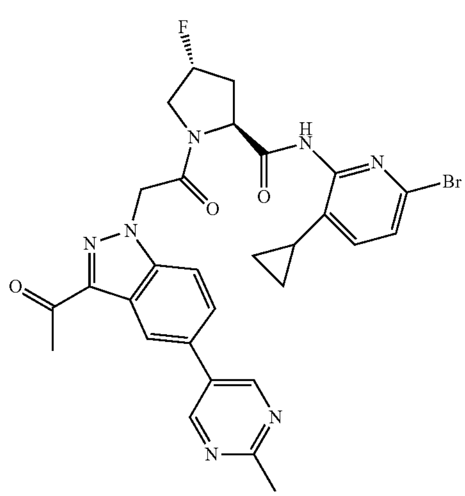 [SMILES: CC(=O)c1nn(CC(=O)N2C[C@H](F)C[C@H]2C(=O)Nc2nc(Br)ccc2C2CC2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-cyclopropylpyridin-2-yl)-4-fluoropyrrolidine-2-carboxamide | *** | 1.68 (A) | 620 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 539 | 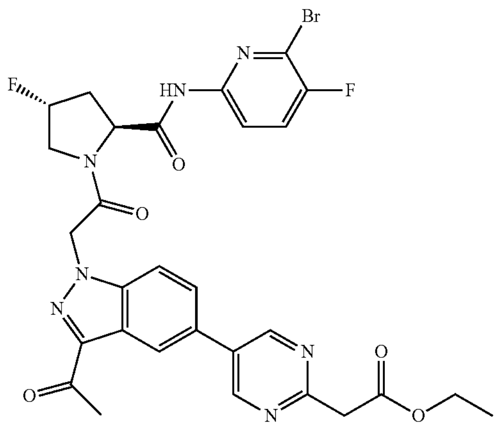 [SMILES: CCOC(=O)Cc1ncc(-c2ccc3c(c2)c(C(C)=O)nn3CC(=O)N2C[C@H](F)C[C@H]2C(=O)Nc2ccc(F)c(Br)n2)cn1] | ethyl 2-(5-(3-acetyl-1-(2-((2S,4R)-2-((6-bromo-5-fluoropyridin-2-yl)carbamoyl)-4-fluoropyrrolidin-1-yl)-2-oxoethyl)-1H-indazol-5-yl)pyrimidin-2-yl)acetate | *** | 2.00 (A) | 670 |
| 540 | 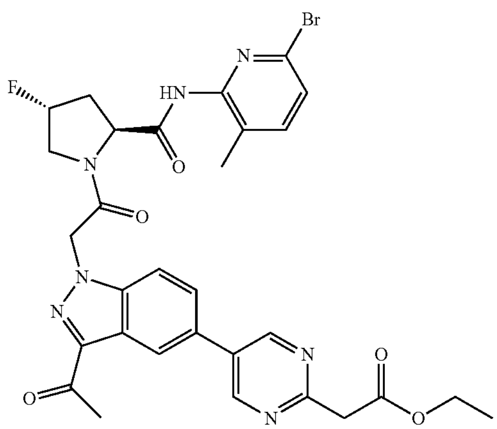 [SMILES: CCOC(=O)Cc1ncc(-c2ccc3c(c2)c(C(C)=O)nn3CC(=O)N2C[C@H](F)C[C@H]2C(=O)Nc2nc(Br)ccc2C)cn1] | ethyl 2-(5-(3-acetyl-1-(2-((2S,4R)-2-((6-bromo-3-methylpyridin-2-yl)carbamoyl)-4-fluoropyrrolidin-1-yl)-2-oxoethyl)-1H-indazol-5-yl)pyrimidin-2-yl)acetate | *** | 1.77 (A) | 666 |
| 541 | 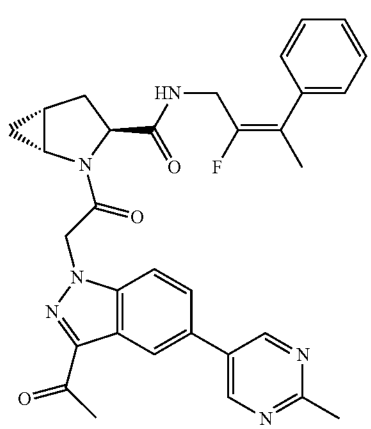 [SMILES: CC(=O)c1nn(CC(=O)N2[C@@H]3C[C@@H]3C[C@H]2C(=O)NC/C(F)=C(/C)c2ccccc2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((E)-2-fluoro-3-phenylbut-2-en-1-yl)-2-azabicyclo[3.1.0]hexane-3-carboxamide | *** | 1.95 (A) | 566 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 542 | 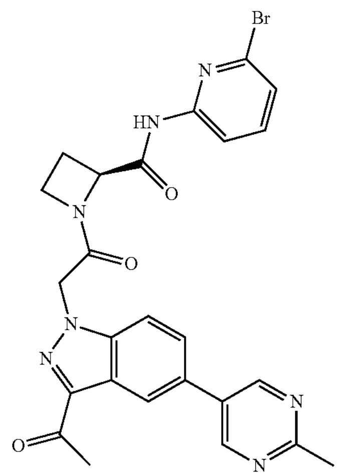 [SMILES: CC(=O)c1nn(CC(=O)N2CC[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)azetidine-2-carboxamide | *** | 10.44 (D) | 550 (M + 2) |
| 543 | 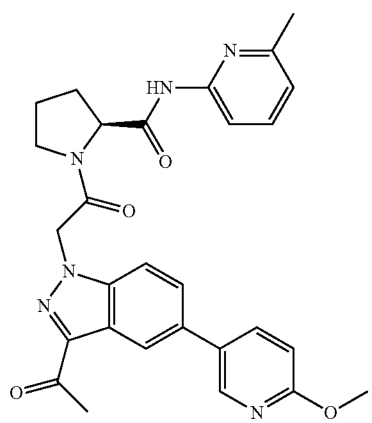 [SMILES: COc1ccc(-c2ccc3c(c2)c(C(C)=O)nn3CC(=O)N2CCC[C@H]2C(=O)Nc2cccc(C)n2)cn1] | (S)-1-(2-(3-acetyl-5-(6-methoxypyridin-3-yl)-1H-indazol-1-yl)acetyl)-N-(6-methylpyridin-2-yl)pyrrolidine-2-carboxamide | ** | 11.84 (D) | 513 |
| 544 | 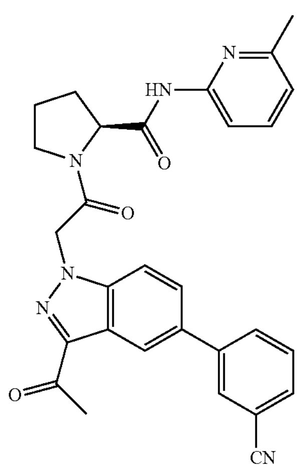 [SMILES: CC(=O)c1nn(CC(=O)N2CCC[C@H]2C(=O)Nc2cccc(C)n2)c2ccc(-c3cccc(C#N)c3)cc12] | (S)-1-(2-(3-acetyl-5-(3-cyanophenyl)-1H-indazol-1-yl)acetyl)-N-(6-methylpyridin-2-yl)pyrrolidine-2-carboxamide | ** | 12.35 (D) | 507 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 545 | 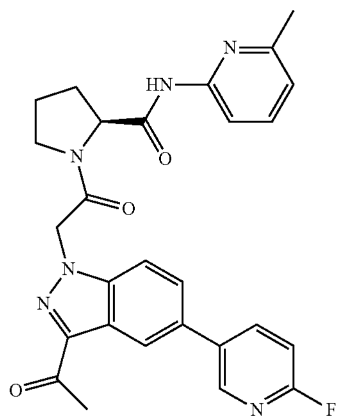 [SMILES: CC(=O)c1nn(CC(=O)N2CCC[C@H]2C(=O)Nc2cccc(C)n2)c2ccc(-c3ccc(F)nc3)cc12] | (S)-1-(2-(3-acetyl-5-(6-fluoropyridin-3-yl)-1H-indazol-1-yl)acetyl)-N-(6-methylpyridin-2-yl)pyrrolidine-2-carboxamide | ** | 11.64 (D) | 501 |
| 546 | 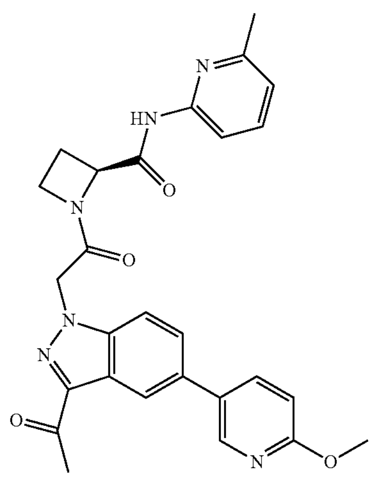 [SMILES: COc1ccc(-c2ccc3c(c2)c(C(C)=O)nn3CC(=O)N2CC[C@H]2C(=O)Nc2cccc(C)n2)cn1] | (S)-1-(2-(3-acetyl-5-(6-methoxypyridin-3-yl)-1H-indazol-1-yl)acetyl)-N-(6-methylpyridin-2-yl)azetidine-2-carboxamide | * | 11.64 (D) | 499 |
| 547 | 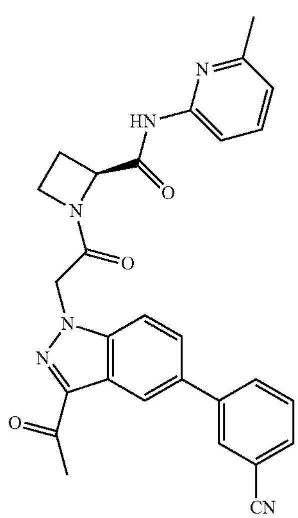 [SMILES: CC(=O)c1nn(CC(=O)N2CC[C@H]2C(=O)Nc2cccc(C)n2)c2ccc(-c3cccc(C#N)c3)cc12] | (S)-1-(2-(3-acetyl-5-(3-cyanophenyl)-1H-indazol-1-yl)acetyl)-N-(6-methylpyridin-2-yl)azetidine-2-carboxamide | * | 12.17 (D) | 493 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 548 | 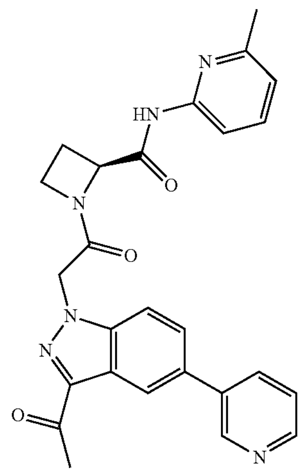 [SMILES: CC(=O)c1nn(CC(=O)N2CC[C@H]2C(=O)Nc2cccc(C)n2)c2ccc(-c3cccnc3)cc12] | (S)-1-(2-(3-acetyl-5-(pyridin-3-yl)-1H-indazol-1-yl)acetyl)-N-(6-methylpyridin-2-yl)azetidine-2-carboxamide | * | 10.11 (D) | 469 |
| 549 | 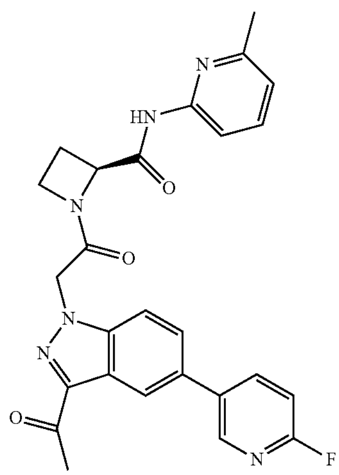 [SMILES: CC(=O)c1nn(CC(=O)N2CC[C@H]2C(=O)Nc2cccc(C)n2)c2ccc(-c3ccc(F)nc3)cc12] | (S)-1-(2-(3-acetyl-5-(6-fluoropyridin-3-yl)-1H-indazol-1-yl)acetyl)-N-(6-methylpyridin-2-yl)azetidine-2-carboxamide | * | 11.35 (D) | 487 |
| 550 | 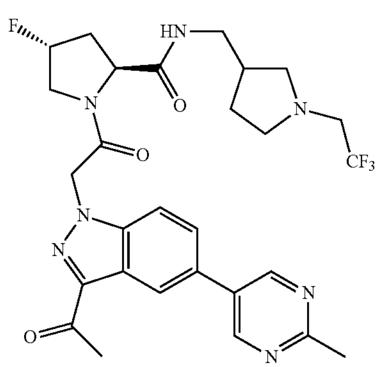 [SMILES: CC(=O)c1nn(CC(=O)N2C[C@H](F)C[C@H]2C(=O)NCC2CCN(CC(F)(F)F)C2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-((1-(2,2,2-trifluoroethyl)pyrrolidin-3-yl)methyl)pyrrolidine-2-carboxamide | ** | 9.32 (D) | 590 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 551 | 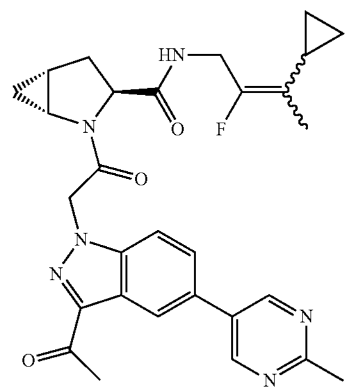 | (1R,3S,5R)-2-(2-(3-acetyl-5-(2-methylpyrimidin-5-yl)-1H-indazol-1-yl)acetyl)-N-(3-cyclopropyl-2-fluorobut-2-en-1-yl)-2-azabicyclo[3.1.0]hexane-3-carboxamide | *** | 1.70 (A) | 531 |
| 554 | 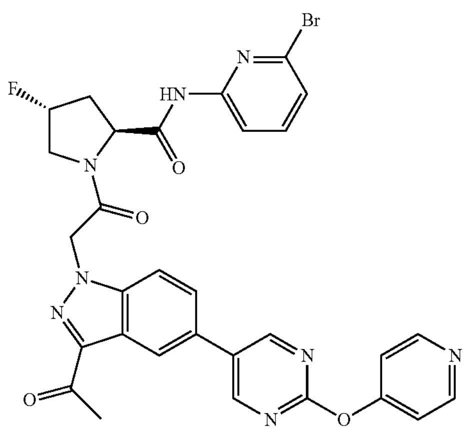 [SMILES: CC(=O)c1nn(CC(=O)N2C[C@H](F)C[C@H]2C(=O)Nc2cccc(Br)n2)c2ccc(-c3cnc(Oc4ccncc4)nc3)cc12] | (2S,4R)-1-(2-(3-acetyl-5-(2-(pyridin-4-yloxy)pyrimidin-5-yl)-1H-indazol-1-yl)acetyl)-N-(6-bromopyridin-2-yl)-4-fluoropyrrolidine-2-carboxamide | *** | 1.69 (A) | 659 |
| 555 | 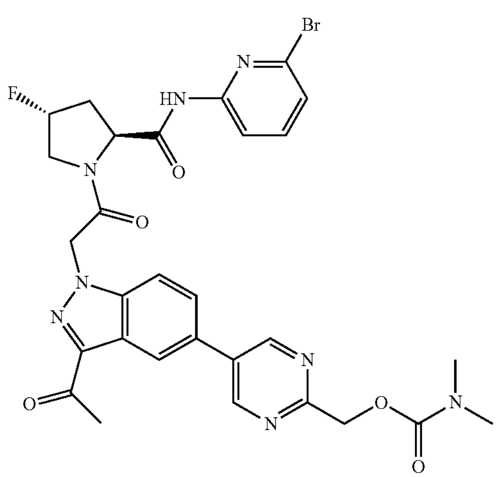 [SMILES: CC(=O)c1nn(CC(=O)N2C[C@H](F)C[C@H]2C(=O)Nc2cccc(Br)n2)c2ccc(-c3cnc(COC(=O)N(C)C)nc3)cc12] | (5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidin-2-yl)methyl dimethylcarbamate | *** | 1.79 (A) | 667 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 556 | 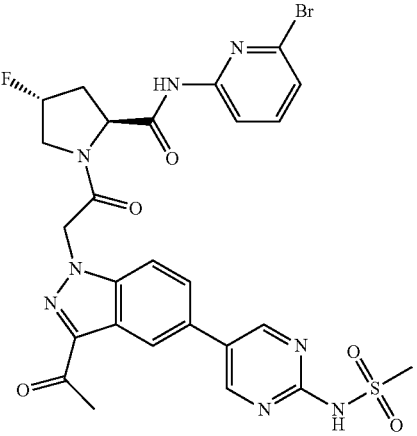 [SMILES: CC(=O)c1nn(CC(=O)N2C[C@H](F)C[C@H]2C(=O)Nc2cccc(Br)n2)c2ccc(-c3cnc(NS(C)(=O)=O)nc3)cc12] | (2S,4R)-1-(2-(3-acetyl-5-(2-(methylsulfonamido)pyrimidin-5-yl)-1H-indazol-1-yl)acetyl)-N-(6-bromopyridin-2-yl)-4-fluoropyrrolidine-2-carboxamide | *** | 1.63 (A) | 659 |
| 557 | 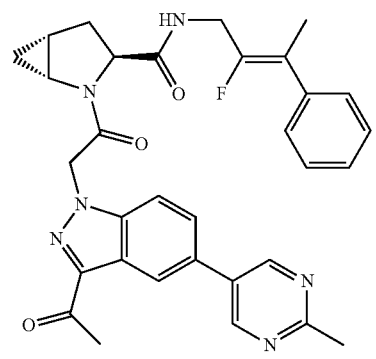 [SMILES: CC(=O)c1nn(CC(=O)N2[C@@H]3C[C@@H]3C[C@H]2C(=O)NC/C(F)=C(\C)c2ccccc2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((Z)-2-fluoro-3-phenylbut-2-en-1-yl)-2-azabicyclo[3.1.0]hexane-3-carboxamide | *** | 1.87 (A) | 567 |
| 558 | 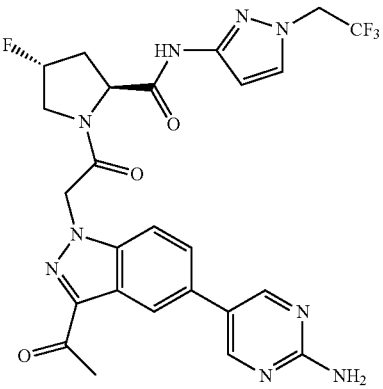 [SMILES: CC(=O)c1nn(CC(=O)N2C[C@H](F)C[C@H]2C(=O)Nc2ccn(CC(F)(F)F)n2)c2ccc(-c3cnc(N)nc3)cc12] | (2S,4R)-1-(2-(3-acetyl-5-(2-aminopyrimidin-5-yl)-1H-indazol-1-yl)acetyl)-4-fluoro-N-(1-(2,2,2-trifluoroethyl)-1H-pyrazol-3-yl)pyrrolidine-2-carboxamide | *** | 1.23 (A) | 574 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 559 | 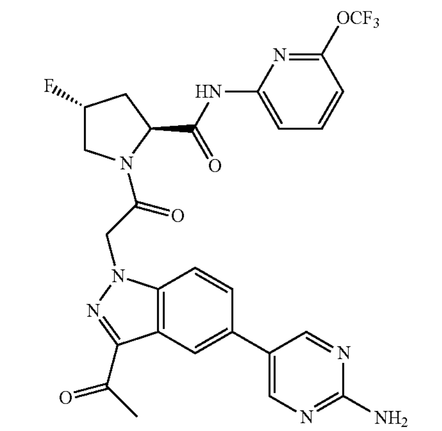 | (2S,4R)-1-(2-(3-acetyl-5-(2-aminopyrimidin-5-yl)-1H-indazol-1-yl)acetyl)-4-fluoro-N-(6-(trifluoromethoxy)pyridin-2-yl)pyrrolidine-2-carboxamide | *** | 1.74 (A) | 586 |
| 560 | 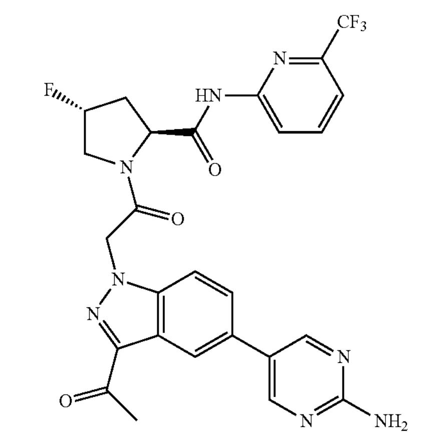 | (2S,4R)-1-(2-(3-acetyl-5-(2-aminopyrimidin-5-yl)-1H-indazol-1-yl)acetyl)-4-fluoro-N-(6-(trifluoromethyl)pyridin-2-yl)pyrrolidine-2-carboxamide | *** | 1.63 (A) | 571 |
| 561 | 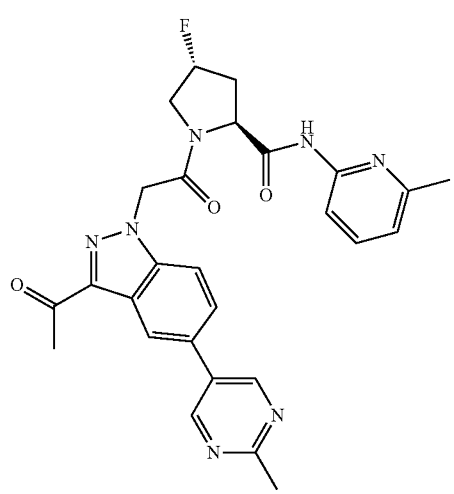 [SMILES: CC(=O)c1nn(CC(=O)N2C[C@H](F)C[C@H]2C(=O)Nc2cccc(C)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-methylpyridin-2-yl)pyrrolidine-2-carboxamide | *** | 1.35 (A) | 515 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 562 | 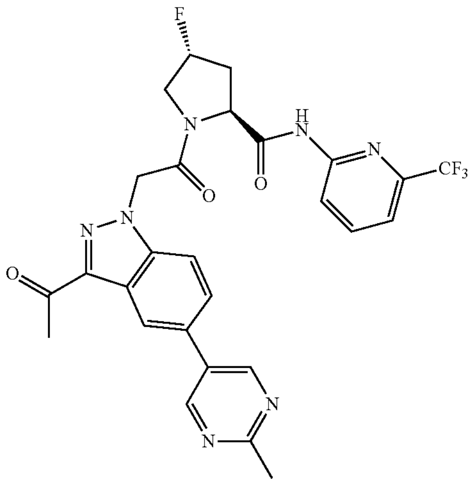 [SMILES: CC(=O)c1nn(CC(=O)N2C[C@H](F)C[C@H]2C(=O)Nc2cccc(C(F)(F)F)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-(trifluoromethyl)pyridin-2-yl)pyrrolidine-2-carboxamide | *** | 1.81 (A) | 570 |
| 563 | 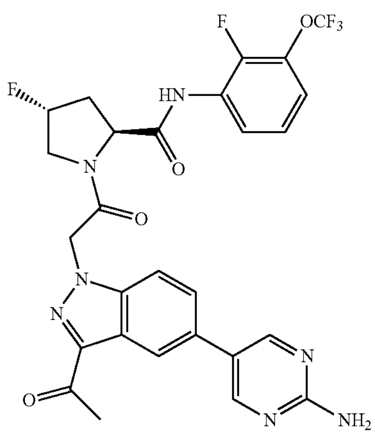 [SMILES: CC(=O)c1nn(CC(=O)N2C[C@H](F)C[C@H]2C(=O)Nc2cccc(OC(F)(F)F)c2F)c2ccc(-c3cnc(N)nc3)cc12] | (2S,4R)-1-(2-(3-acetyl-5-(2-aminopyrimidin-5-yl)-1H-indazol-1-yl)acetyl)-4-fluoro-N-(2-fluoro-3-(trifluoromethoxy)phenyl)pyrrolidine-2-carboxamide | *** | 1.81 (A) | 604 |
| 564 | 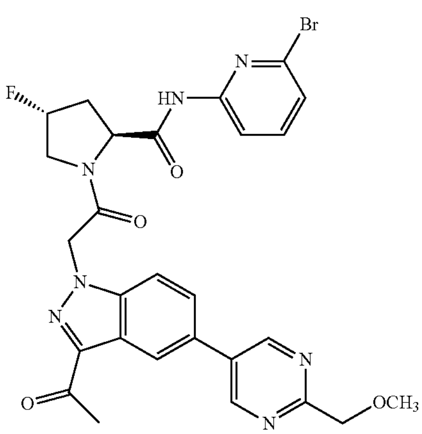 [SMILES: COCc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(3-acetyl-5-(2-(methoxymethyl)pyrimidin-5-yl)-1H-indazol-1-yl)acetyl)-N-(6-bromopyridin-2-yl)-4-fluoropyrrolidine-2-carboxamide | ND | 1.48 (A) | 610 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 565 | 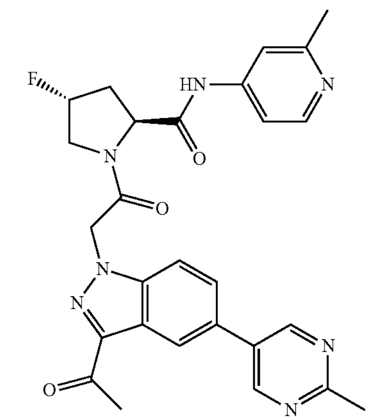 [SMILES: CC(=O)c1nn(CC(=O)N2C[C@H](F)C[C@H]2C(=O)Nc2ccnc(C)c2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(2-methylpyridin-4-yl)pyrrolidine-2-carboxamide | ** | 1.02 (A) | 516 |
| 566 | 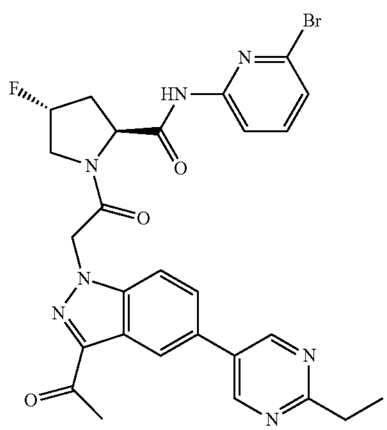 [SMILES: CCc1ncc(-c2ccc3c(c2)c(C(C)=O)nn3CC(=O)N2C[C@H](F)C[C@H]2C(=O)Nc2cccc(Br)n2)cn1] | (2S,4R)-1-(2-(3-acetyl-5-(2-ethylpyrimidin-5-yl)-1H-indazol-1-yl)acetyl)-N-(6-bromopyridin-2-yl)-4-fluoropyrrolidine-2-carboxamide | *** | 1.90 (A) | 594 |
| 567 | 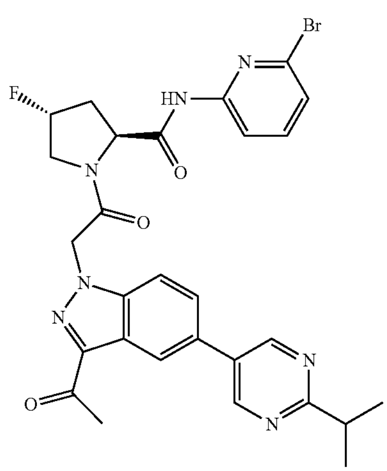 [SMILES: CC(=O)c1nn(CC(=O)N2C[C@H](F)C[C@H]2C(=O)Nc2cccc(Br)n2)c2ccc(-c3cnc(C(C)C)nc3)cc12] | (2S,4R)-1-(2-(3-acetyl-5-(2-isopropylpyrimidin-5-yl)-1H-indazol-1-yl)acetyl)-N-(6-bromopyridin-2-yl)-4-fluoropyrrolidine-2-carboxamide | *** | 2.15 (A) | 608 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 568 | 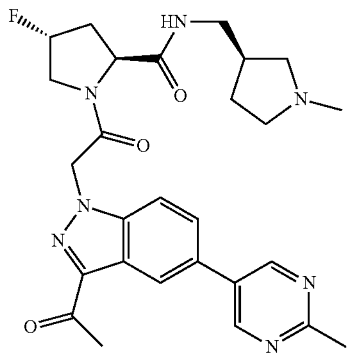 [SMILES: CC(=O)c1nn(CC(=O)N2C[C@H](F)C[C@H]2C(=O)NC[C@@H]2CCN(C)C2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(((S)-1-methylpyrrolidin-3-yl)methyl)pyrrolidine-2-carboxamide | * | 6.39 (D) | 522 |
| 569 | 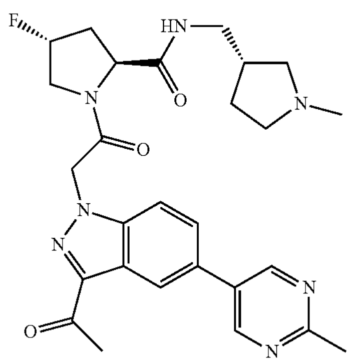 [SMILES: CC(=O)c1nn(CC(=O)N2C[C@H](F)C[C@H]2C(=O)NC[C@H]2CCN(C)C2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(((R)-1-methylpyrrolidin-3-yl)methyl)pyrrolidine-2-carboxamide | * | 6.40 (D) | 522 |
| 570 | 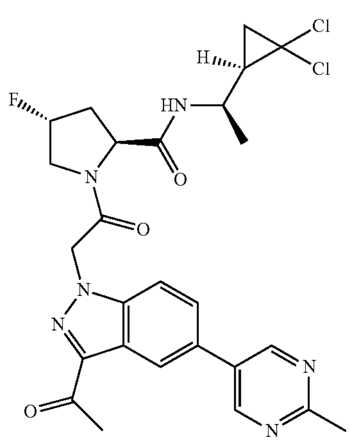 [SMILES: CC(=O)c1nn(CC(=O)N2C[C@H](F)C[C@H]2C(=O)N[C@H](C)[C@H]2CC2(Cl)Cl)c2ccc(-c3cnc(C)nc3)cc12] | (2S,4R)-1-(2-(3-acetyl-5-(2-methylpyrimidin-5-yl)-1H-indazol-1-yl)acetyl)-N-((R)-1-((R)-2,2-dichlorocyclopropyl)ethyl)-4-fluoropyrrolidine-2-carboxamide | *** | 9.85 (D) | 562 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 571 | 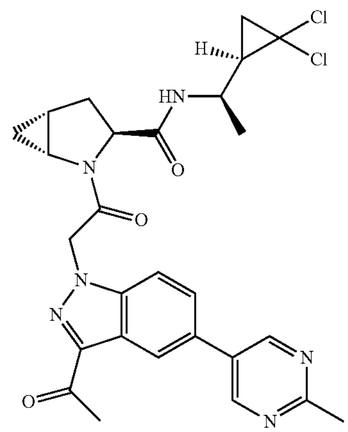 [SMILES: CC(=O)c1nn(CC(=O)N2[C@@H]3C[C@@H]3C[C@H]2C(=O)N[C@H](C)[C@H]2CC2(Cl)Cl)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((R)-1-((R)-2,2-dichlorocyclopropyl)ethyl)-2-azabicyclo[3.1.0]hexane-3-carboxamide | | 9.99 (D) | 556 |
| 572 | 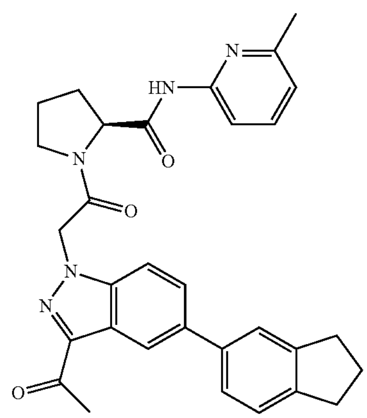 [SMILES: CC(=O)c1nn(CC(=O)N2CCC[C@H]2C(=O)Nc2cccc(C)n2)c2ccc(-c3ccc4c(c3)CCC4)cc12] | (S)-1-(2-(3-acetyl-5-(2,3-dihydro-1H-inden-5-yl)-1H-indazol-1-yl)acetyl)-N-(6-methylpyridin-2-yl)pyrrolidine-2-carboxamide | ** | 14.49 (D) | 522 |
| 573 | 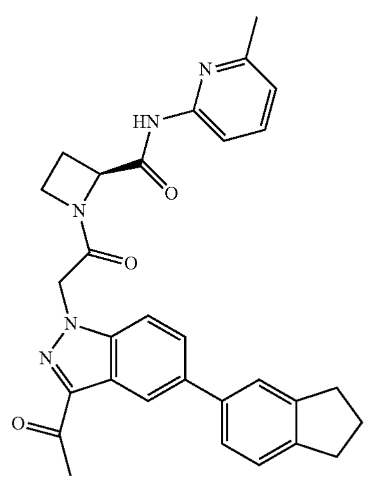 [SMILES: CC(=O)c1nn(CC(=O)N2CC[C@H]2C(=O)Nc2cccc(C)n2)c2ccc(-c3ccc4c(c3)CCC4)cc12] | (S)-1-(2-(3-acetyl-5-(2,3-dihydro-1H-inden-5-yl)-1H-indazol-1-yl)acetyl)-N-(6-methylpyridin-2-yl)azetidine-2-carboxamide | * | 14.43 (D) | 508 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 574 | 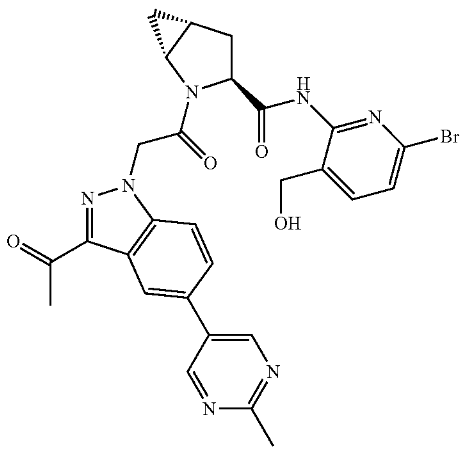 [SMILES: CC(=O)c1nn(CC(=O)N2[C@@H]3C[C@@H]3C[C@H]2C(=O)Nc2nc(Br)ccc2CO)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-(hydroxymethyl)pyridin-2-yl)-2-azabicyclo[3.1.0]hexane-3-carboxamide | *** | 1.36 (A) | 604 |
| 575 | 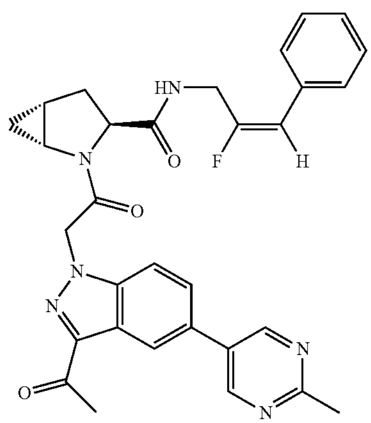 [SMILES: CC(=O)c1nn(CC(=O)N2[C@@H]3C[C@@H]3C[C@H]2C(=O)NC/C(F)=C\c2ccccc2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((E)-2-fluoro-3-phenylallyl)-2-azabicyclo[3.1.0]hexane-3-carboxamide | *** | 1.83 (A) | 553 |
| 576 | 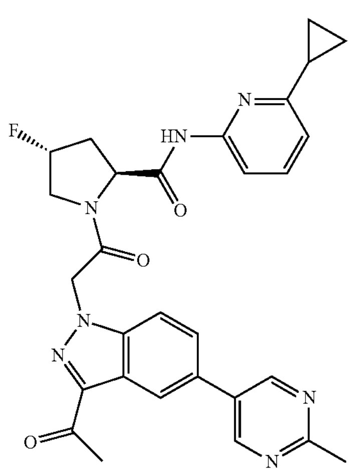 [SMILES: CC(=O)c1nn(CC(=O)N2C[C@H](F)C[C@H]2C(=O)Nc2cccc(C3CC3)n2)c2ccc(-c3cnc(C)nc3)cc12] | (2S,4R)-1-(2-(3-acetyl-5-(2-methylpyrimidin-5-yl)-1H-indazol-1-yl)acetyl)-N-(6-cyclopropylpyridin-2-yl)-4-fluoropyrrolidine-2-carboxamide | *** | 1.72 (A) | 542 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 577 | 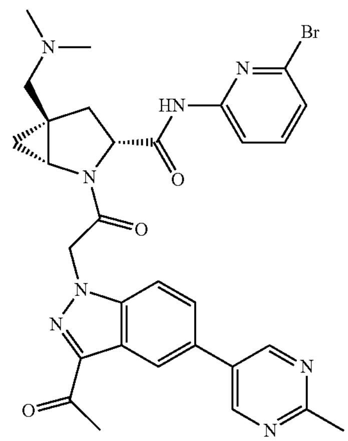 [SMILES: CC(=O)c1nn(CC(=O)N2[C@@H](C(=O)Nc3cccc(Br)n3)C[C@@]3(CN(C)C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromopyridin-2-yl)-5-((dimethylamino)methyl)-2-azabicyclo[3.1.0]hexane-3-carboxamide | *** | 2.13 (B) | 631 |
| 578 | 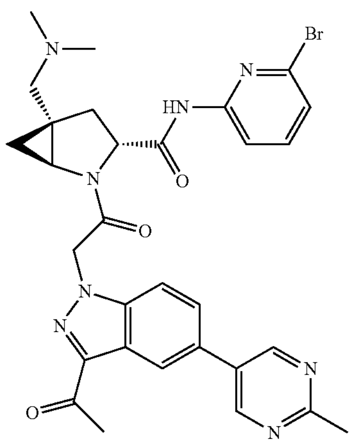 [SMILES: CC(=O)c1nn(CC(=O)N2[C@@H](C(=O)Nc3cccc(Br)n3)C[C@]3(CN(C)C)C[C@H]23)c2ccc(-c3cnc(C)nc3)cc12] | (1S,3S,5S)-2-(2-(3-acetyl-5-(2-methylpyrimidin-5-yl)-1H-indazol-1-yl)acetyl)-N-(6-bromopyridin-2-yl)-5-((dimethylamino)methyl)-2-azabicyclo[3.1.0]hexane-3-carboxamide | *** | 2.93 (B) | 631 |
| 579 | 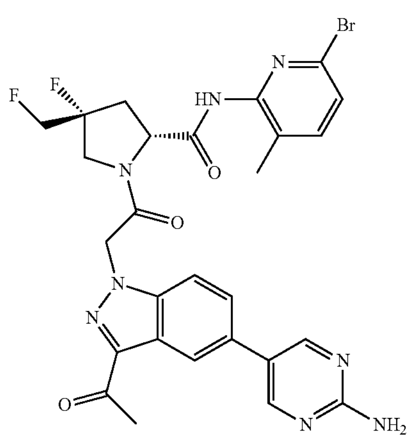 [SMILES: CC(=O)c1nn(CC(=O)N2C[C@@](F)(CF)C[C@@H]2C(=O)Nc2nc(Br)ccc2C)c2ccc(-c3cnc(N)nc3)cc12] | (2S,4R)-1-(2-(3-acetyl-5-(2-aminopyrimidin-5-yl)-1H-indazol-1-yl)acetyl)-N-(6-bromo-3-methylpyridin-2-yl)-4-fluoro-4-(fluoromethyl)pyrrolidine-2-carboxamide | *** | 2.62 (B) | 627 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 580 | 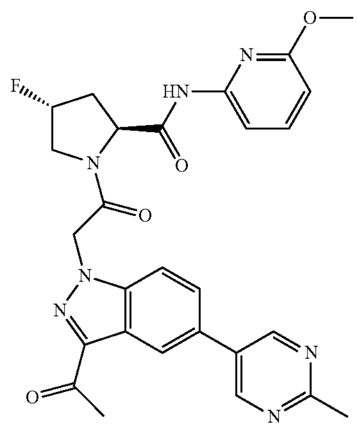 [SMILES: COc1cccc(NC(=O)[C@@H]2C[C@@H](F)CN2C(=O)Cn2nc(C(C)=O)c3cc(-c4cnc(C)nc4)ccc32)n1] | (2S,4R)-1-(2-(3-acetyl-5-(2-methylpyrimidin-5-yl)-1H-indazol-1-yl)acetyl)-4-fluoro-N-(6-methoxypyridin-2-yl)pyrrolidine-2-carboxamide | *** | 1.55 (A) | 532 |
| 581 | 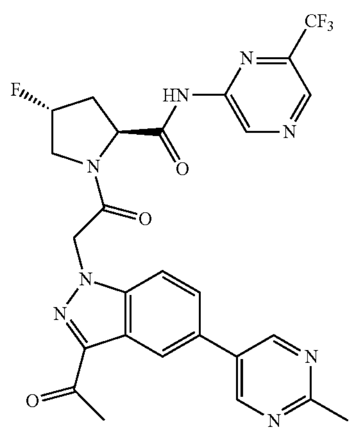 | (2S,4R)-1-(2-(3-acetyl-5-(2-methylpyrimidin-5-yl)-1H-indazol-1-yl)acetyl)-4-fluoro-N-(6-(trifluoromethyl)pyrazin-2-yl)pyrrolidine-2-carboxamide | *** | 1.64 (A) | 571 |
| 582 | 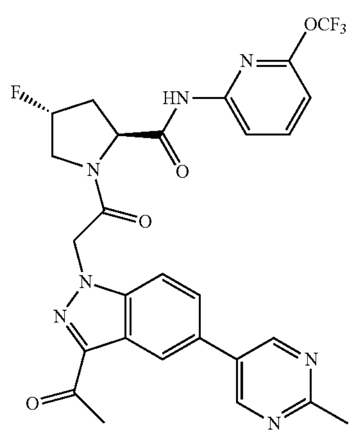 | (2S,4R)-1-(2-(3-acetyl-5-(2-methylpyrimidin-5-yl)-1H-indazol-1-yl)acetyl)-N-(6-(difluoromethoxy)pyridin-2-yl)-4-fluoropyrrolidine-2-carboxamide | *** | 1.77 (A) | 568 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 583 | 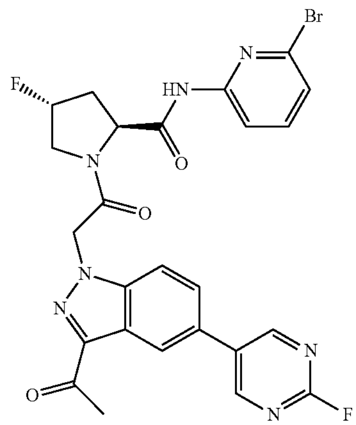 | (2S,4R)-1-(2-(3-acetyl-5-(2-fluoropyrimidin-5-yl)-1H-indazol-1-yl)acetyl)-N-(6-bromopyridin-2-yl)-4-fluoropyrrolidine-2-carboxamide | *** | 1.94 (A) | 584 |
| 584 | 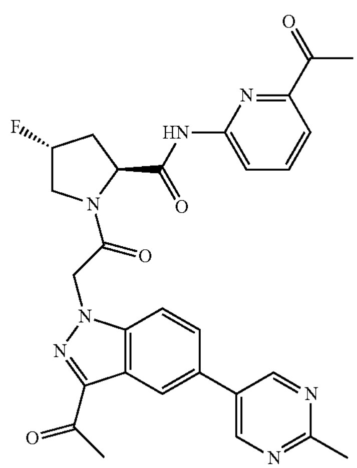 [SMILES: CC(=O)c1cccc(NC(=O)[C@@H]2C[C@@H](F)CN2C(=O)Cn2nc(C(C)=O)c3cc(-c4cnc(C)nc4)ccc32)n1] | (2S,4R)-1-(2-(3-acetyl-5-(2-methylpyrimidin-5-yl)-1H-indazol-1-yl)acetyl)-N-(6-acetylpyridin-2-yl)-4-fluoropyrrolidine-2-carboxamide | *** | 1.43 (A) | 544 |
| 585 | 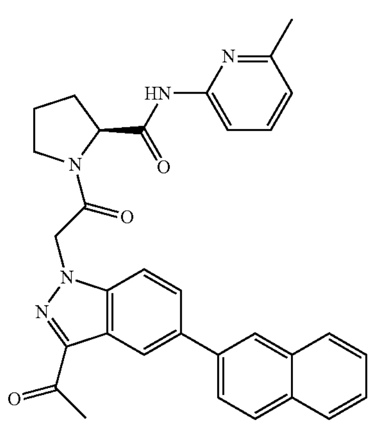 [SMILES: CC(=O)c1nn(CC(=O)N2CCC[C@H]2C(=O)Nc2cccc(C)n2)c2ccc(-c3ccc4ccccc4c3)cc12] | (S)-1-(2-(3-acetyl-5-(naphthalen-2-yl)-1H-indazol-1-yl)acetyl)-N-(6-methylpyridin-2-yl)pyrrolidine-2-carboxamide | * | 14.17 (D) | 532 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 586 | 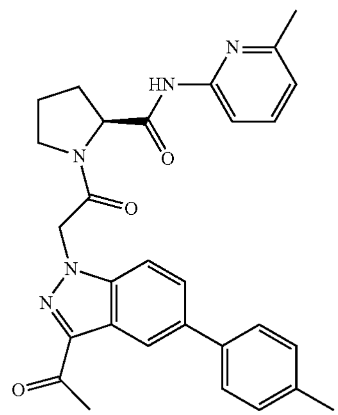 [SMILES: CC(=O)c1nn(CC(=O)N2CCC[C@H]2C(=O)Nc2cccc(C)n2)c2ccc(-c3ccc(C)cc3)cc12] | (S)-1-(2-(3-acetyl-5-(6-methylpyridin-3-yl)-1H-indazol-1-yl)acetyl)-N-(6-methylpyridin-2-yl)pyrrolidine-2-carboxamide | ** | 10.46 (D) | 497 |
| 587 | 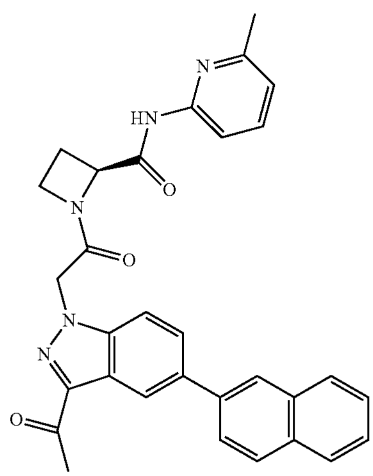 [SMILES: CC(=O)c1nn(CC(=O)N2CC[C@H]2C(=O)Nc2cccc(C)n2)c2ccc(-c3ccc4ccccc4c3)cc12] | (S)-1-(2-(3-acetyl-5-(naphthalen-2-yl)-1H-indazol-1-yl)acetyl)-N-(6-methylpyridin-2-yl)azetidine-2-carboxamide | * | 14.07 (D) | 518 |
| 588 | 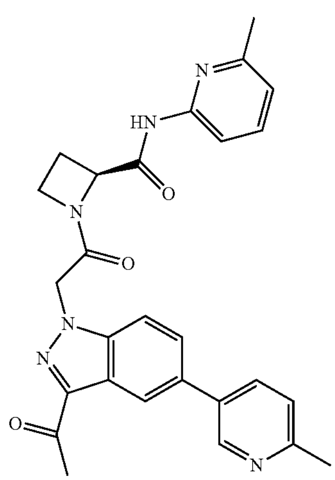 [SMILES: CC(=O)c1nn(CC(=O)N2CC[C@H]2C(=O)Nc2cccc(C)n2)c2ccc(-c3ccc(C)nc3)cc12] | (S)-1-(2-(3-acetyl-5-(6-methylpyridin-3-yl)-1H-indazol-1-yl)acetyl)-N-(6-methylpyridin-2-yl)azetidine-2-carboxamide | * | 10.32 (D) | 483 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 589 | 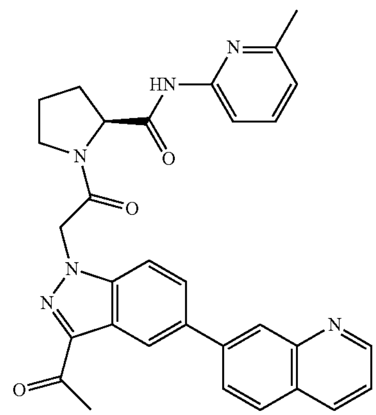 [SMILES: CC(=O)c1nn(CC(=O)N2CCC[C@H]2C(=O)Nc2cccc(C)n2)c2ccc(-c3ccc4cccnc4c3)cc12] | (S)-1-(2-(3-acetyl-5-(quinolin-7-yl)-1H-indazol-1-yl)acetyl)-N-(6-methylpyridin-2-yl)pyrrolidine-2-carboxamide | *** | 11.53 (D) | 533 |
| 590 | 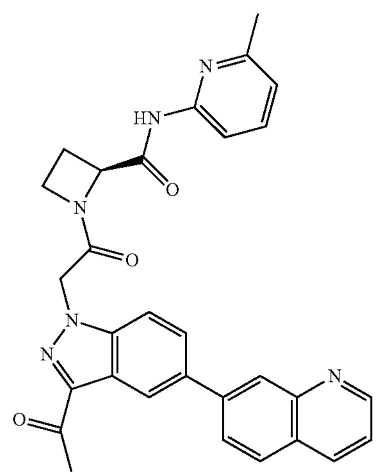 [SMILES: CC(=O)c1nn(CC(=O)N2CC[C@H]2C(=O)Nc2cccc(C)n2)c2ccc(-c3ccc4cccnc4c3)cc12] | (S)-1-(2-(3-acetyl-5-(quinolin-7-yl)-1H-indazol-1-yl)acetyl)-N-(6-methylpyridin-2-yl)azetidine-2-carboxamide | ** | 11.39 (D) | 519 |
| 591 | 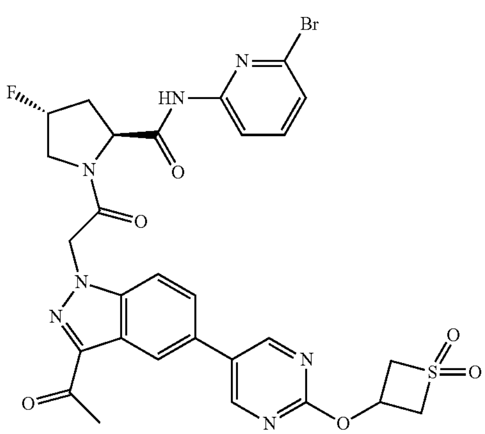 [SMILES: CC(=O)c1nn(CC(=O)N2C[C@H](F)C[C@H]2C(=O)Nc2cccc(Br)n2)c2ccc(-c3cnc(OC4CS(=O)(=O)C4)nc3)cc12] | (2S,4R)-1-(2-(3-acetyl-5-(2-((1,1-dioxidothietan-3-yl)oxy)pyrimidin-5-yl)-1H-indazol-1-yl)acetyl)-N-(6-bromopyridin-2-yl)-4-fluoropyrrolidine-2-carboxamide | *** | 11.69 (C) | 686 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 592 | 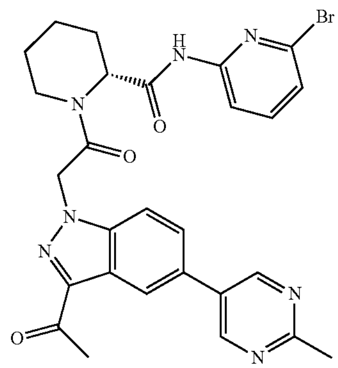 [SMILES: CC(=O)c1nn(CC(=O)N2CCCC[C@@H]2C(=O)Nc2cccc(Br)n2)c2ccc(-c3cnc(C)nc3)cc12] | (R)-1-(2-(3-acetyl-5-(2-methylpyrimidin-5-yl)-1H-indazol-1-yl)acetyl)-N-(6-bromopyridin-2-yl)piperidine-2-carboxamide | * | 11.80 (D) | 576 |
| 593 | 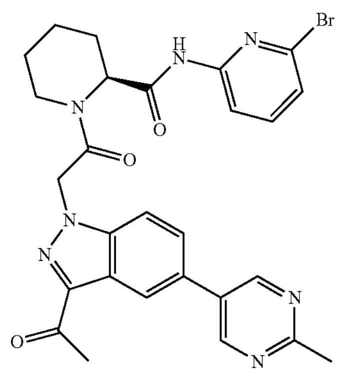 [SMILES: CC(=O)c1nn(CC(=O)N2CCCC[C@H]2C(=O)Nc2cccc(Br)n2)c2ccc(-c3cnc(C)nc3)cc12] | (S)-1-(2-(3-acetyl-5-(2-methylpyrimidin-5-yl)-1H-indazol-1-yl)acetyl)-N-(6-bromopyridin-2-yl)piperidine-2-carboxamide | *** | 11.79 (D) | 576 |
| 594 | 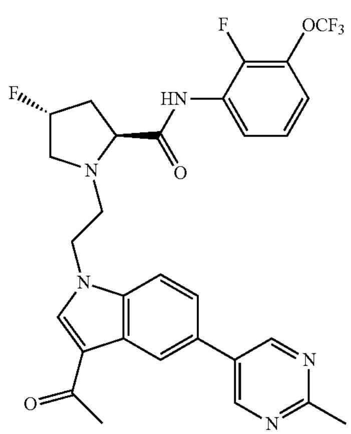 [SMILES: CC(=O)c1cn(CCN2C[C@H](F)C[C@H]2C(=O)Nc2cccc(OC(F)(F)F)c2F)c2ccc(-c3cnc(C)nc3)cc12] | (2S,4R)-1-(2-(3-acetyl-5-(2-methylpyrimidin-5-yl)-1H-indol-1-yl)ethyl)-4-fluoro-N-(2-fluoro-3-(trifluoromethoxy)phenyl)pyrrolidine-2-carboxamide | * | 11.43 (D) | 588 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 596 | 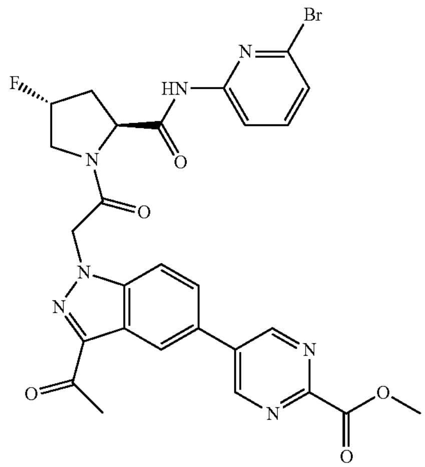 [SMILES: COC(=O)c1ncc(-c2ccc3c(c2)c(C(C)=O)nn3CC(=O)N2C[C@H](F)C[C@H]2C(=O)Nc2cccc(Br)n2)cn1] | methyl 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxylate | *** | 1.66 (A) | 624 |
| 597 | 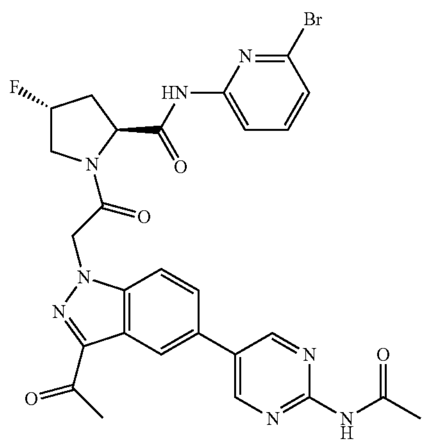 | (2S,4R)-1-(2-(5-(2-acetamidopyrimidin-5-yl)-3-acetyl-1H-indazol-1-yl)acetyl)-N-(6-bromopyridin-2-yl)-4-fluoropyrrolidine-2-carboxamide | *** | 1.50 (A) | 623 |
| 598 | 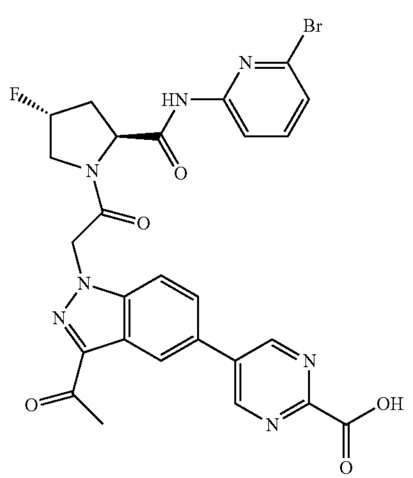 [SMILES: CC(=O)c1nn(CC(=O)N2C[C@H](F)C[C@H]2C(=O)Nc2cccc(Br)n2)c2ccc(-c3cnc(C(=O)O)nc3)cc12] | 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxylic acid | *** | 1.38 (A) | 610 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 599 | 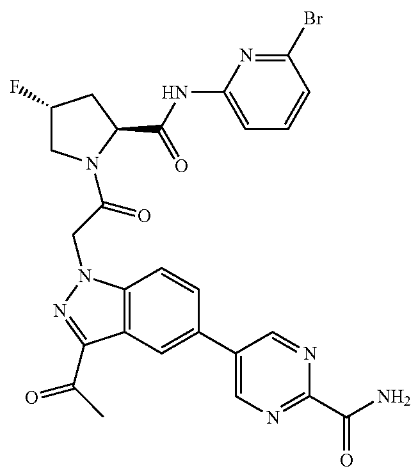 [SMILES: CC(=O)c1nn(CC(=O)N2C[C@H](F)C[C@H]2C(=O)Nc2cccc(Br)n2)c2ccc(-c3cnc(C(N)=O)nc3)cc12] | 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)pyrimidine-2-carboxamide | *** | 1.43 (A) | 609 |
| 600 | 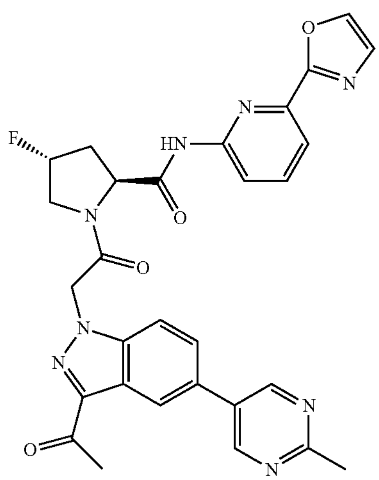 [SMILES: CC(=O)c1nn(CC(=O)N2C[C@H](F)C[C@H]2C(=O)Nc2cccc(-c3ncco3)n2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(6-(oxazol-2-yl)pyridin-2-yl)pyrrolidine-2-carboxamide | *** | 1.39 (A) | 569 |
| 601 | 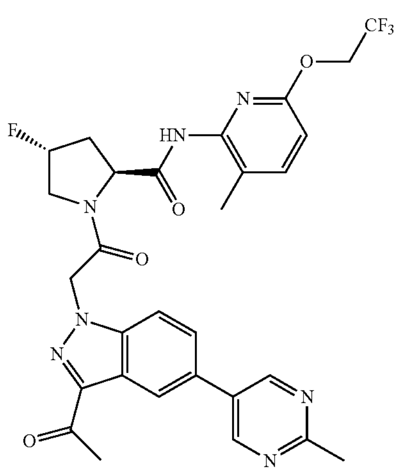 [SMILES: CC(=O)c1nn(CC(=O)N2C[C@H](F)C[C@H]2C(=O)Nc2nc(OCC(F)(F)F)ccc2C)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(3-methyl-6-(2,2,2-trifluoroethoxy)pyridin-2-yl)pyrrolidine-2-carboxamide | *** | 1.85 (A) | 614 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 602 | 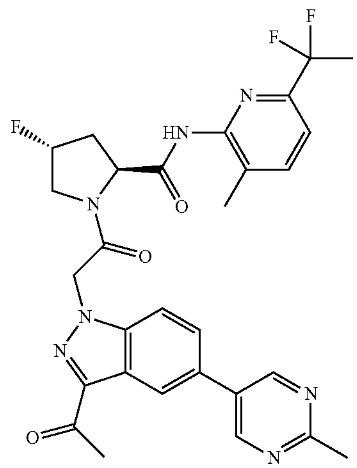 [SMILES: CC(=O)c1nn(CC(=O)N2C[C@H](F)C[C@H]2C(=O)Nc2nc(C(C)(F)F)ccc2C)c2ccc(-c3cnc(C)nc3)cc12] | (2S,4R)-1-(2-(3-acetyl-5-(2-methylpyrimidin-5-yl)-1H-indazol-1-yl)acetyl)-N-(6-(1,1-difluoroethyl)-3-methylpyridin-2-yl)-4-fluoropyrrolidine-2-carboxamide | *** | 1.61 (A) | 580 |
| 603 | 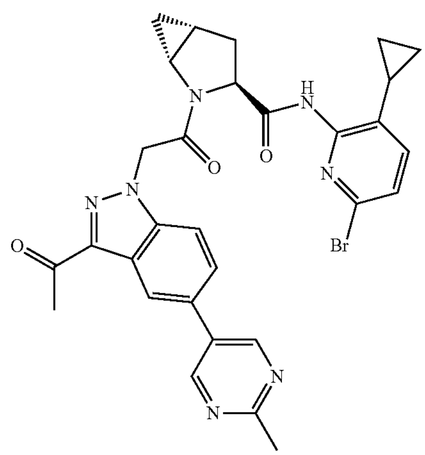 [SMILES: CC(=O)c1nn(CC(=O)N2[C@@H]3C[C@@H]3C[C@H]2C(=O)Nc2nc(Br)ccc2C2CC2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-cyclopropylpyridin-2-yl)-2-azabicyclo[3.1.0]hexane-3-carboxamide | *** | 1.77 (A) | 614 |
| 604 | 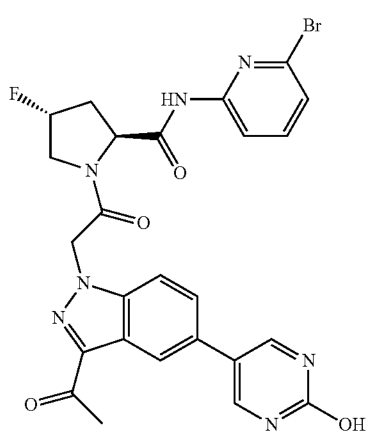 | (2S,4R)-1-(2-(3-acetyl-5-(2-hydroxypyrimidin-5-yl)-1H-indazol-1-yl)acetyl)-N-(6-bromopyridin-2-yl)-4-fluoropyrrolidine-2-carboxamide | *** | 1.28 (A) | 582 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 605 | 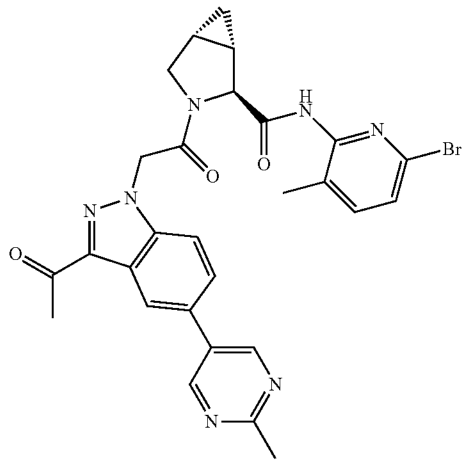 [SMILES: CC(=O)c1nn(CC(=O)N2C[C@@H]3C[C@@H]3[C@H]2C(=O)Nc2nc(Br)ccc2C)c2ccc(-c3cnc(C)nc3)cc12] | (1S,2S,5R)-3-(2-(3-acetyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide | *** | 9.90 (D) | 590 (M + 2) |
| 606 | 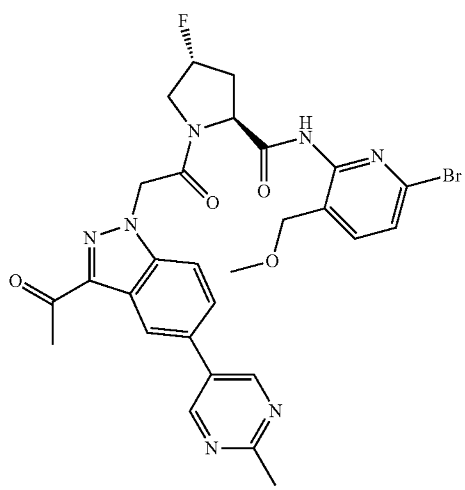 [SMILES: COCc1ccc(Br)nc1NC(=O)[C@@H]1C[C@@H](F)CN1C(=O)Cn1nc(C(C)=O)c2cc(-c3cnc(C)nc3)ccc21] | (2S,4R)-1-(2-(3-acetyl-5-(2-methylpyrimidin-5-yl)-1H-indazol-1-yl)acetyl)-N-(6-bromo-3-(methoxymethyl)pyridin-2-yl)-4-fluoropyrrolidine-2-carboxamide | *** | 1.53 (A) | 624 |
| 607 | 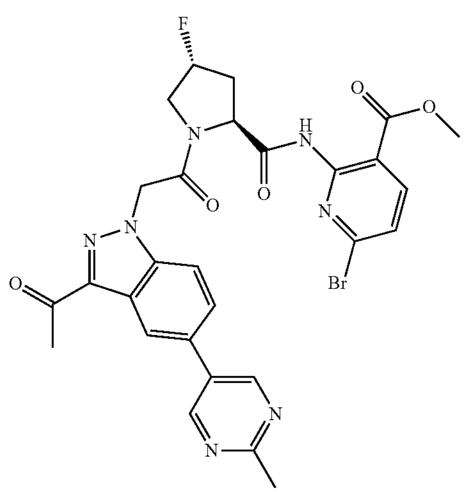 [SMILES: COC(=O)c1ccc(Br)nc1NC(=O)[C@@H]1C[C@@H](F)CN1C(=O)Cn1nc(C(C)=O)c2cc(-c3cnc(C)nc3)ccc21] | methyl 2-((2S,4R)-1-(2-(3-acetyl-5-(2-methylpyrimidin-5-yl)-1H-indazol-1-yl)acetyl)-4-fluoropyrrolidine-2-carboxamido)-6-bromonicotinate | *** | 1.67 (A) | 638 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 608 | 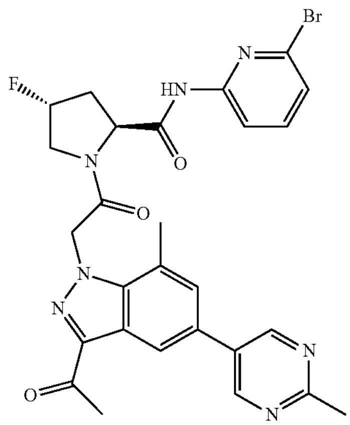 | (2S,4R)-1-(2-(3-acetyl-7-methyl-5-(2-methylpyrimidin-5-yl)-1H-indazol-1-yl)acetyl)-N-(6-bromopyridin-2-yl)-4-fluoropyrrolidine-2-carboxamide | *** | 1.78 (A) | 596 |
| 609 | 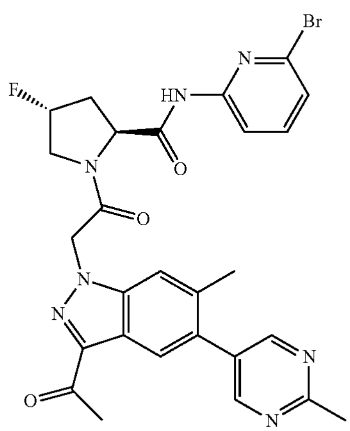 | (2S,4R)-1-(2-(3-acetyl-6-methyl-5-(2-methylpyrimidin-5-yl)-1H-indazol-1-yl)acetyl)-N-(6-bromopyridin-2-yl)-4-fluoropyrrolidine-2-carboxamide | *** | 1.77 (A) | 596 |
| 610 | 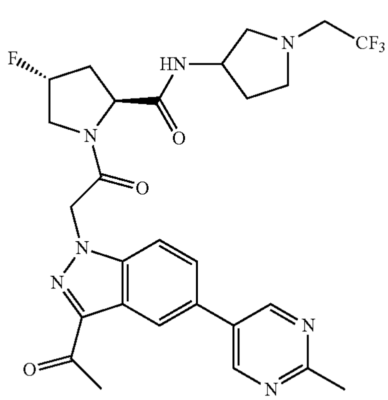 [SMILES: CC(=O)c1nn(CC(=O)N2C[C@H](F)C[C@H]2C(=O)NC2CCN(CC(F)(F)F)C2)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-(1-(2,2,2-trifluoroethyl)pyrrolidin-3-yl)pyrrolidine-2-carboxamide | ** | 2.25 (B) | 576 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 611 | 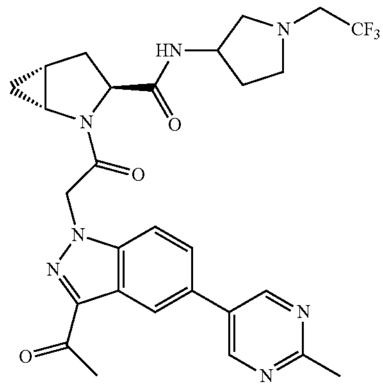 [SMILES: CC(=O)c1nn(CC(=O)N2[C@@H]3C[C@@H]3C[C@H]2C(=O)NC2CCN(CC(F)(F)F)C2)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(1-(2,2,2-trifluoroethyl)pyrrolidin-3-yl)-2-azabicyclo[3.1.0]hexane-3-carboxamide | *** | 2.45 (B) | 570 |
| 612 | 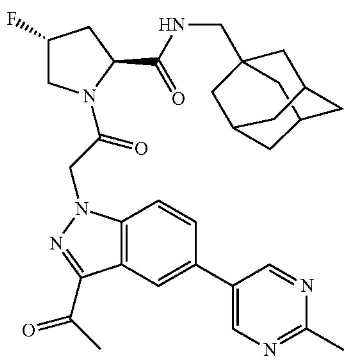 [SMILES: CC(=O)c1nn(CC(=O)N2C[C@H](F)C[C@H]2C(=O)NCC23CC4CC(CC(C4)C2)C3)c2ccc(-c3cnc(C)nc3)cc12] | (2S,4R)-1-(2-(3-acetyl-5-(2-methylpyrimidin-5-yl)-1H-indazol-1-yl)acetyl)-N-(((3S,5S,7S)-adamantan-1-yl)methyl)-4-fluoropyrrolidine-2-carboxamide | *** | 11.90 (D) | 573 |
| 613 | 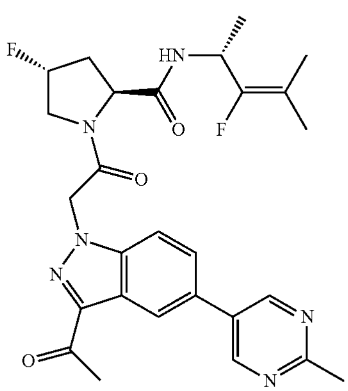 [SMILES: CC(=O)c1nn(CC(=O)N2C[C@H](F)C[C@H]2C(=O)N[C@H](C)C(F)=C(C)C)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-((R)-3-fluoro-4-methylpent-3-en-2-yl)pyrrolidine-2-carboxamide | ** | 10.27 (D) | 525 |
| 614 | 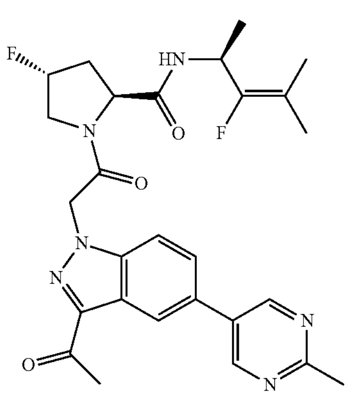 [SMILES: CC(=O)c1nn(CC(=O)N2C[C@H](F)C[C@H]2C(=O)N[C@@H](C)C(F)=C(C)C)c2ccc(-c3cnc(C)nc3)cc12] | (2S,4R)-1-(2-(3-acetyl-5-(2-methylpyrimidin-5-yl)-1H-indazol-1-yl)acetyl)-4-fluoro-N-((S)-3-fluoro-4-methylpent-3-en-2-yl)pyrrolidine-2-carboxamide | *** | 10.14 (D) | 525 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 615 | 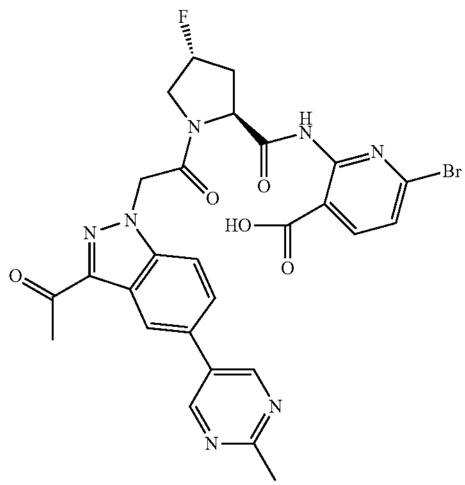 [SMILES: CC(=O)c1nn(CC(=O)N2C[C@H](F)C[C@H]2C(=O)Nc2nc(Br)ccc2C(=O)O)c2ccc(-c3cnc(C)nc3)cc12] | 2-((2S,4R)-1-(2-(3-acetyl-5-(2-methylpyrimidin-5-yl)-1H-indazol-1-yl)acetyl)-4-fluoropyrrolidine-2-carboxamido)-6-bromonicotinic acid | *** | 1.27 (A) | 624 |
| 616 | 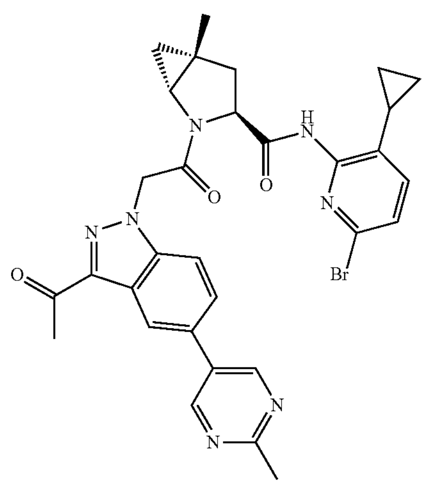 [SMILES: CC(=O)c1nn(CC(=O)N2[C@H](C(=O)Nc3nc(Br)ccc3C3CC3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(6-bromo-3-cyclopropylpyridin-2-yl)-5-methyl-2-azabicyclo[3.1.0]hexane-3-carboxamide | *** | 1.97 (A) | 628 |
| 617 | 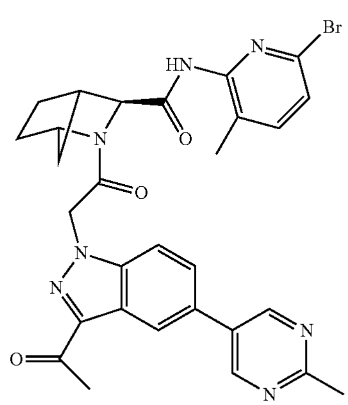 [SMILES: CC(=O)c1nn(CC(=O)N2C3CCC(C3)[C@H]2C(=O)Nc2nc(Br)ccc2C)c2ccc(-c3cnc(C)nc3)cc12] | (3R,4S)-2-(2-(3-acetyl-5-(2-methylpyrimidin-5-yl)-1H-indazol-1-yl)acetyl)-N-(6-bromo-3-methylpyridin-2-yl)-2-azabicyclo[2.2.1]heptane-3-carboxamide | *** | 1.67 (A) | 604 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 618 | 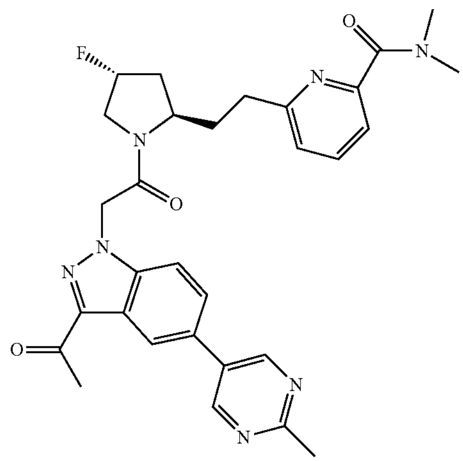 [SMILES: CC(=O)c1nn(CC(=O)N2C[C@H](F)C[C@H]2CCc2cccc(C(=O)N(C)C)n2)c2ccc(-c3cnc(C)nc3)cc12] | 6-((2S,4R)-1-(2-(3-acetyl-5-(2-methylpyrimidin-5-yl)-1H-indazol-1-yl)acetyl)-4-fluoropyrrolidine-2-carboxamido)-N,N-dimethylpicolinamide | ** | 1.20 (A) | 573 |
| 619 | 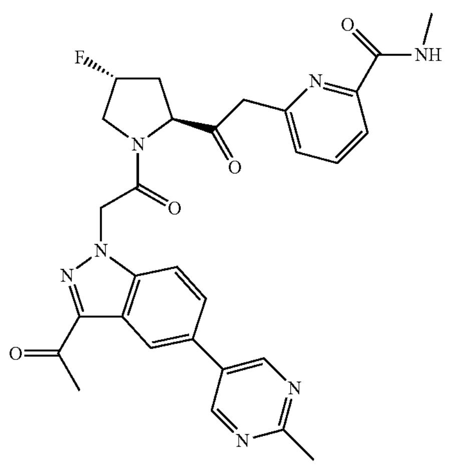 [SMILES: CNC(=O)c1cccc(CC(=O)[C@@H]2C[C@@H](F)CN2C(=O)Cn2nc(C(C)=O)c3cc(-c4cnc(C)nc4)ccc32)n1] | 6-((2S,4R)-1-(2-(3-acetyl-5-(2-methylpyrimidin-5-yl)-1H-indazol-1-yl)acetyl)-4-fluoropyrrolidine-2-carboxamido)-N-methylpicolinamide | ** | 1.21 (A) | 559 |
| 620 | 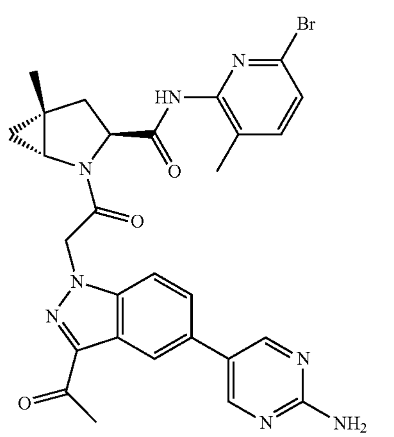 [SMILES: CC(=O)c1nn(CC(=O)N2[C@H](C(=O)Nc3nc(Br)ccc3C)C[C@@]3(C)C[C@@H]23)c2ccc(-c3cnc(N)nc3)cc12] | (1R,3S,5R)-2-(2-(3-acetyl-5-(2-aminopyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.64 (A) | 603 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 621 | 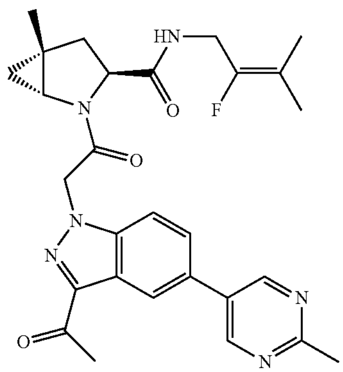 [SMILES: CC(=O)c1nn(CC(=O)N2[C@H](C(=O)NCC(F)=C(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(2-fluoro-3-methylbut-2-en-1-yl)-5-methyl-2-azabicyclo[3.1.0]hexane-3-carboxamide | *** | 10.61 (D) | 519 |
| 622 | 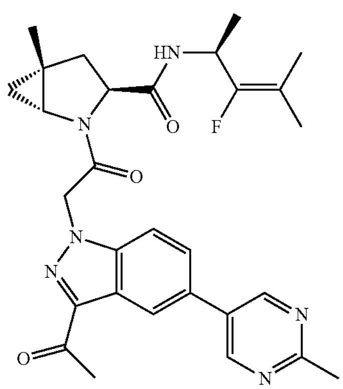 [SMILES: CC(=O)c1nn(CC(=O)N2[C@H](C(=O)N[C@@H](C)C(F)=C(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((S)-3-fluoro-4-methylpent-3-en-2-yl)-5-methyl-2-azabicyclo[3.1.0]hexane-3-carboxamide | *** | 13.31 (C) | 533 |
| 623 | 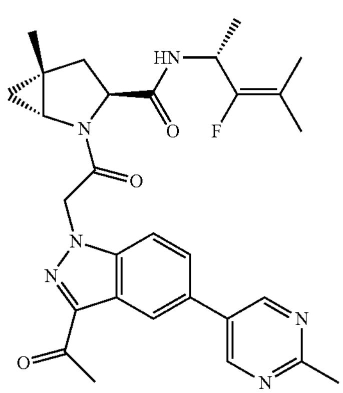 [SMILES: CC(=O)c1nn(CC(=O)N2[C@H](C(=O)N[C@H](C)C(F)=C(C)C)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((R)-3-fluoro-4-methylpent-3-en-2-yl)-5-methyl-2-azabicyclo[3.1.0]hexane-3-carboxamide | *** | 11.25 (D) | 533 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 624 | 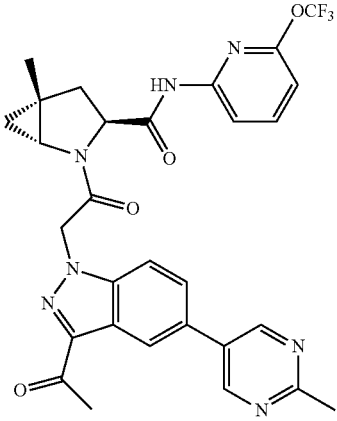 [SMILES: CC(=O)c1nn(CC(=O)N2[C@H](C(=O)Nc3cccc(OC(F)(F)F)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(6-(trifluoromethoxy)pyridin-2-yl)-2-azabicyclo[3.1.0]hexane-3-carboxamide | *** | 11.61 (D) | 594 |
| 625 | 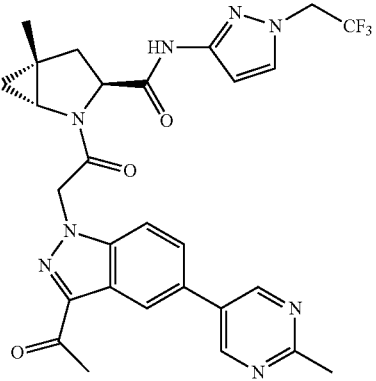 [SMILES: CC(=O)c1nn(CC(=O)N2[C@H](C(=O)Nc3ccn(CC(F)(F)F)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(1-(2,2,2-1H-pyrazol-3-yl)-2-azabicyclo[3.1.0]hexane-3-carboxamide | *** | 12.54 (C) | 581 |
| 626 | 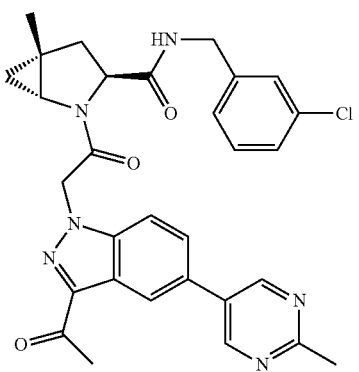 [SMILES: CC(=O)c1nn(CC(=O)N2[C@H](C(=O)NCc3cccc(Cl)c3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(3-chlorobenzyl)-5-methyl-2-azabicyclo[3.1.0]hexane-3-carboxamide | *** | 11.18 (D) | 558 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 627 | 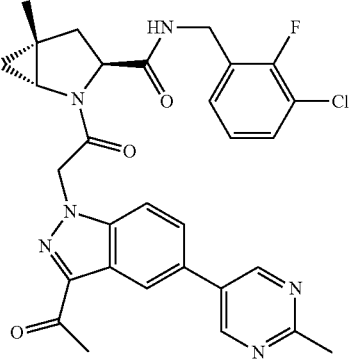 [SMILES: CC(=O)c1nn(CC(=O)N2[C@H](C(=O)NCc3cccc(Cl)c3F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(3-chloro-2-fluorobenzyl)-5-methyl-2-azabicyclo[3.1.0]hexane-3-carboxamide | *** | 11.40 (D) | 576 |
| 628 | 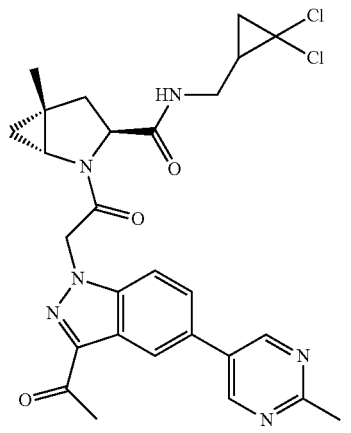 [SMILES: CC(=O)c1nn(CC(=O)N2[C@H](C(=O)NCC3CC3(Cl)Cl)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((2,2-dichlorocyclopropyl)methyl)-5-methyl-2-azabicyclo[3.1.0]hexane-3-carboxamide | *** | 10.75 (D) | 556 |
| 629 | 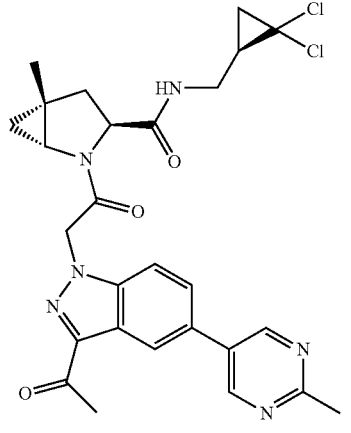 [SMILES: CC(=O)c1nn(CC(=O)N2[C@H](C(=O)NC[C@H]3CC3(Cl)Cl)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-((R)-1-((R)-2,2-dichlorocyclopropyl)ethyl)-5-methyl-2-azabicyclo[3.1.0]hexane-3-carboxamide | *** | 10.99 (D) | 570 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 630 | 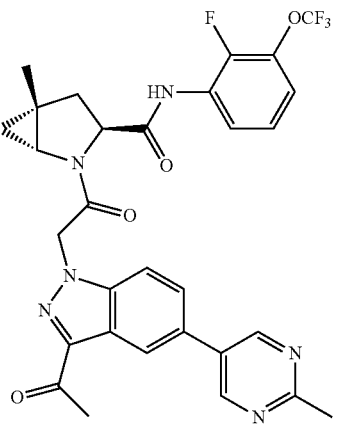 [SMILES: CC(=O)c1nn(CC(=O)N2[C@H](C(=O)Nc3cccc(OC(F)(F)F)c3F)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-N-(2-fluoro-3-(trifluoromethoxy)phenyl)-5-methyl-2-azabicyclo[3.1.0]hexane-3-carboxamide | *** | 12.84 (D) | 611 |
| 631 | 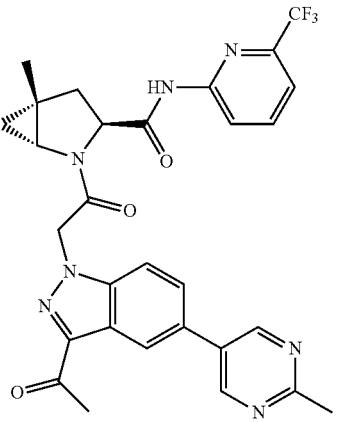 [SMILES: CC(=O)c1nn(CC(=O)N2[C@H](C(=O)Nc3cccc(C(F)(F)F)n3)C[C@@]3(C)C[C@@H]23)c2ccc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(6-(trifluoromethyl)pyridin-2-yl)-2-azabicyclo[3.1.0]hexane-3-carboxamide | *** | 11.27 (D) | 578 |
| 632 | 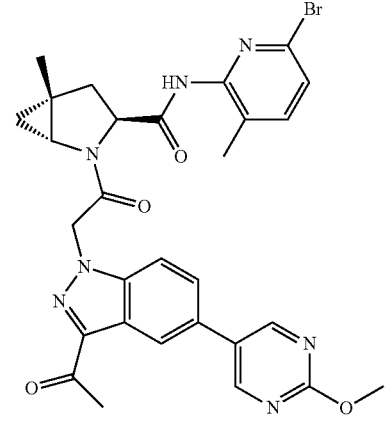 [SMILES: COc1ncc(-c2ccc3c(c2)c(C(C)=O)nn3CC(=O)N2[C@H](C(=O)Nc3nc(Br)ccc3C)C[C@@]3(C)C[C@@H]23)cn1] | (1R,3S,5R)-2-(2-(3-acetyl-5-(2-methoxypyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.97 (A) | 618 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 633 | 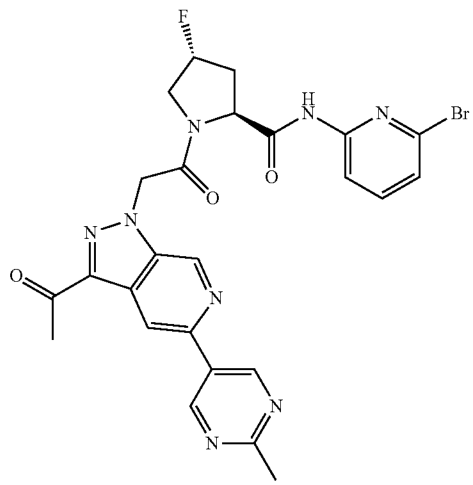 [SMILES: CC(=O)c1nn(CC(=O)N2C[C@H](F)C[C@H]2C(=O)Nc2cccc(Br)n2)c2cnc(-c3cnc(C)nc3)cc12] | (2S,4R)-1-(2-(3-acetyl-5-(2-methylpyrimidin-5-yl)-1H-pyrazolo[3,4-c]pyridin-1-yl)acetyl)-N-(6-bromopyridin-2-yl)-4-fluoropyrrolidine-2-carboxamide | *** | 1.57 (A) | 581 |
| 634 | 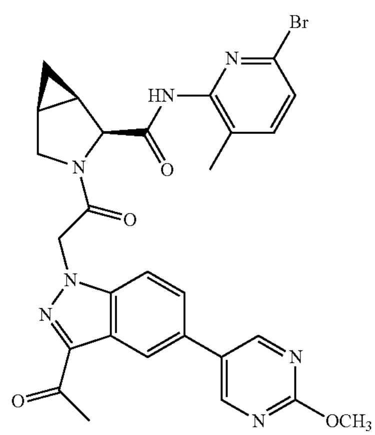 [SMILES: COc1ncc(-c2ccc3c(c2)c(C(C)=O)nn3CC(=O)N2C[C@H]3C[C@H]3[C@H]2C(=O)Nc2nc(Br)ccc2C)cn1] | (1R,2S,5S)-3-(2-(3-acetyl-5-(2-methoxypyrimidin-5-yl)-1H-indazol-1-yl)acetyl)-N-(6-bromo-3-methylpyridin-2-yl)-3-azabicyclo[3.1.0]hexane-2-carboxamide | *** | 1.75 (A) | 604 |
| 635 | 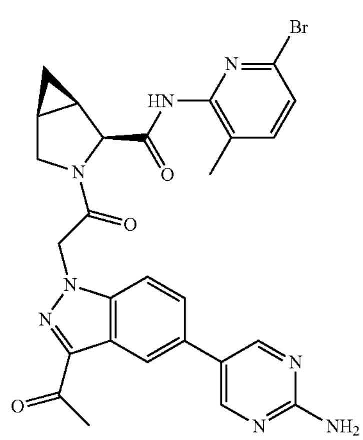 [SMILES: CC(=O)c1nn(CC(=O)N2C[C@H]3C[C@H]3[C@H]2C(=O)Nc2nc(Br)ccc2C)c2ccc(-c3cnc(N)nc3)cc12] | (1R,2S,5S)-3-(2-(3-acetyl-5-(2-aminopyrimidin-5-yl)-1H-indazol-1-yl)acetyl)-N-(6-bromo-3-methylpyridin-2-yl)-3-azabicyclo[3.1.0]hexane-2-carboxamide | *** | 1.43 (A) | 589 |

TABLE 3-continued

Additional Non-limiting Examples of Compounds of Formula I

| Comp No. | Structure | Name | IC₅₀ (Stars) | RT min (Method A,B,C or D) | MS (M + 1) |
|---|---|---|---|---|---|
| 636 | 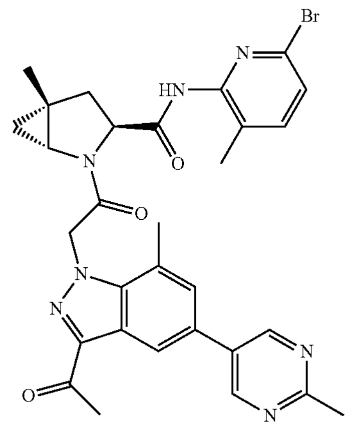 [SMILES: CC(=O)c1nn(CC(=O)N2[C@H](C(=O)Nc3nc(Br)ccc3C)C[C@@]3(C)C[C@@H]23)c2c(C)cc(-c3cnc(C)nc3)cc12] | (1R,3S,5R)-2-(2-(3-acetyl-7-methyl-5-(2-methylpyrimidin-5-yl)-1H-indazol-1-yl)acetyl)-N-(6-bromo-3-methylpyridin-2-yl)-5-methyl-2-azabicyclo[3.1.0]hexane-3-carboxamide | *** | 1.89 (A) | 616 |
| 637 | 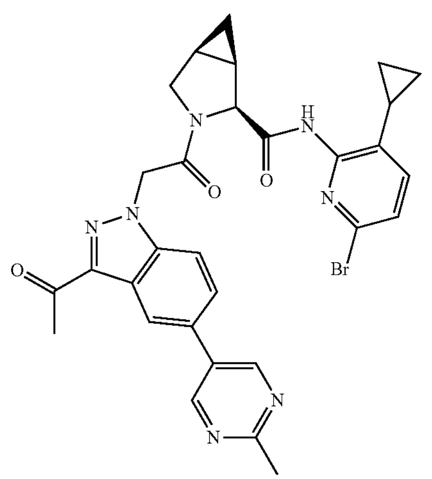 [SMILES: CC(=O)c1nn(CC(=O)N2C[C@H]3C[C@H]3[C@H]2C(=O)Nc2nc(Br)ccc2C2CC2)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(6-bromo-3-cyclopropylpyridin-2-yl)-3-azabicyclo[3.1.0]hexane-2-carboxamide | *** | 1.75 (A) | 614 |
| 638 | 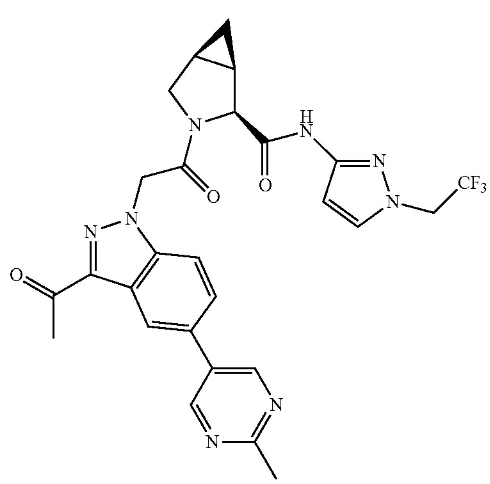 [SMILES: CC(=O)c1nn(CC(=O)N2C[C@H]3C[C@H]3[C@H]2C(=O)Nc2ccn(CC(F)(F)F)n2)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(1-(2,2,2-trifluoroethyl)-1H-pyrazol-3-yl)-3-azabicyclo[3.1.0]hexane-2-carboxamide | *** | 1.49 (A) | 567 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 639 | 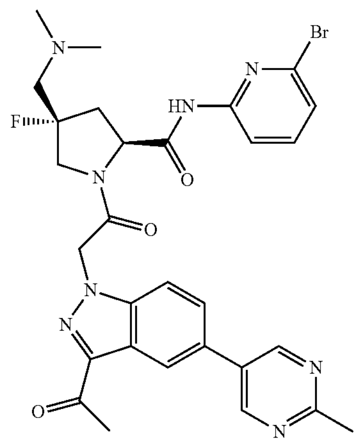 [SMILES: CC(=O)c1nn(CC(=O)N2C[C@@](F)(CN(C)C)C[C@H]2C(=O)Nc2cccc(Br)n2)c2ccc(-c3cnc(C)nc3)cc12] | (2S,4S)-1-(2-(3-acetyl-5-(2-methylpyrimidin-5-yl)-1H-indazol-1-yl)acetyl)-N-(6-bromopyridin-2-yl)-4-((dimethylamino)methyl)-4-fluoropyrrolidine-2-carboxamide | *** | 2.28 (B) | 637 |
| 640 | 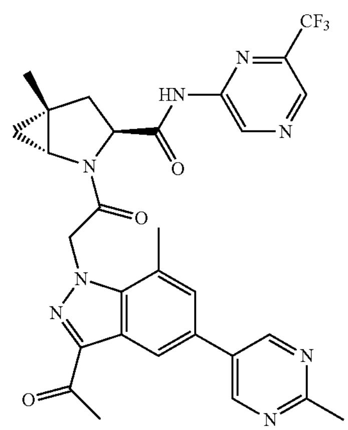 [SMILES: CC(=O)c1nn(CC(=O)N2[C@H](C(=O)Nc3cncc(C(F)(F)F)n3)C[C@@]3(C)C[C@@H]23)c2c(C)cc(-c3cnc(C)nc3)cc12] | (1R,3S,5R)-2-(2-(3-acetyl-5-(2-methylpyrimidin-5-yl)-1H-indazol-1-yl)acetyl)-5-methyl-N-(6-(trifluoromethyl)pyrazin-2-yl)-2-azabicyclo[3.1.0]hexane-3-carboxamide | *** | 11.37 (D) | 579 |
| 641 | 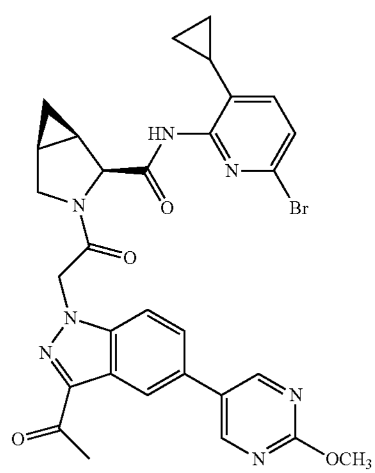 [SMILES: COc1ncc(-c2ccc3c(c2)c(C(C)=O)nn3CC(=O)N2C[C@H]3C[C@H]3[C@H]2C(=O)Nc2nc(Br)ccc2C2CC2)cn1] | (1R,2S,5S)-3-(2-(3-acetyl-5-(2-methoxypyrimidin-5-yl)-1H-indazol-1-yl)acetyl)-N-(6-bromo-3-cyclopropylpyridin-2-yl)-3-azabicyclo[3.1.0]hexane-2-carboxamide | *** | 1.92 (A) | 630 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 642 | 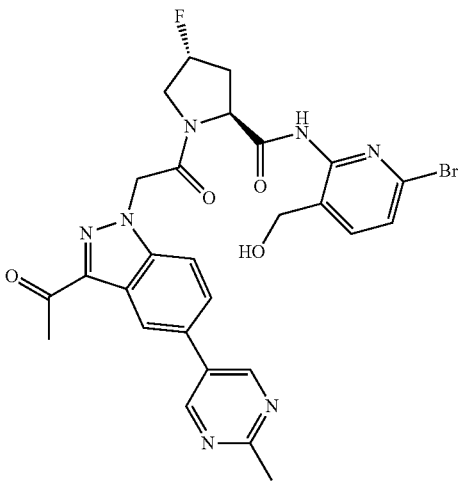 [SMILES: CC(=O)c1nn(CC(=O)N2C[C@H](F)C[C@H]2C(=O)Nc2nc(Br)ccc2CO)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-(hydroxymethyl)pyridin-2-yl)-4-fluoropyrrolidine-2-carboxamide | | | |
| 643 | 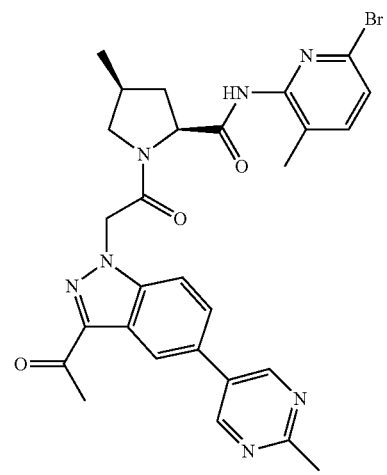 [SMILES: CC(=O)c1nn(CC(=O)N2C[C@@H](C)C[C@H]2C(=O)Nc2nc(Br)ccc2C)c2ccc(-c3cnc(C)nc3)cc12] | (2S,4S)-1-(2-(3-acetyl-5-(2-methylpyrimidin-5-yl)-1H-indazol-1-yl)acetyl)-N-(6-bromo-3-methylpyridin-2-yl)-4-methylpyrrolidine-2-carboxamide | *** | 1.67 (A) | 590 |
| 644 | 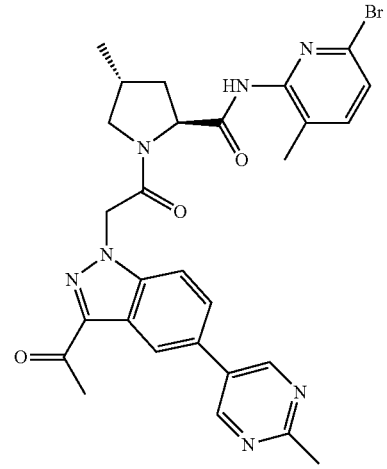 [SMILES: CC(=O)c1nn(CC(=O)N2C[C@H](C)C[C@H]2C(=O)Nc2nc(Br)ccc2C)c2ccc(-c3cnc(C)nc3)cc12] | (2S,4R)-1-(2-(3-acetyl-5-(2-methylpyrimidin-5-yl)-1H-indazol-1-yl)acetyl)-N-(6-bromo-3-methylpyridin-2-yl)-4-methylpyrrolidine-2-carboxamide | *** | 1.70 (A) | 590 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 645 | 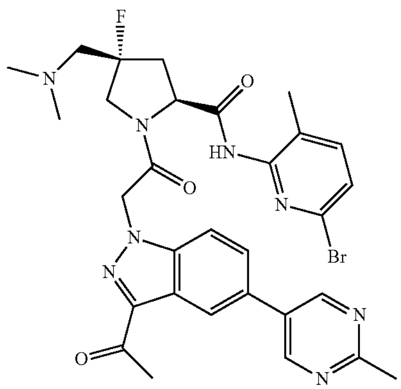 | (2S,4S)-1-(2-(3-acetyl-5-(2-methylpyrimidin-5-yl)-1H-indazol-1-yl)acetyl)-N-(6-bromo-3-methylpyridin-2-yl)-4-((dimethylamino)methyl)-4-fluoropyrrolidine-2-carboxamide | *** | 2.28 (B) | 651 |
| 646 | 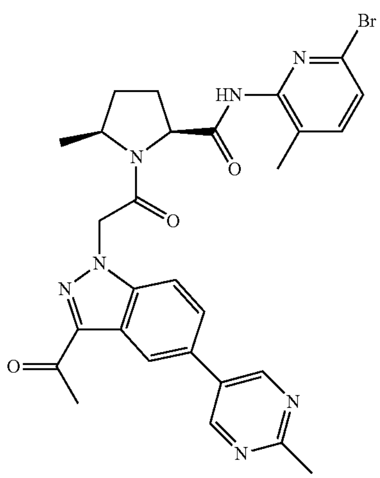 [SMILES: CC(=O)c1nn(CC(=O)N2[C@@H](C)CC[C@H]2C(=O)Nc2nc(Br)ccc2C)c2ccc(-c3cnc(C)nc3)cc12] | (2S,5S)-1-(2-(3-acetyl-5-(2-methylpyrimidin-5-yl)-1H-indazol-1-yl)acetyl)-N-(6-bromo-3-methylpyridin-2-yl)-5-methylpyrrolidine-2-carboxamide | *** | 1.70 (A) | 592 |
| 647 | 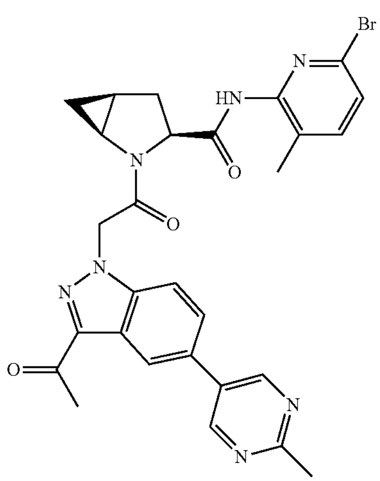 [SMILES: CC(=O)c1nn(CC(=O)N2[C@H](C(=O)Nc3nc(Br)ccc3C)C[C@@H]3C[C@@H]32)c2ccc(-c3cnc(C)nc3)cc12] | (1S,3S,5S)-2-(2-(3-acetyl-5-(2-methylpyrimidin-5-yl)-1H-indazol-1-yl)acetyl)-N-(6-bromo-3-methylpyridin-2-yl)-2-azabicyclo[3.1.0]hexane-3-carboxamide | *** | 1.67 (A) | 590 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 648 | 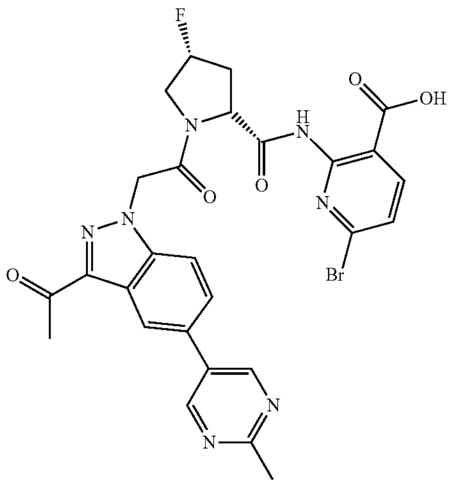 | 2-((2R,4R)-1-(2-(3-acetyl-5-(2-methylpyrimidin-5-yl)-1H-indazol-1-yl)acetyl)-4-fluoropyrrolidine-2-carboxamido)-6-bromonicotinic acid | * | 1.19 (A) | 624 |
| 649 | 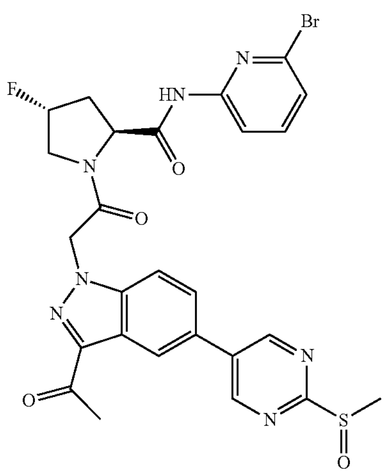 [SMILES: CC(=O)c1nn(CC(=O)N2C[C@H](F)C[C@H]2C(=O)Nc2cccc(Br)n2)c2ccc(-c3cnc(S(C)=O)nc3)cc12] | (2S,4R)-1-(2-(3-acetyl-5-(2-(methylsulfinyl)pyrimidin-5-yl)-1H-indazol-1-yl)acetyl)-N-(6-bromopyridin-2-yl)-4-fluoropyrrolidine-2-carboxamide | *** | 1.51 (A) | 629 |
| 651 | 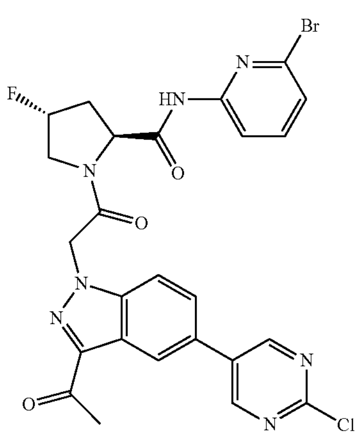 [SMILES: CC(=O)c1nn(CC(=O)N2C[C@H](F)C[C@H]2C(=O)Nc2cccc(Br)n2)c2ccc(-c3cnc(Cl)nc3)cc12] | (2S,4R)-1-(2-(3-acetyl-5-(2-chloropyrimidin-5-yl)-1H-indazol-1-yl)acetyl)-N-(6-bromopyridin-2-yl)-4-fluoropyrrolidine-2-carboxamide | * | 2.05 (A) | 600 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 652 | 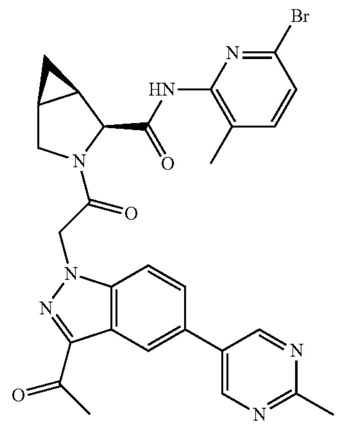 [SMILES: CC(=O)c1nn(CC(=O)N2C[C@H]3C[C@H]3[C@H]2C(=O)Nc2nc(Br)ccc2C)c2ccc(-c3cnc(C)nc3)cc12] | (1R,2S,5S)-3-(2-(3-acetyl-7-methyl-5-(2-methylpyrimidin-5-yl)-1H-indazol-1-yl)acetyl)-N-(6-bromo-3-methylpyridin-2-yl)-3-azabicyclo[3.1.0]hexane-2-carboxamide | *** | 1.71 (A) | 602 |
| 654 | 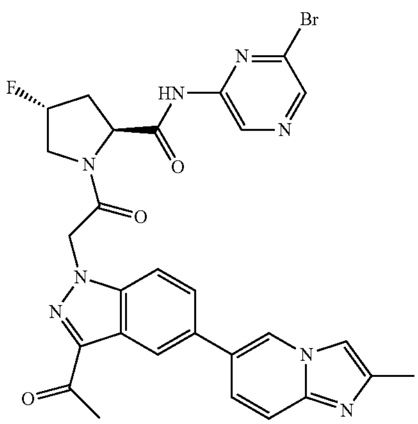 | (2S,4R)-1-(2-(3-acetyl-5-(2-methylimidazo[1,2-a]pyridin-6-yl)-1H-indazol-1-yl)acetyl)-N-(6-bromopyrazin-2-yl)-4-fluoropyrrolidine-2-carboxamide | *** | 1.26 (A) | 619 |
| 655 | 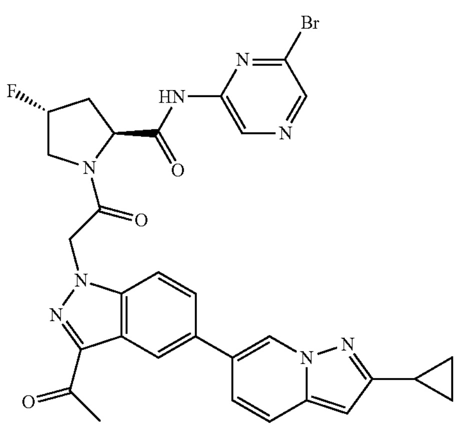 [SMILES: CC(=O)c1nn(CC(=O)N2C[C@H](F)C[C@H]2C(=O)Nc2cncc(Br)n2)c2ccc(-c3ccc4cc(C5CC5)nn4c3)cc12] | (2S,4R)-1-(2-(3-acetyl-5-(2-cyclopropylpyrazolo[1,5-a]pyrimidin-6-yl)-1H-indazol-1-yl)acetyl)-N-(6-bromopyrazin-2-yl)-4-fluoropyrrolidine-2-carboxamide | *** | 2.00 (A) | 646 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 656 | 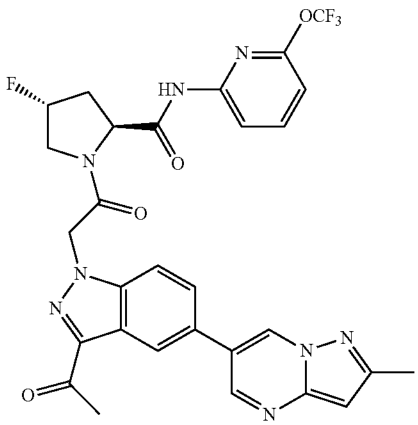 | (2S,4R)-1-(2-(3-acetyl-5-(2-methylpyrazolo[1,5-a]pyrimidin-6-yl)-1H-indol-1-yl)acetyl)-4-fluoro-N-(6-(trifluoromethoxy)pyridin-2-yl)pyrrolidine-2-carboxamide | *** | 2.00 (A) | 624 |
| 657 | 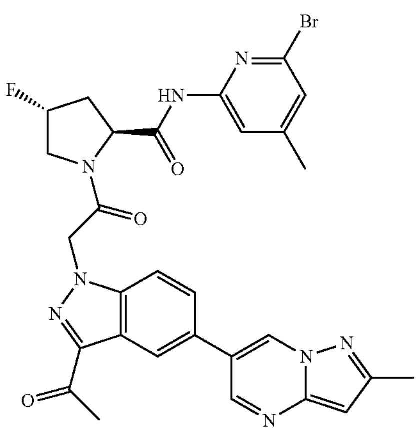 | (2S,4R)-1-(2-(3-acetyl-5-(2-methylpyrazolo[1,5-a]pyrimidin-6-yl)-1H-indol-1-yl)acetyl)-N-(6-bromo-4-methylpyridin-2-fluoropyrrolidine-2-carboxamide | *** | 1.94 (A) | 632 |
| 658 | 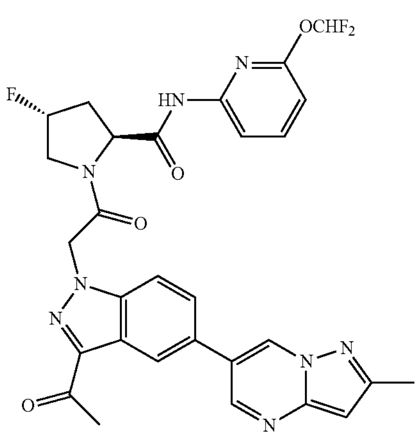 | (2S,4R)-1-(2-(3-acetyl-5-(2-methylpyrazolo[1,5-a]pyrimidin-6-yl)-1H-indazol-1-yl)acetyl)-N-(6-(difluoromethoxy)pyridin-2-yl)-4-fluoropyrrolidine-2-carboxamide | *** | 2.00 (A) | 607 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 659 | 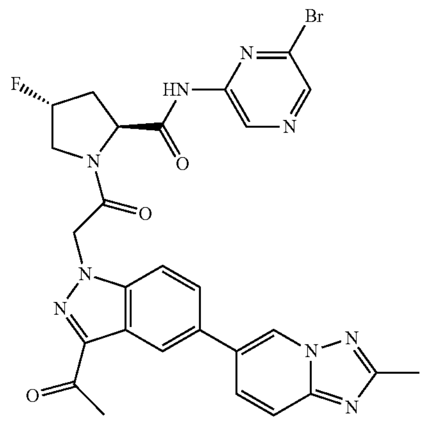 | (1R,3S,5R)-2-(2-(3-acetyl-5-(2-methyl-[1,2,4]triazolo[1,5-a]pyridin-6-yl)-1H-indazol-1-yl)acetyl)-N-(6-bromopyrazin-2-yl)-2-azabicyclo[3.1.0]hexane-3-carboxamide | *** | 1.69 (A) | 614 |
| 660 | 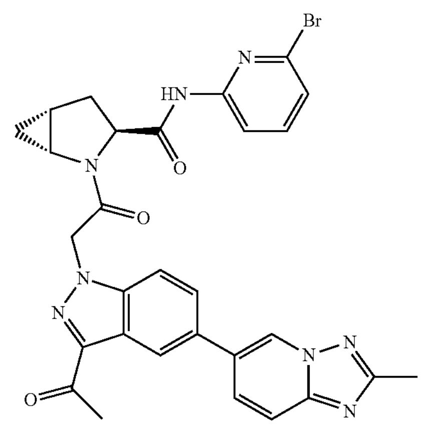 [SMILES: CC(=O)c1nn(CC(=O)N2[C@@H]3C[C@@H]3C[C@H]2C(=O)Nc2cccc(Br)n2)c2ccc(-c3ccc4nc(C)nn4c3)cc12] | (1R,3S,5R)-2-(2-(3-acetyl-5-(2-methyl-[1,2,4]triazolo[1,5-a]pyridin-6-yl)-1H-indazol-1-yl)acetyl)-N-(6-bromopyridin-2-yl)-2-azabicyclo[3.1.0]hexane-3-carboxamide | *** | 1.87 (A) | 613 |
| 661 | 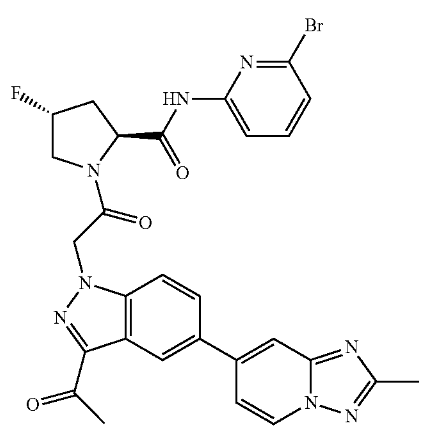 [SMILES: CC(=O)c1nn(CC(=O)N2C[C@H](F)C[C@H]2C(=O)Nc2cccc(Br)n2)c2ccc(-c3ccn4nc(C)nc4c3)cc12] | (2S,4R)-1-(2-(3-acetyl-5-(2-methyl-[1,2,4]triazolo[1,5-a]pyridin-7-yl)-1H-indazol-1-yl)acetyl)-N-(6-bromopyridin-2-yl)-4-fluoropyrrolidine-2-carboxamide | *** | 1.70 (A) | 619 |

TABLE 3-continued

Additional Non-limiting Examples of Compounds of Formula I

| Comp No. | Structure | Name | IC<sub>5</sub> (Stars) | RT min (Method A,B,C or D) | MS (M + 1) |
|---|---|---|---|---|---|
| 662 | 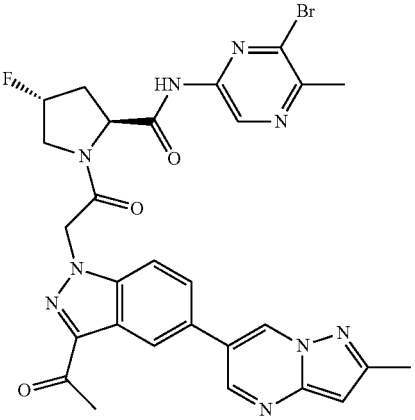 | (2S,4R)-1-(2-(3-acetyl-5-(2-methylpyrazolo[1,5-a]pyrimidin-6-yl)-1H-indazol-1-yl)acetyl)-N-(6-bromo-5-methylpyrazin-2-yl)-4-fluoropyrrolidine-2-carboxamide | *** | 1.86 (A) | 634 |
| 663 | 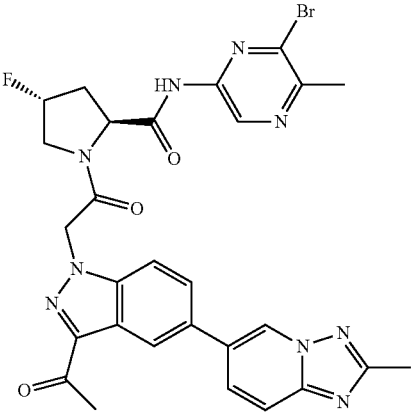 | (2S,4R)-1-(2-(3-acetyl-5-(2-methyl-[1,2,4]triazolo[1,5-a]pyridin-6-yl)-1H-indazol-1-yl)acetyl)-N-(6-bromo-5-methylpyrazin-2-yl)-4-fluoropyrrolidine-2-carboxamide | *** | 1.66 (A) | 634 |
| 664 | 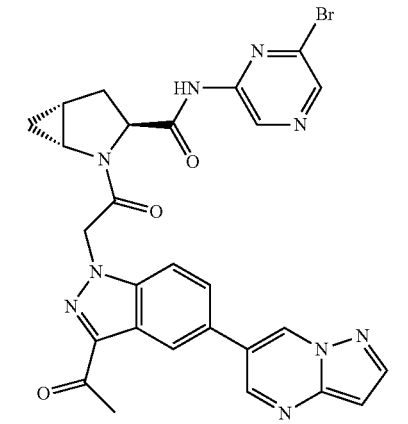 | (1R,3S,5R)-2-(2-(3-acetyl-5-(pyrazolo[1,5-a]pyrimidin-6-yl)-1H-indazol-1-yl)acetyl)-N-(6-bromopyrazin-2-yl)-2-azabicyclo[3.1.0]hexane-3-carboxamide | *** | 1.77 (A) | 600 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 665 | 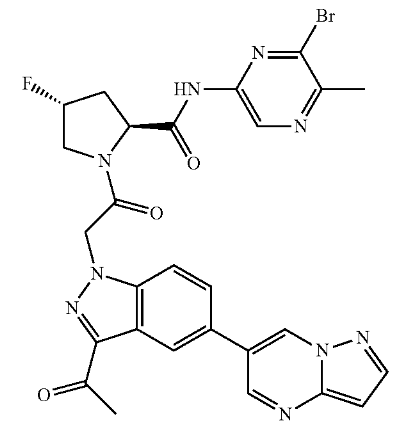 | (2S,4R)-1-(2-(3-acetyl-5-(pyrazolo[1,5-a]pyrimidin-6-yl)-1H-indazol-1-yl)acetyl)-N-(6-bromo-5-methylpyrazin-2-yl)-4-fluoropyrrolidine-2-carboxamide | *** | 1.75 (A) | 620 |
| 666 | 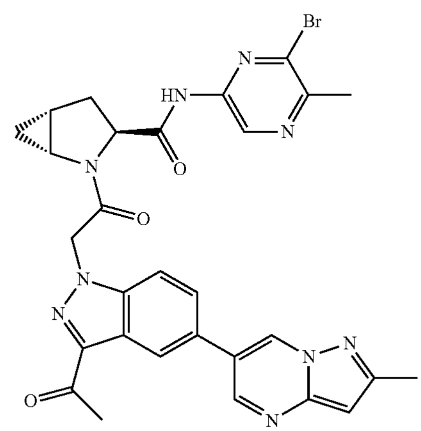 [SMILES: CC(=O)c1nn(CC(=O)N2[C@@H]3C[C@@H]3C[C@H]2C(=O)Nc2cnc(C)c(Br)n2)c2ccc(-c3cnc4cc(C)nn4c3)cc12] | (1R,3S,5R)-2-(2-(3-acetyl-5-(2-methylpyrazolo[1,5-a]pyrimidin-6-yl)-1H-indazol-1-yl)acetyl)-N-(6-bromo-5-methylpyrazin-2-yl)-2-azabicyclo[3.1.0]hexane-3-carboxamide | *** | 1.99 (A) | 628 |
| 667 | 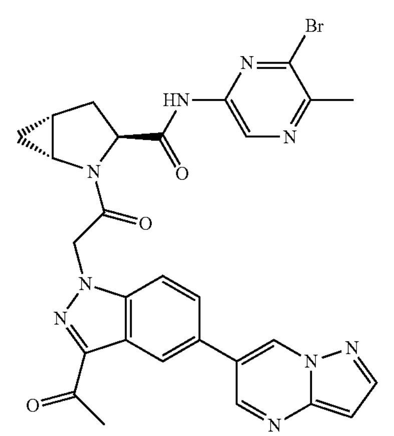 [SMILES: CC(=O)c1nn(CC(=O)N2[C@@H]3C[C@@H]3C[C@H]2C(=O)Nc2cnc(C)c(Br)n2)c2ccc(-c3cnc4ccnn4c3)cc12] | (1R,3S,5R)-2-(2-(3-acetyl-5-(pyrazolo[1,5-a]pyrimidin-6-yl)-1H-indazol-1-yl)acetyl)-N-(6-bromo-5-methylpyrazin-2-yl)-2-azabicyclo[3.1.0]hexane-3-carboxamide | *** | 1.88 (A) | 614 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 668 | 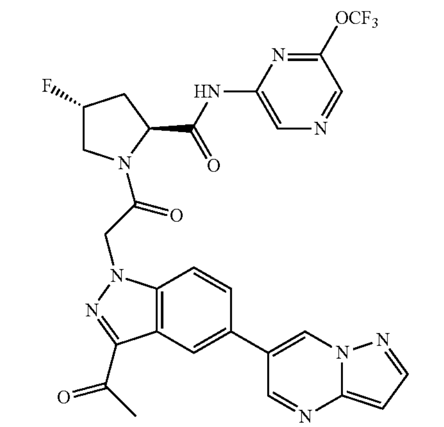 [SMILES: CC(=O)c1nn(CC(=O)N2C[C@H](F)C[C@H]2C(=O)Nc2cncc(OC(F)(F)F)n2)c2ccc(-c3cnc4ccnn4c3)cc12] | (2S,4R)-1-(2-(3-acetyl-5-(pyrazolo[1,5-a]pyrimidin-6-yl)-1H-indazol-1-yl)acetyl)-4-fluoro-N-(6-(trifluoromethoxy)pyridin-2-yl)pyrrolidine-2-carboxamide | *** | 2.02 (A) | 611 |
| 669 | 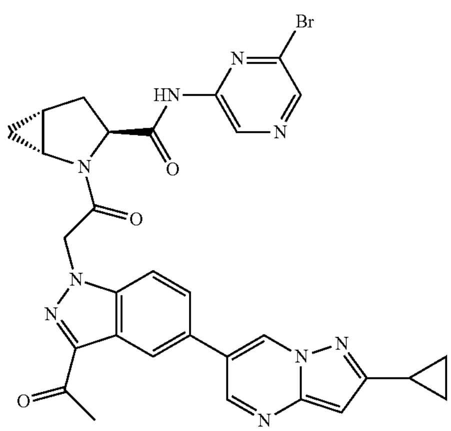 [SMILES: CC(=O)c1nn(CC(=O)N2[C@@H]3C[C@@H]3C[C@H]2C(=O)Nc2cncc(Br)n2)c2ccc(-c3cnc4cc(C5CC5)nn4c3)cc12] | (1R,3S,5R)-2-(2-(3-acetyl-5-(2-cyclopropylpyrazolo[1,5-a]pyrimidin-6-yl)-1H-indazol-1-yl)acetyl)-N-(6-bromopyrazin-2-yl)-2-azabicyclo[3.1.0]hexane-3-carboxamide | *** | 2.12 (A) | 640 |
| 670 | 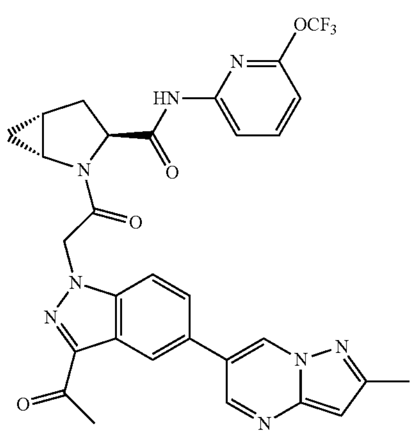 [SMILES: CC(=O)c1nn(CC(=O)N2[C@@H]3C[C@@H]3C[C@H]2C(=O)Nc2cccc(OC(F)(F)F)n2)c2ccc(-c3cnc4cc(C)nn4c3)cc12] | (1R,3S,5R)-2-(2-(3-acetyl-5-(2-methylpyrazolo[1,5-a]pyrimidin-6-yl)-1H-indazol-1-yl)acetyl)-N-(6-(trifluoromethoxy)pyridin-2-yl)-2-azabicyclo[3.1.0]hexane-3-carboxamide | *** | 2.23 (A) | 619 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 671 | 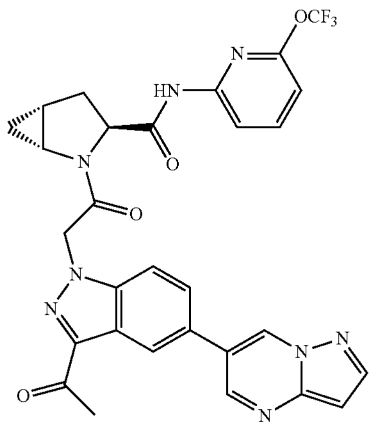 [SMILES: CC(=O)c1nn(CC(=O)N2[C@@H]3C[C@@H]3C[C@H]2C(=O)Nc2cccc(OC(F)(F)F)n2)c2ccc(-c3cnc4ccnn4c3)cc12] | (1R,3S,5R)-2-(2-(3-acetyl-5-(pyrazolo[1,5-a]pyrimidin-6-yl)-1H-indazol-1-yl)acetyl)-N-(6-(trifluoromethoxy)pyridin-2-yl)-2-azabicyclo[3.1.0]hexane-3-carboxamide | *** | 2.13 (A) | 605 |
| 672 | 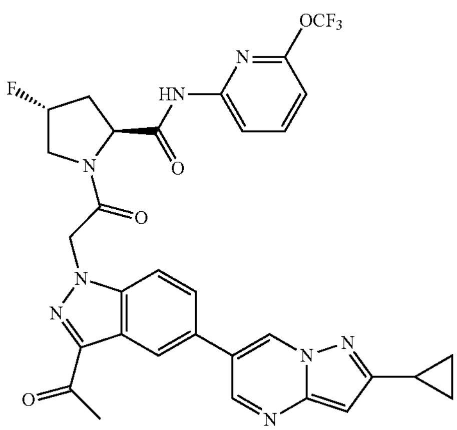 | (2S,4R)-1-(2-(3-acetyl-5-(2-cyclopropylpyrazolo[1,5-a]pyrimidin-6-yl)-1H-indazol-1-yl)acetyl)-4-fluoro-N-(6-(trifluoromethoxy)pyridin-2-yl)pyrrolidine-2-carboxamide | *** | 2.35 (A) | 651 |
| 673 | 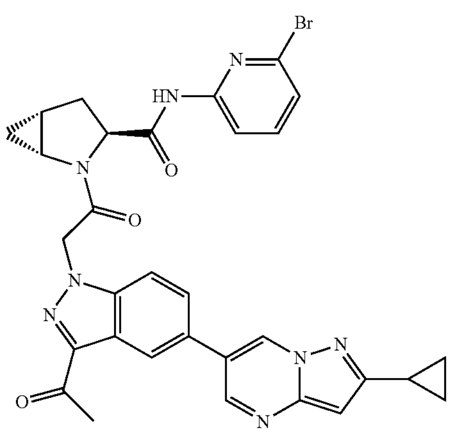 | (1R,3S,5R)-2-(2-(3-acetyl-5-(2-cyclopropylpyrazolo[1,5-a]pyrimidin-6-yl)-1H-indazol-1-yl)acetyl)-N-(6-bromopyridin-2-yl)-2-azabicyclo[3.1.0]hexane-3-carboxamide | *** | 2.28 (A) | 639 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 674 | 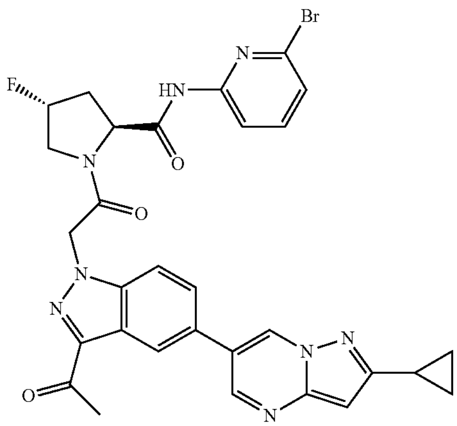 [SMILES: CC(=O)c1nn(CC(=O)N2C[C@H](F)C[C@H]2C(=O)Nc2cccc(Br)n2)c2ccc(-c3cnc4cc(C5CC5)nn4c3)cc12] | (2S,4R)-1-(2-(3-acetyl-5-(2-cyclopropylpyrazolo[1,5-a]pyrimidin-6-yl)-1H-indazol-1-yl)acetyl)-N-(6-bromopyridin-2-yl)-4-fluoropyrrolidine-2-carboxamide | *** | 2.16 (A) | 645 |
| 675 | 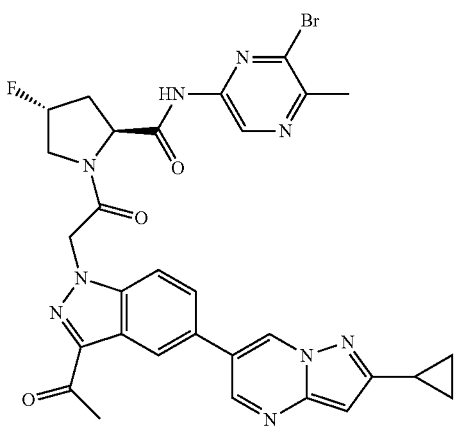 [SMILES: CC(=O)c1nn(CC(=O)N2C[C@H](F)C[C@H]2C(=O)Nc2cnc(C)c(Br)n2)c2ccc(-c3cnc4cc(C5CC5)nn4c3)cc12] | (2S,4R)-1-(2-(3-acetyl-5-(2-cyclopropylpyrazolo[1,5-a]pyrimidin-6-yl)-1H-indazol-1-yl)acetyl)-N-(6-bromo-5-methylpyrazin-2-yl)-4-fluoropyrrolidine-2-carboxamide | *** | 2.11 (A) | 660 |
| 676 | 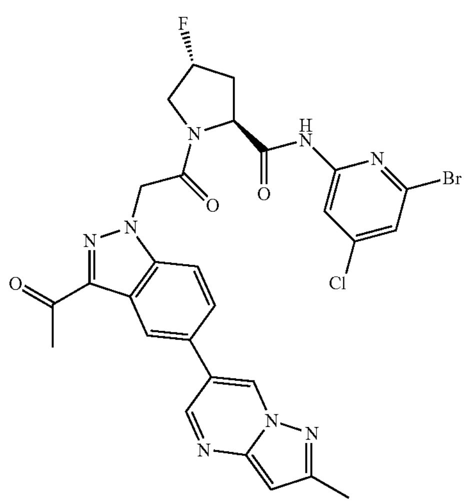 [SMILES: CC(=O)c1nn(CC(=O)N2C[C@H](F)C[C@H]2C(=O)Nc2cc(Cl)cc(Br)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-N-(6-bromo-4-chloropyridin-2-yl)-4-fluoropyrrolidine-2-carboxamide | *** | 2.21 (A) | 653 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 677 | 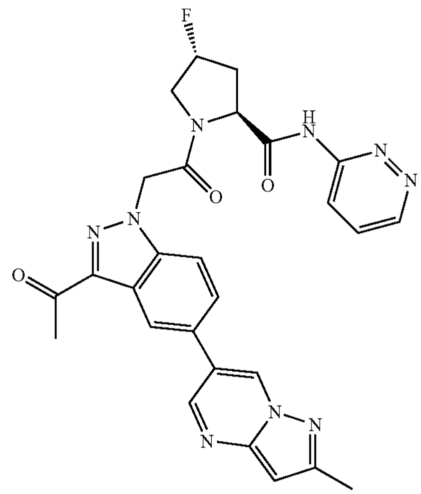 [SMILES: CC(=O)c1nn(CC(=O)N2C[C@H](F)C[C@H]2C(=O)Nc2cccnn2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-4-fluoro-N-(pyridazin-3-yl)pyrrolidine-2-carboxamide | *** | 1.32 (A) | 541 |
| 678 | 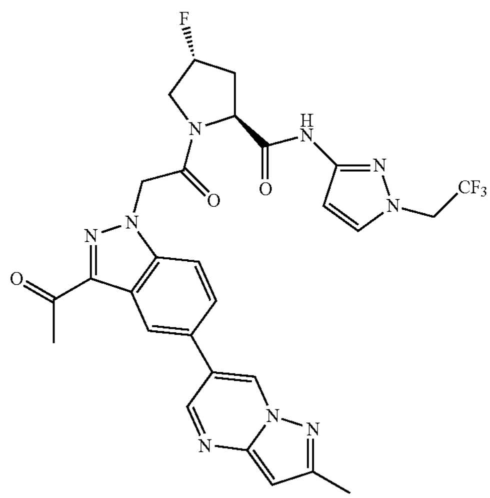 [SMILES: CC(=O)c1nn(CC(=O)N2C[C@H](F)C[C@H]2C(=O)Nc2ccn(CC(F)(F)F)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-4-fluoro-N-(1-(2,2,2-trifluoroethyl)-1H-pyrazol-3-yl)pyrrolidine-2-carboxamide | *** | 1.66 (A) | 612 |
| 679 | 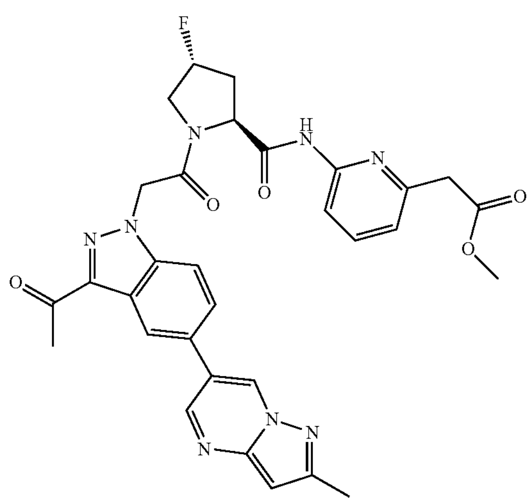 [SMILES: COC(=O)Cc1cccc(NC(=O)[C@@H]2C[C@@H](F)CN2C(=O)Cn2nc(C(C)=O)c3cc(-c4cnc5cc(C)nn5c4)ccc32)n1] | methyl 2-(6-((2S,4R)-1-(2-(3-acetyl-5-(2-methylpyrazolo[1,5-a]pyrimidin-6-yl)-1H-indazol-1-yl)acetyl)-4-fluoropyrrolidine-2-carboxamido)pyridin-2-yl)acetate | *** | 1.67 (A) | 613 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 680 | 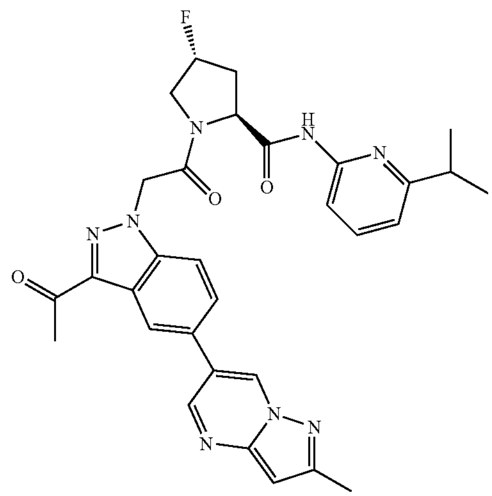 [SMILES: CC(=O)c1nn(CC(=O)N2C[C@H](F)C[C@H]2C(=O)Nc2cccc(C(C)C)n2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-4-fluoro-N-(6-isopropylpyridin-2-yl)pyrrolidine-2-carboxamide | *** | 2.04 (A) | 583 |
| 681 | 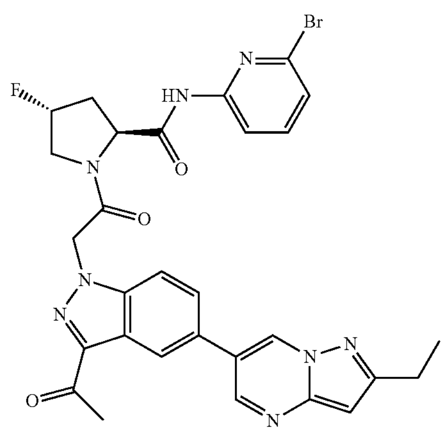 | (2S,4R)-1-(2-(3-acetyl-5-(2-ethylpyrazolo[1,5-a]pyrimidin-6-yl)-1H-indazol-1-yl)acetyl)-N-(6-bromopyridin-2-yl)-4-fluoropyrrolidine-2-carboxamide | *** | 2.11 (A) | 633 |
| 682 | 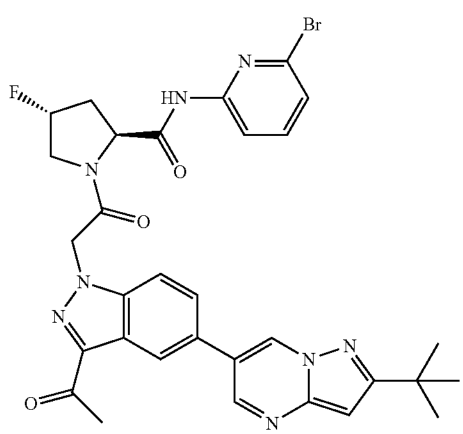 [SMILES: CC(=O)c1nn(CC(=O)N2C[C@H](F)C[C@H]2C(=O)Nc2cccc(Br)n2)c2ccc(-c3cnc4cc(C(C)(C)C)nn4c3)cc12] | (2S,4R)-1-(2-(3-acetyl-5-(2-(tert-butyl)pyrazolo[1,5-a]pyrimidin-6-yl)-1H-indazol-1-yl)acetyl)-N-(6-bromopyridin-2-yl)-4-fluoropyrrolidine-2-carboxamide | *** | 2.49 (A) | 661 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 683 | 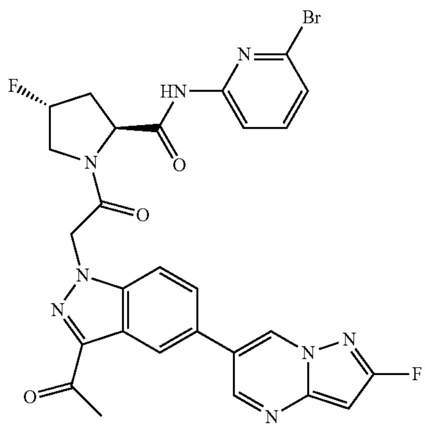 [SMILES: CC(=O)c1nn(CC(=O)N2C[C@H](F)C[C@H]2C(=O)Nc2cccc(Br)n2)c2ccc(-c3cnc4cc(F)nn4c3)cc12] | (2S,4R)-1-(2-(3-acetyl-5-(2-fluoropyrazolo[1,5-a]pyrimidin-6-yl)-1H-indazol-1-yl)acetyl)-N-(6-bromopyridin-2-yl)-4-fluoropyrrolidine-2-carboxamide | *** | 2.09 (A) | 623 |
| 684 | 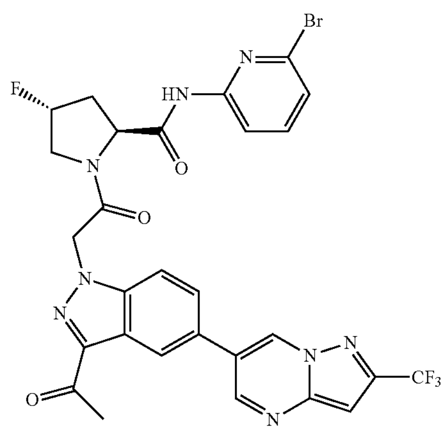 [SMILES: CC(=O)c1nn(CC(=O)N2C[C@H](F)C[C@H]2C(=O)Nc2cccc(Br)n2)c2ccc(-c3cnc4cc(C(F)(F)F)nn4c3)cc12] | (2S,4R)-1-(2-(3-acetyl-5-(2-(trifluoromethyl)pyrazolo[1,5-a]pyrimidin-6-yl)-1H-indazol-1-yl)acetyl)-N-(6-bromopyridin-2-yl)-4-fluoropyrrolidine-2-carboxamide | *** | 2.43 (A) | 673 |
| 685 | 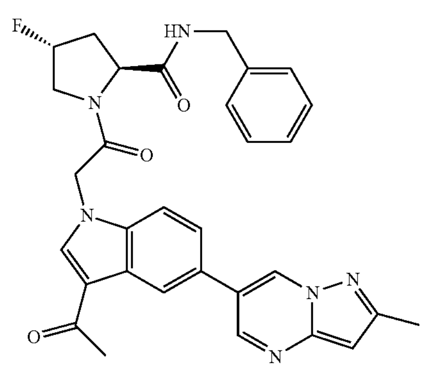 [SMILES: CC(=O)c1cn(CC(=O)N2C[C@H](F)C[C@H]2C(=O)NCc2ccccc2)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-N-benzyl-4-fluoropyrrolidine-2-carboxamide | *** | 10.17 (D) | 553 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 686 | 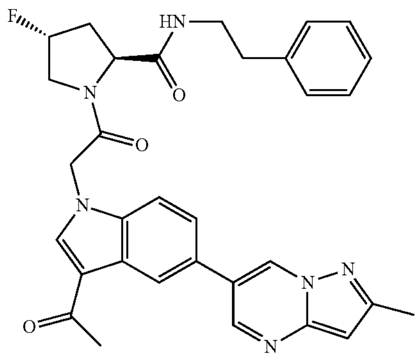 [SMILES: CC(=O)c1cn(CC(=O)N2C[C@H](F)C[C@H]2C(=O)NCCc2ccccc2)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-4-fluoro-N-phenethylpyrrolidine-2-carboxamide | *** | 12.53 (C) | 567 |
| 687 | 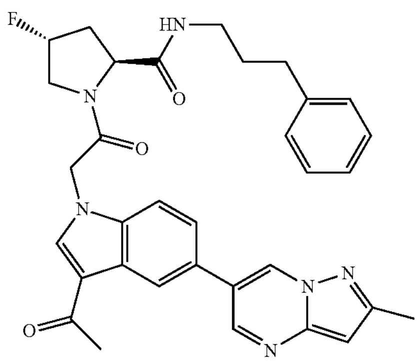 [SMILES: CC(=O)c1cn(CC(=O)N2C[C@H](F)C[C@H]2C(=O)NCCCc2ccccc2)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-4-fluoro-N-(3-phenylpropyl)pyrrolidine-2-carboxamide | *** | 10.85 (D) | 581 |
| 688 | 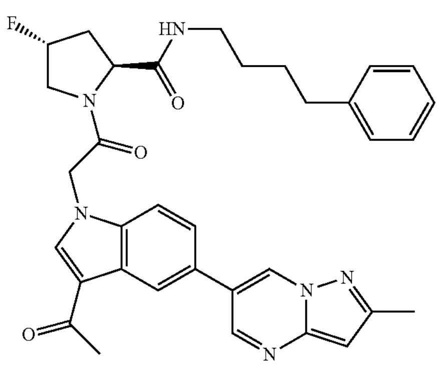 [SMILES: CC(=O)c1cn(CC(=O)N2C[C@H](F)C[C@H]2C(=O)NCCCCc2ccccc2)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)acetyl)-4-fluoro-N-(4-phenylbutyl)pyrrolidine-2-carboxamide | *** | 11.26 (D) | 595 |
| 689 | 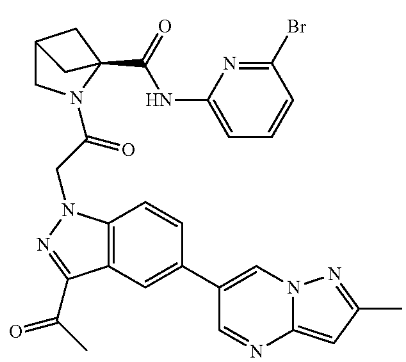 | 2-(2-(3-acetyl-5-(2-methylpyrazolo[1,5-a]pyrimidin-6-yl)-1H-indazol-1-yl)acetyl)-N-(6-bromopyridin-2-yl)-2-azabicyclo[2.1.1]hexane-1-carboxamide | *** | 1.94 (A) | 613 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 691 | 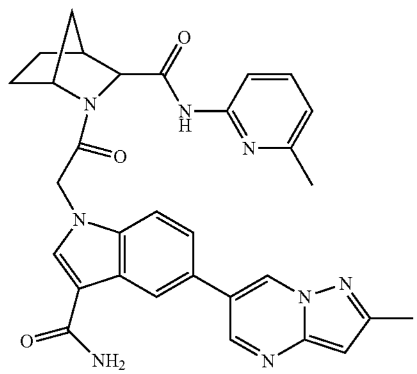 [SMILES: Cc1cccc(NC(=O)C2C3CCC(C3)N2C(=O)Cn2cc(C(N)=O)c3cc(-c4cnc5cc(C)nn5c4)ccc32)n1] | 5-(2-methylpyrazolo[1,5-a]pyrimidin-6-yl)-1-(2-((1R,4S)-3-((6-methylpyridin-2-yl)carbamoyl)-2-azabicyclo[2.2.1]heptan-2-yl)-2-oxoethyl)-1H-indole-3-carboxamide | ** | 2.69 (B) | 563 |
| 692 | 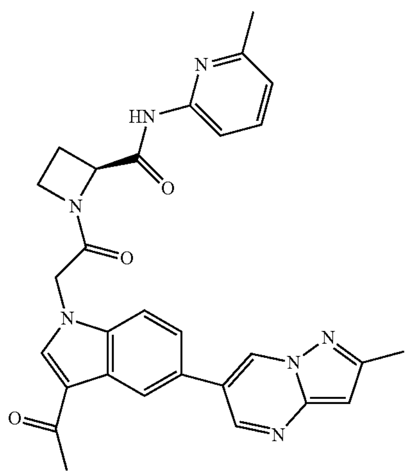 [SMILES: CC(=O)c1cn(CC(=O)N2CC[C@H]2C(=O)Nc2cccc(C)n2)c2ccc(-c3cnc4cc(C)nn4c3)cc12] | (S)-1-(2-(3-acetyl-5-(2-methylpyrazolo[1,5-a]pyrimidin-6-yl)-1H-indol-1-yl)acetyl)-N-(6-methylpyridin-2-yl)azetidine-2-carboxamide | ** | 9.80 (D) | 522 |
| 693 | 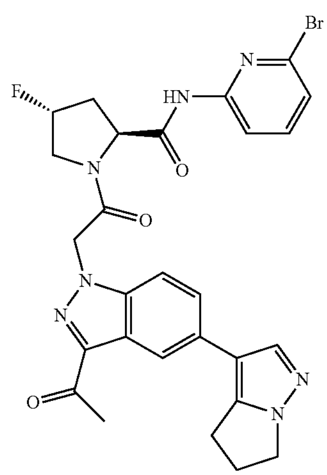 [SMILES: CC(=O)c1nn(CC(=O)N2C[C@H](F)C[C@H]2C(=O)Nc2cccc(Br)n2)c2ccc(-c3cnn4c3CCC4)cc12] | (2S,4R)-1-(2-(3-acetyl-5-(5,6-dihydro-4H-pyrrolo[1,2-b]pyrazol-3-yl)-1H-indazol-1-yl)acetyl)-N-(6-bromopyridin-2-yl)-4-fluoropyrrolidine-2-carboxamide | *** | 1.81 (A) | 594 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 695 | 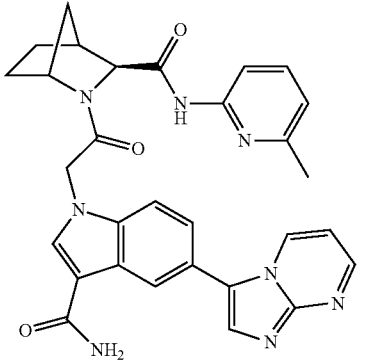 [SMILES: Cc1cccc(NC(=O)[C@@H]2C3CCC(C3)N2C(=O)Cn2cc(C(N)=O)c3cc(-c4cnc5ncccn45)ccc32)n1] | 5-(imidazo[1,2-a]pyrimidin-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | * | 2.29 (B) | 549 |
| 696 | 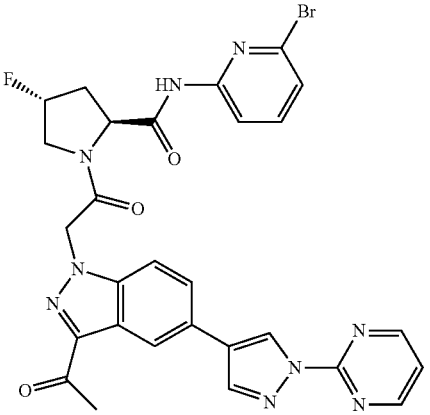 [SMILES: CC(=O)c1nn(CC(=O)N2C[C@H](F)C[C@H]2C(=O)Nc2cccc(Br)n2)c2ccc(-c3cnn(-c4ncccn4)c3)cc12] | (2S,4R)-1-(2-(3-acetyl-5-(1-(pyrimidin-2-yl)-1H-pyrazol-4-yl)-1H-indazol-1-yl)acetyl)-N-(6-bromopyridin-2-yl)-4-fluoropyrrolidine-2-carboxamide | *** | 1.76 (A) | 632 |
| 697 | 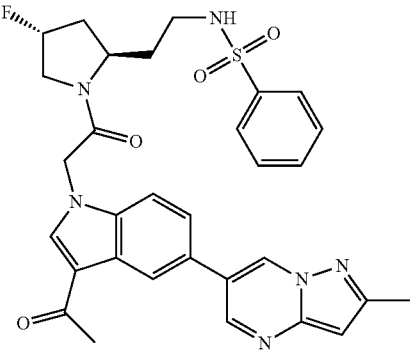 [SMILES: CC(=O)c1cn(CC(=O)N2C[C@H](F)C[C@H]2CCNS(=O)(=O)c2ccccc2)c2ccc(-c3cnc4cc(C)nn4c3)cc12] | N-(2-((2R,4R)-1-(2-(3-acetyl-5-(2-methylpyrazolo[1,5-a]pyrimidin-6-yl)-1H-indol-1-yl)acetyl)-4-fluoropyrrolidin-2-yl)ethyl)benzenesulfonamide | ** | 12.51 (C) | 603 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 698 | 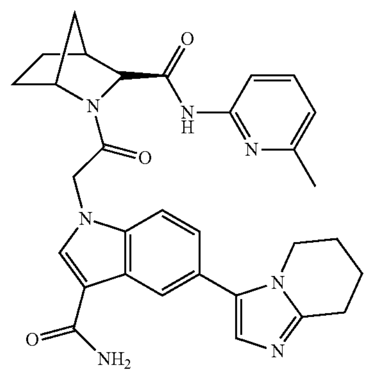 | 1-(2-((1R,3R,4S)-3-((6-methylpyridin-2-yl)carbamoyl)-2-azabicyclo[2.2.1]heptan-2-yl)-2-oxoethyl)-5-(5,6,7,8-tetrahydroimidazo[1,2-a]pyridin-3-yl)-1H-indole-3-carboxamide | * | 3.14 (B) | 552 |
| 699 | 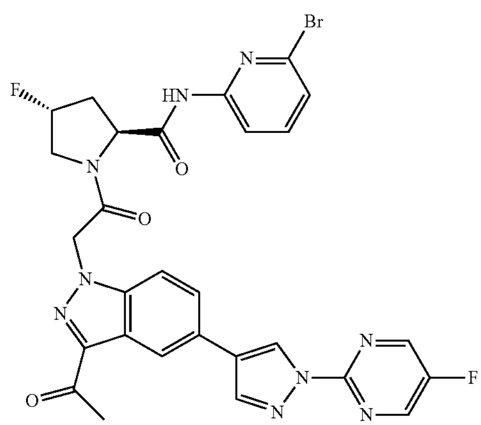 [SMILES: CC(=O)c1nn(CC(=O)N2C[C@H](F)C[C@H]2C(=O)Nc2cccc(Br)n2)c2ccc(-c3cnn(-c4ncc(F)cn4)c3)cc12] | (2S,4R)-1-(2-(3-acetyl-5-(1-(5-fluoropyrimidin-2-yl)-1H-pyrazol-4-yl)-1H-indazol-1-yl)acetyl)-N-(6-bromopyridin-2-yl)-4-fluoropyrrolidine-2-carboxamide | *** | 1.92 (A) | 650 |
| 700 | 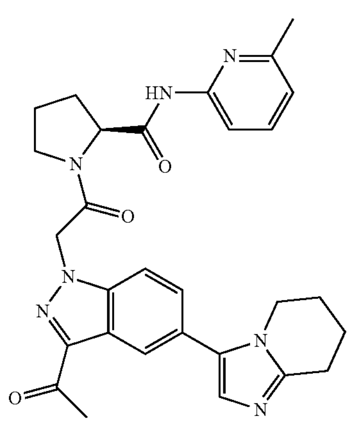 [SMILES: CC(=O)c1nn(CC(=O)N2CCC[C@H]2C(=O)Nc2cccc(C)n2)c2ccc(-c3cnc4n3CCCC4)cc12] | (S)-1-(2-(3-acetyl-5-(5,6,7,8-tetrahydroimidazo[1,2-a]pyridin-3-yl)-1H-indazol-1-yl)acetyl)-N-(6-methylpyridin-2-yl)pyrrolidine-2-carboxamide | ** | 9.31 (D) | 526 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 701 | 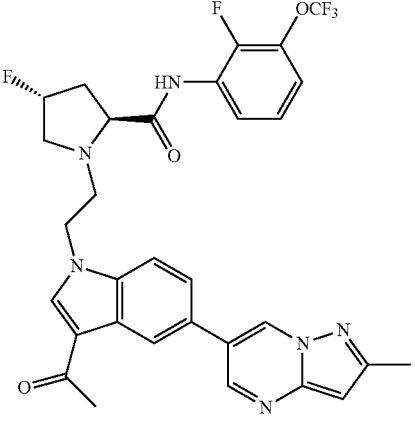 [SMILES: CC(=O)c1cn(CCN2C[C@H](F)C[C@H]2C(=O)Nc2cccc(OC(F)(F)F)c2F)c2ccc(-c3cnc4cc(C)nn4c3)cc12] | (2S,4R)-1-(2-(3-acetyl-5-(2-methylpyrazolo[1,5-a]pyrimidin-6-yl)-1H-indol-1-yl)ethyl)-4-fluoro-N-(2-fluoro-3-(trifluoromethoxy)phenyl)pyrrolidine-2-carboxamide | * | 12.59 (D) | 627 |
| 702 | 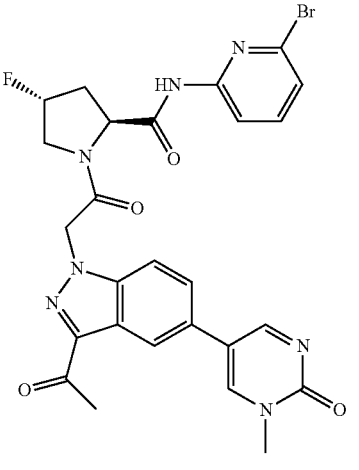 [SMILES: CC(=O)c1nn(CC(=O)N2C[C@H](F)C[C@H]2C(=O)Nc2cccc(Br)n2)c2ccc(-c3cnc(=O)n(C)c3)cc12] | (2S,4R)-1-(2-(3-acetyl-5-(1-methyl-2-oxo-1,2-dihydropyrimidin-5-yl)-1H-indazol-1-yl)acetyl)-N-(6-bromopyridin-2-yl)-4-fluoropyrrolidine-2-carboxamide | *** | 1.38 (A) | 596 |
| 703 | 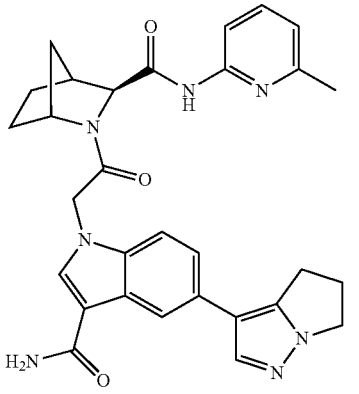 [SMILES: Cc1cccc(NC(=O)[C@@H]2C3CCC(C3)N2C(=O)Cn2cc(C(N)=O)c3cc(-c4cnn5c4CCC5)ccc32)n1] | 5-(5,6-dihydro-4H-pyrrolo[1,2-b]pyrazol-3-yl)-1-(2-((1R,3S,4S)-3-((6-methylpyridin-2-yl)carbamoyl)-2-azabicyclo[2.2.1]heptan-2-yl)-2-oxoethyl)-1H-indole-3-carboxamide | | 1.98 (B) | 538 |

TABLE 3-continued

Additional Non-limiting Examples of Compounds of Formula I

| Comp No. | Structure | Name | IC5 (Stars) | RT min (Method A,B,C or D) | MS (M + 1) |
|---|---|---|---|---|---|
| 704 | 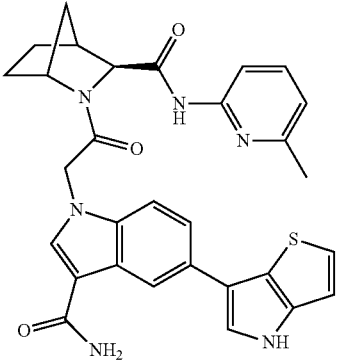 [SMILES: Cc1cccc(NC(=O)[C@@H]2C3CCC(C3)N2C(=O)Cn2cc(C(N)=O)c3cc(-c4c[nH]c5ccsc45)ccc32)n1] | 1-(2-((1R,3S,4S)-3-((6-methylpyridin-2-yl)carbamoyl)-2-azabicyclo[2.2.1]heptan-2-yl)-2-oxoethyl)-5-(1H-thieno[3,2-c]pyrazol-3-yl)-1H-indole-3-carboxamide | * | 2.89 (B) | 554 |
| 705 | 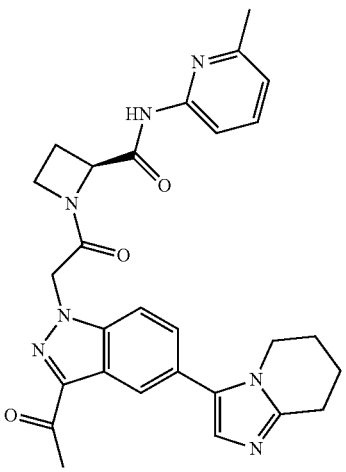 [SMILES: CC(=O)c1nn(CC(=O)N2CC[C@H]2C(=O)Nc2cccc(C)n2)c2ccc(-c3cnc4n3CCCC4)cc12] | (S)-1-(2-(3-acetyl-5-(5,6,7,8-tetrahydroimidazo[1,2-a]pyridin-3-yl)-1H-indazol-1-yl)acetyl)-N-(6-methylpyridin-2-yl)azetidine-2-carboxamide | * | 9.15 (D) | 512 |
| 706 | 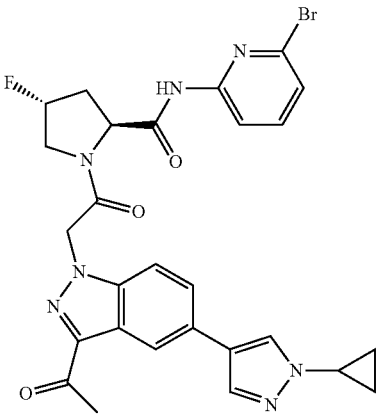 [SMILES: CC(=O)c1nn(CC(=O)N2C[C@H](F)C[C@H]2C(=O)Nc2cccc(Br)n2)c2ccc(-c3cnn(C4CC4)c3)cc12] | (2S,4R)-1-(2-(3-acetyl-5-(1-cyclopropyl-1H-pyrazol-4-yl)-1H-indazol-1-yl)acetyl)-N-(6-bromopyridin-2-yl)-4-fluoropyrrolidine-2-carboxamide | *** | 1.94 (A) | 594 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 707 | 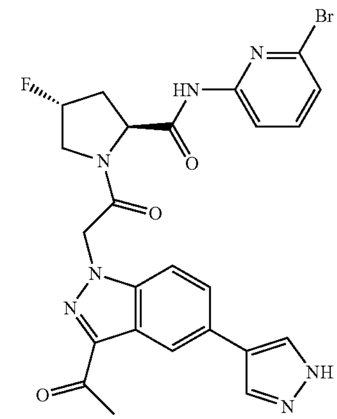 [SMILES: CC(=O)c1nn(CC(=O)N2C[C@H](F)C[C@H]2C(=O)Nc2cccc(Br)n2)c2ccc(-c3cn[nH]c3)cc12] | (2S,4R)-1-(2-(3-acetyl-5-(1H-pyrazol-4-yl)-1H-indazol-1-yl)acetyl)-N-(6-bromopyridin-2-yl)-4-fluoropyrrolidine-2-carboxamide | *** | 1.56 (A) | 554 |
| 708 | 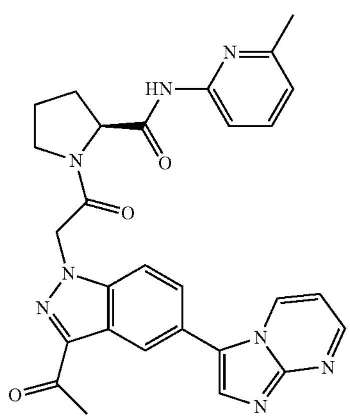 [SMILES: CC(=O)c1nn(CC(=O)N2CCC[C@H]2C(=O)Nc2cccc(C)n2)c2ccc(-c3cnc4ncccn34)cc12] | (S)-1-(2-(3-acetyl-5-(imidazo[1,2-a]pyrimidin-3-yl)-1H-indazol-1-yl)acetyl)-N-(6-methylpyridin-2-yl)pyrrolidine-2-carboxamide | *** | 8.59 (D) | 523 |
| 709 | 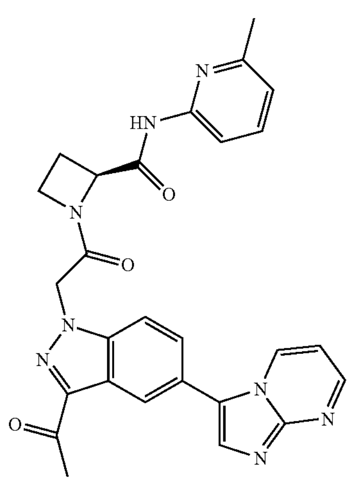 [SMILES: CC(=O)c1nn(CC(=O)N2CC[C@H]2C(=O)Nc2cccc(C)n2)c2ccc(-c3cnc4ncccn34)cc12] | (S)-1-(2-(3-acetyl-5-(imidazo[1,2-a]pyrimidin-3-yl)-1H-indazol-1-yl)acetyl)-N-(6-methylpyridin-2-yl)azetidine-2-carboxamide | *** | 8.67 (D) | 509 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 710 | 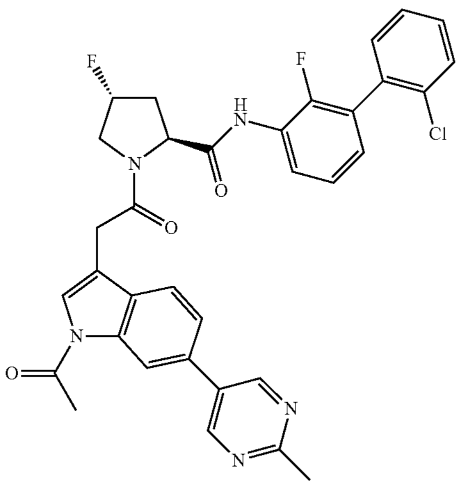 [SMILES: CC(=O)n1cc(CC(=O)N2C[C@H](F)C[C@H]2C(=O)Nc2cccc(-c3ccccc3Cl)c2F)c2ccc(-c3cnc(C)nc3)cc21] | (2S,4R)-1-(2-(1-acetyl-6-(2-methylpyrimidin-5-yl)-1H-indol-3-yl)acetyl)-N-(2'-chloro-2-fluoro-[1,1'-biphenyl]-3-yl)-4-fluoropyrrolidine-2-carboxamide | *** | 2.02 (A) | 628 |
| 711 | 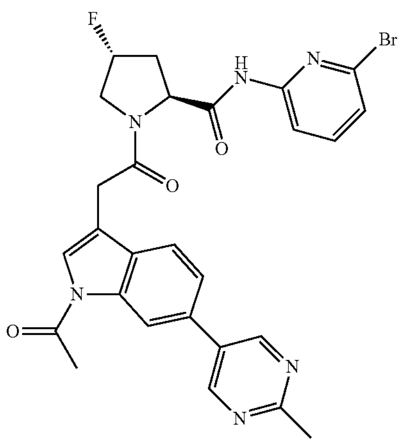 [SMILES: CC(=O)n1cc(CC(=O)N2C[C@H](F)C[C@H]2C(=O)Nc2cccc(Br)n2)c2ccc(-c3cnc(C)nc3)cc21] | (2S,4R)-1-(2-(1-acetyl-6-(2-methylpyrimidin-5-yl)-1H-indol-3-yl)acetyl)-N-(6-bromopyridin-2-yl)-4-fluoropyrrolidine-2-carboxamide | *** | 1.69 (A) | 579 |
| 714 | 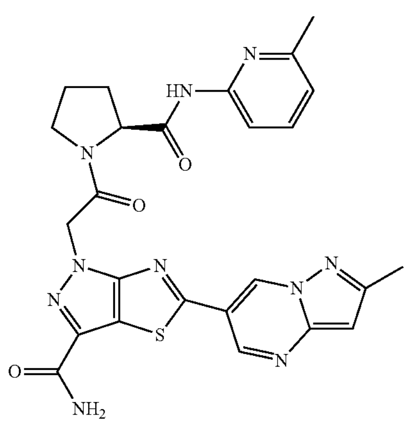 [SMILES: Cc1cccc(NC(=O)[C@@H]2CCCN2C(=O)Cn2nc(C(N)=O)c3sc(-c4cnc5cc(C)nn5c4)nc32)n1] | 1-(2-((2S,4R)-4-fluoro-2-((6-methylpyridin-2-yl)carbamoyl)pyrrolidin-1-yl)-2-oxoethyl)-5-(2-methylpyrazolo[1,5-a]pyrimidin-6-yl)-1H-pyrazolo[3,4-d]thiazole-3-carboxamide | * | 1.90 (B) | 563 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 715 | 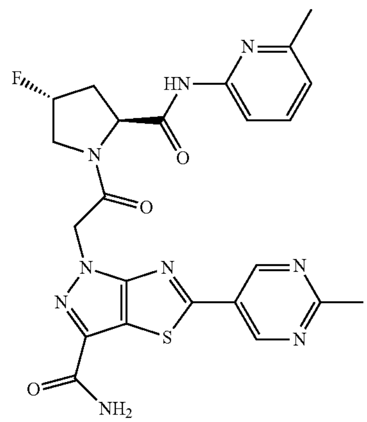 [SMILES: Cc1cccc(NC(=O)[C@@H]2C[C@@H](F)CN2C(=O)Cn2nc(C(N)=O)c3sc(-c4cnc(C)nc4)nc32)n1] | 1-(2-((2S,4R)-4-fluoro-2-((6-methylpyridin-2-yl)carbamoyl)pyrrolidin-1-yl)-2-oxoethyl)-5-(2-methylpyrimidin-5-yl)-1H-pyrazolo[3,4-d]thiazole-3-carboxamide | * | 3.24 (B) | 524 |
| 716 | 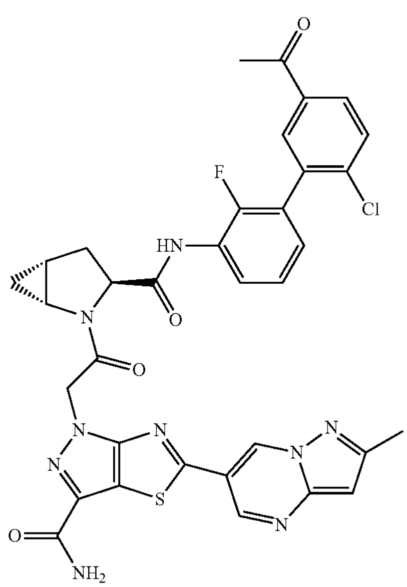 [SMILES: CC(=O)c1ccc(Cl)c(-c2cccc(NC(=O)[C@@H]3C[C@H]4C[C@H]4N3C(=O)Cn3nc(C(N)=O)c4sc(-c5cnc6cc(C)nn6c5)nc43)c2F)c1] | 1-(2-((1R,3S,5R)-3-((5'-acetyl-2'-chloro-2-fluoro-[1,1'-biphenyl]-3-yl)carbamoyl)-2-azabicyclo[3.1.0]hexan-2-yl)-2-oxoethyl)-5-(2-methylpyrazolo[1,5-a]pyrimidin-6-yl)-1H-pyrazolo[3,4-d]thiazole-3-carboxamide | *** | 3.47 (B) | 712 |

TABLE 3-continued

Additional Non-limiting Examples of Compounds of Formula I

| Comp No. | Structure | Name | IC₅ (Stars) | RT min (Method A,B,C or D) | MS (M + 1) |
|---|---|---|---|---|---|
| 717 | 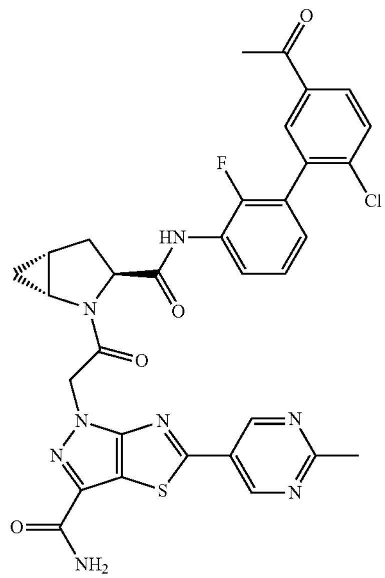 [SMILES: CC(=O)c1ccc(Cl)c(-c2cccc(NC(=O)[C@@H]3C[C@H]4C[C@H]4N3C(=O)Cn3nc(C(N)=O)c4sc(-c5cnc(C)nc5)nc43)c2F)c1] | 1-(2-((1R,3S,5R)-3-((5'-acetyl-2'-chloro-2-fluoro-[1,1'-biphenyl]-3-yl)carbamoyl)-2-azabicyclo[3.1.0]hexan-2-yl)-2-oxoethyl)-5-(2-methylpyrimidin-5-yl)-1H-pyrazolo[3,4-d]thiazole-3-carboxamide | *** | 3.29 (B) | 673 |
| 721 | 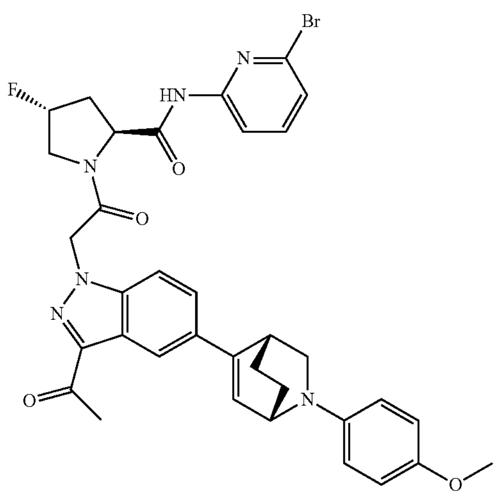 [SMILES: COc1ccc(N2C[C@@H]3CC[C@H]2C=C3c2ccc3c(c2)c(C(C)=O)nn3CC(=O)N2C[C@H](F)C[C@H]2C(=O)Nc2cccc(Br)n2)cc1] | (2S,4R)-1-(2-(3-acetyl-5-((1S,4R)-2-(4-methoxyphenyl)-2-azabicyclo[2.2.2]oct-5-en-5-yl)-1H-indazol-1-yl)acetyl)-N-(6-bromopyridin-2-yl)-4-fluoropyrrolidine-2-carboxamide | *** | 14.58 (D) | 700 (M − 1) |
| 722 | 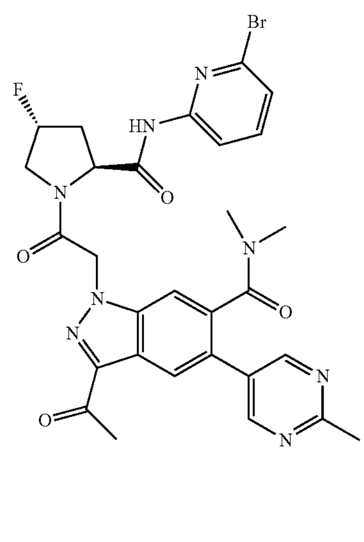 [SMILES: CC(=O)c1nn(CC(=O)N2C[C@H](F)C[C@H]2C(=O)Nc2cccc(Br)n2)c2cc(C(=O)N(C)C)c(-c3cnc(C)nc3)cc12] | 3-acetyl-1-(2-((2S,4R)-2-((6-bromopyridin-2-yl)carbamoyl)-4-fluoropyrrolidin-1-yl)-2-oxoethyl)-N,N-dimethyl-5-(2-methylpyrimidin-5-yl)-1H-indazole-6-carboxamide | *** | 1.48 (A) | 651 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 723 | 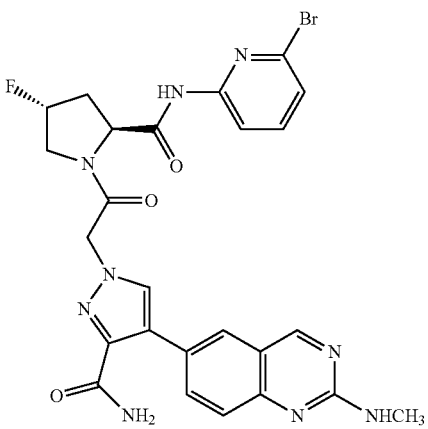 [SMILES: CNc1ncc2cc(-c3cn(CC(=O)N4C[C@H](F)C[C@H]4C(=O)Nc4cccc(Br)n4)nc3C(N)=O)ccc2n1] | 1-(2-((2S,4R)-2-((6-bromopyridin-2-yl)carbamoyl)-4-fluoropyrrolidin-1-yl)-2-oxoethyl)-4-(2-(methylamino)quinazolin-6-yl)-1H-pyrazole-3-carboxamide | * | 1.13 (A) | 596 |
| 724 | 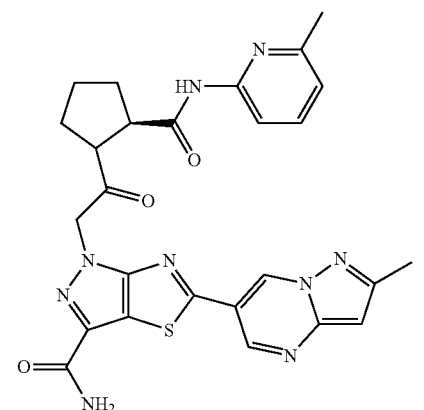 | 1-(2-((2S,4R)-4-fluoro-2-((6-methylpyridin-2-yl)carbamoyl)pyrrolidin-1-yl)-2-oxoethyl)-5-(2-methylpyrazolo[1,5-a]pyrimidin-6-yl)-1H-pyrazolo[3,4-d]thiazole-3-carboxamide | * | 1.90 (B) | 563 |
| 726 | 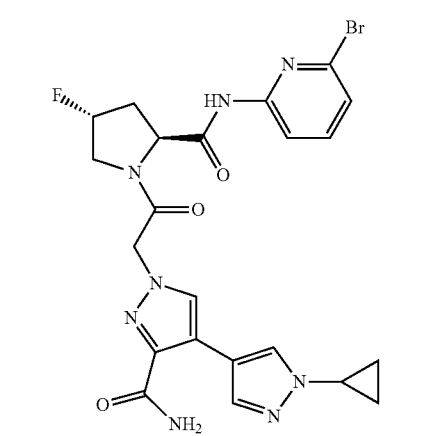 [SMILES: NC(=O)c1nn(CC(=O)N2C[C@H](F)C[C@H]2C(=O)Nc2cccc(Br)n2)cc1-c1cnn(C2CC2)c1] | 1-(2-((2S,4R)-2-((6-bromopyridin-2-yl)carbamoyl)-4-fluoropyrrolidin-1-yl)-2-oxoethyl)-1'-cyclopropyl-1H,1'H-[4,4'-bipyrazole]-3-carboxamide | * | 1.28 (A) | 545 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 727 | 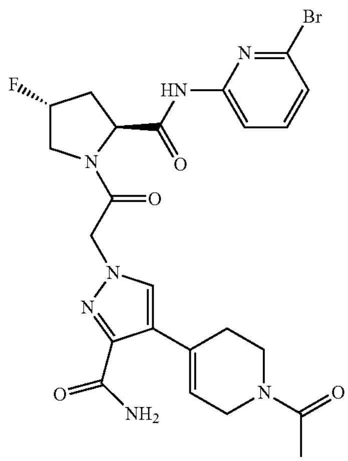 [SMILES: CC(=O)N1CC=C(c2cn(CC(=O)N3C[C@H](F)C[C@H]3C(=O)Nc3cccc(Br)n3)nc2C(N)=O)CC1] | 4-(1-acetyl-1,2,3,6-tetrahydropyridin-4-yl)-1-(2-((2S,4R)-2-((6-bromopyridin-2-yl)carbamoyl)-4-fluoropyrrolidin-1-yl)-2-oxoethyl)-1H-pyrazole-3-carboxamide | * | 1.08 (A) | 562 |
| 729 | 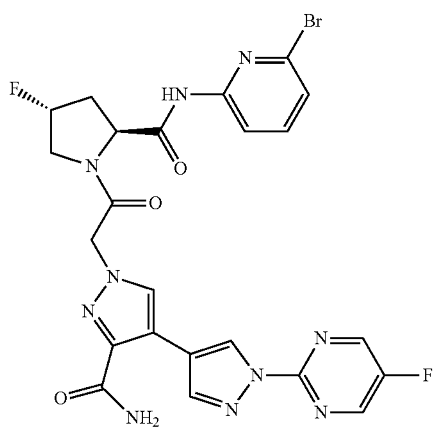 [SMILES: NC(=O)c1nn(CC(=O)N2C[C@H](F)C[C@H]2C(=O)Nc2cccc(Br)n2)cc1-c1cnn(-c2ncc(F)cn2)c1] | 1-(2-((2S,4R)-2-((6-bromopyridin-2-yl)carbamoyl)-4-fluoropyrrolidin-1-yl)-2-oxoethyl)-1'-(5-fluoropyrimidin-2-yl)-1H, 1'H-[4,4'-bipyrazole]-3-carboxamide | * | 1.32 (A) | 601 |
| 730 | 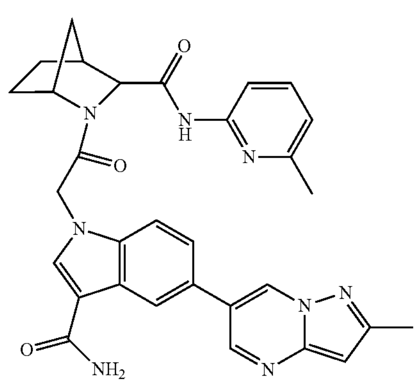 [SMILES: Cc1cccc(NC(=O)C2C3CCC(C3)N2C(=O)Cn2cc(C(N)=O)c3cc(-c4cnc5cc(C)nn5c4)ccc32)n1] | 5-(2-methylpyrazolo[1,5-a]pyrimidin-6-yl)-1-(2-((1R,4S)-3-((6-methylpyridin-2-yl)carbamoyl)-2-azabicyclo[2.2.1]heptan-2-yl)-2-oxoethyl)-1H-indole-3-carboxamide | ** | 2.69 (B) | 563 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 731 | 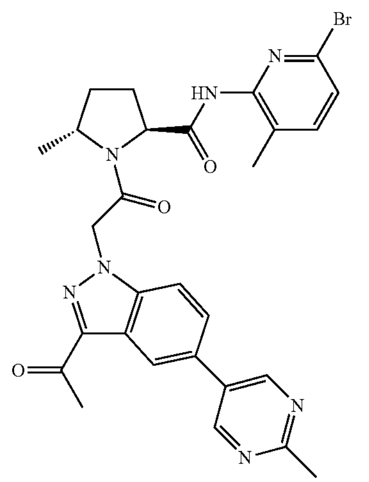 [SMILES: CC(=O)c1nn(CC(=O)N2[C@H](C)CC[C@H]2C(=O)Nc2nc(Br)ccc2C)c2ccc(-c3cnc(C)nc3)cc12] | (2S,5R)-1-(2-(3-acetyl-5-(2-methylpyrimidin-5-yl)-1H-indazol-1-yl)acetyl)-N-(6-bromo-3-methylpyridin-2-yl)-5-methylpyrrolidine-2-carboxamide | *** | 1.64 (A) | 592 |
| 732 | 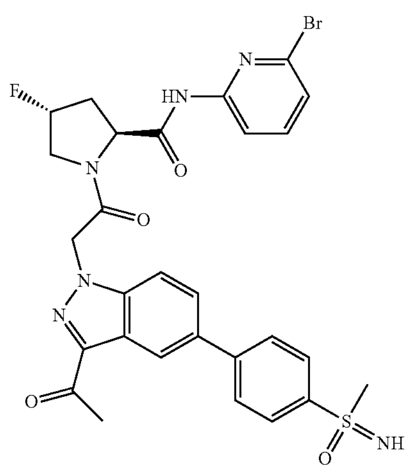 [SMILES: CC(=O)c1nn(CC(=O)N2C[C@H](F)C[C@H]2C(=O)Nc2cccc(Br)n2)c2ccc(-c3ccc(S(C)(=N)=O)cc3)cc12] | (2S,4R)-1-(2-(3-acetyl-5-(2-(S-methylsulfonimidoyl)pyrimidin-5-yl)-1H-indazol-1-yl)acetyl)-N-(6-bromopyridin-2-yl)-4-fluoropyrrolidine-2-carboxamide | *** | 1.46 (A) | 643 |
| 733 | 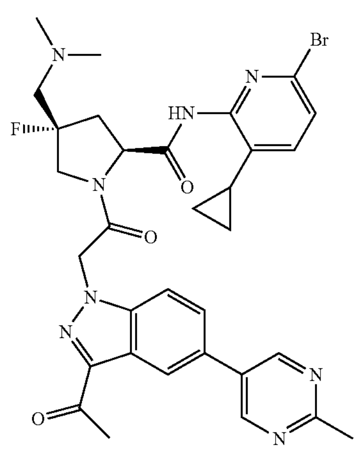 [SMILES: CC(=O)c1nn(CC(=O)N2C[C@@](F)(CN(C)C)C[C@H]2C(=O)Nc2nc(Br)ccc2C2CC2)c2ccc(-c3cnc(C)nc3)cc12] | (1s,4s)-2-(2-(3-acetyl-5-(2-methylpyrimidin-5-yl)-1H-indazol-1-yl)acetyl)-N-(6-bromopyridin-2-yl)-2-azabicyclo[2.2.2]octane-3-carboxamide | ** | 2.09 (A) | 601 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 734 | 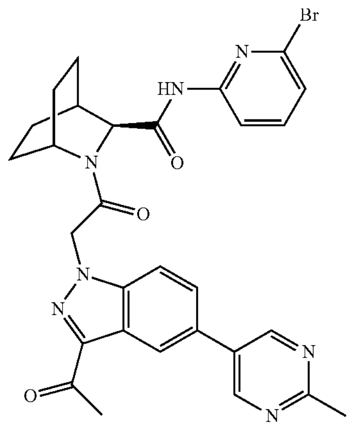 [SMILES: CC(=O)c1nn(CC(=O)N2C3CCC(CC3)[C@H]2C(=O)Nc2cccc(Br)n2)c2ccc(-c3cnc(C)nc3)cc12] | (1s,4s)-2-(2-(3-acetyl-5-(2-methylpyrimidin-5-yl)-1H-indazol-1-yl)acetyl)-N-(6-bromopyridin-2-yl)-2-azabicyclo[2.2.2]octane-3-carboxamide | *** | 1.89 (A) | 601 |
| 735 | 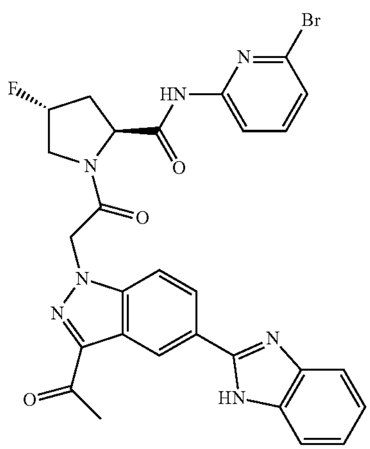 [SMILES: CC(=O)c1nn(CC(=O)N2C[C@H](F)C[C@H]2C(=O)Nc2cccc(Br)n2)c2ccc(-c3nc4ccccc4[nH]3)cc12] | (2S,4R)-1-(2-(3-acetyl-5-(1H-benzo[d]imidazol-2-yl)-1H-indazol-1-yl)acetyl)-N-(6-bromopyridin-2-yl)-4-fluoropyrrolidine-2-carboxamide | *** | 2.45 (A) | 603 |
| 737 | 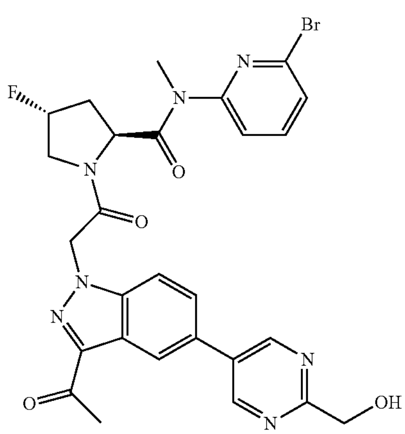 [SMILES: CC(=O)c1nn(CC(=O)N2C[C@H](F)C[C@H]2C(=O)N(C)c2cccc(Br)n2)c2ccc(-c3cnc(CO)nc3)cc12] | (2S,4R)-1-(2-(3-acetyl-5-(2-(hydroxymethyl)pyrimidin-5-yl)-1H-indazol-1-yl)acetyl)-N-(6-bromopyridin-2-yl)-4-fluoro-N-methylpyrrolidine-2-carboxamide | *** | 1.48 (A) | 610 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 738 | 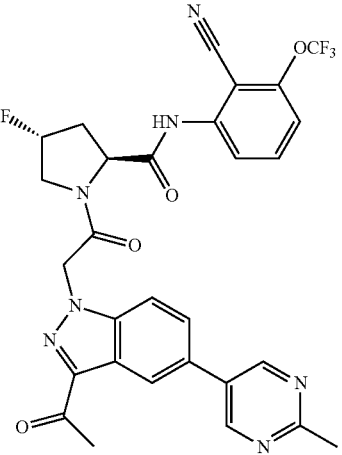 [SMILES: CC(=O)c1nn(CC(=O)N2C[C@H](F)C[C@H]2C(=O)Nc2cccc(OC(F)(F)F)c2C#N)c2ccc(-c3cnc(C)nc3)cc12] | (2S,4R)-1-(2-(3-acetyl-5-(2-methylpyrimidin-5-yl)-1H-indazol-1-yl)acetyl)-N-(2-cyano-3-(trifluoromethoxy)phenyl)-4-fluoropyrrolidine-2-carboxamide | *** | 1.76 (A) | 686 |
| 739 | 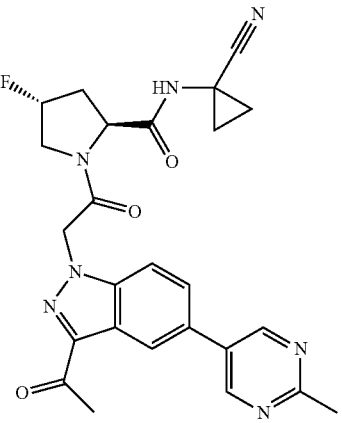 [SMILES: CC(=O)c1nn(CC(=O)N2C[C@H](F)C[C@H]2C(=O)NC2(C#N)CC2)c2ccc(-c3cnc(C)nc3)cc12] | (2S,4R)-1-(2-(3-acetyl-5-(2-methylpyrimidin-5-yl)-1H-indazol-1-yl)acetyl)-N-(1-cyanocyclopropyl)-4-fluoropyrrolidine-2-carboxamide | *** | 2.00 (B) | 490 |
| 741 | 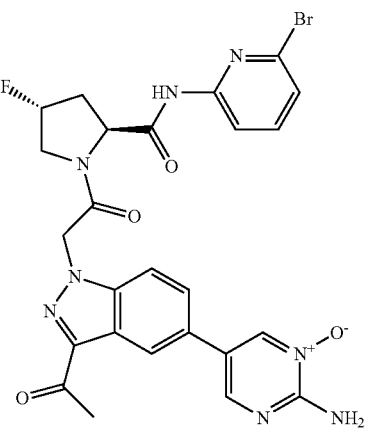 | 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)-2-aminopyrimidine 1-oxide | *** | 2.06 (B) | 597 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 742 | 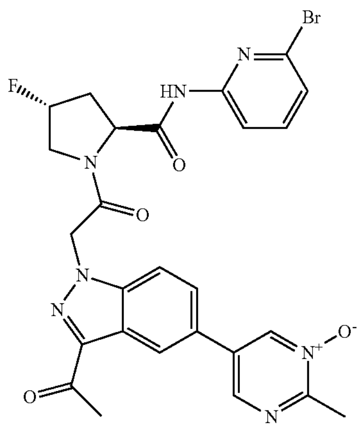 [SMILES: CC(=O)c1nn(CC(=O)N2C[C@H](F)C[C@H]2C(=O)Nc2cccc(Br)n2)c2ccc(-c3cnc(C)[n+]([O-])c3)cc12] | 5-(3-acetyl-1-(2-((2S,4R)-2-((6-bromopyridin-2-yl)carbamoyl)-4-fluoropyrrolidin-1-yl)-2-oxoethyl)-1H-indazol-5-yl)-2-methylpyrimidine 1-oxide | *** | 2.75 (B) | 596 |
| 743 | 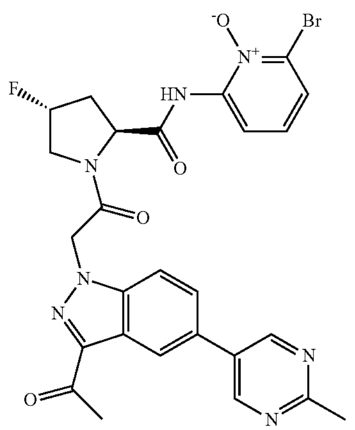 | 2-((2S,4R)-1-(2-(3-acetyl-5-(2-methylpyrimidin-5-yl)-1H-indazol-1-yl)acetyl)-4-fluoropyrrolidine-2-carboxamido)-6-bromopyridine 1-oxide | ** | 2.06 (B) | 596 |
| 744 | 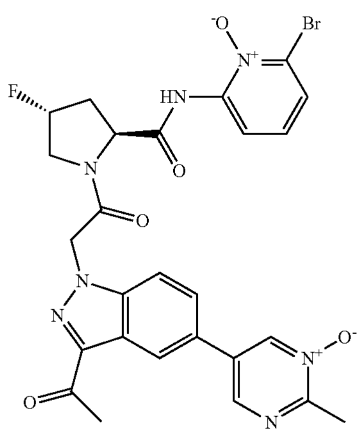 | 5-(3-acetyl-1-(2-((2S,4R)-2-((6-bromo-1-oxidopyridin-2-yl)carbamoyl)-4-fluoropyrrolidin-1-yl)-2-oxoethyl)-1H-indazol-5-yl)-2-methylpyrimidine 1-oxide | ** | 1.87 (B) | 612 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 745 | 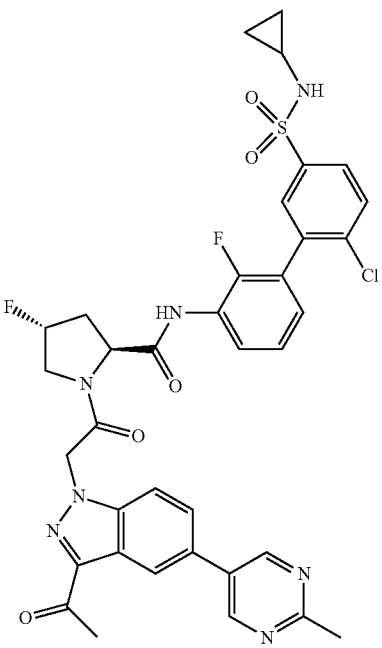 [SMILES: CC(=O)c1nn(CC(=O)N2C[C@H](F)C[C@H]2C(=O)Nc2cccc(-c3cc(S(=O)(=O)NC4CC4)ccc3Cl)c2F)c2ccc(-c3cnc(C)nc3)cc12] | (2S,4R)-1-(2-(3-acetyl-5-(2-methylpyrimidin-5-yl)-1H-indazol-1-yl)acetyl)-N-(2'-chloro-5'-(N-cyclopropylsulfamoyl)-2-fluoro-[1,1'-biphenyl]-3-yl)-4-fluoropyrrolidine-2-carboxamide | *** | | |
| 746 | 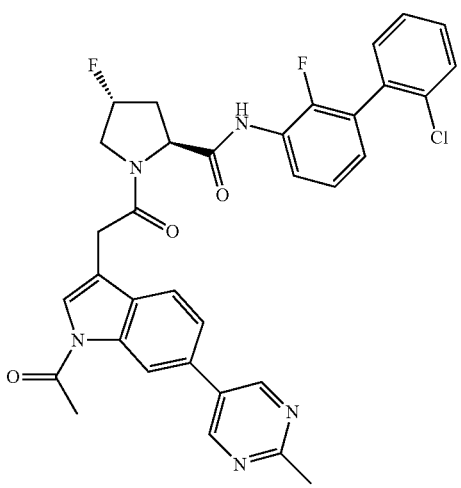 [SMILES: CC(=O)n1cc(CC(=O)N2C[C@H](F)C[C@H]2C(=O)Nc2cccc(-c3ccccc3Cl)c2F)c2ccc(-c3cnc(C)nc3)cc21] | (2S,4R)-1-(2-(1-acetyl-6-(2-methylpyrimidin-5-yl)-1H-indol-3-yl)acetyl)-N-(2'-chloro-2-fluorobiphenyl-3-yl)-4-fluoropyrrolidine-2-carboxamide | *** | 2.02 (A) | 628 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 747 | 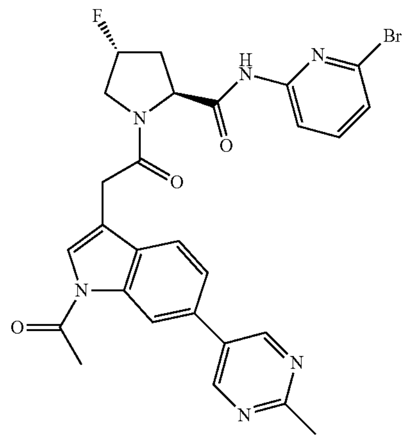 [SMILES: CC(=O)n1cc(CC(=O)N2C[C@H](F)C[C@H]2C(=O)Nc2cccc(Br)n2)c2ccc(-c3cnc(C)nc3)cc21] | (2S,4R)-1-(2-(1-acetyl-6-(2-methylpyrimidin-5-yl)-1H-indol-3-yl)acetyl)-N-(6-bromopyridin-2-yl)-4-fluoropyrrolidine-2-carboxamide | *** | 1.69 (A) | 579 |
| 748 | 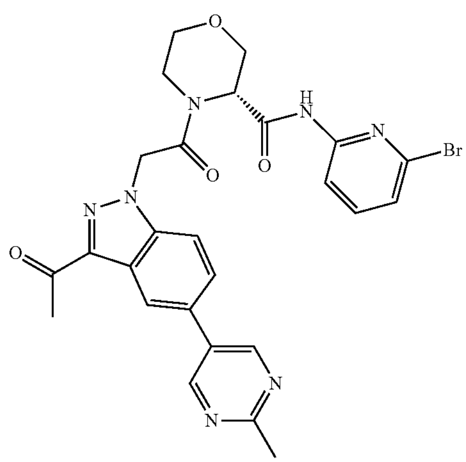 [SMILES: CC(=O)c1nn(CC(=O)N2CCOC[C@@H]2C(=O)Nc2cccc(Br)n2)c2ccc(-c3cnc(C)nc3)cc12] | (R)-4-(2-(3-acetyl-5-(2-methylpyrimidin-5-yl)-1H-indazol-1-yl)acetyl)-N-(6-bromopyridin-2-yl)morpholine-3-carboxamide | *** | 1.65 (A) | 578 |
| 749 | 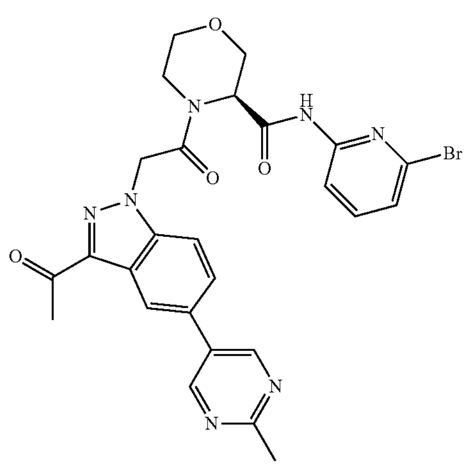 [SMILES: CC(=O)c1nn(CC(=O)N2CCOC[C@H]2C(=O)Nc2cccc(Br)n2)c2ccc(-c3cnc(C)nc3)cc12] | (S)-4-(2-(3-acetyl-5-(2-methylpyrimidin-5-yl)-1H-indazol-1-yl)acetyl)-N-(6-bromopyridin-2-yl)morpholine-3-carboxamide | *** | 1.65 (A) | 578 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 750 | 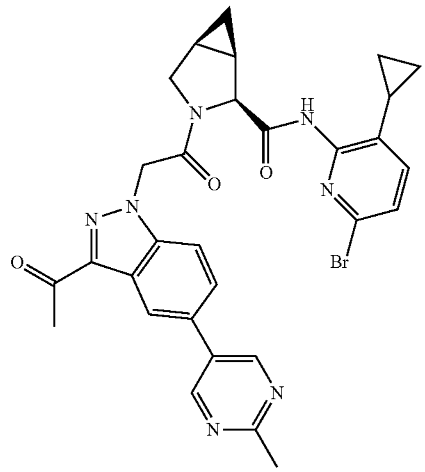 [SMILES: CC(=O)c1nn(CC(=O)N2C[C@H]3C[C@H]3[C@H]2C(=O)Nc2nc(Br)ccc2C2CC2)c2ccc(-c3cnc(C)nc3)cc12] | (1R,2S,5S)-3-(2-(3-acetyl-5-(2-methylpyrimidin-5-yl)-1H-indazol-1-yl)acetyl)-N-(6-bromo-3-cyclopropylpyridin-2-yl)-3-azabicyclo[3.1.0]hexane-2-carboxamide | *** | 1.75 (A) | 614 |
| 751 | 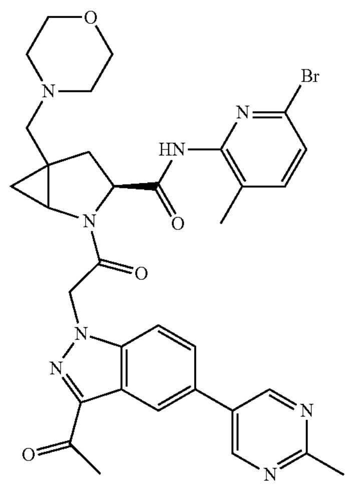 [SMILES: CC(=O)c1nn(CC(=O)N2C3CC3(CN3CCOCC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-(morpholinomethyl)-2-azabicyclo[3.1.0]hexane-3-carboxamide | ** | 1.33 (A) | 686 |
| 752 | 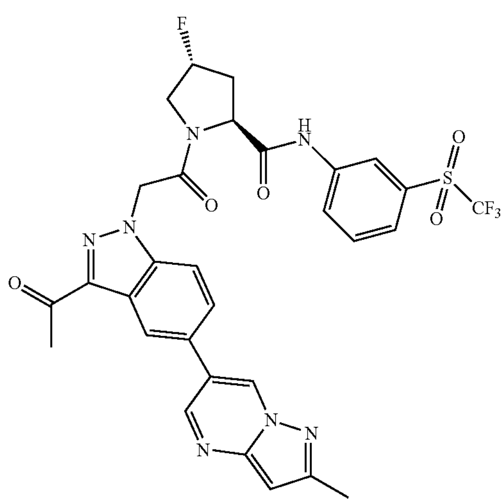 [SMILES: CC(=O)c1nn(CC(=O)N2C[C@H](F)C[C@H]2C(=O)Nc2cccc(S(=O)(=O)C(F)(F)F)c2)c2ccc(-c3cnc4cc(C)nn4c3)cc12] | (2S,4R)-1-(2-(3-acetyl-5-(2-methylpyrazolo[1,5-a]pyrimidin-6-yl)-1H-indazol-1-yl)acetyl)-4-fluoro-N-(3-((trifluoromethyl)sulfonyl)phenyl)pyrrolidine-2-carboxamide | *** | 2.13 (A) | 672 |

TABLE 3-continued

Additional Non-limiting Examples of Compounds of Formula I

| Comp No. | Structure | Name | IC$_5$ (Stars) | RT min (Method A,B,C or D) | MS (M + 1) |
|---|---|---|---|---|---|
| 753 | 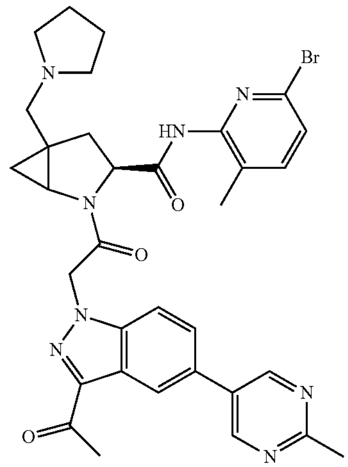 [SMILES: CC(=O)c1nn(CC(=O)N2C3CC3(CN3CCCC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-(pyrrolidin-1-ylmethyl)-2-azabicyclo[3.1.0]hexane-3-carboxamide | ** | 3.48 (B) | 671 |
| 754 | 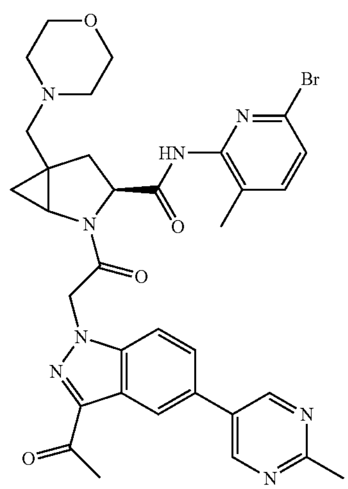 [SMILES: CC(=O)c1nn(CC(=O)N2C3CC3(CN3CCOCC3)C[C@H]2C(=O)Nc2nc(Br)ccc2C)c2ccc(-c3cnc(C)nc3)cc12] | (3S)-2-(2-(3-acetyl-5-(2-methylpyrimidin-5-yl)-1H-indazol-1-yl)acetyl)-N-(6-bromo-3-methylpyridin-2-yl)-5-(morpholinomethyl)-2-azabicyclo[3.1.0]hexane-3-carboxamide | ** | 3.61 (B) | 687 |

Example 8. Human Factor D Assay

Human Factor D (purified from human serum, Complement Technology, Inc.) at 80 nM final concentration was incubated with test compound at various concentrations for 5 minutes at room temperature in 50 mM Tris, 1M NaCl, pH 7.5. A synthetic substrate Z-L-Lys-SBzl and DTNB (Ellman's reagent) are added to final concentrations of 100 μM each. Absorbance at 405 nm ($A_{405}$) was recorded at 30 second intervals for 30 minutes using a microplate spectrophotometer. IC$_{50}$ values are calculated by nonlinear regression of complement Factor D reaction rates as a function of test compound concentration.

Example 9. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) was determined by titration. In the assay, NHS (Complement Technology) was diluted in GVB$^0$ Buffer (0.1% gelatin, 5 mM Veronal, 145 mM NaCl, 0.025% NaN$_3$, pH 7.3, Complement Technology) plus 10 mM Mg-EGTA and incubated with test compound at various concentrations for 15 minutes at 37° C. RE (Complement Technology) freshly suspended in GVB$^0$ plus 10 mM Mg-EGTA are added to a final concentration of 1×10$^8$ cells/mL and reactions are incubated for 30 minutes at 37° C. Positive control reactions (100% lysis) consist of GVB$^0$ plus 10 mM Mg-EGTA with NHS and RE but without test compound; negative control reactions (0% lysis) consist of GVB$^0$ plus 10 mM Mg-EGTA with RE only. Samples are centrifuged at 2000 g for 3 minutes and supernatants collected. Absorbance at 405 nm ($A_{405}$) was recorded using a microplate spectrophotometer. IC$_{50}$ values are calculated by nonlinear regression from the percentage of hemolysis as a function of test compound concentration.

Example 10. An Advantageous Effect of Combination Therapy

The combinatorial efficacy of two compounds on the complement alternative pathway (CAP) was assessed by determining the effect of two compounds mixed together at various concentrations with Normal Human Serum (NHS) on the hemolysis of rabbit erythrocytes (RE) or the production of terminal complement complex (TCC). In both assays the two test compounds were prepared individually in seven-point dilution series, with an eighth sample for each containing solvent alone, and each of the 64 possible combinations was tested in duplicate or triplicate wells.

In the hemolysis assay, NHS (Complement Technology) diluted to 10% in GVB$^0$ Buffer (0.1% gelatin, 5 mM Veronal, 145 mM NaCl, 0.025% NaN$_3$, pH 7.3, Complement Technology) plus 10 mM Mg-EGTA was incubated with the compounds at various concentrations for 15 minutes at 37° C. RE (Complement Technology) freshly suspended in GVB$^0$ plus 10 mM Mg-EGTA was added to a final concentration of 1×10$^8$ cells/mL and reactions were incubated for 30 minutes at 37° C. Positive control reactions consist of GVB$^0$ plus Mg-EGTA with NHS and RE but without test compounds; negative control reactions consist of GVB$^0$ plus Mg-EGTA with RE only. Samples were centrifuged at 2000 g for 3 minutes and supernatants collected. Absorbance at 405 nM ($A_{405}$) was recorded using a microplate spectrophotometer.

The assay for TCC production was conducted using the Complement system Alternative Pathway Wieslab assay kit (Euro Diagnostica). NHS diluted to 5.56% in the provided diluent was incubated with each compound in the wells of the provided assay plates for 60 minutes at 37° C. The wells were emptied and washed with the provided wash solution, incubated with 100 L enzyme-linked detection antibody at 37° C. for 30 minutes, emptied and washed again, and incubated with 100 μL substrate at room temperature for 30 minutes. The provided quantitation standards were used as described by the manufacturer. Positive control reactions consist of diluent with NHS but without test compounds; negative control reactions consist of diluent only. After the 30 minute incubation, the $A_{405}$ of each well was recorded using a microplate spectrophotometer. TCC production was quantitated from $A_{405}$ by reference to the quantitation standards.

Combinatorial effects in both assays were analyzed using the three-dimensional surface-graphing method of Prichard, M. N. and C. Shipman, Jr., Antiviral Research 1990, 14: 181-205, wherein the X-axis and Y-axis indicate test compound concentrations and the Z-axis indicates the difference between measured inhibition and a theoretically determined additive inhibition. For an additive combinatorial relationship the surface graph will resemble a horizontal plane of zero height, whereas positive surface peaks indicate greater inhibition than expected and therefore synergy, and negative surface peaks indicate less inhibition than expected and therefore antagonism.

Figure 10A:
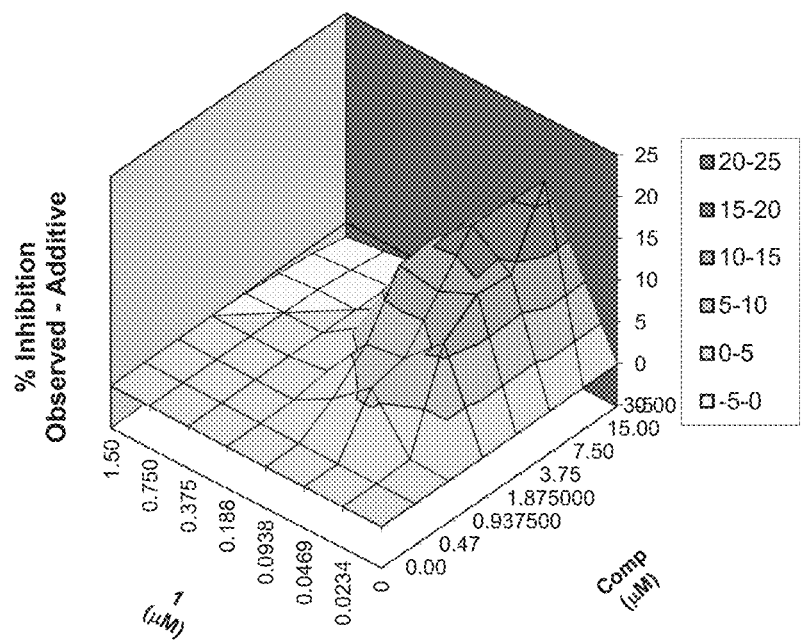
FIG. 10A and FIG. 10B are graphs showing the advantageous effect (% inhibition of the complement alternative pathway (CAP) versus increasing concentration of drug) of the combined administration of a complement Factor D Inhibitor described herein (μM) with the peptidic complement C3 inhibitor compstatin (μM) as measured in a rabbit erythrocyte (RE) hemolysis assay as shown and described in Example 10.
Figure 10B:
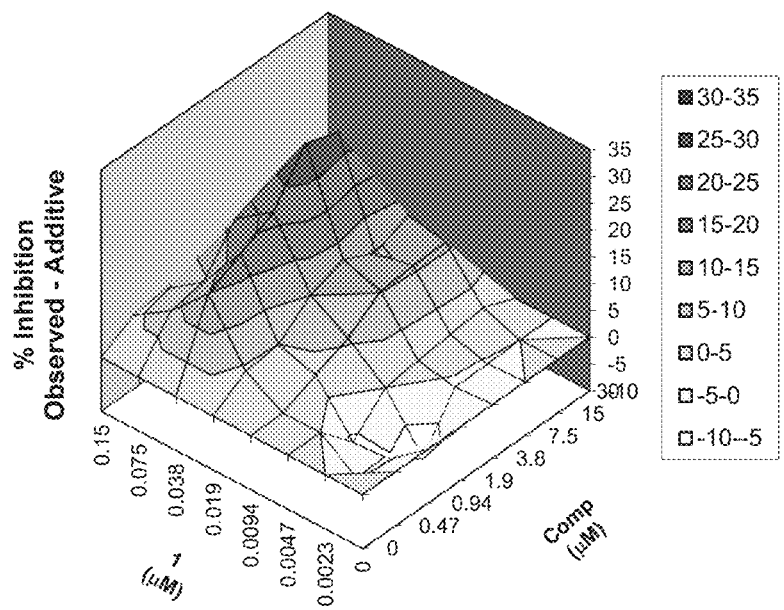
Figure 11A:
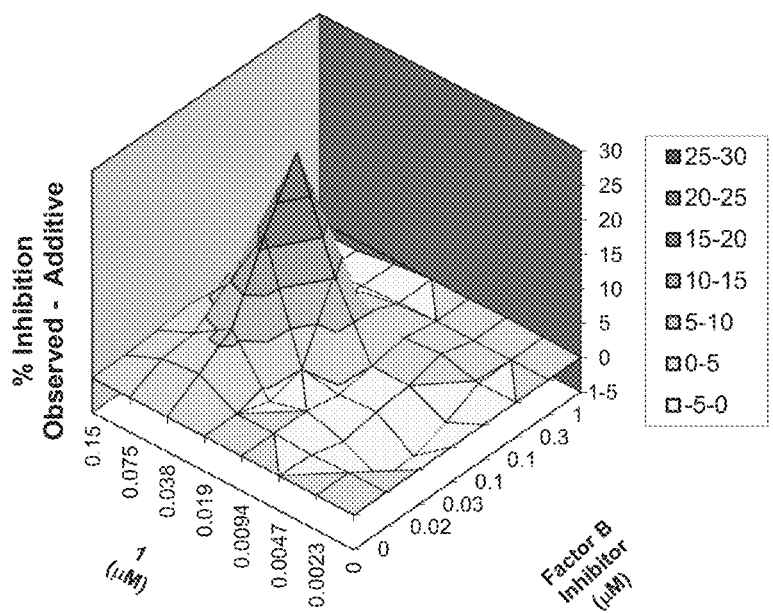
FIG. 11A and FIG. 11B are graphs showing the advantageous effect (% inhibition of the complement alternative pathway (CAP) versus increasing concentration of drug) of the combined administration of a complement Factor D Inhibitor described herein (μM) with Complement Factor B Inhibitor (μM) (Compound 84 in WO2013/192345) as measured in a rabbit erythrocyte (RE) hemolysis assay as shown and described in Example 10.
Figure 11B:
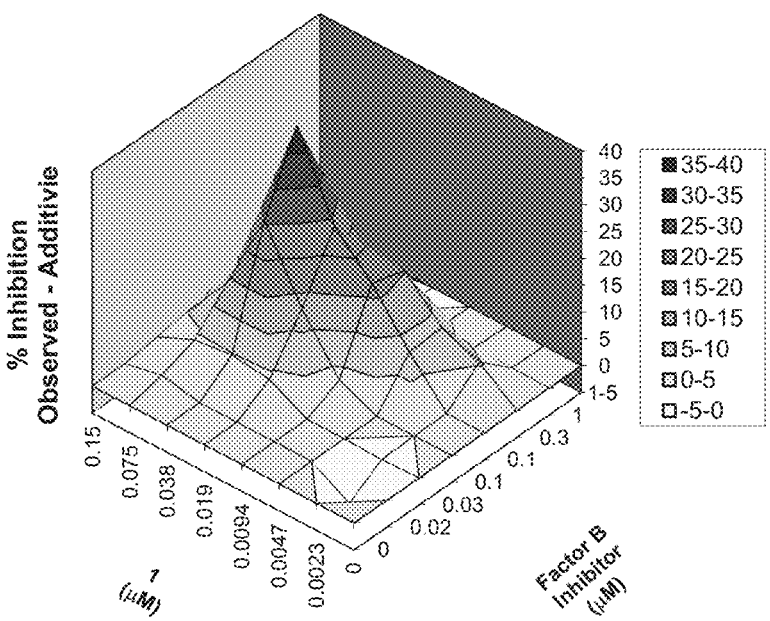
Figure 12A:
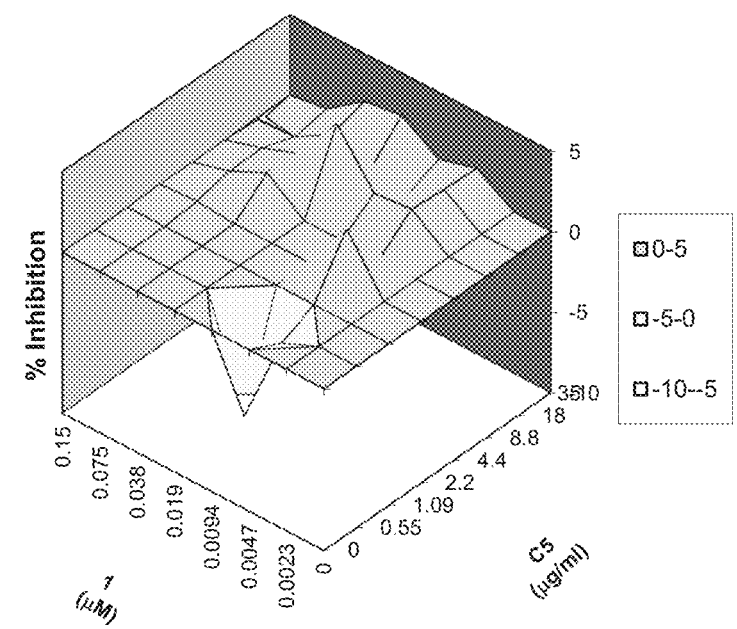
FIG. 12A and FIG. 12B are graphs showing the advantageous effect (% inhibition of the complement alternative pathway (CAP) versus increasing concentration of drug) of the combined administration of a complement Factor D Inhibitor described herein (μM) and an anti-C5 antibody (µg/ml) as measured in an ELISA assay for terminal complement complex (TCC) production as shown and described in Example 10.
Figure 12B:
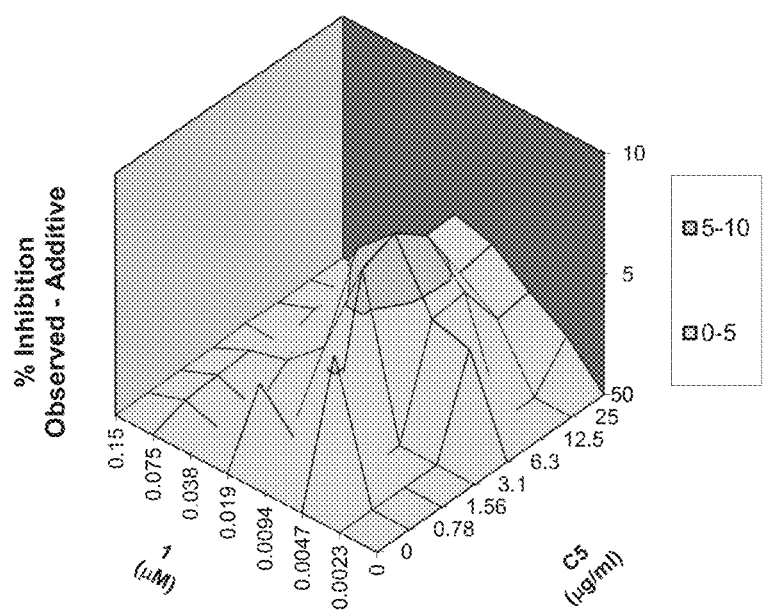
Figure 13A:
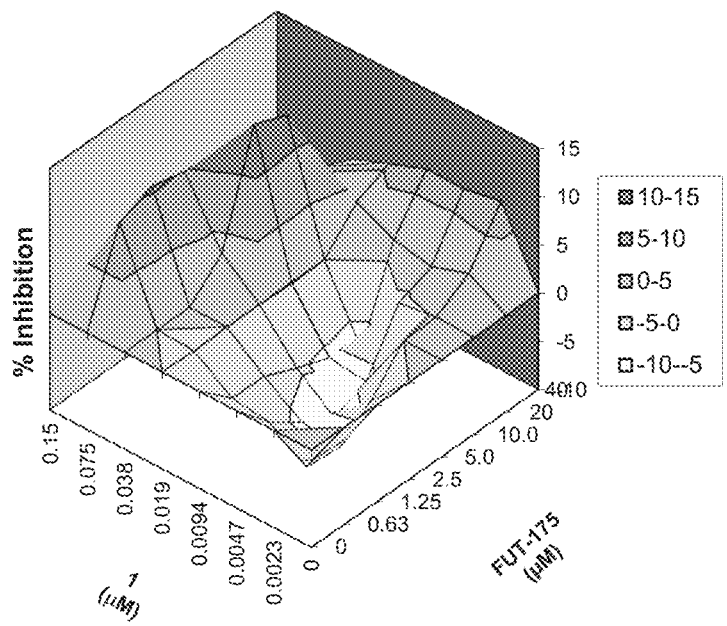
FIG. 13A and FIG. 13B are graphs showing the advantageous effect (% inhibition of the complement alternative pathway (CAP) versus increasing concentration of drug) of a complement Factor D Inhibitor described herein (µM) and FUT-175 (µM) as measured in a rabbit erythrocyte (RE) hemolysis assay as shown and described in Example 10.
Figure 13B:
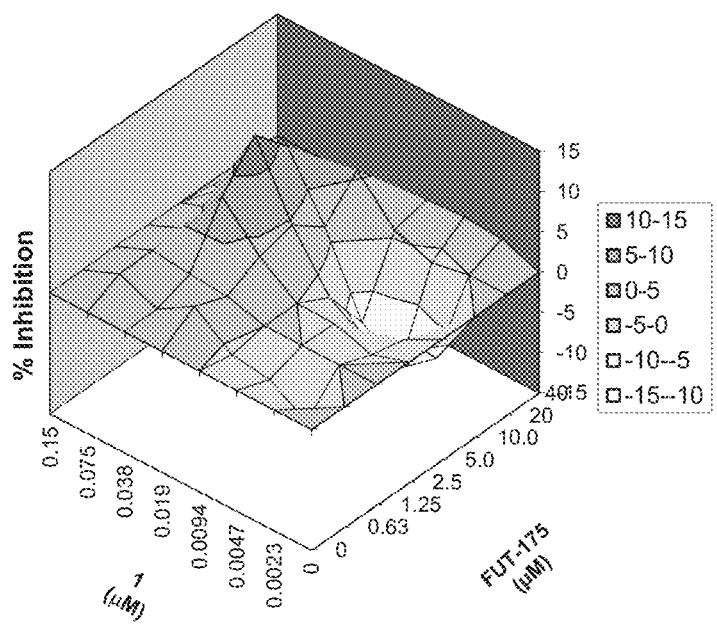

Combinatorial efficacy of a complement Factor D inhibitor as described herein (designated in the Figure as "1", which for clarity was not Compound 1 in Table 1) and the peptidic complement C3 inhibitor compstatin (Tocris Bioscience) was shown in FIG. 10A and FIG. 10B. Combinatorial efficacy of a complement Factor D inhibitor as described herein (1) and a complement Factor B inhibitor (See structure below in this Example; See compound 84 in WO2013/192345) was shown in FIG. 11A and FIG. 11B. Combinatorial efficacy of a Complement Factor D inhibitor as described herein (1) and a monoclonal antibody directed against complement C5 protein (anti-C5, Quidel A217, murine monoclonal antibody to human complement C5, isotype IgG1K) was shown in FIG. 12A and FIG. 12B. Combinatorial efficacy of a complement Factor D inhibitor as described herein (1) and the broad spectrum inhibitor FUT-175 (BD Biosciences) was shown in FIG. 13A and FIG. 13B.

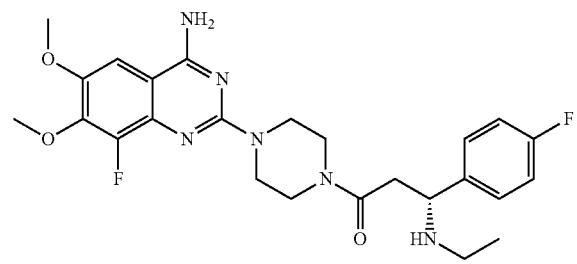

Structure of Complement Factor B Inhibitor

TABLE 4

Effect of Combination Therapy

| Complement Factor D inhibitor of the present invention ("1") combination with | Synergy Volume (μM$^2$ · % inhibition) | Antagonism Volume (μM$^2$ · % inhibition) |
|---|---|---|
| Compstatin | 244 ± 104 | −17 ± 15 |
| Complement Factor B inhibitor | 157 ± 99 | −18 ± 10 |
| Anti-C5 monoclonal Antibody | 57 ± 44 | −4 ± 5 |
| FUT-175 | 95 ± 37 | −59 ± 11 |

Synergy and antagonism volumes are the summed volumes of peaks respectively above and below the Z=0 plane on the surface graph. Volumes are determined using 95% confidence limits to assure significance. Compounds are considered additive for volumes between −25 and 25. Compounds are considered slightly synergistic for volumes between 25 and 50, moderately synergistic for volumes between 50 and 100, and strongly synergistic for volumes greater than 100. Compounds are considered slightly antagonistic for volumes between −25 and −50, moderately antagonistic for volumes between −50 and −100, and strongly antagonistic for volumes less than −100. Results are presented as means±standard deviations from two or three independent experiments.

This specification has been described with reference to embodiments of the invention. However, one of ordinary skill in the art appreciates that various modifications and changes can be made without departing from the scope of the invention as set forth in the claims below. Accordingly, the specification was to be regarded in an illustrative rather than a restrictive sense, and all such modifications are intended to be included within the scope of invention.

We claim:
1. A compound of structure:

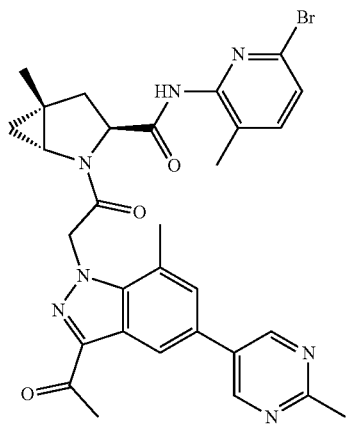 [SMILES: CC(=O)c1nn(CC(=O)N2[C@H](C(=O)Nc3nc(Br)ccc3C)C[C@@]3(C)C[C@@H]23)c2c(C)cc(-c3cnc(C)nc3)cc12]

or a pharmaceutically acceptable salt thereof.

2. A compound of structure:

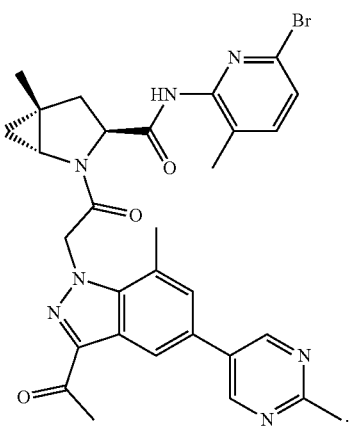 [SMILES: CC(=O)c1nn(CC(=O)N2[C@H](C(=O)Nc3nc(Br)ccc3C)C[C@@]3(C)C[C@@H]23)c2c(C)cc(-c3cnc(C)nc3)cc12]

3. A pharmaceutical composition comprising a compound of structure:

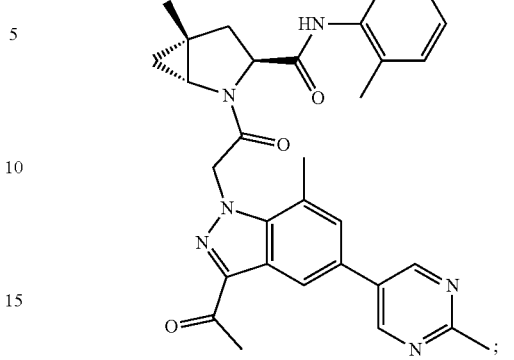

or a pharmaceutically acceptable salt thereof; in a pharmaceutically acceptable carrier.

4. The pharmaceutical composition of claim 3 for the treatment of a human.

5. The pharmaceutical composition of claim 4, wherein the composition is for oral administration.

6. The pharmaceutical composition of claim 4, wherein the composition is for topical administration.

7. The pharmaceutical composition of claim 4 wherein the composition is for ocular delivery.

8. The pharmaceutical composition of claim 4, wherein the composition is for intravitreal delivery.

9. The pharmaceutical composition of claim 4, wherein the composition is for subchoroidal delivery.

10. The pharmaceutical composition of claim 4, wherein the composition is for suprachoroidal delivery.

11. The pharmaceutical composition of claim 4, wherein the composition is in a tablet dosage form.

12. The pharmaceutical composition of claim 4, wherein the composition is in a capsule dosage form.

13. The pharmaceutical composition of claim 4, wherein the composition is for intravenous administration.

14. The pharmaceutical composition of claim 4, wherein the composition is for transdermal administration.

15. The pharmaceutical composition of claim 4, wherein the composition is for parenteral administration.

16. The pharmaceutical composition of claim 4 to treat atypical hemolytic uremic syndrome.

17. The pharmaceutical composition of claim 4 to treat paroxysmal nocturnal hemoglobinuria.

18. The pharmaceutical composition of claim 4 to treat C3 glomerulonephritis.

* * * * *